US012630527B2

(12) United States Patent
Rana

(10) Patent No.: US 12,630,527 B2
(45) Date of Patent: May 19, 2026

(54) BROAD SPECTRUM ANTI-CANCER COMPOUNDS

(71) Applicant: The Regents of the University of California, Oakland, CA (US)

(72) Inventor: Tariq M. Rana, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 982 days.

(21) Appl. No.: 17/768,980

(22) PCT Filed: Oct. 14, 2020

(86) PCT No.: PCT/US2020/055568
§ 371 (c)(1),
(2) Date: Apr. 14, 2022

(87) PCT Pub. No.: WO2021/076617
PCT Pub. Date: Apr. 22, 2021

(65) Prior Publication Data

US 2023/0322715 A1 Oct. 12, 2023

Related U.S. Application Data

(60) Provisional application No. 63/074,421, filed on Sep. 3, 2020, provisional application No. 63/059,939, filed on Jul. 31, 2020, provisional application No. 62/971,701, filed on Feb. 7, 2020, provisional application No. 62/914,914, filed on Oct. 14, 2019.

(51) Int. Cl.

| | |
|---|---|
| ***C07D 401/14*** | (2006.01) |
| ***C07D 207/337*** | (2006.01) |
| ***C07D 239/70*** | (2006.01) |
| ***C07D 413/06*** | (2006.01) |
| ***C07D 413/14*** | (2006.01) |
| ***C07D 471/04*** | (2006.01) |
| ***C07D 473/22*** | (2006.01) |
| ***C07D 487/04*** | (2006.01) |
| ***C07D 491/107*** | (2006.01) |
| ***C07D 513/04*** | (2006.01) |

(52) U.S. Cl.
CPC ....... *C07D 401/14* (2013.01); *C07D 207/337* (2013.01); *C07D 239/70* (2013.01); *C07D 413/06* (2013.01); *C07D 413/14* (2013.01); *C07D 471/04* (2013.01); *C07D 473/22* (2013.01); *C07D 487/04* (2013.01); *C07D 491/107* (2013.01); *C07D 513/04* (2013.01)

(58) Field of Classification Search
CPC ............................... C07D 401/14; A61P 35/00
See application file for complete search history.

(56) References Cited

U.S. PATENT DOCUMENTS

| | | | |
|---|---|---|---|
| 2009/0105209 | A1 | 4/2009 | Dewdney et al. |
| 2016/0213780 | A1 | 7/2016 | Skaar et al. |
| 2016/0264934 | A1 | 9/2016 | Giallourakis et al. |

FOREIGN PATENT DOCUMENTS

| | | | |
|---|---|---|---|
| EP | 0726266 | 8/1996 | |
| WO | WO 2001/054507 | 8/2001 | |
| WO | WO 2005/082859 | 9/2005 | |
| WO | WO 2009/006389 | 1/2009 | |
| WO | WO-2010142752 A1 * | 12/2010 | ............. A61P 37/08 |
| WO | WO 2011/140488 | 11/2011 | |
| WO | WO 2018/157843 | 9/2018 | |
| WO | WO 2018/169994 | 9/2018 | |
| WO | WO 2019/209757 | 10/2019 | |

OTHER PUBLICATIONS

Chemical Abstracts Service Registry No. 1775430-19-7, entry date Jun. 8, 2015 (Year: 2015).*

Extended European Search Report in European Appln. No. 20877361.4, mailed on Aug. 29, 2023, 10 pages.

Adams et al., “Highly specific in vivo tumor targeting by monovalent and divalent forms of 741F8 anti-c-erb B-2 single-chain Fv,” Cancer Research, Sep. 1, 1993, 53(17):4026-4034.

Aik et al., “Structural basis for inhibition of the fat mass and obesity associated protein (FTO),” Journal of Medicinal Chemistry, May 9, 2013, 56(9):3680-3688.

Angelin et al., “Foxp3 Reprograms T Cell Metabolism to Function in Low-Glucose, High-Lactate Environments,” Cell Metabolism, 2017, 25(6): 20 pages.

Antanaviciute et al., “m6a Viewer: software for the detection, analysis, and visualization of N6-methyladenosine peaks from m6A-seq/ME-RIP sequencing data,” RNA, Oct. 1, 2017, 23(10):1493-1501.

(Continued)

*Primary Examiner* — John S Kenyon
*Assistant Examiner* — Sara Elizabeth Bell
(74) *Attorney, Agent, or Firm* — Fish & Richardson P.C.

(57) ABSTRACT

Described herein, inter alia, are compounds for treating cancer and methods of use. This disclosure features chemical entities (e.g., small hairpin RNAs (shRNAs), micro RNA (miRNAs), small interfering RNA (siRNAs), small molecule inhibitors, antisense nucleic acids, peptides, viruses, CRISPR-sgRNAs, or combinations thereof) that inhibit one or more of m6A writers (e.g., methyltransferase like 3 (Mettl3 or MT-A70) or methyltransferase like-14 (Mettl14)), m6Am writers (e.g., phosphorylated CTD interacting factor I (PCIF 1), or Mettl3/14), m6A erasers (e.g., fat-mass and obesity-associated protein (FTO) or ALKB homolog 5 (ALKBH5)), m6Am erasers (e.g., FTO), m6A readers (e.g., YTH domain-containing family proteins (YTHs)), YTF domain family member 1 (YTHDF 1), YTF domain family member 2 (YTHDF 2), YTF domain family member 3 (YTHDF 3), or tyrosine-protein phosphatase non-receptor type 2 (PTPN2).

16 Claims, 344 Drawing Sheets

Specification includes a Sequence Listing.

(56) References Cited

OTHER PUBLICATIONS

Baenke et al., "Functional screening identifies MCT4 as a key regulator of breast cancer cell metabolism and survival," The Journal of Pathology, Oct. 2015, 237(2):152-165.
Bao et al., "Glioma stem cells promote radioresistance by preferential activation of the DNA damage response," Nature, Dec. 2006, 444(7120):756-760.
Barbieri et al., "Promoter-bound METTL3 maintains myeloid leukaemia by m6A-dependent translation control," Nature, Dec. 2017, 552(7683):126-1231.
Benitez et al., "PTEN regulates glioblastoma oncogenesis through chromatin-associated complexes of DAXX and histone H3.3," Nature Communications, May 12, 2017, 8(1):1-15.
Berge et al., "Pharmaceutical salts," Journal of Pharmaceutical Sciences, Jan. 1, 1977, 66(1):1-19.
Bleau et al., "The ABCG2 resistance network of glioblastoma," Cell Cycle, Sep. 15, 2009, 8(18):2937-2945.
Bradshaw et al., "Cancer stem cells in glioblastoma multiforme," Frontiers in Surgery, Aug. 26, 2016, 3(48): 1-8.
Buchet-Poyau et al., "Identification and characterization of human Mex-3 proteins, a novel family of evolutionarily conserved RNA-binding proteins differentially localized to processing bodies," Nucleic Acids Research, Feb. 1, 2007, 35(4):1289-300.
Chavali et al., "Neurodevelopmental protein Musashi-1 interacts with the Zika genome and promotes viral replication," Science, Jul. 7, 2017 357(6346): 14 pages.
Chen et al., "Development of cell-active N 6-methyladenosine RNA demethylase FTO inhibitor," Journal of the American Chemical Society, Oct. 31, 2012, 134(43):17963-17971.
Chen et al., "Elements of cancer immunity and the cancer-immune set point," Nature, 541(7637), 321-330.
Chen, et al., "A restricted cell population propagates glioblastoma growth after chemotherapy," Nature, 2012 488(7412), 522-526.
Condamine et al., "Regulation of Tumor Metastasis by Myeloid-Derived Suppressor Cells," Annual Review of Medicine, 2015,66(1), 97-110.
Cross et al., "Comparison of Several Molecular Docking Programs: Pose Prediction and Virtual Screening Accuracy," Journal of Chemical Information and Modeling, 2009 49(6), 1455-1474.
Cui et al., "Downregulation of TLX induces TET3 expression and inhibits glioblastoma stem cell self-renewal and tumorigenesis," Nature Communications, Feb. 3, 2016, 7(1):1-15.
Cui et al., "m6A RNA Methylation Regulates the Self-Renewal and Tumorigenesis of Glioblastoma Stem Cells," Cell Reports, 2017, 18(11), 2622-2634.
Dang et al., "Zika Virus Depletes Neural Progenitors in Human Cerebral Organoids through Activation of the Innate Immune Receptor TLR3," Cell Stem Cell, 2016, 19(2), 258-265.
Deng et al., "RNA N6-methyladenosine modification in cancers: current status and perspectives," Cell Research, May 2018, 28(5):507-517.
Deng et al., "Role of N6-methyladenosine modification in cancer," Current Opinion in Genetics & Development, Feb. 1, 2018, 48:1-7.
Dominissini et al., "Topology of the human and mouse m6A RNA methylomes revealed by m6A-seq," Nature, 2012, 485(7397), 201-206.
Dranoff, "GM-CSF-secreting melanoma vaccines," Oncogene, May 2003, 22(20):3188-3192.
Eichhorn et al., "USP15 stabilizes TGF-β receptor I and promotes oncogenesis through the activation of TGF-β signaling in glioblastoma," Nature Medicine, Mar. 2012, 18(3):429-435.
Engel et al., "The role of m6A/m-RNA methylation in stress response regulation," Neuron, Jul. 25, 2018, 99(2):389-403.
Friesner et al., "Extra precision glide: Docking and scoring incorporating a model of hydrophobic enclosure for protein-ligand complexes," Journal of Medicinal Chemistry, Oct. 19, 2006, 49(21):6177-6196.
Friesner et al., "Glide: A New Approach for Rapid, Accurate Docking and Scoring. 1. Method and Assessment of Docking Accuracy," Journal of Medicinal Chemistry, 2004, 47(7), 1739-1749.
Fujimura et al., "Crosstalk between regulatory T cells (Tregs) and myeloid derived suppressor cells (MDSCs) during melanoma growth," Oncoimmunology, Nov. 1, 2012, 1(8):1433-1434.
Geula et al., "m6A mRNA methylation facilitates resolution of naïve pluripotency toward differentiation," Science, Feb. 27, 2015, 347(6225):1002-1006.
Godlewski et al., "MicroRNAs and glioblastoma; the stem cell connection," Cell Death & Differentiation, Feb. 2010, 17(2):221-228.
Gonzales-Van et al., "Making the mark: the role of adenosine modifications in the life cycle of RNA viruses," Cell Host & Microbe, Jun. 14, 2017, 21(6):661-669.
Gruber et al., "Efficient tumor cell lysis mediated by a bispecific single chain antibody expressed in *Escherichia coli*," The Journal of Immunology, Jun. 1, 1994, 152(11):5368-5374.
Halgren et al., "Glide: A New Approach for Rapid, Accurate Docking and Scoring. 2. Enrichment Factors in Database Screening," Journal of Medicinal Chemistry, 2004, 47(7), 1750-1759.
Han et al., "Anti-tumour immunity controlled through mRNA m6A methylation and YTHDF1 in dendritic cells," Nature, Feb. 2019, 566(7743):270-274.
Heddleston et al., "Glioma stem cell maintenance: the role of the microenvironment," Current Pharmaceutical Design, Aug. 1, 2011, 17(23):2386-2401.
Holliger et al., ""Diabodies": small bivalent and bispecific antibody fragments," Proceedings of the National Academy of Sciences, Jul. 15, 1993, 90(14):6444-6448.
Hopkins et al., "The role of ligand efficiency metrics in drug discovery," Nature Reviews Drug Discovery, Feb. 2014, 13(2):105-121.
Hu et al., "Minibody: a novel engineered anti-carcinoembryonic antigen antibody fragment (single-chain Fv-CH3) which exhibits rapid, high-level targeting of xenografts," Cancer Research, Jul. 1, 1996, 56(13):3055-3061.
Huang et al., "Meclofenamic acid selectively inhibits FTO demethylation of m6A over ALKBH5," Nucleic Acids Research, Jan. 9, 2015, 43(1):373-384.
Huang et al., "Small-molecule targeting of oncogenic FTO demethylase in acute myeloid leukemia," Cancer Cell, Apr. 15, 2019, 35(4):677-691.
Hugo et al., "Genomic and transcriptomic features of response to anti-PD-1 therapy in metastatic melanoma," Cell, Mar. 24, 2016, 165(1):35-44.
Inda et al., "Tumor heterogeneity is an active process maintained by a mutant EGFR-induced cytokine circuit in glioblastoma," Genes & Development, Aug. 15, 2010, 24(16):1731-1745.
International Preliminary Report on Patentability in International Appln. PCT/US2020/055568, dated Apr. 28, 2022, 11 pages.
International Search Report and Written Opinion in International Appln. PCT/US2020/055568, dated Mar. 22, 2021, 19 pages.
Irwin et al., "ZINC: A Free Tool to Discover Chemistry for Biology," Journal of Chemical Information and Modeling, 2012, 52(7), 1757-1768.
Jacobson et al., "A hierarchical approach to all-atom protein loop prediction," Proteins: Structure, Function, and Bioinformatics, May 1, 2004, 55(2):351-367.
Jacobson et al., "On the role of the crystal environment in determining protein side-chain conformations," Journal of Molecular Biology, Jul. 12, 2002, 320(3):597-608.
Jia et al., "N6-Methyladenosine in nuclear RNA is a major substrate of the obesity-associated FTO," Nature Chemical Biology, 2011, 7(12), 885-887.
Johnson et al., "Glioblastoma survival in the United States before and during the temozolomide era," Journal of Neuro-Oncology, Apr. 2012, 107(2):359-364.
Johnson et al., "Lipophilic efficiency as an important metric in drug design," Journal of Medicinal Chemistry, Mar. 28, 2018, 61(15):6401-6420.

(56) References Cited

OTHER PUBLICATIONS

Johnson et al., "Using the Golden Triangle to optimize clearance and oral absorption," Bioorganic & Medicinal Chemistry Letters, Oct. 1, 2009, 19(19):5560-5564.
Katz et al., "Analysis and design of RNA sequencing experiments for identifying isoform regulation," Nature Methods, Dec. 2010, 7(12):1009-1015.
Katz et al., "Quantitative visualization of alternative exon expression from RNA-seq data," Bioinformatics, Jul. 15, 2015, 31(14):2400-2402.
Ke et al., "m6A mRNA modifications are deposited in nascent pre-mRNA and are not required for splicing but do specify cytoplasmic turnover," Genes & Development, 2017, 31(10), 990-1006.
Kim et al., "Eradication of metastatic mouse cancers resistant to immune checkpoint blockade by suppression of myeloid-derived cells," Proceedings of the National Academy of Sciences, Aug. 12, 2014, 111(32):11774-11779.
Kostelny et al., "Formation of a bispecific antibody by the use of leucine zippers," The Journal of Immunology, Mar. 1, 1992, 148(5):1547-1553.
Kotani et al., "Alternative exon skipping biases substrate preference of the deubiquitylase USP15 for mysterin/RNF213, the moyamoya disease susceptibility factor," Scientific Reports, Mar. 9, 2017, 7(1):1-12.
Lan et al., "Fate mapping of human glioblastoma reveals an invariant stem cell hierarchy," Nature, 2017, 549(7671), 227-232.
Lathia et al., "Cancer stem cells in glioblastoma," Genes & Development, 2015, 29(12), 1203-1217.
Li et al., "m6A mRNA methylation controls T cell homeostasis by targeting the IL-7/STAT5/SOCS pathways," Nature, 2017, 548(7667): 338-342.
Li et al., "Rhein inhibits AlkB repair enzymes and sensitizes cells to methylated DNA damage," Journal of Biological Chemistry, May 20, 2016, 291(21):11083-11093.
Lichinchi et al., "Dynamics of the human and viral m6A RNA methylomes during HIV-1 infection of T cells," Nature Microbiology, 2016, 1(4): 1-9.
Linder et al., "Single-nucleotide-resolution mapping of m6A and m6Am throughout the transcriptome," Nat Methods, 2015, 12(8):767-772.
Louloupi et al., "Transient N-6-methyladenosine transcriptome sequencing reveals a regulatory role of m6A in splicing efficiency," Cell Reports, 23(12): 3429-3437.
Manguso et al., "In vivo CRISPR screening identifies Ptpn2 as a cancer immunotherapy target," Nature, Jul. 2017, 547(7664):413-418.
Matsumura et al., "HGF regulates VEGF expression via the c-Met receptor downstream pathways, PI3K/Akt, MAPK and STAT3, in CT26 murine cells," International Journal of Oncology, 2013, 42(2):535-542.
Mauer et al., "FTO controls reversible m6Am RNA methylation during snRNA biogenesis," Nature Chemical Biology, Apr. 2019, 15(4):340-347.
Mauer et al., "Reversible methylation of m6Am in the 5' cap controls mRNA stability," Nature, 2016, 541(7637), 371-375.
McCafferty et al., "Phage antibodies: filamentous phage displaying antibody variable domains," Nature, Dec. 1990, 348(6301):552-554.
McCartney et al., "Engineering disulfide-linked single-chain Fv dimers [(sFv') 2] with improved solution and targeting properties: anti-digoxin 26-10 (sFv') 2 and anti-c-erbB-2 741F8 (sFv') 2 made by protein folding and bonded through C-terminal cysteinyl peptides," Protein Engineering, Design and Selection, Mar. 1, 1995, 8(3):301-314.
Meng et al., "Mettl14 is required for mouse postimplantation development by facilitating epiblast maturation," The FASEB Journal, Jan. 2019, 33(1):1179-1187.
Meyer et al., "Comprehensive analysis of mRNA methylation reveals enrichment in 3' UTRs and near stop codons," Cell, Jun. 22, 2012, 149(7):1635-1646.
Meyer et al., "Rethinking m6A Readers, Writers, and Erasers," Annual Review of Cell and Developmental Biology, 2017, 33(1), 319-342.
Neufeld et al., "Semaphorins in Angiogenesis and Tumor Progression," Cold Spring Harbor Perspectives in Medicine, 2011, 2(1): 14 pages.
Pack et al., "Miniantibodies: use of amphipathic helixes to produce functional, flexibly linked dimeric FV fragments with high avidity in *Escherichia coli*," Biochemistry, Feb. 1, 1992, 31(6):1579-1584.
Paris et al., "Targeting the RNA m6A reader YTHDF2 selectively compromises cancer stem cells in acute myeloid leukemia," Cell Stem Cell, Jul. 3, 2019, 25(1):137-148.
Patil et al., "Reading m6A in the transcriptome: m6A-binding proteins," Trends in Cell Biology, Feb. 1, 2018, 28(2):113-127.
Pilotto et al., "MET exon 14 juxtamembrane splicing mutations: clinical and therapeutical perspectives for cancer therapy," Annals of Translational Medicine, Jan. 2017, 5(1): 11 pages.
PubChem SID 165304044, "MCULE-2138096859," retrieved on Jul. 22, 2022, retrieved from <https://pubchem.ncbi.nlm.nih.gov/substance/165304044>, 6 pages.
PubChem SID 227143154, "SCHEMBL874448," retrieved on Jul. 22, 2022, retrieved from <https://pubchem.ncbi.nlm.nih.gov/substance/227143154>, 8 pages.
PubChem SID 240880404, "SCHEMBL15955199," retrieved on Jan. 15, 2021, retrieved from <https://pubchem.ncbi.nlm.nih.gov/substance/240880404>, 8 pages.
PubChem SID 257043394, "ZINC3625808," retrieved on Jan. 15, 2021, retrieved from <https://pubchem.ncbi.nlm.nih.gov/substance/257043394>, 6 pages.
PubChem SID 311936688, "SCHEMBL17206065," retrieved on Jan. 15, 2021, retrieved from <https://pubchem.ncbi.nlm.nih.gov/substance/311936688>, 8 pages.
PubChem SID 329231780, "(2S,4S)-1-(4-cyanobenzoyl)-N-cyclopropy1-4-phenoxytetrahydro-1H-pyrrole-2-carboxamide," retrieved on Jan. 15, 2021, retrieved from <https://pubchem.ncbi.nlm.nih.gov/substance/329231780>, 6 pages.
PubChem SID 329606212, "SCHEMBL18260193," retrieved on Jul. 22, 2022, retrieved from <https://pubchem.ncbi.nlm.nih.gov/substance/329606212>, 8 pages.
PubChem SID 371458521, "(3-Phenyloxetan-3-y1)methanamine," retrieved on Jan. 15, 2021, retrieved from<https://pubchem.ncbi.nlm.nih.gov/substance/371458521>, 6 pages.
PubChem SID 374086899, "2-Chloroquinazolin-4-amine," retrieved on Jan. 15, 2021, retrieved from <https://pubchem.ncbi.nlm.nih.gov/substance/374086899>, 6 pages.
PubChem SID 374398465, "156973-09-0," retrieved on Jan. 15, 2021, retrieved from <https://pubchem.ncbi.nlm.nih.gov/substance/374398465>, 6 pages.
PubChem SID 377956480, "3-(Furan-2-y1)-1H-pyrazole," retrieved on Jul. 22, 2022,retrieved from <https://pubchem.ncbi.nlm.nih.gov/substance/377956480>, 6 pages.
Raymer et al., "Lead-like drugs: A perspective: Miniperspective," Journal of Medicinal Chemistry, Jul. 27, 2018, 61(23):10375-10384.
Rose et al., "Inhibition of 2-oxoglutarate dependent oxygenases," Chemical Society Reviews, 2011,40(8): 36 pages.
Schwartz et al., "Perturbation of m6A writers reveals two distinct classes of mRNA methylation at internal and 5' sites," Cell Reports, Jul. 10, 2014, 8(1):284-926.
Setiady et al., "In vivo depletion of CD4+ FOXP3+ Treg cells by the PC61 anti-CD25 monoclonal antibody is mediated by FcγRIII+ phagocytes," European Journal of Immunology, Mar. 2010, 40(3):780-786.
Shi et al., "Where, when, and how: context-dependent functions of RNA methylation writers, readers, and erasers," Molecular Cell, May 16, 2019, 74(4):640-650.
Singh et al., "Identification of human brain tumour initiating cells," Nature, Nov. 2004, 432(7015):396-401.
Stupp et al., "Effects of radiotherapy with concomitant and adjuvant temozolomide versus radiotherapy alone on survival in glioblastoma in a randomised phase III study: 5-year analysis of the EORTC-NCIC trial," The Lancet Oncology, 10(5), 459-466.

(56) References Cited

OTHER PUBLICATIONS

Su et al., "R-2HG exhibits anti-tumor activity by targeting FTO/m6A/MYC/CEBPA signaling," Cell, Jan. 11, 2018, 172(1-2):90-105.

Sullivan et al., "Quantification of microenvironmental metabolites in murine cancers reveals determinants of tumor nutrient availability," Elife, Apr. 16, 2019, 8: 27 pages.

Sun et al., "MCT4 promotes cell proliferation and invasion of castration-resistant prostate cancer PC-3 cell line," EXCLI Journal, 2019, 18:187-194.

Sundar et al., "The role of cancer stem cells in glioblastoma," Neurosurgical Focus, Dec. 1, 2014, 37(6):E6, 9 pages.

Svensen et al., "Fluorescent RNA Aptamers as a Tool to Study RNA-Modifying Enzymes," Cell Chemical Biology, 2016, 23(3), 415-425.

Tang et al., "ALKBH5-dependent m6A demethylation controls splicing and stability of long 3'-UTR mRNAs in male germ cells," Proceedings of the National Academy of Sciences, Jan. 9, 2018, 115(2):E325-E333.

Vargas et al., "Fc-optimized anti-CD25 depletes tumor-infiltrating regulatory T cells and synergizes with PD-1 blockade to eradicate established tumors," Immunity, Apr. 18, 2017, 46(4):577-586.

Villain et al., "miR-126-5p promotes retinal endothelial cell survival through SetD5 regulation in neurons," Development, Jan. 1, 2018, 145(1): 15 pages.

Vu et al., "The N6-methyladenosine (m6A)-forming enzyme METTL3 controls myeloid differentiation of normal hematopoietic and leukemia cells," Nature Medicine, Nov. 2017, 23(11):1369-1376.

Wagner et al., "Tumor interstitial fluid formation, characterization, and clinical implications," Frontiers in Oncology, May 26, 2015, 5(115): 12 pages.

Wang et al., "Fluorescein derivatives as bifunctional molecules for the simultaneous inhibiting and labeling of FTO protein," Journal of the American Chemical Society, Nov. 4, 2015, 137(43):13736-13739.

Wang et al., "Reading RNA methylation codes through methyl-specific binding proteins," RNA Biology, Jun. 1, 2014, 11(6):669-672.

Wei et al., "Differential m6A, m6Am, and m1A demethylation mediated by FTO in the cell nucleus and cytoplasm," Molecular Cell, Sep. 20, 2018, 71(6):973-985.

Weiss et al., "Sulfonamides as selective NaV1. 7 inhibitors: optimizing potency and pharmacokinetics while mitigating metabolic liabilities," Journal of Medicinal Chemistry, Jul. 27, 2017, 60(14):5969-5989.

Yang et al., "Dynamic transcriptomic m6A decoration: writers, erasers, readers and functions in RNA metabolism," Cell Research, 2018, 28(6), 616-624.

Yang et al., "m6A mRNA demethylase FTO regulates melanoma tumorigenicity and response to anti-PD-1 blockade," Nature Communications, 2019 10(1): 14 pages.

Yau et al., "Genome-Wide CRISPR Screen for Essential Cell Growth Mediators in Mutant KRAS Colorectal CancersGenome-Wide CRISPR Screen of KRAS-Mutant Tumor Xenografts," Cancer Research, Nov. 15, 2017, 77(22):6330-6339.

Zhang et al., "A review in research progress concerning m6A methylation and immunoregulation," Frontiers in Immunology, Apr. 26, 2019, 10: 9 pages.

Zhang et al., "Model-based Analysis of ChIP-Seq (MACS)," Genome Biology, 2008,9(9), R137-R137.9.

Zheng et al., "ALKBH5 is a Mammalian RNA Demethylase that Impacts RNA Metabolism and Mouse Fertility," Molecular Cell, 2013, 49(1), 18-29.

Zhu et al., "Remodeling domain interfaces to enhance heterodimer formation," Protein Science, Apr. 1997, 6(4):781-788.

* cited by examiner

F strategy for M-MDSC and G-MDSC

Scheme 1. Synthesis of FTO Inhibitors

A

B

Meclofenamic Acid $IC_{50}$ against FTO

| Log Concentration (nM) | Normalized Activity (%) | Standard Deviation |
|---|---|---|
| 0 | 100 | |
| 4.60206 | 35.2986 | 8.2784 |
| 4.30103 | 42.39851 | 5.5013 |
| 4 | 57.1947 | 13.49285 |
| 3.69897 | 61.395 | 12.1987 |
| 3 | 73.2957 | 13.2957 |

DMSO Control

| DMSO Concentration (%) | Normalized Activity (%) | Standard Deviation |
|---|---|---|
| 0 | 100 | |
| 0.1 | 101.251 | 3.1804 |
| 0.2 | 100.092 | 1.933 |
| 0.5 | 98.781 | 1.9726 |
| 1 | 92.3781 | 2.525 |
| 5 | 80.1264 | 1.16 |
| 10 | 58.3666 | 5.6681 |

1st Generation Library
$IC_{50}$s from 1 - >>40 μM
Oxetane Library
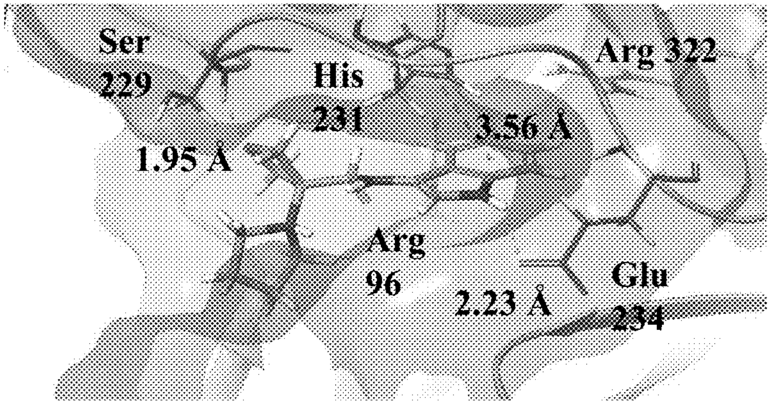
TR-FTO-11 N $IC_{50}$ = 110 nM
$IC_{50}$s from 240 nM - >>40 μM
3rd Generation Library
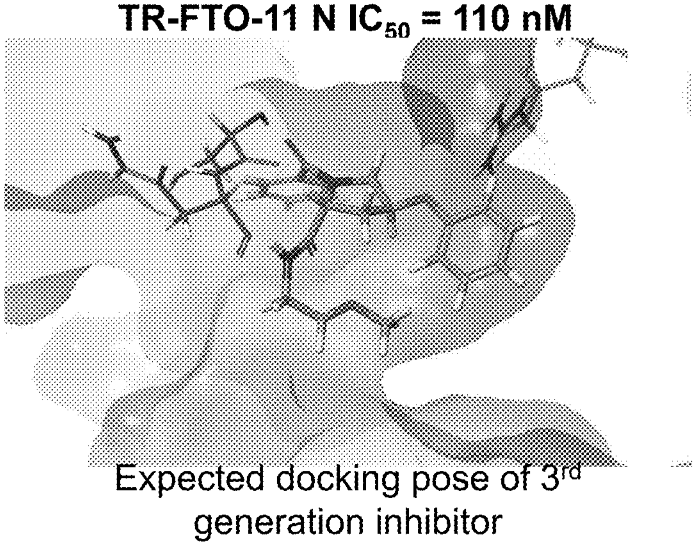
Expected docking pose of 3rd generation inhibitor
Fig. 60

| Structure | Name | Enzymatic $IC_{50}$ FTO | Enzymatic $IC_{50}$ ALKBH5 |
|---|---|---|---|
| 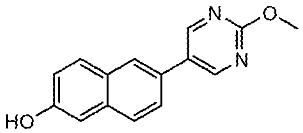 | FTO-2 | 2.18 ± 1.3 | 85.5 ± 5.7 |
| 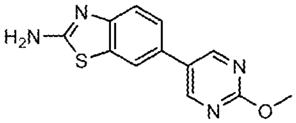 | FTO-4 | 3.39 ± 2.5 | 39.4 ± 3.1 |
| 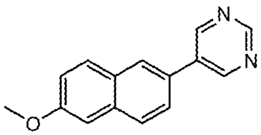 | FTO-5 | 13.38 ± 2.3 | > 40 |
| 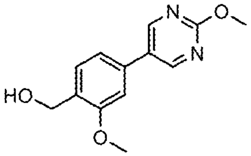 | FTO-6 | 13.8 ± 2.4 | 64.4 ± 6.3 |
| 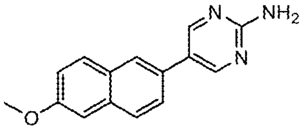 | FTO-12 | 18.3 ± 1.7 | > 40 |
| 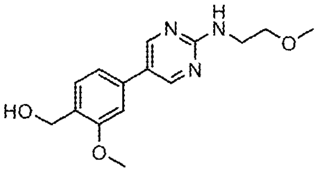 | FTO-20 | 17.2 ± 2.9 | 90.2 ± 7.8 |
Fig. 61

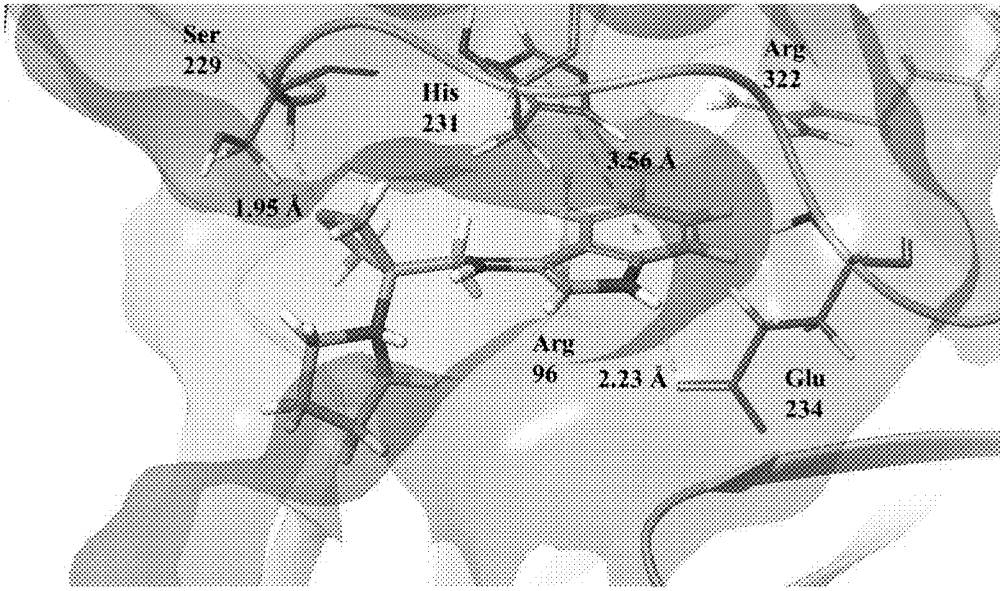
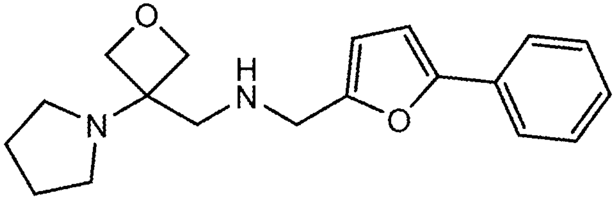
TR-FTO-35 N
FTO $IC_{50}$ = 65 nM
ALKBH5 $IC_{50}$ = >40 μM
TS576 $EC_{50}$ = μM
logD = 1.14
LLE = 6.05
Fig. 65

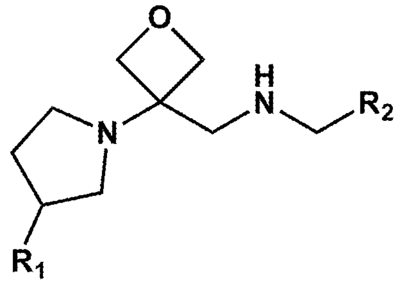
| Compound | $R_1$ | $R_2$ | FTO $IC_{50}$ (μM) | ALKBH5 $IC_{50}$ (μM) | elogD | Compound | $R_1$ | $R_2$ | FTO $IC_{50}$ (μM) | ALKBH5 $IC_{50}$ (μM) | elogD |
|---|---|---|---|---|---|---|---|---|---|---|---|
| TR-FTO-02 | H | 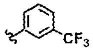 | 4.3 | 19.5 | 1.02 | TR-FTO-31 | H | 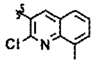 | 0.95 | 51.2 | 1.56 |
| TR-FTO-09 | H | 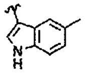 | 0.35 | >40 | 0.87 | TR-FTO-35 | H | 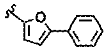 | 0.07 | 55.0 | 1.14 |
| TR-FTO-11 | H | 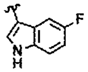 | 0.11 | 6.6 | 1.01 | TR-FTO-37 | H | 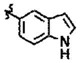 | 0.81 | 3.3 | 0.75 |
| TR-FTO-12 | H | 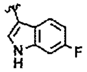 | 0.83 | 2.3 | 0.71 | TR-FTO-38 | H | 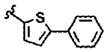 | 0.27 | 3.4 | 1.57 |
| TR-FTO-13 | H | 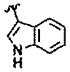 | 1.0 | >40 | 0.77 | TR-FTO-39 | H | 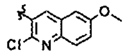 | 1.7 | 0.92 | 1.12 |
| TR-FTO-14 | H | 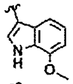 | 0.87 | >40 | 0.40 | TR-FTO-40 | H | 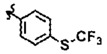 | 0.16 | 3.0 | 1.29 |
| TR-FTO-16 | H | 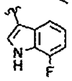 | 2.2 | 0.87 | 0.70 | TR-FTO-42 | H | 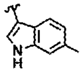 | 3.0 | 13.4 | 0.66 |
| TR-FTO-17 | H | 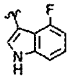 | 1.3 | 2.5 | 0.64 | TR-FTO-44 | F | 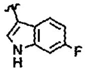 | 0.44 | 17.2 | 0.95 |
| TR-FTO-18 | H | 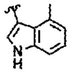 | 1.1 | 41.3 | 0.71 | TR-FTO-45 | F | 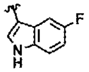 | 0.90 | 30.5 | 1.03 |
| TR-FTO-27 | H | 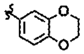 | 0.67 | 5.9 | 0.55 | TR-FTO-47 | F | 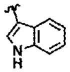 | 2.1 | >40 | 0.38 |
| TR-FTO-30 | H | 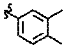 | 0.35 | 9.9 | 0.87 | TR-FTO-48 | F | 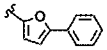 | 2.0 | 2.6 | 1.34 |
Fig. 66

| Structure | Name | clogP | Permeability (nm/s) Caco-2 | MDCK | Enzymatic $IC_{50}$ FTO (μM) |
|---|---|---|---|---|---|
| 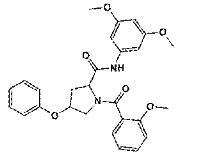 | TR-FTO 2-01 | 4.92 | 3581 | 1964 | 0.61 ± 0.17 |
| 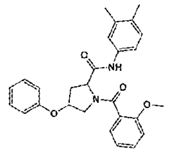 | TR-FTO 2-02 | 5.27 | 2892 | 1559 | 0.19 ± 0.03 |
| 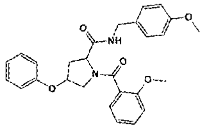 | TR-FTO 2-03 | 4.56 | 2524 | 1733 | 1.24 ± 0.65 |
| 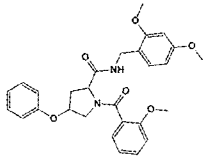 | TR-FTO 2-04 | 4.30 | 1539 | 1355 | 6.67 ± 2.31 |
| Structure | Name | clogP | Permeability (nm/s) Caco-2 | MDCK | Enzymatic $IC_{50}$ FTO (μM) |
|---|---|---|---|---|---|
| 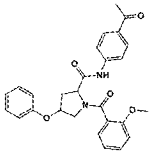 | TR-FTO 2-05 | 4.19 | 1132 | 565 | 8.31 ± 2.07 |
| 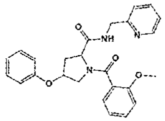 | TR-FTO 2-06 | 3.84 | 2391 | 1403 | 12.46 ± 2.70 |
| 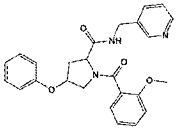 | TR-FTO 2-07 | 3.48 | 1835 | 1040 | 0.17 ± 0.03 |
| 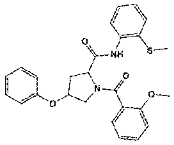 | TR-FTO 2-08 | 4.98 | 2524 | 2168 | 10.35 ± 2.29 |
| 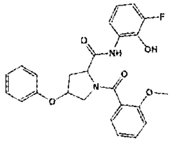 | TR-FTO 2-09 | 4.34 | 2541 | 2309 | > 40 |
Fig. 68

$R_1$ = H, COOH, $COOCH_3$
Y = OH, SH $R_2$ = Ar

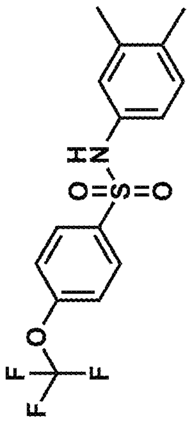
TR-ALKBH5-34
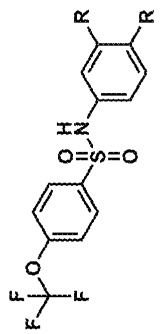
R = $CF_3$, $OCH_3$, $OCF_3$
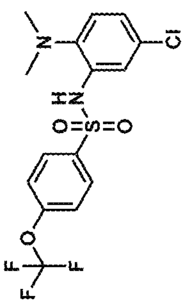
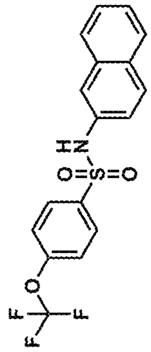
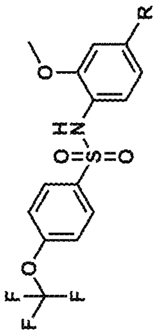
R = F, $CH_3$
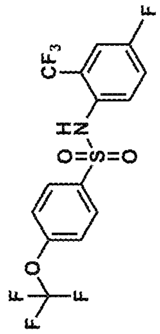
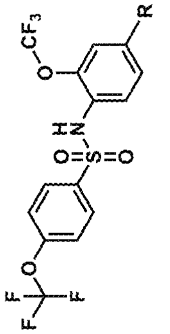
R = F, $CH_3$
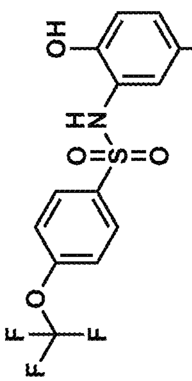
TR-ALKBH5-29
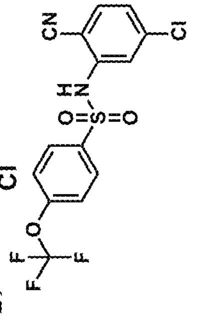
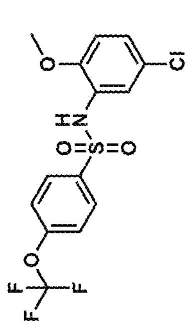
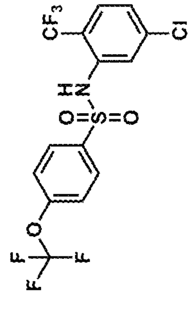
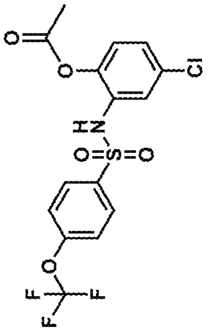
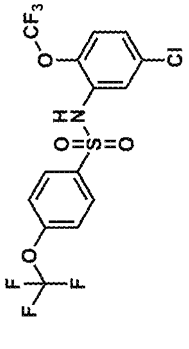
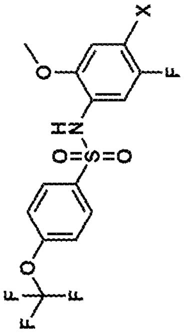
X = F, Cl
Fig. 81

| Structure | Docking Score | Structure | Docking Score |
| --- | --- | --- | --- |
| 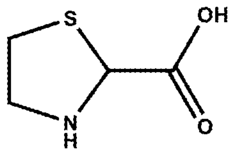 | -8.92 | 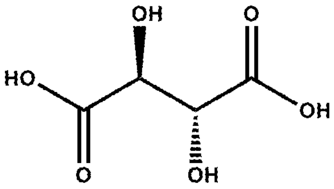 | -11.73 |
| 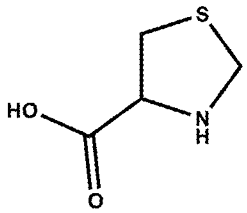 | -9.10 | 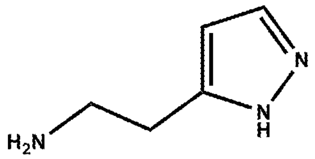 | -7.59 |
| 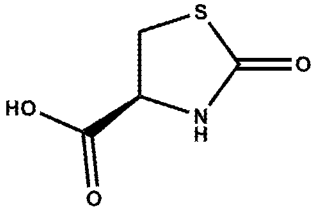 | -8.60 | 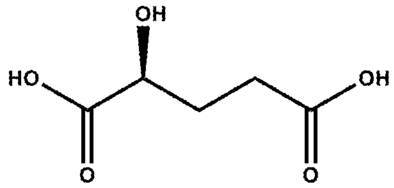 | -10.01 |
| 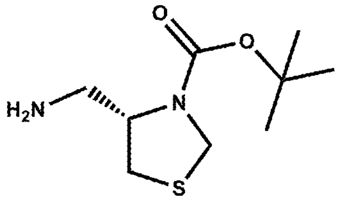 | -9.03 | 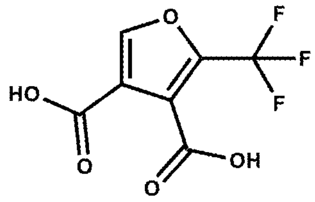 | -8.89 |
Fig. 83

| Structure | Name | Enzymatic $IC_{50}$ ALKBH5 | Enzymatic $IC_{50}$ FTO | elogD | Structure | Name | Enzymatic $IC_{50}$ ALKBH5 | Enzymatic $IC_{50}$ FTO | elogD |
|---|---|---|---|---|---|---|---|---|---|
| 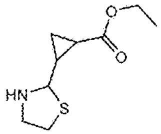 | ALK-01 | 17.5 | 103.3 | 0.58 | 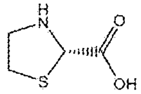 | ALK-06 | 7.95 | >40 | 0.89 |
| 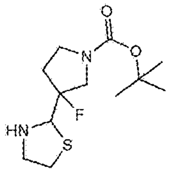 | ALK-02 | 16.6 | >40 | 1.40 | 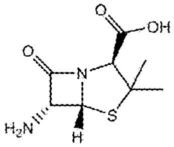 | ALK-07 | 10.0 | >40 | 0.95 |
| 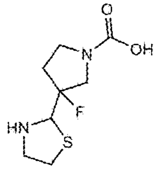 | ALK-03 | >40 | >40 | 0.62 | 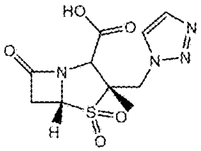 | ALK-08 | 9.9 | >40 | 0.36 |
| 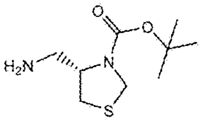 | ALK-04 | 0.9 | >40 | 0.29 | 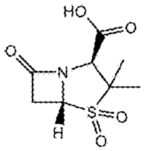 | ALK-09 | 5.7 | >40 | 0.41 |
| 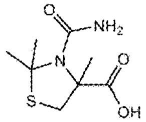 | ALK-05 | 19.8 | >40 | 0.16 | 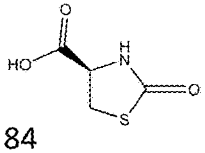 | ALK-10 | 1.7 | >40 | 0.54 |
Fig. 84

$R_1$ = H, COOH, $COOCH_3$
Y = OH, SH $R_2$ = Ar

| Structure | Name | Enzymatic $IC_{50}$ ALKBH5 | Enzymatic $IC_{50}$ FTO | elogD | Structure | Name | Enzymatic $IC_{50}$ ALKBH5 | Enzymatic $IC_{50}$ FTO | elogD |
|---|---|---|---|---|---|---|---|---|---|
| 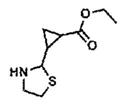 | ALK-01 | 17.5 ± 4.5 | >40 | 0.58 | 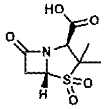 | ALK-09 | 3.8 ± 2.3 | >40 | 0.41 |
| 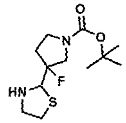 | ALK-02 | 16.6 ± 2.7 | >40 | 1.40 | 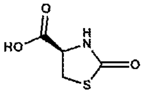 | ALK-10 | 1.7 ± 1.1 | >40 | 0.54 |
| 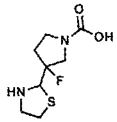 | ALK-03 | >40 | >40 | 0.62 | 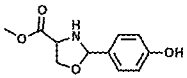 | ALK-13 | 6.7 ± 1.8 | >40 | 2.12 |
| 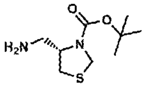 | ALK-04 | 0.9 ± 0.7 | >40 | 0.29 | 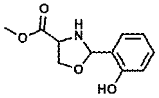 | ALK-16 | 8.2 ± 2.3 | >40 | 1.44 |
| 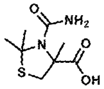 | ALK-05 | 19.8 ± 1.8 | >40 | 0.16 | 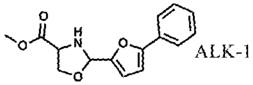 | ALK-18 | 5.4 ± 0.7 | 14.2 ± 3.1 | 0.73 |
| 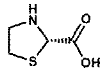 | ALK-06 | 8.8 ± 1.1 | >40 | 0.89 | 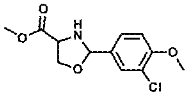 | ALK-23 | 2.8 ± 0.5 | >40 | 3.01 |
| 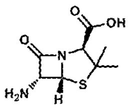 | ALK-07 | 10.0 ± 2.8 | >40 | 0.95 | 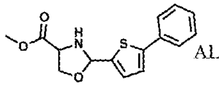 | ALK-25 | 0.9 ± 0.2 | >40 | 1.17 |
| 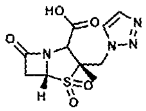 | ALK-08 | 9.9 ± 1.3 | >40 | 0.36 | 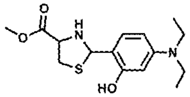 | ALK-30 | 1.4 ± 0.4 | >40 | 0.67 |
Fig. 86

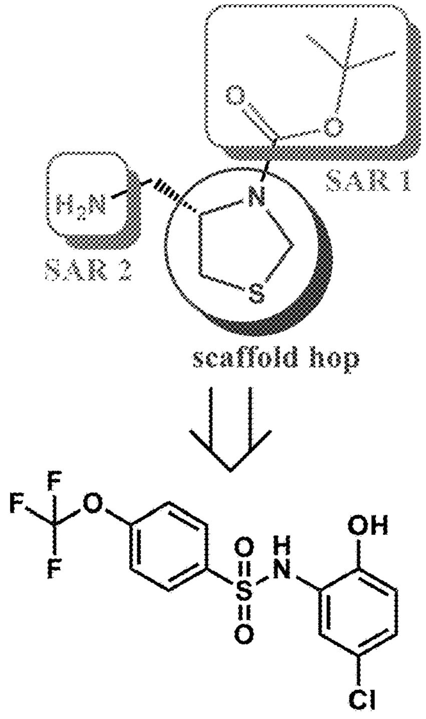
TR-ALKBH5-29
ALKBH5 $IC_{50}$ = 0.11 μM
FTO $IC_{50}$ = >40 μM
TS576 $EC_{50}$ = 30 μM
logD = 0.89
LLE = 6.11
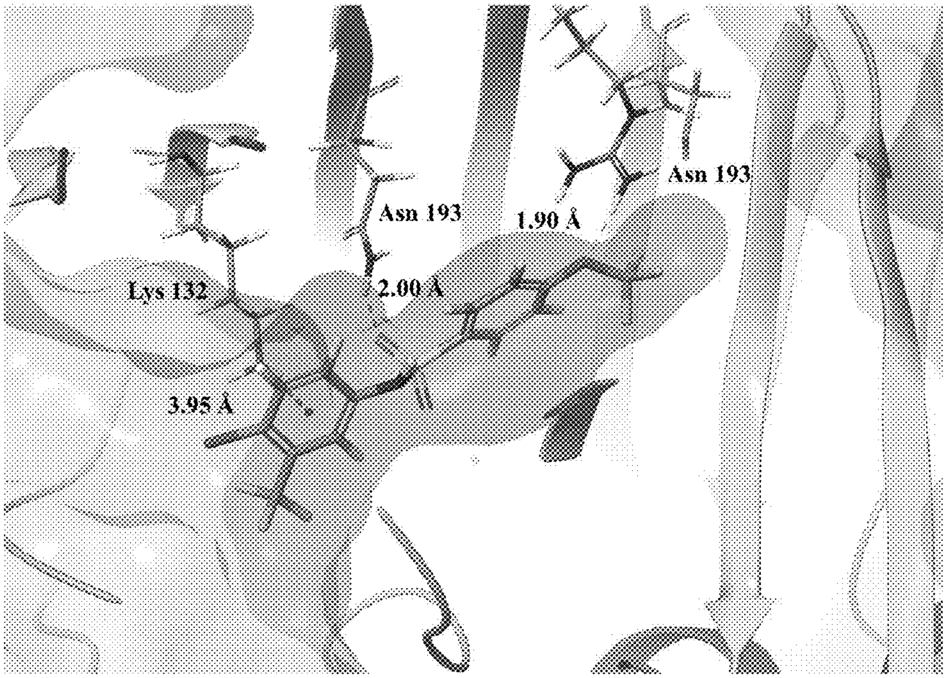
Fig. 89

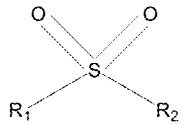
| Compound | $R_1$ | $R_2$ | ALKBH5 $IC_{50}$ (μM) | FTO $IC_{50}$ (μM) | elogD | Compound | $R_1$ | $R_2$ | ALKBH5 $IC_{50}$ (μM) | FTO $IC_{50}$ (μM) | elogD |
|---|---|---|---|---|---|---|---|---|---|---|---|
| TR-ALKBH5-04 | 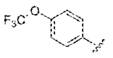 | 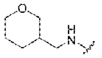 | 0.24 | 19.7 | 0.37 | TR-ALKBH5-33 | 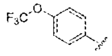 | 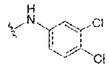 | 2.6 | >40 | 1.24 |
| TR-ALKBH5-05 | 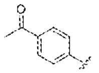 | 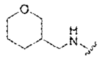 | 1.9 | >40 | 1.12 | TR-ALKBH5-34 | 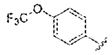 | 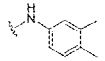 | 23.3 | >40 | 0.60 |
| TR-ALKBH5-08 | 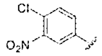 | 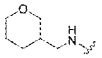 | 0.50 | 6.4 | 0.89 | TR-ALKBH5-36 | 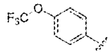 | 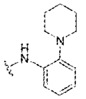 | 0.40 | 23.2 | 1.13 |
| TR-ALKBH5-25 | 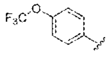 | 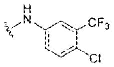 | 1.6 | >40 | 1.50 | TR-ALKBH5-38 | 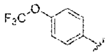 | 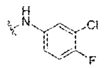 | 1.9 | 27.6 | 2.58 |
| TR-ALKBH5-27 | 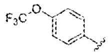 | 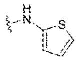 | 2.0 | >40 | 0.36 | TR-ALKBH5-39 | 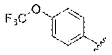 | 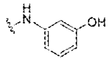 | 3.1 | >40 | 1.60 |
| TR-ALKBH5-29 | 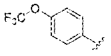 | 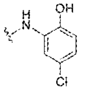 | 0.11 | >40 | 0.88 | TR-ALKBH5-40 | 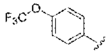 | 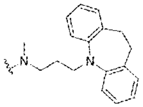 | 2.3 | 59.4 | 2.05 |
| TR-ALKBH5-30 | 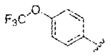 | 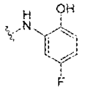 | 1.0 | >40 | 0.81 | TR-ALKBH5-41 | 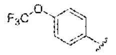 | 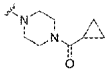 | 0.45 | >40 | 0.79 |
| TR-ALKBH5-31 | 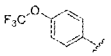 | 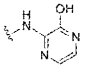 | 13.7 | >40 | 2.33 | TR-ALKBH5-42 | 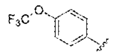 | 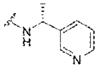 | 0.25 | 285 | 0.83 |
| TR-ALKBH5-32 | 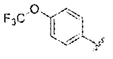 | 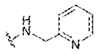 | 2.2 | >40 | 2.25 | | | | | | |
Fig. 90

TR-ALKBH5-34

R = $CF_3$, $OCH_3$, $OCF_3$

R = F, $CH_3$

R = F, $CH_3$

TR-ALKBH5-29

X = F, Cl

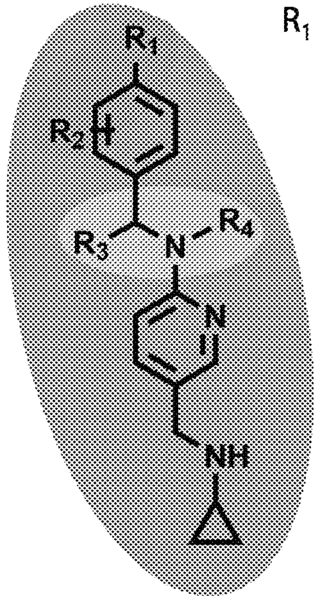
$R_1 = OCH_3, CF_3$
$R_2$ = Hydrogen bond acceptor $OCH_3$, N
$R_3, R_4 = H, CH_3,$
Possible substitution of the isopropyl amine
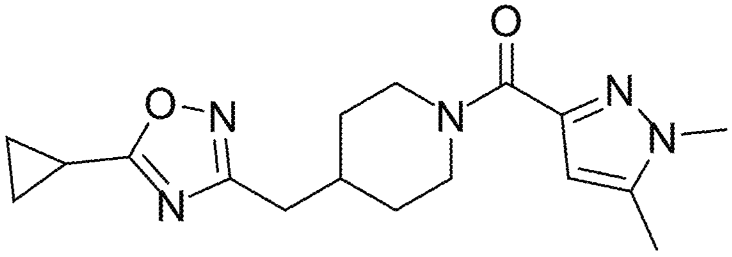
TR-YTH-04N
Fig. 104

Pharmacophore Model for 1st Generation YTH Inhibitors
$R_2$ = Hydrogen bond acceptor $OCH_3$, N
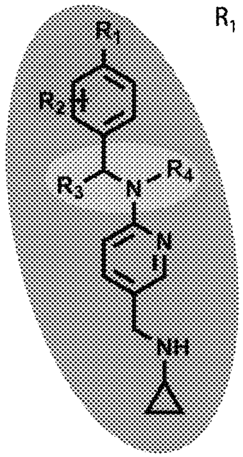
$R_1 = OCH_3, CF_3$
$R_3, R_4 = H, CH_3,$
Possible substitution of the isopropyl amine
Replacing the isopropyl amine moeity with a dimethyl amine improves selectivity towards YTHDF2
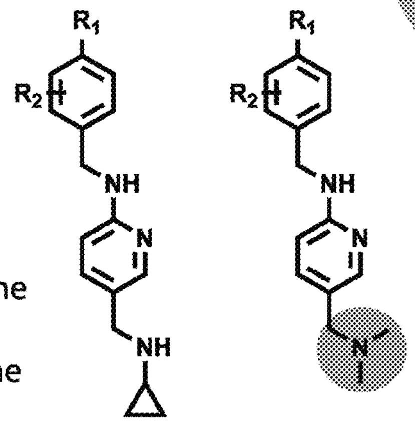
Fig. 105

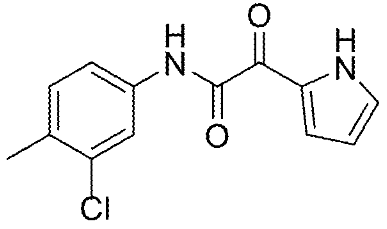
TR-YTH-03N
$K_i$F1 = 0.94 ± 0.62 nM
$K_i$F2 = 1.55 ± 0.8 nM
clogP = 3.12
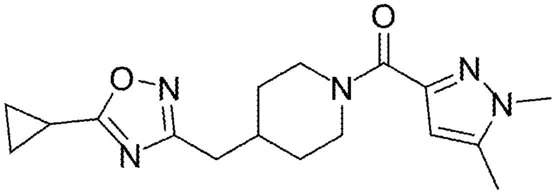
TR-YTH-04N
$K_i$F1 = 497 ± 44 pM
$K_i$F2 = 320 ± 91 pM
clogP = 2.58
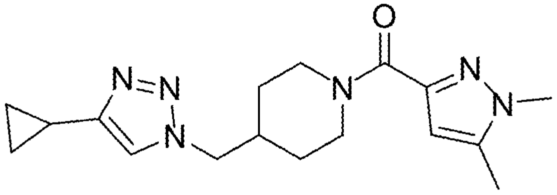
TR-YTH-05N
$K_i$F1 = 333 ± 48 pM
$K_i$F2 = 315 ± 44 pM
clogP = 3.08
Fig. 107

YTH compounds in CCD841CON

DMSO
YTH-2
YTH-10

OD(490nm)

0.4  0.3  0.2  0.1  0.0

0uM  0.1uM  0.5uM  1uM  5uM  10uM  30uM 1 2 3 4 5

TR-K-01 to 010

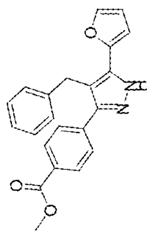
TR-K-01
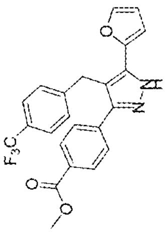
TR-K-02
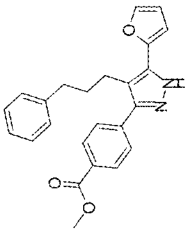
TR-K-03
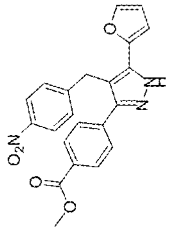
TR-K-04
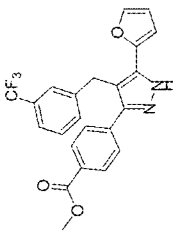
TR-K-05
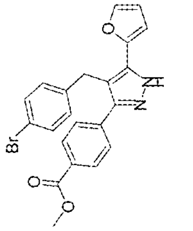
TR-K-06
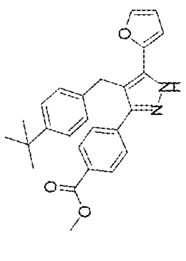
TR-K-07
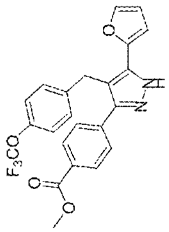
TR-K-08
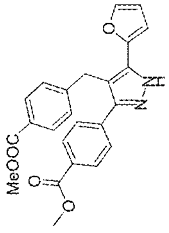
TR-K-09
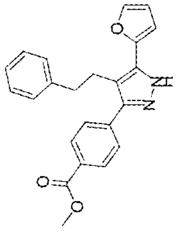
TR-K-010
Fig. 118

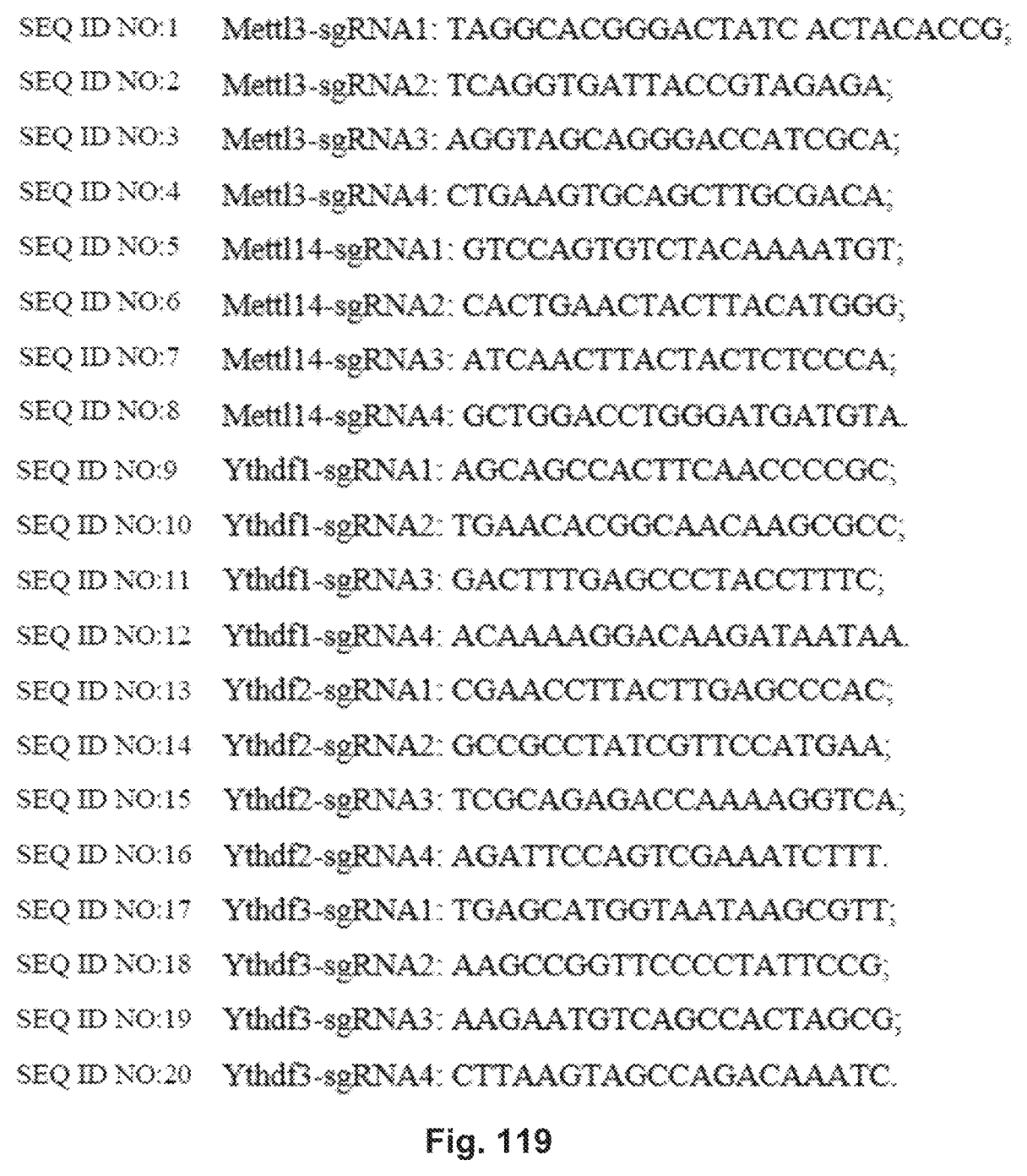

SEQ ID NO:1 Mettl3-sgRNA1: TAGGCACGGGACTATC ACTACACCG;
SEQ ID NO:2 Mettl3-sgRNA2: TCAGGTGATTACCGTAGAGA;
SEQ ID NO:3 Mettl3-sgRNA3: AGGTAGCAGGGACCATCGCA;
SEQ ID NO:4 Mettl3-sgRNA4: CTGAAGTGCAGCTTGCGACA;
SEQ ID NO:5 Mettl14-sgRNA1: GTCCAGTGTCTACAAAATGT;
SEQ ID NO:6 Mettl14-sgRNA2: CACTGAACTACTTACATGGG;
SEQ ID NO:7 Mettl14-sgRNA3: ATCAACTTACTACTCTCCCA;
SEQ ID NO:8 Mettl14-sgRNA4: GCTGGACCTGGGATGATGTA.
SEQ ID NO:9 Ythdf1-sgRNA1: AGCAGCCACTTCAACCCCGC;
SEQ ID NO:10 Ythdf1-sgRNA2: TGAACACGGCAACAAGCGCC;
SEQ ID NO:11 Ythdf1-sgRNA3: GACTTTGAGCCCTACCTTTC;
SEQ ID NO:12 Ythdf1-sgRNA4: ACAAAAGGACAAGATAATAA.
SEQ ID NO:13 Ythdf2-sgRNA1: CGAACCTTACTTGAGCCCAC;
SEQ ID NO:14 Ythdf2-sgRNA2: GCCGCCTATCGTTCCATGAA;
SEQ ID NO:15 Ythdf2-sgRNA3: TCGCAGAGACCAAAAGGTCA;
SEQ ID NO:16 Ythdf2-sgRNA4: AGATTCCAGTCGAAATCTTT.
SEQ ID NO:17 Ythdf3-sgRNA1: TGAGCATGGTAATAAGCGTT;
SEQ ID NO:18 Ythdf3-sgRNA2: AAGCCGGTTCCCCTATTCCG;
SEQ ID NO:19 Ythdf3-sgRNA3: AAGAATGTCAGCCACTAGCG;
SEQ ID NO:20 Ythdf3-sgRNA4: CTTAAGTAGCCAGACAAATC.

Fig. 119

| | Name | Sequence |
|---|---|---|
| SEQ ID NO:21 | METTL3-sg1-UP | CACCGGAGTTGATTGAGGTAAAGCG |
| SEQ ID NO:22 | METTL3-sg1-DN | AAACCGCTTTACCTCAATCAACTCC |
| SEQ ID NO:23 | METTL3-sg2-UP | CACCGCTTGCTCTTACACAGAGTGT |
| SEQ ID NO:24 | METTL3-sg2-DN | AAACACACTCTGTGTAAGAGCAAGC |
| SEQ ID NO:25 | ALKBH5-alkbh5-sg1-UP | CACCGCCTGTACAACGAGCACACGG |
| SEQ ID NO:26 | ALKBH5-alkbh5-sg1-DN | AAACCCGTGTGCTCGTTGTACAGGC |
| SEQ ID NO:27 | ALKBH5-sg2-UP | CACCGGAGGCGCGCAAGGTGAAGAG |
| SEQ ID NO:28 | ALKBH5-sg2-DN | AAACCTCTTCACCTTGCGCGCCTCC |
| SEQ ID NO:29 | alkbh5-sg2-UP | CACCGGTCACGCTCCCCCTGCGCAC |
| SEQ ID NO:30 | alkbh5-sg2-DN | AAACGTGCGCAGGGGGAGCGTGACC |
| SEQ ID NO:31 | WTAP-GPPsg2-UP | CACCGGAAGTGTCGAATGCTTATCC |
| SEQ ID NO:32 | WTAP-GPPsg2-DN | AAACGGATAAGCATTCGACACTTCC |
| SEQ ID NO:33 | WTAP(H/M)-GPPsg3-UP | CACCGGAGCTTAAAAGCAGTCAGGA |
| SEQ ID NO:34 | WTAP(H/M)-GPPsg3-DN | AAACTCCTGACTGCTTTTAAGCTCC |
| SEQ ID NO:35 | Rbm15-sg3-UP | CACCGGACTGAGGTCCCGACCACGC |
| SEQ ID NO:36 | Rbm15-sg3-DN | AAACGCGTGGTCGGGACCTCAGTCC |
| SEQ ID NO:37 | Rbm15-sg6-UP | CACCGGTCAAGCCCAAGCGCTCCCG |
| SEQ ID NO:38 | Rbm15-sg6-DN | AAACCGGGAGCGCTTGGGCTTGACC |
| SEQ ID NO:39 | Mettl14-sg1-UP | CACCGGTCCAGTGTCTACAAAATGT |
| SEQ ID NO:40 | Mettl14-sg1-DN | AAACACATTTTGTAGACACTGGACC |
| SEQ ID NO:41 | Mettl14-sg4-UP | CACCGGCTGGACCTGGGATGATGTA |
| SEQ ID NO:42 | Mettl14-sg4-DN | AAACTACATCATCCCAGGTCCAGCC |
| SEQ ID NO:43 | METTL14-GPPsg1-UP | CACCGACCATCTTACCACTCTTCCA |
| SEQ ID NO:44 | METTL14-GPPsg1-DN | AAACTGGAAGAGTGGTAAGATGGTC |
| SEQ ID NO:45 | METTL14-GPPsg2-UP | CACCGTAACACGGCACCAATGCTGT |
| SEQ ID NO:46 | METTL14-GPPsg2-DN | AAACACAGCATTGGTGCCGTGTTAC |
| SEQ ID NO:47 | mettl3-sg1-UP | CACCGTAGGCACGGGACTATCACTA |
| SEQ ID NO:48 | mettl3-sg1-DN | AAACTAGTGATAGTCCCGTGCCTAC |
| SEQ ID NO:49 | mettl3-sg2-UP | CACCGTCAGGTGATTACCGTAGAGA |
| SEQ ID NO:50 | mettl3-sg2-DN | AAACTCTCTACGGTAATCACCTGAC |
| SEQ ID NO:51 | ALKBH3-sg1-UP | CACCGCGCTCCTTCCATGATTAACA |
| SEQ ID NO:52 | ALKBH3-sg1-DN | AAACTGTTAATCATGGAAGGAGCGC |
| SEQ ID NO:53 | ALKBH3-sg2-UP | CACCGGTGGAGATGGCTCTTAGCAG |
| SEQ ID NO:54 | ALKBH3-sg2-DN | AAACCTGCTAAGAGCCATCTCCACC |

Fig. 119 (cont.)

| | Name | Sequence |
|---|---|---|
| SEQ ID NO:55 | METTL3-sg1-UP | CACCGGAGTTGATTGAGGTAAAGCG |
| SEQ ID NO:56 | METTL3-sg1-DN | AAACCGCTTTACCTCAATCAACTCC |
| SEQ ID NO:57 | METTL3-sg2-UP | CACCGCTTGCTCTTACACAGAGTGT |
| SEQ ID NO:58 | METTL3-sg2-DN | AAACACACTCTGTGTAAGAGCAAGC |
| SEQ ID NO:59 | ALKBH5-alkbh5-sg1-UP | CACCGCCTGTACAACGAGCACACGG |
| SEQ ID NO:60 | ALKBH5-alkbh5-sg1-DN | AAACCCGTGTGCTCGTTGTACAGGC |
| SEQ ID NO:61 | ALKBH5-sg2-UP | CACCGGAGGCGCGCAAGGTGAAGAG |
| SEQ ID NO:62 | ALKBH5-sg2-DN | AAACCTCTTCACCTTGCGCGCCTCC |
| SEQ ID NO:63 | alkbh5-sg2-UP | CACCGGTCACGCTCCCCCTGCGCAC |
| SEQ ID NO:64 | alkbh5-sg2-DN | AAACGTGCGCAGGGGGAGCGTGACC |
| SEQ ID NO:65 | WTAP-GPPsg2-UP | CACCGGAAGTGTCGAATGCTTATCC |
| SEQ ID NO:66 | WTAP-GPPsg2-DN | AAACGGATAAGCATTCGACACTTCC |
| SEQ ID NO:67 | WTAP(H/M)-GPPsg3-UP | CACCGGAGCTTAAAAGCAGTCAGGA |
| SEQ ID NO:68 | WTAP(H/M)-GPPsg3-DN | AAACTCCTGACTGCTTTTAAGCTCC |
| SEQ ID NO:69 | Rbm15-sg3-UP | CACCGGACTGAGGTCCCGACCACGC |
| SEQ ID NO:70 | Rbm15-sg3-DN | AAACGCGTGGTCGGGACCTCAGTCC |
| SEQ ID NO:71 | Rbm15-sg6-UP | CACCGGTCAAGCCCAAGCGCTCCCG |
| SEQ ID NO:72 | Rbm15-sg6-DN | AAACCGGGAGCGCTTGGGCTTGACC |
| SEQ ID NO:73 | Mettl14-sg1-UP | CACCGGTCCAGTGTCTACAAAATGT |
| SEQ ID NO:74 | Mettl14-sg1-DN | AAACACATTTTGTAGACACTGGACC |
| SEQ ID NO:75 | Mettl14-sg4-UP | CACCGGCTGGACCTGGGATGATGTA |
| SEQ ID NO:76 | Mettl14-sg4-DN | AAACTACATCATCCCAGGTCCAGCC |
| SEQ ID NO:77 | METTL14-GPPsg1-UP | CACCGACCATCTTACCACTCTTCCA |
| SEQ ID NO:78 | METTL14-GPPsg1-DN | AAACTGGAAGAGTGGTAAGATGGTC |
| SEQ ID NO:79 | METTL14-GPPsg2-UP | CACCGTAACACGGCACCAATGCTGT |
| SEQ ID NO:80 | METTL14-GPPsg2-DN | AAACACAGCATTGGTGCCGTGTTAC |
| SEQ ID NO:81 | mettl3-sg1-UP | CACCGTAGGCACGGGACTATCACTA |
| SEQ ID NO:82 | mettl3-sg1-DN | AAACTAGTGATAGTCCCGTGCCTAC |
| SEQ ID NO:83 | mettl3-sg2-UP | CACCGTCAGGTGATTACCGTAGAGA |
| SEQ ID NO:84 | mettl3-sg2-DN | AAACTCTCTACGGTAATCACCTGAC |
| SEQ ID NO:85 | ALKBH3-sg1-UP | CACCGCGCTCCTTCCATGATTAACA |
| SEQ ID NO:86 | ALKBH3-sg1-DN | AAACTGTTAATCATGGAAGGAGCGC |
| SEQ ID NO:87 | ALKBH3-sg2-UP | CACCGGTGGAGATGGCTCTTAGCAG |
| SEQ ID NO:88 | ALKBH3-sg2-DN | AAACCTGCTAAGAGCCATCTCCACC |

Fig. 119 (cont.)

| | |
|---|---|
| **NTC:** | 5'-CCGCAGGTATGCACGCGT-3' |
| **METTL3-1:** | 5'-CCGGGCAAGTATGTTCACTATGAAACTCGAGTTTCATAGTGAACATACTTGCTTTTTG-3' |
| **METTL3-2:** | 5'-CCGGGCCAAGGAACAATCCATTGTTCTCGAGAACAATGGATTGTTCCTTGGCTTTTTG-3' |
| **METTL14-1:** | 5'-CCGGCCATGTACTTACAAGCCGATACTCGAGTATCGGCTTGTAAGTACATGGTTTTT-3' |
| **METTL14-2:** | 5'-CCGGGCCGTGGACGAGAAAGAAATACTCGAGTATTTCTTTCTCGTCCACGGCTTTTT-3' |
| **ALKBH5-1:** | 5'-CCGGGAAAGGCTGTTGGCATCAATACTCGAGTATTGATGCCAACAGCCTTTCTTTTTG-3' |
| **ALKBH5-2:** | 5'-CCGGCCACCCAGCTATGCTTCAGATCTCGAGATCTGAAGCATAGCTGGGTGGTTTTTG-3' |
| **FTO-1:** | 5'-CCGGCGGTTCACAACCTCGGTTTAGCTCGAGCTAAACCGAGGTTGTGAACCGTTTTTG-3' |
| **FTO-2:** | 5'-CCGGTCACCAAGGAGACTGCTATTTCTCGAGAAATAGCAGTCTCCTTGGTGATTTTTG-3' |
| **YTHDF1-1:** | 5'-CCGGCCCTACCTGTCCAGCTATTACCTCGAGGTAATAGCTGGACAGGTAGGGTTTTTG-3' |
| **YTHDF1-2:** | 5'-CCGGCCCGAAAGAGTTTGAGTGGAACTCGAGTTCCACTCAAACTCTTTCGGGTTTTTG-3' |
| **YTHDF2-1:** | 5'-CCGGGCTACTCTGAGGACGATATTCCTCGAGGAATATCGTCCTCAGAGTAGCTTTTTG-3' |
| **YTHDF2-2:** | 5'-CCGGCGGTCCATTAATAACTATAACCTCGAGGTTATAGTTATTAATGGACCGTTTTTG-3' |
| **YTHDF3-1:** | 5'-CCGGTAAGTCAAAGAAGACGTATTACTCGAGTAATACGTCTTCTTTGACTTATTTTTG-3' |
| **YTHDF3-2:** | 5'-CCGGGAAGTCTGTTGTGGACTATAACTCGAGTTATAGTCCACAACAGACTTCTTTTTG-3' |

Fig. 120

TR-FTO-11 N

ALKBH5 $IC_{50}$ = 0.11 μM

FTO $IC_{50}$ = >6.6 μM logD = 1.01

LLE = 5.94

TR-YTH-08

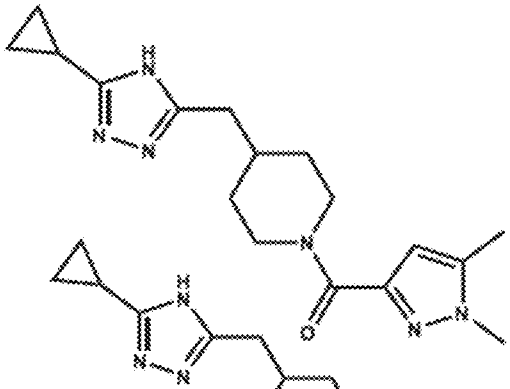
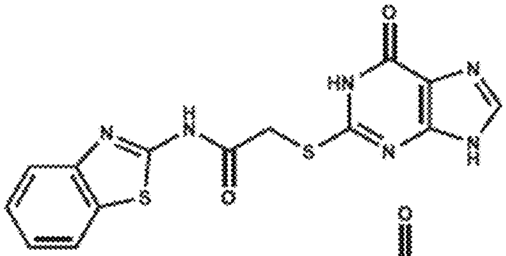
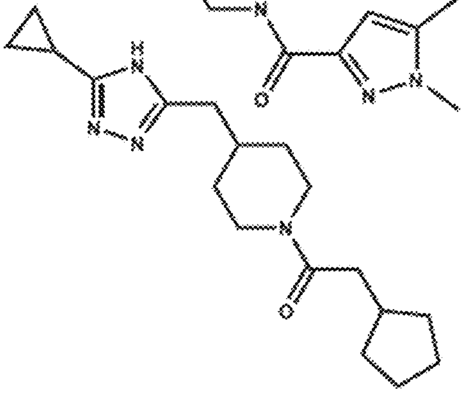
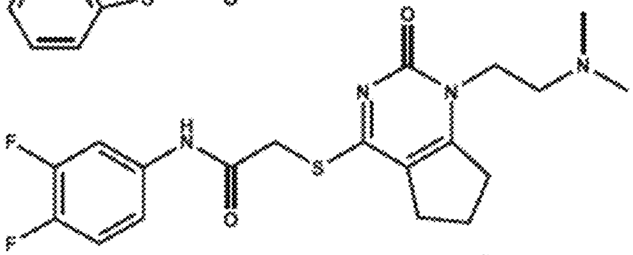
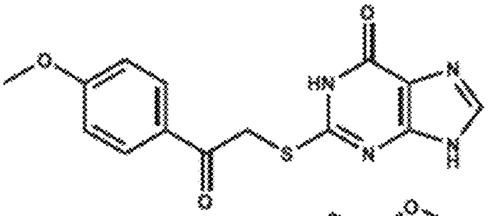
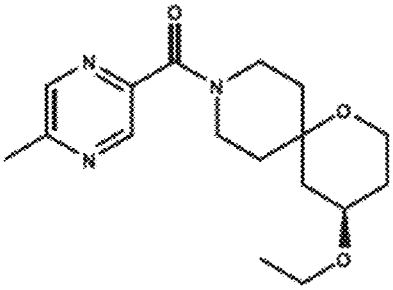
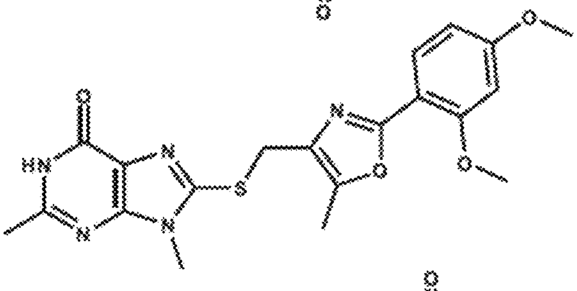
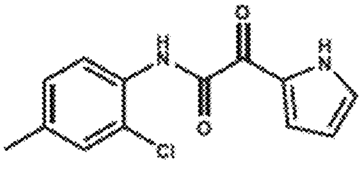
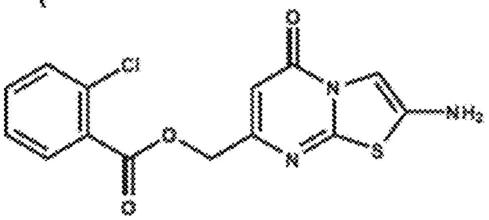
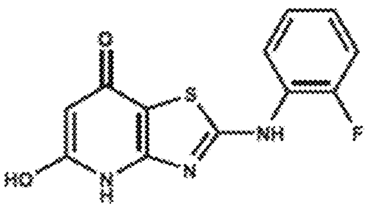
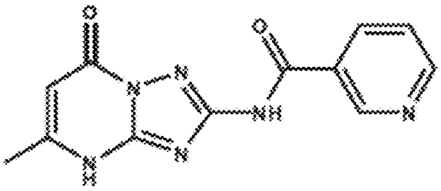
Fig. 127 (cont.)

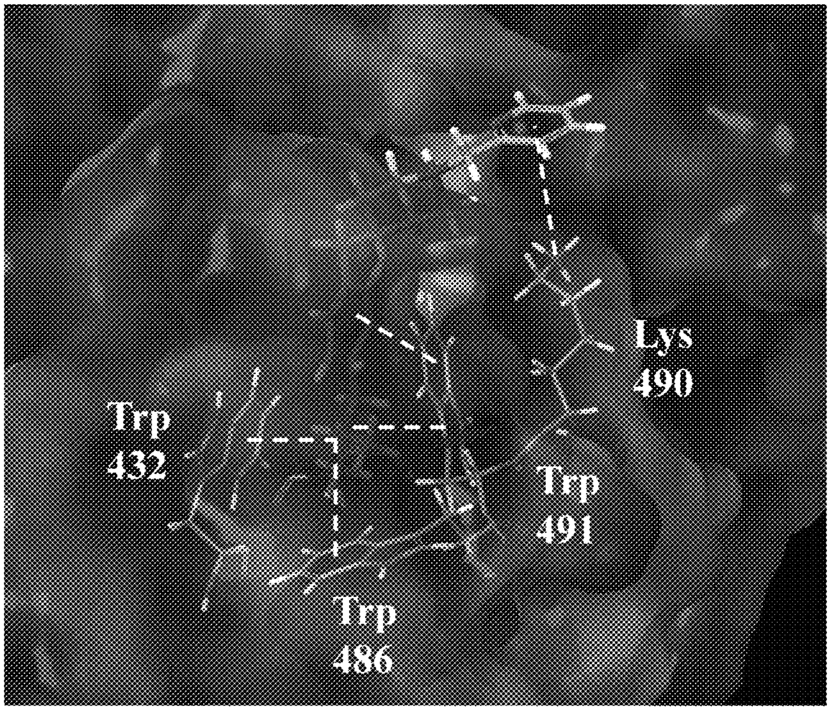
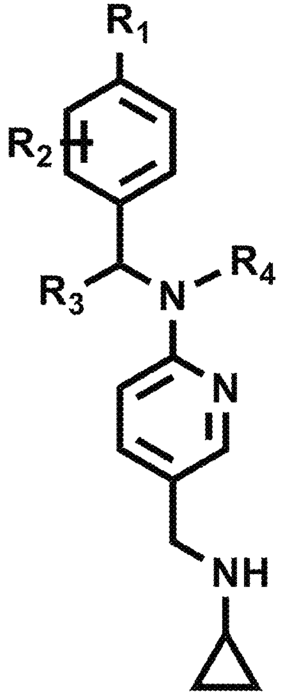
$R_1$ = $OCH_3$, $CF_3$
$R_2$ = Hydrogen bond acceptor $OCH_3$, N
$R_3$, $R_4$ = H, $CH_3$,
Possible substitution of the isopropyl amine
FIG. 128

SEQUENCE LISTING

```
<160> NUMBER OF SEQ ID NOS: 141

<210> SEQ ID NO 1
<211> LENGTH: 25
<212> TYPE: DNA
<213> ORGANISM: Artificial Sequence
<220> FEATURE:
<223> OTHER INFORMATION: Synthetic guide sequence

<400> SEQUENCE: 1

taggcacggg actatcacta caccg                                25


<210> SEQ ID NO 2
<211> LENGTH: 20
<212> TYPE: DNA
<213> ORGANISM: Artificial Sequence
<220> FEATURE:
<223> OTHER INFORMATION: Synthetic guide sequence

<400> SEQUENCE: 2

tcaggtgatt accgtagaga                                      20


<210> SEQ ID NO 3
```

-continued

<211> LENGTH: 20
<212> TYPE: DNA
<213> ORGANISM: Artificial Sequence
<220> FEATURE:
<223> OTHER INFORMATION: Synthetic guide sequence

<400> SEQUENCE: 3
aggtagcagg gaccatcgca 20

<210> SEQ ID NO 4
<211> LENGTH: 20
<212> TYPE: DNA
<213> ORGANISM: Artificial Sequence
<220> FEATURE:
<223> OTHER INFORMATION: Synthetic guide sequence

<400> SEQUENCE: 4
ctgaagtgca gcttgcgaca 20

<210> SEQ ID NO 5
<211> LENGTH: 20
<212> TYPE: DNA
<213> ORGANISM: Artificial Sequence
<220> FEATURE:
<223> OTHER INFORMATION: Synthetic guide sequence

<400> SEQUENCE: 5
gtccagtgtc tacaaaatgt 20

<210> SEQ ID NO 6
<211> LENGTH: 20
<212> TYPE: DNA
<213> ORGANISM: Artificial Sequence
<220> FEATURE:
<223> OTHER INFORMATION: Synthetic guide sequence

<400> SEQUENCE: 6
cactgaacta cttacatggg 20

<210> SEQ ID NO 7
<211> LENGTH: 20
<212> TYPE: DNA
<213> ORGANISM: Artificial Sequence
<220> FEATURE:
<223> OTHER INFORMATION: Synthetic guide sequence

<400> SEQUENCE: 7
atcaacttac tactctccca 20

<210> SEQ ID NO 8
<211> LENGTH: 20
<212> TYPE: DNA
<213> ORGANISM: Artificial Sequence
<220> FEATURE:
<223> OTHER INFORMATION: Synthetic guide sequence

<400> SEQUENCE: 8
gctggacctg ggatgatgta 20

<210> SEQ ID NO 9
<211> LENGTH: 20
<212> TYPE: DNA
<213> ORGANISM: Artificial Sequence
<220> FEATURE:
<223> OTHER INFORMATION: Synthetic guide sequence

<400> SEQUENCE: 9
agcagccact tcaaccccgc 20

<210> SEQ ID NO 10
<211> LENGTH: 20
<212> TYPE: DNA
<213> ORGANISM: Artificial Sequence
<220> FEATURE:
<223> OTHER INFORMATION: Synthetic guide sequence

<400> SEQUENCE: 10
tgaacacggc aacaagcgcc 20

<210> SEQ ID NO 11
<211> LENGTH: 20
<212> TYPE: DNA
<213> ORGANISM: Artificial Sequence
<220> FEATURE:
<223> OTHER INFORMATION: Synthetic guide sequence

<400> SEQUENCE: 11
gactttgagc cctacctttc 20

<210> SEQ ID NO 12
<211> LENGTH: 19
<212> TYPE: DNA
<213> ORGANISM: Artificial Sequence
<220> FEATURE:
<223> OTHER INFORMATION: Synthetic guide sequence

<400> SEQUENCE: 12
acaaaaggac aagataata 19

<210> SEQ ID NO 13
<211> LENGTH: 20
<212> TYPE: DNA
<213> ORGANISM: Artificial Sequence
<220> FEATURE:
<223> OTHER INFORMATION: Synthetic guide sequence

<400> SEQUENCE: 13
cgaaccttac ttgagcccac 20

<210> SEQ ID NO 14
<211> LENGTH: 20
<212> TYPE: DNA
<213> ORGANISM: Artificial Sequence
<220> FEATURE:
<223> OTHER INFORMATION: Synthetic guide sequence

<400> SEQUENCE: 14
gccgcctatc gttccatgaa 20

<210> SEQ ID NO 15
<211> LENGTH: 20
<212> TYPE: DNA
<213> ORGANISM: Artificial Sequence
<220> FEATURE:
<223> OTHER INFORMATION: Synthetic guide sequence

<400> SEQUENCE: 15
tcgcagagac caaaaggtca 20

<210> SEQ ID NO 16
<211> LENGTH: 20
<212> TYPE: DNA

<213> ORGANISM: Artificial Sequence
<220> FEATURE:
<223> OTHER INFORMATION: Synthetic guide sequence

<400> SEQUENCE: 16
agattccagt cgaaatcttt 20

<210> SEQ ID NO 17
<211> LENGTH: 20
<212> TYPE: DNA
<213> ORGANISM: Artificial Sequence
<220> FEATURE:
<223> OTHER INFORMATION: Synthetic guide sequence

<400> SEQUENCE: 17
tgagcatggt aataagcgtt 20

<210> SEQ ID NO 18
<211> LENGTH: 20
<212> TYPE: DNA
<213> ORGANISM: Artificial Sequence
<220> FEATURE:
<223> OTHER INFORMATION: Synthetic guide sequence

<400> SEQUENCE: 18
aagccggttc ccctattccg 20

<210> SEQ ID NO 19
<211> LENGTH: 20
<212> TYPE: DNA
<213> ORGANISM: Artificial Sequence
<220> FEATURE:
<223> OTHER INFORMATION: Synthetic guide sequence

<400> SEQUENCE: 19
aagaatgtca gccactagcg 20

<210> SEQ ID NO 20
<211> LENGTH: 20
<212> TYPE: DNA
<213> ORGANISM: Artificial Sequence
<220> FEATURE:
<223> OTHER INFORMATION: Synthetic guide sequence

<400> SEQUENCE: 20
cttaagtagc cagacaaatc 20

<210> SEQ ID NO 21
<211> LENGTH: 25
<212> TYPE: DNA
<213> ORGANISM: Artificial Sequence
<220> FEATURE:
<223> OTHER INFORMATION: Synthetic primer

<400> SEQUENCE: 21
caccggagtt gattgaggta aagcg 25

<210> SEQ ID NO 22
<211> LENGTH: 25
<212> TYPE: DNA
<213> ORGANISM: Artificial Sequence
<220> FEATURE:
<223> OTHER INFORMATION: Synthetic primer

<400> SEQUENCE: 22
aaaccgcttt acctcaatca actcc 25

-continued

<210> SEQ ID NO 23
<211> LENGTH: 25
<212> TYPE: DNA
<213> ORGANISM: Artificial Sequence
<220> FEATURE:
<223> OTHER INFORMATION: Synthetic primer

<400> SEQUENCE: 23
caccgcttgc tcttacacag agtgt 25

<210> SEQ ID NO 24
<211> LENGTH: 25
<212> TYPE: DNA
<213> ORGANISM: Artificial Sequence
<220> FEATURE:
<223> OTHER INFORMATION: Synthetic primer

<400> SEQUENCE: 24
aaacacactc tgtgtaagag caagc 25

<210> SEQ ID NO 25
<211> LENGTH: 25
<212> TYPE: DNA
<213> ORGANISM: Artificial Sequence
<220> FEATURE:
<223> OTHER INFORMATION: Synthetic primer

<400> SEQUENCE: 25
caccgcctgt acaacgagca cacgg 25

<210> SEQ ID NO 26
<211> LENGTH: 25
<212> TYPE: DNA
<213> ORGANISM: Artificial Sequence
<220> FEATURE:
<223> OTHER INFORMATION: Synthetic primer

<400> SEQUENCE: 26
aaacccgtgt gctcgttgta caggc 25

<210> SEQ ID NO 27
<211> LENGTH: 25
<212> TYPE: DNA
<213> ORGANISM: Artificial Sequence
<220> FEATURE:
<223> OTHER INFORMATION: Synthetic primer

<400> SEQUENCE: 27
caccggaggc gcgcaaggtg aagag 25

<210> SEQ ID NO 28
<211> LENGTH: 25
<212> TYPE: DNA
<213> ORGANISM: Artificial Sequence
<220> FEATURE:
<223> OTHER INFORMATION: Synthetic primer

<400> SEQUENCE: 28
aaacctcttc accttgcgcg cctcc 25

<210> SEQ ID NO 29
<211> LENGTH: 25
<212> TYPE: DNA
<213> ORGANISM: Artificial Sequence
<220> FEATURE:

-continued

<223> OTHER INFORMATION: Synthetic primer

<400> SEQUENCE: 29
caccggtcac gctccccctg cgcac 25

<210> SEQ ID NO 30
<211> LENGTH: 25
<212> TYPE: DNA
<213> ORGANISM: Artificial Sequence
<220> FEATURE:
<223> OTHER INFORMATION: Synthetic primer

<400> SEQUENCE: 30
aaacgtgcgc agggggagcg tgacc 25

<210> SEQ ID NO 31
<211> LENGTH: 25
<212> TYPE: DNA
<213> ORGANISM: Artificial Sequence
<220> FEATURE:
<223> OTHER INFORMATION: Synthetic primer

<400> SEQUENCE: 31
caccggaagt gtcgaatgct tatcc 25

<210> SEQ ID NO 32
<211> LENGTH: 25
<212> TYPE: DNA
<213> ORGANISM: Artificial Sequence
<220> FEATURE:
<223> OTHER INFORMATION: Synthetic primer

<400> SEQUENCE: 32
aaacggataa gcattcgaca cttcc 25

<210> SEQ ID NO 33
<211> LENGTH: 25
<212> TYPE: DNA
<213> ORGANISM: Artificial Sequence
<220> FEATURE:
<223> OTHER INFORMATION: Synthetic primer

<400> SEQUENCE: 33
caccggagct taaaagcagt cagga 25

<210> SEQ ID NO 34
<211> LENGTH: 25
<212> TYPE: DNA
<213> ORGANISM: Artificial Sequence
<220> FEATURE:
<223> OTHER INFORMATION: Synthetic primer

<400> SEQUENCE: 34
aaactcctga ctgcttttaa gctcc 25

<210> SEQ ID NO 35
<211> LENGTH: 25
<212> TYPE: DNA
<213> ORGANISM: Artificial Sequence
<220> FEATURE:
<223> OTHER INFORMATION: Synthetic primer

<400> SEQUENCE: 35
caccggacrg aggtcccgac cacgc 25

<210> SEQ ID NO 36
<211> LENGTH: 25
<212> TYPE: DNA
<213> ORGANISM: Artificial Sequence
<220> FEATURE:
<223> OTHER INFORMATION: Synthetic primer

<400> SEQUENCE: 36
aaacgcgtgg tcgggacctc agtcc 25

<210> SEQ ID NO 37
<211> LENGTH: 25
<212> TYPE: DNA
<213> ORGANISM: Artificial Sequence
<220> FEATURE:
<223> OTHER INFORMATION: Synthetic primer

<400> SEQUENCE: 37
caccggtcaa gcccaagcgc tcccg 25

<210> SEQ ID NO 38
<211> LENGTH: 25
<212> TYPE: DNA
<213> ORGANISM: Artificial Sequence
<220> FEATURE:
<223> OTHER INFORMATION: Synthetic primer

<400> SEQUENCE: 38
aaaccgggag cgcttgggct tgacc 25

<210> SEQ ID NO 39
<211> LENGTH: 25
<212> TYPE: DNA
<213> ORGANISM: Artificial Sequence
<220> FEATURE:
<223> OTHER INFORMATION: Synthetic primer

<400> SEQUENCE: 39
caccggtcca gtgtctacaa aatgt 25

<210> SEQ ID NO 40
<211> LENGTH: 25
<212> TYPE: DNA
<213> ORGANISM: Artificial Sequence
<220> FEATURE:
<223> OTHER INFORMATION: Synthetic primer

<400> SEQUENCE: 40
aaacacattt tgtagacact ggacc 25

<210> SEQ ID NO 41
<211> LENGTH: 25
<212> TYPE: DNA
<213> ORGANISM: Artificial Sequence
<220> FEATURE:
<223> OTHER INFORMATION: Synthetic primer

<400> SEQUENCE: 41
caccggctgg acctgggatg atgta 25

<210> SEQ ID NO 42
<211> LENGTH: 25
<212> TYPE: DNA
<213> ORGANISM: Artificial Sequence
<220> FEATURE:
<223> OTHER INFORMATION: Synthetic primer

<400> SEQUENCE: 42
aaactacatc atcccaggtc cagcc 25

<210> SEQ ID NO 43
<211> LENGTH: 24
<212> TYPE: DNA
<213> ORGANISM: Artificial Sequence
<220> FEATURE:
<223> OTHER INFORMATION: Synthetic primer

<400> SEQUENCE: 43
caccgaccat chaccactct tcca 24

<210> SEQ ID NO 44
<211> LENGTH: 25
<212> TYPE: DNA
<213> ORGANISM: Artificial Sequence
<220> FEATURE:
<223> OTHER INFORMATION: Synthetic primer

<400> SEQUENCE: 44
aaactggaag agtggtaaga tggtc 25

<210> SEQ ID NO 45
<211> LENGTH: 25
<212> TYPE: DNA
<213> ORGANISM: Artificial Sequence
<220> FEATURE:
<223> OTHER INFORMATION: Synthetic primer

<400> SEQUENCE: 45
caccgtaaca cggcaccaat gctgt 25

<210> SEQ ID NO 46
<211> LENGTH: 25
<212> TYPE: DNA
<213> ORGANISM: Artificial Sequence
<220> FEATURE:
<223> OTHER INFORMATION: Synthetic primer

<400> SEQUENCE: 46
aaacacagca ttggtgccgt gttac 25

<210> SEQ ID NO 47
<211> LENGTH: 25
<212> TYPE: DNA
<213> ORGANISM: Artificial Sequence
<220> FEATURE:
<223> OTHER INFORMATION: Synthetic primer

<400> SEQUENCE: 47
caccgtaggc acgggactat cacta 25

<210> SEQ ID NO 48
<211> LENGTH: 25
<212> TYPE: DNA
<213> ORGANISM: Artificial Sequence
<220> FEATURE:
<223> OTHER INFORMATION: Synthetic primer

<400> SEQUENCE: 48
aaactagtga tagtcccgtg cctac 25

<210> SEQ ID NO 49
<211> LENGTH: 25

-continued

<212> TYPE: DNA
<213> ORGANISM: Artificial Sequence
<220> FEATURE:
<223> OTHER INFORMATION: Synthetic primer

<400> SEQUENCE: 49
caccgtcagg tgattaccgt agaga 25

<210> SEQ ID NO 50
<211> LENGTH: 25
<212> TYPE: DNA
<213> ORGANISM: Artificial Sequence
<220> FEATURE:
<223> OTHER INFORMATION: Synthetic primer

<400> SEQUENCE: 50
aaactctcta cggtaatcac ctgac 25

<210> SEQ ID NO 51
<211> LENGTH: 25
<212> TYPE: DNA
<213> ORGANISM: Artificial Sequence
<220> FEATURE:
<223> OTHER INFORMATION: Synthetic primer

<400> SEQUENCE: 51
caccgcgctc cttccatgat taaca 25

<210> SEQ ID NO 52
<211> LENGTH: 25
<212> TYPE: DNA
<213> ORGANISM: Artificial Sequence
<220> FEATURE:
<223> OTHER INFORMATION: Synthetic primer

<400> SEQUENCE: 52
aaactgttaa tcatggaagg agcgc 25

<210> SEQ ID NO 53
<211> LENGTH: 25
<212> TYPE: DNA
<213> ORGANISM: Artificial Sequence
<220> FEATURE:
<223> OTHER INFORMATION: Synthetic primer

<400> SEQUENCE: 53
caccggtgga gatggctctt agcag 25

<210> SEQ ID NO 54
<211> LENGTH: 25
<212> TYPE: DNA
<213> ORGANISM: Artificial Sequence
<220> FEATURE:
<223> OTHER INFORMATION: Synthetic primer

<400> SEQUENCE: 54
aaacctgcta agagccatct ccacc 25

<210> SEQ ID NO 55
<211> LENGTH: 25
<212> TYPE: DNA
<213> ORGANISM: Artificial Sequence
<220> FEATURE:
<223> OTHER INFORMATION: Synthetic primer

<400> SEQUENCE: 55

-continued caccggagtt gattgaggta aagcg 25

<210> SEQ ID NO 56
<211> LENGTH: 25
<212> TYPE: DNA
<213> ORGANISM: Artificial Sequence
<220> FEATURE:
<223> OTHER INFORMATION: Synthetic primer

<400> SEQUENCE: 56
aaaccgcttt acctcaatca actcc 25

<210> SEQ ID NO 57
<211> LENGTH: 25
<212> TYPE: DNA
<213> ORGANISM: Artificial Sequence
<220> FEATURE:
<223> OTHER INFORMATION: Synthetic primer

<400> SEQUENCE: 57
caccgcttgc tcttacacag agtgt 25

<210> SEQ ID NO 58
<211> LENGTH: 25
<212> TYPE: DNA
<213> ORGANISM: Artificial Sequence
<220> FEATURE:
<223> OTHER INFORMATION: Synthetic primer

<400> SEQUENCE: 58
aaacacactc tgtgtaagag caagc 25

<210> SEQ ID NO 59
<211> LENGTH: 25
<212> TYPE: DNA
<213> ORGANISM: Artificial Sequence
<220> FEATURE:
<223> OTHER INFORMATION: Synthetic primer

<400> SEQUENCE: 59
caccgcctgt acaacgagca cacgg 25

<210> SEQ ID NO 60
<211> LENGTH: 25
<212> TYPE: DNA
<213> ORGANISM: Artificial Sequence
<220> FEATURE:
<223> OTHER INFORMATION: synthetic primer

<400> SEQUENCE: 60
aaacccgtgt gctcgttgta caggc 25

<210> SEQ ID NO 61
<211> LENGTH: 25
<212> TYPE: DNA
<213> ORGANISM: Artificial Sequence
<220> FEATURE:
<223> OTHER INFORMATION: Synthetic primer

<400> SEQUENCE: 61
caccggaggc gcgcaaggtg aagag 25

<210> SEQ ID NO 62
<211> LENGTH: 25
<212> TYPE: DNA
<213> ORGANISM: Artificial Sequence
<220> FEATURE:
<223> OTHER INFORMATION: Synthetic primer

<400> SEQUENCE: 62
aaacctcttc accttgcgcg cctcc 25

<210> SEQ ID NO 63
<211> LENGTH: 25
<212> TYPE: DNA
<213> ORGANISM: Artificial Sequence
<220> FEATURE:
<223> OTHER INFORMATION: Synthetic primer

<400> SEQUENCE: 63
caccggtcac gctcccectg cgcac 25

<210> SEQ ID NO 64
<211> LENGTH: 25
<212> TYPE: DNA
<213> ORGANISM: Artificial Sequence
<220> FEATURE:
<223> OTHER INFORMATION: Synthetic primer

<400> SEQUENCE: 64
aaacgtgcgc agggggagcg tgacc 25

<210> SEQ ID NO 65
<211> LENGTH: 25
<212> TYPE: DNA
<213> ORGANISM: Artificial Sequence
<220> FEATURE:
<223> OTHER INFORMATION: Synthetic primer

<400> SEQUENCE: 65
caccggaagt gtcgaatgct tatcc 25

<210> SEQ ID NO 66
<211> LENGTH: 25
<212> TYPE: DNA
<213> ORGANISM: Artificial Sequence
<220> FEATURE:
<223> OTHER INFORMATION: Synthetic primer

<400> SEQUENCE: 66
aaacggataa gcattcgaca cttcc 25

<210> SEQ ID NO 67
<211> LENGTH: 25
<212> TYPE: DNA
<213> ORGANISM: Artificial Sequence
<220> FEATURE:
<223> OTHER INFORMATION: Synthetic primer

<400> SEQUENCE: 67
caccggagct taaaagcagt cagga 25

<210> SEQ ID NO 68
<211> LENGTH: 25
<212> TYPE: DNA
<213> ORGANISM: Artificial Sequence
<220> FEATURE:
<223> OTHER INFORMATION: Synthetic primer

<400> SEQUENCE: 68
aaactcctga ctgcttttaa gctcc 25

<210> SEQ ID NO 69
<211> LENGTH: 25
<212> TYPE: DNA
<213> ORGANISM: Artificial Sequence
<220> FEATURE:
<223> OTHER INFORMATION: Synthetic primer

<400> SEQUENCE: 69
caccggactg aggtcccgac cacgc 25

<210> SEQ ID NO 70
<211> LENGTH: 25
<212> TYPE: DNA
<213> ORGANISM: Artificial Sequence
<220> FEATURE:
<223> OTHER INFORMATION: Synthetic primer

<400> SEQUENCE: 70
aaacgcgtgg tcgggacctc agtcc 25

<210> SEQ ID NO 71
<211> LENGTH: 25
<212> TYPE: DNA
<213> ORGANISM: Artificial Sequence
<220> FEATURE:
<223> OTHER INFORMATION: Synthetic primer

<400> SEQUENCE: 71
caccggtcaa gcccaagcgc tcccg 25

<210> SEQ ID NO 72
<211> LENGTH: 25
<212> TYPE: DNA
<213> ORGANISM: Artificial Sequence
<220> FEATURE:
<223> OTHER INFORMATION: Synthetic primer

<400> SEQUENCE: 72
aaaccgggag cgcttgggct tgacc 25

<210> SEQ ID NO 73
<211> LENGTH: 25
<212> TYPE: DNA
<213> ORGANISM: Artificial Sequence
<220> FEATURE:
<223> OTHER INFORMATION: Synthetic primer

<400> SEQUENCE: 73
caccggtcca gtgtctacaa aatgt 25

<210> SEQ ID NO 74
<211> LENGTH: 25
<212> TYPE: DNA
<213> ORGANISM: Artificial Sequence
<220> FEATURE:
<223> OTHER INFORMATION: Synthetic primer

<400> SEQUENCE: 74
aaacacattt tgtagacact ggacc 25

<210> SEQ ID NO 75
<211> LENGTH: 25
<212> TYPE: DNA
<213> ORGANISM: Artificial Sequence
<220> FEATURE:
<223> OTHER INFORMATION: Synthetic primer

<400> SEQUENCE: 75
caccggctgg acctgggatg atgta 25

<210> SEQ ID NO 76
<211> LENGTH: 25
<212> TYPE: DNA
<213> ORGANISM: Artificial Sequence
<220> FEATURE:
<223> OTHER INFORMATION: Synthetic primer

<400> SEQUENCE: 76
aaactacatc atcccaggtc cagcc 25

<210> SEQ ID NO 77
<211> LENGTH: 24
<212> TYPE: DNA
<213> ORGANISM: Artificial Sequence
<220> FEATURE:
<223> OTHER INFORMATION: Synthetic primer

<400> SEQUENCE: 77
caccgaccat chaccactct tcca 24

<210> SEQ ID NO 78
<211> LENGTH: 25
<212> TYPE: DNA
<213> ORGANISM: Artificial Sequence
<220> FEATURE:
<223> OTHER INFORMATION: Synthetic primer

<400> SEQUENCE: 78
aaactggaag agtggtaaga tggtc 25

<210> SEQ ID NO 79
<211> LENGTH: 25
<212> TYPE: DNA
<213> ORGANISM: Artificial Sequence
<220> FEATURE:
<223> OTHER INFORMATION: Synthetic primer

<400> SEQUENCE: 79
caccgtaaca cggcaccaat gctgt 25

<210> SEQ ID NO 80
<211> LENGTH: 25
<212> TYPE: DNA
<213> ORGANISM: Artificial Sequence
<220> FEATURE:
<223> OTHER INFORMATION: Synthetic primer

<400> SEQUENCE: 80
aaacacagca ttggtgccgt gttac 25

<210> SEQ ID NO 81
<211> LENGTH: 25
<212> TYPE: DNA
<213> ORGANISM: Artificial Sequence
<220> FEATURE:
<223> OTHER INFORMATION: Synthetic primer

<400> SEQUENCE: 81
caccgtaggc acgggactat cacta 25

<210> SEQ ID NO 82

<211> LENGTH: 25
<212> TYPE: DNA
<213> ORGANISM: Artificial Sequence
<220> FEATURE:
<223> OTHER INFORMATION: Synthetic primer

<400> SEQUENCE: 82
aaactagtga tagtcccgtg cctac 25

<210> SEQ ID NO 83
<211> LENGTH: 25
<212> TYPE: DNA
<213> ORGANISM: Artificial Sequence
<220> FEATURE:
<223> OTHER INFORMATION: Synthetic primer

<400> SEQUENCE: 83
caccgtcagg tgattaccgt agaga 25

<210> SEQ ID NO 84
<211> LENGTH: 25
<212> TYPE: DNA
<213> ORGANISM: Artificial Sequence
<220> FEATURE:
<223> OTHER INFORMATION: Synthetic primer

<400> SEQUENCE: 84
aaactctcta cggtaatcac ctgac 25

<210> SEQ ID NO 85
<211> LENGTH: 25
<212> TYPE: DNA
<213> ORGANISM: Artificial Sequence
<220> FEATURE:
<223> OTHER INFORMATION: Synthetic primer

<400> SEQUENCE: 85
caccgcgctc cttccatgat taaca 25

<210> SEQ ID NO 86
<211> LENGTH: 25
<212> TYPE: DNA
<213> ORGANISM: Artificial Sequence
<220> FEATURE:
<223> OTHER INFORMATION: Synthetic primer

<400> SEQUENCE: 86
aaactgttaa tcatggaagg agcgc 25

<210> SEQ ID NO 87
<211> LENGTH: 25
<212> TYPE: DNA
<213> ORGANISM: Artificial Sequence
<220> FEATURE:
<223> OTHER INFORMATION: Synthetic primer

<400> SEQUENCE: 87
caccggtgga gatggctctt agcag 25

<210> SEQ ID NO 88
<211> LENGTH: 25
<212> TYPE: DNA
<213> ORGANISM: Artificial Sequence
<220> FEATURE:
<223> OTHER INFORMATION: Synthetic primer

<400> SEQUENCE: 88

-continued aaacctgcta agagccatct ccacc                                                      25

<210> SEQ ID NO 89
<211> LENGTH: 18
<212> TYPE: DNA
<213> ORGANISM: Artificial Sequence
<220> FEATURE:
<223> OTHER INFORMATION: Synthetic primer

<400> SEQUENCE: 89
ccgcacgtat gcacccgt                                                              18

<210> SEQ ID NO 90
<211> LENGTH: 58
<212> TYPE: DNA
<213> ORGANISM: Artificial Sequence
<220> FEATURE:
<223> OTHER INFORMATION: Synthetic primer

<400> SEQUENCE: 90
ccgggcaagt atgttcacta tgaaactcga gtttcatagt gaacatactt gctttttg       58

<210> SEQ ID NO 91
<211> LENGTH: 58
<212> TYPE: DNA
<213> ORGANISM: Artificial Sequence
<220> FEATURE:
<223> OTHER INFORMATION: Synthetic primer

<400> SEQUENCE: 91
ccgggccaag gaacaatcca ttgttctcga gaacaatgga ttgttccttg gctttttg       58

<210> SEQ ID NO 92
<211> LENGTH: 57
<212> TYPE: DNA
<213> ORGANISM: Artificial Sequence
<220> FEATURE:
<223> OTHER INFORMATION: Synthetic primer

<400> SEQUENCE: 92
ccggccatgt acttacaagc cgatactcga gtatcggctt gtaagtacat ggttttt        57

<210> SEQ ID NO 93
<211> LENGTH: 59
<212> TYPE: DNA
<213> ORGANISM: Artificial Sequence
<220> FEATURE:
<223> OTHER INFORMATION: Synthetic primer

<400> SEQUENCE: 93
ccgggccgtg gacgagagaa agaaatactc gagtatttct ttctcgtcca cggcttttt      59

<210> SEQ ID NO 94
<211> LENGTH: 58
<212> TYPE: DNA
<213> ORGANISM: Artificial Sequence
<220> FEATURE:
<223> OTHER INFORMATION: Synthetic primer

<400> SEQUENCE: 94
ccgggaaagg ctgttggcat caatactcga gtattgatgc caacagcctt tctttttg       58

<210> SEQ ID NO 95
<211> LENGTH: 58
<212> TYPE: DNA

<213> ORGANISM: Artificial Sequence
<220> FEATURE:
<223> OTHER INFORMATION: Synthetic primer

<400> SEQUENCE: 95
ccggccaccc agctatgctt cagatctcga gatctgaagc atagctgggt ggtttttg 58

<210> SEQ ID NO 96
<211> LENGTH: 58
<212> TYPE: DNA
<213> ORGANISM: Artificial Sequence
<220> FEATURE:
<223> OTHER INFORMATION: Synthetic primer

<400> SEQUENCE: 96
ccggcggttc acaacctcgg tttagctcga gctaaaccga ggttgtgaac cgtttttg 58

<210> SEQ ID NO 97
<211> LENGTH: 59
<212> TYPE: DNA
<213> ORGANISM: Artificial Sequence
<220> FEATURE:
<223> OTHER INFORMATION: Synthetic primer

<400> SEQUENCE: 97
ccgggtcacc aaggagactg ctatttctcg agaaatagca gtctccttgg tgattttg 59

<210> SEQ ID NO 98
<211> LENGTH: 58
<212> TYPE: DNA
<213> ORGANISM: Artificial Sequence
<220> FEATURE:
<223> OTHER INFORMATION: Synthetic primer

<400> SEQUENCE: 98
ccggccctac ctgtccagct attacctcga ggtaatagct ggacaggtag ggtttttg 58

<210> SEQ ID NO 99
<211> LENGTH: 58
<212> TYPE: DNA
<213> ORGANISM: Artificial Sequence
<220> FEATURE:
<223> OTHER INFORMATION: Synthetic primer

<400> SEQUENCE: 99
ccggcccgaa agagtttgag tggaactcga gttccactca aactctttcg ggtttttg 58

<210> SEQ ID NO 100
<211> LENGTH: 58
<212> TYPE: DNA
<213> ORGANISM: Artificial Sequence
<220> FEATURE:
<223> OTHER INFORMATION: Synthetic primer

<400> SEQUENCE: 100
ccgggctact ctgaggacga tattcctcga ggaatatcgt cctcagagta gctttttg 58

<210> SEQ ID NO 101
<211> LENGTH: 58
<212> TYPE: DNA
<213> ORGANISM: Artificial Sequence
<220> FEATURE:
<223> OTHER INFORMATION: Synthetic primer

<400> SEQUENCE: 101
ccggcggtcc attaataact ataacctcga ggttatagtt attaatggac cgtttttg 58

<210> SEQ ID NO 102
<211> LENGTH: 58
<212> TYPE: DNA
<213> ORGANISM: Artificial Sequence
<220> FEATURE:
<223> OTHER INFORMATION: Synthetic primer

<400> SEQUENCE: 102
ccggtaagtc aaagaagacg tattactcga gtaatacgtc ttctttgact tatttttg 58

<210> SEQ ID NO 103
<211> LENGTH: 58
<212> TYPE: DNA
<213> ORGANISM: Artificial Sequence
<220> FEATURE:
<223> OTHER INFORMATION: Synthetic primer

<400> SEQUENCE: 103
ccgggaagtc tgttgtggac tataactcga gttatagtcc acaacagact tctttttg 58

<210> SEQ ID NO 104
<211> LENGTH: 20
<212> TYPE: DNA
<213> ORGANISM: Artificial Sequence
<220> FEATURE:
<223> OTHER INFORMATION: Synthetic primer

<400> SEQUENCE: 104
ctatgagccc gaccctatta 20

<210> SEQ ID NO 105
<211> LENGTH: 20
<212> TYPE: DNA
<213> ORGANISM: Artificial Sequence
<220> FEATURE:
<223> OTHER INFORMATION: Synthetic primer

<400> SEQUENCE: 105
gtctcagctt gacagtgaac 20

<210> SEQ ID NO 106
<211> LENGTH: 19
<212> TYPE: DNA
<213> ORGANISM: Artificial Sequence
<220> FEATURE:
<223> OTHER INFORMATION: Synthetic primer

<400> SEQUENCE: 106
acctagagac cagctcatt 19

<210> SEQ ID NO 107
<211> LENGTH: 20
<212> TYPE: DNA
<213> ORGANISM: Artificial Sequence
<220> FEATURE:
<223> OTHER INFORMATION: Synthetic primer

<400> SEQUENCE: 107
caagttctgg gagtcgttag 20

<210> SEQ ID NO 108
<211> LENGTH: 19
<212> TYPE: DNA
<213> ORGANISM: Artificial Sequence
<220> FEATURE:

<223> OTHER INFORMATION: Synthetic primer

<400> SEQUENCE: 108
gatggactca gcagctcta 19

<210> SEQ ID NO 109
<211> LENGTH: 20
<212> TYPE: DNA
<213> ORGANISM: Artificial Sequence
<220> FEATURE:
<223> OTHER INFORMATION: Synthetic primer

<400> SEQUENCE: 109
gctggagtta tgtccctttc 20

<210> SEQ ID NO 110
<211> LENGTH: 20
<212> TYPE: DNA
<213> ORGANISM: Artificial Sequence
<220> FEATURE:
<223> OTHER INFORMATION: Synthetic primer

<400> SEQUENCE: 110
gctgcatatc tgcctgtatt 20

<210> SEQ ID NO 111
<211> LENGTH: 21
<212> TYPE: DNA
<213> ORGANISM: Artificial Sequence
<220> FEATURE:
<223> OTHER INFORMATION: Synthetic primer

<400> SEQUENCE: 111
ctcaatgttc ttcctctgtc c 21

<210> SEQ ID NO 112
<211> LENGTH: 18
<212> TYPE: DNA
<213> ORGANISM: Artificial Sequence
<220> FEATURE:
<223> OTHER INFORMATION: Synthetic primer

<400> SEQUENCE: 112
aagtgagcct cagcaatg 18

<210> SEQ ID NO 113
<211> LENGTH: 18
<212> TYPE: DNA
<213> ORGANISM: Artificial Sequence
<220> FEATURE:
<223> OTHER INFORMATION: Synthetic primer

<400> SEQUENCE: 113
gcagaacctg aagcaaga 18

<210> SEQ ID NO 114
<211> LENGTH: 18
<212> TYPE: DNA
<213> ORGANISM: Artificial Sequence
<220> FEATURE:
<223> OTHER INFORMATION: Synthetic primer

<400> SEQUENCE: 114
tcctacagcc ggaagatt 18

<210> SEQ ID NO 115
<211> LENGTH: 21
<212> TYPE: DNA
<213> ORGANISM: Artificial Sequence
<220> FEATURE:
<223> OTHER INFORMATION: Synthetic primer

<400> SEQUENCE: 115
gttccaggtc agtgatgtat t 21

<210> SEQ ID NO 116
<211> LENGTH: 20
<212> TYPE: DNA
<213> ORGANISM: Artificial Sequence
<220> FEATURE:
<223> OTHER INFORMATION: Synthetic primer

<400> SEQUENCE: 116
ccacttcctg ctgtttctct 20

<210> SEQ ID NO 117
<211> LENGTH: 20
<212> TYPE: DNA
<213> ORGANISM: Artificial Sequence
<220> FEATURE:
<223> OTHER INFORMATION: Synthetic primer

<400> SEQUENCE: 117
ttggtcagga ataccacagc 20

<210> SEQ ID NO 118
<211> LENGTH: 20
<212> TYPE: DNA
<213> ORGANISM: Artificial Sequence
<220> FEATURE:
<223> OTHER INFORMATION: Synthetic primer

<400> SEQUENCE: 118
cccacgtcaa ggagtatttc 20

<210> SEQ ID NO 119
<211> LENGTH: 17
<212> TYPE: DNA
<213> ORGANISM: Artificial Sequence
<220> FEATURE:
<223> OTHER INFORMATION: Synthetic primer

<400> SEQUENCE: 119
tcttctctgg gttggca 17

<210> SEQ ID NO 120
<211> LENGTH: 18
<212> TYPE: DNA
<213> ORGANISM: Artificial Sequence
<220> FEATURE:
<223> OTHER INFORMATION: Synthetic primer

<400> SEQUENCE: 120
gtcacctgct gctttcat 18

<210> SEQ ID NO 121
<211> LENGTH: 21
<212> TYPE: DNA
<213> ORGANISM: Artificial Sequence
<220> FEATURE:
<223> OTHER INFORMATION: Synthetic primer

<400> SEQUENCE: 121
gggtctacac agagagacat a 21

<210> SEQ ID NO 122
<211> LENGTH: 21
<212> TYPE: DNA
<213> ORGANISM: Artificial Sequence
<220> FEATURE:
<223> OTHER INFORMATION: Synthetic primer

<400> SEQUENCE: 122
tcgaggaacc ctagtgataa g 21

<210> SEQ ID NO 123
<211> LENGTH: 21
<212> TYPE: DNA
<213> ORGANISM: Artificial Sequence
<220> FEATURE:
<223> OTHER INFORMATION: Synthetic primer

<400> SEQUENCE: 123
ttgaggtctt tgagggattt g 21

<210> SEQ ID NO 124
<211> LENGTH: 20
<212> TYPE: DNA
<213> ORGANISM: Artificial Sequence
<220> FEATURE:
<223> OTHER INFORMATION: Synthetic primer

<400> SEQUENCE: 124
catcctgctg ggtctgagtg 20

<210> SEQ ID NO 125
<211> LENGTH: 20
<212> TYPE: DNA
<213> ORGANISM: Artificial Sequence
<220> FEATURE:
<223> OTHER INFORMATION: Synthetic primer

<400> SEQUENCE: 125
attctcactg gcccgtcatc 20

<210> SEQ ID NO 126
<211> LENGTH: 20
<212> TYPE: DNA
<213> ORGANISM: Artificial Sequence
<220> FEATURE:
<223> OTHER INFORMATION: Synthetic primer

<400> SEQUENCE: 126
ggctgcgaca aagttgaagt 20

<210> SEQ ID NO 127
<211> LENGTH: 20
<212> TYPE: DNA
<213> ORGANISM: Artificial Sequence
<220> FEATURE:
<223> OTHER INFORMATION: Synthetic primer

<400> SEQUENCE: 127
cgagcttgct tggatctggg 20

<210> SEQ ID NO 128
<211> LENGTH: 20

<212> TYPE: DNA
<213> ORGANISM: Artificial Sequence
<220> FEATURE:
<223> OTHER INFORMATION: Synthetic primer

<400> SEQUENCE: 128
tggtggagta tggcagcaac 20

<210> SEQ ID NO 129
<211> LENGTH: 20
<212> TYPE: DNA
<213> ORGANISM: Artificial Sequence
<220> FEATURE:
<223> OTHER INFORMATION: Synthetic primer

<400> SEQUENCE: 129
cccagtacac cactaacgca 20

<210> SEQ ID NO 130
<211> LENGTH: 20
<212> TYPE: DNA
<213> ORGANISM: Artificial Sequence
<220> FEATURE:
<223> OTHER INFORMATION: Synthetic primer

<400> SEQUENCE: 130
gcctagcctt gatgaaagaa 20

<210> SEQ ID NO 131
<211> LENGTH: 20
<212> TYPE: DNA
<213> ORGANISM: Artificial Sequence
<220> FEATURE:
<223> OTHER INFORMATION: Synthetic primer

<400> SEQUENCE: 131
gaatacagga gtgggttcac 20

<210> SEQ ID NO 132
<211> LENGTH: 18
<212> TYPE: DNA
<213> ORGANISM: Artificial Sequence
<220> FEATURE:
<223> OTHER INFORMATION: Synthetic primer

<400> SEQUENCE: 132
gtcggtgtga acggattt 18

<210> SEQ ID NO 133
<211> LENGTH: 22
<212> TYPE: DNA
<213> ORGANISM: Artificial Sequence
<220> FEATURE:
<223> OTHER INFORMATION: Synthetic primer

<400> SEQUENCE: 133
ggagtcatac tggaacatgt ag 22

<210> SEQ ID NO 134
<211> LENGTH: 20
<212> TYPE: DNA
<213> ORGANISM: Artificial Sequence
<220> FEATURE:
<223> OTHER INFORMATION: Synthetic primer

<400> SEQUENCE: 134
aactttgctt tccctggtta 20

<210> SEQ ID NO 135
<211> LENGTH: 20
<212> TYPE: DNA
<213> ORGANISM: Artificial Sequence
<220> FEATURE:
<223> OTHER INFORMATION: Synthetic primer

<400> SEQUENCE: 135
aacaaagtct ggcctgtatc 20

<210> SEQ ID NO 136
<211> LENGTH: 20
<212> TYPE: DNA
<213> ORGANISM: Artificial Sequence
<220> FEATURE:
<223> OTHER INFORMATION: Synthetic primer

<400> SEQUENCE: 136
gagtctgtgt gggttcaaac 20

<210> SEQ ID NO 137
<211> LENGTH: 20
<212> TYPE: DNA
<213> ORGANISM: Artificial Sequence
<220> FEATURE:
<223> OTHER INFORMATION: Synthetic primer

<400> SEQUENCE: 137
aaaagaagag tgagcagggc 20

<210> SEQ ID NO 138
<211> LENGTH: 27
<212> TYPE: DNA
<213> ORGANISM: Artificial Sequence
<220> FEATURE:
<223> OTHER INFORMATION: Synthetic primer

<400> SEQUENCE: 138
cacaaaatgg attttgtaaa caaagac 27

<210> SEQ ID NO 139
<211> LENGTH: 22
<212> TYPE: DNA
<213> ORGANISM: Artificial Sequence
<220> FEATURE:
<223> OTHER INFORMATION: Synthetic primer

<400> SEQUENCE: 139
tactaaagtg accgttctcc tc 22

-continued
<210> SEQ ID NO 140
<211> LENGTH: 23
<212> TYPE: DNA
<213> ORGANISM: Artificial Sequence
<220> FEATURE:
<223> OTHER INFORMATION: Synthetic primer
<400> SEQUENCE: 140
ggacattggg ataggcatac aac 23
<210> SEQ ID NO 141
<211> LENGTH: 18
<212> TYPE: DNA
<213> ORGANISM: Artificial Sequence
<220> FEATURE:
<223> OTHER INFORMATION: Synthetic primer
<400> SEQUENCE: 141
ggcggcagcc tcacagag 18

BROAD SPECTRUM ANTI-CANCER COMPOUNDS

CROSS REFERENCE TO RELATED APPLICATIONS

This application is a National Stage Application under 35 U.S.C. § 371 and claims the benefit of International Application No. PCT/US2020/055568, filed Oct. 14, 2020, which claims the benefit of U.S. Provisional Application Ser. No. 62/914,914, filed on Oct. 14, 2019; U.S. Provisional Application Ser. No. 62/971,701, filed on Feb. 7, 2020; U.S. Provisional Application Ser. No. 63/059,939, filed on Jul. 31, 2020; and U.S. Provisional Application Ser. No. 63/074,421, filed on Sep. 3, 2020, each of which is incorporated herein by reference in its entirety.

STATEMENT AS TO RIGHTS TO INVENTIONS MADE UNDER FEDERALLY SPONSORED RESEARCH AND DEVELOPMENT

This invention was made in part with Government support under grant nos. CA177322, DA039562, DA049524, DA046171, and NS118250 awarded by the National Institutes of Health. The Government has certain rights in the invention.

SEQUENCE LISTING

This application contains a Sequence Listing that has been submitted electronically as an ASCII text file named Sequence Listing.txt. The ASCII text file, created on Apr. 11, 2022, is 26.6 kilobytes in size. The material in the ASCII text file is hereby incorporated by reference in its entirety.

BACKGROUND $N^6$-Methyladenosine (m6A) is present in 0.1-0.4% of all adenosines in global cellular RNAs and accounts for ~50% of all methylated ribonucleotides. $N^6$-Methyladenosine (m6A) occurs primarily in two consensus sequence motifs, G m6A C (~70%) and A m6A C (~30%). Long internal exons, locations upstream of stop codons, and the 3'-UTR of mRNA are preferred modification sites for m6A, implying roles involving translational control, influencing affinities of RNA binding proteins or unique m6A-derived transcriptome topology. There are several proteins involved in m6A regulation with different roles: the m6A methyltransferases (the "writers"), the m6A demethyltransferases (the "erasers"), and the effectors recognizing m6A (the "readers"). A variety of cytopathologic processes involving nuclear RNA export, splicing, mRNA stability, circRNA translation, miRNA biogenesis, and lncRNA metabolism have been linked to aberrant levels of m6A. In addition, m6A modification has been associated with numerous physiological and pathological phenomena, including obesity, immunoregulation, yeast meiosis, plant development, and carcinogenesis. Disclosed herein, inter alia, are solutions to these and other problems in the art.

SUMMARY

This disclosure features chemical entities (e.g., small hairpin RNAs (shRNAs), micro RNA (miRNAs), small interfering RNA (siRNAs), small molecule inhibitors, antisense nucleic acids, peptides, viruses, CRISPR-sgRNAs, or combinations thereof) that inhibit one or more of m6A writers (e.g., methyltransferase like 3 (Mettl3 or MT-A70) or methyltransferase like-14 (Mettl14)), m6Am writers (e.g., phosphorylated CTD interacting factor 1 (PCIF1), or Mettl3/14), m6A erasers (e.g., fat-mass and obesity-associated protein (FTO) or ALKB homolog 5 (ALKBH5)), m6Am erasers (e.g., FTO), m6A readers (e.g., YTH domain-containing family proteins (YTHs)), YTF domain family member 1 (YTHDF 1), YTF domain family member 2 (YTHDF 2), YTF domain family member 3 (YTHDF 3), or tyrosine-protein phosphatase non-receptor type 2 (PTPN2). Said chemical entities are useful, e.g., in treating cancer, enhancing immunotherapy outcome, or killing cancer stem cells. This disclosure also features compositions containing the same as well as methods of using and making the same.

Accordingly, in one aspect, provided herein are compounds of Formula (PT1)

Formula (PT1)

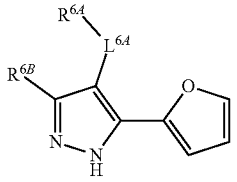

or a pharmaceutically acceptable salt thereof, wherein:

$L^{6A}$ is a bond or $C_{1-4}$ alkylene;

$R^{6A}$ is selected from the group consisting of: $C_{6-10}$ aryl and 5-10 membered heteroaryl, each optionally substituted with from 1-4 $R^{a6}$;

$R^{6B}$ is selected from the group consisting of: $C_{6-10}$ aryl and 5-10 membered heteroaryl, each optionally substituted with from 1-4 $R^{b6}$;

each occurrence of $R^{a6}$ and $R^{b6}$ is independently selected from the group consisting of: halo; cyano; $C_{1-6}$ alkyl; $C_{1-6}$ haloalkyl; $C_{1-6}$ alkoxy; $C_{1-6}$ haloalkoxy; $C_{1-6}$ thioalkoxy; $C(=O)C_{1-6}$ alkyl; $C(=O)OC_{1-6}$ alkyl; C(O)NR'R"; $S(O)_2C_{1-6}$ alkyl; $S(O)_2NR'R"$; —OH; NR'R"; and $NO_2$; and each occurrence of R' and R" is independently H, $C_{1-3}$ alkyl, or $C_{3-6}$ cycloalkyl.

Compounds of Formula (PT1) are useful e.g., as small molecule inhibitors of PTPN2. Non-limiting examples of Formula (PT1) compounds include the compounds in Table 1000.

Also provided herein are compounds of Formula (Y1):

Formula (Y1)

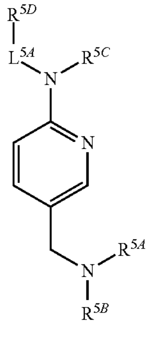

or a pharmaceutically acceptable salt thereof, wherein:

$R^{5A}$ and $R^{5B}$ are independently selected from the group consisting of: H, $C_{1-6}$ alkyl, and $C_{3-6}$ cycloalkyl, wherein the $C_{1-6}$ alkyl and $C_{3-6}$ alkyl are optionally substituted with from 1-4 $R^{a5}$;

$R^{5C}$ is H or $C_{1-6}$ alkyl;

$L^{5A}$ is a bond or $C_{1-6}$ alkylene;

$R^{5D}$ is selected from the group consisting of: $C_{6-10}$ aryl and 5-10 membered, each optionally substituted with from 1-4 $R^{b5}$;

each occurrence of $R^{a5}$ and $R^{b5}$ is independently selected from the group consisting of: a hydrogen bond acceptor group; halo; cyano; $C_{1-6}$ alkyl; $C_{1-6}$ haloalkyl; $C_{1-6}$ alkoxy; $C_{1-6}$ haloalkoxy; $C_{1-6}$ thioalkoxy; $C_{1-6}$ thiohaloalkoxy; $C({=}O)C_{1-6}$ alkyl; $C({=}O)OC_{1-6}$ alkyl; C(O)NR'R"; $S(O)_2C_{1-6}$ alkyl; $S(O)_2NR'R"$; —OH; NR'R"; $NR'C({=}O)C_{1-6}$ alkyl; $NR'C({=}O)OC_{1-6}$ alkyl; NR'C(═O)NR'R"; and $NO_2$; and each occurrence of R' and R" is independently H, $C_{1-3}$ alkyl, or $C_{3-6}$ cycloalkyl.

Compounds of Formula (Y1) are useful e.g., as inhibitors of YTH domain-containing family proteins (YTHs). Non-limiting examples of Formula (Y1) compounds include the compounds in Table 400.

Also provided herein are compounds of Formula (Y2):

Formula (Y2)

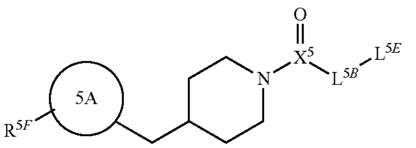

or a pharmaceutically acceptable salt thereof, wherein:

$R^{5F}$ is selected from the group consisting of: $R^{c5}$ and $R^{d5}$;

Ring 5A is a 5-membered heteroarylene optionally substituted with from 1-2 $R^{c5}$;

$X^5$ is C, S, or S(═O);

$L^{5B}$ is a bond or $CH_2$;

$R^{5E}$ is NR'R", or $R^{5E}$ is selected from the group consisting of: $C_{1-6}$ alkyl; $C_{1-6}$ haloalkyl; $C_{6-10}$ aryl; 5-10 membered heteroaryl; $C_{3-12}$ cycloalkyl; and 4-10 membered heterocyclyl, each of which is optionally substituted with from 1-4 $R^{e5}$;

each occurrence of $R^{c5}$ and $R^{e5}$ is independently selected from the group consisting of: halo; cyano; $C_{1-6}$ alkyl; $C_{1-6}$ haloalkyl; $C_{1-6}$ alkoxy; $C_{1-6}$ haloalkoxy; $C_{1-6}$ thioalkoxy; $C({=}O)C_{1-6}$ alkyl; $C({=}O)OC_{1-6}$ alkyl; C(O)NR'R"; $S(O)_2C_{1-6}$ alkyl; $S(O)_2NR'R"$; —OH; NR'R"; $NR'C({=}O)C_{1-6}$ alkyl; $NR'C({=}O)OC_{1-6}$ alkyl; NR'C(═O)NR'R"; and $NO_2$;

$R^{d5}$ is selected from the group consisting of: $C_{6-10}$ aryl; 5-10 membered heteroaryl; $C_{3-12}$ cycloalkyl; and 4-10 membered heterocyclyl, each of which is optionally substituted with from 1-4 $R^{e5}$; and each occurrence of R' and R" is independently H, $C_{1-3}$ alkyl, or $C_{3-6}$ cycloalkyl.

Compounds of Formula (Y2) are useful e.g., as inhibitors of YTH domain-containing family proteins (YTHs). Non-limiting examples of Formula (Y2) compounds include the compounds in Table 600.

Also provided herein are compounds in Table 500, which are useful e.g., as inhibitors of YTH domain-containing family proteins (YTHs).

Also provided herein are compounds of Formula (F1A) or (F1B):

Formula (F1A)

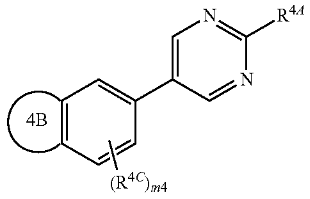

Formula (F1B)

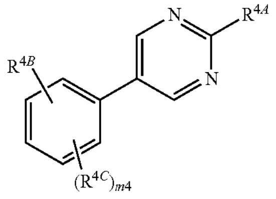

or a pharmaceutically acceptable salt thereof, wherein:

$R^{4A}$ is selected from the group consisting of: H, $C_{1-6}$ alkoxy, $C_{1-6}$ haloalkoxy, NR'R", and $NR'—(CH_2)_{n4}—R^{4D}$;

n4 is 2, 3, or 4;

$R^{4D}$ is $C_{1-6}$ alkoxy, $C_{1-6}$ haloalkoxy, —OH, or NR'R";

m4 is 0, 1, or 2;

$R^{4C}$ is selected from the group consisting of: halo; cyano; $C_{1-6}$ alkoxy; $C_{1-6}$ haloalkoxy; $C_{1-6}$ alkyl; $C_{1-6}$ haloalkyl; —OH; and NR'R";

Ring 4B is phenyl or 5-6 membered heteroaryl each optionally substituted with from 1-3 substituents independently selected from the group consisting of: halo; cyano; $C_{1-6}$ alkoxy; $C_{1-6}$ haloalkoxy; $C_{1-6}$ alkyl; $C_{1-6}$ haloalkyl; —OH; and NR'R";

$R^{4B}$ is selected from the group consisting of:

$-(L^{4A})_{p4}-R^{4E}$; and $C_{1-6}$ alkyl which is optionally substituted with from 1-3 substituents independently selected from the group consisting of: halo; cyano; $C_{1-6}$ alkoxy; $C_{1-6}$ haloalkoxy; $C_{1-6}$ alkyl; $C_{1-6}$ haloalkyl; —OH; and NR'R";

p4 is 0, 1, 2, or 3;

each $L^{4A}$ is independently selected from the group consisting of: —O—, —$CH_2$—, —C(═O)—, —N(R')—, and —$S(O)_{0-2}$—;

$R^{4E}$ is selected from the group consisting of $C_{6-10}$ aryl, 5-10 membered heteroaryl, $C_{3-10}$ cycloalkyl, and 4-10 membered heterocyclyl, each optionally substituted with from 1-3 substituents independently selected from the group consisting of: halo; cyano; $C_{1-6}$ alkoxy; $C_{1-6}$ haloalkoxy; $C_{1-6}$ alkyl; $C_{1-6}$ haloalkyl; —OH; and NR'R"; and each occurrence of R' and R" is independently H, $C_{1-3}$ alkyl, or $C_{3-6}$ cycloalkyl.

Compounds of Formula (F1A) and (F1B) are useful e.g., as inhibitors of fat-mass and obesity-associated protein (FTO). Non-limiting examples of Formula (F1A) and (F1B) compounds include the compounds in Table 100.

Also provided herein are compounds of Formula (F2):

Formula (F2)

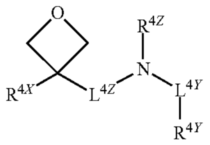

or a pharmaceutically acceptable salt thereof, wherein:

$R^{4X}$ is phenyl, $C_{3-6}$ cycloalkyl, 5-6 membered heterocyclyl, or 5-6 membered heteroaryl, each of which is optionally substituted with from 1-3 substituents independently selected from the group consisting of: halo; cyano; $C_{1-6}$ alkoxy; $C_{1-6}$ haloalkoxy; $C_{1-6}$ alkyl; $C_{1-6}$ haloalkyl; —OH; and NR'R";

$L^{4Z}$ is $C_{1-3}$ alkylene;

$R^{4Z}$ is H or $-L^{4Y}-R^{4Y}$;

each $L^{4Y}$ is independently a bond or $C_{1-3}$ alkylene;

each $R^{4Y}$ is independently selected from the group consisting of $C_{6-10}$ aryl, 5-10 membered heteroaryl, and 7-10 membered fused heterocyloalkyl-aryl, each of which is optionally substituted with from 1-3 substituents independently selected from the group consisting of: $R^{a4}$, $R^{b4}$, and $-(L^{b4})_{b4}-R^{b4}$;

each occurrence of $R^{a4}$ is selected from the group consisting of: independently selected from the group consisting of: halo; cyano; $C_{1-6}$ alkoxy; $C_{1-6}$ haloalkoxy; $C_{1-6}$ alkyl; hydroxy-$C_{1-6}$ alkyl; $C_{1-6}$ haloalkyl; $C_{1-6}$ thioalkoxy; $C_{1-6}$ thiohaloalkoxy; —OH; $NO_2$; and NR'R";

b4 is 1, 2, or 3;

each $L^{b4}$ is independently selected from the group consisting of: —O—, —$CH_2$—, —C(=O)—, —N(R')—, and —$S(O)_{0-2}$—;

each $R^{b4}$ is independently selected from the group consisting of $C_{6-10}$ aryl, 5-10 membered heteroaryl, $C_{3-10}$ cycloalkyl, and 4-10 membered heterocyclyl, each optionally substituted with from 1-3 substituents independently selected from the group consisting of: halo; cyano; $C_{1-6}$ alkoxy; $C_{1-6}$ haloalkoxy; $C_{1-6}$ alkyl; $C_{1-6}$ haloalkyl; —OH; and NR'R"; and each occurrence of R' and R" is independently H, $C_{1-3}$ alkyl, or $C_{3-6}$ cycloalkyl.

Compounds of Formula (F2) are useful e.g., as inhibitors of fat-mass and obesity-associated protein (FTO). Non-limiting examples of Formula (F2) compounds include the compounds in Table 200.

Also provided herein are compounds of Formula (F3):

Formula (F3)

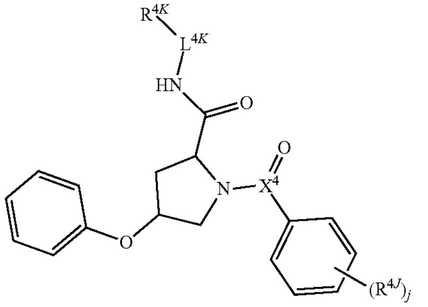

or a pharmaceutically acceptable salt thereof, wherein:

$L^{4K}$ is a bond or $CH_2$;

$R^{4K}$ is selected from the group consisting of: $C_{6-10}$ aryl and 5-10 membered heteroaryl, each optionally substituted with from 1-4 $R^{4L}$;

$X^4$ is C, S, or S(O);

j is 0, 1, 2, or 3;

each occurrence $R^{4J}$ and $R^{4L}$ is independently selected from the group consisting of: halo; cyano; $C_{1-6}$ alkyl; $C_{1-6}$ haloalkyl; $C_{1-6}$ alkoxy; $C_{1-6}$ haloalkoxy; $C_{1-6}$ thioalkoxy; $C_{1-6}$ thiohaloalkoxy; C(=O)$C_{1-6}$ alkyl; C(=O)O$C_{1-6}$ alkyl; C(O)NR'R"; $S(O)_2C_{1-6}$ alkyl; $S(O)_2$NR'R"; —OH; NR'R"; and $NO_2$; and each occurrence of R' and R" is independently H, $C_{1-3}$ alkyl, or $C_{3-6}$ cycloalkyl.

Compounds of Formula (F3) are useful e.g., as inhibitors of fat-mass and obesity-associated protein (FTO). Non-limiting examples of Formula (F3) compounds include the compounds in Table 300.

Also provided herein are compounds of Formula (A1):

Formula (A1)

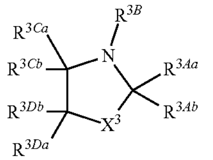

or a pharmaceutically acceptable salt thereof, wherein:

$X^3$ is selected from the group consisting of: O, S, and $S(O)_{1-2}$;

$R^{3Aa}$ and $R^{3Ab}$ are independently H, $C_{1-6}$ alkyl, C(=O)OH, C(=O)O$C_{1-6}$ alkyl, C(=O)NR'R", 4-10 membered heterocyclyl, $C_{6-10}$ aryl, $C_{3-10}$ cycloalkyl, and 5-10 membered heteroaryl, wherein the 4-10 membered heterocyclyl, $C_{6-10}$ aryl, $C_{3-10}$ cycloalkyl, and 5-10 membered heteroaryl are each optionally substituted with from 1-4 $R^{a3}$; or $R^{3Aa}$ and $R^{3Ab}$ combine to form =O;

$R^{3B}$ is selected from the group consisting of: H; C(=O)NR'R"; C(=O)O$C_{1-6}$ alkyl;

or $R^{3Aa}$ and $R^{3B}$ taken together with the ring atoms connecting them form a fused ring including from 4-6 ring atoms, wherein the fused ring is optionally substituted with from 1-4 substituents independently selected from the group consisting of: =O and $R^{a3}$;

$R^{3Ca}$, $R^{3Cb}$, $R^{3Da}$, and $R^{3Db}$ are each independently selected from the group consisting of: C(=O)OH; C(=O)$C_{1-6}$ alkyl; C(=O)NR'R"; $C_{1-6}$ alkyl optionally substituted with from 1-4 $R^{a3}$; and $-L^{3E}-R^{3E}$;

each $L^{3E}$ is independently a bond or $CH_2$;

each $R^{3E}$ is independently selected from the group consisting of: 4-10 membered heterocyclyl, $C_{6-10}$ aryl, $C_{3-10}$ cycloalkyl, and 5-10 membered heteroaryl, each optionally substituted with from 1-4 $R^{a3}$;

each occurrence of $R^{a3}$ is independently selected from the group consisting of: halo; cyano; $C_{1-6}$ alkyl; $C_{1-6}$ haloalkyl; $C_{6-10}$ aryl optionally substituted with $C_{1-3}$ alkyl and/or halo; $C_{1-6}$ alkoxy; $C_{1-6}$ haloalkoxy; $C_{1-6}$ thioalkoxy; $C_{1-6}$ thiohaloalkoxy; C(=O)$C_{1-6}$ alkyl; C(=O)O$C_{1-6}$ alkyl; C(=O)OH; C(O)NR'R"; $S(O)_2C_{1-6}$ alkyl; $S(O)_2$NR'R"; —OH; NR'R"; and $NO_2$; and each occurrence of R' and R" is independently H, $C_{1-3}$ alkyl, or $C_{3-6}$ cycloalkyl.

Compounds of Formula (A1) are useful e.g., as inhibitors of ALKB homolog 5 (ALKBH5). Non-limiting examples of Formula (A1) compounds include the compounds in Table 700.

Also provided herein are compounds of Formula (A2A), (A2B), or (A2C):

Formula (A2A)

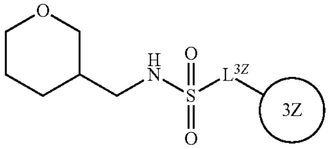

Formula (A2B)

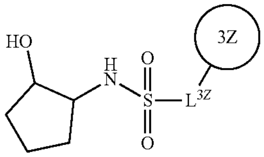

Formula (A2C)

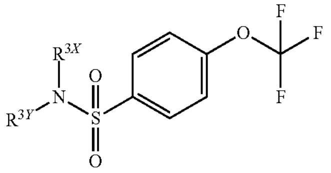

or a pharmaceutically acceptable salt thereof, wherein:

Ring 3Z is selected from the group consisting of: $C_{6-10}$ aryl; 5-10 membered heteroaryl; $C_{3-10}$ cycloalkyl; and 4-10 membered heterocyclyl, each optionally substituted with from 1-4 $R^{b3}$;

$R^{3X}$ is H or $C_{1-6}$ alkyl;

$R^{3Y}$ is $-L^{3W}-R^{3W}$;

$-L^{3W}$ and $-L^{3Z}$ are each independently a bond or $C_{1-4}$ alkylene optionally substituted with from 1-4 $R^{b3}$;

$R^{3W}$ is selected from the group consisting of: $C_{6-10}$ aryl; 5-10 membered heteroaryl; $C_{3-10}$ cycloalkyl; and 4-10 membered heterocyclyl, each optionally substituted with from 1-4 $R^{b3}$, or $R^{3W}$ is

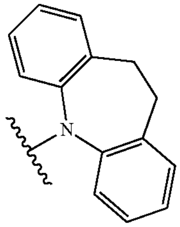 [SMILES: *N1c2ccccc2CCc2ccccc21]

optionally substituted with from 1-4 $R^{b3}$; or $R^{3X}$ and $R^{3Y}$ taken together with the nitrogen to which each is attached forms a 5-8 membered heterocyclyl optionally substituted with from 1-4 $R^{b3}$;

each occurrence of $R^{b3}$ is independently selected from the group consisting of: halo; cyano; $C_{1-6}$ alkyl; $C_{1-6}$ haloalkyl; $C_{6-10}$ aryl optionally substituted with $C_{1-3}$ alkyl and/or halo; $C_{1-6}$ alkoxy; $C_{1-6}$ haloalkoxy; $C_{1-6}$ thioalkoxy; $C_{1-6}$ thiohaloalkoxy; $C(=O)C_{1-6}$ alkyl; $C(=O)C_{3-6}$ cycloalkyl; $OC(=O)C_{1-6}$ alkyl; $C(=O)OC_{1-6}$ alkyl; $C(=O)OH$; C(O)NR'R"; $S(O)_2C_{1-6}$ alkyl; $S(O)_2NR'R"$; —OH; oxo; NR'R"; $NO_2$; $C_{3-6}$ cycloalkyl; and 4-8 membered heterocyclyl; and each occurrence of R' and R" is independently H, $C_{1-3}$ alkyl, or $C_{3-6}$ cycloalkyl.

Compounds of Formula (A2A), (A2B), or (A2C) are useful e.g., as inhibitors of ALKB homolog 5 (ALKBH5). Non-limiting examples of Formula (A2A), (A2B), or (A2C) compounds include the compounds in Table 800.

Also provided herein are compounds of Formula (A3):

Formula (A3)

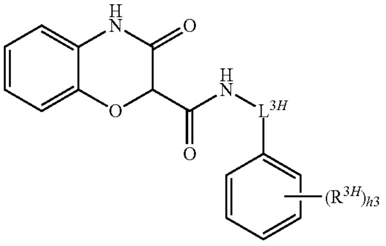

or a pharmaceutically acceptable salt thereof, wherein:

$L^{3H}$ is a bond or $CH_2$;

h3 is 0, 1, 2, or 3;

each occurrence $R^{3H}$ is independently selected from the group consisting of: halo; cyano; $C_{1-6}$ alkyl; $C_{1-6}$ haloalkyl; $C_{6-10}$ aryl optionally substituted with $C_{1-3}$ alkyl and/or halo; $C_{1-6}$ alkoxy; $C_{1-6}$ haloalkoxy; $C_{1-6}$ thioalkoxy; $C_{1-6}$ thiohaloalkoxy; $C(=O)C_{1-6}$ alkyl; $C(=O)C_{3-6}$ cycloalkyl; $OC(=O)C_{1-6}$ alkyl; $C(=O)OC_{1-6}$ alkyl; $C(=O)OH$; C(O)NR'R"; $S(O)_2C_{1-6}$ alkyl; $S(O)_2NR'R"$; —OH; NR'R"; $NO_2$; $C_{3-6}$ cycloalkyl; and 4-8 membered heterocyclyl; and each occurrence of R' and R" is independently H, $C_{1-3}$ alkyl, or $C_{3-6}$ cycloalkyl.

Compounds of Formula (A3) are useful e.g., as inhibitors of ALKB homolog 5 (ALKBH5). In some embodiments of Formula (A3), the compound is selected from the group consisting of the compounds in Table 900, or a pharmaceutically acceptable salt thereof.

Also provided herein are compounds of Formula (M1):

Formula (M1)

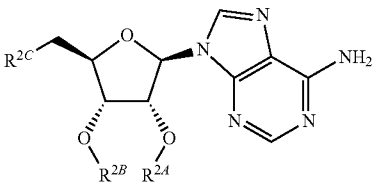

or a pharmaceutically acceptable salt thereof, wherein:

$R^{2A}$ and $R^{2B}$ are each independently H or $C_{1-3}$ alkyl; or $R^{2A}$ and $R^{2B}$ taken together with the atoms connecting them form a 5-8 membered ring which is optionally substituted with from 1-3 $C_{1-3}$ alkyl;

$R^{2C}$ is $—N(R^{2E})-L^{2C}-R^{2D}$ or -(5-6 heteroarylene)-$L^{2C}$-$R^{2D}$;

$R^{2E}$ is H or $-L^{2C}-R^{2D}$;

each $L^2c$ is independently $C_{1-3}$ alkylene; and each $R^{2D}$ is independently selected from the group consisting of:

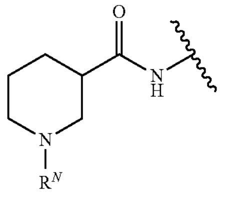

and

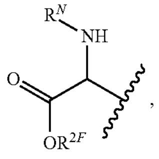

wherein each $R^N$ is independently H, $C_{1-6}$ alkyl, C(=O)$OC_{1-6}$ alkyl, or C(=O)$C_{1-6}$ alkyl, and $R^{2F}$ is H or $C_{1-6}$ alkyl.

Compounds of Formula (M1) are useful e.g., as inhibitors of methyltransferase like 3 (Mettl3 or MT-A70) or methyltransferase like-14 (Mettl14). In some embodiments of Formula (M1), the compound is selected from the group consisting of the compounds in Table 1200.

Also provided herein are compounds of Formula (M2):

Formula (M2)

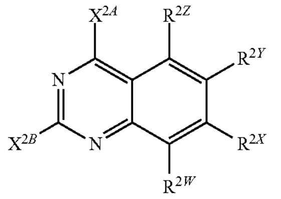

or a pharmaceutically acceptable salt thereof, wherein:

each $R^{2Z}$, $R^{2Y}$, $R^{2X}$, and $R^{2W}$ are independently selected from the group consisting of: H, halo, cyano, $C_{1-6}$ alkyl, $C_{1-6}$ haloalkyl, $C_{1-6}$ alkoxy, $C_{1-6}$ haloalkoxy, OH, and NR'R";

$X^{2A}$ is independently selected from the group consisting of: $NH_2$, NH($C_{1-10}$ alkyl), N($C_{1-10}$ alkyl)$_2$,

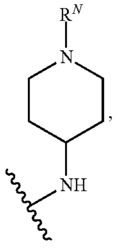

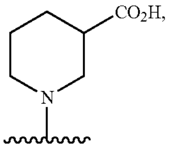

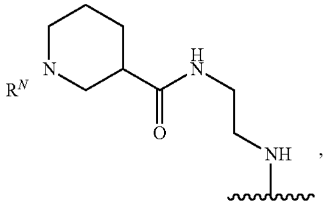

, and

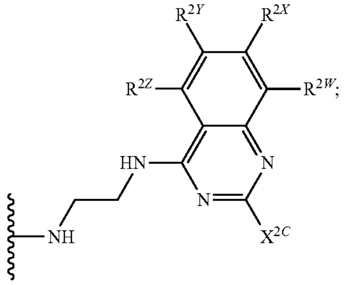

$X^{2B}$ and $X^{2C}$ are independently selected from the group consisting of: halo, $NH_2$, NH($C_{1-10}$ alkyl), N($C_{1-10}$ alkyl)$_2$,

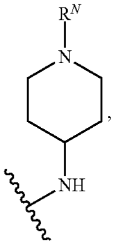

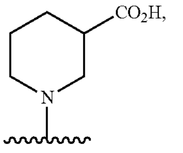

and

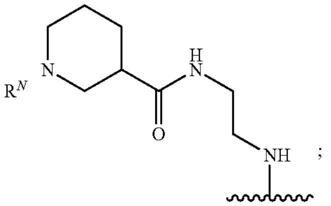

;

each $R^N$ is independently H, $C_{1-6}$ alkyl, C(=O)$OC_{1-6}$ alkyl, or C(=O)$C_{1-6}$ alkyl; and each occurrence of R' and R" is independently H or $C_{1-6}$ alkyl.

Compounds of Formula (M2) are useful e.g., as inhibitors of methyltransferase like 3 (Mettl3 or MT-A70) or methyltransferase like-14 (Mettl14). In some embodiments of Formula (M2), the compound is selected from the group consisting of the compounds in Table 1310, or a pharmaceutically acceptable salt thereof.

Also provided herein provided herein are compounds selected from the group consisting of the compounds in Table 1100, or a pharmaceutically acceptable salt thereof. Compounds of Table 1100 are useful e.g., as inhibitors of methyltransferase like 3 (Mettl3 or MT-A70) or methyltransferase like-14 (Mettl14).

Also provided herein are pharmaceutical compositions comprising:

(i) an inhibitor, wherein the inhibitor inhibits one or more of methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), or tyrosine-protein phosphatase non-receptor type 2 (PTPN2); and (ii) a pharmaceutically acceptable carrier.

In some embodiments, the inhibitor inhibits (e.g., selectively inhibits) a target selected from the group consisting of: methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), and tyrosine-protein phosphatase non-receptor type 2 (PTPN2).

Also provided herein are methods of treating a subject in need thereof, the method comprising:

administering to the subject a therapeutically effective amount of an inhibitor, wherein the inhibitor inhibits one or more of methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), or tyrosine-protein phosphatase non-receptor type 2 (PTPN2).

In some embodiments, the inhibitor inhibits (e.g., selectively inhibits) a target selected from the group consisting of: methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), and tyrosine-protein phosphatase non-receptor type 2 (PTPN2).

Also provided herein are methods of enhancing immunotherapy outcomes in a subject in need thereof, the method comprising:

administering to the subject an inhibitor, wherein the inhibitor inhibits one or more of methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), or tyrosine-protein phosphatase non-receptor type 2 (PTPN2).

In some embodiments, the inhibitor inhibits (e.g., selectively inhibits) a target selected from the group consisting of: methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), and tyrosine-protein phosphatase non-receptor type 2 (PTPN2).

Also provided herein are methods of treating cancer in a subject in need thereof, the method comprising: co-administering to the subject:

(i) a therapeutically effective amount of an inhibitor, wherein the inhibitor inhibits one or more of methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), or tyrosine-protein phosphatase non-receptor type 2 (PTPN2); and (ii) an immunotherapy (e.g., an immunotherapy selected from the group consisting of an immune checkpoint inhibitor, an oncolytic virus therapy, a cell-based therapy, and a cancer vaccine).

In some embodiments, the inhibitor inhibits (e.g., selectively inhibits) a target selected from the group consisting of: methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), and tyrosine-protein phosphatase non-receptor type 2 (PTPN2).

Also provided herein are methods of killing cancer stem cells in a subject in need thereof, the method comprising:

administering to the subject an inhibitor, wherein the inhibitor inhibits one or more of methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), or tyrosine-protein phosphatase non-receptor type 2 (PTPN2).

In some embodiments, the inhibitor inhibits (e.g., selectively inhibits) a target selected from the group consisting of: methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), and tyrosine-protein phosphatase non-receptor type 2 (PTPN2).

The inhibitor in the foregoing compositions and/or methods can include any of the chemical entities described herein. In some embodiments, the inhibitor is a compound selected from the group consisting of a compound of Formula (PT1) (e.g., a compound of Table 1000), a compound of Formula (Y1) (e.g., a compound of Table 400), a compound of Formula (Y2) (e.g., a compound of Table 600), a compound of Table 500, a compound of Formula (F1A) or (F1B) (e.g., a compound of Table 100), a compound of Formula (F2) (e.g., a compound of Table 200), a compound of Formula (F3) (e.g., a compound of Table 300), a compound of Formula (A1) (e.g., a compound of Table 700), a compound of Formula (A2A), (A2B), or (A2C) (e.g., a compound of Table 800), a compound of Formula (A3) (e.g., a compound of Table 900), a compound of Table 1100, a compound of Formula M1 (e.g., a compound of Table 1200), and a compound of Formula M2 (e.g., a compound of Table 1310), or a pharmaceutically acceptable salt thereof. In some embodiments, the inhibitor is a polynucleotide described in FIG. 119 or 120.

BRIEF DESCRIPTION OF THE DRAWINGS

(FIG. 13C) Generation or Flo knockout B16 melanoma cells using lentivirus 1B16 cells were infected with lentivirus of 4 sgs/gene and selected with puromycin for at least 72 hrs, Western blots were used to determine the CRISPR-Cas9 knockout editing efficiency.

(FIG. 14A) Tumor growth of C57Bl_/6J mice inoculated with B16-NTC control (11-9) or B16-Alkbh5 KO cells (11-8), and treated with GVAX vaccine cells and PI)I antibody. All the mice were survived after 12 days of tumor cells implantation and treatments. (FIG. 14B) Tumor growth OfCS7BL/6J mice inoculated with B16-NIC control (n-9) or Fto KO cells (11-6), and treated with CiVtVX vaccine cells and PI)I antibody All the mice were survived after 12 days of tumor cells implantation and treatments (FIG. 14C) Tumor growth of individual mouse implanted with NTC control B16 cells (n-9) and treated with G VAX vaccine cells and PI) I antibody until day IS after tumor cell injection. (FIG. 14D) Tumor growth of individual mouse implanted with Alkbh5 B16 cells (n-8) and treated with G VAX vaccine cells and PI) I antibody until day 15 after tumor cell injection. (FIG. 14E) Tumor growth of individual mouse implanted with Fto B16 cells (11-6) and treated with GVAX vaccine cells and PDI antibody until day 15 after tumor cell injection. (FIG. 14F) Tumor growth Of C 57B136J female mice subcutaneously injected with O SXI 06B 16-FTO melanoma stable cells transduced with N TC sgRNAs, Alkbh5 sgRNAs. or Fto sgRNAs at day 0 without any treatment Methods: C57BW6J female mice at the age of 9-12 weeks were subcutaneously injected with O, 5×106 B 16-FTO melanoma stable cells transduced with NTC sgRNAs, Alkbhs sgRNAs, or Fto sgRNAs at day Each mouse was then treated with GVAX cells expressing GM-CSF at day 1 and day 4 on the opposite flank to the site of tumor inoculatiorv PD-1 Ab were intraperitoneal (i r) administrated to each mouse at the dose of 200 μg/mouse either twice or three times at day 6, 9, 12. Tumor volume was estimated using the formula: (L/2. Death was defined when a growing tumor reached 2.0 cm in the longest dimension.

(FIG. 15B) Quantification of CD,IS+, CD8+, CD4+, NK cells, Treg cells and GZMB+CD4+ or GZMB+CD8+ immune cells in NTC, Alkbh5 KO or Fto KO mouse B 16 tumors after GVAX and PDI antibody combined therapy.

(FIG. 16A) m6A levels of total RNA obtained from mouse B 16 tumors with or without immunotherapy. (FIG. 16B) m6A levels of total RNA from NTC, AlkbhS KO or Fto KO mouse B 16 tumors after GVAX and PDI antibody combined therapy.

FIG. 27A. X-ray crystal structure of human FTO in complex with meclofenamic acid (MA) (PDB ID: 4QKN). The docking site for in silico screening is shown in green spheres.

FIG. 27B. Surface representation of human FTO in complex with MA in green (PDB ID: 4QKN).

FIG. 27C. Predicted binding pose of FTO-02 at the MA binding site. A water mediated hydrogen bond is expected between the pyrimidine ring of FTO-02 and the backbone of Glu 234. A π-π stacking interaction is observed with His 231. FIG. 27D. Predicted binding pose of FTO-18 at the 2 MA binding site Of FTC). A benzene ring Of FTO- 18 is observed to form 71-71 stacking interactions with His 231 and Tyr 108, and the pyrimidine ring of FTO-18 is expected to form a hydrogen bond to Arg 322. Tyr 295 and Arg 316 are predicted to form a bifurcated hydrogen bond to the alcohol group of FTO-18.

FIG. 28A. Synthesis of FTO inhibitors by Suzuki coupling. FIG. 28B. Sigmoidal dose-response curves for F TO-02. Inhibition against FTO is shown in blue and inhibition of ALKBH5 is shown in red. FIG. 28C. Sigmoidal dose- response curves for FTO-04. Inhibition against FTO is shown in blue and inhibition of ALKBH5 is shown in red. FIG. 28D. Sigmoidal dose-response curves for FTO-12. Inhibition against FTO is shown in blue and inhibition of ALKBH5 is shown in red. FIG. 28E. Double reciprocal plot for FTO-02. FTO-02 inhibits FTO by a competitive mechanism. FIG. 28F. Double reciprocal plot for FTO-04. FTO-04 inhibits FTO by a competitive mechanism.

FIGS. 29A and 29B. Size of neurosphere and tumorospheres as quantified by ImageJ. Box and whisker plots show 10-90 percentile. N neurospheres per group. p<0.01, **p<0.0001, by Student's t test. FIG. 29C. Bright field images of neurosphere and tumorospheres after 2 days treatment with FTO-04 inhibitor to normal human neural stem cells (hNSC), and glioblastoma cell lines (TS576, GBM-GSC-23 and GBM-6). FIG. 29D. Size of neurosphere and tumorospheres as quantified by ImageJ. Box and whisker plots show 10-90 percentile. N>50 neurospheres per group. * *p<0.01, ****p<0.0001, by Student's t test.

FIG. 31A: Representative images of TS576 cells derived tumorosphere after lentivirus knocking down of F TO (shControl and shFTO). FIG. 31B: Tumorosphere size was quantified by ImageJ and the size distribution is shown in control and FTO KD group. Box and whisker plots show 10-90 percentile. N>50 neurospheres per group. **p<0.01 by Student's t test. FIG. 31C: qRT-PCR showing lentivirus KD efficiency of FTO in TS576. FIG. 31D: m6A dot blot assays using mRNA Of TS576 glioblastoma cells knockdown with shControl and shFTO lentivirus.

FIG. 60. Design and Synthesis of Compound Libraries: 3 Chemical Scaffolds.

FIG. 61. Selective Inhibitors of FTO.

FIG. 65. Docking pose of TR-FTO-11 N bound to FTO. Hydrogen bonds are observed with Ser 229 and Glu 234. The indole ring of TR-FTO-11 N is expected to form π-π stacking interactions with His 231. The fluorine atom on position 6 of the indole ring is within hydrogen bonding distance of Arg 96 and Arg 322 (2.25 and 2.51 Å, respectively).

FIG. 66. Oxetane Library of FTO Inhibitors

FIG. 68. FTO 3rd Generation Inhibitors.

FIG. 81. Analogs of TR-ALKBH5-29 and 34.

FIG. 83. Depiction of docking scores of various compounds.

FIG. 84. Depiction of enzymatic attributes of various compounds.

FIG. 86. Depiction of enzymatic attributes of various compounds.

FIG. 89. Rational Design of Sulfonamide Library of ALKBH5 Inhibitors

FIG. 90. Structures, enzymatic IC50s, and log D values for select sulfonamide inhibitors of ALKBH5

FIG. 105. Depiction of pharmacophore model for YTH inhibitors.

FIG. 107. Depiction of Ki and c log P of inhibitors.

FIG. 118. Depiction of other exemplary PTPN2 inhibitors.

FIG. 119 shows exemplary CRISPR-sgRNAs that can inhibit one or more of methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), or tyrosine-protein phosphatase non-receptor type 2 (PTPN2).

FIG. 120 shows exemplary polynucleotides that can inhibit one or more of methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), or tyrosine-protein phosphatase non-receptor type 2 (PTPN2).

Figure 124:
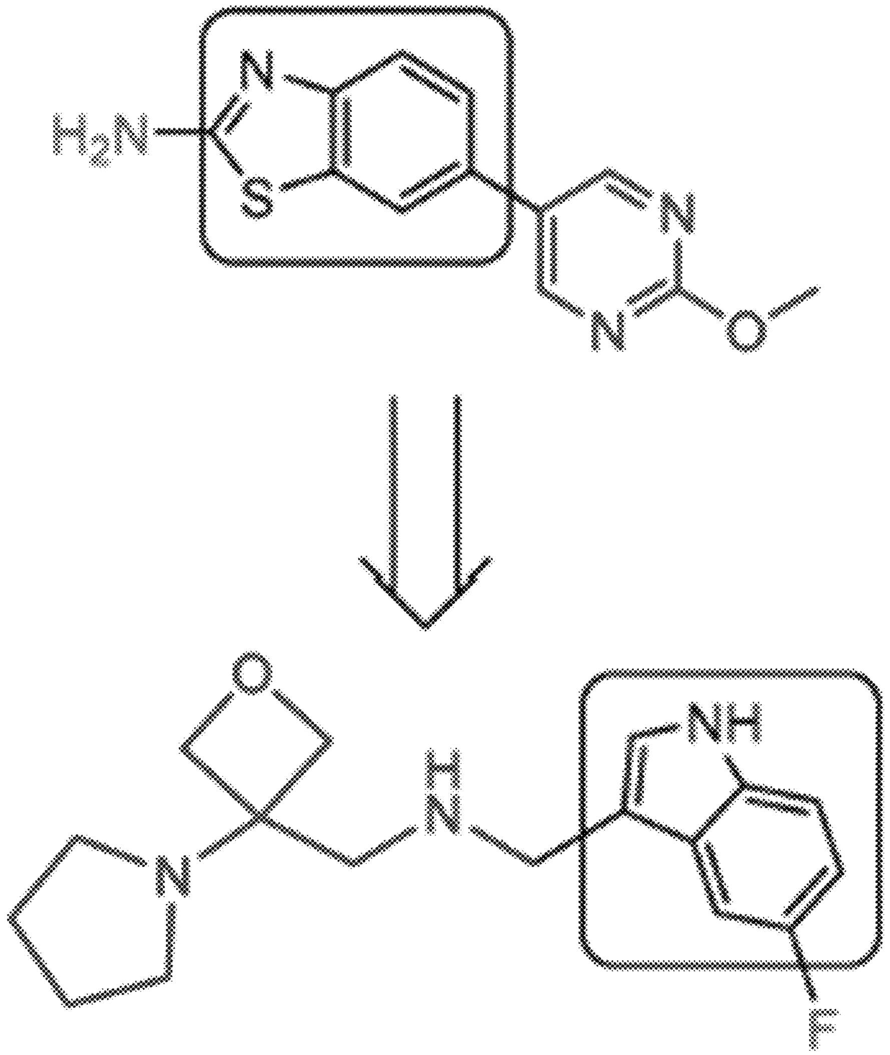
Figure 124:
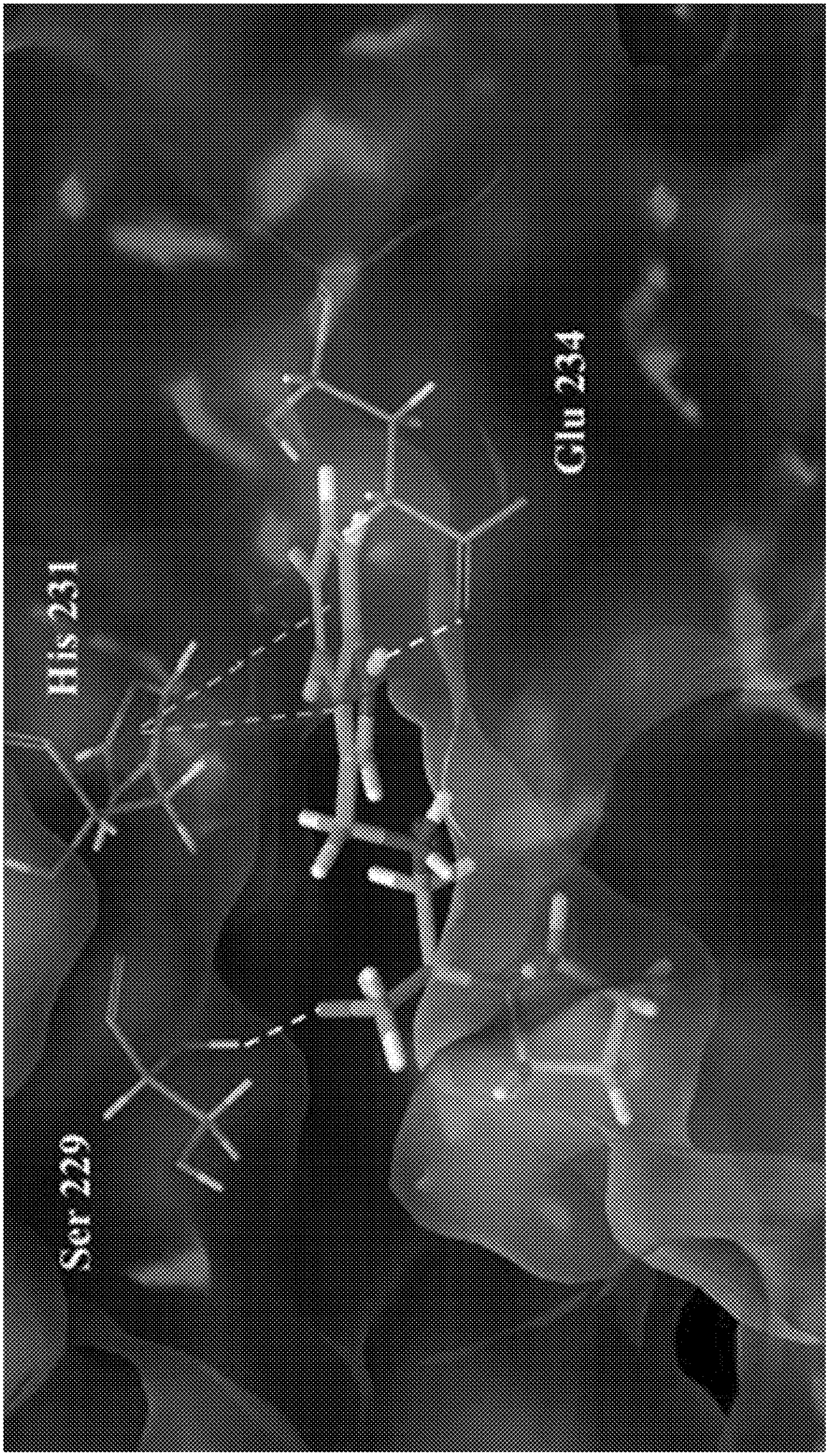

FIG. 124. Depiction of structure-based design of oxetane library.

Figure 125:
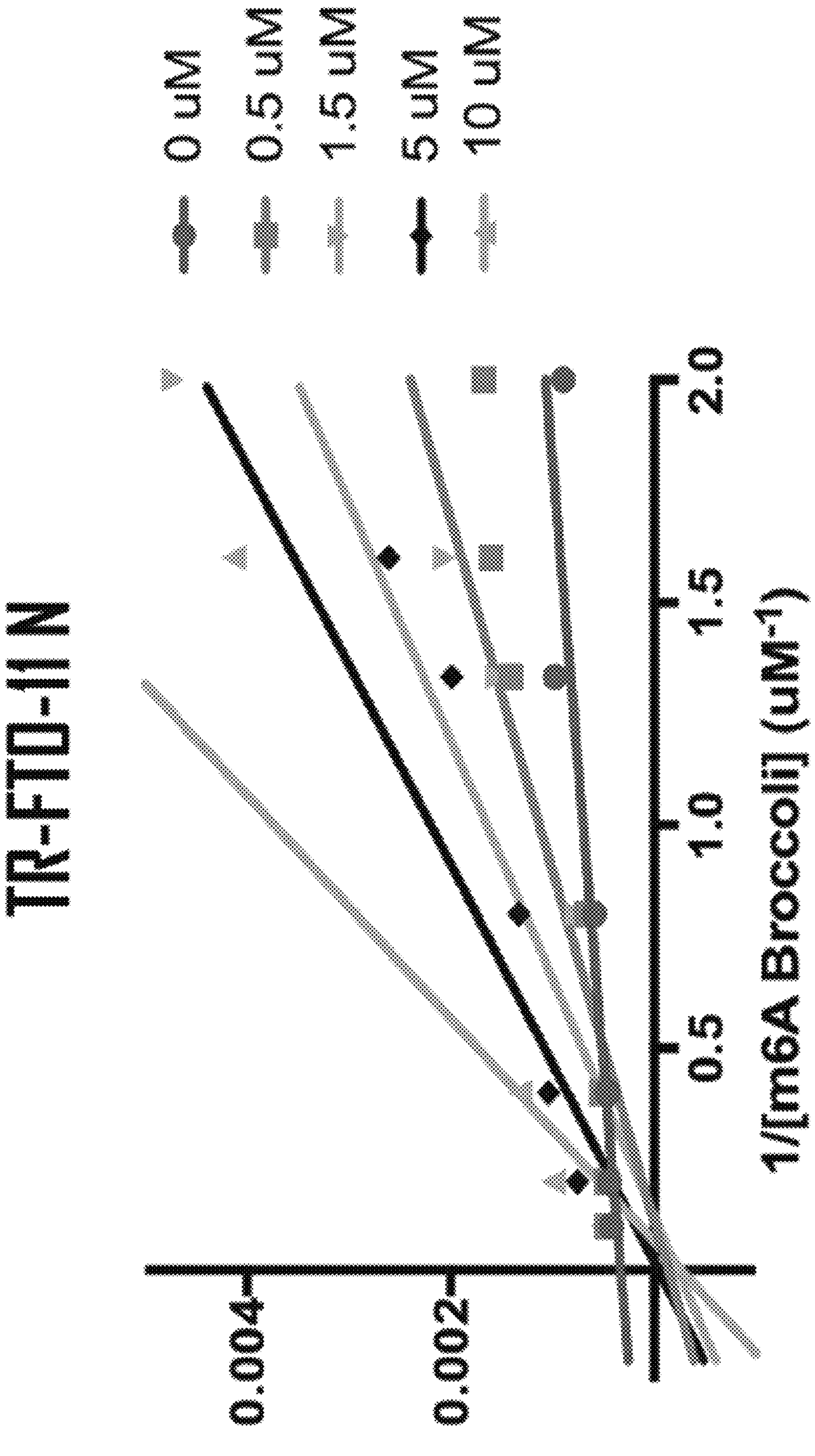
Figure 125:
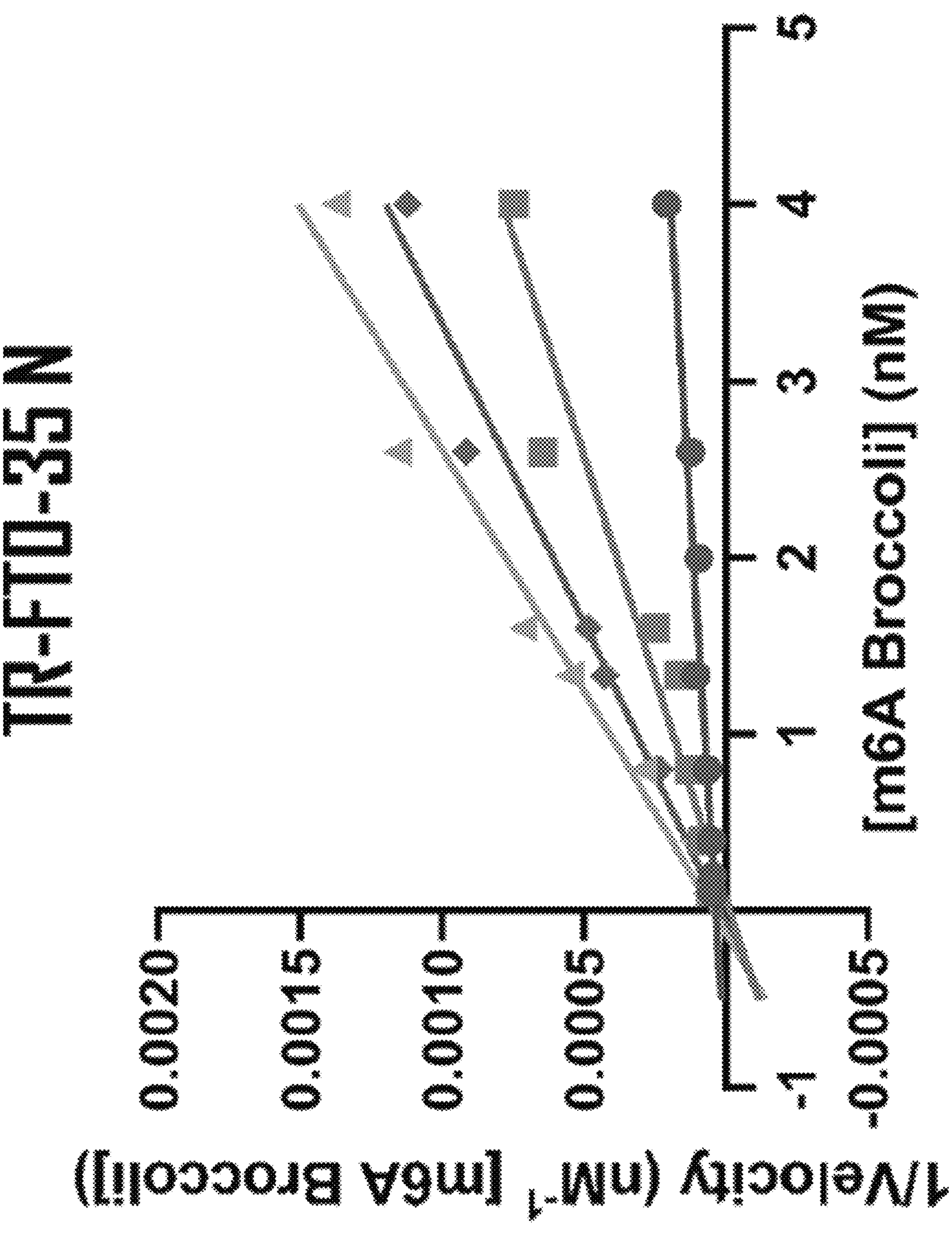
Figure 125:
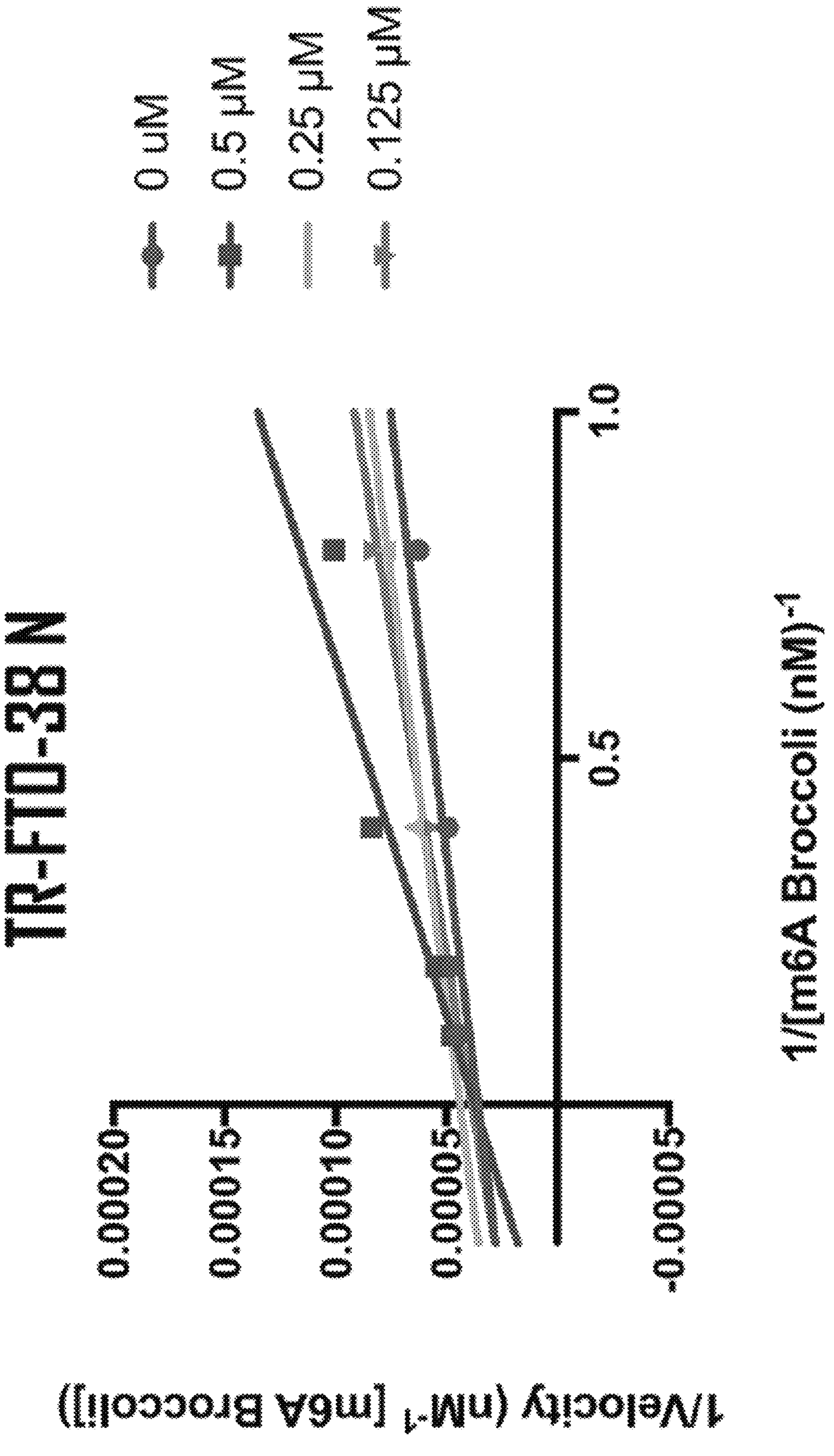
Figure 125:
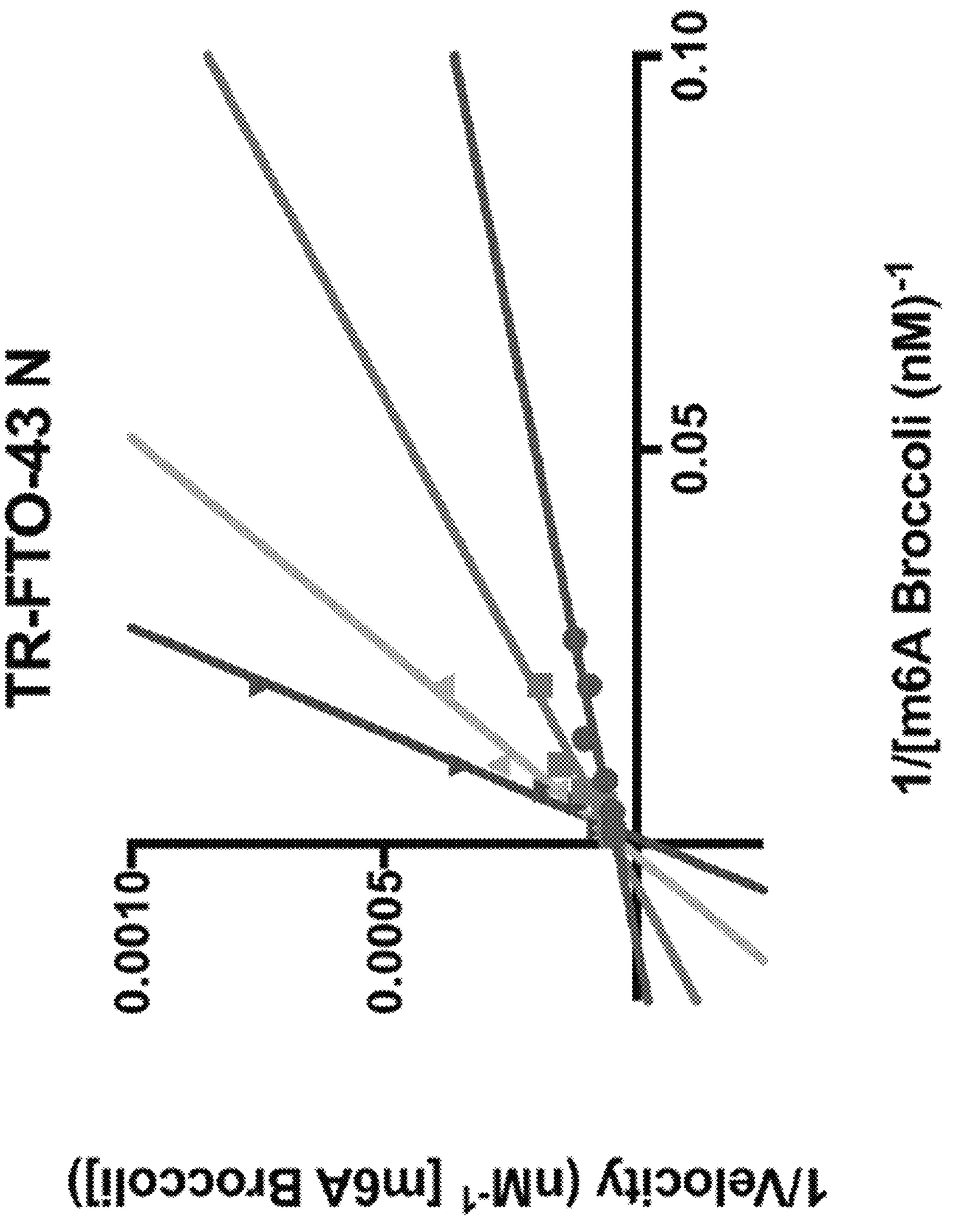
Figure 125:
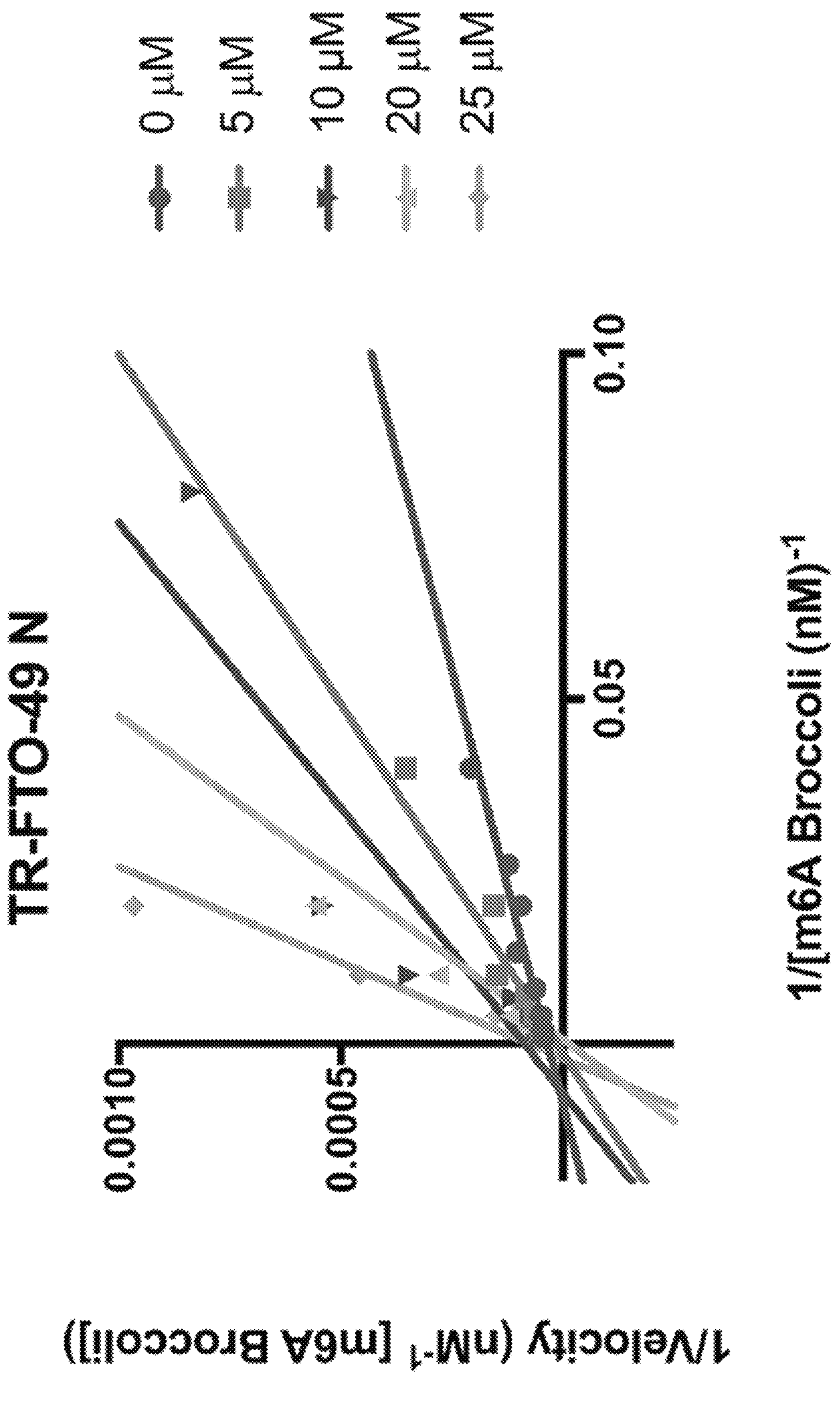

FIG. 125. Plots showing oxetane compounds inhibit FTO competitively.

Figure 126:
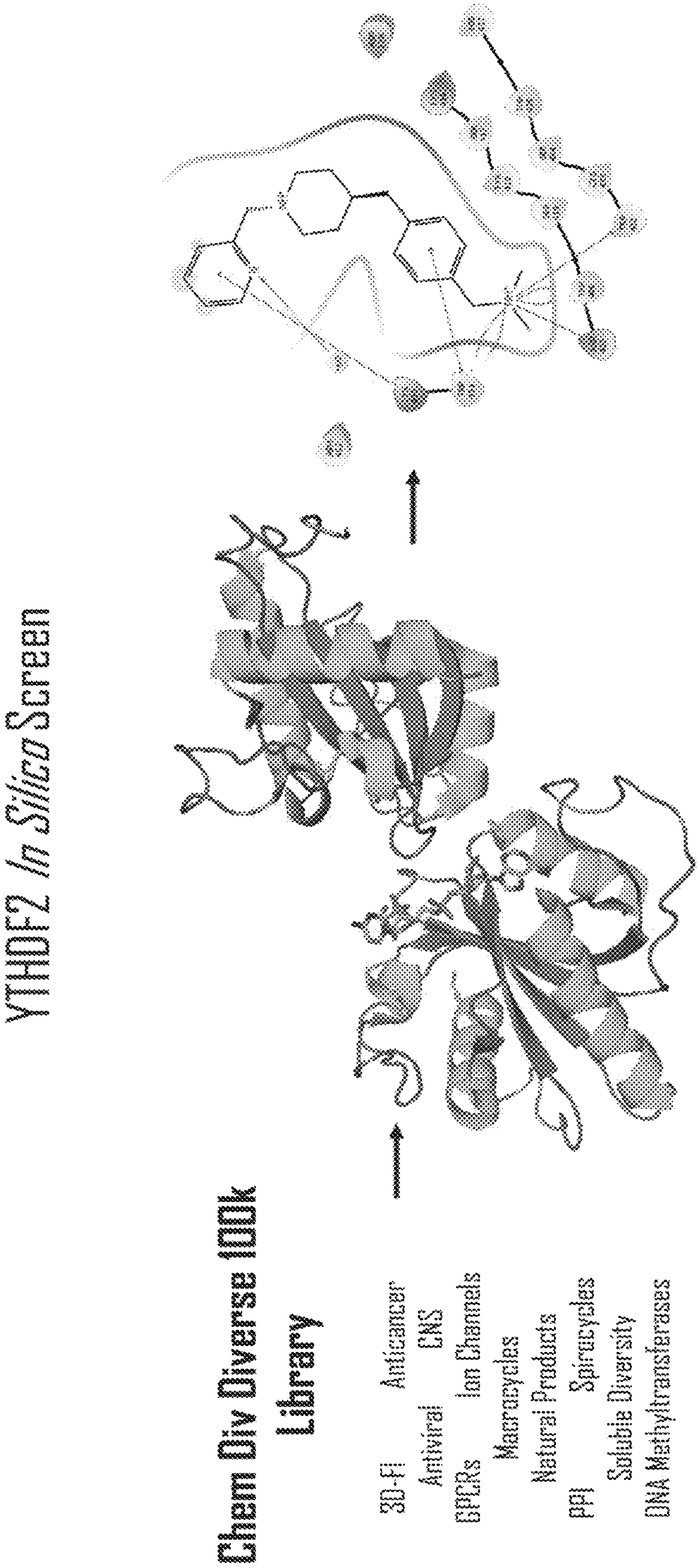

FIG. 126. Depiction of YTHDF2 in silico screen.

Figure 127:
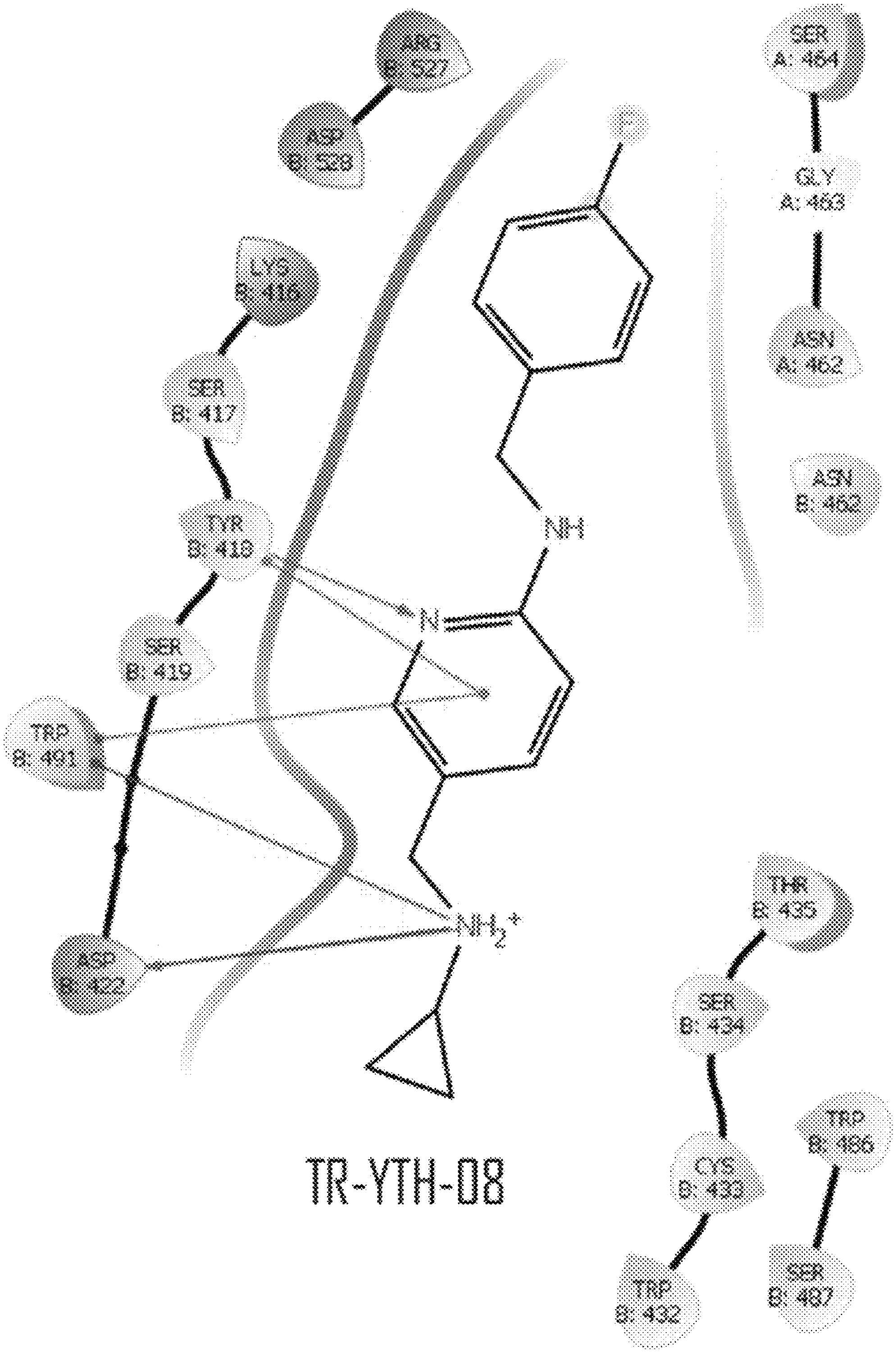

FIG. 127. Depiction of example hits from YTHDF2 in silico screen.

FIG. 128. Depiction of YTH library pharmacophore model.

DETAILED DESCRIPTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $-CH_2O-$ is equivalent to $-OCH_2-$.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, $-CH_2CH_2CH_2CH_2-$. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-S-CH_2$, $-S(O)-CH_3$, $-CH_2-CH_2-S(O)_2-CH_3$, $-CH=CH-O-CH_3$, $-Si(CH_3)_3$, $-CH_2-CH=N-OCH_3$, $-CH=CH-N(CH_3)-CH_3$, $-O-CH_3$, $-O-CH_2-CH_3$, and —CN. Up to two or three heteroatoms may be consecutive, such as, for example, $-CH_2-NH-OCH_3$ and $-CH_2-O-Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, $-CH_2-CH_2-S-CH_2-CH_2-$ and $-CH_2-S-CH_2-CH_2-NH-CH_2-$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $-C(O)_2R'-$ represents both $-C(O)_2R'-$ and $-R'C(O)_2-$. As described above, heteroalkyl groups, as used herein, include those groups that are attached to the remainder of the molecule through a heteroatom, such as $-C(O)R'$, $-C(O)NR'$, $-NR'R''$, $-OR'$, $-SR'$, and/or $-SO_2R'$. Where "heteroalkyl" is recited, followed by recitations of specific heteroalkyl groups, such as $-NR'R''$ or the like, it will be understood that the terms heteroalkyl and $-NR'R''$ are not redundant or mutually exclusive. Rather, the specific heteroalkyl groups are recited to add clarity.

Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "~" denotes the point of attachment of a chemical moiety to the remainder of a molecule or chemical formula.

The term "oxo," as used herein, means an oxygen that is double bonded to a carbon atom.

The term "alkylsulfonyl," as used herein, means a moiety having the formula $—S(O_2)—R'$, where R' is a substituted or unsubstituted alkyl group as defined above. R' may have a specified number of carbons (e.g., "$C_1$-$C_4$ alkylsulfonyl").

The term "alkylarylene" as an arylene moiety covalently bonded to an alkylene moiety (also referred to herein as an alkylene linker). In embodiments, the alkylarylene group has the formula:

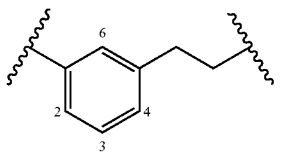

or

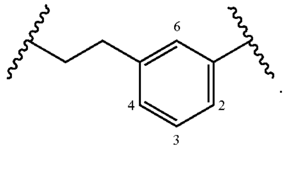

An alkylarylene moiety may be substituted (e.g. with a substituent group) on the alkylene moiety or the arylene linker (e.g. at carbons 2, 3, 4, or 6) with halogen, oxo, $—N_3$, $—CF_3$, $—CCl_3$, $—CBr_3$, $—CI_3$, —CN, —CHO, —OH, $—NH_2$, —COOH, $—CONH_2$, $—NO_2$, —SH, $—SO_2CH_3$, $—SO_3H$, $—OSO_3H$, $—SO_2NH_2$, $—NHNH_2$, $—ONH_2$, $—NHC(O)NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', $—CO_2R'$, —CONR'R", —OC(O)NR'R", —NR"C(O)R', —NR'—C(O)NR"R'", $—NR"C(O)_2R'$, —NR—C(NR'R"R'")=NR"", —NR—C(NR'R")=NR'", —S(O)R', $—S(O)_2R'$, $—S(O)_2NR'R"$, $—NRSO_2R'$, —NR'NR"R'", —ONR'R", —NR'C(O)NR"NR'"R"", —CN, $—NO_2$, $—NR'SO_2R"$, —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., $—CF_3$ and $—CH_2CF_3$) and acyl (e.g., $—C(O)CH_3$, $—C(O)CF_3$, $—C(O)CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', $—CO_2R'$, —CONR'R", —OC(O)NR'R", —NR"C(O)R', —NR'—C(O)NR"R'", $—NR"C(O)_2R'$, —NR—C(NR'R"R'")=NR"", —NR—C(NR'R")=NR'", —S(O)R', $—S(O)_2R'$, $—S(O)_2NR'R"$, $—NRSO_2R'$, —NR'NR"R'", —ONR'R", —NR'C(O)NR"NR'"R"", —CN, $—NO_2$, —R', $—N_3$, $—CH(Ph)_2$, fluoro($C_1$-$C_4$)alkoxy, and fluoro($C_1$-$C_4$)alkyl, $—NR'SO_2R"$, —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula $-T-C(O)-(CRR')_q-U-$, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula $-A-(CH_2)_r-B-$, wherein A and B are independently —CRR'—, —O—, —NR—, —S—, —S(O)—, $—S(O)_2—$, $—S(O)_2NR'—$, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula $—(CRR')_s—X'—(C''R''R''')_d—$, where s and d are independently integers of from 0 to 3, and X' is —O—, —NR'—, —S—, —S(O)—, $—S(O)_2—$, or $—S(O)_2NR'—$. The substituents R, R', R'', and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(i) oxo, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(a) oxo, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the terms "bioconjugate" and "bioconjugate linker" refers to the resulting association between atoms or molecules of "bioconjugate reactive groups" or "bioconjugate reactive moieties". The association can be direct or indirect. For example, a conjugate between a first bioconjugate reactive group (e.g., —$NH_2$, —C(O)OH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., -sulfo-N-hydroxysuccinimide moiety) is covalently attached to the second bioconjugate reactive group (e.g. an amine).

Useful bioconjugate reactive moieties used for bioconjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido or maleimide groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold, or react with maleimides;

(h) amine or sulfhydryl groups (e.g., present in cysteine), which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) metal silicon oxide bonding;

(m) metal bonding to reactive phosphorus groups (e.g. phosphines) to form, for example, phosphate diester bonds;

(n) azides coupled to alkynes using copper catalyzed cycloaddition click chemistry; and (o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable agent" or "detectable moiety" is a composition detectable by appropriate means such as spectroscopic, photochemical, biochemical, immunochemical, chemical, magnetic resonance imaging, or other physical means. For example, useful detectable agents include $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$ $^{77}As$, $^{86}Y$, $^{90}Y$, $^{89}Sr$, $^{89}Zr$, $^{94}Tc$, $^{94}Tc$, $^{99m}Tc$, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-1581}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$ $^{213}Bi$, $^{223}Ra$, $^{225}Ac$, Cr, V, Mn, Fe, Co, Ni, Cu, La, Ce, Pr, Nd, Pm, Sm, Eu, Gd, Tb, Dy, Ho, Er, Tm, Yb, Lu, $^{32}P$, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{77}As$, $^{86}Y$, $^{90}Y$ $^{89}Sr$, $^{89}Zr$, $^{94}Tc$, $^{94}Tc$, $^{99m}Tc$, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-1581}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$ and $^{225}Ac$. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "leaving group" is used in accordance with its ordinary meaning in chemistry and refers to a moiety (e.g., atom, functional group, molecule) that separates from the molecule following a chemical reaction (e.g., bond formation, reductive elimination, condensation, cross-coupling reaction) involving an atom or chemical moiety to which the leaving group is attached, also referred to herein as the "leaving group reactive moiety", and a complementary reactive moiety (i.e. a chemical moiety that reacts with the leaving group reactive moiety) to form a new bond between the remnants of the leaving groups reactive moiety and the complementary reactive moiety. Thus, the leaving group reactive moiety and the complementary reactive moiety form a complementary reactive group pair. Non limiting examples of leaving groups include hydrogen, hydroxide, organotin moieties (e.g., organotin heteroalkyl), halogen (e.g., Br), perfluoroalkylsulfonates (e.g. triflate), tosylates, mesylates, water, alcohols, nitrate, phosphate, thioether, amines, ammonia, fluoride, carboxylate, phenoxides, boronic acid, boronate esters, and alkoxides. In embodiments, two molecules with leaving groups are allowed to contact, and upon a reaction and/or bond formation (e.g., acyloin condensation, aldol condensation, Claisen condensation, Stille reaction) the leaving groups separates from the respective molecule. In embodiments, a leaving group is a bioconjugate reactive moiety. In embodiments, at least two leaving groups (e.g., $R^1$ and $R^{13}$) are allowed to contact such that the leaving groups are sufficiently proximal to react, interact or physically touch. In embodiments, the leaving groups is designed to facilitate the reaction.

The term "protecting group" is used in accordance with its ordinary meaning in organic chemistry and refers to a moiety covalently bound to a heteroatom, heterocycloalkyl, or heteroaryl to prevent reactivity of the heteroatom, heterocycloalkyl, or heteroaryl during one or more chemical reactions performed prior to removal of the protecting group. Typically a protecting group is bound to a heteroatom (e.g., O) during a part of a multipart synthesis wherein it is not desired to have the heteroatom react (e.g., a chemical reduction) with the reagent. Following protection the protecting group may be removed (e.g., by modulating the pH). In embodiments the protecting group is an alcohol protecting group. Non-limiting examples of alcohol protecting groups include acetyl, benzoyl, benzyl, methoxymethyl ether (MOM), tetrahydropyranyl (THP), and silyl ether (e.g., trimethylsilyl (TMS)). In embodiments the protecting group is an amine protecting group. Non-limiting examples of amine protecting groups include carbobenzyloxy (Cbz), tert-butyloxycarbonyl (BOC), 9-Fluorenylmethyloxycarbonyl (FMOC), acetyl, benzoyl, benzyl, carbamate, p-methoxybenzyl ether (PMB), and tosyl (Ts).

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or $-CH_3$). Likewise, for a linker variable (e.g., $L^1$, $L^2$, or $L^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

The term "exogenous" refers to a molecule or substance (e.g., a compound, nucleic acid or protein) that originates from outside a given cell or organism. For example, an "exogenous promoter" as referred to herein is a promoter that does not originate from the plant it is expressed by. Conversely, the term "endogenous" or "endogenous promoter" refers to a molecule or substance that is native to, or originates within, a given cell or organism.

The term "lipid moiety" is used in accordance with its ordinary meaning in chemistry and refers to a hydrophobic molecule which is typically characterized by an aliphatic hydrocarbon chain. In embodiments, the lipid moiety includes a carbon chain of 3 to 100 carbons. In embodiments, the lipid moiety includes a carbon chain of 5 to 50 carbons. In embodiments, the lipid moiety includes a carbon chain of 5 to 25 carbons. In embodiments, the lipid moiety includes a carbon chain of 8 to 525 carbons. Lipid moieties may include saturated or unsaturated carbon chains, and may be optionally substituted. In embodiments, the lipid moiety is optionally substituted with a charged moiety at the terminal end. In embodiments, the lipid moiety is an alkyl or heteroalkyl optionally substituted with a carboxylic acid moiety at the terminal end.

A charged moiety refers to a functional group possessing an abundance of electron density (i.e. electronegative) or is deficient in electron density (i.e. electropositive). Non-limiting examples of a charged moiety includes carboxylic acid, alcohol, phosphate, aldehyde, and sulfonamide. In embodiments, a charged moiety is capable of forming hydrogen bonds.

The term "coupling reagent" is used in accordance with its plain ordinary meaning in the arts and refers to a substance (e.g., a compound or solution) which participates in chemical reaction and results in the formation of a covalent bond (e.g., between bioconjugate reactive moieties, between a bioconjugate reactive moiety and the coupling reagent). In embodiments, the level of reagent is depleted in the course of a chemical reaction. This is in contrast to a solvent, which typically does not get consumed over the course of the chemical reaction. Non-limiting examples of coupling reagents include benzotriazol-1-yl-oxytripyrrolidinophosphonium hexafluorophosphate (PyBOP), 7-Azabenzotriazol-1-yloxy)tripyrrolidinophosphonium hexafluorophosphate (PyAOP), 6-Chloro-benzotriazole-1-yloxy-tris-pyrrolidinophosphonium hexafluorophosphate (PyClock), 1-[Bis(dimethylamino)methylene]-1H-1,2,3-triazolo[4,5-b] pyridinium 3-oxid hexafluorophosphate (HATU), or 2-(1H-benzotriazol-1-yl)-1,1,3,3-tetramethyluronium hexafluorophosphate (HBTU).

The term "solution" is used in accor and refers to a liquid mixture in which the minor component (e.g., a solute or compound) is uniformly distributed within the major component (e.g., a solvent).

The term "organic solvent" as used herein is used in accordance with its ordinary meaning in chemistry and refers to a solvent which includes carbon. Non-limiting examples of organic solvents include acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol, dimethyl ether), 1,2-dimethoxyethane (glyme, DME), dimethylformamide (DMF), dimethyl sulfoxide (DMSO), 1,4-dioxane, ethanol, ethyl acetate, ethylene glycol, glycerin, heptane, hexamethylphosphoramide (HMPA), hexamethylphosphorous, triamide (HMPT), hexane, methanol, methyl t-butyl ether (MTBE), methylene chloride, N-methyl-2-pyrrolidinone (NMP), nitromethane, pentane, petroleum ether (ligroine), 1-propanol, 2-propanol, pyridine, tetrahydrofuran (THF), toluene, triethyl amine, o-xylene, m-xylene, or p-xylene. In embodiments, the organic solvent is or includes chloroform, dichloromethane, methanol, ethanol, tetrahydrofuran, or dioxane.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The terms "bind" and "bound" as used herein is used in accordance with its plain and ordinary meaning and refers to the association between atoms or molecules. The association can be direct or indirect. For example, bound atoms or molecules may be direct, e.g., by covalent bond or linker (e.g. a first linker or second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like).

The term "capable of binding" as used herein refers to a moiety (e.g. a compound as described herein) that is able to measurably bind to a target (e.g., a NF-κB, a Toll-like receptor protein). In embodiments, where a moiety is capable of binding a target, the moiety is capable of binding with a Kd of less than about 10 μM, 5 μM, 1 μM, 500 nM, 250 nM, 100 nM, 75 nM, 50 nM, 25 nM, 15 nM, 10 nM, 5 nM, 1 nM, or about 0.1 nM.

As used herein, the term "conjugated" when referring to two moieties means the two moieties are bonded, wherein the bond or bonds connecting the two moieties may be covalent or non-covalent. In embodiments, the two moieties are covalently bonded to each other (e.g. directly or through a covalently bonded intermediary). In embodiments, the two moieties are non-covalently bonded (e.g. through ionic bond(s), van der waal's bond(s)/interactions, hydrogen bond (s), polar bond(s), or combinations or mixtures thereof).

The term "non-nucleophilic base" as used herein refers to any sterically hindered base that is a poor nucleophile.

The term "nucleophile" as used herein refers to a chemical species that donates an electron pair to an electrophile to form a chemical bond in relation to a reaction. All molecules or ions with a free pair of electrons or at least one pi bond can act as nucleophiles.

The term "strong acid" as used herein refers to an acid that is completely dissociated or ionized in an aqueous solution. Examples of common strong acids include hydrochloric acid (HCl), nitric acid ($HNO_3$), sulfuric acid ($H_2SO_4$), hydrobromic acid (HBr), hydroiodic acid (HI), perchloric acid ($HClO_4$), or chloric acid ($HClO_3$).

The term "carbocation stabilizing solvent" as used herein refers to any polar protic solvent capable of forming dipole-dipole interactions with a carbocation, thereby stabilizing the carbocation.

The terms "disease" or "condition" refer to a state of being or health status of a patient or subject capable of being treated with the compounds or methods provided herein. The disease may be a cancer. The disease may be an autoimmune disease. The disease may be an inflammatory disease. The disease may be an infectious disease. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

The terms "lung disease," "pulmonary disease," "pulmonary disorder," etc. are used interchangeably herein. The term is used to broadly refer to lung disorders characterized by difficulty breathing, coughing, airway discomfort and inflammation, increased mucus, and/or pulmonary fibrosis. Examples of lung diseases include lung cancer, cystic fibrosis, asthma, Chronic Obstructive Pulmonary Disease (COPD), bronchitis, emphysema, bronchiectasis, pulmonary edema, pulmonary fibrosis, sarcoidosis, pulmonary hypertension, pneumonia, tuberculosis, Interstitial Pulmonary Fibrosis (IPF), Interstitial Lung Disease (ILD), Acute Interstitial Pneumonia (AIP), Respiratory Bronchiolitis-associated Interstitial Lung Disease (RBILD), Desquamative Interstitial Pneumonia (DIP), Non-Specific Interstitial Pneumonia (NSIP), Idiopathic Interstitial Pneumonia (IIP), Bronchiolitis obliterans, with Organizing Pneumonia (BOOP), restrictive lung disease, or pleurisy.

As used herein, the term "inflammatory disease" refers to a disease or condition characterized by aberrant inflammation (e.g. an increased level of inflammation compared to a control such as a healthy person not suffering from a disease). Examples of inflammatory diseases include autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis.

As used herein, the term "cancer" refers to all types of cancer, neoplasm or malignant tumors found in mammals (e.g. humans), including leukemias, lymphomas, carcinomas and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3)

the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cunateous T-cell lymphoma, peripheral T-cell lymphoma, anaplastic large cell lymphoma, mycosis fungoides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. "Metastatic cancer" is also called "Stage IV cancer." Cancer occurs at an originating site, e.g., breast, which site is referred to as a primary tumor, e.g., primary breast cancer.

Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The terms "cutaneous metastasis" or "skin metastasis" refer to secondary malignant cell growths in the skin, wherein the malignant cells originate from a primary cancer site (e.g., breast). In cutaneous metastasis, cancerous cells from a primary cancer site may migrate to the skin where they divide and cause lesions. Cutaneous metastasis may result from the migration of cancer cells from breast cancer tumors to the skin.

The term "visceral metastasis" refer to secondary malignant cell growths in the internal organs (e.g., heart, lungs, liver, pancreas, intestines) or body cavities (e.g., pleura, peritoneum), wherein the malignant cells originate from a primary cancer site (e.g., head and neck, liver, breast). In visceral metastasis, cancerous cells from a primary cancer site may migrate to the internal organs where they divide and cause lesions. Visceral metastasis may result from the migration of cancer cells from liver cancer tumors or head and neck tumors to internal organs.

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

As used herein, the term "inflammatory disease" refers to a disease or condition characterized by aberrant inflammation (e.g. an increased level of inflammation compared to a control such as a healthy person not suffering from a disease). Examples of inflammatory diseases include traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis.

As used herein, the term "neurodegenerative disorder" refers to a disease or condition in which the function of a subject's nervous system becomes impaired. Examples of neurodegenerative diseases that may be treated with a compound, pharmaceutical composition, or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, chronic fatigue syndrome, Cockayne syndrome, Corticobasal degeneration, Creutzfeldt-Jakob disease, frontotemporal dementia, Gerstmann-Sträussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, myalgic encephalomyelitis, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, progressive supranuclear palsy, or Tabes dorsalis.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

The term "prevent" refers to a decrease in the occurrence of disease symptoms in a patient. As indicated above, the prevention may be complete (no detectable symptoms) or partial, such that fewer symptoms are observed than would likely occur absent treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of*

*Pharmaceutical Compounding* (1999); Pickar, Dosage Calculations (1999); and *Remington: The Science and Practice of Pharmacy,* 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *Spodoptera*) and human cells. Cells may be useful when they are naturally nonadherent or have been treated not to adhere to surfaces, for example by trypsinization.

A "stem cell" is a cell characterized by the ability of self-renewal through mitotic cell division and the potential to differentiate into a tissue or an organ. Among mammalian stem cells, embryonic stem cells (ES cells) and somatic stem cells (e.g., HSC) can be distinguished. Embryonic stem cells reside in the blastocyst and give rise to embryonic tissues, whereas somatic stem cells reside in adult tissues for the purpose of tissue regeneration and repair. A "neural stem cell" as provided herein refers to a stem cell capable to self-renew through mitotic cell division and to differentiate into a neural cell (e.g., glia cell, neuron, astrocyte, oligodendrocyte).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

Cancer model organism, as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

An "anticancer agent" as used herein refers to a molecule (e.g. compound, peptide, protein, nucleic acid, 0103) used to treat cancer through destruction or inhibition of cancer cells or tissues. Anticancer agents may be selective for certain cancers or certain tissues. In embodiments, anticancer agents herein may include epigenetic inhibitors and multi-kinase inhibitors.

"Anti-cancer agent" and "anticancer agent" are used in accordance with their plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclix-imab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene;

parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL.sub.2), interferon alfa-2a; interferon alfa-2b; interferon alfa-nl; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR—OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*Pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

An "epigenetic inhibitor" as used herein, refers to an inhibitor of an epigenetic process, such as DNA methylation (a DNA methylation Inhibitor) or modification of histones (a Histone Modification Inhibitor). An epigenetic inhibitor may be a histone-deacetylase (HDAC) inhibitor, a DNA methyltransferase (DNMT) inhibitor, a histone methyltransferase (HMT) inhibitor, a histone demethylase (HDM) inhibitor, or a histone acetyltransferase (HAT). Examples of HDAC inhibitors include Vorinostat, romidepsin, CI-994, Belinostat, Panobinostat, Givinostat, Entinostat, Mocetinostat, SRT501, CUDC-101, JNJ-26481585, or PCI24781. Examples of DNMT inhibitors include azacitidine and decitabine. Examples of HMT inhibitors include EPZ-5676. Examples of HDM inhibitors include pargyline and tranylcypromine. Examples of HAT inhibitors include CCT077791 and garcinol.

A "multi-kinase inhibitor" is a small molecule inhibitor of at least one protein kinase, including tyrosine protein kinases and serine/threonine kinases. A multi-kinase inhibitor may include a single kinase inhibitor. Multi-kinase inhibitors may block phosphorylation. Multi-kinases inhibitors may act as covalent modifiers of protein kinases. Multi-kinase inhibitors may bind to the kinase active site or to a secondary or tertiary site inhibiting protein kinase activity. A multi-kinase inhibitor may be an anti-cancer multi-kinase inhibitor. Exemplary anti-cancer multi-kinase inhibitors include dasatinib, sunitinib, erlotinib, bevacizumab, vatalanib, vemurafenib, vandetanib, cabozantinib, poatinib, axitinib, ruxolitinib, regorafenib, crizotinib, bosutinib, cetuximab, gefitinib, imatinib, lapatinib, lenvatinib, mubritinib, nilotinib, panitumumab, pazopanib, trastuzumab, or sorafenib.

"Selective" or "selectivity" or the like of a compound refers to the compound's ability to discriminate between molecular targets (e.g. a compound having selectivity toward HMT SUV39H1 and/or HMT G9a). For example, a compound or inhibitor as provided herein can be 10-fold more selective, 20-fold more selective, 50-fold more selective, 100-fold more selective, 200-fold more selective, 400-fold more selective, 500-fold more selective, 1000-fold more selective, etc. Selectivity can be determined using any known inhibitor assay, including, for example, the assays provided herein.

"Specific", "specifically", "specificity", or the like of a compound refers to the compound's ability to cause a particular action, such as inhibition, to a particular molecular target with minimal or no action to other proteins in the cell (e.g. a compound having specificity towards HMT SUV39H1 and/or HMT G9a displays inhibition of the activity of those HMTs whereas the same compound displays little-to-no inhibition of other HMTs such as DOT1, EZH1, EZH2, GLP, MLL1, MLL2, MLL3, MLL4, NSD2, SET1b, SET7/9, SET8, SETMAR, SMYD2, SUV39H2).

The term "infection" or "infectious disease" refers to a disease or condition that can be caused by organisms such as a bacterium, virus, fungi or any other pathogenic microbial agents. In embodiments, the infectious disease is caused by a pathogenic bacteria. Pathogenic bacteria are bacteria which cause diseases (e.g., in humans). In embodiments, the infectious disease is a bacteria associated disease (e.g., tuberculosis, which is caused by *Mycobacterium tuberculosis*). Non-limiting bacteria associated diseases include pneumonia, which may be caused by bacteria such as *Streptococcus* and *Pseudomonas*; or foodborne illnesses, which can be caused by bacteria such as *Shigella, Campylobacter*, and *Salmonella*. Bacteria associated diseases also includes tetanus, typhoid fever, diphtheria, syphilis, and leprosy. In embodiments, the disease is Bacterial vaginosis (i.e. bacteria that change the vaginal microbiota caused by an overgrowth of bacteria that crowd out the Lactobacilli species that maintain healthy vaginal microbial populations) (e.g., yeast infection, or *Trichomonas vaginalis*); Bacterial meningitis (i.e. a bacterial inflammation of the meninges); Bacterial pneumonia (i.e. a bacterial infection of the lungs); Urinary tract infection; Bacterial gastroenteritis; or Bacterial skin infections (e.g. impetigo, or cellulitis). In embodiments, the infectious disease is a *Campylobacter jejuni, Enterococcus faecalis, Haemophilus influenzae, Helicobacter pylori, Klebsiella pneumoniae, Legionella pneumophila, Neisseria gonorrhoeae, Neisseria meningitides, Staphylococcus aureus, Streptococcus pneumonia*, or *Vibrio cholera* infection.

The terms "immune response" and the like refer, in the usual and customary sense, to a response by an organism that protects against disease. The response can be mounted by the innate immune system or by the adaptive immune system, as well known in the art.

The terms "modulating immune response" and the like refer to a change in the immune response of a subject as a consequence of administration of an agent, e.g., a compound as disclosed herein, including embodiments thereof. Accordingly, an immune response can be activated or deactivated as a consequence of administration of an agent, e.g., a compound as disclosed herein, including embodiments thereof.

"B Cells" or "B lymphocytes" refer to their standard use in the art. B cells are lymphocytes, a type of white blood cell (leukocyte), that develops into a plasma cell (a "mature B cell"), which produces antibodies. An "immature B cell" is a cell that can develop into a mature B cell. Generally, pro-B cells undergo immunoglobulin heavy chain rearrangement to become pro B pre B cells, and further undergo immunoglobulin light chain rearrangement to become an immature B cells. Immature B cells include T1 and T2 B cells.

"T cells" or "T lymphocytes" as used herein are a type of lymphocyte (a subtype of white blood cell) that plays a central role in cell-mediated immunity. They can be distinguished from other lymphocytes, such as B cells and natural killer cells, by the presence of a T-cell receptor on the cell surface. T cells include, for example, natural killer T (NKT) cells, cytotoxic T lymphocytes (CTLs), regulatory T (Treg) cells, and T helper cells. Different types of T cells can be distinguished by use of T cell detection agents.

A "memory T cell" is a T cell that has previously encountered and responded to its cognate antigen during prior infection, encounter with cancer or previous vaccination. At a second encounter with its cognate antigen memory T cells can reproduce (divide) to mount a faster and stronger immune response than the first time the immune system responded to the pathogen.

A "regulatory T cell" or "suppressor T cell" is a lymphocyte which modulates the immune system, maintains tolerance to self-antigens, and prevents autoimmune disease.

As used herein, the term "cardiovascular disorder" or "cardiovascular disease" is used in accordance with its plain ordinary meaning. In embodiments, cardiovascular diseases that may be treated with a compound, pharmaceutical composition, or method described herein include, but are not limited to, stroke, heart failure, hypertension, hypertensive heart disease, myocardial infarction, angina pectoris, tachycardia, cardiomyopathy, rheumatic heart disease, cardiomyopathy, heart arrhythmia, congenital heart disease, valvular heart disease, carditis, aortic aneurysms, peripheral artery disease, thromboembolic disease, and venous thrombosis.

The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms "variable heavy chain," "$V_H$," or "VH" refer to the variable region of an immunoglobulin heavy chain, including an Fv, scFv, dsFv or Fab; while the terms "variable light chain," "$V_L$" or "VL" refer to the variable region of an immunoglobulin light chain, including of an Fv, scFv, dsFv or Fab.

Examples of antibody functional fragments include, but are not limited to, complete antibody molecules, antibody fragments, such as Fv, single chain Fv (scFv), complementarity determining regions (CDRs), VL (light chain variable region), VH (heavy chain variable region), Fab, F(ab)2' and any combination of those or any other functional portion of an immunoglobulin peptide capable of binding to target antigen (see, e.g., FUNDAMENTAL IMMUNOLOGY (Paul ed., 4th ed. 2001). As appreciated by one of skill in the art, various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries (see, e.g., McCafferty et al., (1990) *Nature* 348:552). The term "antibody" also includes bivalent or bispecific molecules, diabodies, triabodies, and tetrabodies. Bivalent and bispecific molecules are described in, e.g., Kostelny et al. (1992) *J. Immunol.* 148:1547, Pack and Pluckthun (1992) *Biochemistry* 31:1579, Hollinger et al. (1993), *PNAS. USA* 90:6444, Gruber et al. (1994) *J Immunol.* 152:5368, Zhu et al. (1997)

*Protein Sci.* 6:781, Hu et al. (1996) *Cancer Res.* 56:3055, Adams et al. (1993) *Cancer Res.* 53:4026, and McCartney, et al. (1995) *Protein Eng.* 8:301.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

The terms "virus" or "virus particle" are used according to its plain ordinary meaning within Virology and refers to a virion including the viral genome (e.g. DNA, RNA, single strand, double strand), viral capsid and associated proteins, and in the case of enveloped viruses (e.g. herpesvirus), an envelope including lipids and optionally components of host cell membranes, and/or viral proteins.

The term "viral structural protein" as used herein, refers to a viral protein that is a structural component of a virus (e.g., a virus which is capable of encoding a protein). In embodiments, the virus structural protein is an RNA virus structural protein. In embodiments, the RNA virus structural protein is a viral premembrane protein (prM), viral envelope protein (Env), a capsid protein (C) or a membrane protein (M).

The term "plaque forming units" is used according to its plain ordinary meaning in Virology and refers to a unit of measurement based on the number of plaques per unit volume of a sample. In some embodiments the units are based on the number of plaques that could form when infecting a monolayer of susceptible cells. Plaque forming unit equivalents are units of measure of inactivated virus. In some embodiments, plaque forming unit equivalents are derived from plaque forming units for a sample prior to inactivation. In embodiments, plaque forming units are abbreviated "Pfu".

The term "RNA virus" as used herein refers, in the usual and customary sense, to a a virus that has RNA (ribonucleic acid) as its genetic material. In embodiments, the RNA is single-stranded RNA (e.g., ssRNA). In embodiments, the RNA is positive (+) single-stranded RNA (e.g., Bymoviruses, comoviruses, nepoviruses, nodaviruses, picornaviruses, potyviruses, sobemoviruses, luteoviruses (e.g., beet western yellows virus, barley yellow dwarf virus, potato leafroll virus), Carmoviruses, dianthoviruses, flaviviruses, pestiviruses, statoviruses, tombusviruses, single-stranded RNA bacteriophages, hepatitis C virus, Alphaviruses, carlaviruses, furoviruses, hordeiviruses, potexviruses, rubiviruses, tobraviruses, tricornaviruses, tymoviruses, apple chlorotic leaf spot virus, or hepatitis E virus). In embodiments, the RNA is double-stranded RNA (e.g., dsRNA).

The terms "viral infection" or "viral disease" or "viral infectious disease" or "virus infection" as used interchangeably herein refers, in the usual and customary sense, to the presence of a virus (e.g., RNA virus) within a subject. In embodiments, a viral infection refers to the presence of a virus (e.g., RNA virus) within a subject that is capable of replicating and/or generating virus particles. In embodiments, the viral infection refers to the presence of a virus (e.g., RNA virus) within a subject that is capable of infecting a second subject. A viral infection can be present in any body issue and the subject may present symptoms such as fever, red eyes, joint pain, headache, and a maculopapular rash, or the subject may be asymptomatic. Diagnosis of a viral infection may be determined by testing bodily fluids (e.g., blood, urine, or saliva) for the presence of the virus's RNA or for antibodies. In embodiments, the virus may be present within a subject but may be latent.

The terms "multiplicity of infection" or "MOI" are used according to its plain ordinary meaning in Virology and refers to the ratio of components (e.g., poxvirus) to the target (e.g., cell) in a given area. In embodiments, the area is assumed to be homogenous.

The term "replicate" is used in accordance with its plain ordinary meaning and refers to the ability of a cell or virus to produce progeny. A person of ordinary skill in the art will immediately understand that the term replicate when used in connection with DNA, refers to the biological process of producing two identical replicas of DNA from one original DNA molecule. In the context of a virus, the term "replicate" includes the ability of a virus to replicate (duplicate the viral genome and packaging said genome into viral particles) in a host cell and subsequently release progeny viruses from the host cell, which results in the lysis of the host cell. A "replication-competent" virus as provided herein refers to a virus (chimeric poxvirus) that is capable of replicating in a cell (e.g., a cancer cell). Similarly, an "oncolytic virus" as referred to herein, is a virus that is capable of infecting and killing cancer cells. As the infected cancer cells are destroyed by oncolysis, they release new infectious virus particles or virions to help destroy the remaining tumor. In embodiments, the chimeric poxvirus is able to replicate in a cancer cell. In embodiments, the chimeric poxvirus does not detectably replicate in a healthy cell relative to a standard control. In embodiments, the chimeric poxvirus provided herein has an increased oncolytic activity compared to its parental virus. In embodiments, the oncolytic activity (ability to induce cell death in an infected cell) is more than 1.5, 2, 3, 4, 5, 6, 7, 8, 9, 10, 100, 10000, 10000 times increased compared to the oncolytic activity of a parental virus (one of the viruses used to form the chimeric virus provided herein).

The term "vaccine" is used according to its plain ordinary meaning within medicine and Immunology and refers to a composition including an antigenic component for administration to a subject (e.g., human), which elicits an immune response to the antigenic component. In some embodiments a vaccine is a therapeutic. In some embodiments, a vaccine is prophylactic. In some embodiments a vaccine includes one or more adjuvants. Vaccines can be prophylactic (e.g. preventing or ameliorating the effects of a future infection by any natural or pathogen, or of an anticipated occurrence of cancer in a predisposed subject) or therapeutic (e.g., treating cancer in a subject who has been diagnosed with the cancer). The administration of vaccines is referred to vaccination. A vaccine typically contains an agent that resembles a disease-causing microorganism (e.g., RNA virus, viral structural protein, or virus particle) and is often made from weakened or killed forms of the virus (e.g., RNA virus), its toxins or one of its surface proteins. The agent stimulates the body's immune system to recognize the agent as a threat, destroy it, and recognize and destroy any of these microorganisms that it later encounters.

The term "vaccine formulation" as used herein refers, in the usual and customary sense, to a vaccine including an immunogenic agent (e.g., a compound as disclosed herein) and optionally one or more pharmaceutically acceptable excipients and vaccine adjuvants.

The terms "antigen" and "epitope" interchangeably refer to the portion of a molecule (e.g., a polypeptide) which is specifically recognized by a component of the immune system, e.g., an antibody, a T cell receptor, or other immune receptor such as a receptor on natural killer (NK) cells. As used herein, the term "antigen" encompasses antigenic epitopes and antigenic fragments thereof.

The term "immune response" used herein encompasses, but is not limited to, an "adaptive immune response", also known as an "acquired immune response" in which adaptive immunity elicits immunological memory after an initial response to a specific pathogen or a specific type of cells that is targeted by the immune response, and leads to an enhanced response to that target on subsequent encounters. The induction of immunological memory can provide the basis of vaccination. The response can be mounted by the innate immune system or by the adaptive immune system, as well known in the art.

The terms "modulating immune response" and the like refer to a change in the immune response of a subject as a consequence of administration of an agent, e.g., a compound as disclosed herein, including embodiments thereof. Accordingly, an immune response can be activated or deactivated as a consequence of administration of an agent, e.g., a compound as disclosed herein, including embodiments thereof.

The term "viral shedding" is used according to its plain ordinary meaning in Medicine and Virology and refers to the production and release of virus from an infected cell. In some embodiments, the virus is released from a cell of a subject. In some embodiments virus is released into the environment from an infected subject. In some embodiments the virus is released from a cell within a subject. In some embodiments, the methods of treatment described herein refer to a reduction in viral shedding from a subject.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

A "synergistic amount" as used herein refers to the sum of a first amount (e.g., an amount of a compound provided herein) and a second amount (e.g., a therapeutic agent) that results in a synergistic effect (i.e. an effect greater than an additive effect). Therefore, the terms "synergy", "synergism", "synergistic", "combined synergistic amount", and "synergistic therapeutic effect" which are used herein interchangeably, refer to a measured effect of the compound administered in combination where the measured effect is greater than the sum of the individual effects of each of the compounds provided herein administered alone as a single agent.

In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the compound provided herein when used separately from the therapeutic agent. In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the therapeutic agent when used separately from the compound provided herein.

The term "vaccine" refers to a composition that can provide active acquired immunity to and/or therapeutic effect (e.g. treatment) of a particular disease or a pathogen. A vaccine typically contains one or more agents that can induce an immune response in a subject against a pathogen or disease, i.e. a target pathogen or disease. The immunogenic agent stimulates the body's immune system to recognize the agent as a threat or indication of the presence of the target pathogen or disease, thereby inducing immunological memory so that the immune system can more easily recognize and destroy any of the pathogen on subsequent exposure. Vaccines can be prophylactic (e.g. preventing or ameliorating the effects of a future infection by any natural or pathogen, or of an anticipated occurrence of cancer in a predisposed subject) or therapeutic (e.g., treating cancer in a subject who has been diagnosed with the cancer). The administration of vaccines is referred to vaccination. In some examples, a vaccine composition can provide nucleic acid, e.g. mRNA that encodes antigenic molecules (e.g. peptides) to a subject. The nucleic acid that is delivered via the vaccine composition in the subject can be expressed into antigenic molecules and allow the subject to acquire immunity against the antigenic molecules. In the context of the vaccination against infectious disease, the vaccine composition can provide mRNA encoding antigenic molecules that are associated with a certain pathogen, e.g. one or more peptides that are known to be expressed in the pathogen (e.g. pathogenic bacterium or virus). In the context of cancer vaccine, the vaccine composition can provide mRNA encoding certain peptides that are associated with cancer, e.g. peptides that are substantially exclusively or highly expressed in cancer cells as compared to normal cells. The subject, after vaccination with the cancer vaccine composition, can have immunity against the peptides that are associated with cancer and kill the cancer cells with specificity.

The term "immune response" used herein encompasses, but is not limited to, an "adaptive immune response", also known as an "acquired immune response" in which adaptive immunity elicits immunological memory after an initial response to a specific pathogen or a specific type of cells that is targeted by the immune response, and leads to an enhanced response to that target on subsequent encounters. The induction of immunological memory can provide the basis of vaccination.

The term "immunogenic" or "antigenic" refers to a compound or composition that induces an immune response, e.g., cytotoxic T lymphocyte (CTL) response, a B cell response (for example, production of antibodies that specifically bind the epitope), an NK cell response or any combinations thereof, when administered to an immunocompetent subject. Thus, an immunogenic or antigenic composition is a composition capable of eliciting an immune response in an immunocompetent subject. For example, an immunogenic or antigenic composition can include one or more immunogenic epitopes associated with a pathogen or a specific type of cells that is targeted by the immune response. In addition, an immunogenic composition can include isolated nucleic acid constructs (such as DNA or RNA) that encode one or more immunogenic epitopes of the antigenic polypeptide that can be used to express the epitope (s) (and thus be used to elicit an immune response against this polypeptide or a related polypeptide associated with the targeted pathogen or type of cells).

The term "EC50" or "half maximal effective concentration" as used herein refers to the concentration of a molecule (e.g., antibody, chimeric antigen receptor or bispecific antibody) capable of inducing a response which is halfway between the baseline response and the maximum response after a specified exposure time. In embodiments, the EC50 is the concentration of a molecule (e.g., antibody, chimeric antigen receptor or bispecific antibody) that produces 50% of the maximal possible effect of that molecule.

An "inhibitor" refers to a compound (e.g. compounds described herein) that reduces activity when compared to a control, such as absence of the compound or a compound with known inactivity.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating", "activator" and the like in reference to a protein-inhibitor interaction means positively affecting (e.g. increasing) the activity or function of the protein relative to the activity or function of the protein in the absence of the activator. In embodiments activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein.

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "modulator" refers to a composition that increases or decreases the level of a target molecule or the function of a target molecule or the physical state of the target of the molecule relative to the absence of the modulator.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease or infection (e.g. a protein associated disease, a cancer (e.g., cancer, inflammatory disease, autoimmune disease, or infectious disease)) means that the disease or infection is caused by (in whole or in part), a symptom of the disease or infection is caused by (in whole or in part) the substance or substance activity or function, or a side-effect of the compound (e.g., toxicity) is caused by (in whole or in part) the substance or substance activity or function. As used herein, what is described as being associated with a disease, if a causative agent, could be a target for treatment of the disease.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extra-cellular components (e.g. proteins, nucleic acids, small molecules, ions, lipids) that conveys a change in one component to one or more other components, which in turn may convey a change to additional components, which is optionally propagated to other signaling pathway components.

In this disclosure, "comprises," "comprising," "containing" and "having" and the like can have the meaning ascribed to them in U.S. Patent law and can mean "includes," "including," and the like. "Consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

II. Compounds

In an aspect is provided a compound or derivative thereof as disclosed herein.

Disclosed herein are compounds and derivatives. Non-limiting embodiments are disclosed in one or more of U.S. Provisional Application Ser. No. 62/914,914, filed on Oct. 14, 2019; U.S. Provisional Application Ser. No. 62/971,701, filed on Feb. 7, 2020; U.S. Provisional Application Ser. No. 63/059,939, filed on Jul. 31, 2020; and U.S. Provisional Application Ser. No. 63/074,421, filed on Sep. 3, 2020, each of which is incorporated herein by reference in its entirety (including the appendices incorporated therein).

Accordingly, in one aspect, provided herein are compounds of Formula (PT1)

Formula (PT1)

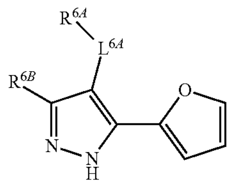

or a pharmaceutically acceptable salt thereof, wherein:

$L^{6A}$ is a bond or $C_{1-4}$ alkylene;

$R^{6A}$ is selected from the group consisting of: $C_{6-10}$ aryl and 5-10 membered heteroaryl, each optionally substituted with from 1-4 $R^{a6}$;

$R^{6B}$ is selected from the group consisting of: $C_{6-10}$ aryl and 5-10 membered heteroaryl, each optionally substituted with from 1-4 $R^{b6}$;

each occurrence of $R^{a6}$ and $R^{b6}$ is independently selected from the group consisting of: halo; cyano; $C_{1-6}$ alkyl; $C_{1-6}$ haloalkyl; $C_{1-6}$ alkoxy; $C_{1-6}$ haloalkoxy; $C_{1-6}$ thio-alkoxy; C(═O)$C_{1-6}$ alkyl; C(═O)O$C_{1-6}$ alkyl; C(O)NR'R"; $S(O)_2C_{1-6}$ alkyl; $S(O)_2$NR'R"; —OH; NR'R"; and $NO_2$; and each occurrence of R' and R" is independently H, $C_{1-3}$ alkyl, or $C_{3-6}$ cycloalkyl.

Compounds of Formula (PT1) are useful e.g., as small molecule inhibitors of PTPN2.

In some embodiments of Formula (PT1), $L^{6A}$ is $C_{1-4}$ alkylene, such as straight chain $C_{1-4}$ alkylene. In some embodiments, $L^{6A}$ is —$CH_2$—. In some embodiments, $L^{6A}$ is —$CH_2CH_2$—. In some embodiments, $L^{6A}$ is —$CH_2CH_2CH_2$—.

In some embodiments of Formula (PT1), $R^{6A}$ is $C_{6-10}$ aryl optionally substituted with from 1-4 $R^{a6}$. In some embodiments, $R^{6A}$ is phenyl optionally substituted with from 1-2 $R^{a6}$. In some embodiments, $R^{6A}$ is unsubstituted phenyl. In some embodiments, $R^{6A}$ is

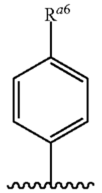

or

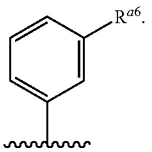

In some embodiments of Formula (PT1), each $R^{a6}$ is independently selected from the group consisting of: $C_{1-6}$ alkyl (e.g., tert-butyl); $C_{1-6}$ haloalkyl (e.g., —$CF_3$); $NO_2$; C(═O)O$C_{1-6}$ alkyl (e.g., C(═O)OMe); halo (e.g., —Br); $C_{1-6}$ alkoxy; and $C_{1-6}$ haloalkoxy (e.g., —$OCF_3$).

In some embodiments of Formula (PT1), $R^{6B}$ is $C_{6-10}$ aryl optionally substituted with from 1-4 $R^{b6}$. In some embodiments, $R^{6B}$ is phenyl substituted with from 1-2 $R^{b6}$. In some embodiments, $R^{6B}$ is

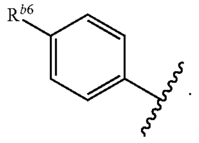

In some embodiments, $R^{6B}$ is

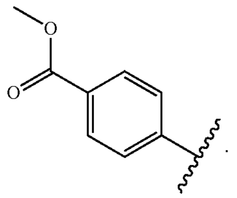 [SMILES: *c1ccc(C(=O)OC)cc1]

In some embodiments of Formula (PT1), the compound is selected from the group consisting of the compounds in Table 1000, or a pharmaceutically acceptable salt thereof.

In one aspect, provided herein are compounds of Formula (Y1):

Formula (Y1)

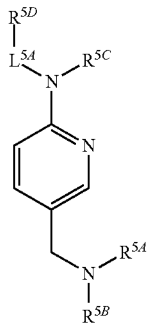

or a pharmaceutically acceptable salt thereof, wherein:

$R^{5A}$ and $R^{5B}$ are independently selected from the group consisting of: H, $C_{1-6}$ alkyl, and $C_{3-6}$ cycloalkyl, wherein the $C_{1-6}$ alkyl and $C_{3-6}$ alkyl are optionally substituted with from 1-4 $R^{a5}$;

$R^{5C}$ is H or $C_{1-6}$ alkyl;

$L^{5A}$ is a bond or $C_{1-6}$ alkylene;

$R^{5D}$ is selected from the group consisting of: $C_{6-10}$ aryl and 5-10 membered, each optionally substituted with from 1-4 $R^{b5}$;

each occurrence of $R^{a5}$ and $R^{b5}$ is independently selected from the group consisting of: a hydrogen bond acceptor group; halo; cyano; $C_{1-6}$ alkyl; $C_{1-6}$ haloalkyl; $C_{1-6}$ alkoxy; $C_{1-6}$ haloalkoxy; $C_{1-6}$ thioalkoxy; $C_{1-6}$ thiohaloalkoxy; C(=O)$C_{1-6}$ alkyl; C(=O)O$C_{1-6}$ alkyl; C(O)NR'R"; $S(O)_2C_{1-6}$ alkyl; $S(O)_2$NR'R"; —OH; NR'R"; NR'C(=O)$C_{1-6}$ alkyl; NR'C(=O)O$C_{1-6}$ alkyl; NR'C(=O)NR'R"; and $NO_2$; and each occurrence of R' and R" is independently H, $C_{1-3}$ alkyl, or $C_{3-6}$ cycloalkyl.

Compounds of Formula (Y1) are useful e.g., as inhibitors of YTH domain-containing family proteins (YTHs).

In some embodiments of Formula (Y1), $R^{5A}$ and $R^{5B}$ are independently selected $C_{1-6}$ alkyl, each optionally substituted with from 1-4 $R^{a5}$. In some embodiments, $R^{5A}$ and $R^{5B}$ are independently selected $C_{1-6}$ alkyl. In some embodiments, $R^{5A}$ and $R^{5B}$ are each methyl. In some embodiments, $R^{5A}$ is H; and $R^{5B}$ is $C_{3-6}$ cycloalkyl which is optionally substituted with from 1-4 $R^{a5}$. In some embodiments, $R^{5A}$ is H; and $R^{5B}$ is cyclopropyl which is optionally substituted with from 1-4 $R^{a5}$. For example, $R^{5A}$ can be H; and $R^{5B}$ can be cyclopropyl.

In some embodiments of Formula (Y1), $R^{5C}$ is H.

In some embodiments of Formula (Y1), $R^{5C}$ is $C_{1-6}$ alkyl, such as $C_{1-3}$ alkyl, such as methyl.

In some embodiments of Formula (Y1), $L^{5A}$ is $C_{1-6}$ alkylene. In some embodiments, $L^{5A}$ is —$CH_2$—. In some embodiments, $L^{5A}$ is —CH($C_{1-3}$ alkyl)-. For example, —CH(Me)-.

In some embodiments of Formula (Y1), $L^{5A}$ is a bond.

In some embodiments of Formula (Y1), $R^{5D}$ is $C_{6-10}$ aryl which is optionally substituted with from 1-4 $R^{b5}$.

In some embodiments of Formula (Y1), $R^{5D}$ is phenyl optionally substituted with from 1-2 $R^{b5}$, such as wherein $R^{5D}$ is

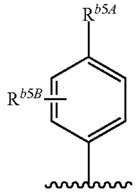, wherein $R^{b5A}$ is $R^{b5}$, and $R^{b5B}$ is H or $R^{b5}$, optionally $R^{b5A}$ is $OCH_3$ or $CF_3$.

In some embodiments of Formula (Y1), $R^{5D}$ is 5-10 membered heteroaryl which is optionally substituted with from 1-4 $R^{b5}$.

In some embodiments of Formula (Y1), $R^{5D}$ is 6-membered heteroaryl, such as pyridyl, which is optionally substituted with from 1-2 $R^{b5}$.

In some embodiments of Formula (Y1), each occurrence of $R^{a5}$ and $R^{b5}$ is independently selected from the group consisting of: halo; cyano; $C_{1-6}$ alkyl; $C_{1-6}$ haloalkyl; $C_{1-6}$ alkoxy; $C_{1-6}$ haloalkoxy; $C_{1-6}$ thioalkoxy; $C_{1-6}$ thiohaloalkoxy; C(=O)$C_{1-6}$ alkyl; C(=O)O$C_{1-6}$ alkyl; C(O)NR'R"; $S(O)_2C_{1-6}$ alkyl; $S(O)_2$NR'R"; —OH; NR'R"; NR'C(=O)$C_{1-6}$ alkyl; NR'C(=O)O$C_{1-6}$ alkyl; NR'C(=O)NR'R"; and $NO_2$;

In some embodiments of Formula (Y1), each occurrence of $R^{b5}$ is independently selected from the group consisting of $C_{1-6}$ alkoxy (e.g., OMe); $C_{1-6}$ thioalkoxy (e.g., —SMe); $C_{1-6}$ alkyl (e.g., methyl); $C_{1-6}$ haloalkyl (e.g., —$CF_3$); and halo (e.g., —F).

In some embodiments of Formula (Y1), the compound is a compound selected from the group consisting of the compounds in Table 400, or a pharmaceutically acceptable salt thereof.

In another aspect, provided herein are compounds of Formula (Y2):

Formula (Y2)

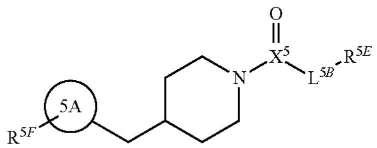

or a pharmaceutically acceptable salt thereof, wherein:

$R^{5F}$ is selected from the group consisting of: $R^{c5}$ and $R^{d5}$;

Ring 5A is a 5-membered heteroarylene optionally substituted with from 1-2 $R^{c5}$;

$X^5$ is C, S, or S(=O);

$L^{5B}$ is a bond or $CH_2$;

$R^{5E}$ is NR'R", or $R^{5E}$ is selected from the group consisting of: $C_{1-6}$ alkyl; $C_{1-6}$ haloalkyl; $C_{6-10}$ aryl; 5-10 membered heteroaryl; $C_{3-12}$ cycloalkyl; and 4-10 membered heterocyclyl, each of which is optionally substituted with from 1-4 $R^{e5}$;

each occurrence of $R^{c5}$ and $R^{e5}$ is independently selected from the group consisting of: halo; cyano; $C_{1-6}$ alkyl; $C_{1-6}$ haloalkyl; $C_{1-6}$ alkoxy; $C_{1-6}$ haloalkoxy; $C_{1-6}$ thioalkoxy; C(=O)$C_{1-6}$ alkyl; C(=O)O$C_{1-6}$ alkyl; C(O)NR'R"; $S(O)_2C_{1-6}$ alkyl; $S(O)_2$NR'R"; —OH; NR'R"; NR'C(=O)$C_{1-6}$ alkyl; NR'C(=O)O$C_{1-6}$ alkyl; NR'C(=O)NR'R"; and $NO_2$;

$R^{d5}$ is selected from the group consisting of: $C_{6-10}$ aryl; 5-10 membered heteroaryl; $C_{3-12}$ cycloalkyl; and 4-10 membered heterocyclyl, each of which is optionally substituted with from 1-4 $R^{e5}$; and each occurrence of R' and R" is independently H, $C_{1-3}$ alkyl, or $C_{3-6}$ cycloalkyl.

Compounds of Formula (Y2) are useful e.g., as inhibitors of YTH domain-containing family proteins (YTHs).

In some embodiments of Formula (Y2), Ring 5A is triazolylene (e.g., 1,2,3-triazolylene).

In some embodiments, Ring 5A is

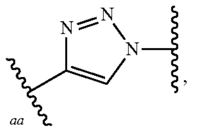

wherein aa represents the point of attachment to $R^{5F}$.

In some embodiments of Formula (Y2), Ring 5A is oxadiazolylene.

In some embodiments, Ring 5A is

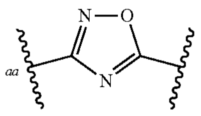

or

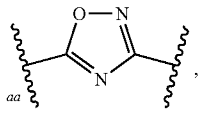

wherein aa represents the point of attachment to $R^{5F}$.

In some embodiments of Formula (Y2), $R^{5F}$ is $R^{d5}$.

In some embodiments, $R^{5F}$ is selected from the group consisting of $C_{6-10}$ aryl (e.g., $C_6$ aryl) and 5-10 membered heteroaryl (e.g., 5-6 membered heteroaryl), each of which is optionally substituted with from 1-4 $R^{e5}$. In some embodiments, $R^{5F}$ is selected from the group consisting of phenyl and pyridyl, each optionally substituted with from 1-2 $R^{e5}$, such as unsubstituted phenyl or pyridyl.

In some embodiments, $R^{5F}$ is 4-10 membered heterocyclyl, which is optionally substituted with from 1-4 $R^{e5}$. In some embodiments, $R^{5F}$ is pyrrolidinyl which is optionally substituted with from 1-2 $C_{1-3}$ alkyl, such as

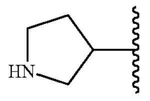

or

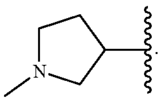

In some embodiments, $R^{5F}$ is $C_{3-12}$ cycloalkyl optionally substituted with from 1-4 $R^{e5}$, such as wherein $R^5$ is adamantly.

In some embodiments, $R^{5F}$ is $C_{1-6}$ alkyl or $C_{1-6}$ haloalkyl, such as methyl, isopropyl, or $CF_3$.

In some embodiments, $R^{5F}$ is halo, such as —Cl.

In some embodiments of Formula (Y2), $X^5$ is C.

In some embodiments of Formula (Y2), $X^5$ is S(O).

In some embodiments of Formula (Y2), $L^{5B}$ is a bond.

In some embodiments of Formula (Y2), $L^{5B}$ is $CH_2$.

In some embodiments of Formula (Y2), $R^{5E}$ is 5-10 membered heteroaryl which is optionally substituted with from 1-4 $R^{e5}$.

In some embodiments of Formula (Y2), $R^{5E}$ is 5-membered heteroaryl which is optionally substituted with from 1-4 $R^{e5}$.

In some embodiments of Formula (Y2), $R^{5E}$ is pyrazolyl optionally substituted with from 1-2 $R^{e5}$, such as wherein $R^{5E}$ is

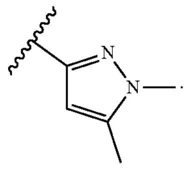 [SMILES: *c1cc(C)n(C)n1]

In some embodiments of Formula (Y2), $R^{5E}$ is furanyl optionally substituted with from 1-2 $R^{e5}$.

In some embodiments of Formula (Y2), $R^{5E}$ is phenyl optionally substituted with from 1-2 $R^{e5s}$.

In some embodiments of Formula (Y2), each occurrence of $R^{e5}$ is independently selected from the group consisting of $C_{1-6}$ alkoxy (e.g., methoxy); $C_{1-6}$ alkyl (e.g., methyl); $C_{1-6}$ haloalkyl (e.g., —$CF_3$); and $C_{1-6}$ haloalkoxy.

In some embodiments of Formula (Y2), $R^{5E}$ is N($C_{1-3}$ alkyl)$_2$, such as $NMe_2$.

In some embodiments of Formula (Y2), $R^{5E}$ is $C_{1-6}$ alkyl, such as methyl.

In some embodiments of Formula (Y2), the compound is selected from the group consisting of the compounds in Table 600, or a pharmaceutically acceptable salt thereof.

In another aspect, provided herein are compounds selected from the group consisting of the compounds in Table 500, or a pharmaceutically acceptable salt thereof. Compounds of Table 500 are useful e.g., as inhibitors of YTH domain-containing family proteins (YTHs).

In another aspect, provided herein are compounds of Formula (F1A) or (F1B):

Formula (F1A)

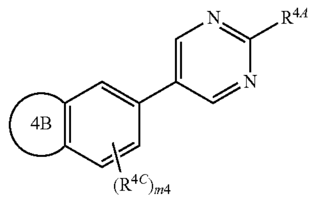

Formula (F1B)

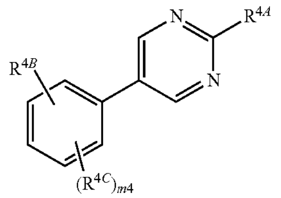

or a pharmaceutically acceptable salt thereof, wherein:

$R^{4A}$ is selected from the group consisting of: H, $C_{1-6}$ alkoxy, $C_{1-6}$ haloalkoxy, NR'R", and NR'—$(CH_2)_{n4}$—$R^{4D}$;

n4 is 2, 3, or 4;

$R^{4D}$ is $C_{1-6}$ alkoxy, $C_{1-6}$ haloalkoxy, —OH, or NR'R";

m4 is 0, 1, or 2;

$R^{4C}$ is selected from the group consisting of: halo; cyano; $C_{1-6}$ alkoxy; $C_{1-6}$ haloalkoxy; $C_{1-6}$ alkyl; $C_{1-6}$ haloalkyl; —OH; and NR'R";

Ring 4B is phenyl or 5-6 membered heteroaryl each optionally substituted with from 1-3 substituents independently selected from the group consisting of: halo; cyano; $C_{1-6}$ alkoxy; $C_{1-6}$ haloalkoxy; $C_{1-6}$ alkyl; $C_{1-6}$ haloalkyl; —OH; and NR'R";

$R^{4B}$ is selected from the group consisting of:

-$(L^{4A})_{p4}$-$R^{4E}$; and $C_{1-6}$ alkyl which is optionally substituted with from 1-3 substituents independently selected from the group consisting of: halo; cyano; $C_{1-6}$ alkoxy; $C_{1-6}$ haloalkoxy; $C_{1-6}$ alkyl; $C_{1-6}$ haloalkyl; —OH; and NR'R";

p4 is 0, 1, 2, or 3;

each $L^{4A}$ is independently selected from the group consisting of: —O—, —$CH_2$—, —C(=O)—, —N(R')—, and —$S(O)_{0-2}$—;

$R^{4E}$ is selected from the group consisting of $C_{6-10}$ aryl, 5-10 membered heteroaryl, $C_{3-10}$ cycloalkyl, and 4-10 membered heterocyclyl, each optionally substituted with from 1-3 substituents independently selected from the group consisting of: halo; cyano; $C_{1-6}$ alkoxy; $C_{1-6}$ haloalkoxy; $C_{1-6}$ alkyl; $C_{1-6}$ haloalkyl; —OH; and NR'R"; and each occurrence of R' and R" is independently H, $C_{1-3}$ alkyl, or $C_{3-6}$ cycloalkyl.

Compounds of Formula (F1A) and (F1B) are useful e.g., as inhibitors of fat-mass and obesity-associated protein (FTO).

In some embodiments of Formula (F1A) or (F1B), $R^{4A}$ is $C_{1-6}$ alkoxy, such as methoxy.

In some embodiments of Formula (F1A) or (F1B), $R^{4A}$ is NR'R", such as $NH_2$.

In some embodiments of Formula (F1A) or (F1B), $R^{4A}$ is NR'—$(CH_2)_{n4}$—$R^{4D}$.

In some embodiments of Formula (F1A) or (F1B), n4 is 2.

In some embodiments of Formula (F1A) or (F1B), $R^{4D}$ is $C_{1-6}$ alkoxy, such as methoxy.

In some embodiments of Formula (F1A) or (F1B), $R^{4D}$ is NH—$CH_2CH_2$—OMe.

In some embodiments of Formula (F1A) or (F1B), m4 is 0.

In some embodiments of Formula (F1A) or (F1B), m4 is 1, optionally wherein $R^{4C}$ is $C_{1-6}$ alkoxy, such as methoxy.

In some embodiments, the compound is a compound of Formula (F1A).

In some embodiments of Formula (F1A), Ring 4B is phenyl which is optionally substituted with from 1-3 substituents independently selected from the group consisting of: halo; cyano; $C_{1-6}$ alkoxy; $C_{1-6}$ haloalkoxy; $C_{1-6}$ alkyl; $C_{1-6}$ haloalkyl; —OH; and NR'R".

In some embodiments of Formula (F1A), Ring 4B is selected from the group consisting of:

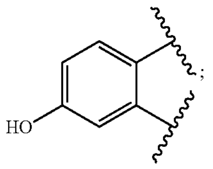
;
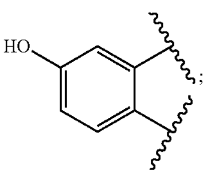
;
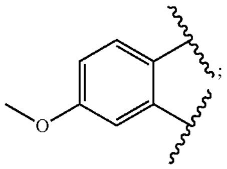
; and
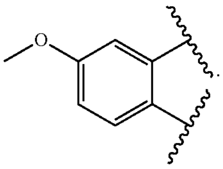
.

In some embodiments of Formula (F1A), Ring 4B is 5-6 membered heteroaryl, which is optionally substituted with from 1-3 substituents independently selected from the group consisting of: halo; cyano; $C_{1-6}$ alkoxy; $C_{1-6}$ haloalkoxy; $C_{1-6}$ alkyl; $C_{1-6}$ haloalkyl; —OH; and NR'R".

In some embodiments of Formula (F1A), Ring 4B is selected from the group consisting of:

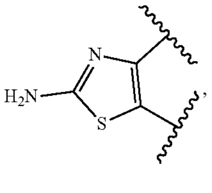
,
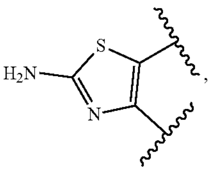
,
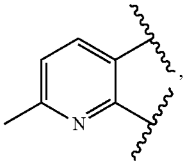
, and
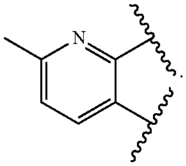
.

In some embodiments, the compound is a compound of Formula (F1B).

In some embodiments of Formula (F1B), $R^{4B}$ is -$(L^{4A})_{p4}$-$R^{4E}$.

In some embodiments of Formula (F1B), $R^{4B}$ is —$OCH_2R^{4E}$, —$OR^{4E}$, or —$NHR^{4E}$.

In some embodiments of Formula (F1B), $R^{4E}$ is phenyl optionally substituted with from 1-3 substituents independently selected from the group consisting of: halo; cyano; $C_{1-6}$ alkoxy; $C_{1-6}$ haloalkoxy; $C_{1-6}$ alkyl; $C_{1-6}$ haloalkyl; —OH; and NR'R", such as unsubstituted phenyl.

In some embodiments of Formula (F1A) or (F1B), the compound is selected from the group consisting of the compounds in Table 100, or a pharmaceutically acceptable salt thereof.

In another aspect, provided herein are compounds of Formula (F2):

Formula (F2)

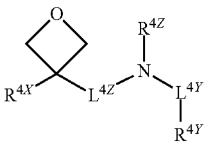

or a pharmaceutically acceptable salt thereof, wherein:

$R^{4X}$ is phenyl, $C_{3-6}$ cycloalkyl, 5-6 membered heterocyclyl, or 5-6 membered heteroaryl, each of which is optionally substituted with from 1-3 substituents independently selected from the group consisting of: halo; cyano; $C_{1-6}$ alkoxy; $C_{1-6}$ haloalkoxy; $C_{1-6}$ alkyl; $C_{1-6}$ haloalkyl; —OH; and NR'R";

$L^{4Z}$ is $C_{1-3}$ alkylene;

$R^{4Z}$ is H or -$L^{4Y}$-$R^{4Y}$;

each $L^{4Y}$ is independently a bond or $C_{1-3}$ alkylene;

each $R^{4Y}$ is independently selected from the group consisting of $C_{6-10}$ aryl, 5-10 membered heteroaryl, and 7-10 membered fused heterocyloalkyl-aryl, each of which is optionally substituted with from 1-3 substituents independently selected from the group consisting of: $R^{a4}$, $R^{b4}$, and -$(L^{b4})_{b4}$-$R^{b4}$;

each occurrence of $R^{a4}$ is selected from the group consisting of: independently selected from the group consisting of: halo; cyano; $C_{1-6}$ alkoxy; $C_{1-6}$ haloalkoxy; $C_{1-6}$ alkyl; hydroxy-$C_{1-6}$ alkyl; $C_{1-6}$ haloalkyl; $C_{1-6}$ thioalkoxy; $C_{1-6}$ thiohaloalkoxy; —OH; $NO_2$; and NR'R"; 4 is 1, 2, or 3;

each $L^{b4}$ is independently selected from the group consisting of: —O—, —$CH_2$—, —C(═O)—, —N(R')—, and —$S(O)_{0-2}$—;

each $R^{b4}$ is independently selected from the group consisting of $C_{6-10}$ aryl, 5-10 membered heteroaryl, $C_{3-10}$ cycloalkyl, and 4-10 membered heterocyclyl, each optionally substituted with from 1-3 substituents independently selected from the group consisting of: halo; cyano; $C_{1-6}$ alkoxy; $C_{1-6}$ haloalkoxy; $C_{1-6}$ alkyl; $C_{1-6}$ haloalkyl; —OH; and NR'R"; and each occurrence of R' and R" is independently H, $C_{1-3}$ alkyl, or $C_{3-6}$ cycloalkyl.

Compounds of Formula (F2) are useful e.g., as inhibitors of fat-mass and obesity-associated protein (FTO).

In some embodiments of Formula (F2), $R^{4X}$ is 5-6 membered heterocyclyl which is optionally substituted with from 1-3 substituents independently selected from the group consisting of: halo; cyano; $C_{1-6}$ alkoxy; $C_{1-6}$ haloalkoxy; $C_{1-6}$ alkyl; $C_{1-6}$ haloalkyl; —OH; and NR'R".

In some embodiments of Formula (F2), $R^{4X}$ is pyrrolidinyl optionally substituted with halo.

In some embodiments of Formula (F2), $R^{4X}$ is or

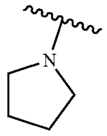

or

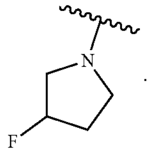

.

In some embodiments of Formula (F2), $R^{4X}$ is 5-6 membered heteroaryl (e.g., 5-membered heteroaryl) which is optionally substituted with from 1-3 substituents independently selected from the group consisting of: halo; cyano; $C_{1-6}$ alkoxy; $C_{1-6}$ haloalkoxy; $C_{1-6}$ alkyl; $C_{1-6}$ haloalkyl; —OH; and NR'R", such as wherein $R^{4X}$ is thienyl (e.g., thien-3-yl) or imidazolyl.

In some embodiments of Formula (F2), $R^{4X}$ is $C_{3-6}$ cycloalkyl (e.g., cyclopentyl) which is optionally substituted with from 1-3 substituents independently selected from the group consisting of: halo; cyano; $C_{1-6}$ alkoxy; $C_{1-6}$ haloalkoxy; $C_{1-6}$ alkyl; $C_{1-6}$ haloalkyl; —OH; and NR'R", such as wherein RX is cyclopentyl.

In some embodiments of Formula (F2), $L^{4Z}$ is $CH_2$.

In some embodiments of Formula (F2), $R^{4Z}$ is H.

In some embodiments of Formula (F2), $R^{4Z}$ is -$L^{4Y}$-$R^{4Y}$.

In some embodiments of Formula (F2), each $L^{4Y}$ is $CH_2$

In some embodiments of Formula (F2), each $R^{4Y}$ is independently selected from the group consisting of: $C_{6-10}$ aryl, 5-10 membered heteroaryl, and 7-10 membered fused heterocyloalkyl-aryl, each of which is optionally substituted with from 1-3 substituents independently selected from the group consisting of: $R^{a4}$ and $R^{b4}$.

In some embodiments of Formula (F2), each $R^{4Y}$ is independently 8-10 membered bicyclic heteroaryl optionally substituted with from 1-3 $R^{a4}$.

In some embodiments of Formula (F2), each $R^{4Y}$ is indolyl (e.g., indol-3-yl or indol-5-yl (e.g., indol-3-yl)) or quinolinyl (e.g., quinolin-3-yl), each optionally substituted with from 1-3 $R^{a4}$.

In some embodiments of Formula (F2), $R^{4Y}$ is

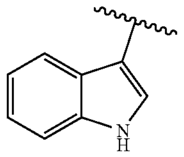

or

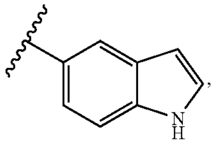

, each optionally substituted with from 1-2 $R^{a4}$.

In some embodiments of Formula (F2), each $R^{4Y}$ is 5-6 membered monocyclic heteroaryl substituted with $R^{b4}$ and further optionally substituted with from 1-2 $R^{a4}$.

In some embodiments of Formula (F2), the $R^{b4}$ is optionally substituted phenyl, such as unsubstituted phenyl.

In some embodiments of Formula (F2), $R^{4Y}$ is furanyl or thienyl, each of which is substituted with $R^{b4}$ and further optionally substituted with from 1-2 $R^{a4}$, optionally wherein the $R^{b4}$ is optionally substituted phenyl, such as unsubstituted phenyl.

In some embodiments of Formula (F2), $R^{4Y}$ is

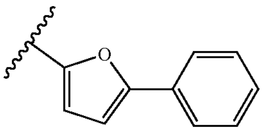

or

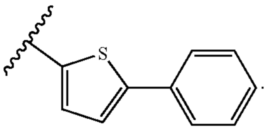

.

In some embodiments of Formula (F2), $R^{4Y}$ is $C_{6-10}$ aryl (such as phenyl or indanyl), each optionally substituted with from 1-4 $R^{a4}$.

In some embodiments of Formula (F2), $R^{4Y}$ is phenyl optionally substituted with from 1-2 $R^{a4}$.

In some embodiments of Formula (F2), $R^{4Y}$ is 7-10 membered fused heterocyloalkyl-aryl, such as benzodioxanyl, which is optionally substituted with from 1-2 $R^{a4}$.

In some embodiments of Formula (F2), $R^4$ is

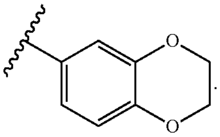 [SMILES: *c1ccc2c(c1)OCCO2]

.

In some embodiments of Formula (F2), the compound is selected from the group consisting of the compounds in Table 200, or a pharmaceutically acceptable salt thereof.

In another aspect, provided herein are compounds of Formula (F3):

Formula (F3)

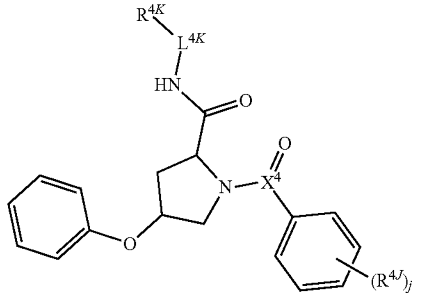

or a pharmaceutically acceptable salt thereof, wherein:

$L^{4K}$ is a bond or $CH_2$;

$R^{4K}$ is selected from the group consisting of: $C_{6-10}$ aryl and 5-10 membered heteroaryl, each optionally substituted with from 1-4 $R^{4L}$;

$X^4$ is C, S, or S(O);

j is 0, 1, 2, or 3;

each occurrence $R^{4J}$ and $R^{4L}$ is independently selected from the group consisting of: halo; cyano; $C_{1-6}$ alkyl; $C_{1-6}$ haloalkyl; $C_{1-6}$ alkoxy; $C_{1-6}$ haloalkoxy; $C_{1-6}$ thioalkoxy; $C_{1-6}$ thiohaloalkoxy; C(═O)$C_{1-6}$ alkyl; C(═O)O$C_{1-6}$ alkyl; C(O)NR'R"; $S(O)_2C_{1-6}$ alkyl; $S(O)_2$NR'R"; —OH; NR'R"; and $NO_2$; and each occurrence of R' and R" is independently H, $C_{1-3}$ alkyl, or $C_{3-6}$ cycloalkyl.

Compounds of Formula (F3) are useful e.g., as inhibitors of fat-mass and obesity-associated protein (FTO).

In some embodiments of Formula (F3), $L^{4K}$ is a bond.

In some embodiments of Formula (F3), $L^{4K}$ is $CH_2$.

In some embodiments of Formula (F3), $R^{4K}$ is phenyl optionally substituted with from 1-4 $R^{4L}$.

In some embodiments of Formula (F3), $R^{4K}$ is 6-membered heteroaryl, such as pyridyl, which is optionally substituted with from 1-4 $R^{4L}$.

In some embodiments of Formula (F3), each occurrence of $R^{4L}$ is independently selected from the group consisting of: halo (e.g., —F); cyano; $C_{1-6}$ alkyl (e.g., methyl); $C_{1-6}$ haloalkyl (e.g., $CF_3$); $C_{1-6}$ alkoxy (e.g., —OMe); $C_{1-6}$ haloalkoxy (e.g., —$OCF_3$); $C_{1-6}$ thioalkoxy (e.g., —SMe); $C_{1-6}$ thiohaloalkoxy; C(═O)$C_{1-6}$ alkyl (e.g., C(═O)Me); C(═O)O$C_{1-6}$ alkyl (e.g., C(═O)OMe); and OH.

In some embodiments of Formula (F3), $X^4$ is C.

In some embodiments of Formula (F3), $X^4$ is S(O).

In some embodiments of Formula (F3), j is 1, 2, or 3.

In some embodiments of Formula (F3), one occurrence of $R^{4J}$ is $C_{1-6}$ alkoxy, $C_{1-6}$ haloalkoxy, $C_{1-6}$ thioalkoxy, or $C_{1-6}$ halothioalkoxy.

In some embodiments of Formula (F3), one occurrence of $R^{4J}$ is $C_{1-6}$ alkoxy, $C_{1-6}$ haloalkoxy, $C_{1-6}$ thioalkoxy, or $C_{1-6}$ halothioalkoxy; and said occurrence of $R^{4J}$ is ortho to $X^4$, such as wherein said occurrence of $R^{4J}$ is $C_{1-6}$ alkoxy (e.g., methoxy).

In some embodiments of Formula (F3), one occurrence of $R^{4J}$ is $C_{1-6}$ alkoxy, $C_{1-6}$ haloalkoxy, $C_{1-6}$ thioalkoxy, or $C_{1-6}$ halothioalkoxy; and said occurrence of $R^{4J}$ is para to $X^4$, such as wherein said occurrence of $R^{4J}$ is $C_{1-6}$ alkoxy (e.g., methoxy).

In some embodiments of Formula (F3), the

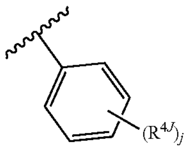

moiety is

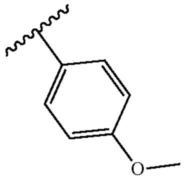

or

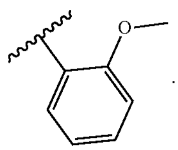

.

In some embodiments of Formula (F3), the compound has the following formula:

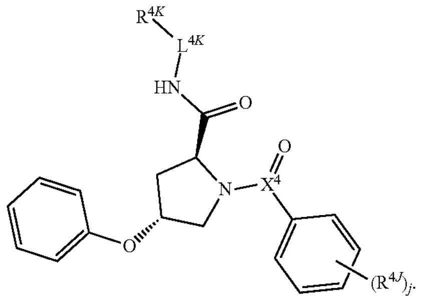

In some embodiments of Formula (F3), the compound is selected from the group consisting of the compounds in Table 300, or a pharmaceutically acceptable salt thereof.

In another aspect, provided herein are compounds of Formula (A1):

Formula (A1)

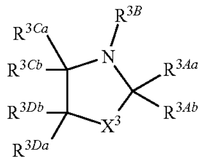

or a pharmaceutically acceptable salt thereof, wherein:

$X^3$ is selected from the group consisting of: 0, S, and $S(O)_{1-2}$;

$R^{3Aa}$ and $R^{3Ab}$ are independently H, $C_{1-6}$ alkyl, C(═O)OH, C(═O)O$C_{1-6}$ alkyl, C(═O)NR'R", 4-10 membered heterocyclyl, $C_{6-10}$ aryl, $C_{3-10}$ cycloalkyl, and 5-10 membered heteroaryl, wherein the 4-10 membered heterocyclyl, $C_{6-10}$ aryl, $C_{3-10}$ cycloalkyl, and 5-10 membered heteroaryl are each optionally substituted with from 1-4 $R^{a3}$; or $R^{3Aa}$ and $R^{3Ab}$ combine to form ═O;

$R^{3B}$ is selected from the group consisting of: H; C(═O)NR'R"; C(═O)O$C_{1-6}$ alkyl;

or $R^{3Aa}$ and $R^{3B}$ taken together with the ring atoms connecting them form a fused ring including from 4-6 ring atoms, wherein the fused ring is optionally substituted with from 1-4 substituents independently selected from the group consisting of: =O and $R^{a3}$;

$R^{3Ca}$, $R^{3Cb}$, $R^{3Da}$, and $R^{3Db}$ are each independently selected from the group consisting of: C(=O)OH; C(=O)$C_{1-6}$ alkyl; C(=O)NR'R"; $C_{1-6}$ alkyl optionally substituted with from 1-4 $R^{a3}$; and $-L^{3E}-R^{3E}$;

each $L^{3E}$ is independently a bond or $CH_2$;

each $R^{3E}$ is independently selected from the group consisting of: 4-10 membered heterocyclyl, $C_{6-10}$ aryl, $C_{3-10}$ cycloalkyl, and 5-10 membered heteroaryl, each optionally substituted with from 1-4 $R^{a3}$;

each occurrence of $R^{a3}$ is independently selected from the group consisting of: halo; cyano; $C_{1-6}$ alkyl; $C_{1-6}$ haloalkyl; $C_{6-10}$ aryl optionally substituted with $C_{1-3}$ alkyl and/or halo; $C_{1-6}$ alkoxy; $C_{1-6}$ haloalkoxy; $C_{1-6}$ thioalkoxy; $C_{1-6}$ thiohaloalkoxy; C(=O)$C_{1-6}$ alkyl; C(=O)O$C_{1-6}$ alkyl; C(=O)OH; C(O)NR'R"; $S(O)_2C_{1-6}$ alkyl; $S(O)_2$NR'R"; —OH; NR'R"; and $NO_2$; and each occurrence of R' and R" is independently H, $C_{1-3}$ alkyl, or $C_{3-6}$ cycloalkyl.

Compounds of Formula (A1) are useful e.g., as inhibitors of ALKB homolog 5 (ALKBH5).

In some embodiments of Formula (A1), $X^3$ is S.

In some embodiments of Formula (A1), $X^3$ is $S(O)_2$.

In some embodiments of Formula (A1), $X^3$ is O.

In some embodiments of Formula (A1), $R^{3Aa}$ is 4-10 membered heterocyclyl or $C_{3-10}$ cycloalkyl, which is substituted with C(=O)O$C_{1-6}$ alkyl or C(=O)OH, and further optionally substituted with from 1-2 $R^{a3}$; and $R^{3Ab}$ is H.

In some embodiments of Formula (A1), $R^{3Aa}$ is phenyl optionally substituted with from 1-3 $R^{a3}$; and $R^{3Ab}$ is H.

In some embodiments of Formula (A1), $R^{3Aa}$ is phenyl substituted with —OH, $C_{1-6}$ alkoxy, or $C_{1-6}$ haloalkoxy, and further optionally substituted with from 1-2 $R^{a3}$; and $R^{3Ab}$ is H.

In some embodiments of Formula (A1), $R^{3Aa}$ is 5-6 membered heteroaryl (e.g., furanyl or thienyl) substituted with phenyl and further optionally substituted with from 1-2 $R^{a3}$; and $R^{3Ab}$ is H.

In some embodiments of Formula (A1), $R^{3Aa}$ is

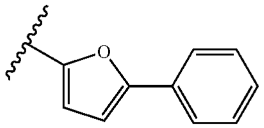

or

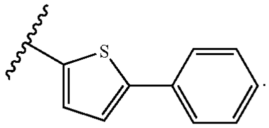

In some embodiments of Formula (A1), $R^{3Aa}$ and $R^{3Ab}$ are independently $C_{1-6}$ alkyl, such as $C_{1-3}$ alkyl, such as methyl.

In some embodiments of Formula (A1), $R^{3Aa}$ and $R^{3Ab}$ are both H.

In some embodiments of Formula (A1), $R^{3Aa}$ and $R^{3Ab}$ combine to form =O.

In some embodiments of Formula (A1), $R^{3B}$ is H.

In some embodiments of Formula (A1), $R^{3B}$ is C(=O)O$C_{1-6}$ alkyl such as C(=O)O-tBu.

In some embodiments of Formula (A1), $R^{3B}$ is C(=O)NR'R", such as C(=O)$NH_2$.

In some embodiments of Formula (A1), $R^{3Aa}$ and $R^{3B}$ together with the ring atoms connecting them form:

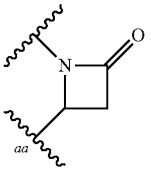

or

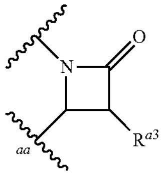

(e.g.,

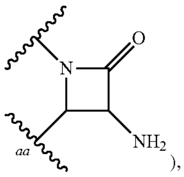

), wherein aa is the point of attachment to $X^3$.

In some embodiments of Formula (A1), $R^{3Ca}$ is C(=O)OH; C(=O)$C_{1-6}$ alkyl; or C(=O)NR'R".

In some embodiments of Formula (A1), $R^{3Cb}$ is H or $C_{1-6}$ alkyl, such as H or methyl. In some embodiments of Formula (A1), $R^{3Ca}$ and $R^{3Cb}$ are both H.

In some embodiments of Formula (A1), $R^{3Da}$ and $R^{3Db}$ are both H.

In some embodiments of Formula (A1), $R^{3Da}$ and $R^{3Db}$ are independently $C_{1-6}$ alkyl, such as methyl.

In some embodiments of Formula (A1), $R^{3Da}$ is $C_{1-6}$ alkyl such as methyl; and $R^{3Db}$ is $-L^{3E}-R^{3E}$, optionally wherein $R^{3E}$ is 5-6 membered heteroaryl.

In some embodiments of Formula (A1), the compound is selected from the group consisting of the compounds in Table 700, or a pharmaceutically acceptable salt thereof.

In another aspect, provided herein are compounds of Formula (A2A), (A2B), or (A2C):

Formula (A2A)

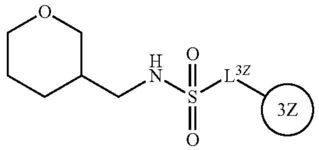

Formula (A2B)

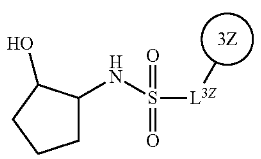

Formula (A2C)

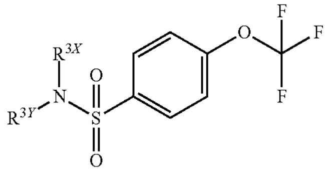

or a pharmaceutically acceptable salt thereof, wherein:

Ring 3Z is selected from the group consisting of: $C_{6-10}$ aryl; 5-10 membered heteroaryl; $C_{3-10}$ cycloalkyl; and 4-10 membered heterocyclyl, each optionally substituted with from 1-4 $R^{b3}$;

$R^{3X}$ is H or $C_{1-6}$ alkyl;

$R^{3Y}$ is $-L^{3W}-R^{3W}$;

-$L^{3W}$ and -$L^{3Z}$ are each independently a bond or $C_{1-4}$ alkylene optionally substituted with from 1-4 $R^{b3}$;

$R^{3W}$ is selected from the group consisting of: $C_{6-10}$ aryl; 5-10 membered heteroaryl; $C_{3-10}$ cycloalkyl; and 4-10 membered heterocyclyl, each optionally substituted with from 1-4 $R^{b3}$, or $R^{3W}$ is

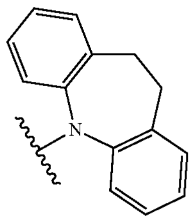 [SMILES: *N1c2ccccc2CCc2ccccc21]

optionally substituted with from 1-4 $R^{b3}$; or $R^{3X}$ and $R^{3Y}$ taken together with the nitrogen to which each is attached forms a 5-8 membered heterocyclyl optionally substituted with from 1-4 $R^{b3}$;

each occurrence of $R^{b3}$ is independently selected from the group consisting of: halo; cyano; $C_{1-6}$ alkyl; $C_{1-6}$ haloalkyl; $C_{6-10}$ aryl optionally substituted with $C_{1-3}$ alkyl and/or halo; $C_{1-6}$ alkoxy; $C_{1-6}$ haloalkoxy; $C_{1-6}$ thioalkoxy; $C_{1-6}$ thiohaloalkoxy; C(═O)$C_{1-6}$ alkyl; C(═O)$C_{3-6}$ cycloalkyl; OC(═O)$C_{1-6}$ alkyl; C(═O)O$C_{1-6}$ alkyl; C(═O)OH; C(O)NR'R"; $S(O)_2C_{1-6}$ alkyl; $S(O)_2$NR'R"; —OH; oxo; NR'R"; $NO_2$; $C_{3-6}$ cycloalkyl; and 4-8 membered heterocyclyl; and each occurrence of R' and R" is independently H, $C_{1-3}$ alkyl, or $C_{3-6}$ cycloalkyl.

Compounds of Formula (A2A), (A2B), or (A2C) are useful e.g., as inhibitors of ALKB homolog 5 (ALKBH5).

In some embodiments of Formula (A2A), (A2B), or (A2C), the compound is a compound of Formula (A2A).

In some embodiments, the compound is a compound of Formula (A2B).

In some embodiments, the compound is a compound of Formula (A2A).

In some embodiments of Formula (A2A) or (A2B), Ring 3Z is phenyl substituted with from 1-4 $R^{b3}$.

In some embodiments of Formula (A2A) or (A2B), one occurrence of $R^{b3}$ is $C_{1-6}$ haloalkoxy (e.g., $OCF_3$), C(═O)$C_{1-6}$ alkyl (e.g., C(═O)Me)), or $NO_2$.

In some embodiments of Formula (A2A) or (A2B), Ring 3Z is selected from the group consisting of:

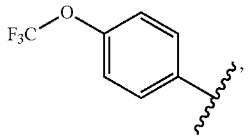, 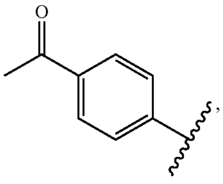, and

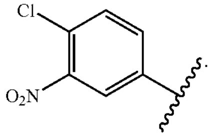.

In some embodiments of Formula (A2A) or (A2B), Ring 3Z is naphthyl or 5-10 membered heteroaryl each optionally substituted with from 1-4 $R^{b3}$, such as wherein Ring 3Z is pyridyl, furanyl, thienyl, chromenonyl, or imidazolyl, each optionally substituted with from 1-4 $R^{b3}$.

In some embodiments of Formula (A2A) or (A2B), $L^{3Z}$ is a bond.

In some embodiments of Formula (A2A) or (A2B), $L^{3Z}$ is $C_{1-3}$ alkylene optionally substituted with from 1-3 substituents independently selected from the group consisting of halo and —OH.

In some embodiments, the compound is a compound of Formula (A2C).

In some embodiments of Formula (A2C), $R^{3X}$ is H.

In some embodiments of Formula (A2C), $R^{3X}$ is $C_{1-6}$ alkyl such as methyl.

In some embodiments of Formula (A2C), $L^{3W}$ is a bond.

In some embodiments of Formula (A2C), $L^{3W}$ is $C_{1-3}$ alkylene optionally substituted with from 1-3 substituents independently selected from the group consisting of halo and —OH.

In some embodiments of Formula (A2C), $R^{3W}$ is phenyl optionally substituted with from 1-4 $R^{b3}$.

In some embodiments of Formula (A2C), $R^{3W}$ is selected from the group consisting of:

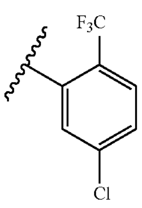
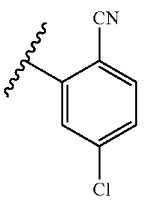
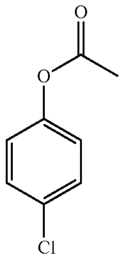

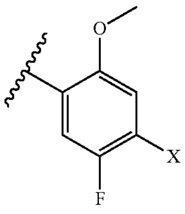

X = F, Cl

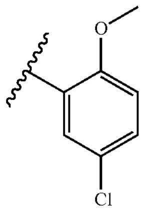
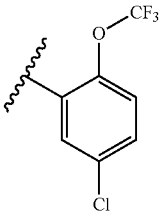

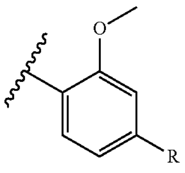

R = F, $CH_3$

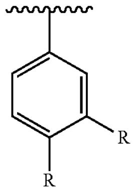

R = $CF_3$, $OCH_3$, $OCF_3$

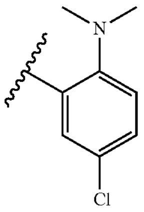

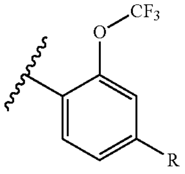

R = F, $CH_3$

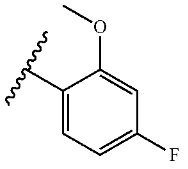

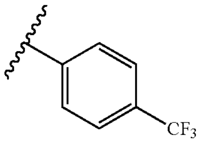
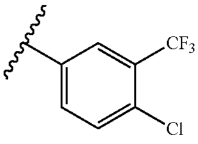

-continued

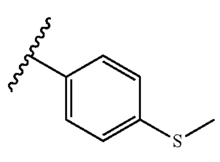
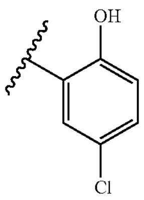
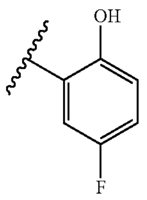

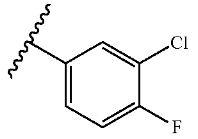
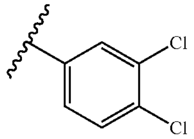

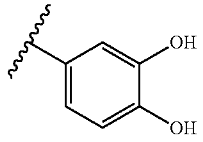
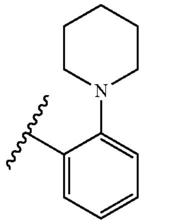

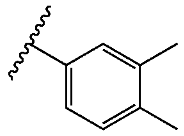
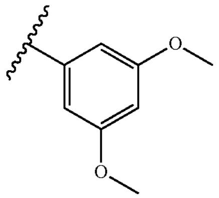

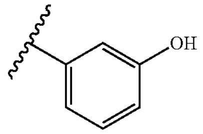

In some embodiments of Formula (A2C), $R^{3W}$ is naphthyl or 5-10 membered heteroaryl each optionally substituted with from 1-4 $R^{b3}$.

In some embodiments of Formula (A2C), $R^{3W}$ is pyridyl, pyrazinyl, furanyl, thienyl, chromenonyl, or imidazolyl, each optionally substituted with from 1-4 $R^{b3}$.

In some embodiments of Formula (A2C), $R^{3W}$ is selected from the group consisting of:

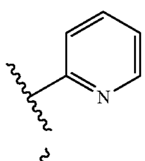, 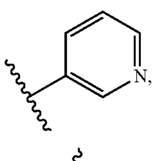, 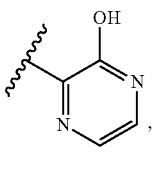,

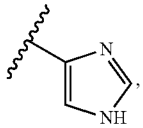, and 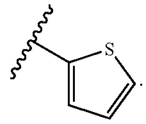.

In some embodiments of Formula (A2C), $R^{3X}$ and $R^{3Y}$ taken together with the nitrogen to which each is attached forms a 5-8 membered heterocyclyl optionally substituted with from 1-4 $R^{b3}$.

In some embodiments of Formula (A2C), $R^{3W}$ is

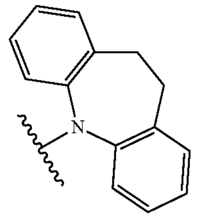 [SMILES: *N1c2ccccc2CCc2ccccc21]

optionally substituted with from 1-4 $R^{b3}$.

In some embodiments of Formula (A2C), $R^{3X}$ and $R^{3Y}$ taken together with the nitrogen to which each is attached forms

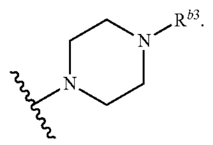

In some embodiments of Formula (A2A), (A2B), or (A2C), the compound is selected from the group consisting of the compounds in Table 800, or a pharmaceutically acceptable salt thereof.

In another aspect, provided herein are compounds of Formula (A3):

Formula (A3)

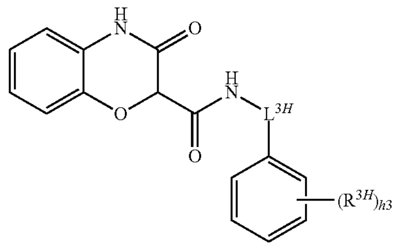

or a pharmaceutically acceptable salt thereof, wherein:

$L^{3H}$ is a bond or $CH_2$;

h3 is 0, 1, 2, or 3;

each occurrence $R^{3H}$ is independently selected from the group consisting of: halo; cyano; $C_{1-6}$ alkyl; $C_{1-6}$ haloalkyl; $C_{6-10}$ aryl optionally substituted with $C_{1-3}$ alkyl and/or halo; $C_{1-6}$ alkoxy; $C_{1-6}$ haloalkoxy; $C_{1-6}$ thioalkoxy; $C_{1-6}$ thiohaloalkoxy; $C(=O)C_{1-6}$ alkyl; $C(=O)C_{3-6}$ cycloalkyl; $OC(=O)C_{1-6}$ alkyl; $C(=O)OC_{1-6}$ alkyl; $C(=O)OH$; $C(O)NR'R''$; $S(O)_2C_{1-6}$ alkyl; $S(O)_2NR'R''$; —OH; NR'R''; $NO_2$; $C_{3-6}$ cycloalkyl; and 4-8 membered heterocyclyl; and each occurrence of R' and R'' is independently H, $C_{1-3}$ alkyl, or $C_{3-6}$ cycloalkyl.

Compounds of Formula (A3) are useful e.g., as inhibitors of ALKB homolog 5 (ALKBH5).

In some embodiments of Formula (A3), $L^3H$ is a bond.

In some embodiments of Formula (A3), $L^3H$ is $CH_2$.

In some embodiments of Formula (A3), h3 is 1 or 2.

In some embodiments of Formula (A3), each $R^{3H}$ is independently selected from the group consisting of: halo (e.g., —F or —Cl); $C_{1-6}$ alkyl (e.g., methyl); $C_{1-6}$ haloalkyl (e.g., —$CF_3$); $C_{1-6}$ alkoxy (e.g., OMe); $C_{1-6}$ haloalkoxy; $C_{1-6}$ thioalkoxy (e.g., —SMe); and C(═O)O$C_{1-6}$ alkyl (e.g., C(═O)OMe).

In some embodiments of Formula (A3), the compound is selected from the group consisting of the compounds in Table 900, or a pharmaceutically acceptable salt thereof.

In another aspect, provided herein are compounds of Formula (M1):

Formula (M1)

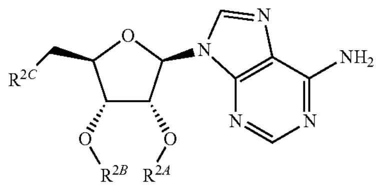

or a pharmaceutically acceptable salt thereof, wherein:

$R^{2A}$ and $R^{2B}$ are each independently H or $C_{1-3}$ alkyl; or $R^{2A}$ and $R^{2B}$ taken together with the atoms connecting them form a 5-8 membered ring which is optionally substituted with from 1-3 $C_{1-3}$ alkyl;

$R^{2C}$ is —N($R^{2E}$)-$L^{2C}$-$R^{2D}$ or -(5-6 heteroarylene)-$L^{2C}$-$R^{2D}$;

$R^{2E}$ is H or -$L^{2C}$-$R^{2D}$;

each $L^{2C}$ is independently $C_{1-3}$ alkylene; and each $R^{2D}$ is independently selected from the group consisting of:

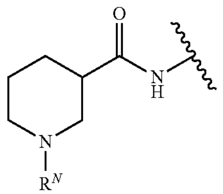

and

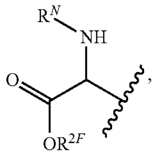

, wherein each $R^N$ is independently H, $C_{1-6}$ alkyl, C(═O)O$C_{1-6}$ alkyl, or C(═O)$C_{1-6}$ alkyl, and $R^{2F}$ is H or $C_{1-6}$ alkyl.

Compounds of Formula (M1) are useful e.g., as inhibitors of methyltransferase like 3 (Mettl3 or MT-A70) or methyltransferase like-14 (Mettl14).

In some embodiments of Formula (M1), $R^{2A}$ and $R^{2B}$ are both H.

In some embodiments of Formula (M1), $R^{2A}$ and $R^{2B}$ taken together with the atoms connecting them form

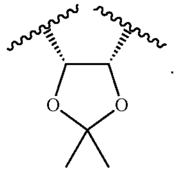 [SMILES: *[C@@H]1OC(C)(C)O[C@@H]1*]

.

In some embodiments of Formula (M1), $R^{2C}$ is —N($R^{2E}$)-$L^{2C}$-$R^{2D}$.

In some embodiments of Formula (M1), $R^{2E}$ is H.

In some embodiments of Formula (M1), $R^{2E}$ is -$L^{2C}$-$R^{2D}$.

In some embodiments of Formula (M1), each $L^{2C}$ is —$CH_2CH_2$—.

In some embodiments of Formula (M1), each $R^{2D}$ is

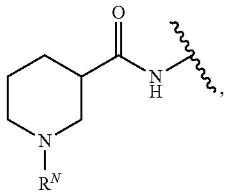

, such as

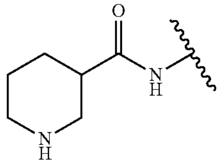

or

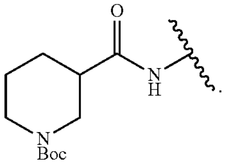

.

In some embodiments of Formula (M1), each $R^{2D}$ is

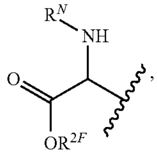

, such as

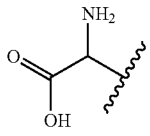

or

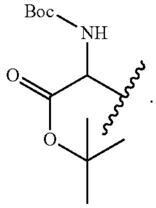

.

In some embodiments of Formula (M1), one $R^{2D}$ is

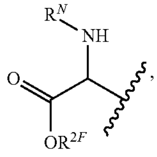

, such as

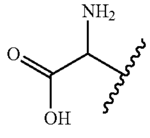

or

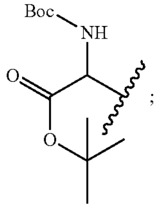

;

and the other $R^{2D}$ is

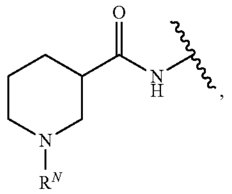

such as

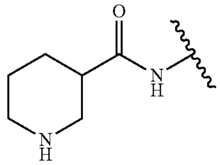

or

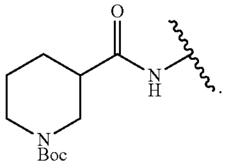

In some embodiments of Formula (M1), $R^{2C}$ is -(5-6 heteroarylene)-$L^{2C}$-$R^{2D}$.

In some embodiments of Formula M) $R^{2C}$ is

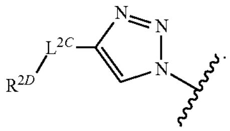

In some embodiments of Formula (M1), $L^{2C}$ is —$CH_2$—.

In some embodiments of Formula (M1), $L^{2D}$ is

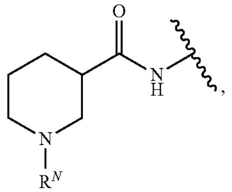

such as

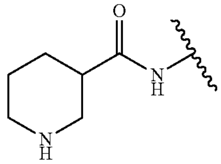

or

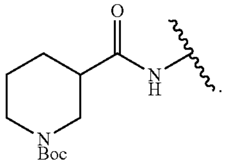

In some embodiments of Formula (M1), the compound is selected from the group consisting of the compounds in Table 1200.

In another aspect, provided herein are compounds of Formula (M2):

Formula (M2)

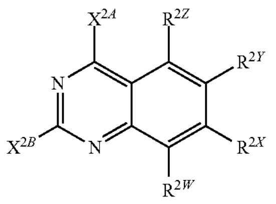

or a pharmaceutically acceptable salt thereof, wherein:

each $R^{2Z}$, $R^{2Y}$, $R^{2X}$, and $R^{2W}$ are independently selected from the group consisting of: H, halo, cyano, $C_{1-6}$ alkyl, $C_{1-6}$ haloalkyl, $C_{1-6}$ alkoxy, $C_{1-6}$ haloalkoxy, OH, and NR'R";

$X^{2A}$ is independently selected from the group consisting of: $NH_2$, $NH(C_{1-10}$ alkyl), $N(C_{1-10}$ alkyl$)_2$,

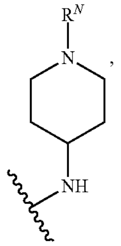

,

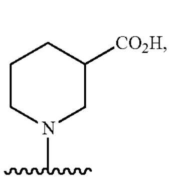

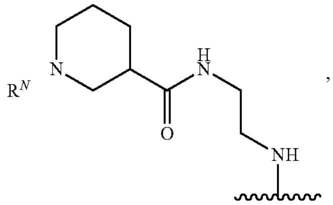

, and

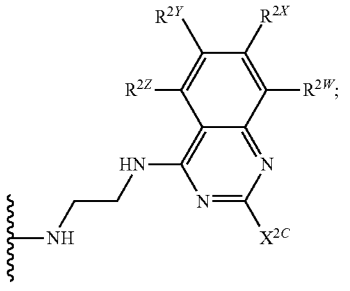

$X^{2B}$ and $X^{2C}$ are independently selected from the group consisting of: halo, $NH_2$, $NH(C_{1-10}$ alkyl), $N(C_{1-10}$ alkyl$)_2$,

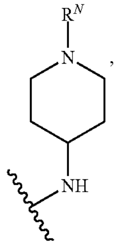

,

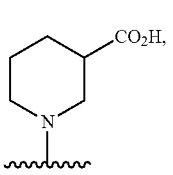

and

-continued

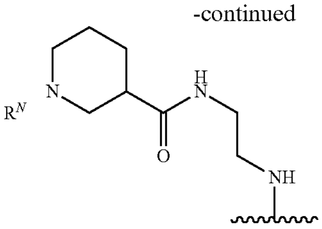

;

each $R^N$ is independently H, $C_{1-6}$ alkyl, C(═O)O$C_{1-6}$ alkyl, or C(═O)$C_{1-6}$ alkyl; and each occurrence of R' and R" is independently H or $C_{1-6}$ alkyl.

In some embodiments of Formula (M2), the compound is other than:

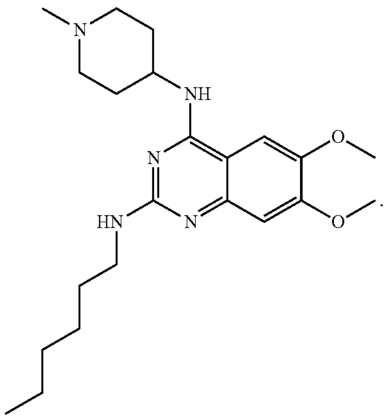 [SMILES: CCCCCCNc1nc(NC2CCN(C)CC2)c2cc(OC)c(OC)cc2n1]

Compounds of Formula (M2) are useful e.g., as inhibitors of methyltransferase like 3 (Mettl3 or MT-A70) or methyltransferase like-14 (Mettl14).

In some embodiments of Formula (M2), $R^{2Z}$ and $R^{2W}$ is H.

In some embodiments of Formula (M2), each of $R^{2X}$ and $R^{2Y}$ is independently $C_{1-6}$ alkoxy, such as methoxy.

In some embodiments of Formula (M2), $X^{2B}$ is halo, such as —Cl.

In some embodiments of Formula (M2), $X^{2B}$ is $NH_2$.

In some embodiments of Formula (M2), $X^{2B}$ is NH($C_{1-10}$ alkyl), such as NH($C_{4-10}$ alkyl), such as

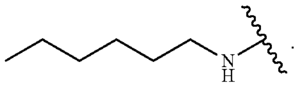 [SMILES: *NCCCCCC]

In some embodiments of Formula (M2), $X^{2B}$ is

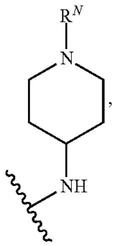

such as

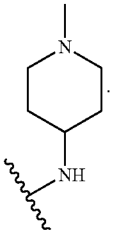 [SMILES: *NC1CCN(C)CC1]

In some embodiments of Formula (M2), $X^{2B}$ is

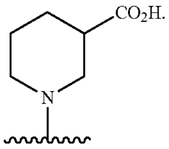 [SMILES: *N1CCCC(C(=O)O)C1]

In some embodiments of Formula (M2), $X^{2A}$ is NH($C_{1-10}$ alkyl), such as NH($C_{4-10}$ alkyl), such as

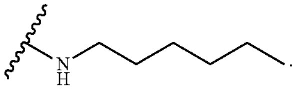 [SMILES: *NCCCCCC]

In some embodiments of Formula (M2), $X^{2A}$ is $NH_2$.

In some embodiments of Formula (M2), $X^{2A}$ is

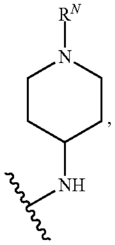

such as

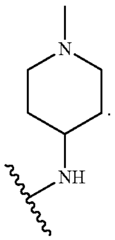 [SMILES: *NC1CCN(C)CC1]

In some embodiments of Formula (M2), $X^{2A}$ is

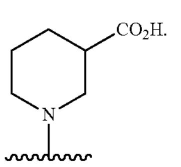 [SMILES: *N1CCCC(C(=O)O)C1]

In some embodiments of Formula (M2), $X^{2A}$ is

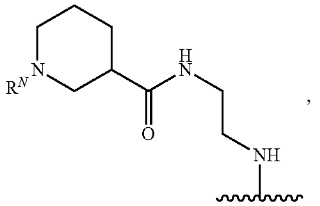 [SMILES: *NCCNC(=O)C1CCCNC1]

such as

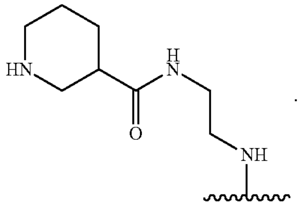 [SMILES: *NCCNC(=O)C1CCCNC1]

In some embodiments of Formula (M2), $X^{2A}$ is

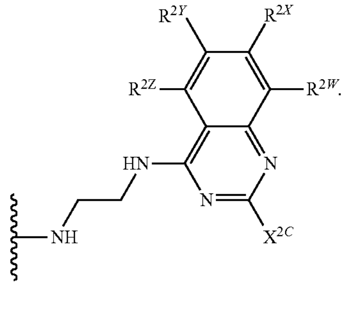

In some embodiments of Formula (M2), $X^{2C}$ is halo.

In some embodiments of Formula (M2), $X^{2C}$ is $NH(C_{1-10}$ alkyl), such as $NH(C_{4-10}$ alkyl), such as

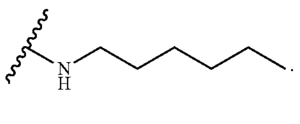 [SMILES: *NCCCCCC]

In some embodiments of Formula (M2), the compound is selected from the group consisting of the compounds in Table 1310, or a pharmaceutically acceptable salt thereof.

In another aspect, provided herein are compounds selected from the group consisting of the compounds in Table 1100, or a pharmaceutically acceptable salt thereof.

Compounds of Table 1100 are useful e.g., as inhibitors of methyltransferase like 3 (Mettl3 or MT-A70) or methyltransferase like-14 (Mettl14).

Also provided herein are polynucleotides (e.g., small hairpin RNAs (shRNAs), micro RNA (miRNAs), small interfering RNA (siRNAs), antisense nucleic acids, CRISPR-sgRNAs) that inhibit one or more of one or more of methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), or tyrosine-protein phosphatase non-receptor type 2 (PTPN2).

In some embodiments, the polynucleotide inhibits (e.g., selectively inhibits) a target selected from the group consisting of: methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), and tyrosine-protein phosphatase non-receptor type 2 (PTPN2).

In some embodiments, the polynucleotide has a nucleotide sequence identity of at least 75% (e.g., at least 80%, at least 85%, at least 90%, at least 95%, at least 97%, at least 98%, at least 99%) of a polynucleotide sequence of any one of Examples B1 to B-10. In some embodiments, the polynucleotide is selected from a polynucleotide sequence of any one of Examples B1 to B-10.

In some embodiments, the polynucleotide has a nucleotide sequence identity of at least 75% (e.g., at least 80%, at least 85%, at least 90%, at least 95%, at least 97%, at least 98%, at least 99%) of a polynucleotide sequence of any one of FIG. 119 or 120. In some embodiments, the polynucleotide is selected from a polynucleotide sequence of any one of FIG. 119 or 120.

III. Pharmaceutical Compositions

Also provided herein are pharmaceutical compositions comprising:

(i) an inhibitor, wherein the inhibitor inhibits one or more m6A writers (e.g., methyltransferase like 3 (Mettl3 or MT-A70) or methyltransferase like-14 (Mettl14)), m6Am writers (e.g., phosphorylated CTD interacting factor 1 (PCIF1), or Mettl3/14), m6A erasers (e.g., fat-mass and obesity-associated protein (FTO) or ALKB homolog 5 (ALKBH5)), m6Am erasers (e.g., FTO), m6A readers (e.g., YTH domain-containing family proteins (YTHs)), YTF domain family member 1 (YTHDF 1), YTF domain family member 2 (YTHDF 2), YTF domain family member 3 (YTHDF 3), or tyrosine-protein phosphatase non-receptor type 2 (PTPN2); and (ii) a pharmaceutically acceptable carrier.

Accordingly, in some embodiments, provided herein are pharmaceutical compositions comprising:

(i) an inhibitor, wherein the inhibitor inhibits one or more of methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), or tyrosine-protein phosphatase non-receptor type 2 (PTPN2); and (ii) a pharmaceutically acceptable carrier.

In some embodiments, the inhibitor inhibits (e.g., selectively inhibits) a target selected from the group consisting of: methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), and tyrosine-protein phosphatase non-receptor type 2 (PTPN2).

In some embodiments, the inhibitor comprises a therapeutic agent.

In some embodiments, the therapeutic agent comprises at least one of a small hairpin RNA (shRNA), a micro RNA (miRNA), a small interfering RNA (siRNA), a small molecule inhibitor, an antisense nucleic acid, a peptide, a virus, a CRISPR-sgRNA, or combinations thereof.

In some embodiments, the therapeutic agent comprises a gene-editing factor.

In some embodiments, the gene-editing factor comprises CRISPR/Cas9 reagents.

In some embodiments, the therapeutic agent comprises is a lentivirus.

In some embodiments, the lentivirus comprises a lentiviral vector encoding at least one of a small hairpin RNA (shRNA), a microRNA (miRNA), a small interfering RNA (siRNA), a small molecule inhibitor, an antisense nucleic acid, a peptide, a virus, a CRISPR-sgRNA, or combinations thereof.

In some embodiments, the lentivirus encodes a gene, wherein the gene expresses a protein gene product, wherein the protein gene product is selected from methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), or tyrosine-protein phosphatase non-receptor type 2 (PTPN2).

In some embodiments, the gene expresses a wild type protein gene product.

In some embodiments, the gene expresses a protein gene product comprising a mutation. In some embodiments, the mutation is a suppressor mutation. In some embodiments, the mutation is a dominant mutation.

In some embodiments, the therapeutic agent is an antisense nucleic acid directed to a gene, wherein the gene expresses a protein gene product, wherein the protein gene product is selected from methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), or tyrosine-protein phosphatase non-receptor type 2 (PTPN2).

In some embodiments, the inhibitor is a compound selected from the group consisting of a compound of Formula (PT1) (e.g., a compound of Table 1000), a compound of Formula (Y1) (e.g., a compound of Table 400), a compound of Formula (Y2) (e.g., a compound of Table 600), a compound of Table 500, a compound of Formula (F1A) or (F1B) (e.g., a compound of Table 100), a compound of Formula (F2) (e.g., a compound of Table 200), a compound of Formula (F3) (e.g., a compound of Table 300), a compound of Formula (A1) (e.g., a compound of Table 700), a compound of Formula (A2A), (A2B), or (A2C) (e.g., a compound of Table 800), a compound of Formula (A3) (e.g., a compound of Table 900), a compound of Table 1100, a compound of Formula M1 (e.g., a compound of Table 1200), and a compound of Formula M2 (e.g., a compound of Table 1310), or a pharmaceutically acceptable salt thereof, In some embodiments, the inhibitor is a polynucleotide as defined in FIG. 119 or 120.

In some embodiments, the inhibitor inhibits tyrosine-protein phosphatase non-receptor type 2 (PTPN2). In some embodiments, the inhibitor comprises at least one of a small hairpin RNA (shRNA), micro RNA (miRNA), a small interfering RNA (siRNA), a small molecule inhibitor, an antisense nucleic acid, a peptide, a virus, a CRISPR-sgRNA, or combinations thereof. In some embodiments, the inhibitor is a CRISPR-sgRNA, such as a CRISPR-sgRNA defined in FIG. 119. In some embodiments, inhibitor is a small hairpin RNA (shRNA), a micro RNA (miRNA) or a small interfering RNA (siRNA), such as a polynucleotide as defined in FIG. 120. In some embodiments, the inhibitor is a small molecule inhibitor. In some embodiments, the inhibitor is a compound of Formula (PT1) (e.g., a compound of Table 1000), or a pharmaceutically acceptable salt thereof.

In some embodiments, the inhibitor inhibits one or more of YTH domain-containing family proteins (YTHs). In some embodiments, wherein the inhibitor comprises at least one of a small hairpin RNA (shRNA), a micro RNA (miRNA), a small interfering RNA (siRNA), a small molecule inhibitor, an antisense nucleic acid, a peptide, a virus, a CRISPR-sgRNA, or combinations thereof. In some embodiments, the inhibitor is a CRISPR-sgRNA, such as a CRISPR-sgRNA defined in FIG. 119. In some embodiments, the inhibitor is a small hairpin RNA (shRNA), a micro RNA (miRNA) or a small interfering RNA (siRNA), such as a polynucleotide as defined in FIG. 120. In some embodiments, the inhibitor is a small molecule. In some embodiments, the inhibitor is a compound of Formula (Y1) (e.g., a compound of Table 400), or a pharmaceutically acceptable salt thereof. In some embodiments, the inhibitor is a compound of Table 500, or a pharmaceutically acceptable salt thereof. In some embodiments, the inhibitor is a compound a compound of Formula (Y2) (e.g., a compound of Table 600), or a pharmaceutically acceptable salt thereof.

In some embodiments, the inhibitor inhibits fat-mass and obesity-associated protein (FTO). In some embodiments, the inhibitor comprises at least one of a small hairpin RNA (shRNA), a micro RNA (miRNA), a small interfering RNA (siRNA), a small molecule inhibitor, an antisense nucleic acid, a peptide, a virus, a CRISPR-sgRNA, or combinations thereof. In some embodiments, the inhibitor is a CRISPR-sgRNA, such as a CRISPR-sgRNA defined in FIG. 119. In some embodiments, the inhibitor is a small hairpin RNA (shRNA), a micro RNA (miRNA) or a small interfering RNA (siRNA), such as a polynucleotide as defined in FIG. 120. In some embodiments, the inhibitor is a small molecule inhibitor. In some embodiments, the inhibitor is a compound of Formula (F1A) or (F1B) (e.g., a compound of Table 100). In some embodiments, the inhibitor is a compound of Formula (F2) (e.g., a compound of Table 200), or a pharmaceutically acceptable salt thereof. In some embodiments, the inhibitor is a compound of Formula (F3) (e.g., a compound of Table 300), or a pharmaceutically acceptable salt thereof.

In some embodiments, the inhibitor inhibits ALKB homolog 5 (ALKBH5). In some embodiments, the inhibitor comprises at least one of a small hairpin RNA (shRNA), a micro RNA (miRNA), a small interfering RNA (siRNA), a small molecule inhibitor, an antisense nucleic acid, a peptide, a virus, a CRISPR-sgRNA, or combinations thereof. In some embodiments, the inhibitor is a CRISPR-sgRNA, such as a CRISPR-sgRNA defined in FIG. 119. In some embodiments, the inhibitor is a small hairpin RNA (shRNA), a micro RNA (miRNA) or a small interfering RNA (siRNA), such as a polynucleotide as defined in FIG. 120. In some embodiments, the inhibitor is a small molecule inhibitor. In some embodiments, the inhibitor is a compound of Formula (A1) (e.g., a compound of Table 700), or a pharmaceutically acceptable salt thereof. In some embodiments, the inhibitor is a compound of Formula (A2A), (A2B), or (A2C) (e.g., a compound of Table 800), or a pharmaceutically acceptable salt thereof. In some embodiments, the inhibitor is a compound of Formula (A3) (e.g., a compound of Table 900), or a pharmaceutically acceptable salt thereof.

In some embodiments, the inhibitor inhibits methyltransferase like 3 (Mettl3 or MT-A70) and/or methyltransferase like-14 (Mettl14). In some embodiments, the inhibitor comprises at least one of a small hairpin RNA (shRNA), a micro RNA (miRNA), a small interfering RNA (siRNA), a small molecule inhibitor, an antisense nucleic acid, a peptide, a virus, a CRISPR-sgRNA, or combinations thereof. In some embodiments, the inhibitor is a CRISPR-sgRNA, such as a CRISPR-sgRNA defined in FIG. 119. In some embodiments, the inhibitor is a small hairpin RNA (shRNA), a micro RNA (miRNA) or a small interfering RNA (siRNA), such as a polynucleotide as defined in FIG. 120. In some embodiments, the inhibitor is a small molecule inhibitor. In some embodiments, the inhibitor is a compound of Table 1100, or a pharmaceutically acceptable salt thereof. In some embodiments, the inhibitor is a compound of Formula M1 (e.g., a compound of Table 1200), or a pharmaceutically acceptable salt thereof. In some embodiments, the inhibitor is a compound of Formula M2 (e.g., a compound of Table 1310), or a pharmaceutically acceptable salt thereof, In some embodiments, the inhibitor inhibits phosphorylated CTD interacting factor 1 (PCIF1). In some embodiments, the inhibitor comprises at least one of a small hairpin RNA (shRNA), a micro RNA (miRNA), a small interfering RNA (siRNA), a small molecule inhibitor, an antisense nucleic acid, a peptide, a virus, a CRISPR-sgRNA, or combinations thereof. In some embodiments, the inhibitor is a CRISPR-sgRNA, such as a CRISPR-sgRNA defined in FIG. 119. In some embodiments, the inhibitor is a small hairpin RNA (shRNA), a micro RNA (miRNA) or a small interfering RNA (siRNA), such as a polynucleotide as defined in FIG. 120. In some embodiments, the inhibitor is a small molecule inhibitor.

In some embodiments, the inhibitor inhibits YTF domain family member 2 (YTHDF 2) or YTF domain family member 3 (YTHDF 3). In some embodiments, the inhibitor comprises at least one of a small hairpin RNA (shRNA), a micro RNA (miRNA), a small interfering RNA (siRNA), a small molecule inhibitor, an antisense nucleic acid, a peptide, a virus, a CRISPR-sgRNA, or combinations thereof. In some embodiments, the inhibitor is a CRISPR-sgRNA, such as a CRISPR-sgRNA defined in FIG. 119. In some embodiments, the inhibitor is a small hairpin RNA (shRNA), a micro RNA (miRNA) or a small interfering RNA (siRNA), such as a polynucleotide as defined in FIG. 120. In some embodiments, the inhibitor is a small molecule inhibitor.

In an aspect is provided a pharmaceutical composition including a compound described herein and a pharmaceutically acceptable excipient.

Disclosed herein are pharmaceutical compositions including an inhibitor (e.g., a compound) described herein and a pharmaceutically acceptable excipient. Non-limiting embodiments are disclosed in one or more of U.S. Provisional Application Ser. No. 62/914,914, filed on Oct. 14, 2019; U.S. Provisional Application Ser. No. 62/971,701, filed on Feb. 7, 2020; U.S. Provisional Application Ser. No. 63/059,939, filed on Jul. 31, 2020; and U.S. Provisional Application Ser. No. 63/074,421, filed on Sep. 3, 2020, each of which is incorporated herein by reference in its entirety (including the appendices incorporated therein).

Also provided herein, inter alia, are compositions that inhibit the activity of demethylases FTO (fat mass and obesity-associated protein) or ALKBH5. Both of these demethylases are expressed by cancer stem cells (e.g., glioblastoma stem cells). Inhibition of FTO and/or ALKBH5 was found to reduce the size of neuro organoids established from glioblastoma cancer stem cells. The compositions provided herein as inhibitors of FTO or ALKBH5 include small molecules, shRNA, siRNA, miRNA, antisense nucleic acids, and CRISPRsgRNAs compositions designed to inhibit the activity of these demethylases. Inhibition may be achieved through direct binding to the demethylase (e.g., via small molecules), prevention of translations and/or degradation of mRNA (e.g., via antisense nucleic acids, shRNA, siRNA, miRNA), or gene silencing (i.e., prevention of translation) using, e.g., CRISPR-sgRNA compositions.

Small molecules have been designed to inhibit the activity of FTO or ALKBH5. Non-limiting examples of ALKBH5 inhibitors include: a compound of Formula (A1) (e.g., a compound of Table 700), a compound of Formula (A2A), (A2B), or (A2C) (e.g., a compound of Table 800), or a compound of Formula (A3) (e.g., a compound of Table 900), or a pharmaceutically acceptable salt thereof. Thus, in one aspect is provided a compound of Formula (A1) (e.g., a compound of Table 700), a compound of Formula (A2A), (A2B), or (A2C) (e.g., a compound of Table 800), or a compound of Formula (A3) (e.g., a compound of Table 900), or a pharmaceutically acceptable salt thereof. In an aspect is provided a pharmaceutical composition including a pharmaceutically acceptable excipient and a compound of Formula (A1) (e.g., a compound of Table 700), a compound of Formula (A2A), (A2B), or (A2C) (e.g., a compound of Table 800), or a compound of Formula (A3) (e.g., a compound of Table 900), or a pharmaceutically acceptable salt thereof. Non-limiting examples of FTO inhibitors include: a compound of Formula (F1A) or (F1B) (e.g., a compound of Table 100), a compound of Formula (F2) (e.g., a compound of Table 200), or a compound of Formula (F3) (e.g., a compound of Table 300), or a pharmaceutically acceptable salt thereof. Thus, in one aspect is provided a compound of Formula (F1A) or (F1B) (e.g., a compound of Table 100), a compound of Formula (F2) (e.g., a compound of Table 200), or a compound of Formula (F3) (e.g., a compound of Table 300), or a pharmaceutically acceptable salt thereof. In an aspect is provided a pharmaceutical composition including a pharmaceutically acceptable excipient and a compound of Formula (F1A) or (F1B) (e.g., a compound of Table 100), a compound of Formula (F2) (e.g., a compound of Table 200), or a compound of Formula (F3) (e.g., a compound of Table 300), or a pharmaceutically acceptable salt thereof.

shRNAs have also been engineered to inhibit the activity of FTO or ALKBH5. FIG. 120 shows shRNAs useful for inhibiting demethylases including FTO and ALKBH5. Therefore, in one aspect is provided a nucleic acid having a sequence shown in FIG. 120. In an aspect is provided a pharmaceutical composition including a pharmaceutically acceptable excipient and a nucleic acid having a sequence shown in FIG. 120.

CRISPR-sgRNA compositions have been designed to inhibit the activity of FTO or ALKBH5. FIG. 119 shows sgRNAs for use in accordance with standard CRISPR methods known in the art that are useful for inhibiting demethylases including FTO and ALKBH5. In an aspect is provided a CRISPR-sgRNA composition, wherein the sgRNA has a sequence shown in FIG. 119. In an aspect is provided a pharmaceutical composition including a pharmaceutically acceptable excipient and a CRISPR-sgRNA composition, wherein the sgRNA has a sequence shown in FIG. 119.

IV. Methods of Use

In one aspect, provided herein are methods of treating a subject in need thereof, comprising administering to the subject a therapeutically effective amount of an inhibitor, wherein the inhibitor inhibits m6A writers (e.g., methyltransferase like 3 (Mettl3 or MT-A70) or methyltransferase like-14 (Mettl14)), m6Am writers (e.g., phosphorylated CTD interacting factor 1 (PCIF1), or Mettl3/14), m6A erasers (e.g., fat-mass and obesity-associated protein (FTO) or ALKB homolog 5 (ALKBH5)), m6Am erasers (e.g., FTO), m6A readers (e.g., YTH domain-containing family proteins (YTHs)), YTF domain family member 1 (YTHDF 1), YTF domain family member 2 (YTHDF 2), YTF domain family member 3 (YTHDF 3), or tyrosine-protein phosphatase non-receptor type 2 (PTPN2)

In some embodiments, provided herein are methods of treating a subject in need thereof, the method comprising:

administering to the subject a therapeutically effective amount of an inhibitor, wherein the inhibitor inhibits one or more of methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), or tyrosine-protein phosphatase non-receptor type 2 (PTPN2).

In some embodiments, the inhibitor inhibits (e.g., selectively inhibits) a target selected from the group consisting of: methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), and tyrosine-protein phosphatase non-receptor type 2 (PTPN2).

In some embodiments, the subject has been identified or diagnosed as having a cancer.

In some embodiments, the cancer is selected from List AA and List AB defined infra. In some embodiments, the cancer is melanoma, glioblastoma (GBM), colorectal cancer (CRC), gastric cancer, acute myeloid leukemia (AML), lung squamous cell carcinoma (LUSC), breast cancer, ovarian cancer, endometrial cancer, esophageal cancer, pancreatic cancer, or head and neck cancer.

Also provided herein are methods of enhancing immunotherapy outcomes in a subject in need thereof, the method comprising:

administering to the subject an inhibitor, wherein the inhibitor inhibits m6A writers (e.g., methyltransferase like 3 (Mettl3 or MT-A70) or methyltransferase like-14 (Mettl14)), m6Am writers (e.g., phosphorylated CTD interacting factor 1 (PCIF1), or Mettl3/14), m6A erasers (e.g., fat-mass and obesity-associated protein (FTO) or ALKB homolog 5 (ALKBH5)), m6Am erasers (e.g., FTO), m6A readers (e.g., YTH domain-containing family proteins (YTHs)), YTF domain family member 1 (YTHDF 1), YTF domain family member 2 (YTHDF 2), YTF domain family member 3 (YTHDF 3), or tyrosine-protein phosphatase non-receptor type 2 (PTPN2).

In some embodiments, provided herein are methods of enhancing immunotherapy outcomes in a subject in need thereof, the method comprising:

administering to the subject an inhibitor, wherein the inhibitor inhibits one or more of methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), or tyrosine-protein phosphatase non-receptor type 2 (PTPN2).

In some embodiments, the inhibitor inhibits (e.g., selectively inhibits) a target selected from the group consisting of: methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), and tyrosine-protein phosphatase non-receptor type 2 (PTPN2).

In some embodiments, the subject has been identified or diagnosed as having a cancer. In some embodiments, the cancer is selected from List AA and List AB defined infra.

In some embodiments, the cancer is melanoma, glioblastoma (GBM), colorectal cancer (CRC), gastric cancer, acute myeloid leukemia (AML), lung squamous cell carcinoma (LUSC), breast cancer, ovarian cancer, endometrial cancer, esophageal cancer, pancreatic cancer, or head and neck cancer.

Also provided herein are methods of treating cancer in a subject in need thereof, the method comprising: co-administering to the subject:

(i) a therapeutically effective amount of an inhibitor, wherein the inhibitor inhibits m6A writers (e.g., methyltransferase like 3 (Mettl3 or MT-A70) or methyltransferase like-14 (Mettl14)), m6Am writers (e.g., phosphorylated CTD interacting factor 1 (PCIF1), or Mettl3/14), m6A erasers (e.g., fat-mass and obesity-associated protein (FTO) or ALKB homolog 5 (ALKBH5)), m6Am erasers (e.g., FTO), m6A readers (e.g., YTH domain-containing family proteins (YTHs)), YTF domain family member 1 (YTHDF 1), YTF domain family member 2 (YTHDF 2), YTF domain family member 3 (YTHDF 3), or tyrosine-protein phosphatase non-receptor type 2 (PTPN2); and (ii) an immunotherapy (e.g., an immunotherapy selected from an immune checkpoint inhibitor, an oncolytic virus therapy, a cell-based therapy (e.g., CAR-T cell therapy), and a cancer vaccine).

In some embodiments, provided herein are methods of treating cancer in a subject in need thereof, the method comprising: co-administering to the subject:

(iii) a therapeutically effective amount of an inhibitor, wherein the inhibitor inhibits one or more of methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), or tyrosine-protein phosphatase non-receptor type 2 (PTPN2); and (iv) an immunotherapy (e.g., an immunotherapy selected from an immune checkpoint inhibitor, an oncolytic virus therapy, a cell-based therapy (e.g., CAR-T cell therapy), and a cancer vaccine).

In some embodiments, the method further comprises administering to the subject one or more additional anticancer therapies selected from a chemotherapeutic agent, ionizing radiation, a therapeutic antibody, or gene therapy.

In some embodiments, the inhibitor inhibits (e.g., selectively inhibits) a target selected from the group consisting of: methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), and tyrosine-protein phosphatase non-receptor type 2 (PTPN2).

In some embodiments, the immunotherapy comprises administering anti-PD-1, anti-CTLA-4, or GVAX.

In some embodiments, the subject has been identified or diagnosed as having a cancer. In some embodiments, the cancer is selected from List AA and List AB defined infra. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, lung squamous cell carcinoma, head and neck carcinoma, endometrial cancer, cervical cancer, liver cancer, and hepatocellular carcinoma. In some embodiments, the cancer is melanoma, glioblastoma (GBM), colorectal cancer (CRC), gastric cancer, acute myeloid leukemia (AML), lung squamous cell carcinoma (LUSC), breast cancer, ovarian cancer, endometrial cancer, esophageal cancer, pancreatic cancer, or head and neck cancer.

Also provided herein are methods of killing cancer stem cells in a subject in need thereof, the method comprising:

administering to the subject an inhibitor, wherein the inhibitor inhibits m6A writers (e.g., methyltransferase like 3 (Mettl3 or MT-A70) or methyltransferase like-14 (Mettl14)), m6Am writers (e.g., phosphorylated CTD interacting factor 1 (PCIF1), or Mettl3/14), m6A erasers (e.g., fat-mass and obesity-associated protein (FTO) or ALKB homolog 5 (ALKBH5)), m6Am erasers (e.g., FTO), m6A readers (e.g., YTH domain-containing family proteins (YTHs)), YTF domain family member 1 (YTHDF 1), YTF domain family member 2 (YTHDF 2), YTF domain family member 3 (YTHDF 3), or tyrosine-protein phosphatase non-receptor type 2 (PTPN2).

In some embodiments, provided herein are methods of killing cancer stem cells in a subject in need thereof, the method comprising:

administering to the subject an inhibitor, wherein the inhibitor inhibits one or more of methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), or tyrosine-protein phosphatase non-receptor type 2 (PTPN2).

In some embodiments, the inhibitor inhibits (e.g., selectively inhibits) a target selected from the group consisting of: methyltransferase like 3 (Mettl3 or MT-A70), methyltransferase like-14 (Mettl14), phosphorylated CTD interacting factor 1 (PCIF1), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), and tyrosine-protein phosphatase non-receptor type 2 (PTPN2).

In some embodiments, the subject has been identified or diagnosed as having a cancer. In some embodiments, the cancer is selected from List AA and List AB defined infra. In some embodiments, the cancer is melanoma, glioblastoma (GBM), colorectal cancer (CRC), gastric cancer, acute myeloid leukemia (AML), lung squamous cell carcinoma (LUSC), breast cancer, ovarian cancer, endometrial cancer, esophageal cancer, pancreatic cancer, or head and neck cancer.

In some embodiments of one or more methods herein, the inhibitor is a compound selected from the group consisting of a compound of Formula (PT1) (e.g., a compound of Table 1000), a compound of Formula (Y1) (e.g., a compound of Table 400), a compound of Formula (Y2) (e.g., a compound of Table 600), a compound of Table 500, a compound of Formula (F1A) or (F1B) (e.g., a compound of Table 100), a compound of Formula (F2) (e.g., a compound of Table 200), a compound of Formula (F3) (e.g., a compound of Table 300), a compound of Formula (A1) (e.g., a compound of Table 700), a compound of Formula (A2A), (A2B), or (A2C) (e.g., a compound of Table 800), a compound of Formula (A3) (e.g., a compound of Table 900), a compound of Table 1100, a compound of Formula M1 (e.g., a compound of Table 1200), and a compound of Formula M2 (e.g., a compound of Table 1310), or a pharmaceutically acceptable salt thereof, In some embodiments of one or more methods herein, the inhibitor is a polynucleotide as defined in FIG. 119 or 120.

In some embodiments of one or more methods herein, the inhibitor inhibits Tyrosine-protein phosphatase non-receptor type 2 (PTPN2). In some embodiments, the inhibitor comprises at least one of a small hairpin RNA (shRNA), micro RNA (miRNA), a small interfering RNA (siRNA), a small molecule inhibitor, an antisense nucleic acid, a peptide, a virus, a CRISPR-sgRNA, or combinations thereof. In some embodiments, the inhibitor is a CRISPR-sgRNA, such as a CRISPR-sgRNA defined in FIG. 119. In some embodiments, inhibitor is a small hairpin RNA (shRNA), a micro RNA (miRNA) or a small interfering RNA (siRNA), such as a polynucleotide as defined in FIG. 120. In some embodiments, the inhibitor is a small molecule inhibitor. In some embodiments, the inhibitor is a compound of Formula (PT1) (e.g., a compound of Table 1000), or a pharmaceutically acceptable salt thereof.

In some embodiments of one or more methods herein, the inhibitor inhibits one or more of YTH domain-containing family proteins (YTHs). In some embodiments, wherein the inhibitor comprises at least one of a small hairpin RNA (shRNA), a micro RNA (miRNA), a small interfering RNA (siRNA), a small molecule inhibitor, an antisense nucleic acid, a peptide, a virus, a CRISPR-sgRNA, or combinations thereof. In some embodiments, the inhibitor is a CRISPR-sgRNA, such as a CRISPR-sgRNA defined in FIG. 119. In some embodiments, the inhibitor is a small hairpin RNA (shRNA), a micro RNA (miRNA) or a small interfering RNA (siRNA), such as a polynucleotide as defined in FIG. 120. In some embodiments, the inhibitor is a small molecule. In some embodiments, the inhibitor is a compound of Formula (Y1) (e.g., a compound of Table 400), or a pharmaceutically acceptable salt thereof. In some embodiments, the inhibitor is a compound of Table 500, or a pharmaceutically acceptable salt thereof. In some embodiments, the inhibitor is a compound a compound of Formula (Y2) (e.g., a compound of Table 600), or a pharmaceutically acceptable salt thereof.

In some embodiments of one or more methods herein, the inhibitor inhibits fat-mass and obesity-associated protein (FTO). In some embodiments, the inhibitor comprises at least one of a small hairpin RNA (shRNA), a micro RNA (miRNA), a small interfering RNA (siRNA), a small molecule inhibitor, an antisense nucleic acid, a peptide, a virus, a CRISPR-sgRNA, or combinations thereof. In some embodiments, the inhibitor is a CRISPR-sgRNA, such as a CRISPR-sgRNA defined in FIG. 119. In some embodiments, the inhibitor is a small hairpin RNA (shRNA), a micro RNA (miRNA) or a small interfering RNA (siRNA), such as a polynucleotide as defined in FIG. 120. In some embodiments, the inhibitor is a small molecule inhibitor. In some embodiments, the inhibitor is a compound of Formula (F1A) or (F1B) (e.g., a compound of Table 100). In some embodiments, the inhibitor is a compound of Formula (F2) (e.g., a compound of Table 200), or a pharmaceutically acceptable salt thereof. In some embodiments, the inhibitor is a compound of Formula (F3) (e.g., a compound of Table 300), or a pharmaceutically acceptable salt thereof.

In some embodiments of one or more methods herein, the inhibitor inhibits ALKB homolog 5 (ALKBH5). In some embodiments, the inhibitor comprises at least one of a small hairpin RNA (shRNA), a micro RNA (miRNA), a small interfering RNA (siRNA), a small molecule inhibitor, an antisense nucleic acid, a peptide, a virus, a CRISPR-sgRNA, or combinations thereof. In some embodiments, the inhibitor is a CRISPR-sgRNA, such as a CRISPR-sgRNA defined in FIG. 119. In some embodiments, the inhibitor is a small hairpin RNA (shRNA), a micro RNA (miRNA) or a small interfering RNA (siRNA), such as a polynucleotide as defined in FIG. 120. In some embodiments, the inhibitor is a small molecule inhibitor. In some embodiments, the inhibitor is a compound of Formula (A1) (e.g., a compound of Table 700), or a pharmaceutically acceptable salt thereof. In some embodiments, the inhibitor is a compound of Formula (A2A), (A2B), or (A2C) (e.g., a compound of Table 800), or a pharmaceutically acceptable salt thereof. In some embodiments, the inhibitor is a compound of Formula (A3) (e.g., a compound of Table 900), or a pharmaceutically acceptable salt thereof.

In some embodiments of one or more methods herein, the inhibitor inhibits methyltransferase like 3 (Mettl3 or MT-A70) and/or methyltransferase like-14 (Mettl14). In some embodiments, the inhibitor comprises at least one of a small hairpin RNA (shRNA), a micro RNA (miRNA), a small interfering RNA (siRNA), a small molecule inhibitor, an antisense nucleic acid, a peptide, a virus, a CRISPR-sgRNA, or combinations thereof. In some embodiments, the inhibitor is a CRISPR-sgRNA, such as a CRISPR-sgRNA defined in FIG. 119. In some embodiments, the inhibitor is a small hairpin RNA (shRNA), a micro RNA (miRNA) or a small interfering RNA (siRNA), such as a polynucleotide as defined in FIG. 120. In some embodiments, the inhibitor is a small molecule inhibitor. In some embodiments, the inhibitor is a compound of Table 1100, or a pharmaceutically acceptable salt thereof. In some embodiments, the inhibitor is a compound of Formula M1 (e.g., a compound of Table 1200), or a pharmaceutically acceptable salt thereof. In some embodiments, the inhibitor is a compound of Formula M2 (e.g., a compound of Table 1310), or a pharmaceutically acceptable salt thereof, In some embodiments of one or more methods herein, the inhibitor inhibits phosphorylated CTD interacting factor 1 (PCIF1). In some embodiments, the inhibitor comprises at least one of a small hairpin RNA (shRNA), a micro RNA (miRNA), a small interfering RNA (siRNA), a small molecule inhibitor, an antisense nucleic acid, a peptide, a virus, a CRISPR-sgRNA, or combinations thereof. In some embodiments, the inhibitor is a CRISPR-sgRNA, such as a CRISPR-sgRNA defined in FIG. 119. In some embodiments, the inhibitor is a small hairpin RNA (shRNA), a micro RNA (miRNA) or a small interfering RNA (siRNA), such as a polynucleotide as defined in FIG. 120. In some embodiments, the inhibitor is a small molecule inhibitor.

In some embodiments of one or more methods herein, the inhibitor inhibits YTF domain family member 2 (YTHDF 2) or YTF domain family member 3 (YTHDF 3). In some embodiments, the inhibitor comprises at least one of a small hairpin RNA (shRNA), a micro RNA (miRNA), a small interfering RNA (siRNA), a small molecule inhibitor, an antisense nucleic acid, a peptide, a virus, a CRISPR-sgRNA, or combinations thereof. In some embodiments, the inhibitor is a CRISPR-sgRNA, such as a CRISPR-sgRNA defined in FIG. 119. In some embodiments, the inhibitor is a small hairpin RNA (shRNA), a micro RNA (miRNA) or a small interfering RNA (siRNA), such as a polynucleotide as defined in FIG. 120. In some embodiments, the inhibitor is a small molecule inhibitor.

In some embodiments of one or more methods herein, the cancer is selected from the group consisting of:

[List AA]

1) breast cancers, including, for example ER+ breast cancer, ER- breast cancer, her2− breast cancer, her2+ breast cancer, stromal tumors such as fibroadenomas, phyllodes tumors, and sarcomas, and epithelial tumors such as large duct papillomas; carcinomas of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms. Further examples of breast cancers can include luminal A, luminal B, basal A, basal B, and triple negative breast cancer, which is estrogen receptor negative (ER−), progesterone receptor negative, and her2 negative (her2−). In some embodiments, the breast cancer may have a high risk Oncotype score;

2) cardiac cancers, including, for example sarcoma, e.g., angiosarcoma, fibrosarcoma, rhabdomyosarcoma, and liposarcoma; myxoma; rhabdomyoma; fibroma; lipoma and teratoma;

3) lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

4) gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

5) genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

6) liver cancers, including, for example, hepatoma, e.g., hepatocellular carcinoma; cholangiocarcinoma; hepatoblastoma; angiosarcoma; hepatocellular adenoma; and hemangioma;

7) bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

8) nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, oligodendrocytoma, schwannoma, retinoblastoma, and congenital tumors; and cancers of the spinal cord, e.g., neurofibroma, meningioma, glioma, and sarcoma;

9) gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa theca cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

10) hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenstrom's macroglobulinemia;

11) skin cancers and skin disorders, including, for example, malignant melanoma and metastatic melanoma, basal cell carcinoma, squamous cell carcinoma, Kaposi's sarcoma, moles dysplastic nevi, lipoma, angioma, dermatofibroma, keloids, and scleroderma; and 12) adrenal gland cancers, including, for example, neuroblastoma.

In some embodiments of one or more methods herein, the cancer is selected from the group consisting of:

[List AB]

1) astrocytic tumors, e.g., diffuse astrocytoma (fibrillary, protoplasmic, gemistocytic, mixed), anaplastic (malignant) astrocytoma, glioblastoma multiforme (giant cell glioblastoma and gliosarcoma), pilocytic astrocytoma (pilomyxoid astrocytoma), pleomorphic xanthoastrocytoma, subependymal giant cell astrocytoma, and gliomatosis cerebri;

2) oligodendroglial tumors, e.g., oligodendroglioma and anaplastic oligodendroglioma;

3) oligoastrocytic tumors, e.g., oligoastrocytoma and anaplastic oligoastrocytoma;

4) ependymal tumors, e.g., subependymoma, myxopapillary ependymoma, ependymoma, (cellular, papillary, clear cell, tanycytic), and anaplastic (malignant) ependymoma;

5) choroid plexus tumors, e.g., choroid plexus papilloma, atypical choroid plexus papilloma, and choroid plexus carcinoma;

6) neuronal and mixed neuronal -glial tumors, e.g., gangliocytoma, ganglioglioma, dysembryoplastic neuroepithelial tumor (DNET), dysplastic gangliocytoma of the cerebellum (Lhermitte-Duclos), desmoplastic infantile astrocytoma/ganglioglioma, central neurocytoma, anaplastic ganglioglioma, extraventricular neurocytoma, cerebellar liponeurocytoma, Papillary glioneuronal tumor, Rosette-forming glioneuronal tumor of the fourth ventricle, and paraganglioma of the filum terminale;

7) pineal tumors, e.g., pineocytoma, pineoblastoma, papillary tumors of the pineal region, and pineal parenchymal tumor of intermediate differentiation;

8) embryonal tumors, e.g., medulloblastoma (medulloblastoma with extensive nodularity, anaplastic medulloblastoma, desmoplastic, large cell, melanotic, medullomyoblastoma), medulloepithelioma, supratentorial primitive neuroectodermal tumors, and primitive neuroectodermal tumors (PNETs) such as neuroblastoma, ganglioneuroblastoma, ependymoblastoma, and atypical teratoid/rhabdoid tumor;

9) neuroblastic tumors, e.g., olfactory (esthesioneuroblastoma), olfactory neuroepithelioma, and neuroblastomas of the adrenal gland and sympathetic nervous system;
10) glial tumors, e.g., astroblastoma, chordoid glioma of the third ventricle, and angiocentric glioma;
11) tumors of cranial and paraspinal nerves, e.g., schwannoma, neurofibroma Perineurioma, and malignant peripheral nerve sheath tumor;
12) tumors of the meninges such as tumors of meningothelial cells, e.g., meningioma (atypical meningioma and anaplastic meningioma); mesenchymal tumors, e.g., lipoma, angiolipoma, hibernoma, liposarcoma, solitary fibrous tumor, fibrosarcoma, malignant fibrous histiocytoma, leiomyoma, leiomyosarcoma, rhabdomyoma, rhabdomyosarcoma, chondroma, chondrosarcoma, osteoma, osteosarcoma, osteochondroma, haemangioma, epithelioid hemangioendothelioma, haemangiopericytoma, anaplastic haemangiopericytoma, angiosarcoma, Kaposi Sarcoma, and Ewing Sarcoma; primary melanocytic lesions, e.g., diffuse melanocytosis, melanocytoma, malignant melanoma, meningeal melanomatosis; and hemangioblastomas;
13) tumors of the hematopoietic system, e.g., malignant Lymphomas, plasmocytoma, and granulocytic sarcoma;
14) Germ cell tumors, e.g., germinoma, embryonal carcinoma, yolk sac tumor, choriocarcinoma, teratoma, and mixed germ cell tumors;
15) Tumors of the sellar region, e.g., craniopharyngioma, granular cell tumor, pituicytoma, and spindle cell oncocytoma of the adenohypophysis.

Cancers can be solid tumors. In some embodiments, the cancers are metastatic. Cancers can also occur, as in leukemia, as a diffuse tissue. Thus, the term "tumor cell," as provided herein, includes a cell afflicted by any one of the above identified disorders.

A method of treating cancer using a compound or composition as described herein may be combined with existing methods of treating cancers, for example by chemotherapy, irradiation, or surgery (e.g., oophorectomy). In some embodiments, a compound or composition can be administered before, during, or after another anticancer agent or treatment.

In an aspect is provided a method of inhibiting methyltransferase like 3 (Mettl3 or MT-A70), methyltransferase like-14 (Mettl14), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), or tyrosine-protein phosphatase non-receptor type 2 (PTPN2) using a compound as described herein.

In an aspect is provided a method of treating a disease related to methyltransferase like 3 (Mettl3 or MT-A70), methyltransferase like-14 (Mettl14), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), or tyrosine-protein phosphatase non-receptor type 2 (PTPN2) comprising administering an effective amount of a compound as disclosed herein to a subject in need thereof.

In embodiments, the disease is cancer. In embodiments, the cancer is melanoma. In embodiments, the cancer is colon cancer. In embodiments, the cancer is lung cancer. In embodiments, the cancer is gliobastoma (GBM). In embodiments, the disease is melanoma. In embodiments, the disease is colon cancer. In embodiments, the disease is lung cancer. In embodiments, the disease is gliobastoma (GBM).

In an aspect is provided a method of improving immunotherapy outcomes by inhibiting methyltransferase like 3 (Mettl3 or MT-A70), methyltransferase like-14 (Mettl14), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), or tyrosine-protein phosphatase non-receptor type 2 (PTPN2) comprising administering an effective amount of a compound as disclosed herein to a subject in need thereof.

In an aspect is provided a method of treating cancer, said method comprising administering a therapeutically effective amount of an inhibitor of methyltransferase like 3 (Mettl3 or MT-A70), methyltransferase like-14 (Mettl14), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), or tyrosine-protein phosphatase non-receptor type 2 (PTPN2).

In embodiments, the inhibitor is a small molecule, a shRNA, a miRNA, a siRNA, an antisense nucleic acid, or a CRISPR-sgRNA, as disclosed herein.

Disclosed herein are methods of inhibiting methyltransferase like 3 (Mettl3 or MT-A70), methyltransferase like-14 (Mettl14), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), or tyrosine-protein phosphatase non-receptor type 2 (PTPN2) using a compound as described herein. Non-limiting embodiments are disclosed in U.S. Provisional Application Ser. No. 62/914,914, filed on Oct. 14, 2019; U.S. Provisional Application Ser. No. 62/971,701, filed on Feb. 7, 2020; U.S. Provisional Application Ser. No. 63/059,939, filed on Jul. 31, 2020; and U.S. Provisional Application Ser. No. 63/074,421, filed on Sep. 3, 2020, each of which is incorporated herein by reference in its entirety (including the appendices incorporated therein).

Disclosed herein are methods of treating a disease related to methyltransferase like 3 (Mettl3 or MT-A70), methyltransferase like-14 (Mettl14), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), or tyrosine-protein phosphatase non-receptor type 2 (PTPN2) comprising administering an effective amount of a compound of claim 1 to a subject in need thereof. Non-limiting embodiments are disclosed in U.S. Provisional Application Ser. No. 62/914,914, filed on Oct. 14, 2019; U.S. Provisional Application Ser. No. 62/971,701, filed on Feb. 7, 2020; U.S. Provisional Application Ser. No. 63/059,939, filed on Jul. 31, 2020; and U.S. Provisional Application Ser. No. 63/074,421, filed on Sep. 3, 2020, each of which is incorporated herein by reference in its entirety (including the appendices incorporated therein).

Disclosed herein are methods of improving immunotherapy outcomes by inhibiting methyltransferase like 3 (Mettl3 or MT-A70), methyltransferase like-14 (Mettl14), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), or tyrosine-protein phosphatase non-receptor type 2 (PTPN2) comprising administering an effective amount of a compound as disclosed herein to a subject in need thereof. Non-limiting embodiments are disclosed in one or more of U.S. Provisional Application Ser. No. 62/914,914, filed on Oct. 14, 2019; U.S. Provisional Application Ser. No. 62/971,701, filed on Feb. 7, 2020; U.S. Provisional Application Ser. No. 63/059,939, filed on Jul. 31, 2020; and U.S. Provisional Application Ser. No. 63/074,421, filed on Sep. 3, 2020, each of which is incorporated herein by reference in its entirety (including the appendices incorporated therein).

Disclosed herein are methods of treating cancer, said method comprising administering a therapeutically effective amount of an inhibitor of methyltransferase like 3 (Mettl3 or MT-A70), methyltransferase like-14 (Mettl14), fat-mass and obesity-associated protein (FTO), ALKB homolog 5 (ALKBH5), YTH domain-containing family proteins (YTHs), YTF domain family member 1 (YTHDF 1), YTF domain family member 2 (YTHDF 2), YTF domain family member 3 (YTHDF 3), or tyrosine-protein phosphatase non-receptor type 2 (PTPN2). Non-limiting embodiments are disclosed in one or more of U.S. Provisional Application Ser. No. 62/914,914, filed on Oct. 14, 2019; U.S. Provisional Application Ser. No. 62/971,701, filed on Feb. 7, 2020; U.S. Provisional Application Ser. No. 63/059,939, filed on Jul. 31, 2020; and U.S. Provisional Application Ser. No. 63/074,421, filed on Sep. 3, 2020, each of which is incorporated herein by reference in its entirety (including the appendices incorporated therein).

The compositions described herein are contemplated as useful for the treatment of tumors, in particular glioblastomas. More specifically, the compositions provided herein are useful for killing glioblastoma cancer stem cells. Thus, in an aspect is provided a method of killing glioblastoma cancer stem cells, the method including administering a therapeutically effective amount of an inhibitor of ALKBH5 and/or FTO. In embodiments, the FTO inhibitor is a small molecule, a shRNA, a miRNA, a siRNA, an antisense nucleic acid, or a CRISPRsgRNA composition. In embodiments, the FTO inhibitor is an FTO inhibitor as described herein, including embodiments thereof. Non-limiting examples of FTO inhibitors include: a compound of Formula (F1A) or (F1B) (e.g., a compound of Table 100), a compound of Formula (F2) (e.g., a compound of Table 200), or a compound of Formula (F3) (e.g., Table 300), or a pharmaceutically acceptable salt thereof. In embodiments, the ALKBH5 inhibitor is a small molecule, a shRNA, a miRNA, a siRNA, an antisense nucleic acid, or a CRISPR-sgRNA composition. In embodiments, the ALKBH5 inhibitor is an ALKBH5 inhibitor as described herein, including embodiments thereof. Non-limiting examples of ALKBH5 inhibitors include: a compound of Formula (A1) (e.g., a compound of Table 700), a compound of Formula (A2A), (A2B), or (A2C) (e.g., a compound of Table 800), or a compound of Formula (A3) (e.g., a compound of Table 900), or a pharmaceutically acceptable salt thereof.

The compositions provided herein are further contemplated as useful for potentiating immunotherapy. Immunotherapy is a treatment that engages parts of a subject's immune system to kill cancer cells. There are different types of immunotherapy, including monoclonal antibodies designed to target and kill cancer cells, immune checkpoint inhibitors which prevent immune suppression in the tumor environment, cancer vaccines that can start and immune response, and other non-specific immunotherapies designed to boost the immune system in a general way. As described herein, the combination of inhibiting (e.g., knocking-out via CRISPR-sgRNA methods) FTO and/or ALKBH5 in melanoma cells and delivering immunotherapeutic treatments such as anti-PD-1 and GVAX results in a greater reduction in melanoma tumor size compared to immunotherapy alone. Therefore, in an aspect is provided a method of enhancing cancer immunotherapy, the method including co-administering a FTO IO and/or an ALKBH5 inhibitor with immunotherapy. In embodiments, the FTO inhibitor is a small molecule, a shRNA, a miRNA, a siRNA, an antisense nucleic acid, or a CRISPR-sgRNA composition. In embodiments, the FTO inhibitor is an FTO inhibitor as described herein, including embodiments thereof. Non-limiting examples of FTO inhibitors include: a compound of Formula (F1A) or (F1B) (e.g., a compound of Table 100), a compound of Formula (F2) (e.g., a compound of Table 200), or a compound of Formula (F3) (e.g., Table 300), or a pharmaceutically acceptable salt thereof. In embodiments, the ALKBH5 inhibitor is a small molecule, a shRNA, a miRNA, a siRNA, an antisense nucleic acid, or a CRISPR-sgRNA composition. In embodiments, the ALKBH5 inhibitor is an ALKBH5 inhibitor as described herein, including embodiments thereof. Non-limiting examples of ALKBH5 inhibitors include: a compound of Formula (A1) (e.g., a compound of Table 700), a compound of Formula (A2A), (A2B), or (A2C) (e.g., a compound of Table 800), or a compound of Formula (A3) (e.g., a compound of Table 900), or a pharmaceutically acceptable salt thereof. In embodiments, the immunotherapy includes delivery of anti-PD-I, anti-CTLA-4, or GVAX. In embodiments, the immunotherapy includes delivery of a combination of two or more of anti-PD-1, anti-CTLA-4, and GVAX. In embodiments, the immunotherapy includes delivery of anti-PD-I and GVAX. In embodiments, the cancer is melanoma, colon or lung cancer.

It has been suggested that there exists a negative relationship between the amount of T regulatory cells (Tregs) and the immune response to tumors. As described in the Examples section, the combination of inhibiting (e.g., knocking-out via CRISPR-sgRNA methods) FTO and/or ALKBH5 in melanoma cells and delivering immunotherapeutic treatments such as anti PD-1 and GV AX resulted in a decrease in the presence of Tregs in the tumor environment. Thus, in another aspect is a method of reducing T regulatory cells, the method including coadministering a FTO and/or an ALKBH5 inhibitor with immunotherapy. In embodiments, the FTO inhibitor is a small molecule, a shRNA a miRNA, a siRNA, an antisense nucleic acid, or a CRISPR-sgRNA composition. In embodiments, the FTO inhibitor is an FTO inhibitor as described herein, including embodiments thereof. In embodiments, the ALKBH5 inhibitor is a small molecule, a shRNA, a miRNA, a siRNA, an antisense nucleic acid, or a CRISPR-sgRNA composition. In embodiments, the ALKBH5 inhibitor is an ALKBH5 inhibitor as described herein, including embodiments thereof. In embodiments, the immunotherapy includes delivery of anti-PD-I, anti-CTLA-4, or GVAX. In embodiments, the immunotherapy includes delivery of a combination of two or more of anti-PD-I, anti-CTLA-4, and GVAX. In embodiments, the immunotherapy includes delivery of anti-PD-I and GVAX.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example B1: New Targets and Compounds to Enhance Cancer Immunotherapy

Although immune checkpoint blockade (ICB) therapy has revolutionized cancer treatment, many patients do not respond or develop resistance to ICB. N6-methylation of adenosine (m6A) in RNA regulates many pathophysiological processes. Here, we show that deletion of the m6A demethylase Alkbh5 in B16 mouse melanoma cells does not affect tumor growth but markedly potentiates the efficacy of cancer immunotherapy. Alkbh5 has effects on m6A density and splicing events in tumors during immunotherapy. Alkbh5 modulates the metabolite and cytokine content of the tumor microenvironment and the composition of tumor-infiltrating immune cells. Notably, the ALKBH5 gene mutation and expression status of melanoma patients correlate with their response to immunotherapy. Our results suggest that m6A demethylases in tumor cells contribute to the efficacy of immunotherapy and identify ALKBH5 as a potential therapeutic target to enhance immunotherapy outcome in melanoma and potential y other cancers. Similarly, FTO, the m6A RNA reader proteins, YTH domain containing proteins, e.g., YTHDF1, YTHDF2, and YTHDF3, and Mettl3/14 inhibition by CRISPR and small molecules enhanced immunotherapy responses in colon and melanoma cancers. In addition, inhibitors of tyrosine-protein phosphatase non-receptor type 2 (PTPN2) sensitized melanoma tumor to PD-1 therapy. Compounds to inhibit all these targets, mentioned above, are described here.

Introduction

The adaptive immune response is tightly regulated through immune checkpoint pathways that serve to inhibit T cell activation, thereby maintaining self-tolerance and preventing autoimmunity. The two major checkpoints involve interactions between cytotoxic T-lymphocyte antigen 4 (CT LA-4) and programmed cell death protein 1 (PD-1) on T cells and their ligands CD80/CD86 and PD-L1, respectively, which are expressed on various immune cells under physiological conditions. However, expression of these proteins on tumor cells inhibits the T cell activation and enables immune evasion and tumor cell survival. The development of antibodies (Abs) and fusion proteins against PD-1, PD-L1, and CTLA-4, which block negative signaling and enhance the T cell response to tumor antigens, has proven to be a breakthrough in the treatment of solid tumors. Nevertheless, such immune checkpoint blockade (ICB) is ineffective against some tumor types, and many patients who initially respond develop resistance and relapse after ICB. Consequently, understanding the mechanisms of tumor sensitivity, evasion, and resistance to ICB is under intense investigation[1]. One of the proposed mechanisms for the failure of ICB is ineffective T cell infiltration and/or activation due to immunosuppressive conditions within the tumor microenvironment (TME). There is thus an urgent need to develop approaches to increase the sensitivity of tumors to ICBs through combination treatment with molecules that convert an immune suppressive to an immune active TME.

Epitranscriptomics is an emerging field that seeks to identify and understand chemical modifications in RNA; the enzymes that deposit, remove, and interpret the modifications (writers, erasers, and readers, respectively); and their effects on gene expression via regulation of RNA metabolism, function, and localization[2,3]. N6-methyladenosine (m6A) is the most prevalent RNA modification in many species, including mammals. In eukaryotic mRNAs, m6A is abundant in 5'-UTR, 3'-UTRs, and stop codons[4-6]. The m6A modification is catalyzed by a large RNA methyltransferase complex composed of two catalytic subunits (METTL3 and METTL 14), a splicing factor (WTAP), a novel protein (KIAA1429), and other as yet unidentified proteins[2,3]. Conversely, removal of m6A is catalyzed by the RNA demethylases FTO and ALKBH5[2,7,8]. In addition, FTO demethylates N6,2'-O-dimethyladenosine (m6Am) to reduce the stability of target mRNAs and snRNA biogenesis[9,10]. The m6A RNA reader proteins, YTH domain containing proteins, e.g., YTHDF1, YTHDF2, and YTHDF3, specifically[11,12] bind modified RNA and mediate its effects on RNA stability and translation.

In addition to the physiological roles of m6A in regulating RNA metabolism in such crucial processes as stem cell differentiation, circadian rhythms, spermatogenesis, and the stress response[2, 13], increasing evidence supports a pathological role for perturbed m6A metabolism in several disease states. For example, recent studies have shown that the m6A status of mRNA is involved in the regulation of T cell homeostasis viral infection[15] and cancer[16-21].

Here, we employed a mouse model of melanoma to investigate the roles of tumor cell-intrinsic Alkbh5 and Fto functions in modulating the response to immunotherapy. We found that CRISPR-mediated deletion of Alkbh5 or Fto in the B16 mouse melanoma cell line had no effect on tumor growth in untreated mice, but it significantly reduced tumor growth and Alkbh5 KO prolonged mouse survival during immunotherapy. Alkbh5 deficiency altered immune cell infiltration and metabolite composition in the TME. Finally, we show that gene mutation or downregulation of the ALKBH5 in melanoma patients correlates with a positive response to PD-1 blockade with pembrolizumab or nivolumab. Thus, our results identify a major role for tumor m6A demethylases in controlling the efficacy of immunotherapy and suggest that combination treatment with ALKBH5 inhibitors may be a new approach to overcome tumor resistance to ICB.

Results

Deletion of the m6A RNA Demethylases Alkbh5 and Fto Enhances the Efficacy of Immunotherapy.

Figure 1A:
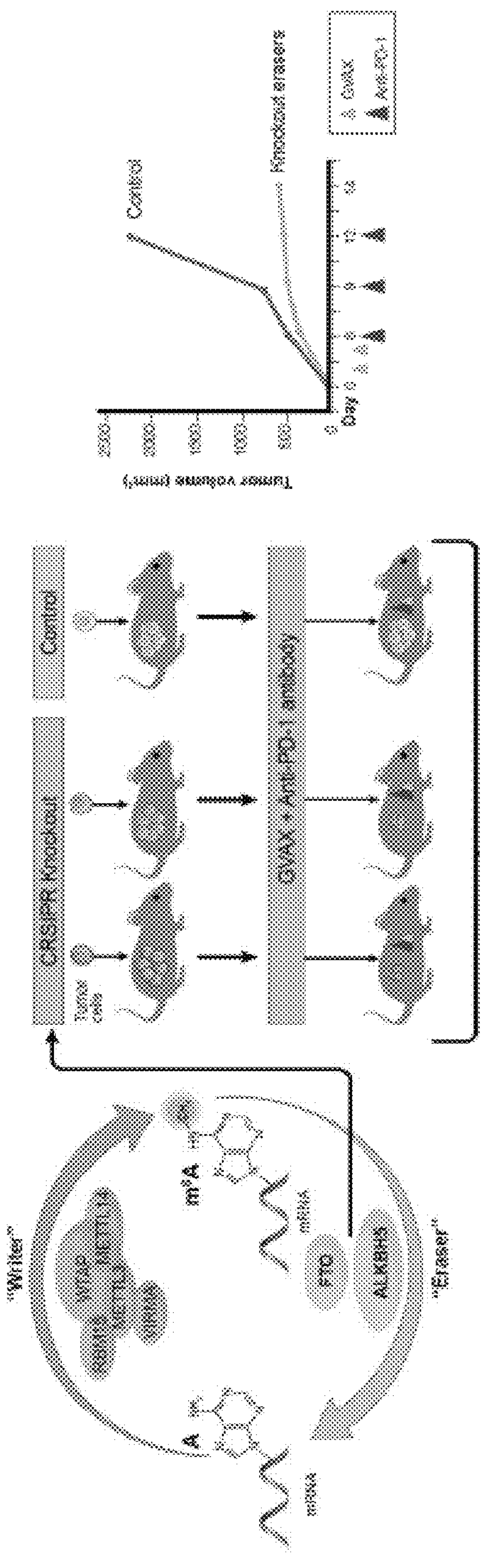
FIG. 1A-1E. Depiction and plots of deletion of the m6A RNA Demethylases Alkbh5 Sensitizes Tumors to Immunotherapy.
Figure 5A:
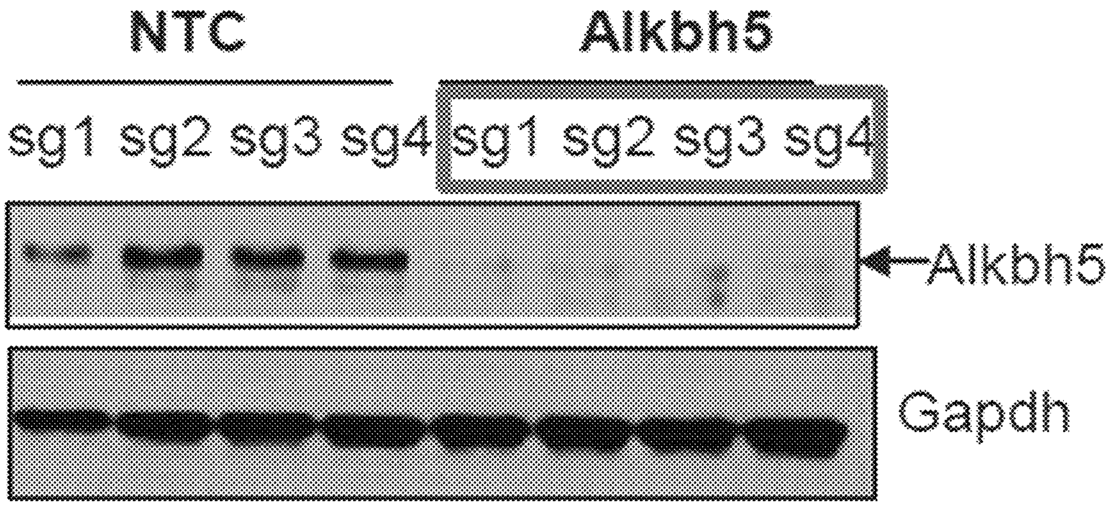
Figure 5B:
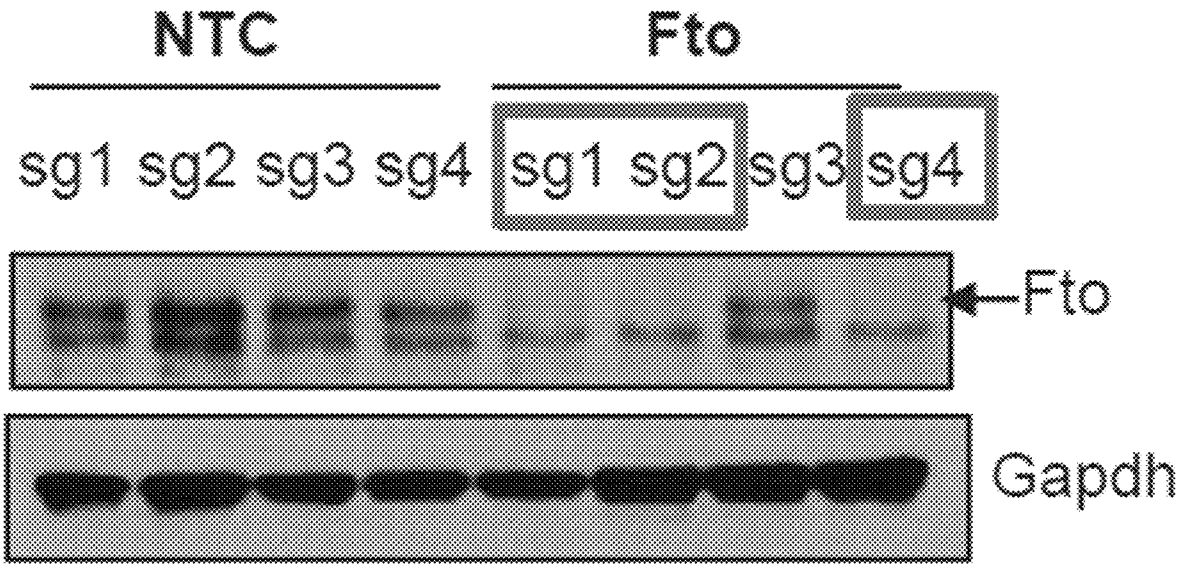
Figure 5C:
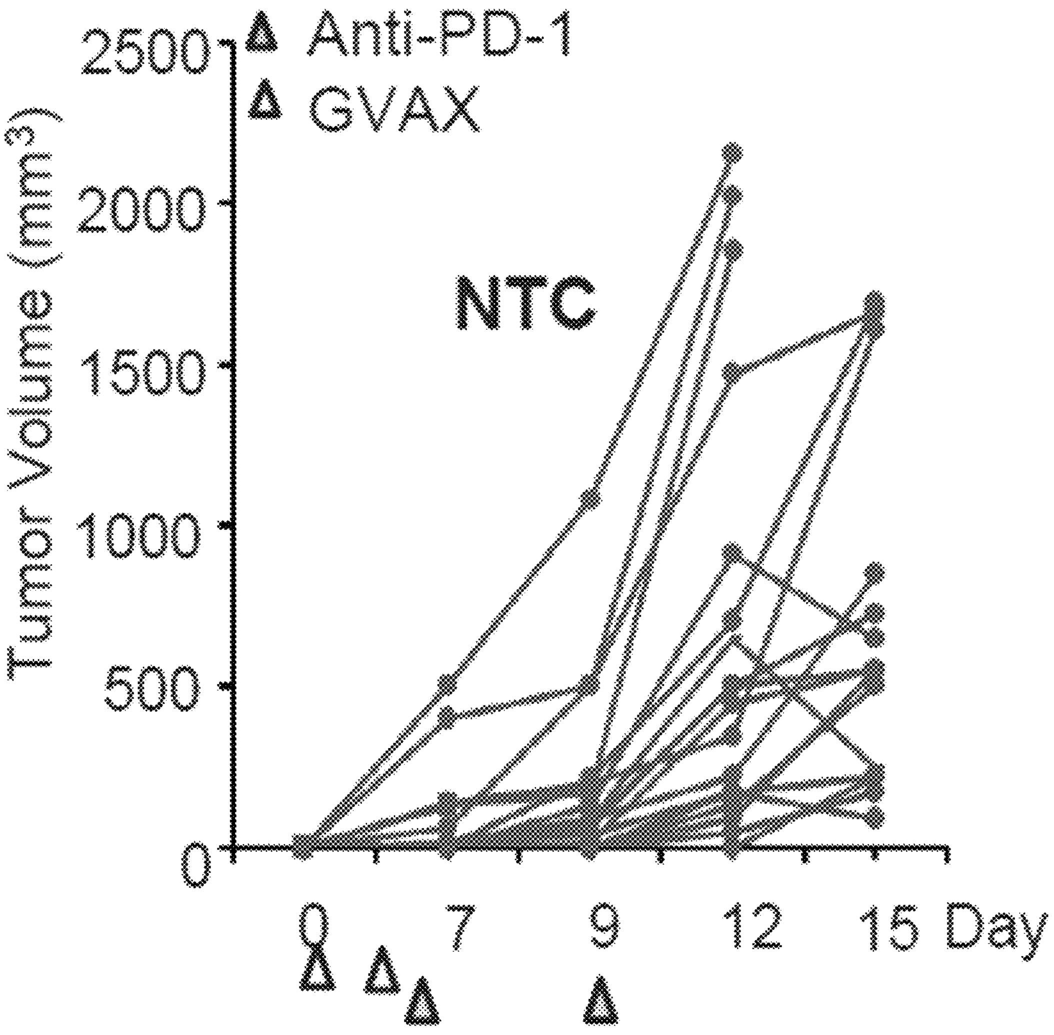
Figure 5D:
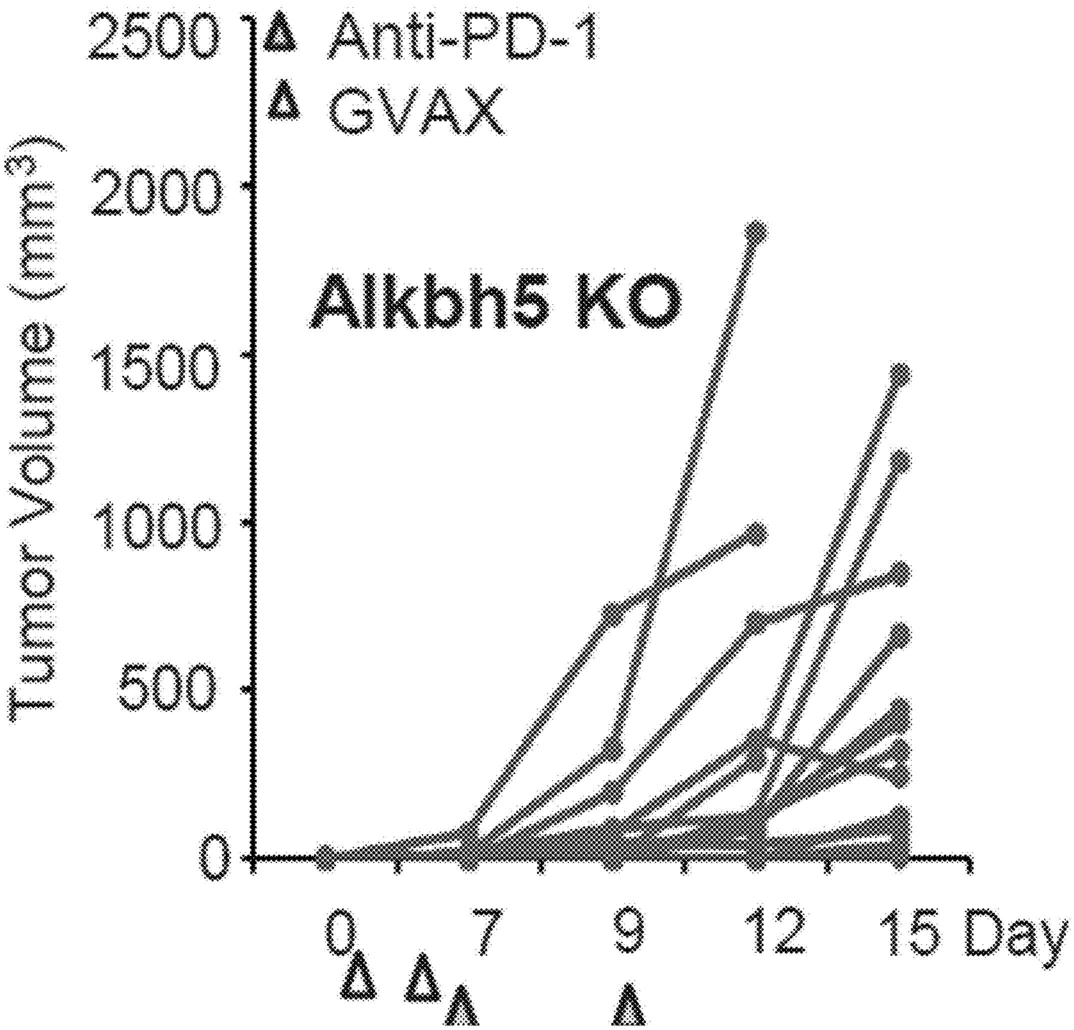
Figure 5E:
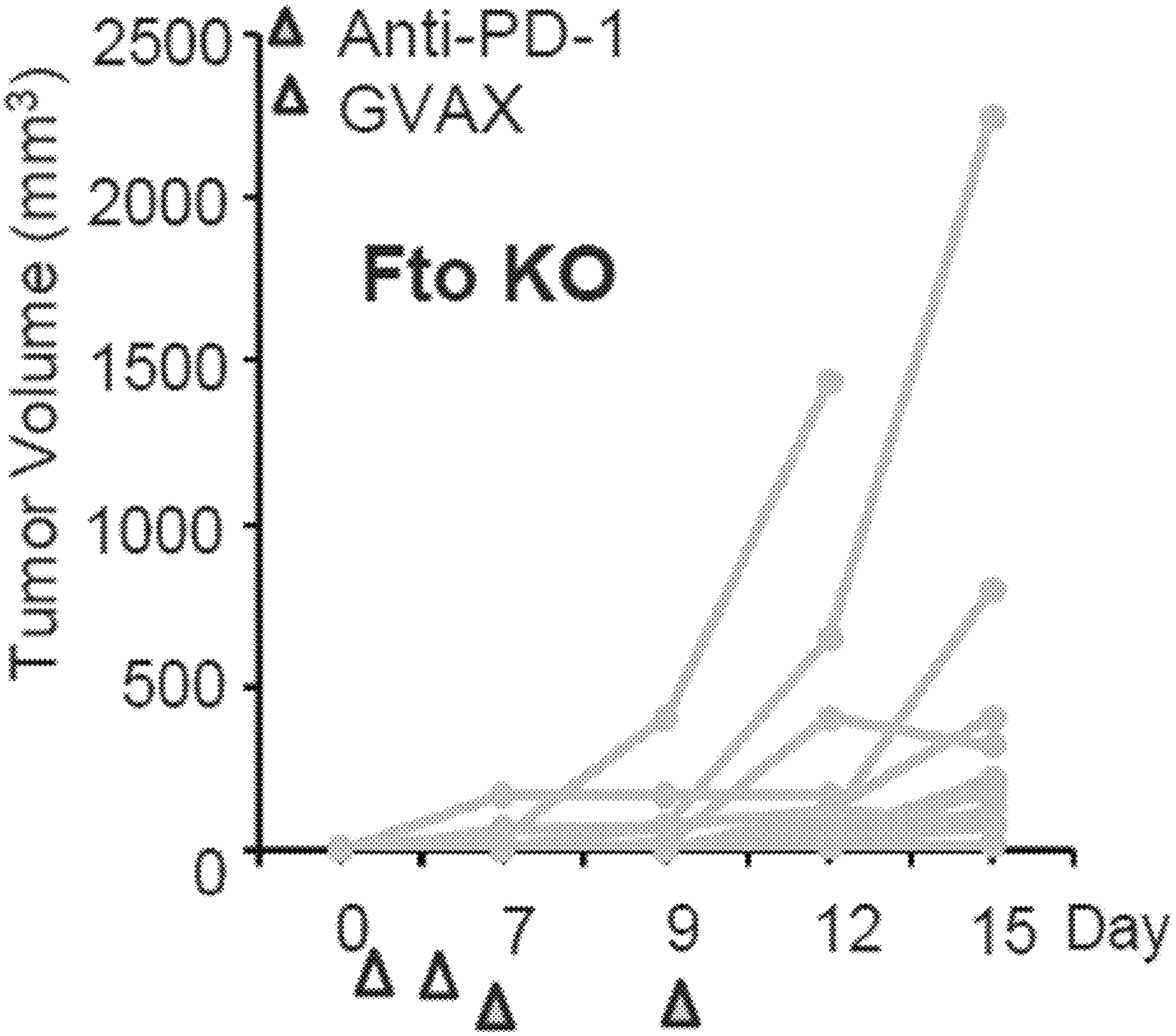
Figure 5F:
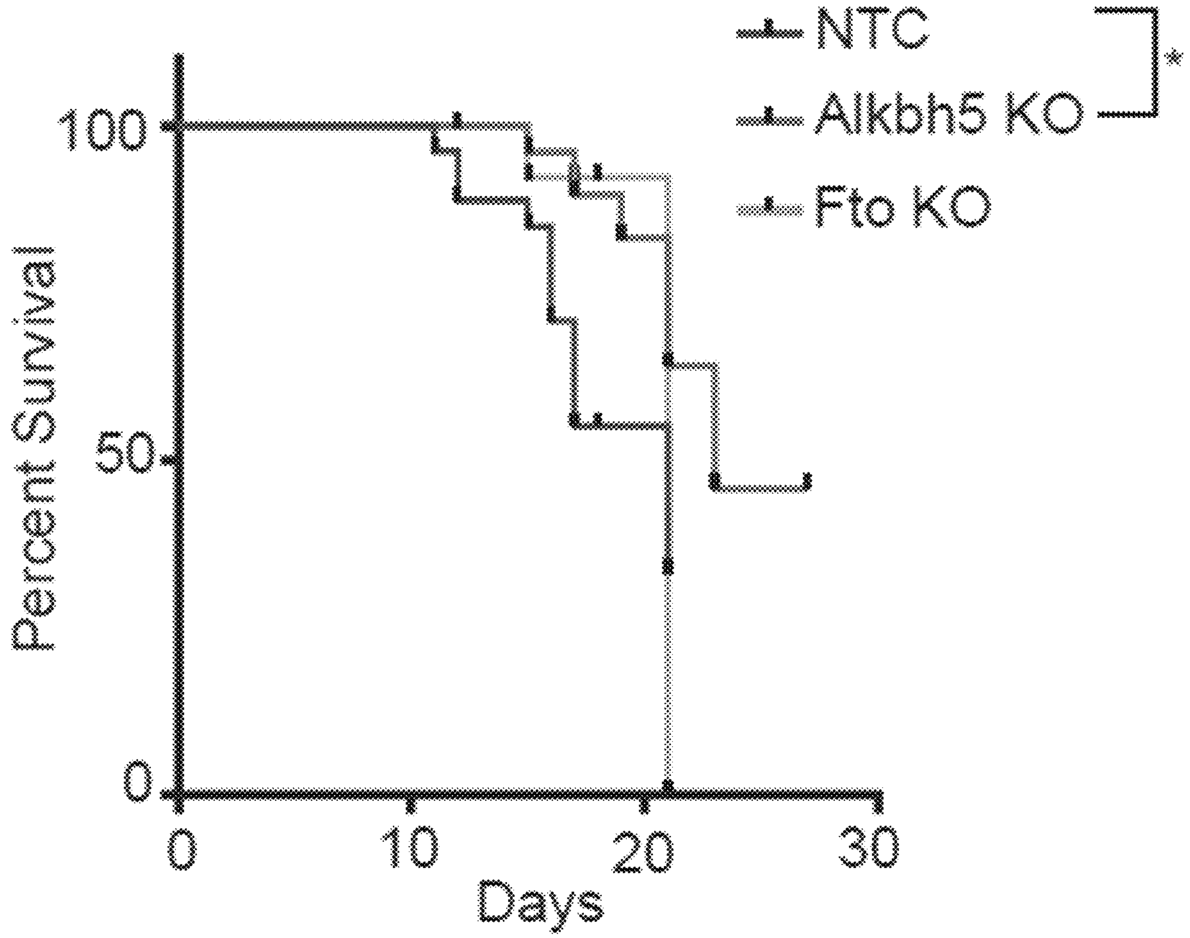

To determine the role of m6A methylation in tumor cells in the response of melanoma to anti-PD-1 therapy, we employed a mouse model using the poorly immunogenic murine melanoma cell line B16. In the standard protocol (FIG. 1A), B16 cells were deleted of Alkbh5 or Fto by CRISPR-Cas9 editing and subcutaneously injected into wild-type syngeneic C57BL/6 mice, which were then vaccinated on days 1 and 4 with GVAX 22 composed of irradiated B16 cells secreting granulocyte-macrophage colony-stimulating factor to induce an anti-tumor T cell response. The mice were then treated with anti-PD-1 Ab on days 6, 9, and 12 (or as indicated for individual experiments) (FIG. 1A). Gene editing was performed with up to four distinct Alkbh5- or Fto-targeting sgRNAs per gene (or non-targeting control sgRNAs, NTC), and B16 lines with complete deletion were selected for further experiments (FIGS. 5A through 5B). Compared with NTC-B16 tumors, growth of Akbh5-knockout (KO) and Fto-KO tumors was significantly reduced by GVAX/anti-PD-1 treatment (FIGS. 1B-1C and 5C-5E) and the survival of Alkbh5-deficient tumor-bearing mice was significantly prolonged (FIG. 5F).

Figure 1B:
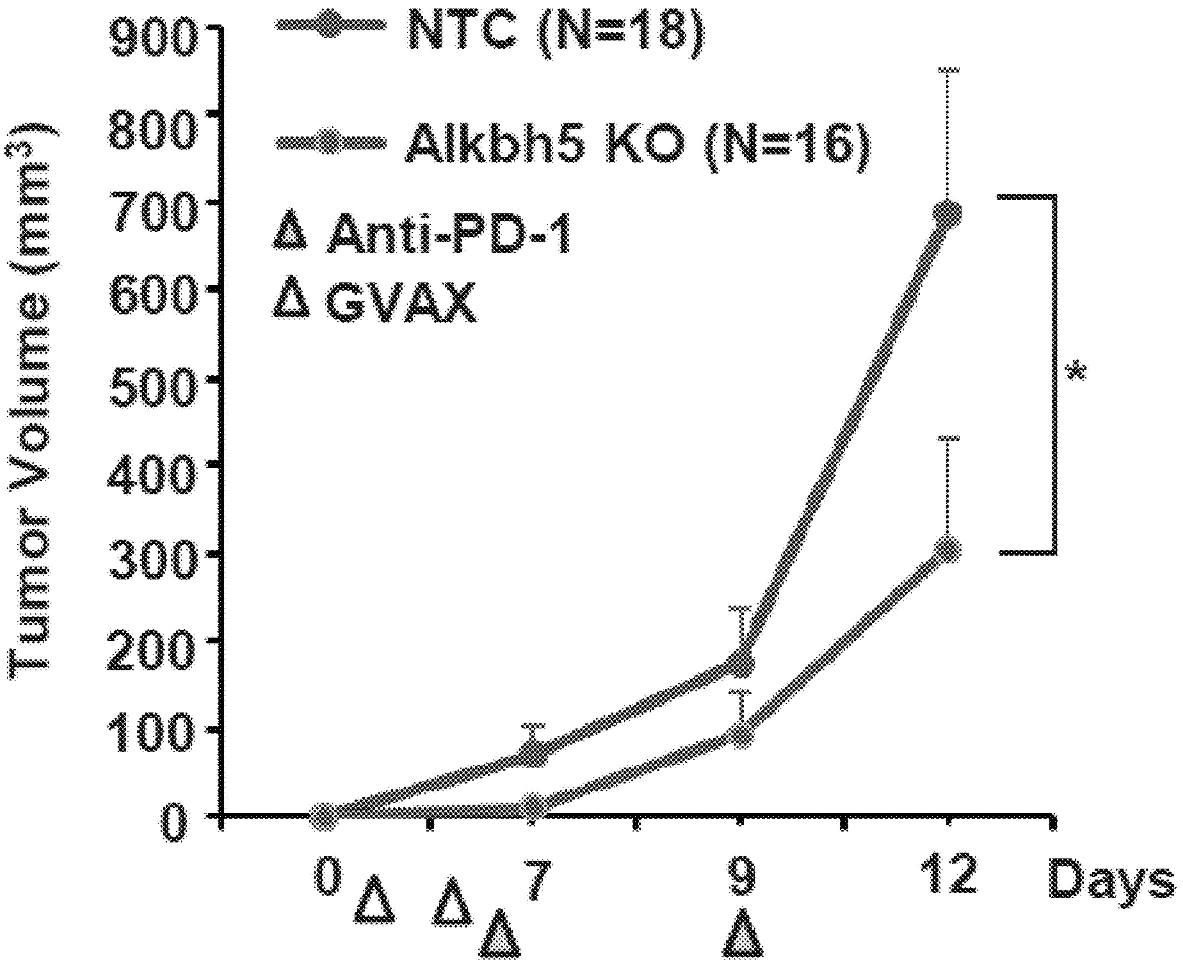
Figure 1C:
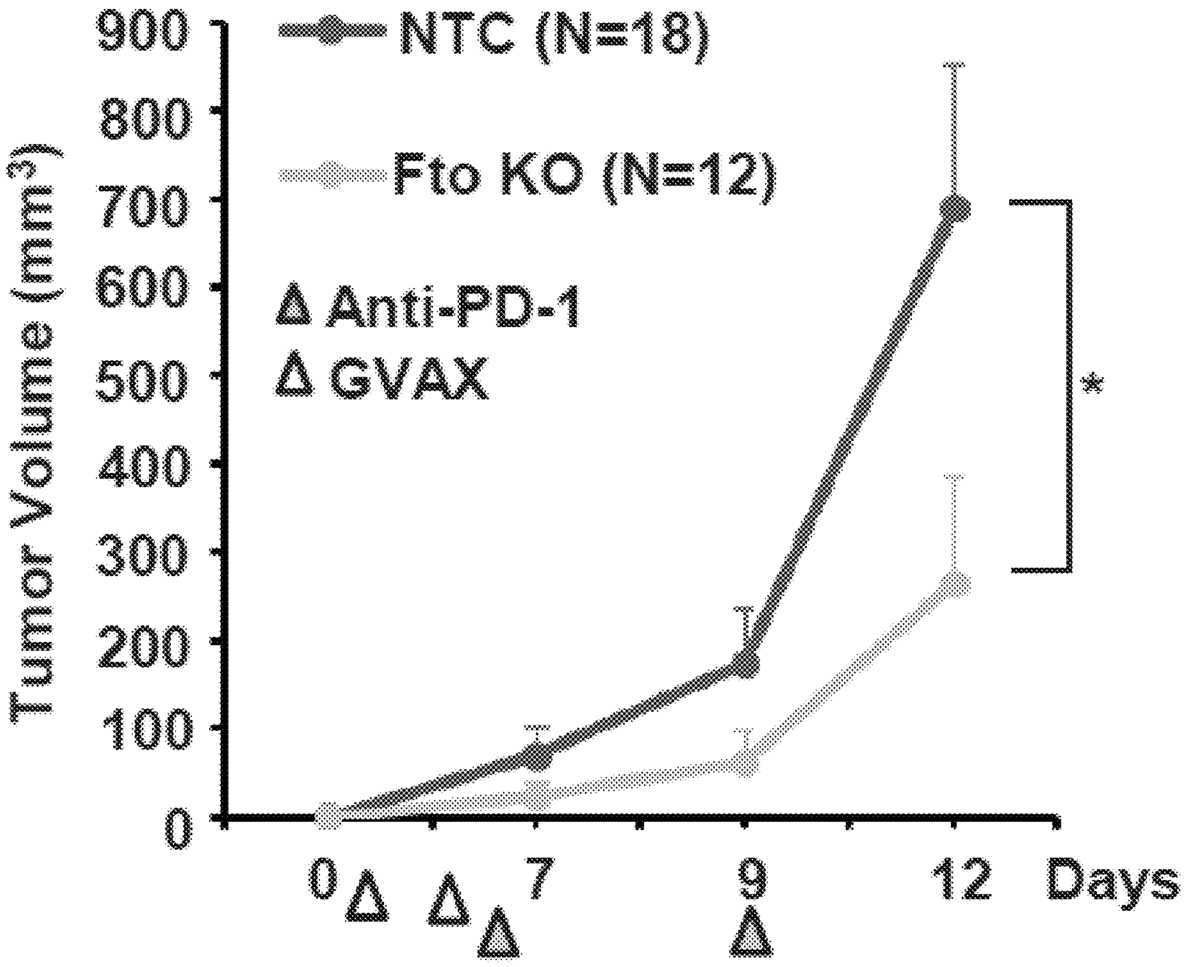
Figure 1D:
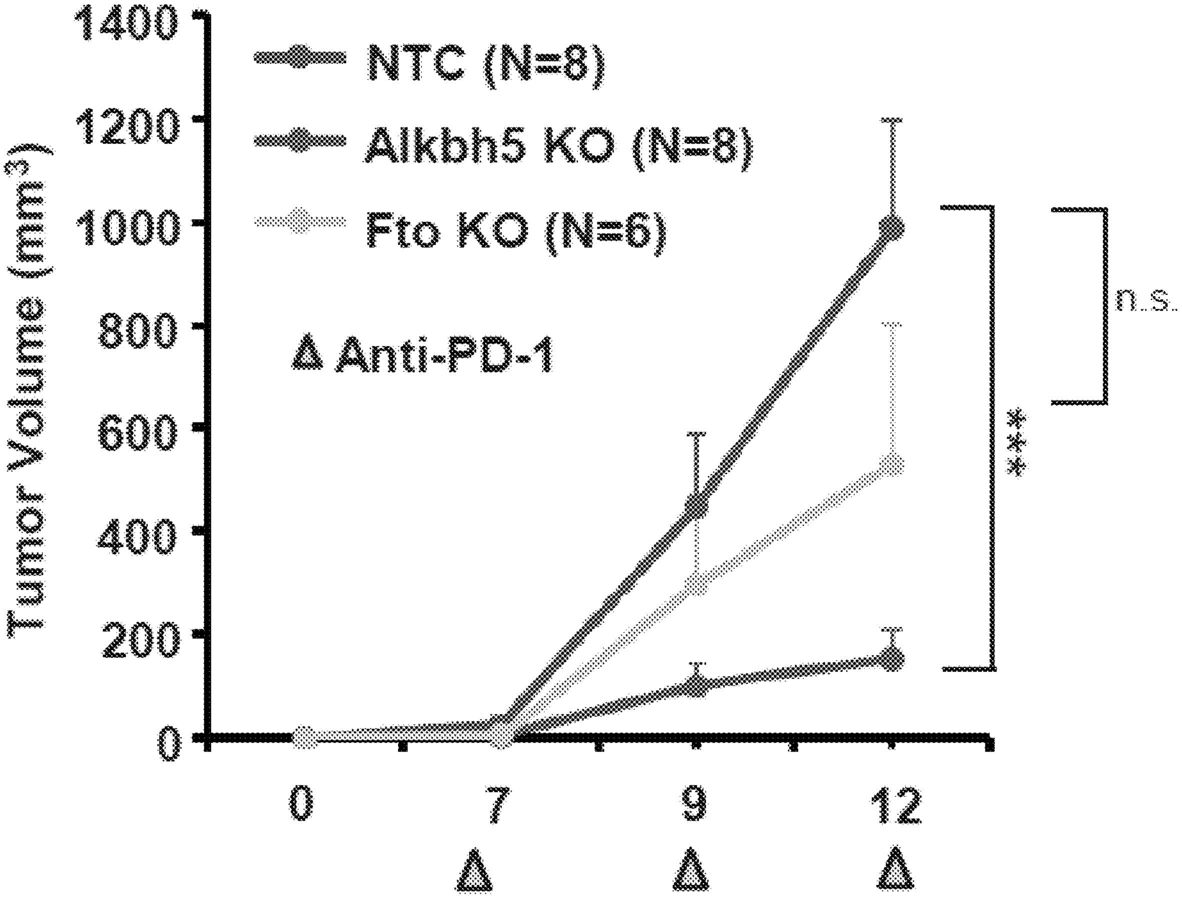

Alkbh5-KO implanted tumors also had significantly reduced tumor growth when treated with anti-PD-1 antibody alone (FIG. 1D). Importantly, there were no significant differences between the growth of NTC, Alkbh5-KO, and Fto-KO B16 cells either in vitro (FIG. 5G) or in vivo in untreated mice (FIG. 5H), indicating that deletion of the m6A demethylases did not intrinsically impair their growth. To examine the mechanisms by which Alkbh5 and Fto KO modulates GVAX/anti-PD-1 therapy, we performed the same experiments in Tcra-deficient mice, which lack the TCRa chain and do not develop mature CD4* and CD8*T cells. In these mice, the effects of Alkbh5 knockout on tumor growth were dampened, but not eliminated (FIGS. 1E and 5I), suggesting that the effect of Alkbh5 in regulating GVAX/anti-PD-1 therapy was partially independent of the host T cell response. Taken together, these data demonstrate that Alkbh5 and Fto expression in B16 melanoma cells is not required for their growth or survival in vitro or in vivo; however, the enzymes play a crucial role in the efficacy of GVAX/anti-PD-1 therapy.

Deletion of Alkbh5 in Melanoma Cells Alters the Recruitment of Immune Cell Subpopulations During Immunotherapy.

Figure 2A:
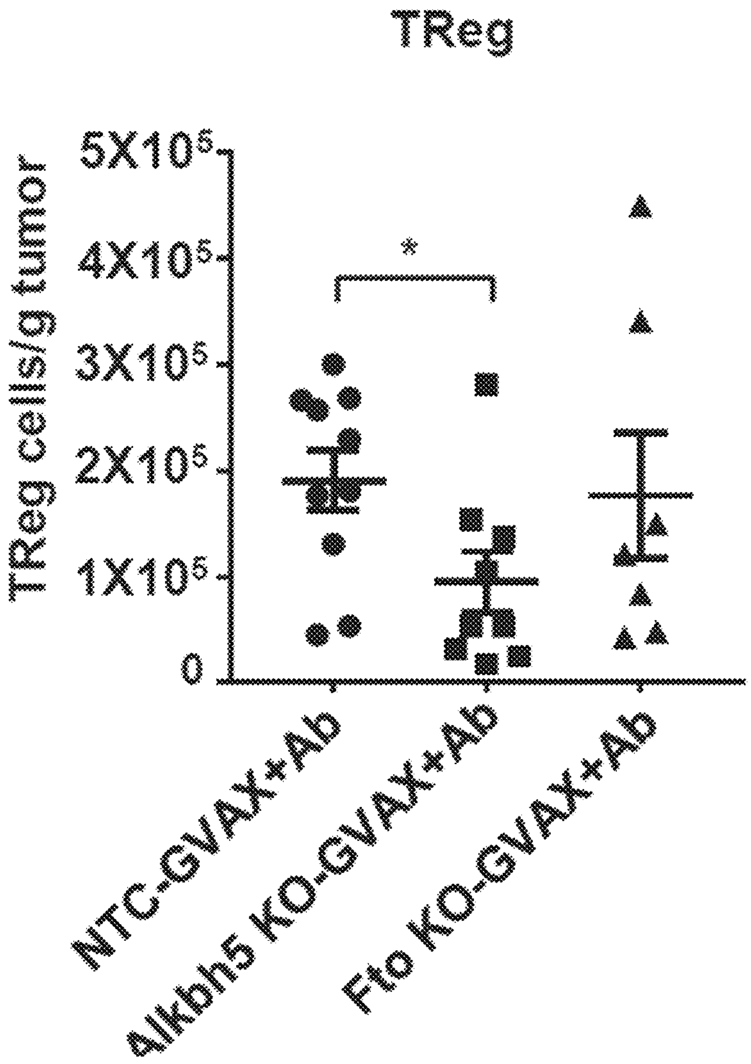
FIG. 2A-2G. Depiction of Deletion of Alkbh5 Modulates Tumor immune cell Infiltration and gene expression During Immunotherapy.
Figure 2B:
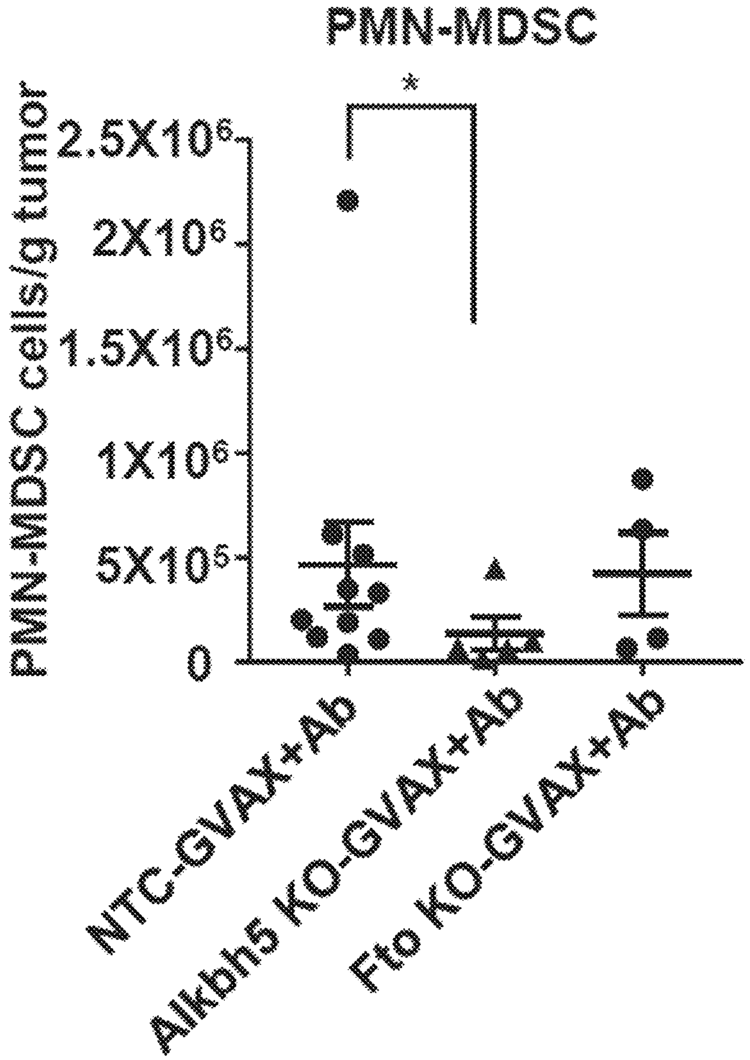
Figure 2C:
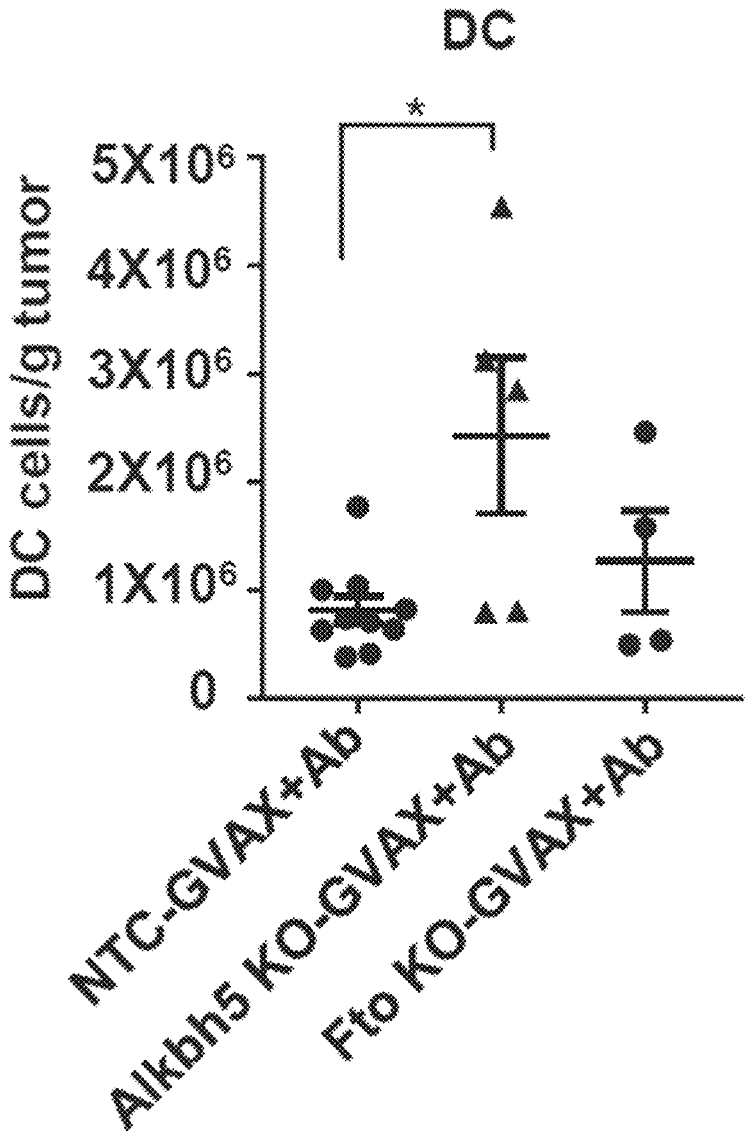
Figure 2D:
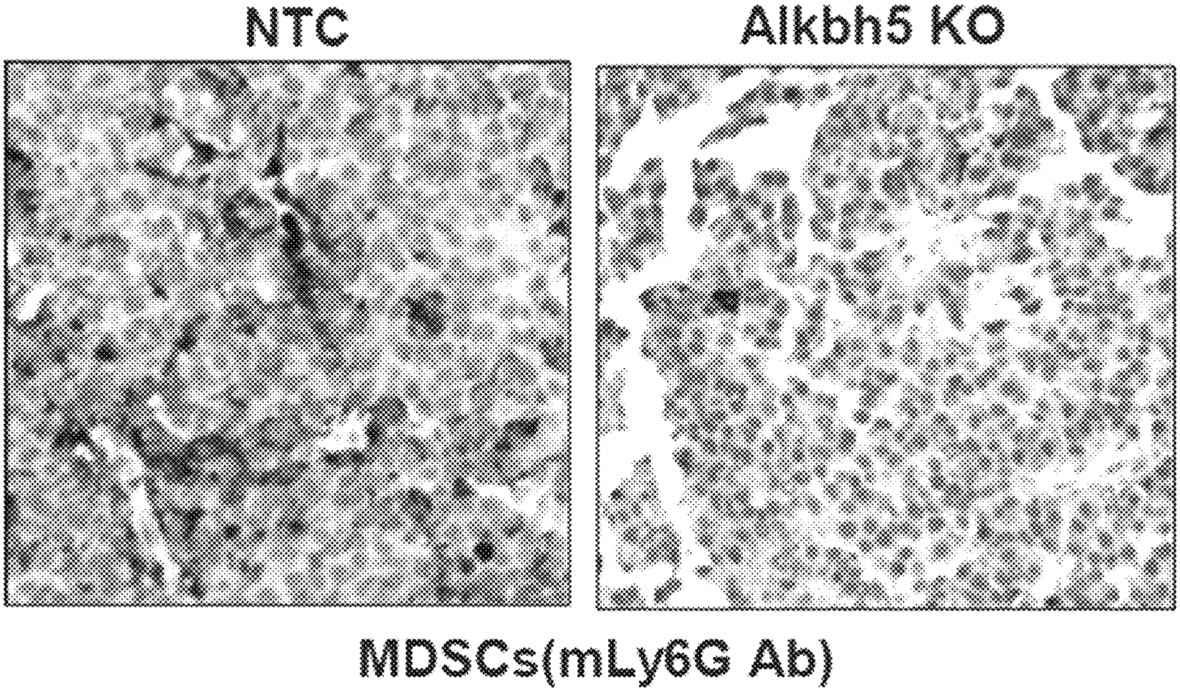
Figure 6A:
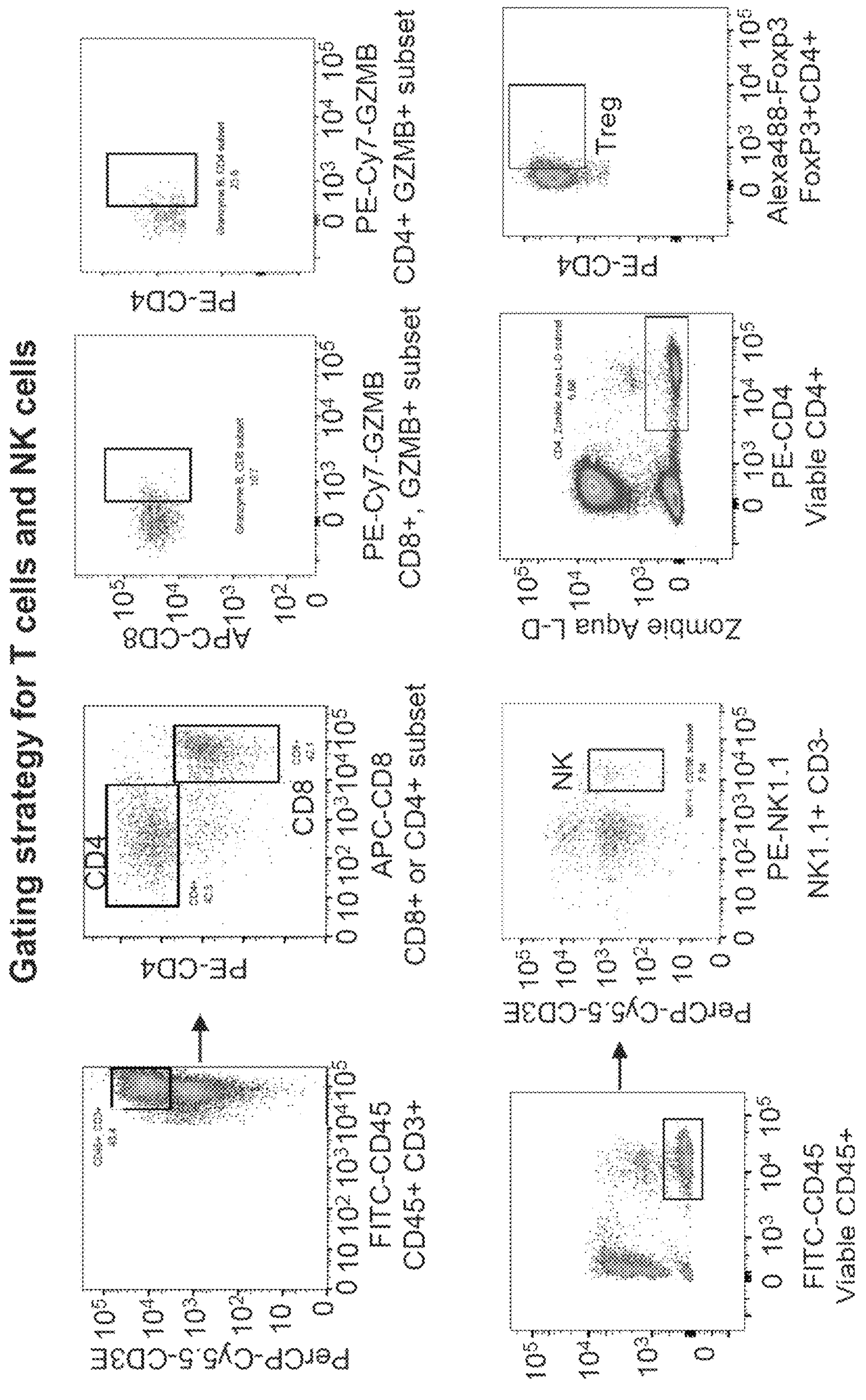
FIG. 6A-6F. Depiction of Deletion of Alkbh5 Modulates Tumor immune cell Infiltration and gene expression During Immunotherapy.
Figure 6B:
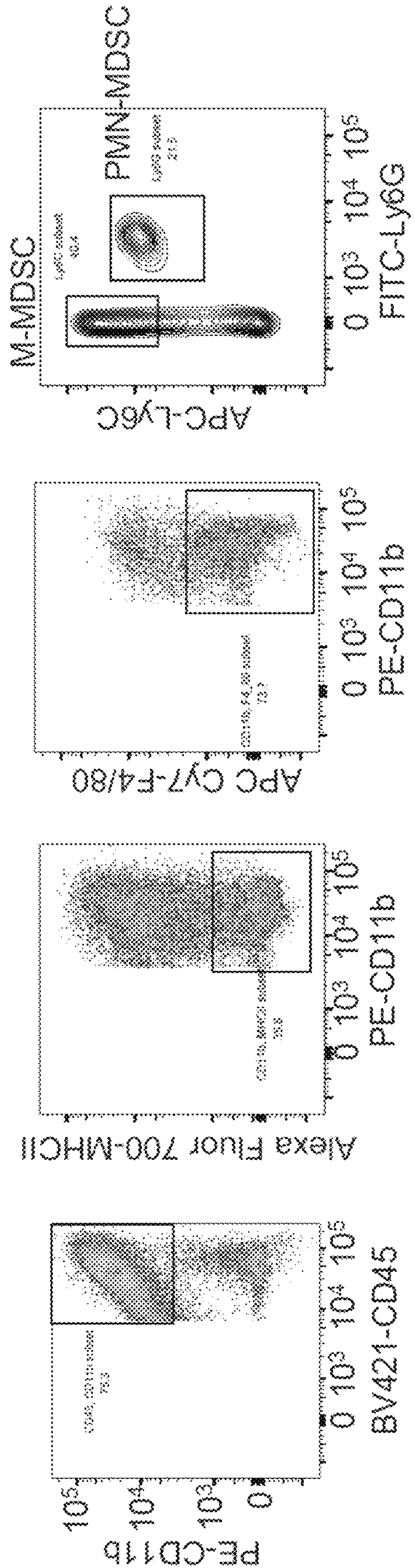
Figure 6C:
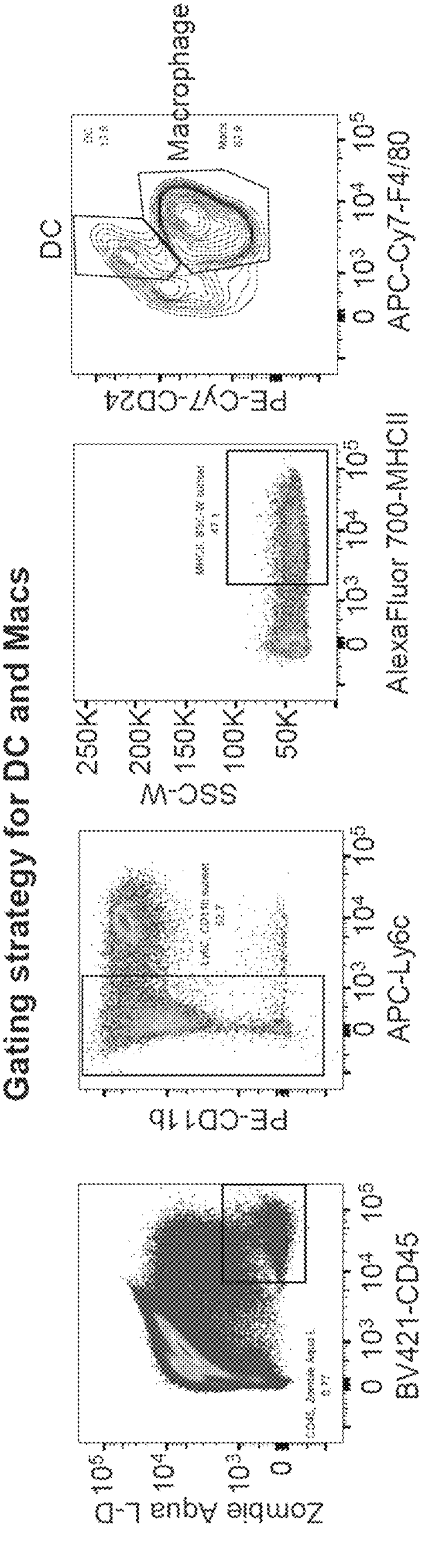
Figure 6D:
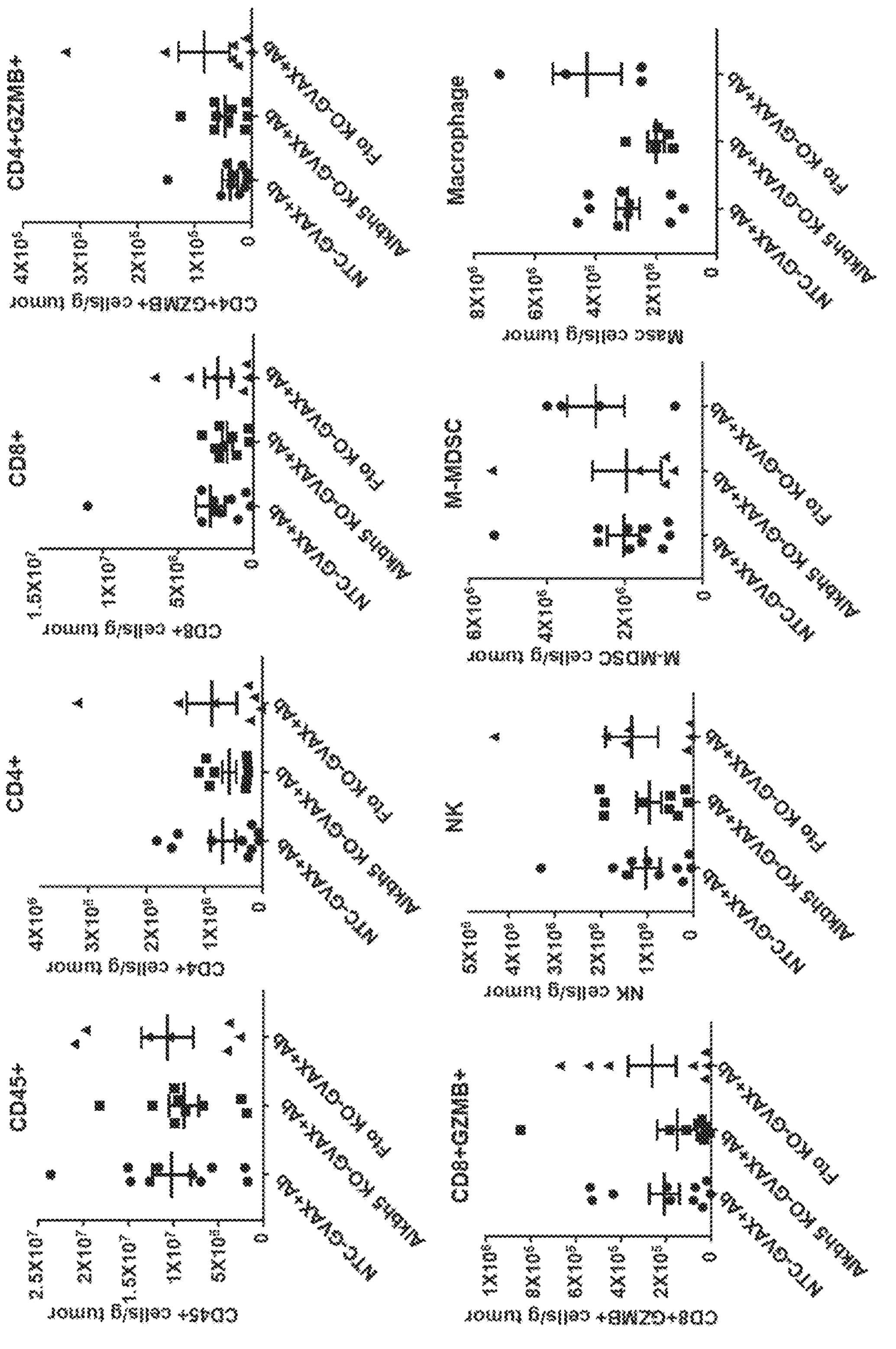
Figure 6E:
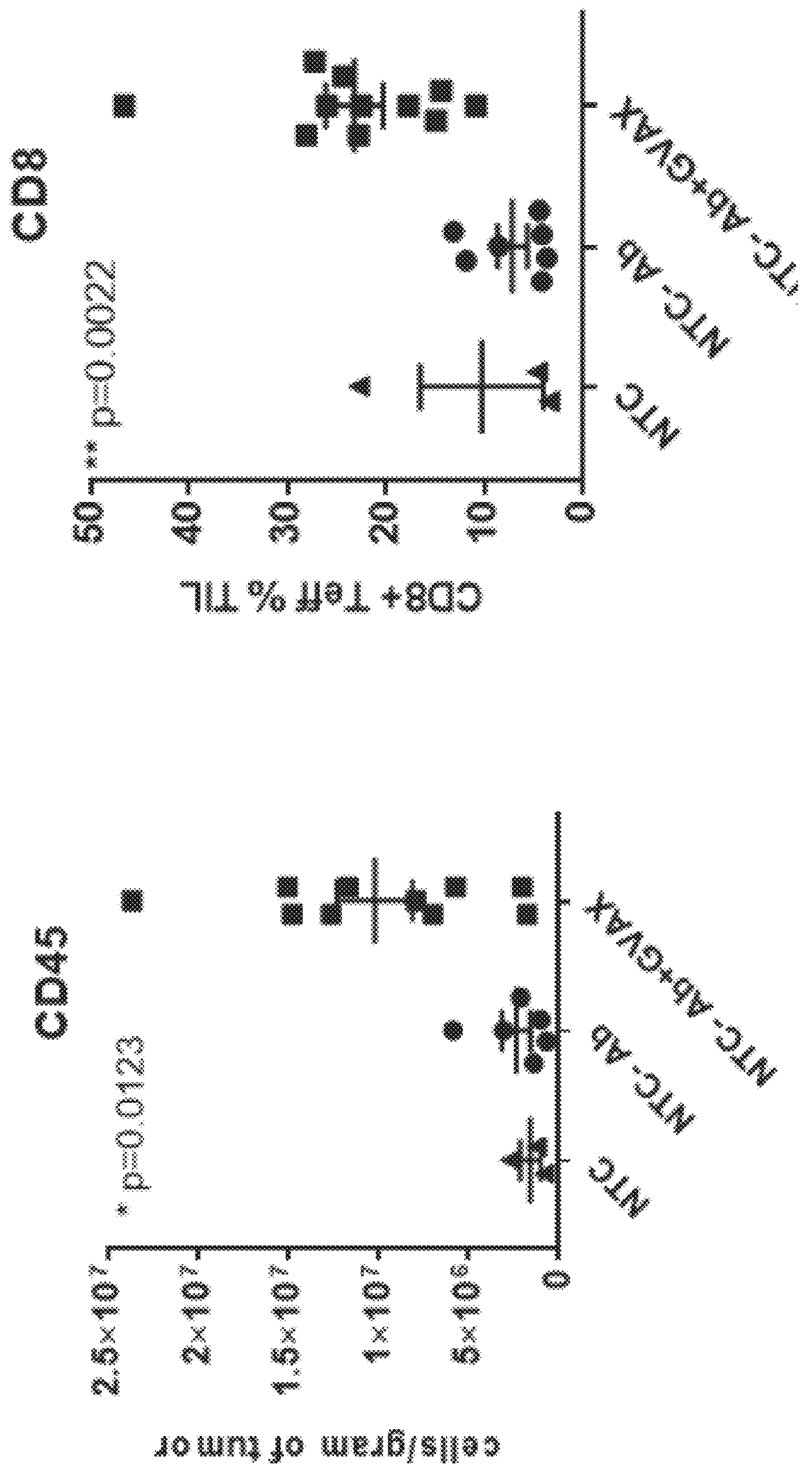
Figure 6F:
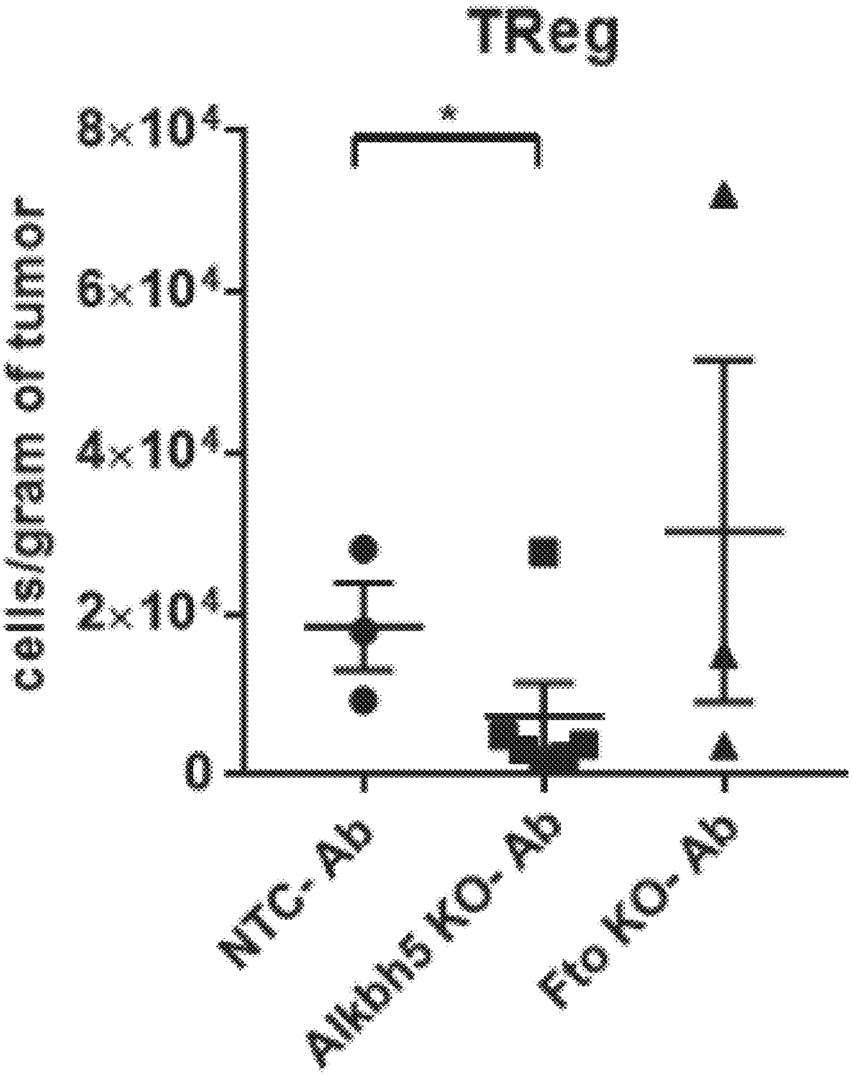

We examined whether Alkbh5 and Fto deletion in tumor cells modulates immune cell recruitment during GVAX/anti-PD-1 therapy by flow cytometric analysis of tumor infiltrates on day 12 (FIG. 6A-6C). Compared with NTC B16 tumors, there is no significant difference in total number of tumor infiltrated lymphocytes (TIL) (CD45+), CD4+, CD8+ cells in Alkbh5 and Fto deficient mouse tumors, although a trend to higher abundance of GZMB+ CD8, GZMB+ CD4 T cell and NK cell numbers in Fto null mice tumor (FIG. 6D). However, the number of infiltrating regulatory T cells (Tregs) and polymorphonuclear myeloid-derived suppressor cells (PMN-MDSCs), but not myeloid (M)-MDSCs, was significantly decreased in Alkbh5-KO tumors compared with N TC tumors during GVAX/anti-PD-1 treatment (FIGS. 2A-2B and 6D-6F). Interestingly, dendritic cells (DCs), but not macrophages, were also significantly elevated in Alkhb5-KO tumors compared with NTC tumors (FIGS. 2C and 6D). To verify the decrease in PMN-MDSCs, we performed immunohistochemical staining and found a marked reduction in the accumulation of MDSCs in Alkbh5-KO tumors compared with NTC tumors on day 12 (FIG. 2D).

Figure 2E:
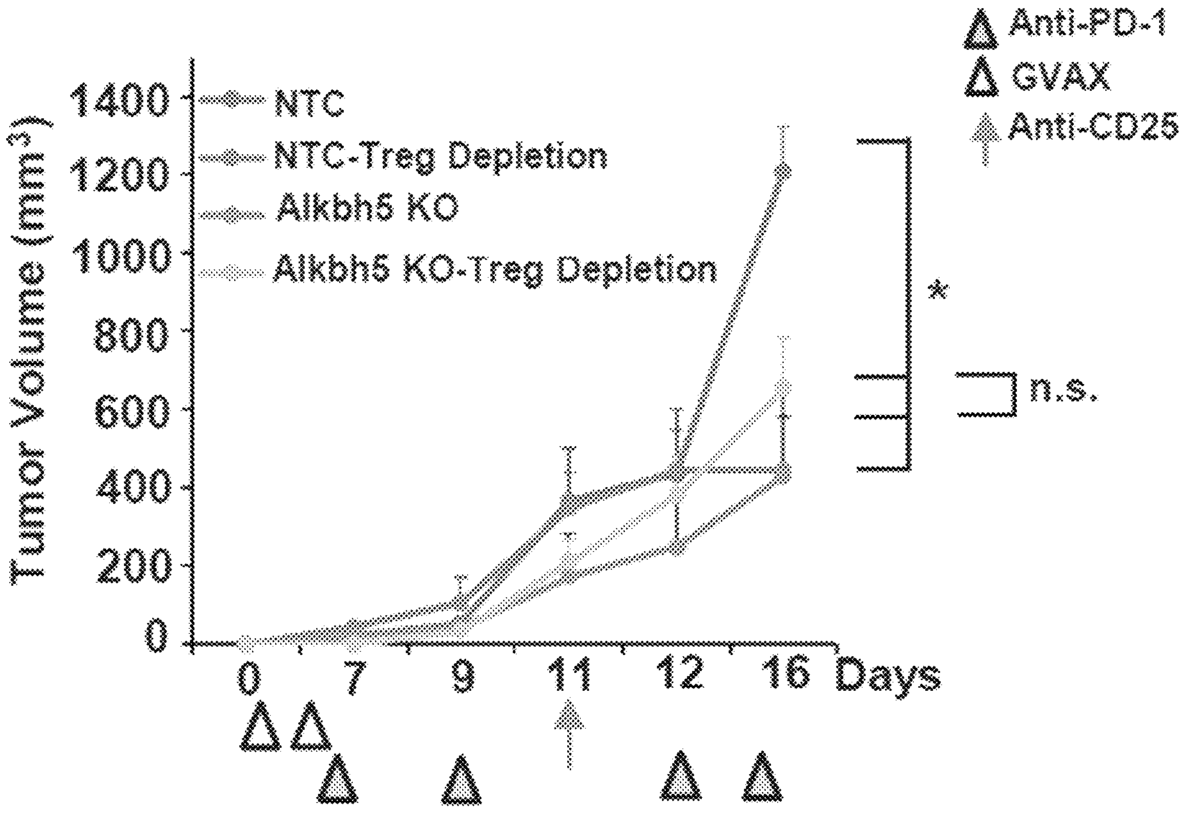

Cross-talk between Tregs and other immune cells is an important contributor to tumor-induced immune suppression; for example, MDSCs can induce Treg amplification and decrease DC differentiation in the tumor microenvironment, and Tregs can greatly inhibit cytotoxic T cell function 23. To assess Treg function in GVAX/anti-PD-1 therapy of melanoma, we monitored the effect on tumor growth after injection of a Treg-depleting anti-CD25 Ab on day 11 of treatment 242s. Treg depletion was found to reduce the growth of NTC B16 tumors but not of Alkbh5-KO tumors (FIG. 2E). These results are consistent with an immunosuppressive role for Tregs during GVAX/anti-PD-1 therapy and also with the observed reduction in Treg infiltration into Alkbh5-KO. Collectively, these data demonstrate that tumor cell expression of Alkbh5 plays a role in modulating the recruitment of immunosuppressive MDSCs and Tregs during GVAX/anti-PD-1 therapy.

M6A Demethylase Deletion Alters the Tumor Cell Transcriptome During Immunotherapy.

Figure 2F:
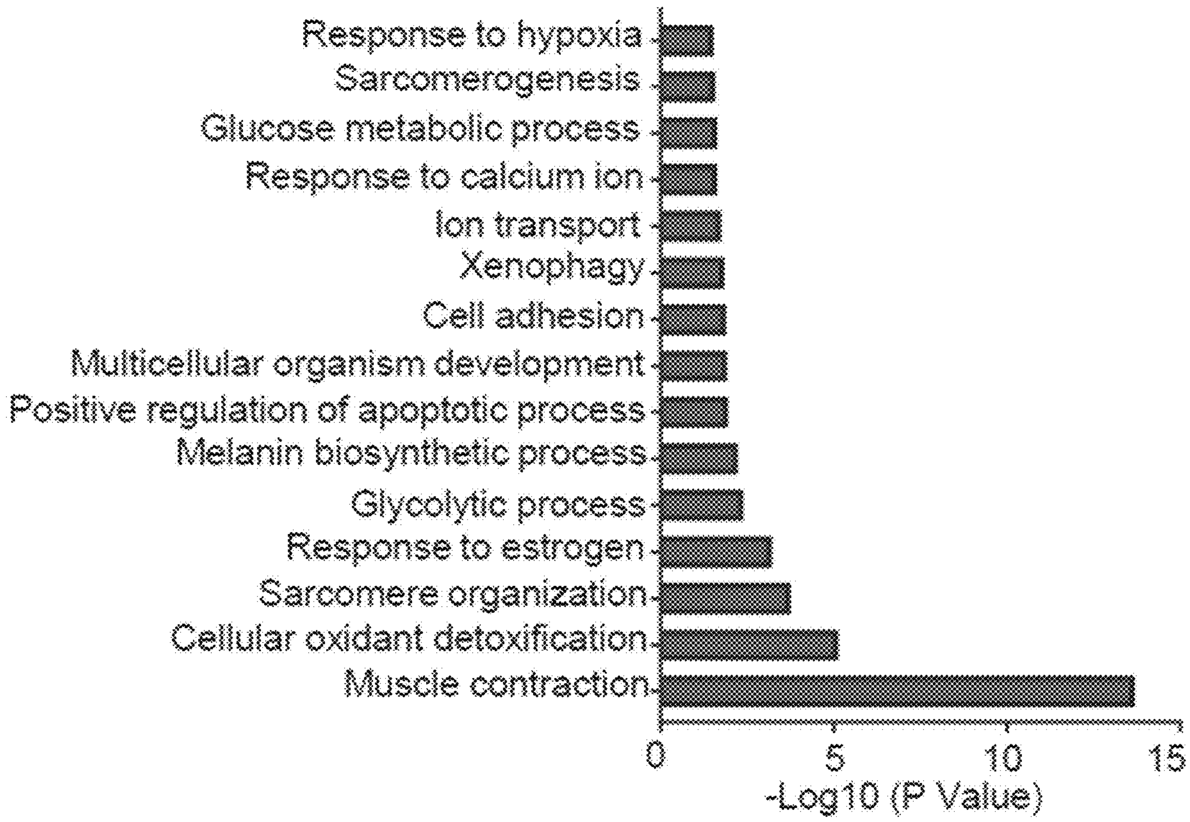
Figure 7A:
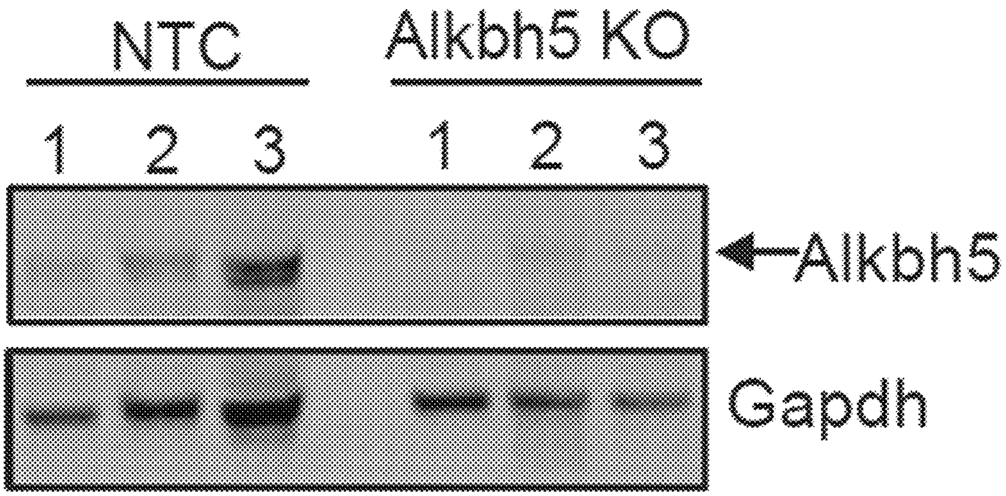
FIG. 7A-7K. Depiction of Deletion of Alkbh5 Modulates Tumor immune cell Infiltration and gene expression During Immunotherapy.
Figure 7B:
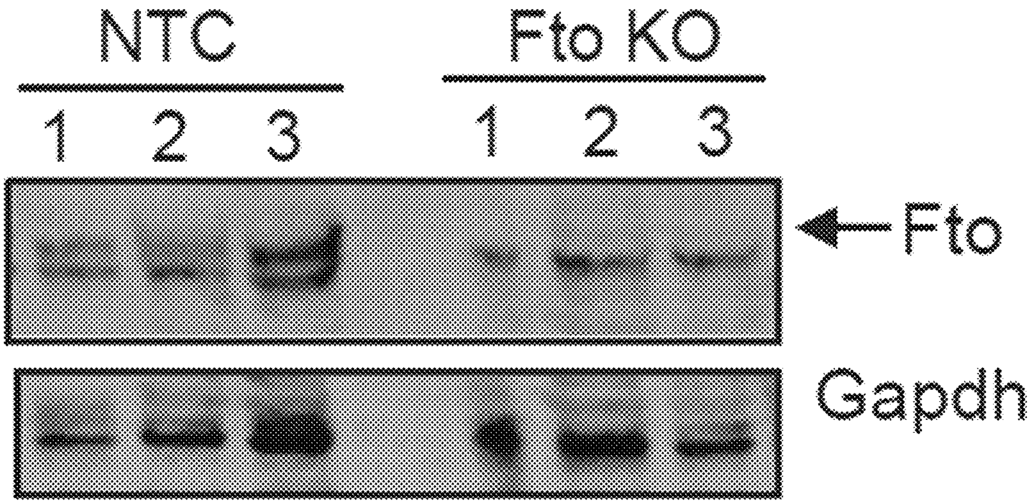
Figure 7C:
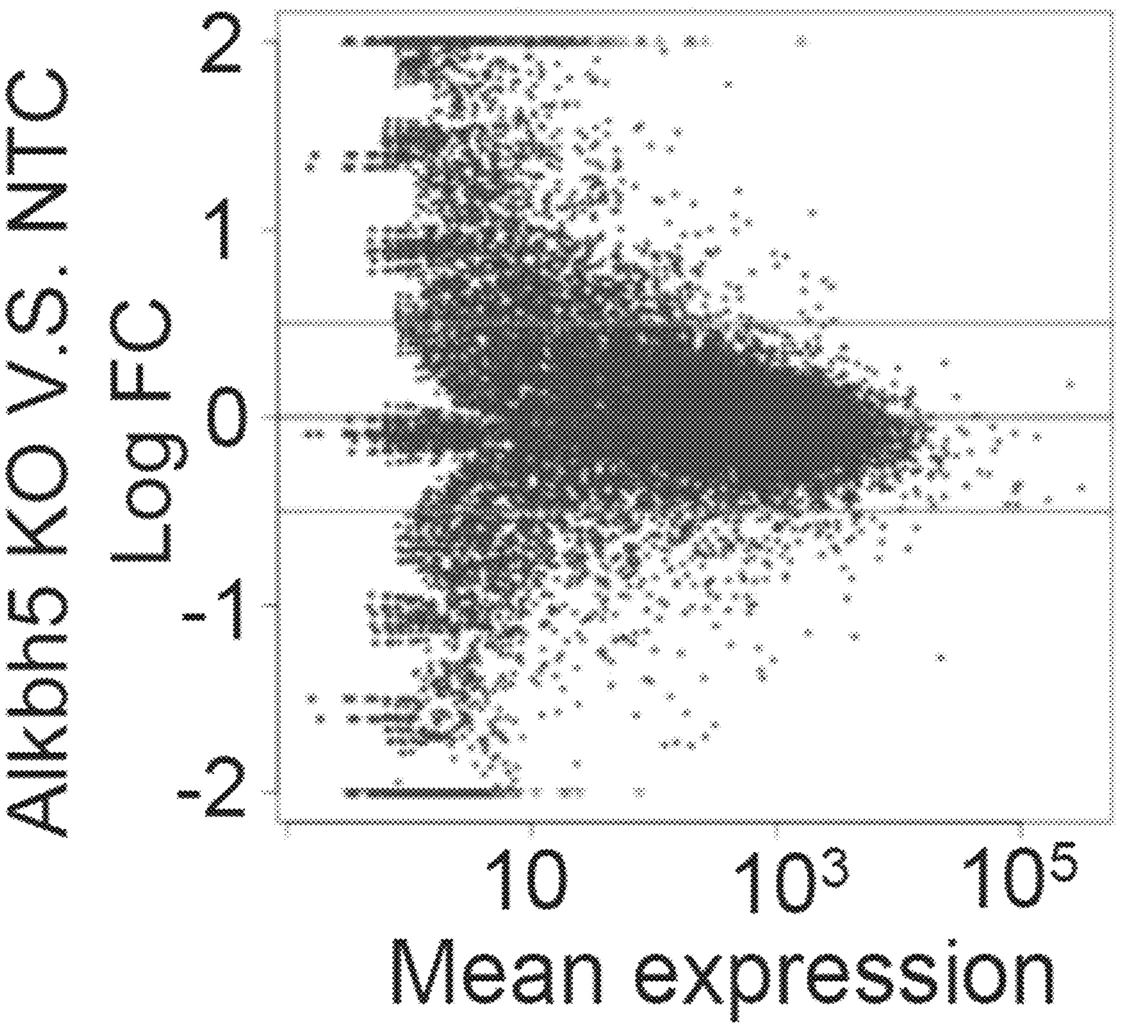
Figure 7D:
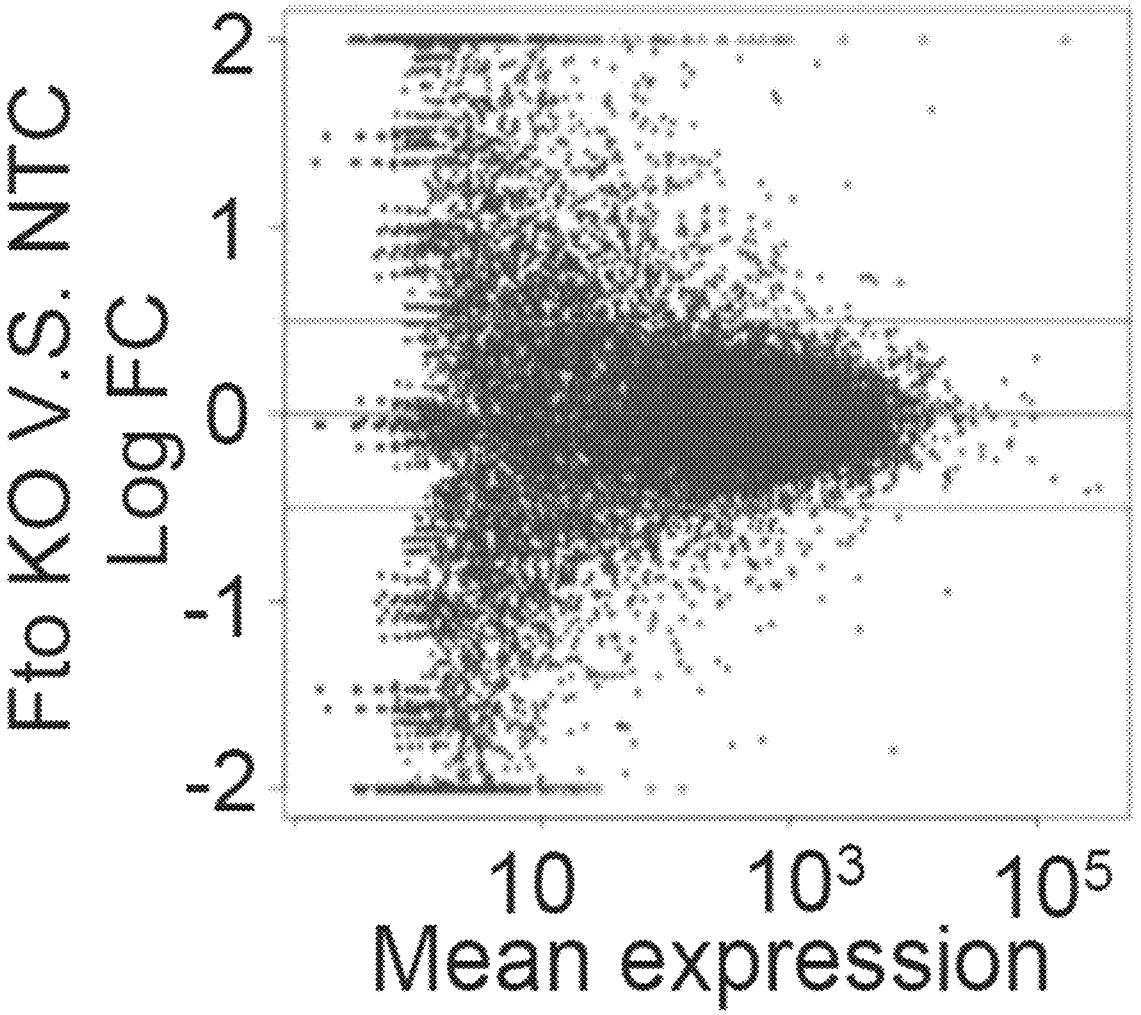
Figure 7E:
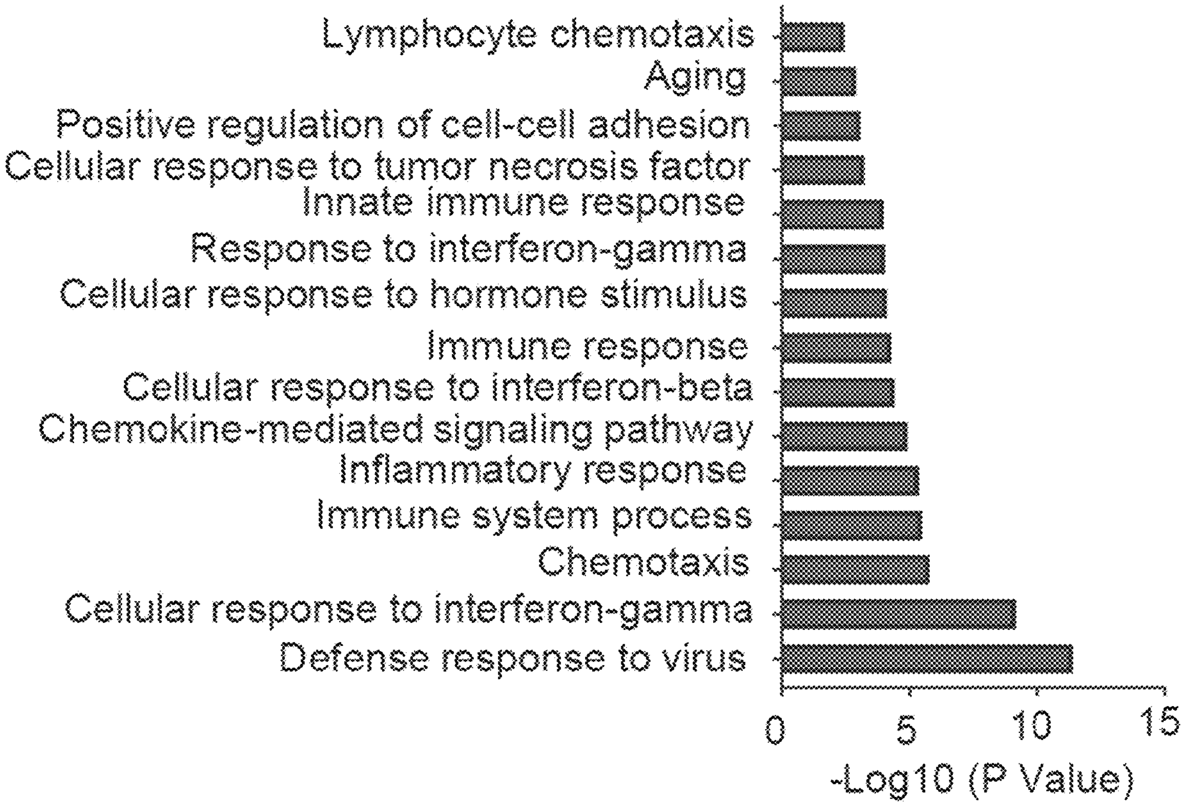
Figure 7F:
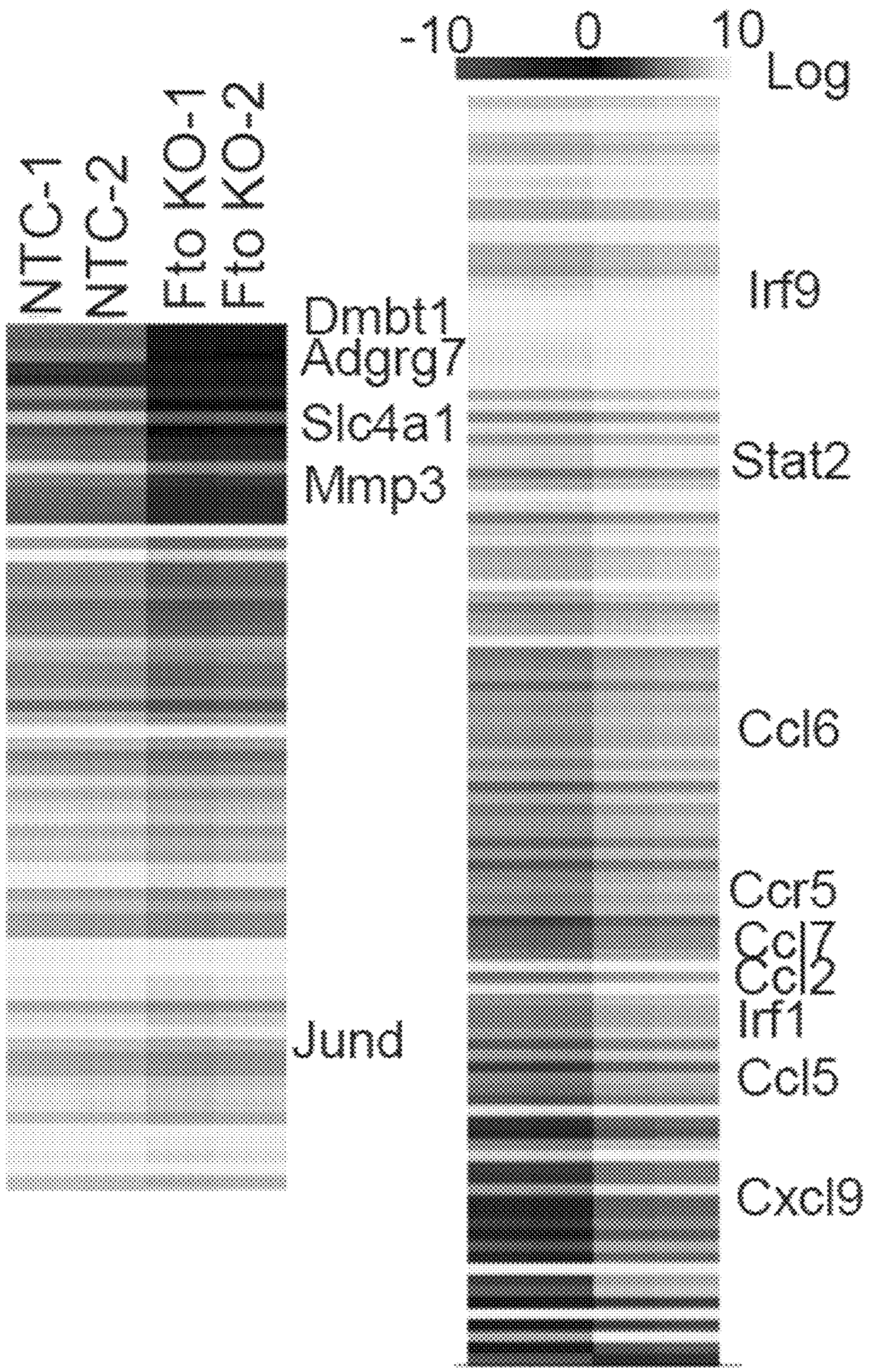
Figure 7G:
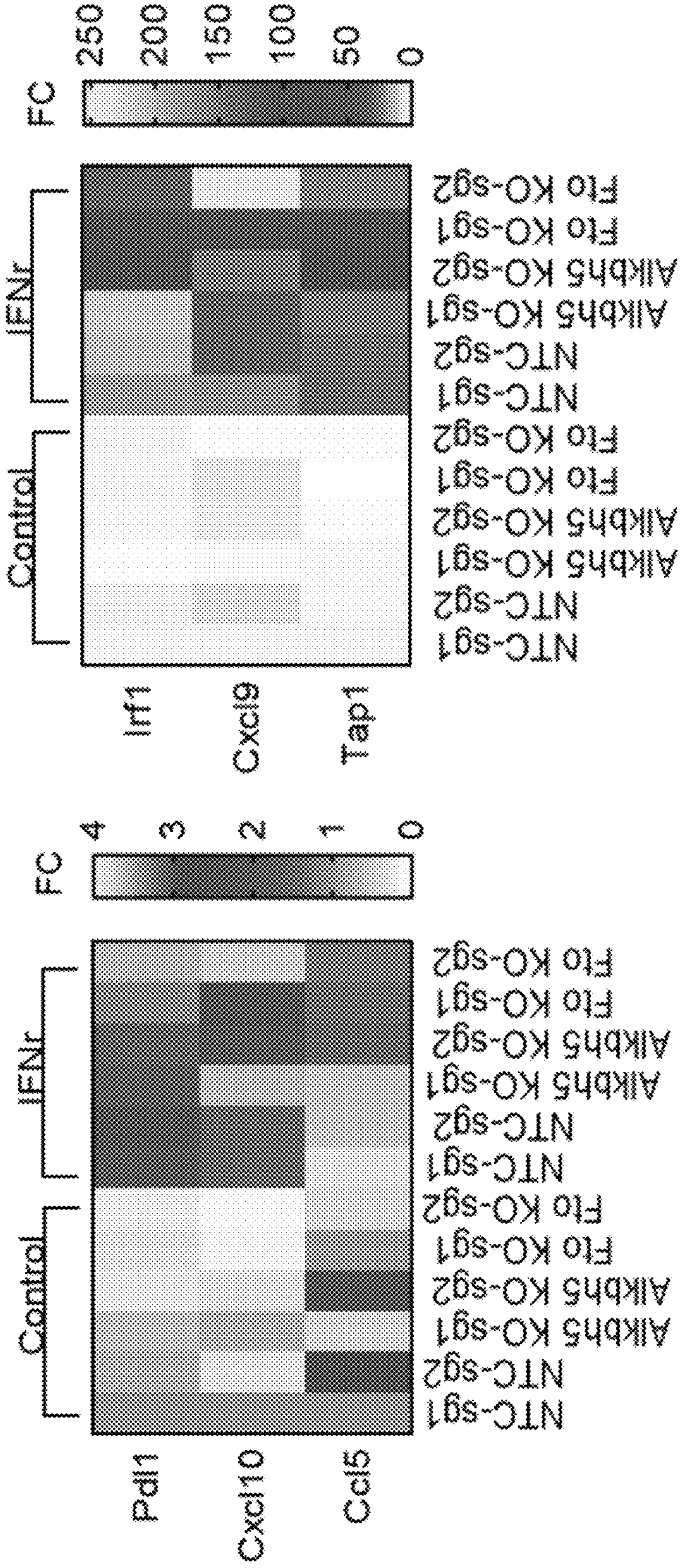

To understand the regulatory role of Alkbh5 and Fto in tumor therapy at the molecular level, we performed RNA-Seq to identify differentially expressed genes (DEGs) in NTC B16 tumors compared Alkbh5-KO or Fto-KO tumors on day 12 of CVAX/anti-PD-1 treatment. Tumors were confirmed to be Alkbh5 or Fto deficient before RNA-Seq analysis (FIG. 7A-7B). Gene ontology (GO) analysis showed that the DEGs in Alkbh5-KO tumors were predominantly involved in metabolic processes, apoptosis, cell adhesion, transport, and hypoxia (FIGS. 2F and 7C). Interestingly, however, DEGs in Fto-KO tumors were mostly immune response-associated genes (FIG. 7D-7E). Indeed further analysis of GO pathways and heatmaps revealed that of the DEGs differed between Alkbh5-KO and Fto-KO B16 tumors. Genes most affected by Alkbh5 KO were associated with regulation of tumor cell survival, adhesion, metastasis and metabolism such as Ralgps2, Mmp3, Epha4, Adgrg7, Reln and Slc16a3/MCT4 (FIG. 2G), whereas those most affected by Fto-KO were associated with interferon-y (IFNY) and chemokine signaling, including RFI, IRF9, STAT 2, Cxc19, Ccl5, and Ccr5 (FIG. 7F). To confirm this result, we exposed NTC, Alkbh5-KO, and Fto-KO B16 cells to IFNY in vitro and analyzed gene expression by qRT-PCR. As shown in FIG. 7G, Fto-KO, but not Alkbh5-KO or NTC tumor cells showed increased expression of the IFNY pathway targets Pdll and Irfl and the chemokines Cxc19, Cxc110, and Cd5 after IFNy stimulation. These results suggest that, during anti-PD-1/GVAX therapy, Alkbh5 expression in B16 melanoma cells predominantly affects cell intrinsic changes and recruitment of immune cells to the TME, while Fto is involved in regulating IFNy and inflammatory chemokine pathways.

Figure 7H:
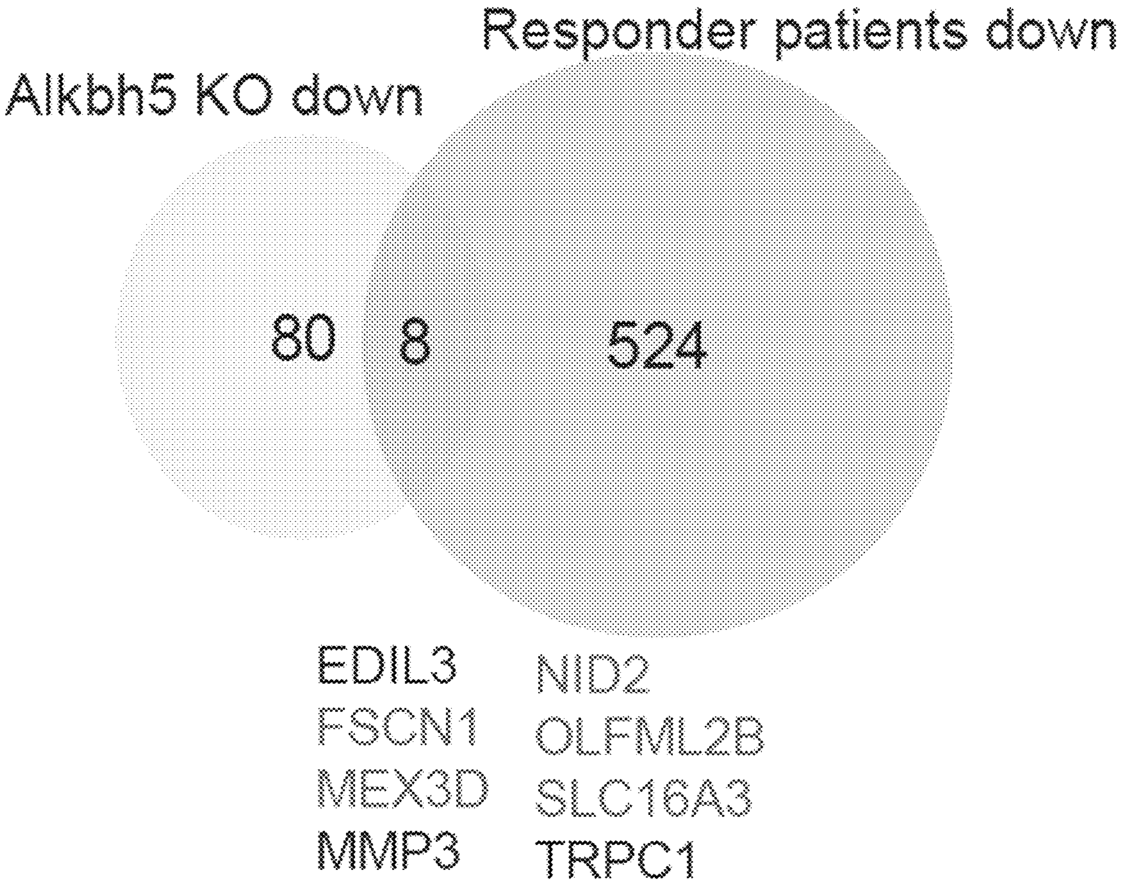
Figure 7I:
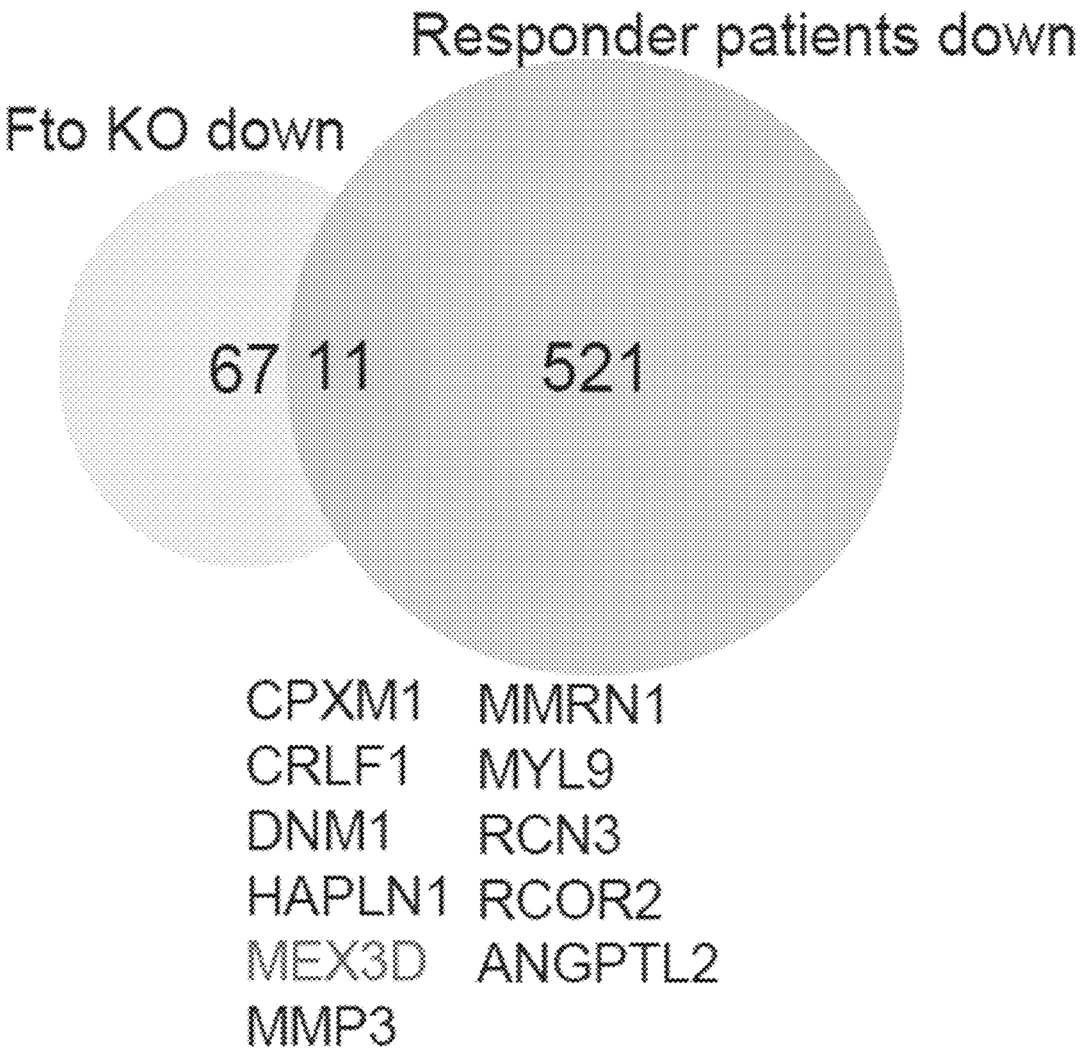
Figure 7J:
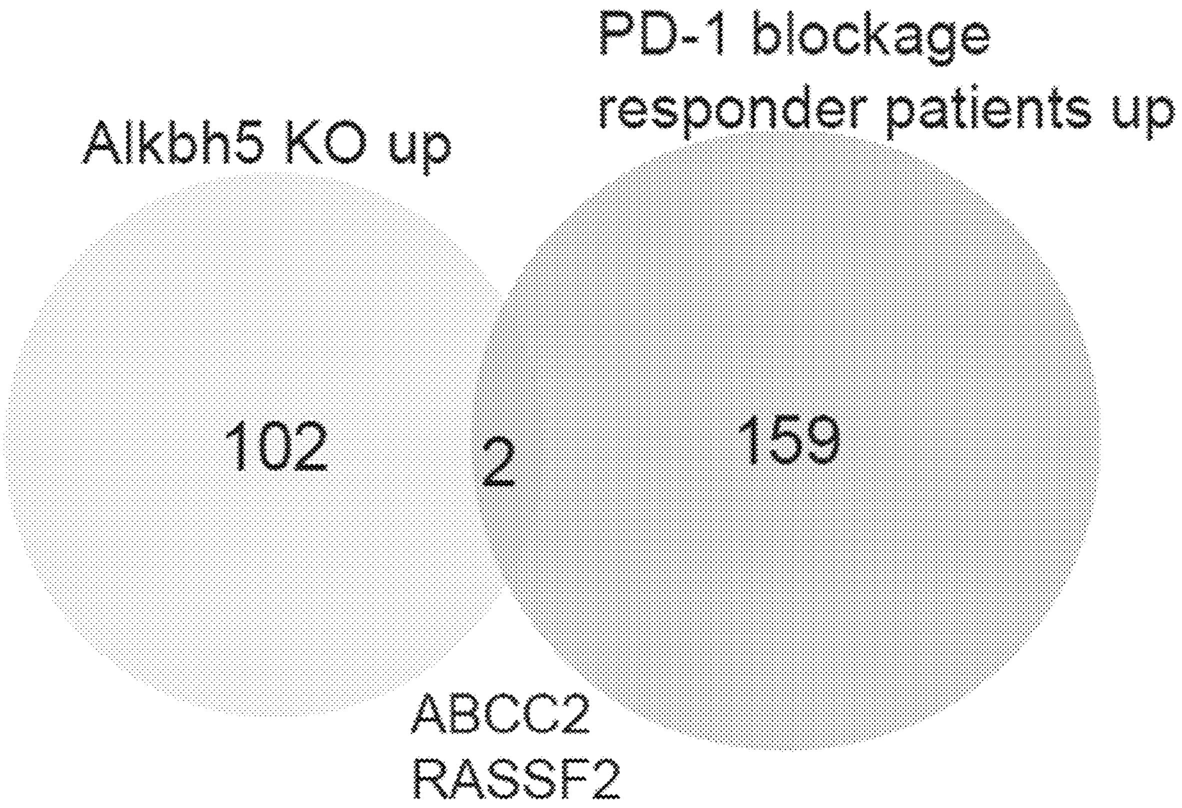
Figure 7K:
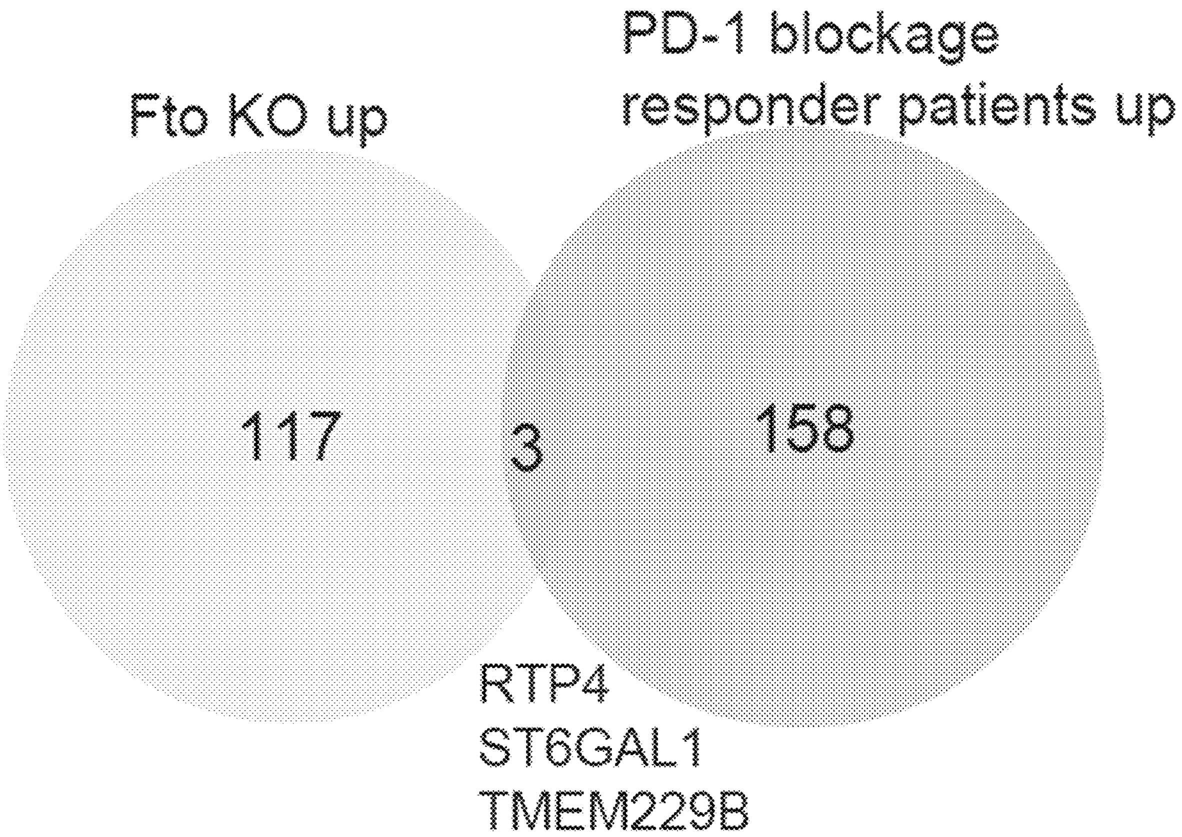

IFNY pathway activation has been shown to be an important indicator of the efficacy of PD-1 blockade in mouse model studies[26], whereas another study of melanoma patients identified associations between anti-PD-1 response and expression of genes involved in mesenchymal transition, inflammatory, wound healing, and angiogenesis, but not IFNY pathway or other gene signatures indicative if sensitivity to ICB 2. Therefore, we analyzed a gene expression dataset from 38 melanoma patients who did (n 21) or did not (n 17) respond to anti-PD-1 therapy, and searched for DEGs that were also identified here as DEGs in B16 tumors with Alkbh5 or Fto KO. This analysis identified 8 genes that were commonly downregulated in Alkbh5-KO B16 tumors and responder melanoma patients, and 11 genes that were commonly downregulated in Fto-KO B16 tumors and responder patients (FIGS. 7H and 7I). Fewer genes were commonly upregulated between these groups (FIGS. 7J and 7K). These results suggest that the downregulated genes conserved among mouse model and patients receiving PD-1 antibody treatment play important roles in regulating cancer immunotherapy response and are potential target genes of Alkbh5 and Fto.

Alkbh5 and Fto Deletion in Melanoma Cells Affects the m6A Epitranscriptome During Immunotherapy.

Figure 3A:
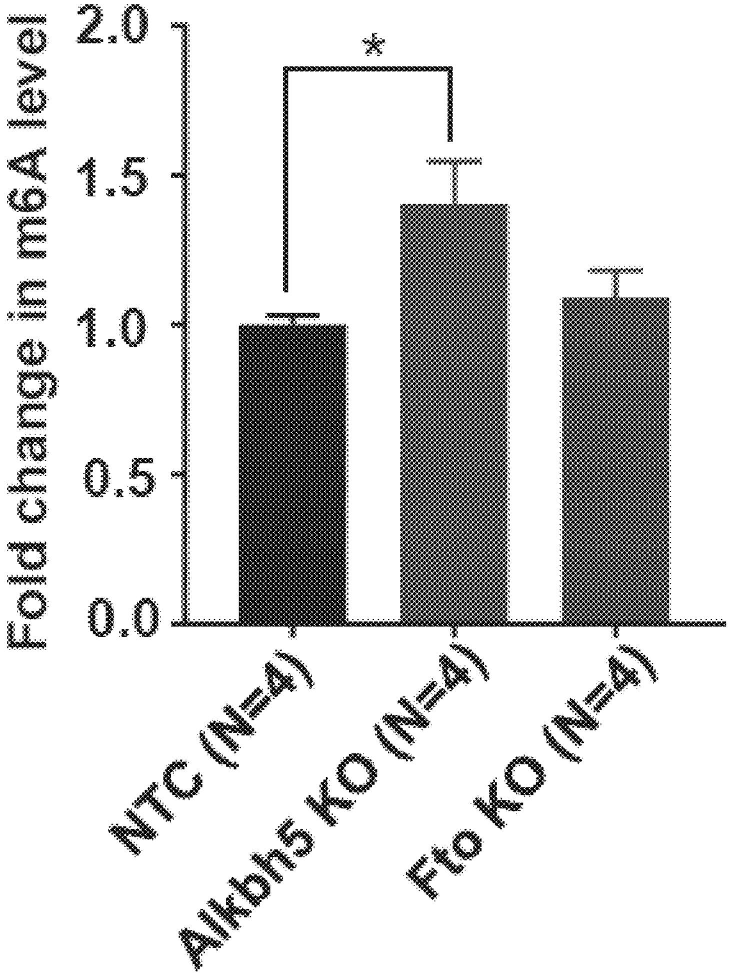
FIG. 3A-3H. Depiction of Alkbh5 Regulates Gene Splicing, and Lactate and Vegfa Contents of TME in B16 Tumors During Immunotherapy FIG. 4A-4F. Depiction of ALKBH5 Expression Influences the Response of Melanoma Patients to Anti-PD-1 Therapy FIG. 5A-5I. Depiction and plots of deletion of the m6A RNA Demethylases Alkbh5 Sensitizes Tumors to Immunotherapy.
Figure 3B:
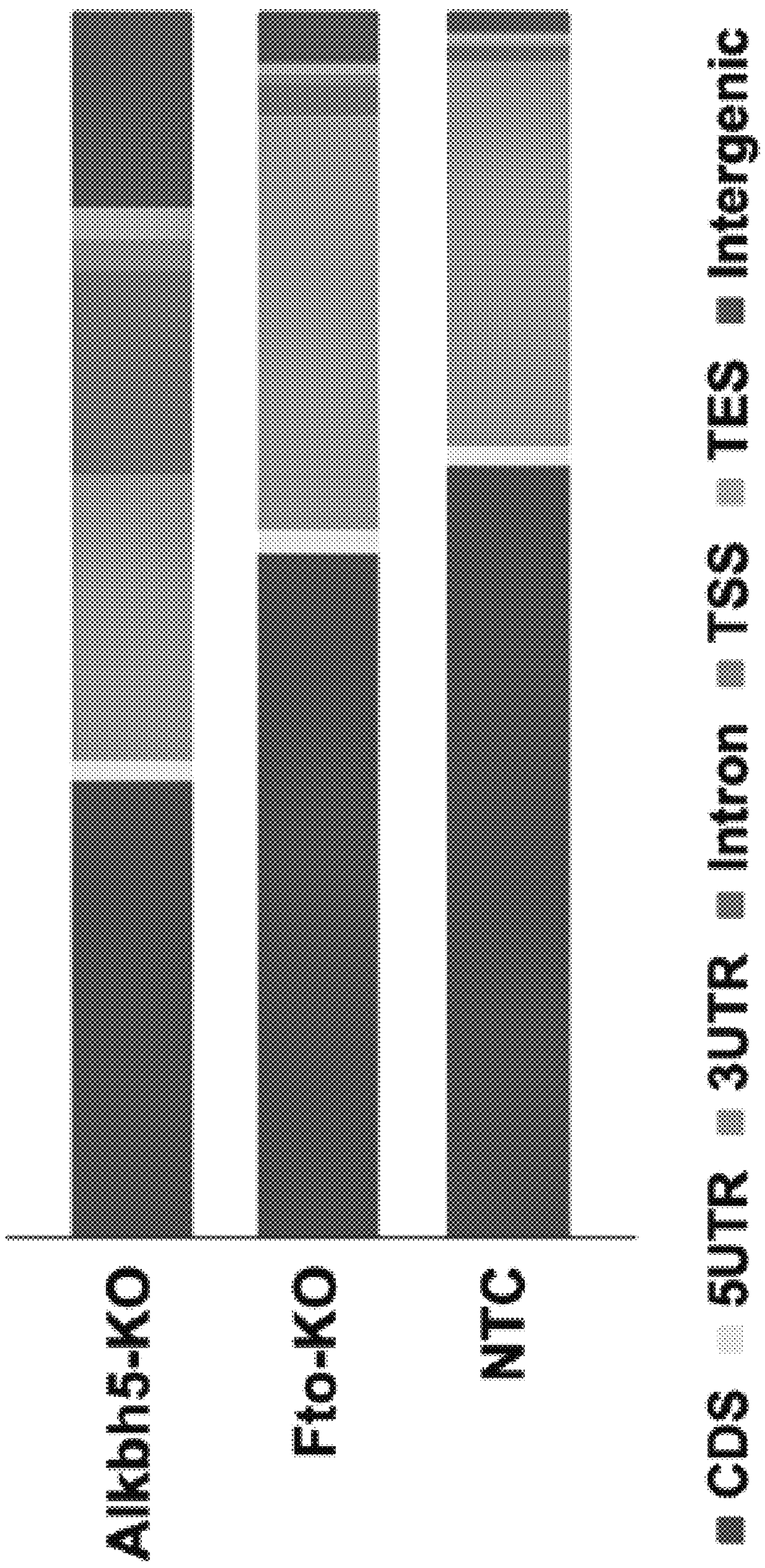
Figure 3C:
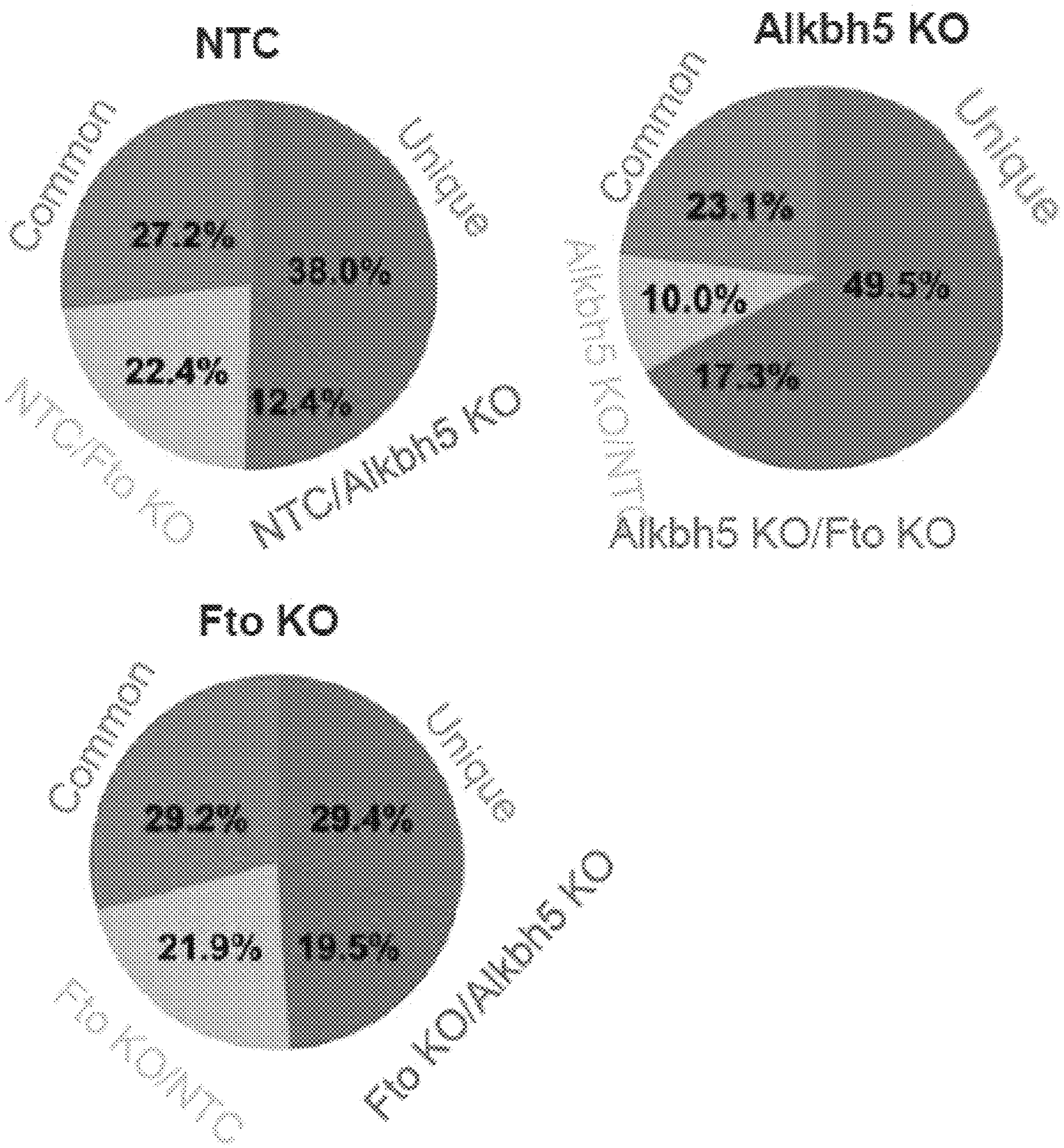
Figure 3D:
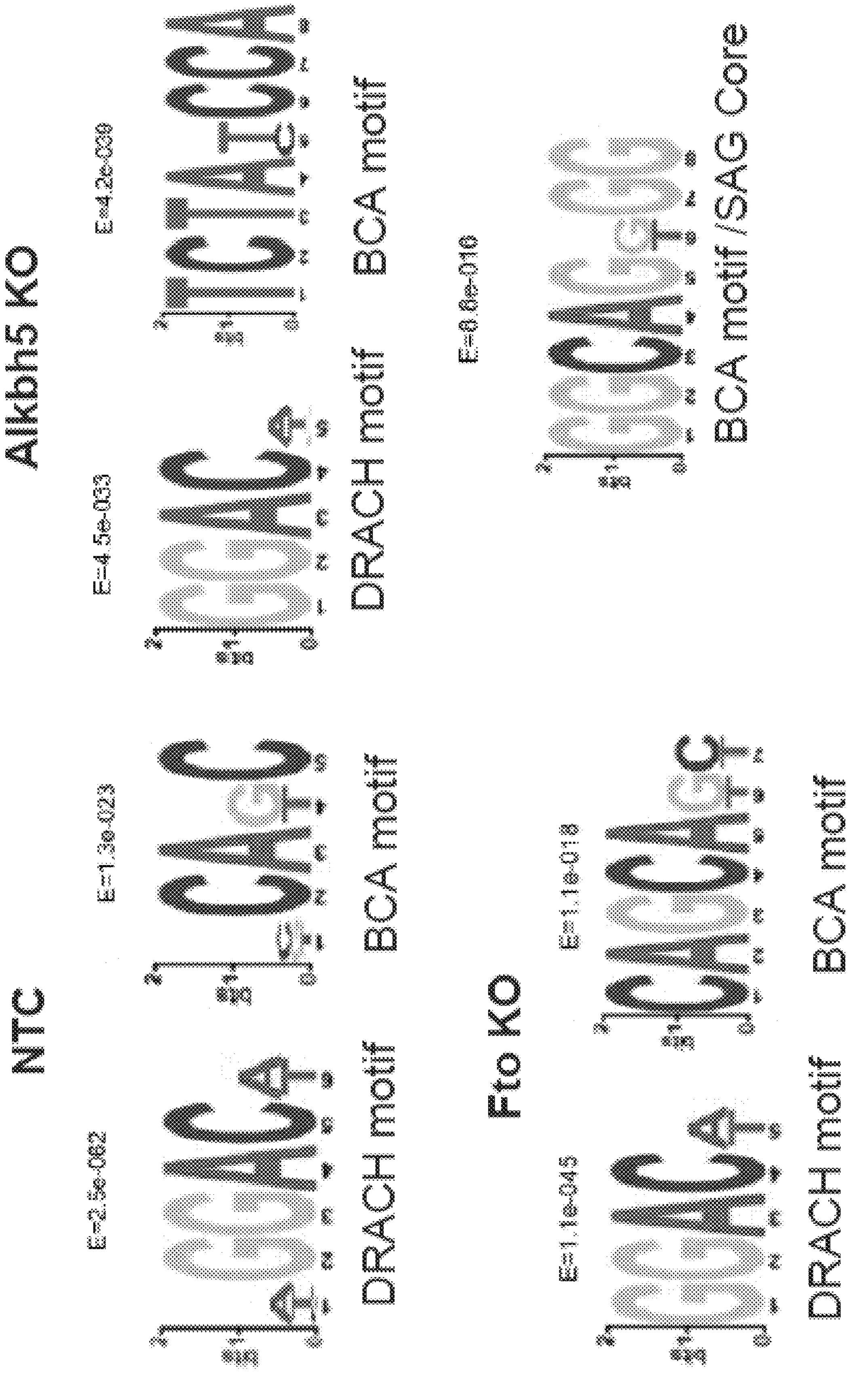
Figure 8A:
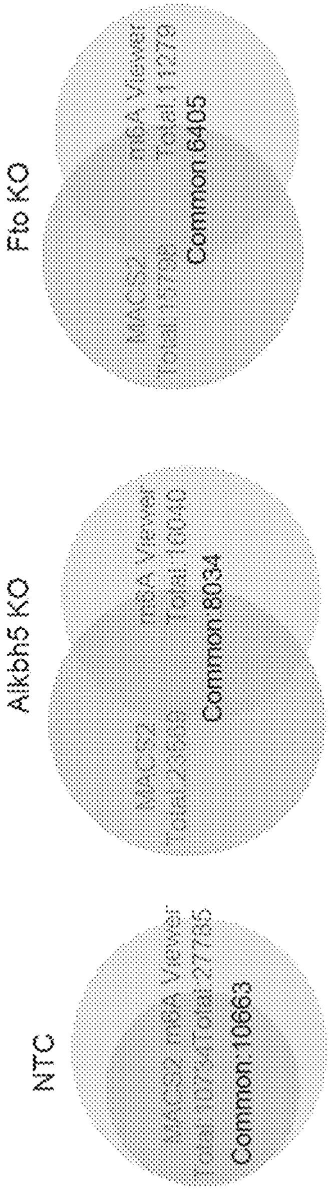
FIG. 8A-8C. Depiction of Alkbh5 Regulates Gene Splicing, and Lactate and Vegfa Contents of TME in B16 Tumors During Immunotherapy FIG. 9A-9I. Depiction of Alkbh5 Regulates Gene Splicing, and Lactate and Vegfa Contents of TME in B16 Tumors During Immunotherapy FIG. 10A-10F. Depiction of Alkbh5 Regulates Gene Splicing, and Lactate and Vegfa Contents of TME in B16 Tumors During Immunotherapy and Depiction of ALKBH5 Expression Influences the Response of Melanoma Patients to Anti-PD-1 Therapy FIG. 11. FTO inhibitors specifically kill Glioblastoma cancer stem cells TSS76 GBM cancer stem cells were used to develop neuro organoid models of cancer and two drug concentrations were tested.
Figure 8B:
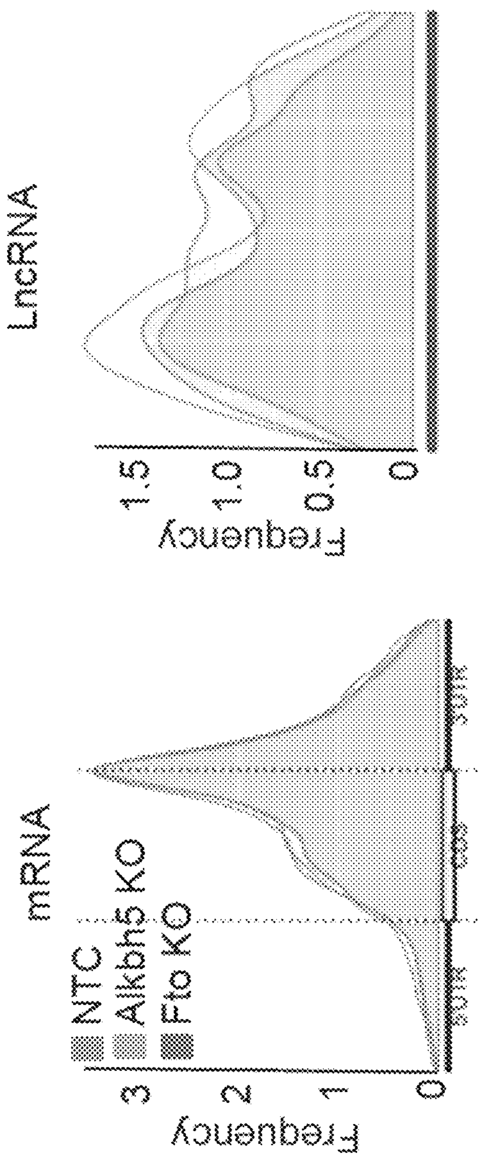

Given the profound importance of m6A in regulating the function of target RNAs and gene expression[28,29], we next examined how Alkbh5 and Fto KO affected content in RNA by LC-MS/MS of B16 tumors on day 12 of GVAX/anti-PD-1 therapy. This analysis revealed that levels of m6A were increased in Alkbh5-KO tumors (FIG. 3A). We then performed m6A RNA immunoprecipitation followed by high-throughput sequencing (MeRIP-Seq) to determine whether the altered gene expression observed in the KO tumors was a consequence of m6A/m6Am demethylation. To obtain the most robust data, we selected only m6A peaks identified by two independent peak calling algorithms and detected in tumors from all biological replicates per group (FIGS. 8A and 8B). In the NTC B16 tumors, the majority of m6A peaks were detected in the coding sequence (CDS) and the 3' and 5' untranslated regions (UTR), which is consistent with previous studies. Notably, the density of m6A peaks in intronic regions was substantially higher in Alkhb5-KO tumors compared with NTC tumors during treatment (FIG. 3B), and Alkbh5-KO tumors had more unique m6A peaks compared with NTC or Fto-KO tumors (FIG. 3C). Analysis of motifs in the m6A peaks showed that the canonical m6A motif DRACH (D: A, G, U; R: A, G; H: A C, U) was the most common motif in all tumor groups. The putative m6Am motif BCA (B C, U, or G; methylatable A) was present in other enriched motifs. One motif enriched in Alkbh5-KO tumors contained the SAG core, which is reminiscent of the SRSF binding site motif known to affect gene splicing (FIG. 3D). These data suggest that Fto and Alkbh5 deletion had some common and some distinct effects on m6A/m6Am peaks in B16 tumors, which might contribute to the different mechanisms through which the two demethylases influence the efficacy of GVAX/anti-PD-1 therapy.

Figure 8C:
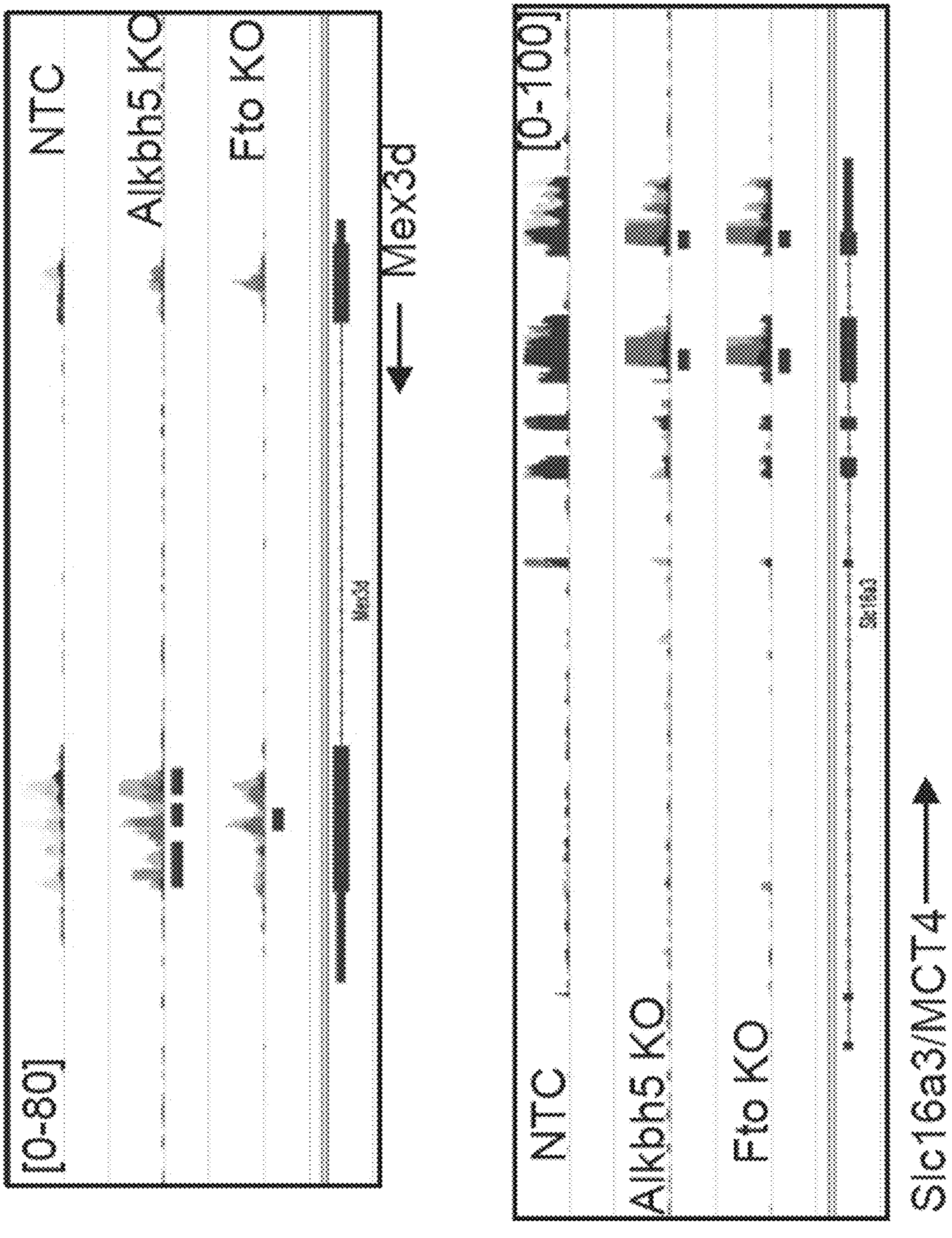

We next examined whether the downregulation of the overlapped genes in Alkbh5 KO or Fto KO tumors (responding better than NTC) and melanoma patients responding to immunotherapy was due to altered levels of m6A (FIGS. 7H and 7I). Five out of eight common downregulated genes had increased m6A peaks in Akbh5 deficient mouse tumor (shown in red, FIG. 7H). While only one of total eleven common genes, Mex3d, had elevated m6A levels in Fto deficient tumors (red in FIG. 8C). m6A peaks in Mex3d, common in both Alkbh5 and Fto downregulated genes, and in Slc16a3/MCT4, found in only Alkbh5 regulated genes, had significantly increased m6A density in the knockout tumors compared to NTC (FIG. 8C). These results suggest that Alkbh5 or Fto knockout increases m6A levels and reduce expression of certain genes involved in immunotherapy resistance. The overall levels of m6A in Fto deficient was not changed, but it did show increase m6A levels at some gene's levels, albeit the number of changed genes were much less than Alkbh5 knockout tumors (e.g. FIG. 8C).

Figure 3E:
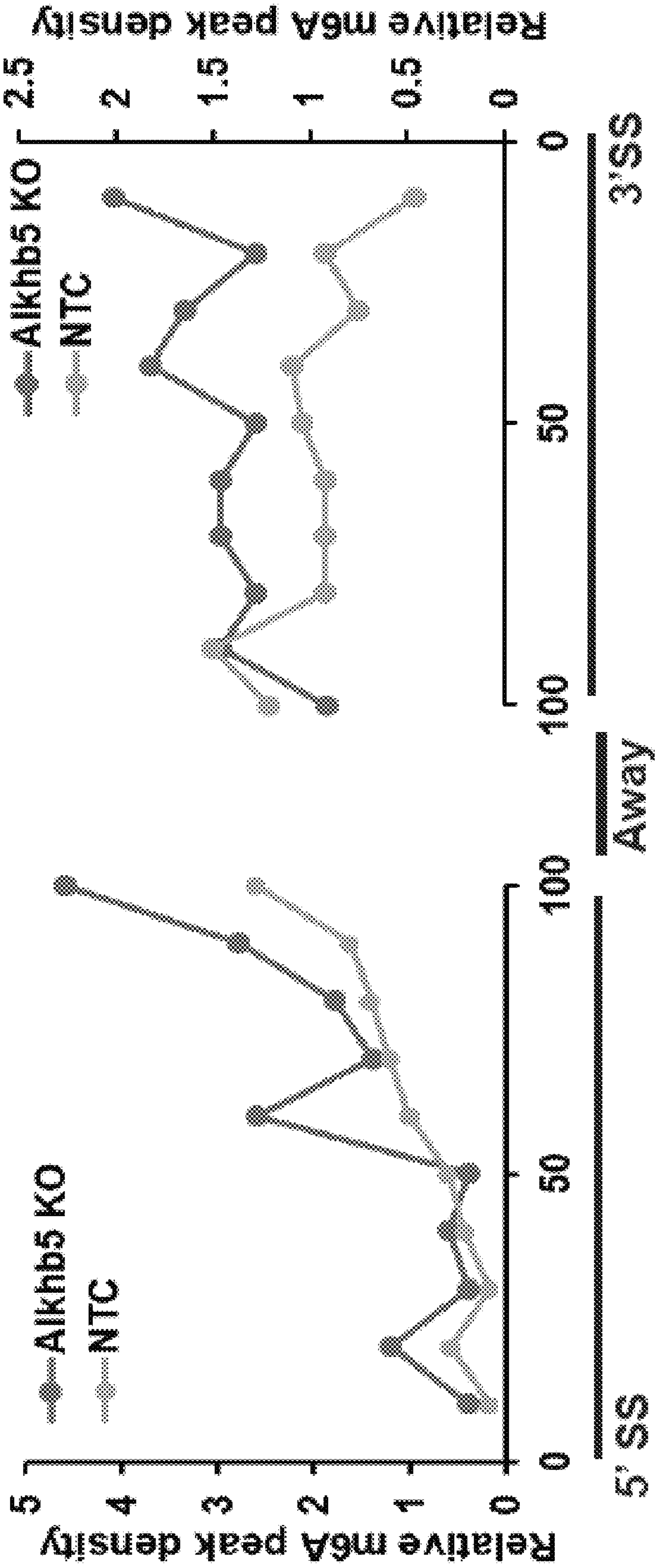
Figure 3F:
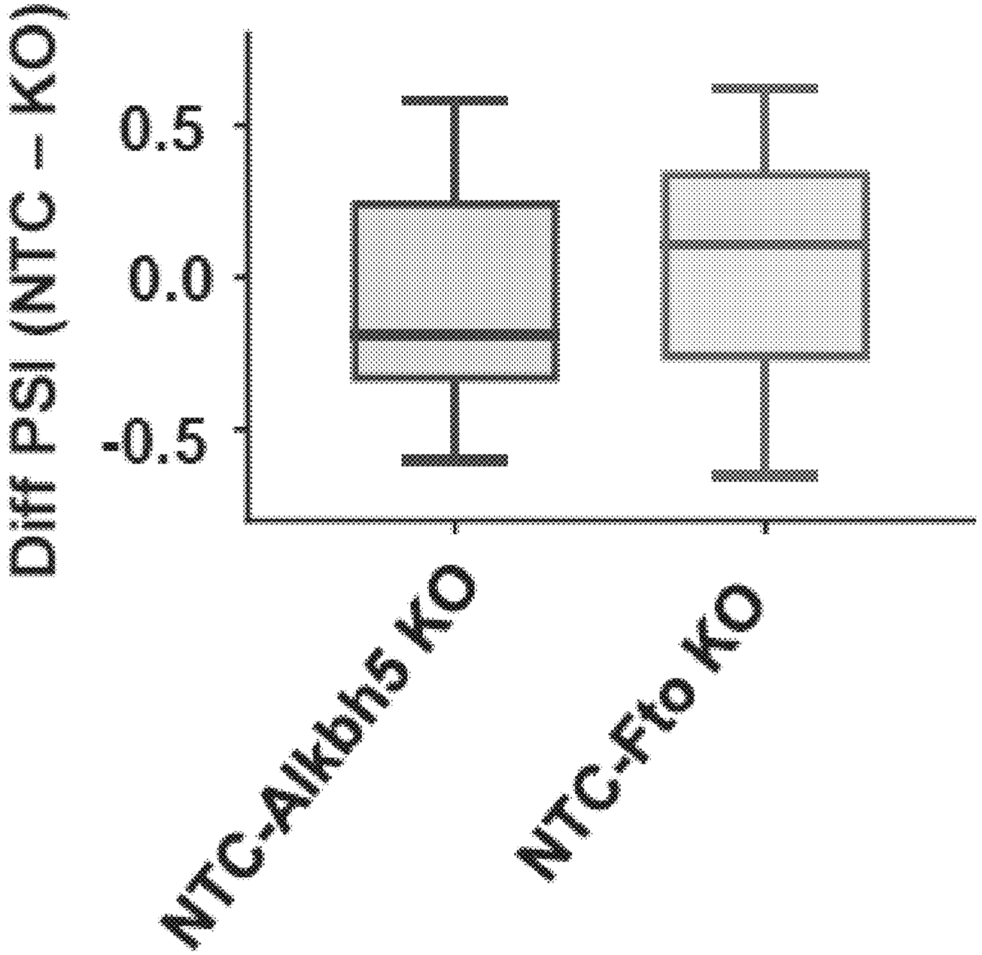
Figure 9A:
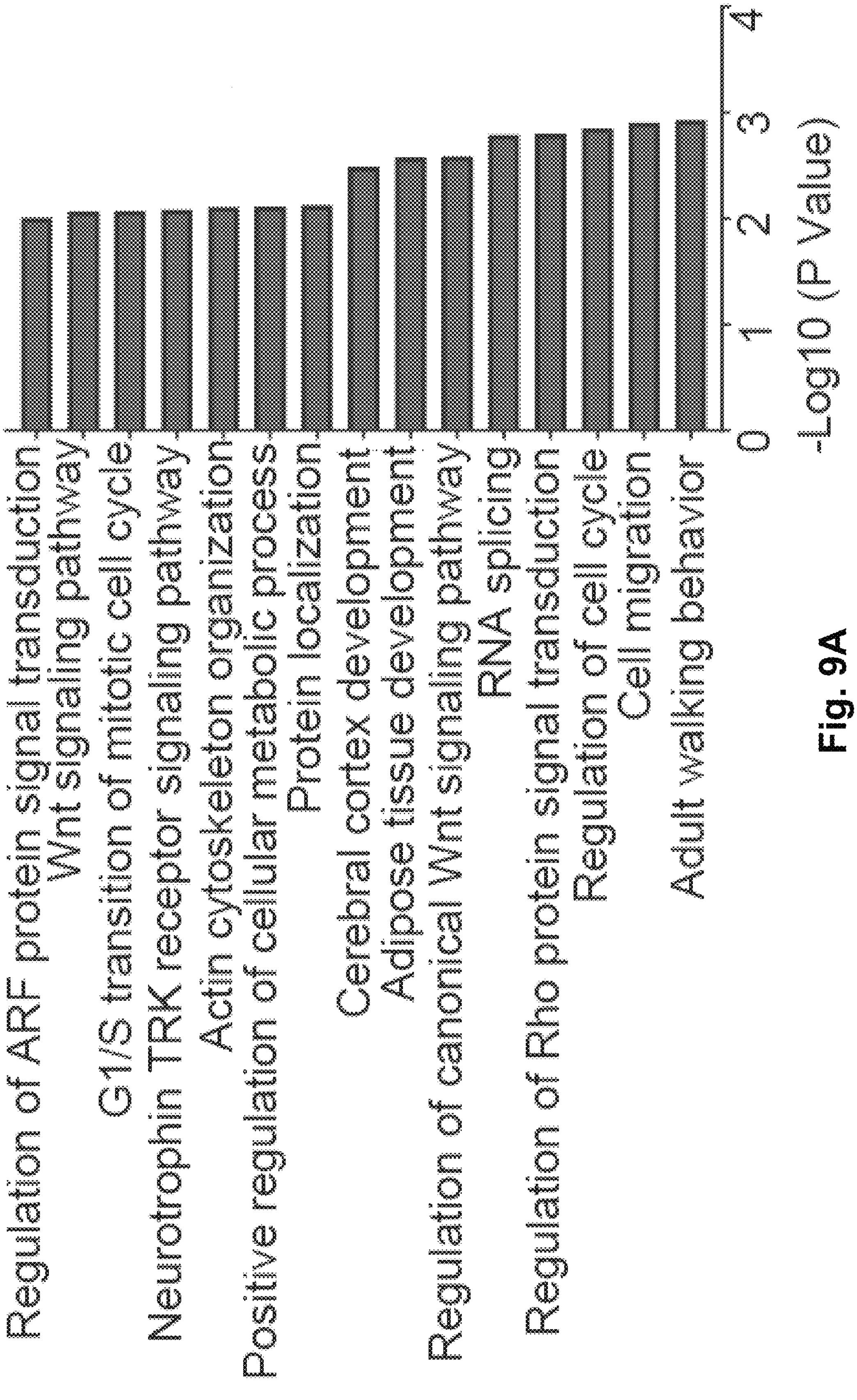
Figure 9B:
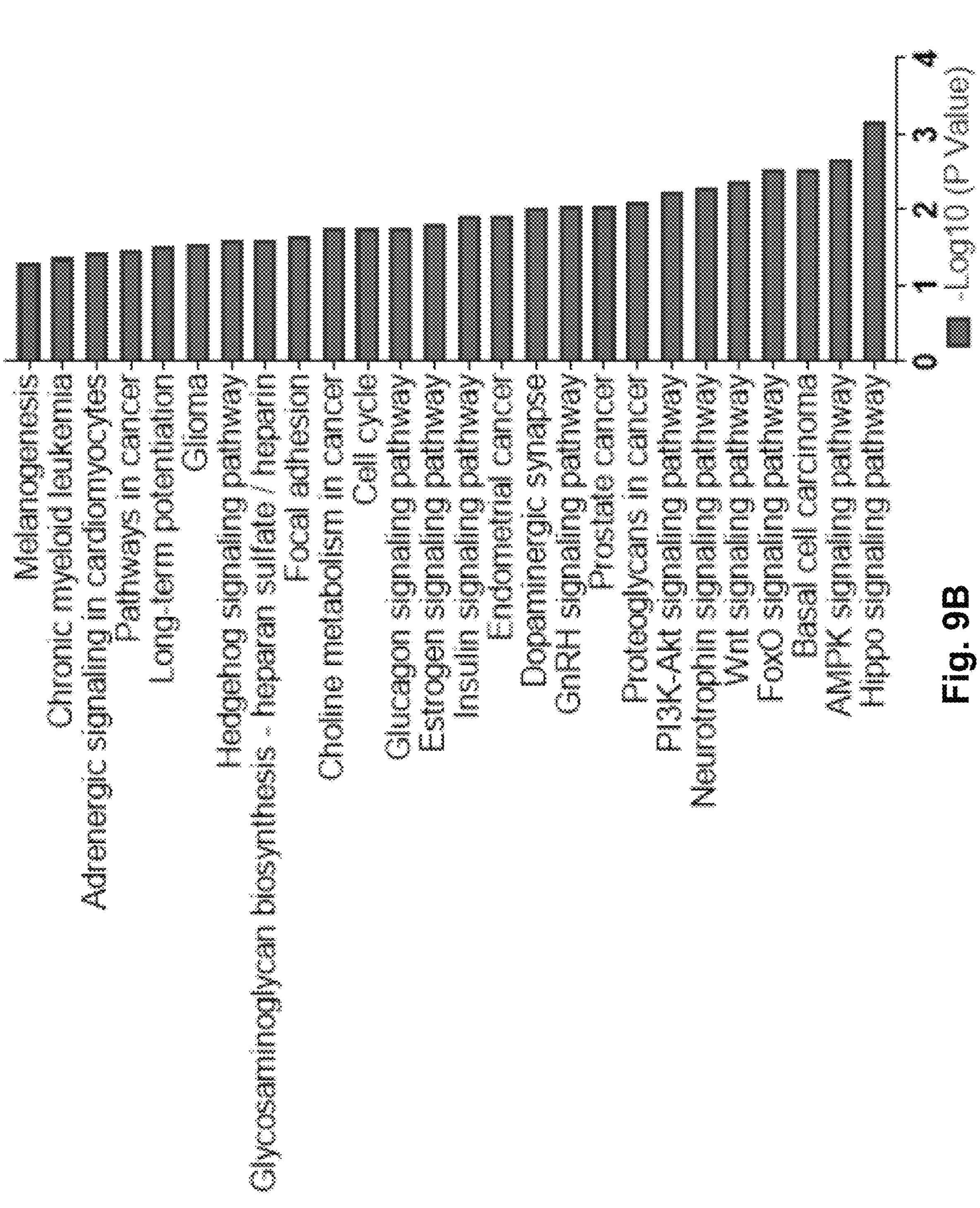

M6A Density is Increased Near Splice Sites and Leads to Aberrant RNA Splicing in Alkbh5-Deficient Tumors Although the regulatory role of m6A deposition in splicing is somewhat controversial[30,31], Alkbh5 has been reported to affect splicing in an m6A demethylase-dependent manner[32]. Our MeRIP-Seq results showed that unique m6A peaks were more prevalent in Akbh5-KO tumors compared with NTC or Fto-KO tumors during GVAX/anti-PD-1 treatment, and that one m6A motif enriched in Alkbh5-KO tumors had a sequence similar to the SRSF binding motif (FIG. 3B-3D)[30]. GO analysis of mRNAs with unique m6A peaks in Alkbh5-KO tumors showed enrichment in splicing, cell cycle, and signaling pathway functions (FIGS. 9A and 9B), suggesting that Alkbh5 also regulates gene expression in B16 cells through effects on mRNA splicing. To test this hypothesis, we examined the location of m6A at 5' or 3' intron-exon splice junctions by positional assessment. Consistent with a previous study using miCLIP[30,31] we found that m6A deposition increased from both 5' and 3' splice sites to the internal exonic regions in NTC control tumors with immunotherapy (FIG. 3E). Surprisingly, we found that in Alkbh5 deficient tumors, the m6A densities were elevated at the both 5' and 3' splice sites, with a dramatic increase at the proximal region to the 3' splicing site (FIG. 3E).

Figure 9C:
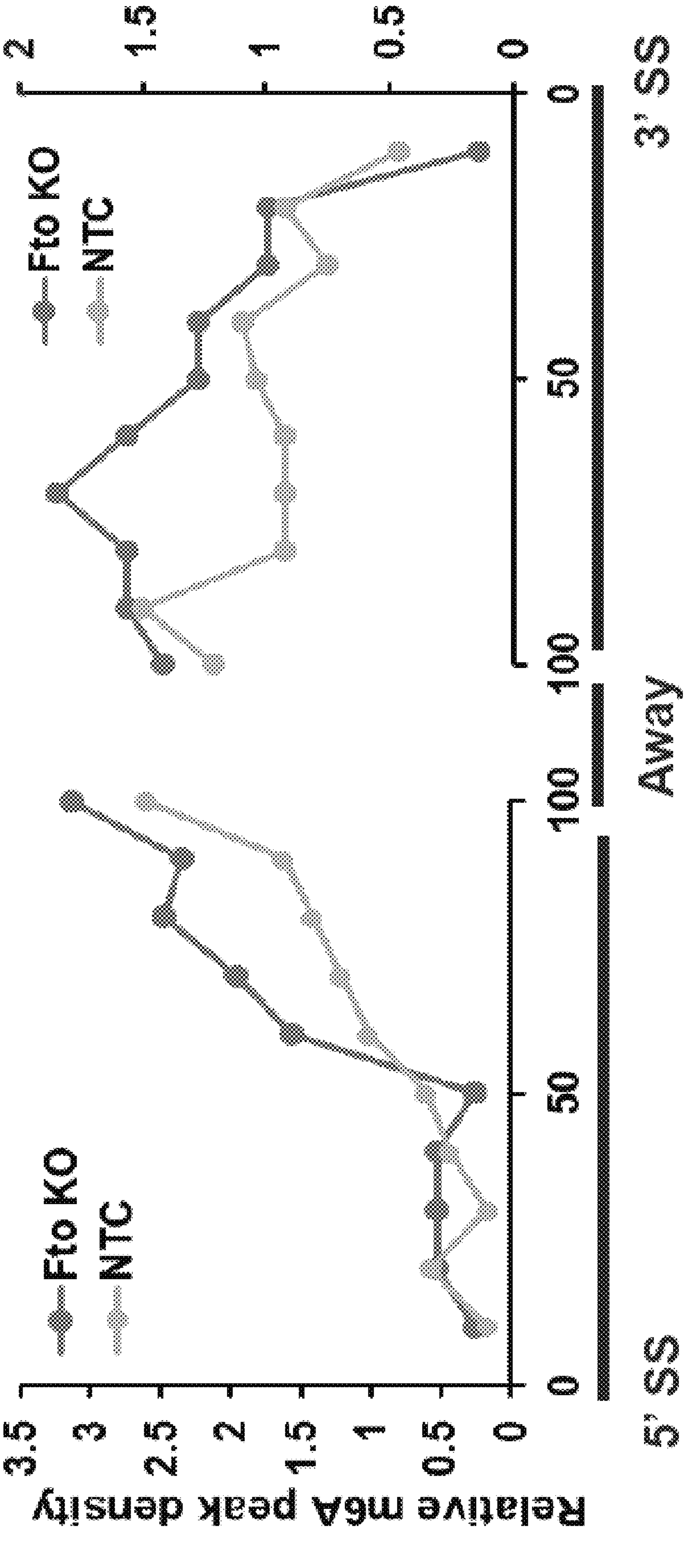
Figure 9D:
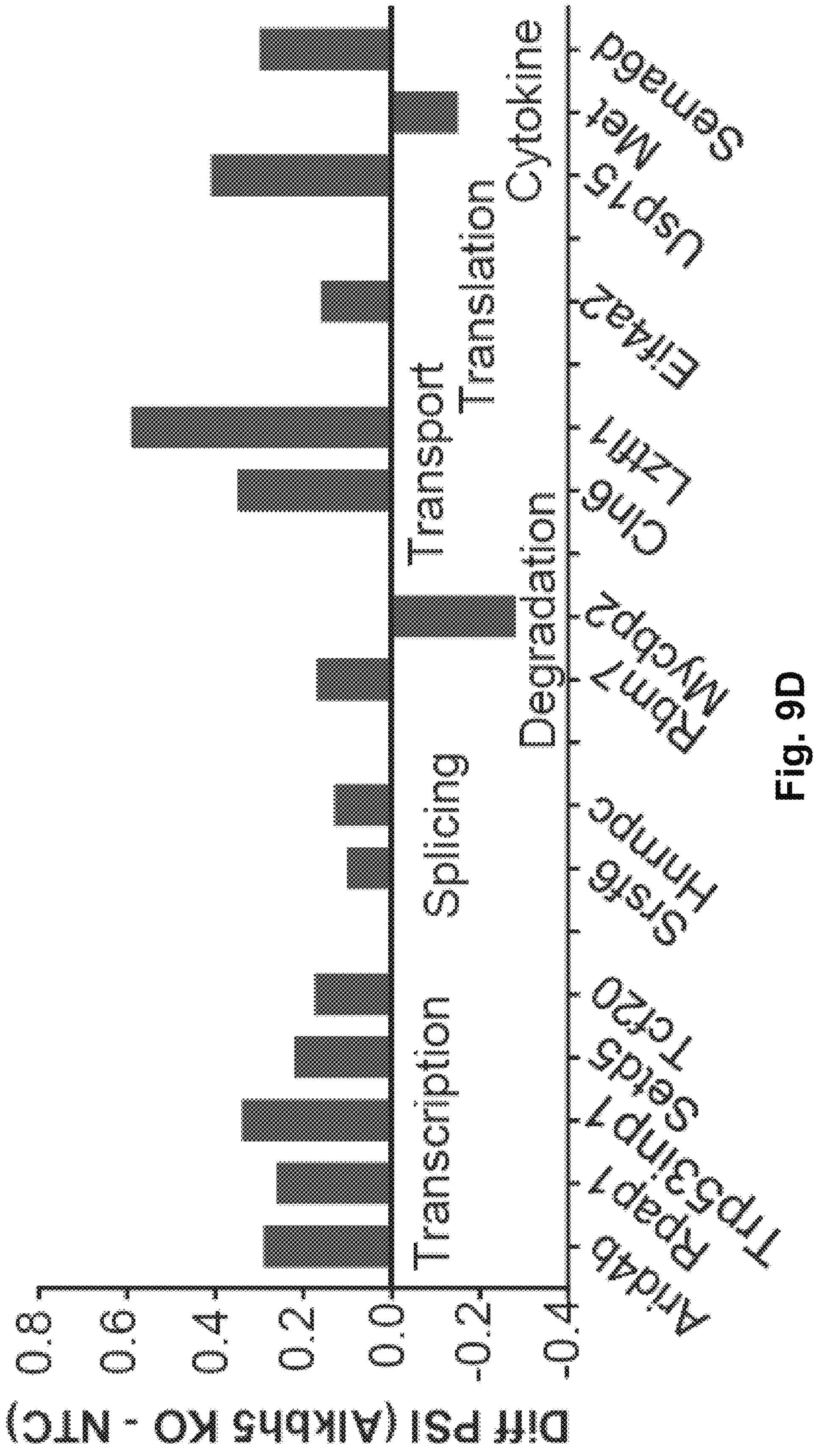
Figure 9E:
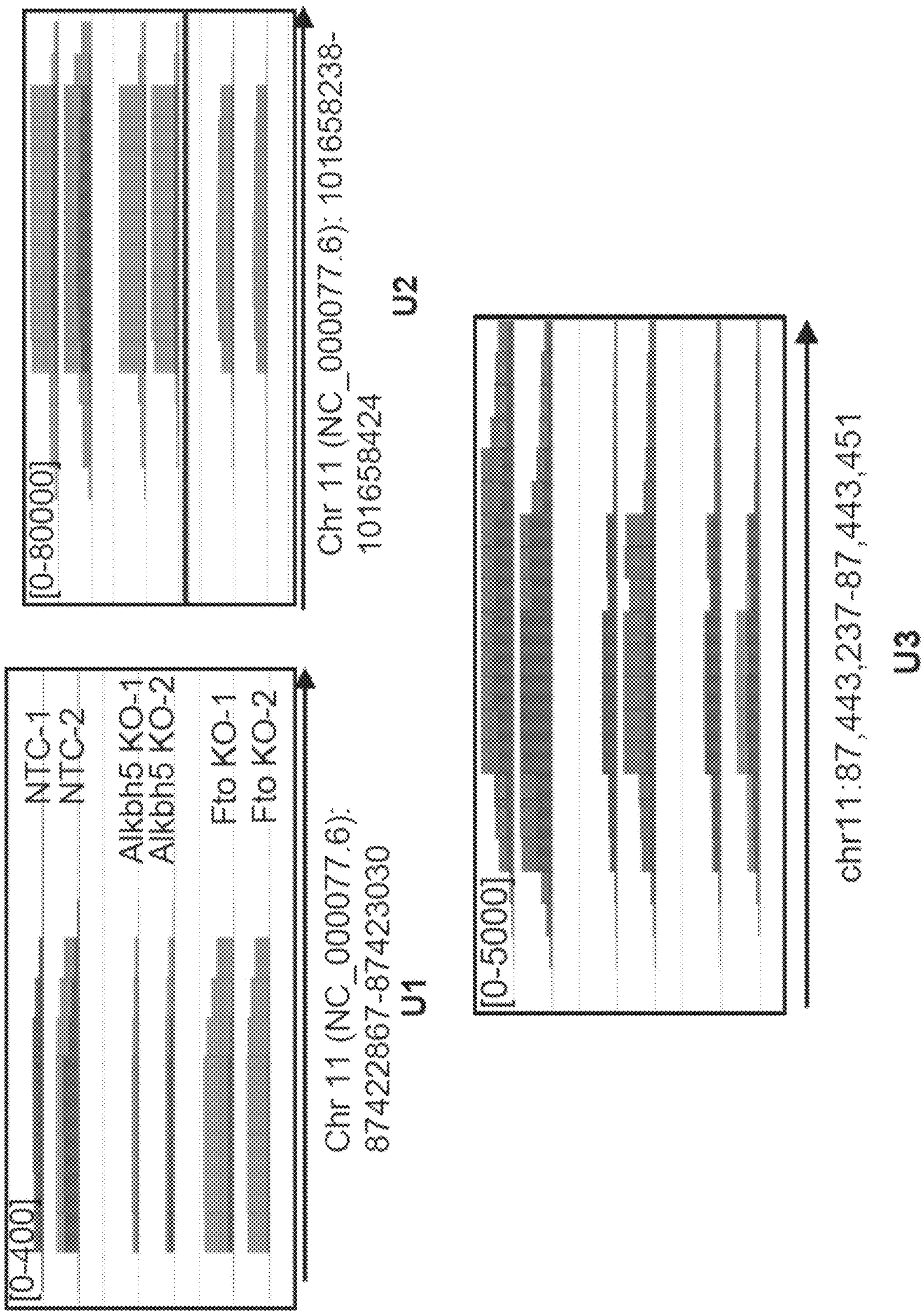
Figure 9F:
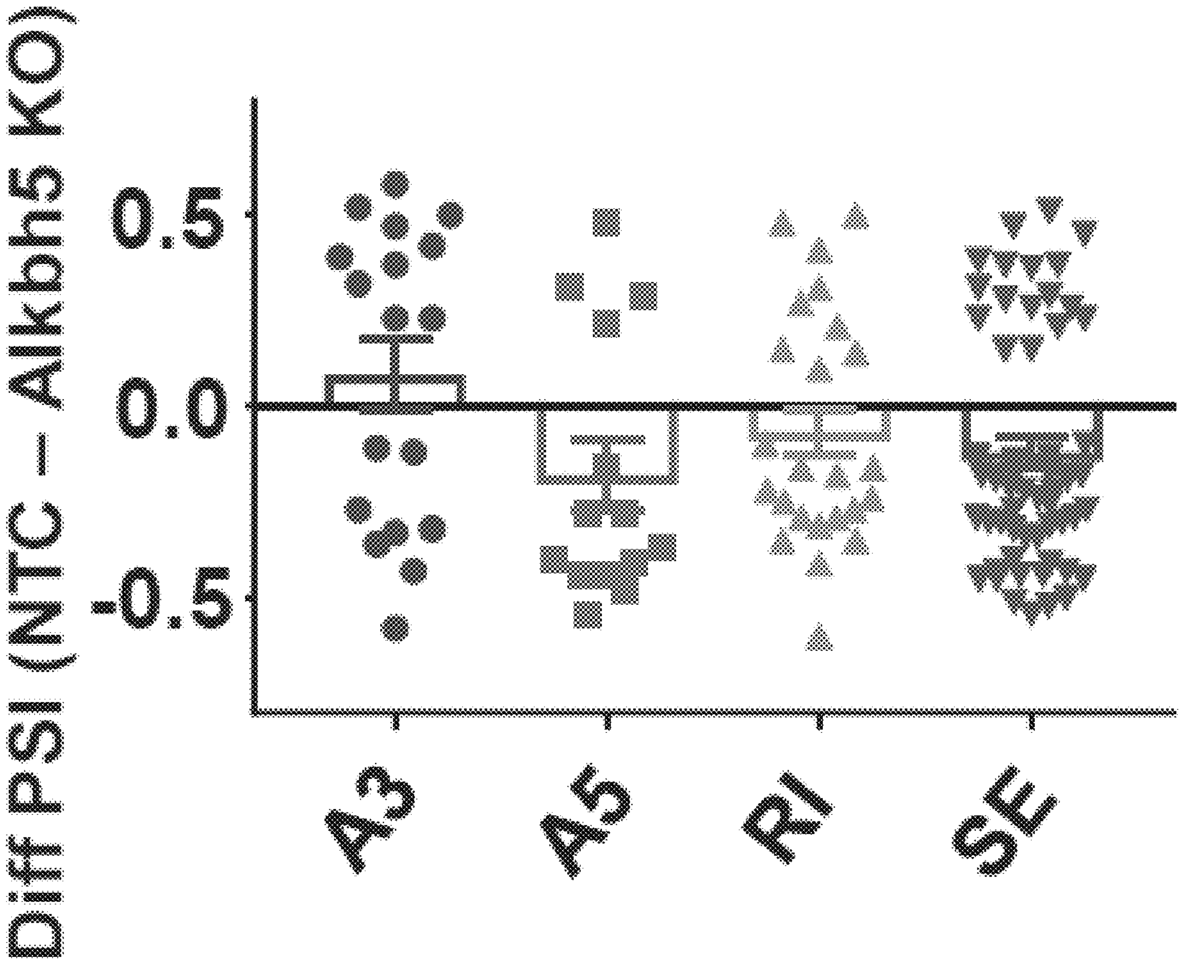
Figure 9G:
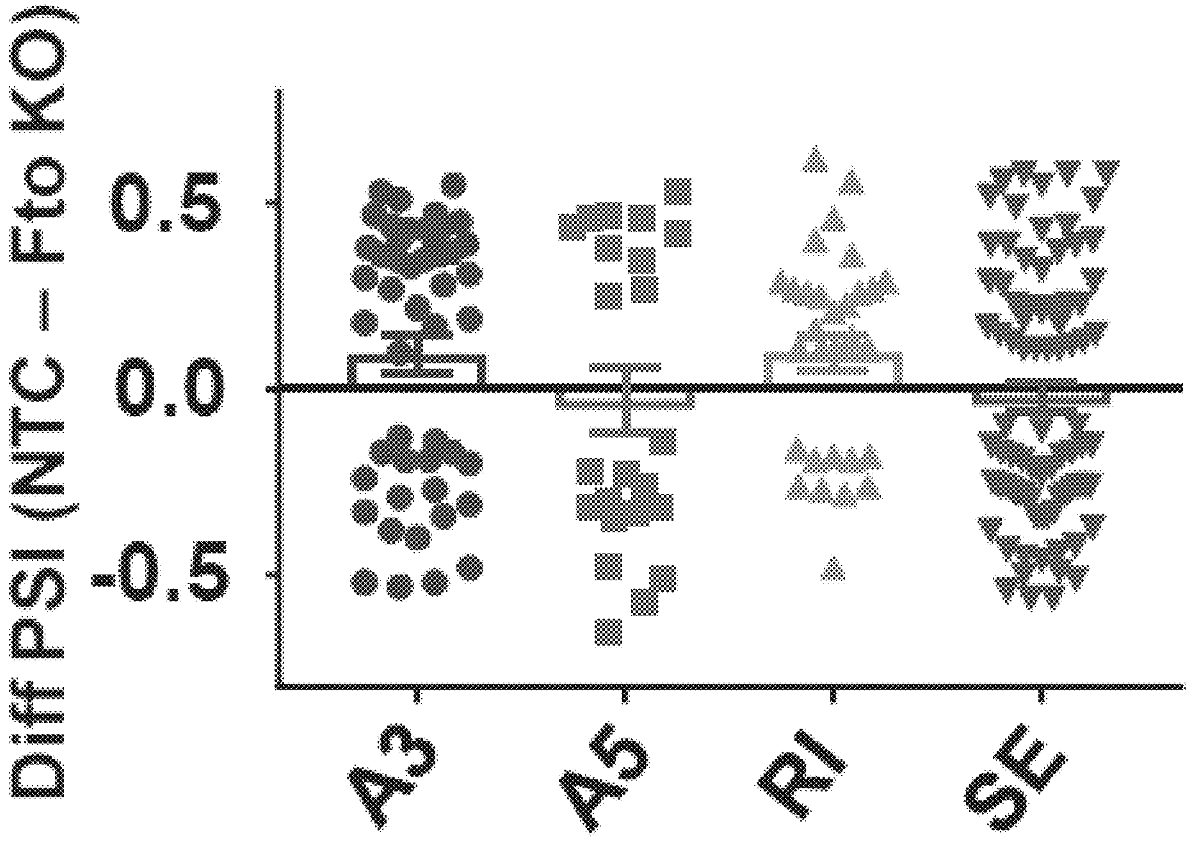
Figure 9H:
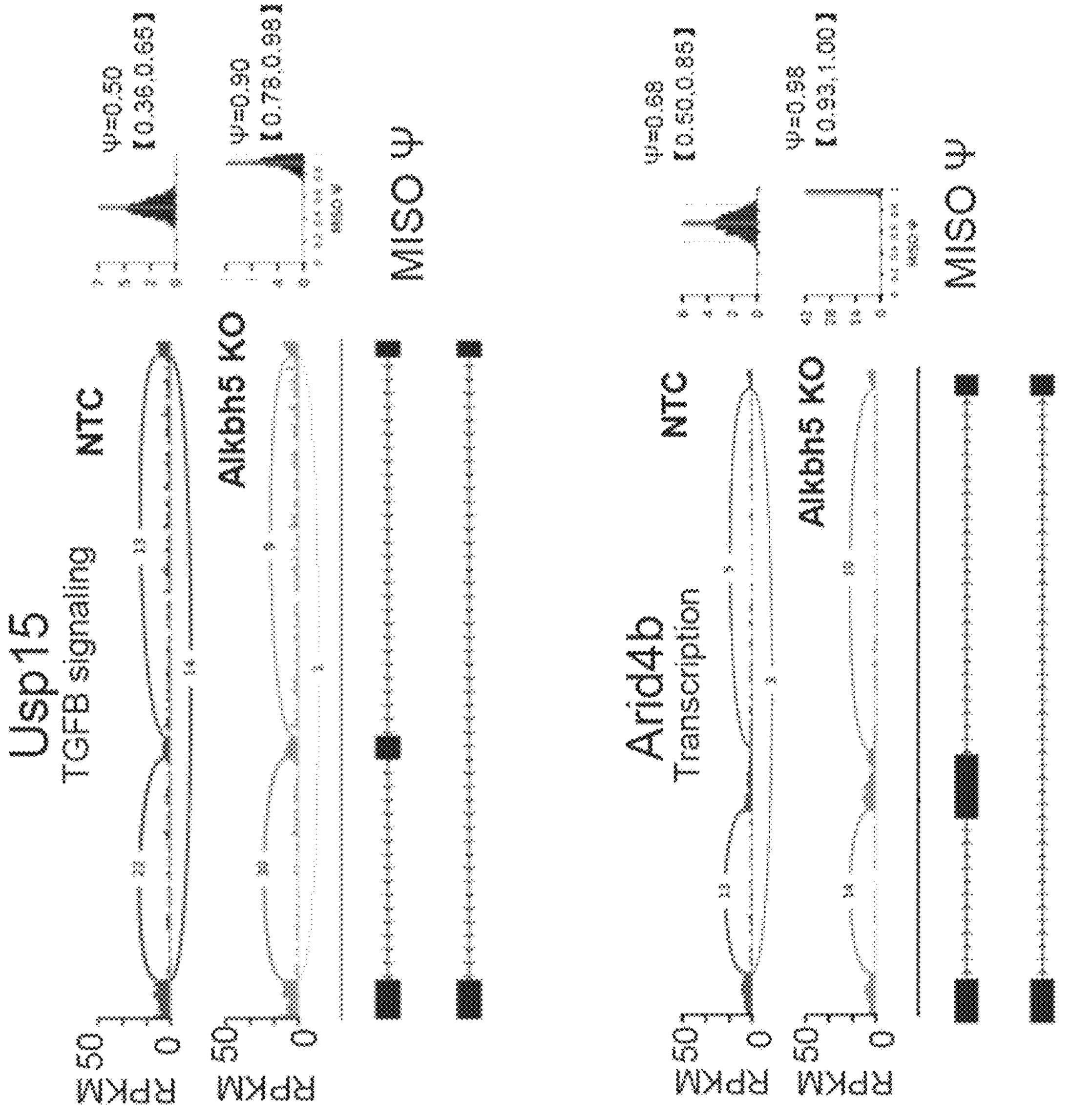
Figure 9H:
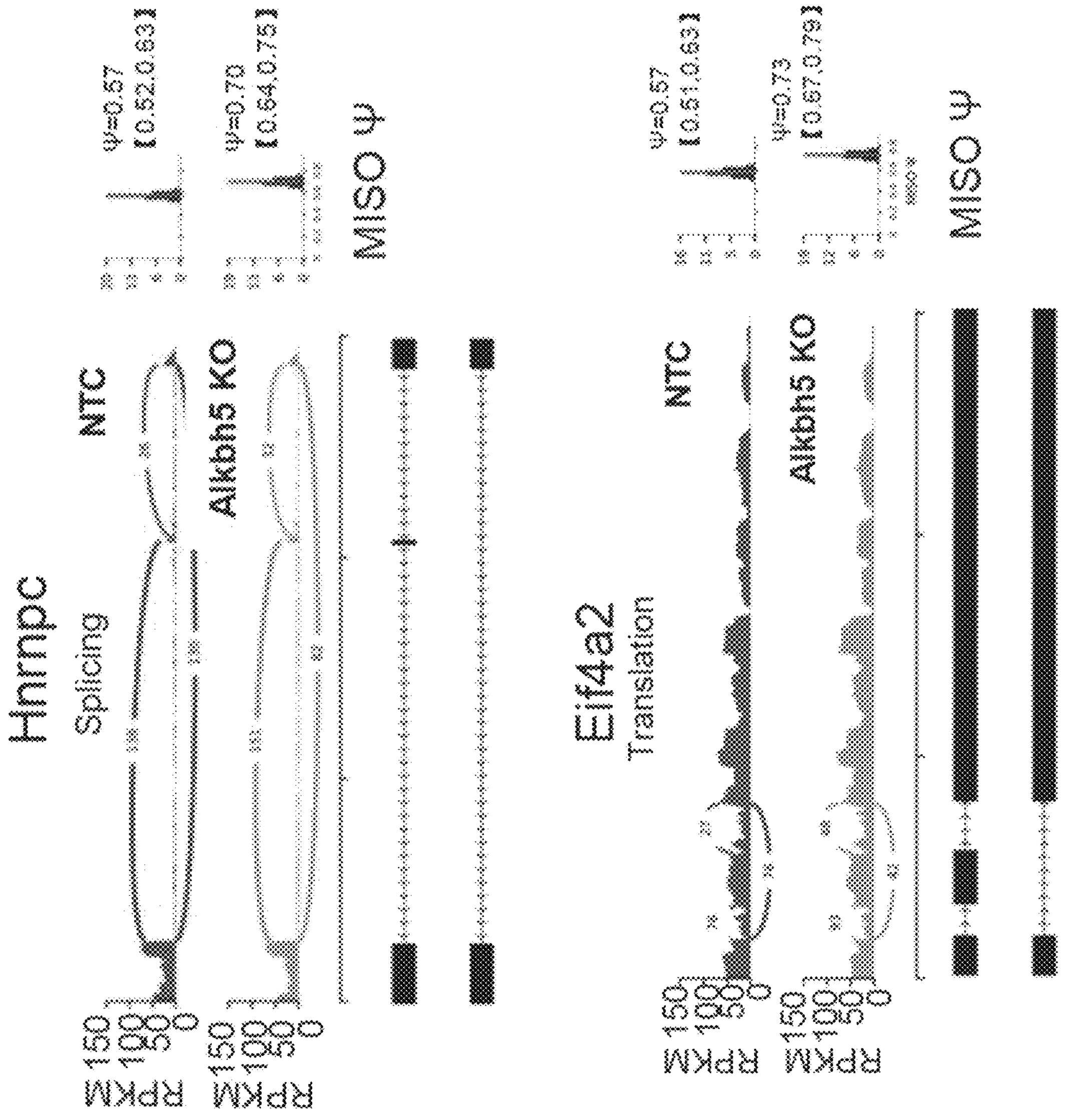

In contrast, m6A deposition at splice sites in Fto-KO tumors was comparable to that in NTC tumors (FIG. 9C) suggesting that Alkbh5 plays a role in gene splicing through depositing m6A modifications near the splicing sites. Changes in m6Am by FTO have been reported to affect snRNA biogenesis and gene splicing, and we observed an increase in m6Am/m6A in UI, 02 and IJ3 snRNAs in Fto-KO tumors compared with NTC tumors (FIG. 9E). To investigate this further, we analyzed our RNA-Seq data using MISO to detect differences in RNA splicing. Although the global splicing profiles were unaffected by Alkbh5 or Fto deletion, the frequency of spliced-in transcripts (as reflected by the percent spliced-in index (PSI) in a subset of genes was increased by Alkbh5 deletion in tumors analyzed during GVAX/anti-PD-1 treatment (Figures Categories of gene functions, where PSI was changed in Alkbh5 KO tumors, included genes involved in important cellular processes such as transcription, splicing, protein degradation, transport, translation and cytokine-related pathways (FIGS. 9D and 9H).

Figure 9I:
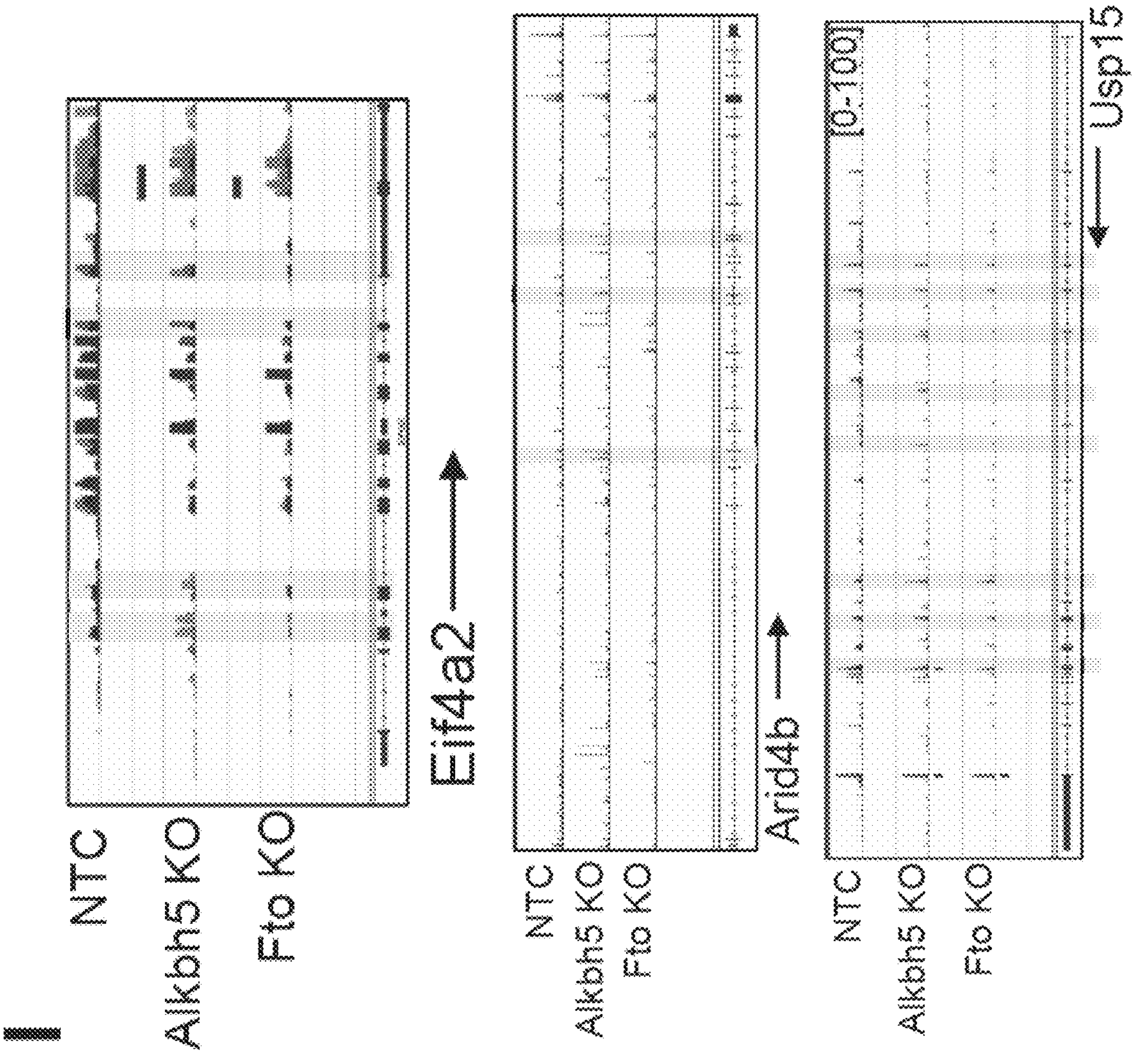

To determine whether changes in m6A deposition were linked with mRNA splicing, we next asked whether the m6A density increased in mRNAs with higher spliced-in frequencies (i.e., higher PSI) in Alkbh5-KO compared with NTC tumors. Indeed, mRNA with high PS due to Alkbh5 KO had higher m6A densities near intron- exon junctions compared with the same mRNAs in NTC tumors; these mRNAs included Usp15, Arid4b, and Eif4a2 (FIG. 9I). Among the genes with altered PSI in Alkbh5-KO tumors after immunotherapy, Sema6d, Setd5 and Met regulate vasculature, the expression and secretion of vascular endothelial growth factor and hepatocyte growth factor, both of which promote MDSC expansion[33-36]. Usp15 affects signaling by transforming growth factor-P, which attracts and activates Tregs. Notably, Met and Uspl 5 are expressed as isoforms that have markedly different functions[37-38], suggesting that gene splicing changes are important for TME composition and eventually affecting the immunotherapy efficacy. Taken together, these data indicate that Alkbh5 regulates the density of m6A near spice sites in multiple mRNAs with functions potentially important to tumor infiltration by immune cells during GVAX/anti-PD-1 therapy.

Alkbh5 Regulates Lactate and Vegfa Accumulation in the Tumor Microenvironment During Immunotherapy Our findings above suggest that Alkbh5 knockout regulates its targets by changing m6A levels which leads to decreased gene expression or altered gene splicing. Some of these genes are involved in regulating cytokines or metabolites in TME such as Slc16a3/MCT4, Usp15, Met (FIGS. 2G and 9H). Therefore, it is important to examine whether in Alkbh5-KO tumors, cytokines or metabolites in TME are altered that consequently modulate tumor infiltrated lymphocyte populations and immunotherapy efficacy (FIGS. 1 and 2).

Figure 3G:
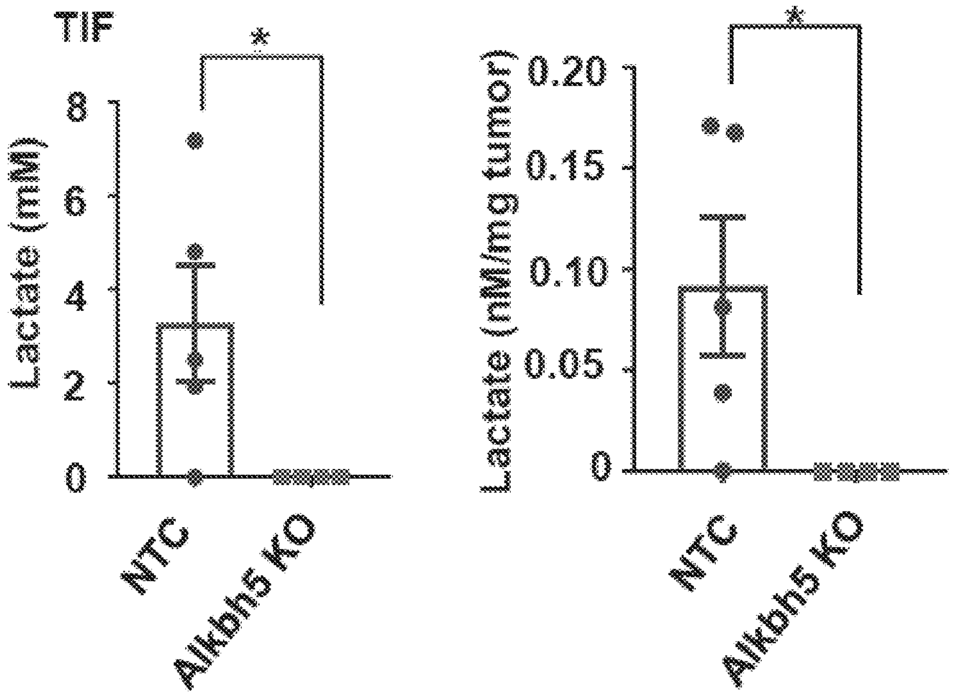
Figure 3H:
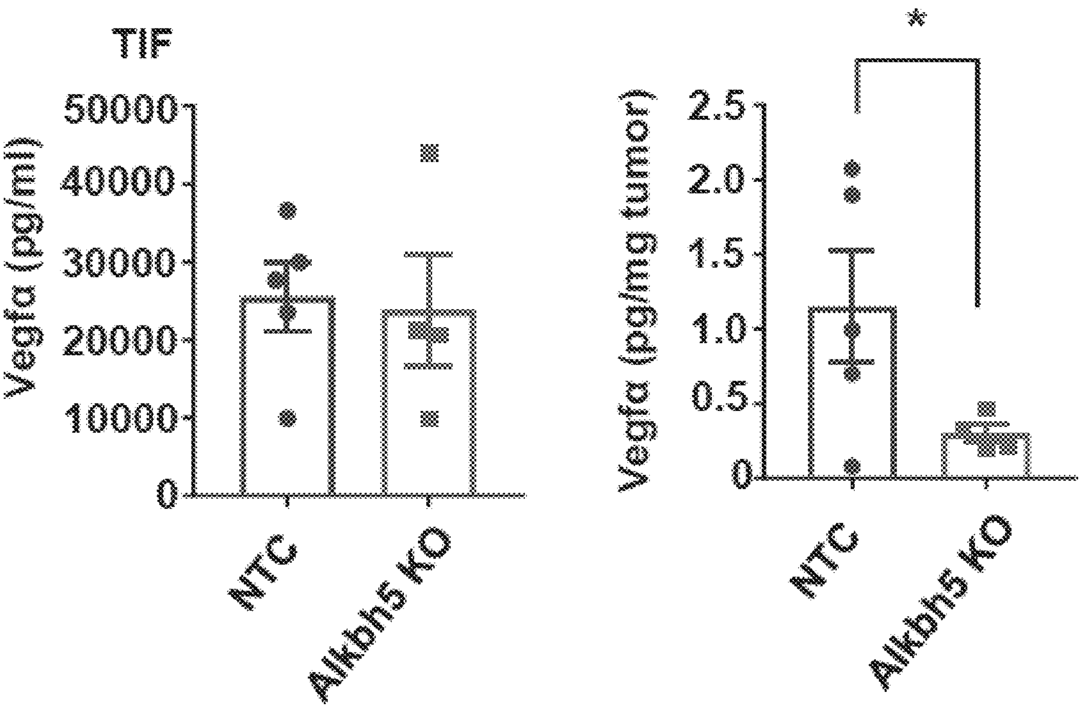
Figure 10A:
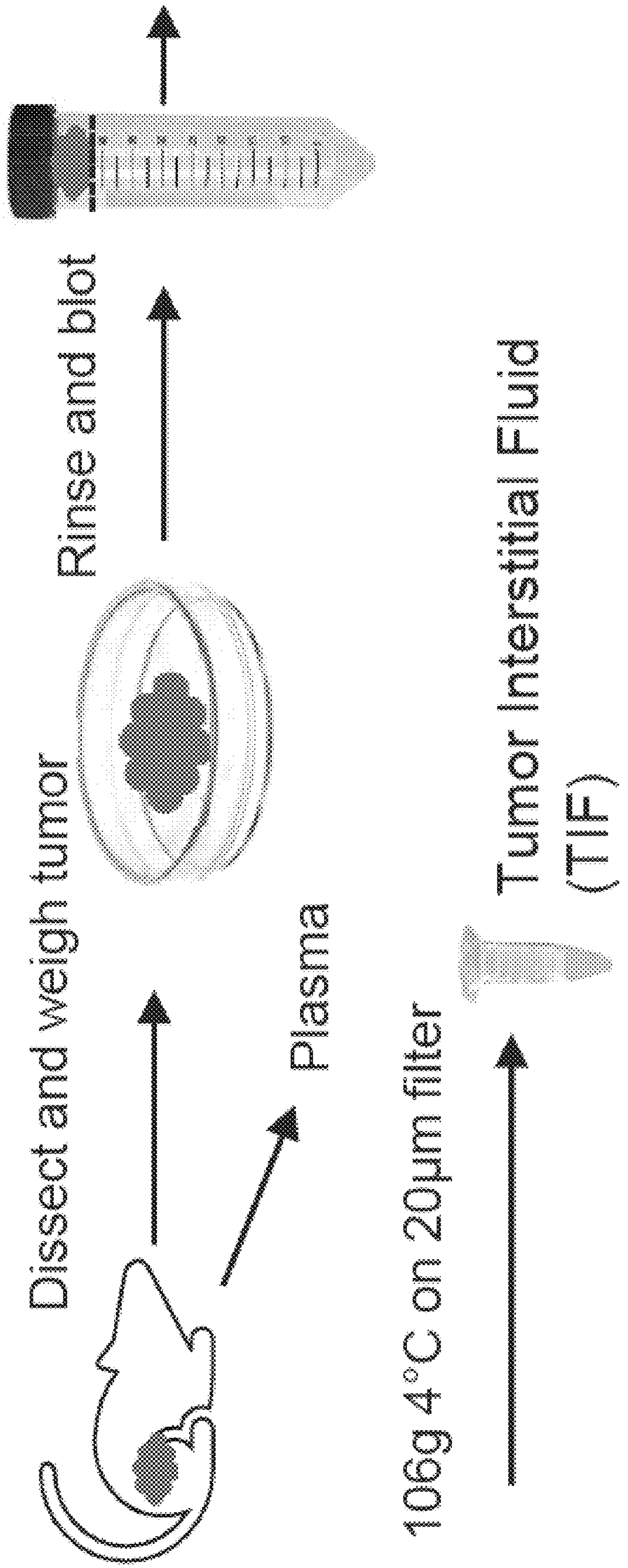
Figure 10B:
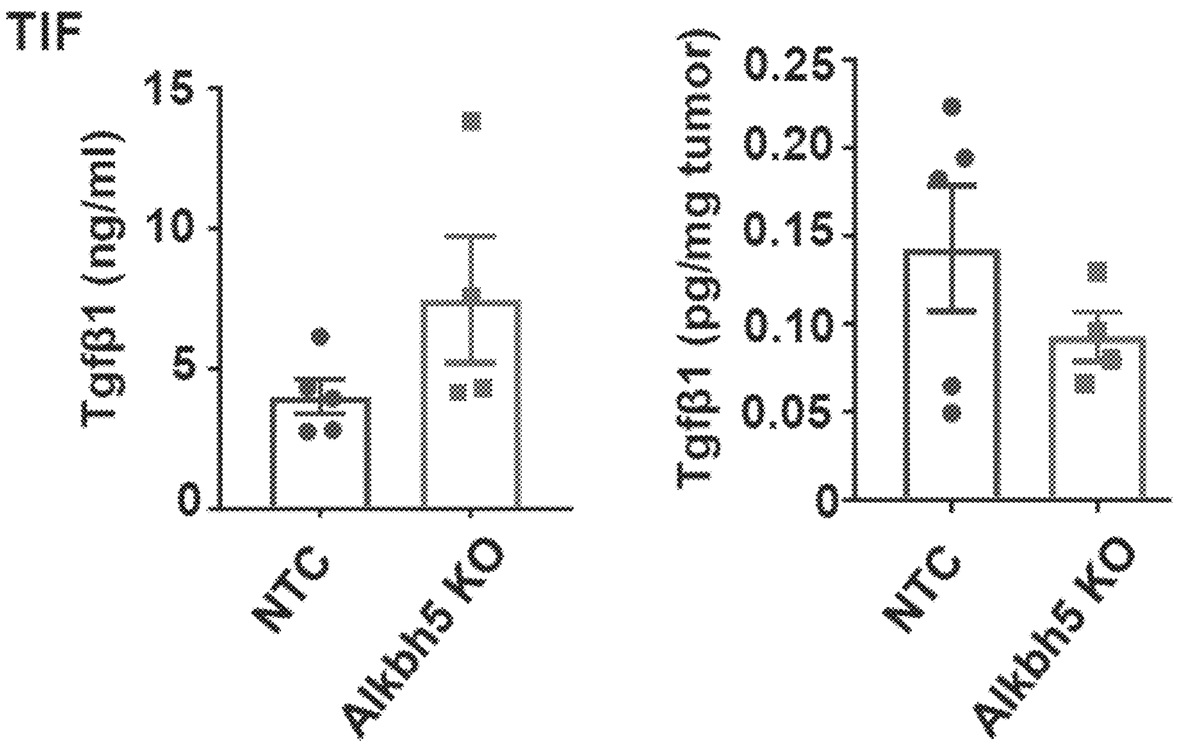
Figure 10C:
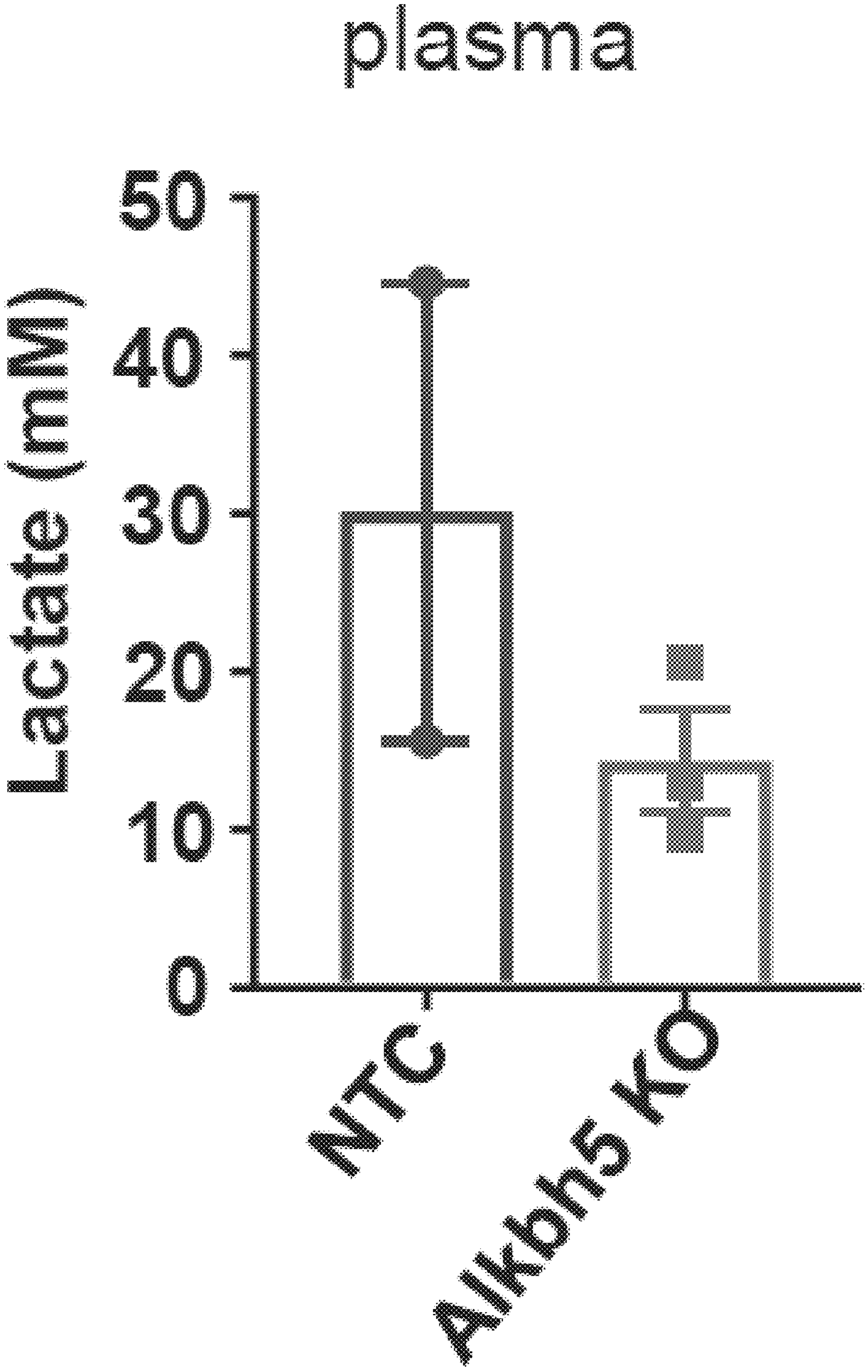
Figure 10D:
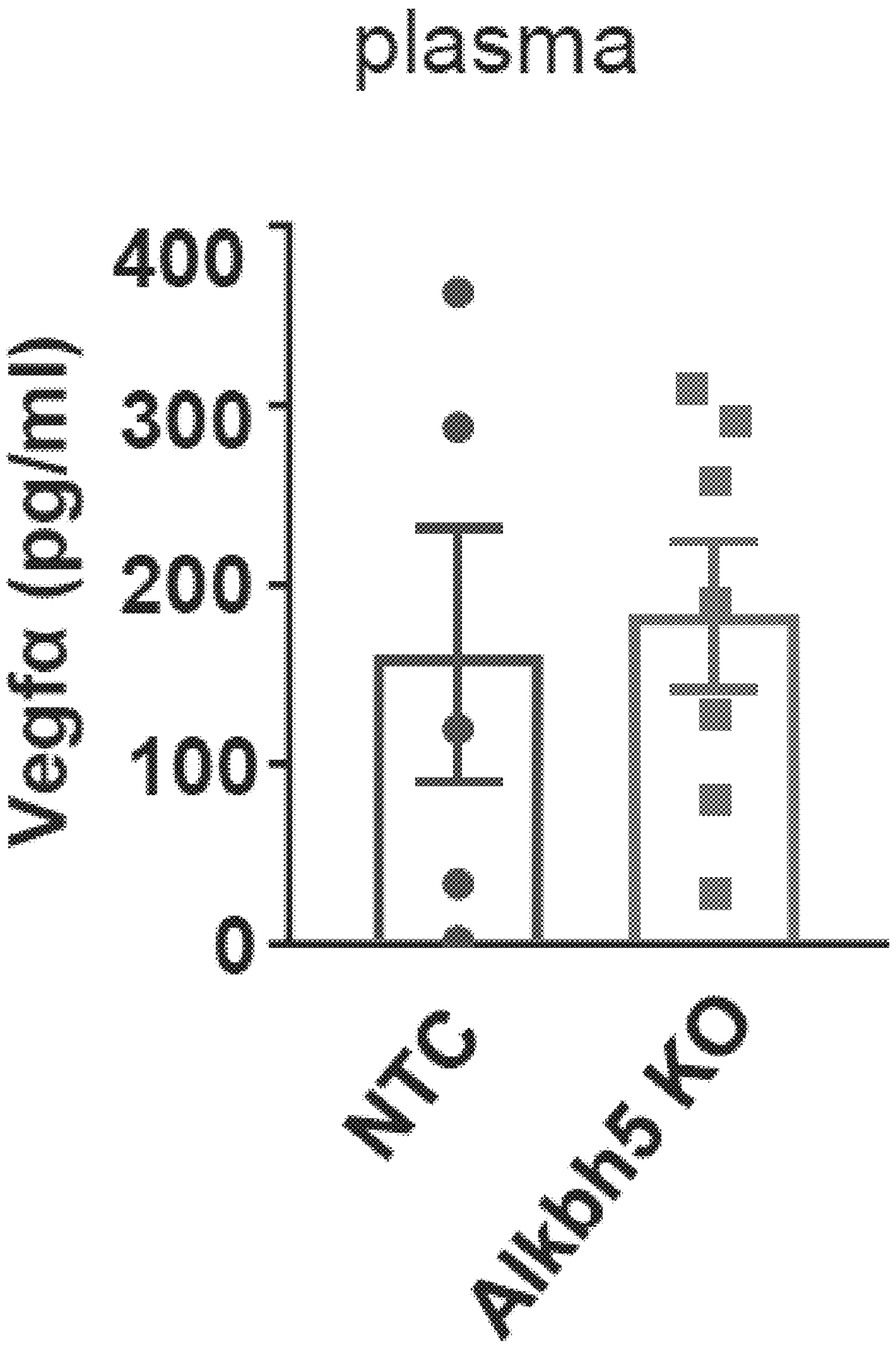
Figure 10E:
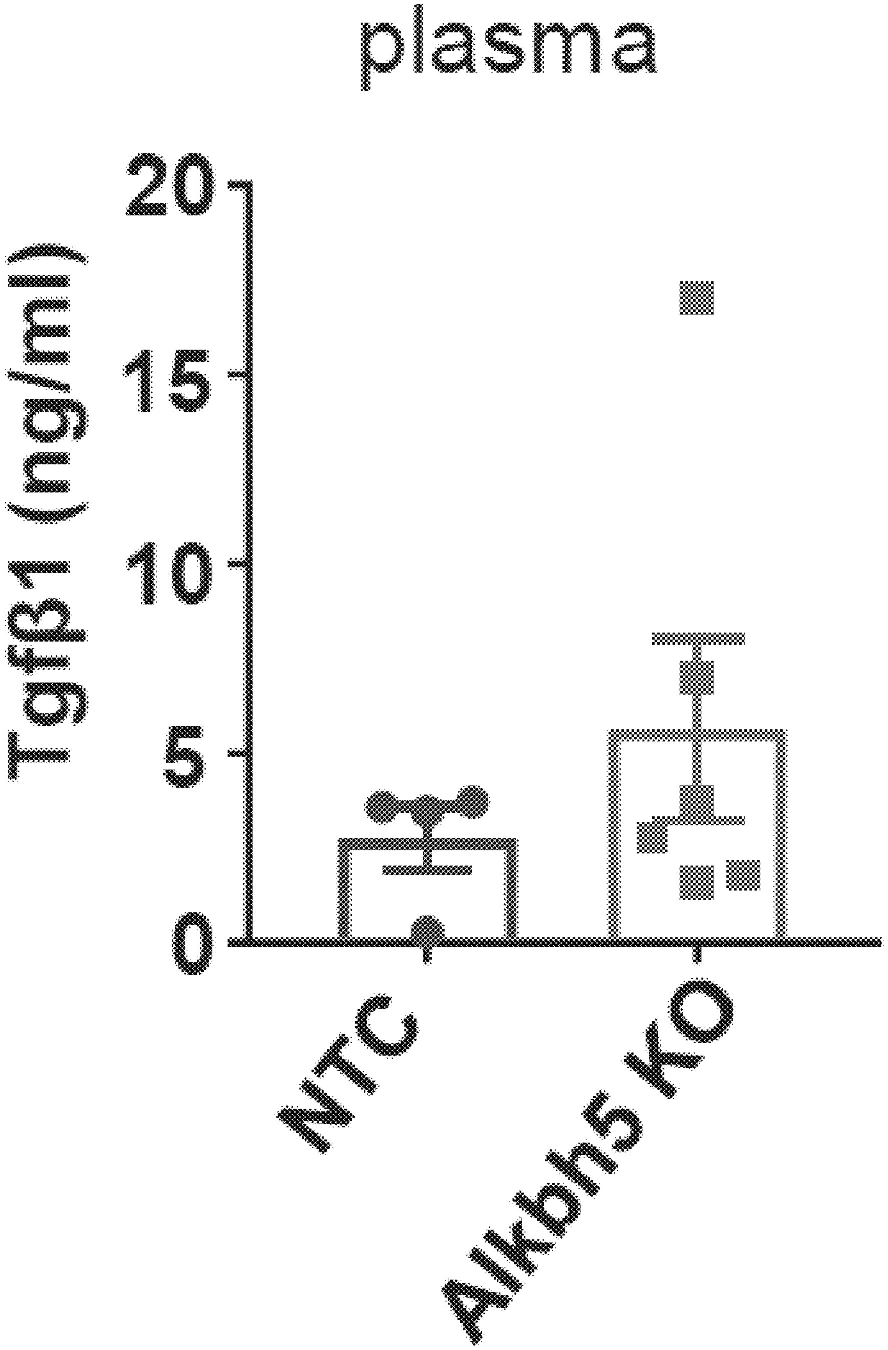

To address these questions, we quantified lactate, Vegfa, and TgfP1 concentrations in the tumor interstitial fluid (TIE), which contains proteins, metabolites, and other noncellular substances present in the TME (FIG. 10A). Indeed, both the lactate concentration in TIF and the total lactate content in the TME were dramatically lower in Alkbh5-KO tumors compared with NTC tumors (FIG. 3G). Similarly, although the Vegfa concentration in TIF was comparable between NTC and Alkbh5-KO tumors, the total Vegfa content in the TME was reduced by Alkbh5 deletion (FIG. 3H). In agreement with a previous study, we also found unat Vegfa levels were much lower in plasma than in TIF[39], showing that our isolation of TIF was successful (FIG. 10D). The lactate and Vegfa levels in plasma did not differ in mice bearing NTC vs Alkbh5-KO tumors, suggesting that the effect of Alkbh5 deletion on lactate and Vegfa levels was restricted to the TME and was not systemic (FIGS. 10C and 10D). In contrast to lactate and Vegfa, we found that the concentration of Tgfßl in TIF was increased by Alkbh5 deletion, whereas the TME content of Tgfßl was reduced only in Alkbh5-deficient tumors (FIGS. 10B and 10E). Collectively, these results showed that Alkbh5 expression in melanoma modulates metabolite and cytokine content in the TME, suggesting another mechanism by which m6A demethylase could modulate the infiltration of immune cells during anti-PD-1/GVAX treatment.

Figure 4A:
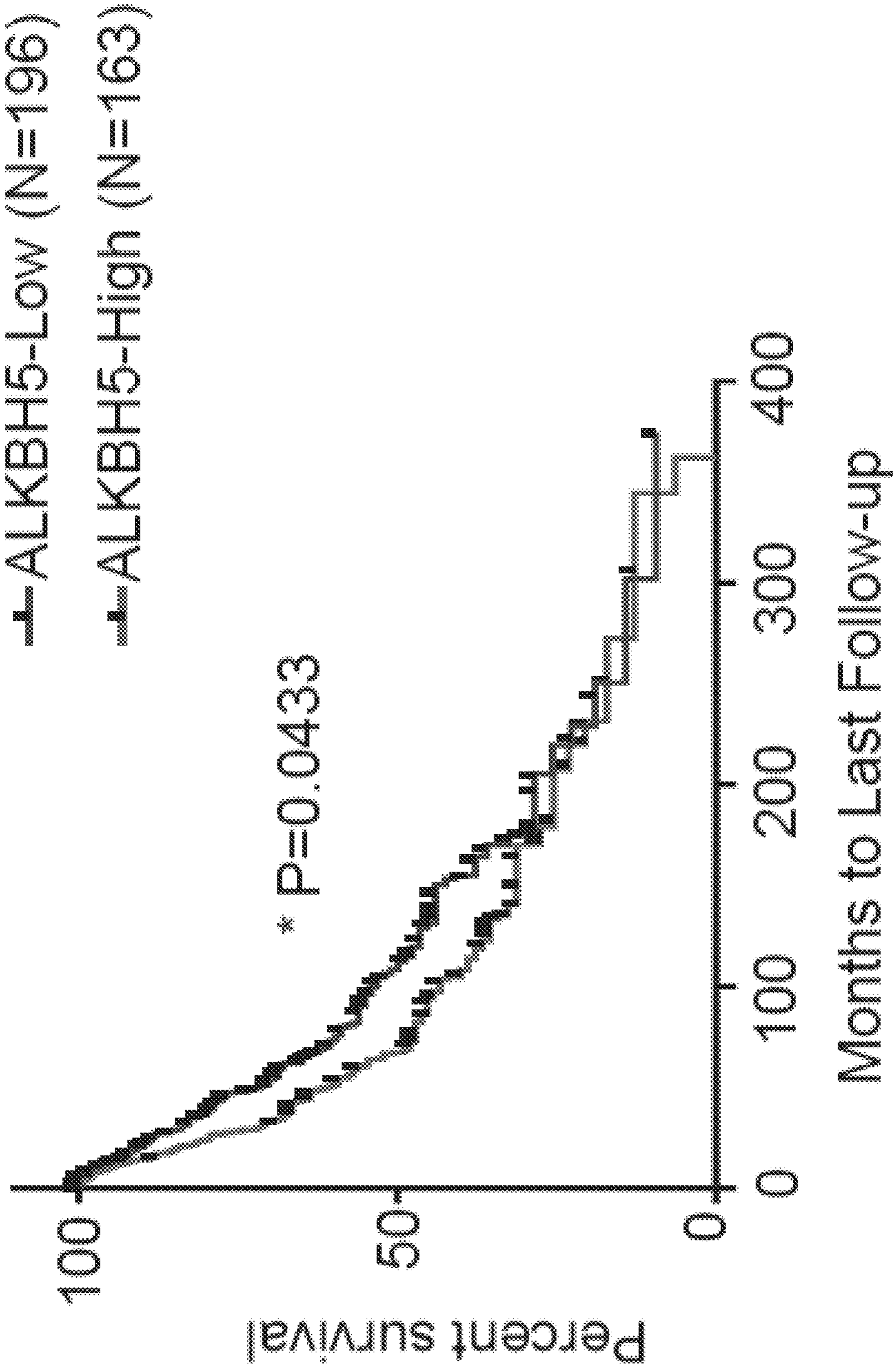
Figure 4B:
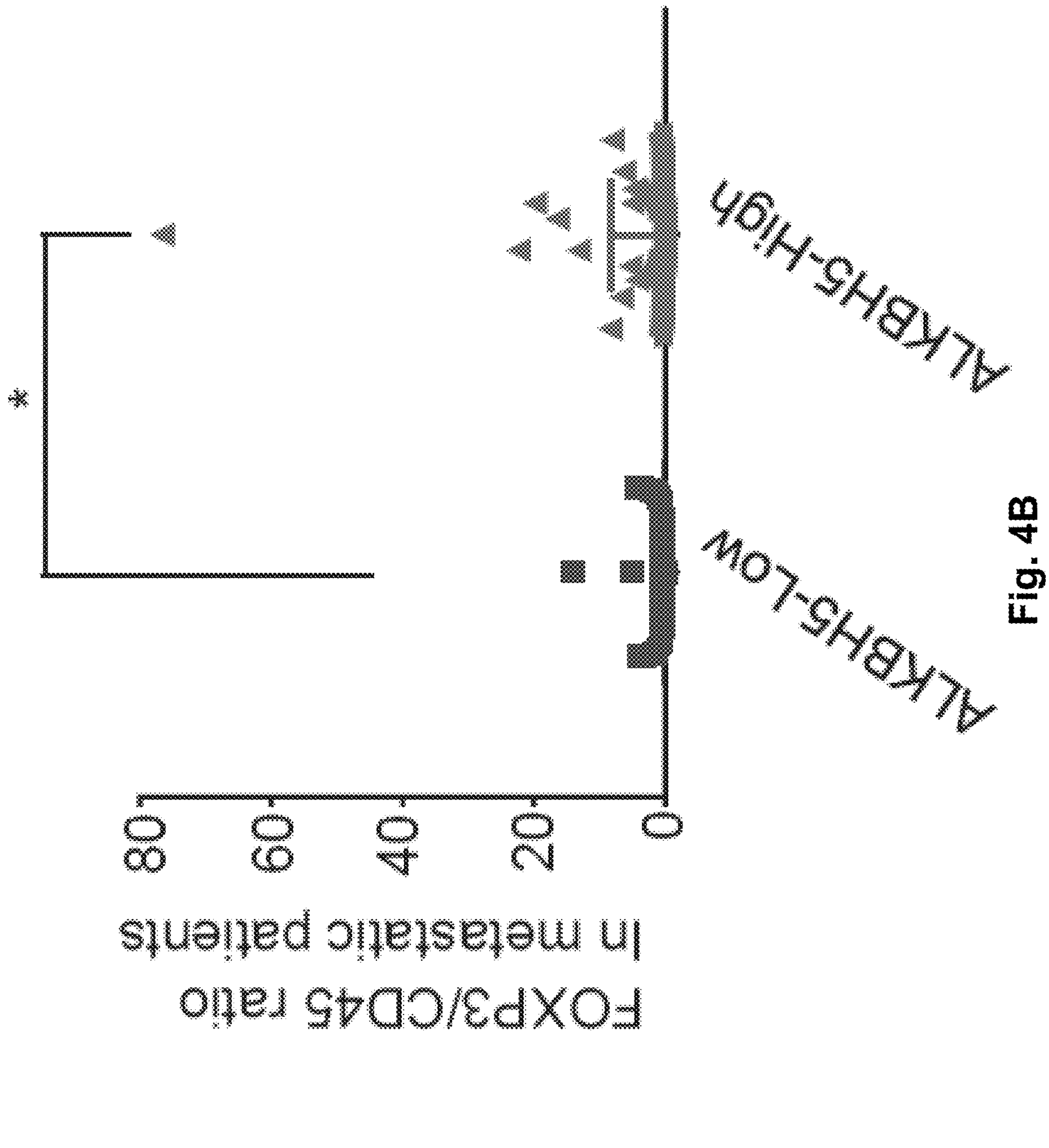

ALKBH5 Mutation/Expression in Melanoma Patients Correlates with the Response to Anti-PD-1 Therapy Our results thus far strongly suggest that ALKBH5 deletion enhances the efficacy of anti-PD-1 therapy. Therefore, we analyzed TCGA database to examine the correlation between expression level of ALKBH5 and survival time in metastatic melanoma patients. In consistent with our findings, low expression of ALKBH5 correlated with better patients' survival (FIG. 4A). Importantly, Treg cell numbers, as indicated by FOXP3/CD45 ratio, were significant lower in patients less expression of ALKBH5 (FIG. 4B).

Figure 4C:
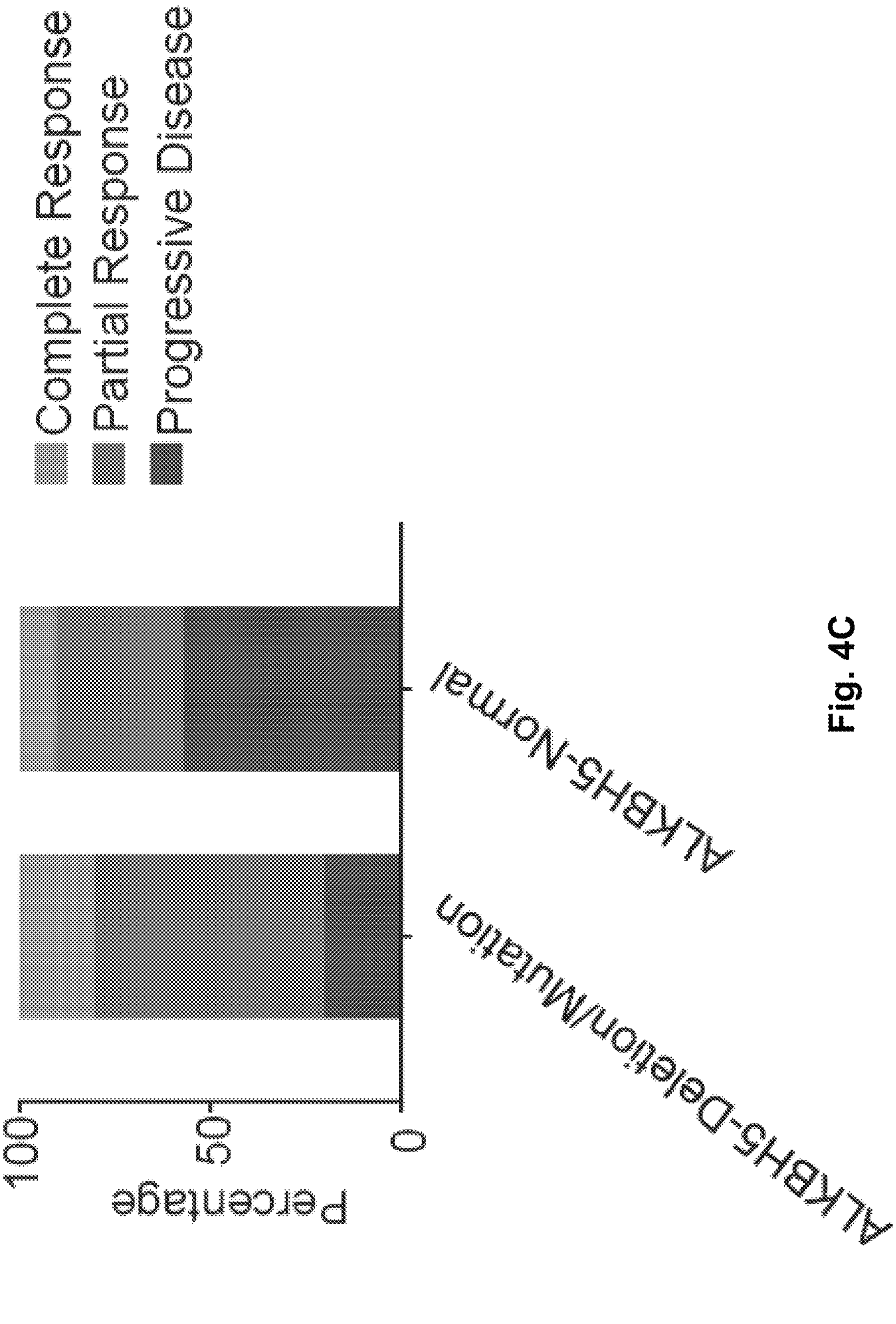
Figure 10F:
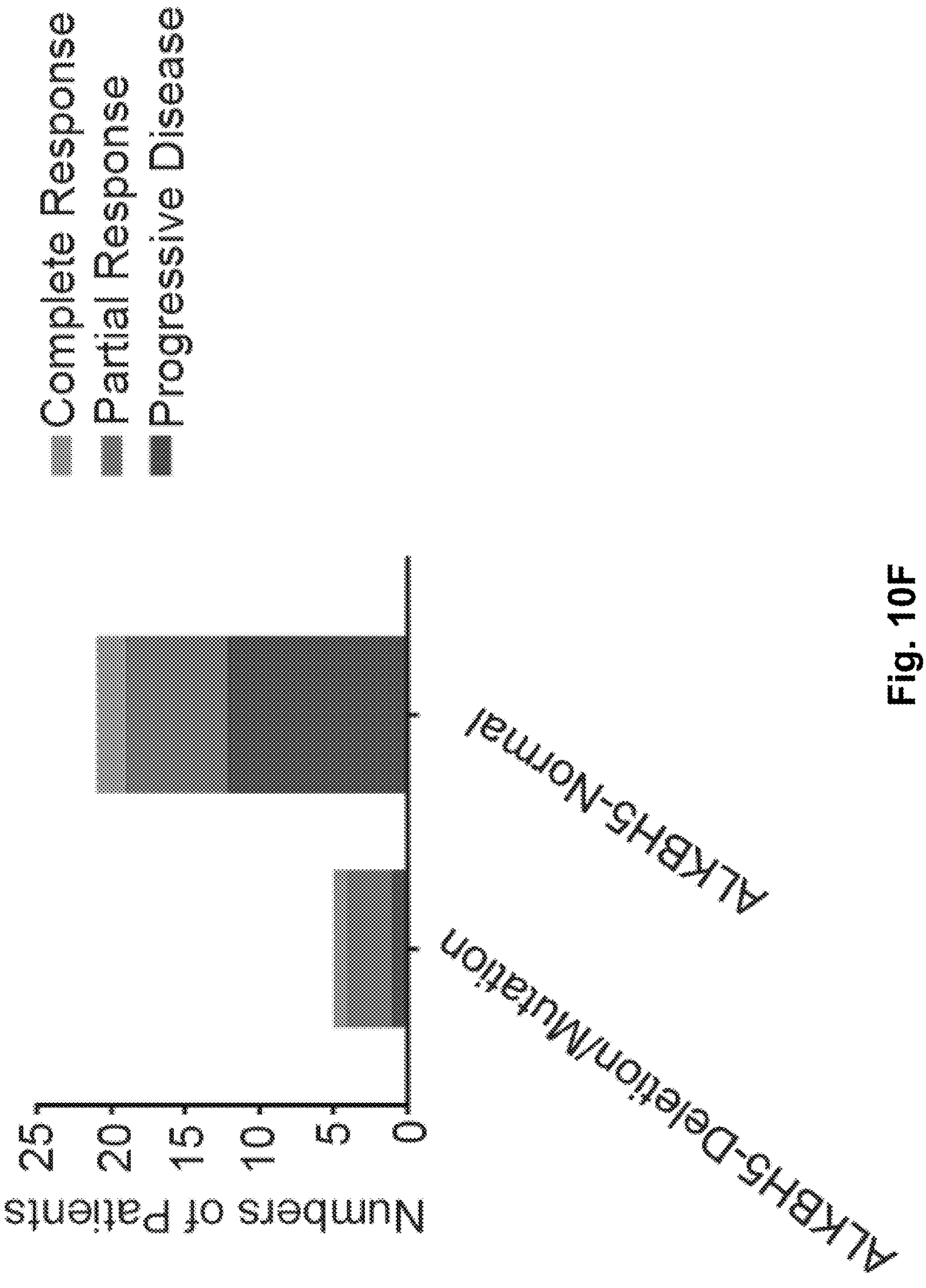

We next determined whether melanoma patients harboring ALKBH5 deletion/mutation were more sensitive to anti-PD-1 therapy than patients carrying wild-type ALKBH5. To this end, we analyzed 26 melanoma patients receiving anti-PD-1 treatment[27] and examined the treatment response according to their ALKBH5 mutation and gene expression status. As shown in FIG. 4C, we found that more patients harboring deleted or mutated ALKBH5 achieved complete or partial responses to pembrolizumab or nivolumab therapy than did patients wild wild-type ALKBH5 (FIGS. 4C and 10F).

Figure 4D:
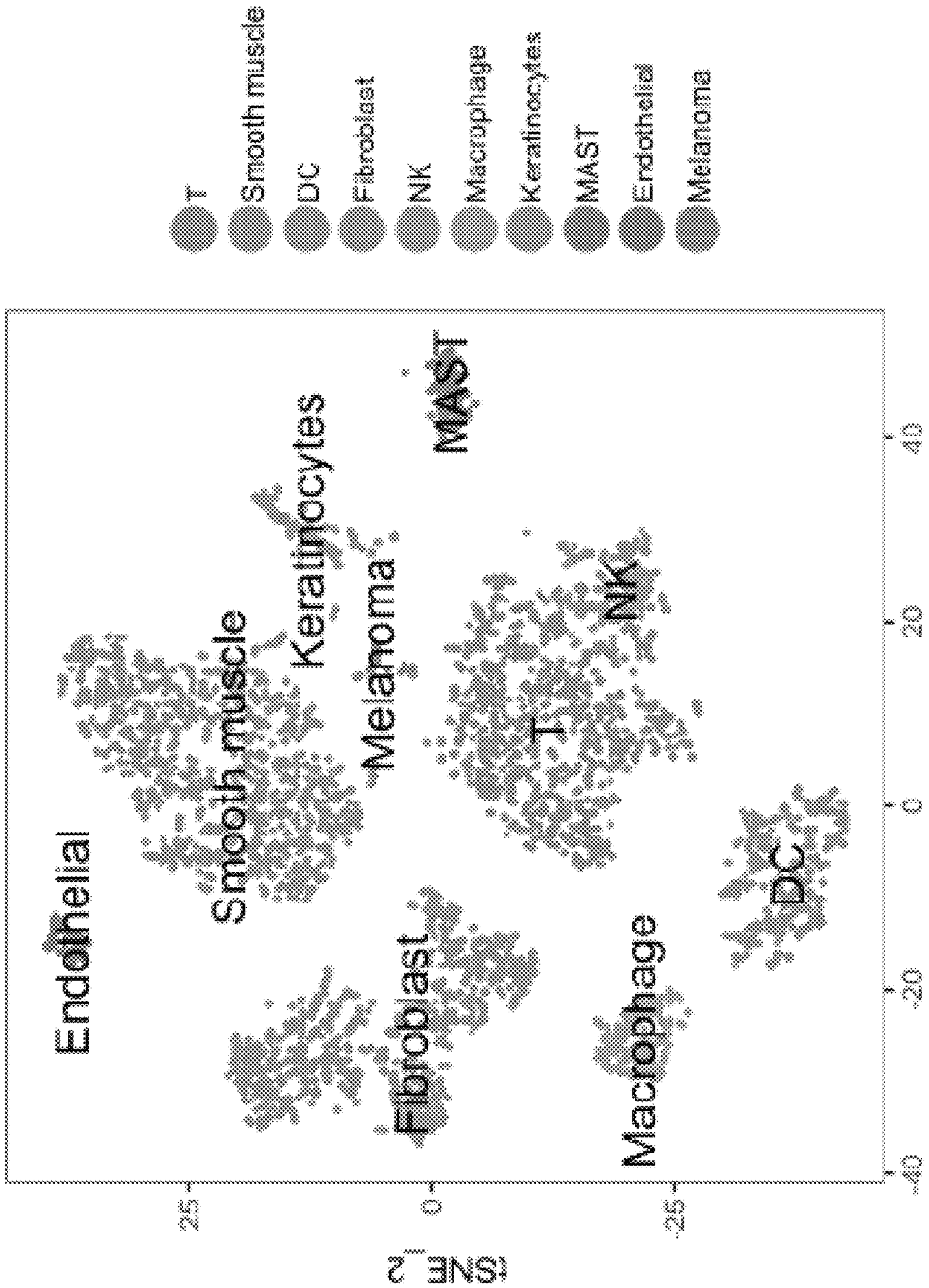
Figure 4E:
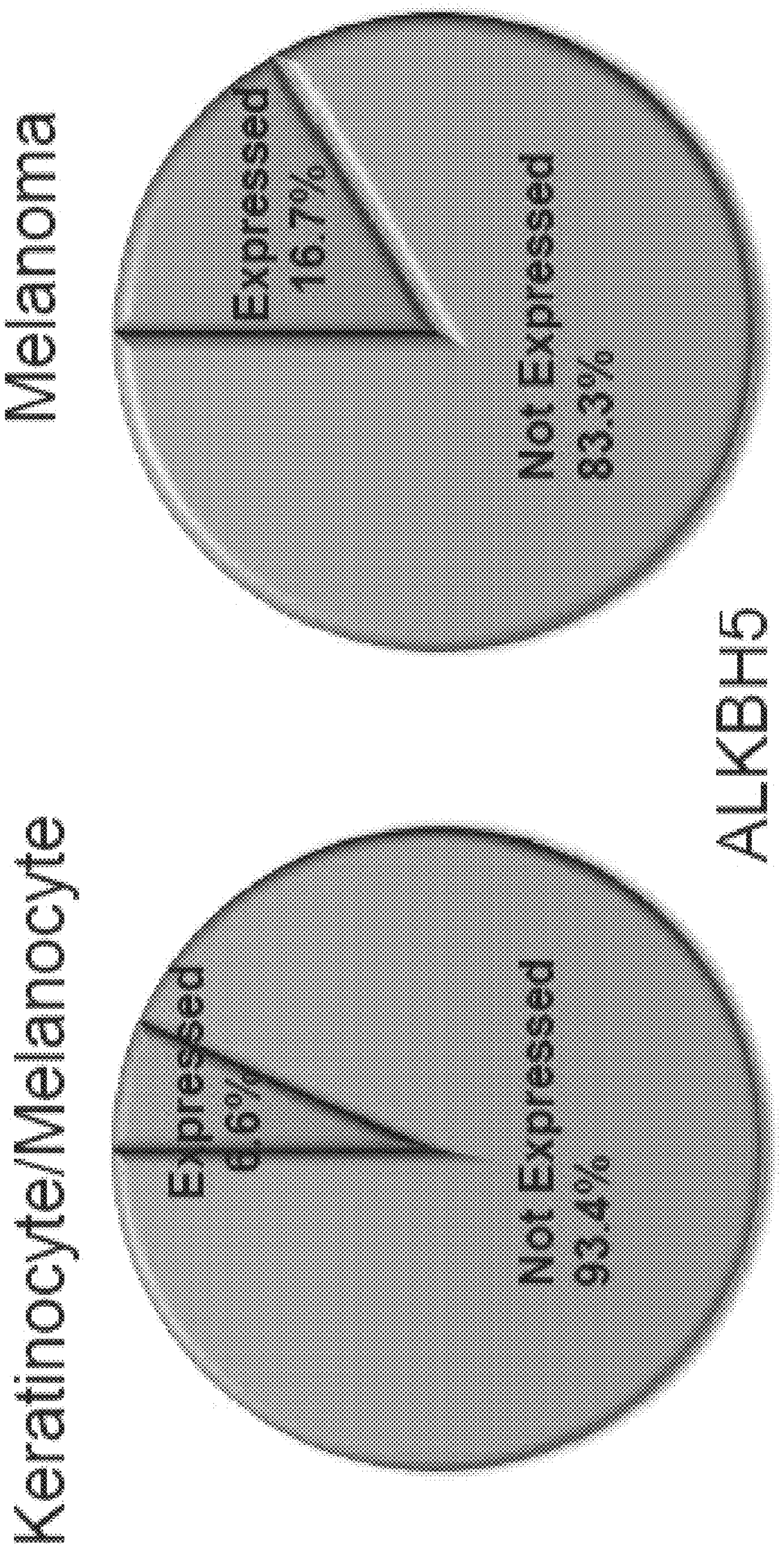

Next, we performed single-cell RNA-Seq on tumor cells obtained from a patient with stage IV melanoma who had responded well to anti-PD-1 therapy. By using scRNA-seq, we were able to examine ALKBH5 expression in the resistant tumor cells in patient receiving PD-1 antibody. We identified 10 cell types in the tumor (FIG. 4D), vittl substantial immune cell infiltration and very few residual melanoma cells, reflecting the response to therapy. We then examined ALKBH5 expression in the tumor cells and found that 16.7% of melanoma cells (16.7%) expressed ALK3H5 compared with only 6.6% of normal keratinocytes and melanocytes surrounding the tumor cells (FIG. 4E). Taken together, these results indicate that tumor expression of ALKBH5 might be a predictive biomarker of patient's survival and response to anti-PD-1 therapy, at least for melanoma patients.

Discussion

Figure 5G:
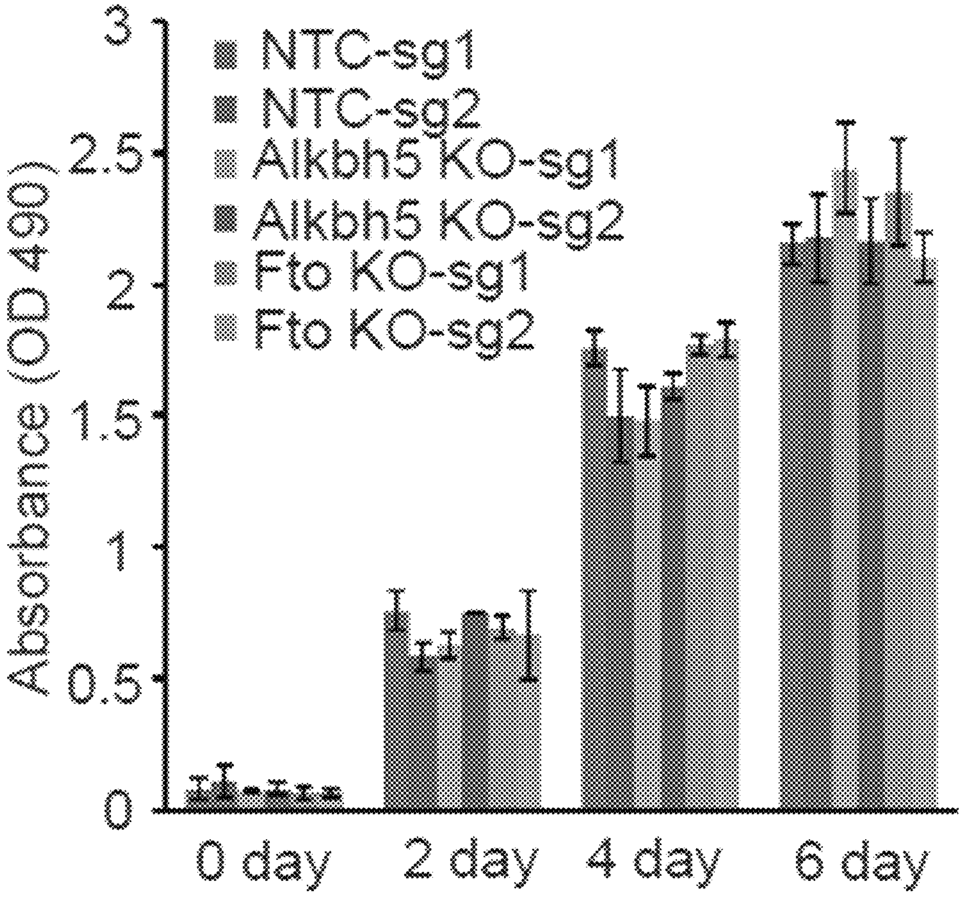
Figure 5H:
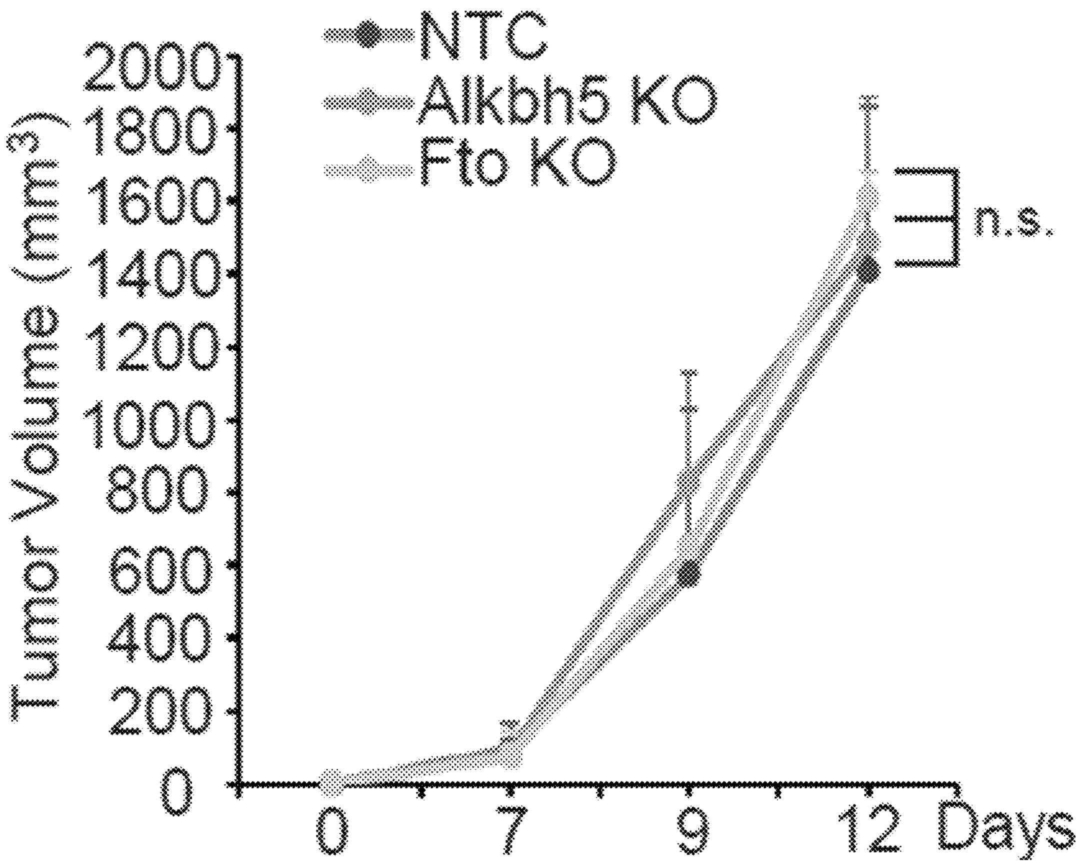
Figure 5I:
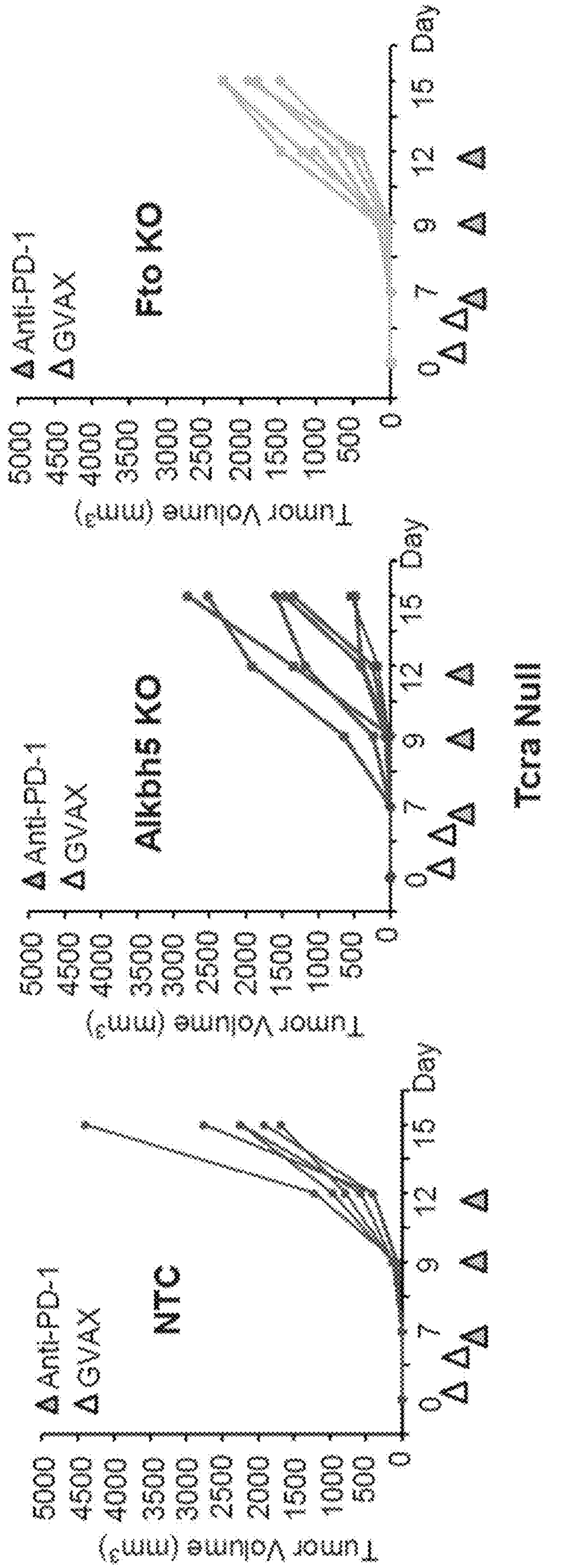

A major challenge facing the future of ICB for cancer is to understand the mechanisms of resistance to ICB and to develop combination therapies that enhance anti-tumor immunity and durable responses. using the poly immunogenic B16 mouse model of melanoma which is resistant to ICS, we discovered that genetic inactivation Of the demethylases Akbh5 and Fto in tumor cells rendered them more susceptible to anti-PD-1/GVAX therapy. The possibility that a similar approach could be employed for clinical applications is supported by the finding that Alkbh5 and Fto KO mice are viable This contrasts with m6A methyltransferases, which are known to be essential for embryonic development and stem cell differentiation[40,41] Notably, a recent study showed that anti-PD-1-blockade responses were enhanced in FTO knockdown tumors[21]. We also observed a similar trend with FTO knockout tumors during PD-1 Ab treatment alone, but it is not as robust as observed for Alkbh5 KO tumors (FIG. 1D). Therefore, Aklbh5 has more obvious effects on PD-1 Ab treatment alone or combined with GVAX compared to Fto (FIG. 1). Besides, it seems that the role of FTO in cell proliferation dominates the effects of FTO for in-vivo tumor growth from the published report[21], which we did not observe (FIGS. 5G and 5H). Overall, our data showed a more dramatic effects of Alkbh5 in regulating immunotherapy compared to Fto, and we further dissected the mechanisms of both proteins in this process.

Tregs and MDSCs are the dominant immunosuppressive cell populations in anti- tumor immunity[23]. In our study, we found that both cell populations were reduced in Alkbh5-KO tumors during GVAX/anti-PD-1 therapy, whereas the abundance of DCs increased. A decrease in tumor infiltration of MDSCs and Tregs was also observed in a mouse model of 4T1 tumors in response to the anti-PD-1/anti-CTLA-4 plus AZAENT treatment d2. Importantly, here we propose the link between m6A demethylase ALKBH5 and the altered tumor infiltrated lymphocytes composition in immunotherapy, providing new target to regulate the mechanism of TME and modulate of immunotherapy outcomes.

Our results showed that the function of Alkbh5 in regulating TME and immunotherapy efficacy was not through IFNY pathway, in accordance with the observation of unchanged infiltrated cytotoxic CD8 T cell population in Alkbh5 deficient tumors. Instead Alkbh5 knockout increased the m6A density in its targets and decreased mRNA expression or enhanced percentage of exon splice-in ratios. For example, Mex3d and Slc16a3/Mct4 mRNA expression was reduced in Alkhb5-KO tumors compared with NTC tumors during GVAX/anti-PD-1 therapy. Mex3d is an RNA- binding protein with putative roles in RNA turnover[43], and Slc16a3/Mct4 is important for pH maintenance, lactate secretion, and non-oxidative glucose metabolism in cancer cells[44]. Reduced lactate concentration in the TME has been linked to impaired Treg expansion and differentiation[45]. This suggests that a similar mechanism may be at play in the Alkbh5-KO B16 tumors analyzed in this study, which displayed reductions in Slc16a3/Mct4 expression, lactate content in TIF, and Treg abundance in the TME. In addition, Slc16a3/Mct4 was reported to regulate VEGF expression in tumor cells 46. Metand Usp15 mRNAs, which exhibited altered spliced-in percentage Alkbh5-KO tumors, are known to regulate HGF, VEGF and TGFB signaling in colon cancer and glioblastoma cells 34•47. We also observed a reduction in the TME level of Vegfa, suggesting that these metabolites and/or cytokines could affect the accumulation and expansion of suppressive Tregs and MDSCs at the tumor sites.

Figure 4F:
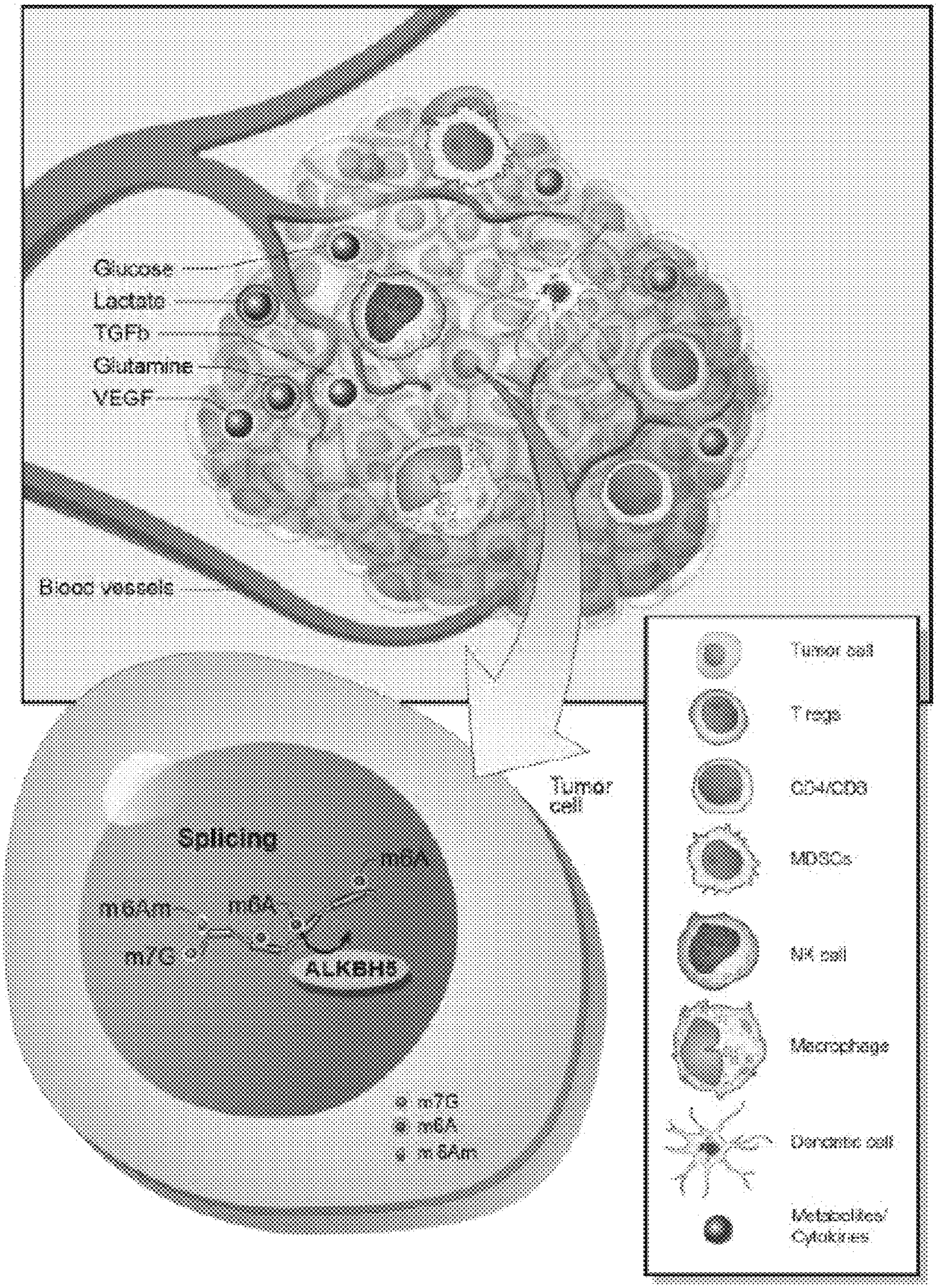

In summary, we have uncovered a previously unknown function for tumor- expressed Alkbh5 in regulating metabolite/cytokine content and filtration of immune cells in the TME during GVAX/anti-PD-1 therapy. Alkbh5-mediated alterations in the density of m6A was found to regulate the splicing and expression of mRNAs with potential roles in the control of tumor growth (FIG. 4F). These findings highlight the importance of m6A demethylation in regulating the tumor response to immunotherapy and suggest that ALKBH5 could be a potential therapeutic target, alone or in combination with ICB, for cancer.

Experimental Procedures

Cell Lines

The mouse B16FIO melanoma cell line was purchased from ATCC. The B16-GM-CSF cell line was a kind gift from Drs. Glenn Dranoff and Michael Dougan (Dana- Farber/Harvard Cancer Center). All cells were cultured in high-glucose DMEM (Thermo Fisher Scientific) supplemented 10% fetal bovine serum (FBS; Gibco) and 50 Ll/ml penicillin-streptomycin (Gibco) in a humidified 5% $C_{02}$ atmosphere.

Human Tumor Specimens

Tumor samples were obtained from a melanoma patient who had been treated with anti-PDI Ab. The procedures were approved by the UCSD Institutional Review Board and the patient provided informed consent.

Mouse Melanoma Model and Treatments

Animal studies and procedures were approved by the UCSD Institutional Animal Care and use Committee. Female C57BL/6J wild-type mice were obtained from The Jackson Laboratory and housed in the UCSD specific-pathogen free facility. 86.12952– TcratmlMcrn/J (Tcra+) mice, which are CDC and CDB• T cell deficient, were obtained from The Jackson Laboratory and bred on-site. For the standard protocol, mice (aged 9-12 weeks at use) were injected subcutaneously (s.c.) with 5×105 B16 cells (NTC control, Fto-KO, or Alkbh5-KO, generated as described below) into the left flank on day 0, and then injected with 1 OE irradiated (100 GY) BIG-GM CSF cells (GVAX) into the opposite flank on days 1 and 4 to elicit an anti-tumor immune response. Mice were then injected intraperitoneally (i p.) with 10 mg/kg (–200 pgimouse) of rat monoclonal anti-mouse RD-I Ab (Bio X Cell, clone 29F. IA 12) on the days as indicated on the figures. For PD-1 Ab treatment alone, mice were implanted with B16 cells and treated with antibody on day 6, 9 and 12. For the Treg depletion experiments, mice were injected as described above and were additionally injected i.p. vittl rat anti-mouse CD25 Ab (Bio X Cell, clone 7D4) on day 11. Tumors were measured every 3 days beginning on day 7. Measurements of the longest dimension (length, L) and the longest perpendicular dimension (width, W) were taken for calculation of tumor volume: (L W2)/2. Mice were euthanized by CO2 inhalation and cervical dislocation when tumors reached 2.0 cm in length, and the day of sacrifice was taken as the date of death for the purpose of the survival experiments.

CRISPR/Cas9-Mediated Generation of Knockout Cell Lines

B16 NTC, Alkbh5 or Fto KO cell lines were generated using at least four sgRNA sequences per gene. sgRNAs were cloned into the PlentiCRISPR V2 vector by Golden Gate assembly. Lentiviruses were generated by co-transfecting HEK293T cells with the sgRNA-expressing vectors (carrying a puromycin resistance gene), a packaging plasmid (psPAX2), and an envelope plasmid (pMD2.G) in DMEM medium. At 14 h after transfection, the medium was replaced with DMEM/IO % FBS. After two days of transfection, the supernatants were collected and used to infect B16 melanoma cells by spin infection. Transduced cells were selected by culture wittl puromycin (Alfa Aesar) at 1 pg/ml for 7 days, and KO efficiency was determined by western blot analysis.

Flow Cytometry of Tumor-infiltrating Immune Cells

Tumors were excised from mice using sterile techniques, weighed, mechanically diced, and then incubated with complete RPMI medium plus collagenase P (2 mg/ml, Sigma-Aldrich) and DNase I (50 ug/ml, Sigma-Aldrich) for 10-20 min with gentle shaking every 5 min. Single-cell suspensions were filtered through a 70-pm filter and resuspended in FACS staining buffer. Red blood cells were lysed by addition of lysis reagent. Cells were incubated with TruStain fcX anti-mouse CD16/32 Abs (BioLegend) and then with either Zombie Aqua Live/Dead fixable dye (BioLegend; for cells to be labeled for surface and intracellular proteins) or Calcein violet 450 AM Live/Dead (eBiosciences; for cells to be labeled only for surface markers). The cells were labeled with the appropriate combinations of Abs against cell surface markers. For intracellular protein staining, cells were fixed, permeabilized, and stained with the appropriate Abs. Finally, the cells were resuspended in FACS staining buffer and analyzed on a BD FACSCanto (UCSD Flow Cytometry core). BD CompBeads were used to optimize fluorescence settings (552845, 3D Biosciences). Fluorescence-minus-one, unstained, and single-stained cells were also used to set gates. The gating strategies for the various cell subsets are shown in FIG. 6.

The following anti-mouse Abs were used for flow cytometry: CD45 (clone 30-FI 1), CD8 (clone 53-6.7), CD4 (Clone RM4-5), CD3E (Clone 145-2C11), NKI.1 (clone PK136), FoxP3 (Clone MF-14), granzyme B (Clone 25-8898-82), CDI 1b (clone M1,'70), Ly6G (clone IAB), Ly6C (clone HKI 0.4), MHC-II (clone M5/114.15.2), F4/80 (BM8), and CD24– (clone M1/69). All Abs were from BioLegend except anti-granzyme B (eBioscience).

qRT-PCR and RNA-Seq

Total RNA was extracted from cultured cells using Quick-RNA Miniprep Plus Kit (Zymo Research) according to the manufacturer's instructions. Freshly dissected mouse tumors were weighed and immediately homogenized in TRIzol (Thermo Fisher Scientific). The lysates were centrifuged, and RNA was isolated from the supernatants using Direct-zol RNA Miniprep Plus kit (Zymo Research). All RNAs were treated with DNase 1. cDNAs were synthesized using an iScript cDNA synthesis kit (Bio-Rad). Gene expression levels were normalized to glyceraldehyde 3-phosphate dehydrogenase (GAPDH) mRNA levels and are expressed as the relative fold-change in expression compared with the control condition.

For RNA-Seq, total RNA was isolated from NTC, Alkbh5-KO, and Fto-KO tumors (two biological replicates). Sequencing was performed by HiSeq 4000 at the IGM Genomics Center, UCSD. Fastqc was used to perform quality control on sequencing data, and Cutadapt was used to remove adapters and trim reads. The preprocessed reads were then aligned to the *Mus musculus* genome (m 19 GENCODE data) using STAR. The raw gene count for each sample was obtained by Htseq2 (strand—reverse) and was normalized using the built-in method (median of ratios) in DEseq2. Differential gene expression was analyzed by DEseq2 using a cut-off p value of 0.05.

MeRIP-Seq

MeRIP-Seq was performed as previously reported 4B with some modifications. Briefly, total RNA was extracted from freshly isolated mouse tumors as described above. Aliquots (15 pg) of high-quality RNA were treated twice with RiboMinus (Invitrogen), and depletion of the majority of rRNAs was confirmed using an Agilent Bioanalyzer. Purified RNA was fragmented to 100-200 nucleotides using Ambion RNA Fragmentation Reagent (AM8740, Life Technologies) and the fragmented RNA was collected by ethanol precipitation. An input sample (10% of total fragmented RNA) was reserved for each sample. Fragmented RNA was incubated with 10 pl rabbit anti-mEA polyclonal Ab (ab151230, Abcam) in IP binding buffer (10 mM Tris-HCl, 150 mM NaCl, 0.1% NP-40, pH 7.4) for 2 h at CC. The mixture was then incubated with 50 pl protein A/G magnetic beads (Thermo Fisher) for 2 h at 40 C, and the beads were collected and washed twice in P wash buffer (10 mM Tris-HCl, 1 M NaCl, 0.1% NP-40, pH 7.4). Bound RNA was eluted from the beads with m6A elution buffer (10 mM Tris-HCl, 1 M NaCl, 0.1% NP40, 25 mM m6A, pH 7.4) and extracted with TR Zol (Thermo Fisher). m6A-containing RNA was dissolved in water and processed for library generation using a TruSeq mRNA library preparation kit (Illumina). Sequencing was performed by HiSeq 4000 at the GM Genomics core, UCSD.

MeRIPSeq Data Analysis

Two pipelines were used to call peaks on each sample based on its paired m6A-RIP/input data: m6A viewer (expected peak length 200, FDR 0.05, peak-deconvolution mode 49) and MACS2 (q-value 0.05, call-summit mode 50). The default peak range for m6A viewer was 200 nucleotides and peaks, and −200 nucleotides for MACS2.

To find the collection of consensus peak for each group, we first identified the common peaks of each group for individual peak-calling tool. For each individual tool, peaks from biological replicates were filtered using adjusted method 51. A peak from one biological replicate was kept if and only if there exist at least one peak whose summit was within 200 nt away from the summit of peak for each of the remaining biological replicates. These kept peaks together built the collection of common peaks for each group. After achieving the set of common peaks for each group within m6A viewer and MACS2 output separately, the collection of consensus peak for each group was generated by finding the overlapping peaks of two set of common peaks from different peak-calling tools. For example, if we denoted the common peaks of NTC from m6A viewer as NTC- view and that from MACS2 as NTC-macs, the final result of consensus peak for NTC group was the set of peaks from NTC-view that have overlapping peaks in NTC-macs, where "overlap" has the same meaning as defined above. With this stringent method, we reduced the possibility of keeping false positive peaks to the least. The collection of consensus peaks of NTC, Akbh5-KO and Fto-KO groups were used for the data visualization by using bedtools and IGV, and motif-finding using MEME-ChiP for each group. We further generated the peak distribution across chromosome region (intron, CDS, and intergenic region) and across gene region (3'UTR, 5'UTR and CDS) using RSeQC and Guitar Plot. According to these results, we noticed some difference in consensus peaks of different groups.

To investigate the difference, for each group, we compared its consensus peaks with these from the rest two groups, to split them into three parts: commonly shared peaks, unique peaks and peaks shared only within two groups. For example, the collection of consensus peaks of NTC group was divided into peaks that are unique in NTC (having no overlapping peaks in Fto-KO and Akbh5-KO group), peaks that were commonly shared in all groups (having overlapping peaks pairwrisely), peaks that were shared with Alkbh5-KO (having overlapping peaks in Alkbh5-KO but not in Fto-KO group) and peaks that were shared Fto-KO (having overlapping peaks in Fto-KO but not in Alkbh5-KO group). We then mapped these peaks to their located genes to generate the according gene list. The gene annotation used here was from GENCODE.

Alternative Splicing and Splice Junction Analysis

The method to compute m6A peak density among the splicing junction is based on the method from the published report 31. The information of long internal exon (with length 200 nt) are extracted from the gene annotation of GENCODE. The consensus peak of each group is mapped to the location of long internal exon and only peaks whose summit is in the region of long internal exon is kept. After this, the long internal exon region is divided into three parts: 5' nearSS (SS: splice site), a 100 bp interval starting from 5' splice site, 3' near-SS, a 100 bp interval ending at 3' splice site and away-from-SS, which is the region in the middle. For example, peak A is in 5' near-SS region, peak B in away-from-SS region and peak C in 3' near-SS region. The reference m6A peak density for each experimental group is the m6A peak density on the away-from-SS region. The away-from-SS region of long interval exon is split into intervals of 10 bp long. For one interval, we examine all transcript and record the number of m6A peaks whose summit is in the interval. Then we divide this number by the number of transcripts containing this interval to get the peak density of the specific interval. The average m6A peak density for all interval in away-SS region is the reference m6A peak density for each group. We use the same method to get the m6A peak density for ten 10 bp intervals of the 5' and 3' near-SS region. This peak density is normalized by dividing according reference m6A peak density of each group to get the relative m6A peak density of each interval in near-SS region. The indexed and sorted input file are then used for alternative splicing analysis by MISO 52 based on the provided alternative splicing event annotation by this software. The ratio between reads including or excluding exons, also known as percent spliced in index (PSI), indicates how efficiently sequences of interest are spliced into transcripts. The output from Alkbh5-KO and Fto- KO groups are compared with that from NTC to find the differential alternative splicing event using PSI-value difference 0.1 and bayes factor 5. We used bayes factor 5 which means that the isoform/exon is more than five times to be differentially expressed than not. The visualization of certain differential splicing events of interest is realized using sashimi-plot Single-Cell RNASeq of a Human Melanoma Specimen Two tissue samples (punch biopsies) were obtained from a patient with stage IV melanoma who had been treated with the anti-PD-1 Ab. Tissues were digested to single-cell suspensions and filtered through a 70 pm nylon mesh. Dead cells were removed with a kit (Stemcell Technologies) and viable cells were counted. The cells were then washed with 0.04% RNase-free bovine serum albumin in PBS and analyzed by single-cell RNA-Seq. Reverse transcription, cDNA amplification, and library preparation were performed using a Chromium Single Cell 3' Library & Gel Bead Kit v2 (IOX Genomics) according to the manufacturer's protocols. Libraries were sequenced on an Illumina HiSeq 4000. Single-cell RNA-Seq data were analyzed using the Cell Ranger Single-Cell Software Suite (IOX Genomics).

Tumor Interstitial Fluid (TIF) Isolation and Analysis

TIF samples were extracted from mouse tumors, and plasma samples were prepared as previously described[54]. Concentrations of lactate, Vegfa, and TgfP1 in both matrices were measured using Lactate BioAssay Systems Assay kits (eBioscience), VEGF-A Mouse ELISA Kit (Invitrogen) and TGF beta-I Human/Mouse ELISA Kit (Invitrogen) according to the manufacturer's instructions. Lactate, Vegfa, and Tgfßl content are presented as the plasma concentration and the TIF concentration and content per unit tumor mass (concentration×TIF volume/tumor weight).

IFNY Stimulation of Melanoma Cells In Vitro

B16 cells were plated at a density of 50000/well in 12-well plates in complete DMEM medium with DPBS (vehicle control) or IFNY (100 ng/ml, BioLegend) for 48 h. The cells were then collected, RNA was extracted, and gene expression levels were determined by qRT-PCR.

Cell Proliferation Assay

B16 cells were plated at a density of 2000/well in 96-well plates in triplicate and incubated for 0, 2, 4, or 6 days before cell numbers were determined by manual counting or by using a CellTiter AQueous One Solution Cell Proliferation Assay kit (Promega).

Western Blot Analysis

Cells or fresh isolated mouse tumors were lysed in lysis buffer (60 mM Tris HCl, 2% SDS, 10% glycerol, complete EDTA-free protease inhibitor, 500 Ll/ml benzonase nuclease) by pipetting or homogenization. Samples were clarified by centrifugation and protein concentrations in the supernatants were determined with a BCA protein assay kit (Pierce). Aliquots of 50-150 pg of protein were resolved by Tris-Glycine or 4-12% Bis-Tris Plus PAGE and the proteins were transferred to PVDF membranes. Membranes were blocked with 5% non-fat milk and incubated overnight at 40 C with Abs against Alkbh5 (AP18410c, Abgent), Fto (27226-1-AP, Proteintech), or GAPDH (14C10, Cell Signaling Technology). After washing, the membranes were incubated for 1 h at RT with secondary Ab. Finally, the blots were developed using ECL and imaged.

Immunohistochemistry

Freshly excised B16 tumors were fixed in 4% paraformaldehyde, dehydrated, embedded in paraffin, sectioned into 5-pm slices, and mounted on slides according to standard procedures. Sections were then incubated with rat anti-mouse Ly6G (RB6-8$C_5$, Abcam) overnight at CC, followed by biotinylated secondary Ab for 1 h at RT, and then incubated with peroxidase conjugated avidin biotin complex for 1 h at RT. Finally, the sections were incubated with AEC chromogen substrate developing agent and imaged using a Keyence microscope. LC-MS/MS Analysis of m6A RNA m6A-containing RNA was analyzed by LC-MS/MS as previously described 4. Total RNA depleted of rRNA were for analysis (100 ng/sample). Samples were obtained from four mice per condition.

Statistical Analysis

Data are presented as the mean standard error (SEM) unless otherwise indicated. Group means were compared by Student's t-test. P<0.05 was considered statistically significant.

Data and Software Availability

Data Resources

The accession number for the sequencing data reported in this paper is NCBI GEO: GSE134388 and will be released with publication.

Figure Legends

FIG. 1. Deletion of the m6A RNA Demethylases Alkbh5 Sensitizes Tumors to Immunotherapy.

(A) Experimental design to investigate the role of m6A RNA methylation in anti-PD-1 therapy. Alkbh5 and Fto were deleted by CRISPR-Cas9 editing of B16 mouse melanoma cells and injected subcutaneously into C57B/J6 wild-type mice ($5\times10^5$/mouse). Control mice received non-targeting control (NTC) B16 cells. Because B16 cells are poorly immunogenic, all mice were injected subcutaneously with GVAX (irradiated BIG-GM-CSF cells) on days 1 and 4 to elicit an anti-B16 immune response. Anti-PD-1 Ab (200 pg/mouse) was injected intraperitoneally on days 6, 9, and 12 (or as indicated for individual experiments).

(B and C) Growth of NTC, Alkbh5 KO and Fto KO (C) B16 tumors in C57BL/6 mice treated as described in Data are the mean SEM of the indicated total number of mice/groups. For each gene, ttlree B16 CRISPR cell lines with 24 mice/line were examined.

(D) Growth of NTC, Alkbh5 KO, and Fto KO BIG tumors in C57BU6 mice treated with anti-PD-1 antibody. Data are the mean±SEM of the indicated total number of mice/groups.

(E) As described for (A) except B16 cells were injected into 36. (TCRa-deficient) mice, which are devoid of mature CD8+ and CD4+ T cells. Data are presented as the mean SEM. *p<0.05. See also FIG. 6.

FIG. 2. Deletion of Alkbh5 Modulates Tumor Immune Cell Infiltration and Gene Expression During Immunotherapy.

(A-C) FACS quantification of immune cells isolated from B16 NTC, Alkbh5-KO, and Fto-KO tumors as described in FIG. 1A. Tumor-infiltrating cells were analyzed using the gating strategies described in FIG. 6A-6C. (A) CD4+ FoxP3+ (T regulatory), (B) CD45+CD11b+Ly6G4Ly6ClOF4/80-MHC-11−(polymorphonuclear, PMN-MDSCs) and (C) CD45+ Ly6C-MHC-1+CD24hi F4/B010 (dendritic cells, DCS) were analyzed. Data are presented as the mean±SEM. Points represent individual mice.

(D) Immunohistochemical staining of Ly6G+ PMN-MDSCs in NTC or Alkbh5-KO tumors isolated from mice on day 12.

(E) Growth of NTC and Alkbh5-KO tumors in mice treated as described in FIG. 1A and additionally injected intraperitoneally with 10 mg/kg of control lgG or Treg-depleting anti-CD25 Ab on day 11. Data are presented as the mean±SEM. *p<0.05 vs NTC control mice.

(F and G) GO analysis (F) and heatmap presentation (G) of differentially expressed genes in Alkbh5-KO tumors compared with NTC tumors. Genes satisfying the cut-off criteria of p<0.05 and logfold-change X) or are shown.

FIG. 3. Alkbh5 Regulates Gene Splicing, and Lactate and Vegfa Contents of TME in B16 Tumors During Immunotherapy (A) LC-MS/MS quantification of m6A in ribosome-depleted total RNA isolated from NTC, Alkbh5-KO, and Fto-KO tumors. Data are presented as the mean SEM fold-change relative to the NTC control in 4 mice/group. *p<0.05,p<0.01, *p<0.001 vs NTC control.

(B) Genomic location of the conserved m6A peaks identified by MeRIP-Seq in B16 tumors from mice treated as described in FIG. 1A. Plot shows the proportion of m6A in the coding sequence (CDS), 5' and 3' UTRs, introns, transcription start site (TSS), transcription end site (TES), and intergenic regions.

(C) Pie charts showing the proportions of common and unique m6A/m6Am peaks in B16 tumors from mice treated as described in FIG. 1A.

(D) Top consensus motifs of MeRIP-Seq peaks identified by MEME in B16 tumors from mice treated as described in FIG. 1A.

(E) The density of m6A in the region of 100 nt exon regions from the 5' splice site ("SS") and the 3' SS. The Relative m6A peak density of a specific position in NTC and Alkbh5 deficient tumors was calculated as the scaled m6A peak density proportional to the average m6A peak density in the internal exonic regions. (F) Difference of PSI was calculated by MISO as NTC control minus either Akbh5 knockout or Fto knockout tumors.

(G) Lactate concentration and total content in tumor interstitial fluid (TIF) isolated from NTC or Alkbh5-KO tumors excised on day 12 from mice treated as described in FIG. 1A. Left panels show absolute lactate concentration in TIF; right panels show lactate content per mg tumor. Data are the presented as the mean±SEM of five (NTC) or four (Alkbh5 KO) mice.

(H) As for (G) except Vegfr was analyzed.

FIG. 4. ALKBH5 Expression Influences the Response of Melanoma Patients to Anti-PD-1 Therapy.

(A) Kaplan-Meier survival rate analysis of TCGA metastasized melanoma patients grouped by ALKBH5 mRNA levels. Patients with follow-up history were included in the analysis; the mean ALKBH5 level for the entire group was used as the cutoff value. ALKBH5 low: NZ196; ALKBH5 high: NZ163.

(B) FOXP3/CD45 expression ratio was calculated for metastatic melanoma patients grouped by ALKBH5 mRNA levels; the mean ALKBH5 level for the entire group was used as the cutoff value. ALKBH5 low: NZ196; ALKBH5 high: NZ163.

(C) Melanoma patients (n 26) carrying wild-type (normal) or deleted/mutated ALKHB5 gene were treated with pembrolizumab or nivolumab anti-PD-1 Ab. The percentage with complete response, partial response, and progressive disease are shown. Data are from GSE78220.

(D) Single-cell RNA-Seq data presented as t-distributed stochastic neighbor embedding (t-SNE) plots. Cells were from a tumor biopsy collected from a melanoma patient who showed a response to anti-PD-1 therapy. Plots show the distribution of identified cells.

(E) ALKBH5 expression in normal keratinocytes/melanocytes and melanoma tumor cells in melanoma patient receiving PD-1 therapy.

(F) Proposed Model for Alkbh5-Mediated Effects on Immunotherapy of Melanoma. Alkbh5-mediated m6A demethylation from target RNAs and/or effects on mRNA splicing alter the secretion of cytokines and metabolites in the tumor microenvironment. We postulate that dysregulation of these events in the tumor cells affect the infiltration of immune cell populations and, subsequently, the efficacy of immunotherapy. Our data provide an evidence of m6A in the cross-talk between tumor-intrinsic alteration and extrinsic microenvironment changes during cancer immunotherapy.

Supplemental Information

FIG. 5 (Related to FIG. 1).

(A and B) Western blot analysis of Alkbh5 (A) and Fto (B) expression in B16 cell lines subjected to CRISPR-Cas9-mediated gene KO. Four lines, each receiving a distinct gene-targeting sgRNA sequence, were generated per gene. NTC cells received nontargeting control sgRNAs. Cell lines with complete deletion (red boxes) were used for the mouse experiments.

(C-E) Tumor growth in individual C57BL/6 mice for the experiments shown in FIGS. 1B and 1C.

(F) Kaplan-tvleier survival curves for mice injected with NTC, Akbh5-KO, and Fto-KO cells and treated as described for FIG. 1A. NTC: N 27 Alkbh5 KO: NZ 28; Fto KO: NE 15. Mice were sacrificed and considered "dead" when the tumor size reached 2 cm at the longest axis.

(G) Proliferation of NTC, Alkbh5.KO, or Fto-KO cells B16 cells in vitro.

Figure 69A:
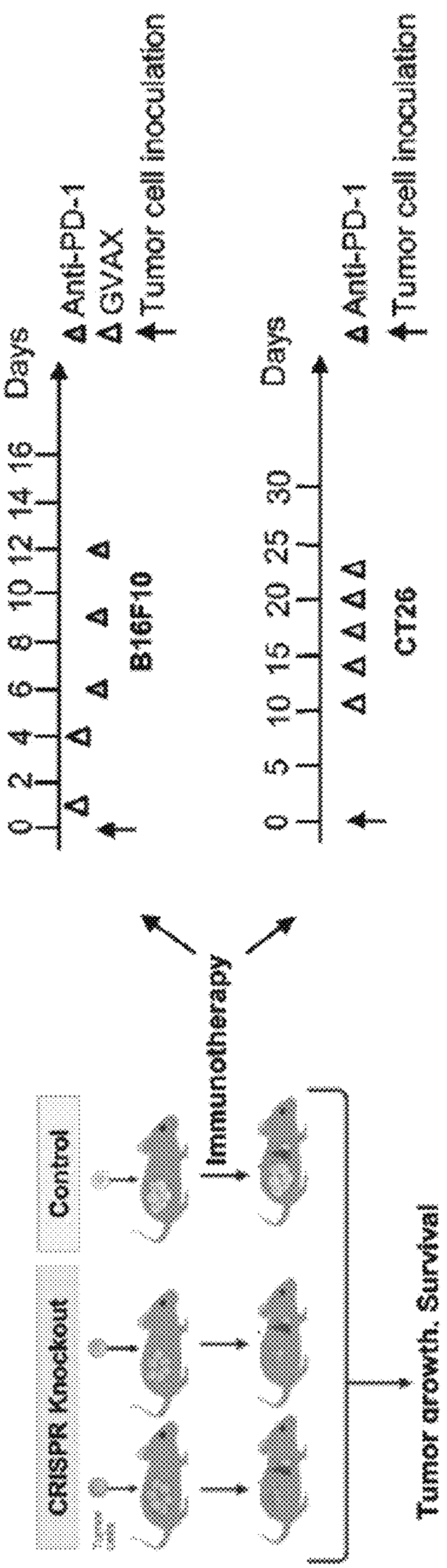
FIG. 69A-69F. Deletion of the m6A RNA demethylase Alkbh5 sensitizes tumors to anti-PD-1 immunotherapy and alters immune cell recruitment. (69A) Experimental design to investigate the role of m6A RNA methylation in anti-PD-1 therapy. Alkbh5 and Fto were deleted by CRISPR/Cas9 editing of B16 mouse melanoma cells and injected subcutaneously into C57BWG wild-type mice (5×IOS per mouse). Control mice received NTC BIG cells. Because BIG cells are poorly immunogenic, all mice were injected subcutaneously with GVAX (irradiated B16 GM-CSF cells) on days 1 and 4 to elicit an anti-B16 immune response. Anti-PD-1 Ab (200 ug per mouse) was injected intraperitoneally on days 6, 9, and 12 (or as indicated for individual experiments). Similar experiments were performed for CT26 cells. The cells were inoculated in BALB/c mice and mice were treated with PD-1 Ab on days 11, 14, 17, 20, and 23. (69B) Growth of NTC and Alkbh5-KO B16 tumors in C57BlJ6 mice treated as described in A. Data are the mean SEM of the indicated total number of mice per group. For each gene, three B 16 CRISPR cell lines with 24 mice per line were examined. (69C) Kaplan-Meier survival curves for mice injected with NTC and Alkbh5-KO B16 cells and treated with GVAX and PD-1 Ab. NTC: n 27; Alkbh5-KO: n 28. Mice were killed and considered "dead" when the tumor size reached 2 cm at the longest axis. (69D) Growth of NT C and Alkbh5-KO CT26 tumors in BALB/c mice treated with anti-PD-1 Ab. Data are the mean SEM Of the indicated total number Of mice per group. (69E) Kaplan-Meier survival curves for mice injected with NTC and Alkbh5-KO CT26 cells and treated as described for D. NTC: n 10; Alkbh5-KO: n 10. Mice were killed and considered "dead" when the tumor size reached 2 cm at the longest axis. (69-F) FACS quantification of immune cells isolated from B16 NTC, Alkbh5-KO, and Fto-KO tumors as described in 69A. Tumor-infiltrating cells were analyzed using the gating strategies as described. CD4* FoxP3* (Treg), (PMN-MD-SCS), and CD24h' F4/8010 (DC) were analyzed. Data are presented as the mean±SEM. Points represent individual mice *P<0.05, P<0.01, *P<0.001

(H) As described for FIG. 69A except injected mice were not treated with CVAX or anti- PD-1 Ab). Data are presented as the mean SEM.

Figure 1E:
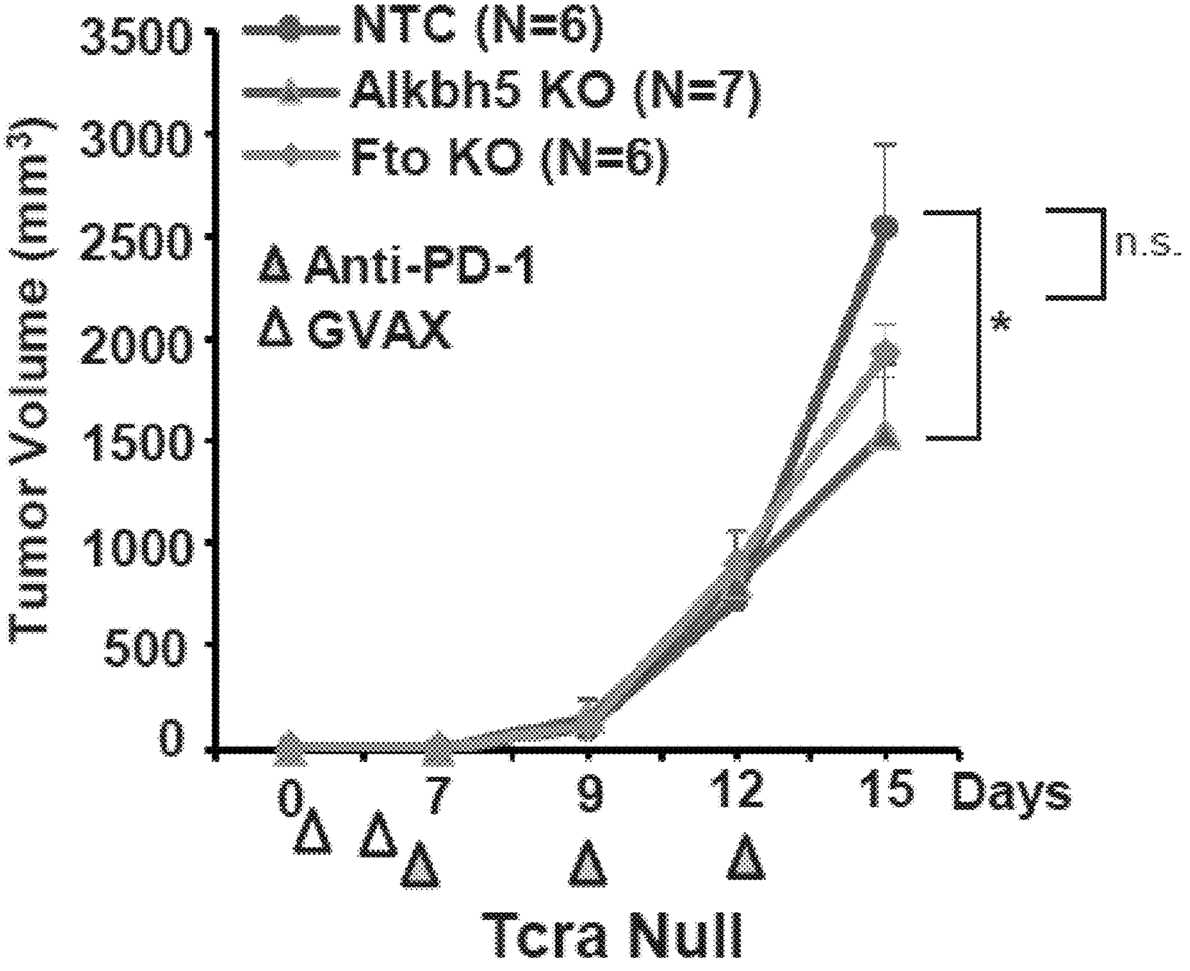
Figure 2G:
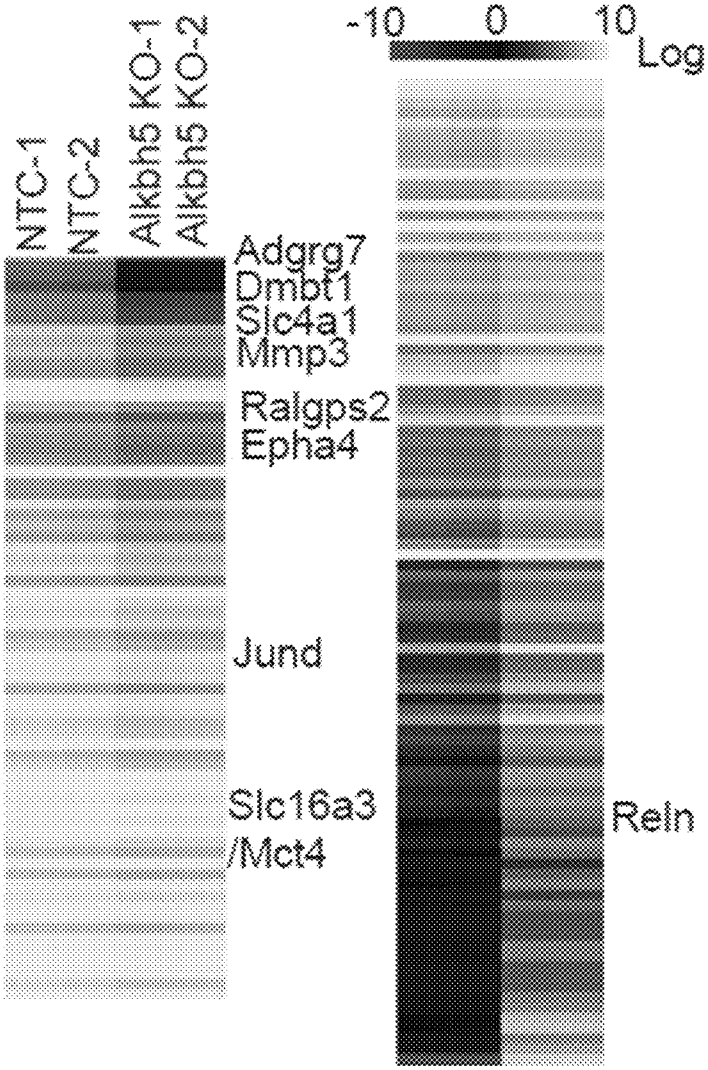

(I) Tumor growth in individual 36.129S2-TcratmlMom/J mice for the experiments shown in FIG. 1E.

FIG. 6 (Related to FIG. 2).

(A-C) Representative dot plots showing the gating strategy for the data shown in FIGS. 2A-C and 6D Populations of interest are indicated by black boxes.

(D) FACS quantification of immune cells isolated from B16 NTC, Alkbh5-KO, and Fto- KO tumors as described in FIG. 1A. Tumor-infiltrating cells were analyzed using the gating strategies described in FIG. 6A-6C. CD45+, CD4+, CD8+, CD4+ granzyme B (GZMB+), CDB+ GZMB+, NKI.1+ (natural killer), CD45+CD11b+Ly6C hi (monocytic myeloid-derived suppressor cells, M-MDSCs), CD45+Ly6C-MHC-ll+ CD2410 F4/80hi (macrophages) were analyzed. Data are presented as the mean±SEM. Points represent individual mice. (E) Flow cytometry of CD45+ and CDB+ cells in tumors excised from mice injected with NTC cells without treatment and treated with anti-PD-1 Ab alone or GVAX and anti-PD-1 Ab). Data are the mean SEM. Points represent individual mice.

(F) Flow cytometry of Tregs in tumors excised from mice injected with NTC, Alkbh5-KO, or Fto-KO B16 cells and treated with anti-PD-1 Ab). Data are the mean SEM. Points represent individual mice. $*P<0.05$ vs control mice.

FIG. 7 (Related to FIG. 2).

(A and B) Western blot verification of effective Alkbh5 or Fto KO in B16 tumors excised from mice treated as described in FIG. 1A. Representative blots with 3 mice/group are shown.

(C and D) MA (log ratio vs mean average) plots of significantly downregulated genes in Alkbh5-KO vs. NTC BIG tumors (C) or Fto-KO vs. NTC B16 tumors (D) excised on day 12 from mice treated as described for FIG. 1A. Genes satisfying the cut-off criteria of p c: 0.05 and logfold-change or <<–0.5 are shown.

(E and F) As for (2F and G) except differentially expressed genes in Fto-KO tumors vs NTC tumors were analyzed.

(G) qRT-PCR analysis of Pdll, Cxc110, cc15, Irfl, Cxc19, and Tapi mRNA levels in NTC, Alkbh5-KO, and Fto-KO cells cultured in vitro in the presence or absence of IFNy 100 ng/ml for 48 h. Data are presented as the fold change (FC, color coded bar) in mRNA level relative to the same cells without IFNY treatment.

(H and I) Venn diagrams showing genes significantly downregulated in Alkbh5-KO vs NTC B16 tumors (H) or Fto-KO vs NTC B16 tumors (l) isolated from mice on day 12 of treatment as described for FIG. 1A (pink circles) and their overlap with genes in melanoma patients who were responders to anti-PD-1 Ab (pembrolizumab or nivolumab) therapy. Dataset is GSE78220. (J and K) As described for (S3H and l) except the Venn diagrams show significantly upregulated genes.

FIG. 8 (Related to FIG. 3).

(A) Venn diagrams of m6A/m6Am peaks detected by MACS2 or m6A viewer peak calling pipeline. The peak numbers shown were the numbers of common peaks of all the animals in each group called by MACS2 or m6A viewer. Common peaks of all biological replicates in each group and called by both peak calling methods were kept for further analysis.

(B) Metagene profiles depicting m6A signals in mRNA and LncRNA gene transcripts.

(C) Genome browser tracks were shown for Mex3d and Slc16a3/Mct4 with called m6A sites by MeRIP and corresponding inputs. Input was indicated by blue color in each track. Bed files of the called peaks were shown under the MeRIP track of each group. Scale of the peak density was set the same for all the groups for a gene and shown in the FIG. 9 (Related to FIG. 3).

(A-B) GO (A) and KEGG (B) analysis of the unique m6A peaks mapped genes in Alkbh5 deficient tumors after immunotherapy.

(C) The density of m6A in the region of 100 nt exon regions from the 5'SS and the 3'SS. The relative m6A peak density of a specific position in NTC and Fto deficient tumors was calculated as the scaled m6A peak density proportional to the average m6A peak density in the internal exonic regions.

(D) Summary of gene function in which PSI were changed in Alkbh5 deficient cells. Representative genes are shown.

(E) Genome browser tracks were shown for snRNA UI, 1-12 and 03 with called m6A sites by MeRlP and corresponding inputs. Input was indicated by blue color in each track. Scale of the peak density was set the same for all the groups for a gene and shown in the corner.

(F-G) Difference of PS was calculated by MISO as NTC control minus either Alkbh5 knockout (F) or Fto knockout (G) tumors. A3: alternative 3 splice site; AS: alternative 5' splice site; RI: intron retention; SE: spliced exon.

(H) Alternative splicing of gene Usp15, Arid4b, Eif4a2 and Hnrnpc in NTC and Alkbh5 deficient tumors after immunotherapy are shown. (I) Genome browser tracks of Eif4a2, Arid4b and Usp15 with called m6A sites by MeRIP and corresponding inputs are shown. Input was indicated by blue color in each track. Increased m6A density near splice site in Alkbh5 deficient tumors are highlighted with green bar.

FIG. 10 (Related to FIGS. 3 and 4).

(A) TIF isolation method from mouse tumors after immunotherapy.

(B) TgfP1 concentration and total content in tumor interstitial fluid (TIF) isolated from NTC or Alkbh5-KO tumors excised on day 12 from mice treated as described in FIG. 1A. Left panels show absolute Tgfßl concentration in TIF; right panels show Tgfßl content per mg tumor. Data are the presented as the mean±SEM of five (NTC) or four (Alkbh5 KO) mice.

(C) Lactate concentration in plasma isolated from NTC or Alkbh5-KO tumors excised on day 12 from mice treated as described in FIG. 1A.

(D) As for (C) except Vegfa was analyzed.

(E) As for (C) except TgfB1 was analyzed.

(F) Number of melanoma patients carrying wild-type (normal) or deleted/mutated ALKBH5 genes who experienced complete response (n 2 and 1, respectively), partial response (n 7 and 3, respectively), and progressive disease (n 12 and 1, respectively) following treatment with anti-PD-1 Ab).

REFERENCES

1. Chen, D. S. & Mellman, I. Elements of cancer immunity and the cancer-immune set point. Nature 541, 321-330, doi:10.1038/nature21349 (2017).
2. Meyer, K. D. & Jaffrey, S. R. Rethinking Readers, Writers, and Erasers. Annu Rev Cell Dev Bio/33, 319-342, doi:10.1146/annurev-cellbio-100616-060758 (2017).
3. Shi, H., Wei, J. & He, C. Where, When, and How: Context-Dependent Functions of RNA Methylation Writers, Readers, and Erasers. Mol Cell 74, 640-650, doi:10.1016/j.molcel.2019.04.025 (2019).
4. Meyer, K. D. et al. Comprehensive analysis of mRNA methylation reveals enrichment in 3' UTRs and near stop codons. Cell 149, 1635-1646, doi:10.1016/j.cell.2012.05.003 (2012).
5. Dominissini, D. et al. Topology of the human and mouse m6A RNA methylomes revealed by m6A-seq. Nature. 485, 201-206, doi:10.1038/nature11112 (2012).
6. Schwartz, S. et al. Perturbation of m6A writers reveals tvvo distinct classes of mRNA methylation at internal and 5' sites. Cell Rep 8, 284-296, doi:10.1016/j.celrep.2014.05.048 (2014).
7. Jia, G. et al. N6-methyladenosine in nuclear RNA is a major substrate of the obesity-associated FTO. Nat Chem Bio/7, 885-887, doi:10.1038/nchembio.687 (2011).
8. Zheng, G. et al. ALKBH5 is a mammalian RNA demethylase that impacts RNA metabolism and mouse fertility. Mol Cell 49, 18-29, doi:10.1016/j.m01cel.2012.10.015 (2013).
9. Mauer, J. et al. Reversible methylation of m(6)Am in the 5' cap controls mRNA stability. Nature 541, 371-375, doi:10.1038/nature21022 (2017).
10. Mauer, J. et al. FTO controls reversible m(6)Am RNA methylation during snRNA biogenesis. Nat Chem Biol 15, 340-347, doi:1 O. 1038/s41589-019-0231-8 (2019).
11. Patil, D. P., Pickering, B. F. & Jaffrey, S. R. Reading m(6)A in the Transcriptome: m(6)A-Binding Proteins. Trends in cell biology 28, 113-127, doi:10.1016/j.tcb.2017.10.001 (2018).
12. Wang, X. & He, C. Reading RNA methylation codes through methyl-specific binding proteins. RNA biology 11, 669-672, doi:10.4161/rna.28829 (2014).
13. Yang, Y., Hsu, P. J., Chen, Y. S. & Yang, Y. G. Dynamic transcriptomic m(6)A decoration: writers, erasers, readers and functions in RNA metabolism. Cell Res 28, 616-624, doi: 10.1038,'s41422-018-0040-8 (2018).
14. Li, H. B. et al. m(6)A mRNA methylation controls T cell homeostasis by targeting the IL-7/STAT5/SOCS pathways. Nature 548, 338-342, doi:10.1038/nature23450 (2017).
15. Gonzales-van Horn, S. R. & Sarnow, P. Making the Mark: The Role of Adenosine Modifications in the Life Cycle of RNA Viruses. Cell host & microbe 21, 661-669, doi:1 O. 1016/j.chom.2017.05.008 (2017).
16. Barbieri, 1. et al. Promoter-bound METTL3 maintains myeloid leukemia by m(6)A-dependent translation control. Nature 552, 126-131, doi:10.1038/nature24678 (2017)
17. Han, D. et al. Anti-tumour immunity controlled through mRNA methylation and YTHDF1 in dendritic cells. Nature 566, 270-274, doi:10.1038/s41586-019-0916-x (2019).
18. Paris, J. et al. Targeting the RNA m(6)A Reader YTHDF2 Selectively Compromises Cancer Stem Cells in Acute Myeloid Leukemia. Cell Stem Cell 25, 137-148 el 36, doi:10.1016/j.stem.2019.03.021 (2019).
19. Su, R. et al. R-2HG Exhibits Anti-tumor Activity by Targeting FTO/m(6)A/MYC/CEBPA Signaling. Cell 172, 90-105 el 23, doi:10.1016/j.cell.2017.11.031 (2018).
20. Vu, L. P. et al. The N(6)-methyladenosine (m(6)A)-forming enzyme METTL3 controls myeloid differentiation of normal hematopoietic and leukemia cells. Nat Med 23, 1369-1376, doi:iO.1038/nm.4416 (2017).
21. Yang, S. at al. mRNA demethylase FTO regulates melanoma tumorigenicity and response to anti-PD-1 blockade. Nat Commun 10, 2782, doi:10.1038’s41467-019-10669-0 (2019).

22. Dranoff, G. GM-CSF-secreting melanoma vaccines. Oncogene 22, 3188-3192, doi:10.1038/sj.onc.1206459 (2003).

23. Fujimura, T., Kambayashi, Y. & Aiba, S. Crosstalk between regulatory T cells (T regs) and myeloid derived suppressor cells (MDSCs) during melanoma growth. Onconimmunology 1, 1433-1434, (2012).

24. Setiady, Y. Y., Coccia, J. A. & Park, P. U. In vivo depletion of CD4+FOXP3+ Treg cells by the PC61 anti-CD25 monoclonal antibody is mediated by Fcgam-maRIII+ phagocytes. Eur J Immuno/40, 780-786, 1002/eji.200gag613 (2010).

25. Arce Vargas, F. et Fc-Optimized Anti-CD25 Depletes Tumor-infiltrating Regulatory T Cells and Synergizes With PD-1 Blockade to Eradicate Established Tumors. Immunity 46, 577-586, doi:10.1016fj.immuni.2017.03.013 (2017).

26. Manguso, R. T. et al. In vivo CRISPR screening identifies Ptpn2 as a cancer immunotherapy target. Nature 547, 413-418, doi:10.1038/nature23270 (2017).

27. Hugo, W. et al. Genomic and Transcriptomic Features of Response to Anti-PD-1 Therapy in Metastatic Melanoma. Cell 165, 35-44, (2016).

28. Wei, J. et al. Differential m(6)A, m(6)Am, and m(1)A Demethylation Mediated by FTO in the Cell Nucleus and Cytoplasm. Mol. Cell 71, 973-985 e975, doi:10.1016/j.molcel.2018.08.011 (2018).

29. Linder. B. et al. Single-nucleotide-resolution mapping of m6A and m6Am throughout the transcriptome. Nat Methods 12, 767-772, (2015).

30. Louloupi, A., Ntini, E., Conrad, T. & Orom, U. A. V. Transient N-6-Methyladenosine Transcriptome Sequencing Reveals a Regulatory Role of m6A in Splicing Efficiency. Cel Rep 23, 3429-3437, doi:10.1016fj.celrep.2018.05.077 (2018).

31. Ke, S. et al. mRNA modifications are deposited in nascent pre-mRNA and are not required for splicing but do specify cytoplasmic turnover. Genes Dev 31, 990-1006, doi:10.1101/gad.301C36.117 (2017).

32. Tang, C. at al. ALKBH5-dependent m6A demethylation controls splicing and stability of long 3'-UTR mRNAs in male germ cells. Proc Natl Acad Sci USA 115, E325-E333, doi:10.1073/pnas.1717794115 (2018).

33. Condamine, T., Ramachandran, I., Youn, J. I. & Gabrilovich, D. I. Regulation Of tumor metastasis by myeloid-derived suppressor cells. Annu Rev Med 66, 97-110, 1146/annurev-med-051013-052304 (2015).

34. Matsumura, A. et al. HGF regulates VEGF expression via the c-Met receptor downstream pathways, P13K/Akt. MAPK and STAT3, in CT26 murine cells. Int J Oncol 42, 535-542, doi: 10.3892/00.2012.1728 (2013).

35. Neufeld. G., Sabag, A. D., Rab'novicz, N. & Kessler, O. Semaphorins in angiogenesis and tumor progression. Cold Spring Harb Perspect Med 2, a006718, doi:10.1101/cshperspect.a006718 (2012).

36. Villain, G. et al. miR-126-5p promotes retinal endothelia cell survival through SetD5 regulation in neurons. Development 145, doi:10.1242/dev.156232 (2018).

37. Kotani, Y. et al. Alternative exon skipping biases substrate preference of the deubiquitylase IJSPI 5 for mysterinJRNF213, the moyamoya disease susceptibility factor. Sci Rep 7, 44293, doi:10.1038/srep44293 (2017).

38. Pilotto, S. et al. MET exon 14 juxtamembrane splicing mutations: clinical and therapeutical perspectives for cancer therapy. Ann Transl Med 5, 2, doi: 10.2103natm.2016.12.33 (2017).

39. Wagner, M. & Wig, H. Tumor Interstitial Fluid Formation, Characterization, and Clinical Implications. Front Oncol 5, 115, doi:1C.3389/fonc.2015.00115 (2015).

40. Geula, S. et al. Stem cells. m6A mRNA methylation facilitates resolution of naive pluripotency toward differentiation. Science 347, 1002-1006, doi:10.1126/science.1261417 (2015).

41. Meng, T. G. et al. Mettl14 is required for mouse postimplantation development by facilitating epiblast maturation. FASEE J 33, 1179-1187, doi: 10.10Wfj201800719R (2019).

42. Kim, K. et al. Eradication of metastatic mouse cancers resistant to immune checkpoint blockade by suppression of myeloid-derived cells. Proc Natl Acad Sci USA 111, 11774-11779, doi:10.1073/pnas.1410626111 (2014).

43. Buchet-Poyau, K. et al. Identification and characterization of human Mex-3 proteins, a novel family of evolutionarily conserved RNA-binding proteins differentially localized to processing bodies. Nucleic Acids Res 35, 1289-1300, doi.:10.1093/nar/gkm016 (2007).

44. Baenke, F. et al. Functional screening MCT4 as a key regulator of breast cancer cell metabolism and survival. J Pathol 237, 152-165, doi:10.1002/path.4562 (2015).

45. Angelin, A. et al. Foxp3 Reprograms T Cell Metabolism to Function in Low-Glucose, High-Lactate Environments. Cell Metab 25, 1282-1293 e1287. (2017).

46. Sun, Q., Hu, L L. Fu, Q. MCT4 promotes cell proliferation and invasion of castration-resistant prostate cancer PC-3 cell ine. EXCL' J 18, 187-194, doi:10.17179/eX-Cli2018-1879 (2019).

47. Eichhorn, P. J. et al. USP15 stabilizes TGF-beta receptor I and promotes oncogenesis through the activation Of TCF-beta signaling in glioblastoma. Nat Med 18, 429-435, doi:10.1038/nm.2619 (2012).

48. Lichinchi, G. et al. Dynamics of the human and viral m(6)A RNA methylomes during HIV-1 infection of T cells. Nat Microbiol 1, 16011, doi:1c.1038/nmicrobiol.2016.11 (2016).

49. Antanaviciute, A. et al. m6aViewer: software for the detection, analysis, and visualization of peaks from sequencing data. RNA 23, 1493-1501, doi: 10.1261frna.0582C$_{6.116}$ (2017).

50. Zhang, Y. et al. Model-based analysis of ChlP-Seq (MACS). Genome Biol 9, R137, doi:10. 1186/gb-2008-9-9-r137 (2008).

51. Engel, M. et al. The Role of Methylation in Stress Response Regulation. Neuron 99, 389-403 e389, (2018)

52. Katz, Y., Wang, E. T., Airoldi, E. M. & Burge. C. B. Analysis and design of RNA sequencing experiments for identifying isoform regulation. Nat Methods 7, 1009-1015, doi:10.103B'nmeth.1528 (2010).

53. Katz, Y. et al. Quantitative visualization of alternative exon expression from RNA-seq data. Bioinformatics 31, 2400-2402, (2015).

54. Sullivan, M. R. et al. Quantification of microenvironmental metabolites in murine cancers reveals determinants of tumor nutrient availability. Elite 8, (2019).

Example B2. Compounds for Immunotherapy and Cancer Stem Cells

Figure 11:
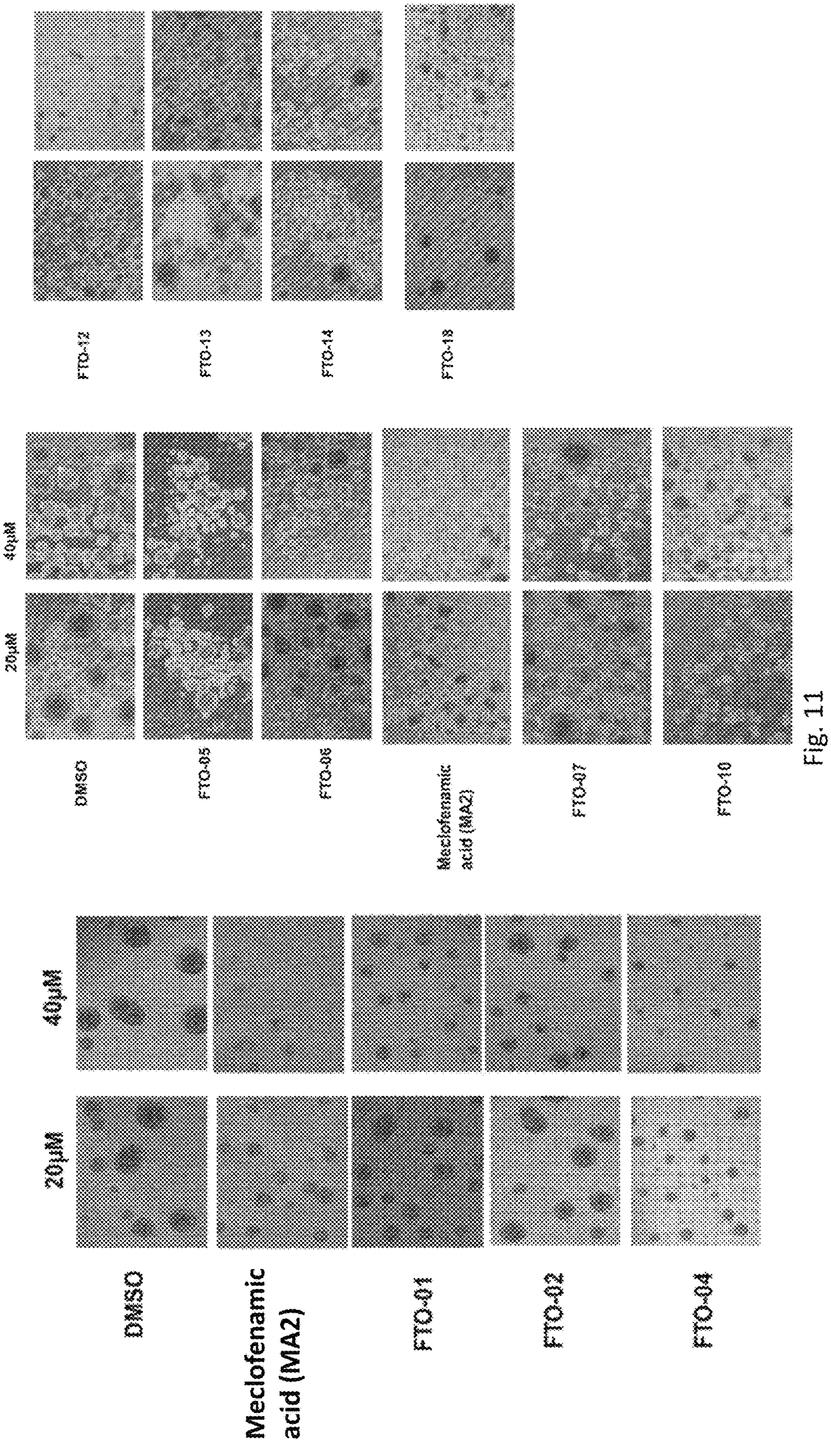
Figure 12:
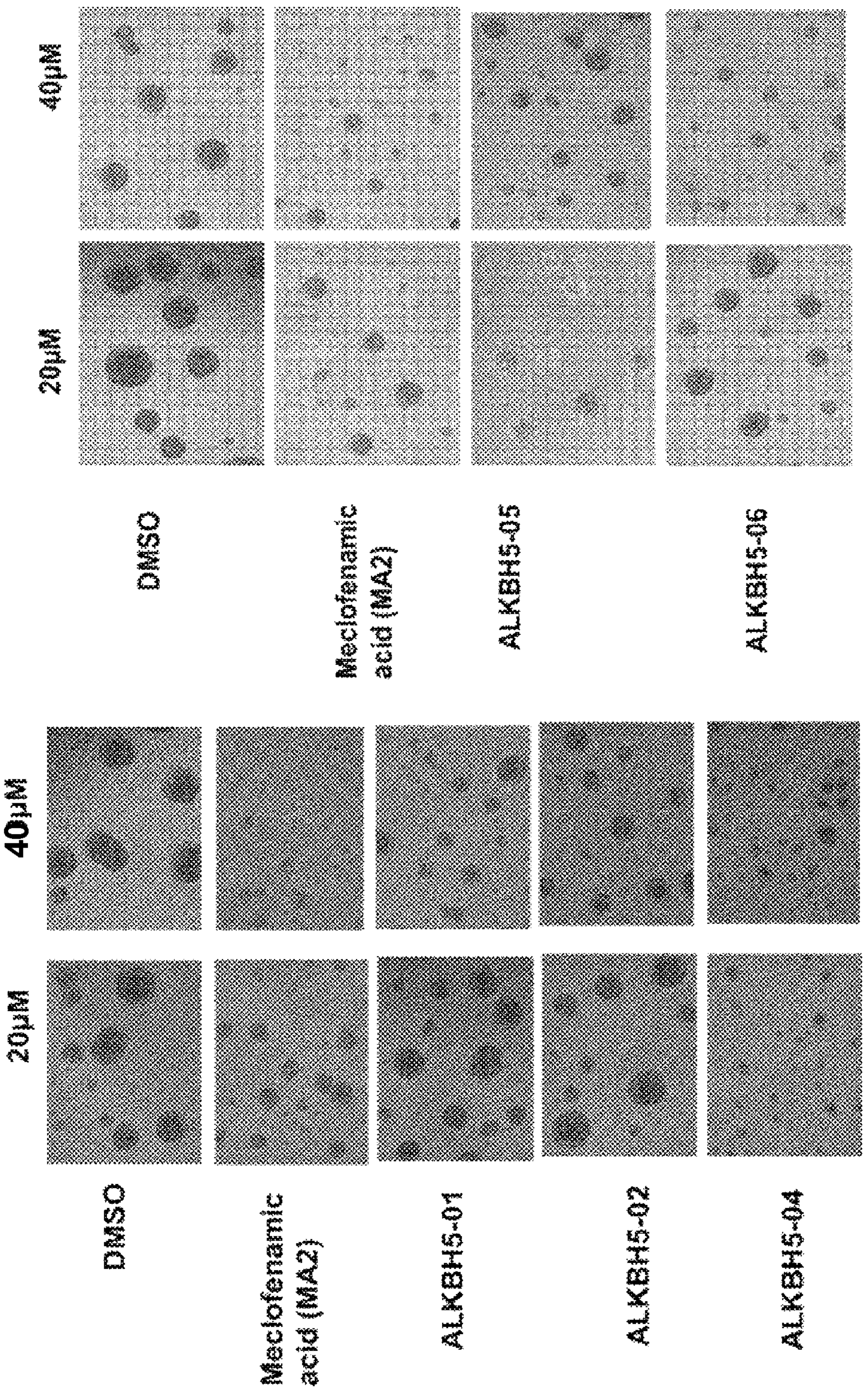
FIG. 12. ALKBHS inhibitors specifically kill Glioblastoma cancer stem cells. TSS76 GBM cancer stem cells were used to develop neuro organoid models or cancer and two drug concentrations were tested.

Glioblastomas are one of the most aggressive brain tumors for which no real cure exists. The invention consists in new compounds (antisense, shRNA, small molecules, CRISPR-sgRNAs) that block two known demethylases FTO (fat mass and obesity-associated protein) and ALKBH5. These demethylases are enzymes expressed by cancer stem cells. In experiments, the inventor used neuro organoids (as in vitro tumor models) established from glioblastoma cancer stem cells. Data showed that the inhibitors were able to reduce the size of the neuro organoids (see FIGS. 11 and 12). The reason for using this type of in vitro tumor models is that established tumor cell lines have shown not to be representative of the gene expression and profiles of real cells.

Figure 13A:
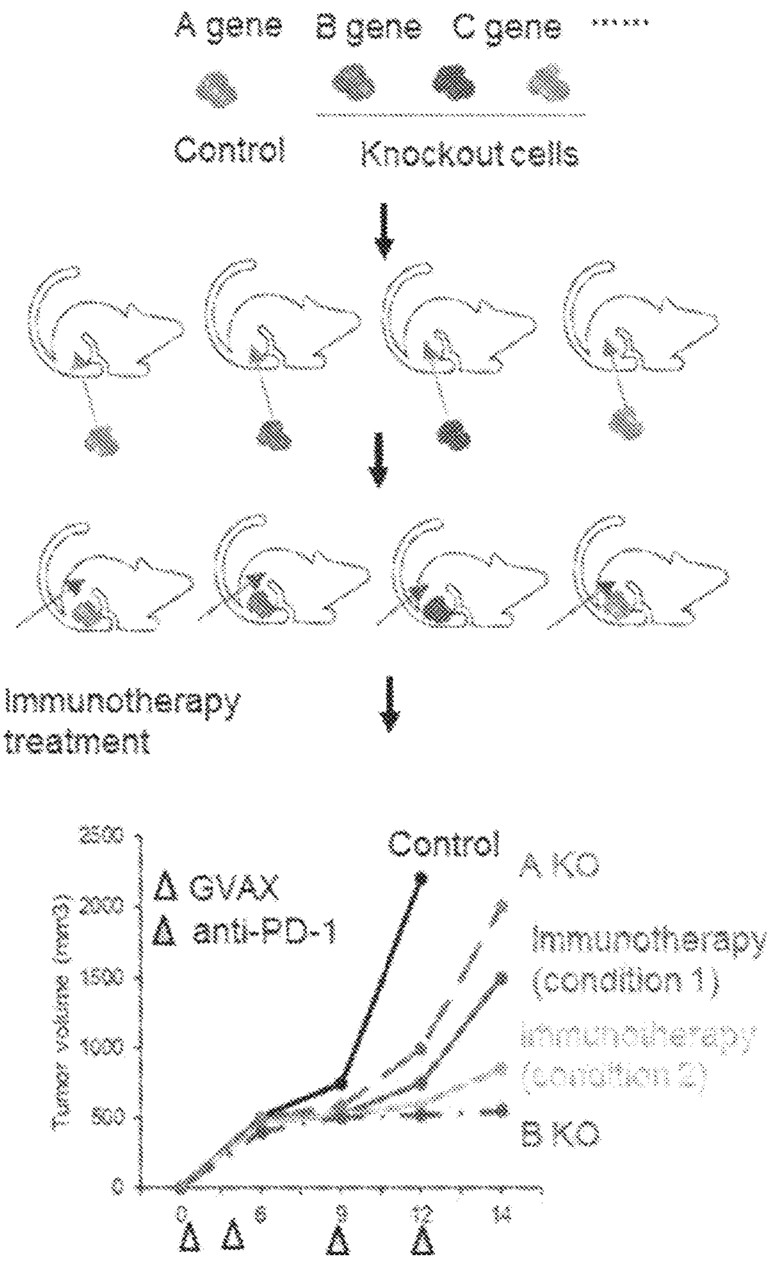
FIG. 13A-13C. Generation Of AlkbhS and Fto knockout B16 melanoma cells using CRISPR-Cas9 and in-vivo model for melanoma immunotherapy (FIG. 13A) Experimental design for in vivo melanoma immunotherapy (FIG. 13B) Generation Of Alkbh5 knockout B16 melanoma cells using lentivirus B16 cells were infected with lentivirus of 4 sgs/gene and selected with puromycin for at least 72 hrs. Western blots were used to determine the CRISPR-Cas9 knockout editing efficiency.
Figure 13B:
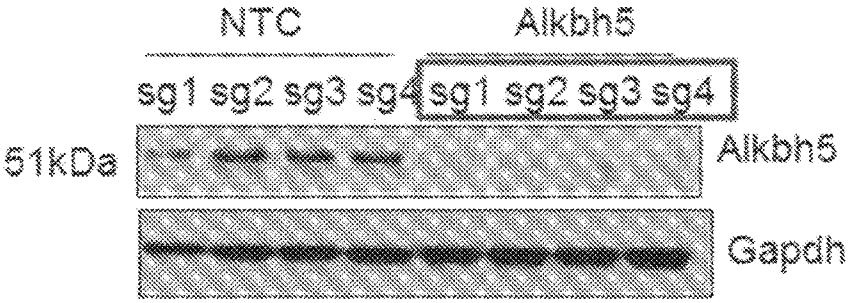
Figure 13C:
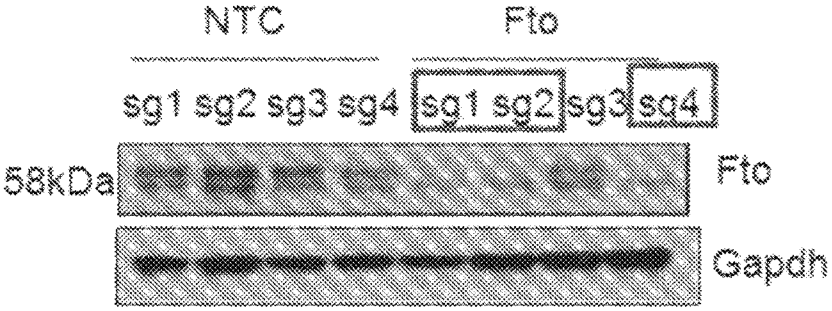
Figure 14A:
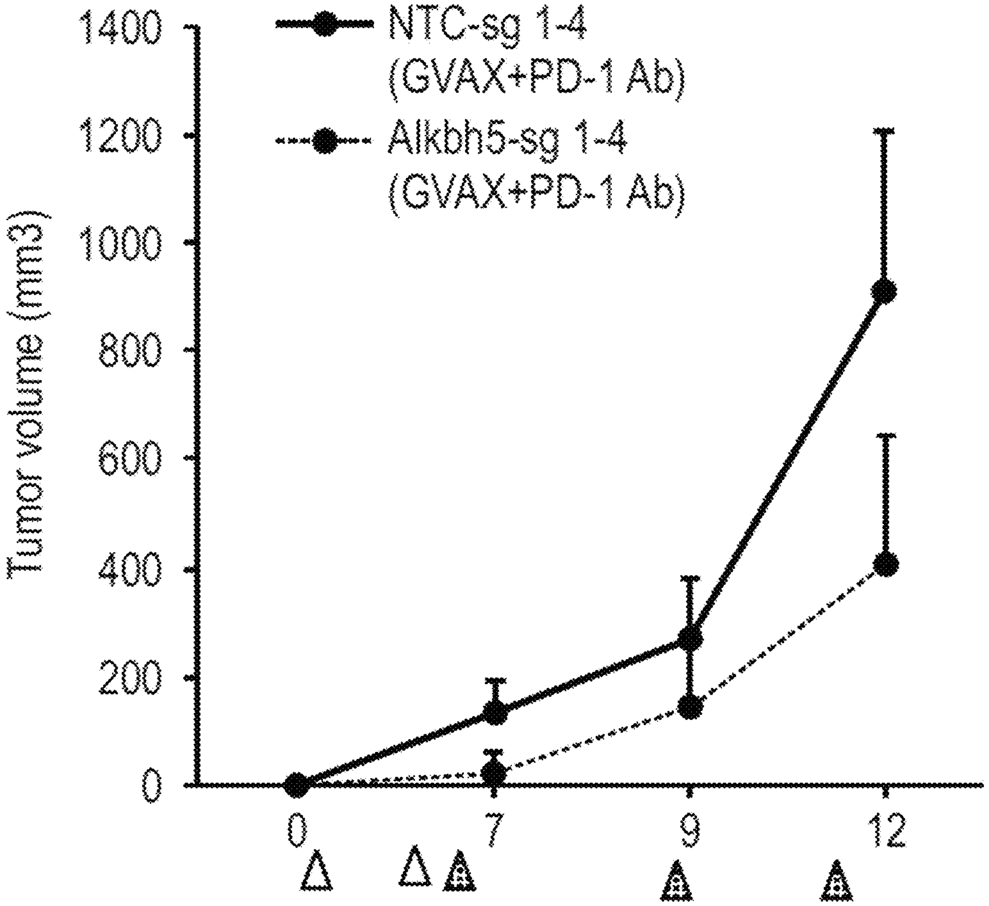
FIG. 14A-14F. Alkbh5 and Fto knockout B16 melanoma cells decreased the tumor growth rate in C57BL,'6J mice after immunotherapy.
Figure 14B:
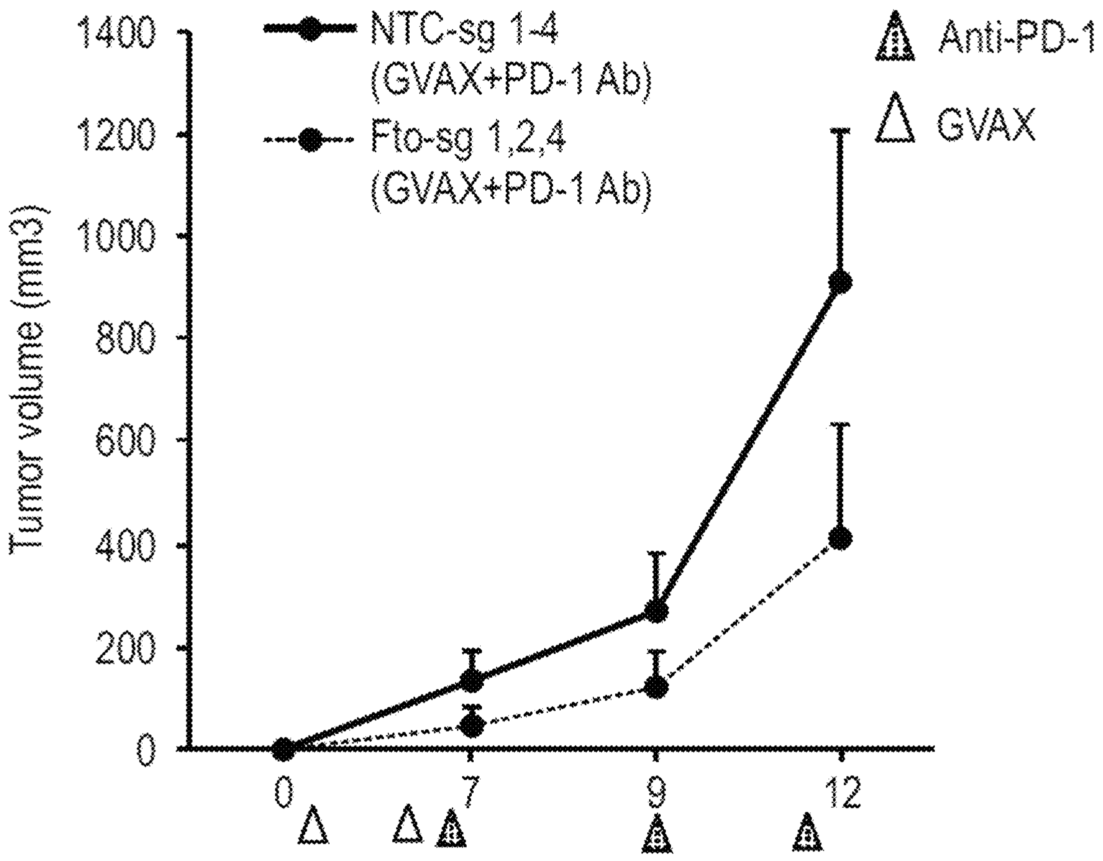
Figure 14C:
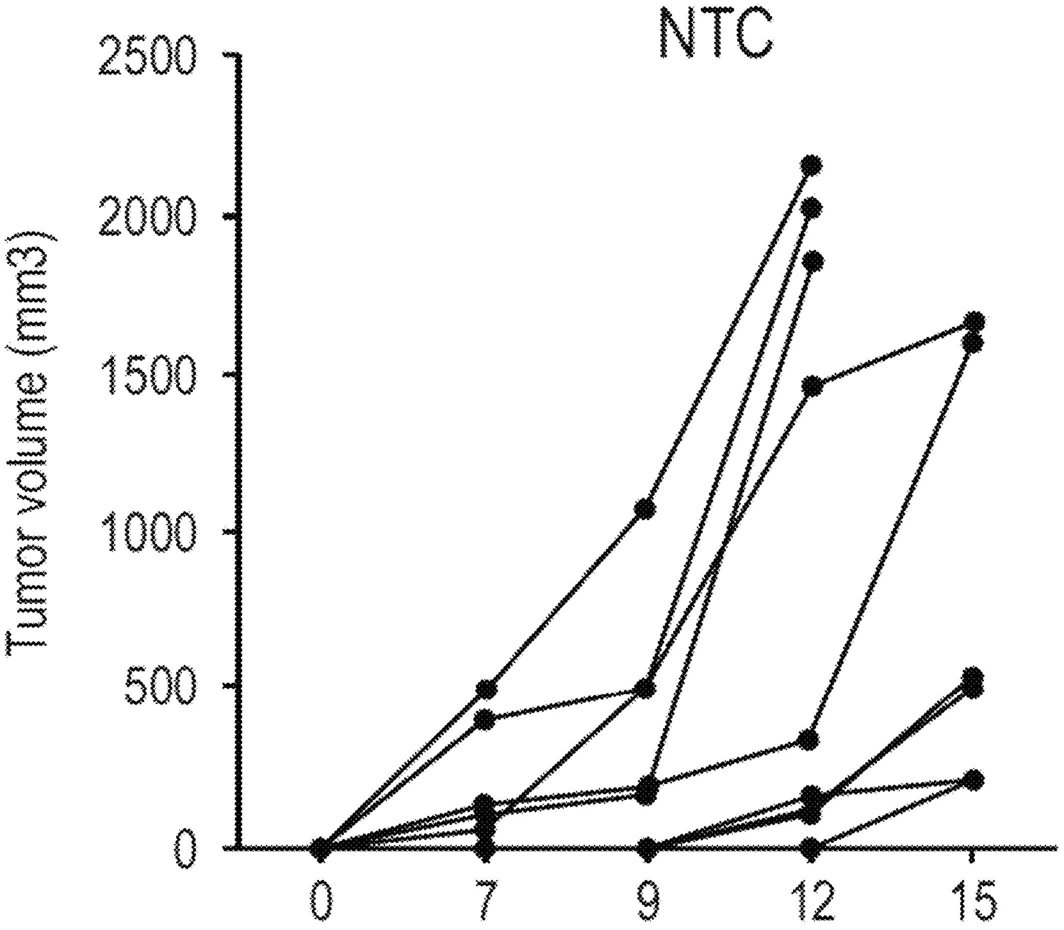
Figure 14D:
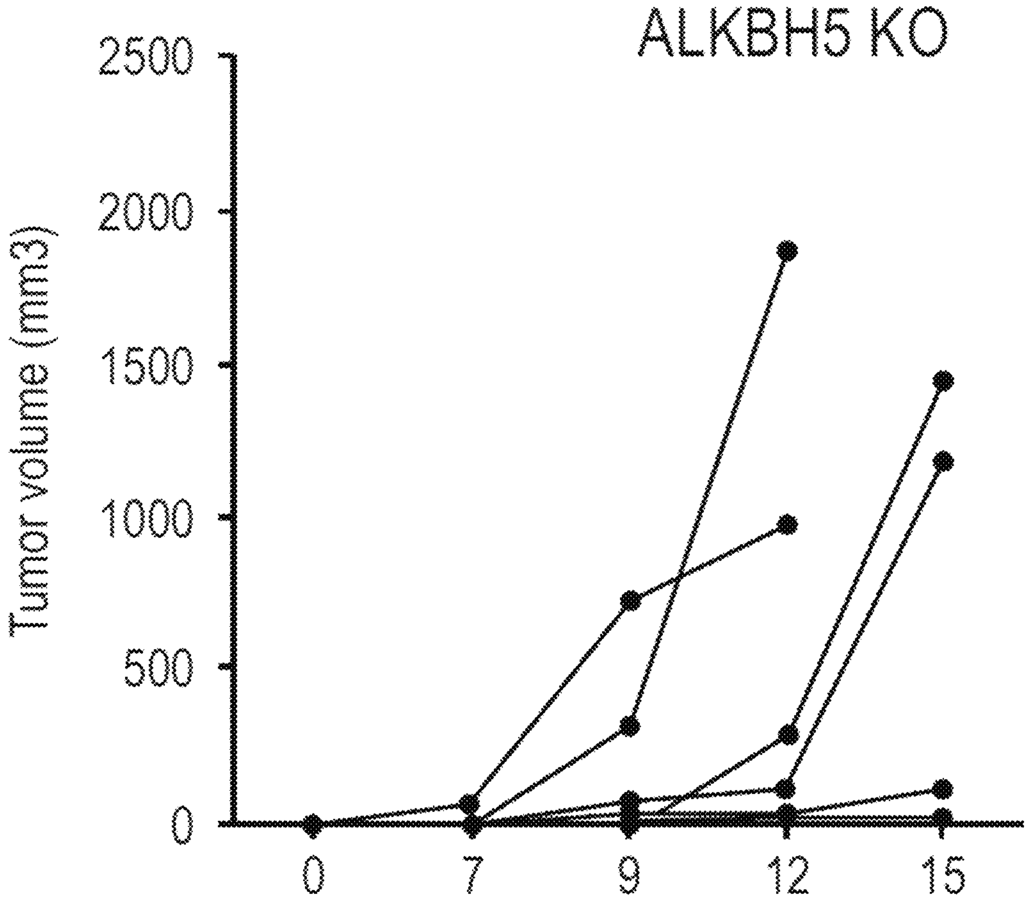
Figure 14E:
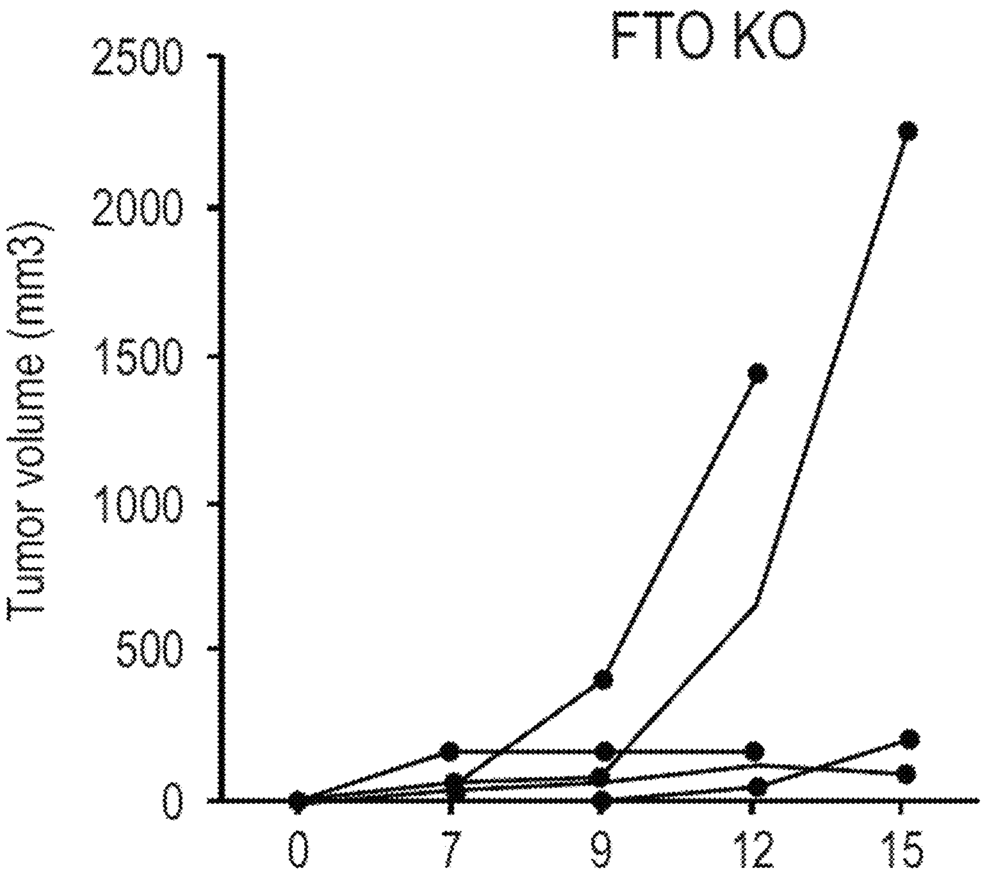
Figure 14F:
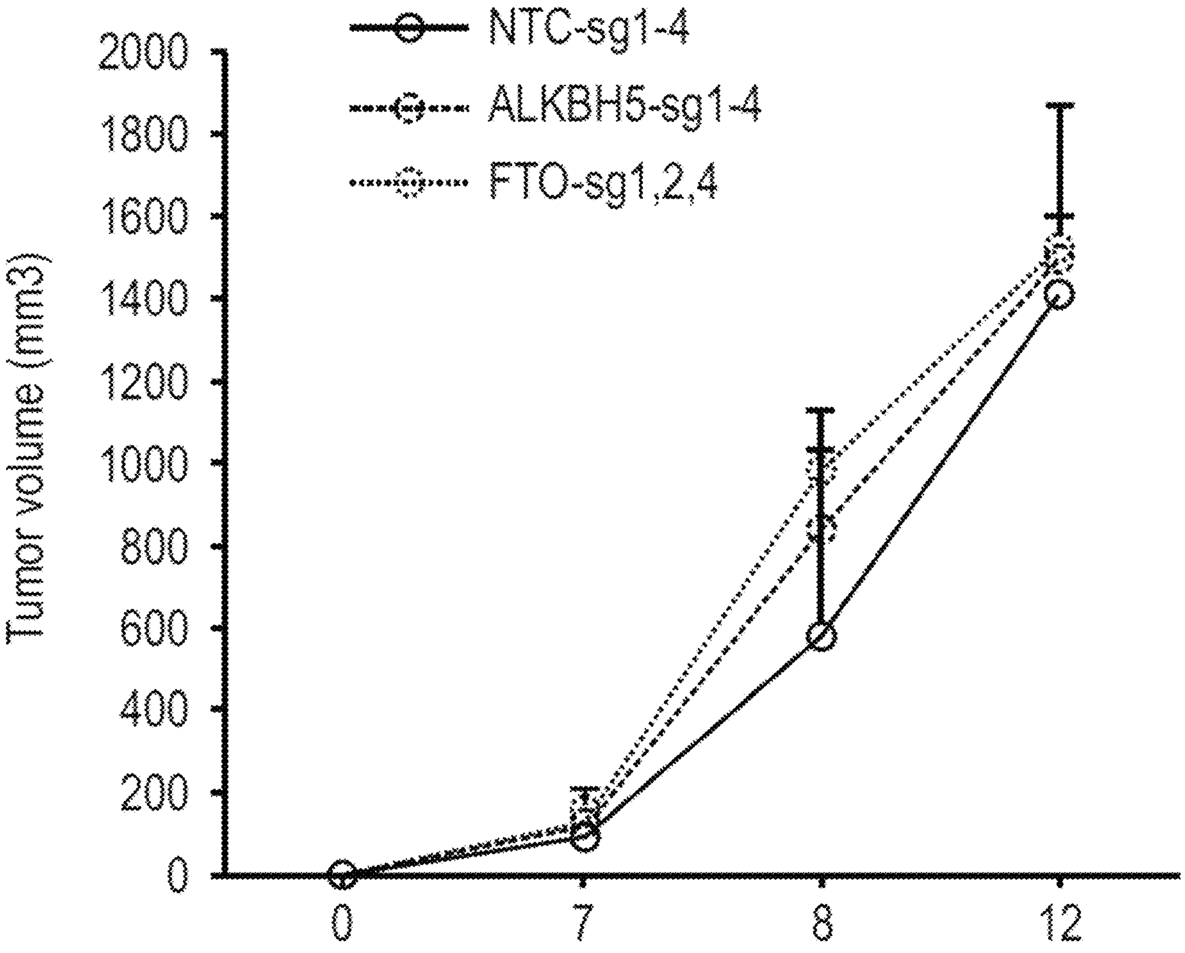
Figure 15A:
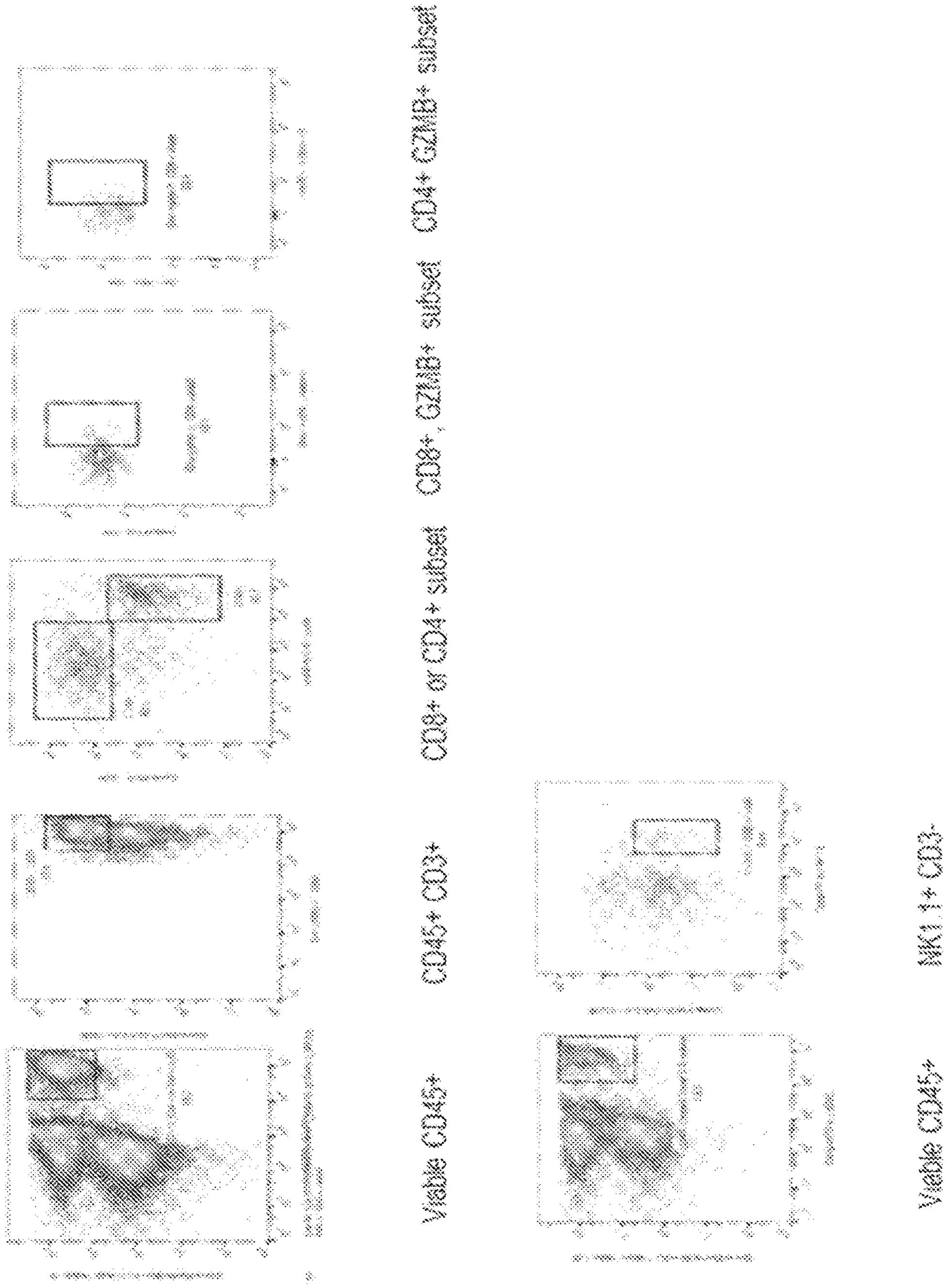
FIG. 15A-15B. Alkbh5 and Fto knockout increases cytotoxic immune cell population from mouse B16 melanoma tumor after immunotherapy with GVAX and PD-1 antibody administration, (FIG. 15A) Representative flow cytometry images for CD45+, CD4+, CD8+, NK cells, GZMB+CD4+ or GZMB+CDS* immune cells from the mouse tumor.
Figure 15B:
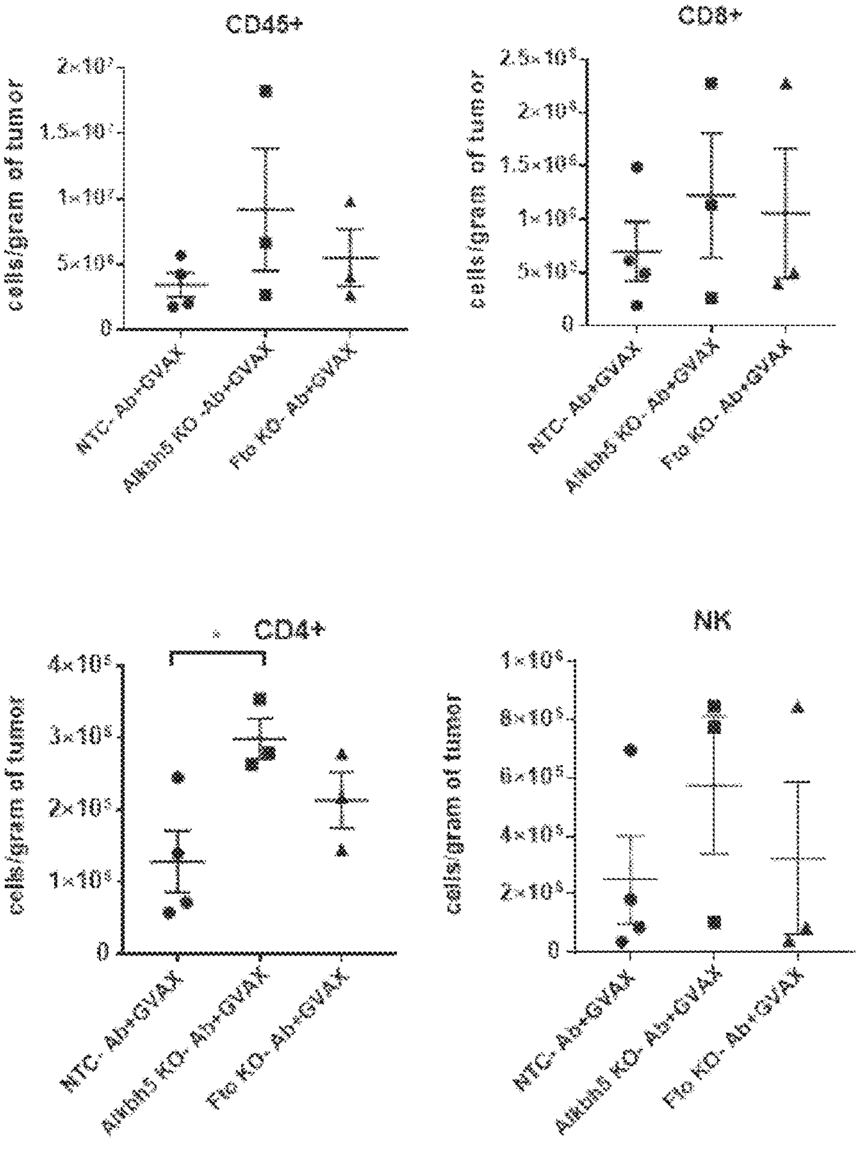
Figure 15B:
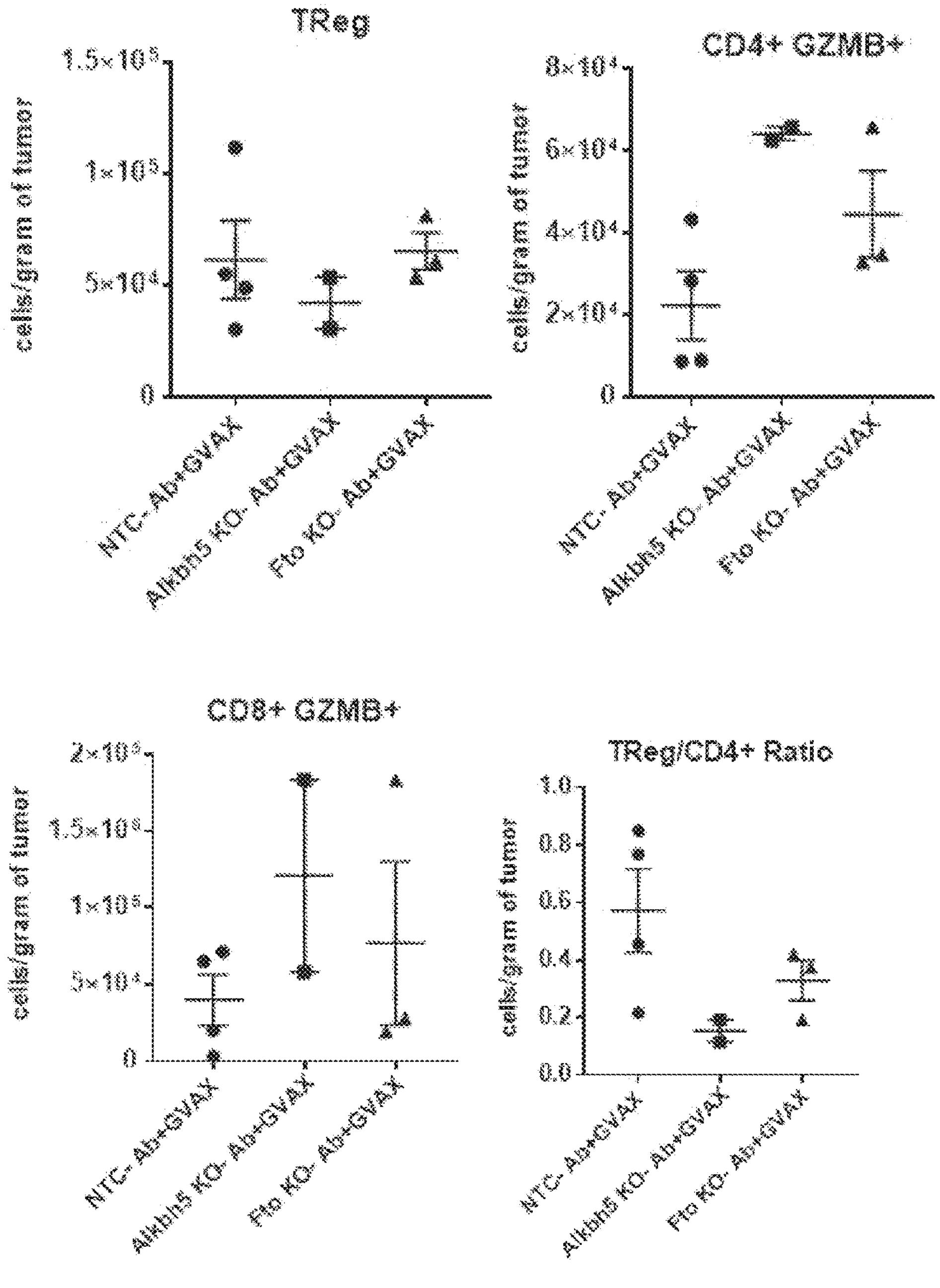
Figure 15B:
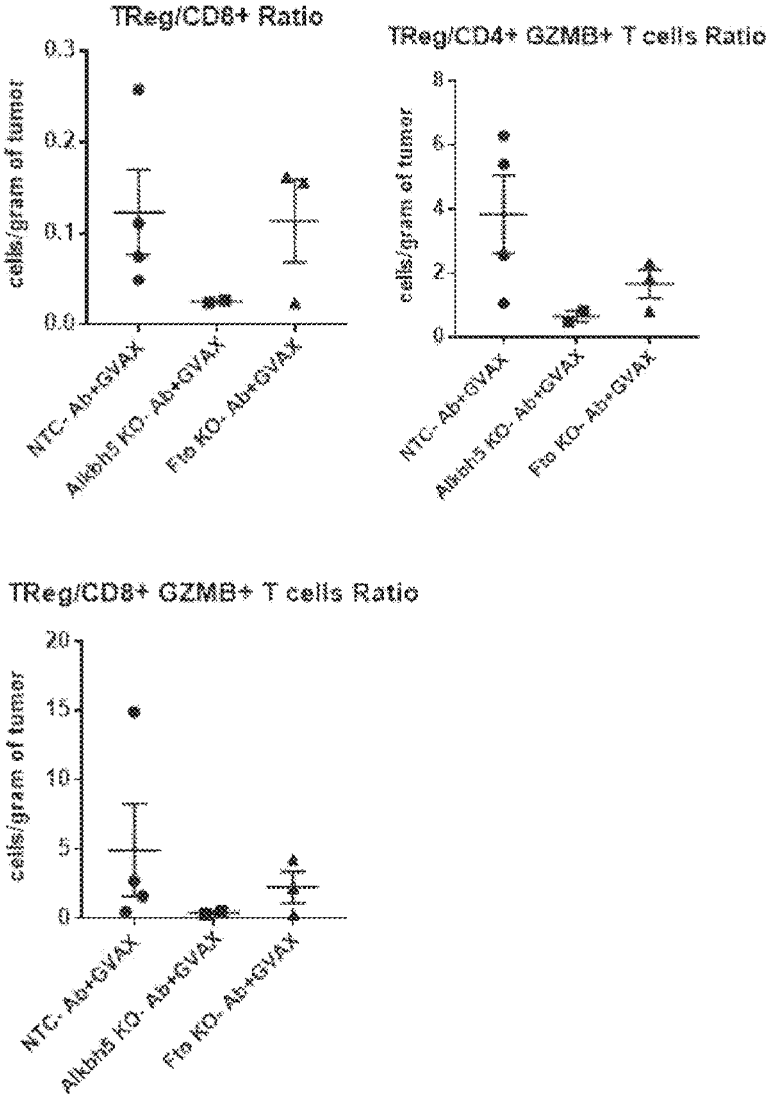

These inhibitors also have use in cancer immunotherapy treatments (e.g melanoma, NSCLC, lung kidney, colon, etc.) to increase the anti-tumor response in patients. In other words, the inhibitors potentidie the immunotherapy effects of anti-PD-1, GRAX, anti-CTLA-4, etc. Many cancer patients are refractory to the immunotherapy treatments, in fact, immunotherapy is effective in only 5%-30% of the cancer patients. In experiments, the inventor compares the effect of injecting B16 melanoma cells in mice vs injecting KO-FTO B16 melanoma cells or ALKBH5-KO B16 melanoma cells (FIG. 13A-13C) with GVAX or anti-PD-1 ab (antibodies) to treat the induced melanomas in these mice The results show that when either of the 2 demethylases are knocked-out (KO), the immunotherapy treatment in this model is more effective (tumor size is reduced, FIGS. 14A-14F). The inventor also surveyed the various immune cell subpopulations and showed a reduction in Treg numbers in mice when FTO and ALKBH5 are knocked-out. High levels of Tregs in cancer patients correlate with a lower immune response to tumors (FIGS. 15A-15B). In other words, inhibiting these two demethylases results in an enhancement of tumor immunotherapies effects, selectively killing cancer stem cells.

The most abundant modification in mammalian mRNA is the m6A modification of methyladenosine. ALKBHS is a mammalian demethylase that oxidatively reverses m6A in mRNA in vitro and in vivo, This demethylation activity of ALKBHS significantly affects mRNA export and RNA metabolism as well as the assembly of mRNA processing factors in nuclear speckles.

FTO (fat mass and obesity-associated protein) belongs to the AlkB family of nonheme (u-KG)-dependent dioxygenases, which catalyze a wide range of biological oxidations FTO is an RNA En words, both FTO and ALKBHS are demethylases that reverse the m6A modification.

Figure 16A:
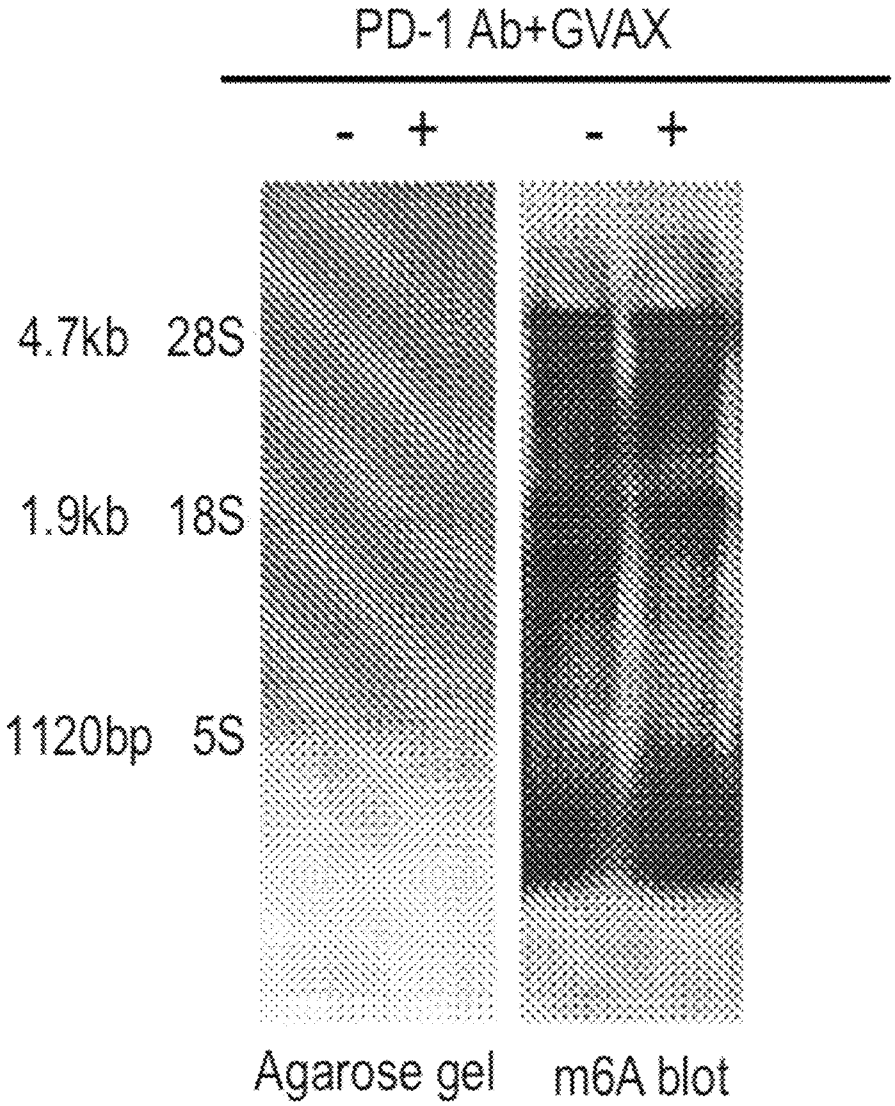
FIG. 16A-16B. Alkbh5 and Flo knockout increases m6A levels in mouse BIO melanoma tumor after immunotherapy with GVAX and PDI antibody treatment.
Figure 16B:
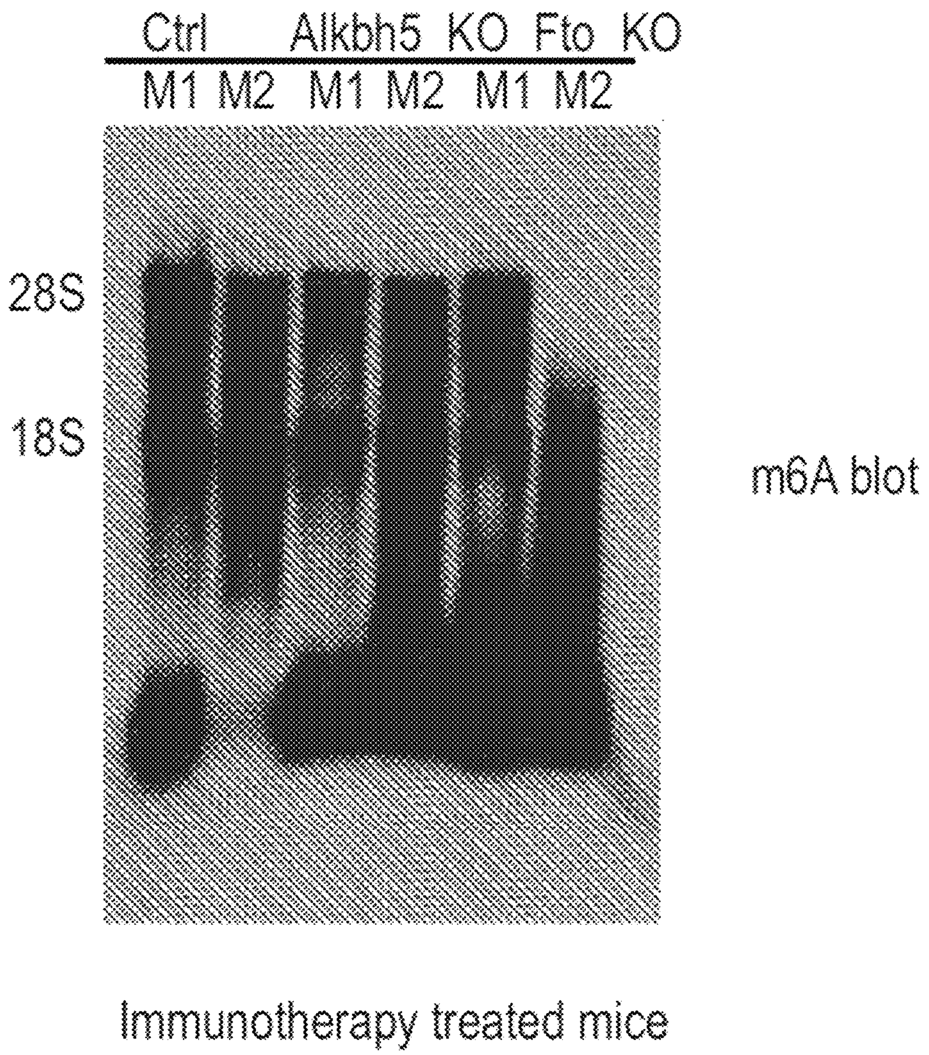

Both FTO and ALKBHS may be inhibited using small molecules, shRNA, antisense nucleic acids, siRNA, miRNA, or CRISPR-sgRNA strategies ALKBH5 and FTC) knockout increases m6A levels in mouse B16 melanoma tumor after immunotherapy with and PD-1 antibody treatment (FIGS. 16A-16B).

Example B3: Broad Spectrum Anti-Cancer Compounds Targeting Epitranscriptomics Machinery: Mettl3/14, ALKBH5, FTO, YTHDF1, YTHDF2, and YTHDF3

Epitranscriptomics is an emerging field that seeks to identify and understand chemical modifications in RNA; the enzymes that deposit remove, and interpret the modifications (writers, erasers, and readers, respectively); and their effects on gene expression via regulation of RNA metabolism, function, and localization[2,3]. N6-methy/adenosine (m6A) is the most prevalent RNA modification in many specks, including mammals. In eukaryotic mRNAs, m6A is abundant in 5'-UTR, 3'-UTRs, and stop codons.[4-6] The m6A modification is catalyzed by a large RNA methyltransferase complex composed of catalytic subunits (METTL3 and METTL14), a splicing factor (WTAP), a novel protein (KIAA1429), and other as yet unidentified proteins. Conversely, removal of m6A is catalyzed by the RNA demethylases EFO and ALKBH5. In addition, FTO demethylases NO,2'-O-dimethyladenosine (m6Am) to reduce the stability of target mRNAs and snRNA biogenesis The m6A RNA reader proteins, YTH domain containing proteins, e.g., YTHDF1, YTHDF2, and YTHDF3, specifically bind modified RNA and mediate its effects on RNA stability and translation.[11,12]

In addition to the physiological roles of m6A in regulating RNA metabolism in such crucial processes as stem cell differentiation, circadian rhythms, spermatogenesis, and the stress response increasing evidence supports a pathological role for perturbed m5A metabolism in several disease states. For example, recent studies have shown that the m6A Status Of mRNA is involved in the regulation of T cell homeostasis[14], viral infections[15], and cancer[16-21]. Here we describe inhibitors for key components of the epitranscriptomics machinery including ALKBH5, FTO, Mettl3/14, and YTHDF1, YTHDF2, and YTHDF3 proteins. These inhibitors caused killing of various cancers as described.

Glioblastoma multiforme (GBM) is the deadliest brain tumor identified in both adults and children, with an average life expectancy of 15 months. GBM is characterized by high rates of both metastasis and recurrence and often resistant to treatment with radiation and chemotherapy. These characteristics have been attributed to the presence of undifferentiated glioblastoma stem-like tumor initiating cells (GSCs). Recent studies have shown that cells depleted in M-methyladenosine (m6A) RNA modifications are resistant to differentiation, and suspected that misregulation of the reversible m6A pathway may play a role in generating tumor-initiating cells and promoting tumorigenesis. In GSCs, knockdown of the m6A demethylases FTO and its homolog alkylation repair homolog protein 5 (ALKBH5) suppresses GSC-induced tumorigenesis and FTO inhibition prolongs lifespan in tumor bearing mice, indicating FTO could be a mechanism for targeting GSCS directly.

By targeting ETO and the m6A modification pathway, we expect to target differentiation pathways directly, allowing us to directly impact GSCs. Previous reports with existing FTO inhibitors have already demonstrated ETO to be an effective target for GSCs in cells and in xenograft models[13]. However, the modest potency and poor pharmacokinetic properties of these inhibitors represents a significant and unaddressed barrier towards developing FTO as GBM therapeutics. Our strategy of expanding the chemical diversity of FTO inhibitors while also integrating consideration of physicochemical properties during all stages of development will significantly progress the development of new GSC-targeting therapeutics for GBM.

After the identification of FTO as an m6A demethylase in 2011, its role in tumorigenesis and poor of multiple cancers, including GBM and acute myeloid leukemia (AML), has gained widespread interest This interest has led to the of several small molecule inhibitors including rhein, which binds FTO and its homolog ALKBH5 indiscriminately, and meclofenarnic acid (MFA). As MFA was identified to increase m6A levels in cells by inhibiting FTO preferentially over ALKBH5, a variety of derivative small-molecule inhibitors were inspired by this structure. One such derivative was recently determined to suppress the proliferation of human-derived AML cell lines in xeno-transplanted mice, validating FTO as a druggable cancer target. However, the cellular efficacy of these analogs is modest and their use in vivo is by poor ADME and PK profiles. To progress the development of FTO inhibitors as anticancer therapeutics, it is essential to identify chemically diverse inhibitors with improved cellular efficacy and physicochemical properties.

We developed high throughput in vitro inflyorescence-based assay that utilized synthetic methylated RNA substrate that can bind the fluorophore DFHB1-lT once demethylated, producing an easily readable fluorescent signal. This assay has been validated for both FTO and ALKBH5, and has used determine $IC_{50}$s of small molecule inhibitors, including MFA, against bath proteins with high Z-factors (>70). The development of this assay has opened the possibility of high throughput in vitro screening of a much higher volume of compounds than has previously been possible. When combined with in silico screening techniques, this assay can now allow for the first high volume screen of chemically diverse FTO inhibitors, allowing identification of new pharmacophores with better potential therapeutic lead development. Our strategy is to combine high throughput virtual screening with this new high throughout in vitro biochemical assay to rapidly a large, diverse set of compounds identify unique FTO inhibitors with physicochemical properties better suited to drug development.

Figure 17A:
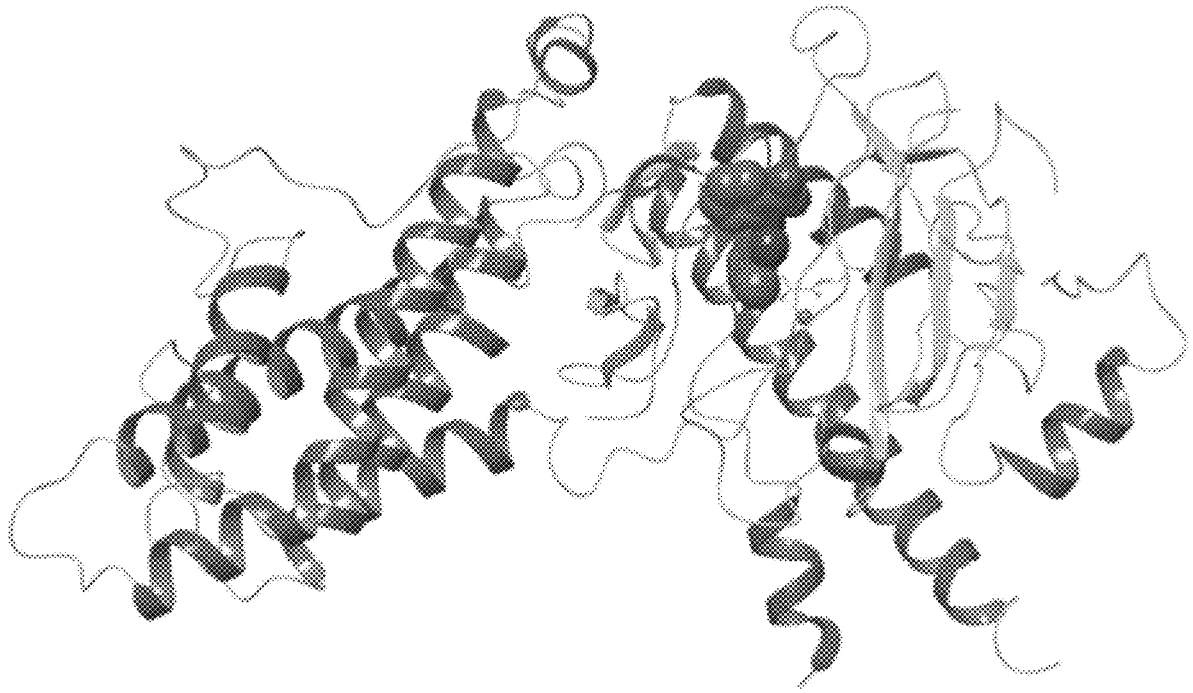
FIG. 17A-17B. Depiction of X-ray crystal structure of human FTO in complex with meclofenamic acid (MFA). The docking site for in silico screening is shown in spheres and surface representation of human FTP in complex with MFA.
Figure 17B:
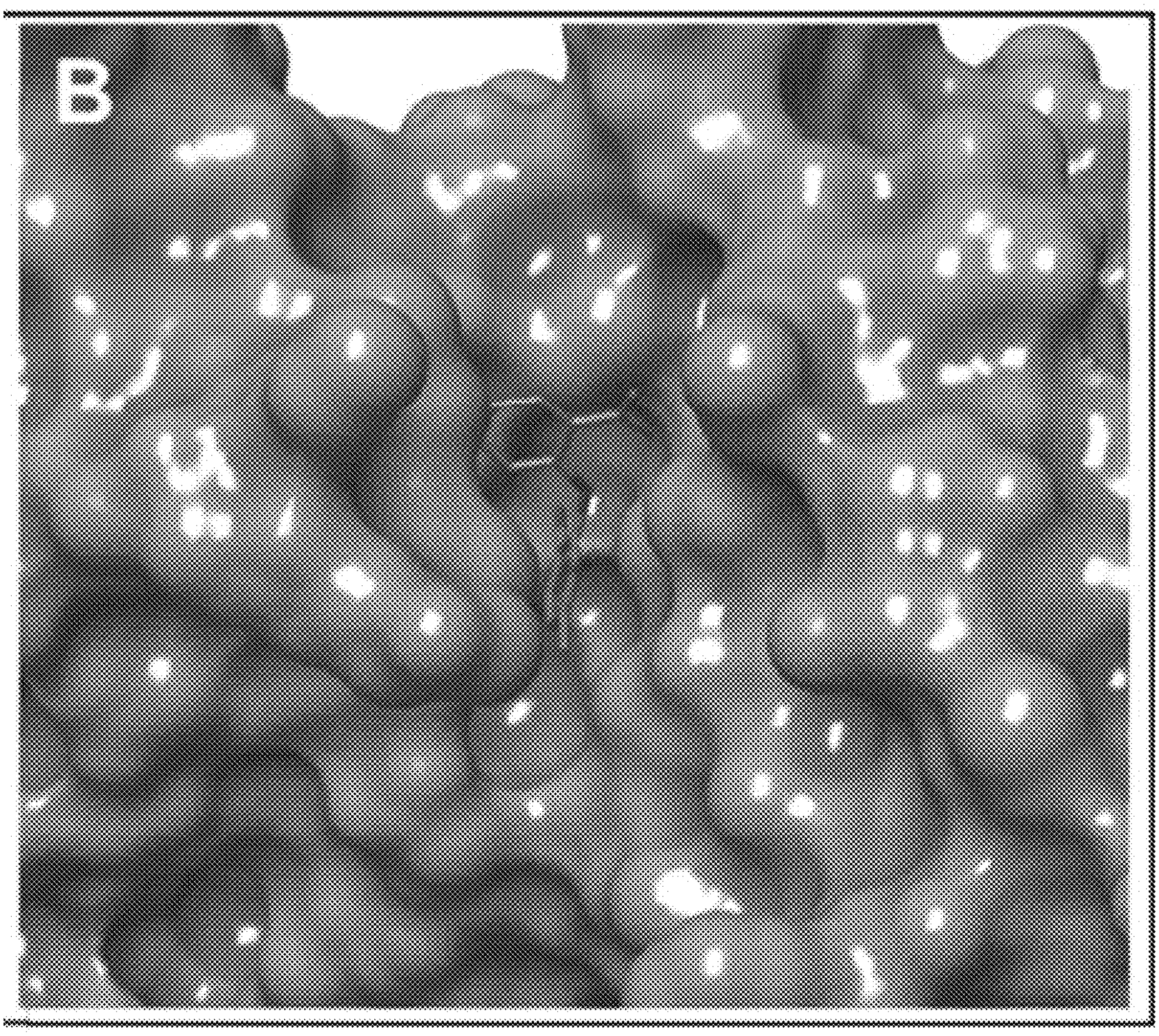

High throughput virtual screening (HTVS) of the ZINC database will be conducted with the molecular modeling program Schrödinger to identify potential inhibitors of FTO. In silico modeling is particularly advantageous approach in this context, as there are few known FTO inhibitors with only moderate in vitro $IC_{50}$s and poor pharmacokinetic profiles. The ZINC is a diverse library of approximately 350,000 small molecules and fragments maintained by the University of California: San Francisco for the purpose of high throughput in silico screening. Screening the ZINC database will increase the chances of developing potent FTO inhibitors with more favorable pharmacokinetic properties by increasing the chemical diversity of the inhibitors being tested experimentally. Screening will target a 5 cubic binding pocket near the alpha-ketoglutarate binding site of FTO (FIG. 17). Several small molecules, such as MFA, have been identified to bind to this site and selectively inhibit demethylation by FTO over the homologue RNA demethylase ALKBH5. Targeting this site will facilitate the development of inhibitors that are selective towards FTO. During the in silico screen, a range of physicochemical properties will be calculated, including measures of lipophilicity (c log P), membrane permeability (Caco-2 and MDCK model diffusion rates), and solubility (polar surface area). There is extensive literature supporting the importance of these properties in identifying leads which are more likely to feature favorable pharmacokinetic profiles, and calculating these parameters the early hit identification stage will allow for selection of leads which are more likely to show improved PK and therefore improved therapeutic potential over existing FTO inhibitors. Initial screening against FTO has identified 30 chemically distinct hits with favorable physicochemical properties for lead development.

Figure 18A:
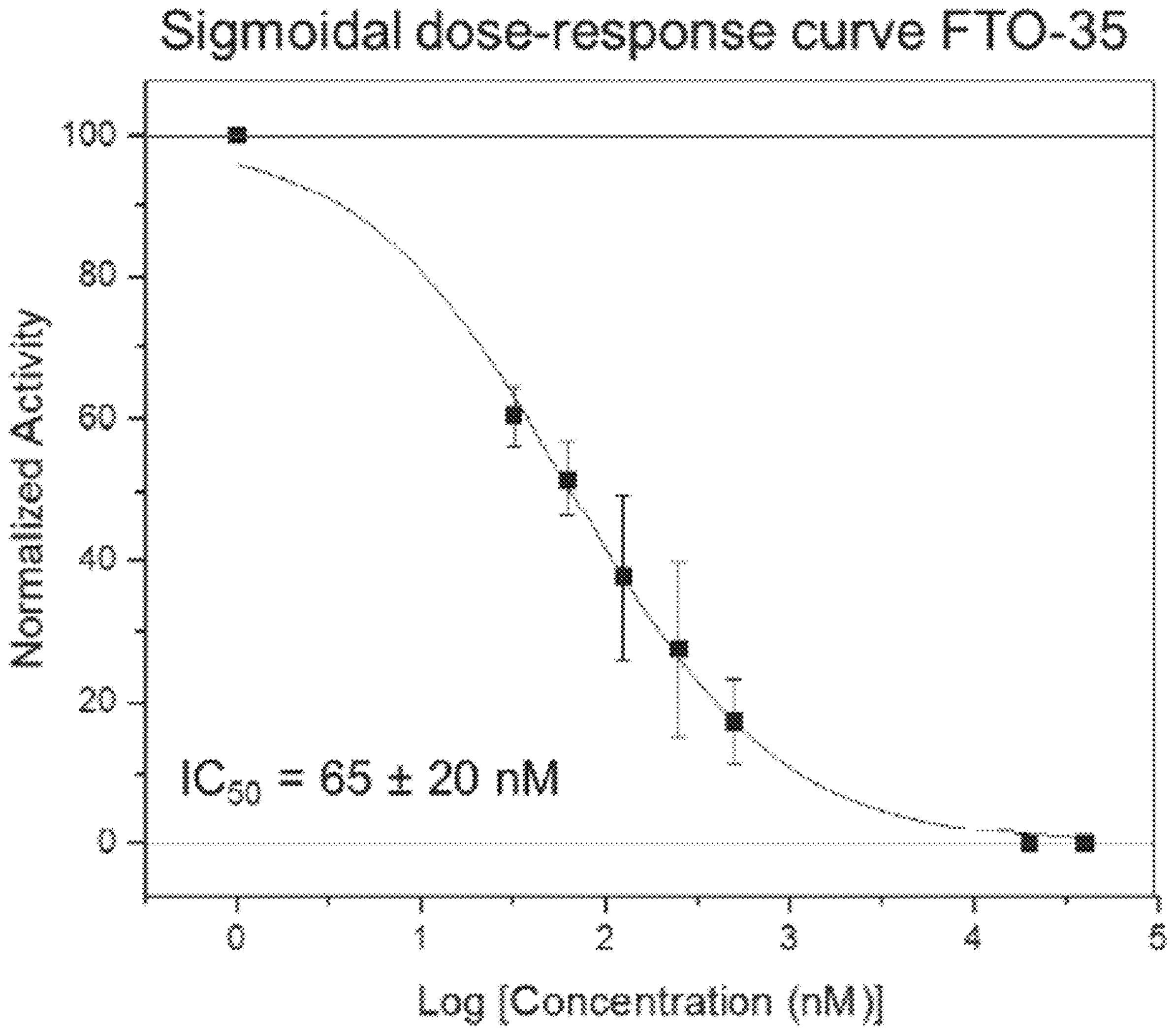
FIG. 18A-18B. Sigmoidal dose-response curve for FTO-35 against FTO and ligand trajectory map. Lipophilic ligand efficiency (LLE) is determined for each compound according to lipophilicity (log D) and enzymatic activity. Compounds with an LLE above 30 are considered promising. Compounds are binned by expected membrane permeability.
Figure 18B:
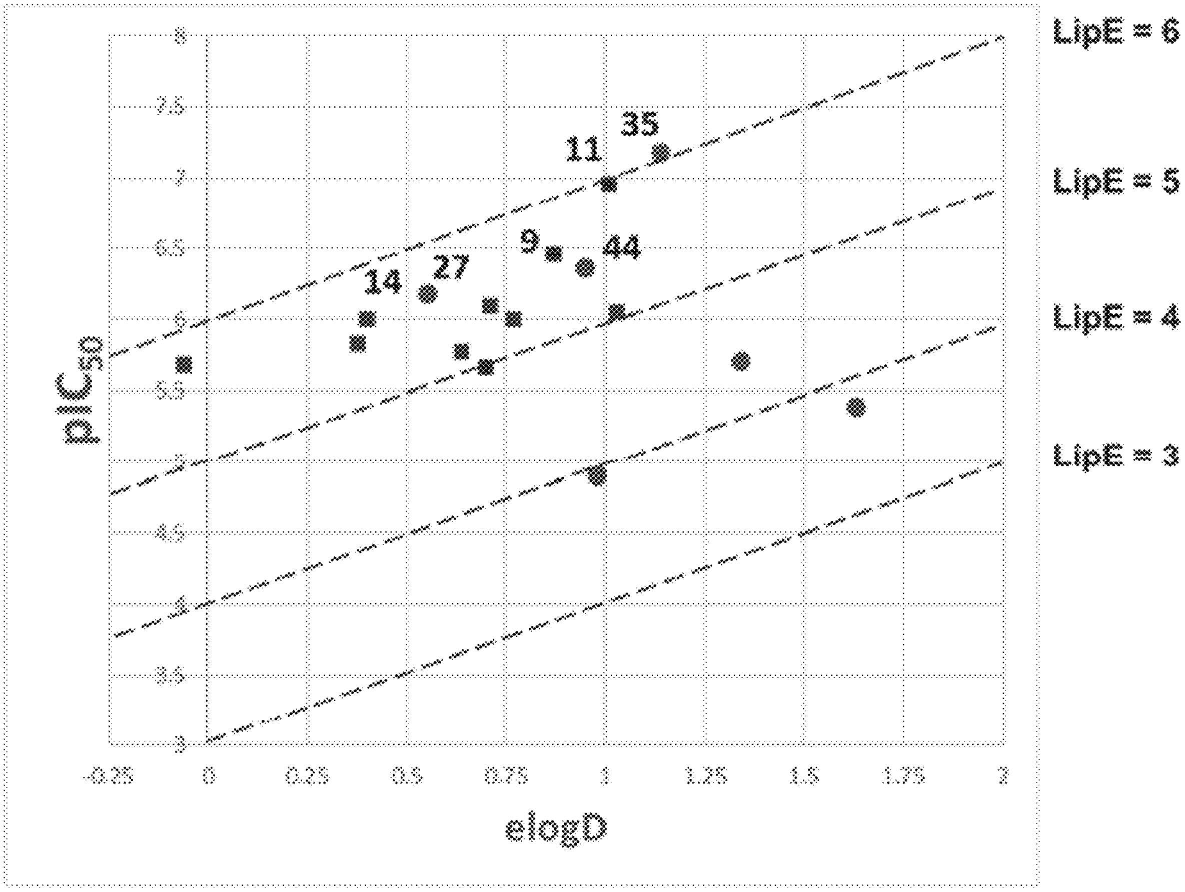
Figure 19:
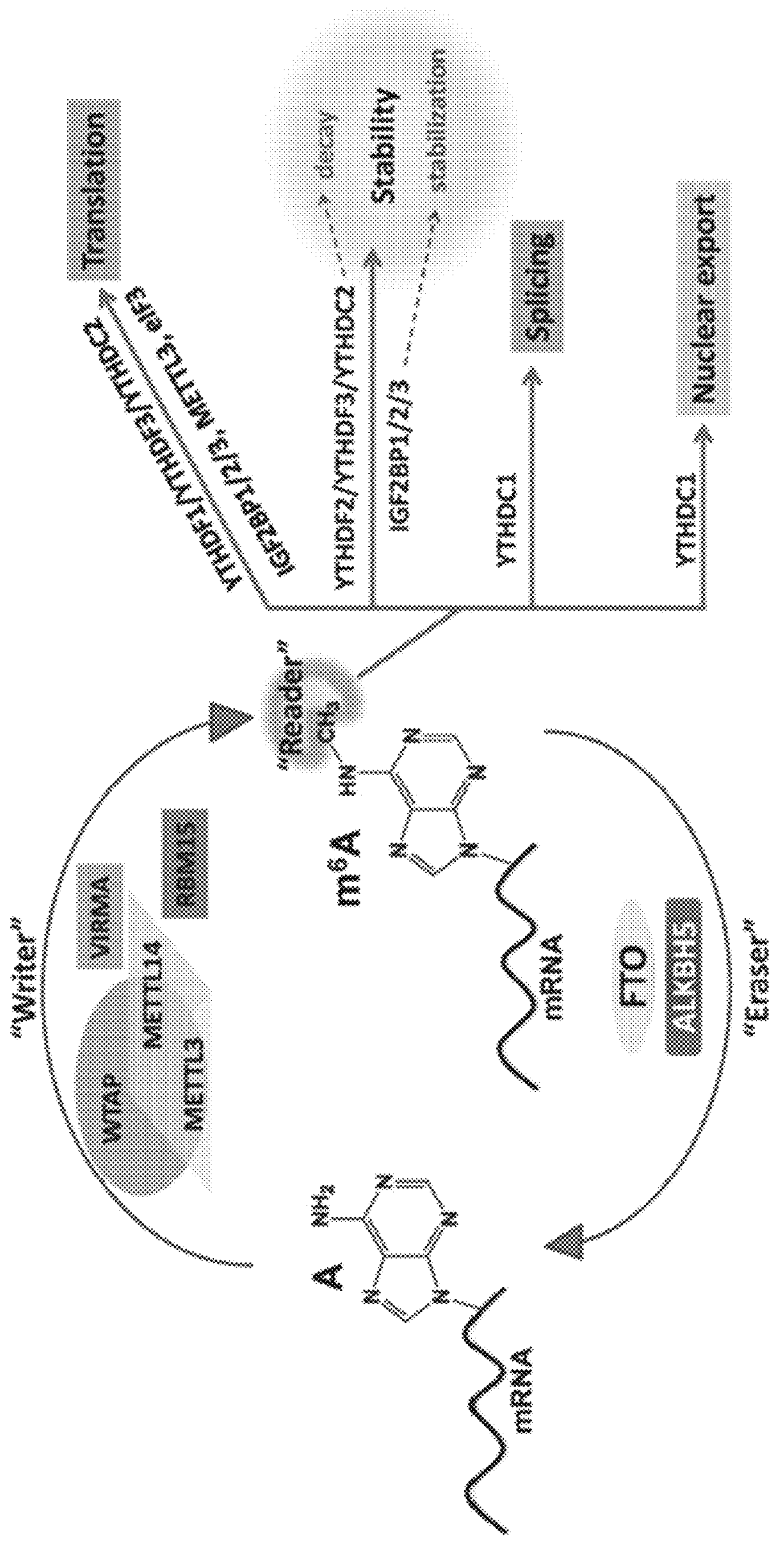
FIG. 19. Depiction of m6A mRNA modification.
Figure 20:
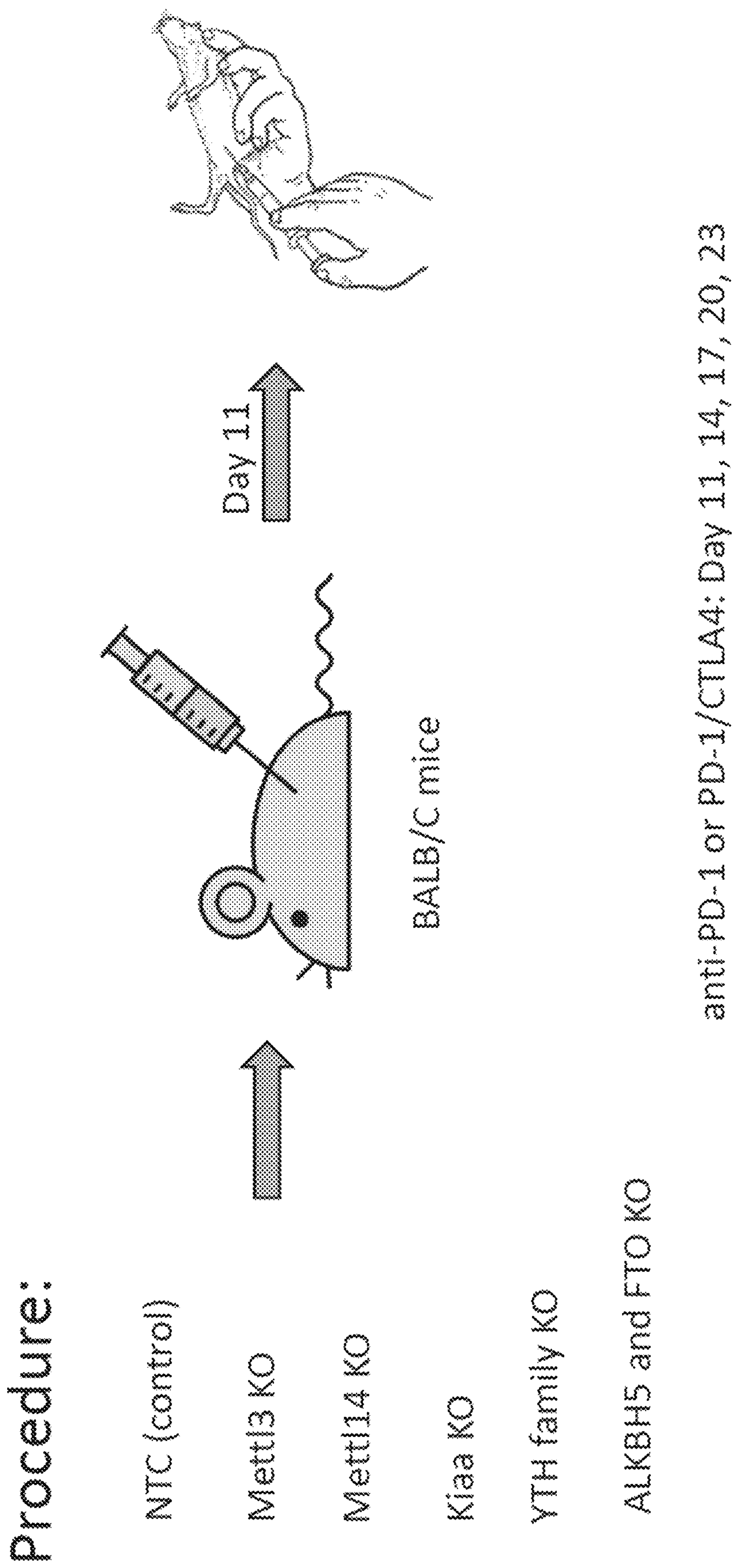
FIG. 20. Depiction of In Vivo immunotherapy procedure.
Figure 21:
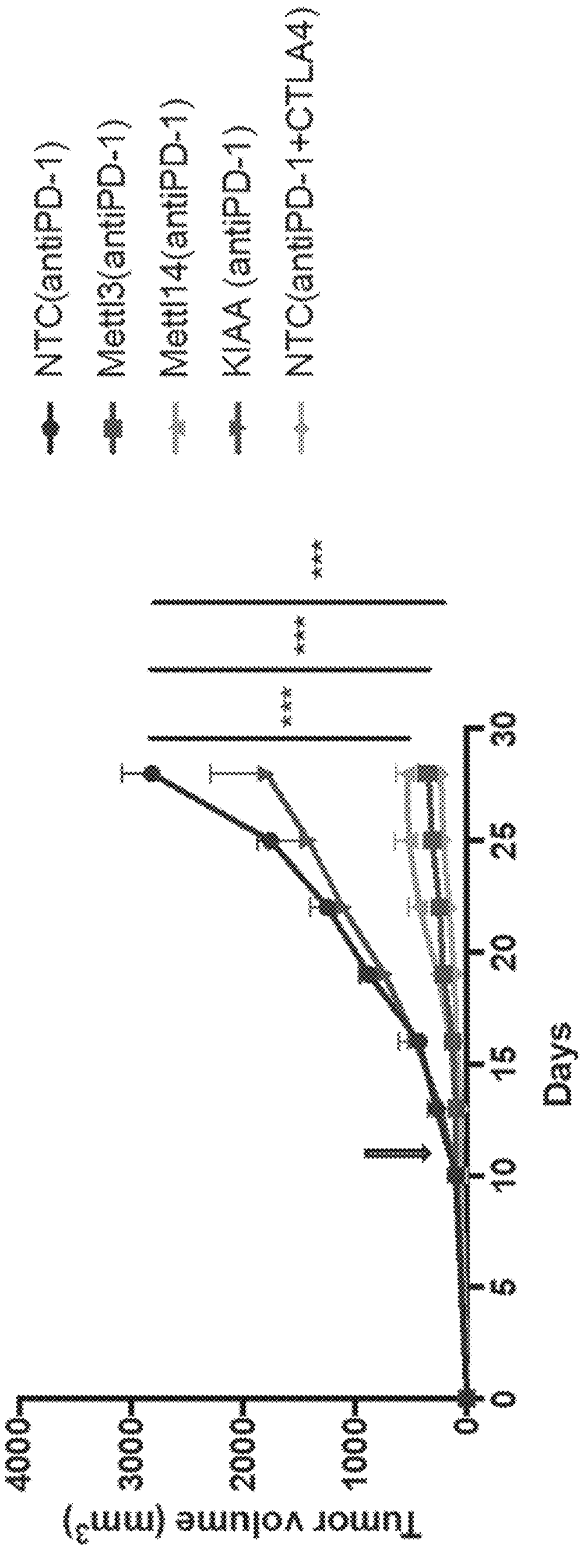
FIG. 21. Depiction of data associated with loss of Mettl3/14 sensitizing tumors to PD-1 checkpoint blockage: colon cancer.
Figure 22:
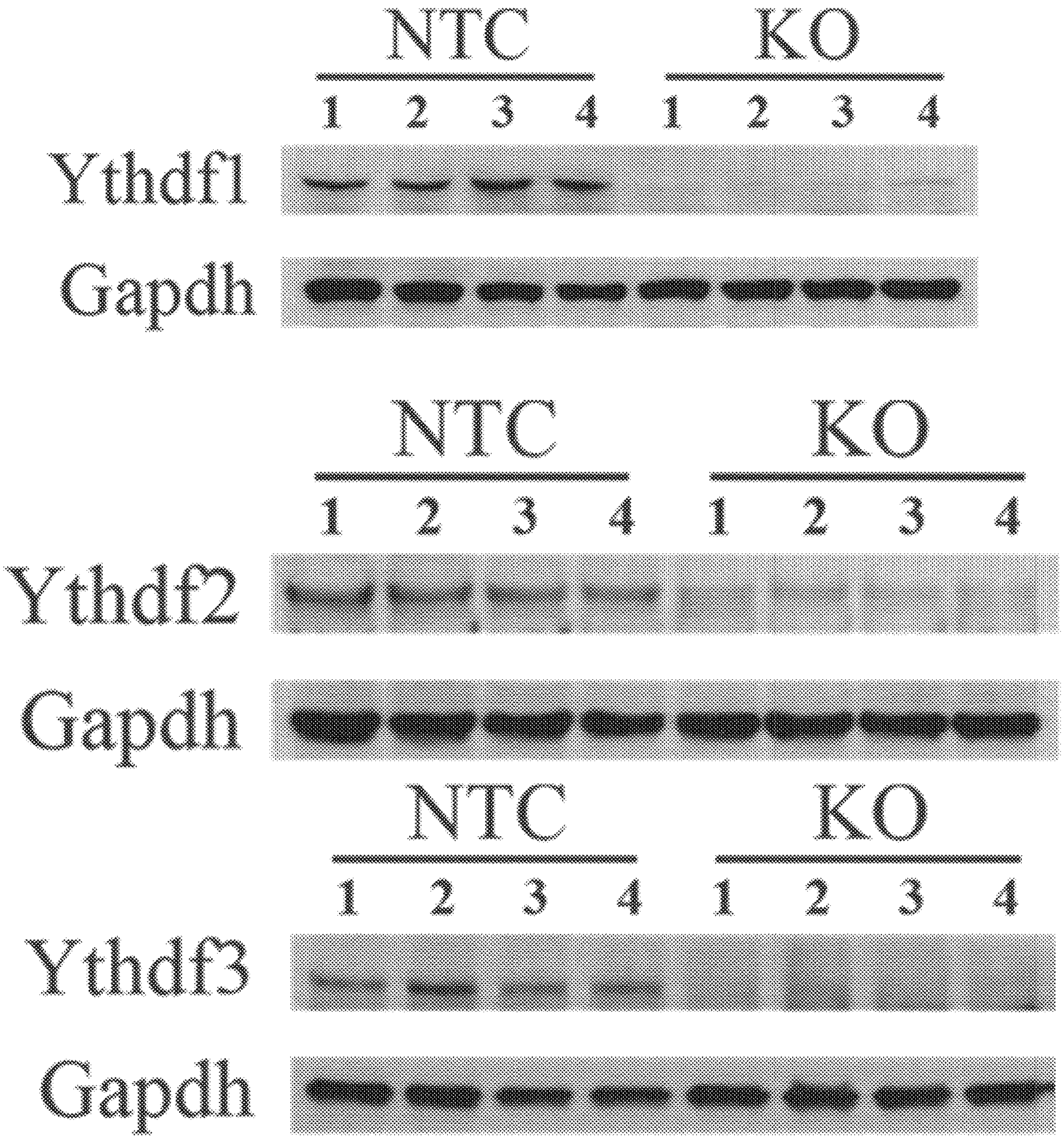
FIG. 22. Depiction of impact of loss of YTH on tumors during PD-1 checkpoint blockage.
Figure 22:
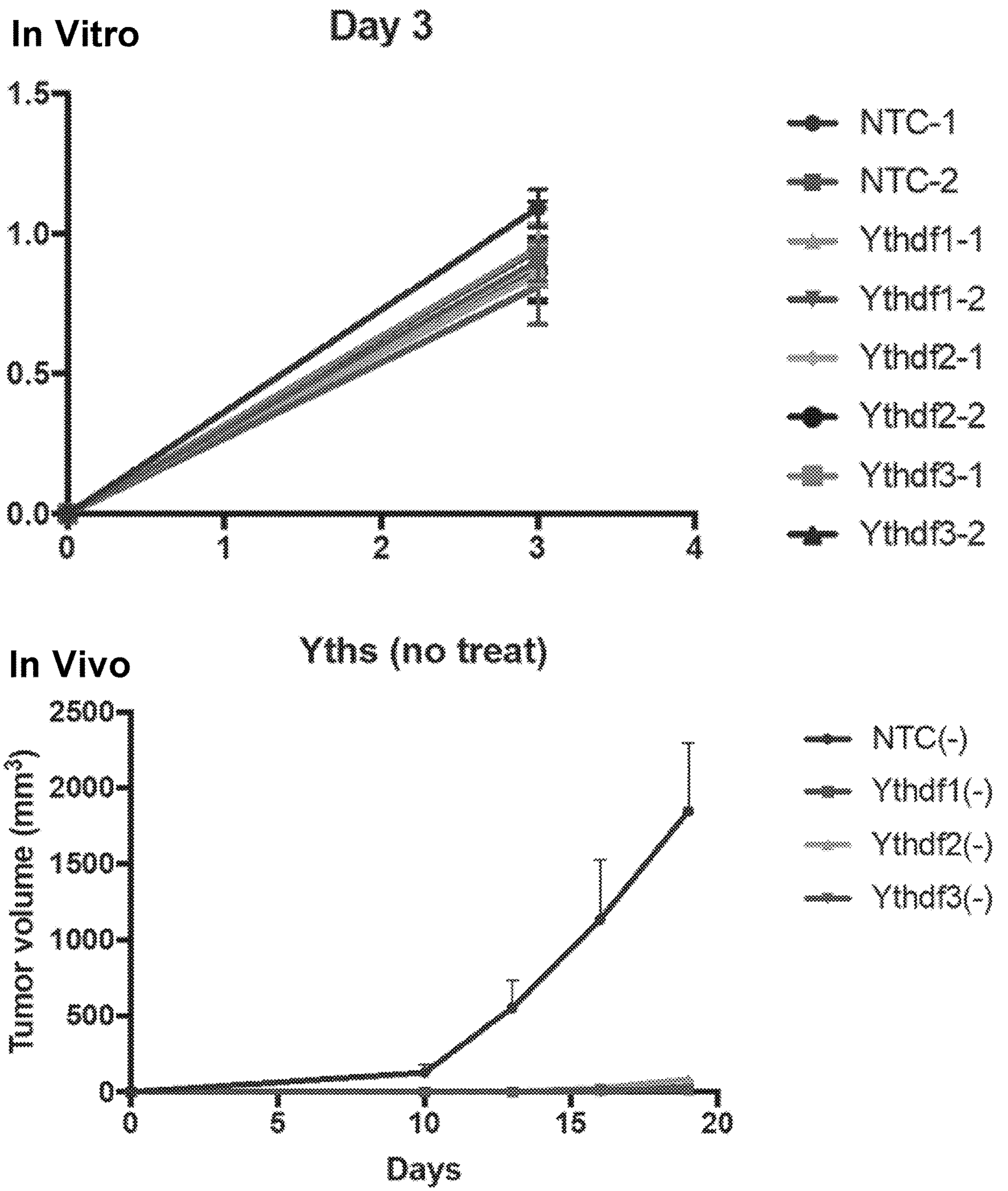
Figure 23:
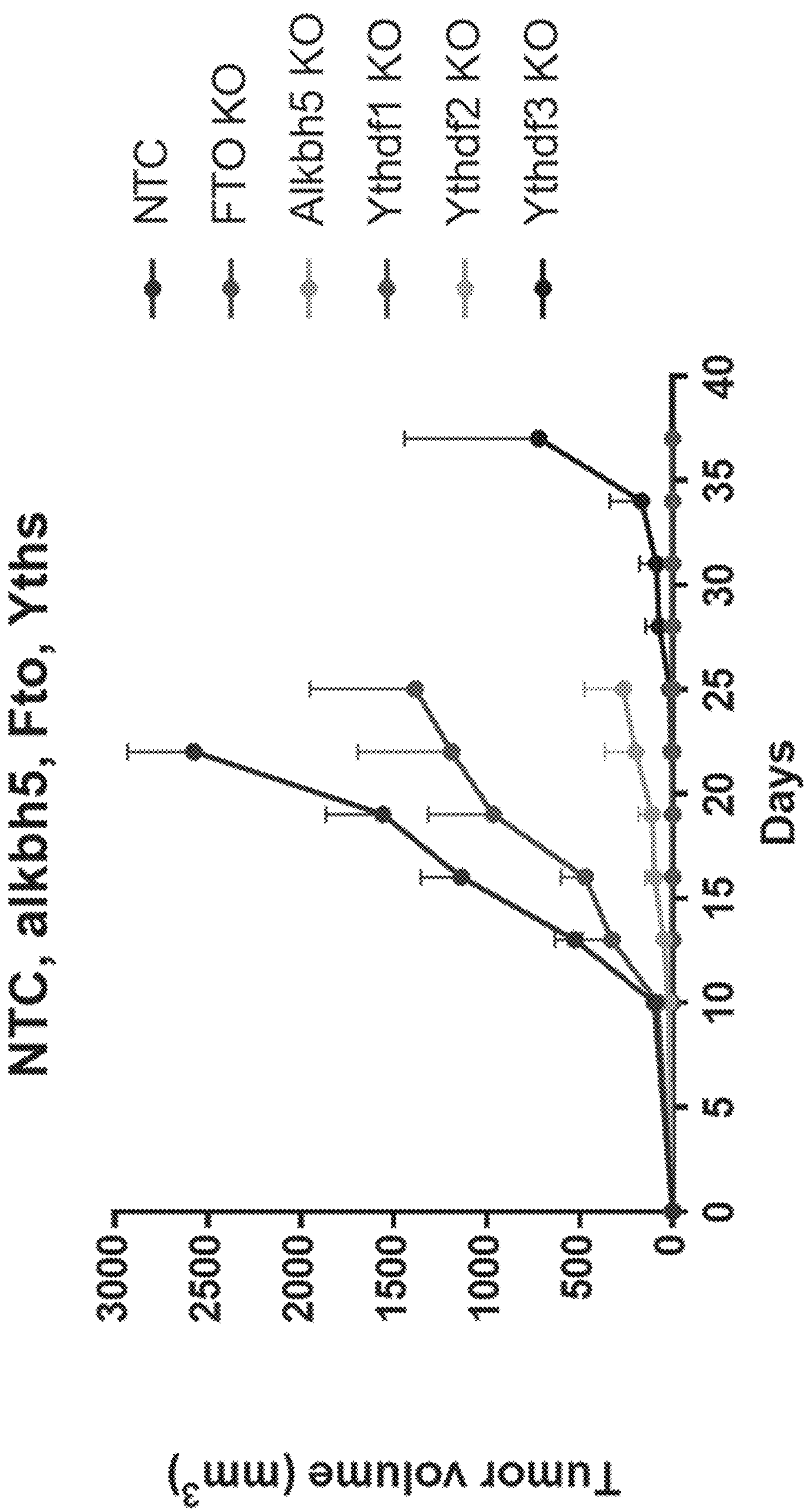
FIG. 23. Depiction of impact of loss of YTH on tumors during PD-1 checkpoint blockage.
Figure 24:
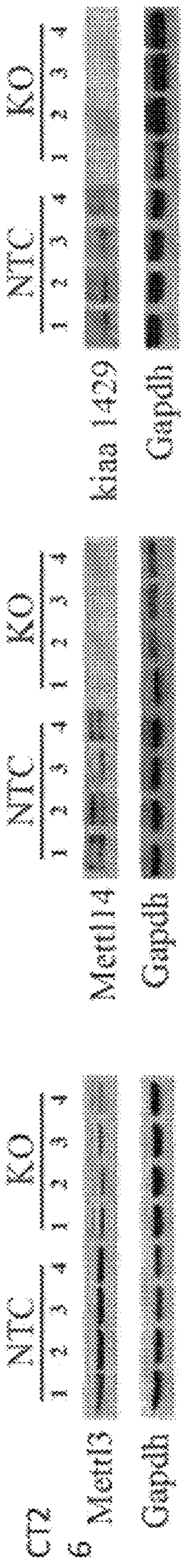
FIG. 24. Depiction of loss of Mettl3/14 on tumors during PD-1 checkpoint blockage.
Figure 24:
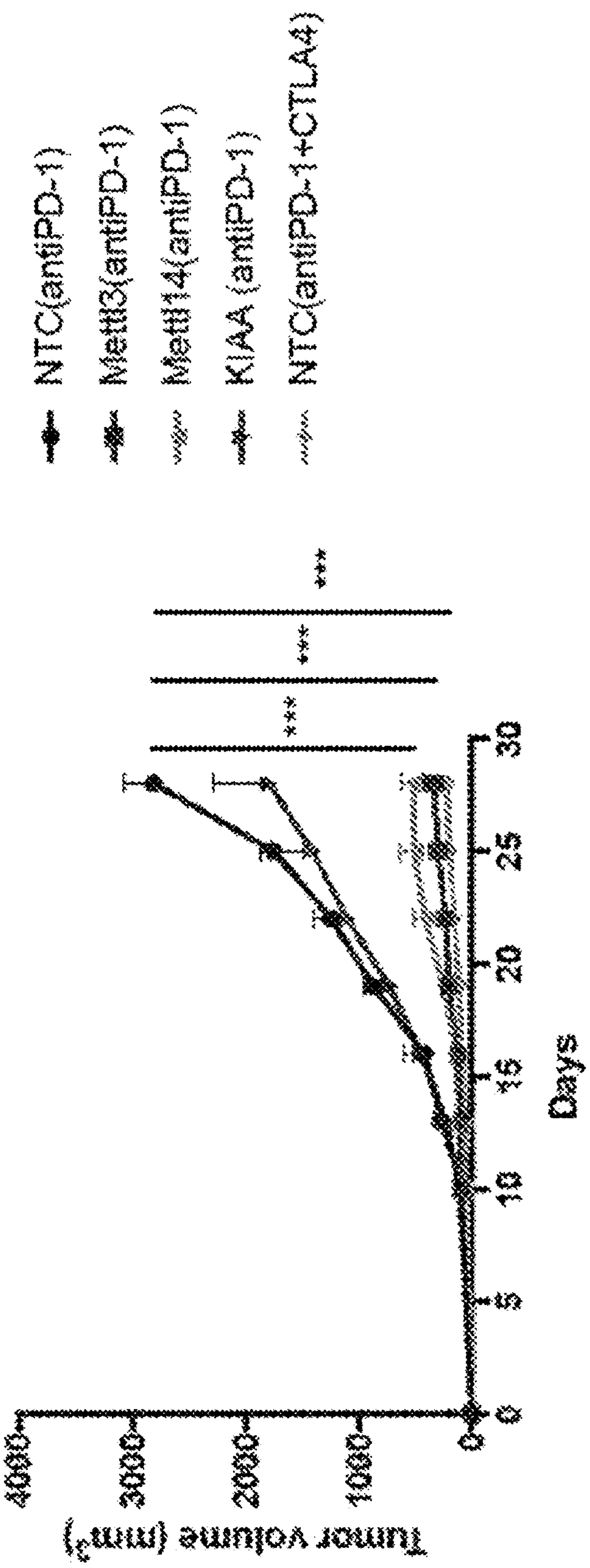
Figure 24:
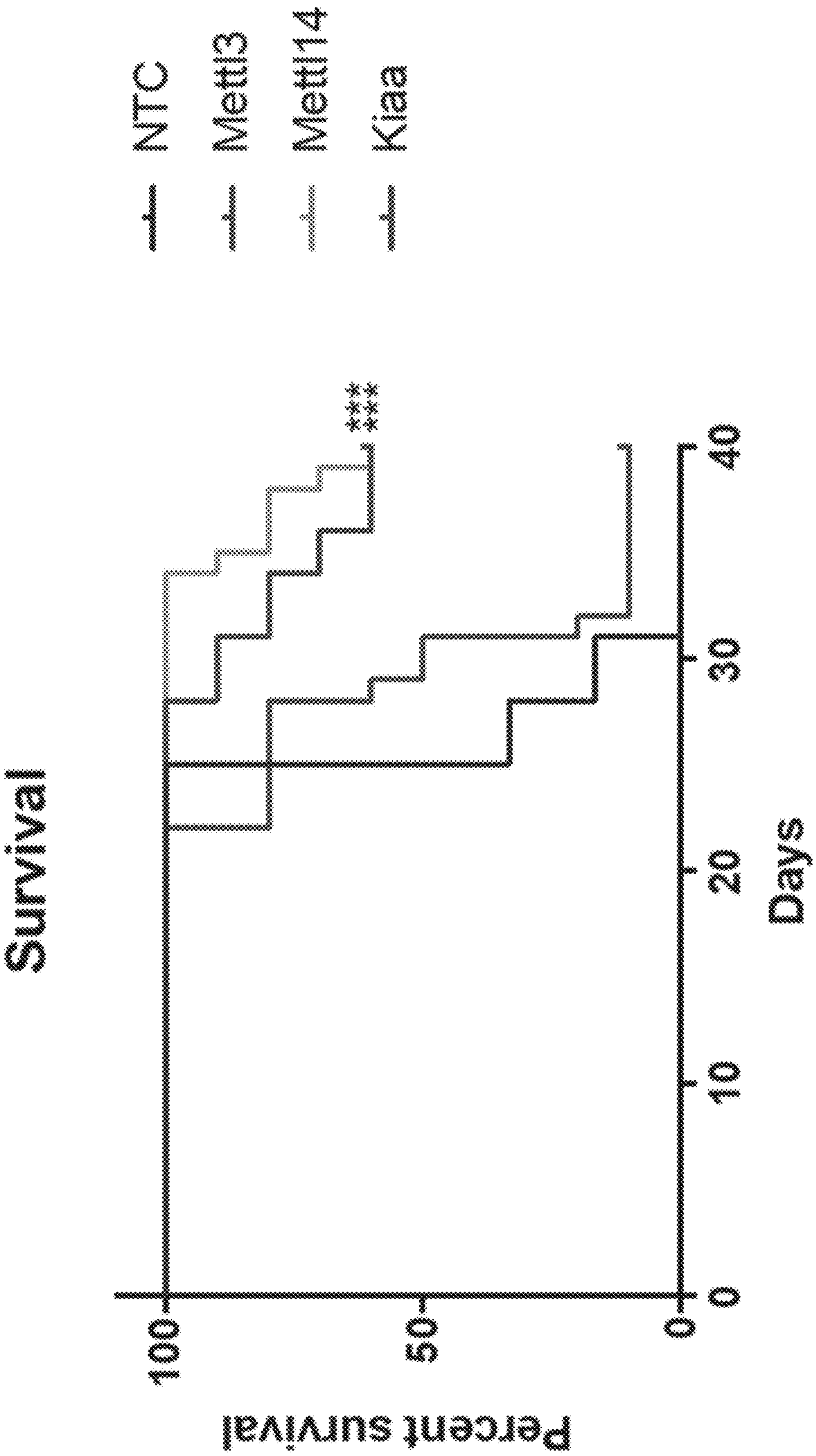
Figure 25:
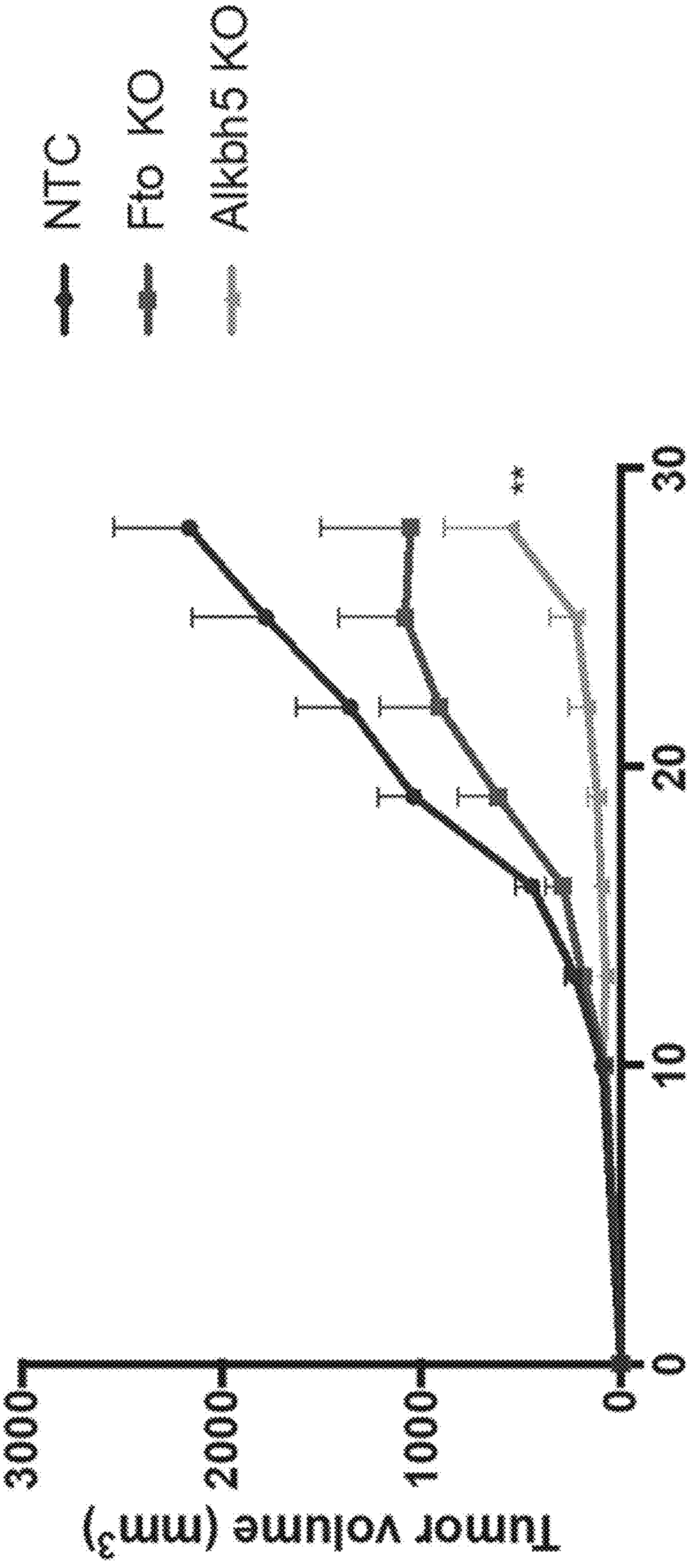
FIG. 25. Depiction of loss of ALKBH5 and FTO on tumors during PD-1 checkpoint blockage.
Figure 25:
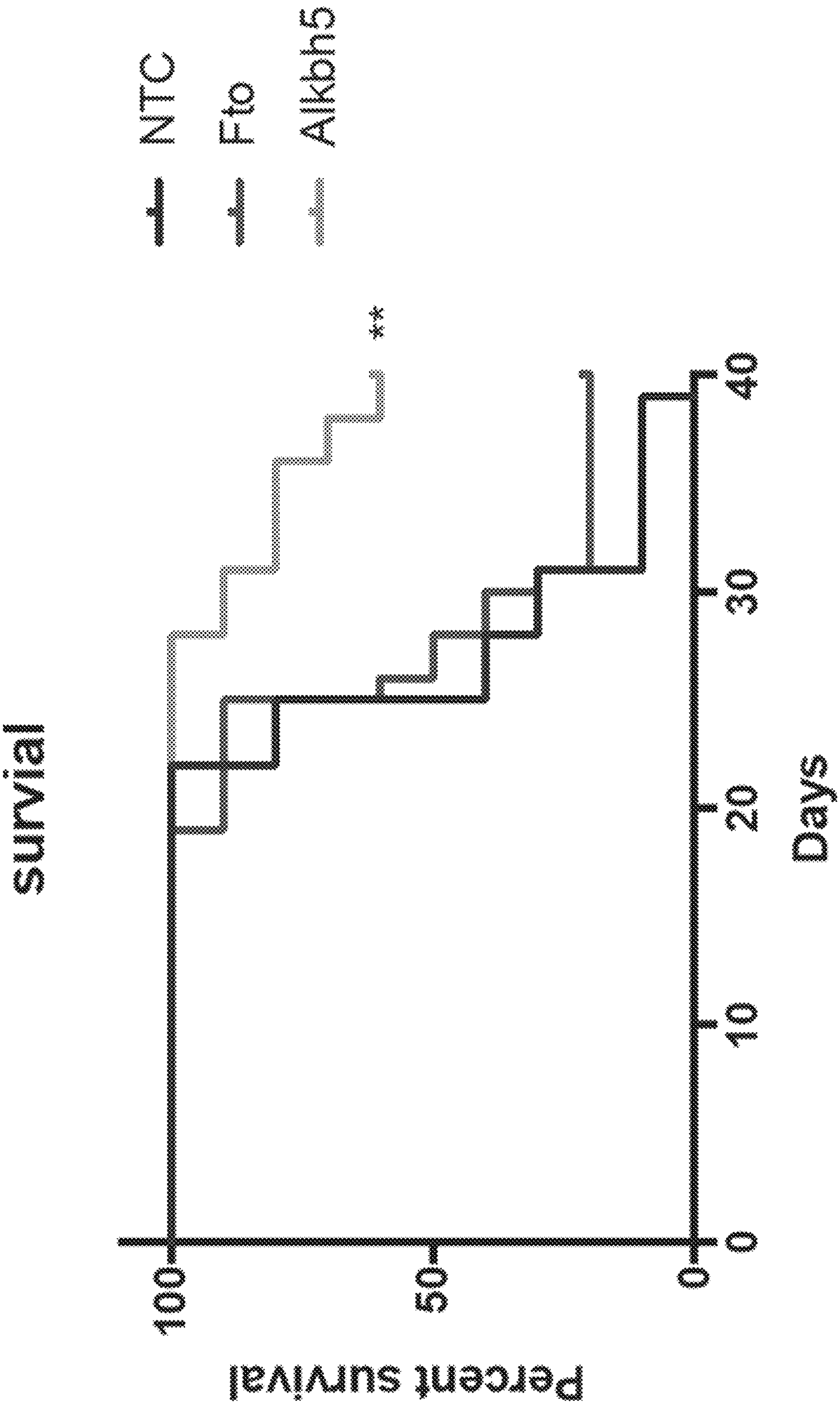
Figure 26:
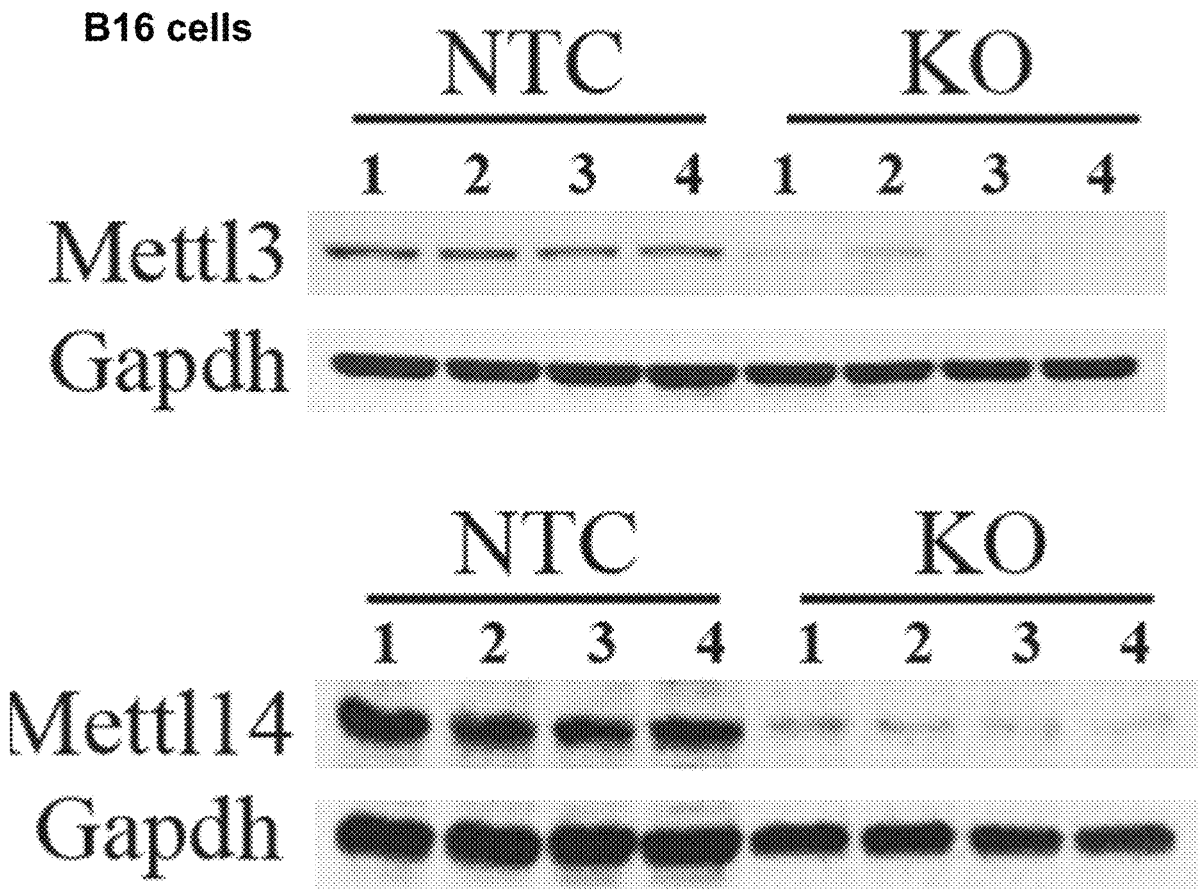
FIG. 26. Depiction of loss of Mettl3/14 on tumors during PD-1 checkpoint blockage.
Figure 26:
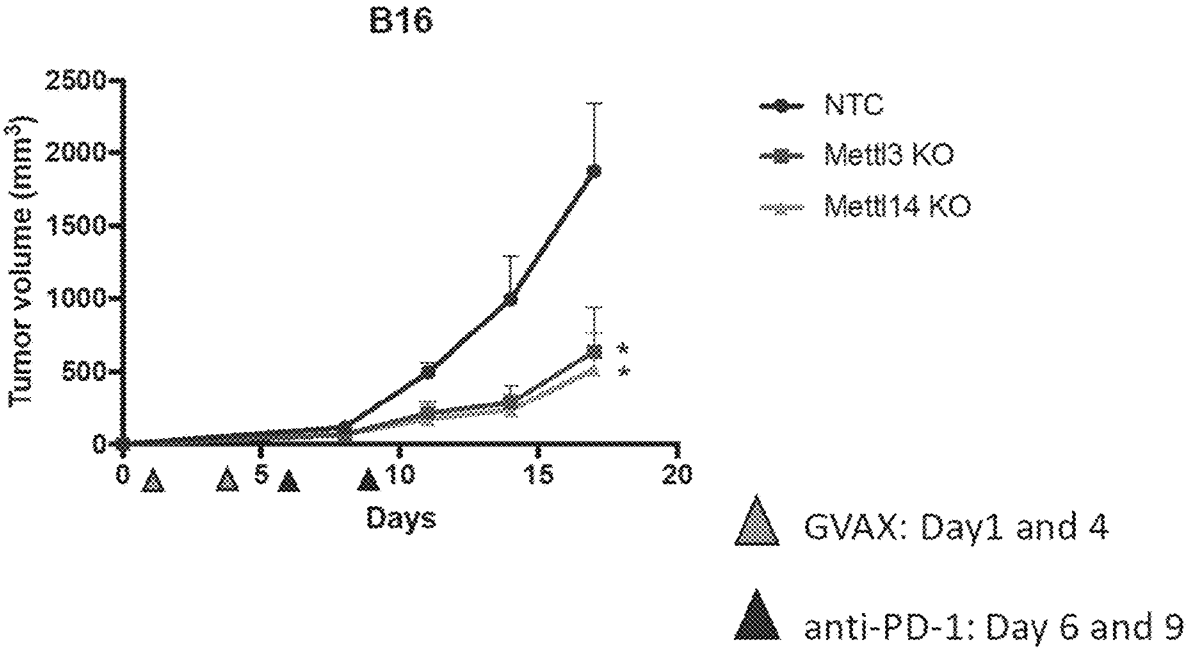

Hit validation and lead optimization of inhibitors through in vitro enzymatic inhibition assays arid structure-based drug design. Following synthesis, inhibitors identified through in silico screening will be experimentally validated by the fluroescent enzymatic inhibition assay developed by the Jaffrey lab and established in our lab can be used to rapidly verify that inhibitors are potent and selective towards FTO. Additionally, compounds maybe rapidly optimized for potency, selectivity, and physiochemical properties using structure-based design prior to call-based testing. Concomitantly, c log P value can be determined for inhibitors which are potent and selective: Meta-analyses of pharmaceutical drug development projects has identified the importance of log P in identifying which are more likely to feature favorable clearance rates and membrane permeability: one such study found that compounds with a molecular weight of 350 g/mol a log P of 1.5 had a 25% success rate of being advanced to clinical trials. Identifying compounds with favorable log P values at this stage will aid in selecting leads which are not only potent, but most likely to possess favorable PK profiles for in vivo models in Aim 3b. To date, IC50 values against FTO have been determined for approximately 75 inhibitors from our initial screening and design, 45 of which have also been screened against ALKBH5. An additional 20 compounds are currently being evaluated for their enzymatic potency against FTO. From the 45 inhibitors screened against both FTO and ALKBH5, 15 selective inhibitors have been identified with nanomolar potency against FTO (FIG. 18). Of these, 10 also display favorable log P values between 1-3.

The glioblastoma stem cell lines can also be used to generate 3D cerebral organoid models, a technique that has already been established in the Rana lab. Evaluation of the most potent inhibitors identified in the initial cellular screen in the 3D organoid models can more accurate understanding of their effects in more physiologically relevant model prior to in vivo study. The m6A individual-nucleotide-resolution cross-linking and immunoprecipitation (miCLIP) method can be used to determine the extent of mRNA binding to FTO ALKBH5 the presence or absence of an inhibitor to determine cellular mechanism of inhibition for the most effective inhibitor. RNA interference and CRISPR/Cas9 system established methods in Rana lab, can be used to generate FTO and ALKBH5 knockouts in GSCs, and quantification of the m6A RNA levels can be used to establish the phenotype of the KO cells. Quantification of the KO cells after treatment with inhibitors can be used verify as cellular, while comparison of the phenotype type after treatment with inhibitors can further validate these targets in cells prior to in vivo studies.

Cell lines were treated with a total of nine 2-fold serial dilutions of inhibitors (3 replicates per dose), using diluent-only treated cells as controls. The known FTO inhibitor MFA and the current standard of care for gliobastoma, temozolomide, will also be used as positive controls. The extent of proliferation and/or cell death will also be evaluated for each cell line to determine the median-effect dose (Dm, equivalent to an EC50). Compounds will be ranked according to their $EC_{50}$s before selecting the best inhibitor for in Vivo mouse models.

The 3D organoid models were grown using the TS576 cell line, as this line is the most suited to the large number of passages required to grow the organoids. To verify the mechanism of inhibition in cells, m6A individual-nucleotide-resolution cross-linking and immunoprecipitation (miCLiP) will be used to quantify the extent of mRNA binding to FTO in the presence or absence of inhibitor. If the inhibitor is bound to FTO, then the mRNA binding to FTO will be decreased. RNA interference and quantification will be performed as described in Chavali at. CRISPR-Cas9 experiments will be performed according to established methods in Rana Lab.

Similarly, compounds for ALKBH5, YTH family, and Mettl3Y14 were designed and analyzed. Chemical structures, biochemical and inhibition data is presented in attached files for these inhibitors.

See table below for roles and mechanisms of m6A regulators in cancer and FIGS. 19-26 for additional data.

| Regulator | Function in cancer |
|---|---|
| FTO | Oncogenic role in AML: promoting leukemogenesis and drug resistance<br>Oncogenic role in GBM: pharmaceutical inhibition of FTO suppresses GBM development |
| ALKBH5 | Oncogenic role in GBM: promoting tumorigenesis and self-renewal/ proliferation of GSCs<br>Oncogenic role in breast cancer: promoting tumorigenesis and proliferation of BCSCs |
| METTL14 | Oncogenic role in AML: promoting LSC/LIC self-renewal and leukemogenesis and inhibiting myeloid differentiation<br>Tumor-suppressor role in GBM: inhibiting tumorigenesis and self-renewal/ proliferation of GSCs<br>Tumor-suppressor role in HCC: inhibiting tumor invasion and metastasis<br>Oncogenic role in HCC: promoting HCC cell proliferation and migration |
| METTL3 | Oncogenic role in AML: promoting leukemogenesis and inhibiting myeloid differentiation<br>Tumor-suppressor role GBM: inhibiting tumorigenesis and self-renewal/ proliferation of GSCs<br>Oncogenic role in GBM: promoting tumorigenesis, GSC maintenance, and radioresistance<br>Oncogenic role in HCC: promoting HCC cell proliferation and migration<br>Oncogenic role in lung cancer: promoting growth, survival and invasion of lung cancer cells |
| IGF2BP1/2/3 | Oncogenic roles in cervical and liver cancer: promoting growth, colony formation, migration and invasion of cervical and liver cancer cells |

| Regulator | $m^6A$-related role | Functional mechanism | Refs. |
|---|---|---|---|
| FTO | $m^6A$ eraser | Targeting ASB2, RARA, MYC, and CEBPA, etc FTO iself is a target of 2HG | 55, 69 |
| | $m^6A$ eraser | N/A | 60 |
| ALKBH5 | $m^6A$ eraser | Targeting FOXM1, etc | 72 |
| | $m^6A$ eraser | Probably targeting NANOG, etc | 73 |
| METTL14 | $m^6A$ writer complex component | Targeting MYB and MYC, etc | 75 |
| | $m^6A$ write complex component | Probably targeting ADAM19, etc | 60 |
| | $m^6A$ write complex component | Inhibiting primary micoRNA (e.g., mir-126) processing | 86 |
| | $m^6A$ write complex component | Targeting SOCS2, etc | 87 |
| METTL3 | $m^6A$ methyltransferase | Probably targeting MYC, 8CL2, PTEN, SP1, and SP2, etc | 82, 83 |
| | $m^6A$ methyltransferase | Probably targeting ADAM19, etc | 60 |
| | $m^6A$ methyltransferase | Targeting SOX2, etc | 85 |
| | $m^6A$ methyltransferase | Targeting SOCS2, etc | 87 |
| | $m^6A$ reader? | Probably targeting EGFR and TAZ, etc | 267 |
| IGF2BP1/2/3 | $m^6A$ readers | Targeting MYC, FSCNT, TK1, and MARCKSL1, etc | 25 |

$m^6A$ $N^6$, AML acute myeloid leukemia, GBM gliobastoma, HCC hepatocellular carcinoma, LSC/LIC leukemia stem/initiating cell, GSC(s) gliobastoma stem(-like) cell(s), N/A data not available

REFERENCES

1. Singh, S. K. et al Identification of human brain tumour initiating cells. Nature 432, 396-401 doi:10.1038/nature03128 (2004).
2. Bao, S. et al. Glioma stem cells promote radioresistance by preferential activation of the DNA damage response. Nature 444, 756-760, doi:10.1038/nature05236 (2006).
3. Godlewski, J., Newton, H. B., Chiocca, E. A. & Lawler, S. E. MicroRNAs and glioblastoma; the stem cell connection. Cell Death Differ 17, 221-228, (2010).
4. Stupp, R. et al. Effects of radiotherapy with concomitant and adjuvant temozolomide versus radiotherapy alone on survival in glioblastoma in a randomised phase Ill study: 5-year analysis Of the EORTC-NCIC trial. Lancet Onco/ 10. 459-466. (2009).
5. Johnson, D. R. O'Neill, B. P. Glioblastoma survival in the United States before and during the temozolomide era. J Neurooncol 107, 359-364, doi:10.1007/s11060-011-07494 (2012).
6. Lathia, D., Mack, S. C, Mulkearns-Hubert, E. E., Valentim, C. L & Rich, J. N. Cancer stem cells in glioblastoma. Genes Dev 29, 1203-1217, (2015).
7. Bradshaw, A. et al. Cancer Stem Cell Hierarchy in Glioblastoma Multiforme. Front Surg 3, 21, (2016).
8. Lan. X. et al. Fate mapping of human glioblastoma reveals an invariant stem cell hierarchy. Nature 549, 227.232, (2017).
9. Heddleston, J. M. et al. Glioma stem cell maintenance: the role of the microenvironment. Curr Pharm Des 17, 2386-2401 (2011).
10. Sundar, S. J., Hsieh, J, K, Manjila, S., Lathia, J. D. & Sloan, A. The role of cancer stem cells in glioblastoma. Neurosurg Focus 37, E6. doi:10.3171/2014.9.FOCUS14494 (2014).
11. Bleau, A. M., Huse, J, T. & Holland, E. C. The ABCG2 resistance network of groblastoma. Cell cycle 8, 2936-2944 (2009).
12. Chen, J. et al. A restricted I population propagates glioblastoma growth after chemotherapy. Nature 488, 522-526, doil10.1038/naturel1287 (2012).
13. Cui, Q. et al. m6A RNA methylation regulates the self-renewal and tumorigenesis of glioblastoma stem cells. Cell Rep 18.2622-2634 (2017).

14. Huang, Y. et al. Meclofenamic acid selective y inhibits FTO demethytlation of m6A over ALKBH5. Nucleic Acids Res 43, 373-384 (2015).
15. Deng, X. et al. Role of N(6)-methyladenosine modification in cancer. Curr Opin Genet Dev 48, 1-7 (2018)
16. Deng, X. et al. RNA modification in cancers: current status and perspectives. Cell Res 28, 507-517 (2018).
17. Rose, N. R. et al. Inhibition of 2-oxoglutarate dependent oxygenases. Chem Soc Rev 40, 4364-4397 (2011).
18. Chen, B. et al. Development of cell-active N6-methyladenosine RNA demethylase FTO inhibitor. J Am Chem Soc 134, 17963-17971 (2012).
19. Aik, W. et al. Structural basis for inhibition of the fat mass and obesity associated protein (FTO)). J Med Chem 56, 3680-3688.
20. Li, Q. et al, Rhein inhibits AlkB repair enzymes and sensitizes cells to methylated DNA damage. J Biol Chem 291, 11083-11093 (2016).
21. Wang, T. et al, Fluorescein derivatives as bifunctional molecules for the simultaneous inhibiting and labeling of FTO protein. J Am Chem Soc 137. 13736-13739 (2015).
22. Huang, Y. et al. Small molecule targeting of oncogenic ETO demethylase in acute myeloid leukemia, Cancer Cell 35, 677-691 (2019).
23. Svensen, N. & Jaffrey, S. R. Fluorescent RNA Aptamers as a Tool to study RNA-Modifying Enzymes. Cell Chem Biol 23, 415-425, doi:10.1016/j.chembiol2015.11.018 (2016).
24. Cross, J. B. et al. Comparison of several molecular programs: pose prediction and virtual screening accuracy. J Chem Inf Model 49, 1455-1474, doi:10.1021/ci900C$_{56}$c (2009).
25. Invin, J. J., Sterling, T., Mysinger, M. M., Bolstad, E. S. R Coleman, R. G. ZINC: a free tool to discover chemistry for biology. J Chem Inf Mode/52, 1757-176B, doi: 10.1021/ci3C$_{01277}$ (2012).
26. Johnson. T. W. Dress, K. R. Edwards, M. Using the golden triangle to optimize clearance and oral absorption. J Bioorg Med Chem Lett 19, 5560-5564 (2009).
27. Johnson. T. W. Ga lego, R. A. Edwards, M. P. Lipophilic efficiency as an important metric in drug design. J Med Chem 61, 6401-6420 (2018).
28. Hopkins, A L. et al. The role of ligand efficiency metrics in drug discovery. NRDD 13, 105-121 (2014).
29. Raymer, B. Bhattacharya, S. K. Lead-like drugs: a perspective. J Med Chem 61, 10375-10384 (2018).
30. Weiss, M. M. et al., Sulfonamides as selective Navl.7 inhibitors: optimizing potency and pharmacokinetics while mitigating metabolic liabilities. J Med Chem 60, 5969-5989 (2017).
31. Dang, J. et al. Zika Virus Depletes Neural progenitors in Human Cerebral Organoids through Activation of the Innate Immune Receptor TLR3. Cell Stem Cell 19, 258-265, doi:10.10160.stem.2016.C4.014 (2016).
32. Linder, B, et al, Single-nucleotide-resolution mapping of m6A and m6Am throughout the transcriptome. Nat Methods 12, 767-772, doi:10.1C38/nmeth.3453 (2015).
33. Chavali, p. L. et al. Neurodevelopmental protein Musashi-1 interacts with the Zika genome and promotes viral replication. Science 357, 83-88, doi:10.1126/science.aamg243 (2017).
34. Rana, T. M. et al, Genome-wide CRISPR screen for essential I growth mediators in mutant KRAS colorectal cancers. Cancer Res, 0.1158'0008-5472.CAN-17-2043 (2017).

Example B4: M6A-RNA Demethylase FTO Inhibitors Impair Self-Renewal in Glioblastoma Stem Cells The role of mRNA modifications in regulation of gene expression, stem-cell maintenance, and differentiation has gained significant interest upon transcriptome-wide mapping of the most abundant internal modification, M-methyladenosine (m6A), which was identified in over 25% of all mRNAs.[1-3] m6A methylation is considered a reversible modification, where addition of the methyl group is controlled by a multiprotein "writer" complex requiring a heterodimer comprised of METTL3 and METTL14 proteins and supported by WTAP, KIAA1429, and RBM15.[4-7] Demethylation is controlled primarily by two "eraser" Fe (II)-α-ketoglutarate-dependent dioxygenases, alkylation repair homolog protein 5 (ALKBH5) and fat mass- and obesity-associated protein (FTO).[8-14] FTO has also been shown to demethylate $N^6$,2'-O-dimethyladenosine (m6Am) modified RNA transcripts.[10, 15-18] An additional host of "reader" proteins composed primarily of the YTH-domain containing family bind m6A RNAs and trigger a variety of downstream fates, including RNA degradation, stabilization, and translation.[3, 19-26]

While the role of m6A modification in stem cell differentiation is well known, the role of this modification in de-differentiation and tumor progression is still emerging. Geula et. al. have shown that pluripotent stem cells depleted in m6A modifications show resistance to differentiation, suggesting that alterations in m6A can alter differentiation pathways.[2] As such pathways are known to be directly linked to acquisition of stem-like cell properties in solid and hematological tumors, it is suspected that m6A misregulation may play a role in the generation of tumor-initiating cells and cancer progression.[27] Recent studies have shown that misregulation of any part of the adenosine-m6A equilibrium is associated with poor prognosis and tumorigenesis in a wide variety of cancers, including acute myeloid leukemia (AML).[28-38] Su et al have shown that FTO regulates MYC/CEBPA expression, and inhibition of FTO by the α-ketoglutarate mimic R-2-hydroxyglutarate reduces proliferation and viability of leukemia cells both in vitro and in vivo.[34] Recently, a new derivative of MA called FB23-2 was also shown to suppress proliferation and promote differentiation in AML cells and prolong survival in AML mouse models.[36]

The m6A methylation machinery has also been identified as a potential therapeutic target in glioblastoma. In 2017, ALKBH5 was shown to be an oncogene for glioblastoma, where shRNA knockdown of ALKBH5 in patient-derived glioblastoma stem cells (GSCs) decreased tumor cell proliferation and tumorigenesis by reducing the expression of FOXM1.[31] Cui et. al. have shown that depletion of m6A by knockdown of either METTL3 or METTL14 leads to growth and self-renewal in GSCs both in vitro and in vivo.[33] Depletion of m6A levels in vivo were further correlated with poor survival outcomes in GSC-grafted mice, while increased m6A levels via overexpression of METTL3 impaired tumor proliferation in multiple GSC lines in vitro.[33] Furthermore, treatment of orthotopically transplanted GSC tumors with the small molecule FTO inhibitor meclofenamic acid (MA) prevented tumor progression in vivo, supporting the role of m6A methylation pathways in GSC growth and self-renewal.[33] Conversely, Visvanathan et. al showed that silencing of Mettl3 impaired neurosphere formation in GSCs and sensitized neurospheres to γ-irradiation via downregulation of SOX2-mediated DNA repair; the authors further demonstrate that knockdown of Mettl3 prolonged lifespan in an intracranial orthotopic mouse model.[39] While the role of m6A methylation in glioblastoma is still unclear, these studies illustrate the emerging interest in the m6A methylation machinery and FTO specifically as potential targets for cancer chemotherapy. However, most existing small molecule inhibitors of FTO show poor pharmacokinetic profiles or inadequate selectivity towards FTO and are considered unsuitable for clinical study. Therefore, it is important to identify novel chemical scaffolds for targeting FTO that may offer advantages over existing selectivity and physicochemical properties.

Figure 27A:
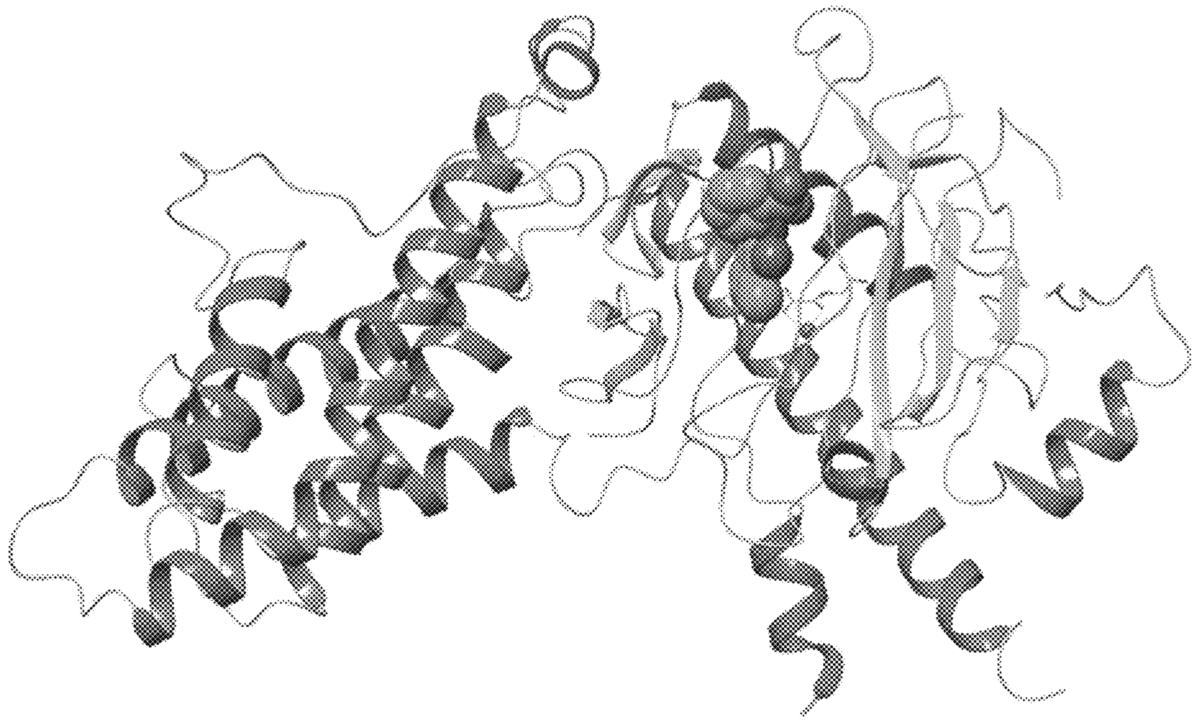
FIG. 27A-27D.
Figure 27B:
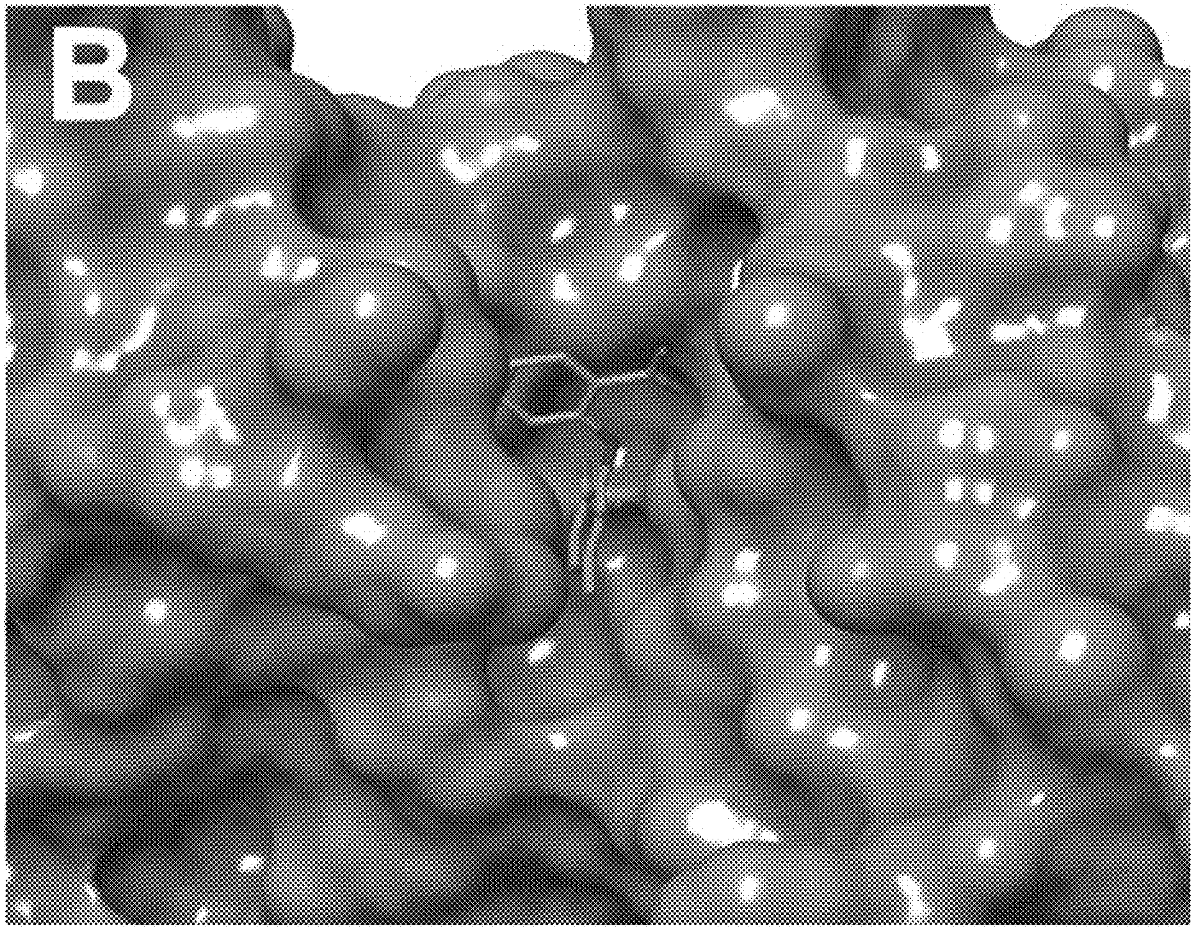
Figure 27C:
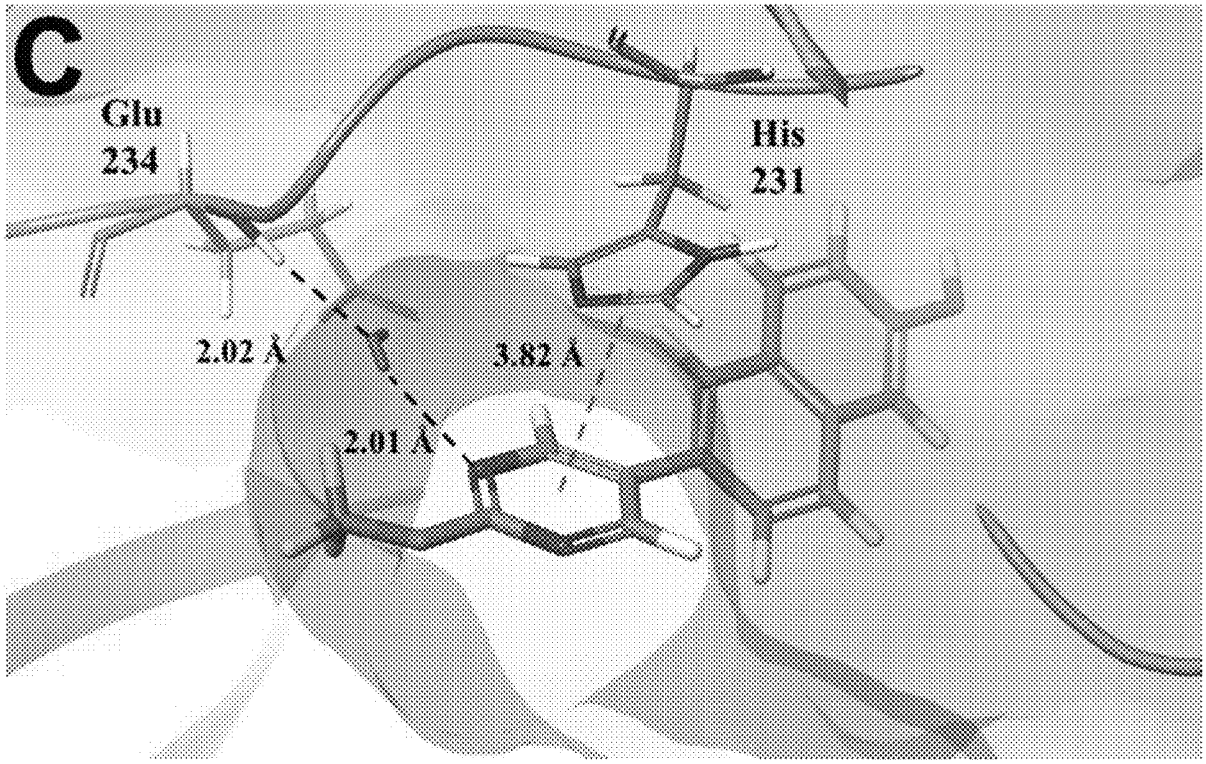
Figure 27D:
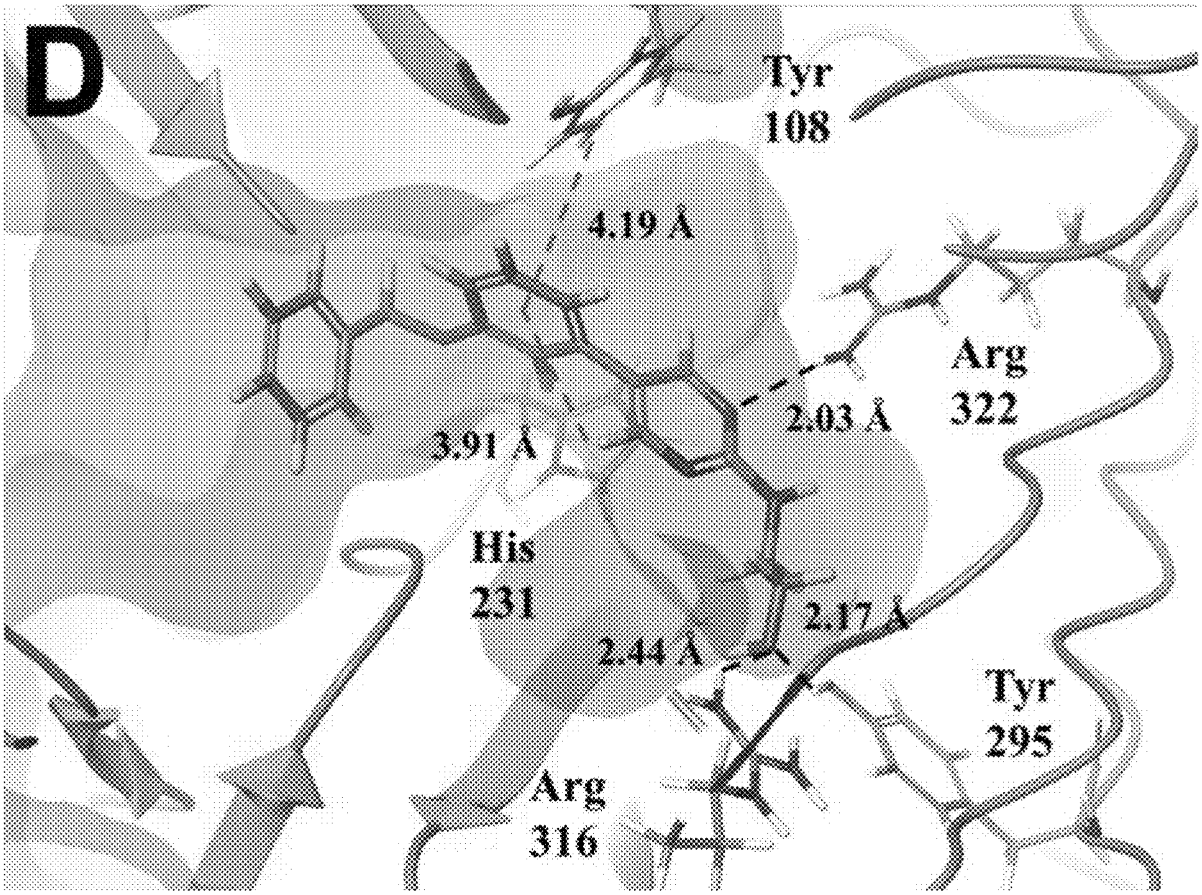

In order to identify chemically distinct inhibitors of FTO, we used a combination of structure-based drug design and molecular docking with the Schrödinger software suite to target the MA binding site of FTO. As MA has previously been shown to preferentially inhibit FTO over ALKBH5, we rationalized that targeting this site would be more likely to identify unique inhibitors that also maintained selectivity against ALKBH5.[40] An x-ray crystal structure of the MA-FTO complex (PDB ID: 4QKN) was first prepared using the Prime module, and the docking grid was defined as a 5×5×5 Å cube centered on MA (FIGS. 27A and 27B).[40] Docking was performed using Glide XP.[41-43] Scaffold hopping of the benzoic acid region identified a pyrimidine scaffold as a promising replacement, and fragment growth was directed towards an unoccupied binding pocket containing residues Glu234, Tyr106, Tyr108, and Arg322. Interactions with these four residues were considered highly favorable. Additional contacts with the nucleotide recognition lid (β3i and β4i, including Val83-Pro93) were considered favorable, as this flexible loop is unique to FTO among homolog α-ketoglutarate dependent dioxygenases and the selectivity of MA towards FTO over ALKBH2, 3, and 5 has been attributed to interactions with this region.[40] Representative docking poses for two inhibitors (FTO-02 and FTO-18) are shown in FIGS. 27C and 27D. Docking poses for FTO-1-20 are in the supporting information (FIGS. 32-51). Hits showing promising docking scores (absolute value ≥7) were also analyzed by QikProp to assess their physicochemical properties. As existing FTO inhibitors fail to progress to clinical applications due to poor pharmacokinetic profiles, it was important to filter our screen for compounds with more favorable physicochemical properties. Priority was placed on compounds with high predicted membrane permeability (>500 nm/s), c log P between 1-4, and low molecular weight (<350 g/mol). These criteria were selected due to multiple studies indicating compounds with low molecular weight and moderate lipophilicity are more likely to show favorable adsorption and clearance rates, and less toxicity due to target promiscuity. As such, controlling the physicochemical properties of inhibitors during the initial screening stages should select for better leads for future optimization and development. Based on these criteria, the top 20 inhibitors were selected for synthesis (Table S1). These parameters were also calculated for MA, FB23-2 and its precursor FB23 (Table S2). Of these, only FB23-2 was found to have a c log P value in between 1-4 (3.46) and all three are predicted to have limited membrane permeability. In Huang et. al, FB23 was shown to have limited cellular efficacy due to poor cellular uptake.[36] FB23-2 was designed to overcome this limitation and the cellular concentration of FB23-2 was found to be ~3-10× greater than that of FB23 in MONOMAC6 and NB4 cells, although still limited.[36] Similarly, our predicted permeability models estimate the rate of passive diffusion for FB23-2 to be ~2.5× greater than that of FB23. Of the 20 compounds selected for synthesis, 15 were predicted to have improved permeability relative to MA, FB23, and FB23-2 while still adhering to the ideal lipophilicity range (Table S1-2).

Compounds were synthesized via Suzuki-Miyaura cross-coupling, affording all compounds on milligram scale in moderate yields (52-75%, Scheme 1, general procedure A). Substituted pyrimidine boronic acids were coupled with a variety of commercially available aryl bromides by tetrakis (triphenylphosphine)palladium in tetrahydrofuran. While most compounds were synthesized without the use of protecting groups, the amino group of the amino-benzothiazole ring in FTO-04 was protected with a tertbutyloxycarbonyl (Boc) group prior to coupling (SI, procedure B). The Boc group was then removed under acidic conditions to obtain FTO-04 (SI, procedure C). After purification by silica gel column chromatography, a total of 20 potential FTO inhibitors were obtained.

Figure 53:
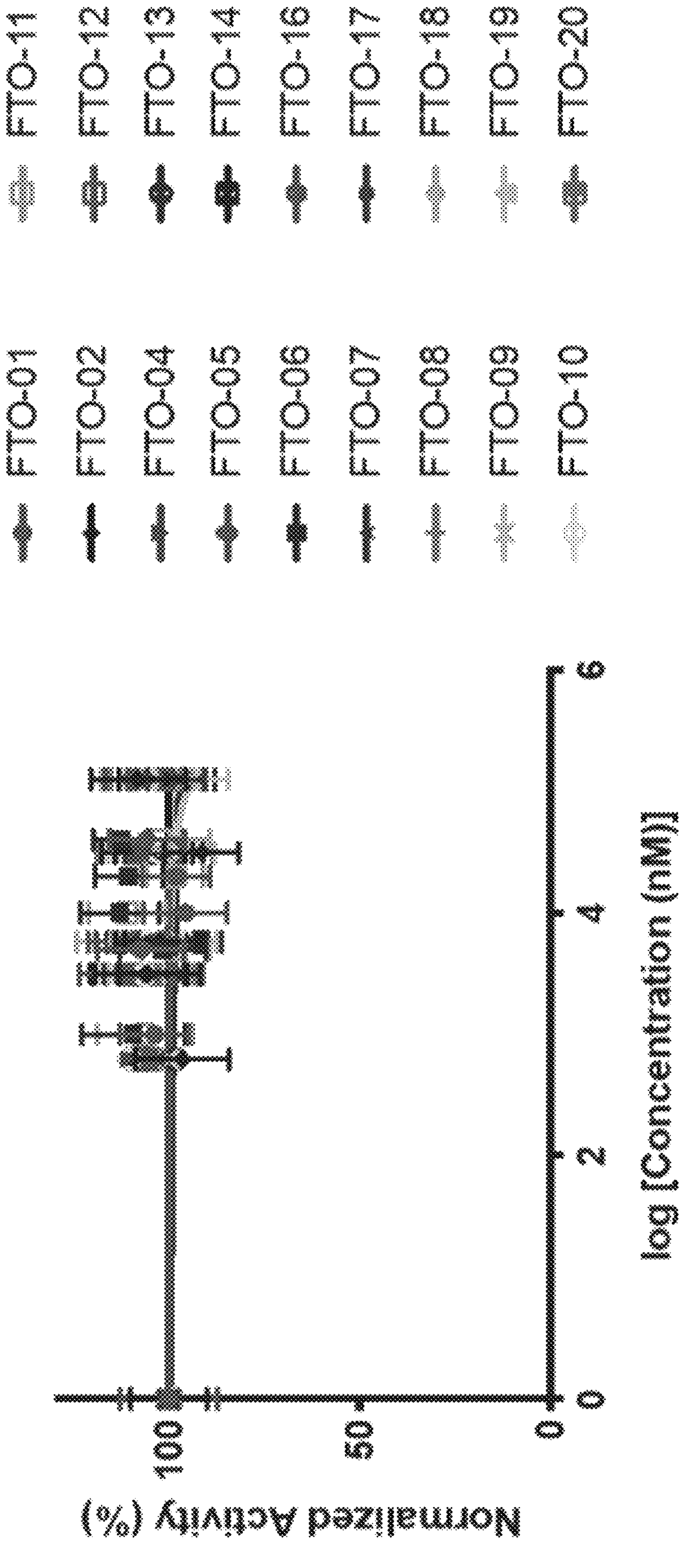
FIG. 53. Demethylation Assay Negative Control. F TO-I-20 do not significantly alter fluorescent signal of the demethylated Broccoli-DHBI-I T complex.
Figure 54:
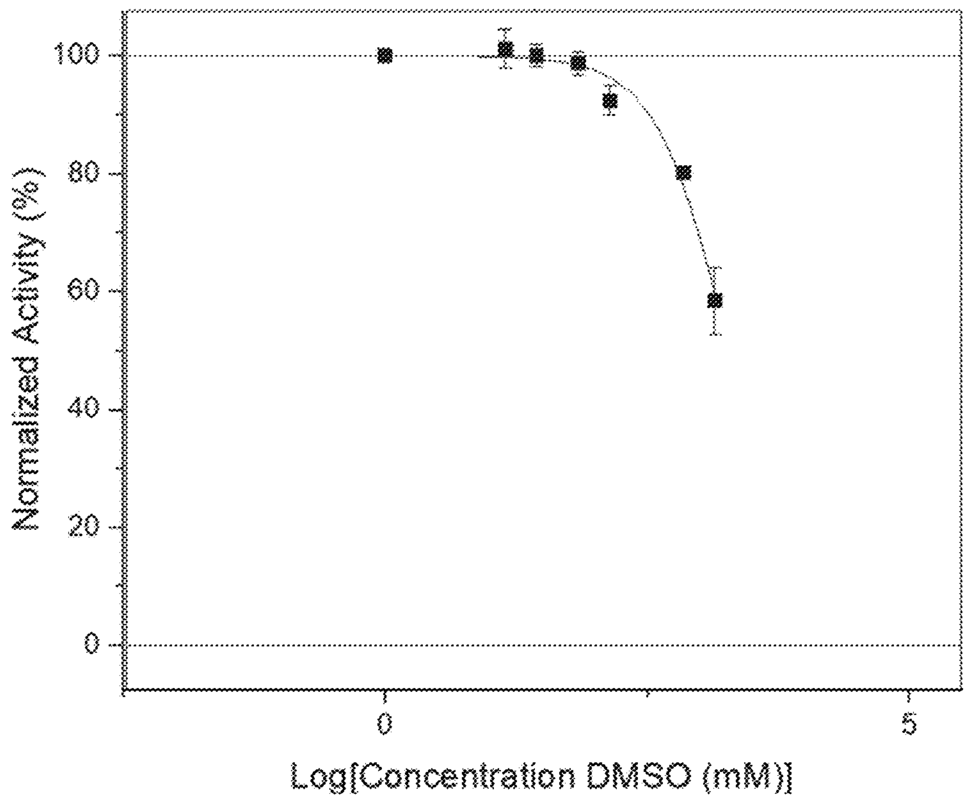
FIG. 54. DMSO Control for Demethylation Assays. DMSO does not significantly impair enzyme function or fluorescent signal until concentrations exceed >1%.
Figure 55A:
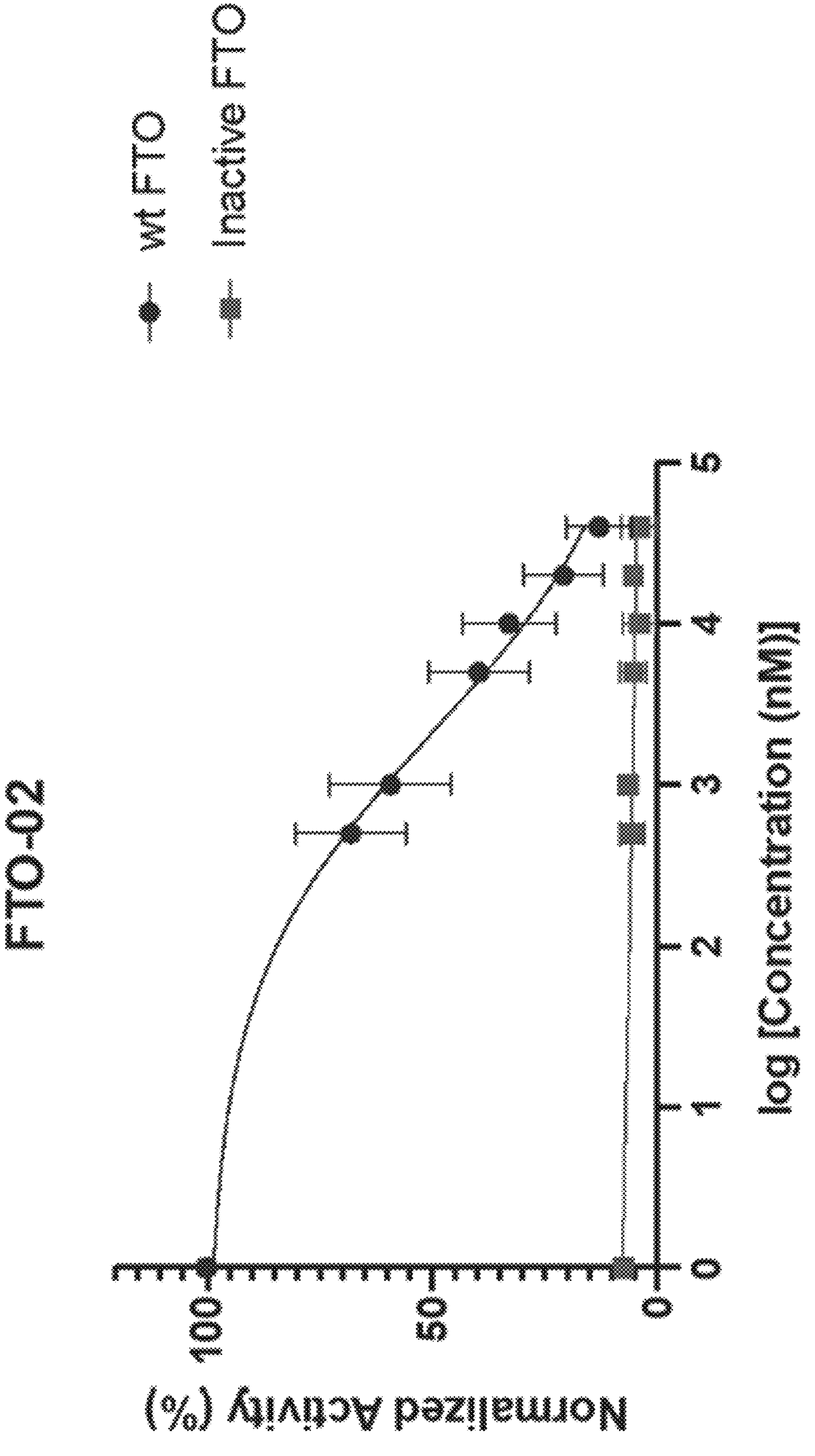
FIG. 55A-55B. Inactive FTO controls, 55A, Normalized activity of wt FTO and inactive FTO in the presence of 0-40 μM FTO-02. 55B. Normalized activity of wt FTO and inactive FTO in the presence of 0-40 μM FTO-04.
Figure 55B:
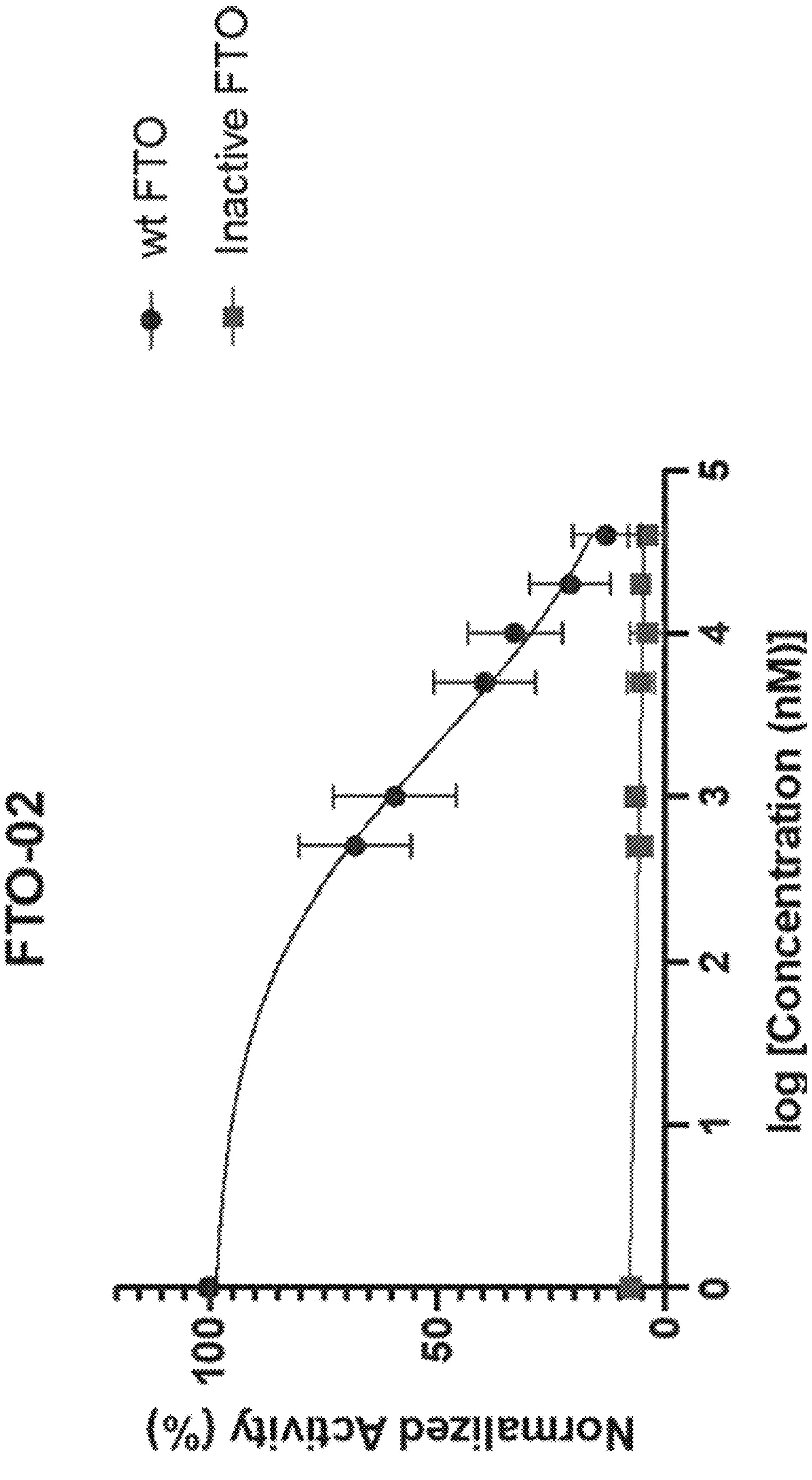

In order to determine their efficacy as FTO inhibitors, the compounds were screened by a fluorescence enzymatic inhibition assay developed previously by the Jaffrey lab.[44] Briefly, a nonfluorescent methylated RNA substrate termed "m6A7-Broccoli" is incubated with FTO in the presence of 2-oxoglutarate (300 μM), $(NH_4)_2Fe(SO_4)_2 \cdot 6H_2O$ (300 μM), and L-ascorbate (2 mM) for 2 hours at room temperature in reaction buffer (50 mM NaHEPES, pH 6). Read buffer (250 mM NaHEPES, pH 9, 1 M KCl, 40 mM $MgCl_2$) containing the small molecule 3,5-difluoro-4-hydroxybenzylidene imidazolinone (DFHBI-1T, 2.2 μM) is added to the reaction mixture and DFHBI-1T binds preferentially to demethylated Broccoli to produce a fluorescent signal after incubation for 2 hours at room temperature. MA was used as a positive control, and the observed $IC_{50}$ was in agreement with literature values ($IC_{50}$=12.5±1.8 μM).[40, 44] The enzymatic activity of FTO was tested at six concentrations of each inhibitor ranging from 0-40 μM in triplicate. As a negative control, the assays were repeated with demethylated Broccoli to ensure that any change in fluorescence was not due to interference with the Broccoli-DHBI-1T complex (FIG. 53); no compounds were observed to significantly alter fluorescence signal at concentrations up to 40 μM. To ensure that DMSO did not interfere with fluorescence signal or enzyme activity, the activity was determined for FTO under concentrations of DMSO ranging from 0-10% (FIG. 54). DMSO was found to interfere with enzyme activity at concentrations >1%; all inhibitor concentrations were restricted to a final concentration of 0.2% DMSO. Compounds FTO-02 and FTO-04 were also screened against FTO without the presence of cofactor 2-oxoglutarate; under these conditions, no fluorescence was observed (FIG. 55). Two compounds, FTO-03 and FTO-15, showed significant precipitation in assay buffer and the dose response could not be determined. All other compounds showed $IC_{50}$s in the micromolar range, with six compounds showing $IC_{50}$s below 15 μM and seven showing $IC_{50}$s above 40 μM (Table 1, Table S1). Of the four pyrimidine scaffolds tested, 2-methoxypyrimidine appeared to be the most potent against FTO, as all compounds with this moiety had an $IC_{50}$ below 15 μM. Compounds with the unsubstituted pyrimidine scaffold varied in $IC_{50}$ from 13 to 41 μM, and both the 2-aminopyrimidine and the pyrimidine-2-aminoethanol scaffolds showed little inhibitory potency. Of the aryl bromides, the 6-methoxynaphthalene and the (2-methoxyphenyl)methanol scaffolds both consistently showed potency towards FTO, where all compounds containing these scaffolds had $IC_{50}$s below 20 μM (Table 1, Table S1). The potency of other aryl bromide scaffolds varied widely and appeared dependent on the corresponding pyrimidine scaffold. In general, compounds containing either the 2-methoxypyrimidine or the 6-methoxynaphthalene were the most potent inhibitors of FTO; the two most potent inhibitors, FTO-02 and FTO-04 ($IC_{50}$=2.2 and 3.4 μM respectively), were found to inhibit FTO approximately 4× more potently than MA ($IC_{50}$=12.5) with comparable potency to FB23-2 (reported $IC_{50}$=2.6 μM).[36]

Figure 56:
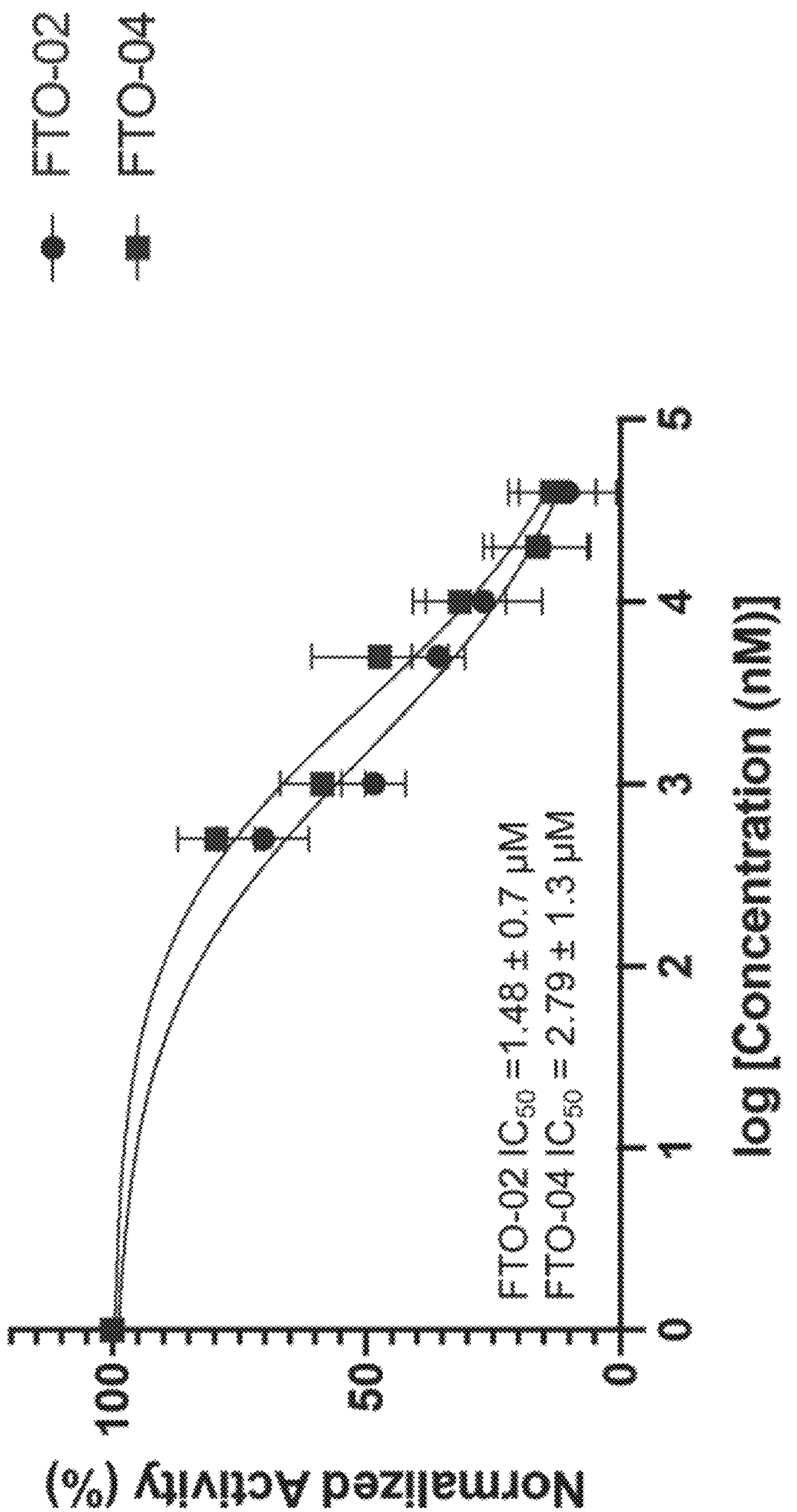
FIG. 56. IC50 curves for FTO-02 and FTO-04 against FTO by ELISA Assay.

The top two inhibitors were also screened against FTO using an ELISA-based inhibition assay as an orthogonal assay control. Biotinylated m6A-RNA was incubated with FTO for 2 hours at room temperature in reaction buffer (50 mM NaHEPES pH 6, 300 μM 2-oxoglutarate, 300 μM $(NH_4)_2Fe(SO_4)_2 \cdot 6H_2O$, and 2 mM L-ascorbate) with 0-40 μM FTO-02 or FTO-04. The reaction mixture was then incubated with neutravidin coated 96-well plates overnight at 4° C., washed and blocked, incubated with $m^6A$-specific antibody for 1 hour at room temperature, washed and blocked, and incubated with horseradish peroxidase-conjugated secondary antibody for 1 hour at room temperature. After extensive washing, the wells were treated with 3,3',5,5'-tetramethylbenzidine (TMB) for 30 minutes at room temperature and the absorbance was measured at 390 nm. Absorbance was normalized to control wells for each concentration of inhibitor without cofactor 2-oxoglutarate to control for non-specific antibody binding, and the data were fit to a sigmoidal dose-response curve in GraphPad Prism 6. These assays reported $IC_{50}$ values consistent with those observed in the Broccoli assays (1.48±0.7 μM FTO-02, 2.79±1.3 μM FTO-04, FIG. 56).

Figure 28A:
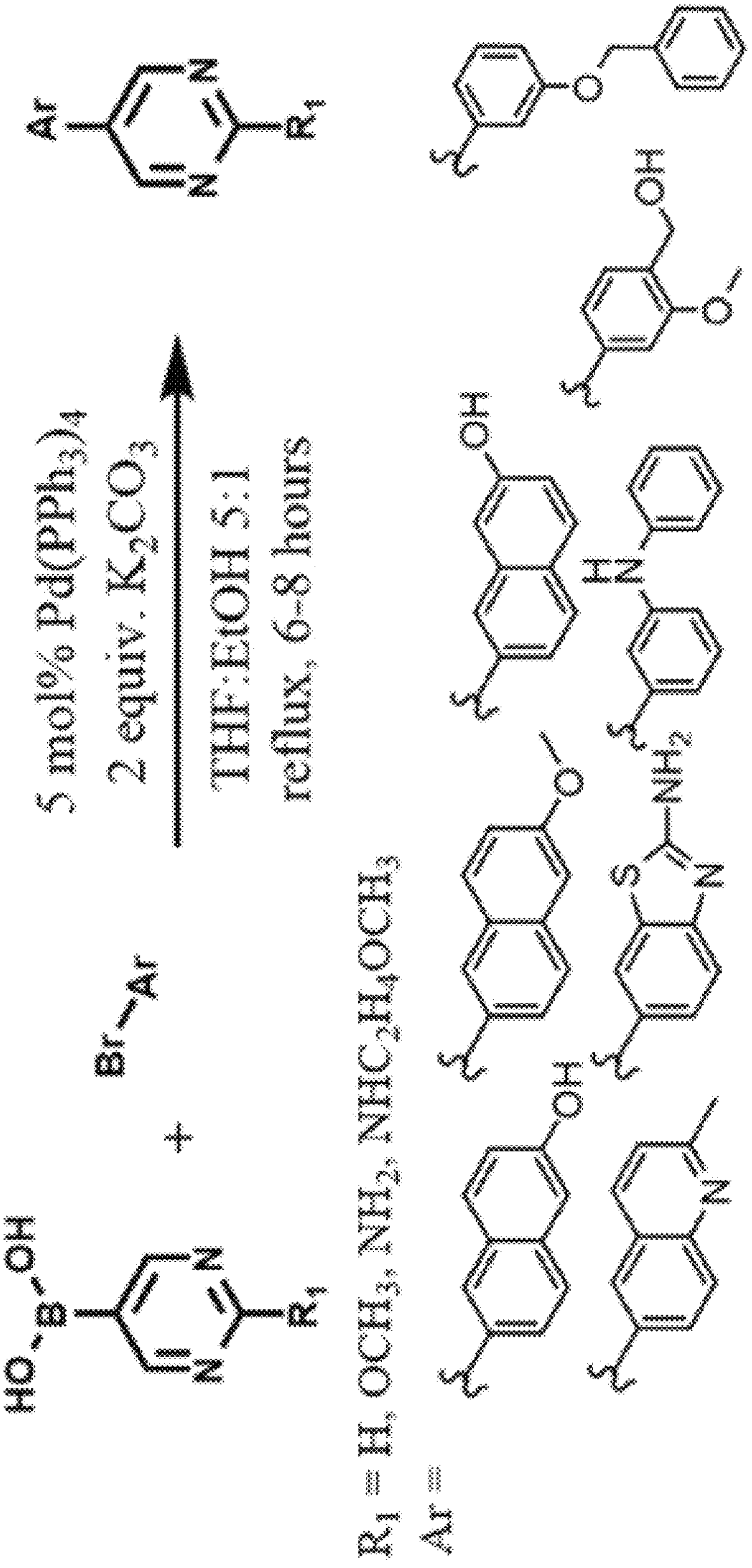
FIG. 28A-28F. FTO Inhibitors are selective and competitive.
Figure 28B:
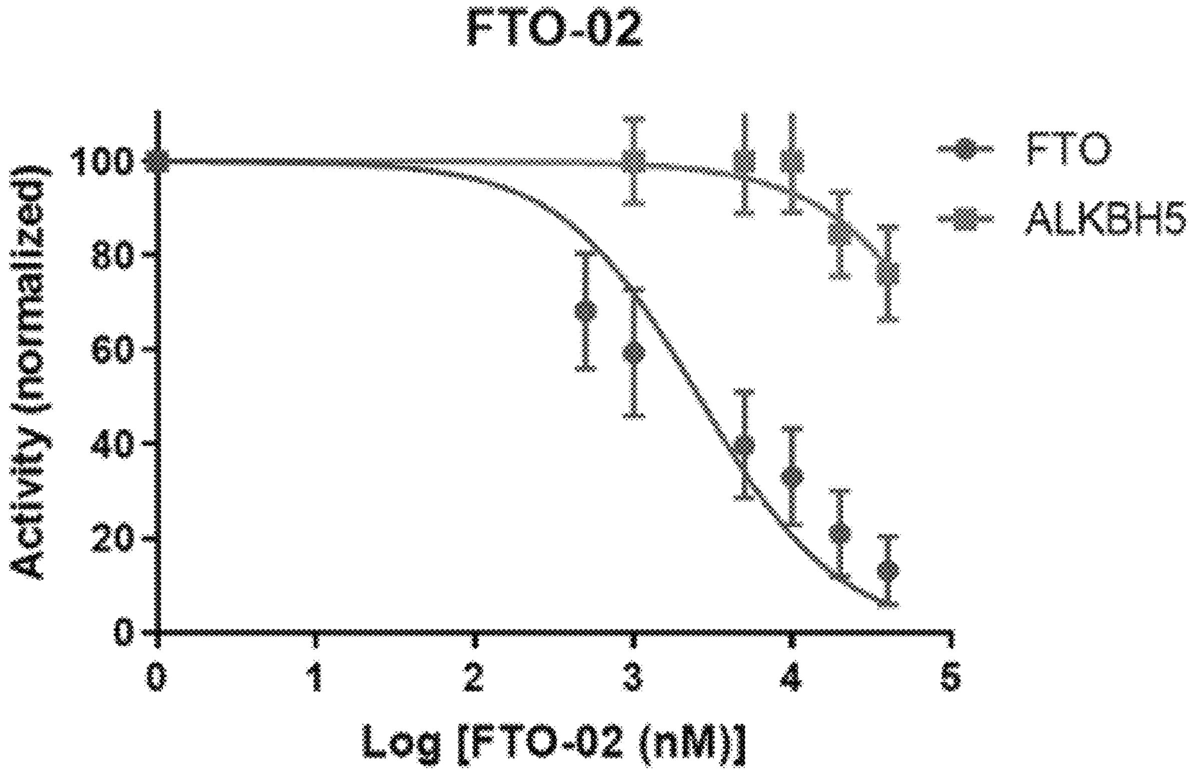
Figure 28C:
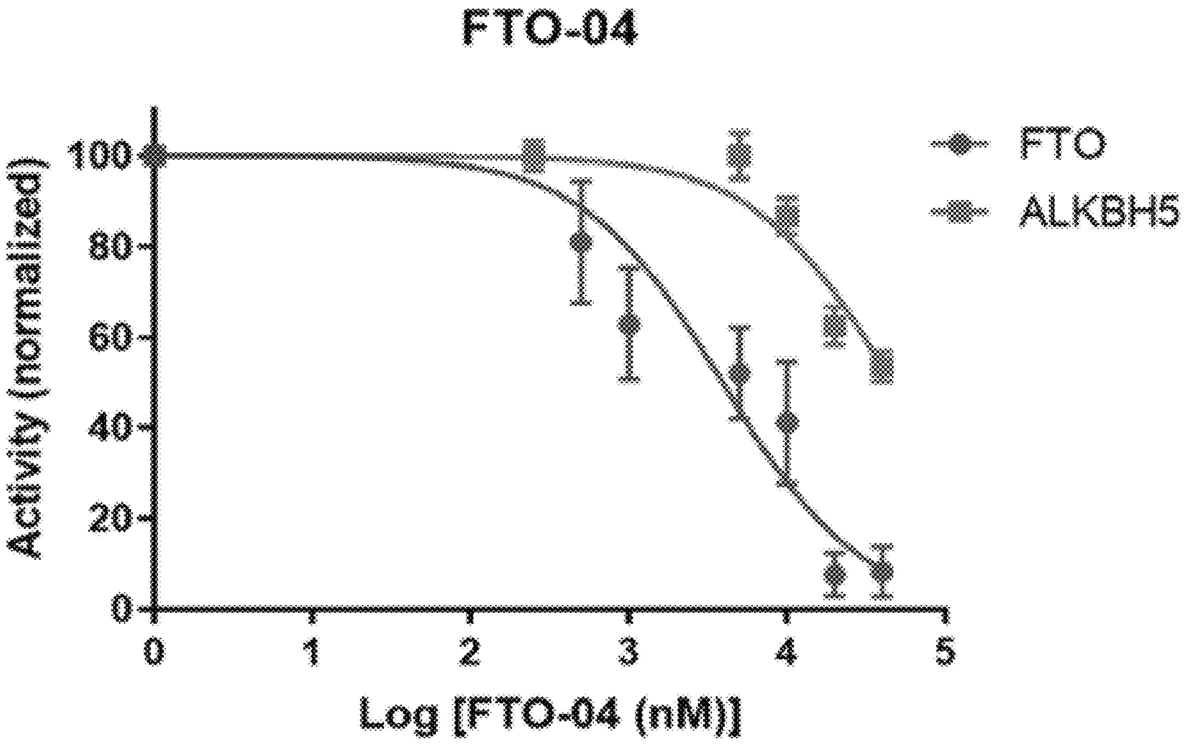
Figure 28D:
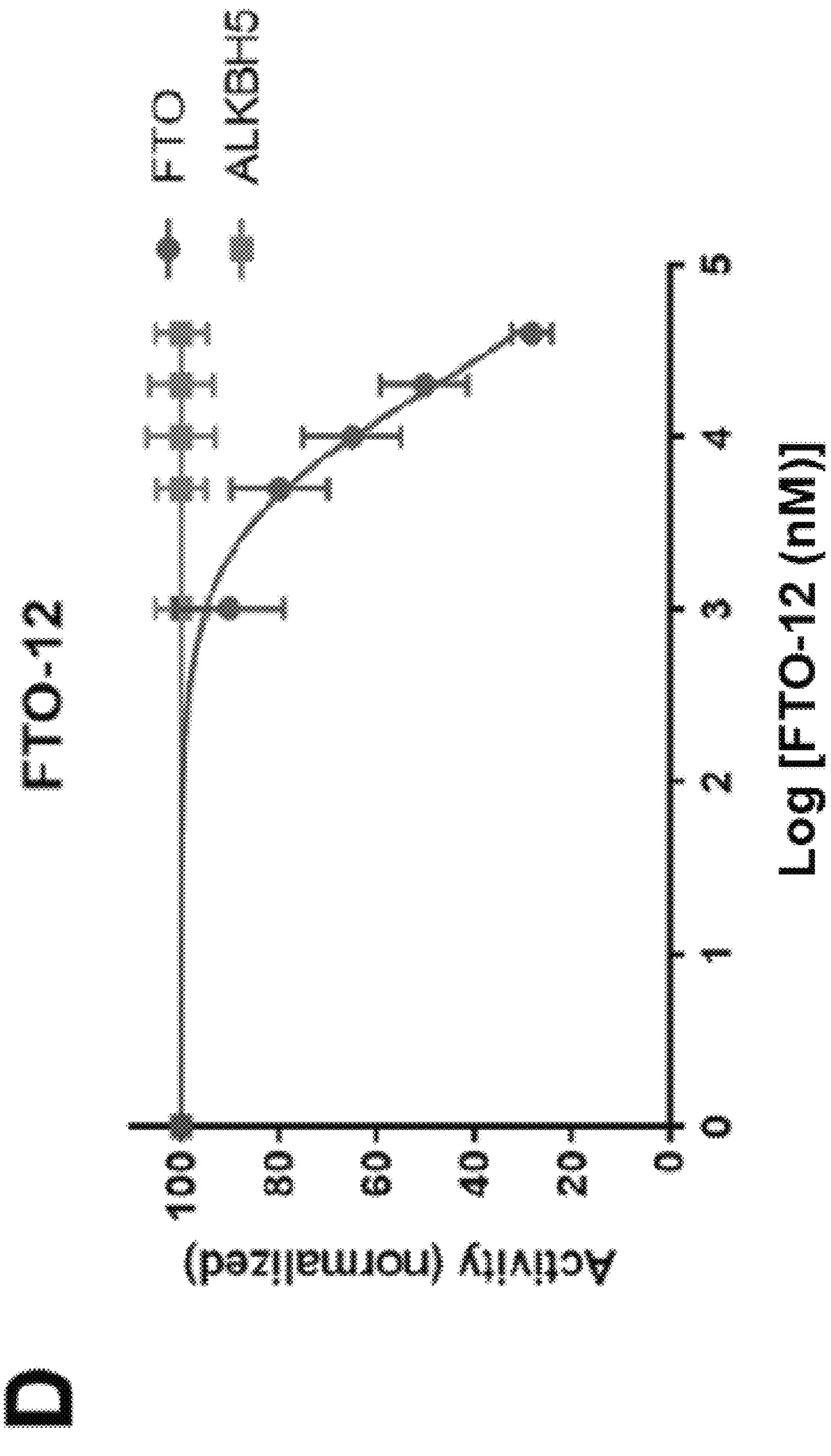

All compounds which did not show precipitation were also screened in the same manner against ALKBH5 to determine if there was any specificity towards FTO (Table 1, Table S1). Of the 18 compounds tested, nine displayed poor activity towards ALKBH5 ($IC_{50}$≥40 μM), and five of these showed no measurable inhibition at the highest concentration measured (FTO-01, FTO-05, FTO-07, FTO-12, and FTO-18). This selectivity against ALKBH5 is comparable to that observed for MA and FB23-2, which are reported to show little to no inhibition of FTO at 50 μM.[36] Importantly, the two most potent inhibitors FTO-02 and FTO-04 (FTO $IC_{50}$=2.2 and 3.4 μM respectively) both reported significant selectivity over ALKBH5 (ALKBH5 $IC_{50}$=85.5 and 39.4 μM respectively), with FTO-02 showing ~40× greater potency towards the target FTO. Compounds FTO-05, FTO-06, FTO-12, and FTO-20 showed a preference for FTO over ALKBH5 of five-fold or higher (Table 1, FIGS. 28B-28D). Four compounds, FTO-08, FTO-10, FTO-11, and FTO-19, were considered equivalent inhibitors towards both demethylases. Interestingly two compounds, FTO-09, and FTO-13, showed a distinct preference towards ALKBH5 over FTO, where FTO-09 was almost ten times more potent towards ALKBH5 ($IC_{50}$=5.2 vs. >40 μM). Both FTO-09 and FTO-13 feature the 2-aminopyrimidine ring previously identified as a poor inhibitor of FTO. In general, three of the five compounds which reported $IC_{50}$s against ALKBH5 below 40 μM contained the -aminopyrimidine ring, suggesting this scaffold preferentially inhibits ALKBH5 over FTO.

Of the six selective inhibitors shown in Table 1, five are predicted to form hydrophobic contacts with residues of the nucleotide recognition lid, specifically residues Val83, Ile85, Leu90, Thr92, Pro93, and Val94. While it has been suggested that the selective inhibition of MA against FTO over ALKBH2, 3, and 5 can be attributed to contacts with this loop, it is unclear if these contacts also control selectivity of FTO-02, 4, 5, 6, 12, and 20 without crystal structures. As ALKBH2, 3, and 5 do not contain this loop, it is likely that inhibitors selective against ALKBH5 will also be selective against ALKBH2 and 3. However, as the fluorescent inhibition assay is not amenable to the DNA methylating enzymes ALKBH2 and 3, off-target inhibition of these enzymes cannot be ruled out.

Figure 28E:
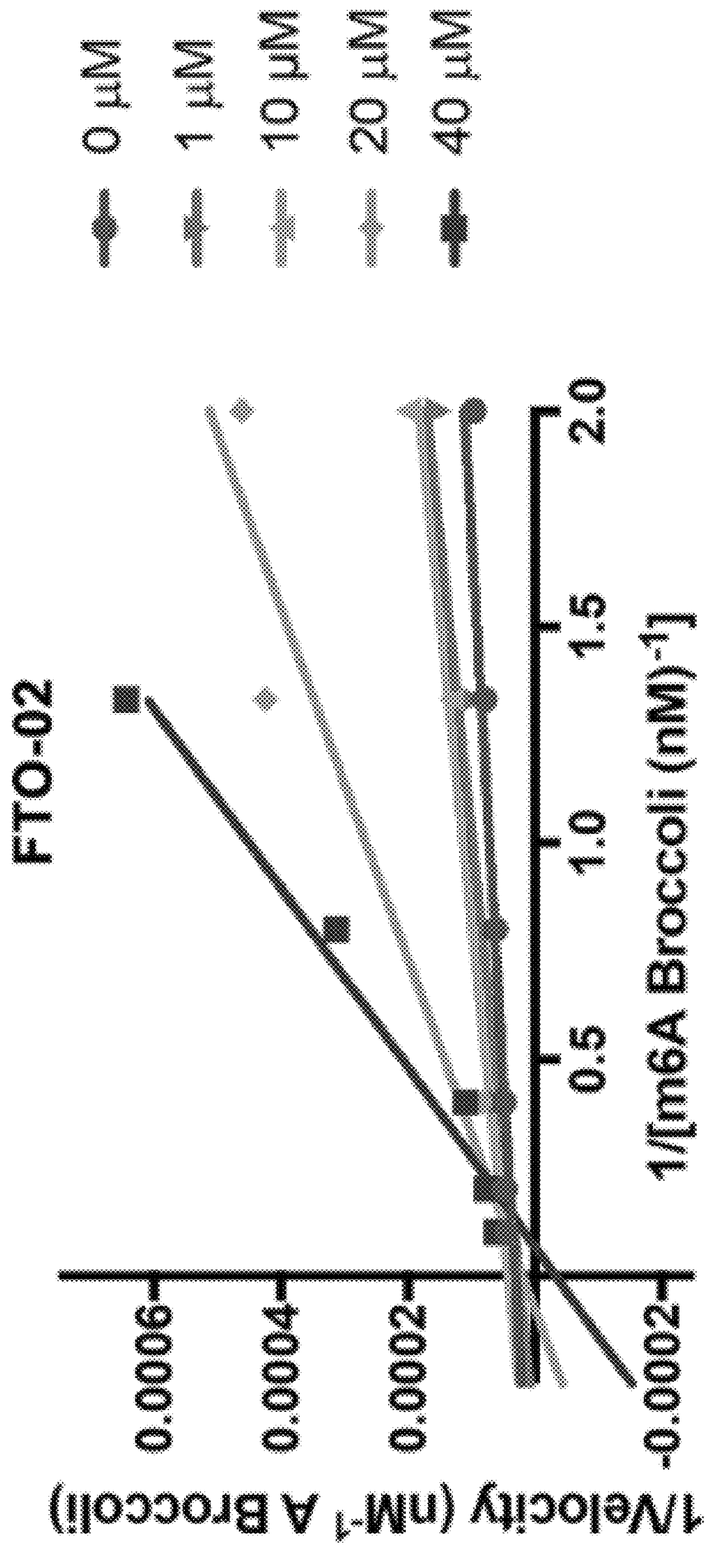
Figure 28F:
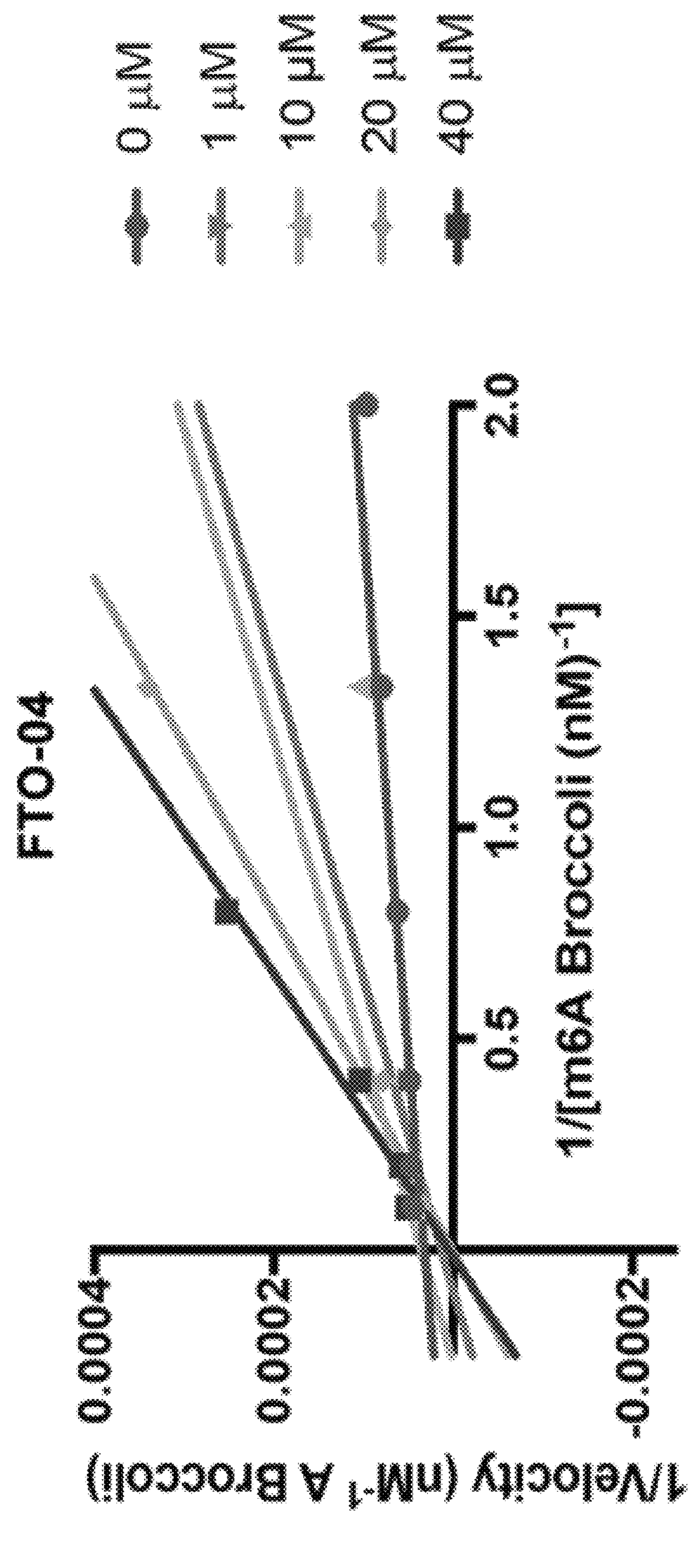
Figure 57A:
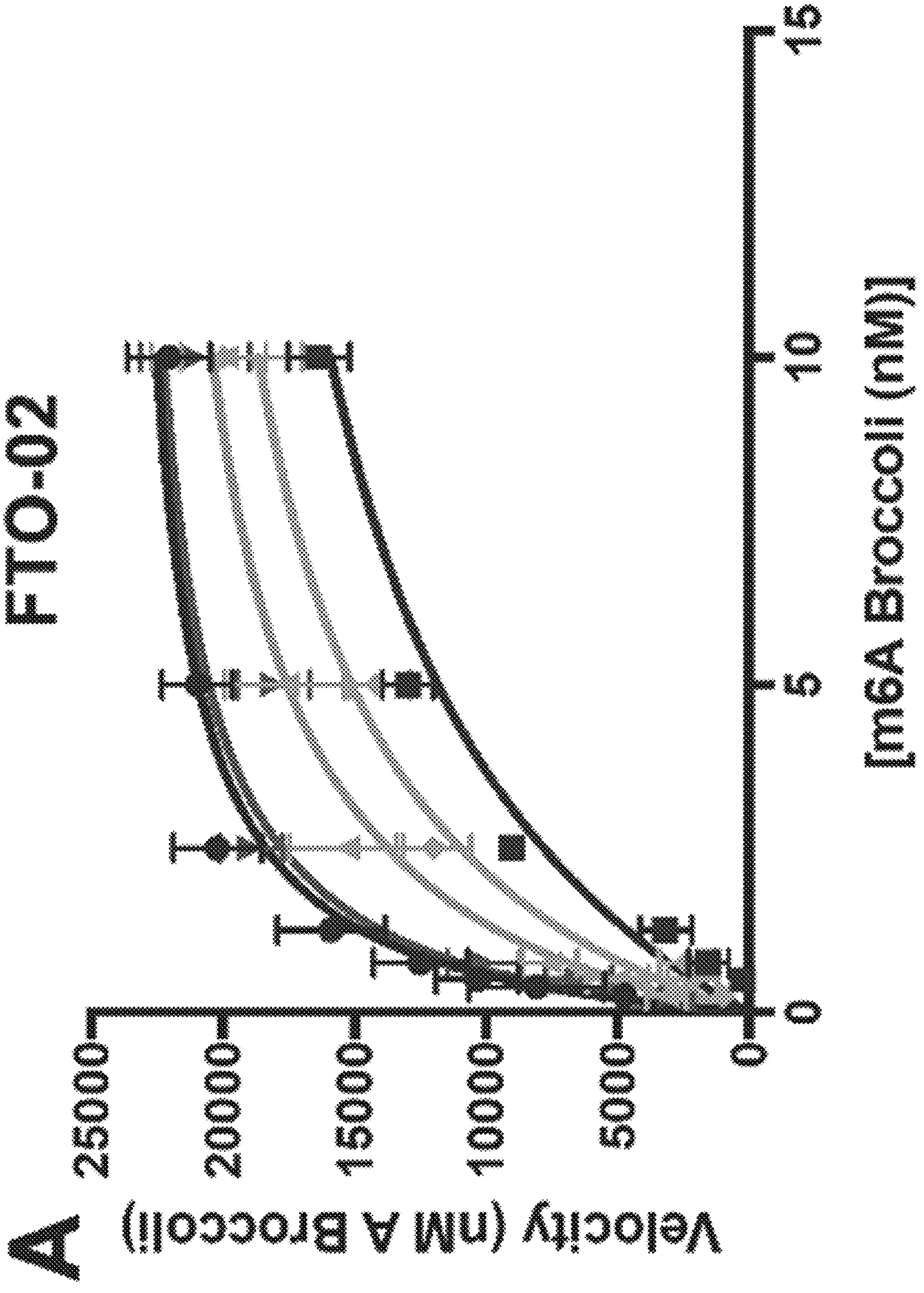
FIG. 57A-57B. Velocity plots for FTO-02 and FTO-04. 57A. FTO-02 approaches a common for all concentrations of inhibitor, consistent with a competitive mechanism of inhibition. 57B. FTO-04 approaches a common for all concentrations of inhibitor, indicating FTO-04 is a competitive inhibitor.
Figure 57B:
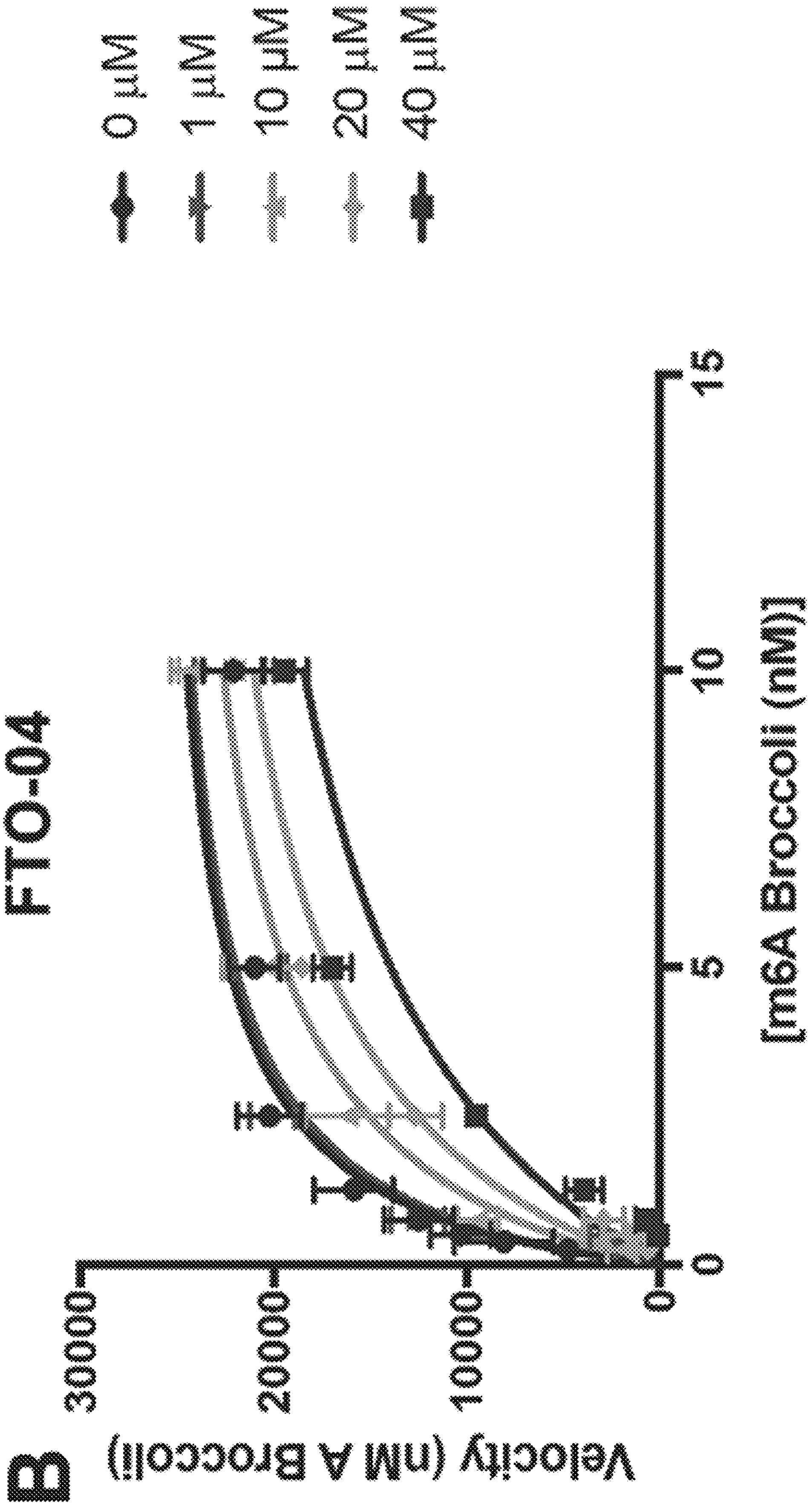

The mechanism of inhibition was established for the two most potent and highly selective inhibitors, FTO-02 and FTO-04, using steady-state inhibition kinetics. The reaction velocity was determined for FTO in the presence of 0, 0.5, 1, 10, and 40 μM inhibitor with a range of ten substrate concentrations between 0 and 10 μM. A plot of the reaction velocity versus substrate concentration shows that $v_{max}$ is reached when substrate concentrations exceed 5 μM, for all concentrations of FTO-02 and FTO-04 (FIGS. 57A-57B). The double-reciprocal plots show all concentrations of FTO-02 and FTO-04 converge on a common y-intercept, indicating $v_{max}$ is independent of the concentration of either inhibitor, supporting a competitive mechanism of inhibition (FIGS. 28E-28F). This mechanism is consistent with the initial in silico modeling targeted towards the MA binding site and the competitive mechanism previously reported for MA.[40]

Recent studies have indicated that the m6A methylation machinery mediates tumorigenesis and self-renewal in glioblastoma stem cells. Depletion of m6A methylation promotes tumor growth both in vitro and in vivo while knockdown of the demethylase ALKBH5 was found to impede tumorigenesis and prolong life span in GSC-derived tumor bearing mice.[31] Additionally, the small molecule FTO inhibitor meclofenamic acid was observed to prolong lifespan in intracranial GSC xenograft mice.[33] However, other reports suggest depletion of m6A methylation can impair tumor growth and sensitize GSC neurospheres to γ-irradiation and prolong lifespan in tumor-bearing mice.[39] While the role of m6A methylation in glioblastoma is still emerging, these data suggest that targeting the m6A methylation machinery to alter m6A levels could prove a promising strategy for treating glioblastoma.

Figure 29A:
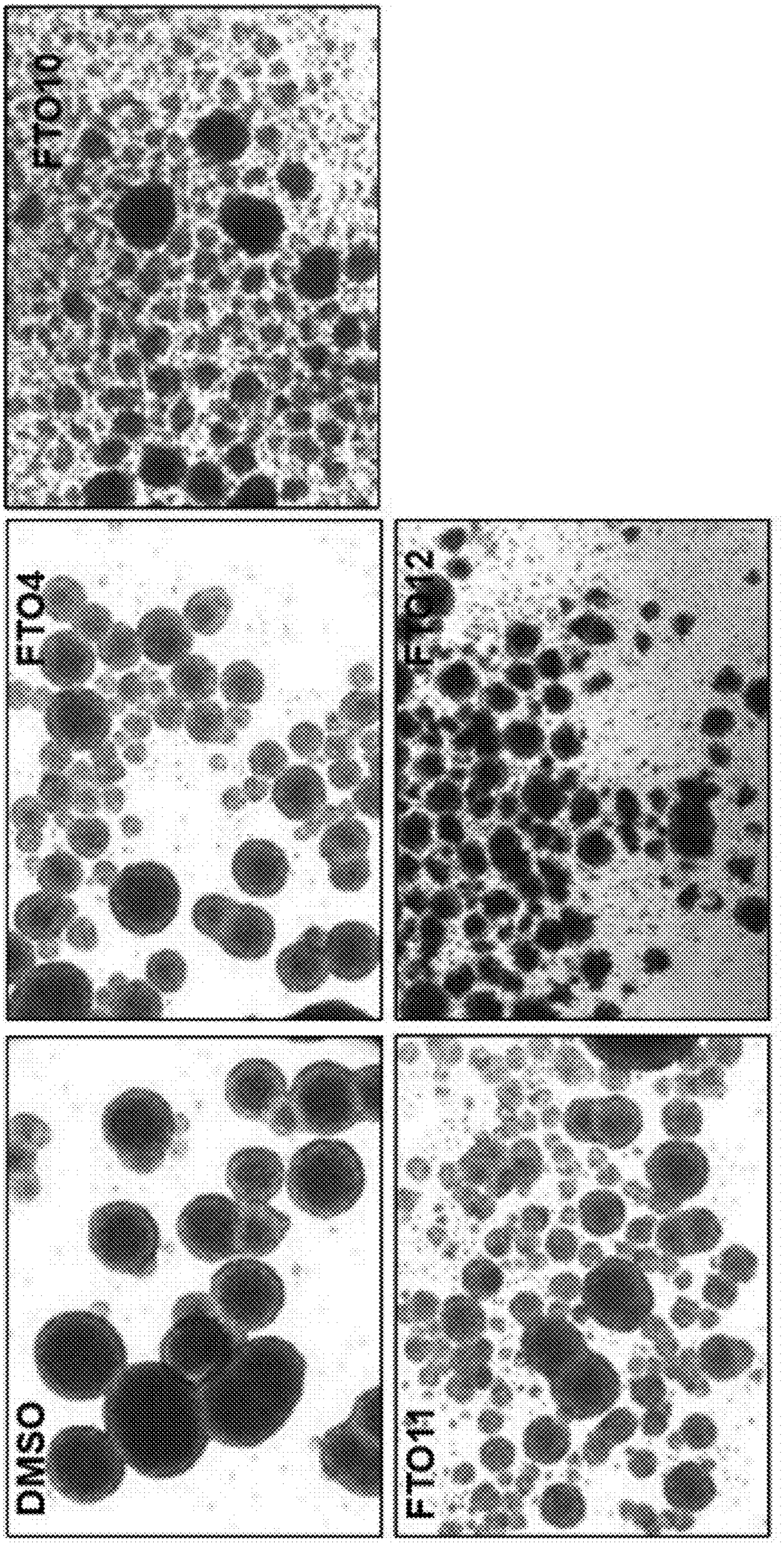
FIG. 29A-29D. FTO inhibitors inhibit the self-renewal of GSC tumorospheres.
Figure 29B:
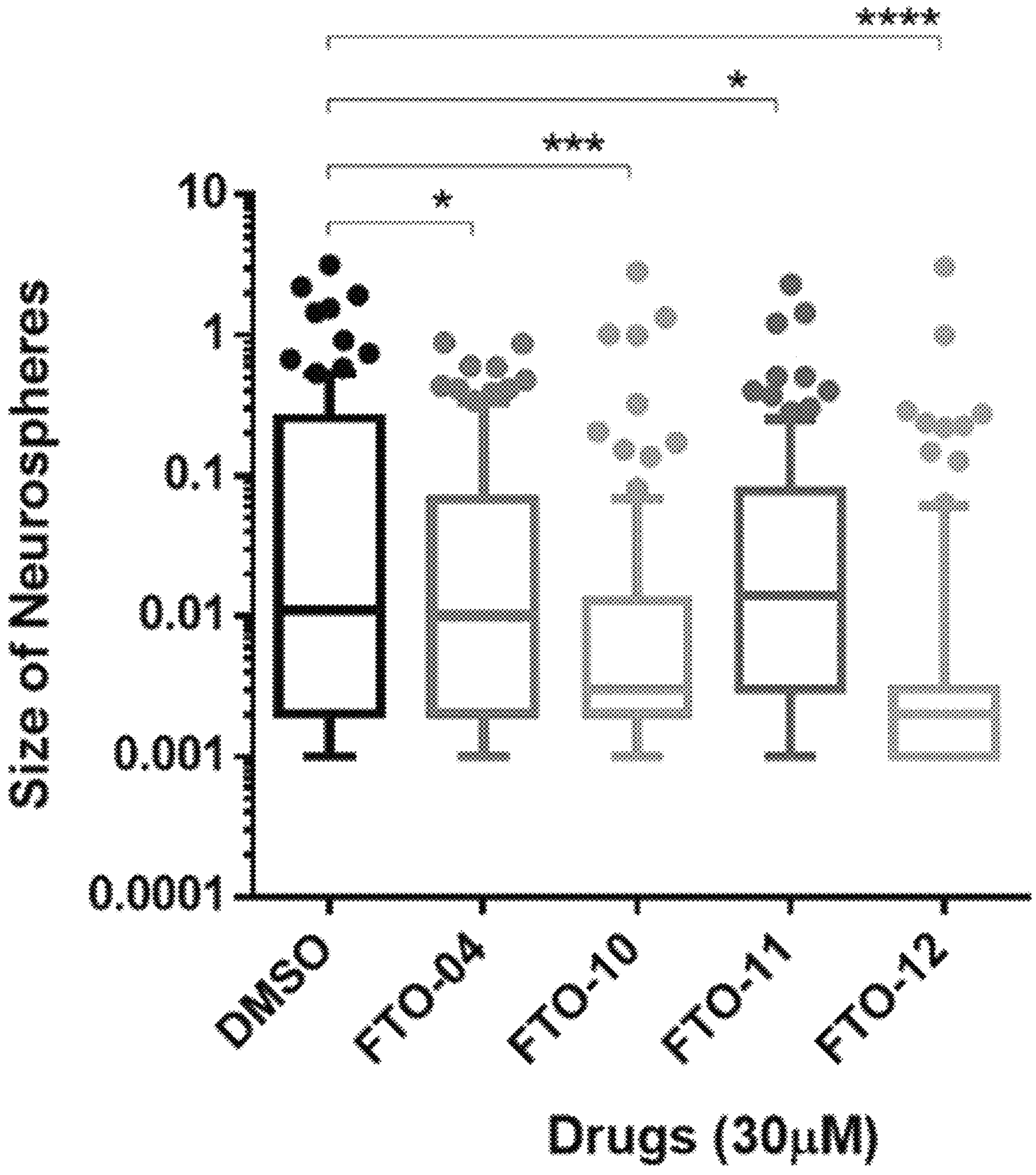
Figure 29C:
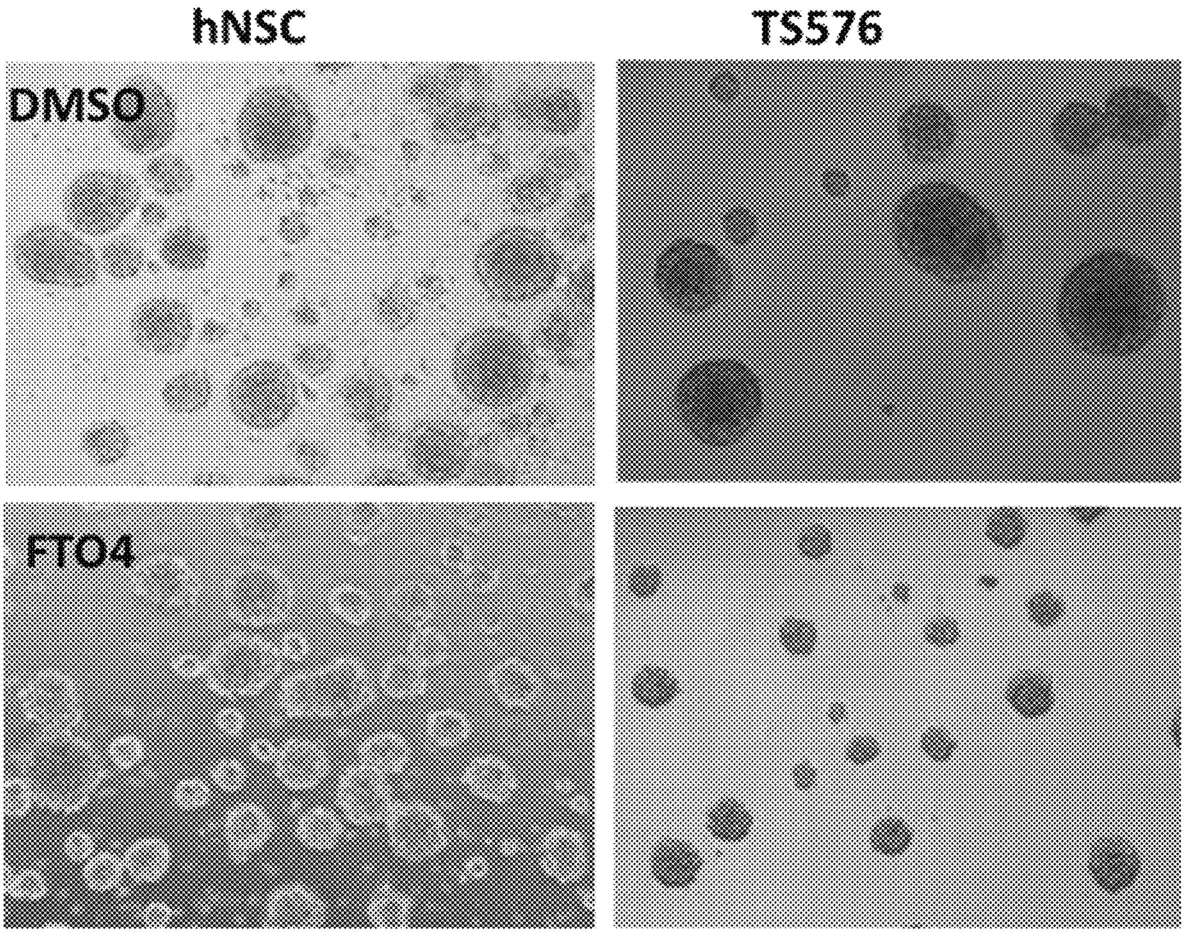
Figure 29C:
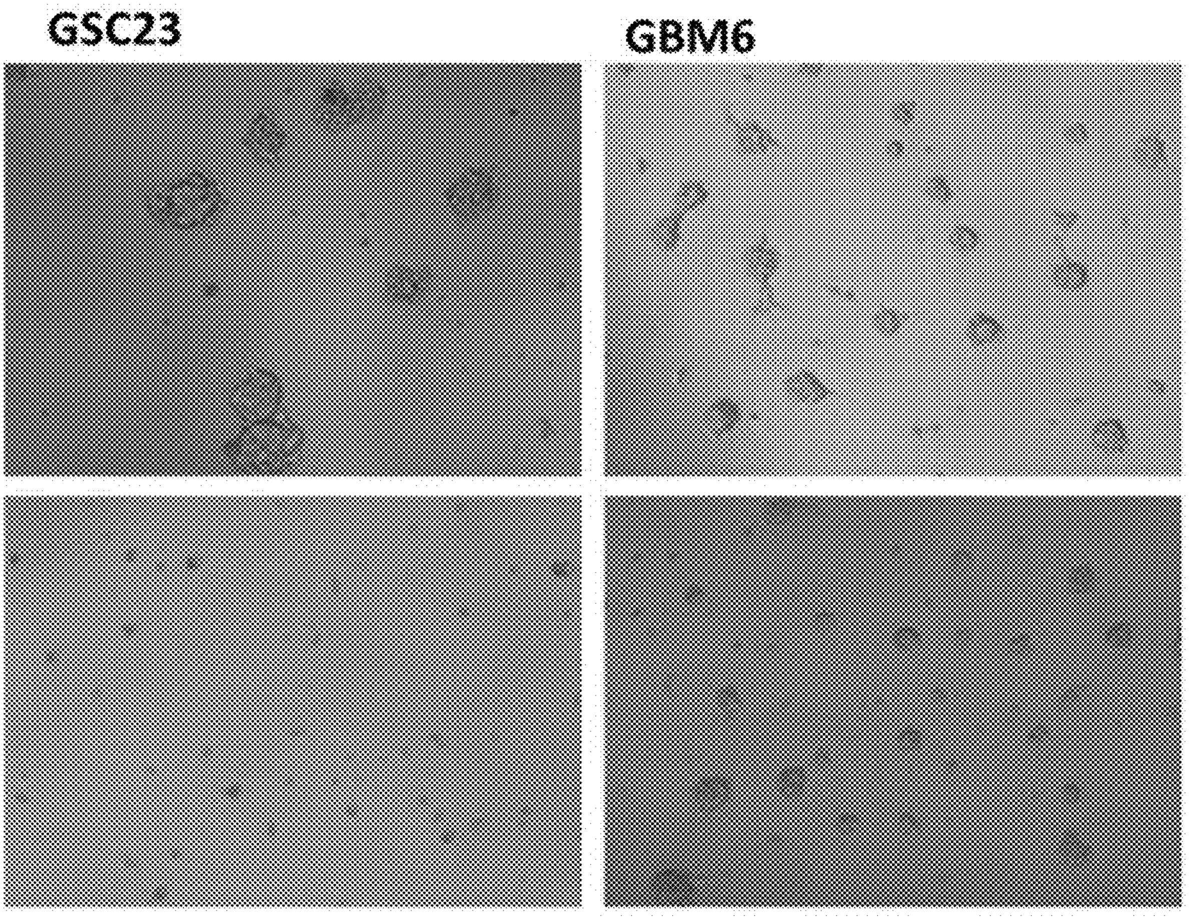
Figure 29D:
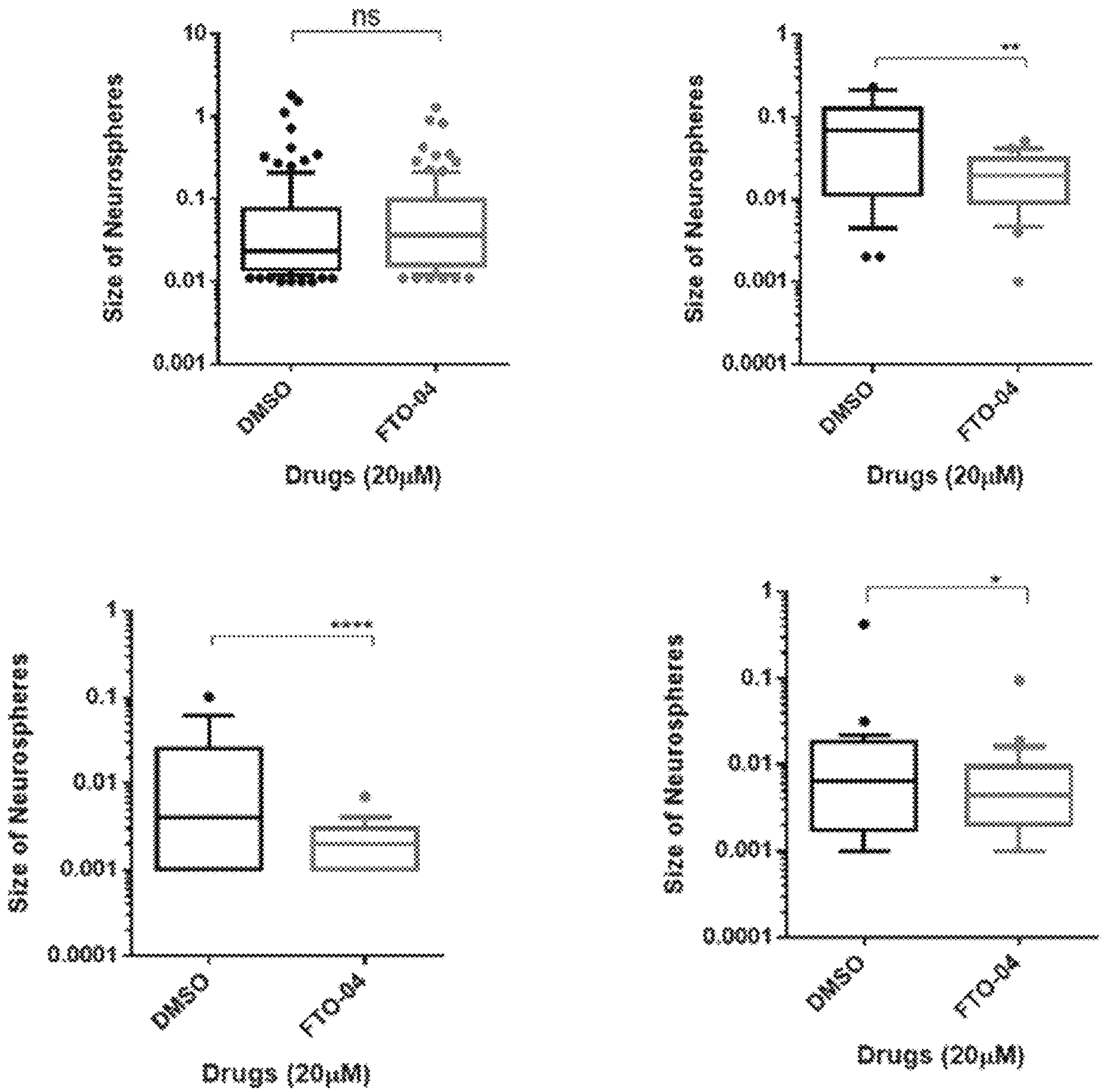
Figure 30:
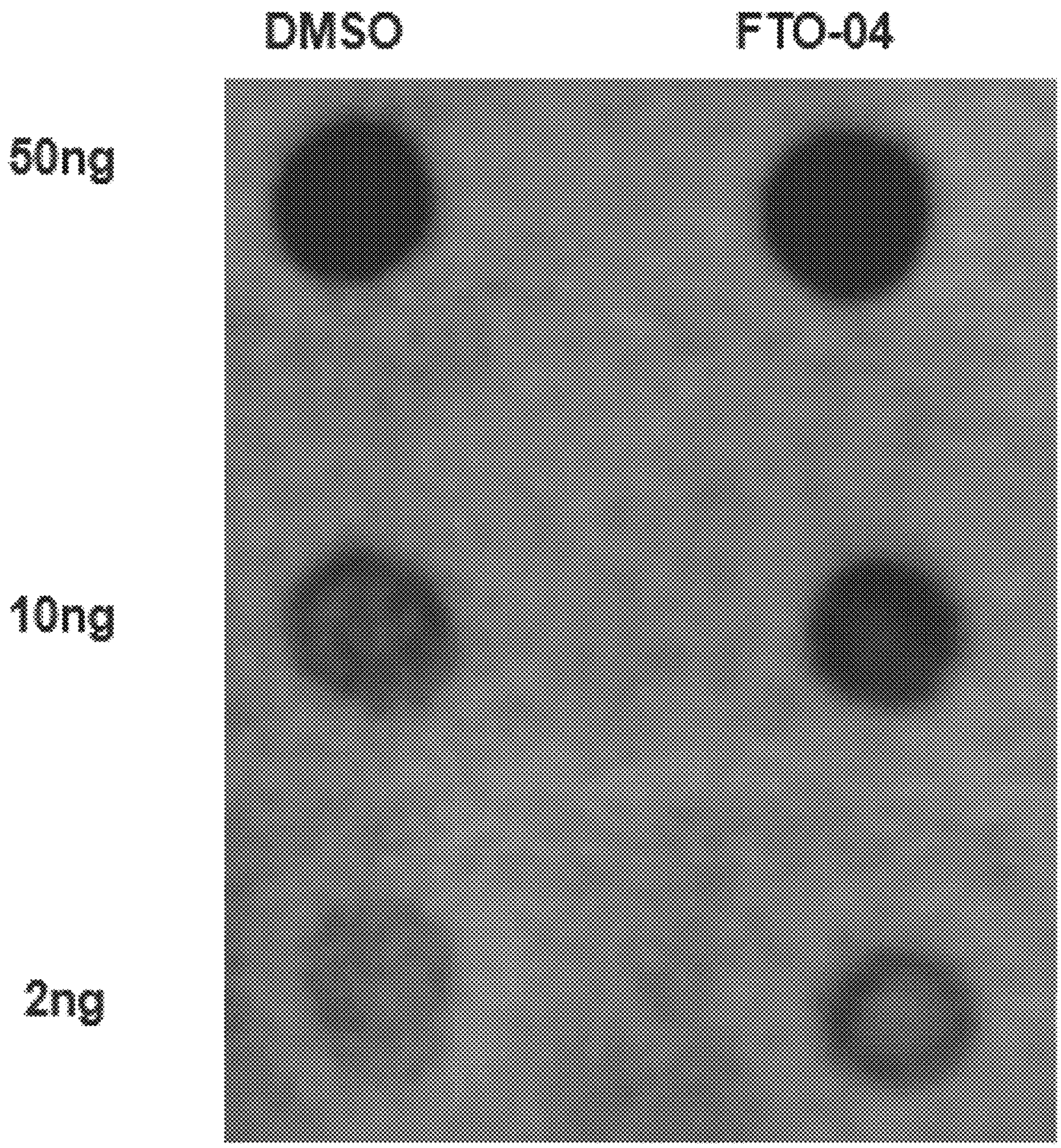
FIG. 30. m6a enrichment in mRNA from TS576 treated with F TO inhibitor: m6A dot blot assays using poly(A)+ mRNA of TS576 glioblastoma stem cells treated with DMSO and FTO inhibitor (F TO-04).
Figure 31A:
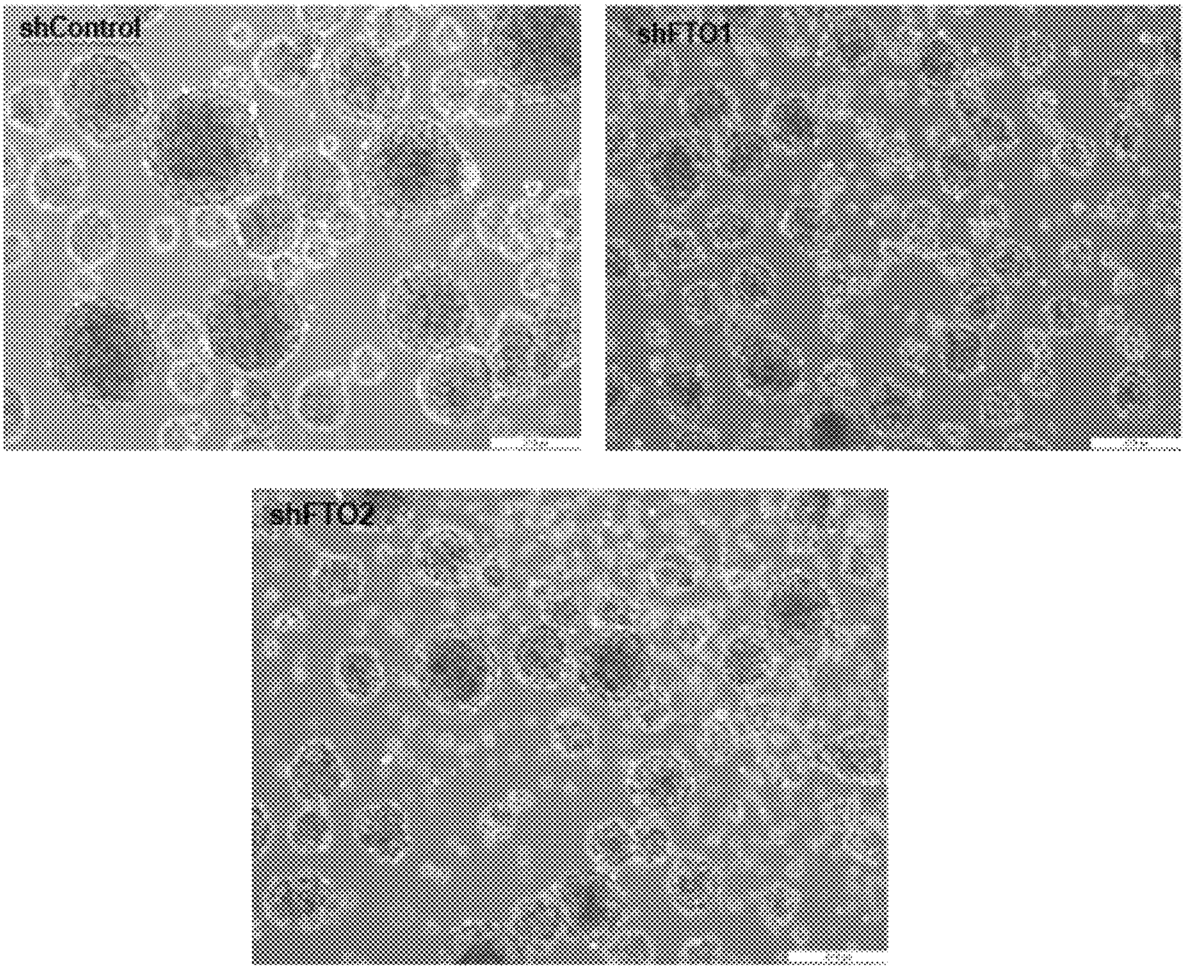
FIG. 31A-31D. Effects of knockdown (KD) of FTO in TS576 cells on size of tumorospheres and m6A level.
Figure 31B:
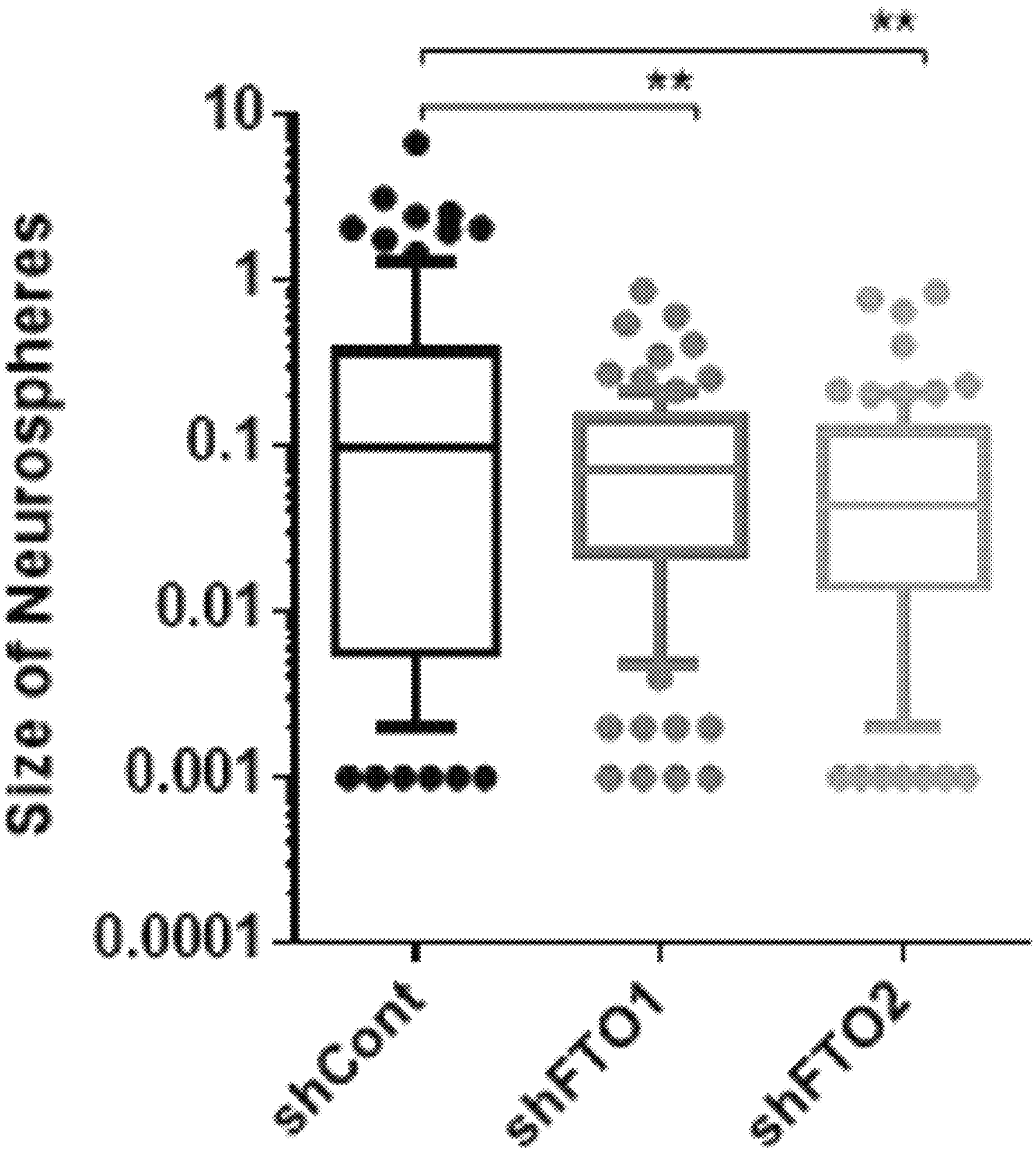
Figure 31C:
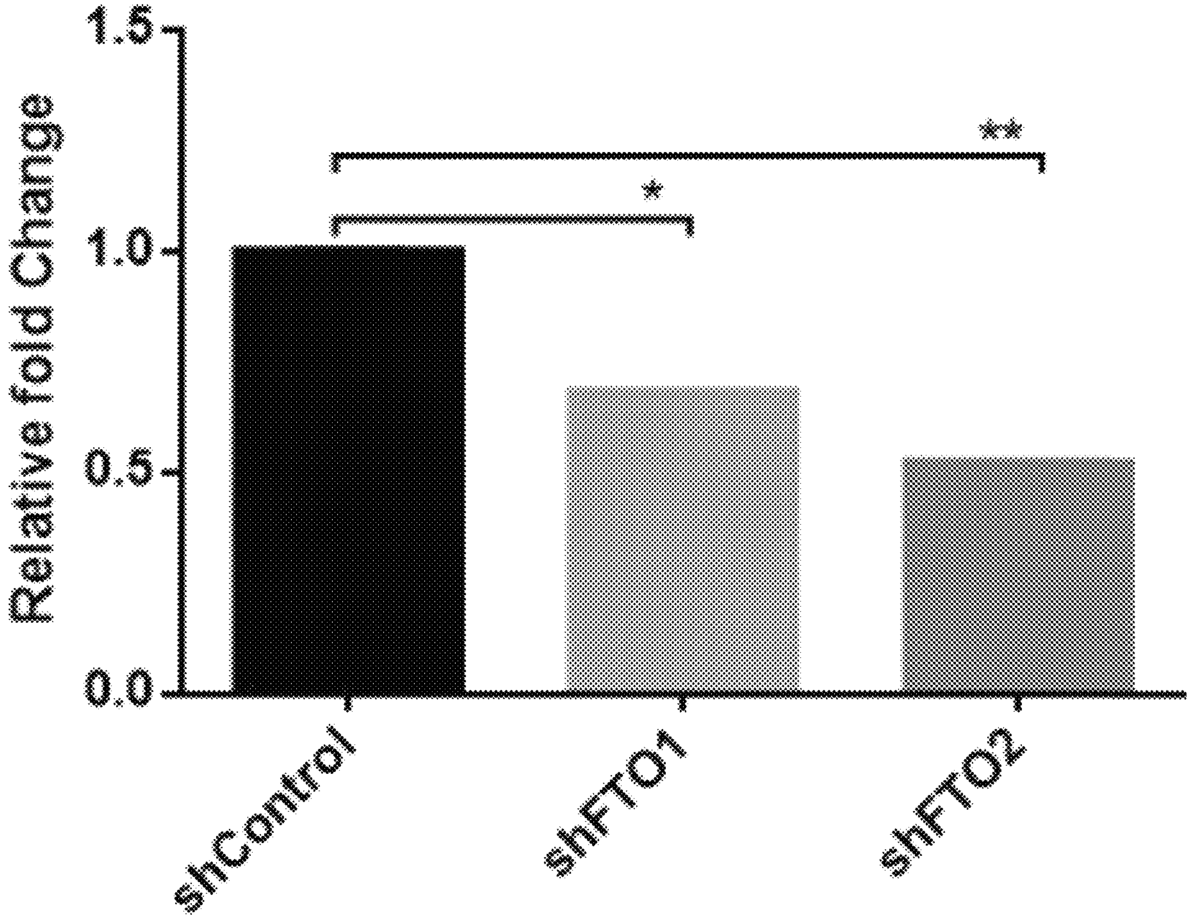
Figure 31D:
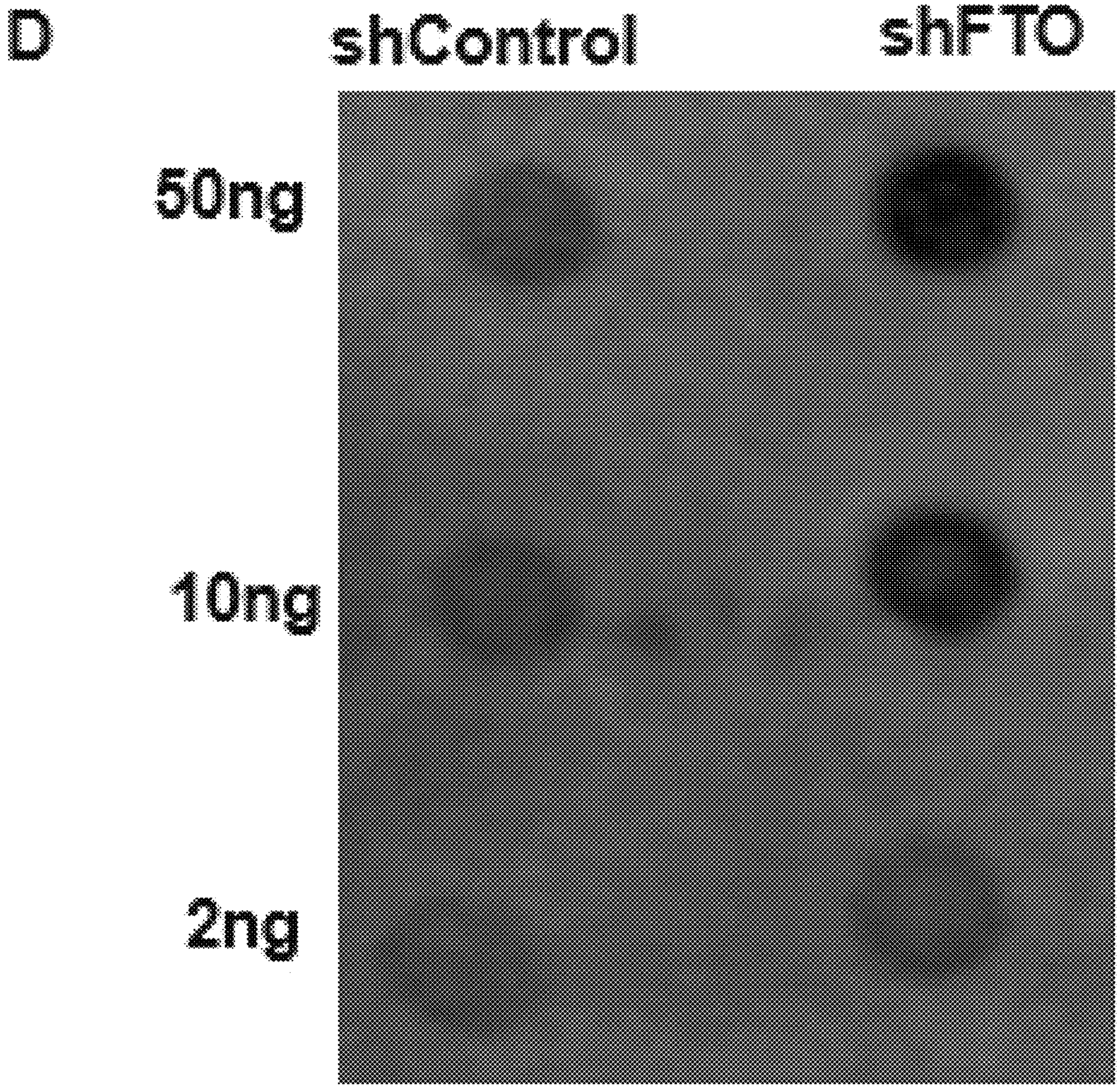
Figure 32:
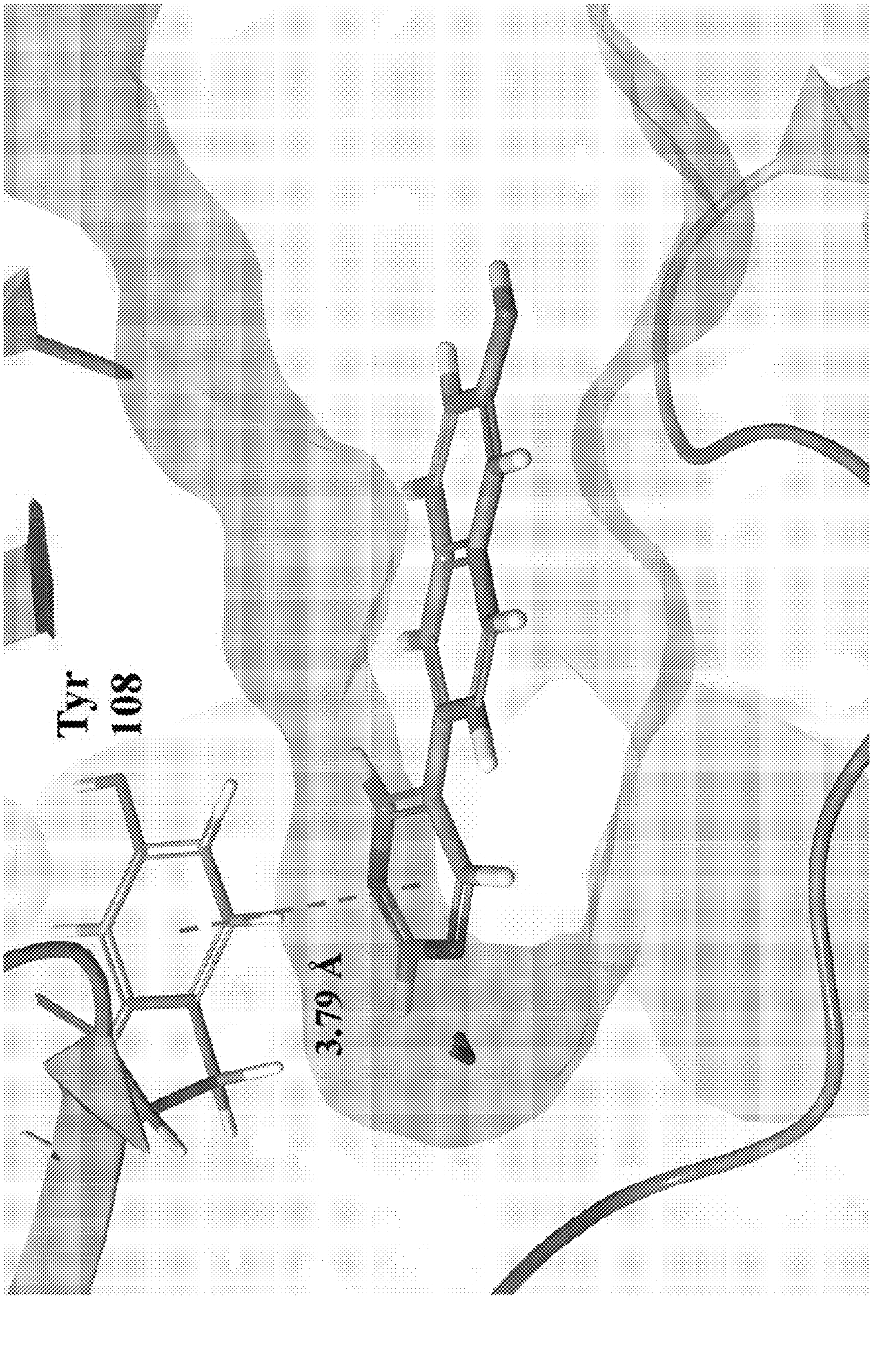
FIG. 32. Predicted binding pose of FTO-OI at the MA binding site of FTO. A π-π stacking interaction is observed with Tyr 108.
Figure 33:
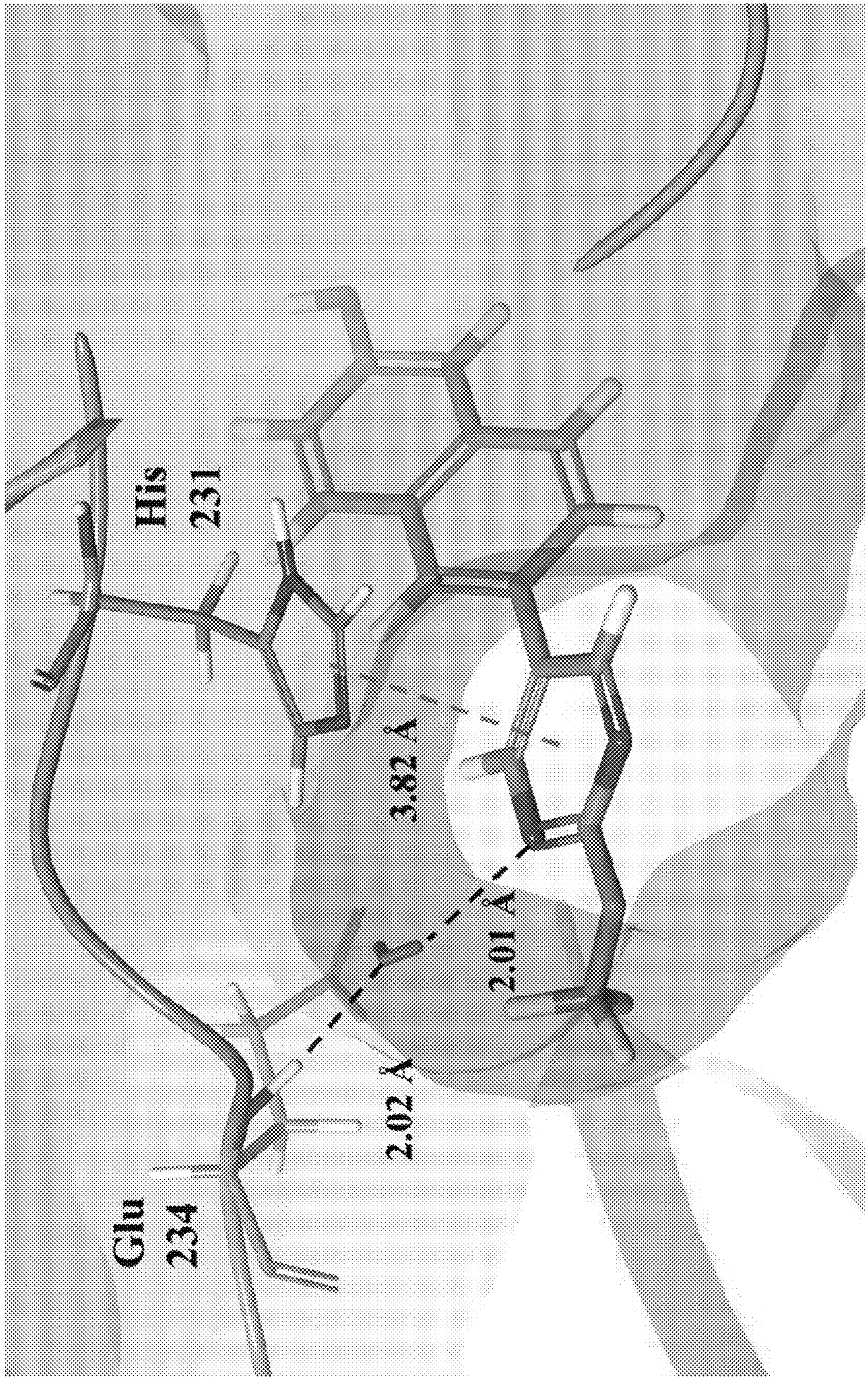
FIG. 33. Predicted binding pose of FTO-02 at the MA binding site of FTO. A water mediated hydrogen bond is expected between the pyrimidine ring of FTO-02 and the backbone of Glu 234. A π-π stacking interaction is observed with His 231.
Figure 34:
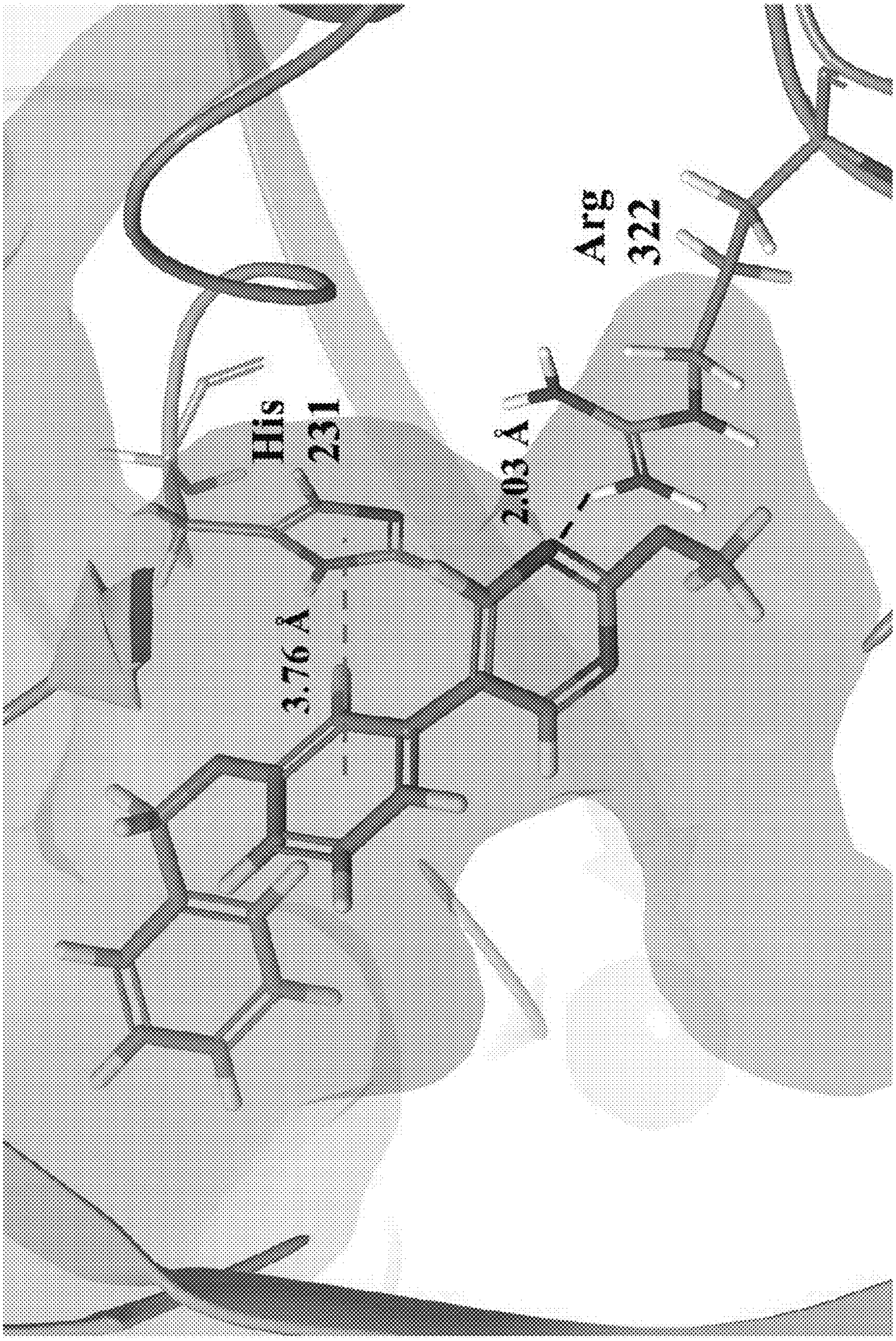
FIG. 34. Predicted binding pose of FTO-03 at the MA binding site of FTO. A π-π stacking interaction is observed with His 231, and a hydrogen bonding interaction is expected between Arg 322 and the pyrimidine ring of FTO-03.
Figure 35:
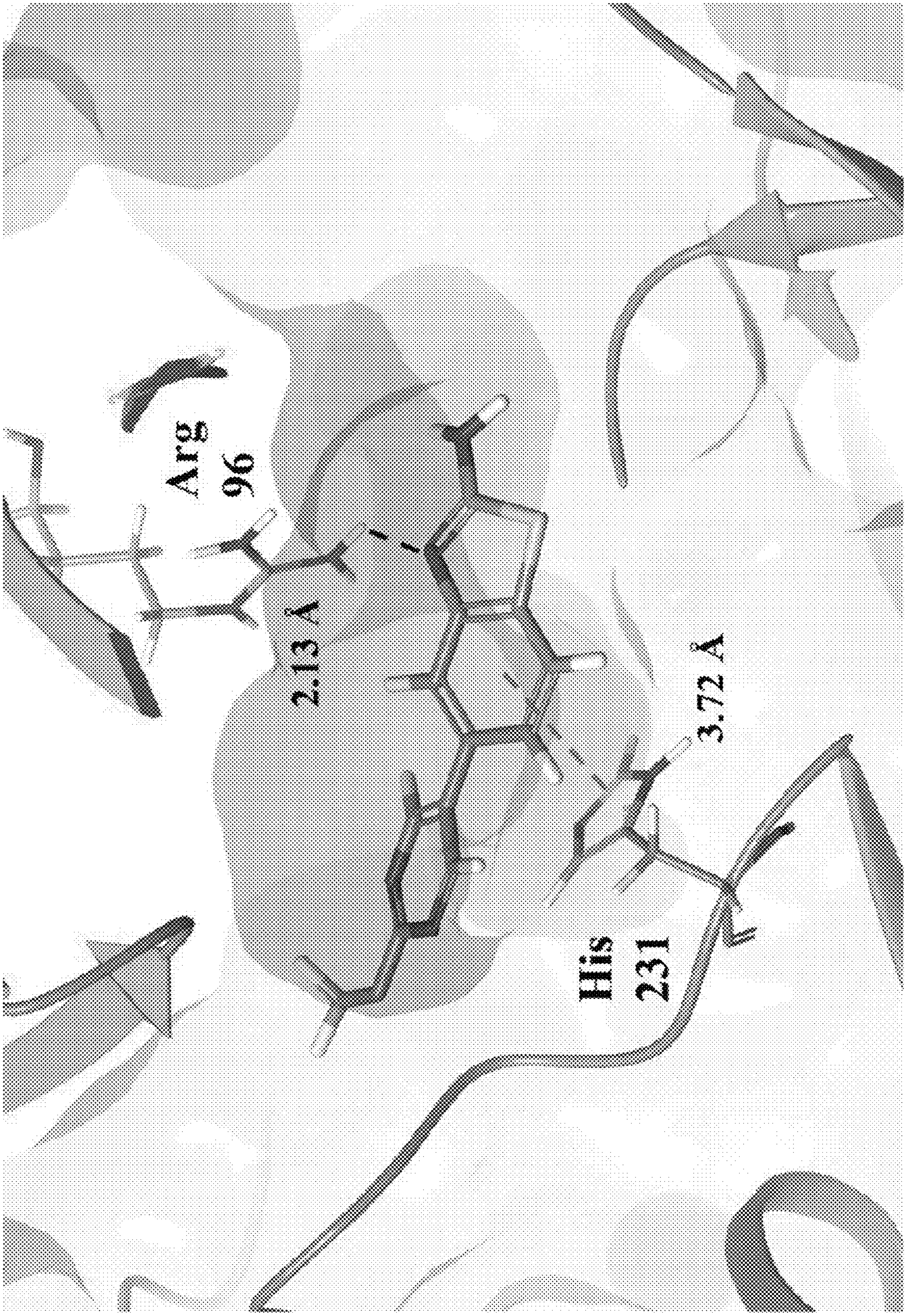
FIG. 35. Predicted binding pose of FTO-04 at the MA binding site of FTO. A π-π stacking interaction is observed with His 231, and a hydrogen bonding interaction is expected between Arg 96 and the benzothiazole ring of FTO-04.
Figure 36:
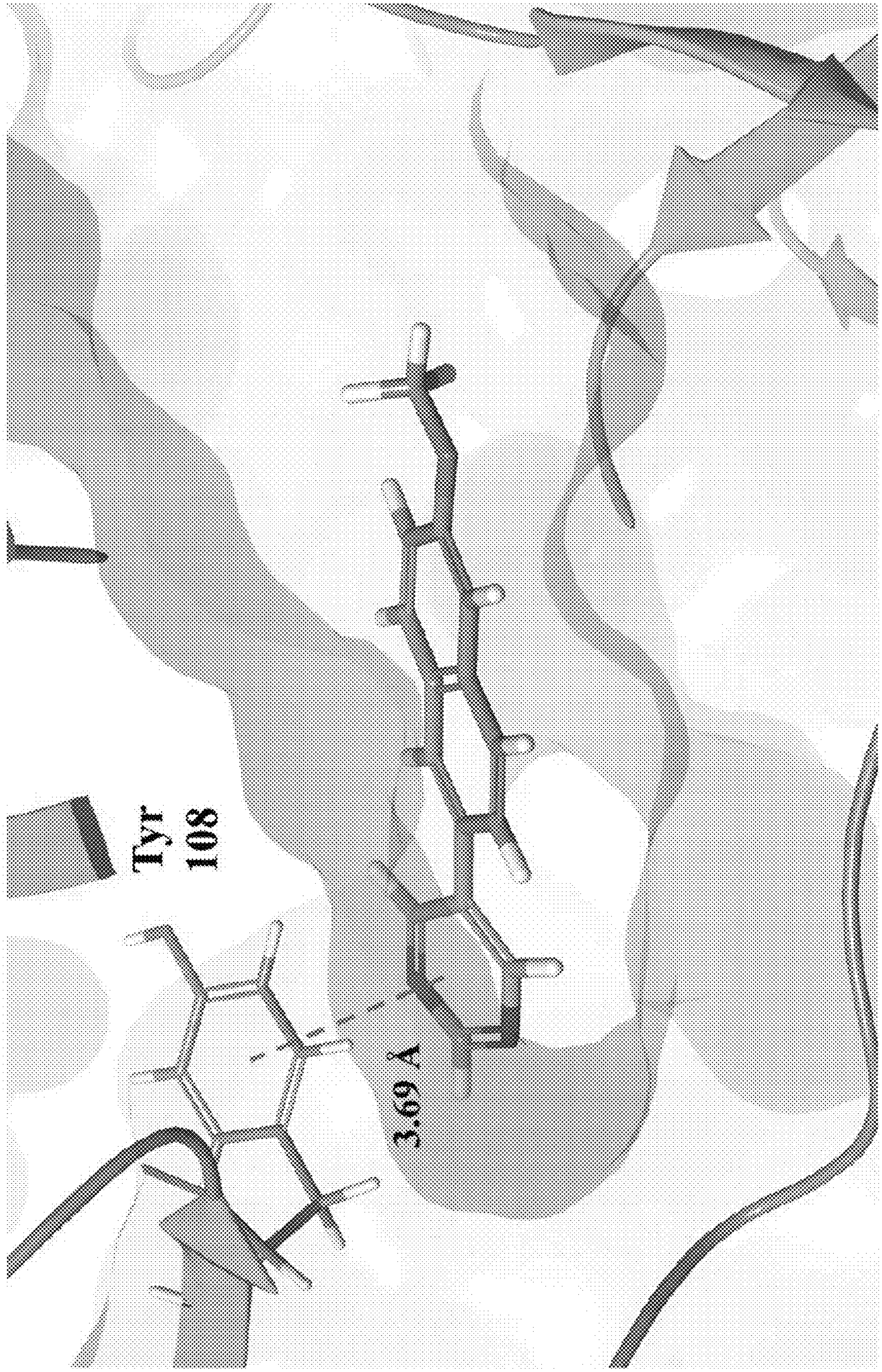
FIG. 36. Predicted binding pose of FTO-OS at the MA binding site of FTO. A π-π stacking interaction is observed with Tyr 108.
Figure 37:
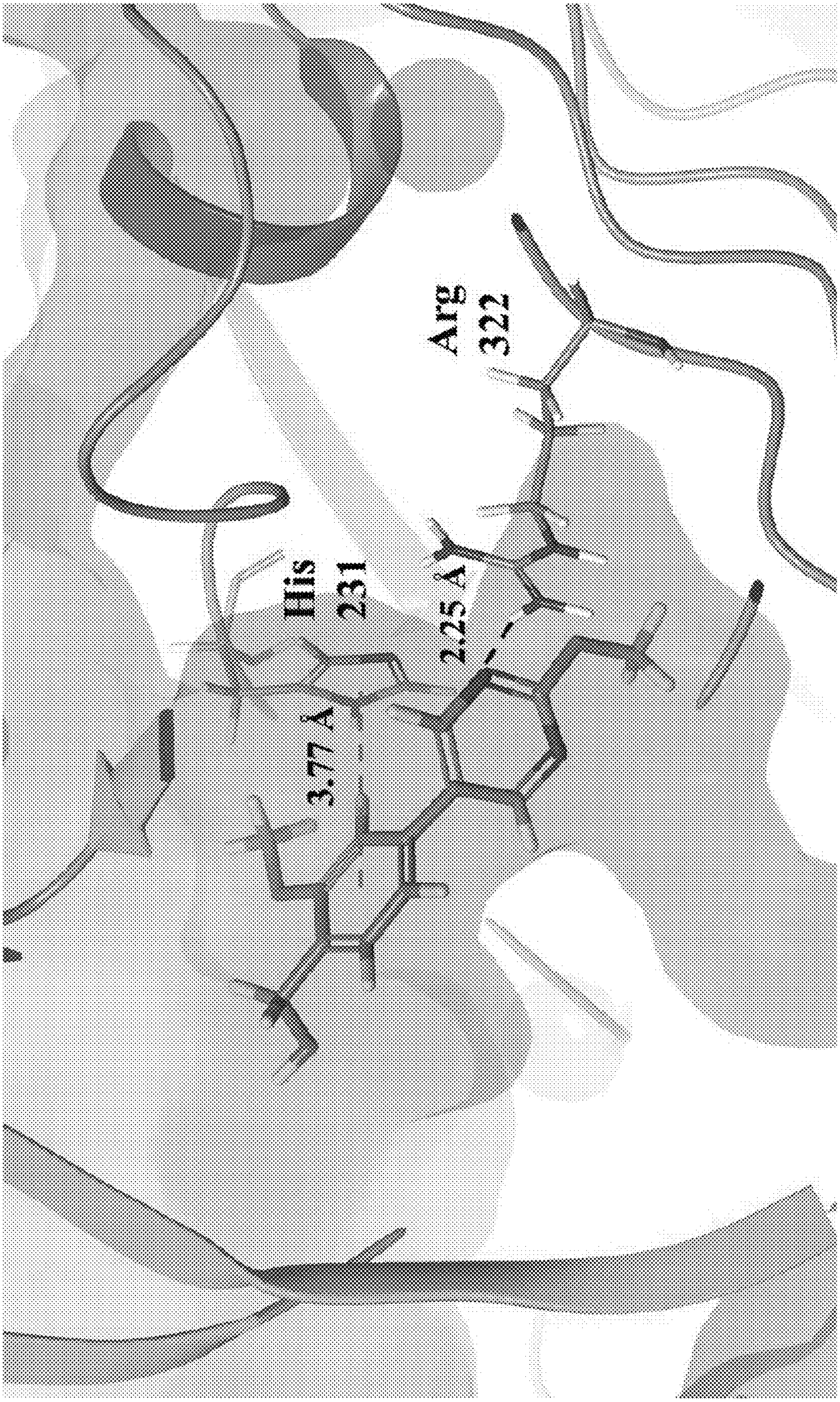
FIG. 37. Predicted binding pose of FTO-06 at the MA binding site of FTO. A hydrogen bond is observed between Arg 322 and the pyrimidine ring of FTO-06, A π-π stacking interaction is observed with His 231.
Figure 38:
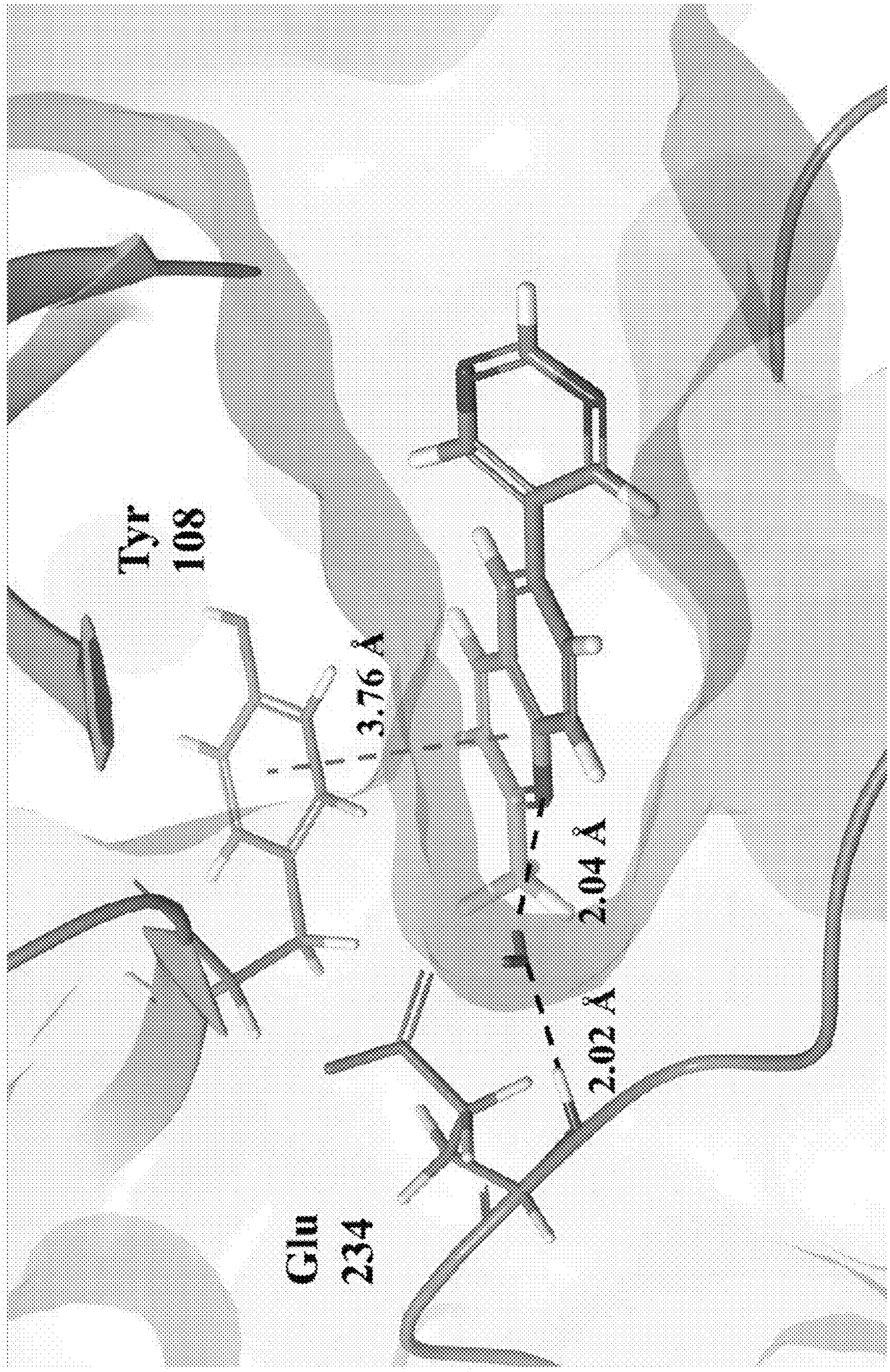
FIG. 38. Predicted binding pose of FTO-07 at the MA binding site of FTO. A water-mediated hydrogen bond is observed between the backbone of Glu 234 and the nitrogen atom of the 2-methylquinoline ring. A π-π stacking interaction is observed with Tyr 108.
Figure 39:
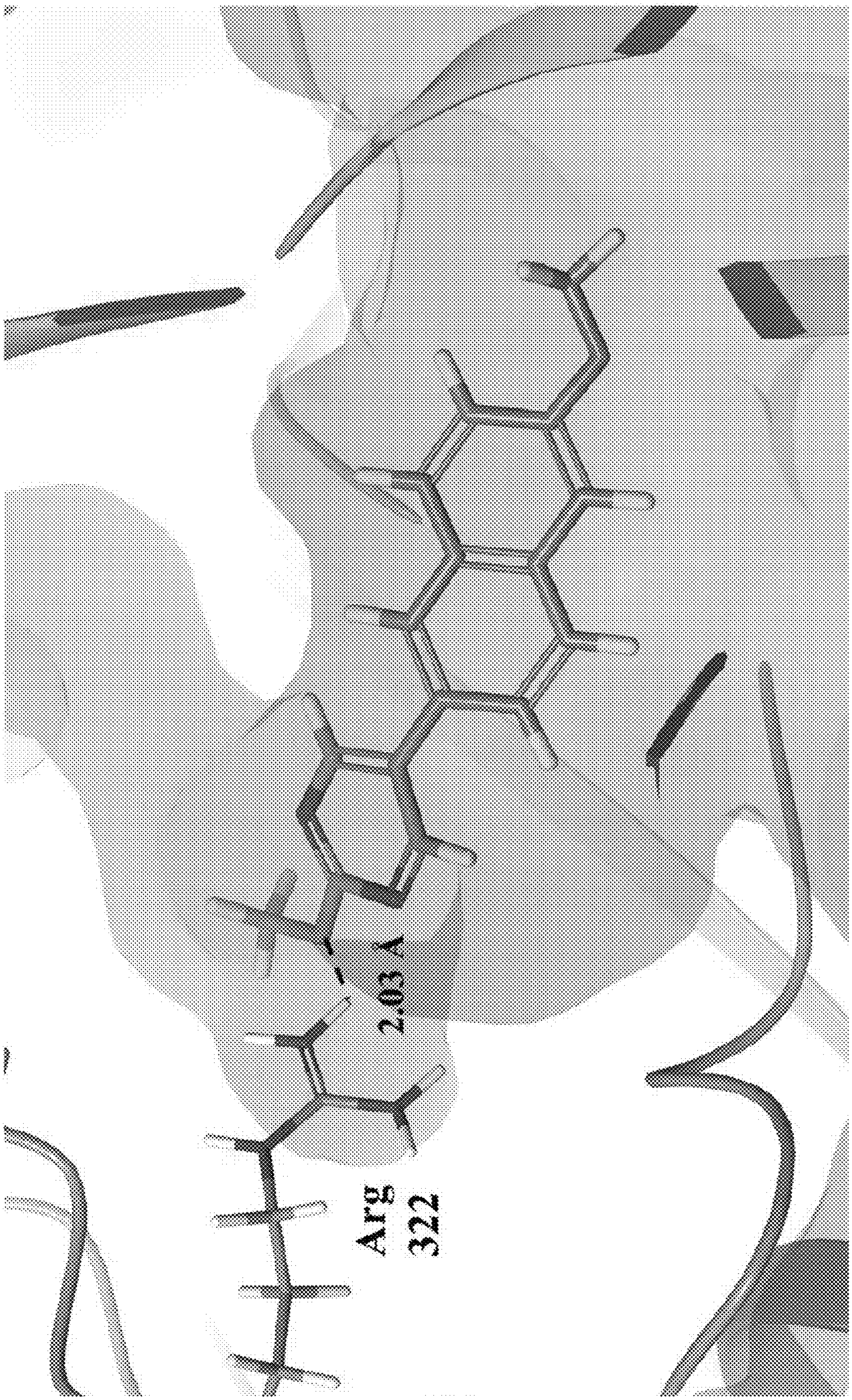
FIG. 39. Predicted binding pose of FTO-08 at the MA binding site of FTO. A hydrogen bond is observed between Arg 322 and the oxygen atom of the 2-methoxypyrimidine ring.
Figure 40:
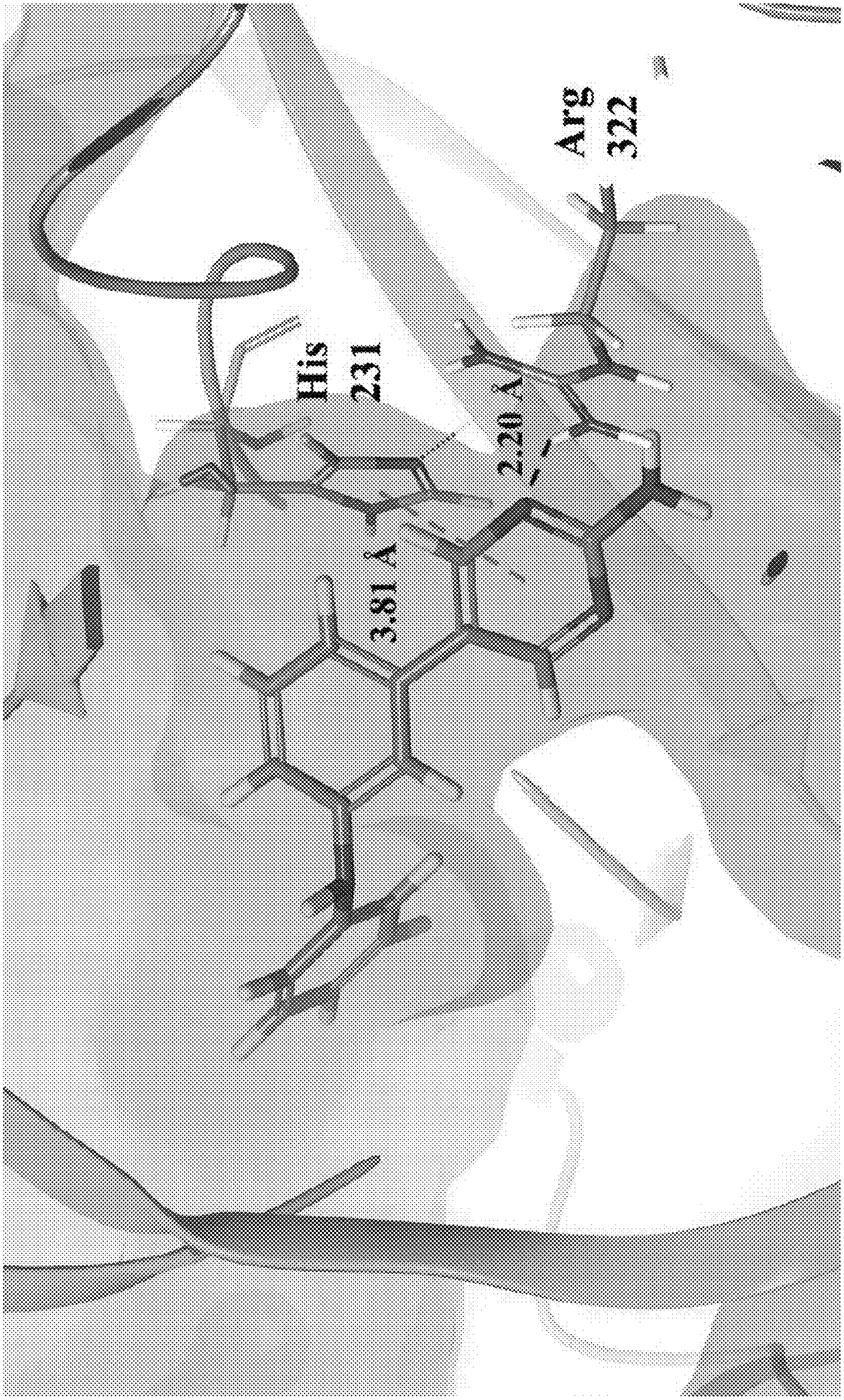
FIG. 40. Predicted binding pose of FTO-09 at the MA binding site. The pyrimidine ring is observed to form a hydrogen bond to Arg 322, and a π-π stacking interaction with His 231.
Figure 41:
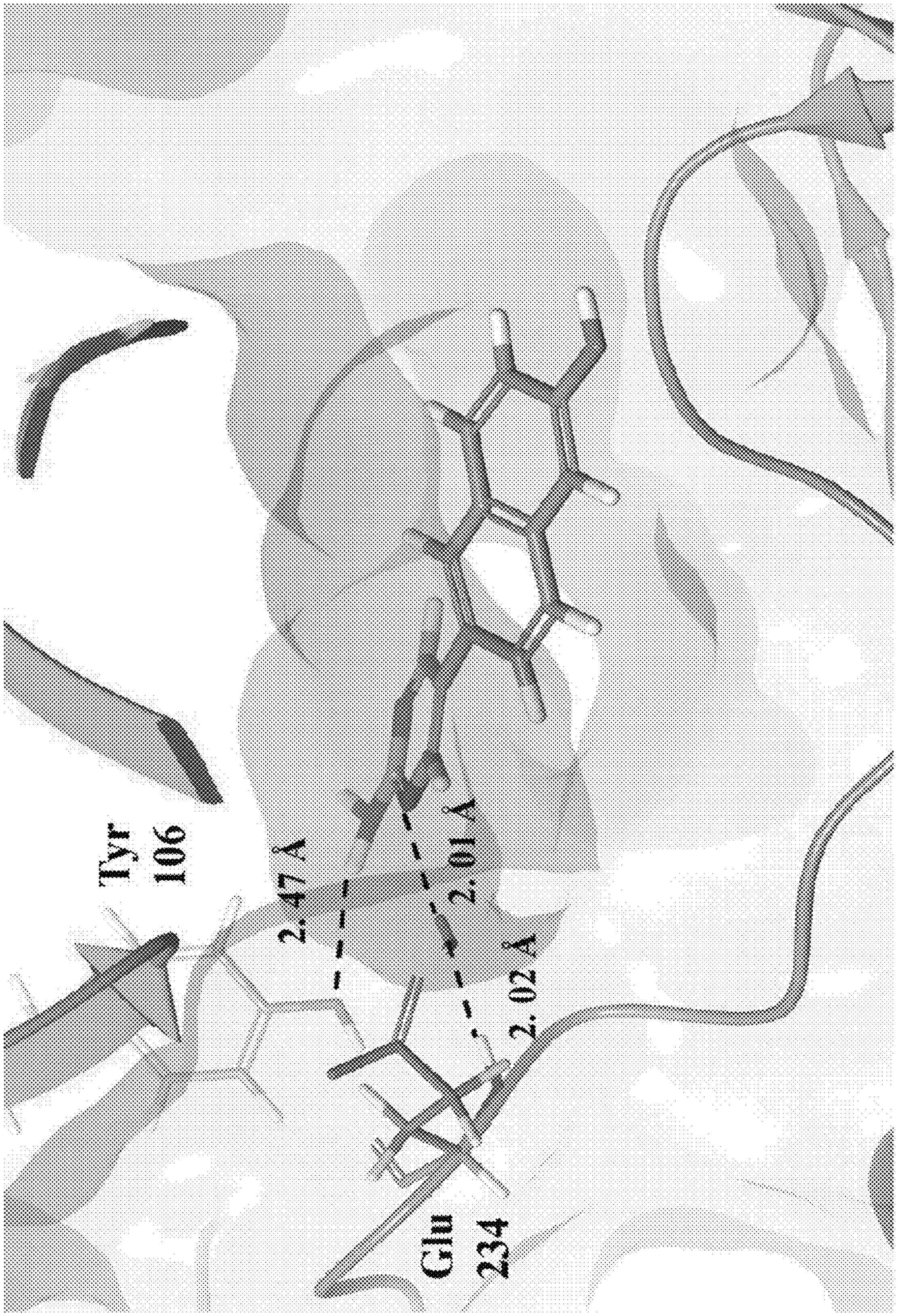
FIG. 41. Predicted binding pose of FTO-10 at the MA binding site of FTO. A water-mediated hydrogen bond is observed between Glu 234 and the pyrimidine ring of FTO-10. A hydrogen bond is observed between the amino group of the 2-aminopyrimidine and Tyr 106.
Figure 42:
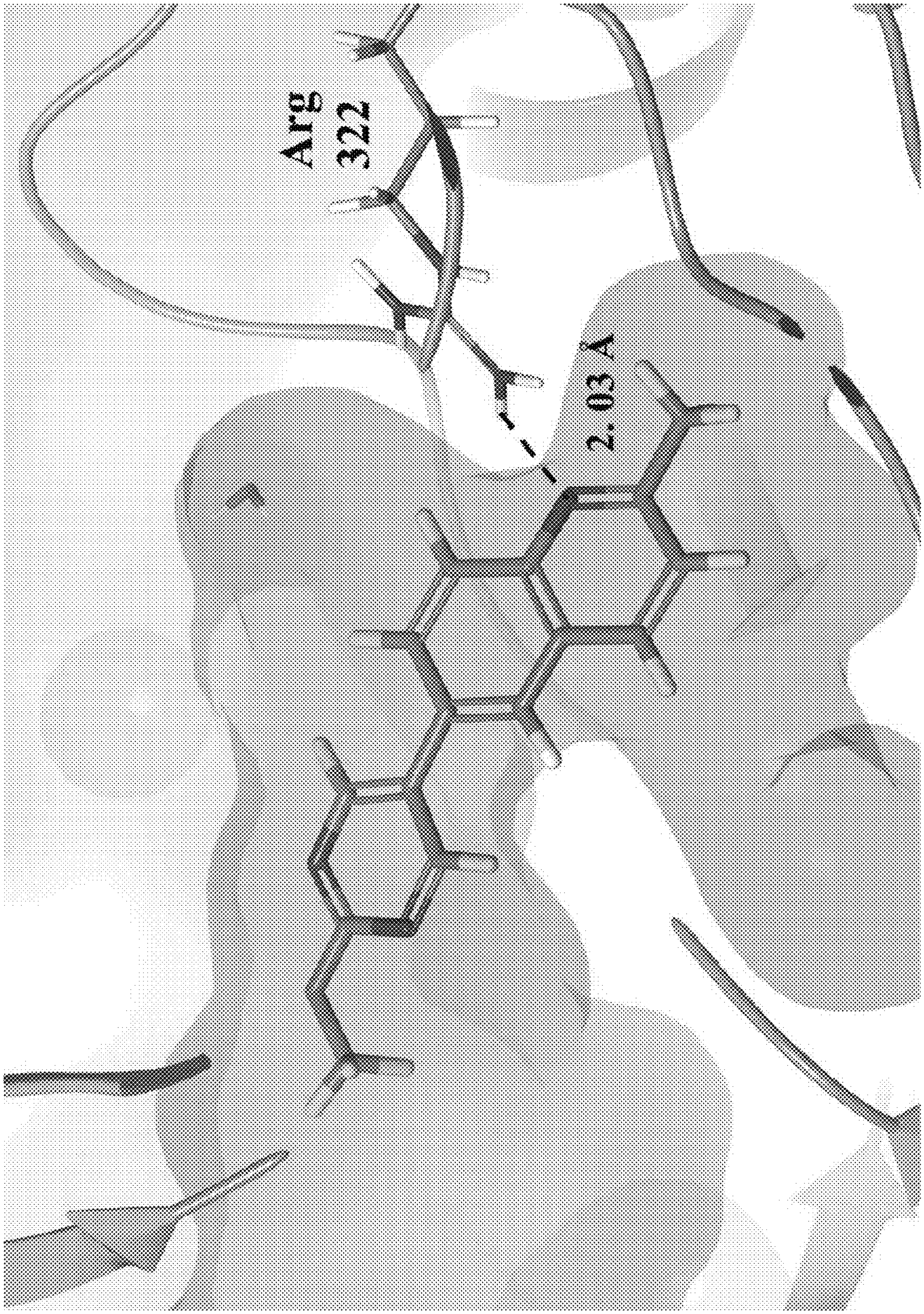
FIG. 42. Predicted binding pose of FTO-I I at the MA binding site of FTO. A hydrogen bond is observed between Arg 322 and the nitrogen atom of the 2-methylquinoline ring.
Figure 43:
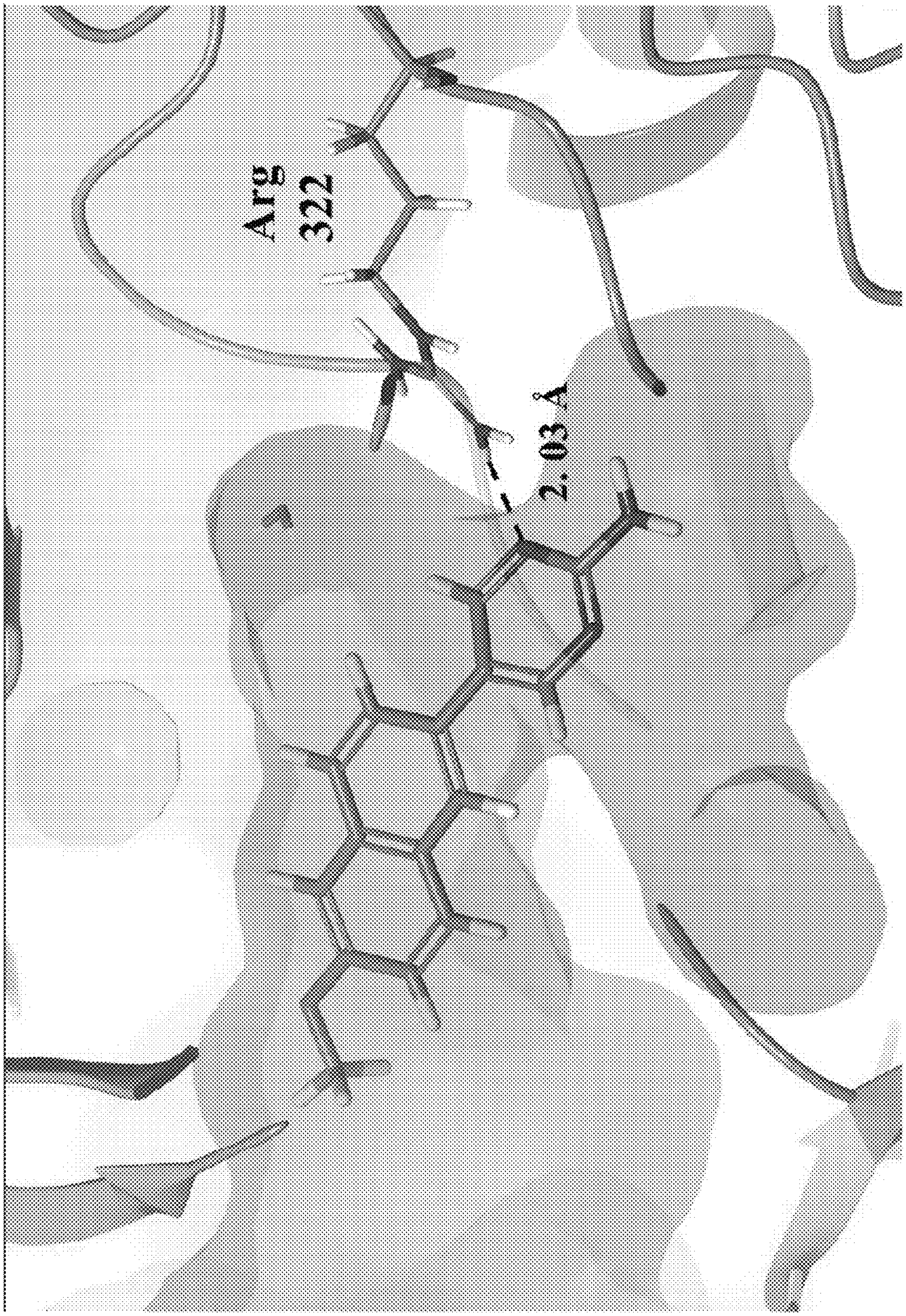
FIG. 43. Predicted binding pose of FTO-12 at the MA binding site of FTO. A hydrogen bond is observed between the pyrimidine ring of FTO-12 and Arg 322.
Figure 44:
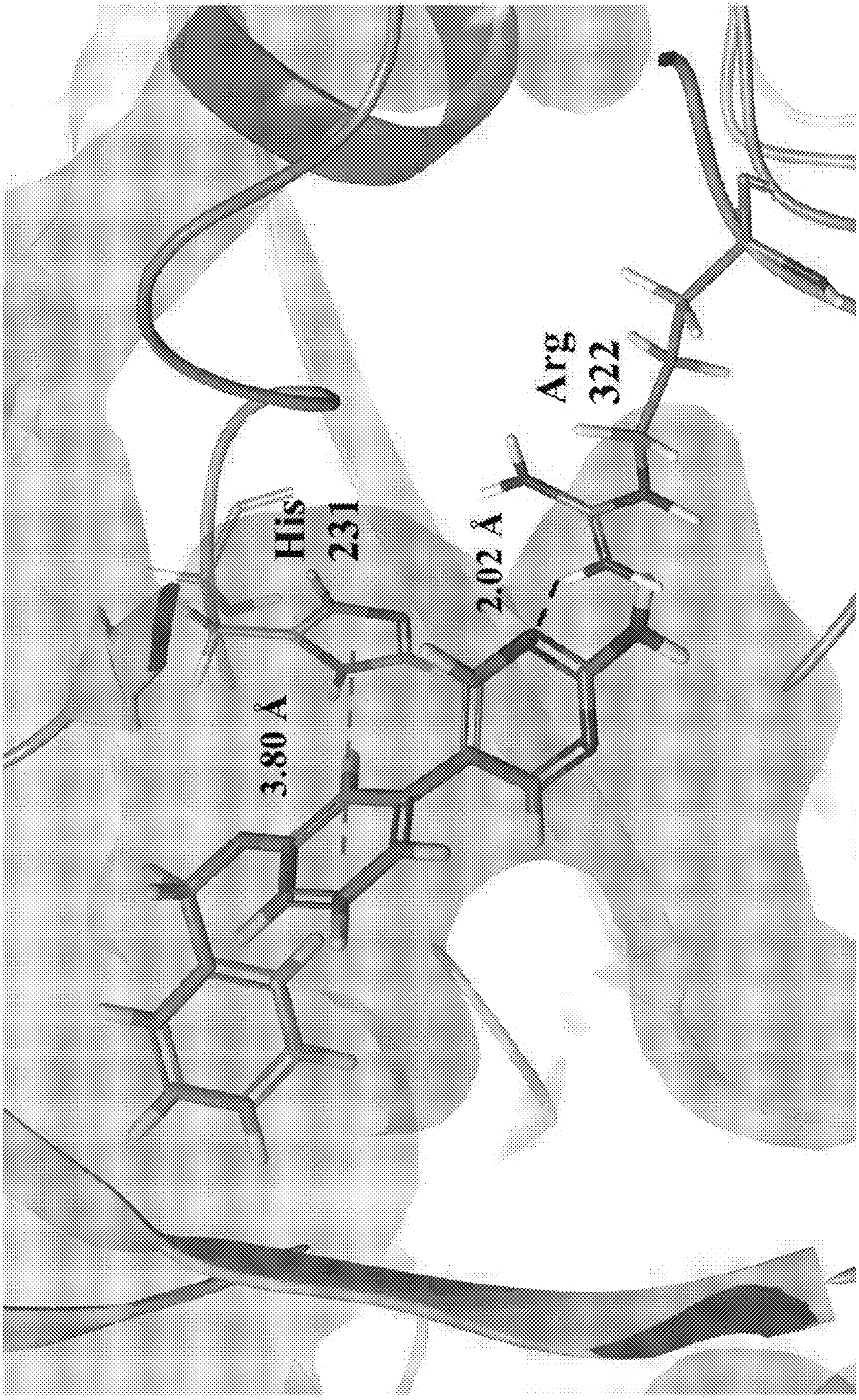
FIG. 44. Predicted binding pose of FTO-13 at the MA binding site of FTO. A benzene ring in FTO-13 is observed to form π-π stacking interactions with His 231 and the pyrimidine ring is predicted to form a hydrogen bond with Arg 322.
Figure 45:
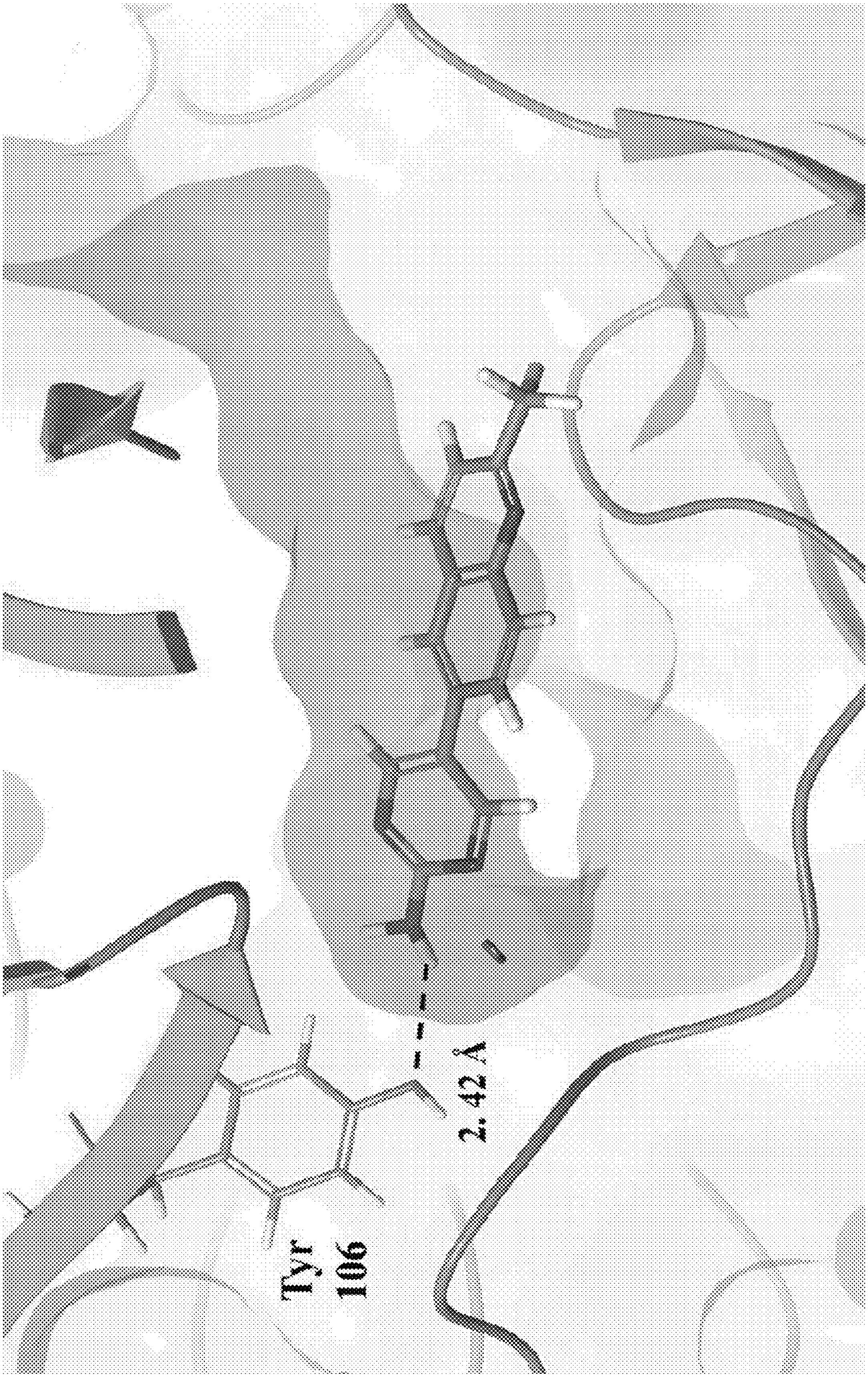
FIG. 45. Predicted binding pose of FTO-14 at the MA binding site of FTO. A hydrogen bond is observed between the amino group of the 2-aminopyrimidine ring of F TO-14 and Tyr 106.
Figure 46:
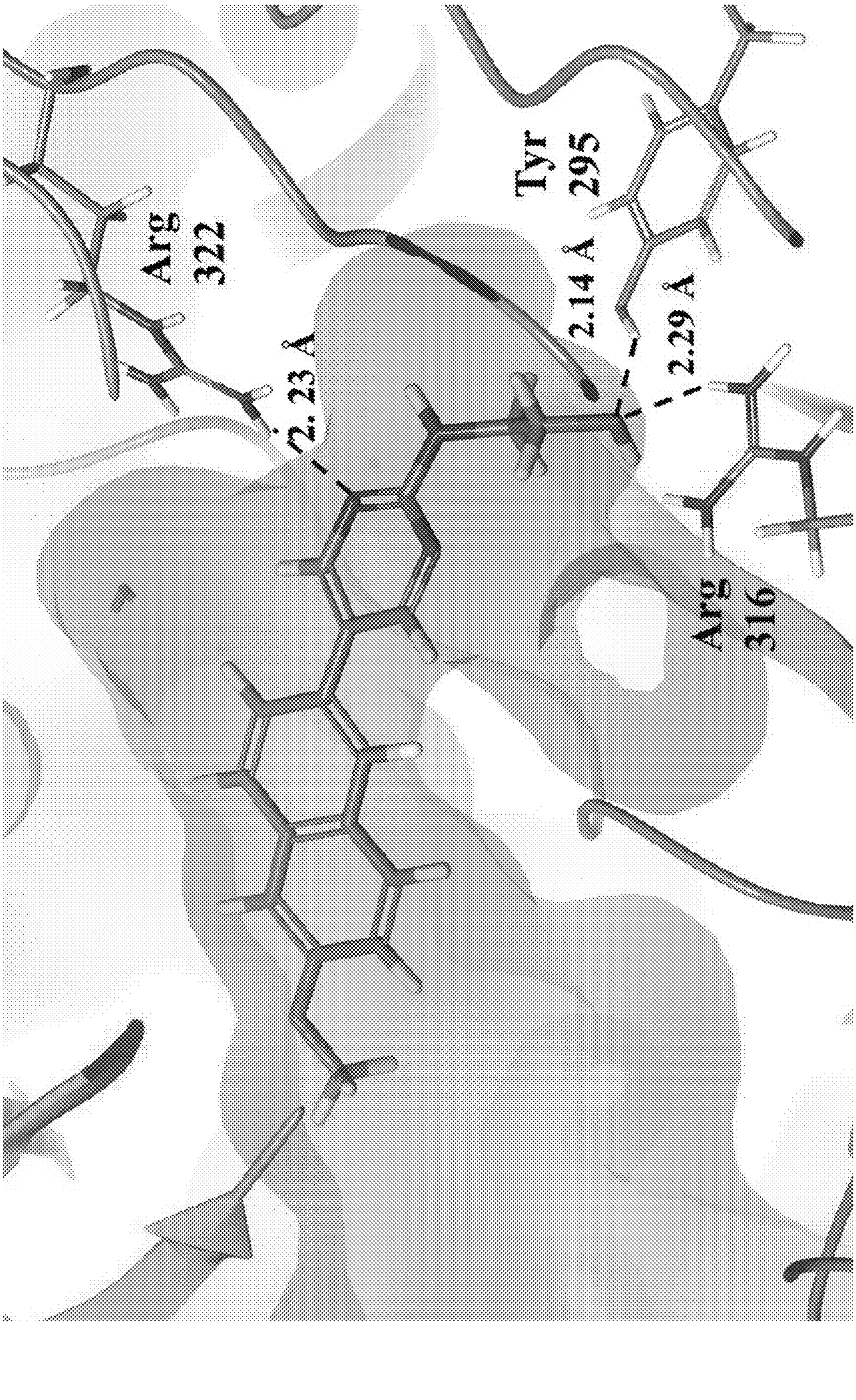
FIG. 46. Predicted binding pose of FTO-15 at the MA binding site of FTO. The pyrimidine ring of FTO-15 is predicted to form a hydrogen bond to Arg 322. Tyr 295 and Arg 316 are observed to form a bifurcated hydrogen bond to the alcohol group of F TO-15.
Figure 47:
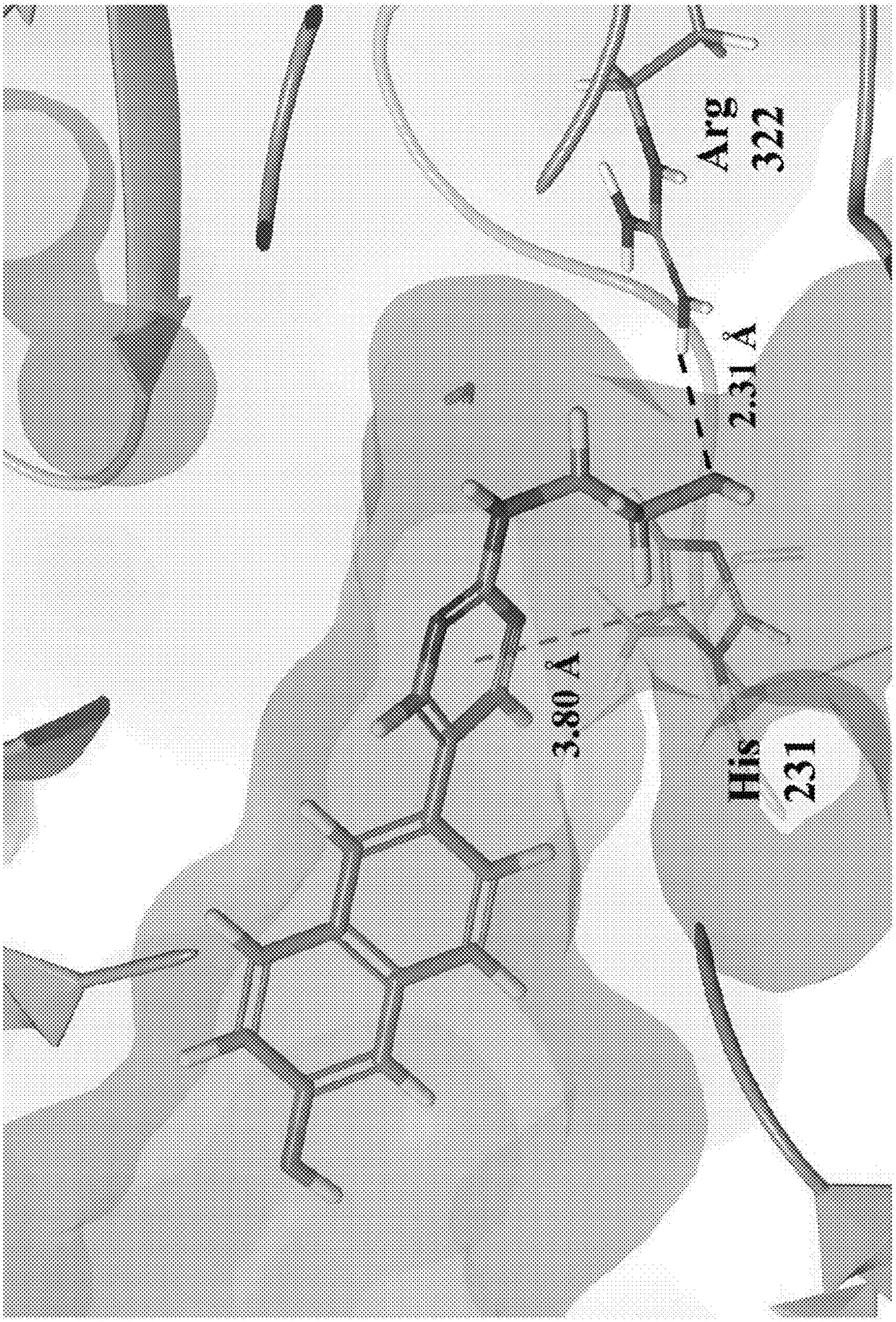
FIG. 47. Predicted binding pose of FTO-16 at the MA binding site of FTO. A π-π stacking interaction is observed between His 231 and the pyrimidine ring of F TO-16. Arg 322 is predicted to form a hydrogen bond to the alcohol group of FTO-16.
Figure 48:
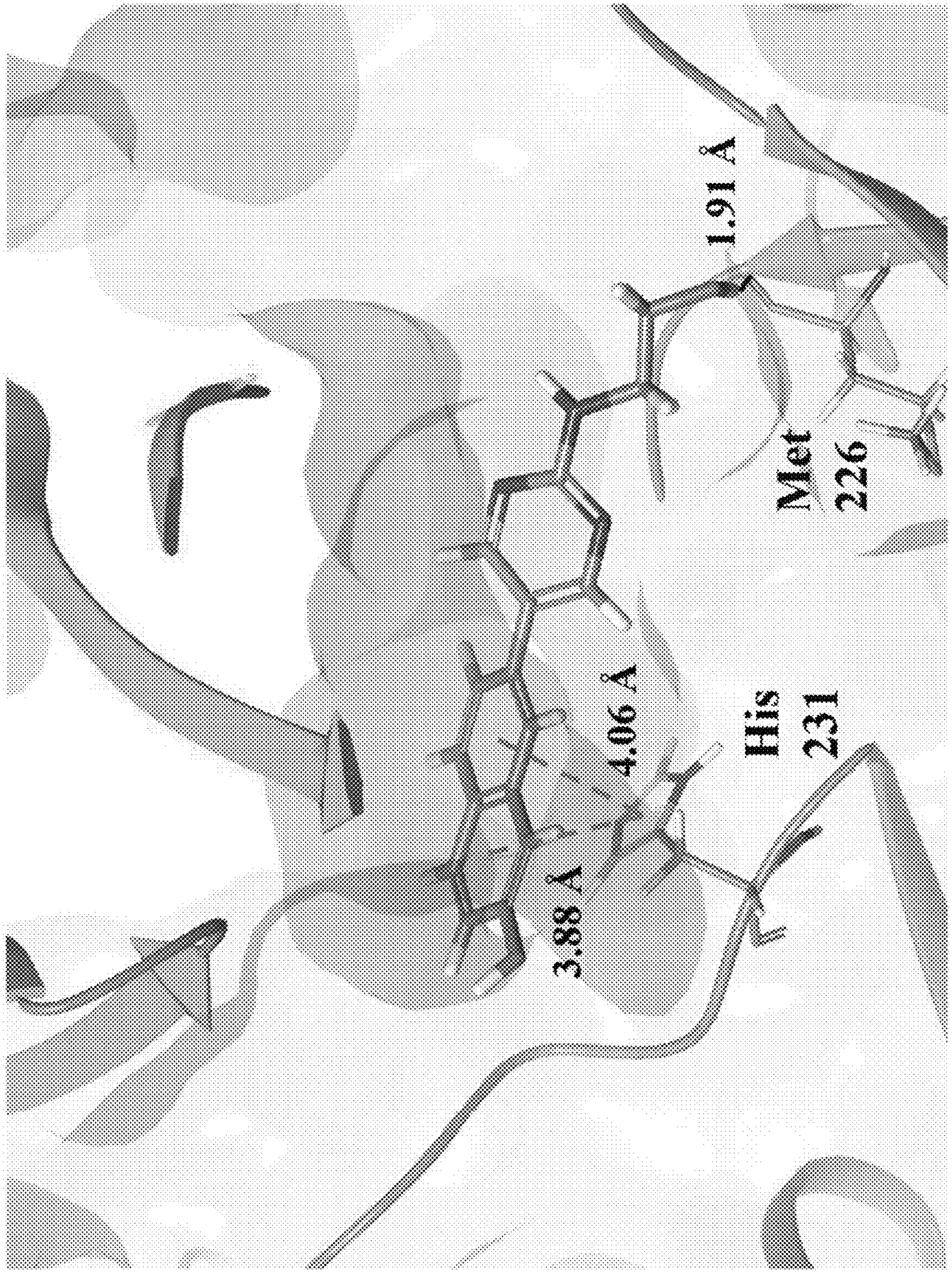
FIG. 48. Predicted binding pose of FTO-17 at the MA binding site of FTO. A π-π stacking interaction is observed between His 231 and the napthol ring of FTO-17. The backbone of Met 226 is predicted to accept a hydrogen bond from the alcohol group of FTO-17.
Figure 49:
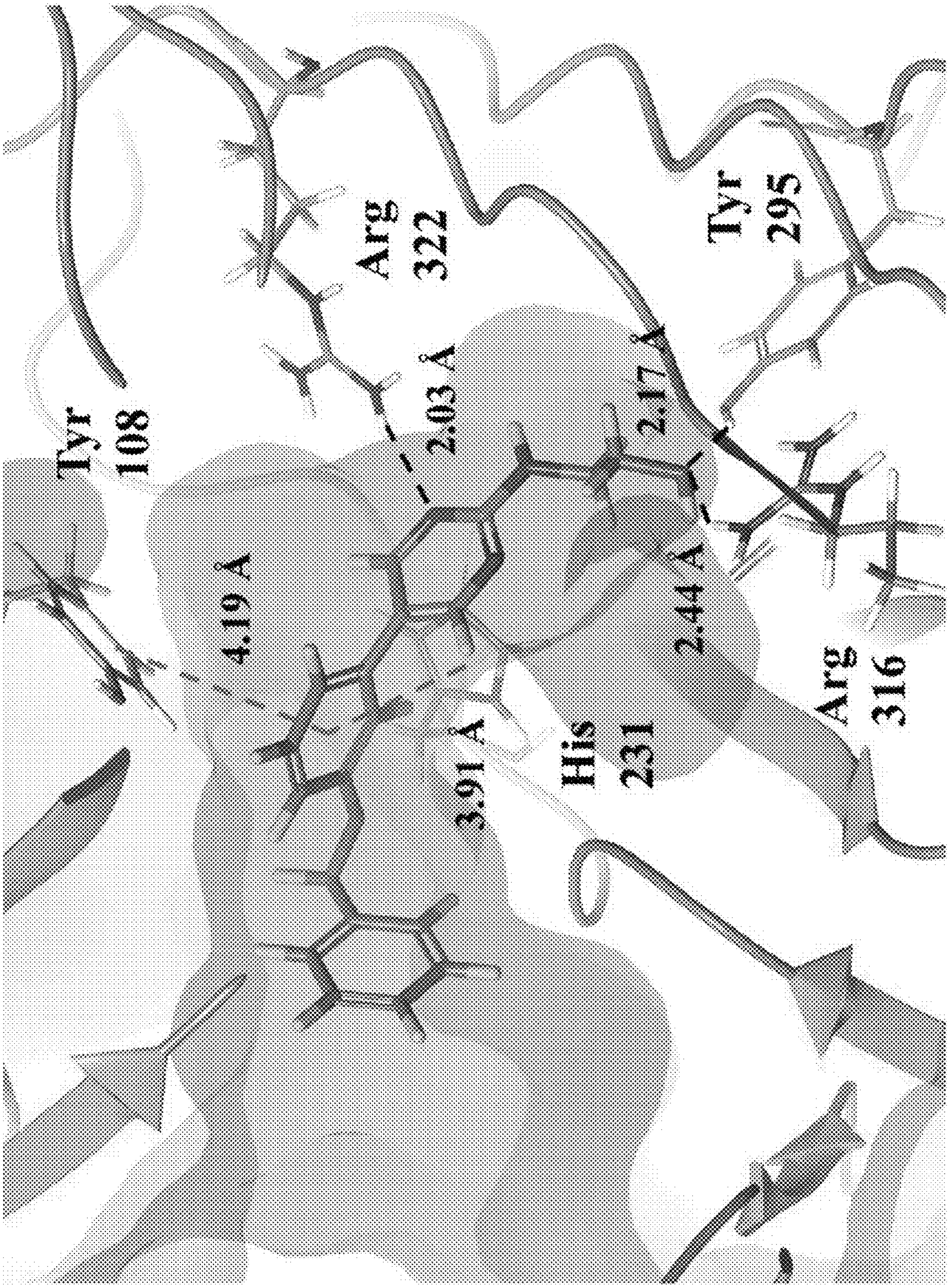
FIG. 49. Predicted binding pose of FTO-18 at the MA binding site of FTO. A benzene ring of FTO-18 is observed to form π-π stacking interactions with His 231 and Tyr 108, and the pyrimidine ring of FTO-18 is expected to form a hydrogen bond to Arg 322. Tyr 295 and Arg 316 are predicted to form a bifurcated hydrogen bond to the alcohol group of FTO-18.
Figure 50:
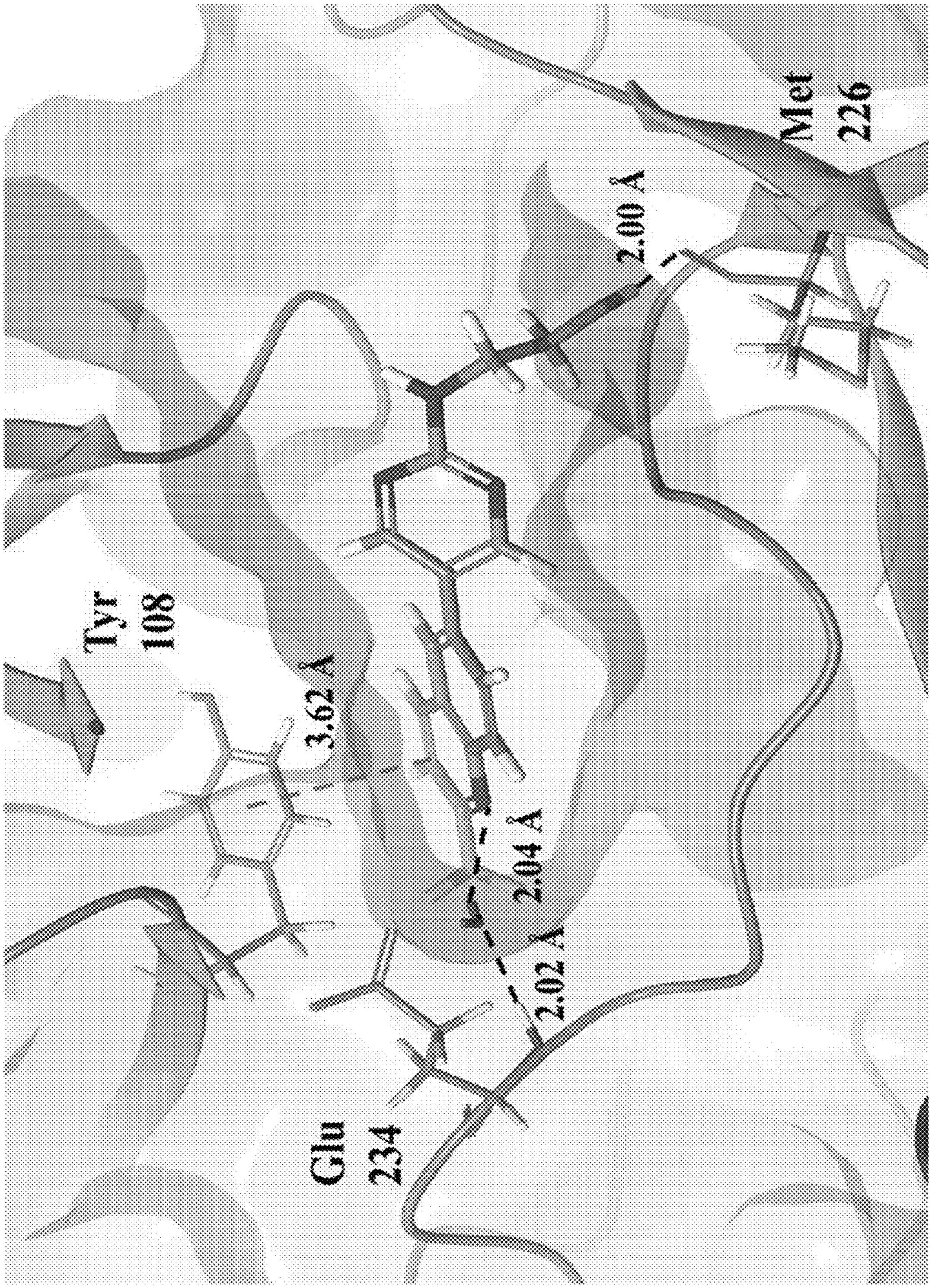
FIG. 50. Predicted binding pose of FTO-19 at the MA binding site of FTO. A water-mediated hydrogen bond is observed between the backbone of Glu 234 and the nitrogen atom of the 2-methylquinoline ring of FTO-19. A stacking interaction is observed between the quinoline ring and Tyr 108.
Figure 51:
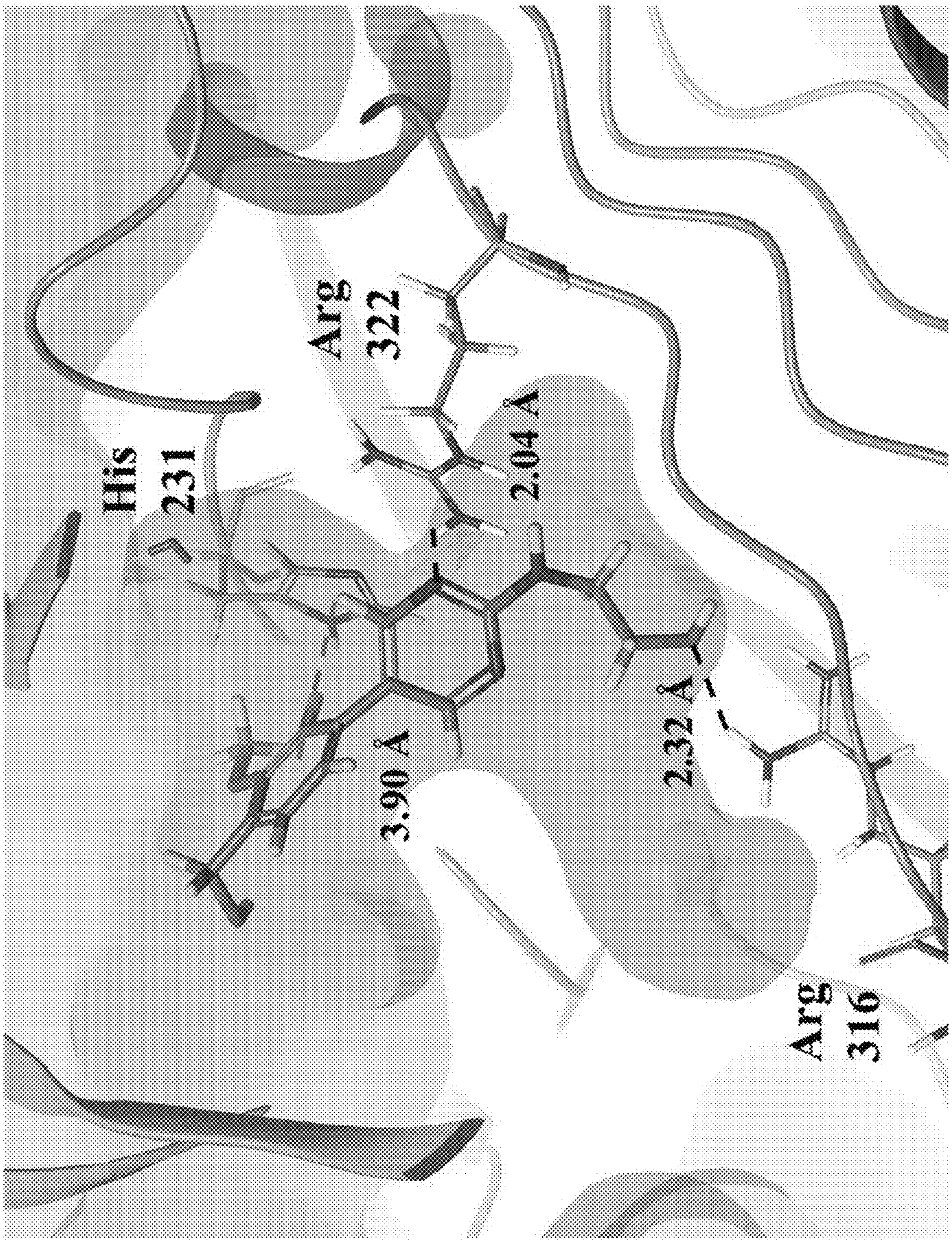
FIG. 51. Predicted binding pose of FTO-20 at the MA binding site of FTO. A π-π stacking interaction is observed with His 231, and hydrogen bonds are predicted with Arg 322 and Arg 316.
Figure 52:
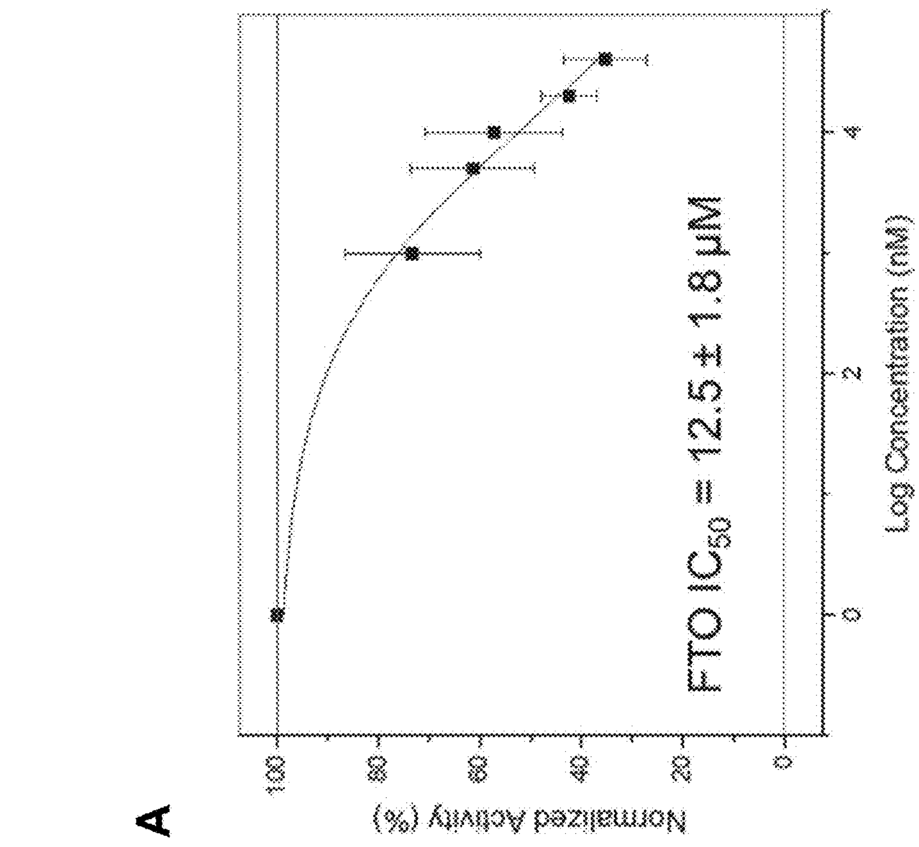
FIG. 52A-52B. Inhibition of FTO by meclofenamic acid. The observed IC50 value of 12.5 11M is comparable to literature values.
Figure 58A:
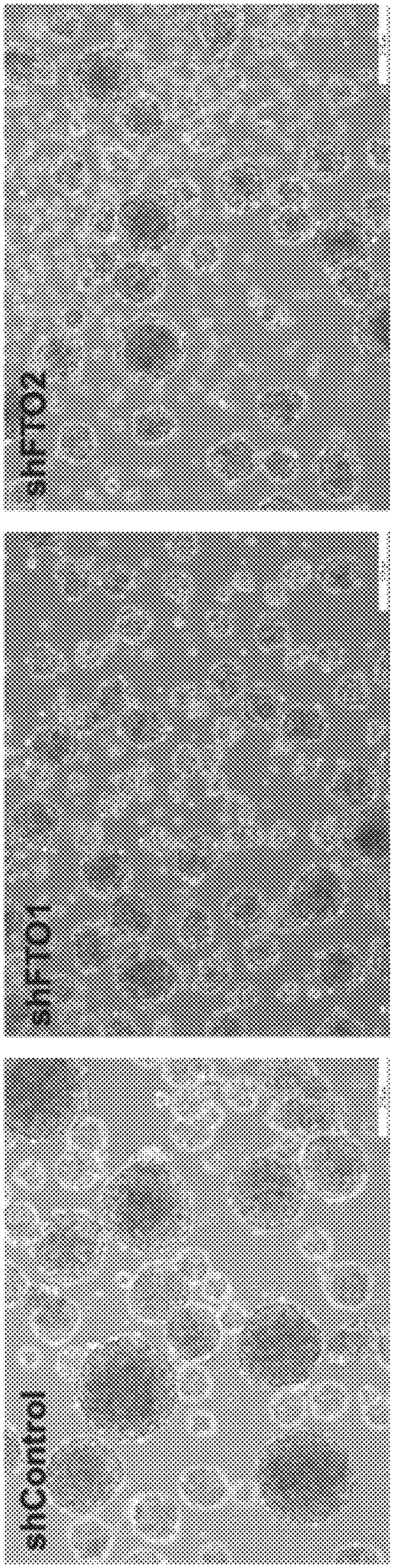
FIG. 58A-58C. Effects of FTO knockdown on tumorsphere size in TS576 cells. 58A. Representative images of TS576 cells derived tumorosphere after lentivirus knocking down of FTO (shControl and shFTO) 58B. Tumorosphere size was quantified by ImageJ and the size distribution is shown in control and F TO KD group. Box and whisker plots show 10-90 percentile. N>50 neurospheres per group. * *p<0.01 by Student's t test. 58C. qRT-PCR showing lentivirus KD efficiency of FTO in TS576.
Figure 58B:
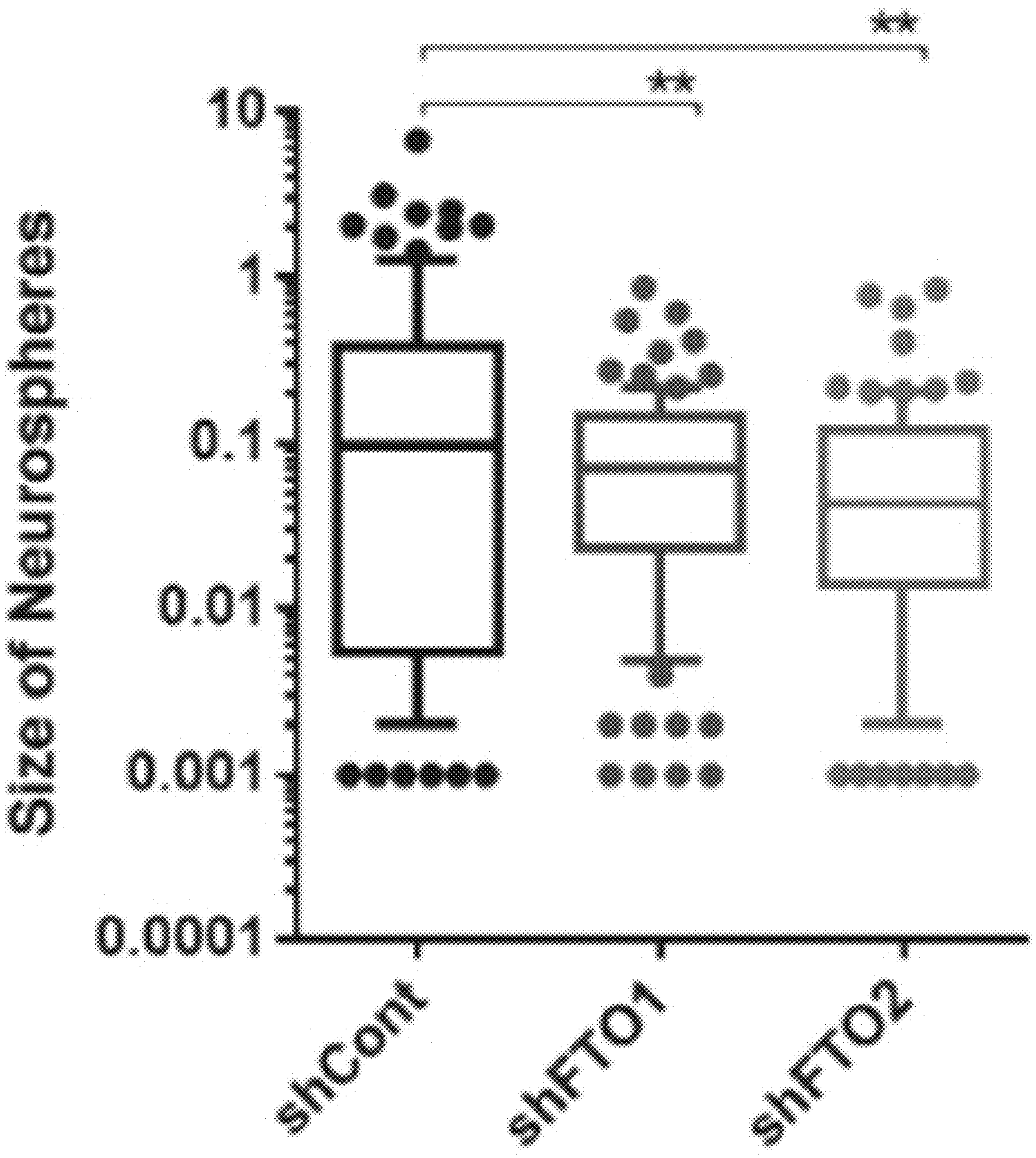
Figure 58C:
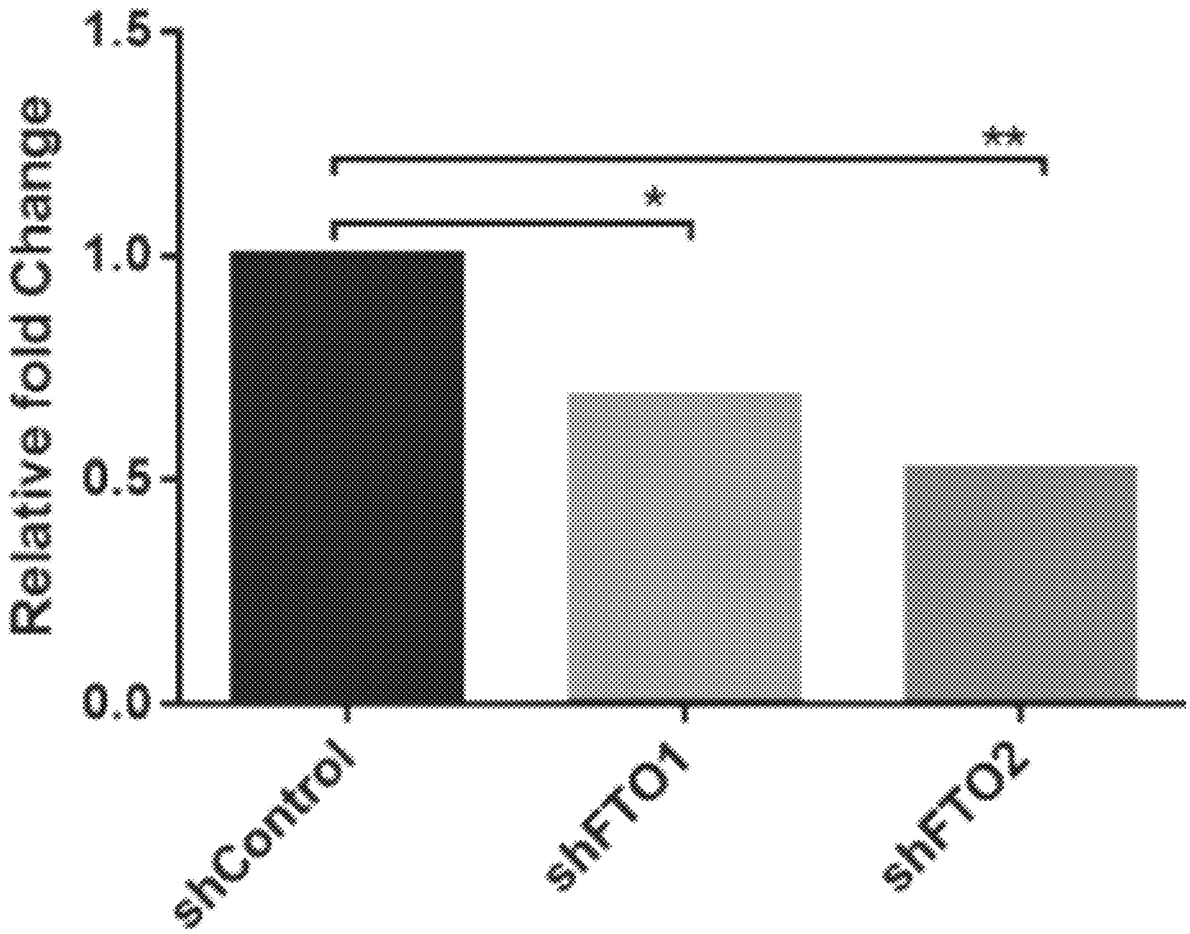

To understand the effects of our FTO inhibitors on the self-renewal properties of GSCs, tumorospheres cultured from the patient-derived GSC line TS576 were treated with 30 μM of FTO-04, FTO-10, FTO-11, or FTO-12 (FIG. 29A-29B; cell line gifted from the Furnari lab).[45, 46] The GSCs were cultured in sphere-forming assays for 24 hours, then treated with either inhibitors or DMSO control for 2 days. The size of the tumorospheres was calculated using ImageJ. The tumorosphere model was chosen over traditional monolayer cell screening assays as it is known to better replicate the tumor microenvironment.[47-51] As misregulation of m6A methylation processes has been associated with hypoxia, the tumorosphere model was considered more a favorable model system.[29, 30, 52] Changes in tumorosphere size after treatment with FTO-04 was also compared to lentiviral knockdown of FTO as a positive control (FIG. 58; knockdown of FTO was found to significantly reduce the size of tumorospheres relative to shControl. As observed in FIG. 29A-29B, all four inhibitors showed a significant reduction in size of the tumorospheres compared to vehicle control. Furthermore, FTO-04 was also shown to significantly decrease the size of tumorospheres cultured from patient-derived TS576, GSC-23 and GBM-6 GSC lines at 20 μM (FIG. 29C-29D; cell lines gifted from the Furnari lab).[45, 46] The assay was repeated for neurospheres derived from healthy neural stem cells (hNSCs), which showed no alteration in neurosphere size after treatment with 20 μM, indicating that inhibition of self-renewal is specific to the GSC lines at this dose (FIG. 29C-29D). Collectively, these data indicate that FTO-04 can significantly impair the self-renewal properties in GSCs to prevent tumorosphere formation without significantly impairing hNSC neurosphere formation.

Figure 59A:
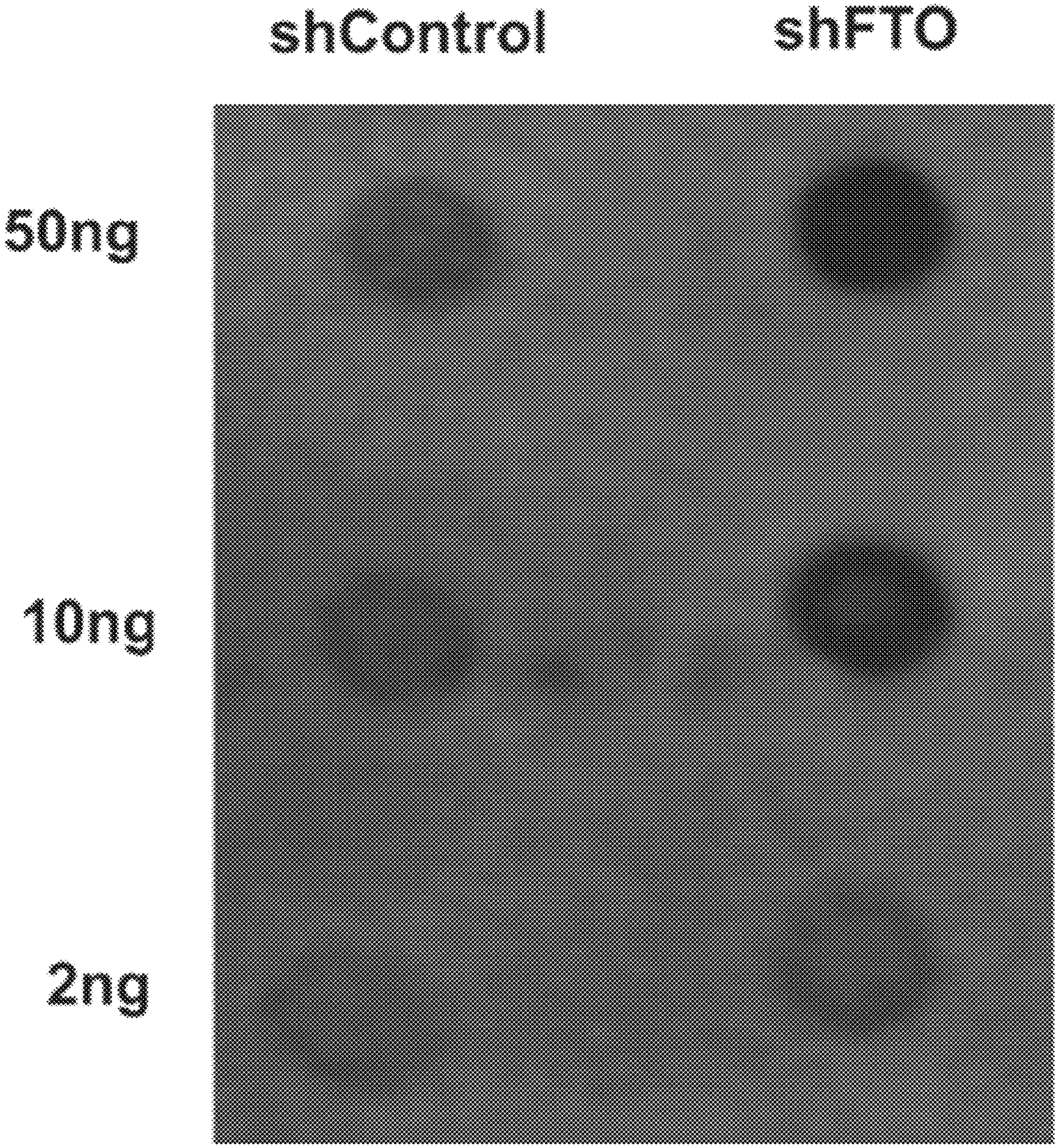
FIG. 59A-59B. m6A mRNA dot blot assays of TS576 treated with shFTO, DMSO, or FTO-04. 59A. m6A dot blot assays using poly(A)+ mRNA of TS576 glioblastoma cells knockdown with shControl and shFTO lentivirus. 59B. m6A dot blot assays using poly(A)+ mRNA of TS576 glioblastoma cells knockdown with DMSO and FTO-04.
Figure 59B:
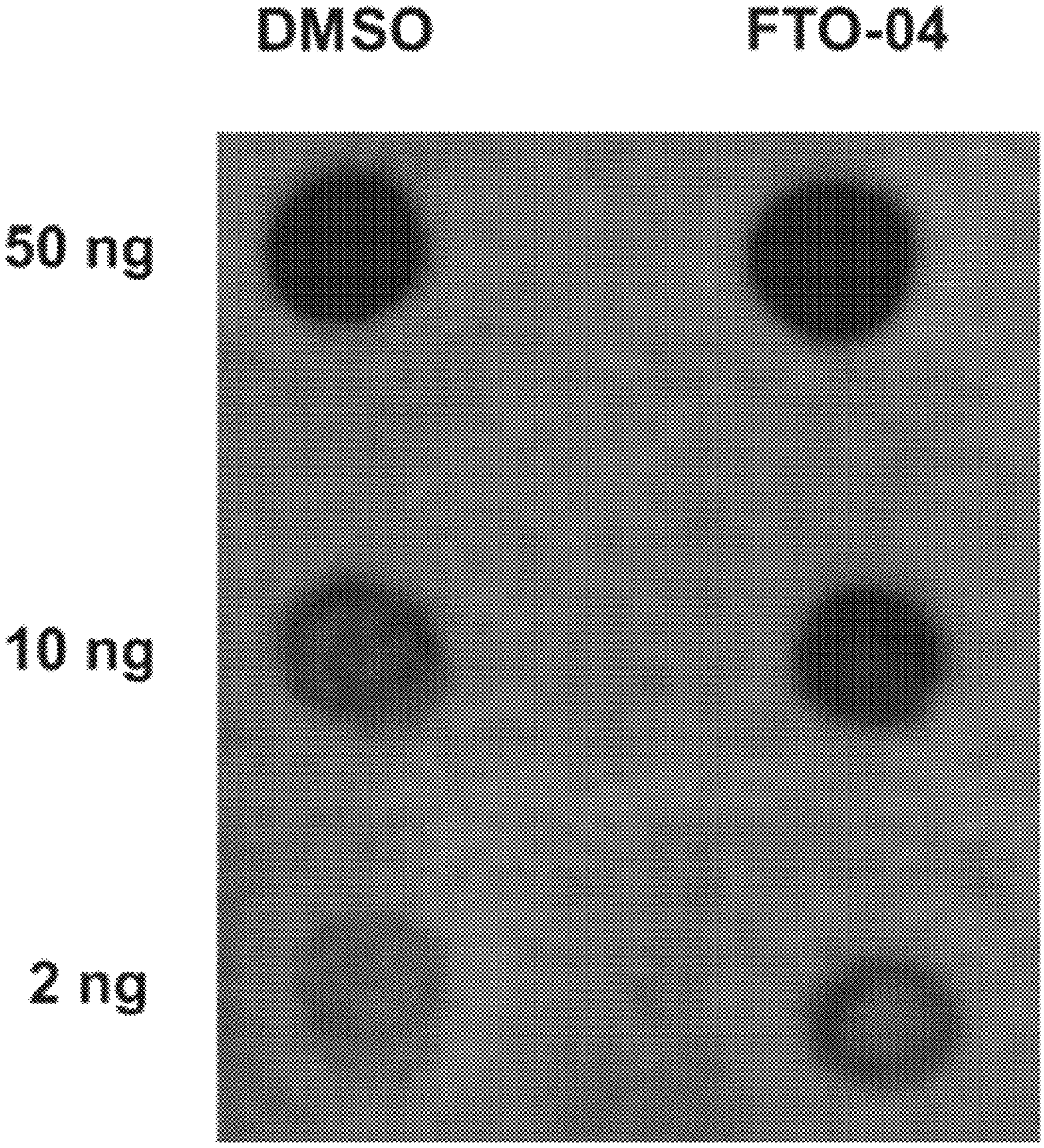
Figure 62:
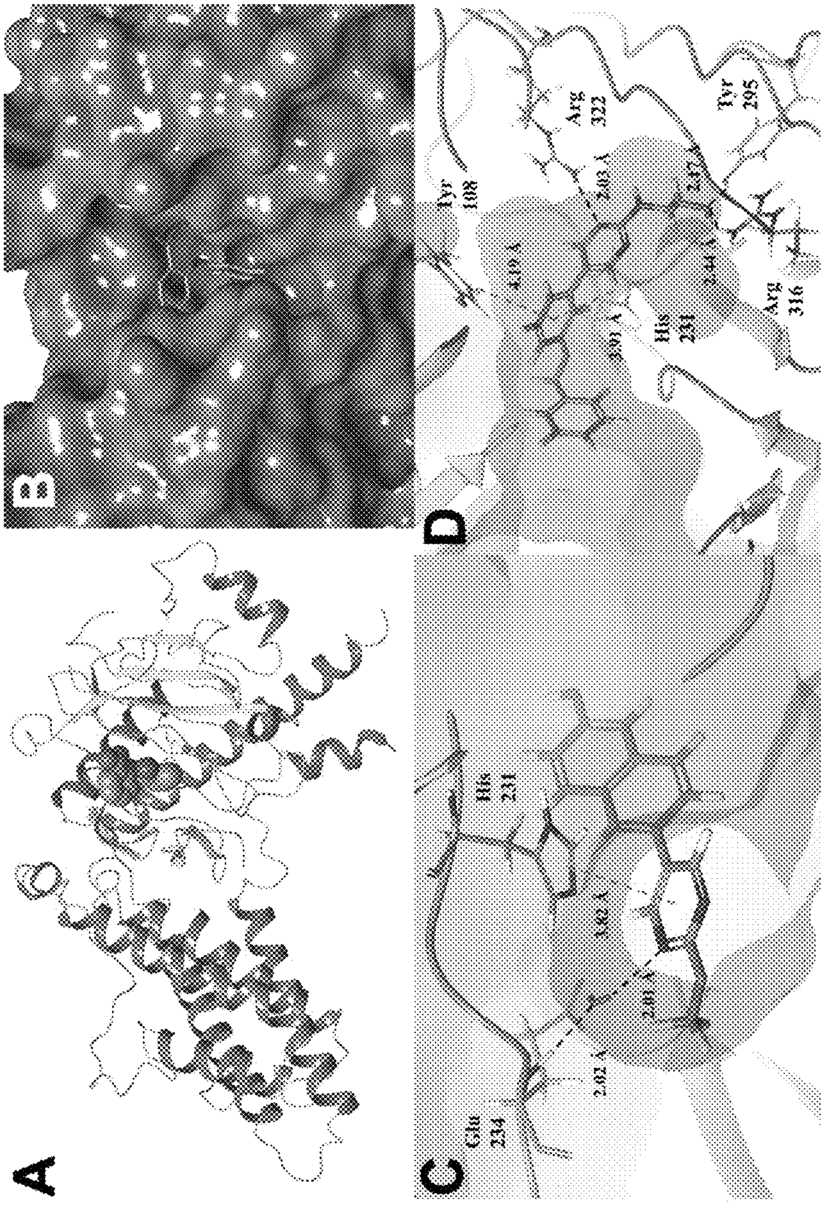
FIG. 62A-62D. Molecular docking targeting the meclofenamic acid binding site of FTO. 62A. X-ray crystal structure of human FTO in complex with meclofenamic acid (MA) (PDB ID: 4QKN). The docking site for in silico screening is shown in green spheres. 62B. Surface representation of human FTO in complex with MA in green (PDB ID: 4QKN). 62C. Predicted binding pose of FTO-02 at the MA binding site. A water mediated hydrogen bond is expected between the pyrimidine ring of FTO-02 and the backbone of Glu 234. A π-π stacking interaction is observed with His 231. 62D. Predicted binding pose of FTO-18 at the MA binding site of FTO. A benzene ring of FTO-18 is observed to form π-π stacking interactions with His 231 and Tyr 108, and the pyrimidine ring of FTO-18 is expected to form a hydrogen bond to Arg 322. Tyr 295 and Arg 316 are predicted to form a bifurcated hydrogen bond to the alcohol group of FTO-18.
Figure 63:
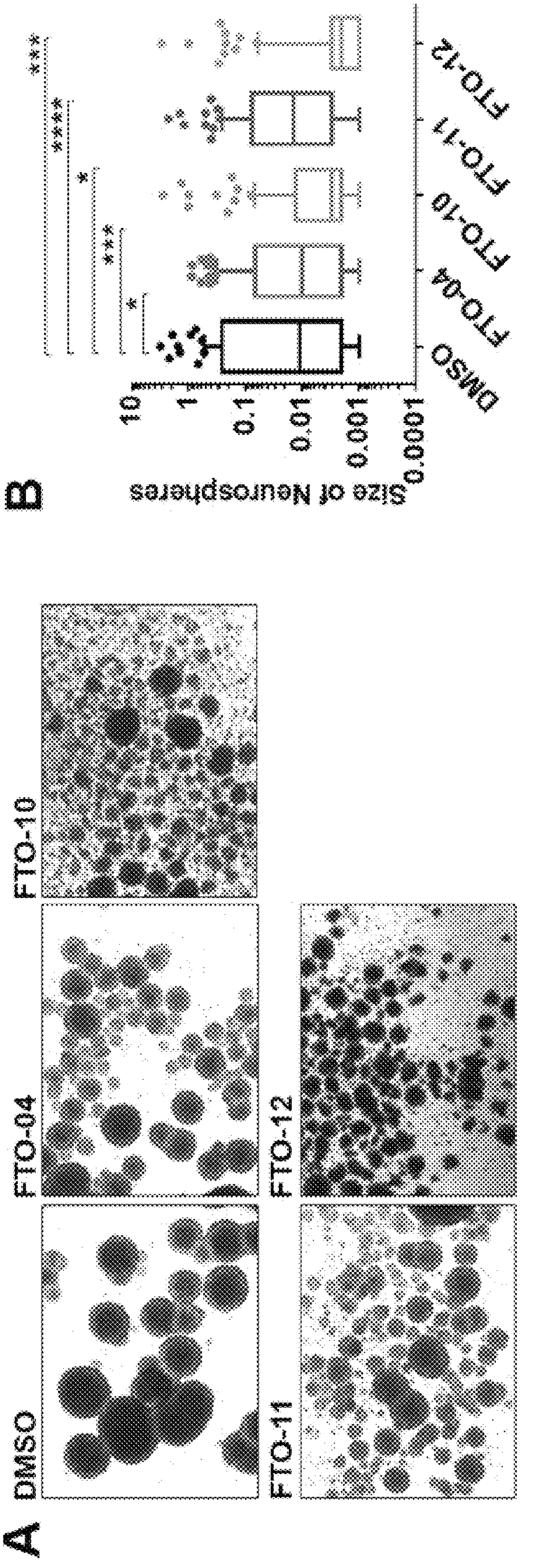
FIG. 63A-63B. FTO inhibitors impair the self-renewal of GSC neurospheres. 63A. Bright field images of neurospheres after 2 days treatment with 30 μM FTO inhibitors in TS576 glioblastoma cells 63B. Size of neurospheres as quantified by ImageJ. Box and whisker plots show 10-90 percentile. N>50 neurospheres per group. p<0.01, **p<0.0001, by Student's t test.
Figure 64:
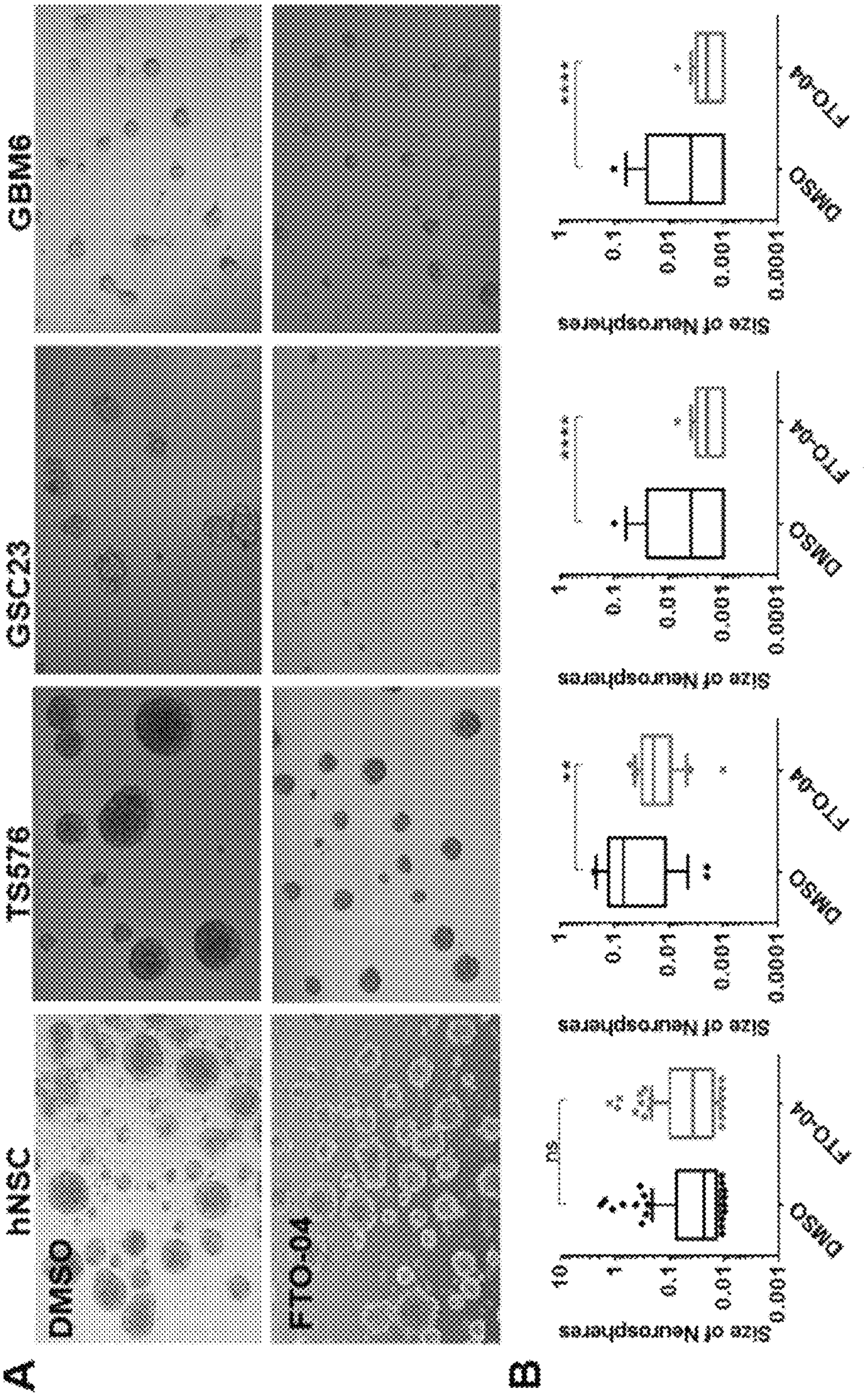
FIG. 64A-64B. FTO-04 inhibits GSC neurospheres formation in multiple patient-derived stem cell lines without impairing hNSC neurosphere growth. 64A. Bright field images of neurospheres after 2 days treatment with FTO-04 inhibitor (20 μM) to normal human neural stem cells (hNSC), and glioblastoma cell lines (TS576, GBM-GSC-23 and GBM-6). 64B. Size of neurospheres as quantified by ImageJ. Box and whisker plots show 10-90 percentile. N>50 neurospheres per group. p<0.01, **p<0.0001, by Student's t test.
Figure 67:
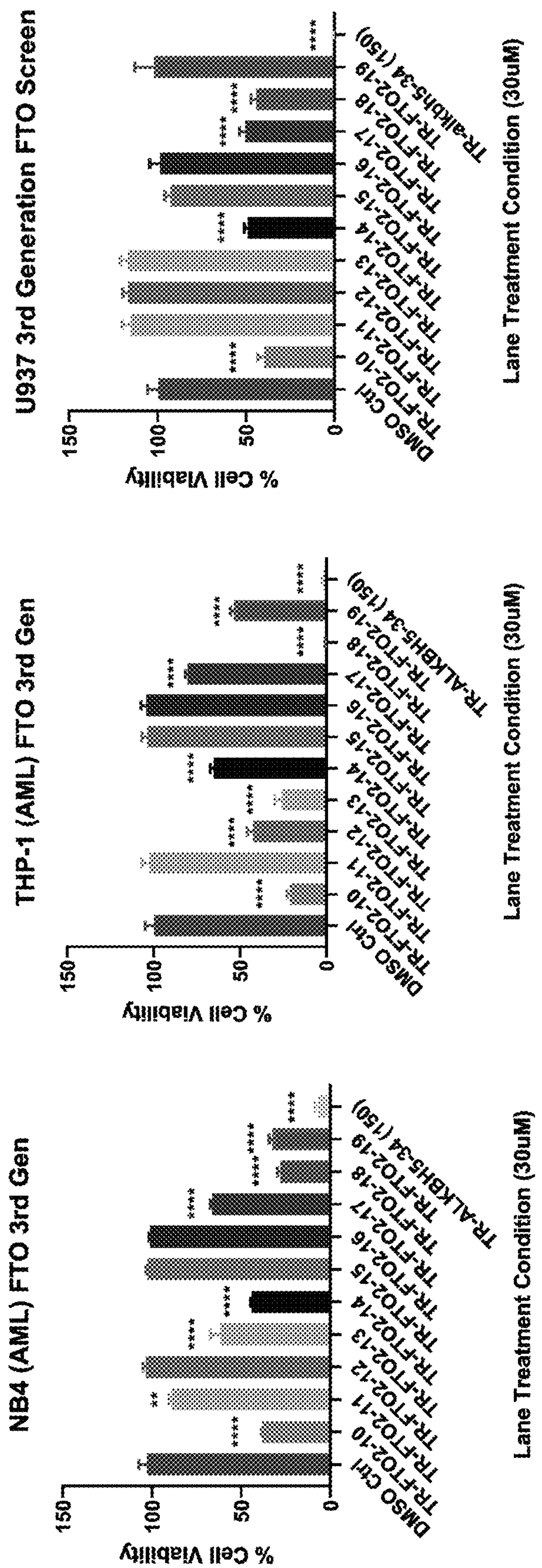
FIG. 67. Plots of cell viability of FTO inhibitors.

Next, we sought to determine if FTO-04 was able to alter m6A levels in purified mRNA from GSCs by m6A dot blot assay. TS576 cells were treated with 2, 10, and 50 ng shControl or shFTO to establish the relative change in m6A mRNA levels due to FTO knockdown. As observed in FIG. 59A, m6A levels significantly increase as concentrations of shFTO increase. TS576 cells were then treated with 2, 10, and 50 ng of either DMSO or FTO-04 (FIG. 59B). While 10 and 50 ng concentrations of DMSO are observed also observed to increase m6A levels, FTO-04 was found to increase m6A mRNA levels significantly compared to DMSO control consistent with the results observed for shFTO. These results indicate that FTO-04 reduces tumorosphere size of GSCs by altering m6A mRNA levels consistent with inhibition of FTO. However, it is important to note that this assay does not distinguish between m6A and m6Am transcripts; it is possible that the increase in m6A mRNA levels is due at least in part to alterations of m6Am transcripts.

As interest in characterizing the role of m6A modification in tumor progression and proliferation gains momentum, it will be critical to identify small molecule inhibitors which can be used as high quality chemical probes both in vitro and in vivo. To that end, it is necessary to identify chemical scaffolds which are not only potent and selective inhibitors, but also have physicochemical properties that are favorable for future in vivo proof of concept models and potential pharmacokinetic development. Collectively, this work represents an important step forward by combining structure-based drug design and a high throughput in vitro inhibition assay system to identify a new chemical class of FTO inhibitors with tightly defined physicochemical properties. Many of these compounds were found to inhibit FTO selectively over ALKBH5 with micromolar potency and the most potent and selective inhibitors FTO-02 and FTO-04 were found to inhibit FTO through a competitive mechanism, consistent with the initial in silico screening at the MA binding site. Importantly, FTO-04 was found to inhibit tumorosphere formation in cultures derived from multiple GSC lines without significantly altering hNSC neurosphere formation. A comparison of m6A mRNA levels in GSCs after FTO knockdown or treatment with FTO-04 indicate that FTO-04 increases m6A mRNA levels in a manner consistent with FTO inhibition. These data indicate that targeting the m6A methylation machinery, and the demethylase FTO specifically, could prove an effective mechanism for treating glioblastoma and identify FTO-04 as a new lead for therapeutic development.

TABLE 1

| Selective Inhibitors of FTO | | | |
|---|---|---|---|
| Structure | Name | Enzymatic $IC_{50}$ FTO | Enzymatic $IC_{50}$ ALKBH5 |
| 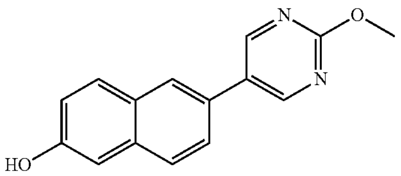 [SMILES: COc1ncc(-c2ccc3cc(O)ccc3c2)cn1] | FTO-2 | 2.18 ± 1.3 | 85.5 ± 5.7 |
| 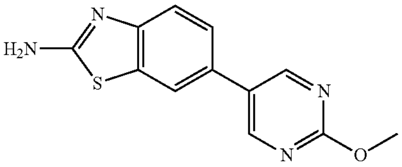 | FTO-4 | 3.39 ± 2.5 | 39.4 ± 3.1 |
| 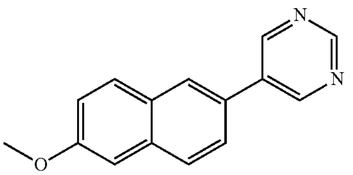 [SMILES: COc1ccc2cc(-c3cncnc3)ccc2c1] | FTO-5 | 13.38 ± 2.3 | >40 |
| 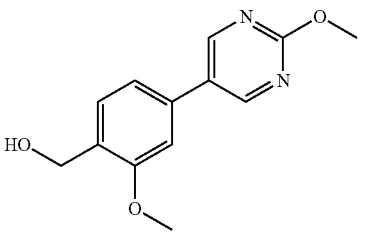 [SMILES: COc1ncc(-c2ccc(CO)c(OC)c2)cn1] | FTO-6 | 13.8 ± 2.4 | 64.4 ± 6.3 |

TABLE 1-continued

| Selective Inhibitors of FTO | | | |
|---|---|---|---|
| Structure | Name | Enzymatic $IC_{50}$ FTO | Enzymatic $IC_{50}$ ALKBH5 |
| 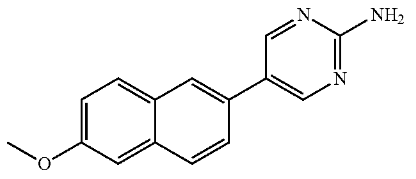 [SMILES: COc1ccc2cc(-c3cnc(N)nc3)ccc2c1] | FTO-12 | 18.3 ± 1.7 | >40 |
| 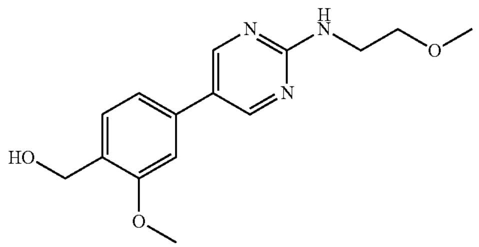 [SMILES: COCCNc1ncc(-c2ccc(CO)c(OC)c2)cn1] | FTO-20 | 17.2 ± 2.9 | 90.2 ± 7.8 |

Experimental Methods

Molecular Modeling with Schrödinger

In silico modeling of FTO inhibitors was performed using the Glide docking module of the Schrödinger 11.5 modeling software suite. A crystal structure of FTO bound to meclofenamic acid (MA) (PDBID: 4QKN) was first refined using Prime. Missing side chains and hydrogen atoms were resolved before docking and the Optimized Potentials for Liquid Simulations All-Atom (OPLS) force field and the Surface generalized Born (SGB) continuum solution model was used to optimize and minimize the crystal structures. The docking grid was generated as a 5x5x5 Å cube centered on MA. Glycerol and α-ketoglutarate were removed from the docking site prior to grid generation. Ligprep was used to generate a minimized 3D structure for all prospective FTO inhibitors using the OPLS 2001 force field. Docking was performed with Glide XP. QikProp was used to predict physicochemical properties such as c log P and membrane permeability in Caco-2 and MDCK cell lines for the 20 most promising compounds.

Protein Expression and Purification

The protein expression and purification protocol was adapted from Svensen and Jaffrey, 2016. *E. coli* BL21 competent cells (New England Biolabs) were transformed with pET28-SUMO-His10-FTO plasmid (a generous gift from the Jaffrey lab) by heat shock and spread on a LB Kanamycin agar plate, then incubated overnight at 37° C. 2-3 colonies were picked and transferred to 5 mL of LB media treated with kanamycin (0.5 mg $mL^{-1}$ final concentration), then grown overnight shaking at 37° C. The overnight culture was then transferred to 2 L of LB kanamycin media and incubated at 37° C. until OD 0.8. The culture was cooled at 4° C. for 20 mins and induced with 0.5 mM isopropyl β-D-1-thiogalactopyranoside (IPTG), then grown shaken at 16° C. Cell pellets were collected by centrifugation (5,000 g for 10 min at 4° C.) and the supernatant was discarded. The pellets were resuspended in B-PER Bacterial Protein Extraction Reagent (6 mL per gram) with DNase 1 (5 U per mL, RNase-free) and incubated at 4° C. for 1 hour. The suspension was centrifuged at 10,000 g for 20 min and the supernatant was transferred to a Talon Metal Affinity Resin column that had been pre-equilibrized with binding buffer (50 mM $NaH_2PO_4$ pH 7.2, 300 mM NaCl, 20 mM imidazole, 1 mM β-mercaptoethanol in RNase-free water). The supernatant was incubated with the affinity resin column at 4° C. for 1 hour with end-over-end rotation. After incubation, the column was washed with 5 bed volumes of binding buffer, then incubated with 1 bed volume of elution buffer (50 mM $NaH_2PO_4$ pH 7.2, 300 mM NaCl, 500 mM imidazole, 5 mM β-mercaptoethanol in RNase-free water) for 20 mins. After incubation, the eluant was collected and the column was incubated again with 1 bed volume of elution buffer; the elution process was repeated until no further protein was collected (3-5 bed volumes total). The eluant was combined and transferred to a Slyde-A-Lyzer Dialysis Cassette (20,000 MWCO, Thermo Scientific) and dialyzed overnight at 4° C. against dialysis buffer (50 mM Tris-HCl pH 7.4, 100 mM NaCl, 5 mM B-mercaptoethanol, 5% (v/v) glycerol in RNase-free water). Protein concentration was measured by absorbance at 280 nm and calculated by Beer-Lambert's Law (A=ε/C, $\varepsilon_{FTO}$=95,340). ALKBH5 was expressed and purified from pET28-SUMO-His10-ALKBH5 plasmid by the same procedure described above.

In Vitro Inhibition Assay Method

The in vitro inhibition assay method was adapted from Svenson and Jaffrey, 2016. All reactions were performed in a 96-well plate with 200 μL assay buffer (50 mM HEPES pH 6, 300 μM 2-oxoglutarate, 300 μM $(NH_4)_2Fe(SO_4)_2·6H_2O$, 2 mM ascorbic acid in RNase-free water) with 7.5 μM $m^6A_7$-Broccoli RNA and 0.250 μM FTO. Inhibitors were added in concentrations ranging from 0.008-40 μM; all inhibitors were dissolved in DMSO and added to a final concentration of 0.2% DMSO. Prior to incubation, 40 μL read buffer (250 mM HEPES pH 9.0, 1 M KCl, 40 mM $MgCl_2$, 2.2 μM DFHBI-1T in RNase-free water) was added to bring the final well volume to 200 μL. After incubation at room temperature for 2 hours, the plates were left at 4° C. overnight (16 hours) to allow DFHBI-1T to bind to $A_7$-Broccoli RNA. Specificity assays were performed by the same method with 0.250 μM ALKBH5. Fluorescence intensity was measured with a BioTek Synergy plate reader with FITC filters (excitation 485 nm, emission 510 nm). Sigmoidal dose-response curves were fitted in GraphPad Prism 6. All assays were performed in triplicate, with additional repetitions added as necessary.

As a negative control, inhibitors were screened at concentrations ranging from 0-40 μM as described above with 7.5 μM demethylated Broccoli instead of $m6A_7$-Broccoli. No compounds were observed to significantly alter fluorescent signal of the A7-Broccoli-DHBI-1T complex at these concentrations (FIG. 53).

Michealis-Menton kinetics was performed using the inhibition assay procedure described above; the activity of FTO concentrations of 0, 0.250, 0.385. 0.500, 0.625, 0.750, 1.25, 2.5, 5, and 10 μM m6A Broccoli were recorded for the following concentrations of FTO-02 N: 0, 0.5, 1, 10, and 40 μM and FTO-04: 0, 1, 10, 20, and 40 μM. The data were fitted in GraphPad Prism 6.

ELISA Assay Methods

The IC50s of FTO-02 and FTO-04 against FTO were determined by ELISA as an orthogonal assay control. 3'-biotinylated m6A-RNA (5'-CCGG(m6A)CUU-3', 0.200 μM) was incubated with 0.250 μM FTO for 2 hours at room temperature in reaction buffer (50 mM NaHEPES pH 6, 300 μM 2-oxoglutarate, 300 μM $(NH_4)_2Fe(SO_4)_2 \cdot 6H_2O$, and 2 mM L-ascorbate) with 0-40 μM FTO-02 or FTO-04. The reaction mixture was then incubated with neutravidin coated 96-well plates (Pierce) overnight at 4° C., washed and blocked, incubated with m6A -specific primary antibody (Abcam ab151230, 1:400 dilution) for 1 hour at room temperature, washed and blocked (phosphate buffer saline with 0.1% tween-20 (PBST); blocked in 5% of non-fat milk in PBST buffer), and incubated with horseradish peroxidase-conjugated secondary antibody (Sigma-Aldrich, A6154, 1:5000 dilution) for 1 hour at room temperature. After extensive washing, the wells were treated with 3,3',5,5'-tetramethylbenzidine (TMB, BM Blue POD substrate by Roche Diagnostics GmbH) for 30 minutes at room temperature and the absorbance was measured at 390 nm. Absorbance was normalized to control wells for each concentration of inhibitor without cofactor 2-oxoglutarate, and the data were fit to a sigmoidal dose-response curve in GraphPad Prism 6.

Synthetic Methods

General Experimental Procedures

All reagents were performed under nitrogen atmosphere. Air sensitive liquids were transferred by syringe through rubber septa. Dry THF was prepared by distillation over calcium hydride. All other reagents and solvents were purchased from commercial sources and used without further purification. All solvents used for column chromatography were reagent grade. Reaction progress was monitored by analytical thin layer chromatography (TLC, silica gel 60, F254, EMD Chemicals) and visualized by UV illumination (254 nm). Compounds were purified by flash column chromatography on silica gel 60 Å (200-400 mesh, 40-63 μm) at medium pressure (20 psi). All compounds were purified to >95% purity. NMR spectra were recorded at ambient temperature on a Brucker 600 MHz spectrophotometer ($^1$H-NMR: 600 MHz and $^{13}$C NMR: 150 MHz). Chemical shift values are reported in parts per million (ppm) relative to the residual solvent peak ($CDCl_3$ or $(CD_3)_2OS$). Coupling constants for $^1$H-NMR are reported in Hz. High Resolution Mass Spectrometry (HRMS) data were acquired on an Agilent 6230 High Resolution time-of-flight mass spectrometer and reported as m/z for the molecular ion [M+H]+.

General Procedure A for Suzuki-Miyaura Cross-Coupling Reactions

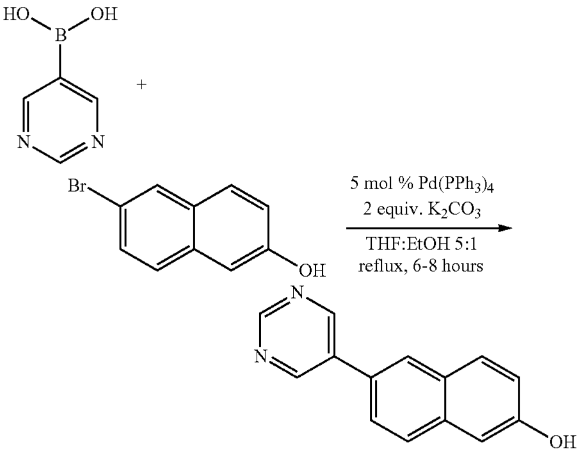

6-bromo-2-naphthol (0.900 g, 4.0 mmol), palladium tetrakisthriphenylphosphine (0.231 g, 0.02 mmol), and potassium carbonate (1.115 g, 8.0 mmol) were placed under nitrogen atmosphere, and dissolved in dry THF (20 mL) to obtain a dark red solution. A syringe was used to transfer pyrimidine-5-boronic acid (0.500 g, 4.0 mmol) in 5 mL dry THF to the stirring solution. The reaction was heated under reflux for 6 hours. The reaction mixture was filtered over Celite and the filter cake was washed with ethyl acetate. The filtrate was concentrated under reduced pressure to obtain the crude product as a yellow solid. The crude product was purified by silica gel column chromatography (Ethyl acetate: Hexanes 2:3, Rf=0.48). Following this procedure, twenty potential FTO inhibitors were obtained with an average yield of 54%.

Procedure B for Synthesis of tert-butyl (6-bromobenzo[d]thiazol-2-yl)carbamate 6-bromobenzo[d]thiazol-2-amine (0.458 g, 2 mmol) and $BOC_2O$ (1.2 eq, 2.4 mmol) were dissolved in THF (30 mL). 4-dimethylaminopyridine (DMAP, 0.1 equivalent) was added to the solution and the reaction was stirred for 3.5 hours at room temperature. The reaction mixture was diluted in ethyl acetate (100 mL) and washed with 0.25 M HCl (50 mL), 2 M $NaHCO_3$ (100 mL), and brine. The organic layers were dried by $Na_2SO_4$, filtered, then concentrated to obtain the crude product. The crude product was used for Suzuki coupling via general method A without further purification.

Procedure C for Boc Deprotection of tert-butyl (6-(2-methoxypyrimidin-5-yl)benzo[d]thiazol-2-yl) carbamate A solution of tert-butyl (6-(2-methoxypyrimidin-5-yl) benzo[d]thiazol-2-yl)carbamate (0.720 g, 2 mmol) in dioxane (40 mL) was treated with 4M HCl in dioxane and stirred at room temperature for 1 hour. The reaction mixture was concentrated, then dissolved in ethyl acetate (100 mL) and extracted with 10% $Na_2CO_3$ (50 mL) and brine (2×50 mL). The organic layers were dried with $Na_2SO_4$, filtered, and concentrated to obtain the crude product as a yellow solid. The crude product was purified by silica gel column chromatography (Ethyl acetate:Hexanes 2:3, Rf=0.48).

Chemical Characterization Data 6-(pyrimidin-5-yl)naphthalen-2-ol (FTO 1)

Prepared according to general procedure A. Yield 0.640 g, 2.88 mmol, 72%. Yellow solid, mp 230° C. $^{1}$H-NMR (600 MHz, d-DMSO): 9.93 (s, 1H), 9.25 (s, 2H), 9.17 (s, 1H), 8.03 (d, J=2.0 Hz, 1H), 7.75 (d, J=8.6 Hz, 1H), 7.65 (d, J=8.6 Hz, 1H), 7.47 (dd, J=8.8, 2.1 Hz, 1H), 7.45 (d, J=8.8 Hz, 1H), 7.13 (d, J=2.5 Hz, 1H). $^{13}$C-NMR (150 MHz, d-DMSO): 156.5, 155.3, 150.3, 150.3, 133.8, 132.8, 132.2, 130.0, 129.5, 129.4, 128.2, 125.2, 115.9, 109.5. HRMS (ESI, M+) m/z calculated for $C_{14}H_{10}N_2O$ 222.0793, found 222.0795.

6-(2-methoxypyrimidin-5-yl)naphthalen-2-ol (FTO 2)

Prepared according to general procedure A. Yield 0.525 g, 2.8 mmol, 52%. Orange solid, mp 230° C. $^{1}$H-NMR (600 MHz, d-DMSO): 9.89 (s, 1H), 9.02 (s, 2H), 8.16 (d, J=2.0 Hz, 1H), 7.82 (d, J=8.7 Hz, 1H), 7.80 (d, J=8.7 Hz, 1H), 7.76 (d, J=2.5 Hz, 1H), 7.75 (d, J=2.5 Hz, 1H), 7.15 (d, J=2.6 Hz, 1H), 3.97 (s, 3H). $^{13}$C-NMR (150 MHz, d-DMSO): 157.8, 155.4, 155.4, 154.7, 133.9, 130.6, 129.3, 128.5, 128.2, 126.7, 125.5. 120.1, 115.9, 106.5, 56.0. HRMS (ESI, M+) m/z calculated for $C_{15}H_{12}N_2O_2$ 252.0899, found 252.0900.

5-(3-(benzyloxy)phenyl)-2-methoxypyrimidine (FTO 3)

Prepared according to general procedure A. Yield 0588 g, 2.01 mmol, 51%. Yellow solid, mp 230° C. $^{1}$H-NMR (600 MHz, $CDCl_3$): 8.71 (s, 2H), 7.47 (d, J=7.3 Hz, 2H), 7.42 (t, J=7.4 Hz, 1H), 7.41 (d, J=6.1 Hz, 2H), 7.40 (d J=2.7 Hz, 1H), 7.36 (t, J=7.3 Hz, 1H), 7.13 (d, J=1.4 Hz, 2H), 7.04 (d, J=1.6 Hz, 1H), 5.14 (s, 2H), 4.07 (s, 3H). $^{13}$C-NMR (150 MHz, d-DMSO): 163.4, 159.7, 156.7, 156.7, 139.7, 136.6, 130.8, 130.8, 128.9, 128.9, 128.4, 127.8, 124.2, 118.4, 114.0, 113.2, 70.4, 55.0. HRMS (ESI, M+) m/z calculated for $C_{18}H_{16}N_2O_2$ 292.1212, found 292.1216.

6-(2-methoxypyrimidin-5-yl)benzo[d]thiazol-2-amine (FTO 4)

Prepared according to general procedure A from tert-butyl (6-bromobenzo[d]thiazol-2-yl)carbamate and (2-methoxy-pyrimidin-5-yl)boronic acid. FTO-04 was purified after Boc deprotection as described in procedure C. Yield 0.723 g, 2.80 mmol, 70%. Yellow solid, mp 230° C. $^{1}$H-NMR (600 MHz, d-DMSO): 8.82 (s, 2H), 7.71 (s, 2H), 7.60 (d, J=8.3 Hz, 1H), 7.47 (d, J=2.0 Hz, 1H), 7.14 (dd, J=8.3, 2.0 Hz, 1H), 3.87 (s, 3H). $^{13}$C-NMR (150 MHz, d-DMSO): 168.7, 157.8, 155.2, 155.0, 155.0, 130.5, 123.8, 123.4, 120.6, 118.9, 55.1. HRMS (ESI, M+) m/z calculated for $C_{12}H_{10}N_4OS$ 258.0575, found 258.0580.

5-(6-methoxynaphthalen-2-yl)pyrimidine (FTO 5)

Prepared according to general procedure A. Yield 0.595 g, 2.52 mmol, 63%. White solid, mp 230° C. $^{1}$H-NMR (600 MHz, d-DMSO): 9.26 (s, 2H), 9.19 (s, 1H), 8.35 (d, J=1.1 Hz, 1H), 7.98 (d, J=8.6 Hz, 1H), 7.92 (dd, J=8.5, 2.1 Hz, 2H), 7.40 (d, J=2.5 Hz, 11H), 7.24 (dd, J=8.9, 2.6 Hz, 1H), 3.90 (s, 3H). $^{13}$C-NMR (150 MHz, d-DMSO): 157.7, 155.3, 150.3, 150.3, 135.0, 134.2, 133.9, 130.6, 129.3, 128.5, 126.7, 125.4, 120.1, 106.5, 56.0. HRMS (ESI, M+) m/z calculated for $C_{15}H_{12}N_2O$ 236.0950, found 236.0593.

(2-methoxy-4-(2-methoxypyrimidin-5-yl)phenyl) methanol (FTO 6)

Prepared according to general procedure A. Yield 0.374 g, 1.52 mmol, 38%. White solid, mp 230° C. $^{1}$H-NMR (600 MHz, d-DMSO): 8.60 (s, 2H), 7.29 (d, J=7.9 Hz, 1H), 7.13 (d, J=1.6 Hz, 1H), 7.11 (t, J=2.7 Hz, 1H), 5.10 (t, J=5.6 Hz, 2H), 3.78 (s, 6H). $^{13}$C-NMR (150 MHz, d-DMSO): 163.4, 157.1, 148.9, 148.9, 136.2, 131.0, 129.1, 123.5, 113.9, 61.1, 58.1, 56.0. HRMS (ESI, M+) m/z calculated for $C_{13}H_{14}N_2O_3$ 246.1004, found 246.1009.

2-methyl-6-(pyrimidin-5-yl)quinoline (FTO-07)

Prepared according to general procedure A. Yield 0.520 g, 2.35 mmol, 59%. White solid, mp 230° C. $^{1}$H-NMR (600 MHz, d-DMSO): 9.26 (s, 1H), 8.68 (s, 2H), 8.24 (d, J=8.4 Hz, 1H), 8.23 (d, J=2.2 Hz, 1H), 7.89 (d, J=8.9 Hz, 11H), 7.83 (dd, J=8.9, 2.2 Hz, 11H), 7.48 (d, J=8.4 Hz, 11H), 2.73 (s, 3H). $^{13}$C-NMR (150 MHz, d-DMSO): 155.0, 154.8, 154.8, 150.5, 150.1, 141.9, 136.8, 130.7, 130.2, 128.7, 128.3, 125.9, 123.1, 24.0. HRMS (ESI, M+) m/z calculated for $C_{14}H_{11}N_3$ 221.0953, found 221.0958.

2-methoxy-5-(6-methoxynaphthalen-2-yl)pyrimidine (FTO 8)

Prepared according to general procedure A. Yield 0.266 g, 1.00 mmol, 25%. White solid, mp 230° C. $^{1}$H-NMR (600 MHz, d-DMSO): 9.05 (s, 2H), 8.23 (d, J=1.1 Hz, 1H), 7.95 (d, J=8.6 Hz, 1H), 7.93 (d, J=2.1 Hz, 1H), 7.89 (d, J=2.1 Hz 11H), 7.37 (d, J=2.5 Hz, 1H), 7.21 (dd, J=8.9, 2.6 Hz, 1H), 3.97 (s, 3H), 3.89 (s, 3H). $^{13}$C-NMR (150 MHz, d-DMSO): 163.5, 157.5, 150.3, 150.3, 133.9, 130.8, 130.3, 129.5, 128.5, 128.3, 124.1, 120.4, 120.1, 106.7, 56.5, 56.0. HRMS (ESI, M+) m/z calculated for $C_{16}H_{14}N_2O_2$ 266.1055, found 266.1058.

5-(3-(phenylamino)phenyl)pyrimidin-2-amine (FTO-09)

Prepared according to general procedure A. Yield 0.441 g, 1.68 mmol, 42%. Yellow solid, mp 230° C. $^{1}$H-NMR (600 MHz, d-DMSO): 8.37 (s, 2H), 7.27 (t, J=7.9 Hz, 2H), 7.15 (t, J=8.6 Hz, 2H), 7.08 (d, J=7.6 Hz, 2H), 7.02 (dd, J=8.2, 1.7 Hz, 1H), 6.92 (d, J=8.9 Hz, 1H), 6.90 (t, J=7.3 Hz, 1H). $^{13}$C-NMR (150 MHz, d-DMSO): 161.5, 150.2, 150.2, 140.1, 139.3, 137.2, 130.5, 129.9, 129.9, 121.4, 120.6, 120.6, 120.6, 120.4, 117.6, 117.6. HRMS (ESI, M+) m/z calculated for $C_{16}H_{14}N_4O$ 262.1218, found 262.1225.

6-(2-aminopyrimidin-5-yl)naphthalen-2-ol (FTO 10)

Prepared according to general procedure A. Yield 0.690 g, 2.91 mmol, 73%. Yellow solid, mp 230° C. $^{1}$H-NMR (600 MHz, d-DMSO): 8.66 (s, 2H), 8.20 (d, J=6 Hz, 1H), 8.01 (s, 1H), 7.78 (d, J=8.8 Hz, 1H), 7.73 (d, J=8.6, 1H), 7.12 (d, J=6 Hz, 1H), 7.09 (dd, J=8.9, 2.4 Hz, 1H), 6.79 (s, 2H), 6.57 (s, 1H). $^{13}$C-NMR (150 MHz, d-DMSO): 158.8, 158.6, 156.5, 156.5, 134.1, 132.6, 130.1, 130.2, 127.6, 127.6, 124.7, 124.0, 122.1, 110.8. HRMS (ESI, M+) m/z calculated for $C_{14}H_{11}N_3O$ 237.0902, found 237.0900.

6-(2-methoxypyrimidin-5-yl)-2-methylquinoline (FTO 11)

Prepared according to general procedure A. Yield 0.302 g, 1.20 mmol, 30%. White solid, mp 230° C. $^1$H-NMR (600 MHz, d-DMSO): 8.53 (s, 2H), 7.96 (d, J=8.4 Hz, 1H), 7.93 (d, J=2.2 Hz, 1H), 7.89 (d, J=8.9 Hz, 1H), 7.74 (dd, J=8.9, 2.2 Hz, 1H), 7.31 (d, J=8.4 Hz, 1H), 4.02 (s, 3H), 2.73 (s, 3H). $^{13}$C-NMR (150 MHz, d-DMSO): 163.4, 155.0, 154.8, 154.8, 150.5, 141.9, 136.8, 130.7, 128.7, 128.3, 125.9, 123.1, 118.4, 50.3, 21.0. HRMS (ESI, M+) m/z calculated for $C_{15}H_{13}N_3O$ 251.1059, found 251.1061.

5-(6-methoxynaphthalen-2-yl)pyrimidin-2-amine (FTO 12)

Prepared according to general procedure A. Yield 0.543 g, 2.16 mmol, 54%. Yellow solid, mp 230° C. $^1$H-NMR (600 MHz, d-DMSO): 8.68 (s, 2H), 8.09 (d, J=2.5 Hz, 1H), 7.87 (d, J=8.8 Hz, 11H), 7.84 (d, J=8.8 Hz, 1H), 7.75 (dd, J=8.5, 1.9 Hz, 1H), 7.33 (d, J=2.5 Hz, 1H), 7.18 (dd, J=8.9, 2.5 Hz, 1H), 6.79 (s, 2H), 3.88 (s, 3H). $^{13}$C-NMR (150 MHz, d-DMSO): 163.4, 157.9, 156.6, 156.6, 133.9, 130.9, 130.4, 129.5, 128.5, 126.7, 123.8, 122.8, 106.5, 56.0, 25.8. HRMS (ESI, M+) m/z calculated for $C_{15}H_{13}N_3O$ 251.1059, found 251.1066.

5-(3-(benzyloxy)phenyl)pyrimidin-2-amine (FTO-13)

Prepared according to general procedure A. Yield 0.566 g, 2.04 mmol, 51%. Yellow solid, mp 230° C. $^1$H-NMR (600 MHz, d-DMSO): 8.70 (s, 2H), 7.43 (d, J=7.3 Hz, 2H), 7.42 (t, J=7.4 Hz, 1H), 7.40 (d, J=6.1 Hz, 2H), 7.39 (d J=2.7 Hz, 11H), 7.36 (t, J=7.3 Hz, 1H), 7.14 (d, J=1.4 Hz, 2H), 7.04 (d, J=1.6 Hz, 1H), 6.79 (s, 2H), 5.05 (s, 2H). $^{13}$C-NMR (150 MHz, d-DMSO): 161.7, 159.7, 150.7, 150.7, 137.0, 136.6, 130.8, 128.9, 128.9, 128.4, 127.8, 127.8, 120.2, 118.4, 114.0, 113.2, 70.4. HRMS (ESI, M+) m/z calculated for $C_{17}H_{15}N_3O$ 277.1215, found 277.1223.

5-(2-methylquinolin-6-yl)pyrimidin-2-amine (FTO 14)

Prepared according to general procedure A. Yield 0.784 g, 3.32 mmol, 83%. Yellow solid, mp 230° C. $^1$H-NMR (600 MHz, d-DMSO): 8.73 (s, 2H), 8.23 (d, J=8.3 Hz, 1H), 8.18 (d, J=8.8 Hz, 1H), 8.00 (d, J=1.7 Hz, 1H), 7.94 (d, J=8.7 Hz, 1H), 7.43 (d, J=8.5 Hz, 1H), 6.87 (s, 2H), 2.65 (s, 3H). $^{13}$C-NMR (150 MHz, d-DMSO): 163.7, 157.9, 156.9, 156.9, 141.9, 138.6, 136.8, 130.7, 128.7, 128.3, 125.9, 123.1, 118.4, 25.5. HRMS (ESI, M+) m/z calculated for $C_{14}H_{12}N_4$ 236.1062, found 236.1070.

N-(2-methoxyethyl)-5-(6-methoxynaphthalen-2-yl) pyrimidin-2-amine (FTO-15)

Prepared according to general procedure A. Yield 0.744 g, 2.52 mmol, 63%. Yellow solid, mp 230° C. $^1$H-NMR (600 MHz, d-DMSO): 8.41 (s, 2H), 8.00 (s, 1H), 7.83 (m, 2H), 7.80 (dd, J=8.7, 2.5 Hz, 1H), 7.71 (dd, J=8.5, 1.7 Hz, 1H), 7.30 (d, J=2.3 Hz, 1H), 7.15 (dd, J=8.9, 2.5 Hz, 1H), 6.73 (s, 1H), 3.87 (s, 3H), 3.48 (m, 2H), 3.27 (s, 3H). $^{13}$C-NMR (150 MHz, d-DMSO): 159.5, 156.7, 150.8, 150.8, 136.1, 134.1, 132.9, 129.7, 128.8, 127.9, 124.2, 120.3, 119.1, 109.7, 72.0, 58.7, 56.3, 43.5. HRMS (ESI, M+) m/z calculated for $C_{18}H_{19}N_3O_2$ 309.1477, found 309.1472.

6-(2-((2-methoxyethyl)amino)pyrimidin-5-yl)naphthalen-2-ol (FTO-16)

Prepared according to general procedure A. Yield 0.378 g, 1.28 mmol, 32%. Yellow solid, mp 230° C. $^1$H-NMR (600 MHz, d-DMSO): 8.29 (s, 2H), 7.93 (s, 1H), 7.68 (dd, J=8.7, 2.5 Hz, 2H), 7.46 (d, J=7.3 Hz, 1H), 7.39 (t, J=7.7 Hz, 1H), 7.32 (t, J=8.0, 1H), 6.90 (dd, J=8.0, 2.0 Hz, 1H), 3.95 (s, 2H), 3.46 (s, 2H), 3.25 (s, 3H). $^{13}$C-NMR (150 MHz, d-DMSO): 159.9, 156.6, 150.3, 150.3, 134.1, 132.2, 130.3, 130.0, 129.0, 128.7, 125.7, 120.5, 116.4, 109.5, 71.8, 43.3, 56.9. HRMS (ESI, M+) m/z calculated for $C_{17}H_{17}N_3O_2$ 295.1321, found 295.1316.

7-(2-((2-methoxyethyl)amino)pyrimidin-5-yl)naphthalen-2-ol (FTO-17)

Prepared according to general procedure A. Yield 0.484 g, 1.68 mmol, 42%. Yellow solid, mp 230° C. $^1$H-NMR (600 MHz, d-DMSO): 8.41 (s, 2H), 7.90 (s, 1H), 7.84 (d, J=8.4 Hz, 1H), 7.73 (d, J=8.3 Hz, 1H), 7.64 (dd J=8.0, 2.0 Hz, 1H), 7.63 (d, J=2.5 Hz, 1H), 7.39 (t, J=7.7 Hz, 1H), 7.13 (d, J=7.3 1H), 3.94 (s, 2H), 3.47 (s, 2H), 3.28 (s, 3H). $^{13}$C-NMR (150 MHz, d-DMSO): 160.2, 156.1, 150.1, 150.1, 135.7, 134.9, 130.0, 129.2, 127.5, 125.5, 124.1, 120.6, 118.8, 109.7, 71.6, 56.5, 43.1. HRMS (ESI, M+) m/z calculated for $C_{17}H_{17}N_3O_2$ 295.1321, found 295.1314.

5-(4-(benzyloxy)phenyl)-N-(2-methoxyethyl)pyrimidin-2-amine (FTO-18)

Prepared according to general procedure A. Yield 0.698 g, 2.08 mmol, 52%. Yellow solid, mp 230° C. $^1$H-NMR (600 MHz, d-DMSO): 8.29 (s, 2H), 7.93 (s, 1H), 7.68 (dd, J=8.7, 2.5 Hz, 2H), 7.46 (d, J=7.3 Hz, 2H), 7.39 (t, J=7.7 Hz, 2H), 7.32 (t, J=8.0, 1H1), 6.90 (dd, J=8.0, 2.0 Hz, 2H), 5.16 (s, 2H), 3.95 (s, 2H), 3.46 (s, 2H), 3.25 (s, 3H). $^{13}$C-NMR (150 MHz, d-DMSO): 159.5, 158.8, 150.1, 150.1, 137.9, 136.6, 130.6, 128.9, 128.9, 128.4, 127.8, 127.8, 120.2, 118.4, 114.0, 113.2, 71.6, 70.7, 58.7, 43.1. HRMS (ESI, M+) m/z calculated for $C_{20}H_{21}N_3O_2$ 335.1634, found 334.1630.

N-(2-methoxyethyl)-5-(2-methylquinolin-6-yl)pyrimidin-2-amine (FTO-19)

Prepared according to general procedure A. Yield 0.503 g, 1.71 mmol, 43%. Yellow solid, mp 230° C. $^1$H-NMR (600 MHz, d-DMSO): 8.70 (s, 2H), 8.24 (d, J=8.3 Hz, 1H), 8.10 (d, J=8.8 Hz, 1H), 8.01 (d, J=1.7 Hz, 1H), 7.93 (s, 1H), 7.89 (d, J=8.7 Hz, 1H), 7.44 (d, J=8.5 Hz, 1H), 3.94 (s, 2H), 3.45 (s, 2H), 3.26 (s, 3H), 2.71 (s, 3H). $^{13}$C-NMR (150 MHz, d-DMSO): 159.8, 158.1, 151.2, 151.2, 150.1, 141.9, 135.6, 133.1, 128.7, 128.3, 125.9, 123.1, 120.2, 71.5, 58.7, 43.1, 25.5. HRMS (ESI, M+) m/z calculated for $C_{17}H_{18}N4_3O$ 294.1481, found 294.1485.

(2-methoxy-4-(2-((2-methoxyethyl)amino)pyrimidin-5-yl)phenyl)methanol (FTO-20)

Prepared according to general procedure A. Yield 0.584 g, 2.02 mmol, 51%. Yellow solid, mp 230° C. $^1$H-NMR (600 MHz, d-DMSO): 8.68 (s, 2H), 7.93 (s, 1H), 7.30 (d, J=7.9 Hz, 1H), 7.13 (d, J=1.6 Hz, 1H), 7.11 (t, J=2.7 Hz, 1H), 5.10 (t, J=5.6 Hz, 2H), 3.94 (s, 2H), 3.77 (s, 3H), 3.45 (s, 2H), 3.26 (s, 3H). $^{13}C$-NMR (150 MHz, d-DMSO): 159.9, 157.1, 148.9, 148.9, 136.2, 131.0, 129.1, 123.5, 119.1, 113.9, 71.5, 61.1, 58.6, 58.1, 43.0. HRMS (ESI, M+) m/z calculated for $C_{15}H_{19}N_3O_3$ 289.1426, found 289.1430.

Glioblastoma Cancer Stem Cells (GSCs) Cultures

Neurosphere Formation Assay

Early passaged GSCs were used to understand the efficacy of ALK-04 on the self-renewal capacity of GSCs by tumor-sphere-formation assay as described earlier[10, 11]. In brief, GSCs were seeded at $4\times10^4$ cells in 24 well plate and cultured for 3 days followed by treatment with ALK-04 inhibitors at 20 μM daily for 3 days. After 3 days of treatment the images of the tumorospheres were imaged with phase contrast microscope and size was measured with Image J, to understand the effects of drugs on the self-renewal of GSCs on sphere formation. This process was also repeated for healthy neural stem cells (hNSCs) treated daily with 20 μM ALK-04 for three days to assess the therapeutic ratio.

m6A Dot Blot Assay

Polyadenylated mRNA were isolated from TS576 cells treated with either DMSO, FTO-04 (30 μM), and control (shControl) or FTO lentivirus (shFTO) knockdown samples by using Magnetic mRNA Isolation Kit (New England Biolabs, S1550S). Isolated mRNA was quantified, serially diluted and denatured at 95° C. for 3 min, then chilled on ice to prevent reformation of secondary structure of mRNA. Denatured mRNA samples were spotted on an Amersham Hybond-N$^+$ membrane (GE Healthcare, RPN3050B) and cross-linked to the membrane with UV radiation. After crosslinking the membrane was washed with phosphate buffer saline with 0.1% tween-20 (PBST) and blocked in 5% of non-fat milk in PBST buffer, and then incubated with anti-m$^6$A antibody (1:1000; abcam) overnight at 4° C. The membrane was then washed as before and incubated in HRP-conjugated secondary antibodies for 1 h at room temperature. The membrane was then developed with Thermo ECL SuperSignal West Femto Maximum Sensitivity Substrate (Thermo Fisher Scientific).

Lentiviral Generation and Infection

Lentiviral particles for shControl, shFTO1 and shFTO2 were prepared by co-transfection of these shRNA plasmids with psPAX.2 (1.2 μg) and pMD2.G (0.6 μg) vectors in 293FT cells using Opti-MEM and Lipofectamine 2K transfection Reagent (Invitrogen). After overnight transfection the supernatant was removed and DMEM/F12 medium with B27 and growth factor containing medium was added to the cells. Virus containing supernatants were collected 24-48 h after transfection and filtered at 0.22 μm and stored at −80° C. Generated shControl and shFTO lentivirus particles were used to infect TS576 cells in the presence of Polybrene (8 jig/ml) (Millipore). After 12 h lentivirus containing medium was replaced with fresh medium and samples were collected after 72 h of infection.

Also see FIGS. 60-68 for additional information.

Table on inhibition Data for FTO Inhibitors against FTO and ALKBH5. C log P and permeability parameters calculated by QikProp.

| Structure | Name | clogP (octanol/water) | Permeability (nm/s) Caco-2 | MDCK | Enzymatic $IC_{50}$ FTO | Enzymatic $IC_{50}$ ALKBH5 |
|---|---|---|---|---|---|---|
| 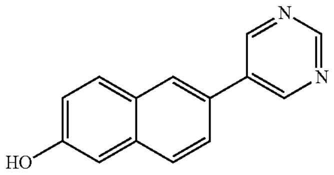 [SMILES: Oc1ccc2cc(-c3cncnc3)ccc2c1] | FTO-1 | 2.04 | 873 | 427 | 41.7 ± 1.2 | >40 |
| 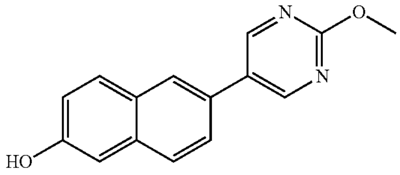 [SMILES: COc1ncc(-c2ccc3cc(O)ccc3c2)cn1] | FTO-2 | 3.00 | 1338 | 677 | 2.18 ± 1.3 | 85.5 ± 5.7 |
| 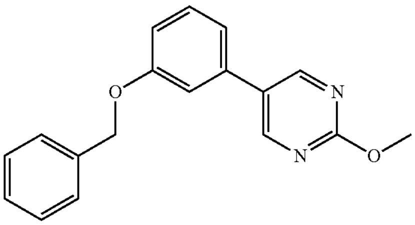 [SMILES: COc1ncc(-c2cccc(OCc3ccccc3)c2)cn1] | FTO-3 | 4.69 | 4410 | 2460 | ND | ND |
| 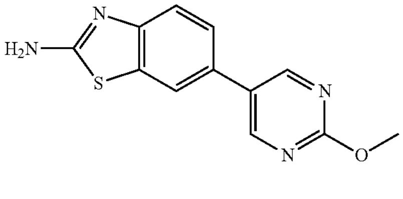 [SMILES: COc1ncc(-c2ccc3nc(N)sc3c2)cn1] | FTO-4 | 2.00 | 632 | 562 | 3.39 ± 2.5 | 39.4 ± 3.1 |

-continued
| Structure | Name | clogP (octanol/water) | Permeability (nm/s) Caco-2 | Permeability (nm/s) MDCK | Enzymatic $IC_{50}$ FTO | Enzymatic $IC_{50}$ ALKBH5 |
|---|---|---|---|---|---|---|
| 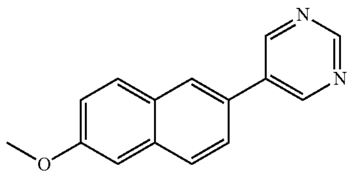 [SMILES: COc1ccc2cc(-c3cncnc3)ccc2c1] | FTO-5 | 2.67 | 2880 | 1552 | 13.38 ± 2.3 | >40 |
| 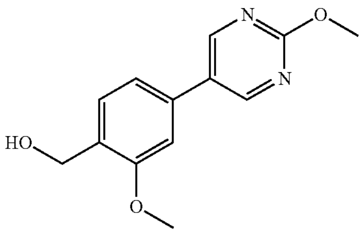 [SMILES: COc1ncc(-c2ccc(CO)c(OC)c2)cn1] | FTO-6 | 2.30 | 1335 | 665 | 13.8 ± 2.4 | 64.4 ± 6.3 |
| 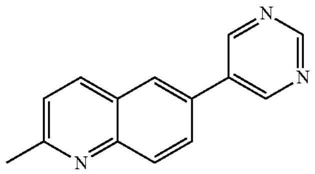 [SMILES: Cc1ccc2cc(-c3cncnc3)ccc2n1] | FTO-7 | 2.27 | 2101 | 1104 | 29.1 ± 2.4 | >40 |
| 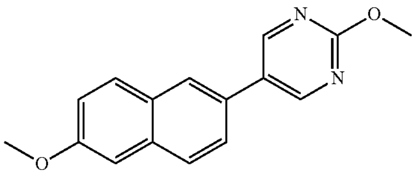 | FTO-8 | 3.75 | 4411 | 2460 | 10.0 ± 1.8 | 16.4 ± 2.1 |
| 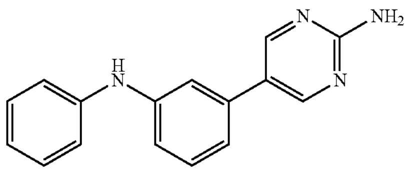 [SMILES: Nc1ncc(-c2cccc(Nc3ccccc3)c2)cn1] | FTO-9 | 2.79 | 624 | 297 | 43.8 ± 2.4 | 5.2 ± 2.9 |
| 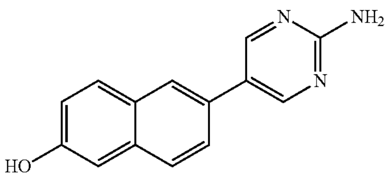 [SMILES: Nc1ncc(-c2ccc3cc(O)ccc3c2)cn1] | FTO-10 | 1.60 | 255 | 113 | 48.1 ± 3.5 | 36.1 ± 3.1 |
| 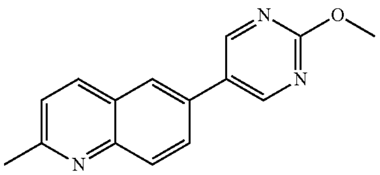 | FTO-11 | 3.35 | 3218 | 1750 | 11.3 ± 1.1 | 19.5 ± 2.7 |

-continued
| Structure | Name | clogP (octanol/water) | Permeability (nm/s) Caco-2 | Permeability (nm/s) MDCK | Enzymatic $IC_{50}$ FTO | Enzymatic $IC_{50}$ ALKBH5 |
|---|---|---|---|---|---|---|
| 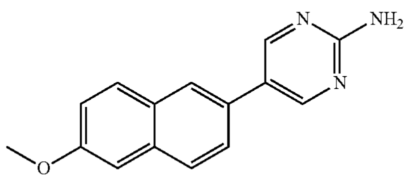 [SMILES: COc1ccc2cc(-c3cnc(N)nc3)ccc2c1] | FTO-12 | 2.48 | 842 | 411 | 18.3 ± 1.7 | >40 |
| 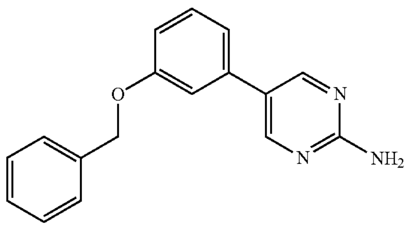 [SMILES: Nc1ncc(-c2cccc(OCc3ccccc3)c2)cn1] | FTO-13 | 3.37 | 842 | 411 | 36.7 ± 3.1 | 14.9 ± 1.8 |
| 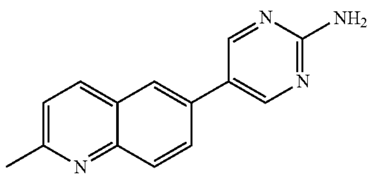 [SMILES: Cc1ccc2cc(-c3cnc(N)nc3)ccc2n1] | FTO-14 | 2.11 | 615 | 292 | 59.6 ± 4.8 | >40 |
| 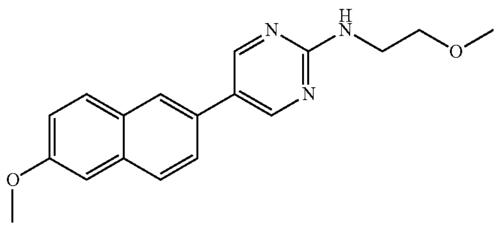 [SMILES: COCCNc1ncc(-c2ccc3cc(OC)ccc3c2)cn1] | FTO-15 | 3.45 | 963 | 475 | ND | ND |
| 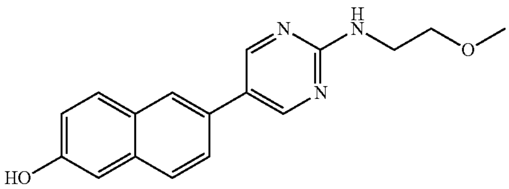 [SMILES: COCCNc1ncc(-c2ccc3cc(O)ccc3c2)cn1] | FTO-16 | 2.89 | 292 | 130 | 46.5 ± 3.1 | >40 |
| 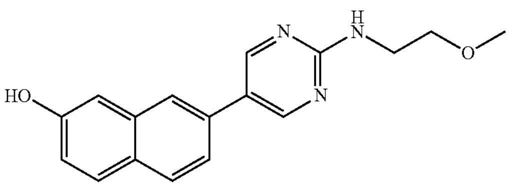 [SMILES: COCCNc1ncc(-c2ccc3ccc(O)cc3c2)cn1] | FTO-17 | 2.89 | 292 | 130 | 51.9 ± 4.7 | >40 |

-continued

| Structure | Name | clogP (octanol/water) | Permeability (nm/s) Caco-2 | Permeability (nm/s) MDCK | Enzymatic $IC_{50}$ FTO | Enzymatic $IC_{50}$ ALKBH5 |
|---|---|---|---|---|---|---|
| 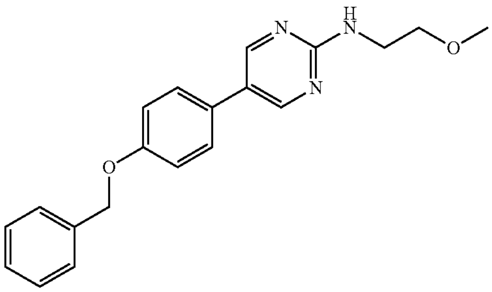 [SMILES: COCCNc1ncc(-c2ccc(OCc3ccccc3)cc2)cn1] | FTO-18 | 3.69 | 963 | 475 | >40 | >40 |
| 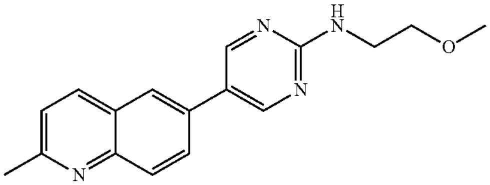 | FTO-19 | 2.44 | 702 | 337 | 25.2 ± 4.9 | 53.5 ± 5.2 |
| 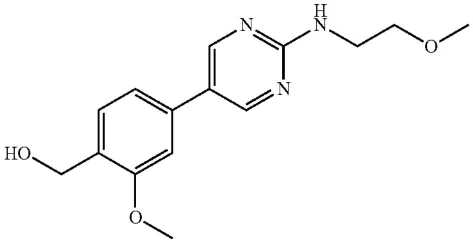 [SMILES: COCCNc1ncc(-c2ccc(CO)c(OC)c2)cn1] | FTO-20 | 1.21 | 2.87 | 128 | 17.2 ± 2.9 | 90.2 ± 7.8 |

ND = Not determined

TABLE S2

Calculated Physicochemical Data for MA, FB23, and FB23-2. ClogP and permeability parameters calculated by QikProp. Inhibition data for MA was obtained as described in the methods. Inhibition data for FB23 and FB23-2 against FTO and ALKBH5 is reported from Huang et. al 2019.

| Structure | Name | clogP (octanol/water) | Permeability (nm/s) Caco-2 | Permeability (nm/s) MDCK | Enzymatic $IC_{50}$ FTO | Enzymatic $IC_{50}$ ALKBH5 |
|---|---|---|---|---|---|---|
| 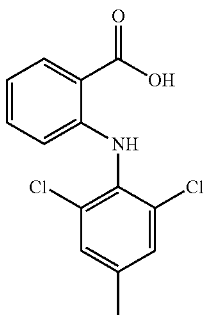 [SMILES: Cc1cc(Cl)c(Nc2ccccc2C(=O)O)c(Cl)c1] | MA | 4.93 | 327 | 638 | 12.5 ± 1.8 | >40 |

TABLE S2-continued

Calculated Physicochemical Data for MA, FB23, and FB23-2. ClogP and permeability parameters calculated by QikProp. Inhibition data for MA was obtained as described in the methods. Inhibition data for FB23 and FB23-2 against FTO and ALKBH5 is reported from Huang et. al 2019.

| Structure | Name | clogP (octanol/water) | Permeability (nm/s) Caco-2 | Permeability (nm/s) MDCK | Enzymatic $IC_{50}$ FTO | Enzymatic $IC_{50}$ ALKBH5 |
|---|---|---|---|---|---|---|
| 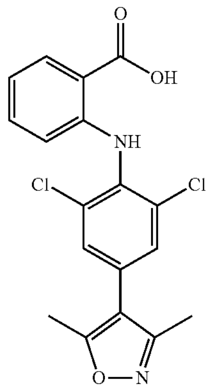 [SMILES: Cc1noc(C)c1-c1cc(Cl)c(Nc2ccccc2C(=O)O)c(Cl)c1] | FB23 | 4.96 | 97 | 210 | 0.06 | >40 |
| 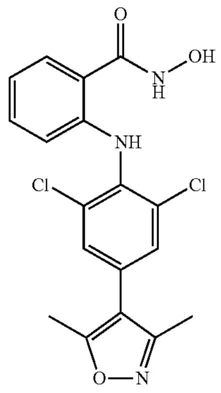 [SMILES: Cc1noc(C)c1-c1cc(Cl)c(Nc2ccccc2C(=O)NO)c(Cl)c1] | FB23-2 | 3.46 | 240 | 428 | 2.6 | >40 |

REFERENCES

1. Meyer, K. D., Saletore, Y., Zumbo, P., Elemento, O., Mason, C. E., and Jaffrey, S. R. (2012) Comprehensive analysis of mRNA methylation reveals enrichment in 3' UTRs and near stop codons, *Cell* 149, 1635-1646.
2. Geula, S., Moshitch-Moshkovitz, S., Dominissini, D., Mansour, A. A., Kol, N., Salmon-Divon, M., Hershkovitz, V., Peer, E., Mor, N., Manor, Y. S., Ben-Haim, M. S., Eyal, E., Yunger, S., Pinto, Y., Jaitin, D. A., Viukov, S., Rais, Y., Krupalnik, V., Chomsky, E., Zerbib, M., Maza, I., Rechavi, Y., Massarwa, R., Hanna, S., Amit, I., Levanon, E. Y., Amariglio, N., Stern-Ginossar, N., Novershtern, N., Rechavi, G., and Hanna, J. H. (2015) Stem cells. m6A mRNA methylation facilitates resolution of naive pluripotency toward differentiation, *Science* 347, 1002-1006.
3. Dominissini, D., Moshitch-Moshkovitz, S., Schwartz, S., Salmon-Divon, M., Ungar, L., Osenberg, S., Cesarkas, K., Jacob-Hirsch, J., Amariglio, N., Kupiec, M., Sorek, R., and Rechavi, G. (2012) Topology of the human and mouse m6A RNA methylomes revealed by m6A-seq, *Nature* 485, 201-206.
4. Liu, J., Yue, Y., Han, D., Wang, X., Fu, Y., Zhang, L., Jia, G., Yu, M., Lu, Z., Deng, X., Dai, Q., Chen, W., and He, C. (2014) A METTL3-METTL14 complex mediates mammalian nuclear RNA N6-adenosine methylation, *Nat Chem Biol* 10, 93-95.
5. Wang, X., Feng, J., Xue, Y., Guan, Z., Zhang, D., Liu, Z., Gong, Z., Wang, Q., Huang, J., Tang, C., Zou, T., and Yin, P. (2016) Structural basis of N(6)-adenosine methylation by the METTL3-METTL14 complex, *Nature* 534, 575-578.
6. Meyer, K. D., and Jaffrey, S. R. (2017) Rethinking m(6)A Readers, Writers, and Erasers, *Annu Rev Cell Dev Biol* 33, 319-342.
7. Shi, H., Wei, J., and He, C. (2019) Where, When, and How: Context-Dependent Functions of RNA Methylation Writers, Readers, and Erasers, *Mol Cell* 74, 640-650.
8. Han, Z., Niu, T., Chang, J., Lei, X., Zhao, M., Wang, Q., Cheng, W., Wang, J., Feng, Y., and Chai, J. (2010) Crystal structure of the FTO protein reveals basis for its substrate specificity, *Nature* 464, 1205-1209.
9. Zou, S., Toh, J. D., Wong, K. H., Gao, Y. G., Hong, W., and Woon, E. C. (2016) N(6)-Methyladenosine: a conformational marker that regulates the substrate specificity of human demethylases FTO and ALKBH5, *Sci Rep* 6, 25677.
10. Mauer, J., Luo, X., Blanjoie, A., Jiao, X., Grozhik, A. V., Patil, D. P., Linder, B., Pickering, B. F., Vasseur, J. J., Chen, Q., Gross, S. S., Elemento, O., Debart, F., Kiledjian, M., and Jaffrey, S. R. (2017) Reversible methylation of m(6)Am in the 5' cap controls mRNA stability, *Nature* 541, 371-375.
11. Zhang, X., Wei, L. H., Wang, Y., Xiao, Y., Liu, J., Zhang, W., Yan, N., Amu, G., Tang, X., Zhang, L., and Jia, G. (2019) Structural insights into FTO's catalytic mechanism for the demethylation of multiple RNA substrates, *Proc Natl Acad Sci USA* 116, 2919-2924.
12. Thalhammer, A., Bencokova, Z., Poole, R., Loenarz, C., Adam, J., O'Flaherty, L., Schodel, J., Mole, D., Giaslakiotis, K., Schofield, C. J., Hammond, E. M., Ratcliffe, P. J., and Pollard, P. J. (2011) Human AlkB homologue 5 is a nuclear 2-oxoglutarate dependent oxygenase and a direct target of hypoxia-inducible factor 1alpha (HIF-1alpha), *PLoS One* 6, e16210.
13. Aik, W., Scotti, J. S., Choi, H., Gong, L., Demetriades, M., Schofield, C. J., and McDonough, M. A. (2014) Structure of human RNA N(6)-methyladenine demethylase ALKBH5 provides insights into its mechanisms of nucleic acid recognition and demethylation, *Nucleic Acids Res* 42, 4741-4754.
14. Xu, C., Liu, K., Tempel, W., Demetriades, M., Aik, W., Schofield, C. J., and Min, J. (2014) Structures of human ALKBH5 demethylase reveal a unique binding mode for specific single-stranded N6-methyladenosine RNA demethylation, *J Biol Chem* 289, 17299-17311.
15. Mauer, J., and Jaffrey, S. R. (2018) FTO, m(6) Am, and the hypothesis of reversible epitranscriptomic mRNA modifications, *FEBS Lett* 592, 2012-2022.
16. Wei, J., Liu, F., Lu, Z., Fei, Q., Ai, Y., He, P. C., Shi, H., Cui, X., Su, R., Klungland, A., Jia, G., Chen, J., and He, C. (2018) Differential m(6)A, m(6)Am, and m(1)A Demethylation Mediated by FTO in the Cell Nucleus and Cytoplasm, *Mol Cell* 71, 973-985 e975.
17. Mauer, J., Sindelar, M., Despic, V., Guez, T., Hawley, B. R., Vasseur, J. J., Rentmeister, A., Gross, S. S., Pellizzoni, L., Debart, F., Goodarzi, H., and Jaffrey, S. R. (2019) FTO controls reversible m(6)Am RNA methylation during snRNA biogenesis, *Nat Chem Biol* 15, 340-347.
18. Koh, C. W. Q., Goh, Y. T., and Goh, W. S. S. (2019) Atlas of quantitative single-base-resolution N(6)-methyl-adenine methylomes, *Nat Commun* 10, 5636.
19. Xu, C., Wang, X., Liu, K., Roundtree, I. A., Tempel, W., Li, Y., Lu, Z., He, C., and Min, J. (2014) Structural basis for selective binding of m6A RNA by the YTHDC1 YTH domain, *Nat Chem Biol* 10, 927-929.
20. Zhu, T., Roundtree, I. A., Wang, P., Wang, X., Wang, L., Sun, C., Tian, Y., Li, J., He, C., and Xu, Y. (2014) Crystal structure of the YTH domain of YTHDF2 reveals mechanism for recognition of N6-methyladenosine, *Cell Res* 24, 1493-1496.
21. Wang, X., Lu, Z., Gomez, A., Hon, G. C., Yue, Y., Han, D., Fu, Y., Parisien, M., Dai, Q., Jia, G., Ren, B., Pan, T., and He, C. (2014) N6-methyladenosine-dependent regulation of messenger RNA stability, *Nature* 505, 117-120.
22. Wang, X., Zhao, B. S., Roundtree, I. A., Lu, Z., Han, D., Ma, H., Weng, X., Chen, K., Shi, H., and He, C. (2015) N(6)-methyladenosine Modulates Messenger RNA Translation Efficiency, *Cell* 161, 1388-1399.
23. Li, F., Zhao, D., Wu, J., and Shi, Y. (2014) Structure of the YTH domain of human YTHDF2 in complex with an m(6)A mononucleotide reveals an aromatic cage for m(6)A recognition, *Cell Res* 24, 1490-1492.
24. Luo, S., and Tong, L. (2014) Molecular basis for the recognition of methylated adenines in RNA by the eukaryotic YTH domain, *Proc Natl Acad Sci USA* 111, 13834-13839.
25. Theler, D., Dominguez, C., Blatter, M., Boudet, J., and Allain, F. H. (2014) Solution structure of the YTH domain in complex with N6-methyladenosine RNA: a reader of methylated RNA, *Nucleic Acids Res* 42, 13911-13919.
26. Patil, D. P., Pickering, B. F., and Jaffrey, S. R. (2018) Reading m(6)A in the Transcriptome: m(6)A-Binding Proteins, *Trends Cell Biol* 28, 113-127.
27. Jaffrey, S. R., and Kharas, M. G. (2017) Emerging links between m6A and misregulated mRNA methylation in cancer, *Genome Med* 9, 2.
28. Boriack-Sjodin, P. A., Ribich, S., and Copeland, R. A. (2018) RNA-modifying proteins as anticancer drug targets, *Nat Rev Drug Discov* 17, 435-453.
29. Panneerdoss, S., Eedunuri, V. K., Yadav, P., Timilsina, S., Rajamanickam, S., Viswanadhapalli, S., Abdelfattah, N., Onyeagucha, B. C., Cui, X., Lai, Z., Mohammad, T. A., Gupta, Y. K., Huang, T. H., Huang, Y., Chen, Y., and Rao, M. K. (2018) Cross-talk among writers, readers, and erasers of m(6)A regulates cancer growth and progression, *Sci Adv* 4, eaar8263.
30. Zhang, C., Zhi, W. I., Lu, H., Samanta, D., Chen, I., Gabrielson, E., and Semenza, G. L. (2016) Hypoxia-inducible factors regulate pluripotency factor expression by ZNF217- and ALKBH5-mediated modulation of RNA methylation in breast cancer cells, *Oncotarget* 7, 64527-64542.
31. Zhang, S., Zhao, B. S., Zhou, A., Lin, K., Zheng, S., Lu, Z., Chen, Y., Sulman, E. P., Xie, K., Bogler, O., Majumder, S., He, C., and Huang, S. (2017) m(6)A Demethylase ALKBH5 Maintains Tumorigenicity of Glioblastoma Stem-like Cells by Sustaining FOXM1 Expression and Cell Proliferation Program, *Cancer Cell* 31, 591-606 e596.
32. Barbieri, I., Tzelepis, K., Pandolfini, L., Shi, J., Millan-Zambrano, G., Robson, S. C., Aspris, D., Migliori, V., Bannister, A. J., Han, N., De Braekeleer, E., Ponstingl, H., Hendrick, A., Vakoc, C. R., Vassiliou, G. S., and Kouzarides, T. (2017) Promoter-bound METTL3 maintains myeloid leukaemia by m(6)A-dependent translation control, *Nature* 552, 126-131.
33. Cui, Q., Shi, H., Ye, P., Li, L., Qu, Q., Sun, G., Sun, G., Lu, Z., Huang, Y., Yang, C. G., Riggs, A. D., He, C., and Shi, Y. (2017) m6A RNA Methylation Regulates the Self-Renewal and Tumorigenesis of Glioblastoma Stem Cells, *Cell Rep* 18, 2622-2634.
34. Su, R., Dong, L., Li, C., Nachtergaele, S., Wunderlich, M., Qing, Y., Deng, X., Wang, Y., Weng, X., Hu, C., Yu, M., Skibbe, J., Dai, Q., Zou, D., Wu, T., Yu, K., Weng, H., Huang, H., Ferchen, K., Qin, X., Zhang, B., Qi, J., Sasaki, A. T., Plas, D. R., Bradner, J. E., Wei, M., Marcucci, G., Jiang, X., Mulloy, J. C., Jin, J., He, C., and Chen, J. (2018) R-2HG Exhibits Anti-tumor Activity by Targeting FTO/m(6)A/MYC/CEBPA Signaling, *Cell* 172, 90-105 e123.
35. Vu, L. P., Pickering, B. F., Cheng, Y., Zaccara, S., Nguyen, D., Minuesa, G., Chou, T., Chow, A., Saletore, Y., MacKay, M., Schulman, J., Famulare, C., Patel, M., Klimek, V. M., Garrett-Bakelman, F. E., Melnick, A., Carroll, M., Mason, C. E., Jaffrey, S. R., and Kharas, M. G. (2017) The N(6)-methyladenosine (m(6)A)-forming enzyme METTL3 controls myeloid differentiation of normal hematopoietic and leukemia cells, *Nat Med* 23, 1369-1376.

36. Huang, Y., Su, R., Sheng, Y., Dong, L., Dong, Z., Xu, H., Ni, T., Zhang, Z. S., Zhang, T., Li, C., Han, L., Zhu, Z., Lian, F., Wei, J., Deng, Q., Wang, Y., Wunderlich, M., Gao, Z., Pan, G., Zhong, D., Zhou, H., Zhang, N., Gan, J., Jiang, H., Mulloy, J. C., Qian, Z., Chen, J., and Yang, C. G. (2019) Small-Molecule Targeting of Oncogenic FTO Demethylase in Acute Myeloid Leukemia, *Cancer Cell* 35, 677-691 e610.

37. Chen, J., and Du, B. (2019) Novel positioning from obesity to cancer: FTO, an m(6)A RNA demethylase, regulates tumour progression, *J Cancer Res Clin Oncol* 145, 19-29.

38. Li, Z., Weng, H., Su, R., Weng, X., Zuo, Z., Li, C., Huang, H., Nachtergaele, S., Dong, L., Hu, C., Qin, X., Tang, L., Wang, Y., Hong, G. M., Huang, H., Wang, X., Chen, P., Gurbuxani, S., Arnovitz, S., Li, Y., Li, S., Strong, J., Neilly, M. B., Larson, R. A., Jiang, X., Zhang, P., Jin, J., He, C., and Chen, J. (2017) FTO Plays an Oncogenic Role in Acute Myeloid Leukemia as a N(6)-Methyladenosine RNA Demethylase, *Cancer Cell* 31, 127-141.

39. Visvanathan, A., Patil, V., Arora, A., Hegde, A. S., Arivazhagan, A., Santosh, V., and Somasundaram, K. (2018) Essential role of METTL3-mediated m(6)A modification in glioma stem-like cells maintenance and radioresistance, *Oncogene* 37, 522-533.

40. Huang, Y., Yan, J., Li, Q., Li, J., Gong, S., Zhou, H., Gan, J., Jiang, H., Jia, G. F., Luo, C., and Yang, C. G. (2015) Meclofenamic acid selectively inhibits FTO demethylation of m6A over ALKBH5, *Nucleic Acids Res* 43, 373-384.

41. Friesner, R. A., Banks, J. L., Murphy, R. B., Halgren, T. A., Klicic, J. J., Mainz, D. T., Repasky, M. P., Knoll, E. H., Shelley, M., Perry, J. K., Shaw, D. E., Francis, P., and Shenkin, P. S. (2004) Glide: a new approach for rapid, accurate docking and scoring. 1. Method and assessment of docking accuracy, *J Med Chem* 47, 1739-1749.

42. Halgren, T. A., Murphy, R. B., Friesner, R. A., Beard, H. S., Frye, L. L., Pollard, W. T., and Banks, J. L. (2004) Glide: a new approach for rapid, accurate docking and scoring. 2. Enrichment factors in database screening, *J Med Chem* 47, 1750-1759.

43. Friesner, R. A., Murphy, R. B., Repasky, M. P., Frye, L. L., Greenwood, J. R., Halgren, T. A., Sanschagrin, P. C., and Mainz, D. T. (2006) Extra precision glide: docking and scoring incorporating a model of hydrophobic enclosure for protein-ligand complexes, *J Med Chem* 49, 6177-6196.

44. Svensen, N., and Jaffrey, S. R. (2016) Fluorescent RNA Aptamers as a Tool to Study RNA-Modifying Enzymes, *Cell Chem Biol* 23, 415-425.

45. Inda, M. M., Bonavia, R., Mukasa, A., Narita, Y., Sah, D. W., Vandenberg, S., Brennan, C., Johns, T. G., Bachoo, R., Hadwiger, P., Tan, P., Depinho, R. A., Cavenee, W., and Furnari, F. (2010) Tumor heterogeneity is an active process maintained by a mutant EGFR-induced cytokine circuit in glioblastoma, *Genes Dev* 24, 1731-1745.

46. Benitez, J. A., Ma, J., D'Antonio, M., Boyer, A., Camargo, M. F., Zanca, C., Kelly, S., Khodadadi-Jamayran, A., Jameson, N. M., Andersen, M., Miletic, H., Saberi, S., Frazer, K. A., Cavenee, W. K., and Furnari, F. B. (2017) PTEN regulates glioblastoma oncogenesis through chromatin-associated complexes of DAXX and histone H3.3, *Nat Commun* 8, 15223.

47. Cheng, L., Huang, Z., Zhou, W., Wu, Q., Donnola, S., Liu, J. K., Fang, X., Sloan, A. E., Mao, Y., Lathia, J. D., Min, W., McLendon, R. E., Rich, J. N., and Bao, S. (2013) Glioblastoma stem cells generate vascular pericytes to support vessel function and tumor growth, *Cell* 153, 139-152.

48. Lv, D., Hu, Z., Lu, L., Lu, H., and Xu, X. (2017) Three-dimensional cell culture: A powerful tool in tumor research and drug discovery, *Oncol Lett* 14, 6999-7010.

49. Dirkse, A., Golebiewska, A., Buder, T., Nazarov, P. V., Muller, A., Poovathingal, S., Brons, N. H. C., Leite, S., Sauvageot, N., Sarkisjan, D., Seyfrid, M., Fritah, S., Stieber, D., Michelucci, A., Hertel, F., Herold-Mende, C., Azuaje, F., Skupin, A., Bjerkvig, R., Deutsch, A., Voss-Bohme, A., and Niclou, S. P. (2019) Stem cell-associated heterogeneity in Glioblastoma results from intrinsic tumor plasticity shaped by the microenvironment, *Nat Commun* 10, 1787.

50. Ishiguro, T., Ohata, H., Sato, A., Yamawaki, K., Enomoto, T., and Okamoto, K. (2017) Tumor-derived spheroids: Relevance to cancer stem cells and clinical applications, *Cancer Sci* 108, 283-289.

51. Colwell, N., Larion, M., Giles, A. J., Seldomridge, A. N., Sizdahkhani, S., Gilbert, M. R., and Park, D. M. (2017) Hypoxia in the glioblastoma microenvironment: shaping the phenotype of cancer stem-like cells, *Neuro Oncol* 19, 887-896.

52. Zhang, C., Samanta, D., Lu, H., Bullen, J. W., Zhang, H., Chen, I., He, X., and Semenza, G. L. (2016) Hypoxia induces the breast cancer stem cell phenotype by HIF-dependent and ALKBH5-mediated m(6)A-demethylation of NANOG mRNA, *Proc Natl Acad Sci USA* 113, E2047-2056.

53. Huang, Y., Yan, J., Li, Q., Li, J., Gong, S., Zhou, H., Gan, J., Jiang, H., Jia, G. F., Luo, C., and Yang, C. G. (2015) Meclofenamic acid selectively inhibits FTO demethylation of m6A over ALKBH5, *Nucleic Acids Res* 43, 373-384.

54. Jacobson, M. P., Friesner, R. A., Xiang, Z., and Honig, B. (2002) On the role of the crystal environment in determining protein side-chain conformations, *J Mol Biol* 320, 597-608.

55. Jacobson, M. P., Pincus, D. L., Rapp, C. S., Day, T. J., Honig, B., Shaw, D. E., and Friesner, R. A. (2004) A hierarchical approach to all-atom protein loop prediction, *Proteins* 55, 351-367.

56. Friesner, R. A., Banks, J. L., Murphy, R. B., Halgren, T. A., Klicic, J. J., Mainz, D. T., Repasky, M. P., Knoll, E. H., Shelley, M., Perry, J. K., Shaw, D. E., Francis, P., and Shenkin, P. S. (2004) Glide: a new approach for rapid, accurate docking and scoring. 1. Method and assessment of docking accuracy, *J Med Chem* 47, 1739-1749.

57. Halgren, T. A., Murphy, R. B., Friesner, R. A., Beard, H. S., Frye, L. L., Pollard, W. T., and Banks, J. L. (2004) Glide: a new approach for rapid, accurate docking and scoring. 2. Enrichment factors in database screening, *J Med Chem* 47, 1750-1759.

58. Friesner, R. A., Murphy, R. B., Repasky, M. P., Frye, L. L., Greenwood, J. R., Halgren, T. A., Sanschagrin, P. C., and Mainz, D. T. (2006) Extra precision glide: docking and scoring incorporating a model of hydrophobic enclosure for protein-ligand complexes, *J Med Chem* 49, 6177-6196.

59. Svensen, N., and Jaffrey, S. R. (2016) Fluorescent RNA Aptamers as a Tool to Study RNA-Modifying Enzymes, *Cell Chem Biol* 23, 415-425.

60. Benitez, J. A., Ma, J., D'Antonio, M., Boyer, A., Camargo, M. F., Zanca, C., Kelly, S., Khodadadi-Jamayran, A., Jameson, N. M., Andersen, M., Miletic, H., Saberi, S., Frazer, K. A., Cavenee, W. K., and Furnari, F.

B. (2017) PTEN regulates glioblastoma oncogenesis through chromatin-associated complexes of DAXX and histone H3.3, *Nat Commun* 8, 15223.
61. Inda, M. M., Bonavia, R., Mukasa, A., Narita, Y., Sah, D. W., Vandenberg, S., Brennan, C., Johns, T. G., Bachoo, R., Hadwiger, P., Tan, P., Depinho, R. A., Cavenee, W., and Furnari, F. (2010) Tumor heterogeneity is an active process maintained by a mutant EGFR-induced cytokine circuit in glioblastoma, *Genes Dev* 24, 1731-1745.
62. Cui, Q., Yang, S., Ye, P., Tian, E., Sun, G., Zhou, J., Sun, G., Liu, X., Chen, C., Murai, K., Zhao, C., Azizian, K. T., Yang, L., Warden, C., Wu, X., D'Apuzzo, M., Brown, C., Badie, B., Peng, L., Riggs, A. D., Rossi, J. J., and Shi, Y. (2016) Downregulation of TLX induces TET3 expression and inhibits glioblastoma stem cell self-renewal and tumorigenesis, *Nature communications* 7, 10637.
63. Cui, Q., Shi, H., Ye, P., Li, L., Qu, Q., Sun, G., Sun, G., Lu, Z., Huang, Y., Yang, C. G., Riggs, A. D., He, C., and Shi, Y. (2017) m6A RNA Methylation Regulates the Self-Renewal and Tumorigenesis of Glioblastoma Stem Cells, *Cell Rep* 18, 2622-2634.

Example B5: ALKBH5 Regulates Anti-PD-1 Therapy Response by Modulating Lactate and Suppressive Immune Cell Accumulation in Tumor Microenvironment Introduction The adaptive immune response is tightly regulated through immune checkpoint pathways that serve to inhibit T cell activation, thereby maintaining self-tolerance and preventing autoimmunity. The two major checkpoints involve interactions between cytotoxic T lymphocyte antigen 4 (CTLA-4) and programmed cell death protein 1 (PD-1) on T cells and their ligands CD80/CD86 and PD-L1, respectively, which are expressed on various immune cells under physiological conditions. However, expression of these proteins on tumor cells inhibits the T cell activation and enables immune evasion and tumor cell survival. The development of antibodies (Abs) and fusion proteins against PD-1, PD-L1, and CTLA-4, which block negative signaling and enhance the T cell response to tumor antigens, has proven to be a breakthrough in the treatment of solid tumors. Nevertheless, such immune checkpoint blockade (ICB) is ineffective against some tumor types, and many patients who initially respond develop resistance and relapse after ICB. Consequently, understanding the mechanisms of tumor sensitivity, evasion, and resistance to ICB is under intense investigation[1]. One of the proposed mechanisms for the failure of ICB is ineffective T cell infiltration and activation due to immunosuppressive conditions within the tumor microenvironment (TME). There is thus an urgent need to develop approaches to increase the sensitivity of tumors to ICBs through combination treatment with molecules that convert an immune-suppressive to an immune-active TME.

Epitranscriptomics is an emerging field that seeks to identify and understand chemical modifications in RNA; the enzymes that deposit, remove, and interpret the modifications (writers, erasers, and readers, respectively); and their effects on gene expression via regulation of RNA metabolism, function, and localization[2, 3]. N6-methyladenosine (m6A) is the most prevalent internal RNA modification in many species, including mammals. In eukaryotic mRNAs, m6A is abundant in 5'UTRs, 3'UTRs, and stop codons[4-6]. The m6A modification is catalyzed by a large RNA methyltransferase complex composed of a catalytic subunit METTL3 and its interacting proteins METTL14, a splicing factor (WTAP), a novel protein (KIAA1429), and other as yet unidentified proteins[2,3]. Conversely, removal of m6A is catalyzed by the RNA demethylases FTO and ALKBH5[7,8]. In addition, FTO demethylates N6,2'-O-dimethyladenosine (m6Am) to reduce the stability of target mRNAs and small nuclear RNA (snRNA) biogenesis[9, 10]. The m6A RNA reader proteins, YTH domain-containing proteins (e.g., YTHDF1, YTHDF2, and YTHDF3), specifically bind modified RNA and mediate its effects on RNA stability and translation[11, 12].

In addition to the physiological roles of m6A in regulating RNA metabolism in such crucial processes as stem cell differentiation, circadian rhythms, spermatogenesis, and the stress response[2, 13], increasing evidence supports a pathological role for perturbed m6A metabolism in several disease states. For example, recent studies have shown that the m6A status of mRNA is involved in the regulation of T cell homeostasis[14], viral infection[15], and cancer[16-21].

Here, we employed well-established ICB mouse models of melanoma and colorectal carcinoma to investigate the roles of tumor cell intrinsic Alkbh5 and Fto functions in modulating the response to immunotherapy. We found that CRISPR-mediated deletion of Alkbh5 or Fto in the B16 mouse melanoma[22] or CT26 colorectal carcinoma[23-25] cell line had no effect on tumor growth in untreated mice, but Alkbh5 knockout (KO) significantly reduced tumor growth and prolonged mouse survival during immunotherapy. Alkbh5 deficiency altered immune cell infiltration and metabolite composition in the TME. In addition, the efficacy of cancer immunotherapy was enhanced by pharmacological inhibition of Alkbh5. Finally, we show that gene mutation or down-regulation of the ALKBH5 in melanoma patients correlates with a positive response to PD-1 blockade with pembrolizumab or nivolumab. Thus, our results identify a major role for tumor m6A demethylase in controlling the efficacy of immunotherapy and suggest that combination treatment with ALKBH5 inhibitors may be an approach to sensitize immunotherapy or to overcome tumor resistance to ICB.

Results

Deletion of the m6A RNA Demethylase Alkbh5 Enhances the Efficacy of Anti-PD-1 Treatment.

Figure 69B:
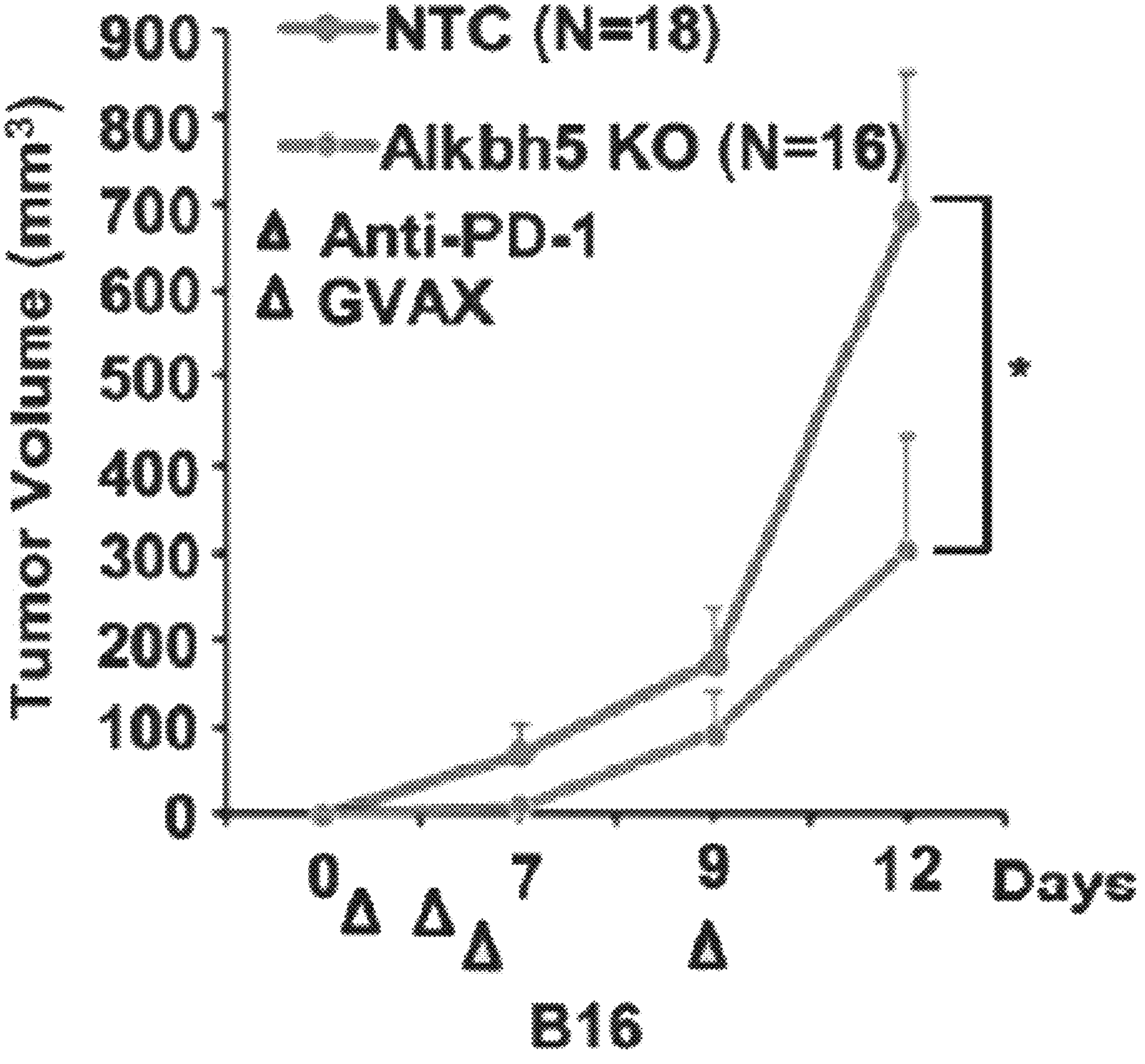
Figure 69C:
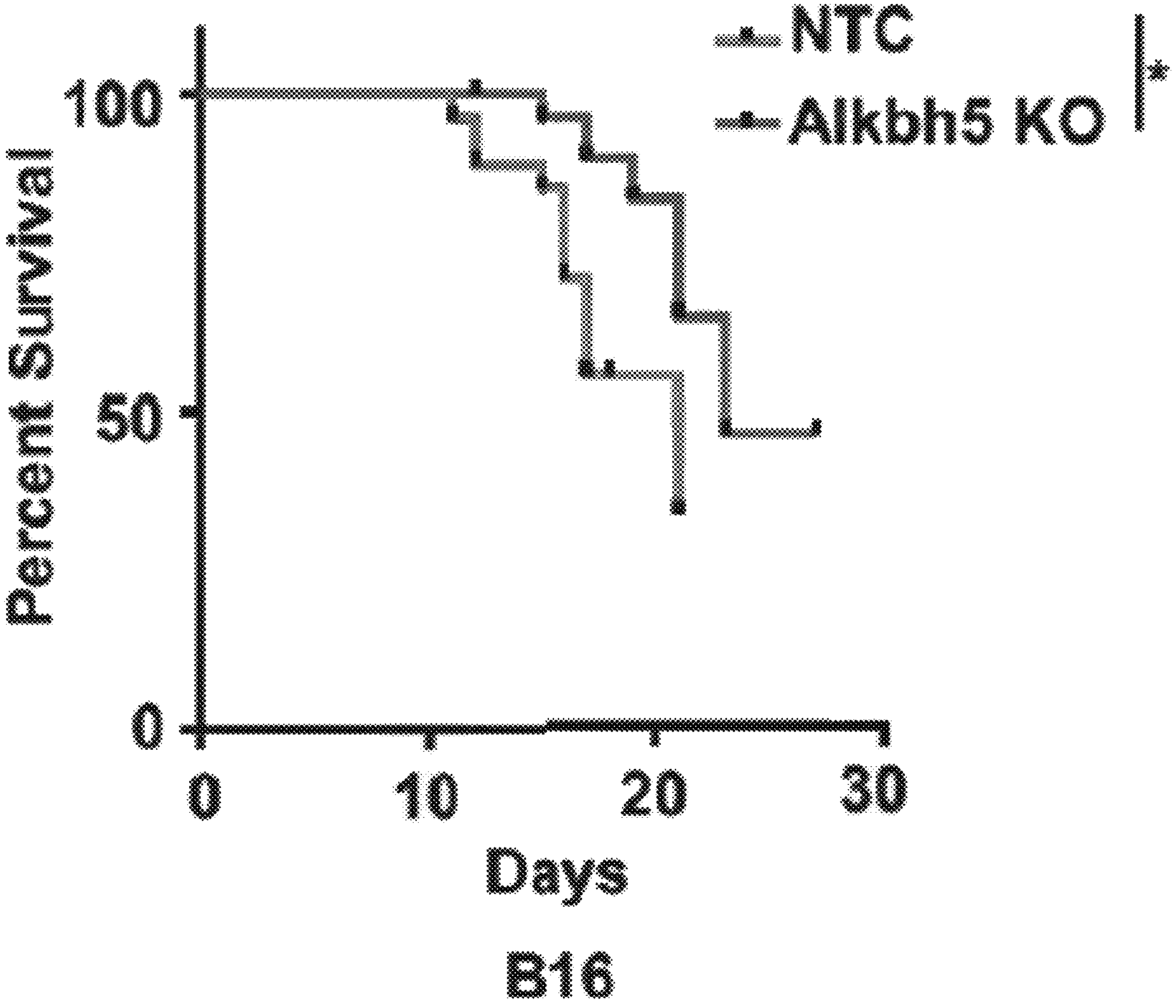
Figure 69D:
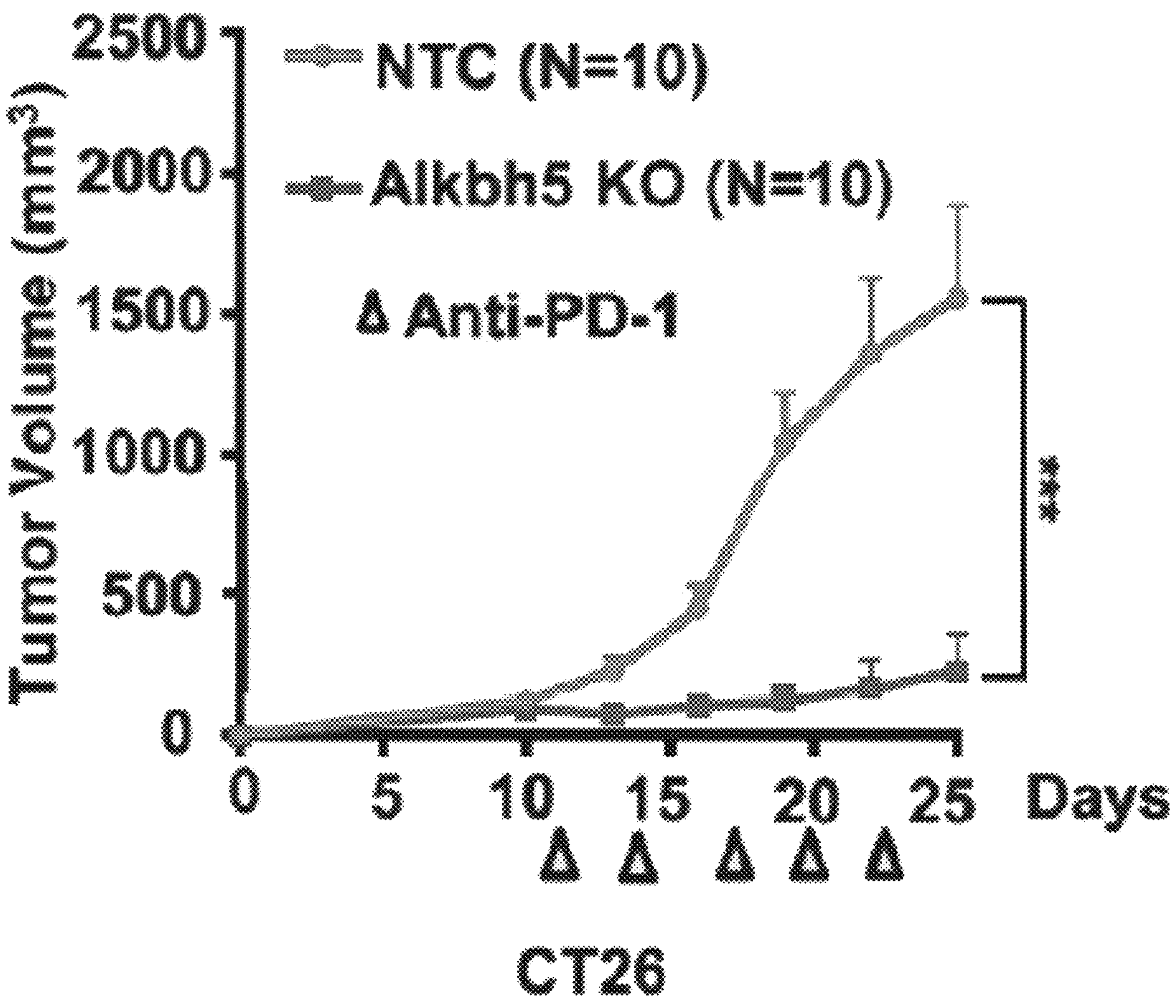

To determine the role of m6A demethylation enzymes in tumor cells in the response to anti-PD-1 therapy, we employed a mouse model using the poorly immunogenic murine melanoma cell line B16 or modestly immunogenic colorectal cancer cell line CT26. In the standard protocol (FIG. 69), B16 cells were deleted of Alkbh5 or Fto by CRISPR/Cas9 editing and subcutaneously injected into wild-type syngeneic C57BL/6 mice, which were then vaccinated on days 1 and 4 with GVAX[26], composed of irradiated B16 cells secreting granulocyte-macrophage colony-stimulating factor (GM-CSF) to induce an antitumor T cell response. The mice were then treated with anti-PD-1 Ab on days 6, 9, and 12 (or as indicated for individual experiments). In the CT26 model, control or KO cells were subcutaneously injected into BALB/c mice, and mice were then treated with anti-PD-1 Ab on days 11, 14, 17, 20, and 23 (FIG. 69A). Gene editing was performed with up to four distinct Alkbh5- or Fto-targeting single-guide RNAs (sgRNAs) per gene (or nontargeting control sgRNAs, NTC), and B16 lines with complete deletion were selected for further experiments (SI Appendix, FIG. 5-S1AB). Compared with NTC-B16 tumors, growth of Alkbh5-KO and Fto-KO tumors was significantly reduced by GVAX/anti-PD-1 treatment (FIG. 69B, and SI Appendix, FIG. 5-S1C,G-I) and the survival of Alkbh5- but not Fto-deficient tumor-bearing mice was significantly prolonged (FIG. 69C and SI Appendix, FIG. 5-S1D).

Figure 69E:
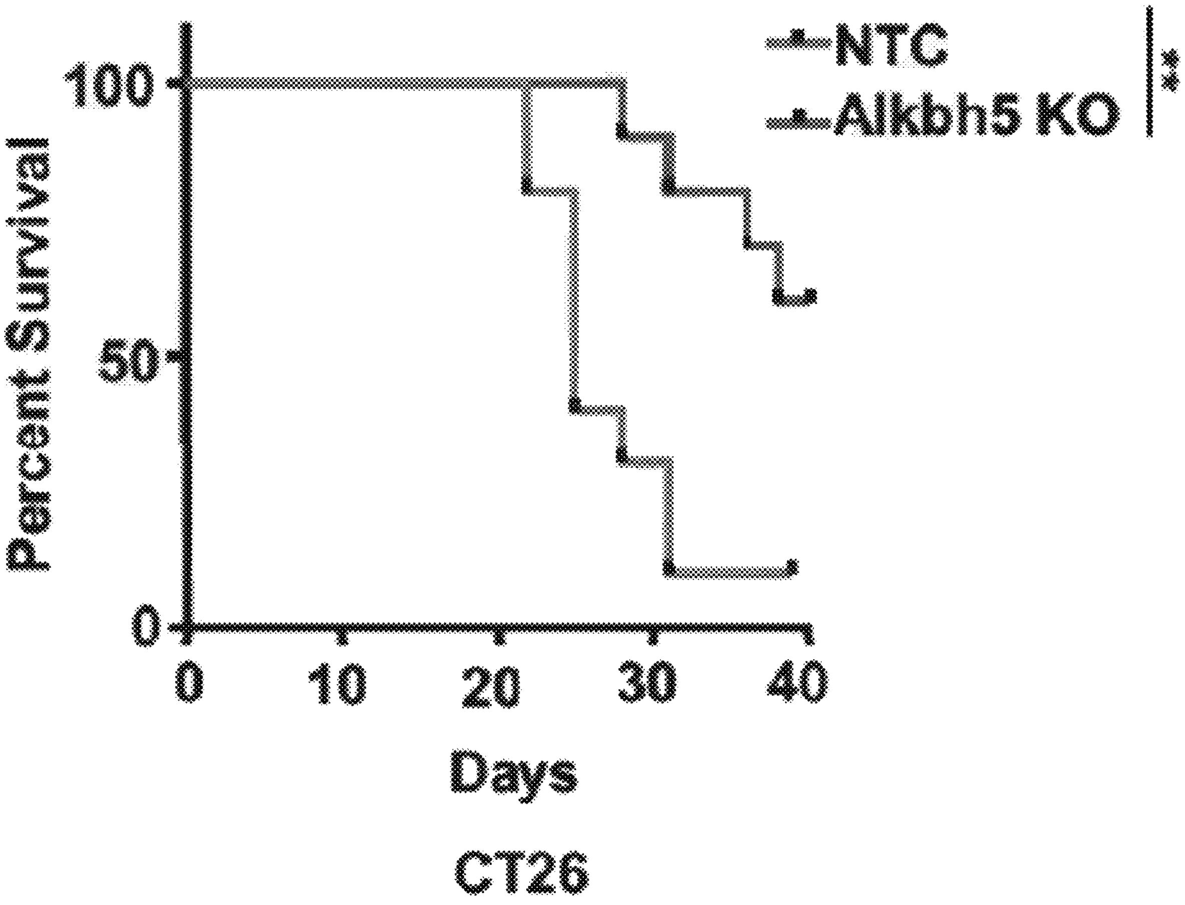

We then sought to determine whether the effects of Alkbh5 and Fto KO reflect a generalizable phenomenon during cancer immunotherapy. For this purpose, we employed a modestly immunogenic colorectal cancer line CT26, which responds to PD-1 Ab treatment[23-25]. Similar to the B16 model, we found the tumor growth of Alkbh5 KO was significantly reduced compared with NTC in CT26 tumors treated with PD-1 Ab. However, FtoKO tumors did not show significant changes although they grew slower than NTC (FIG. 69D and SI Appendix, FIGS. 5-S1E and 5-SIJ-L). As observed in the B16 model, the survival of Alkbh5-deficient tumor-bearing mice were significantly prolonged in CT26 model (FIG. 69E and SI Appendix, FIG. 5-S1F). These data confirmed the role of Alkbh5-KO and Fto-KO tumors in immunotherapy independent of tumor types. Alkbh5 KO showed more dramatic effects than Fto KO in restricting tumor growth and prolonging mouse survival. In addition, there were no significant differences between the growth of NTC, Alkbh5-KO, and Fto-KO B16 cells either in vitro (SI Appendix, FIG. 5-S1M) or in vivo in untreated mice (SI Appendix, FIGS. 5-S1 N and O), indicating that deletion of the m6A demethylases did not intrinsically impair their growth. Taken together, these data demonstrate that Alkbh5 expression is not required for their growth or survival in vitro or in vivo; however, the enzymes play a crucial role in the efficacy of anti-PD-1 therapy.

Deletion of Alkbh5 in Melanoma Cells Alters the Recruitment of Immune Cell Subpopulations During GVAX/Anti-PD-1 Treatment.

Figure 69F:
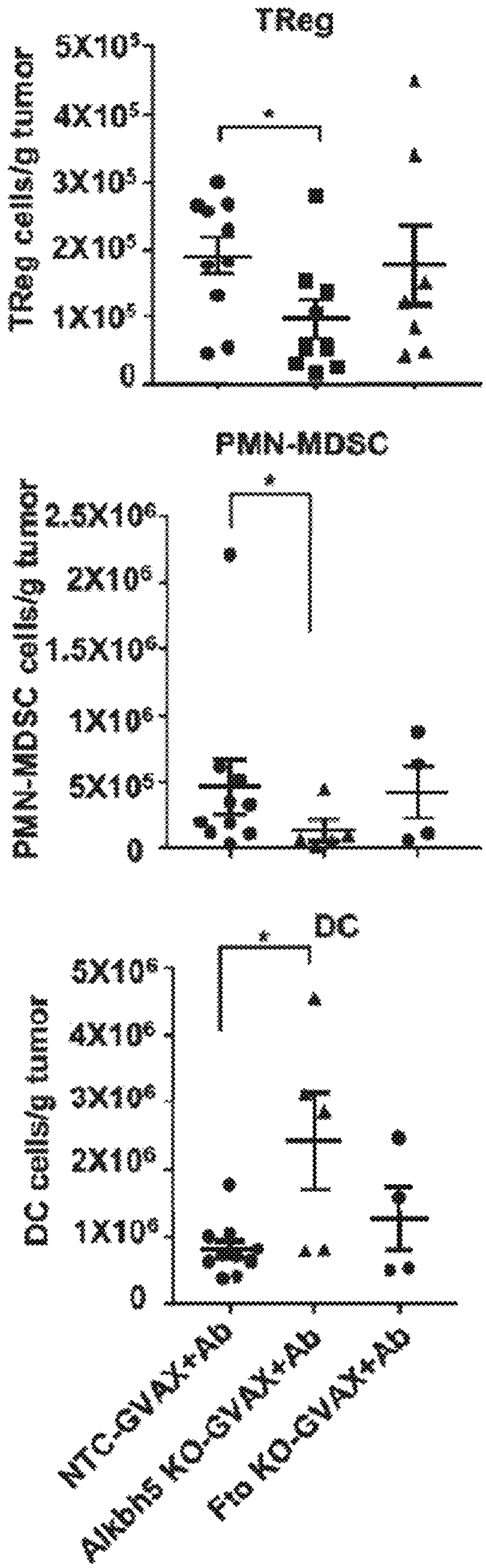
Figure 70A:
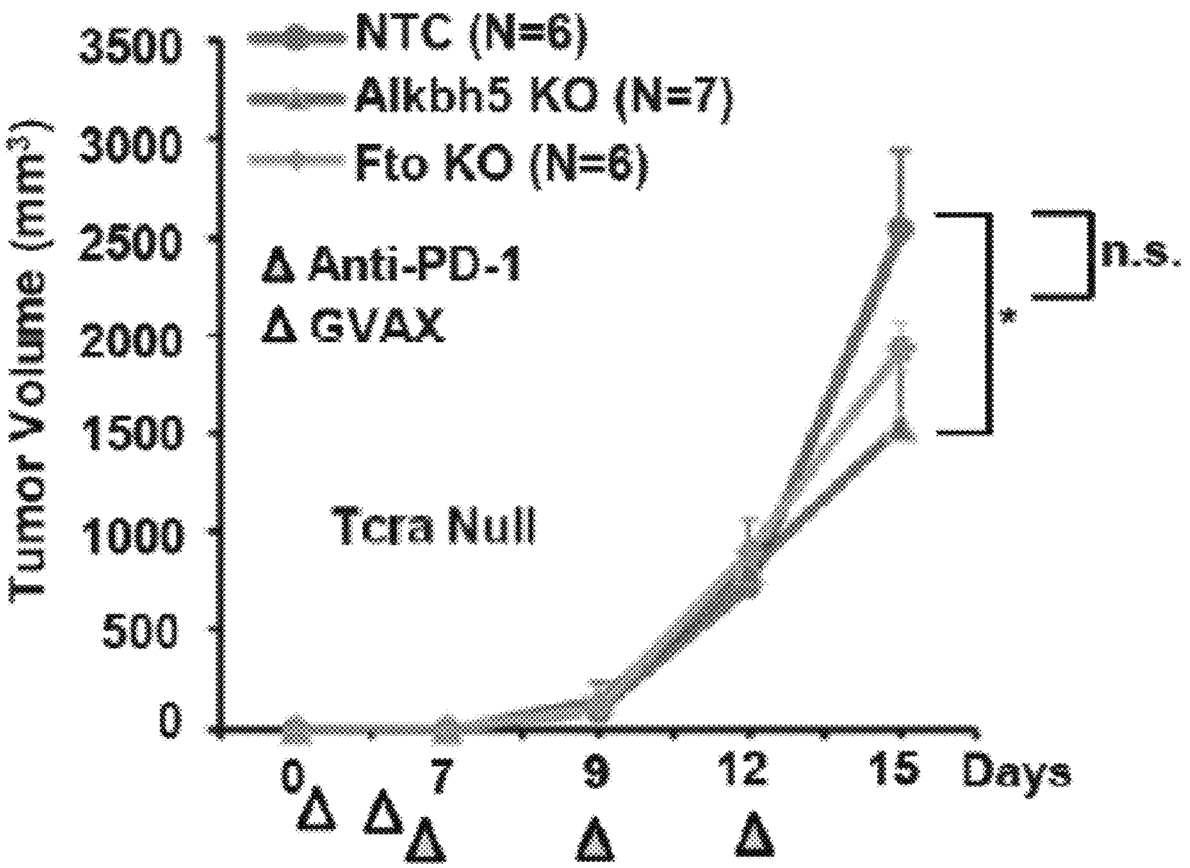
FIG. 70A-70F. Alkbh5 regulates tumor infiltration of Treg and MDSCs and gene expression during GVA)Uanti-PD-1 therapy. (70A) As described for FIG. 69A, except B16 cells were injected into B6.129S2-Tcratml (TCRqx-deficient) mice, which are devoid of mature CD8* and CD4* T cells. Data are presented as the mean±SEM. *P<0.05; n.s., not significant. (70B) Immunohistochemical staining of Ly6G* PMN-MDSCs in NTC or Alkbh5-KO tumors isolated from mice on day 12. Magnification: 50 μm. (70C) Growth of NTC and Alkbh5-KO tumors in mice treated as described in FIG. 69A and additionally injected intraperitoneally with 10 mg/kg of control lgG or Treg-depleting anti-CD25 Ab on day 11. Data are presented as the mean SEM. *P<0.05 vs. NTC control mice. (70D) Growth of NTC and Alkbh5-KO tumors in mice treated as described in FIG. 69A and additionally injected intraperitoneally with 10 mg/kg of control lgG or MDSC-depleting anti-mouse Ly6G/Ly6C (Gr-1) Ab on day 10. Data are presented as the mean SEM. 0.05, **P<0.01 vs. NTC control mice. (70E and 70F) GO analysis (70E) and heatmap presentation (70F) of DEGs in Alkbh5-KO tumors compared with NTC tumors. Genes satisfying the cut-off criteria of P<0.05 and log fold-change>0.5 or <0.5 are shown.
Figure 70B:
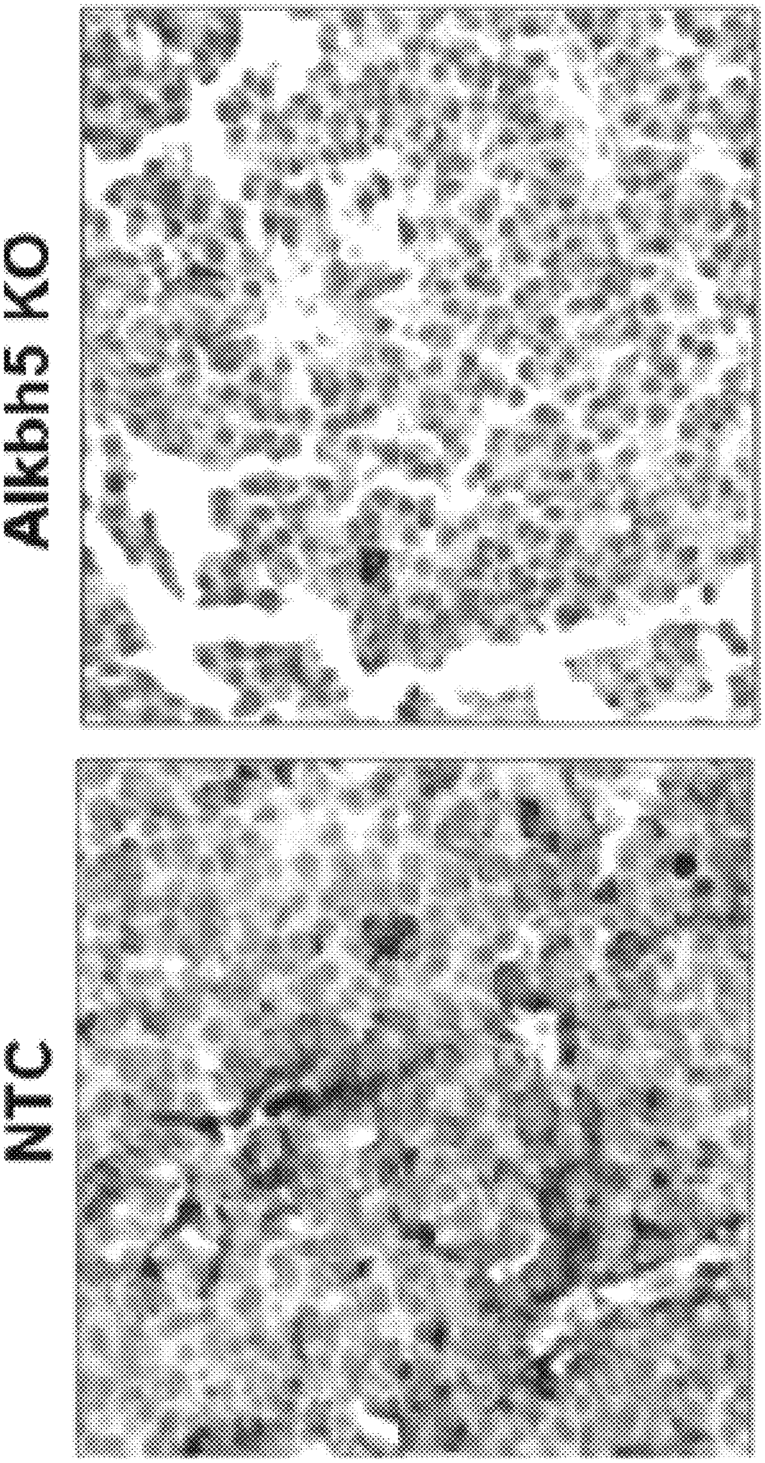

To examine the mechanism by which Alkbh5 modulates GVAX/anti-PD-1 therapy, we examined whether Alkbh5 and Fto deletion in tumor cells modulates immune cell recruitment during GVAX/anti-PD-1 therapy by flow cytometric analysis of tumor infiltrates on day 12 (SI Appendix, FIG. 5-S2 A-C). Compared with NTC B16 tumors, there is no significant difference in total number of tumor infiltrated lymphocytes (CD45+), CD4+, CD8+ cells in Alkbh5− and Fto− deficient mouse tumors, although a trend to higher abundance of granzyme B (GZMB)+ CD8, GZMB+ CD4 T cell, and NK cell numbers in Fto-null mice tumor (SI Appendix, FIG. 5-S2D). However, the number of infiltrating regulatory T cells (Tregs) and polymorphonuclear myeloid derived suppressor cells (PMN- DSCs), but not myeloid (M)-MDSCs, was significantly decreased in Alkbh5-KO tumors compared with NTC tumors during GVAX/anti-PD-1 treatment (FIG. 69F and SI Appendix, FIG. 5-S2 D-F). Interestingly, dendritic cells (DCs), but not macrophages, were also significantly elevated in Alkhb5-KO tumors compared with NTC tumors (FIG. 69F and SI Appendix, FIG. 5-S2 D-F). In contrast, Fto-KO tumors did not show significant changes in MDSC, Tregs, or DC cell populations (FIG. 69F and SI Appendix, FIG. 5-S2 D-F). In accordance with these observations, in Tcra-deficient mice, which lack the TCR-α chain and do not develop mature CD4+ and CD8+ T cells, the effects of Alkbh5 KO but not Fto KO on tumor growth were dampened, but not eliminated (FIG. 70A and SI Appendix, FIG. 5-S2G), suggesting that the effect of Alkbh5 in regulating GVAX/anti-PD-1 therapy was partially independent of the host T cell response. To verify the decrease in PMNMDSCs, we performed immunohistochemical staining and found a marked reduction in the accumulation of MDSCs in Alkbh5-KO tumors compared with NTC tumors on day 12 (FIG. 70B).

Figure 70C:
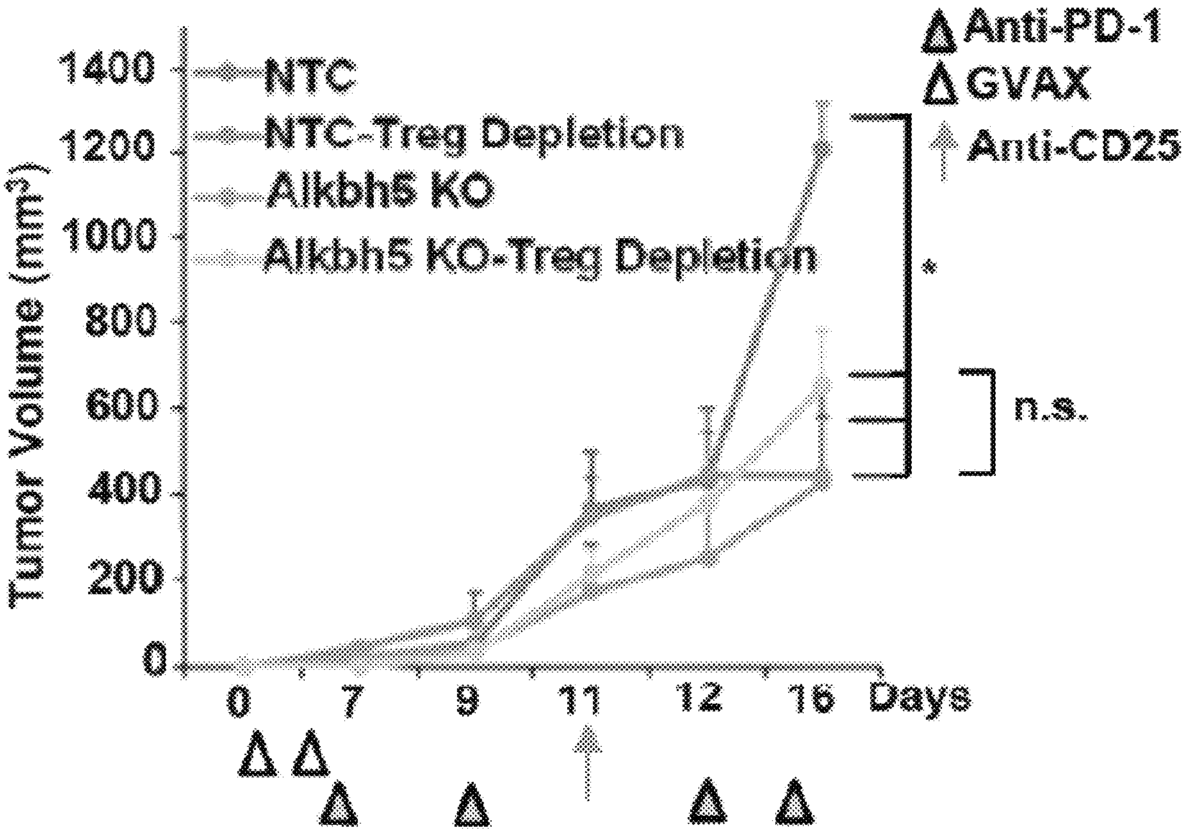
Figure 70D:
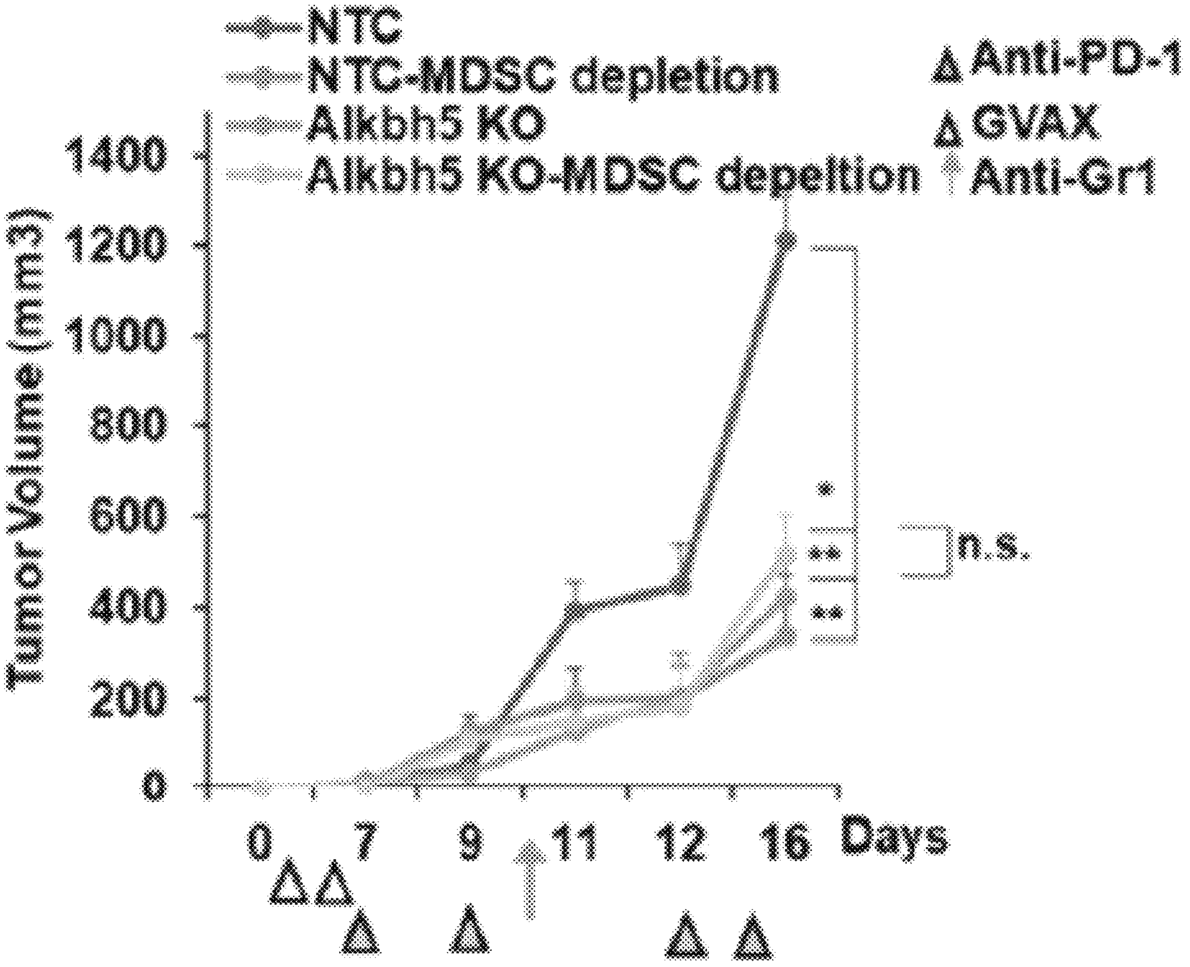

Cross-talk between Tregs and other immune cells is an important contributor to tumor-induced immune suppression; for example, MDSCs can induce Treg amplification and decrease DC differentiation in the TME, and Tregs can greatly inhibit cytotoxic T cell function[27]. To assess Treg function in GVAX/anti-PD-1 therapy of melanoma, we monitored the effect on tumor growth after injection of a Treg-depleting anti-CD25 Ab on day 11 of treatment[28, 29]. We observed that Treg depletion in NTC tumors showed significant decrease in tumor growth (FIG. 70C), while Alkbh5-KO tumors, which had lower numbers of Treg cells than NTC tumors (FIG. 69F), did not show significant effects on tumor growth (FIG. 70C). These data suggest that Treg cells played important roles in the effects of Alkbh5 KO to restrict tumor growth during therapy, since Treg depletion only worked in NTC tumors that had higher Treg cell numbers. Similarly, we also performed MDSC depletion to assess the tumor growth in NTC and Alkbh5-KO tumors during ICB therapy. Our results show that MDSC depletion had an effect similar to Treg depletion while growth kinetics may vary from these deletions in NTC tumors (FIG. 70D). Collectively, these data demonstrate that tumor cell expression of Alkbh5 plays an important role in tumor growth by modulating the recruitment of immunosuppressive MDSCs and Tregs during GVAX/anti-PD-1 therapy.

m6A Demethylase Deletion Alters the Tumor Cell Transcriptome During GVAX/Anti-PD-1 Treatment.

Figure 70E:
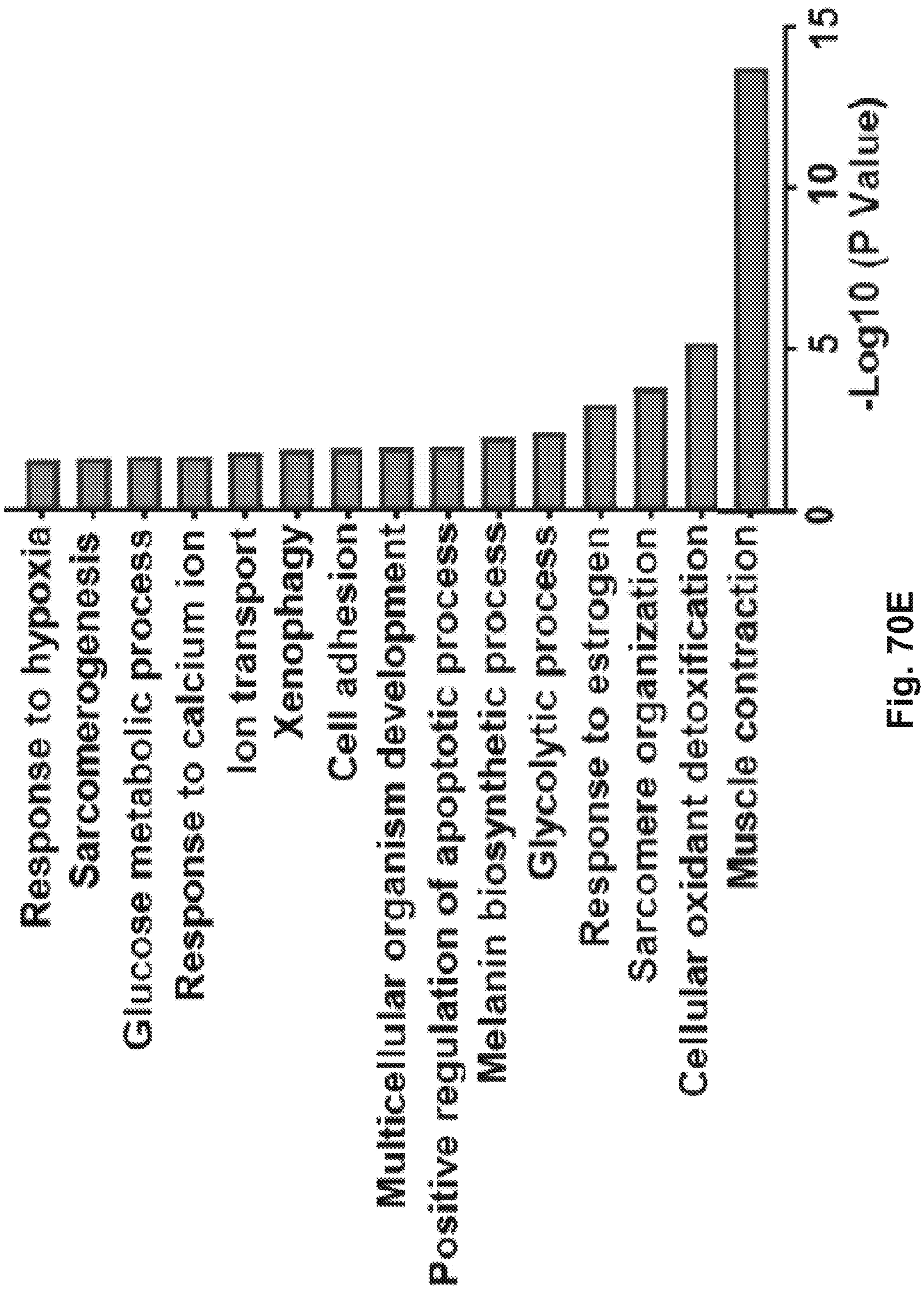

To understand the regulatory role of Alkbh5 and Fto in tumor therapy at the molecular level, we performed RNA-sequencing (RNA-seq) to identify differentially expressed genes (DEGs) in NTC B16 tumors compared with Alkbh5-KO or Fto-KO tumors on day 12 of GVAX/anti-PD-1 treatment. Tumors were confirmed to be Alkbh5- or Ftodeficient before RNA-seq analysis (SI Appendix, FIGS. 5-S3 A and B). Gene ontology (GO) analysis showed that the DEGs in Alkbh5-KO tumors were predominantly involved in metabolic processes, apoptosis, cell adhesion, transport, and hypoxia (FIG. 70E and SI Appendix, FIG. 5-S3C). Interestingly, however, DEGs in Fto-KO tumors were mostly immune response associated genes (SI Appendix, FIGS. 5-S3 D and E). Indeed, further analysis of GO pathways and heatmaps revealed that >80% of the DEGs differed between Alkbh5-KO and Fto-KO B16 tumors. Genes most affected by Alkbh5 KO were associated with regulation of tumor cell survival, adhesion, metastasis, and metabolism, such as Ralgps2, Mmp3, Epha4, Adgrg7, Reln, and Mct4/Slc16a3 (FIG. 70F), whereas those most affected by Fto KO were associated with IFN-γ and chemokine signaling, including IRF1, IRF9, STAT2, Cxcl9, Ccl5, and Ccr5 (SI Appendix, FIG. 5-S3F). To confirm this result, we exposed NTC, Alkbh5-KO, and Fto-KO B16 cells to IFN-γ in vitro and analyzed gene expression by qRT-PCR. As shown in SI Appendix, FIG. 5-S3G, Fto-KO, but not Alkbh5-KO or NTC tumor cells showed increased expression of the IFN-γ pathway targets Pdl1 and Irf1 and the chemokines Cxcl9, Cxcl10, and Ccl5 after IFN-γ stimulation. These results suggest that, during anti-PD-1/GVAX therapy, Alkbh5 expression in B16 melanoma cells predominantly affects cell intrinsic changes and recruitment of immune cells to the TME, while Fto is involved in regulating IFN-γ and inflammatory chemokine pathways.

IFN-γ pathway activation has been shown to be an important indicator of the efficacy of PD-1 blockade in mouse model studies[22], whereas another study of melanoma patients identified associations between anti-PD-1 response and expression of genes involved in mesenchymal transition, inflammatory, wound healing, and angiogenesis, but not the IFN-γ pathway or other gene signatures indicative of sensitivity to ICB[30]. Therefore, we analyzed a gene-expression dataset from 38 melanoma patients who did (n=21) or did not (n=17) respond to anti-PD-1 therapy, and searched for DEGs that were also identified here as DEGs in B16 tumors with Alkbh5 or Fto KO. This analysis identified 8 genes that were commonly down-regulated in Alkbh5-KO B16 tumors and responder melanoma patients, and 11 genes that were commonly down-regulated in Fto-KO B16 tumors and responder patients (SI Appendix, FIGS. 5-S3 I and K). Fewer genes were commonly up-regulated between these groups (SI Appendix, FIGS. 5-S3 H and J). These results suggest that the down-regulated genes conserved among mouse model and patients receiving PD-1 Ab treatment play important roles in regulating cancer immunotherapy response and are potential target genes of Alkbh5 and Fto.

Alkbh5 Deletion in Melanoma Cells Affects the m6A Epitranscriptome During GVAX/Anti-PD-1 Treatment.

Figure 71A:
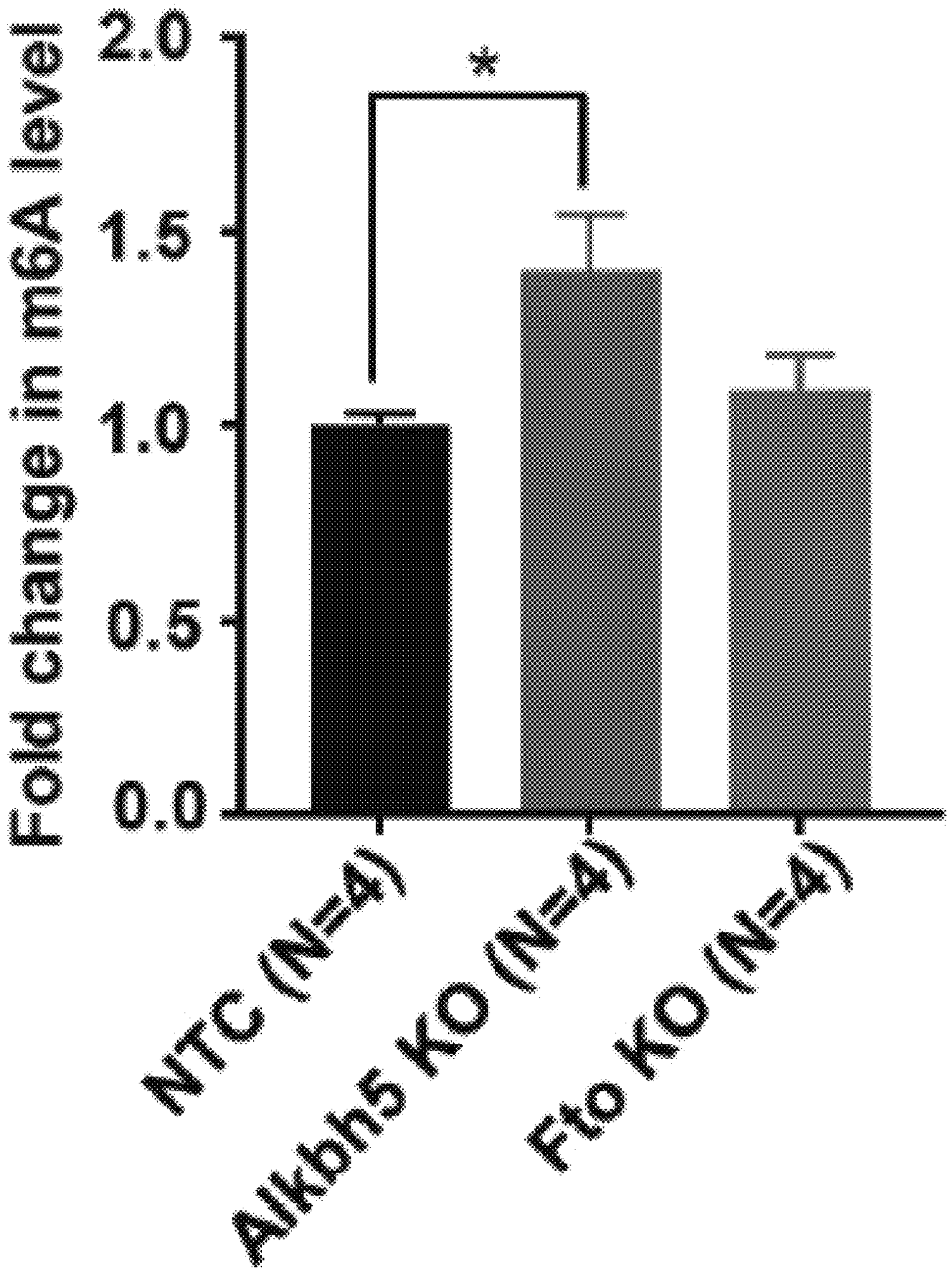
FIG. 71A-71H. Alkbh5 during GVAWanti-PD-1 immunotherapy (71A) LC-MS/MS quantification of m6A in ribosome-depleted total RNA isolated from NTC, Alkbh5XO, and Fto-KO tumors. Data are presented as the mean±SEM fold-change relative to the NTC in four mice per group. *P<0.05 vs. NTC (71B) Genomic location of the conserved m6A peaks identified by MeRIP-Seq in B16 tumors from mice treated as described in FIG. 69A. Plot shows the proportion of m6A in the CDS, 5' and 3' UTRs, introns, transcription Start Site (TSS), transcription end Site (TES), and intergenic regions. (71C) Pie charts showing the proportions of common and unique m6A/m6Am peaks of NTC and AlkhbS-KO B16 tumors from mice treated as described in 71A. (71D) Top consensus motifs of MeRIP-Seq peaks identified by MEME in NTC and Alkbh5-KO B16 tumors from mice treated as described in FIG. 71A. (71E) Genome browser tracks of NTC and AlkhbS-KO tumors after treatment were shown for Slc16A31/Mct4 with called m6A sites by MeRIP and inputs. Input was indicated by blue color in each track. Bed files of the called peaks were shown in the corner. (71F) MeRIP-qPCR of Mct4 gene for both peak 1 and peak 2 regions shown in E. **P<0.01 vs NTC control. (71G) The density of m6A in the region of 100 nt exon regions from the 5' splice site ("SS") and the 3' SS. The relative m6A peak of a specific position in NTC and Alkbh5-deficient tumors was calculated as the scaled m6A peak density proportional to the average rm6A peak density in the internal exonic regions. (71H) Difference of PSI was calculated by MISO as NTC control minus either Alkbh5-KO or Fto-KO tumors.
Figure 71B:
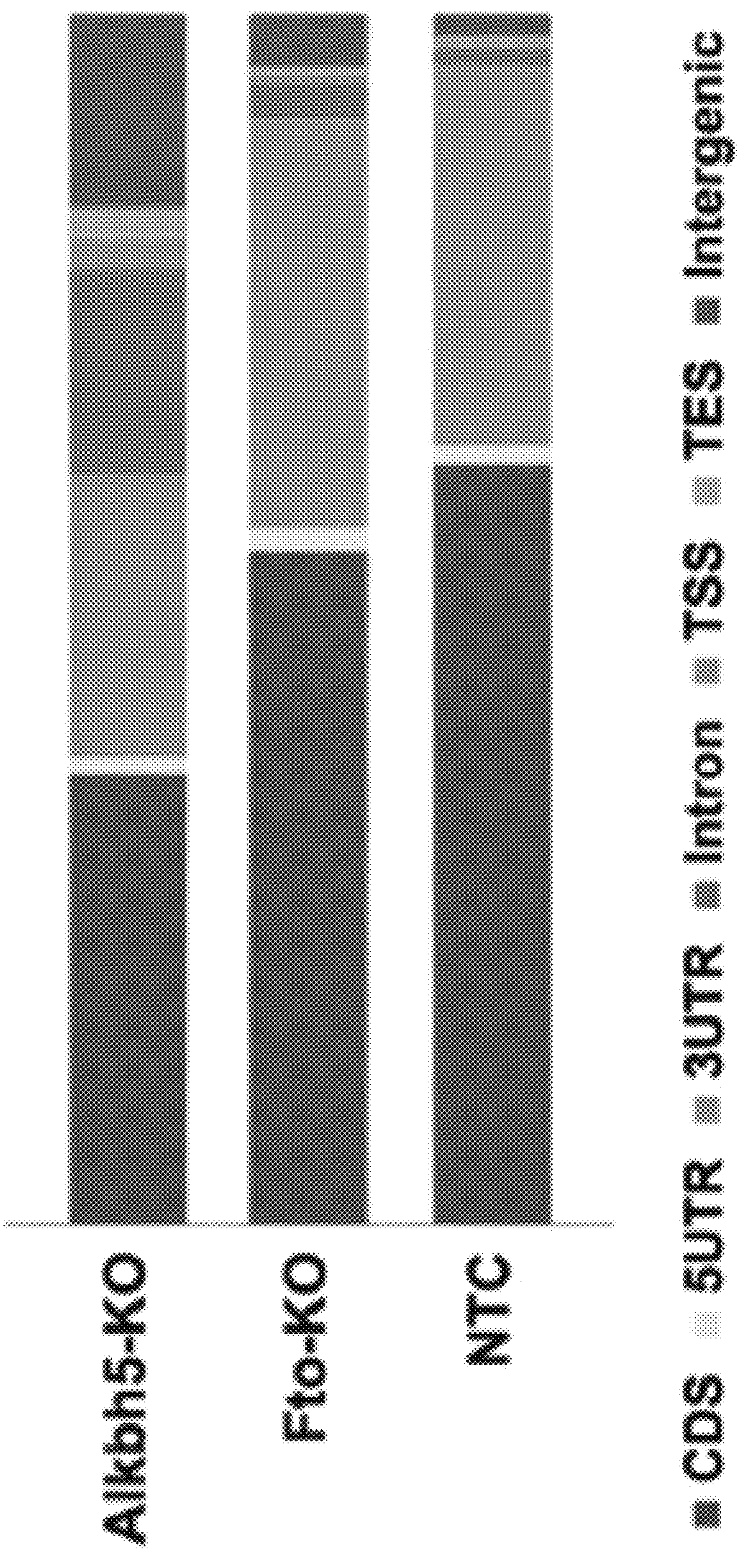
Figure 71C:
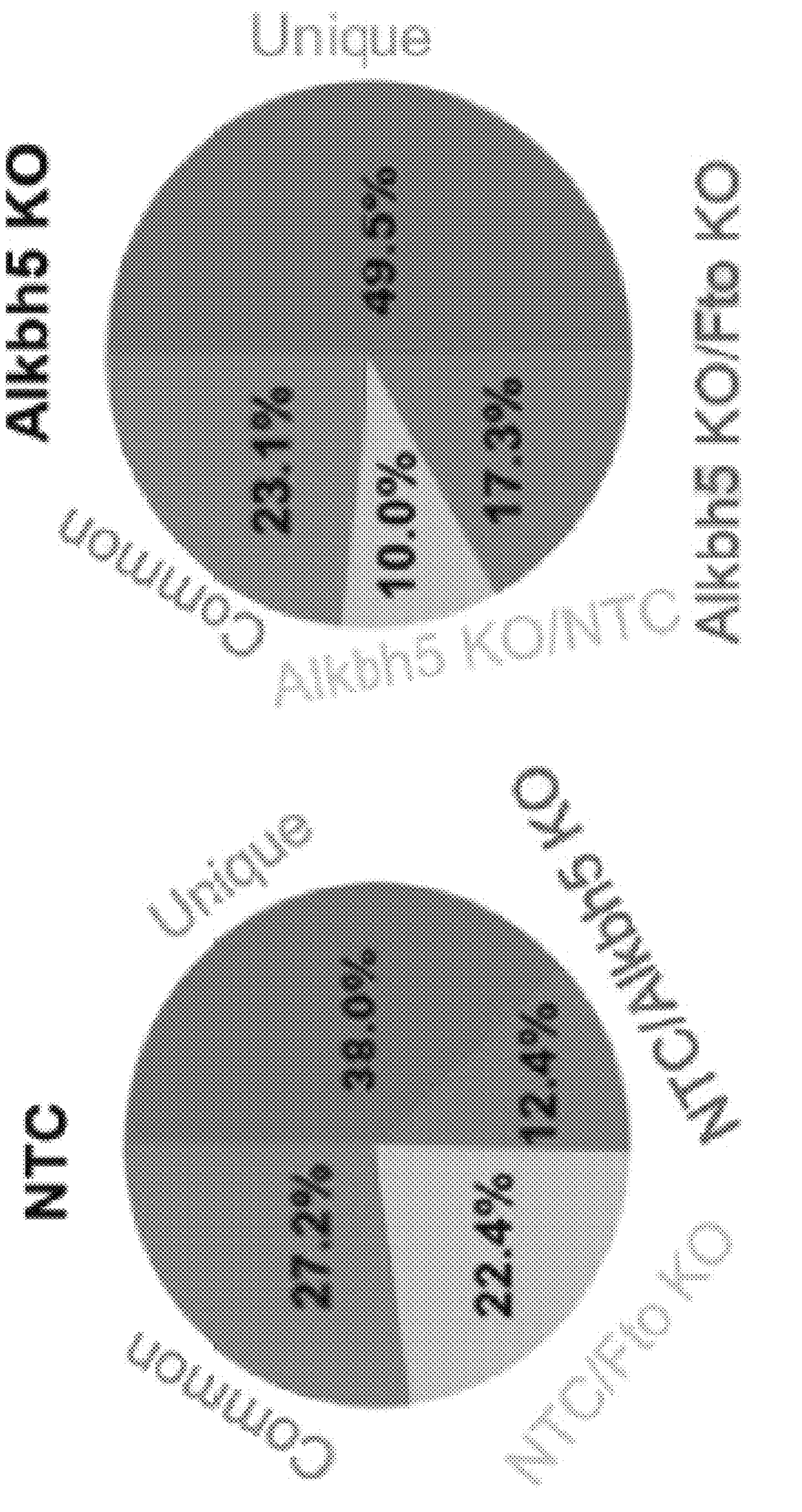
Figure 71D:
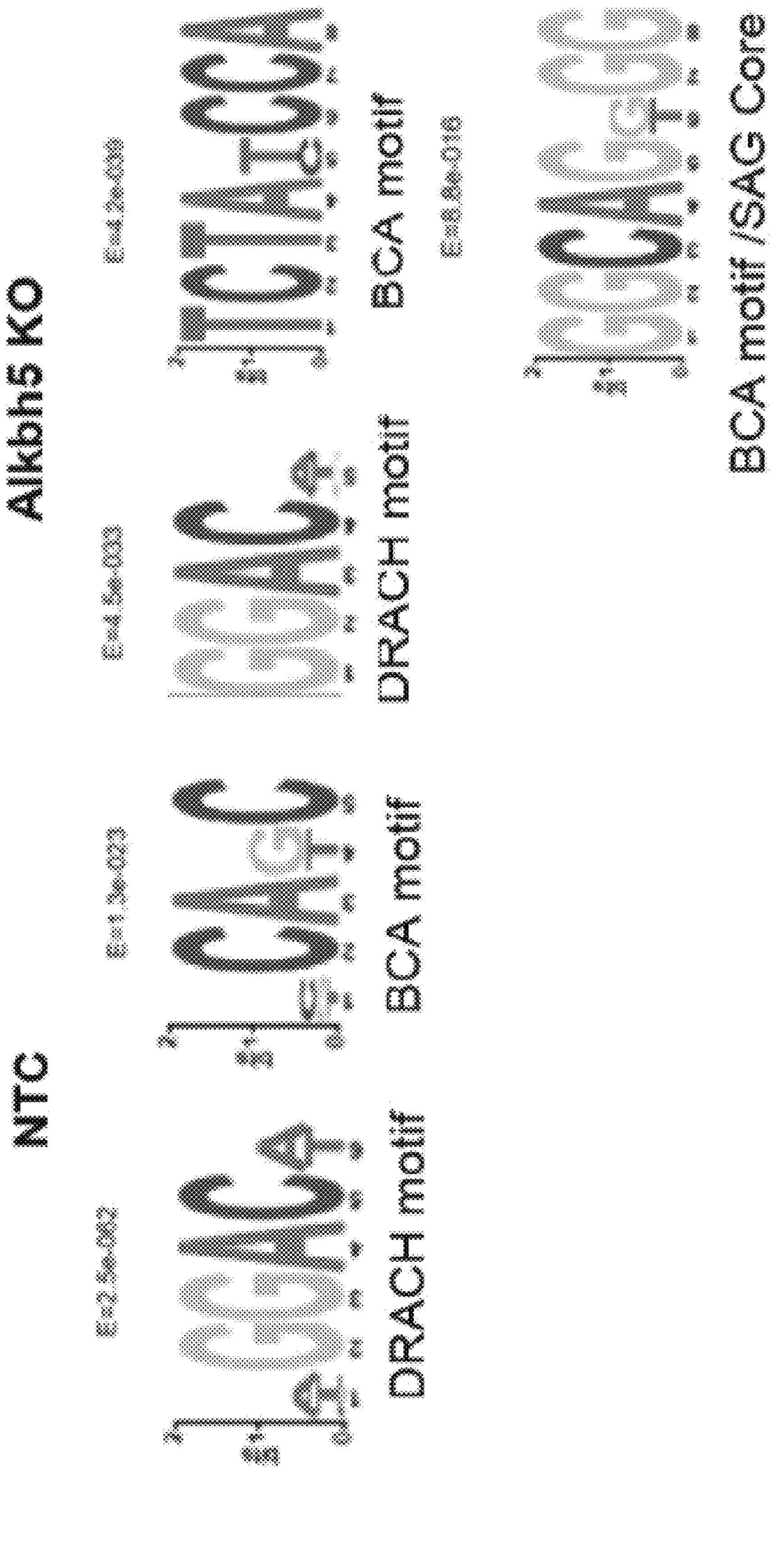

Given the profound importance of m6A in regulating the function of target RNAs and gene expression[31, 32], we next examined how Alkbh5 affected m6Acontent in RNA by LC-MS/MS of B16 tumors on day 12 of GVAX/anti-PD-1 therapy 33-35. This analysis revealed that levels of m6A were significantly increased in Alkbh5-KO but not in Fto-KO tumors (FIG. 71A). We then performed m6A RNA immunoprecipitation followed by high-throughput sequencing (MeRIP-seq) to determine whether the altered gene expression observed in the KO tumors was a consequence of m6A/m6Am demethylation. To obtain the most robust data, we selected only m6A peaks identified by two independent peak calling algorithms and detected in tumors from all biological replicates per group (SI Appendix, FIGS. 5-S4 A and B). In the NTC and Fto-KO B16 tumors, the majority of m6A peaks were detected in the coding sequence (CDS) and the 3'UTR and 5'UTR, which is consistent with previous studies[4, 5, 36]. Notably, the density of m6A peaks in intronic regions was substantially higher in Alkhb5-KO tumors compared with NTC tumors during treatment (FIG. 71B), and Alkbh5-KO tumors had more unique m6A peaks compared with NTC or Fto-KO tumors (FIG. 71C and SI Appendix, FIG. 5-S4C). Analysis of motifs in the m6A peaks showed that the canonical m6A motif DRACH (D=A, G, U; R=A, G; H=A, C, U) was the most common motif in all tumor groups. The putative m6Am motif BCA (B=C, U, or G; A*=methylatable A) was present in other enriched motifs. One motif enriched in Alkbh5-KO tumors contained the SAG core, which is reminiscent of the SRSF binding site motif known to affect gene splicing (FIG. 71D and SI Appendix, FIG. 5-S4D). These data suggest that Fto and Alkbh5 deletion had some common and some distinct effects on m6A/m6Am peaks in B16 tumors, which might contribute to the different mechanisms through which the two demethylases influence the efficacy of GVAX/anti-PD-1 therapy.

Figure 71E:
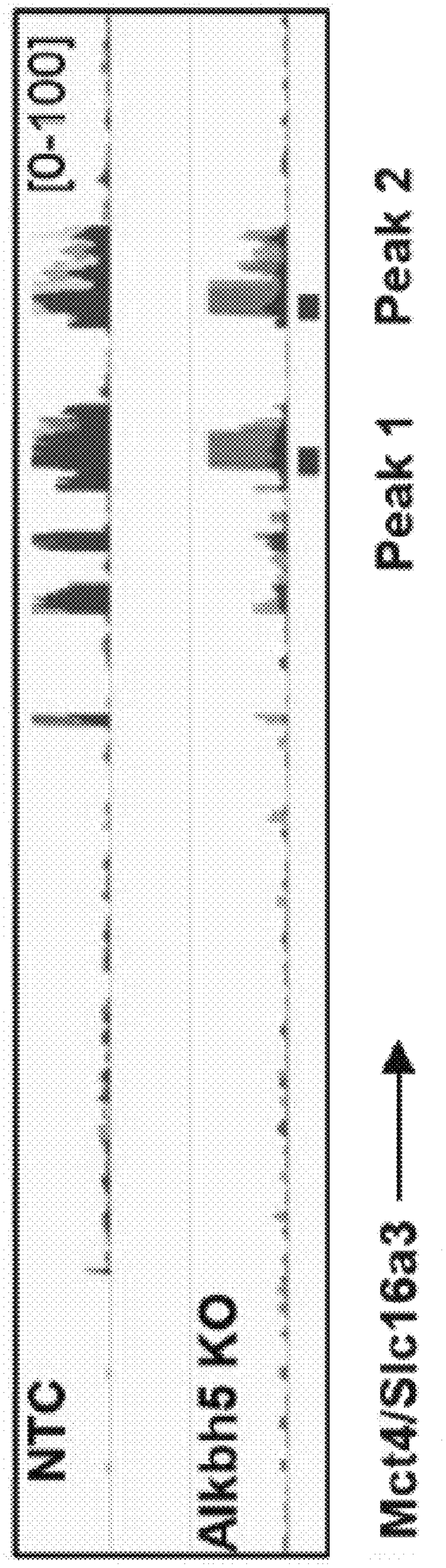
Figure 71F:
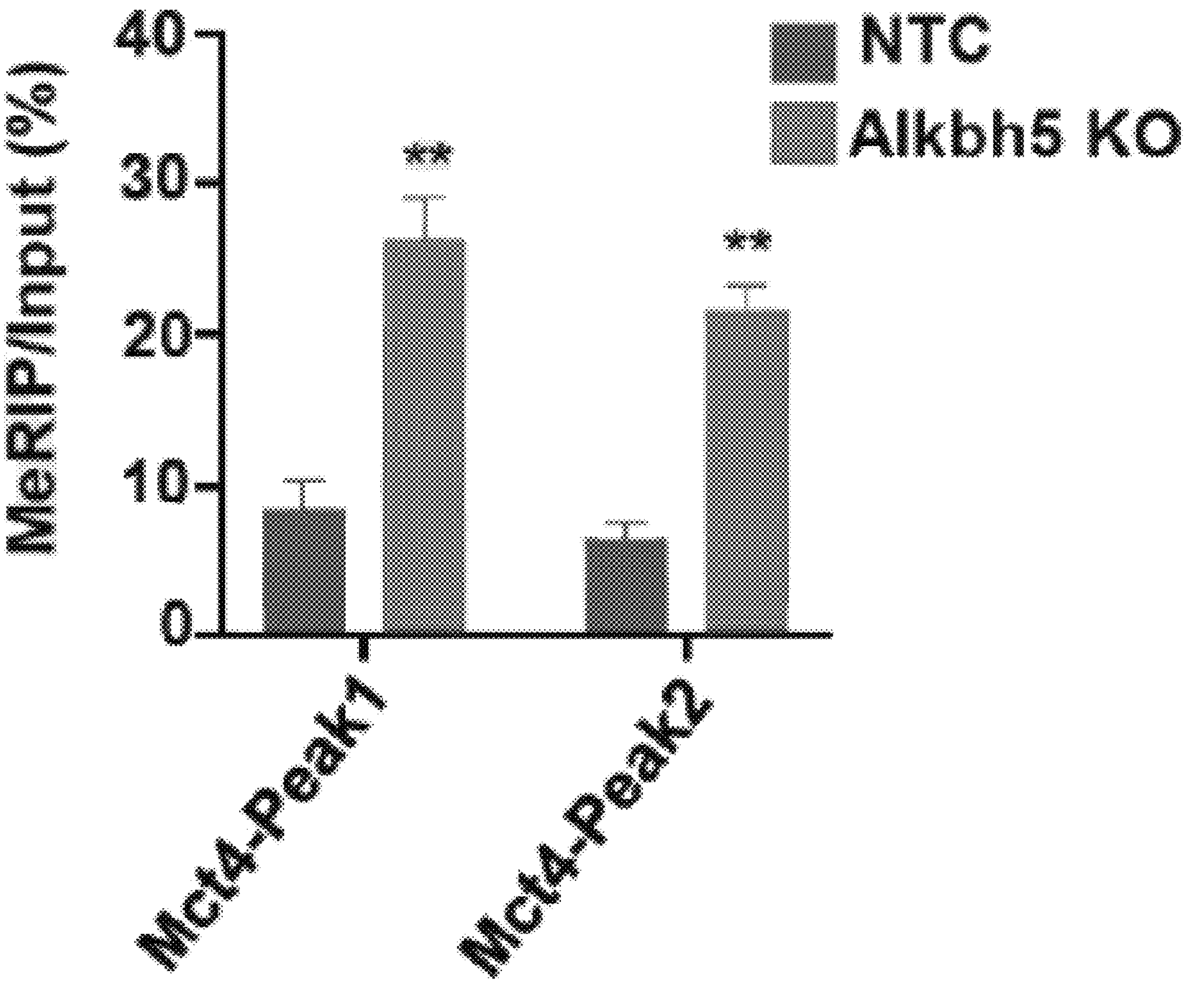

We next examined whether the down-regulation of the overlapped genes in Alkbh5-KO or Fto-KO tumors (responding better than NTC) and melanoma patients responding to immunotherapy was due to altered levels of m6A (SI Appendix, FIGS. 5-S3 I and K). Five of eight common down-regulated genes had increased m6A peaks in Alkbh5-deficient mouse tumor (shown in red in SI Appendix, FIG. 5-S3I). While only 1 of a total of 11 common genes, Mex3d, had elevated m6A levels in Fto-deficient tumors (red in SI Appendix, FIG. 5-S3K). m6A peaks in Mex3d, common in both Alkbh5 and Fto down-regulated genes, increased compared to NTC (SI Appendix, FIG. 5-S4E). Mct4/Slc16a3, found in only Alkbh5 down-regulated genes, had significantly increased m6A density in the Alkbh5-KO tumors compared to NTC (FIGS. 71E and 71F).

These results suggest that Alkbh5 KO increased m6A levels and reduced expression of certain genes involved in immunotherapy resistance. The overall levels of m6A in Fto-deficient tumors was not changed; however, it showed increased m6A at some genes, albeit the number of changed genes were much less than in Alkbh5-KO tumors (e.g., SI Appendix, FIGS. S3 I-K and S4E).

m6A Density is Increased Near Splice Sites and Leads to Aberrant RNA Splicing in Alkbh5-Deficient Tumors.

Figure 71G:
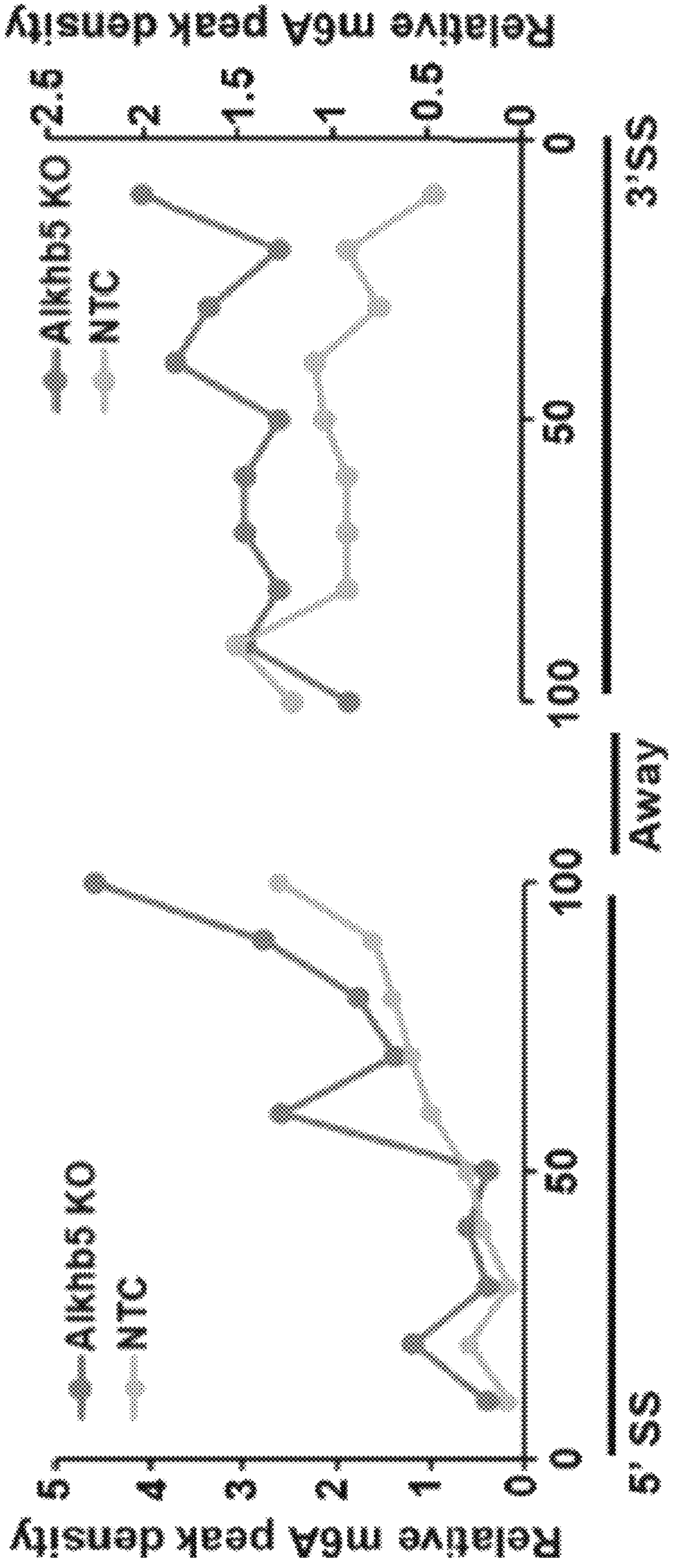

Although the regulatory role of m6A deposition in splicing is somewhat controversial[36, 37], Alkbh5 has been reported to affect splicing in an m6A demethylase-dependent manner 38. Our MeRIP-seq results showed that unique m6A peaks were more prevalent in Alkbh5-KO tumors compared with NTC or Fto-KO tumors during GVAX/anti-PD-1 treatment, and that one m6A motif enriched in Alkbh5-KO tumors had a sequence similar to the SRSF binding motif (FIG. 71B-71D)[36]. GO analysis of mRNAs with unique m6A peaks in Alkbh5-KO tumors showed enrichment in splicing, cell cycle, and signaling pathway functions (SI Appendix, FIGS. 5-S5 A and B), suggesting that Alkbh5 also regulates gene expression in B16 cells through effects on mRNA splicing. To test this hypothesis, we examined the location of m6A at 5' or 3' intron-exon splice junctions by positional assessment. Consistent with a previous study using m6A individual nucleotide-resolution cross-linking and immunoprecipitation[36, 37], we found that m6A deposition increased from both 5' and 3' splice sites to the internal exonic regions in NTC control tumors with immunotherapy (FIG. 71G). Surprisingly, we found that in Alkbh5-deficient tumors, the m6A densities were elevated at the both 5' and 3' splice sites, with a dramatic increase at the proximal region to the 3' splicing site (FIG. 71G). In contrast, m6A deposition at splice sites in Fto-KO tumors was comparable to that in NTC tumors (SI Appendix, FIG. 5-S5C), suggesting that Alkbh5 plays a role in gene splicing through depositing m6A modifications near the splicing sites.

Figure 71H:
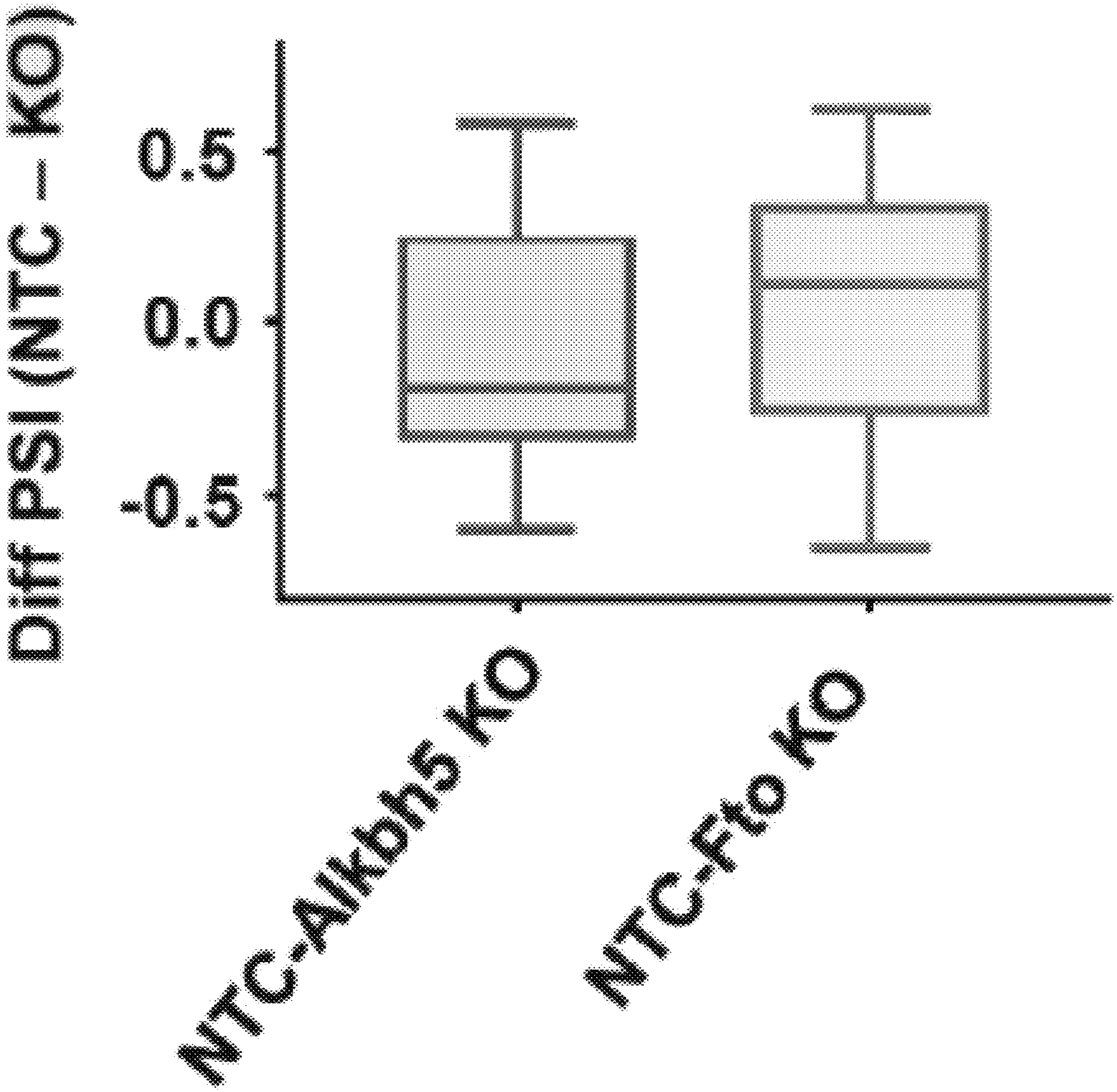

Changes in m6Am by FTO have been reported to affect snRNA biogenesis and gene splicing[10], and we observed an increase in m6Am/m6A in U1, U2, and U3 snRNAs in Fto-KO tumors compared with NTC tumors (SI Appendix, FIG. 5-S5E). To investigate this further, we analyzed our RNA-seq data using MISO to detect differences in RNA splicing. Although the global splicing profiles were unaffected by Alkbh5 or Fto deletion, the frequency of spliced-in transcripts (as reflected by the percent spliced-in index, PSI) in a subset of genes was increased by Alkbh5 deletion in tumors analyzed during GVAX/anti-PD-1 treatment (FIG. 71H and SI Appendix, FIGS. 5G-S5 D, F, and G). Categories of gene functions, where the PSI was changed in Alkbh5-KO tumors, included genes involved in important cellular processes, such as transcription, splicing, protein degradation, transport, translation, and cytokine-related pathways (SI Appendix, FIGS. 5-S5 D and H).

To determine whether changes in m6A deposition were linked with mRNA splicing, we next asked whether the m6A density increased in mRNAs with higher spliced-in frequencies (i.e., higher PSI) in Alkbh5-KO compared with NTC tumors. Indeed, mRNA with high PSI due to Alkbh5 KO had higher m6A densities near intron-exon junctions compared with the same mRNAs in NTC tumors; these mRNAs included Usp15, Arid4b, and Eif4a2 (SI Appendix, FIG. 5-S5I). Among the genes with altered PSI in Alkbh5-KO tumors after immunotherapy, Eif4a2 regulates gene translation, Arid4b regulates gene transcription, and Sema6d, Setd5, and Met regulate vasculature, the expression and secretion of vascular endothelial growth factor, and hepatocyte growth factor, both of which promote MDSC expansion[39-42]. Usp15 affects signaling by transforming growth factor-β, which attracts and activates Tregs. Notably, Met and Usp15 are expressed as isoforms that have markedly different functions[43,44], suggesting that gene-splicing changes may play a role in TME composition and eventually affecting the immunotherapy efficacy. Taken together, these data indicate that Alkbh5 regulates the density of m6A near spice sites in multiple mRNAs with functions potentially important during GVAX/anti-PD-1 therapy.

Alkbh5 Regulates Lactate and Vegfa Accumulation in the TME During GVAX/Anti-PD-1 Treatment.

Our findings above suggest that Alkbh5 KO regulates its targets by changing m6A levels, which leads to decreased gene expression or altered gene splicing. Some of these genes are involved in regulating cytokines (Vegfα and Tgfβ1) or metabolite (lactate) in TME, such as Mct4/Slc16a3, Usp15, Met, and Sema6d (FIGS. 70F, 71E, and 71F, and SI Appendix, FIGS. 5-S5 D and H—I). Therefore, it is important to examine whether in Alkbh5-KO tumors, cytokines, or metabolites in the TME are altered that consequently modulate tumor infiltrated lymphocyte populations and immunotherapy efficacy (FIGS. 69 and 70).

Figure 72A:
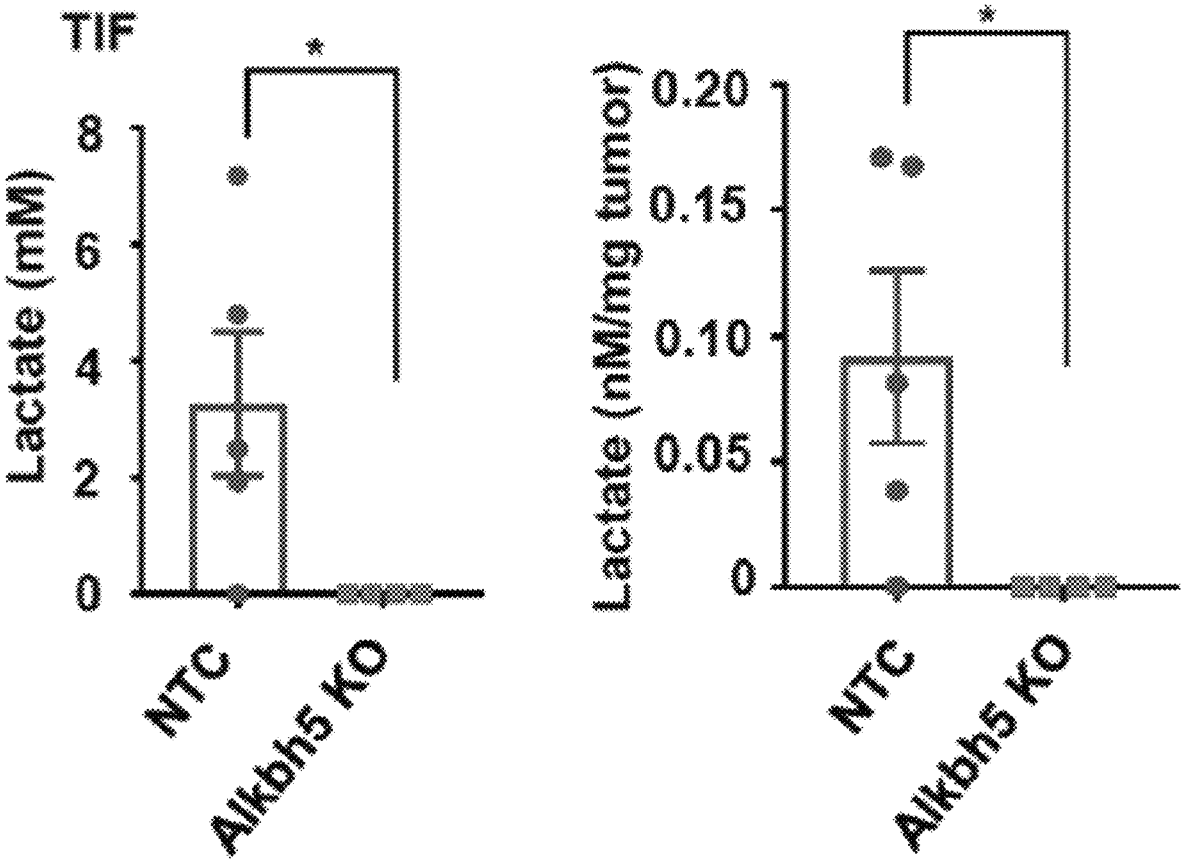
FIG. 72A-72K. Mct4/Slc16a3 is an Alkbh5 target gene and regulates lactate contents, and MDSC accumulation in the TME. (72A) Lactate concentration and total content in TIF isolated from NTC or Alkbh5-KO excised on day 12 from mice treated as described in FIG. 72A (Left) Absolute lactate concentration in TIF; (Right) lactate content per milligram. Data are the presented as the mean±SEM of five (NTC) or four (Alkbh5XO) mice. (72B) As for A, except Vegfa was analyzed. (72C) mRNA decay analysis Of Mct4/Slc16a3 in NTC and Alkbh5-KO B16 cells. NTC and Alkbh5-KO B16 cells were treated with actinomycin D (ActD) at concentration of 5 μg/ml and cells were collected for RNA extraction at indicated time points. Three independent experiments were performed and calculated. *P<0.05 (72D) Mct4 protein levels in NTC, Alkbh5-KO, and Alkbh5-KO cells expressing Mct4 (Alkbh5-KO+ MCt4) B16 cells by Western blotting. (72E) Extracellular lactate concentration in supernatants of NTC, Alkbh5-KO, and Alkbh5-KO+ MCt4 B16 cells. ***P<0.001 (72F) Growth of Alkbh5-KO, and Alkbh5-KO+MCt4 B16 tumors in C57BL/6 mice treated as described in 72A. Data are the mean±SEM of the indicated total number of mice per group. The mice number for each group was NTC=8, Alkbh5-KO=8, Alkbh5-KO+ Mct4=10. (72G) Lactate concentration and total content in TIF isolated from NTC, Alkbh5-KO, and AlkbhS-KO+ MCt4 B16 tumors excised on day 12 from mice treated as described in FIG. 69A. Data are the presented as the mean±SEM. Points represent individual mice. *P<0.05 (72H and 72I) FACS quantification of cells isolated from B16 NTC, Alkbh5-KO, and Alkbh5-KO+MCt4 B16 tumors as described FIG. 69A. Treg cells (72H) and PMN-MDSC cells (72I) were analyzed. Data are presented as the mean±SEM. Pints represent individual mice. *P<0.05 (72J) PCR analysis of alternative splicing of Eif4a2 and Sema6d genes in NTC, Alkbh5-KO, and Alkbh5-KO+Mct4 B16 cells are shown. (72K) Growth of NTC, Alkbh5-KO, Alkbh5-KO+Wild-type Alkbh5 (Alkbh5 KO+Alkbh5 Wt), Alkbh5 KO+catalytically mutant Alkbh5 (Alkbh5 KO+Alkbh5 Mut) in C57BL/6 mice treated as described in FIG. 69A Data are the mean±SEM of the indicated total number of mice per group.
Figure 72B:
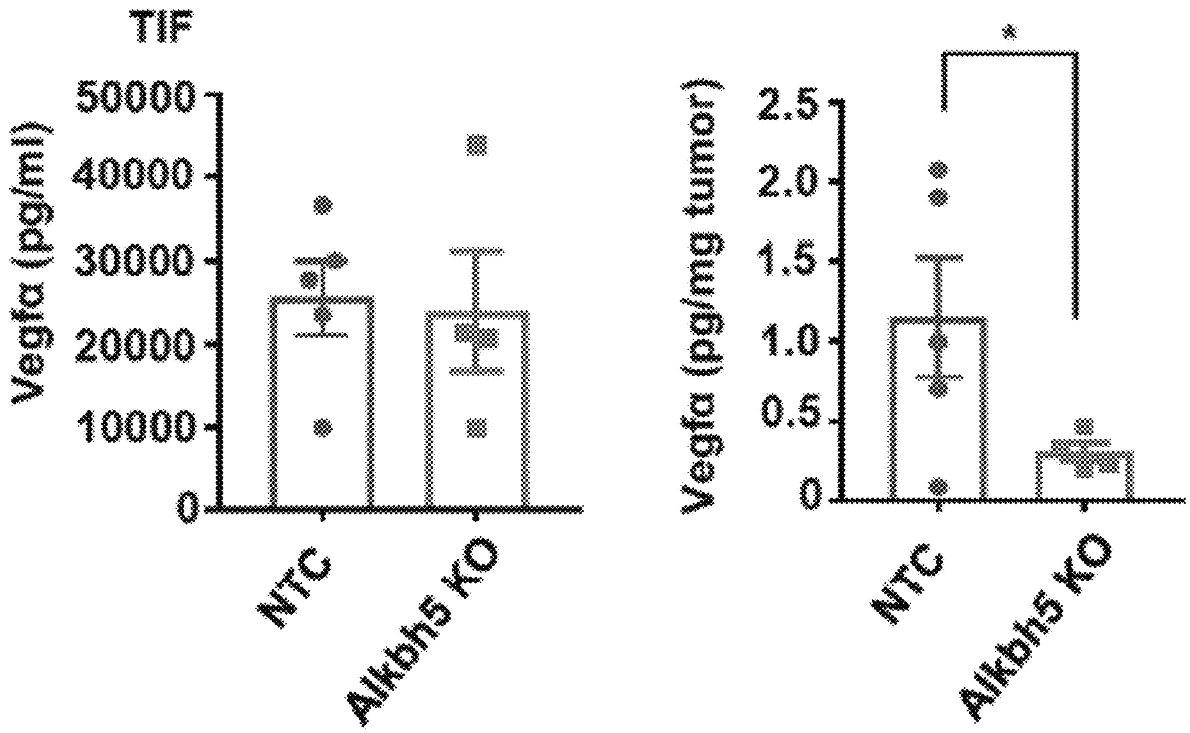

To address these questions, we quantified lactate, Vegfa, and Tgfβ1 concentrations in the tumor interstitial fluid (TIF), which contains proteins, metabolites, and other non-cellular substances present in the TME (SI Appendix, FIG. 5-S6A). Indeed, both the lactate concentration in TIF and the total lactate content in the TME were dramatically reduced in Alkbh5-KO tumors compared with NTC tumors (FIG. 72A). Although the Vegfa concentration in TIF was comparable between NTC and Alkbh5-KO tumors, the total Vegfa content in the TME was reduced by Alkbh5 deletion (FIG. 72B). In agreement with a previous study, we also found that Vegfa levels were much lower in plasma than in TIF 45, showing that our isolation of TIF was successful (SI Appendix, FIG. 5-S6D). The lactate and Vegfa levels in plasma did not differ in mice bearing NTC vs. Alkbh5-KO tumors, suggesting that the effect of Alkbh5 deletion on lactate and Vegfa levels was restricted to the TME and was not systemic (SI Appendix, FIGS. 5-S6 C and D). In contrast to lactate and Vegfa, we found that the concentration of Tgfβ1 in TIF was increased by Alkbh5 deletion, whereas the TME content of Tgfβ1 was reduced only in Alkbh5-deficient tumors (SI Appendix, FIGS. 5-S6 B and E). Collectively, these results showed that Alkbh5 expression in melanoma modulates metabolite and cytokine content with the most significant change of lactate in TIF, suggesting another mechanism by which m6A demethylase could modulate the infiltration of immune cells during anti-PD-1/GVAX treatment.

Mct4/Slc16a3, An Alkbh5 Target Gene, is Involved in Regulating Extracellular Lactate Concentration, Tregs, and MDSC Accumulation in the TME.

Figure 70F:
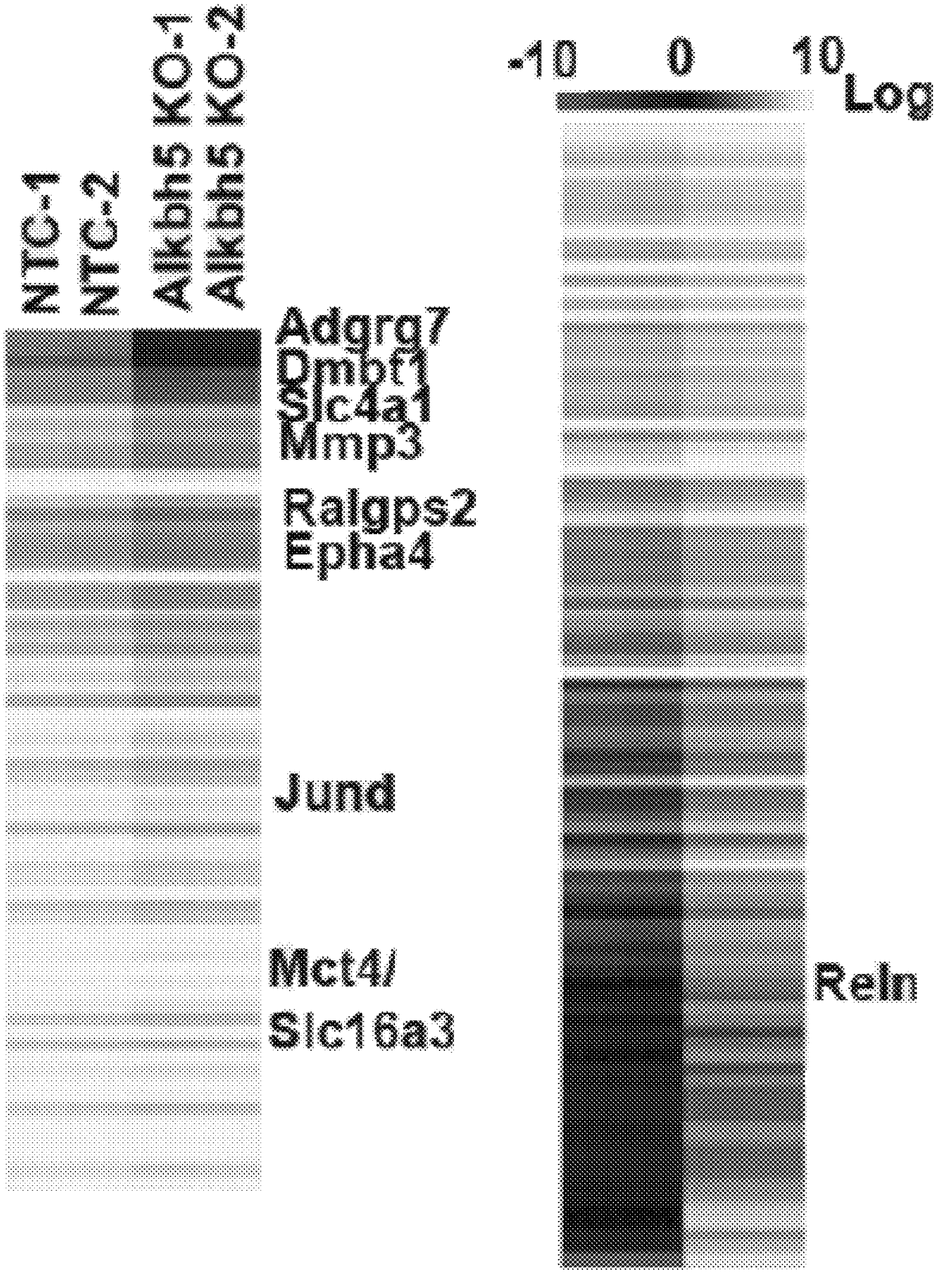
Figure 72C:
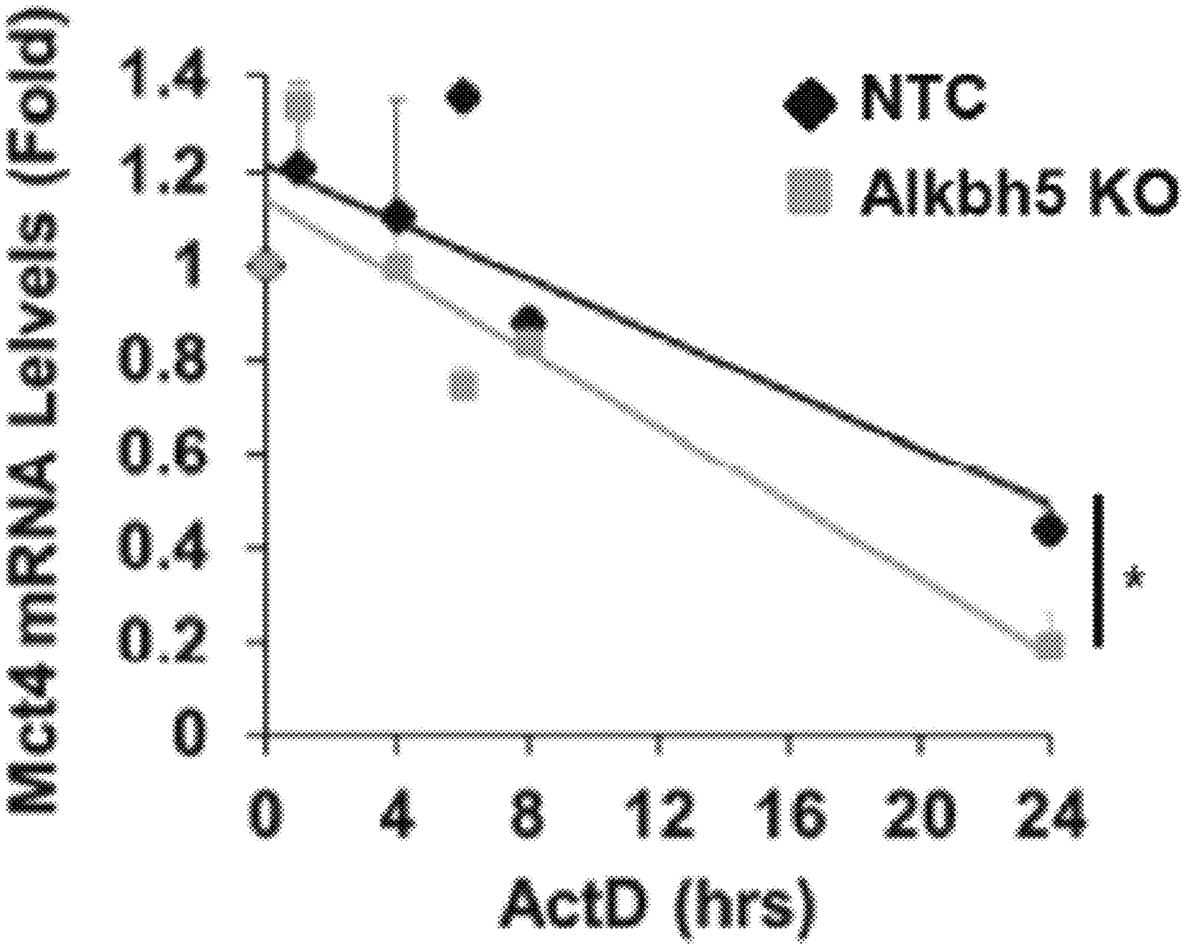

As shown above, we found lactate was the most dramatically decreased metabolite in Alkbh5-KO tumors compared with NTC tumors among all of the Alkbh5-related cytokines and metabolites we examined in the TME (FIGS. 72A and 72B, and SI Appendix, FIG. 5-S6 A-E). In Alkbh5-KO tumors, Mct4/Slc16a3 mRNA level was decreased and m6A density was increased compared with NTC tumors during anti-PD-1/GVAX treatment (FIGS. 70F, 71E, and 71F). Mct4 is a key enzyme catalyzing rapid transport across the plasma membrane of lactate. Lactate is the metabolite that directly affects MDSC and Treg recruitment in tumor sites[46,47]. Therefore, we hypothesized Mct4 is an Alkbh5 target gene in regulating lactate concentration and affecting Tregs and MDSC accumulation in TME during the treatment. To test this hypothesis, we first examined Mct4 expression and RNA stability in NTC and Alkbh5-deficient cells and tumors. We found that Mct4 mRNA levels were lower in Alkbh5-KO than in NTC cells in both B16 and CT26 mouse cell lines, as well as in two other human cell lines when compared ALKBH5 knockdown with control cells (SI Appendix, FIGS. 5-S6 F—I and 5-S9 B and C). In mouse tumors under anti-PD-1/GVAX treatment, both mRNA and protein levels of Mct4 were decreased in Alkbh5-KO tumors compared with NTC (SI Appendix, FIGS. 5-S6 G and H). Next, we performed an mRNA decay assay to determine Mct4 RNA stability in NTC and Alkbh5-KO cells. Our results showed that Mct4 mRNA stability was reduced in Alkbh5-KO cells compared with NTC in both B16 and CT26 cell lines (FIG. 72C and SI Appendix, FIG. 5-S6 J-L). These results strongly suggest that Alkbh5 regulated Mct4 expression by changing its m6A levels and RNA stability.

Figure 72D:
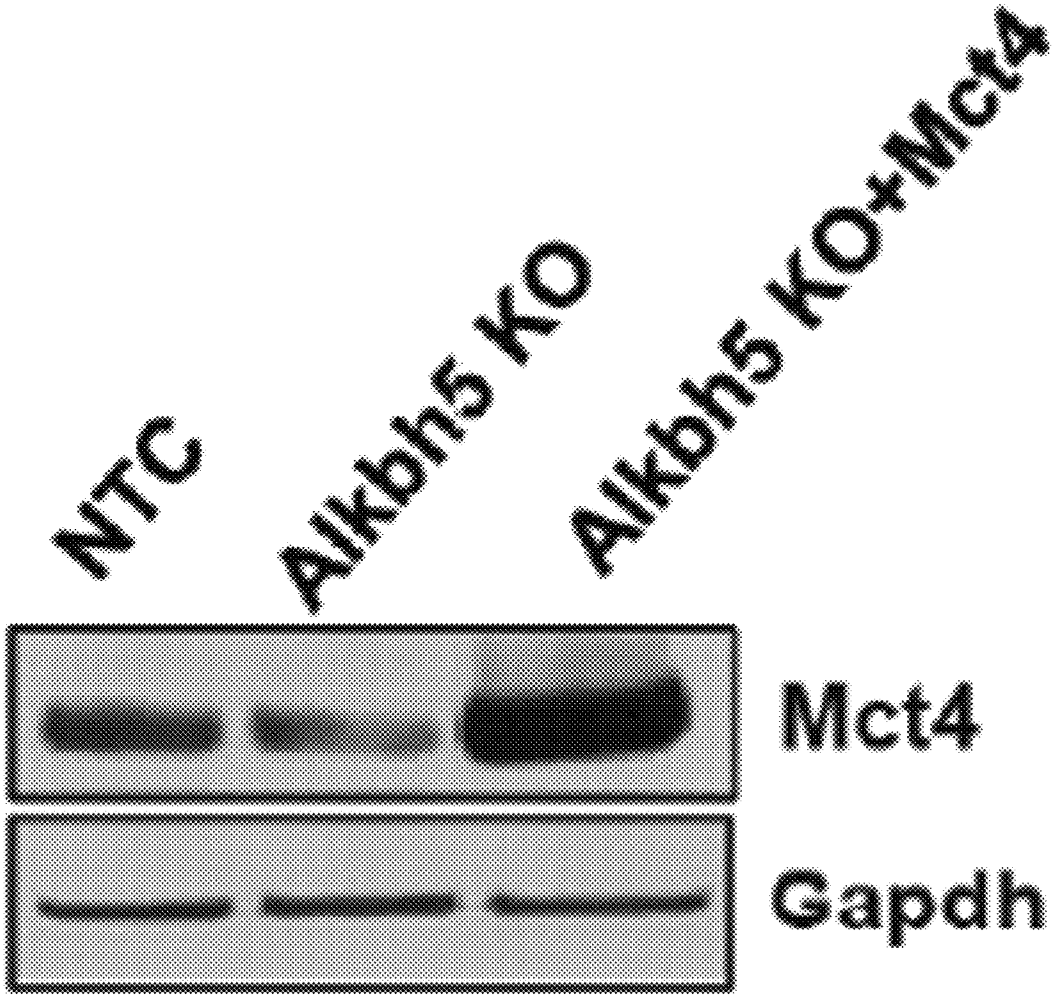
Figure 72E:
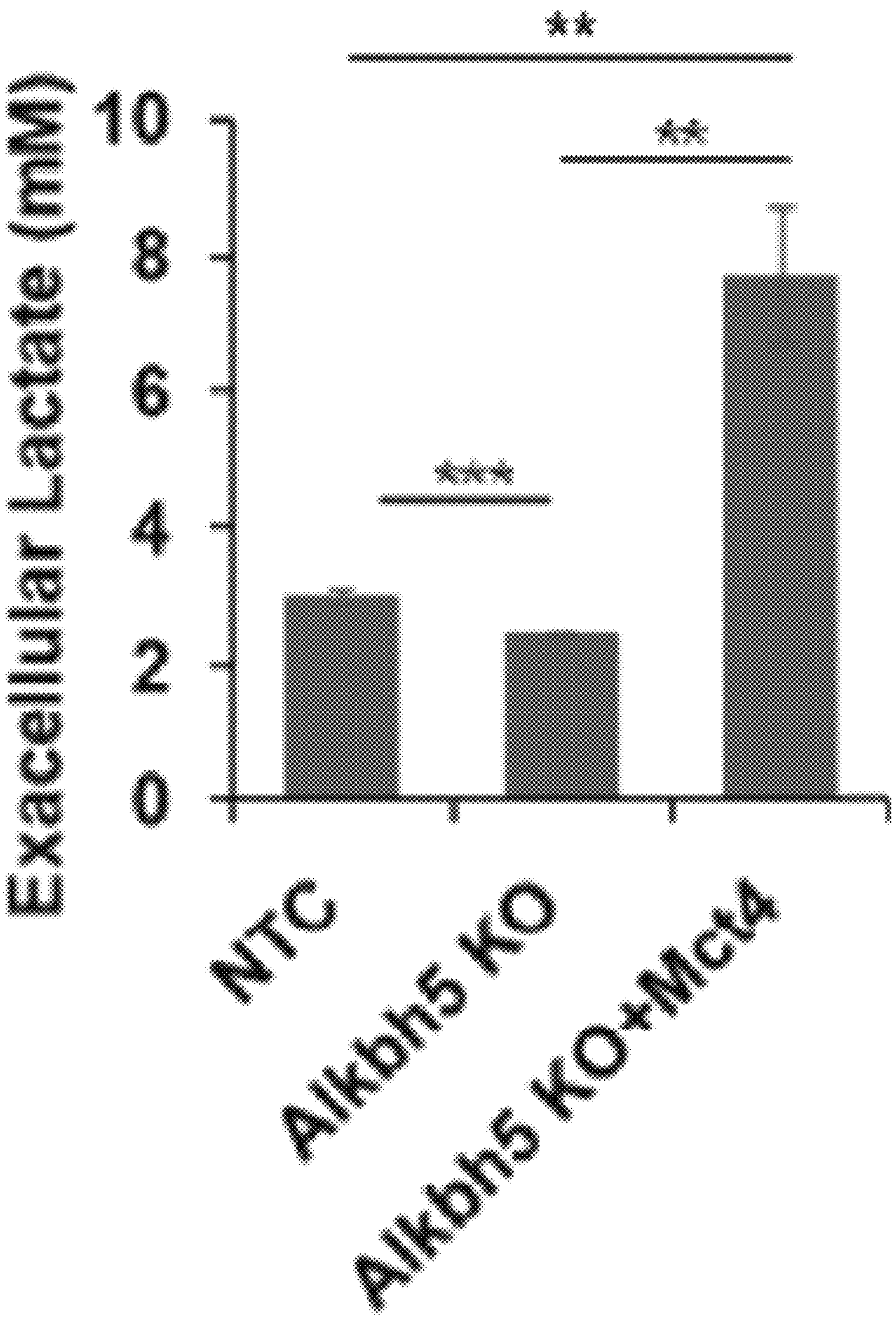

To further delineate the role of Mct4 in Alkbh5 KO tumors during anti-PD-1/GVAX treatment, we constructed a stable cell line expressing Mct4 in Alkbh5-KO cells and examined the function of Mct4 in Alkbh5-KO cells in vitro and in vivo. First, we validated the cell lines by detecting the both mRNA and protein levels of Mct4, and performed in vitro proliferation assay for NTC, Alkbh5-KO, and Alkhb5-KO+Mct4 cells. Results of these analyses showed that there was no difference in cell proliferation of NTC, Alkbh5-KO, and Alkbh5-KO+Mct4 cells in vitro (FIG. 72D and SI Appendix, FIGS. 5-S7 A and B). As Mct4 is a key enzyme mediating transport of lactate across the cell membrane, we examined extracellular lactate concentration in NTC, Alkbh5-KO, and Alkbh5-KO+Mct4 B16 cells. As expected, we observed a reduction of lactate concentration in Alkhb5-KO cells, and an increased level of lactate in Alkhb5-KO+Mct4 cells in vitro (FIG. 72E). Furthermore, we inoculated these cells to mice and treated them with anti-PD-1/GVAX and monitored tumor growth in vivo as described above (FIG. 69). We observed a significantly reduced tumor growth in Alkhb5-KO tumors but not Alkbh5-KO+Mct4 tumors compared with NTC, albeit Alkbh5-KO+Mct4 tumors also grew slower than NTC (FIG. 72). These results suggested that Mct4 was one of the major targets of Alkbh5 during anti-PD-1/GVAX treatment. Next, we isolated tumors and assayed the lactate concentration and amounts in TIF and found that lactate levels were significantly reduced in Alkbh5-KO but not Alkbh5-KO+Mct4 tumors, which was consistent with in vitro assay (FIG. 72G). In accordance with that, flow cytometry analysis of the tumors showed that Tregs and PMNMDSC populations were significantly decreased in in Alkbh5-KO but not Alkbh5-KO+Mct4 tumors (FIGS. 72H and 72I). Altogether, these results show that Mct4 is a key Alkhb5 target gene mediating reduced lactate levels, as well as Tregs and MDSC populations in Alkbh5-KO tumors during the anti-PD-1/GVAX treatment.

Figure 72F:
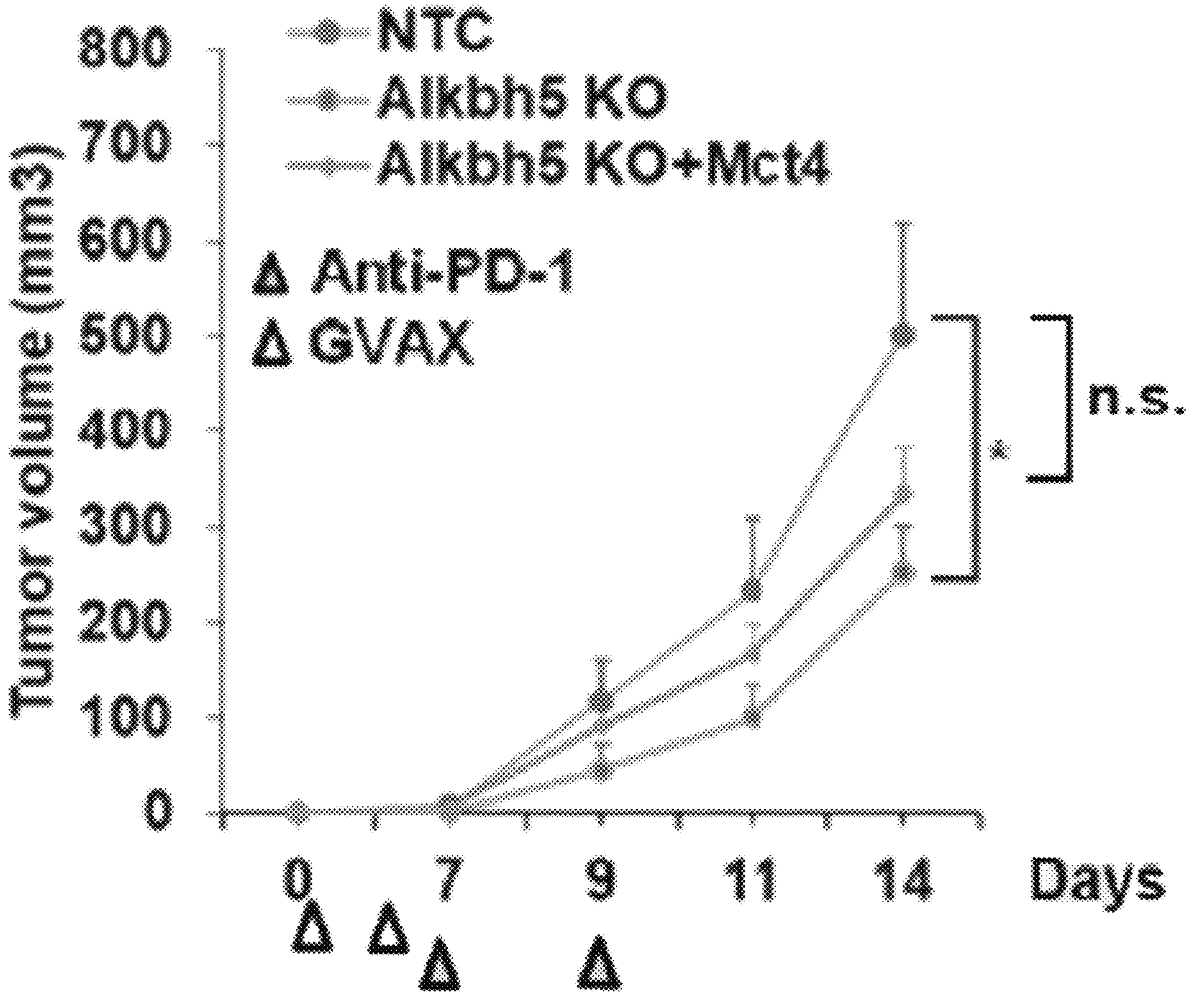
Figure 72G:
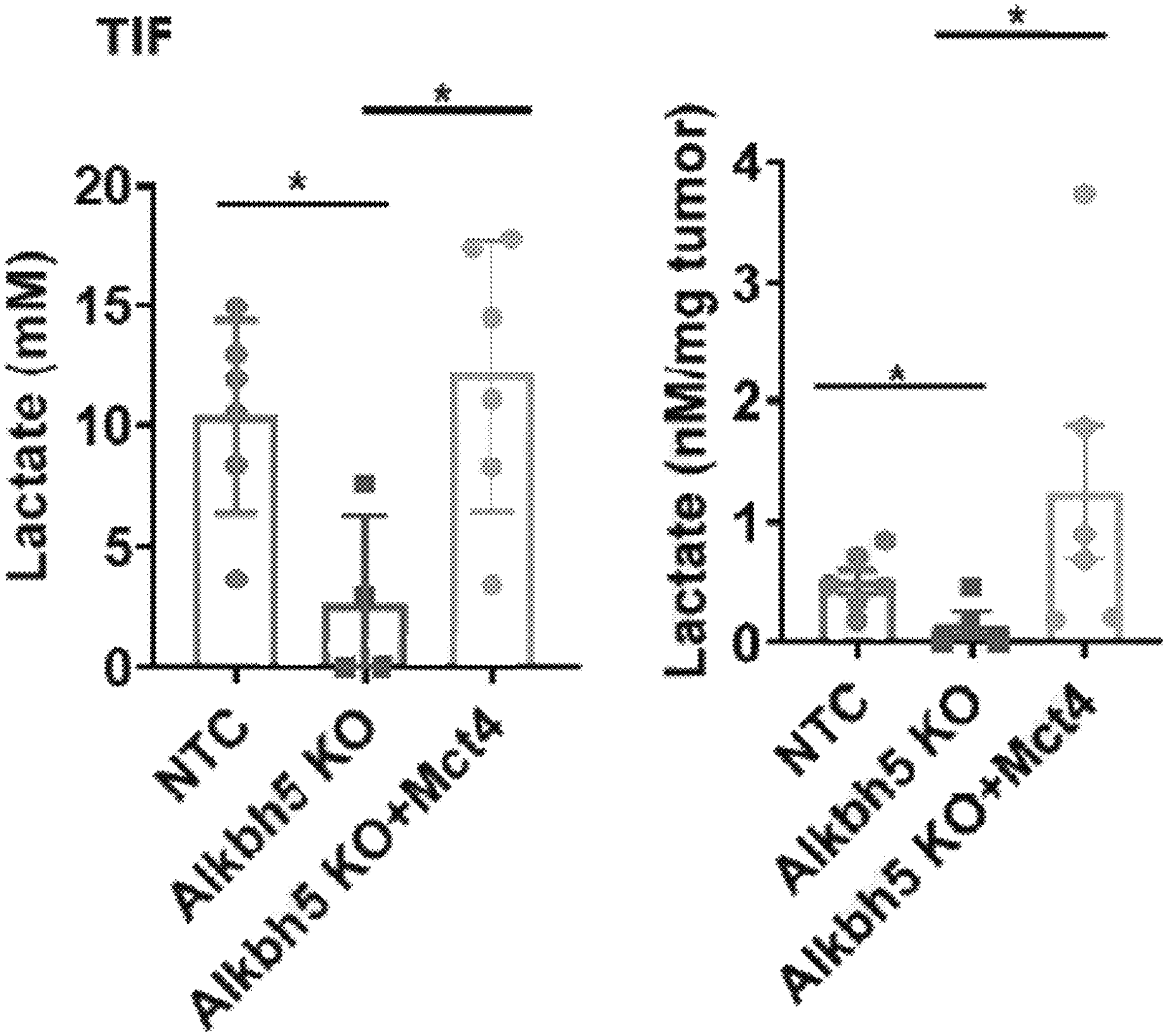
Figure 72H:
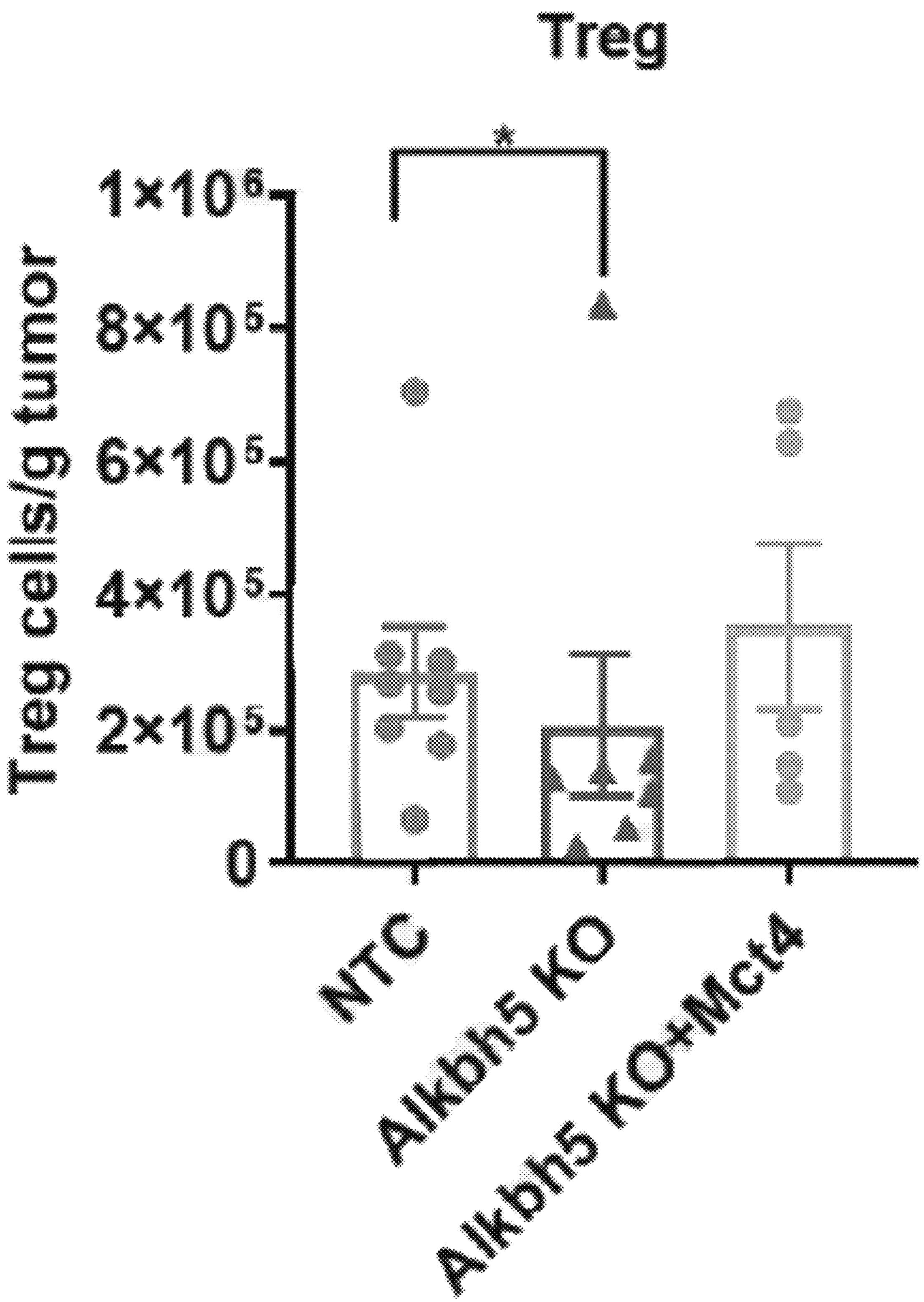
Figure 72I:
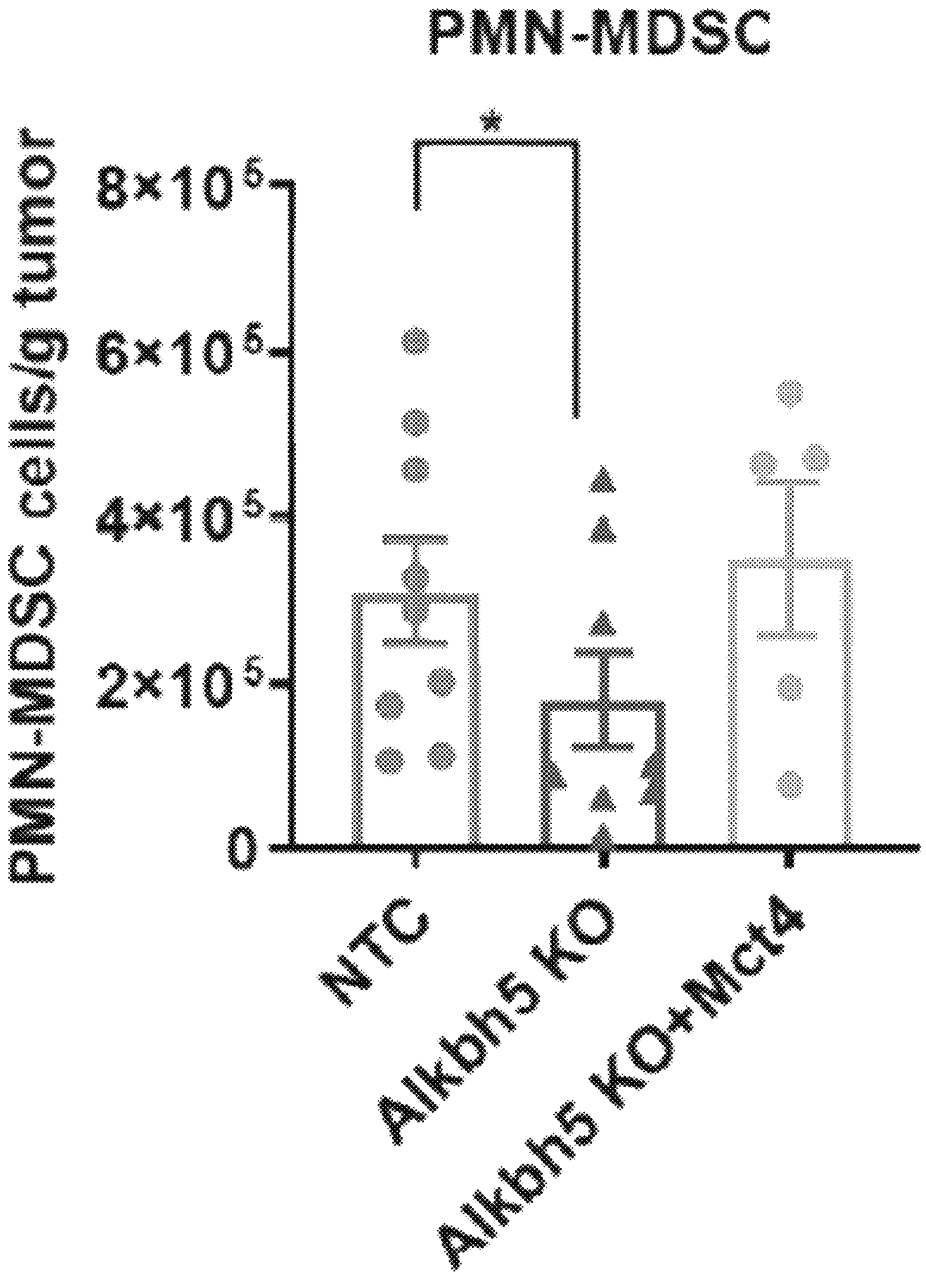
Figure 72J:
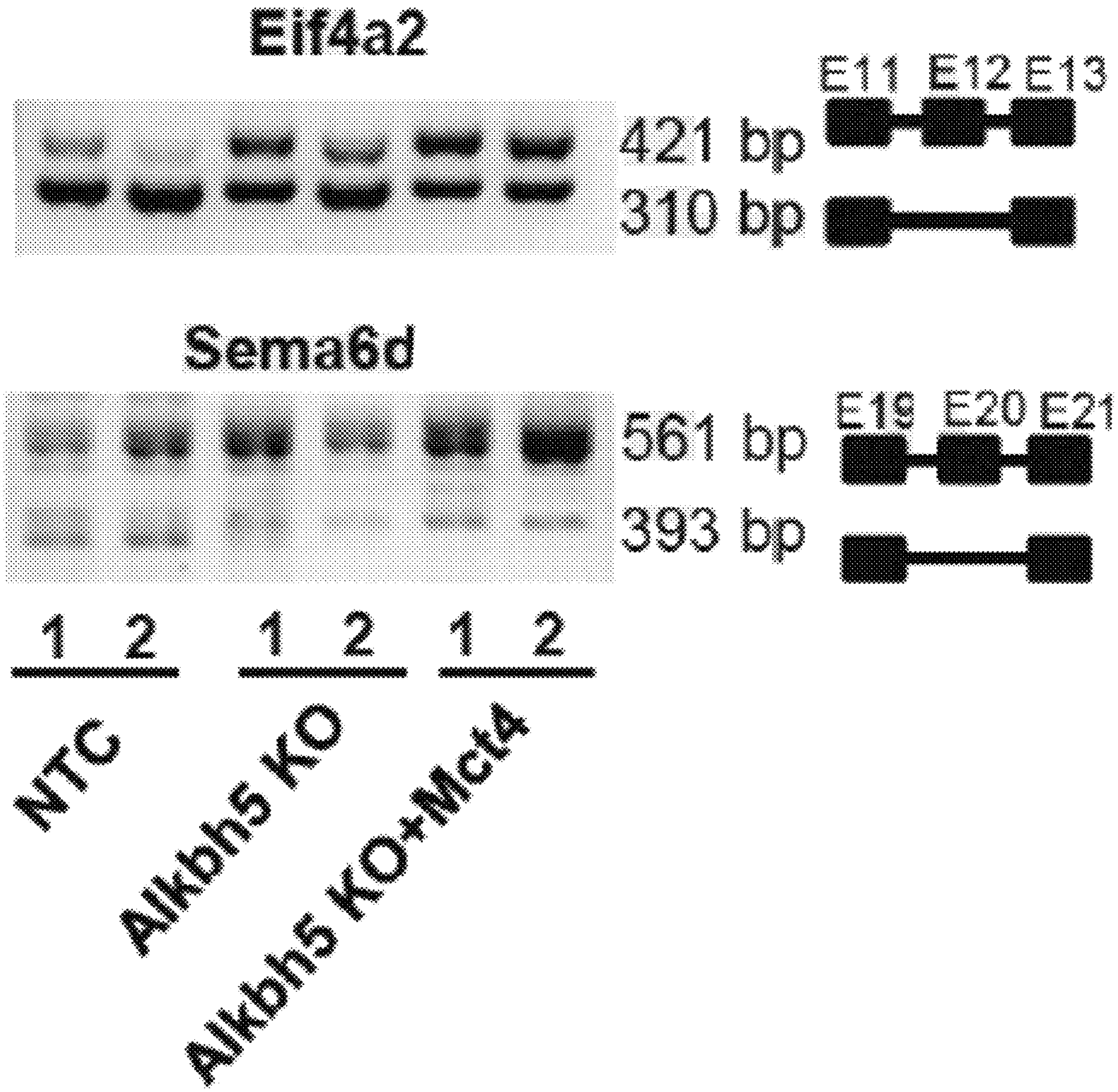

Although not significant, we observed a slower tumor growth in Alkbh5-KO+Mct4 than NTC cells-inoculated mice in vivo (FIG. 72F). We speculate that other factors or events also play roles in Alkbh5-KO tumor, albeit not as significant as Mct4, during anti-PD-1/GVAX treatment. Therefore, we analyzed several genes whose splicing events were altered in Alkbh5-KO tumors, and compared their pattens in NTC, Alkbh5-KO, and Alkbh5-KO+Mct4 cells. The results showed that gene splicing changes remained the same in Alkbh5-KO and Alkbh5-KO+Mct4 cells, such as Eif4a2 and Sema6d, suggesting that besides Mct4, they may play roles in Alkbh5-KO tumors (FIG. 72J and SI Appendix, FIG. 5-S7 C-E).

m6A mRNA Demethylase Activity of Alkbh5 is Indispensable During GVAX/Anti-PD-1 Treatment.

Figure 72K:
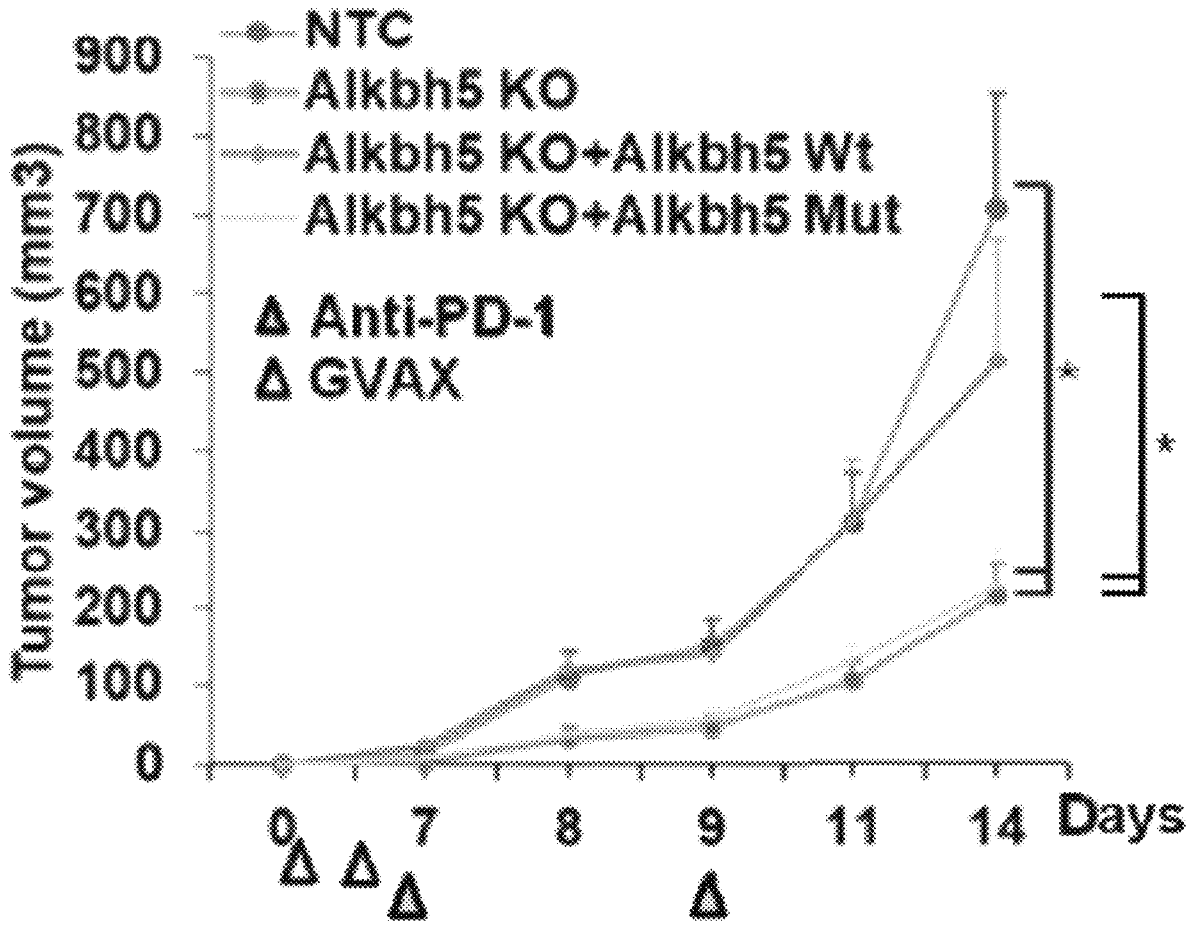

Since Alkbh5 is an m6A RNA de-methylase, we asked whether the m6A demethylase enzymatic activity is essential for the functions of Alkbh5. We constructed stable cell lines by expressing Alkbh5 CRISPR sgRNA-resistant wild-type or H205A/H267A catalytically inactive mutant Icon- served enzymatic sites in human ALKBH5, H204H266[8, 48]1 of Alkhb5 in Alkbh5-KO cells and examined Mct4 expression. Our results showed that wild-type but not mutant Alkbh5 could res- cue Mct4 mRNA and protein levels (SI Appendix, FIG. 5-S8 A-D). We also analyzed gene splicing of Eif4a2 and Sema6d genes, which had altered PSI in Alkbh5-KO tumors, in wild-type and mutant Alkbh5-expressed Alkbh5-KO cell lines. These results showed that Eif4a2 gene splicing was rescued in wild-type but not mutant Alkbh5-expressed Alkbh5-KO cells. MeRIP-seq also showed an increased signal of m6A in Alkhb5-KO cells compared with NTC in the exon-intron junction, which were involved in the alternative splicing of Eif4a2. On the other hand, gene splicing of Sema6d was not affected by the enzymatic activity of Alkbh5, and we did not observe m6A peaks around the spliced exons (SI Appendix, FIG. 5-SSE). These results showed that enzymatic activity of Alkbh5 play important roles in regulating Mct4 RNA and protein expression, as well as certain genes with altered alternative splicing, which was directly affected by m6A and Alkbh5. Furthermore, we performed in vivo tumor growth experiments in mice treated with GVAX/anti-PD-1. As shown in FIG. 72K and SI Appendix, FIG. 5-S9A, expressing wild-type but not catalytically inactive mutant Alkbh5 in Alkbh5-KO cells abolished the tumor restricting effects of Alkbh5 KO during GVAX/anti-PD-1 treatment. Altogether, these results demonstrate that the catalytic activity of Alkbh5 is indispensable for its effects on in vivo tumor growth during GVAX/anti-PD-1 treatment.

ALKBH5 and MCT4/SLC16A3 Levels in Melanoma Patients Correlate with the Response to Anti-PD-1 Therapy.

Figure 73A:
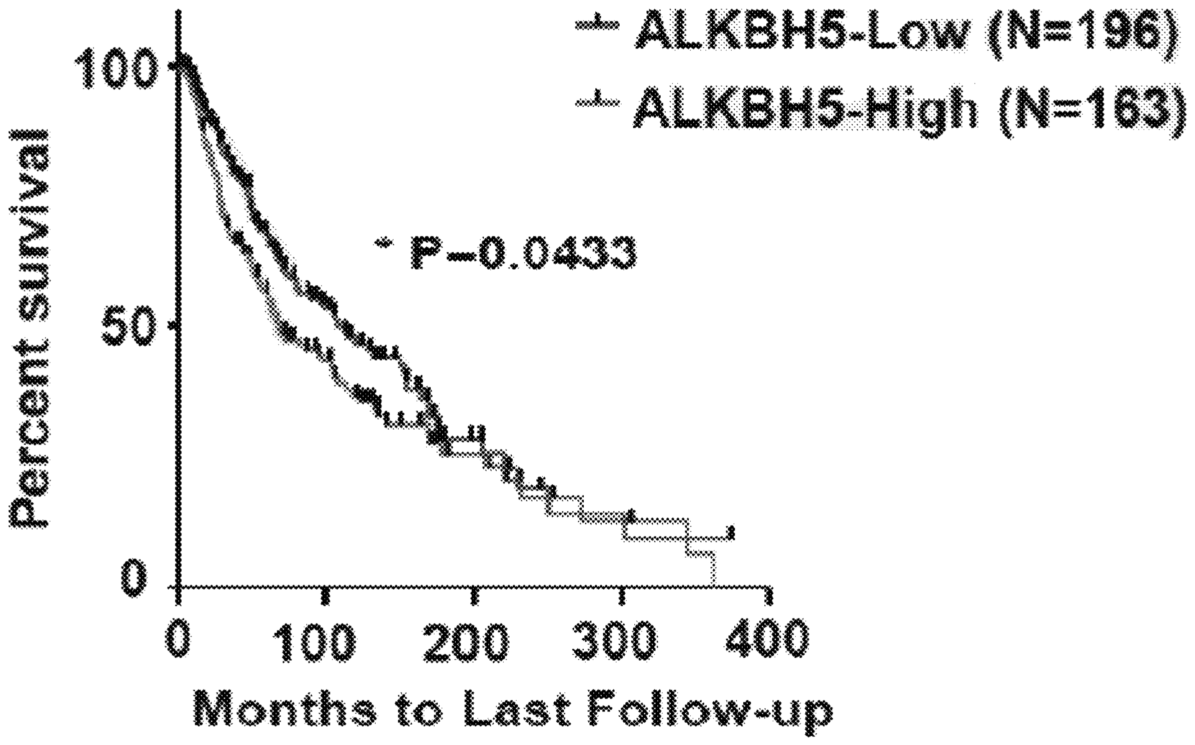
FIG. 73A-73H. ALKBH5 expression influences the response of melanoma patients to antiPD-1 (73A) Kaplan-Meier survival rate analysis of TCGA metastasized melanoma patients grouped by ALKBH5 mRNA levels. Patients with follow-up history were included in the analysis; the mean ALKBH5 level for the entire group was used as the cut-off value. ALKBH5 low n=196, ALKBHS high n=163. (73B) FOXP3/CD45 expression ratio was calculated for metastatic melanoma patients grouped by ALKBH5 mRNA levels; the mean ALKBH5 level for the entire group was used as the Cut-Off value. ALKBH5 low n=196; ALKBH5 high n=163. *P<0.05 (73C) Pearson correlation Of ALKHB5 and SLC16A3/MCT4 in melanoma patients from the TCGA database (n=472). (73D) Melanoma patients (n=26) carrying low or high MCT4/SLC16A3 mRNA expression were treated with pembrolizumab or nivolumab anti-PD-1 Ab (GSE78220). Average expression was used as Cut-off. The percentage with complete response (CR), partial response (PR), and progressive disease (PD) are shown. Data are from GSE78220. (73E) Pearson correlation of ALKHB5 and MCWSLC16A3 in melanoma patients treated With pembrolizumab or nivolumab anti-PD-1 Ab (GSE78220). (73F) Melanoma patients carrying wild-type (normal) or deleted/mutated ALKHB5 gene were treated with pembrolizumab or nivolumab. complete response (CR), partial response (PR), and progressive disease (PD) are shown (GSE78220). (73G) scRNA-Seq data presented as t-distributed stochastic neighbor embedding (t-SNE) plots. Cells were from a tumor biopsy collected from a melanoma patient who showed a response to anti-PD-1 therapy. Plots show the distribution of identified cells. (73H) ALKBH5 expression in normal and melanoma tumor cells in melanoma patient receiving PD- 1 therapy.
Figure 73B:
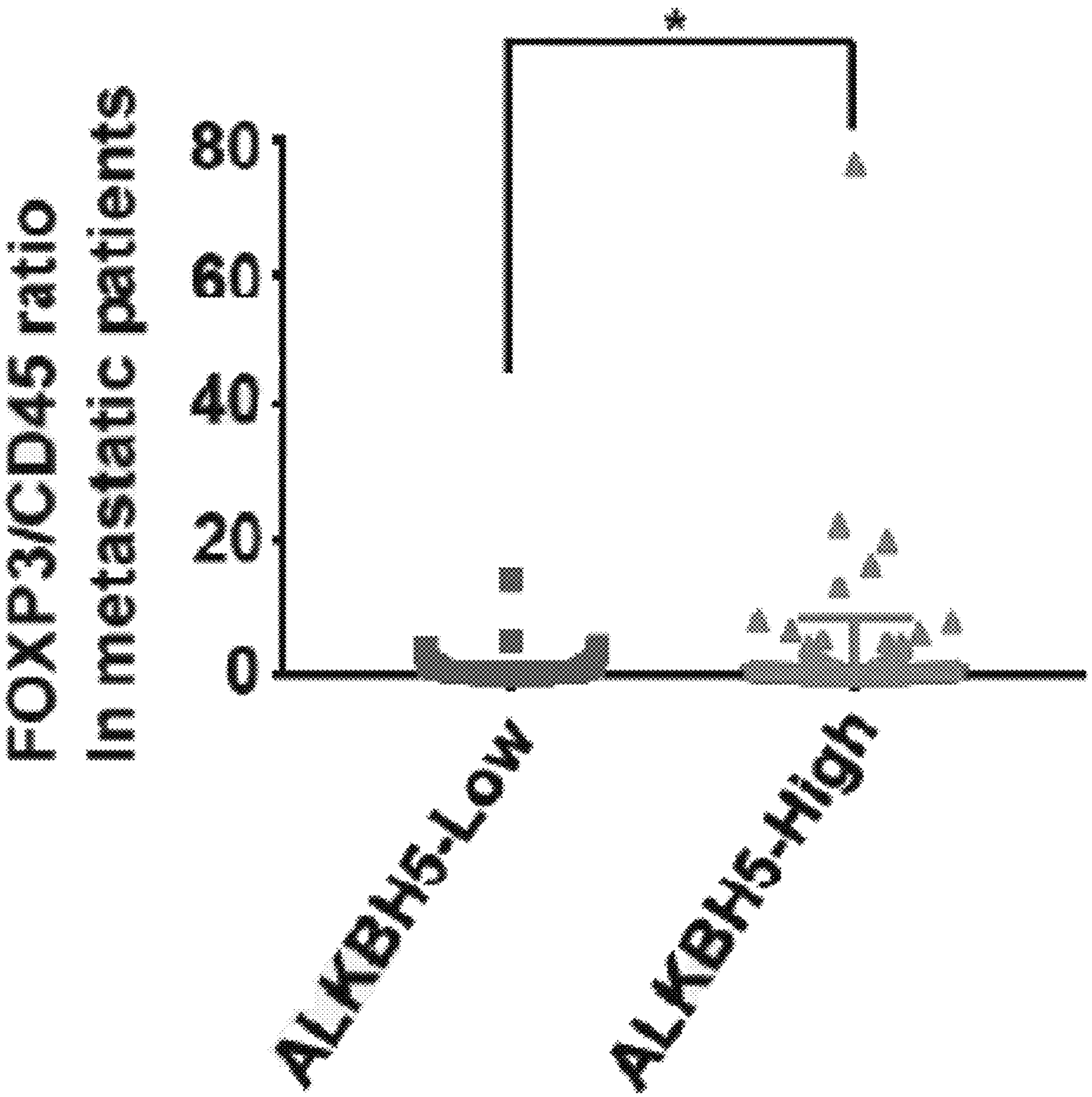
Figure 73C:
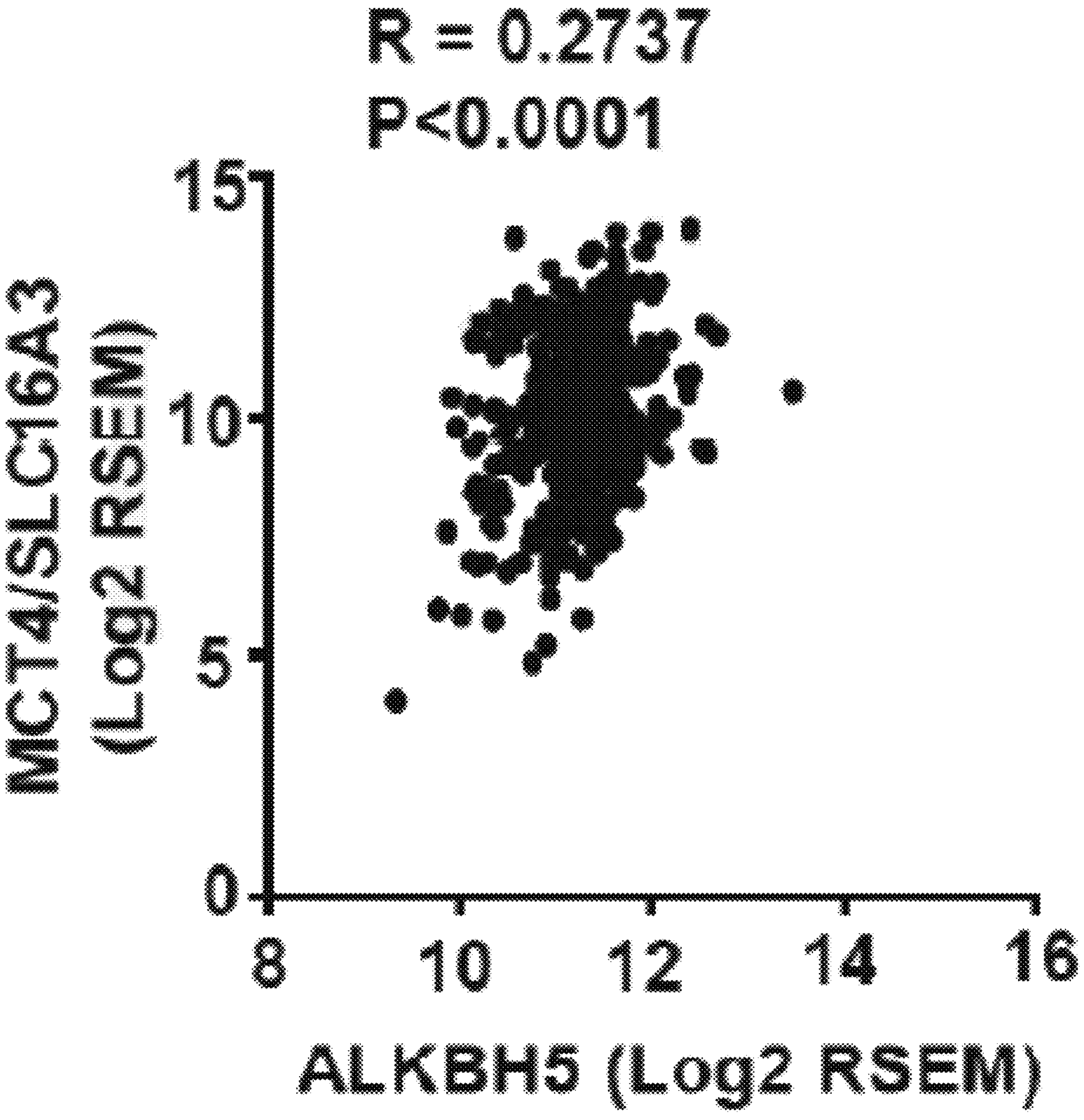

Our results thus far strongly suggest that ALKBH5 deletion enhances the efficacy of anti-PD-1 therapy. Therefore, we analyzed the Cancer Genome Atlas (TCGA) database to examine the correlation between expression level of ALKBH5 and survival time in metastatic melanoma patients. Consistent with our findings, low expression of ALKBH5 correlated with better patients' survival (FIG. 73A). Importantly, Treg cell numbers, as indicated by FOXP3/CD45 ratio, were significant lower in patients with less expression of ALKBH5 (FIG. 73B). As described above, we found that Mct4/Slc16a3 was an important Alkbh5 target gene during immunotherapy, and Mct4 level decreased in Alkbh5-KO tumors during therapy. Mct4 is a key gene to mediate lactate secretion which led to reduced lactate in TIF contents and suppressive immune cell populations of Alkhb5-KO tumors during immunotherapy (FIGS. 70F, 71E, 71F, and 72C-72I). Therefore, we examined the gene expression of ALKBH5 and MCT4/SLC16A3 in the TCGA database. Consistent with our mouse tumor data, we found there is a positive correlation between ALKBH5 and MCT4/SLC16A3 expression in melanoma patients (FIG. 73C). Consistent with our results (FIG. 70 and SI Appendix, FIG. 5-53), our analysis did not show any correlation of ALKBH5 expression with IFN pathway genes IRFI and PDLI (SI Appendix, FIGS. 5-S10B and C). We observed a negative correlation of PBRMI and GZMB, which serves as a positive control for our analysis 49 (SI Appendix, FIG. 5-S10D).

Figure 73D:
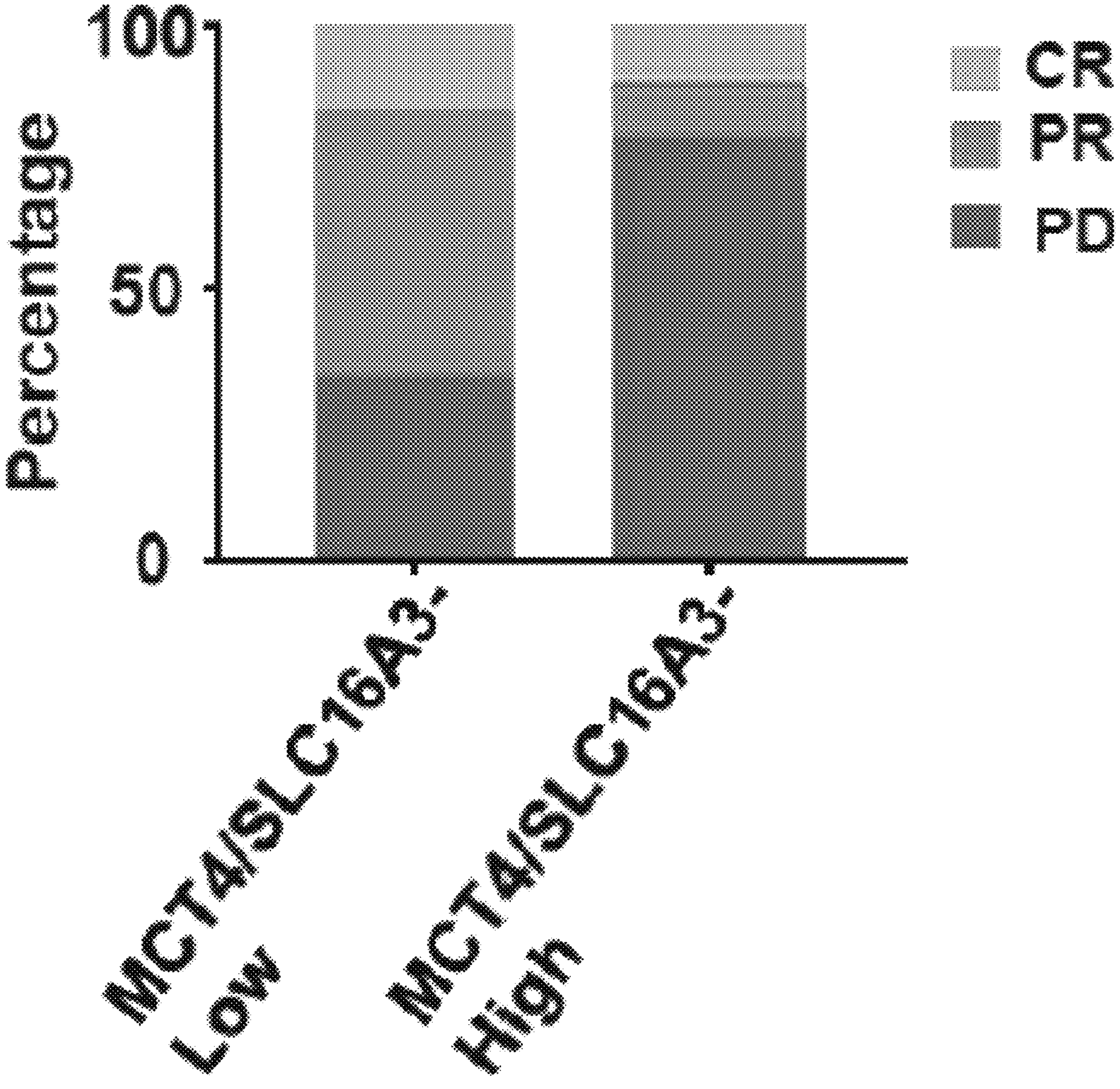
Figure 73E:
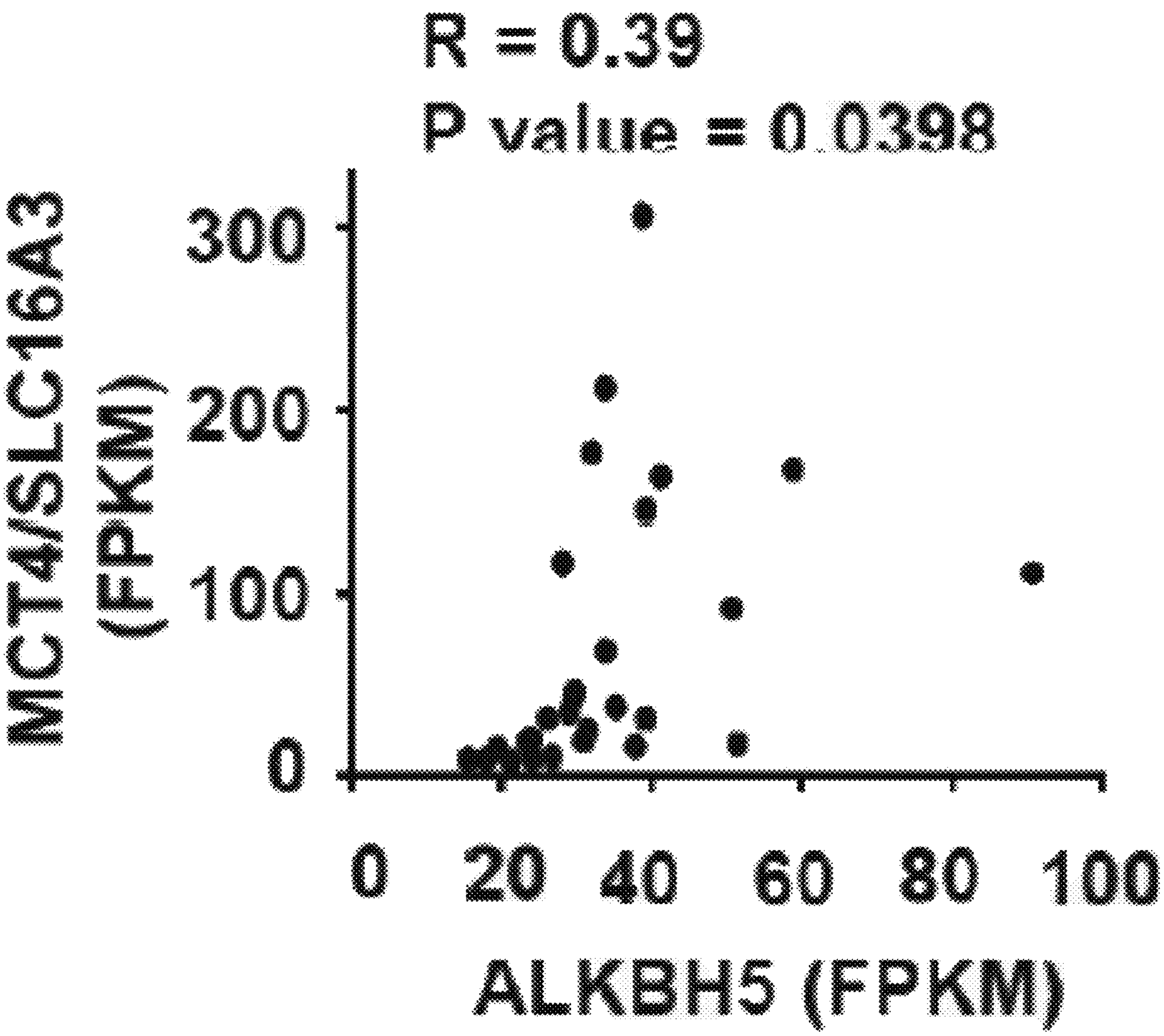
Figure 73F:
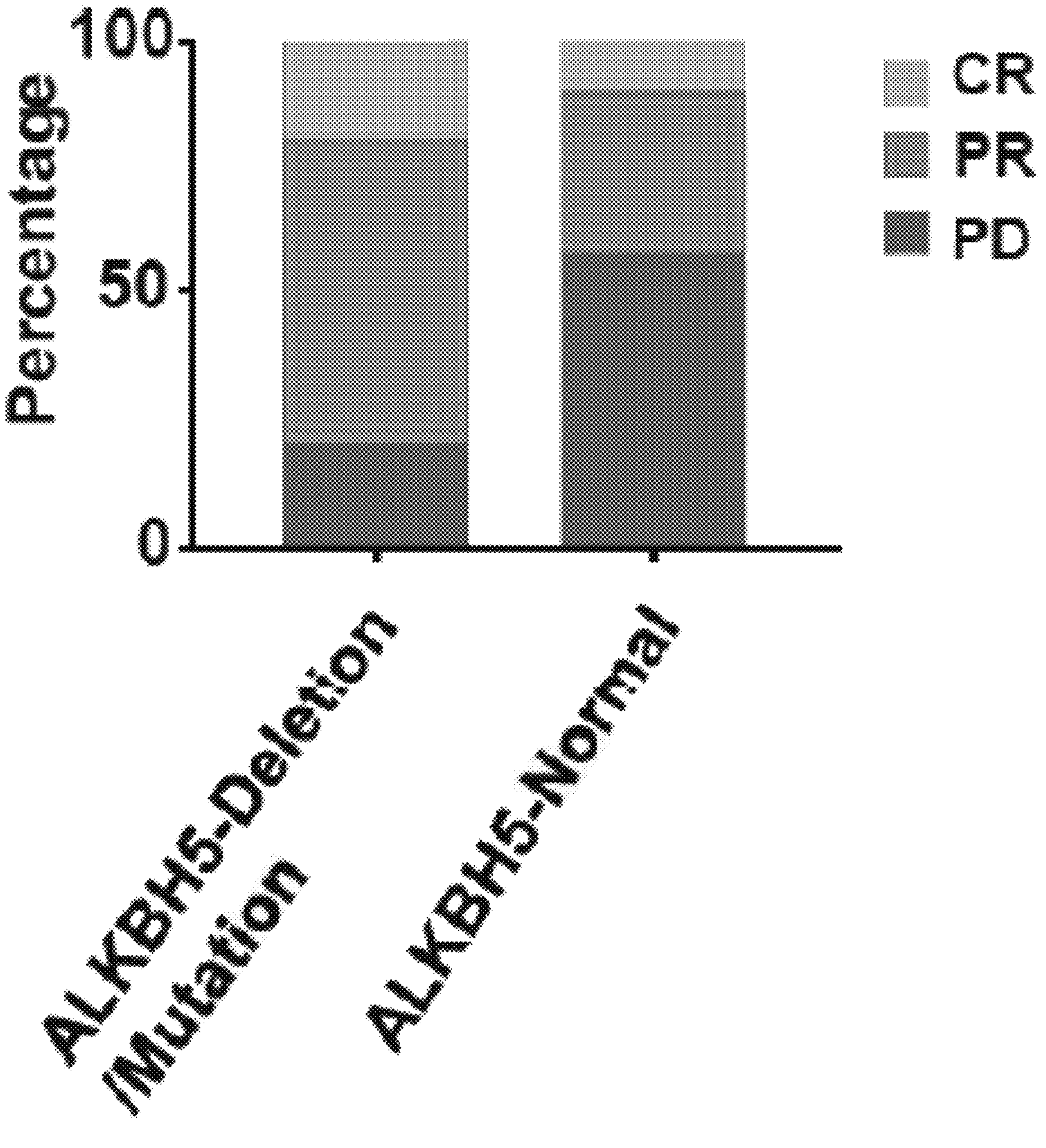

MCT4/SLC16A3 was also found in the down-regulated gene list of 26 melanoma patients receiving pembrolizumab or nivolumab treatment[30]; we then analyzed the percentage of patient response to PD-1 Ab in low- and high-expressed MCT4/SLC16A3 groups. Melanoma patients with low expression of MCT4/SLC16A3 has much higher complete or partial response rate than the high-expression group (FIG. 73D). In the same cohort of melanoma patients receiving pembrolizumab or nivolumab treatment, we also observed a positive correlation of ALKBH5 and MCT4/SLC16A3 expression (FIG. 73E). We next determined whether melanoma patients harboring ALKBH5 deletion/mutation were more sensitive to anti-PD-1 therapy than patients carrying wild-type ALKBH5. To this end, we examined the treatment response according to their ALKBH5 mutation and gene-expression status. As shown in FIG. 73F, we found that more patients harboring deleted or mutated ALKBH5 achieved complete or partial responses to pembrolizumab or nivolumab therapy than did patients with wild-type ALKBH5.

Figure 73G:
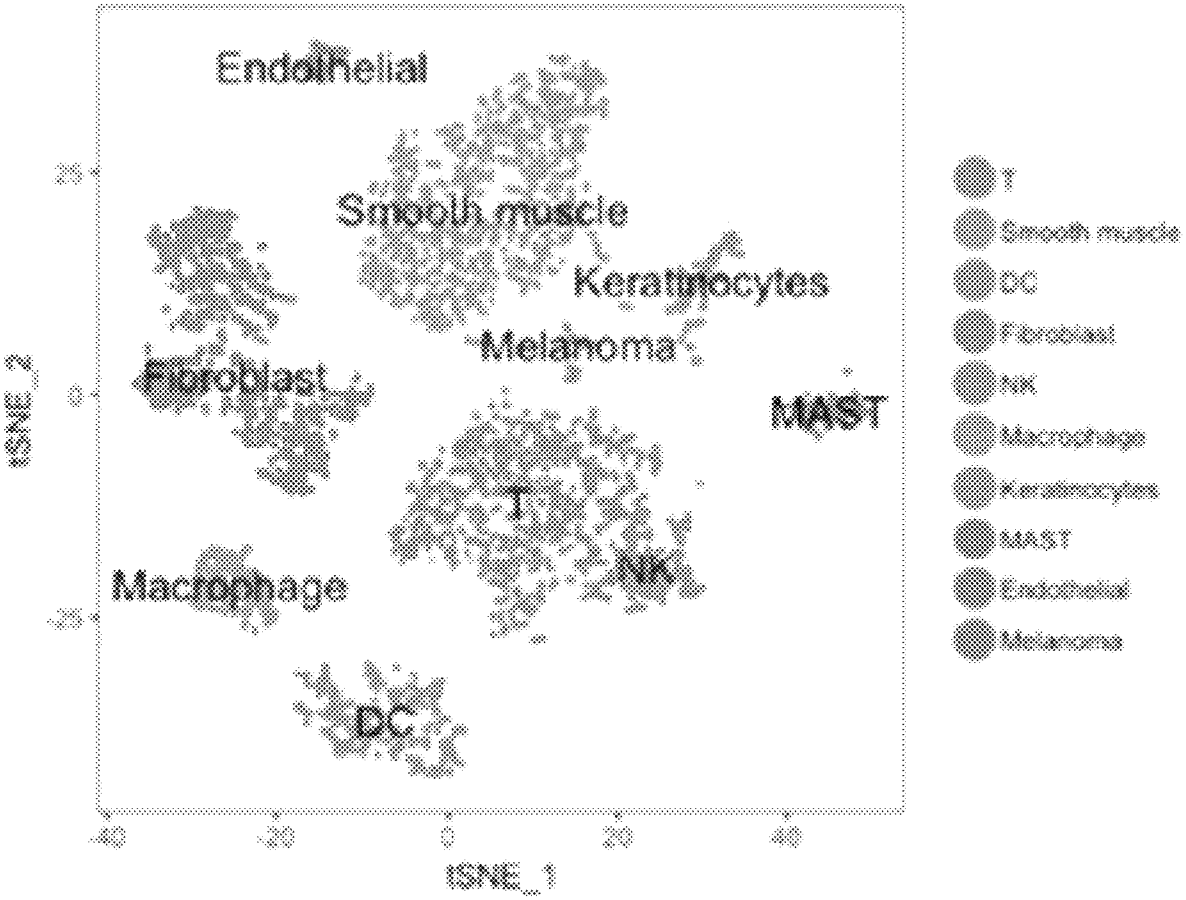
Figure 73H:
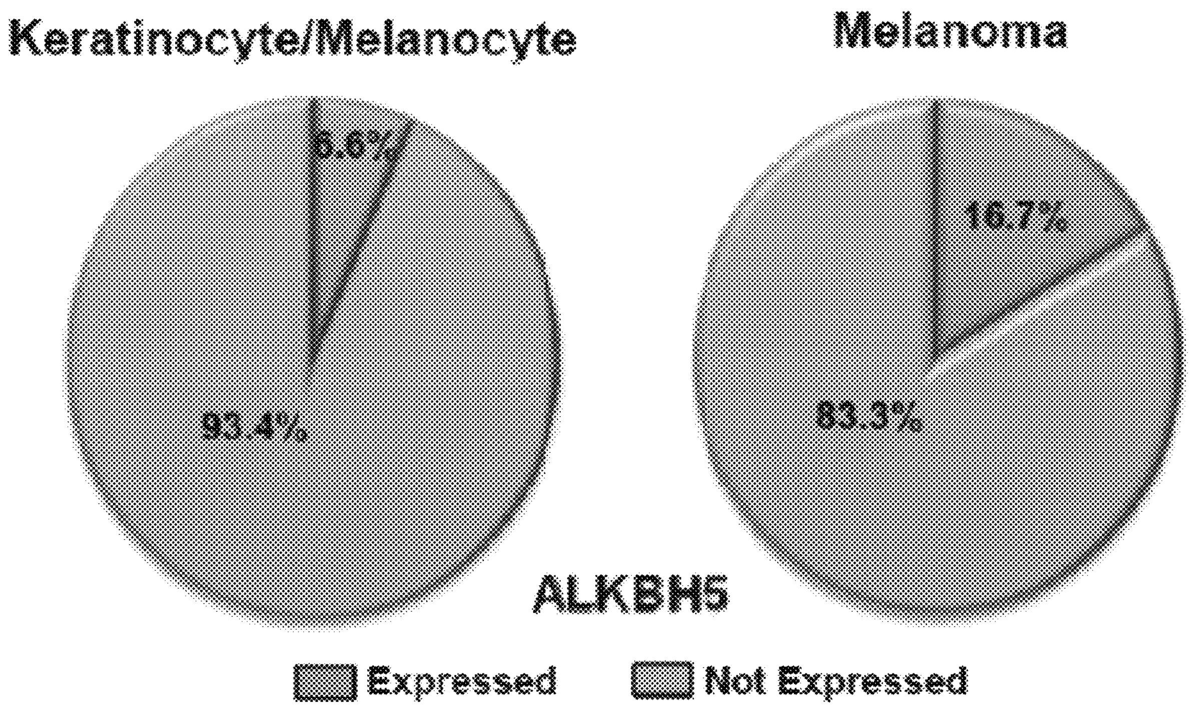

Next, we performed single-cell RNA-seq (scRNA-seq) on tumor cells obtained from a patient with stage IV melanoma who had responded well to anti-PD-1 therapy. By using scRNA-seq, we were able to examine ALKBH5 expression in the resistant tumor cells in patients receiving PD-1 Ab. We identified 10 cell types in the tumor (FIG. 73G), with substantial immune cell infiltration and very few residual melanoma cells, reflecting the response to therapy. We then examined ALKBH5 expression in the tumor cells and found that 16.7% of melanoma cells (16.7%) expressed ALKBH5 compared with only 6.6% of normal keratinocytes and melanocytes surrounding the tumor cells (FIG. 73H). Taken together, these results indicate that tumor expression of ALKBH5 might be a predictive biomarker of patient's survival and response to anti-PD-1 therapy, at least for melanoma patients.

A Small-Molecule Inhibitor of Alkbh5 Enhances the Efficacy of Anti-PD-1 Therapy.

Figure 74A:
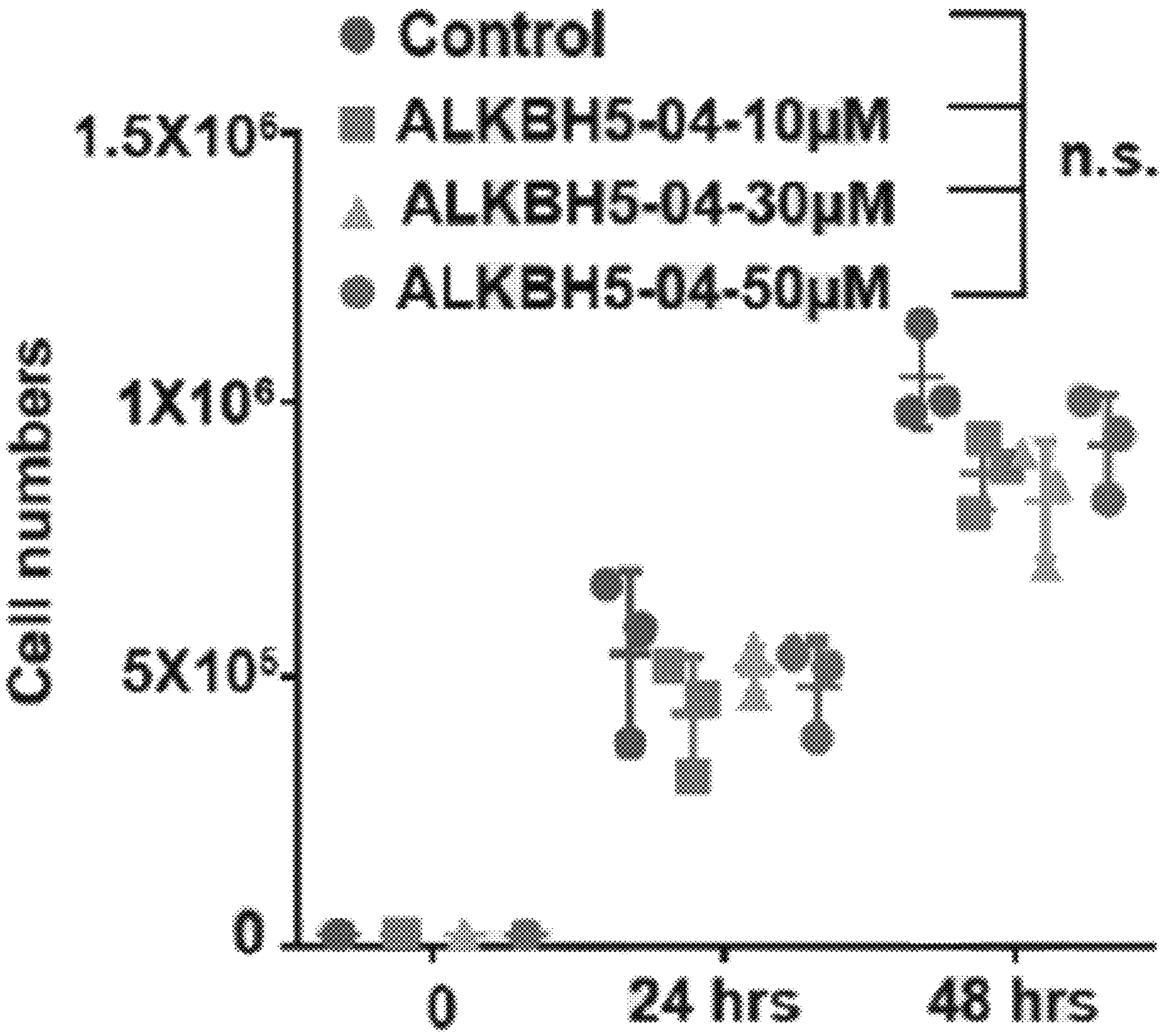
FIG. 74A-74C. ALKBH5 inhibitor enhances efficacy of immunotherapy in combination with GVAX and PD-1 AB. (74A) Proliferation assay of B16 cells treated with DMSO control and 10 μm 30 μm, and 50 μm ALKBH5 inhibitor. (74B) Treatment timeline and B16 growth of control and ALKHB5 inhibitor combined with PD-1 and GVAX immunotherapy. *P<0.05 (74C) Proposed model for ALKBH5-mediated regulation of immunotherapy. ALKBH5 influences anti-PD-1 therapy modifying m6A levels and splicing of specific genes. Inhibition of ALKBH5 mRNA demethylation by CRISPR or a small molecule increased m6A on MCT4/SLC16A3, a lactate which reduced its mRNA levels leading to reduction of lactate in TIFs. Consequently, MDSC and Treg suppressive immune cell populations in the TME are decreased and therapy responses are enhanced.
Figure 74B:
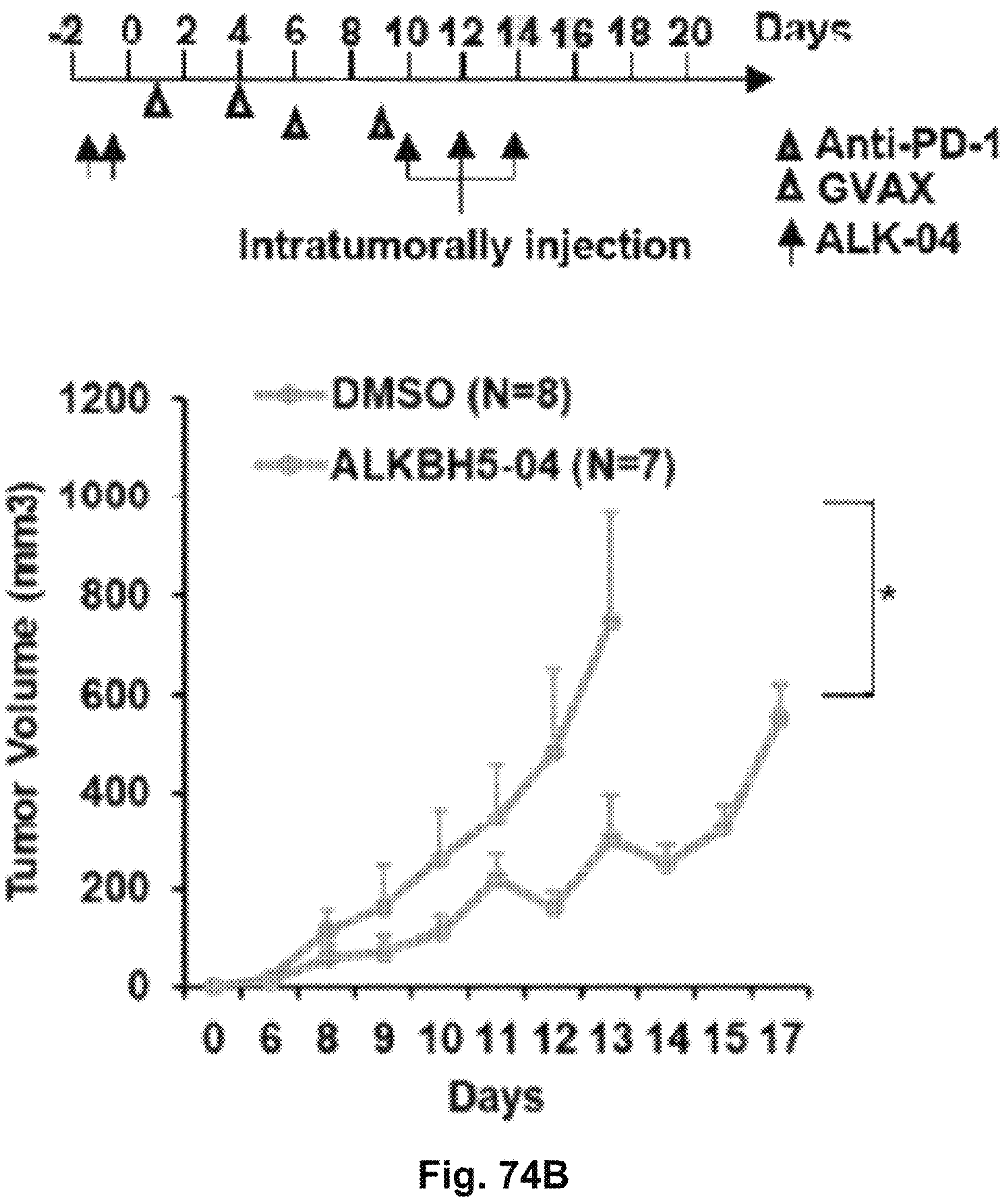

Our results thus far indicate that loss f-m6A demethylase Alkbh5, in B16 melanoma cells, potentiates the efficacy of GVAX/anti-PD-1 therapy. To identify clinically relevant pharmacological inhibitors of Alkbh5, we have identified a specific inhibitor of ALKBH5, named ALK-04, by in silico screening of compounds using the X-ray crystal structure of ALKBH5 (PDB ID code 4NRO) and by performing structure-activity relationship studies on a library of synthesized compounds. First, we tested the cytotoxicity of the inhibitor in vitro, and B16 cells proliferation was not significantly affected by inhibitor treatment (FIG. 72). Next, we compared tumor growth of control and inhibitor-treated mice during immunotherapy. Consistent with our previous findings of Alkbh5-KO tumor, mice treated with ALKBH5 inhibitor significantly reduced tumor growth compared to control (FIG. 74B and SI Appendix, FIG. 5-SIOA). These results confirmed the function of Alkbh5 in restricting the efficacy of immunotherapy and provide a rational for future combinatorial therapy by using an ALKBH5 inhibitor.

Discussion

A major challenge facing the future of ICB for cancer is to understand the mechanisms of resistance to ICB and to develop combination therapies that enhance antitumor immunity and durable responses. Using the poorly immunogenic B16 mouse model of melanoma, which is resistant to ICB, we discovered that genetic inactivation of the demethylases Alkbh5 and Fto in tumor cells rendered them more susceptible to anti-PD-1/GVAX therapy. The possibility that a similar approach could be employed for clinical applications is supported by the finding that Alkbh5 and Fto KO mice are viable[7, 8]. This contrasts with mGA methyltransferases, which are known to be essential for embryonic development and stem cell differentiation[50, 51]. Notably, a recent study showed that anti-PD-1 blockade responses were enhanced in FTO knockdown tumors 21. We also observed a similar trend with FPO—KO tumors during PD-1 Ab treatment, but it is not as robust as observed for Alkbh5-KO tumors (FIG. 69 and SI Appendix, FIG. 5-SI). Therefore, Alklbh5 has more obvious effects on PD-1 Ab treatment alone or combined with GVAX compared to Fto (FIG. 69). Besides, it seems that the role of FPO in cell proliferation dominates the effects of FTO for in vivo tumor growth from the published report[21], which we did not observe in our experiments (SI Appendix, FIG. 5-SI11). Overall, our data showed a more dramatic effects of Alkbh5 in regulating immunotherapy compared to Fto, and we further dissected the mechanisms of Alkbh5 in this process.

Tregs and MDSCs are the dominant immunosuppressive cell populations in antitumor immunity[27]. In our study, we found that both cell populations were reduced in Alkbh5-KO tumors during GVAX/anti-PD-1 therapy, whereas the abundance of DCs increased. A decrease in tumor infiltration of MDSCs and Tregs was also observed in a mouse model of 4T1 tumors in response to the plus AZA/ENT treatment[23]. Importantly, here we propose the link between m6A demethylase ALKBH5 and the altered tumor infiltrated lymphocytes composition during anti-PD-1/GVAX immunotherapy, providing a new target to regulate the mechanism of the TME and modulate of immunotherapy outcomes.

Our results showed that the function of Alkbh5 in regulating the TME and immunotherapy efficacy was not through the IFN—Y pathway, in accordance with the observation of unchanged infiltrated cytotoxic CDS T cell population in Alkbh5-deficient tumors. Instead, Alkbh5-KO increased the m6A density in its targets and decreased mRNA expression or enhanced percentage of exon splice-in ratios. For example, Mex3d and Mct4/Slc16a3 mRNA expression was reduced in Alkhb5-KO tumors compared with NTC tumors during GVAX/anti-PD-1 therapy. Mex3d is an RNA-binding protein with putative roles in RNA turnover[52], and Mct4/Slc16a3 is important for pH maintenance, lactate secretion, and nonoxidative glucose metabolism in cancer cells[53]. Reduced lactate concentration in the TME has been linked to impaired MDSC and Treg expansion and differentiation[46, 47] In this study, we found that Alkbh5 enzymatic activity is indispensable for regulating in vivo tumor growth during GVAX/anti-PD-1 therapy. Mct4/Slc16a3 was one of the major targets of Alkbh5 during this process. Alkbh5-KO B16 tumors displayed reductions in Mct4/Slc16a3 expression, lactate content in TIF, and MDSC and Treg abundance in the TME. Rescue experiments showed that Mct4/Slc16a3 was responsible for regulating lactate concentration and MDSC, Treg accumulation in Alkbh5-KO tumors during the GVAX/anti-PD-1 therapy. In addition, Mct4/Slc16a3 was reported to regulate VEGF expression in tumor cells[54]. We also observed a reduction in the TME level of Vegfa in Alkbh5-KO tumors (FIG. 72B and SI Appendix, FIG. 5-S6H).

Except for Mct4, we also analyzed several genes with altered PSI in the Mct4-expressing Alkbh5-KO cells. Gene splicing did not change in the rescue cells compared with Alkbh5-KO cells (FIG. 72J and SI Appendix, FIG. 5-S7 C-E); these results suggest that gene splicing may play a role independent of Mct4. Previous studies have shown that tumor-specific alternative splicing- derived neoepitopes were related to immunotherapy response[55]. We examined the gene-mutation profiles of several of those genes with altered PSI in melanoma patients, and indeed we found that these genes harbored the mutations that affected gene splicing in patients (SI Appendix, FIG. 5-S7F). The extract role and detailed mechanisms of gene splicing in Alkbh5-KO tumors during GVAX/anti-PD-1 therapy will need further investigations.

Figure 74C:
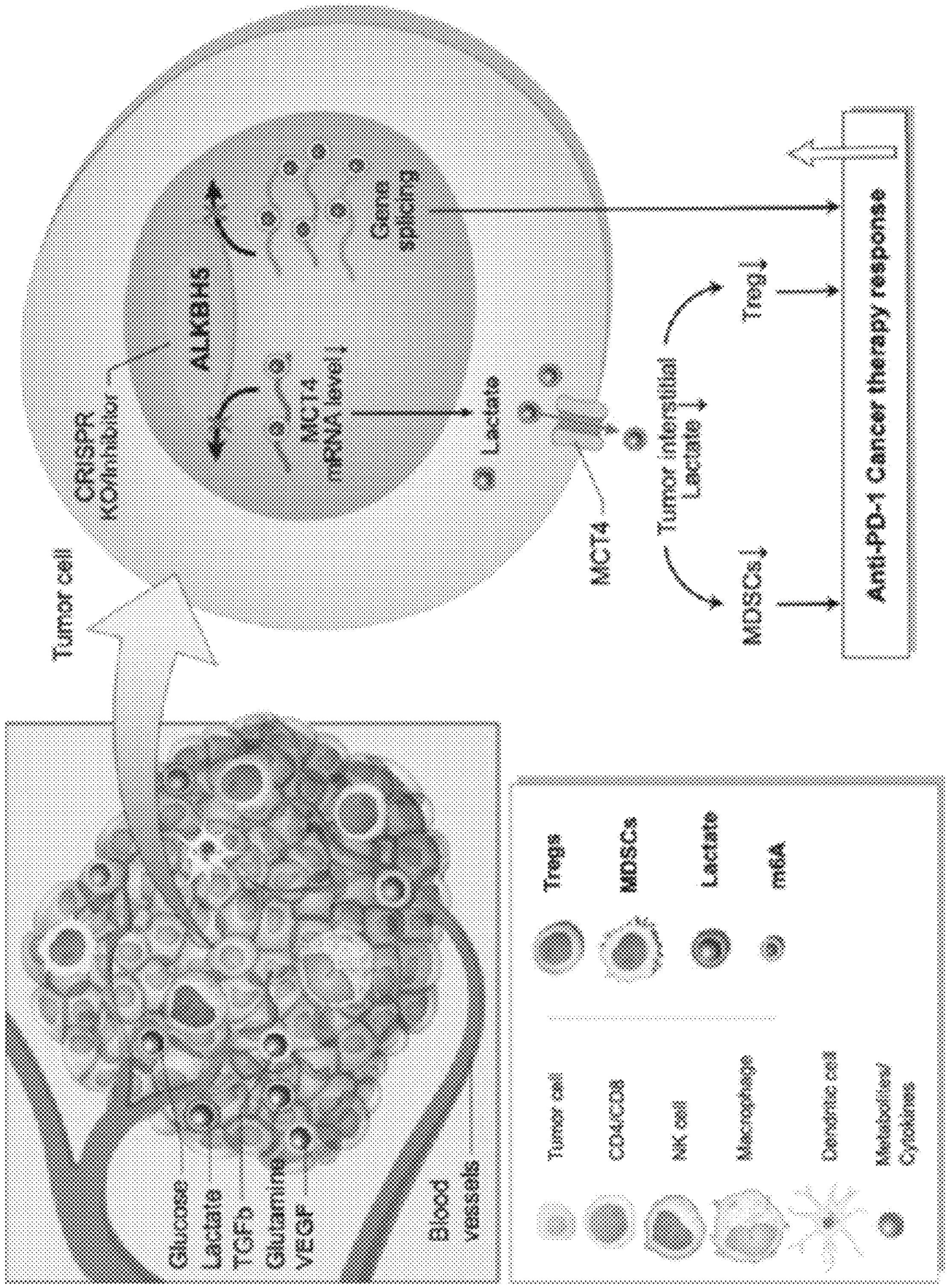
Figure 75:
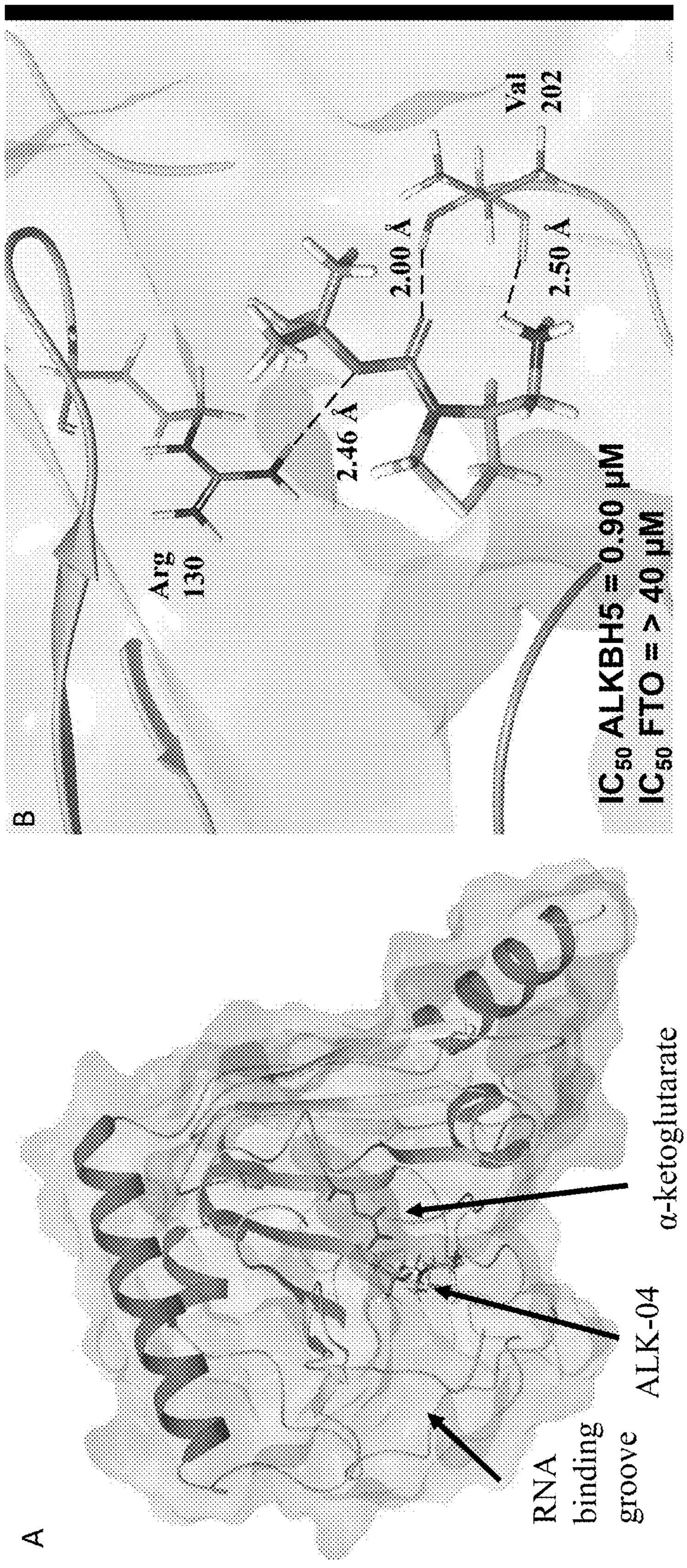
FIG. 75A-75B. Model figure for the docking site and the final pose for ALK-04.
Figure 76:
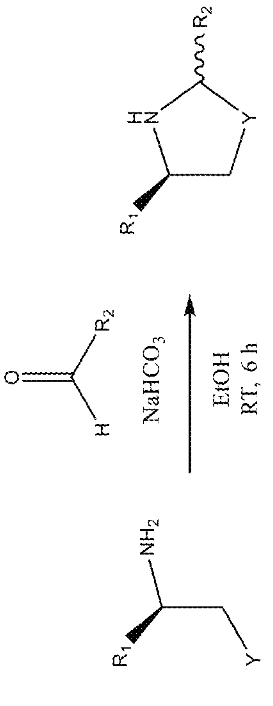
FIG. 76. Synthetic scheme for synthesis of ALK-11-ALK-30.
Figure 77:
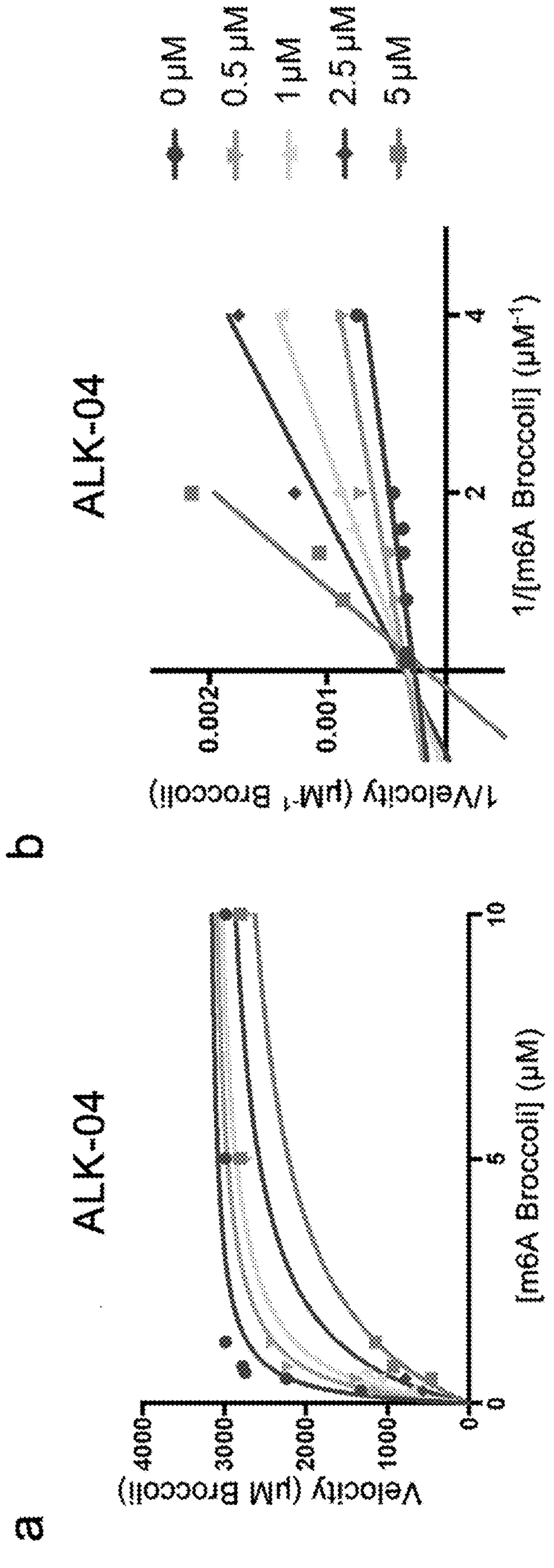
FIG. 77A-77B. Michaelis-Menten kinetics of ALK-04 against ALKBH5.
Figure 78:
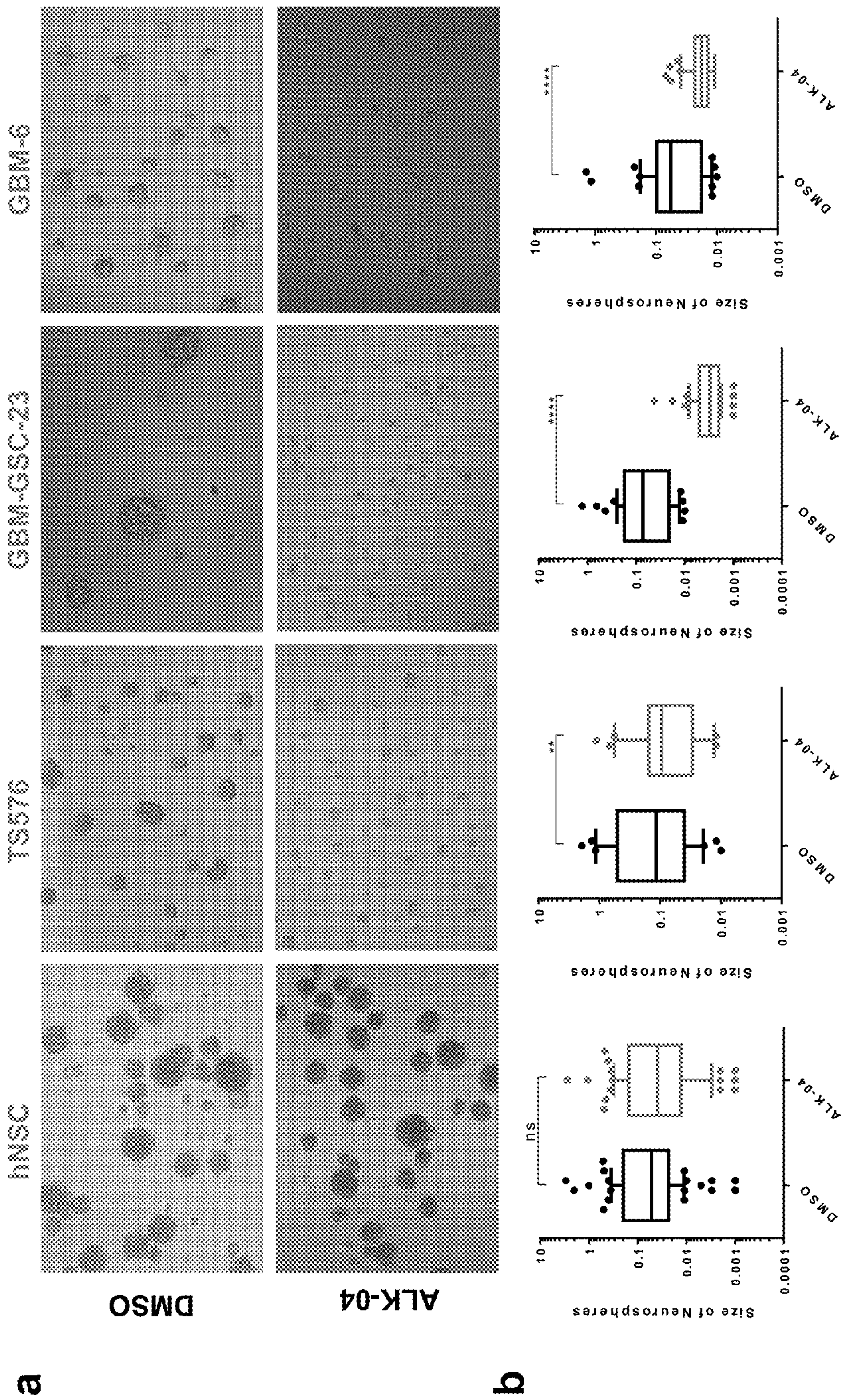
FIG. 78A-78B. Data illustrating inhibition of glioblastoma stem cell neurospheres.
Figure 79:
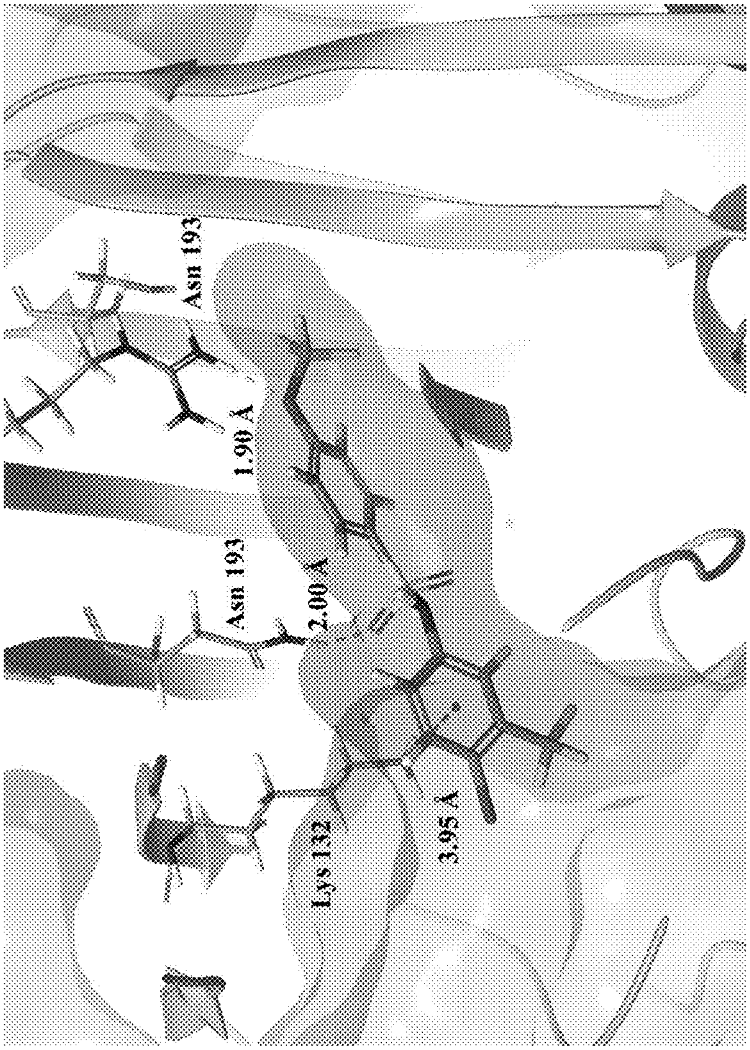
FIG. 79. TOC graphic showing scaffold hop from ALK-04 and representative hit TR-ALKBH5-29.
Figure 80:
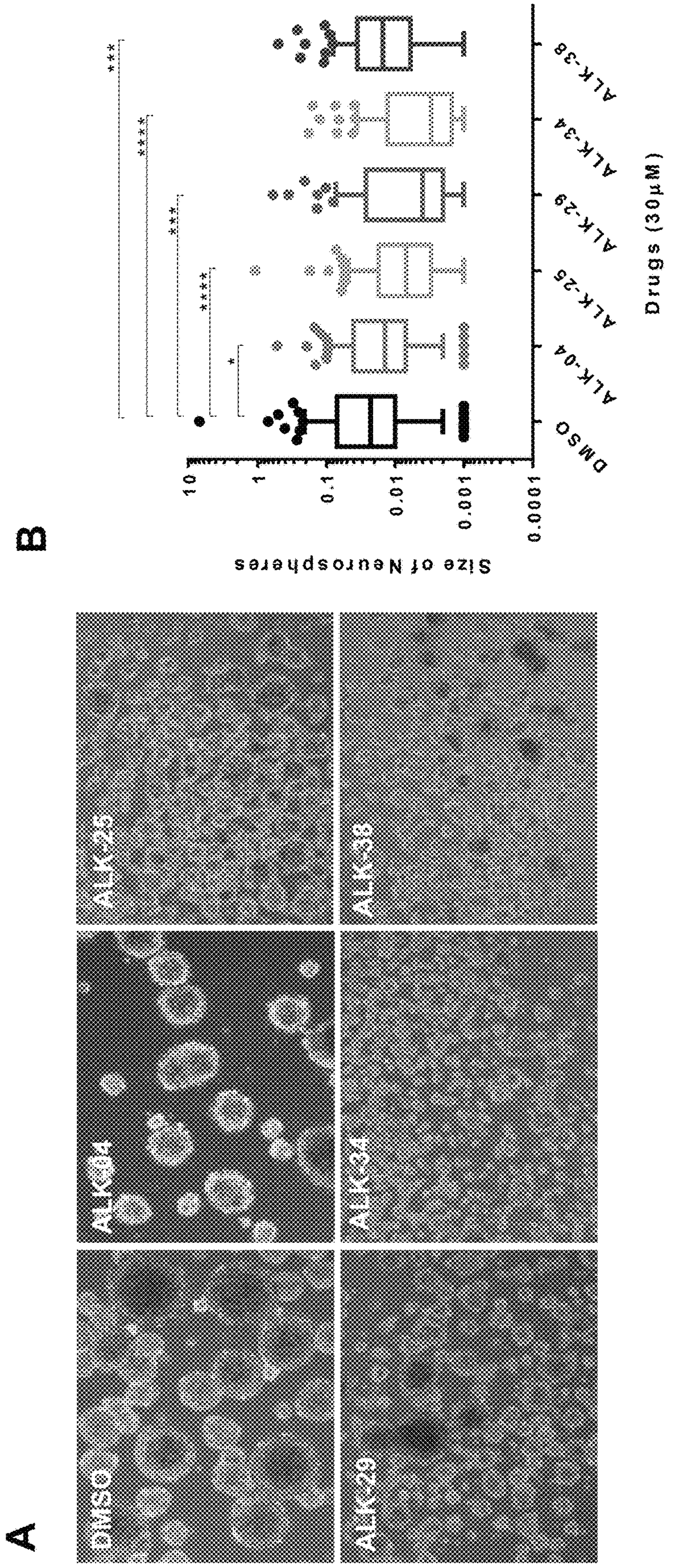
FIG. 80A-80B. Data showing effects of ALKBH5 inhibitors on size of neurosphere.
Figure 82:
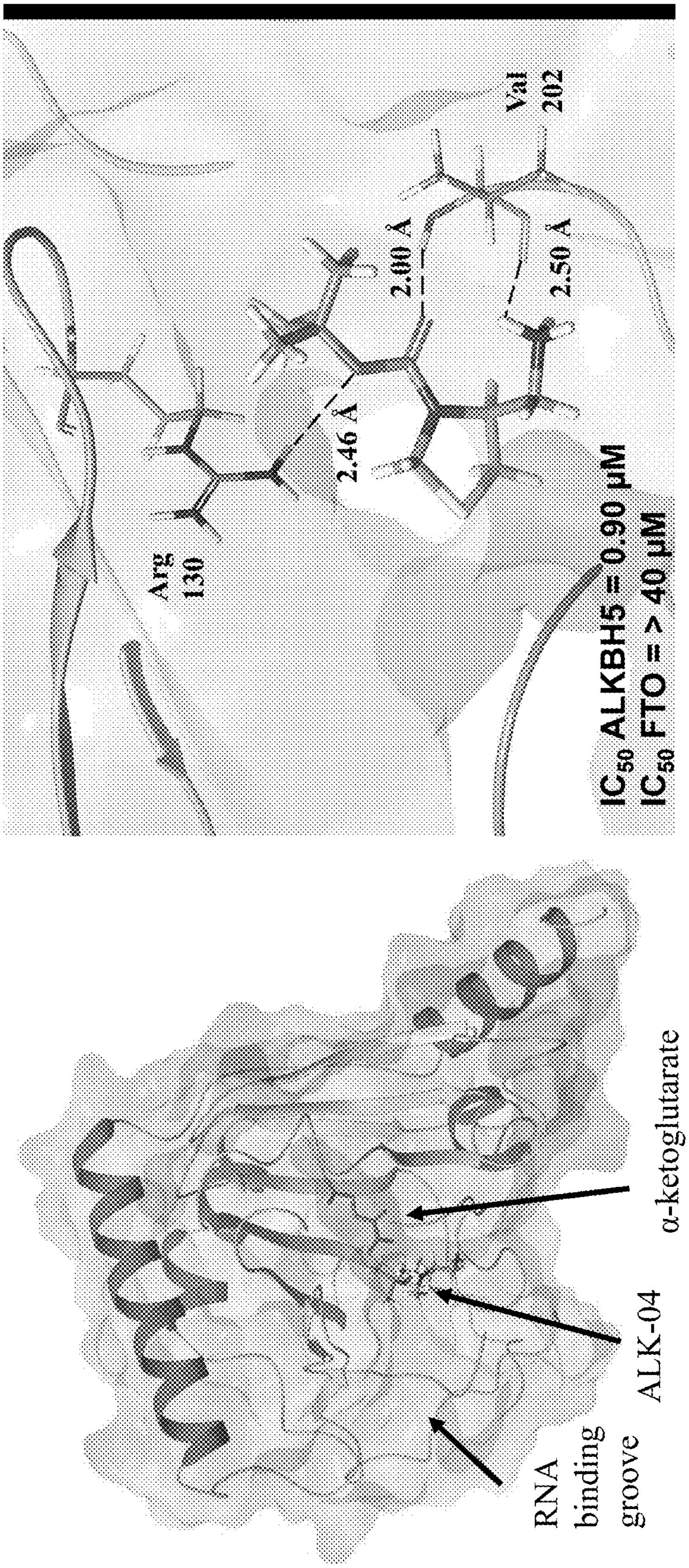
FIG. 82. Depiction of 3D structure.
Figure 85:
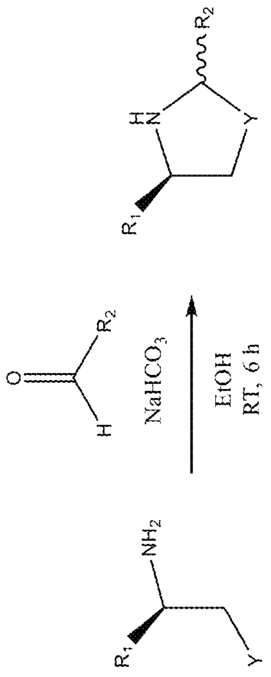
FIG. 85. Depiction of synthesis scheme or ALKBH5 thiazolidine library.
Figure 87:
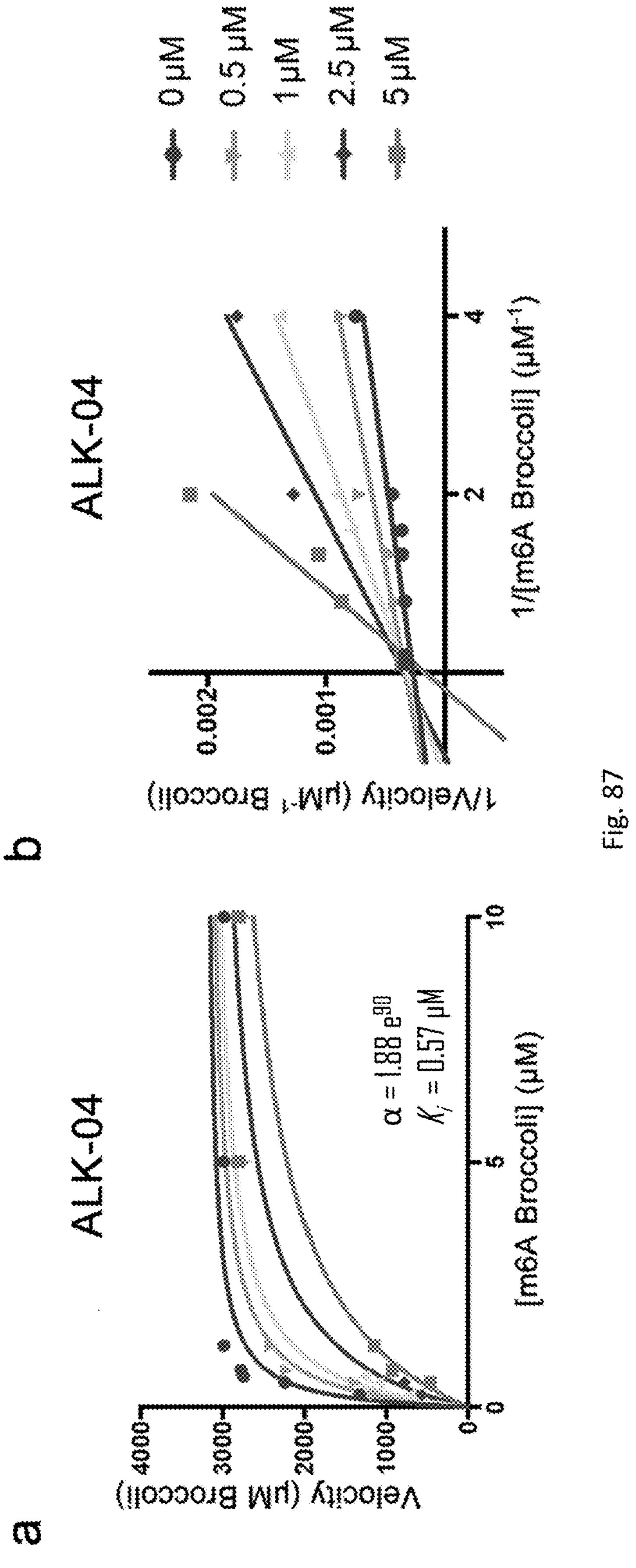
FIG. 87A-87B. Michaelis-Menten kinetics confirms ALK-04 is a competitive inhibitor of ALKBH5.
Figure 88:
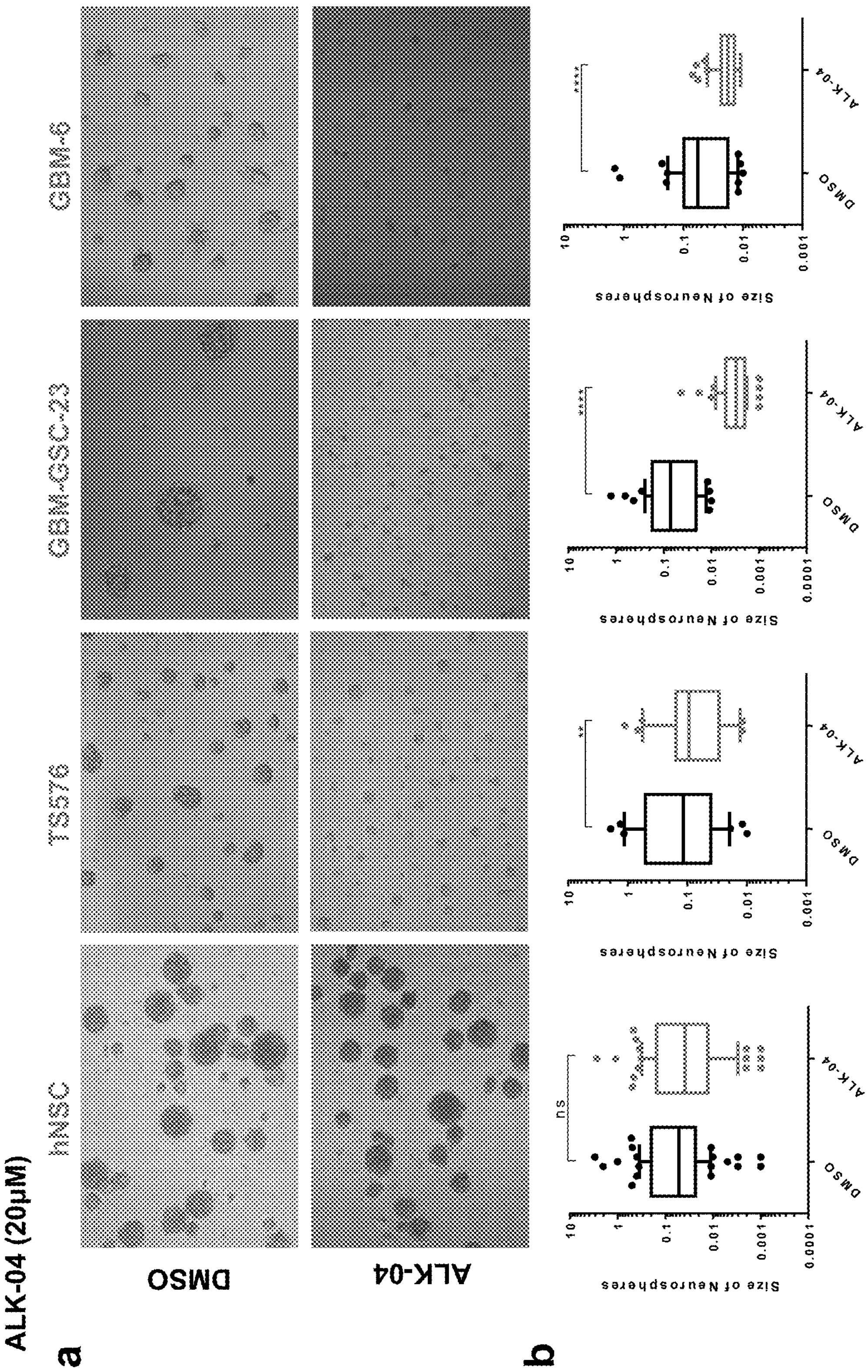
FIG. 88A-88B. Depiction of data from ALK-04 experiments.
Figure 91:
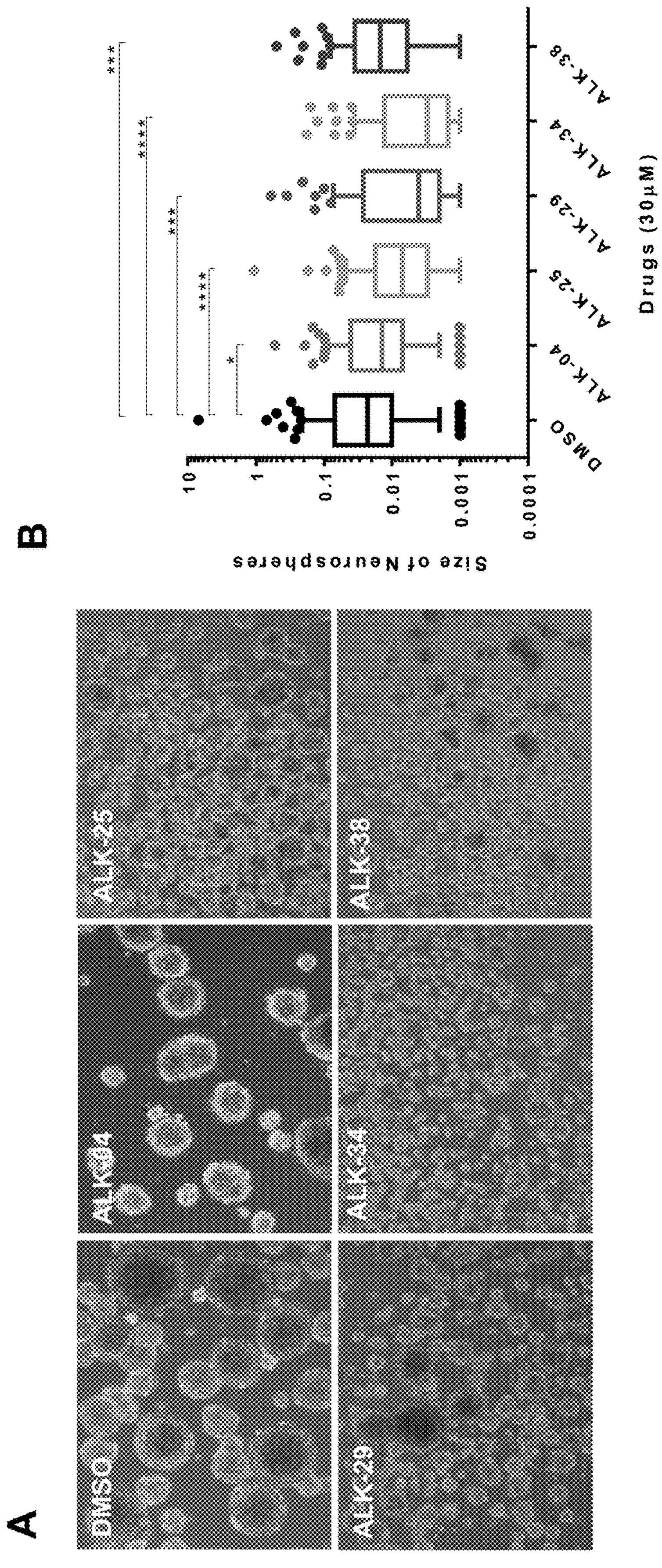
FIG. 91A-91B. Effects of ALKBH5 Inhibitors on size of neurosphere.
Figure 92:
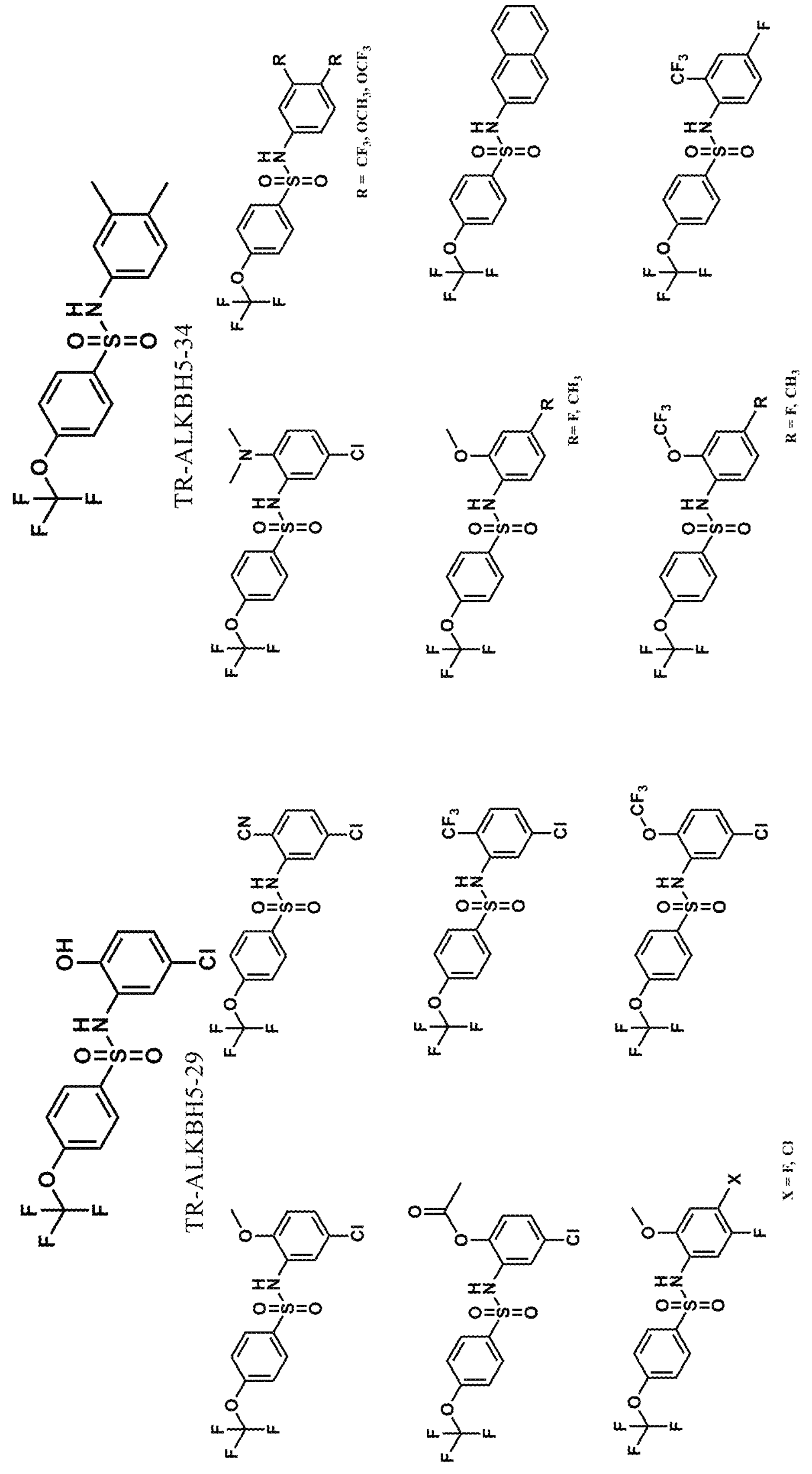
FIG. 92. Analogs of TR-ALKBH5-29 and 34.

In summary, we have uncovered a previously unknown function for tumor-expressed Alkbh5 in regulating metabolite/cytokine content and filtration of immune cells in the TME during GVAX/anti-PD-1 therapy. Alkbh5-mediated alterations in the density of m6A was found to regulate the splicing and expression of mRNAs with potential roles in the control of tumor growth (FIG. 74C). These findings highlight the importance of m6A demethylation in regulating the tumor response to immunotherapy and suggest that ALKBH5 could be a potential therapeutic target, alone or in combination with ICB, for cancer.

Materials and Methods

Tumor samples were obtained from a melanoma patient who had been treated with anti-PD-1 Ab. The procedures were approved by the University of California San Diego Institutional Review Board and the patient provided informed consent. Animal studies and procedures were approved by the University of California San Diego Institutional Animal Care and Use Committee. Details of materials regarding cell lines, mouse strains and human tumor specimens, antibodies, and reagents used for our study can be found in SI Appendix. Detailed methods of mouse models and treatments, CRISPR/Cas9-mediated generation of KO cell lines, flow cytometry analysis of tumor-infiltrating immune cells, qRT-PCR and RNA-seq, MeRIP-seq, MeRIP-seq data analysis, alternative splicing and splice junction analysis, scRNA-seq of human melanoma specimens, TIF isolation and analysis, IFN—Y stimulation of melanoma cells in vitro, cell proliferation assay, Western blot analysis, immunohistochemistry, and LC-MS/MS analysis of m6A RNA can also be found in SI Appendix.

REFERENCES

1. D. S. Chen, I. Mellman, Elements of cancer immunity and the cancer-immune set point. Nature 541, 321-330 (2017).
2. K. D. Meyer, S. R. Jaffrey, Rethinking m6A readers, writers, and erasers. Annu. Rev. Cell Dev. Biol. 33, 319-342 (2017).
3. H. Shi, J. Wei, C. He., Where, when, and how: Context-dependent functions of RNA methylation writers, readers, and erasers. Mol. Cell 74, 640-650 (2019).
4. K. D. Meyer et al., Comprehensive analysis of mRNA methylation reveals enrichment in 3' UTRs and near stop codons. Cell 149, 1635-1646 (2012).
5. D. Dominissini et al., Topology of the human and mouse m6A RNA methylomes revealed by m6A-seq. Nature 485, 201-206 (2012).
6. S. Schwartz et al., Perturbation of m6A writers reveals two distinct classes of mRNA methylation at internal and 5' sites. Cell Rep. 8, 284-296 (2014).
7. G. Jia et al., N6-methyladenosine in nuclear RNA is a major substrate of the obesity associated FTO. Nat. Chem. Biol. 7, 885-887 (2011).

8. G. Zheng et al., ALKBH5 is a mammalian RNA demethylase that impacts RNA metabolism and mouse fertility. Mol. Cell 49, 18-29 (2013).
9. J. Mauer et al., Reversible methylation of m6 Am in the 5' cap controls mRNA stability. Nature 541, 371-375 (2017).
10. J. Mauer et al.; FTO controls reversible m6 Am RNA methylation during snRNA biogenesis. Nat. Chem. Biol. 15, 340-347 (2019).
11. D. P. Patil, B. F. Pickering, S. R. Jaffrey, Reading m6A in the transcriptome: m6 A-Binding proteins. Trends Cell Biol. 28, 113-127 (2018).
12. X. Wang, C. He, Reading RNA methylation codes through methyl-specific binding proteins. RNA Biol. 11, 669-672 (2014).
13. Y. Yang, P. J. Hsu, Y. S. Chen, Y. G. Yang, Dynamic transcriptomic m6A decoration: Writers, erasers, readers and functions in RNA metabolism. Cell Res. 28, 616-624 (2018).
14. H. B. Li et al., m6A mRNA methylation controls T cell homeostasis by targeting the IL7/STAT5/SOCS pathways. Nature 548, 338-342 (2017).
15. S. R. Gonzales-van Horn, P. Sarnow, Making the mark: The role of adenosine modifications in the life cycle of RNA viruses. Cell Host Microbe 21, 661-669 (2017).
16. I. Barbieri et al., Promoter-bound METTL3 maintains myeloid leukaemia by m6A-dependent translation control. Nature 552, 126-131 (2017).
17. D. Han et al., Anti-tumour immunity controlled through mRNA m6A methylation and YTHDF1 in dendritic cells. Nature 566, 270-274 (2019).
18. J. Paris et al., Targeting the RNA m6A reader YTHDF2 selectively compromises cancer stem cells in acute myeloid leukemia. Cell Stem Cell 25, 137-148.e6 (2019).
19. R. Su et al., R-2HG exhibits anti-tumor activity by targeting FTO/m6 A/MYC/CEBPA signaling. Cell 172, 90-105.e23 (2018).
20. L. P. Vu et al., The N6-methyladenosine (m6A)-forming enzyme METTL3 controls myeloid differentiation of normal hematopoietic and leukemia cells. Nat. Med. 23, 1369-1376 (2017).
21. S. Yang et al., m6A mRNA demethylase FTO regulates melanoma tumorigenicity and response to anti-PD-1 blockade. Nat. Commun. 10, 2782 (2019).
22. R. T. Manguso et al., In vivo CRISPR screening identifies Ptpn2 as a cancer immunotherapy target. Nature 547, 413-418 (2017).
23. K. Kim et al., Eradication of metastatic mouse cancers resistant to immune checkpoint blockade by suppression of myeloid-derived cells. Proc. Natl. Acad. Sci. U.S.A. 111, 11774-11779 (2014).
24. T. H. Corbett, D. P. Griswold Jr., B. J. Roberts, J. C. Peckham, F. M. Schabel Jr., Tumor induction relationships in development of transplantable cancers of the colon in mice for chemotherapy assays, with a note on carcinogen structure. Cancer Res. 35, 2434-2439 (1975).
25. L. P. Belnap, P. H. Cleveland, M. E. Colmerauer, R. M. Barone, Y. H. Pilch, Immunogenicity of chemically induced murine colon cancers. Cancer Res. 39, 1174-1179 (1979).
26. G. Dranoff, GM-CSF-secreting melanoma vaccines. Oncogene 22, 3188-3192 (2003).
27. T. Fujimura, Y. Kambayashi, S. Aiba, Crosstalk between regulatory T cells (Tregs) and myeloid derived suppressor cells (MDSCs) during melanoma growth. OncoImmunology 1, 1433-1434 (2012).
28. Y. Y. Setiady, J. A. Coccia, P. U. Park, In vivo depletion of CD4+FOXP3+ Treg cells by the PC61 anti-CD25 monoclonal antibody is mediated by FcgammaRIII+ phagocytes. Eur. J. Immunol. 40, 780-786 (2010).
29. F. Arce Vargas et al.; Melanoma TRACERx Consortium; Renal TRACERx Consortium; Lung TRACERx Consortium, Fc-optimized anti-CD25 depletes tumor-infiltrating regulatory T cells and synergizes with PD-1 blockade to eradicate established tumors. Immunity 46, 577-586 (2017).
30. W. Hugo et al., Genomic and transcriptomic features of response to anti-PD-1 therapy in metastatic melanoma. Cell 165, 35-44 (2016).
31. H. Weng et al., METTL14 inhibits hematopoietic stem/progenitor differentiation and promotes leukemogenesis via mRNA m6A modification. Cell Stem Cell 22, 191-205.e9 (2018).
32. B. Linder et al., Single-nucleotide-resolution mapping of m6A and m6Am throughout the transcriptome. Nat. Methods 12, 767-772 (2015).
33. G. Lichinchi, T. M. Rana, Profiling of N6-methyladenosine in zika virus RNA and host cellular mRNA. Methods Mol. Biol. 1870, 209-218 (2019).
34. G. Lichinchi et al., Dynamics of human and viral RNA methylation during zika virus infection. Cell Host Microbe 20, 666-673 (2016).
35. G. Lichinchi et al., Dynamics of the human and viral m(6)A RNA methylomes during HIV-1 infection of T cells. Nat. Microbiol. 1, 16011 (2016).
36. A. Louloupi, E. Ntini, T. Conrad, U. A. V. Orom, Transient N-6-Methyladenosine transcriptome sequencing reveals a regulatory role of m6A in splicing efficiency. Cell Rep. 23, 3429-3437 (2018).
37. S. Ke et al., m6A mRNA modifications are deposited in nascent pre-mRNA and are not required for splicing but do specify cytoplasmic turnover. Genes Dev. 31, 990-1006 (2017).
38. C. Tang et al., ALKBH5-dependent m6A demethylation controls splicing and stability of long 3'-UTR mRNAs in male germ cells. Proc. Natl. Acad. Sci. U.S.A. 115, E325-E333 (2018).
39. T. Condamine, I. Ramachandran, J. I. Youn, D. I. Gabrilovich, Regulation of tumor metastasis by myeloid-derived suppressor cells. Annu. Rev. Med. 66, 97-1110 (2015).
40. A. Matsumura et al., HGF regulates VEGF expression via the c-Met receptor downstream pathways, PI3K/Akt, MAPK and STAT3, in CT26 murine cells. Int. J. Oncol. 42, 535-542 (2013).
41. G. Neufeld, A. D. Sabag, N. Rabinovicz, O. Kessler, Semaphorins in angiogenesis and tumor progression. Cold Spring Harb. Perspect. Med. 2, a006718 (2012).
42. G. Villain et al., miR-126-5p promotes retinal endothelial cell survival through SetD5 regulation in neurons. Development 145, dev156232 (2018).
43. Y. Kotani et al., Alternative exon skipping biases substrate preference of the deubiquitylase USP15 for mysterin/RNF213, the moyamoya disease susceptibility factor. Sci. Rep. 7, 44293 (2017).
44. S. Pilotto et al., MET exon 14 juxtamembrane splicing mutations: Clinical and therapeutical perspectives for cancer therapy. Ann. Transl. Med. 5, 2 (2017).
45. M. Wagner, H. Wiig, Tumor interstitial fluid formation, characterization, and clinical implications. Front. Oncol. 5, 115 (2015).

46. Z. Husain, P. Seth, V. P. Sukhatme, Tumor-derived lactate and myeloid-derived suppressor cells: Linking metabolism to cancer immunology. OncoImmunology 2, e26383 (2013).
47. A. Angelin et al., Foxp3 reprograms T cell metabolism to function in low-glucose, high-lactate environments. Cell Metab. 25, 1282-1293.e7 (2017).
48. C. Feng et al., Crystal structures of the human RNA demethylase Alkbh5 reveal basis for substrate recognition. J. Biol. Chem. 289, 11571-11583 (2014).
49. D. Pan et al., A major chromatin regulator determines resistance of tumor cells to T cell-mediated killing. Science 359, 770-775 (2018).
50. S. Geula et al., Stem cells. m6A mRNA methylation facilitates resolution of naïve pluripotency toward differentiation. Science 347, 1002-1006 (2015).
51. T. G. Meng et al., Mettl14 is required for mouse postimplantation development by facilitating epiblast maturation. FASEB J. 33, 1179-1187 (2019).
52. K. Buchet-Poyau et al., Identification and characterization of human Mex-3 proteins, a novel family of evolutionarily conserved RNA-binding proteins differentially localized to processing bodies. Nucleic Acids Res. 35, 1289-1300 (2007).
53. F. Baenke et al., Functional screening identifies MCT4 as a key regulator of breast cancer cell metabolism and survival. J. Pathol. 237, 152-165 (2015).
54. Q. Sun, L. L. Hu, Q. Fu, MCT4 promotes cell proliferation and invasion of castrationresistant prostate cancer PC-3 cell line. EXCLI J. 18, 187-194 (2019).
55. L. Frankiw, D. Baltimore, G. Li, Alternative mRNA splicing in cancer immunotherapy. Nat. Rev. Immunol. 19, 675-687 (2019).

Additional embodiments of Example B5 include those disclosed in *PNAS* 2020 117 (33) 20159-20170 (https://doi.org/10.1073/pnas.1918986117) (Reference 56), which is incorporated herein by reference in its entirety (inclusive of the SI appendix).

In Example B5, references to the SI Appendix refers to that of PNAS 2020 117 (33) 20159-20170 (https://doi.org/10.1073/pnas.1918986117) (Reference 56). Figures in the SI Appendix of Reference 56 are referenced as FIG. 5-[X] herein, wherein [X] denotes figure number in the SI Appendix of Reference 56. For example, "SI Appendix, FIG. 5-S1AB" as used herein refers to FIGS. S1 A and B in the SI Appendix of Reference 56. As another example, "SI Appendix, FIG. 5-S7F" refers to FIG. S7F in the SI Appendix of Reference 56.

Also see FIGS. 82 through 92 for additional information.

Example B6: M6A RNA Methyltransferases METTL3/14 Regulate Immune Responses to Anti-PD-1 Therapy Abstract An impressive clinical success has been observed in treating a variety of cancers using immunotherapy with programmed cell death-1 (PD-1) checkpoint blockade. However, limited response in most patients treated with anti-PD-1 antibodies remains a challenge, requiring better understanding of molecular mechanisms limiting immunotherapy. In colorectal cancer (CRC) resistant to immunotherapy, mismatch-repair-proficient or microsatellite instability-low (pMMR-MSI-L) tumors have low mutation burden and constitute ~85% of patients. Here, we show that inhibition of N6-methyladenosine (m6A) mRNA modification by depletion of methyltransferases, Mettl3 and Mettl14, enhanced response to anti-PD-1 treatment in pMMR-MSI-L CRC and melanoma. Mettl3- or Mettl14-deficient tumors increased cytotoxic tumor-infiltrating CD8+ T cells and elevated secretion of IFN-γ, Cxcl9, and Cxcl10 in tumor microenvironment in vivo. Mechanistically, Mettl3 or Mettl14 loss promoted IFN-γ-Stat1-Irf1 signaling through stabilizing the Stat1 and Irf1 mRNA via Ythdf2. Finally, we found a negative correlation between METTL3 or METTL14 and STAT1 in 59 patients with pMMR-MSI-L CRC tumors. Altogether, our findings uncover a new awareness of the function of RNA methylation in adaptive immunity and provide METTL3 and METTL14 as potential therapeutic targets in anticancer immunotherapy.

Introduction

Immunotherapy has become one of the unprecedented treatment modalities for multiple cancers by targeting the interactions between tumor and immune system (Ribas & Wolchok, 2018). The immune system discriminates exogeneous cells from self through the recognition of the major histocompatibility complex (MHC) complex-peptides presented on target cells, e.g., tumor cell, and T cell receptors (TCR) on immune cells (Schreiber et al, 2011; Khalil et al, 2016), whereas this recognition alone is not sufficient for initiation of the immune response. Other regulatory circuits also play important roles to co-inhibit or co-activate immune cells, the former role is typically exploited by cancer cells to evade immunosurveillance (Townsend & Allison, 1993; Sharma & Allison, 2015; Wei et al, 2018b). Among these negative regulatory pathways, PD-1 (programmed cell death-1) and CTLA-4 (cytotoxic T-lymphocyte protein 4) have been targeted by immune checkpoint inhibitors (ICIs) to enhance tumor cell killing by T cells in immunotherapy (Jenkins et al, 2018). Tumors with mutated genome are likely to generate peptide neoantigen to recruit and activate immune cells via MHC complex-TCR recognition in immunotherapy to induce durable response (Samstein et al, 2019). Although impressive success has been observed in the clinical practice of ICIs for tumors with high mutation burden, such as non-small cell lung cancer (NSCLC) and melanoma, while the failure of response or elapse in low-mutation-burden cancer patients treated with ICIs remains common (Alexandrov et al, 2013; Sharma et al, 2017; Ganesh et al, 2019). In addition to mutational load, a number of other useful biomarkers for ICI responses have been identified including interferon signatures (Ayers et al, 2017), checkpoint ligand expression, and inflammation in tumor microenvironments (Kowanetz et al, 2018).

Mismatch-repair deficiency or high level of microsatellite instability (dMMR-MSI-H) in tumors has emerged as an effective biomarker to predict solid tumor responses to ICIs (Le et al, 2017; Mandal et al, 2019). dMMR-MSI-H tumors possess microsatellite instability (MSI) leading to genetic hypermutability and accumulation of thousands of mutations. These studies are exciting and provide a proof of concept that reliable biomarkers could provide important criteria for patient stratification for ICI therapies. However, mismatch-repair-proficient or microsatellite instability-low (pMMR-MSI-L) tumors have low mutation burden and constitute ~85% of CRC patients (Ganesh et al, 2019). Apart from the status of mutation burden, lack of response or being resistant to ICIs also involves the alternations of molecular mechanisms in both cancer and immune system as well as their interface (Sharma et al, 2017). Within these alternations, the abnormality of T cells, the absence of antigen presentation, and the aberrant oncogenic signaling were revealed by recent studies (Sharma et al, 2017). Therefore, new mechanisms governing the response and resistance to ICIs therapy need to be discovered. In addition, mechanism-driven biomarkers should be identified for guiding cancer immunotherapy for pMMR-MSI-L tumors in CRC.

N6-methyladenosine (m6A) is the most abundant chemical modification in mRNA and lncRNA in eukaryotes (Dominissini et al, 2012; Meyer et al, 2012; Yue et al, 2015; Meyer & Jaffrey, 2017). In mammalian cells, this epitranscriptomic mark is installed by methyltransferase machinery comprising a METTL3-METTL14 core and other subunits (Liu et al, 2014; Ping et al, 2014). The reversal of this modification is mediated by the alpha-ketoglutarate-dependent dioxygenases FTO and ALKBH5 (Jia et al, 2011; Zheng et al, 2013). Dynamics of RNA methylation influences a broad range of physiological processes including RNA metabolism and protein translation mainly through the readout of YTH family m6A binding proteins (Wang et al, 2014, 2015; Xiao et al, 2016; Hsu et al, 2017; Li et al, 2017; Nachtergaele & He, 2018). Aberrant m6A RNA methylation is associated with various diseases including cancer (Deng et al, 2018; Wu et al, 2019). Recently, studies have started to provide emerging roles of RNA methylation and its machinery in tumor initiation, differentiation, and progression (Jaffrey & Kharas, 2017; Liu et al, 2019). Moreover, elevation of RNA methylation affects both immune response and melanoma cell sensitivity within anticancer immunotherapy (Han et al, 2019; Yang et al, 2019). Despite this discovery, suppression of m6A had also been observed in the tumorigenesis (Deng et al, 2018). Recently, depletion of ALKBH5 in sensitizing tumors to cancer immunotherapy has been described where ALKBH5 modulates target gene expression and splicing, leading to changes in lactate content of the tumor microenvironment, which regulates the composition of tumor-infiltrating Treg and myeloid-derived suppressor cells (Li et al, 2020). Remarkably, a small-molecule inhibitor of ALKBH5 enhanced the efficacy of cancer immunotherapy (Li et al, 2020). The complex and varied roles of m6A in tumors suggest that much needs to be done to further understand the importance and dynamic of this modification in cancer biology and its clinical application. Besides, apart from total mutation burden, whether RNA methylation pathway involves the insensitivity of refractory cancer in immunotherapy remains unknown.

Here, we present that the disruption of m6A methyltransferases enhanced immunotherapy response in pMMR-MSI-L colorectal cancer through modulating the intratumor microenvironment and tumor-infiltrating cells. Mechanistically, depletion of Mettl3 or Mettl14 enhanced IFN-γ-Stat1-Irf1 signaling through stabilizing the Stat1 and Irf1 mRNA mediated by Ythdf2. Our findings uncovered, a previously unrecognized, mechanism of mRNA methylation in sensitizing pMMR-MSI-L colorectal cancer to PD-1 blockade, thereby providing potential new biomarkers and a therapeutic avenue for this malignant disease refractory to ICIs treatment.

Results

Loss of Mettl3 or Mettl14 Sensitizes Colorectal Carcinoma and Melanoma Tumors to Anti-PD-1 Treatment.

Figure 93A:
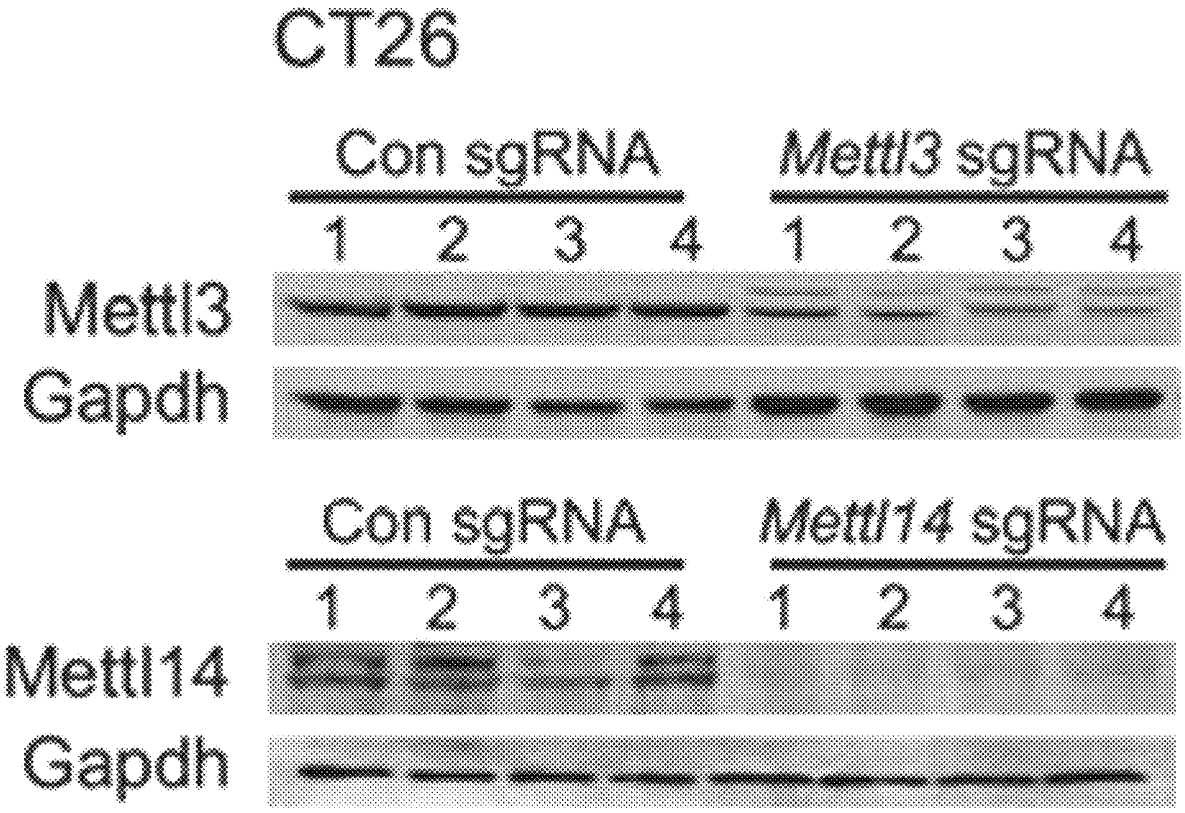
FIG. 93A-93F. Depiction of data showing that depletion of Mettl3 or Mettl14 sensitizes CT26 and B16 tumors to immunotherapy.
Figure 93B:
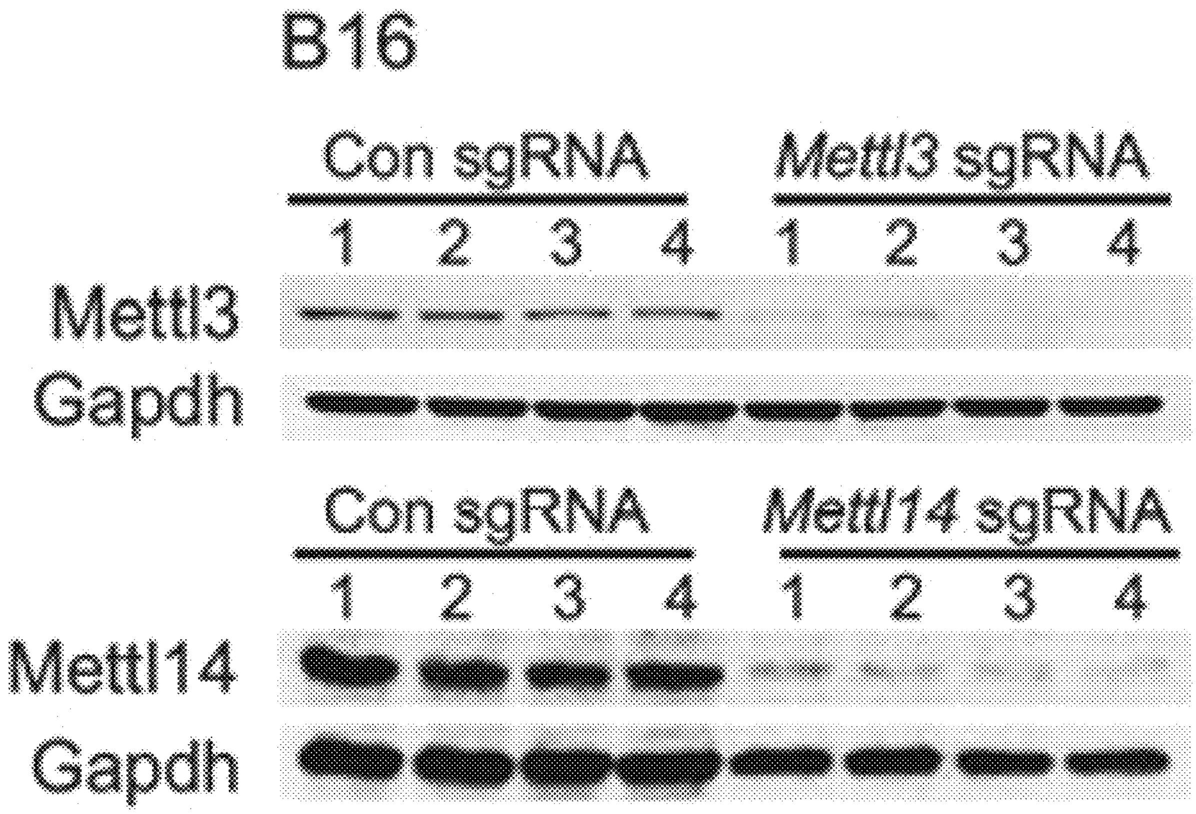
Figure 93C:
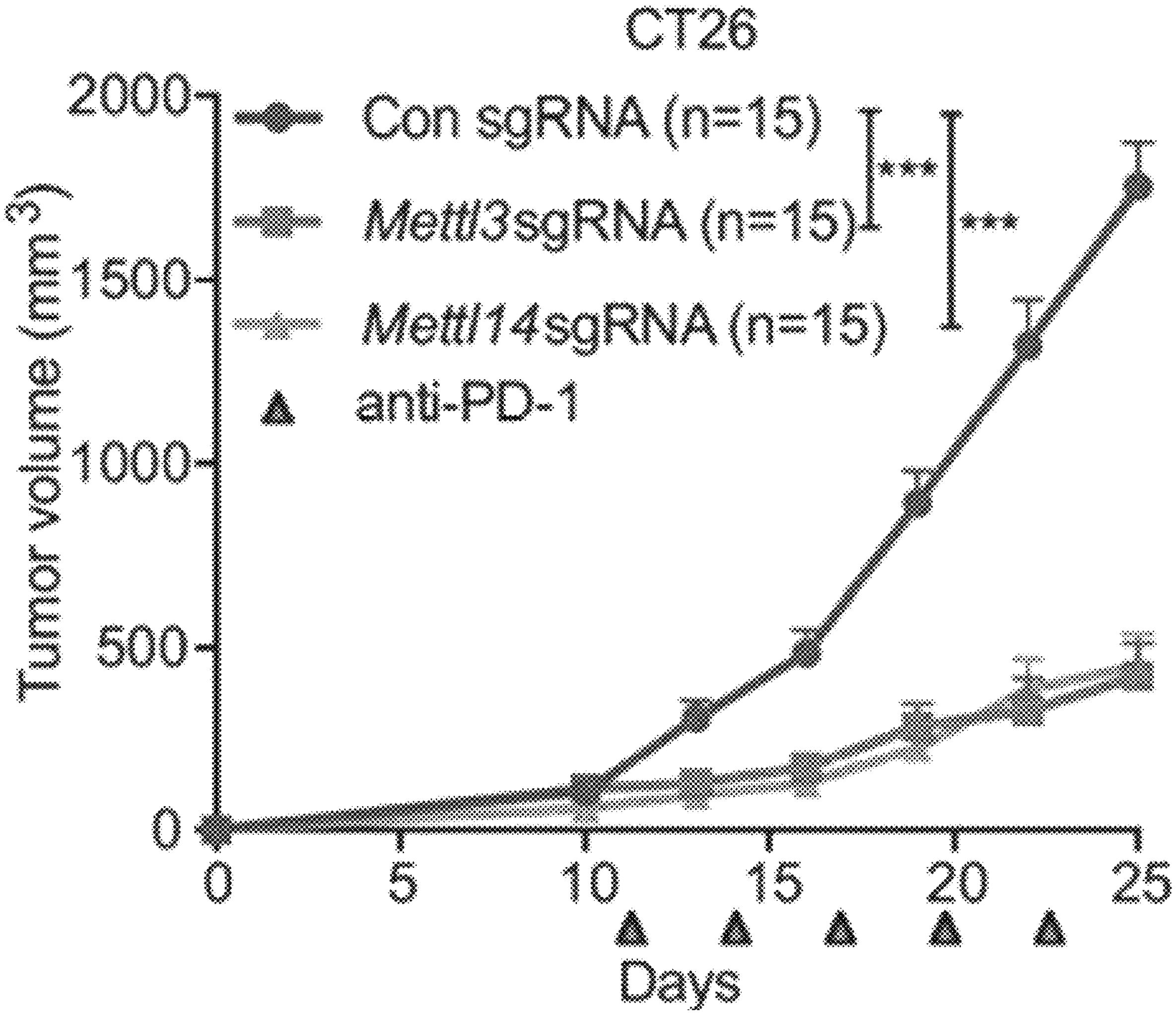
Figure 93D:
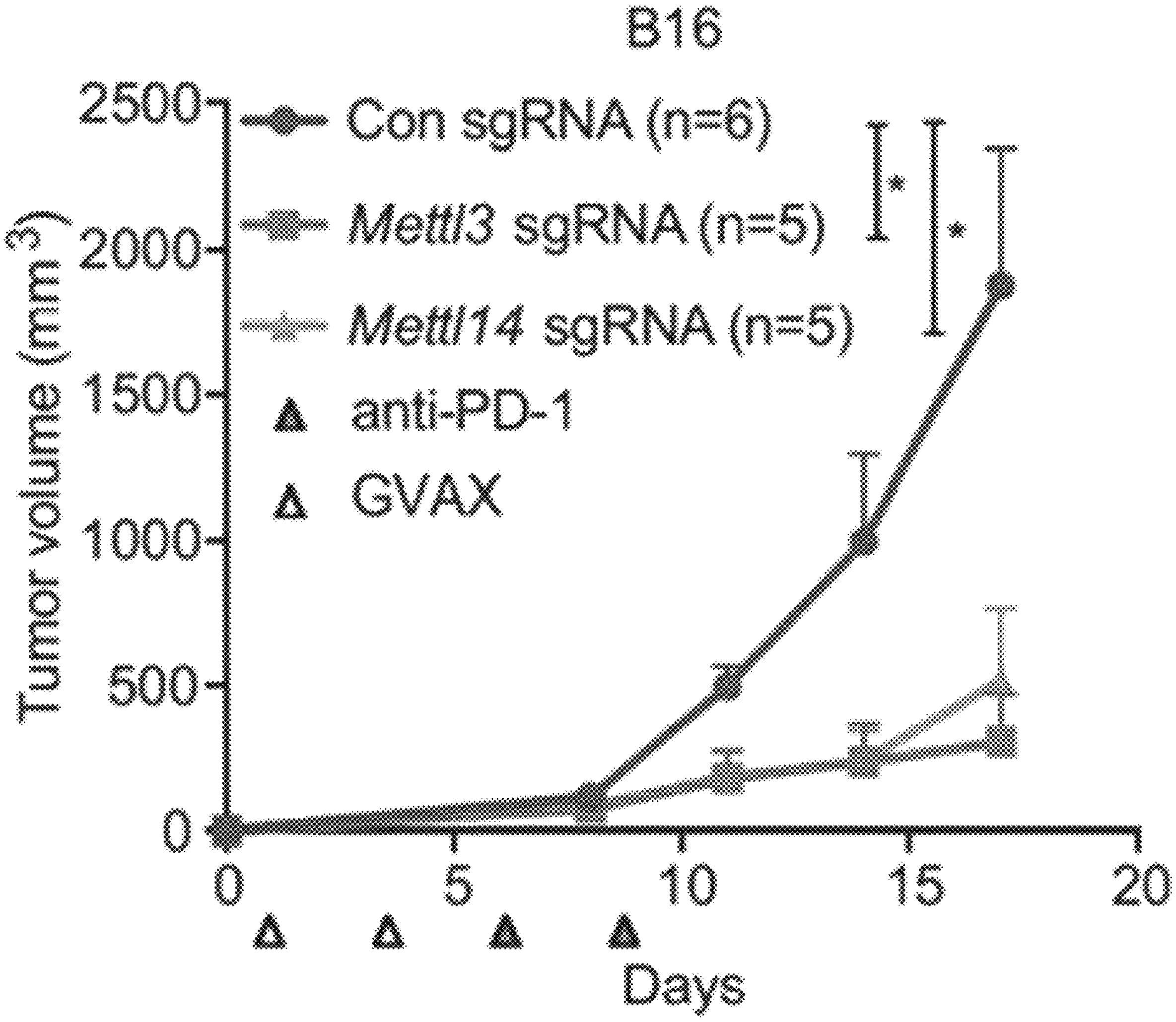
Figure 93E:
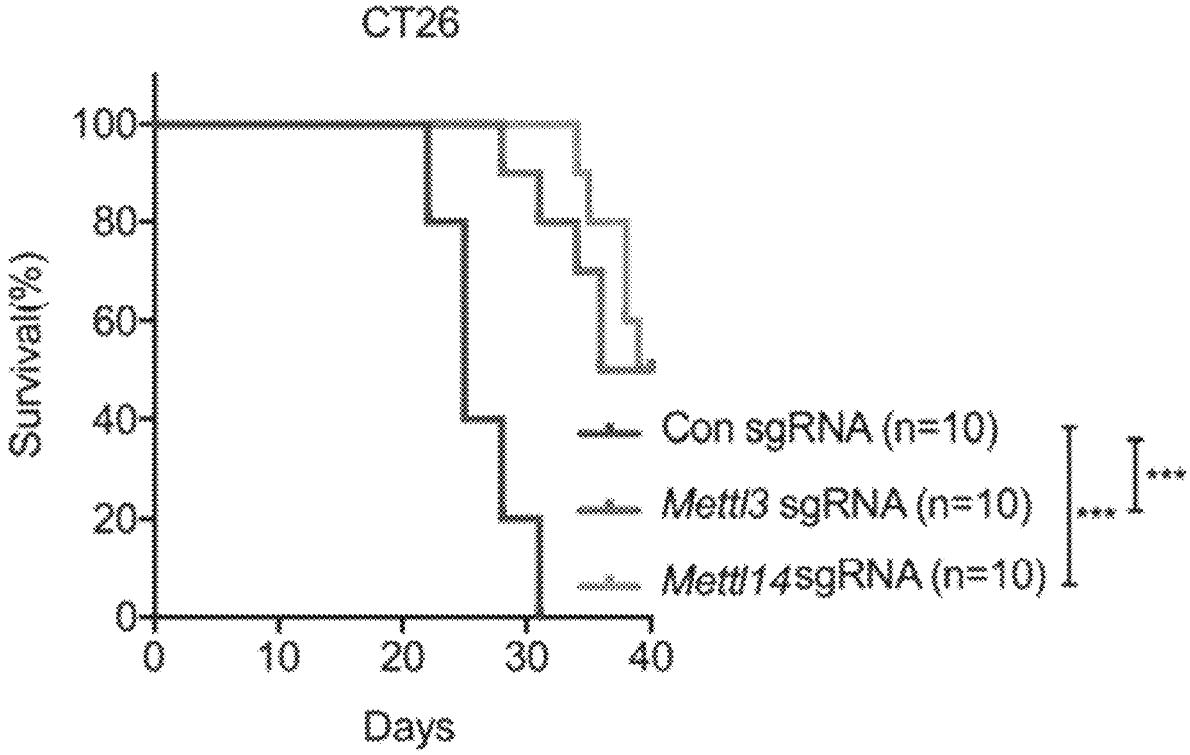
Figure 93F:
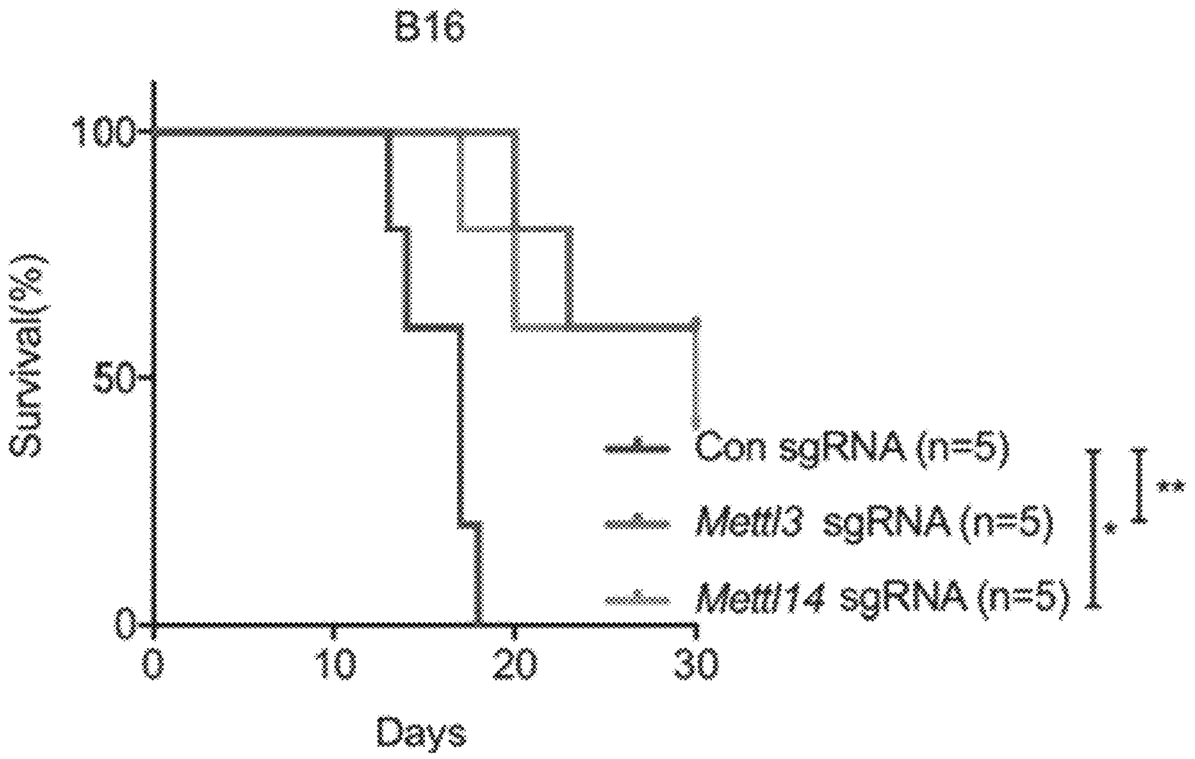
Figure 98A:
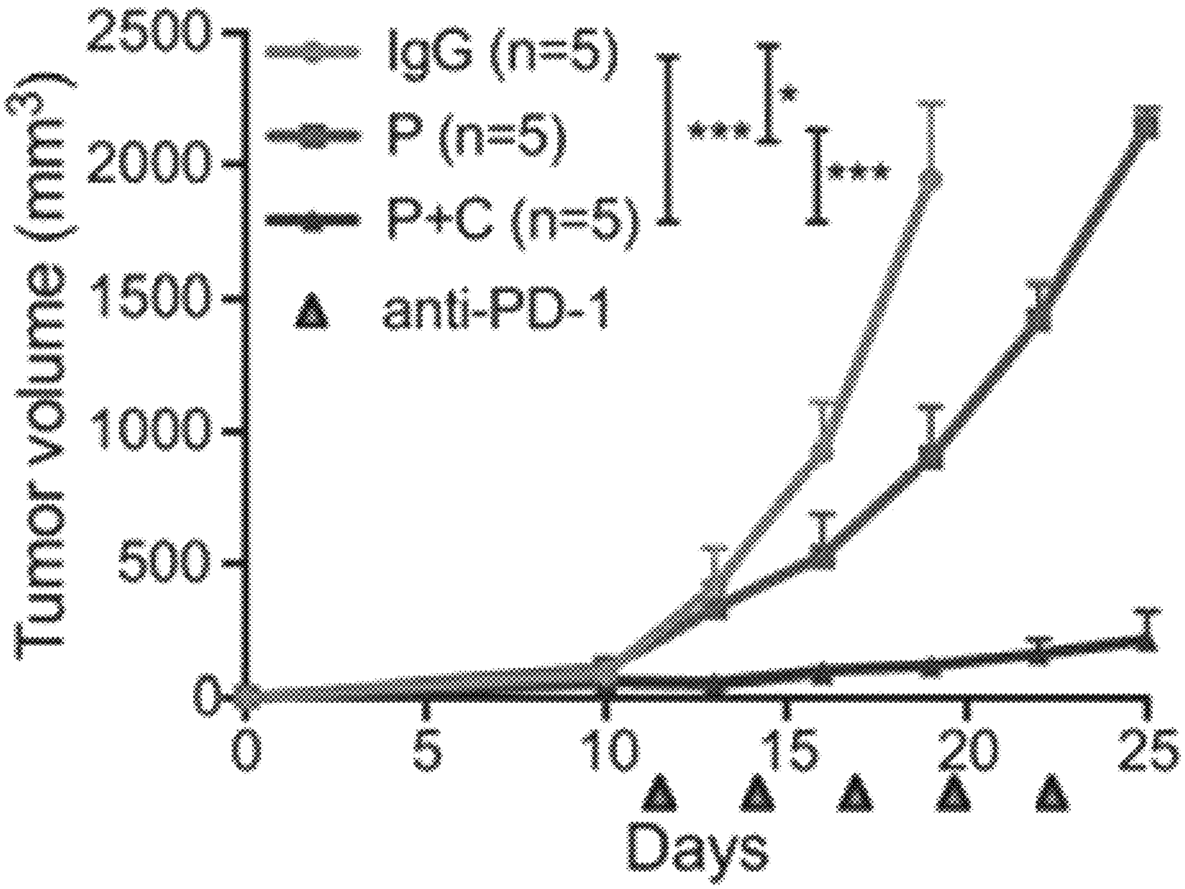
FIG. 98A-98G. Depletion of Mettl3 or Mettl14 enhanced the response to immunotherapy.
Figure 98B:
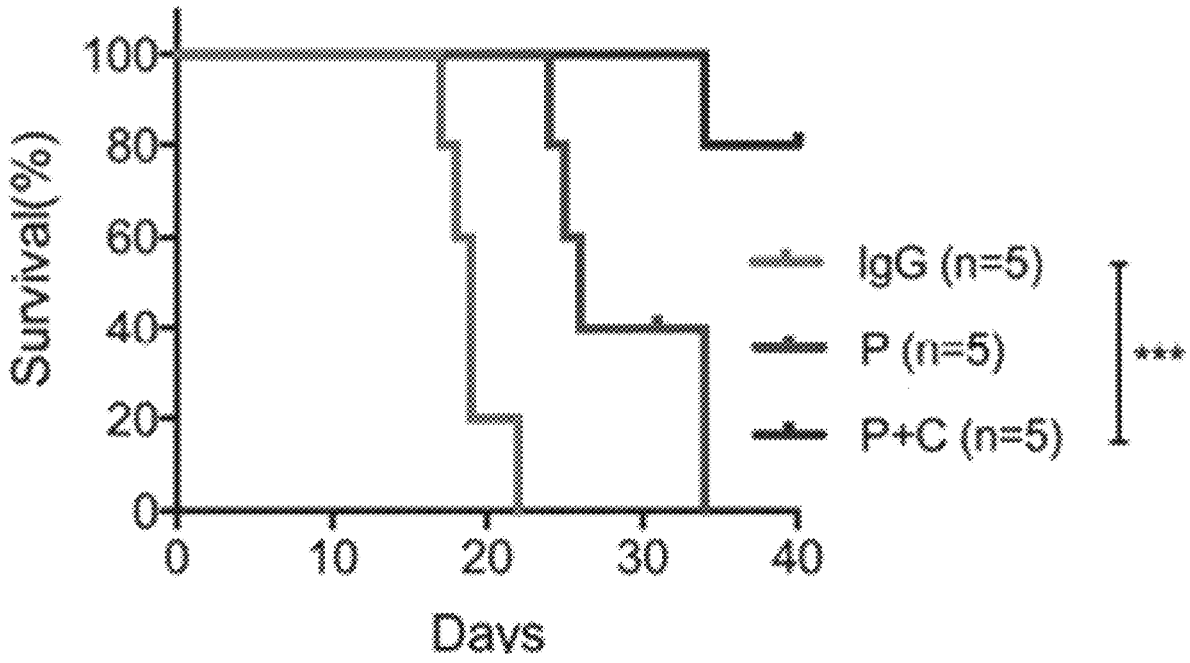
Figure 98C:
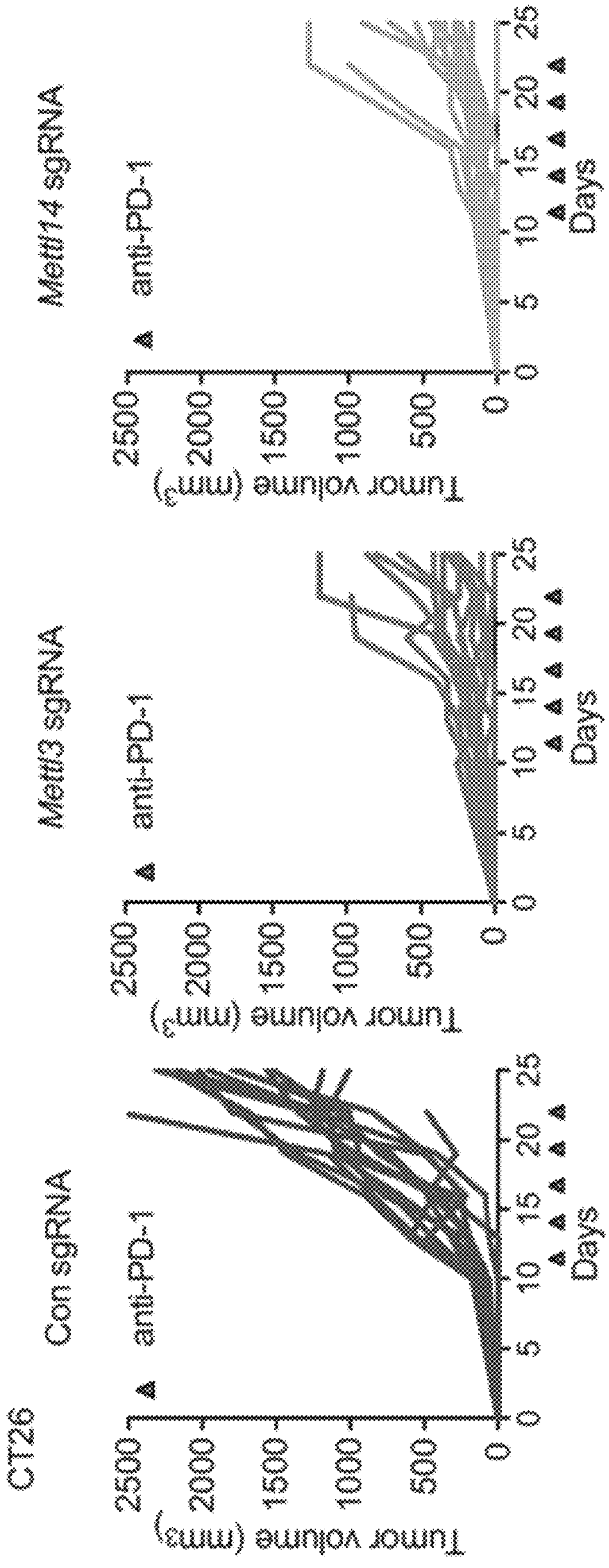
Figure 98D:
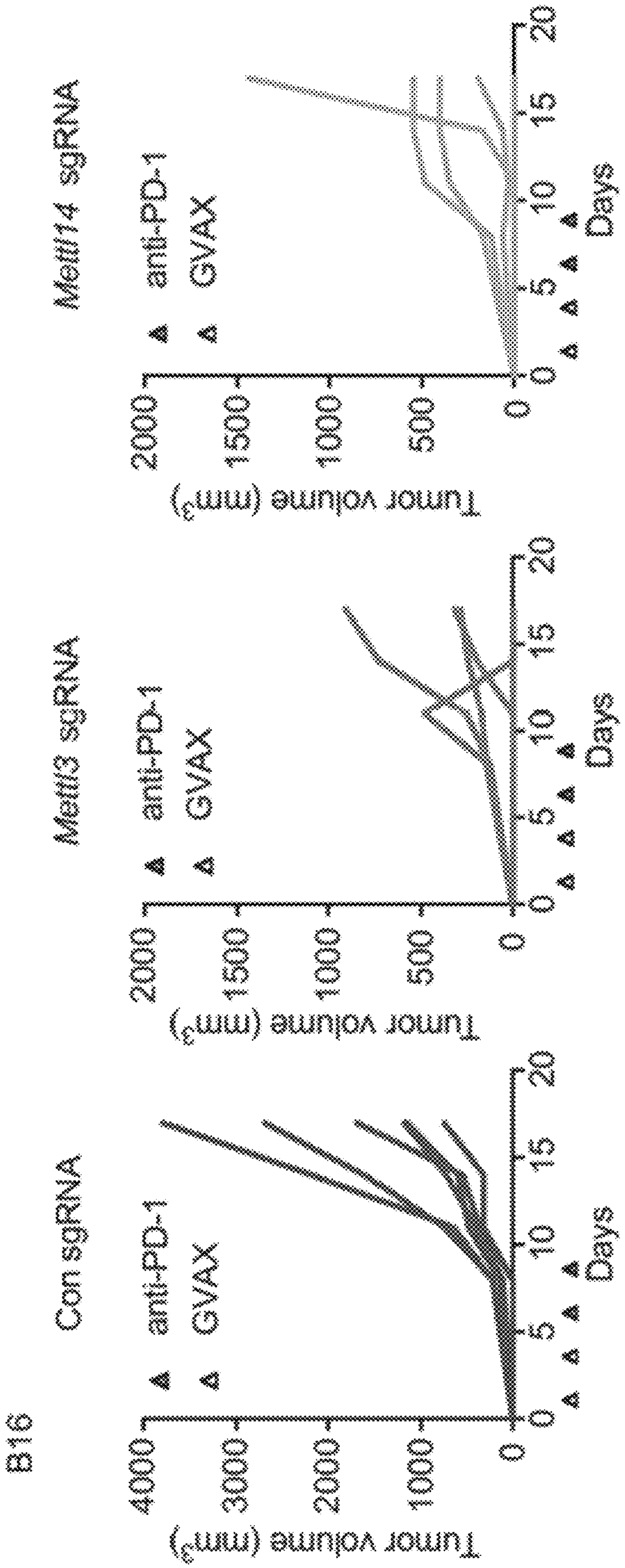
Figure 98E:
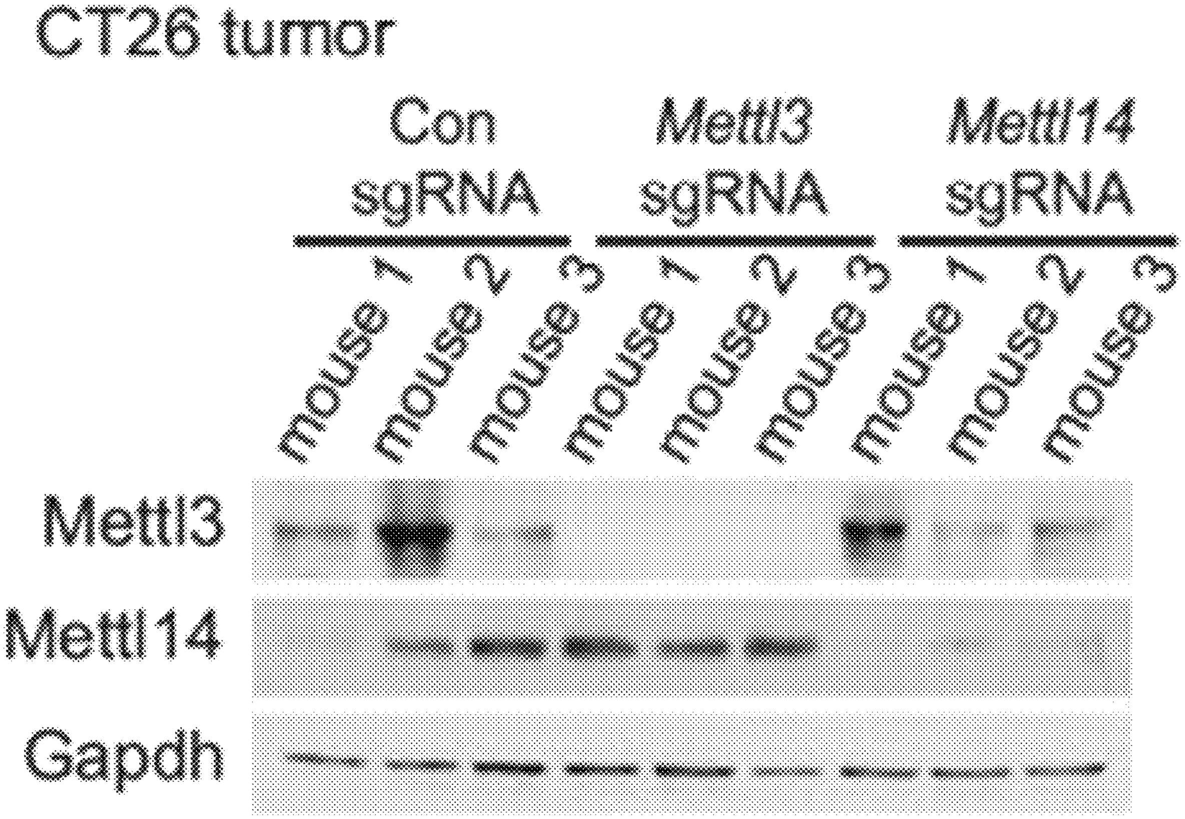
Figure 98F:
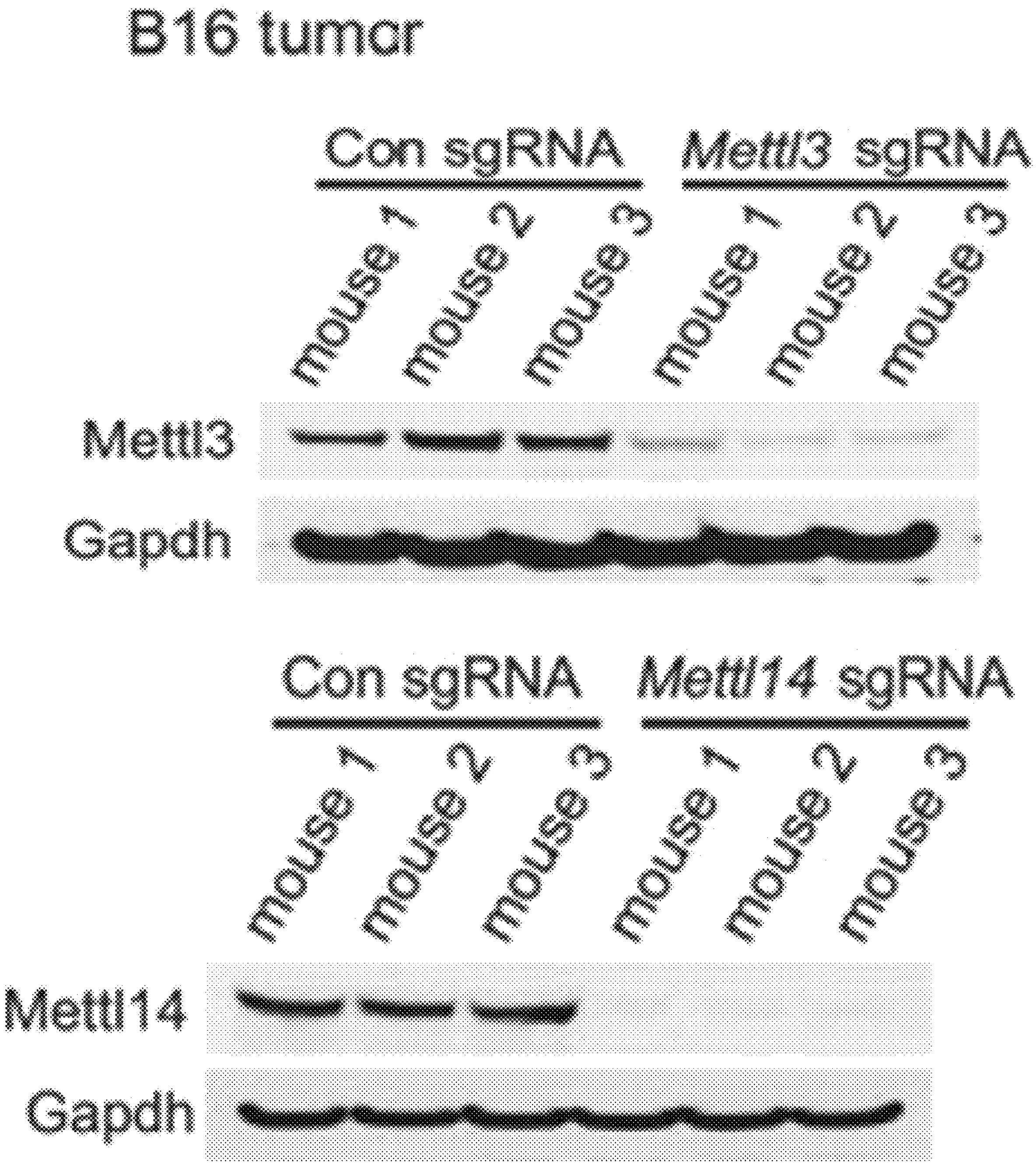
Figure 98G:
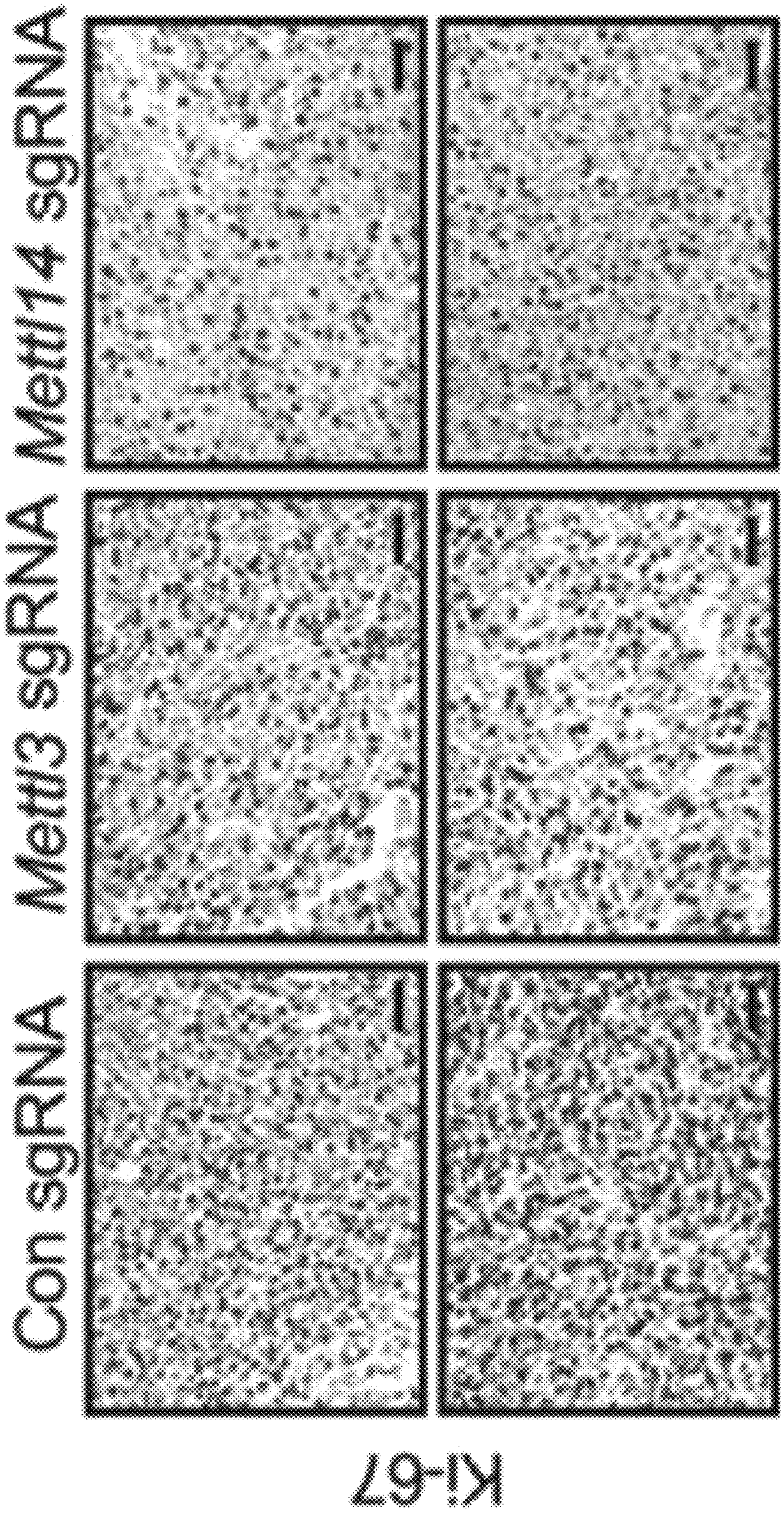
Figure 99A:
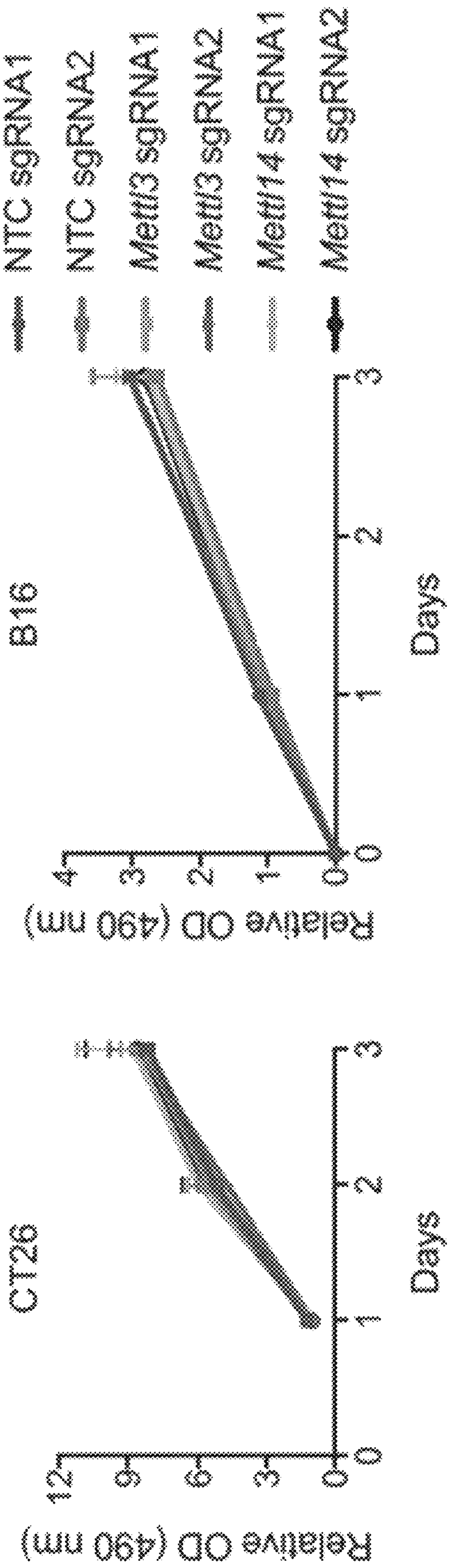
FIG. 99A-99E. Loss of Mettl3 or Mettl14 has no effect to cell proliferation and tumor growth FIG. 100A-100G. Tumor-infiltrating CD8+ T cells and chemokines concentration were altered in Mettl3 or Mettl14 null tumors.

So far, the roles of m6A methyltransferases (METTL3 and METTL14) in cancer immunotherapy have not been investigated. To determine the biological function of METTL3 and METTL14 in this process, we employed mouse models using the modestly immunogenic colorectal cancer cell line CT26 (Kim et al, 2014) and a poorly immunogenic murine melanoma cell line B16 (Manguso et al, 2017). Loss of Mettl3 and Mettl14 CT26 colorectal carcinoma and B16 melanoma cells were generated using sgRNA and validated the effect of depletion by Western blotting (FIGS. 93A and 93B). To establish these mouse models, we first investigated the immune checkpoint-blocking antibody response in CT26 tumors. We treated BALB/c mice bearing CT26 colorectal carcinoma with control IgG, anti-PD-1, or combined anti-PD-1 plus anti-CTLA-4 antibodies. Anti-PD-1 antibody had limited effect on tumor growth and mice survival compared with control IgG antibody treatment, whereas combined anti-PD-1 and anti-CTLA-4 treatment responded better than anti-PD-1 (FIGS. 98A and 98B), consistent with the previous study (Kim et al, 2014) showing resistance to anti-PD-1 treatment in colon cancer immunotherapy. Next, Mettl3- or Mettl14-depleted and control cells were subcutaneously injected into BALB/c mice, and mice were treated with anti-PD-1 antibody. Compared to control, the mice bearing Mettl3- or Mettl14-depleted CT26 tumors showed slower tumor growth (FIG. 93C and FIG. 98C) and prolonged survival (FIG. 93E). We also analyzed the effect of Mettl3 or Mettl14 depletion in a well-established B16 melanoma model where C57BL/6J mice were treated with combination of anti-PD-1 antibody and granulocyte-macrophage colony-stimulating factor (GM-CSF)-secreting irradiated B16 cell vaccine (GVAX), which simulates an adaptive immune response (Manguso et al, 2017). Consistent with the results of CT26, Mettl3- or Mettl14-deficient-B16-tumor-bearing mice exhibited tumor growth inhibition (FIG. 93D and FIG. 98D) and longer survival than controls (FIG. 93F). Additionally, we confirmed that Mettl3 and Mettl14 were efficiently repressed in these mouse tumors by Western blot (FIGS. 98E and 98F) and found the expression of Ki-67 was decreased in Mettl3- or Mettl14-depleted tumors using immunohistochemistry (IHC) staining, which indicated that Mettl3 or Mettl14 null tumors were smaller than control tumors caused reduced proliferation (FIG. 98G). Then, we assessed whether Mettl3 or Mettl14 depletion alone was able to affect cell or tumor growth since Mettl3 and Mettl14 are lethal in particular cancer types such as leukemia (Barbieri et al, 2017; Vu et al, 2017; Weng et al, 2018), glioblastoma (Cui et al, 2017), and hepatocellular carcinoma (Ma et al, 2017; Chen et al, 2018). Our observation revealed that all the cells and tumors with control and Mettl3 or Mettl14 knockout have quite similar cellular proliferation in vitro (FIG. 99A) and tumor volume in vivo (FIG. 99B-99E). Collectively, these results suggested a generalizable role of m6A methyltransferases in colorectal carcinoma and melanoma, where the loss of Mettl3 or Mettl14 sensitizes tumor to the effect of immunotherapy, but not intrinsically impairs their growth alone.

Depletion of Mettl3 or Mettl14 Increased Cytotoxic Tumor-Infiltrating CD8+ T Cells and Altered Tumor Microenvironment.

Figure 94A:
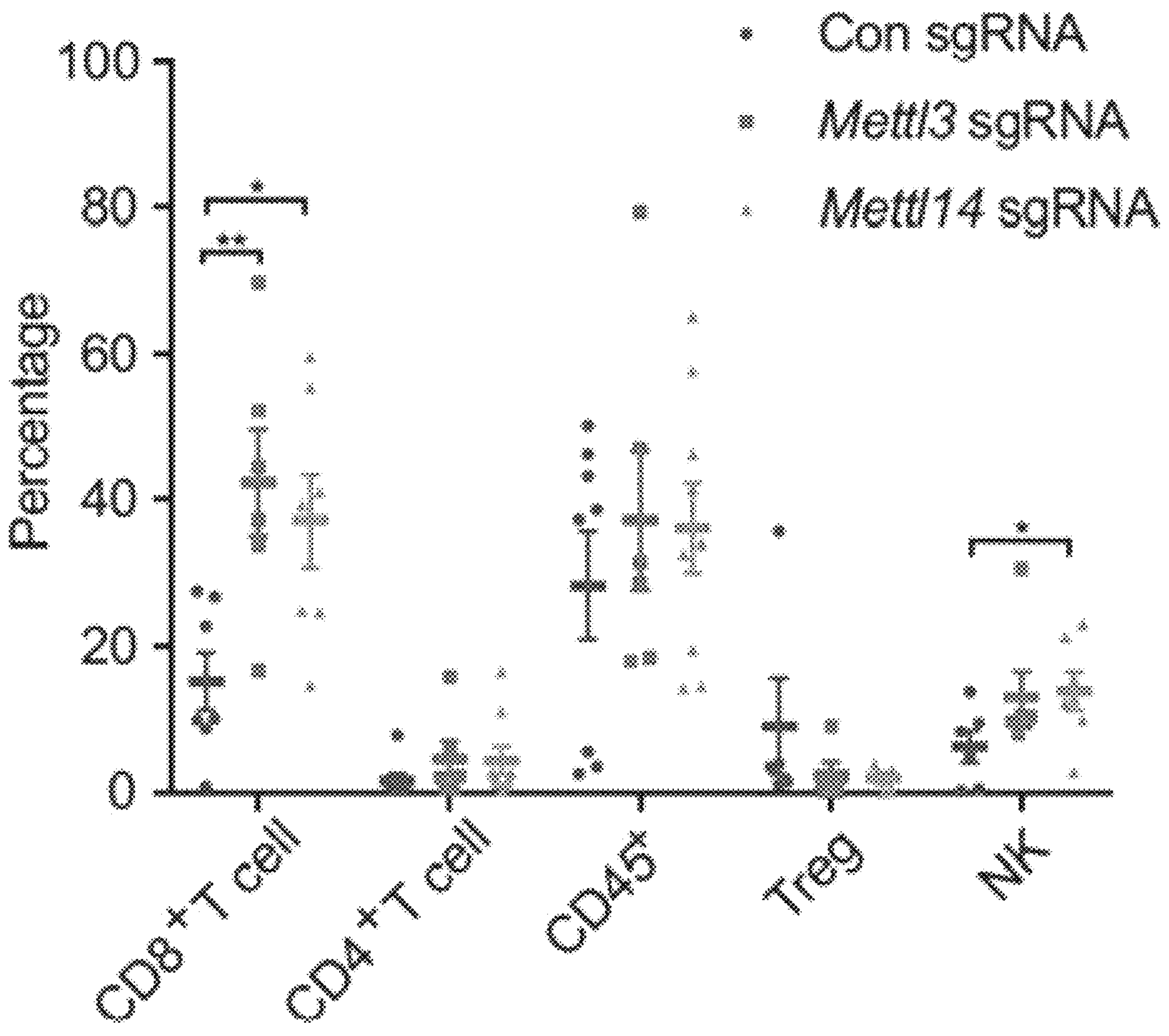
FIG. 94A-94G. Depiction of data showing Mettl3 or Mettl14 deficiency enhances tumor-infiltrating CD8+ T cells and cytokine production.
Figure 94B:
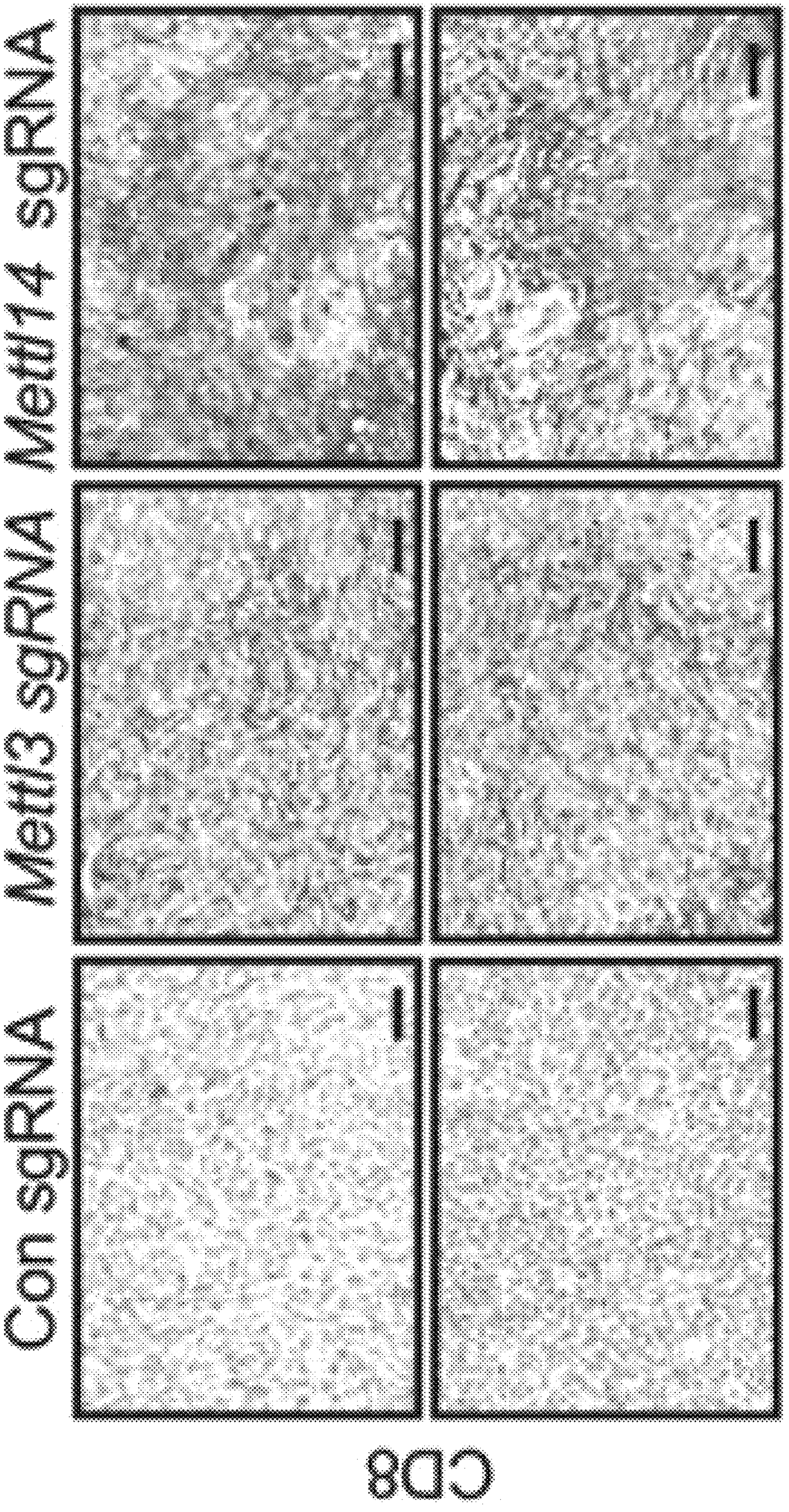
Figure 94C:
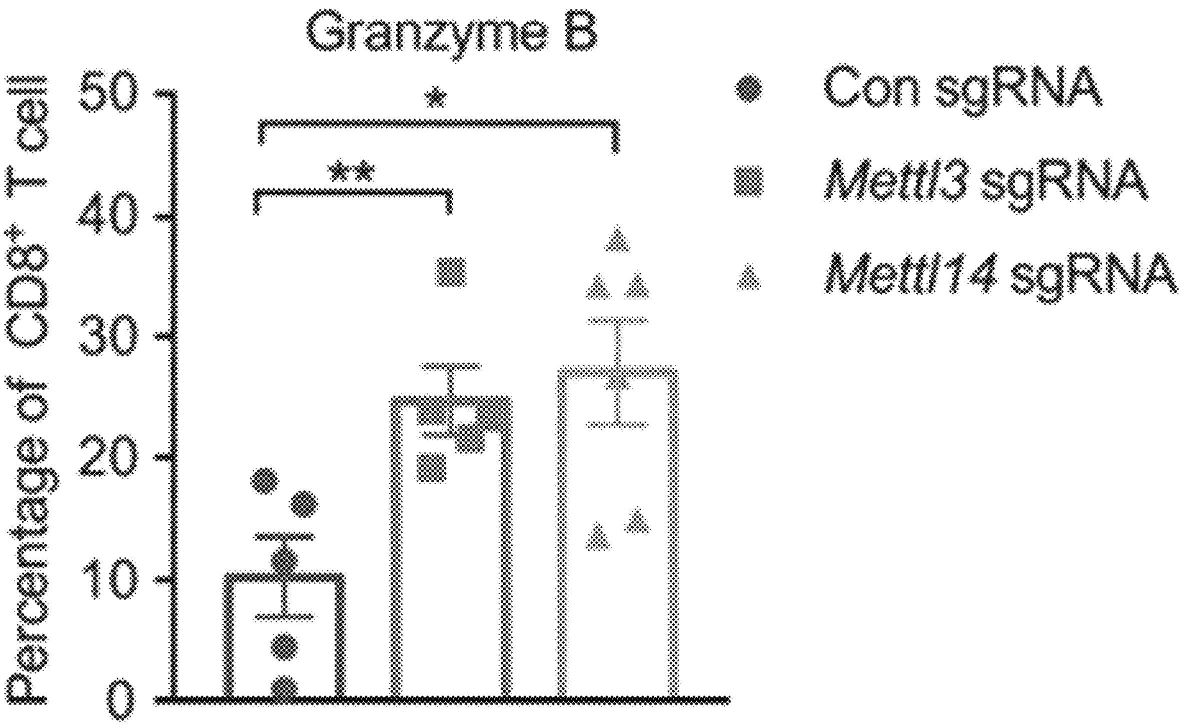
Figure 94D:
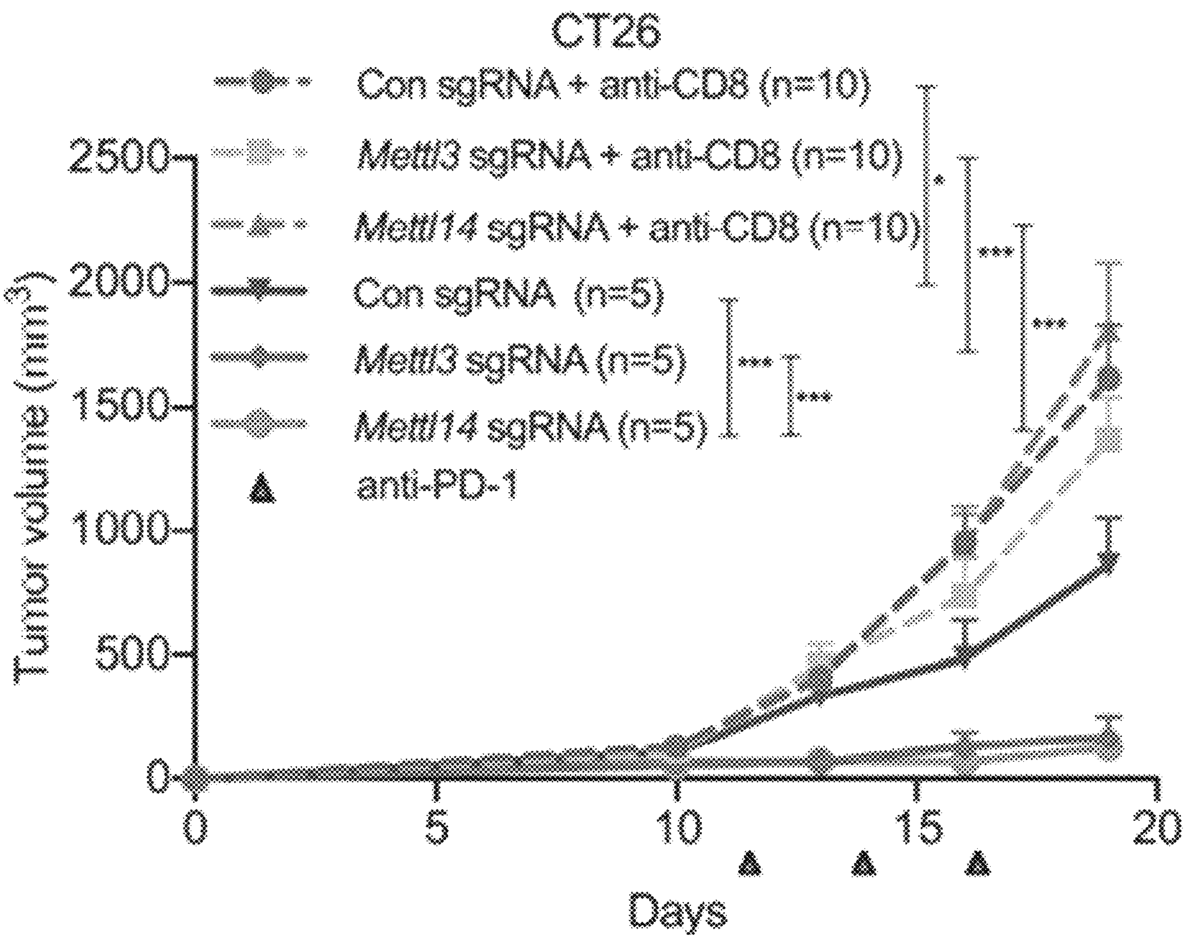
Figure 94E:
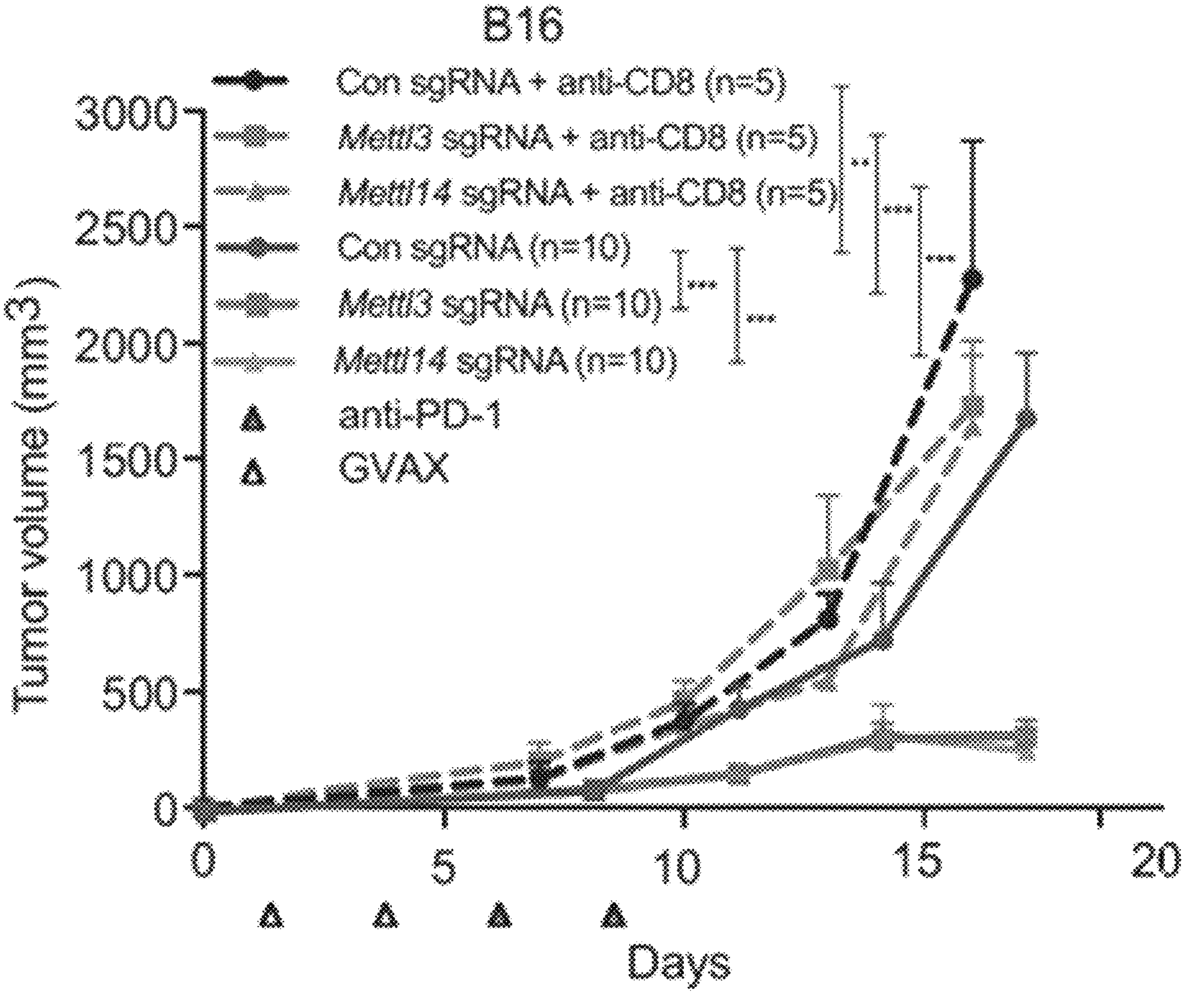
Figure 94F:
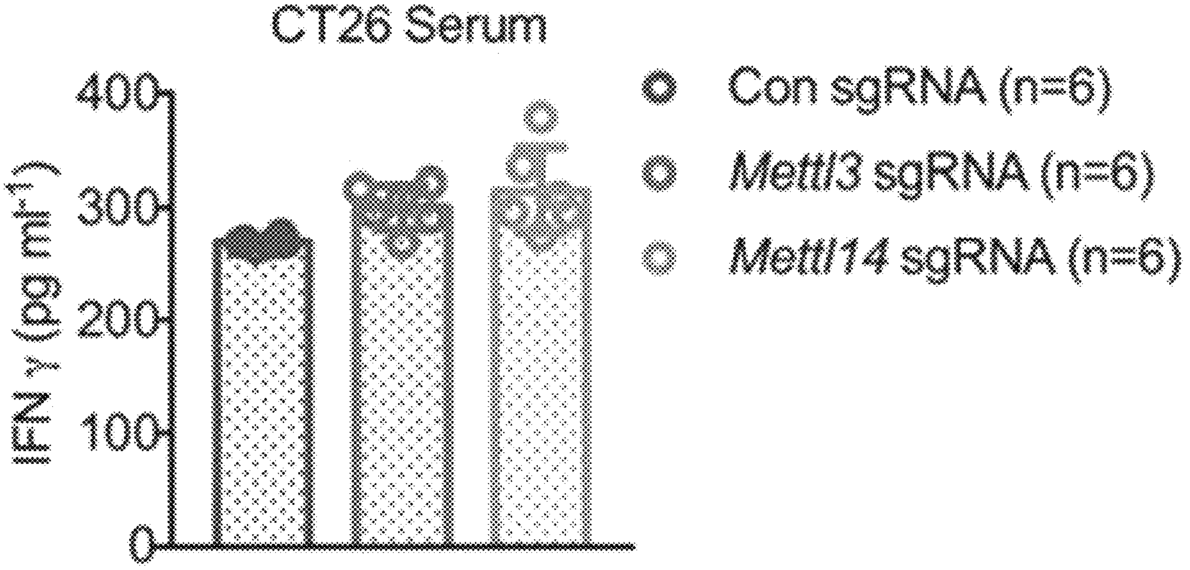
Figure 94G:
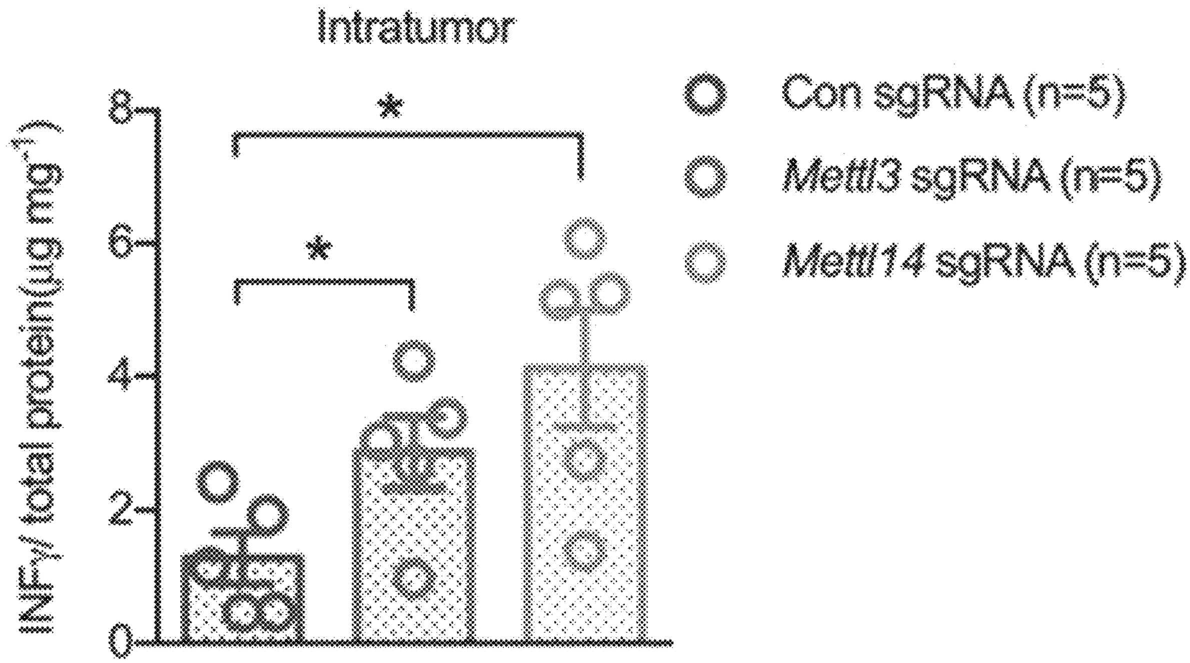
Figure 99B:
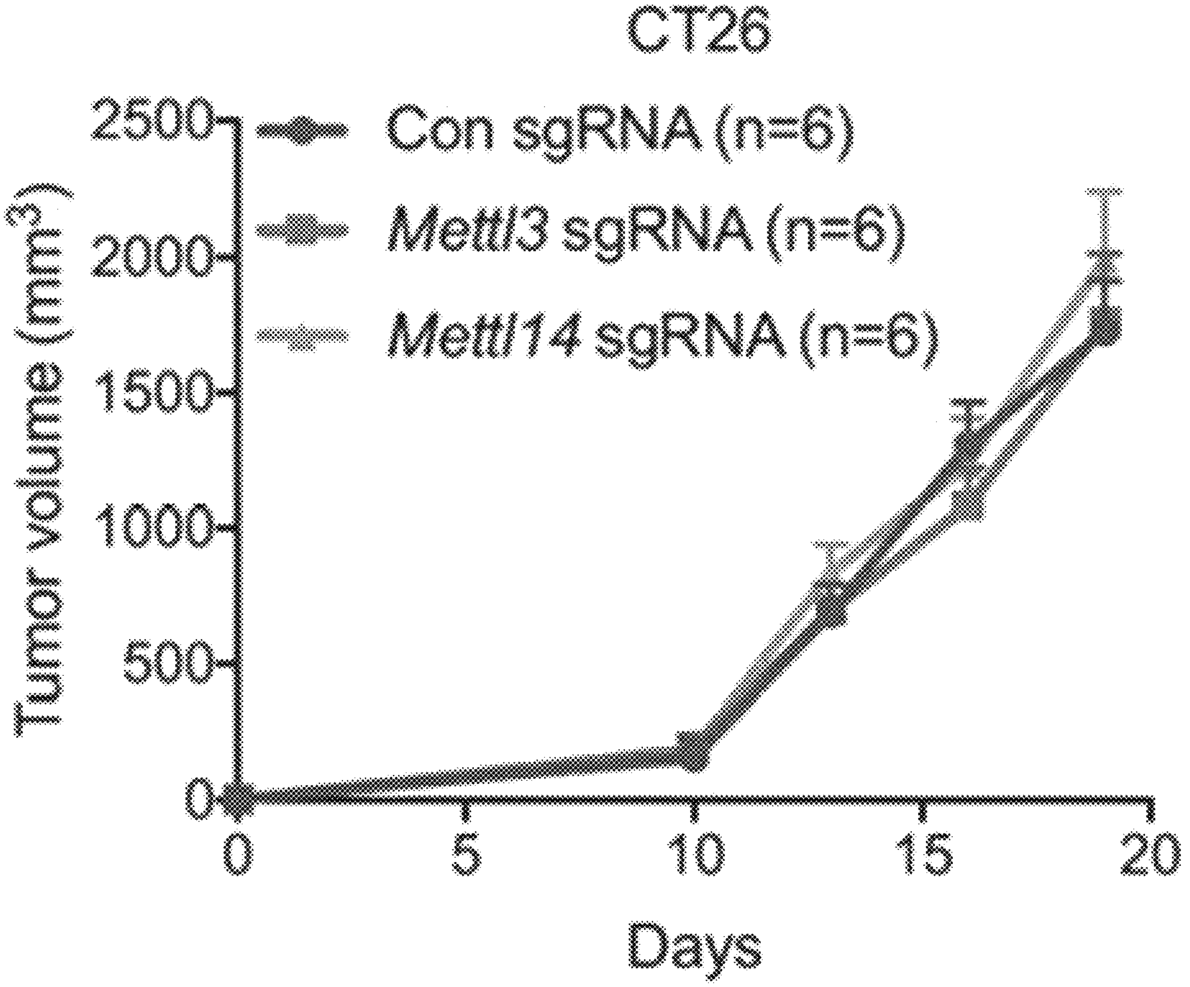
Figure 99C:
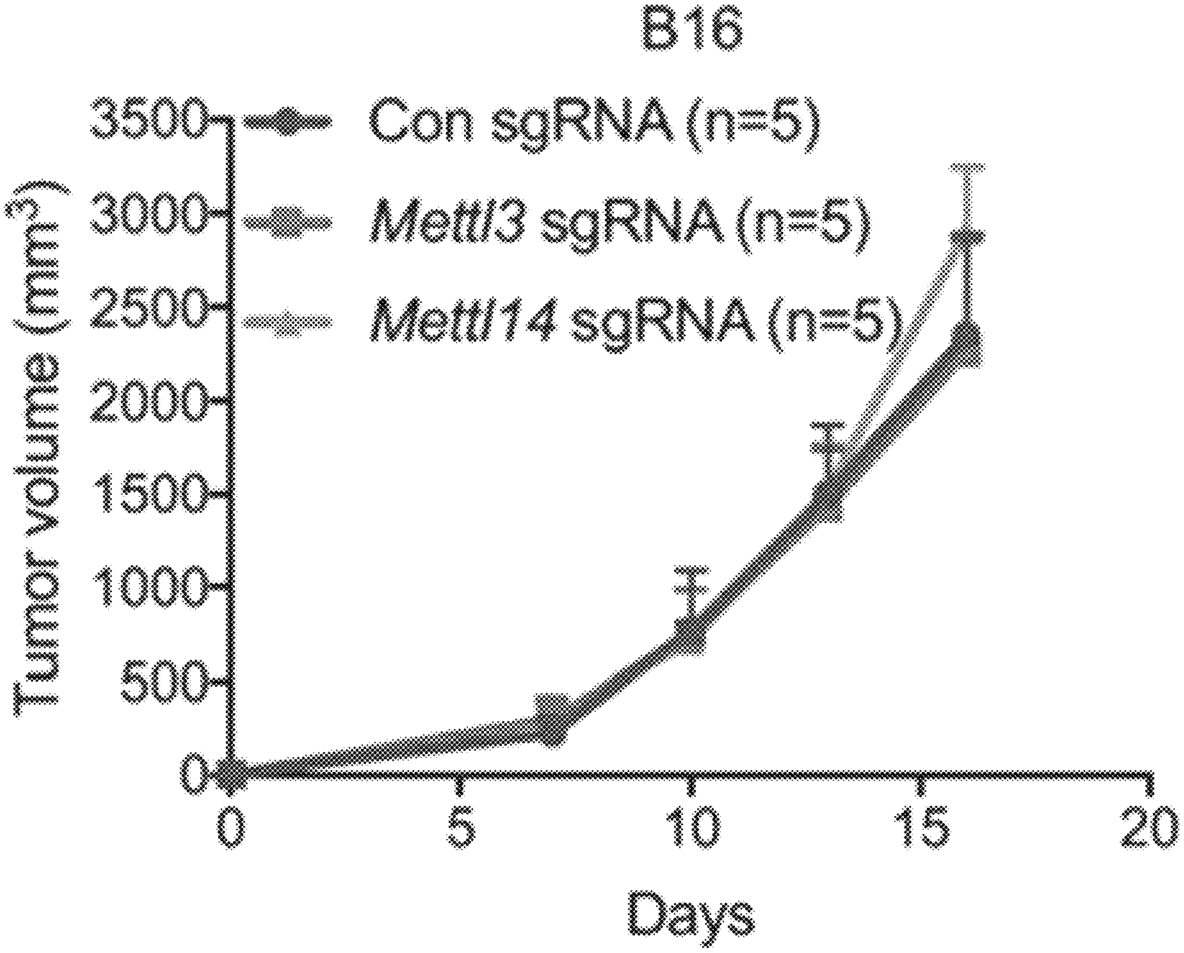

To identify the mechanisms by which depletion of Mettl3 or Mettl14 increased the response to immunotherapy, we analyzed the immune cell components within the CT26 tumor tissues by flow cytometry. The immune infiltrates contained significantly increased CD8+ T cells in both Mettl3 and Mettl14 null tumors compared to control tumors (FIGS. 94, 100A, 10B, and 100 C), whereas no differences in the CD4+ T cells, CD45+ cells, and Treg cells were observed (FIG. 94A). Additionally, the level of natural killer (NK) cells is higher from Mettl14-deficient tumors than that of control tumors (FIG. 94A). In line with the observations of flow cytometry analysis, we also found that Mettl3- and Mettl14-depleted tumors had higher expression of CD8 than that of control (FIG. 94B). Further analysis revealed that Mettl3- and Mettl14-depleted tumors contained a dramatically enhanced granzyme B expression in CD8+ T cells (FIG. 94C). Consistently, compared with control tumors, we observed increased CD8+ T cells and granzyme B expression in CD8+ T cells from Mettl3 and Mettl14 null B16 tumors as well (FIGS. 99B and 99C). Taken together, loss of Mettl3 or Mettl14 improved cytotoxic tumor-infiltrating CD8+ T cells. To further investigate the contributions of CD8+ T cells to the antitumor response of immunotherapy, we depleted CD8+ T cells using an anti-CD8 antibody and monitored the tumor growth from mice bearing control, Mettl3, or Mettl14 null tumors during immunotherapy. Our results showed that enhanced response to immunotherapy caused by depletion of Mettl3 or Mettl14 was completely abolished in both CT26 and B16 tumors (FIGS. 94D and 94E), indicating that CD8+ T cells are essential for controlling tumor growth (Ribas & Wolchok, 2018).

Figure 99D:
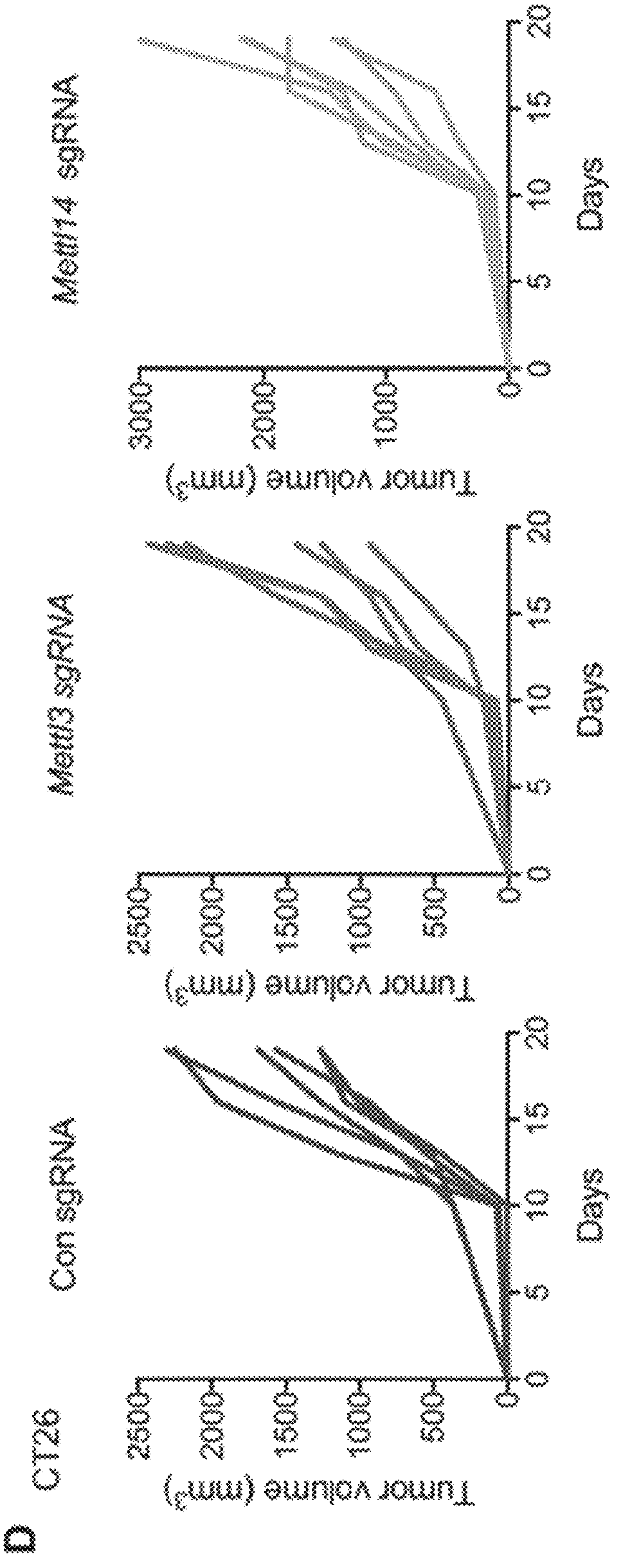
Figure 99E:
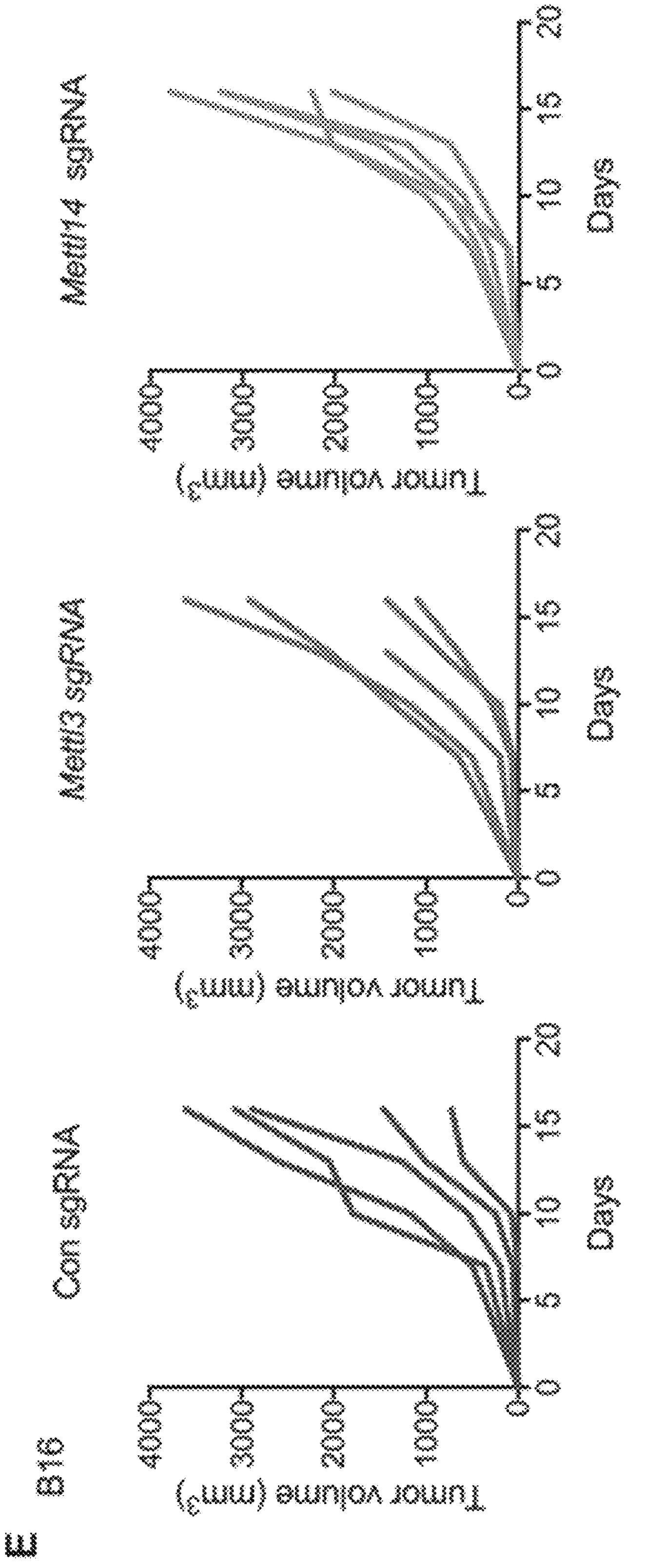

CD8+ T cells are multiple cytokine producers (Paliard et al, 1988), which predominately secrete cytokines including IFN-γ and TNFα (Lichterfeld et al, 2004; Pandiyan et al, 2007). IFN-γ plays an important role in tumor immune surveillance (Castro et al, 2018) via inducing the production of CXCL9 and CXCL10, where these chemokines facilitate recruitment of CD8+ and CD4+ effector T cells to suppress tumor growth (Gorbachev et al, 2007; Tokunaga et al, 2018). To address this question, we then analyzed the secretion of IFN-γ, Cxcl9, and Cxcl10 in both mouse serum and intratumor using ELISA. Our results showed that the production of IFN-γ and Cxcl10 was not significantly changed in mouse serum (FIGS. 94F and 100F) except for Cxcl9 (FIG. 99D). Interestingly, we observed a remarkably increased concentration of IFN-γ (FIG. 94G), Cxcl9 (FIG. 99E), and Cxcl10 (FIG. 100G) in both Mettl3- and Mettl14-deficient intratumor relative to control intratumor. Together, these results indicate a mechanism where Mettl3 or Mettl14 loss enhanced efficacy of immunotherapy through modulating production of cytokines and chemokines in the tumor microenvironment.

Identification of Potential Targets of Mettl3 and Mettl14.

Figure 95A:
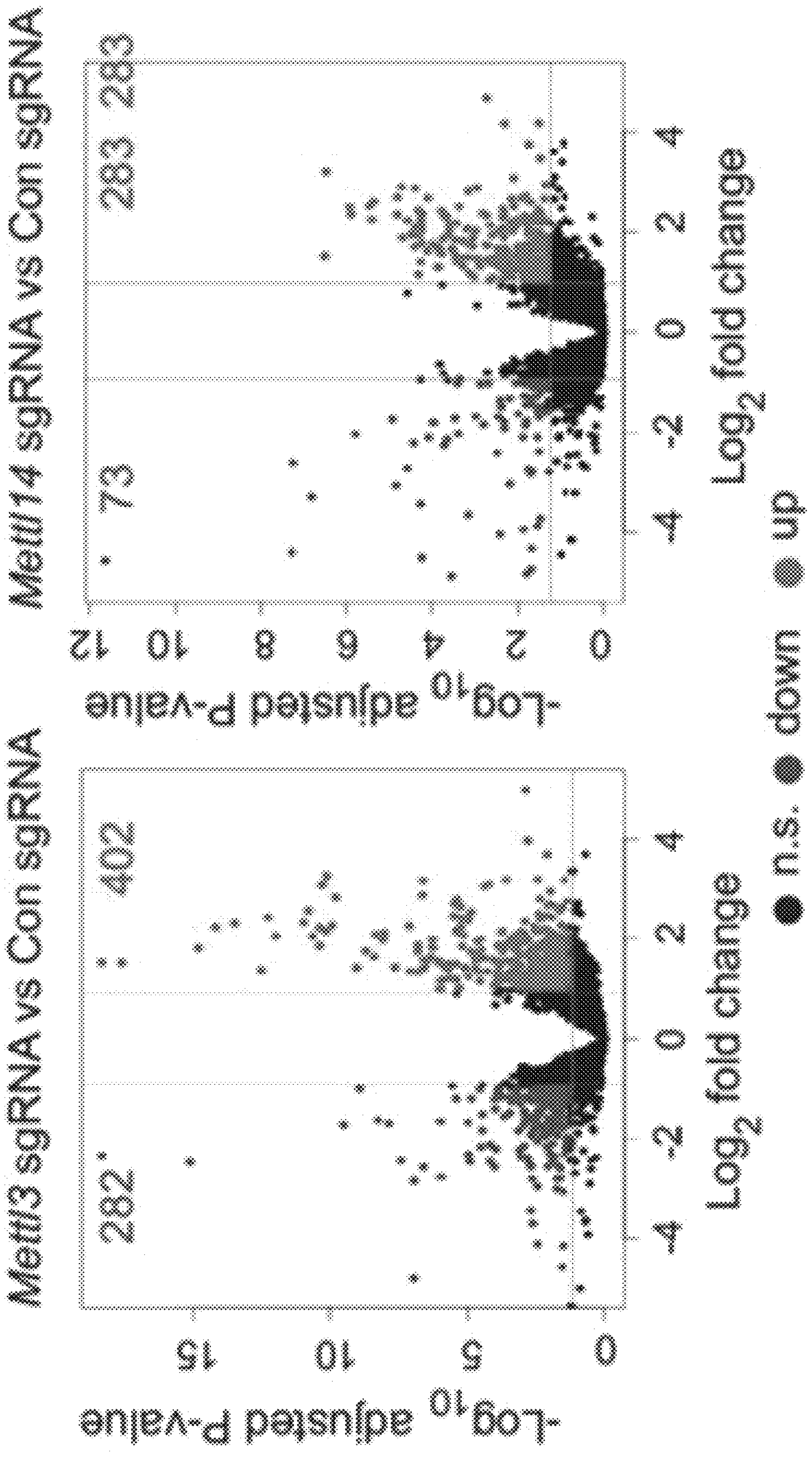
FIG. 95A-95I. Depiction of identification of target genes of Mettl3 and Mettl14 by RNA-seq and m6A-seq.
Figure 95B:
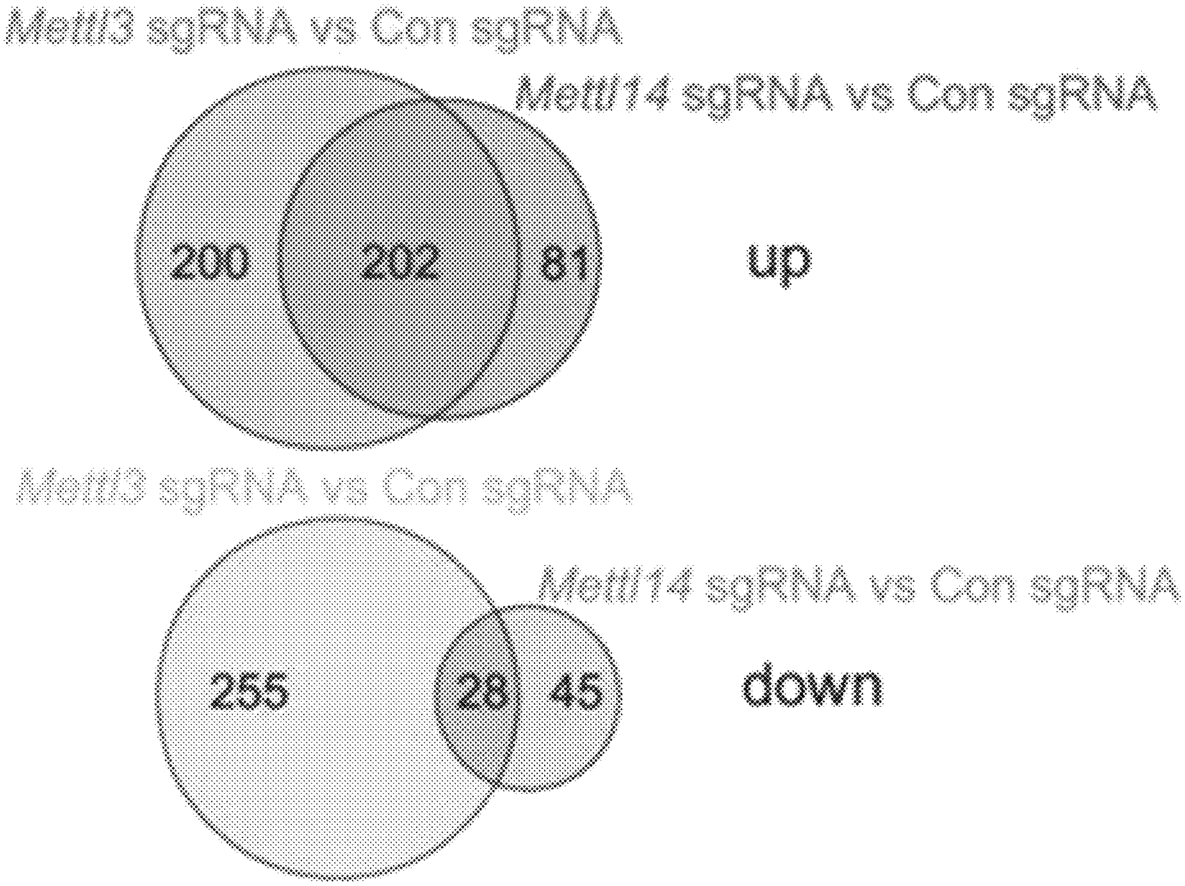
Figure 95C:
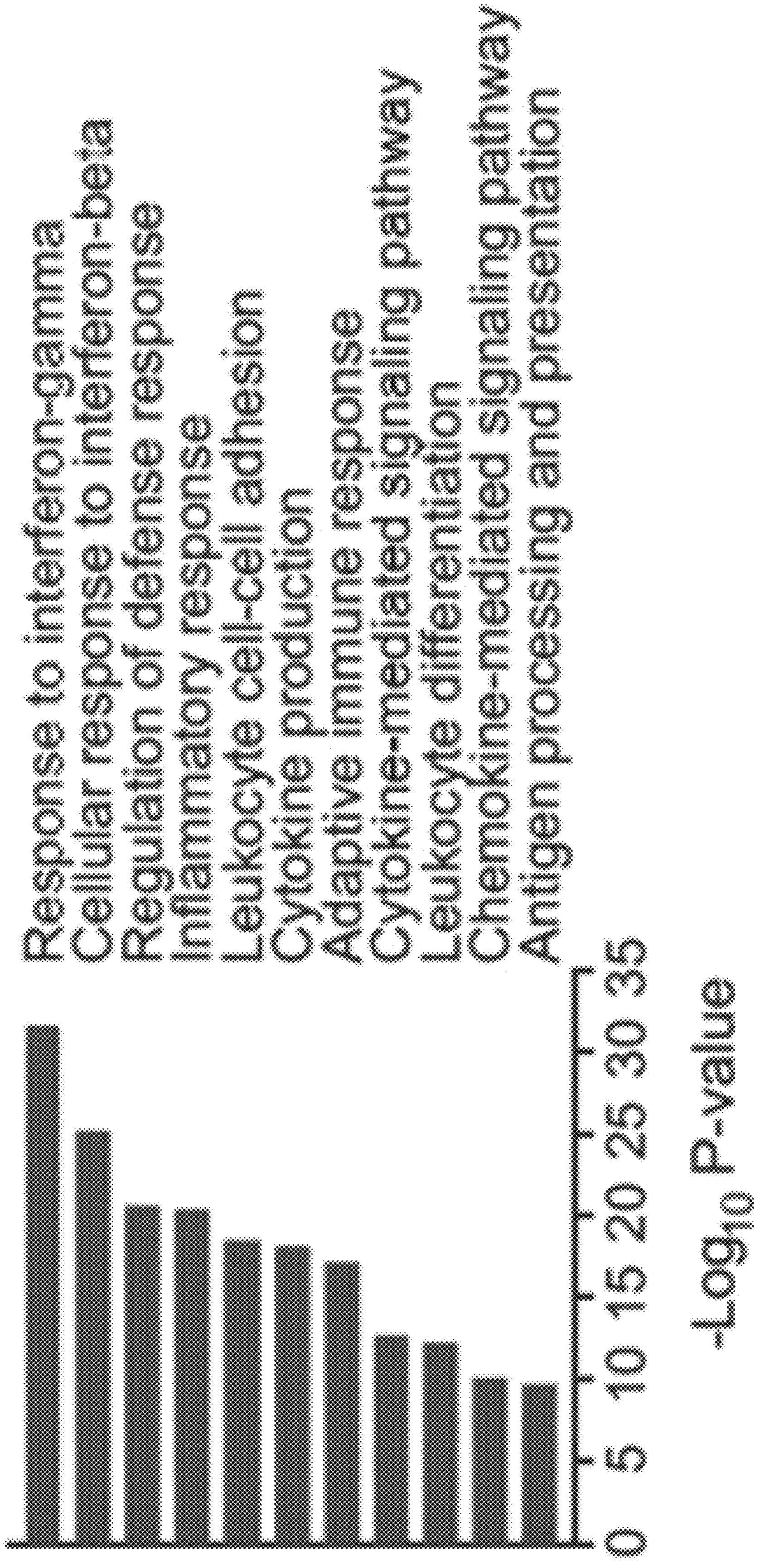
Figure 100A:
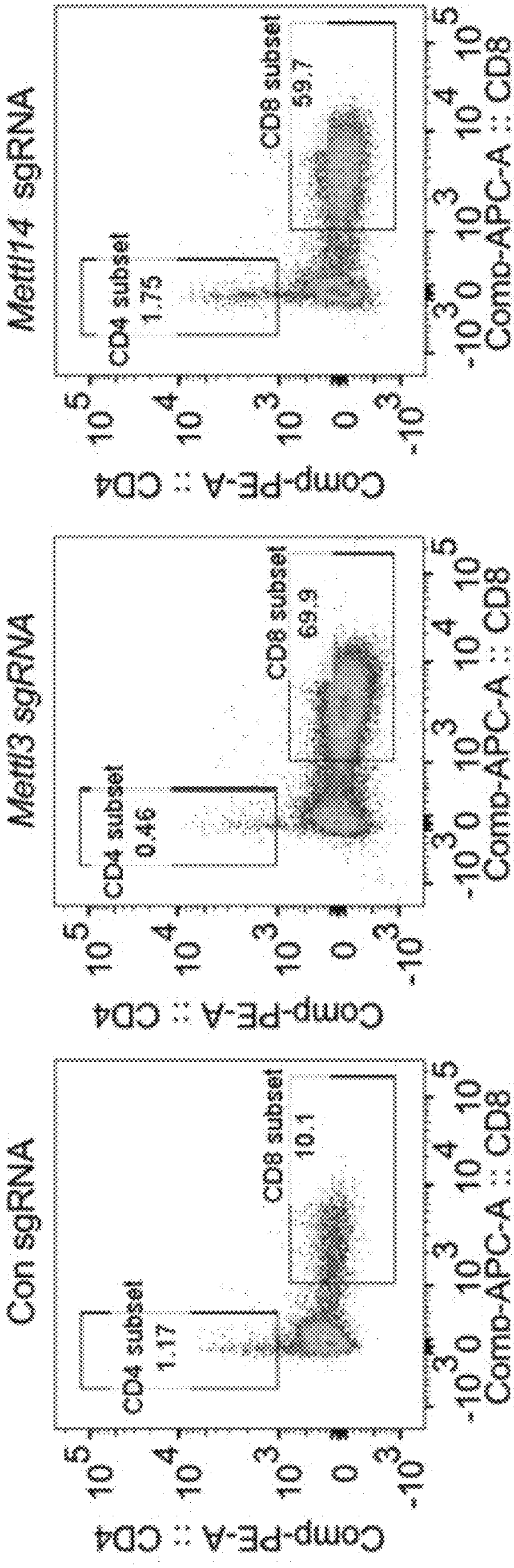
Figure 100B:
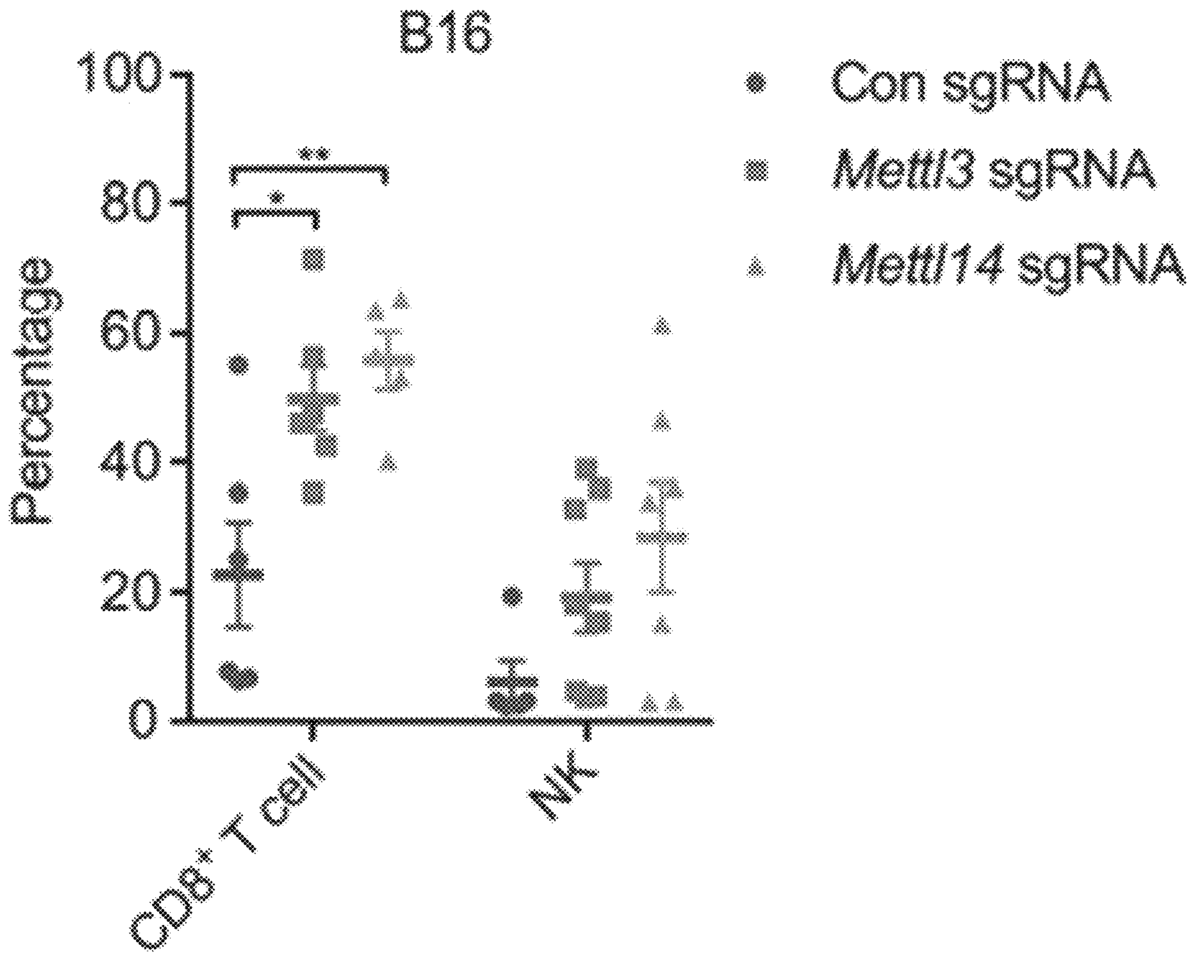
Figure 100C:
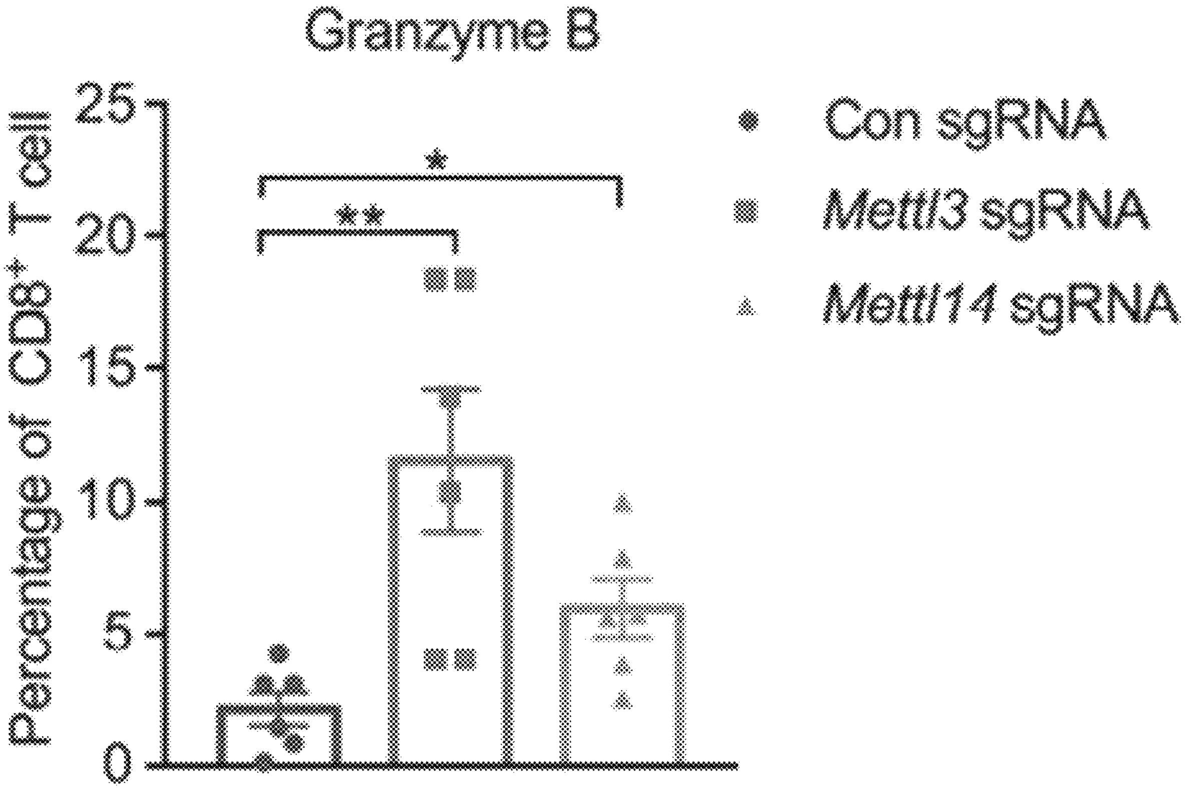
Figure 100D:
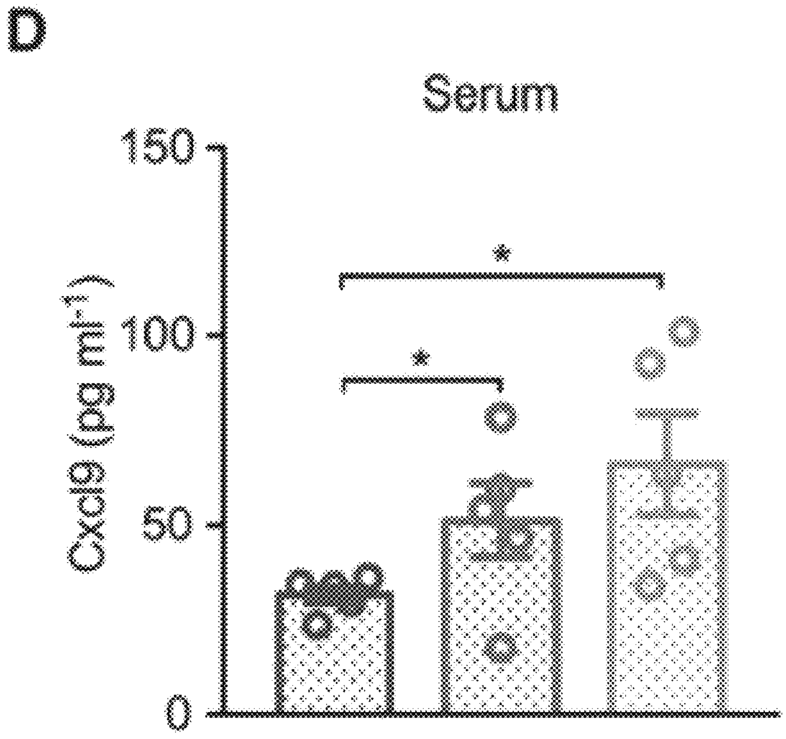
Figure 100E:
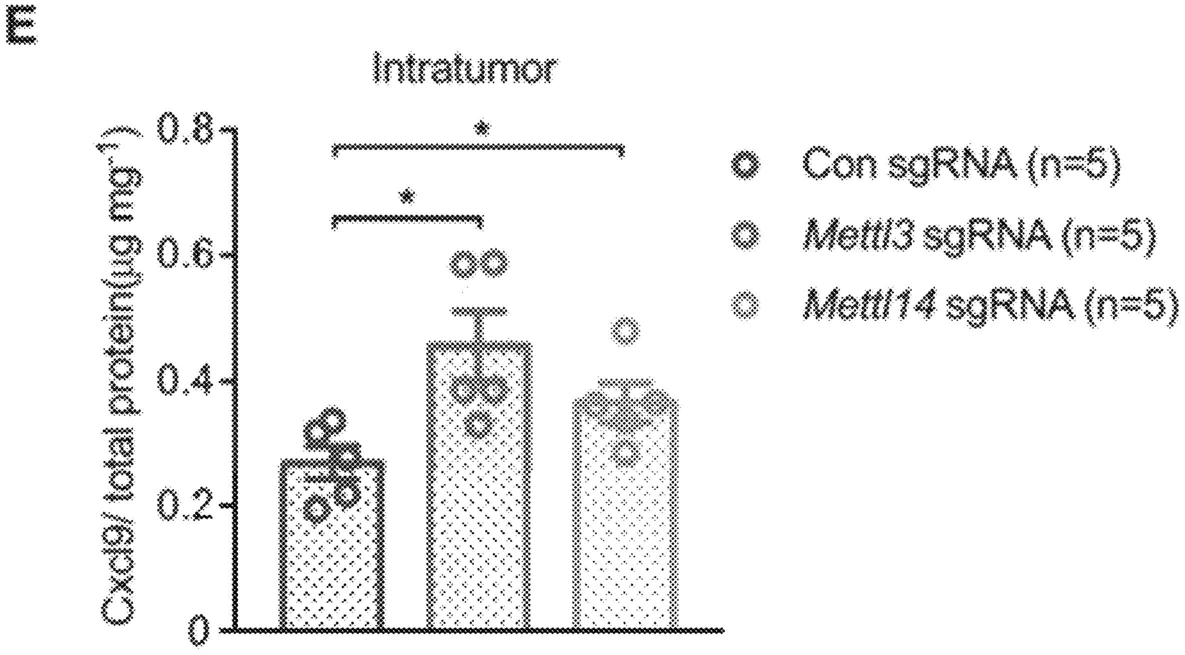
Figure 100F:
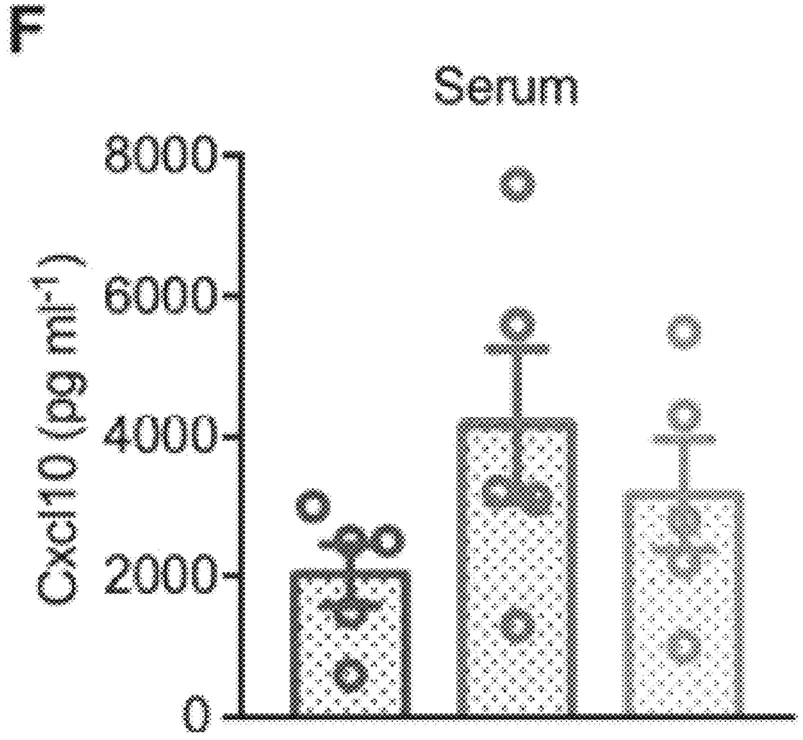
Figure 100G:
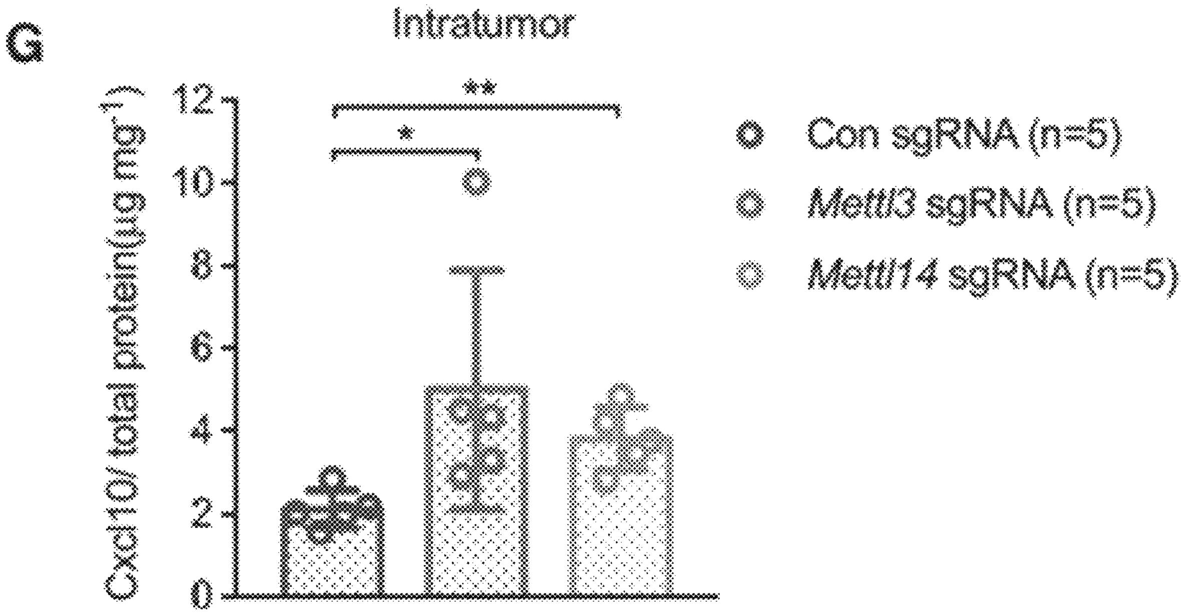
Figure 101A:
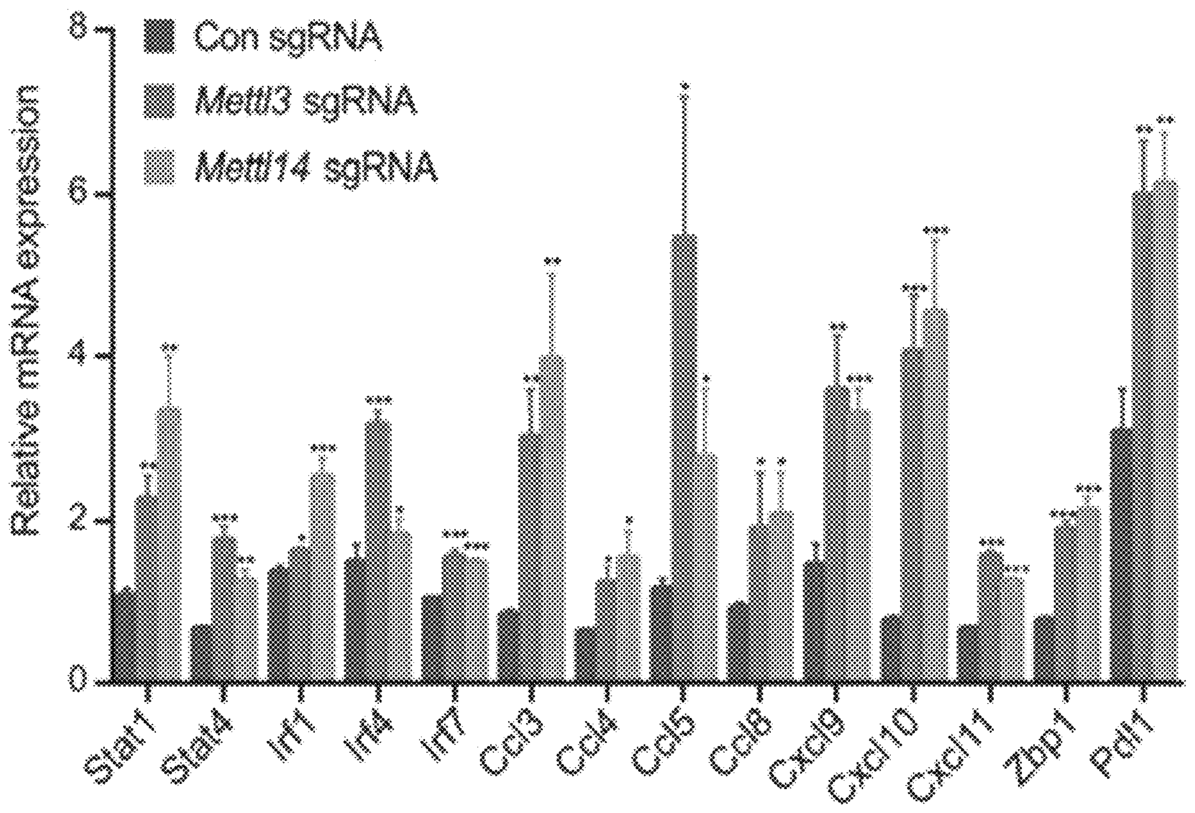
FIG. 101A-101G. Gene expression changes and analysis of m6A modification in Mettl3- or Mettl14-depleted tumors.

To understand the molecular mechanism of Mettl3 and Mettl14 in cancer immunotherapy, we employed RNA sequencing (RNA-seq) to identify the affected genes upon Mettl3 and Mettl14 depletion. Through analysis of our RNA-seq data, we identified the mRNA transcript level of 402 genes was upregulated and 282 genes was downregulated in Mettl3 null tumors compared to control tumors, while 283 genes were increased and 73 genes were decreased in Mettl14-deficient tumors compared with control (FIG. 95A). Furthermore, 230 Mettl3- and Mettl14-dependent genes were altered among both tumors with knockout of Mettl3 and Mettl14 compared to control: including 202 co-upregulated and 28 co-downregulated genes (FIG. 95B, Dataset EV1). Gene ontology (GO) analysis was performed on 202 co-upregulated genes since the limited numbers of co-downregulated genes, and these enriched pathways were mainly associated with responses to interferons, defense, inflammation, leukocyte cell-cell adhesion, cytokine production, adaptive immunity, and antigen processing and presentation (FIG. 95C). Notably, Mettl3- and Mettl14-dependent upregulated genes involved in interferon-gamma and interferon-beta pathways including Stat1, Stat4, Irf1, Irf4, Irf7, and Pdl1, and cytokine/chemokine-mediated signaling pathway such as Ccl5, Cxcl9, and Cxcl10, which was consistent with our previous observation of productions of chemokines (FIGS. 100E and 100G). To validate our RNA-seq results, we performed qRT-PCR and our results showed that all of these genes involved in interferons and cytokine/chemokine pathways were significantly upregulated in Mettl3 and Mettl14 null tumors (FIG. 101A). Together, these findings suggested that the upregulated genes upon Mettl3 and Mettl14 depletion were principally connected with immune response-associated processes.

Figure 95D:
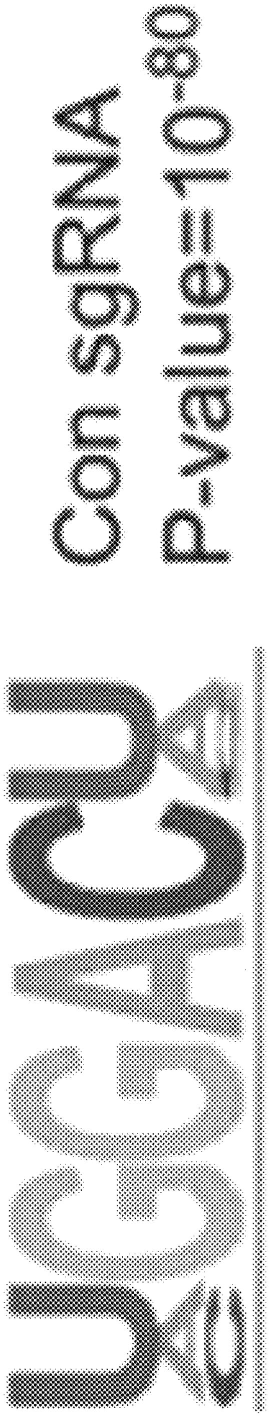
Figure 101B:
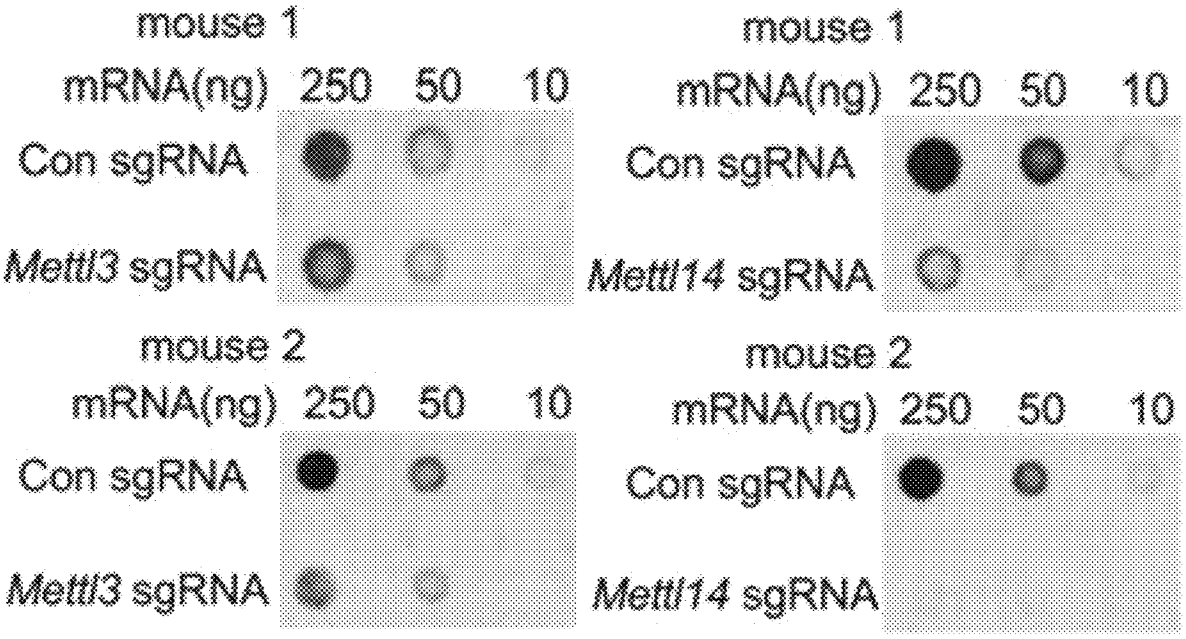
Figure 101C:
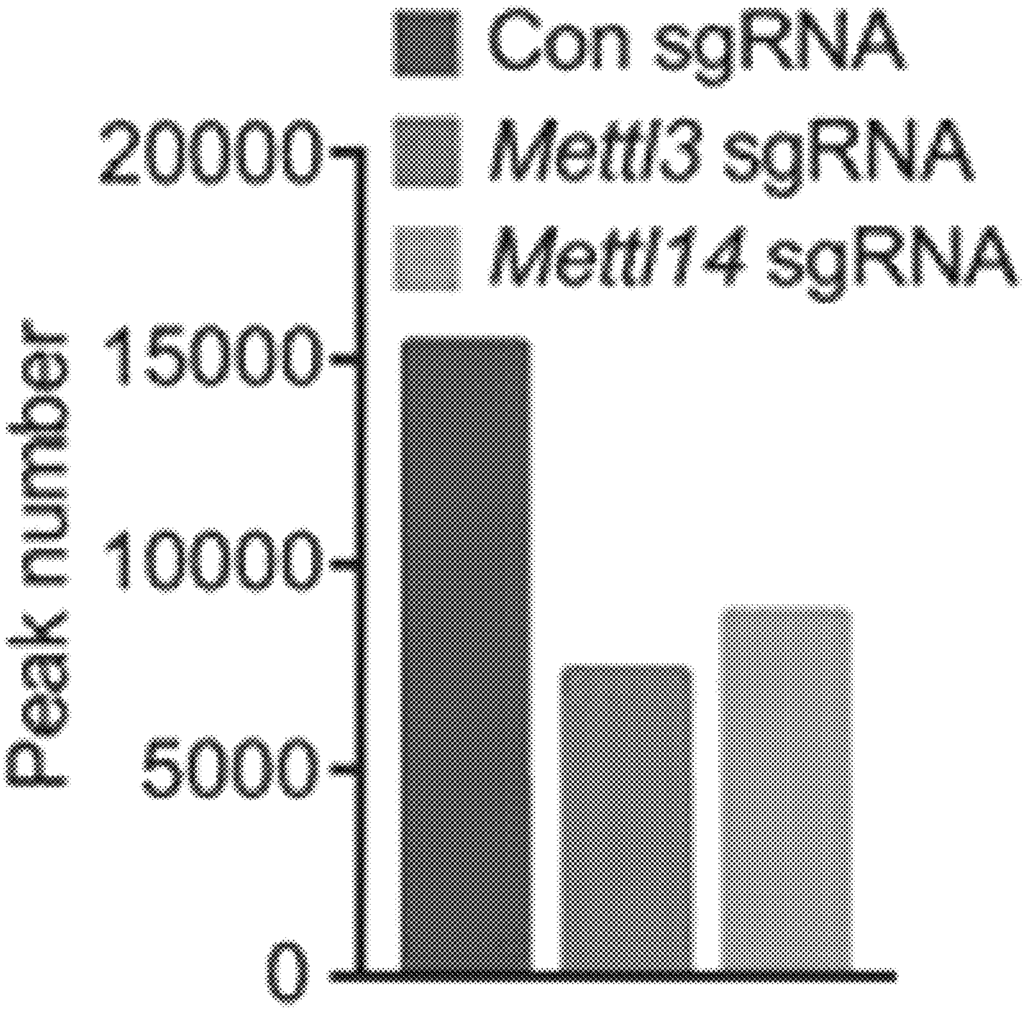
Figure 101D:
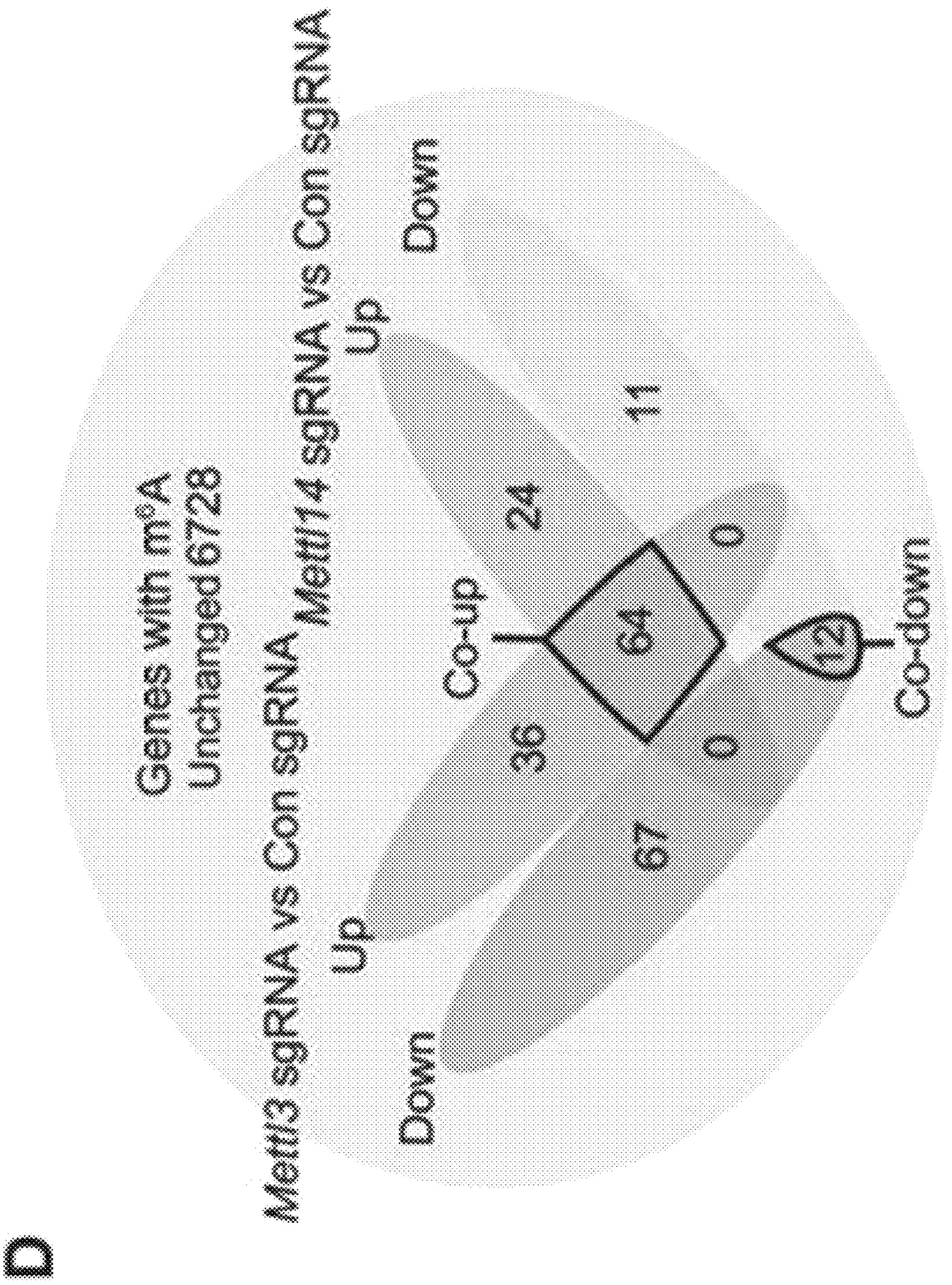
Figure 101E:
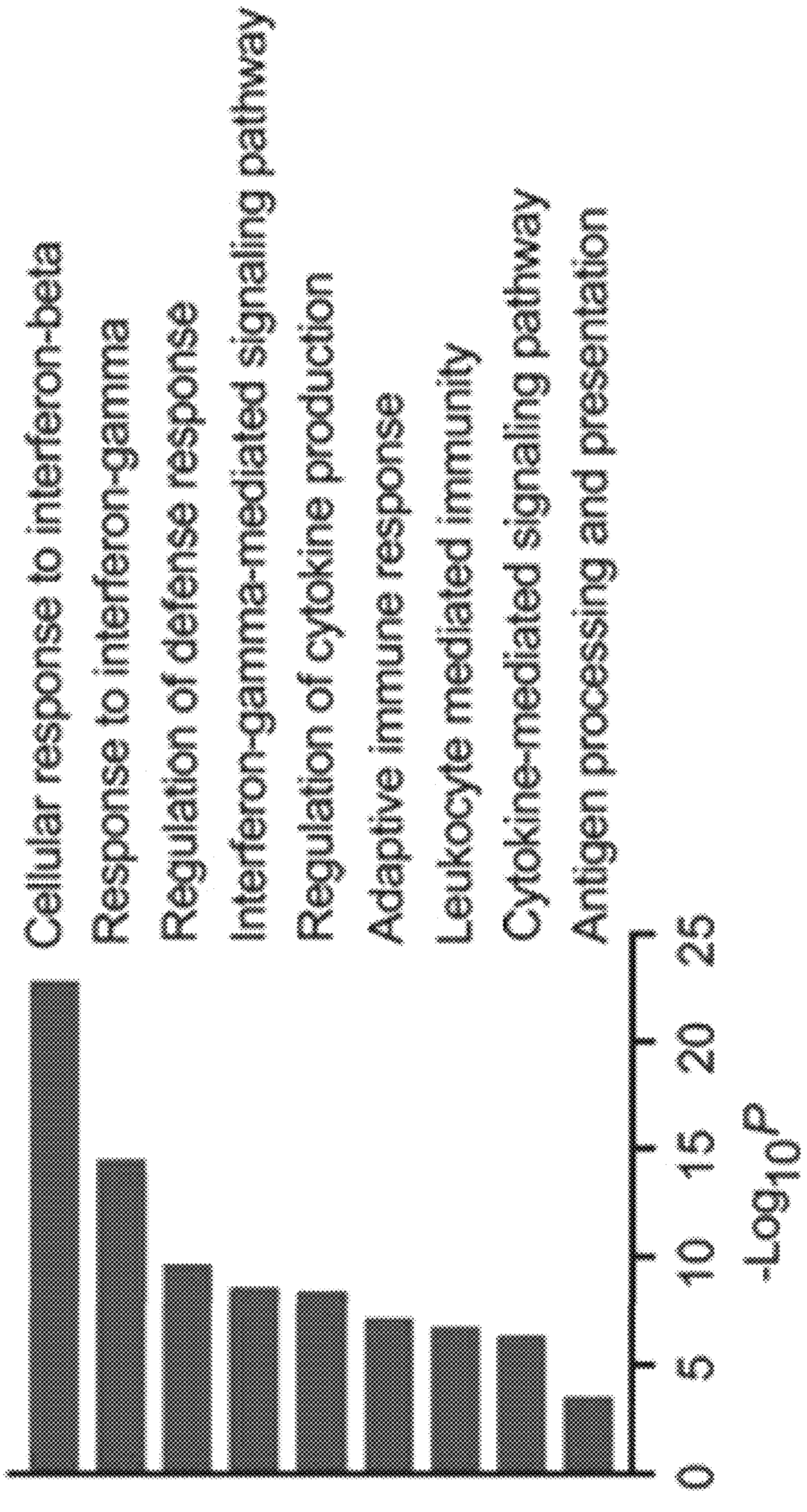
Figure 101F:
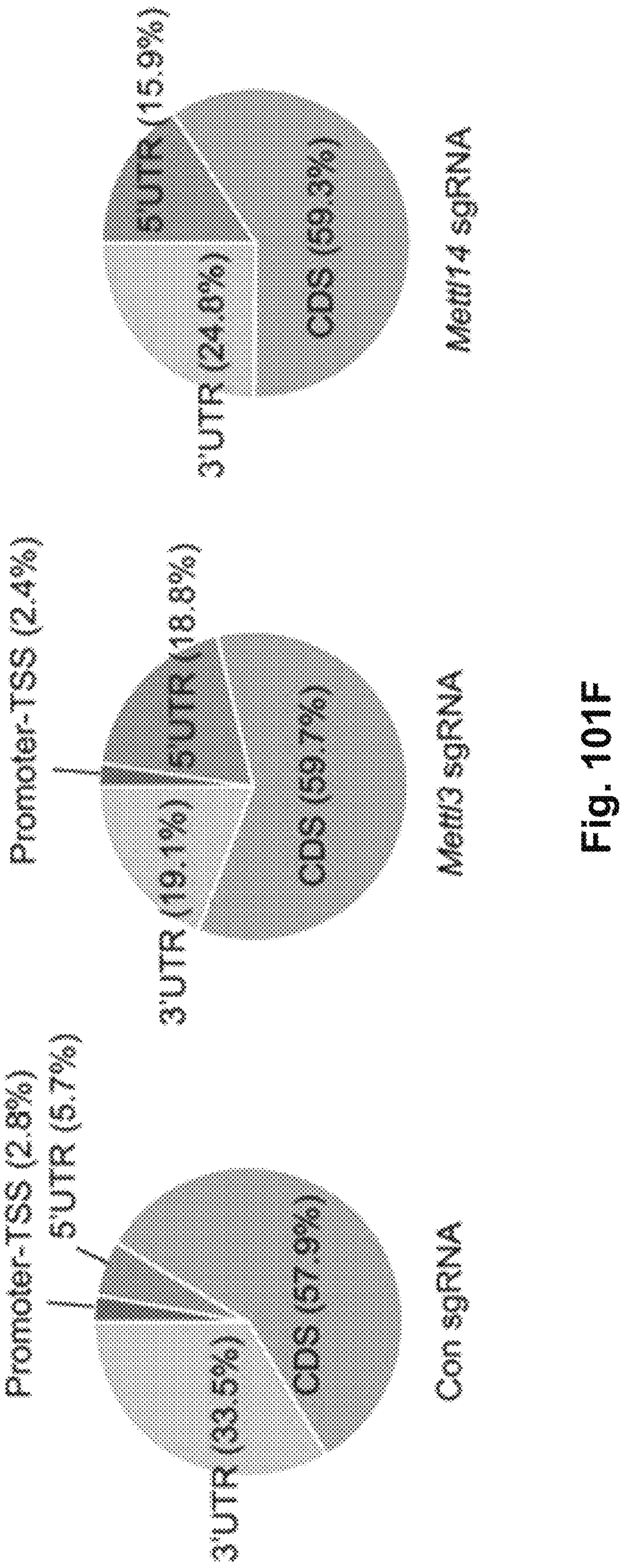
Figure 101G:
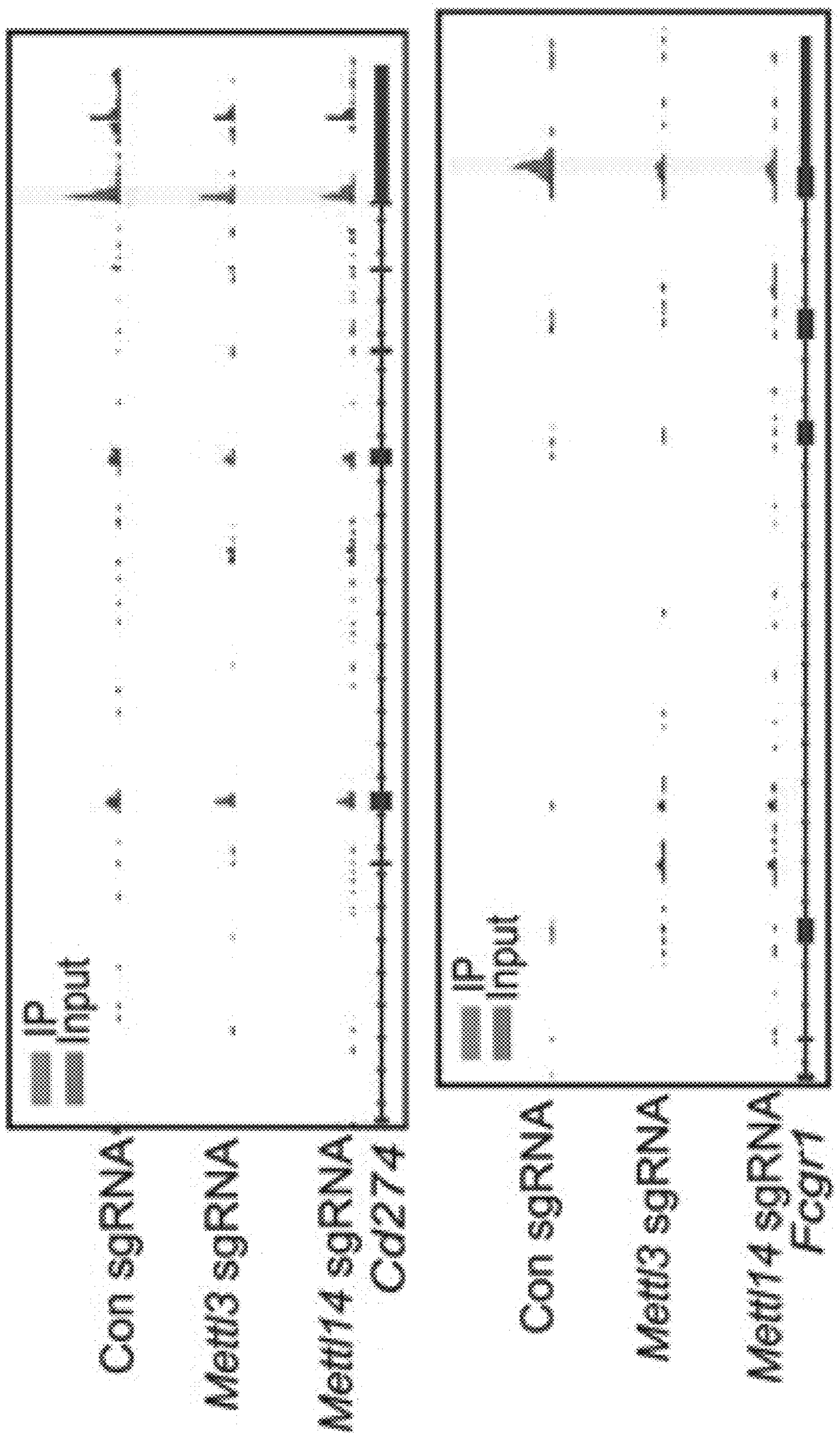
Figure 101G:
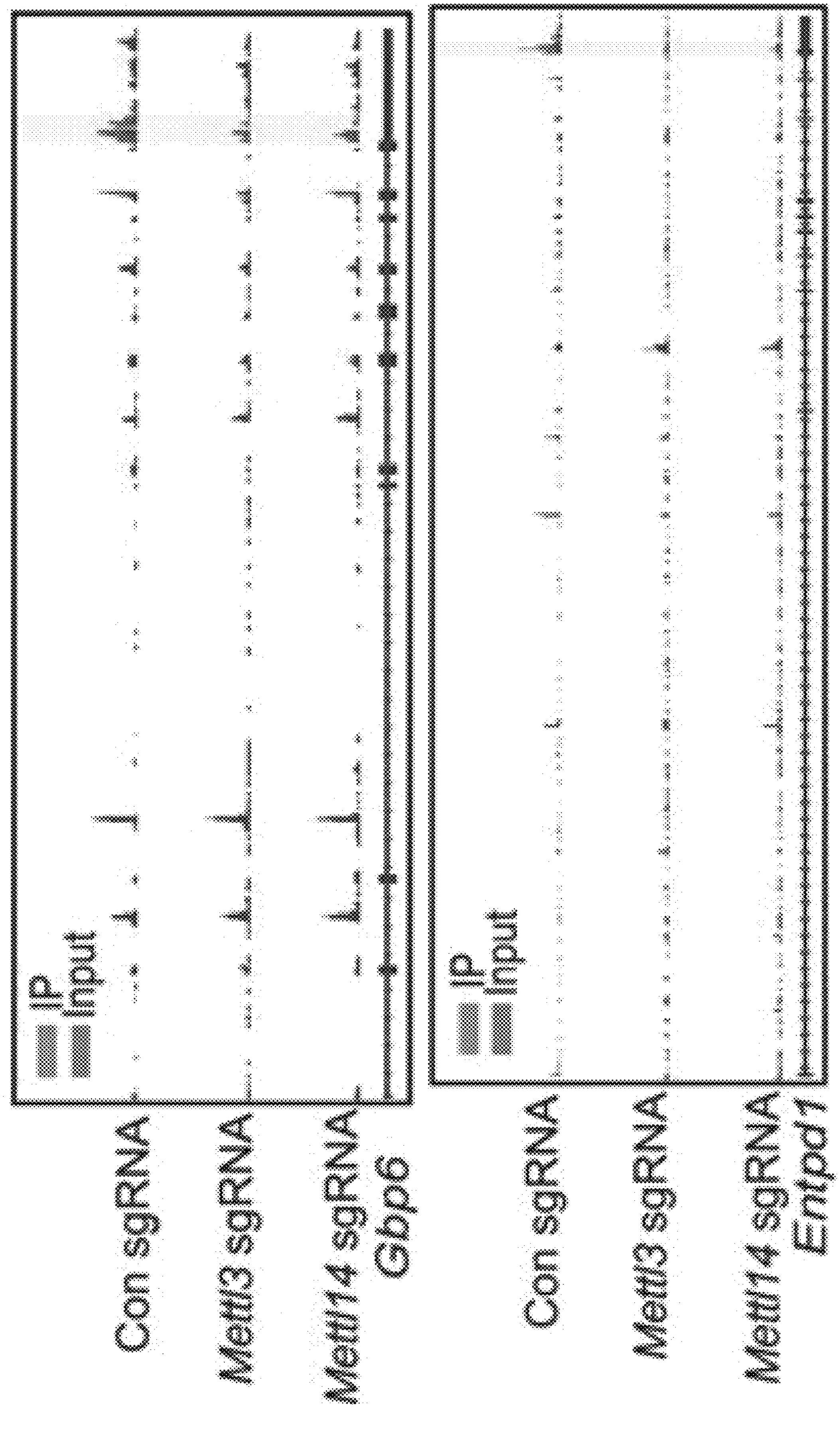

We then asked whether the altered gene expression caused by Mettl3 and Mettl14 depletion was a consequence of suppressed m6A methylation. We first analyzed the total m6A modification levels by dot-blot experiments, which were significantly decreased in the Mettl3 and Mettl14 null tumors compared with control tumors (FIG. 101B). Next, m6A methylome between control and methyltransferase-depleted tumors were compared by antibody-based m6A immunoprecipitation together with high-throughput sequencing (MeRIP-seq) as described previously (Lichinchi et al, 2016a,b; Lichinchi & Rana, 2019). In line with total methylation level changes on mRNA, after combining the peaks in replicates, our analysis identified 16,883 high-confidence m6A peaks in control tumor, whereas 7,701 and 8,794 m6A peaks were identified in Mettl3- and Mettl14-deficient tumors, respectively (FIG. 101C). These results indicate a global loss of m6A methylation in methyltransferase-depleted tumors. To investigate the role of m6A on the regulation of mRNA level, we identified the upregulated, downregulated, and unchanged m6A-containing genes from MeRIP-seq and RNA-seq data. Although the majority of m6A-containing genes (6,728) were unchanged, 64 m6A-containing genes were co-upregulated in both Mettl3- and Mettl14-deficient tumors, whereas only 12 m6A-containing genes were downregulated, which reflected the specific regulatory role of m6A in response to immunotherapy and indicated the destabilization effect of m6A modification on RNA (FIG. 101D). Then, GO analysis was performed on 64 co-upregulated m6A-containing genes, and these enriched pathways were also related to immune response, predominately associated with response to interferons, regulation of cytokine production, adaptive immune response, and defense response, etc. (FIG. 101E, Dataset EV2). Furthermore, depletion of Mettl3 and Mettl14 decreased m6A enrichment in 3'UTR where the majority of m6A control the stability of mRNA, mirrored the upregulated overall genes and m6A-containing genes (FIGS. 101F and 101G). Moreover, previously identified GGACU m6A consensus motif was highly enriched within m6A peaks in the control tumors (FIG. 95D).

Figure 95E:
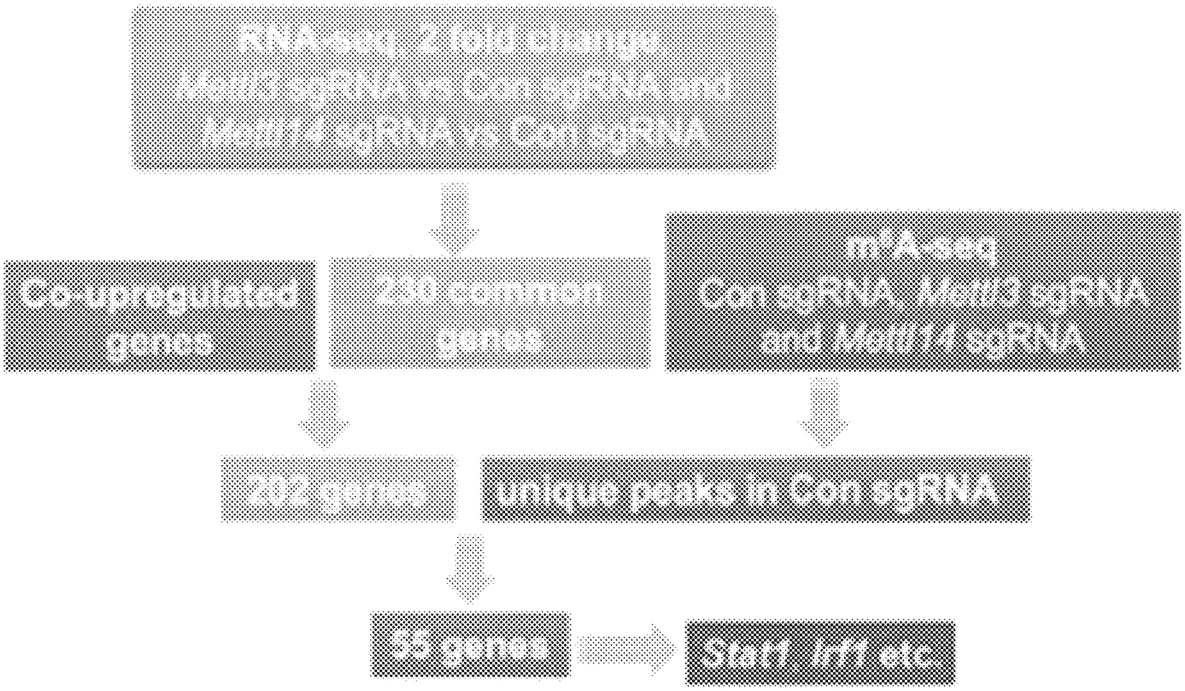
Figure 95F:
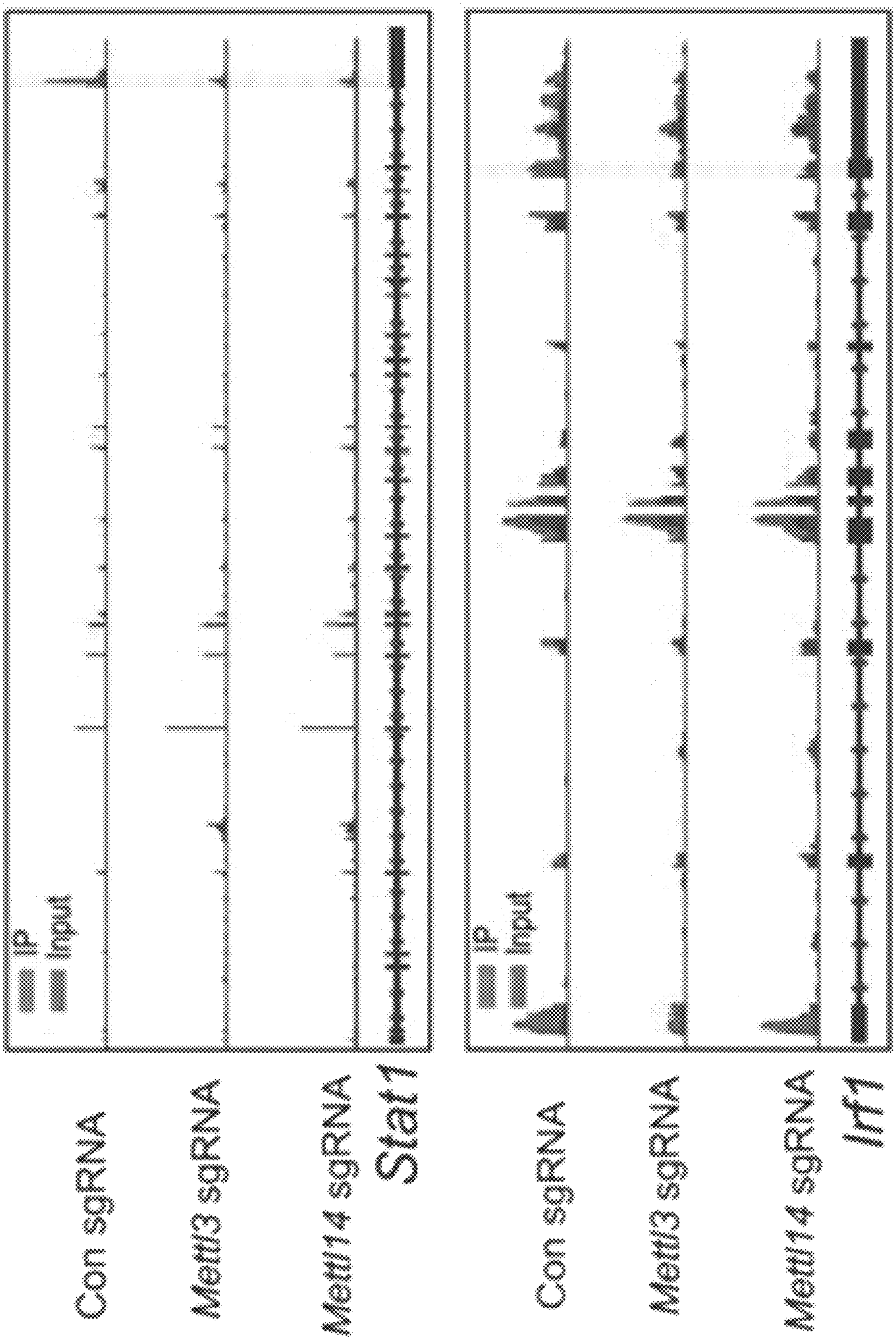
Figure 95G:
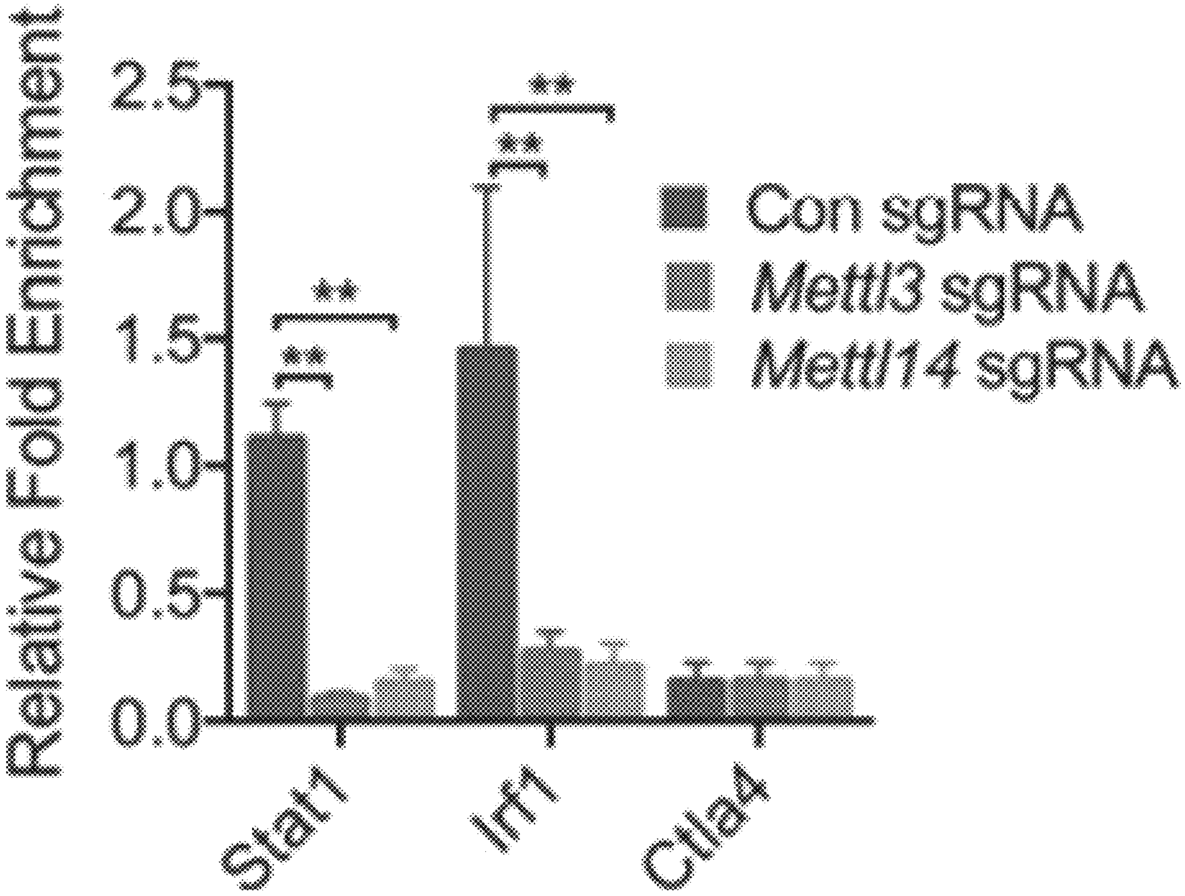
Figure 95H:
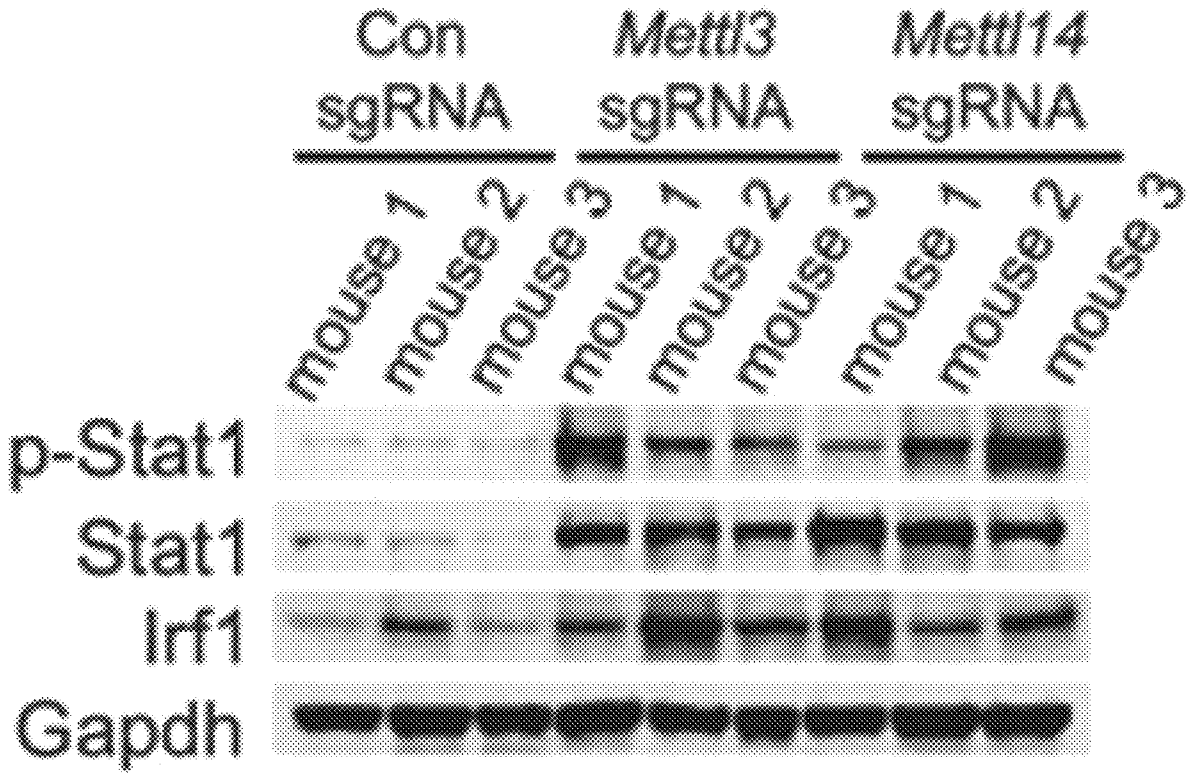
Figure 95I:
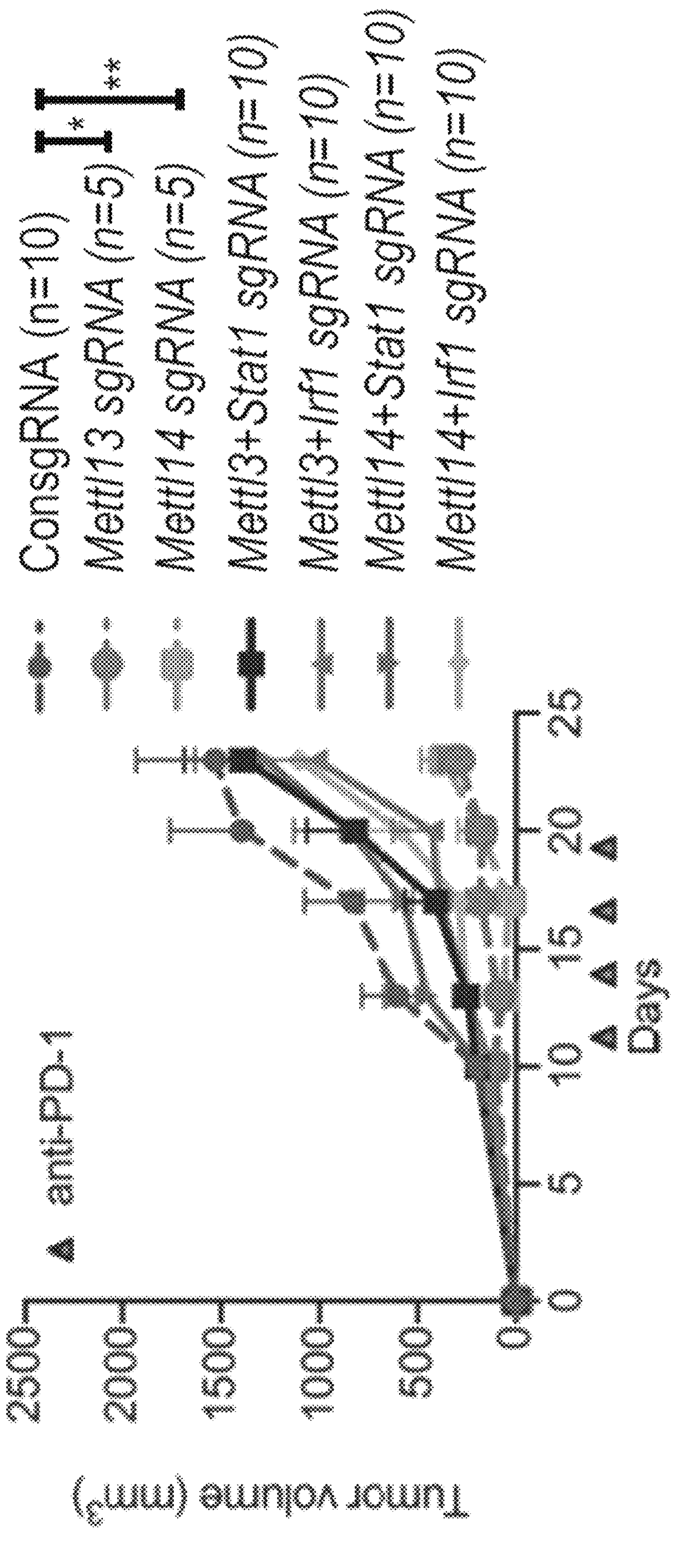
Figure 102A:
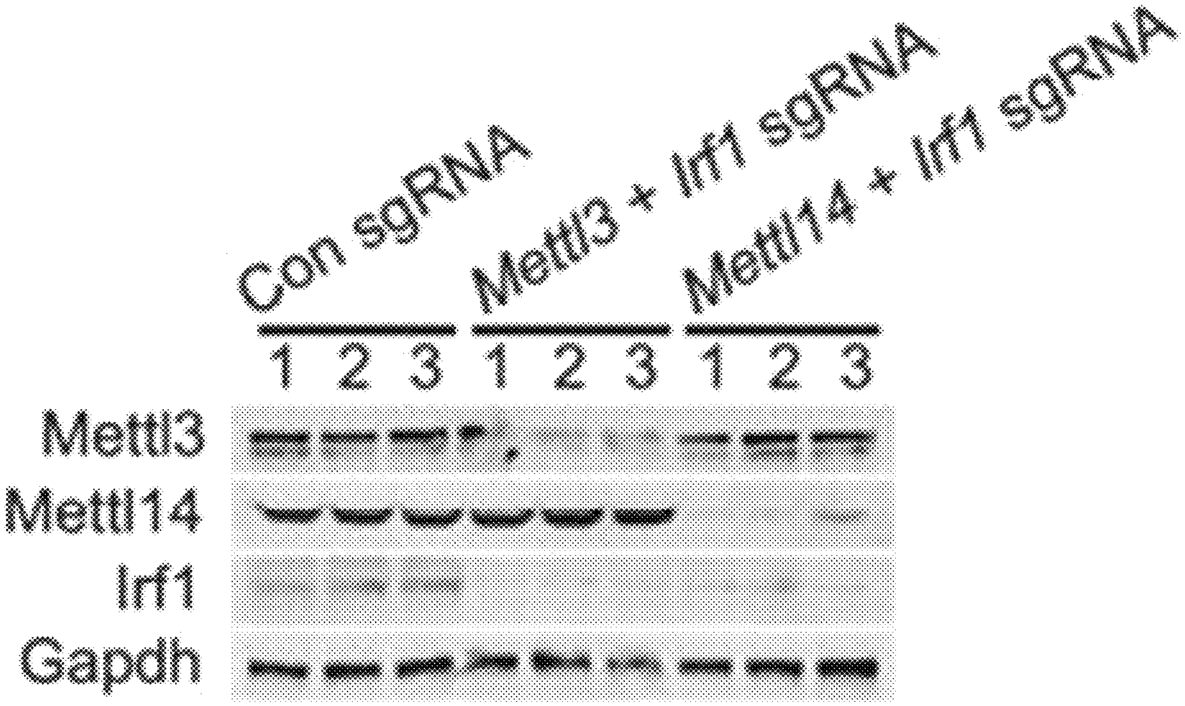
FIG. 102A-102F. Stat1 and Irf1 are targets regulated by Mettl3 and Mettl14.
Figure 102B:
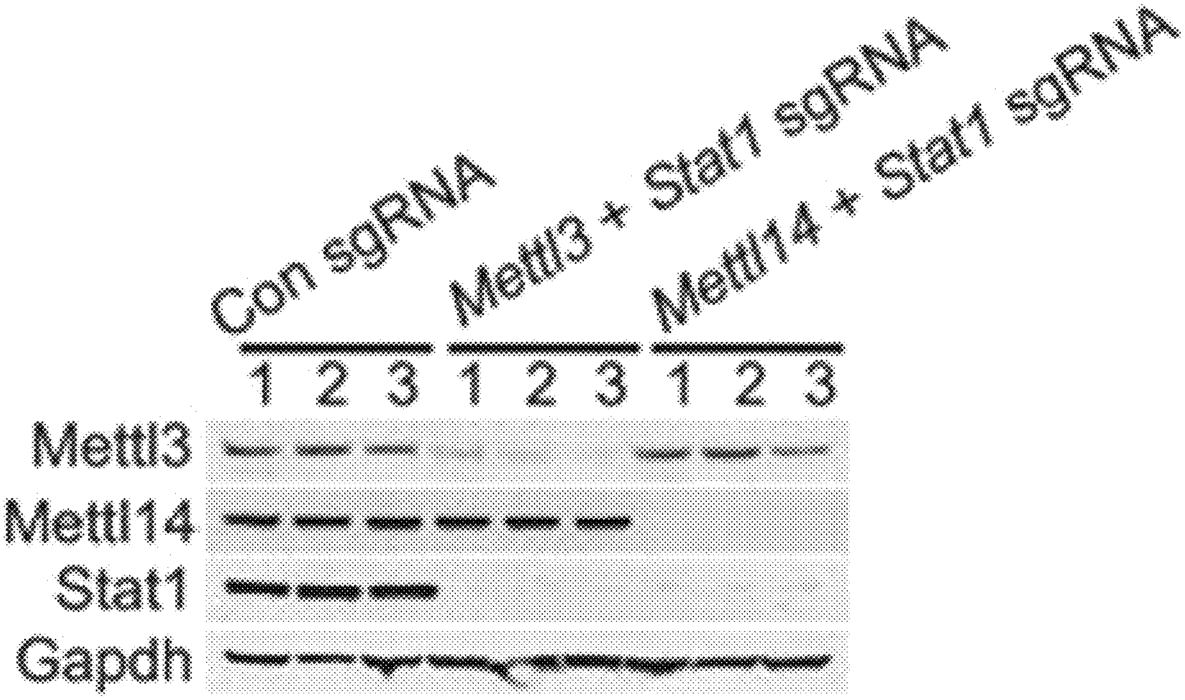
Figure 102C:
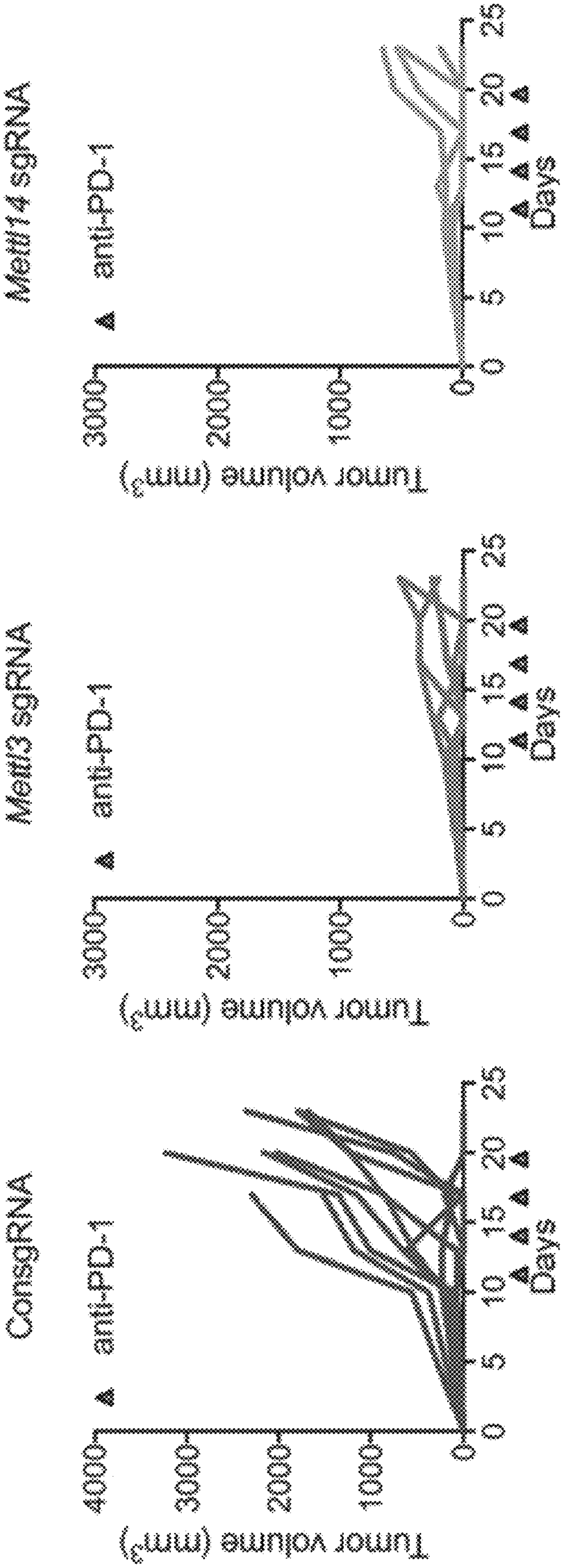
Figure 102D:
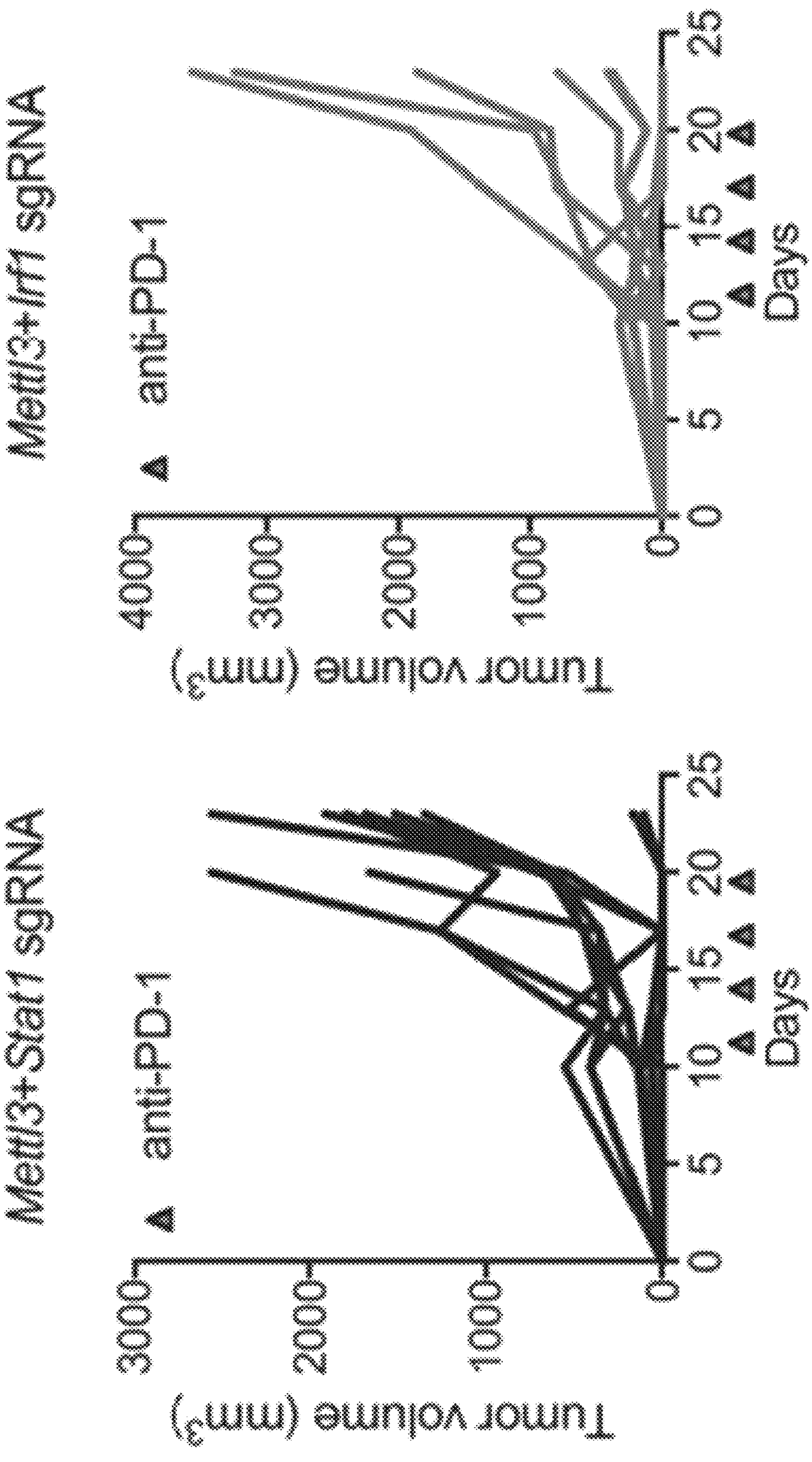
Figure 102E:
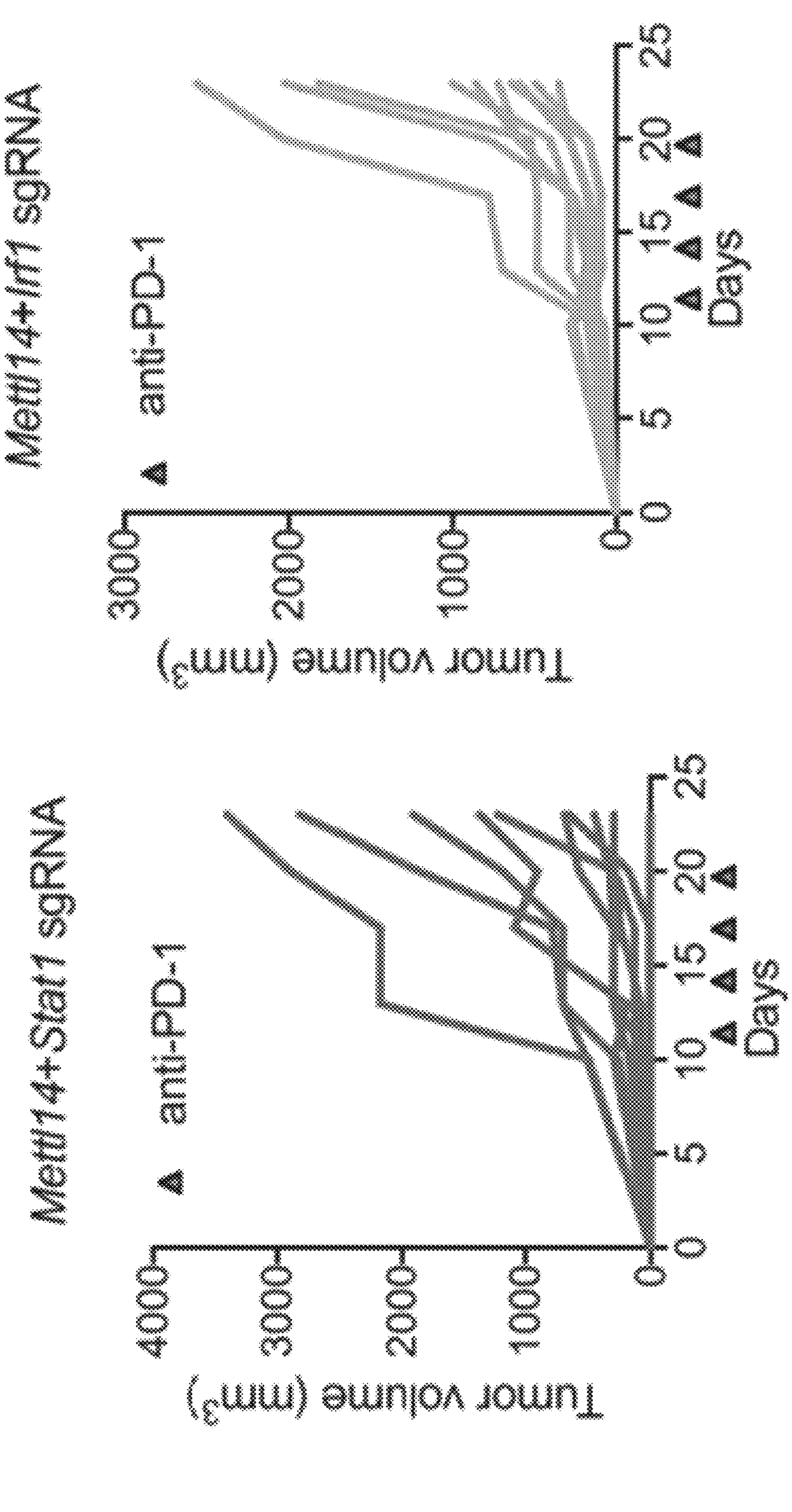
Figure 102F:
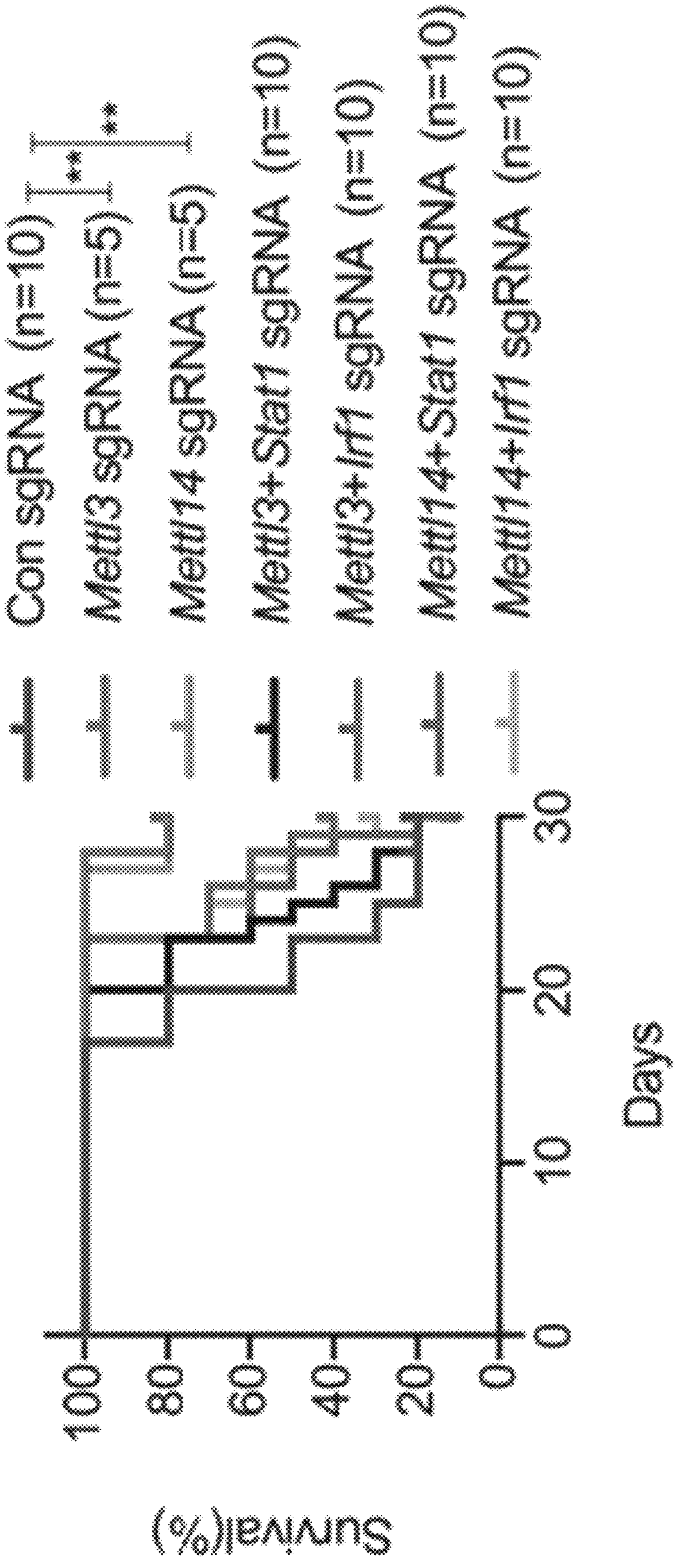

To identify the potential targets of Mettl3 and Mettl14, we developed a workflow scheme outlined in FIG. 95E. We filtered 202 co-upregulated genes enriched in pathways that were found in the RNA-seq with 11,167 m6A peaks which were lost in both Mettl3 and Mettl14 null tumors. This analysis resulted in 55 candidate genes identification including Stat1 and Irf1 (FIG. 95E, Dataset EV3). Given that STAT1 and IRF1 not only act as fundamental role in Janus kinase (JAK)-STAT signaling, which is involved in antiviral and antibacterial response (Ramana et al, 2000; Honda et al, 2006; Pautz et al, 2010), but also play a critical role in IFN-γ signaling (Sharma et al, 2017) and anti-PD-1 response (Garcia-Diaz et al, 2017; Zenke et al, 2018), which results in antitumor effects. Then, we further analyzed our MeRIP-seq data, which showed that Mettl3 and Mettl14 deposit m6A on 3'UTR (near stop codon) of both Stat1 and Irf1, and these two m6A sites have drastically decreased methylation level in Mettl3 and Mettl14 null tumors (FIG. 95F). We further validated these findings by MeRIP-qPCR showing significant decrease in Stat1 and Irf1 mRNA levels in Mettl3 and Mettl14 null tumors demonstrating that our MeRIP-seq data were robust and accurate (FIG. 95G). In agreement with the transcript level of Stat1 and Irf1 validated by qRT-PCR (FIG. 101A), we also observed an increased Stat1, phosphorylated (p-) Stat1 and Irf1 protein levels in the Mettl3 and Mettl14 null tumors (FIG. 95). To further investigate whether the mechanism of enhanced immunotherapy response of Mettl3 or Mettl14 null tumors relies on the increased Stat1 and Irf1, we generated knockout of Stat1 or Irf1 CT26 cells based on the Mettl3- or Mettl14-depleted cells we already had, and then double knockout of Mettl3/Stat1, Mettl3/Irf1, Mettl14/Stat1, or Mettl14/Irf1 CT26 cells were obtained and validated the effect via Western blot (FIGS. 102A and 102B). We next compared the tumor growth of these double knockout cells with tumors lacking Mettl3 or Mettl14 only under immunotherapy. Double loss of Mettl3/Stat1, Mettl3/Irf1, Mettl14/Stat1, and Mettl14/Irf1 reversed the observed effects on Mettl3- or Mettl14-deficient tumor growth (FIGS. 951 and 102C-102E). Moreover, the mice bearing these double knockout of Mettl3/Stat1, Mettl3/Irf1, Mettl14/Stat1, and Mettl14/Irf1 tumors have quite similar survival rate compared to control, whereas shortened survival than depleted Mettl3 or Mettl14 only (FIG. 102F). Thus, these data demonstrate that Stat1 and Irf1 are the main targets regulated by both Mettl3 and Mettl14.

Role of Mettl3 and Mettl14 in Tumor Cells Response to IFN-γ.

Figure 96A:
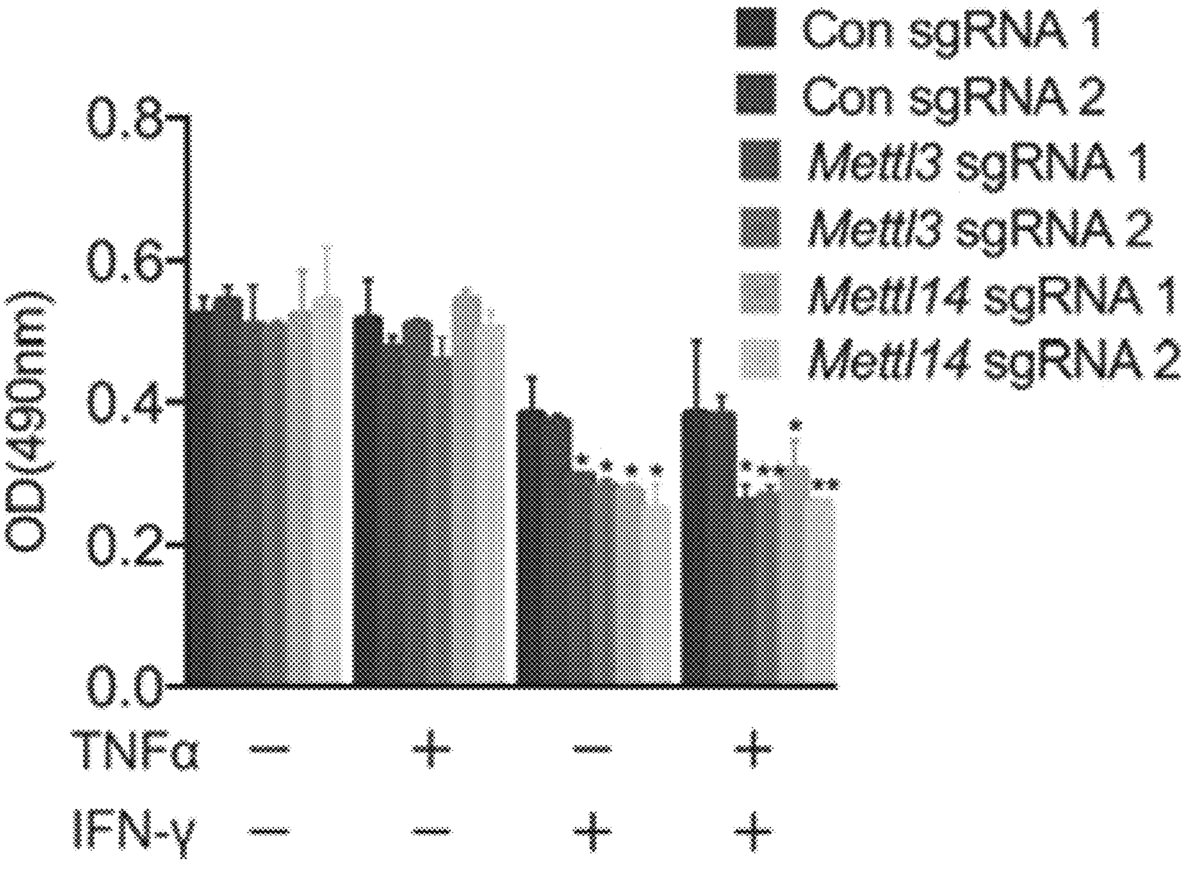
FIG. 96A-96J. Depiction of data showing tumor cells with knockout of Mettl3 or Mettl14 exhibit enhanced response to IFNγ.
Figure 96B:
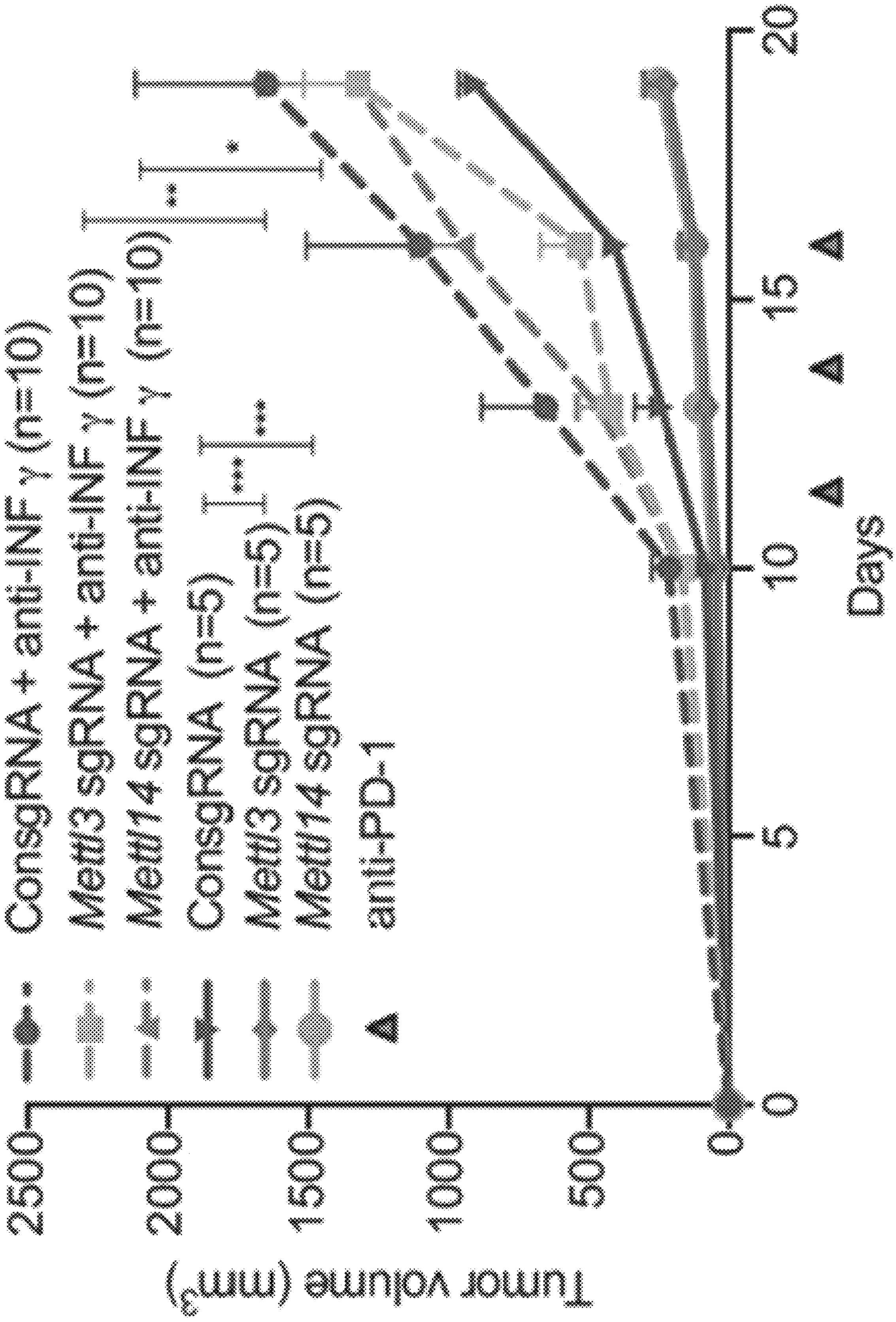
Figure 96C:
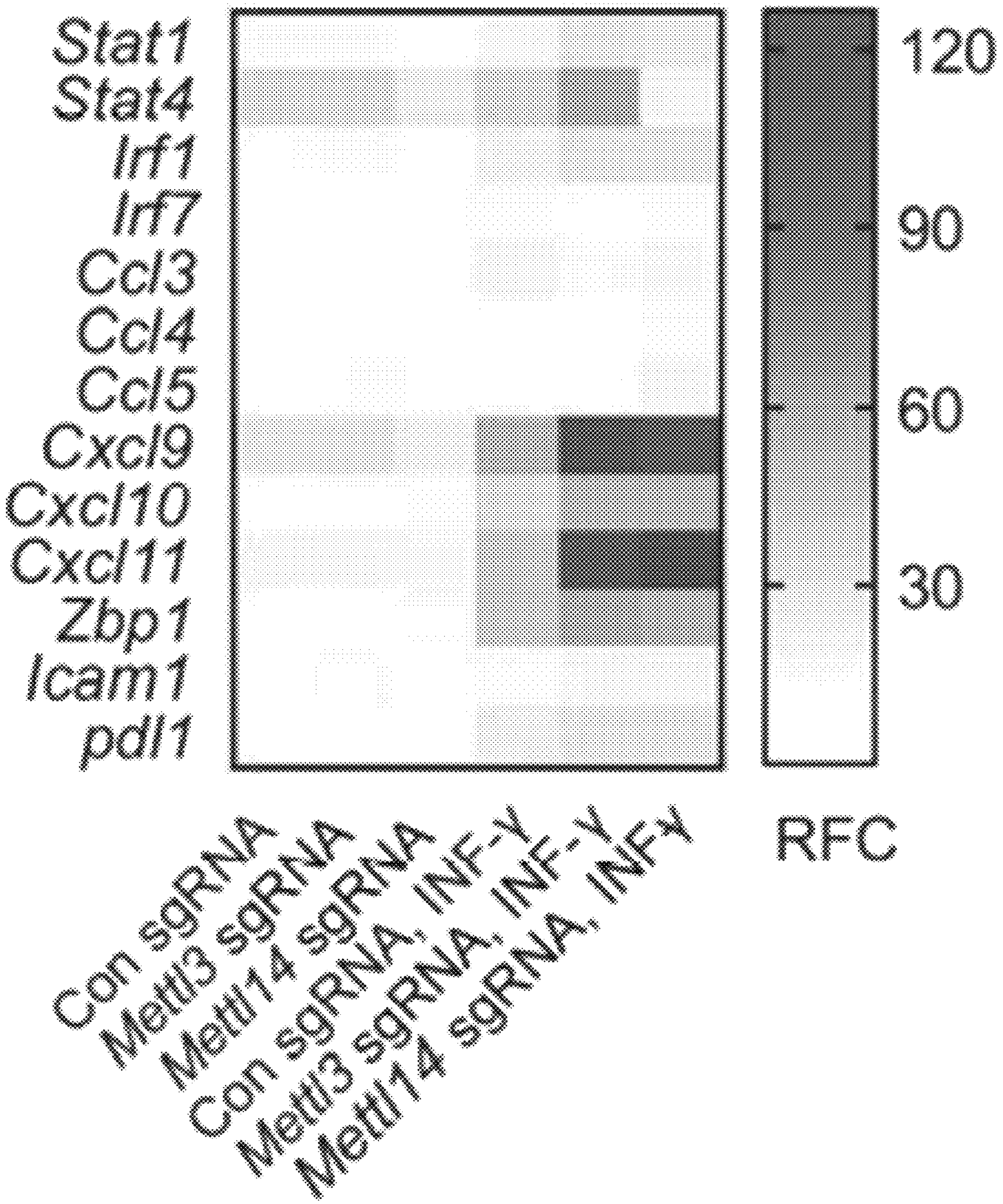
Figure 96D:
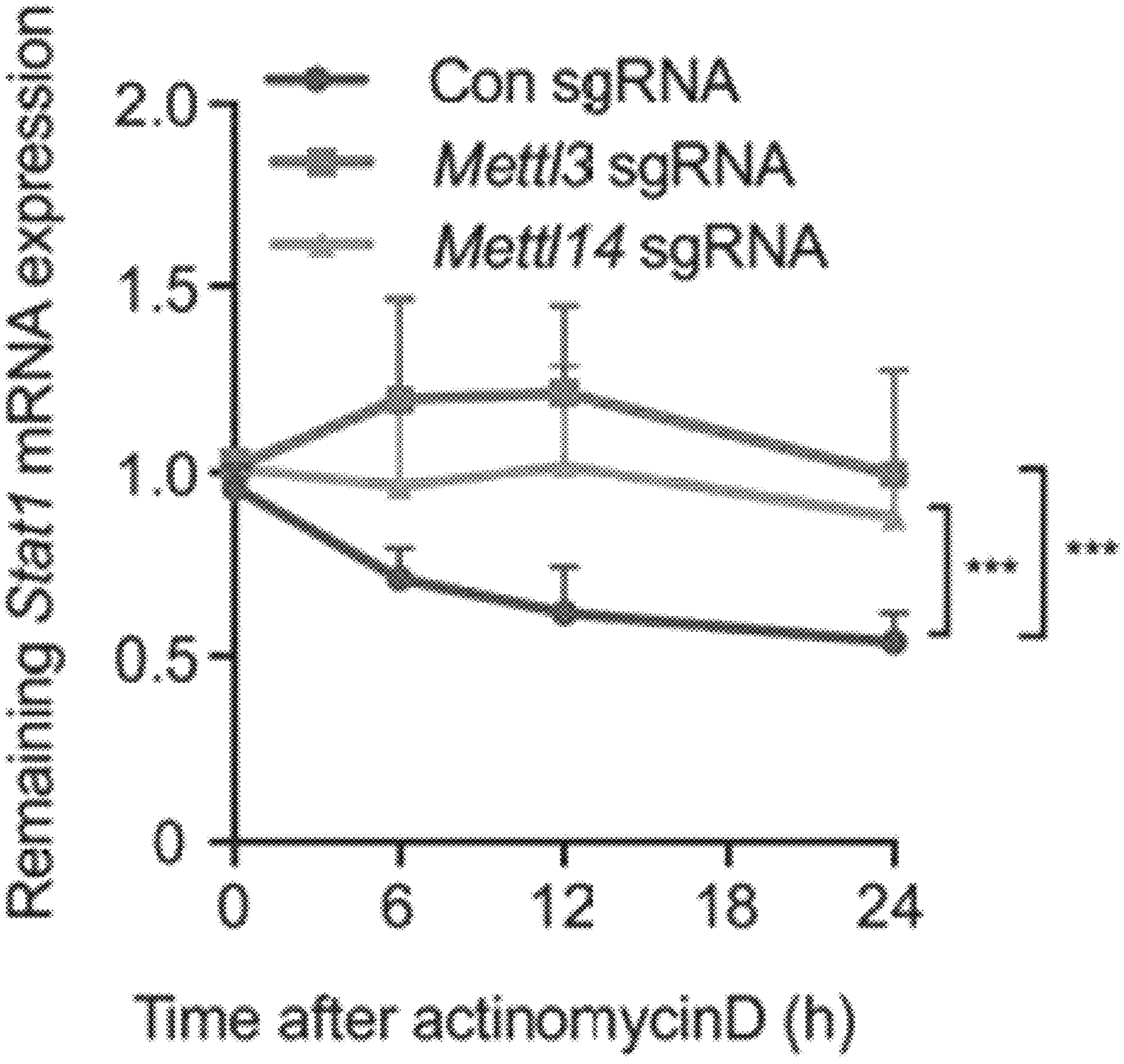
Figure 96E:
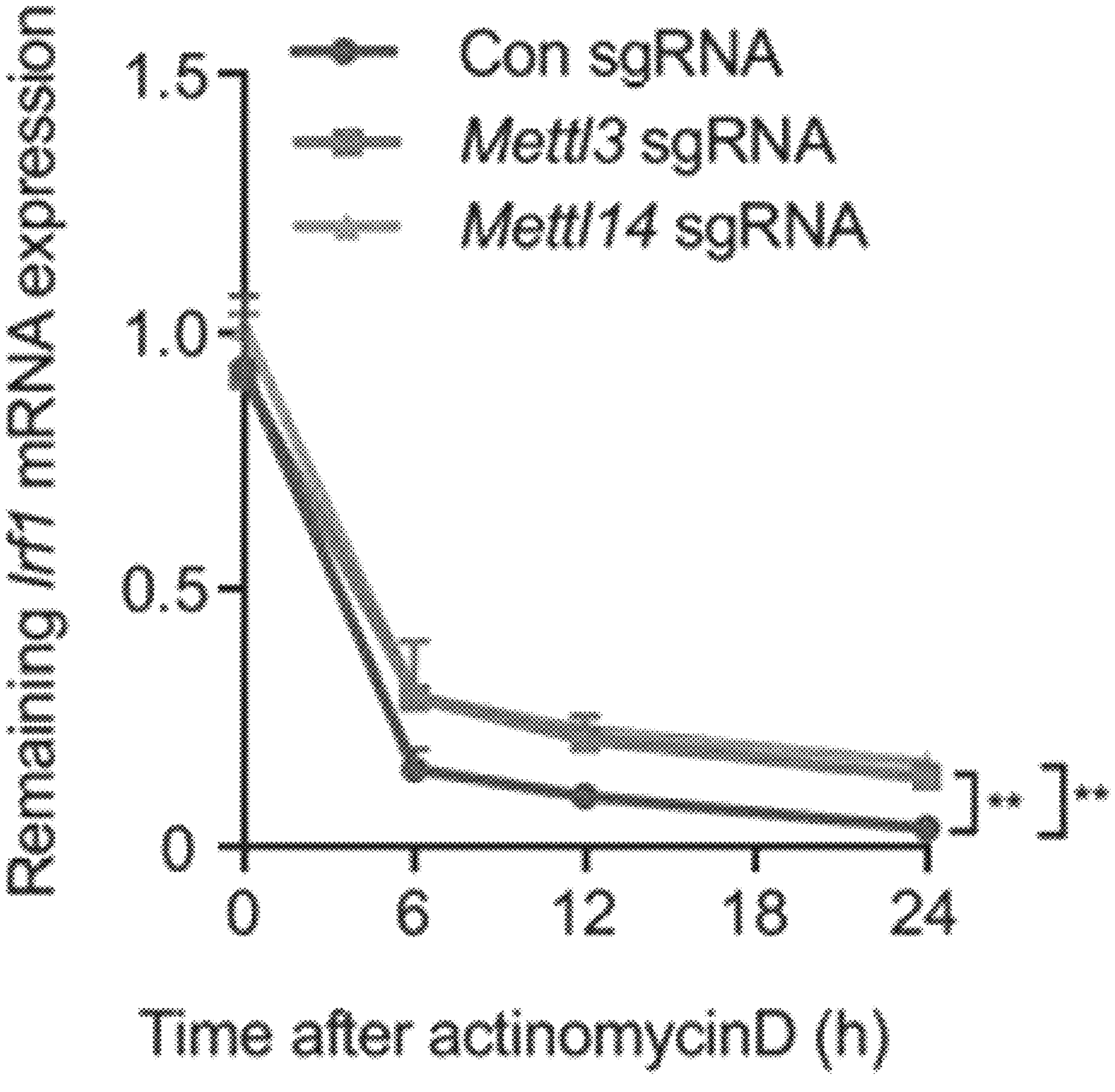

IFN-γ signaling is a key contributor in adaptive and acquired resistance to the checkpoint blockade therapeutic strategy and has impressive effects on antitumor immune responses (Sharma et al, 2017). We next investigated whether depletion of Mettl3 or Mettl14 could improve the response of tumor cells to IFN-7. To this purpose, we first assessed whether IFN-γ has the effect on the growths of cells with knockout of Mettl3 or Mettl14. The results of cellular proliferation assay showed that Mettl3 or Mettl14 deficiency indeed sensitized CT26 cells to IFN-γ, and combined IFN-γ and TNFα-induced growth inhibition, but not TNFα alone, indicating that IFN-γ alone is sufficient to inhibit Mettl3 or Mettl14 deficient cell growth (FIG. 96A). In line with this result, we also found that blocking of INFγ using anti-IFN-γ antibody in BALB/c mice partially reversed the inhibition of tumor growth by Mettl3 or Mettl14 depletion under immunotherapy, suggesting IFN-γ is responsible for the observed Mettl3 or Mettl14 loss-mediated suppression during immunotherapy (FIG. 96B). Furthermore, transcriptional analysis of the Mettl3- or Mettl14-deficient and control CT26 cells with or without the stimulation of IFN-γ by qRT-PCR suggested that an increased expression of IFN-γ pathway genes including Stat1 and Irf1, but no alteration of gene expression in unstimulated conditions (FIG. 96C). Thus, the loss of Mettl3 or Mettl14 increased sensitivity to IFN-γ treatment. To determine whether the increased mRNA levels of Stat1 and Irf1, in Mettl3 and Mettl14 null tumors, are a consequence of enhanced mRNA stability, we determined the half-life of these mRNAs. Control and Mettl3- or Mettl14-deficient cells with stimulation of IFN-γ were treated with actinomycin D for 0, 6, 12, and 24 h, and then, mRNA stability was monitored using qRT-PCR. This analysis revealed that Mettl3- and Mettl14-depleted cells contained more stabilized Stat1 and Irf1 mRNAs than control cells (FIGS. 96D and 96E), and this alternation is consistent with the observation of decreased m6A enrichment in 3'UTR of Stat1 and Irf1 in Mettl3- or Mettl14-depleted tumors (FIG. 95F).

Figure 96F:
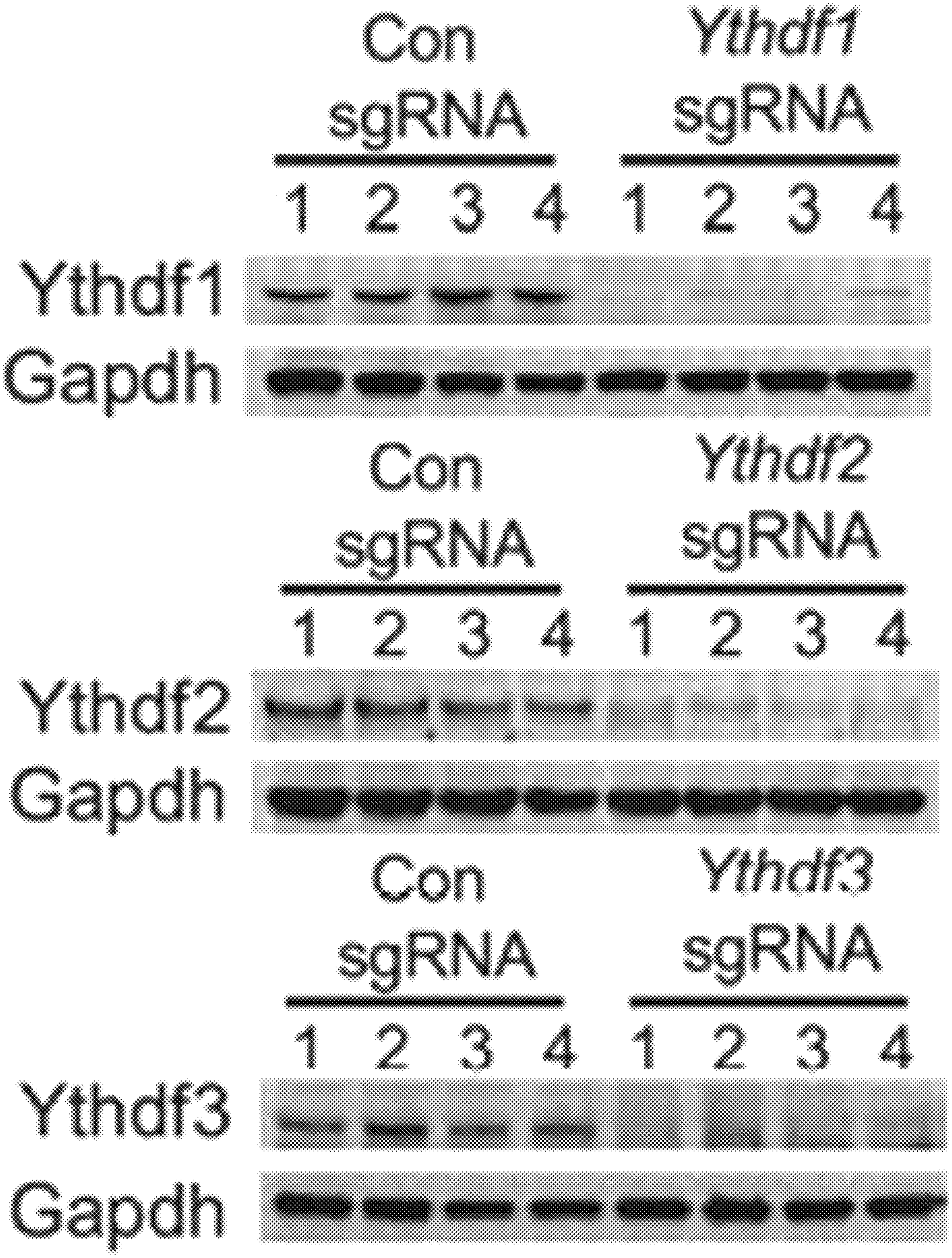
Figure 96G:
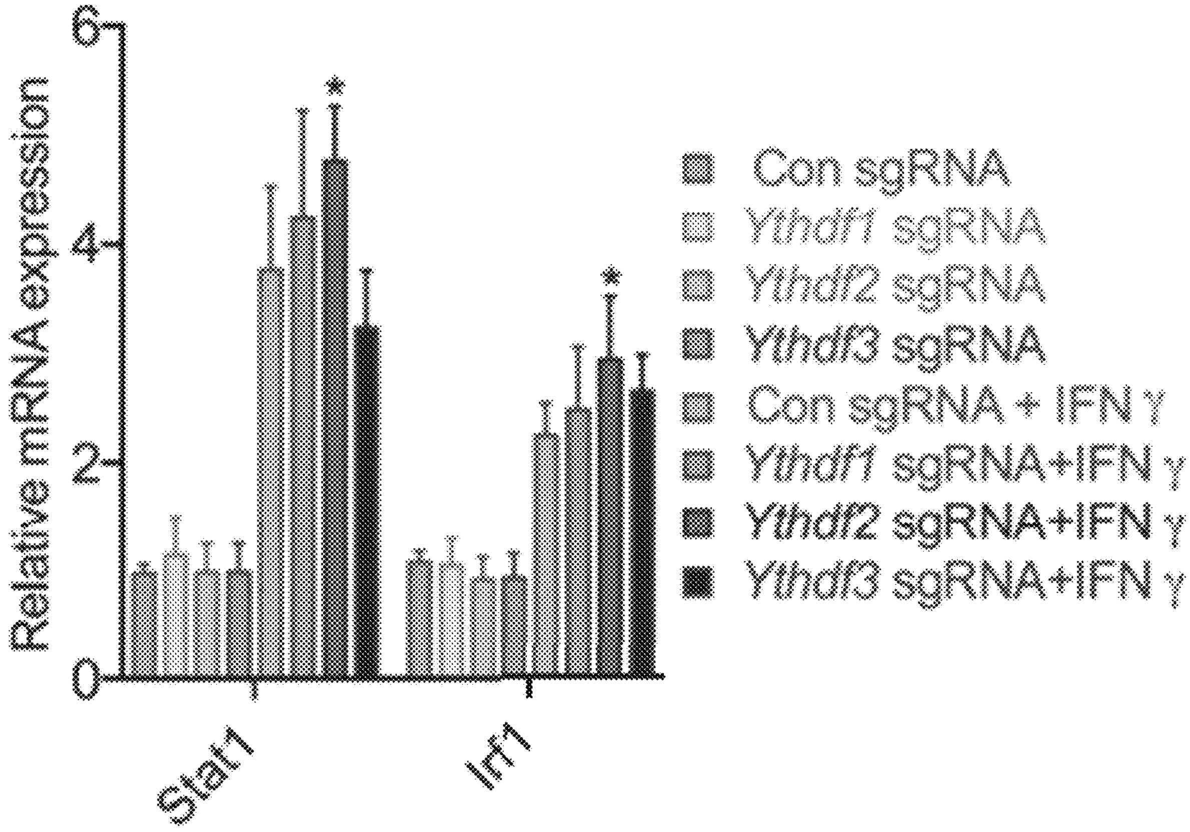
Figure 96H:
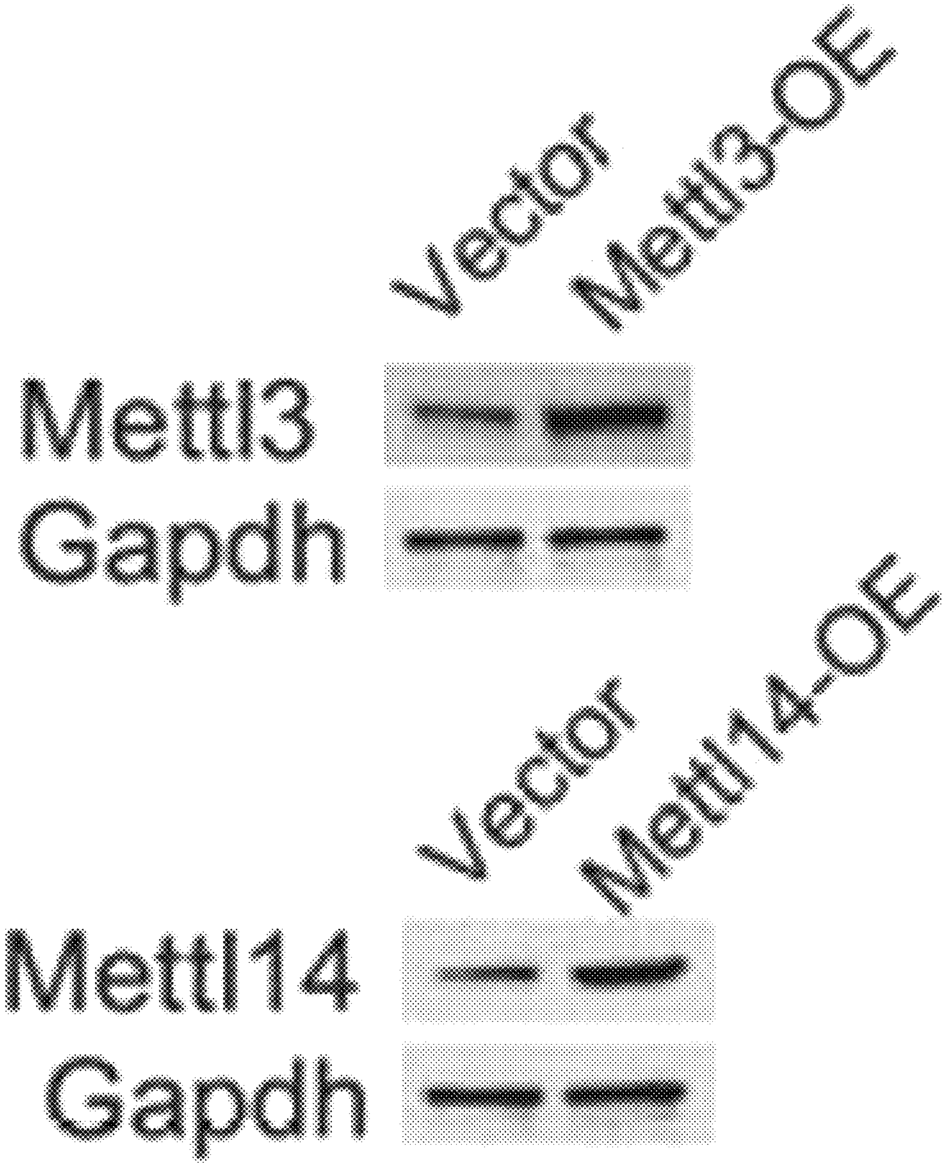
Figure 96I:
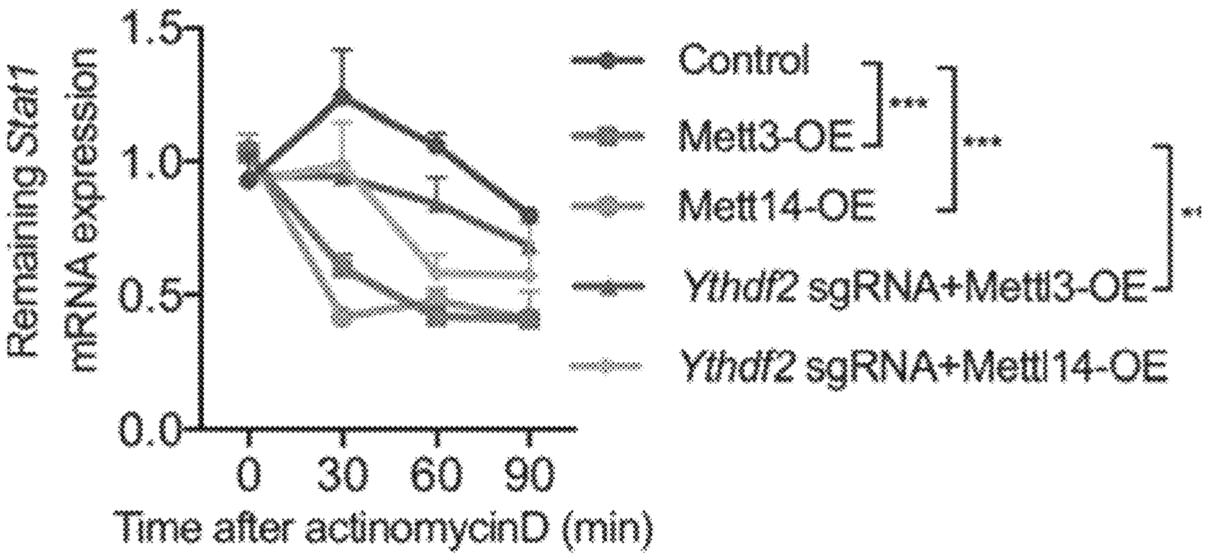
Figure 96J:
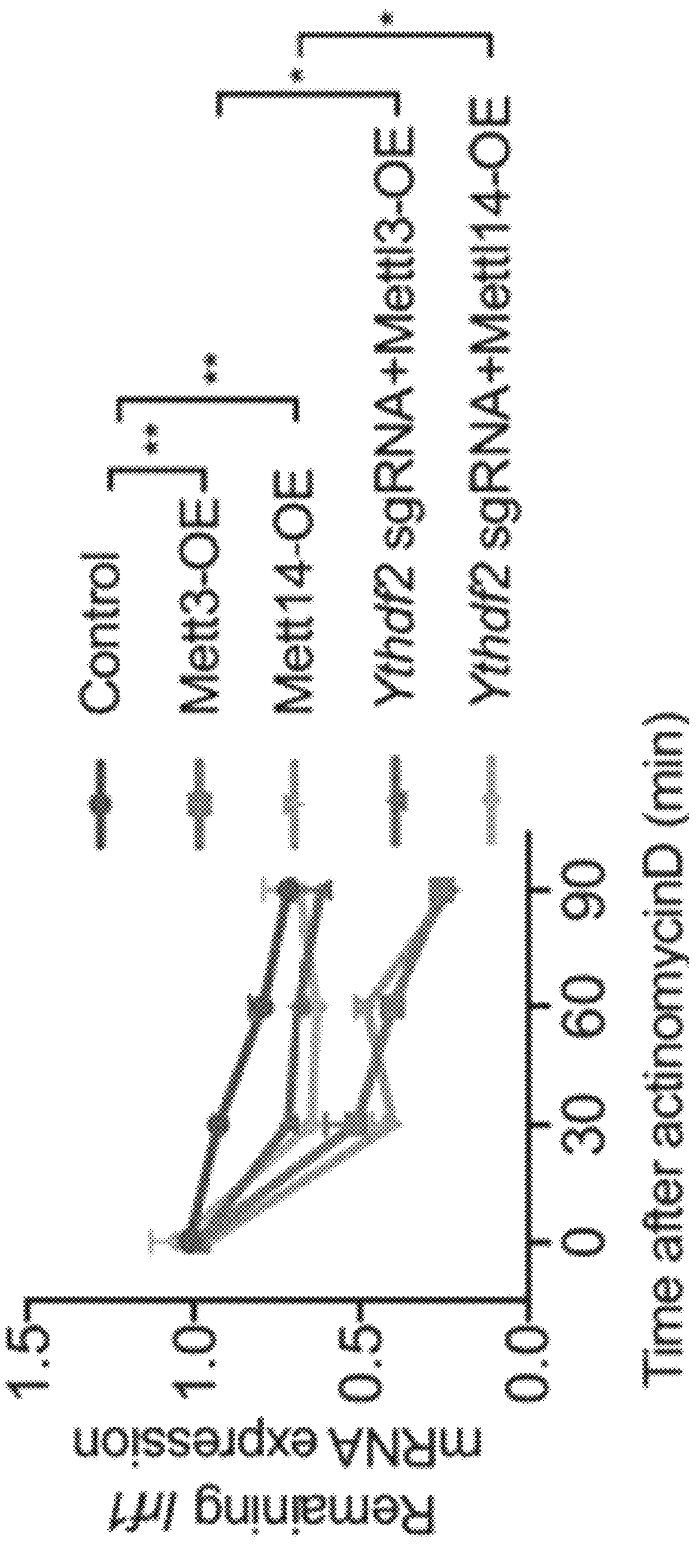

To further explore how Mettl3 and Mettl14 regulate gene expression through its readers, since the downstream functions of m6A rely on its readers-YTH family proteins, we generated knockout of Ythdf1-3 CT26 cells (FIG. 96F) and then analyzed the expression of Stat1 and Irf1 in these Yths-depleted cells with or without treatment of IFN-γ by qRT-PCR. This analysis indicated that loss of Ythdf2 significantly increased the mRNA levels of Stat1 and Irf1 with stimulation of IFN-γ (FIG. 96G). Accordingly, depletion of Ythdf2 partially reversed decreased mRNA stability of Stat1 and Irf1 caused by overexpression of Mettl3 or Mettl14 in cells with stimulation of IFN-γ and then treatment with actinomycin D for 0, 30, 60, and 90 min (FIG. 96H-96J). Altogether, these results support that Ythdf2-mediated mRNA stability controls Stat1 and Irf1 expression of Mettl3 and Mettl14 regulated genes.

METTL3 and METTL14 were Negatively Correlated with STAT1 in Human pMMR-MSI-L CRC Colon Tissue.

Figure 97A:
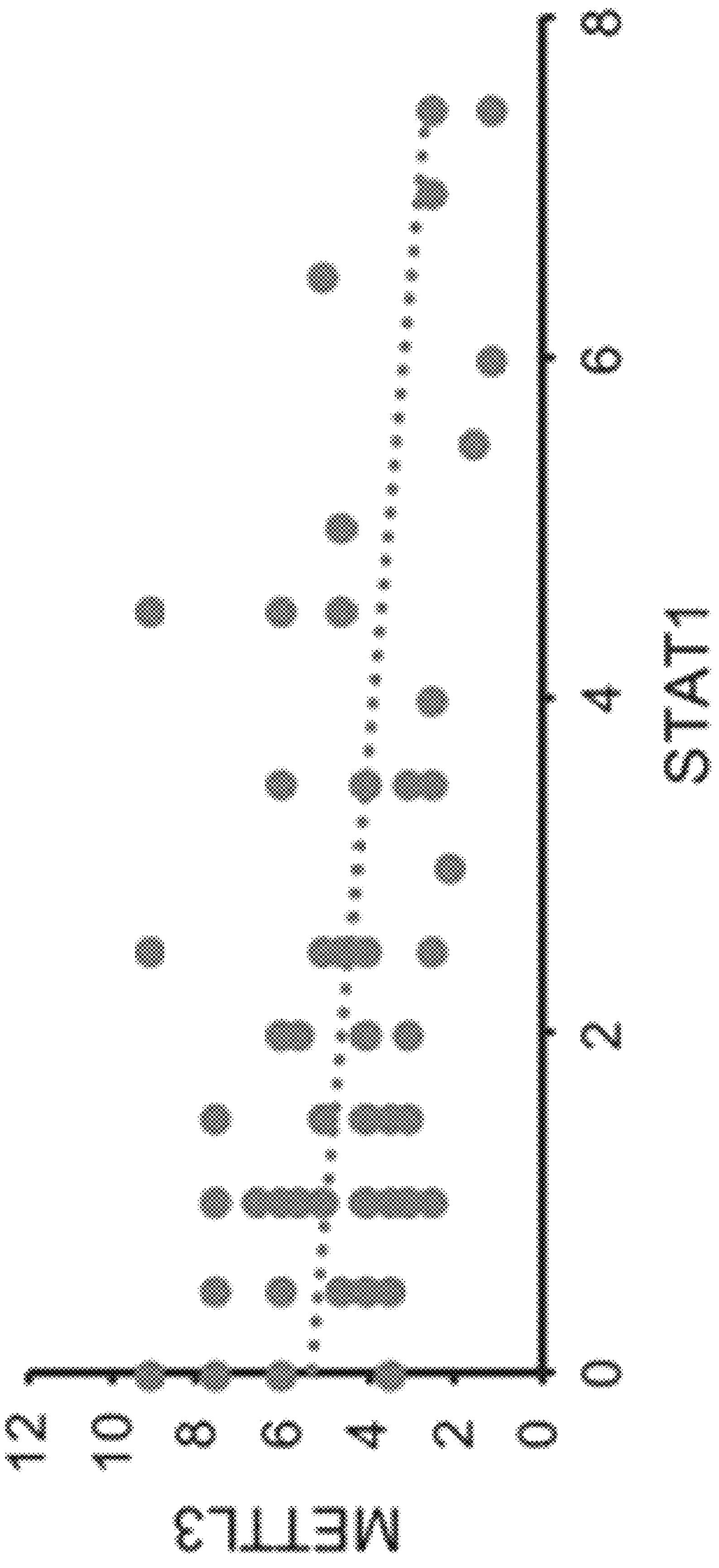
FIG. 97A-97C. Depiction of data showing the negative correlation of METTL3, METTL14, and STAT1 in human pMMR-MSI-L CRC colon tissue.
Figure 97B:
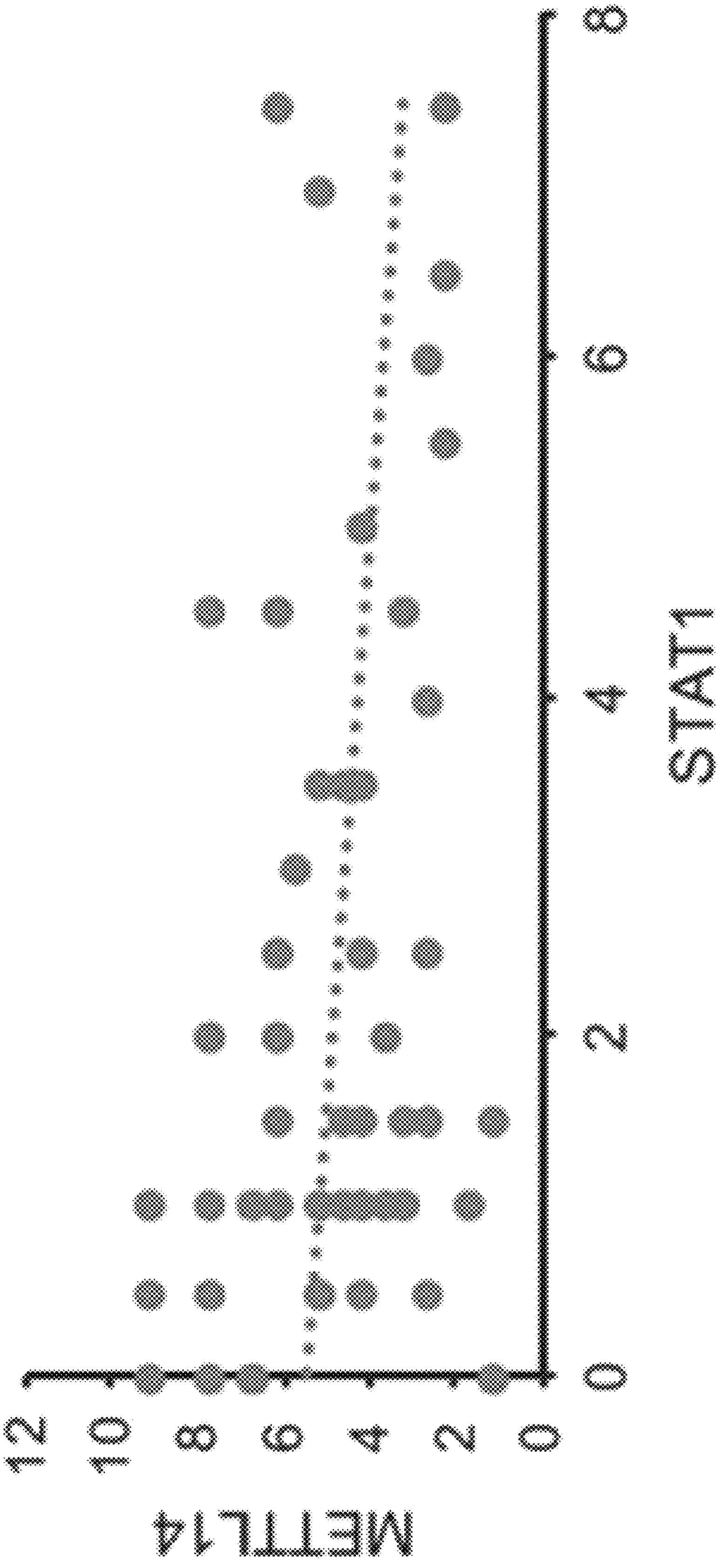

In agreement with our results of mouse model, we found a negative correlation between METTL3 or METTL14 and STAT1 in 59 patients with pMMR-MSI-L CRC tumors using immunohistochemistry (FIGS. 97A and 97B). Together, these results identify METTL3/14-STAT1 axis as a regulator of IFN-γ in pMMR-MSI-L CRC tumors and suggest that METTL3 and METTL14 inhibition could be a viable new strategy to sensitize these CRC tumors which are refractory to currently available immunotherapy treatments.

Discussion

Figure 97C:
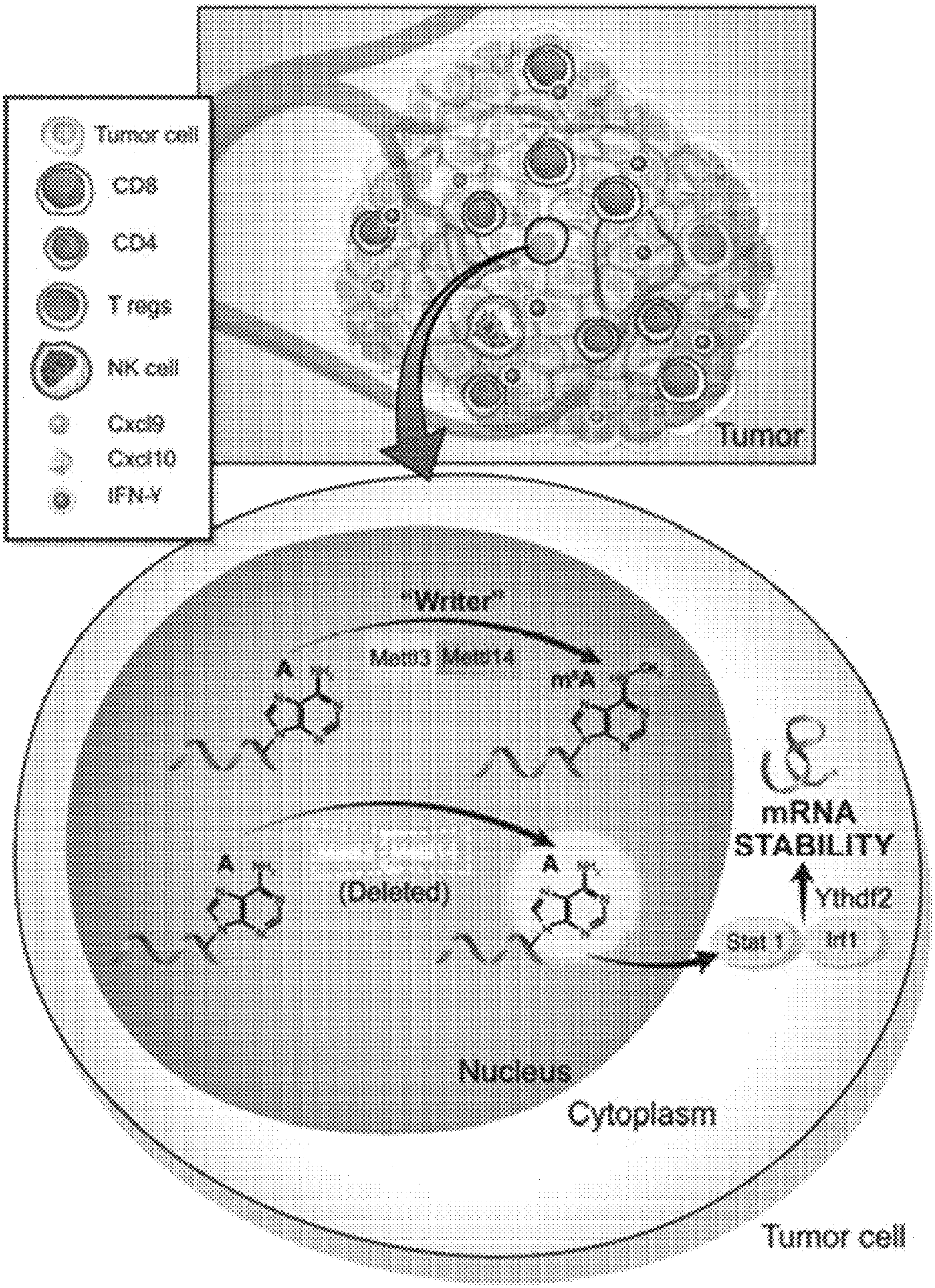

Overall, our work demonstrates that RNA-modifying enzymes play a vital role in tumor survival during immunotherapy. Depletion of Mettl3 or Mettl14, core subunits of RNA methyltransferase, significantly slowed tumor growth and prolonged the survival in mouse bearing CT26 colorectal carcinoma and B16 melanoma with anti-PD1 or anti-PD1/GVAX treatments, respectively. Outside tumor cells, the elevation of CD8+ T cells in both Mettl3 and Mettl14 null tumors and NK cells in Mettl14 null tumors, accompanied by the increased production of cytokines and chemokines including IFN-γ, Cxcl9, and Cxcl10 were detected, demonstrating the immune system and tumor microenvironment were altered under the abolishment of tumor m6A mRNA transferases. Inside tumor cells, the changes of the transcriptome profile in methyltransferase-depleted tumor showed the activation of IFN-γ signaling was pivotal to re-sensitize tumor cells to immunotherapy. Epitranscriptome analysis indicated the loss of m6A modification on the transcripts in IFN-γ-Stat1-Irf1 axis contributed to their stabilization mediated by m6A reader Ythdf2 thereby account for the upregulation of IFN-γ signaling and the change of tumor microenvironment. Furthermore, the depletion of Mettl3 or Mettl14 increased sensitivity to IFN-γ in tumor cells (FIG. 97C). Lastly, based on the in vivo and in vitro observations, a negative correlation between METTL3/14 and STAT1 expression was also revealed in pMMR-MSS colorectal carcinoma patients to further substantiate the clinical value of our discovery.

It is worth noting that depletion of Mettl3 or Mettl14 alone did not affect tumor growth in mice, highlighting the unique role of m6A in the tuning of certain pathways regulating immunotherapy. Previous studies reported that Mettl3 or Mettl14 depletion alone was able to affect cell proliferation or tumor growth in leukemia (Barbieri et al, 2017; Vu et al, 2017; Weng et al, 2018), glioblastoma (Cui et al, 2017), and hepatocellular carcinoma (Ma et al, 2017; Chen et al, 2018). In this study, however, the effect of RNA m6A modification machinery loss on tumors only emerged under immunotherapy. These findings highlight that the function of m6A mRNA modification varies under different physiological context and the role it plays to help tumors undergo specific external stresses like that from the immune system.

IFN-γ-Stat1-Irf1 axis plays an essential role in the interaction between tumor and immune system. The protective role of IFN-γ against implanted, chemically induced, and spontaneous tumors have been recorded in numerous studies since the mid-1990s (Dunn et al, 2002). At the molecular level, our MeRIP-seq and RNA-seq revealed the suppression of m6A on the 3'UTR of Stat1 and Irf1 mRNA coupled with the elevation of their abundance. Accordingly, we also observed increased mRNA expression of Cxc19, Cxcl10 and production of Cxcl9, and Cxcl10 in tumors. Given that the extracellular secretion of Cxcl9-mediated lymphocytic infiltration to the tumor and suppressed tumor growth (Gorbachev et al, 2007), and Cxcl10 level was positively correlated with the number of circulating lymphocytes (Sridharan et al, 2016). Thus, it is likely that the activation of these chemokine genes and the elevation of their level within the intratumor environment, discovered in this study, accounts for the increased CD8+ TILs and intratumor IFN-γ level, explaining the tumor inhibition by PD-1 antibody treatment.

Interestingly, a recent study reported that the knockdown of FTO sensitized melanoma cells to IFN-γ through the increase of m6A enrichment and consequently destabilization of transcripts encoded by melanoma promoting genes, including PD-1, CXCR4, and SOX10 (Yang et al, 2019). At a first glance, this may seem that there is a discrepancy about the role that m6A modification machinery plays in tumor immunosurveillance that could be explained by the use of different experimental mouse model (Yang et al, 2019), but more importantly, our work on Mettl3/14 and the reported FTO findings (Yang et al, 2019) underscore the significance of epitranscriptomic regulation of molecular networks in response to certain stress conditions during tumorigenesis and tumor microenvironment altered by immunotherapy. Three recent reports further support the notion that the role of RNA modification machinery to regulate mechanism of gene expression is more complex that previously envisioned. (a) Changes in m6A mRNA levels by knockdown of either METTL14 or ALKBH5 inhibited cancer growth and invasion (Panneerdoss et al, 2018). ALKBH5/METTL14 formed a positive feedback loop with RNA stability factor HuR to regulate the stability of target transcripts. Further, hypoxia altered the level/activity of RNA modification machinery and expression of specific transcripts in cancer cells (Panneerdoss et al, 2018). (b) By developing and employing a new method, m6A-Crosslinking-Exonuclease-sequencing (m6ACE-seq), to map transcriptome-wide m6A and m6Am at quantitative single-base-resolution, Goh and colleagues discovered that both ALKBH5 and FTO maintained their regulated sites in an unmethylated steady-state (Koh et al, 2019). (c). The role of ALKBH5 in enhancing anti-PD-1 immunotherapy involves regulation of lactate content in the tumor microenvironment and the composition of tumor-infiltrating Treg and myeloid-derived suppressor cells (Li et al, 2020). Remarkably, ALKBH5 inhibition by a small molecule resulted in a similar phenotype and sensitized tumors to immunotherapy, indicating future translational potential of targeting m6A regulating machinery in cancers (Li et al, 2020). However, these studies do not exclude the possibility that specific RNA modifications are written and erased under various stress conditions by translocation of enzymes. Therefore, dynamic imbalance of m6A modification machinery location and function may affect the tumor progression and immunotherapy responses.

Despite the success of immunotherapy in the past decade, pMMR-MSI-L subtype colorectal cancer, the vast majority of CRC patients carried, failed to benefit from any immunotherapy alone (Ganesh et al, 2019). The lack of recruitment of immune cell to the tumor seems the primary reason since microsatellite instability-high (pMMR-MSI-H) colorectal cancer (Llosa et al, 2015), another subtype of CRC that responds well to immunotherapy, is featured by an interferon-rich microenvironment and heavily infiltrated immune cells like CD8+ TILs, CD4+(Th1) TILs, and macrophages (Deschoolmeester et al, 2011). Our results revealed that suppression of m6A modification sensitized tumors to immunotherapy by altering the tumor microenvironment and recruitment of CD8+ TILs. Notably, the growth inhibitory effects in Mettl3/14-depleted tumors we observed in the study were comparable to that of multiple combinatorial immunotherapy regimens (anti-PD-1+anti-CTLA-4). Thus, it is exciting to imagine the possibility that our study opens doors to combine immunotherapy with newly developed methyltransferase inhibitors for CRC therapy.

Taken together, we found the suppression of m6A modification enhanced response to immunotherapy in colorectal carcinoma and melanoma. This sensitization effect in CRC tumors is mediated by the elevated Stat1 and Irf1 expression whose mRNA transcripts were stabilized by the decreased m6A enrichment. This study demonstrates the essential role of m6A writer in the maintenance of tumor surveillance to immunotherapy. The inhibition of m6A writers also provides the opportunity to overcome the barrier in the pMMR-MSI-L colorectal cancer immunotherapy.

Materials and Methods

All studies were conducted in accordance with approved IRB protocols by the University of California, San Diego. All animal work was approved by the Institutional Review Board at the University of California, San Diego, and was performed in accordance with Institutional Animal Care and Use Committee guidelines.

Cell Culture and Viral Infection

CT26 (CRL-2638; murine colon carcinoma) and B16F10 (CRL-6475; murine melanoma) were all purchased from ATCC. B16-GM-CSF cell line was a kind gift from Drs. Glenn Dranoff and Michael Dougan (Dana-Farber/Harvard Cancer Center). These cell lines were cultured in DMEM, RPMI (Gibco) supplemented with 10% fetal bovine serum (Gibco) at 37° C. in 5% $CO_2$ incubators. HEK293FT cells were resuspended in DMEM and co-transfected with CRISPR V2 backbones with the indicated sgRNA, and packaging plasmids psPAX2, and pMD2.G in 10 cm dish using Lipofectamine (Life Technologies, 11668027) in Opti-MEM medium (Gibco). The medium was replaced with fresh completed DMEM after 4-6 h. The supernatant was harvested after 48 h and then infect cells by spin transduction. Finally, cells were selected by puromycin (Alfa Aesar, Thermo Fisher Scientific) or blasticidin (Alfa Aesar, Thermo Fisher Scientific). SgRNA used in this work was as follows:

```
Mettl3-sgRNA1:
TAGGCACGGGACTATC ACTACACCG;

Mettl3-sgRNA2:
TCAGGTGATTACCGTAGAGA;

Mettl3-sgRNA3:
AGGTAGCAGGGACCATCGCA;

Mettl3-sgRNA4:
CTGAAGTGCAGCTTGCGACA;

Mettl14-sgRNA1:
GTCCAGTGTCTACAAAATGT;
```

-continued

Mettl14-sgRNA2:
CACTGAACTACTTACATGGG;

Mettl14-sgRNA3:
ATCAACTTACTACTCTCCCA;

Mettl14-sgRNA4:
GCTGGACCTGGGATGATGTA.

Ythdf1-sgRNA1:
AGCAGCCACTTCAACCCCGC;

Ythdf1-sgRNA2:
TGAACACGGCAACAAGCGCC;

Ythdf1-sgRNA3:
GACTTTGAGCCCTACCTTTC;

Ythdf1-sgRNA4:
ACAAAAGGACAAGATAATAA.

Ythdf2-sgRNA1:
CGAACCTTACTTGAGCCCAC;

Ythdf2-sgRNA2:
GCCGCCTATCGTTCCATGAA;

Ythdf2-sgRNA3:
TCGCAGAGACCAAAAGGTCA;

Ythdf2-sgRNA4:
AGATTCCAGTCGAAATCTTT.

Ythdf3-sgRNA1:
TGAGCATGGTAATAAGCGTT;

Ythdf3-sgRNA2:
AAGCCGGTTCCCCTATTCCG;

Ythdf3-sgRNA3:
AAGAATGTCAGCCACTAGCG;

Ythdf3-sgRNA4:
CTTAAGTAGCCAGACAAATC.

Immunoblotting

Proteins from cells or fresh mice tumors were extracted using RIPA lysis buffer by homogenization followed by centrifugation to remove insoluble material and clarified supernatant was measured using BCA protein assay kit (Bio-Rad). Subsequently, 50-150 μg of protein was resolved by NuPAGE Bis-Tris or 10% Tris-Glycine gels and transferred to PVDF membranes (Bio-Rad). Membranes were blocked in 5% milk TBST buffer and then incubated with the indicated antibodies including Mettl3 (Abcam, ab195352), Mettl14 (Fisher Scientific, ABE1338MI), Gapdh (PROTEINTECH GROUP, HRP-60004), Stat1 (PROTEINTECH GROUP, 10144-2-AP), p-Stat1 (Cell Signaling Technology), Irf1 (PROTEINTECH GROUP, 11335-1-AP), Ythdf1 (PROTEINTECH GROUP, 17479-1-AP), Ythdf2 (PROTEINTECH GROUP, 24744-1-AP), and Ythdf3 (Sigma-Aldrich, Inc., SAB2108258) overnight at 4° C. After being washed, membranes were incubated with HRP-conjugated secondary antibodies at 25° C. for 1 h and visualized on autoradiography film (Genesee Scientific Inc, 30-100) using the enhanced chemiluminescence (ECL) detection system (Thermo Scientific).

Animal Models

BALB/c and C57BL/6J mice (6-8 week) used for study were purchased from The Jackson Laboratory. 2×106 CT26 cells with knockout of Mettl3, Mettl14, Mettl3/Stat1, Mettl3/Irf1, Mettl14/Stat1, or Mettl14/Irf1 and control were suspended in 200 μl of PBS/Matrigel (Corning) (1:1) and then subcutaneously inoculated into flank of each mouse. BALB/c mice bearing CT26 tumors were injected intraperitoneally (i.p.) with 200 μg (10 mg/kg) of anti-CTLA-4 (Bio X Cell, mCD152) and/or anti-PD1 (Bio X Cell, clone 29F.1A12) and IgG (Bio X Cell, clone 2A3, BE0089) antibodies on days 11, 14, 17, 20, and 23 as recommended. (Kim et al, 2014) For the in vivo CD8 depletion study, CT26 tumor-bearing mice were additionally treated i.p. with 200 μg (10 mg/kg) of anti-CD8 antibody (Bio X Cell, clone YTS169.4) twice a week starting on day 8 and also injected i.p. with 200 μg (10 mg/kg) of anti-PD1 antibody as indicated. For the in vivo IFN-γ blocking assay, BALB/c mice bearing the indicated tumors were treated i.p. with 200 μg (10 mg/kg) of anti-IFN-γ antibody (Bio X Cell, Clone: XMG1.2) every 2 days starting on day 7 and also injected i.p. with 200 μg (10 mg/kg) of anti-PD1 antibody as indicated. 0.5×106 B16 cells with knockout of Mettl3, Mettl14, and control were implanted into the left flank, and 1×106 irradiated (100 Gy) B16-GM-CSF cells (GVAX) were injected into the right flank of each C57BL/6J mouse on days 1 and 4. B16 tumor-bearing mice were given a dose of 200 μg (10 mg/kg) of anti-PD1 antibody i.p. on days 6 and 9. For the in vivo depletion study, B16 tumor-bearing mice were treated i.p. with 200 μg (10 mg/kg) of anti-CD8 antibody (Bio X Cell, clone YTS169.4) twice a week starting on day 3 and also injected i.p. with 200 μg (10 mg/kg) of anti-PD1 antibody and GVAX were injected into the right flank as indicated. Tumor volumes were calculated according to the formula: volume (mm3)=(longer diameter× shorter diameter2)/2. Mice were monitored every 2 days as indicated. All animal studies were approved by the Institutional Animal Care and Use Committee of University of California, San Diego.

Flow Cytometry Analysis of Tumor Cells

Tumors with knockout of Mettl3, Mettl14, and control were collected from mice, weighted, mechanically diced, and then digested with 2 mg/ml collagenase P (Sigma-Aldrich) and 50 g/ml DNase I (Sigma-Aldrich) at 37° C. for 30 min. Then, these samples were filtered through 70-μm cell strainers and washed by cell staining buffer (BioLegend). The red blood cells were lysed with lysis buffer (BioLegend, 420301). After counting viable cells and these cells were blocked with TruStain FcX (anti-mouse CD16/32) antibody (BioLegend) and then incubated with Zombie Aqua Live/Dead fixable dye (BioLegend, 423102). Subsequently, specific antibodies recognized cell surface markers were stained. The intracellular staining procedures followed by the BioLegend protocol as recommended. Briefly, cells were fixed with fixation buffer (BioLegend, 420801), permeabilized, and stained with predetermined optimum combination of antibodies. Meanwhile, BD Compensation Beads (BD Biosciences, 552845) were used to optimize fluorescence compensation settings for multicolor flow cytometric analysis. Information about all the antibodies used in the flow cytometry analysis is provided below. CD45 (clone 30-F11), CD3ε (clone 145-2C11), CD4 (clone RM4-5), CD8 (clone 53-6.7), NK1.1 (clone PK136), FoxP3 (clone MF-14), granzyme B (clone QA16A02), and all the antibodies were purchased from BioLegend.

Production of Cytokine/Chemokine Analysis

Intratumoral cytokine extraction from freshly harvested CT26 tumors and serum samples were prepared as described previously (Amsen et al, 2009; Veinalde et al, 2017). The productions of IFN-γ, Cxcl9, and Cxcl10 were measured using IFN-γ Mouse ELISA Kit (Invitrogen, 88-7314-22), mouse CXCL9 ELISA Kit (Fisher Scientific, EMCXCL9), and mouse CXCL10 ELISA Kit (Fisher Scientific, EMCXCL10) according to the manufacturer's instructions, respectively.

RNA Isolation and Quantitative Real-Time PCR

Total RNA was extracted from fresh tumors using Direct-zol RNA MiniPrep Kit (Zymo Research, 11-331) and RNA extraction form cultured cells using Quick-RNA Miniprep Kit (Zymo Research, R1055) following the manufacturer's instructions. Gene expression was analyzed as previously described (Mu et al, 2018). cDNA was generated using the iScript Reverse Transcription Synthesis Kit (Bio-Rad, 1708841) and quantitative real-time PCR was used SsoAdvanced Universal SYBR Green PCR SuperMix (Bio-Rad, 1725270). All primers used for qPCR are listed in Table 1.

RNA-Seq

Total RNA was isolated from CT26 tumors with knockout of Mettl3, Mettl14, and control (five mice tumors for biological replicates in each group). RNA-seq library preparation and sequencing were performed at the IGM Genomics Center, UCSD using Illumina HiSeq 4000. For the analysis, single-end reads were trimmed by cutadapt (v1.18) then mapped to mouse genome (mm10) using HISAT2 (v2.1.0). Transcripts were quantified by HTSeq (0.11.2), and differential expressed genes (DEGs) were then determined by DESeq2.

MeRIP-Seq and MeRIP-qPCR mRNA was isolated from tumors using RiboMinus Transcriptome Isolation Kit (life technology, K1500-02) followed by the procedures as recommended. Purified mRNA samples were fragmented to 100-200 nucleotides with Fragmentation Reagents Kit (Invitrogen, AM8740) according to the manufacturer's protocol. 10% of total fragmented RNA was reserved as an input sample and the rest of fragmented RNA was further used for m6A immunoprecipitation with the anti-N6-methyladenosine (m6A) antibody (abcam, ab151230) in 500 μl IP binding buffer (150 mM NaCl, 10 mM Tris-HCl, pH 7.5, 0.1% NP-40) with RNase inhibitor at 4° C. for 2 h and then adding the washed protein A/G magnetic beads (NEB) by IP binding buffer to the RNA-antibody immunoprecipitation mixture to rotate at 4° C. for 2 h. The collected magnetic beads were washed twice in IP binding buffer, twice in low salt reaction buffer (50 mM NaCl, 10 mM Tris-HCl, pH 7.5, 0.1% NP-40) and twice in high salt reaction buffer (500 mM NaCl, 10 mM Tris-HCl, pH 7.5, 0.1% NP-40). The bound RNA was eluted from beads by adding 30 μl RLT buffer (QIAGEN) and incubated for 5 min at 25° C. Lastly, the eluted RNA was purified by ethanol precipitation and prepared for library generation using a TruSeq mRNA library preparation kit (Illumina). Sequencing was performed at IGM Genomics core, UCSD on an Illumina HiSeq4000 machine. Detection for enriched peaks in m6A immunoprecipitation samples was performed by model-based analysis of ChIP-seq (MACS2) algorithm (v2.1.0), peaks were detected if their FDR was <5% and fold enrichment was higher than 1. High-confidence peaks in both biological replicate samples were found by BEDtools intersect function. De novo motif search was performed by HOMER (v4.10). For m6A-MeRIP-qPCR, we adopted the same protocol above, m6A enrichment was determined by qPCR analysis with indicated primers on LightCycler 480 (Roche Diagnostics). Ctla4 without m6A-modified transcript was used as negative control. (Wang et al, 2019) All primers used for MeRIP-qPCR are listed in Table 1.

Dot-Blot Assays mRNA from fresh tumors was isolated using Magnetic mRNA Isolation Kit (New England Biolabs, S1550S) and then denatured at 95° C. for 3 min, followed by chilling on ice. Quantified mRNA was spotted on an Amersham Hybond-N+ membrane (GE Healthcare, RPN3050B) and crosslinked to the membrane with UV radiation. The membrane was blocked in 5% of non-fat milk PBST buffer and then incubated with anti-m6A antibody (1:2,000; abcam) overnight at 4° C. After incubating with HRP-conjugated secondary antibodies, the membrane was visualized by SuperSignal West Femto Maximum Sensitivity Substrate (Thermo Fisher Scientific).

In Vitro Cytokines Stimulation

Mettl3- or Mettl14-deficient CT26 cells and control cells were cultured in 12-well plates in RPMI/10% FBS with the indicated combinations of cytokines: TNFα (10 ng/ml, PeproTech) and IFN-γ (100 ng/ml, BioLegend). Cells were further analyzed after 60 h.

Cell Proliferation Assays

A total of 2000 cells were plated in the 96-well plate, cells with the indicated sgRNA were determined by CellTiter AQueous One Solution Cell Proliferation Assay kit (Promega, G3580) following the manufacturer's instructions. Briefly, adding 20 μl of CellTiter Reagent into each well of the 96-well plate containing the cells. Incubating the plate at 37° C. in 5% $CO_2$ incubators for 1-2 h, and then record the absorbance at 490 nm.

mRNA Stability Measurements

An mRNA stability measurement assay was performed as previously reported. (Wei et al, 2018a; Wang et al, 2019). Briefly, CT26 cells with knockout of Mettl3, Mettl14, and control or overexpression of Mettl3, Mettl14, and a combination with depletion of Ythdf2 were stimulated with IFN-γ. After 48 h, 5 g/ml of Actinomycin D (Alfa Aesar, AAJ67160XF) was added for 0, 6, 12, and 24 h or 0, 30, 60, 90 min as indicated and then these cells were collected. Subsequently, mRNA levels were quantified by RT-qPCR with gene-specific qPCR primers (Table 1).

Immunohistochemistry

Human colon cancer tissues used in this study were obtained from US Biomax.inc. The staining analysis followed the previous description. (Mu et al, 2018) Briefly, slides of paraffin-embedded from human and mouse tissue were deparaffinized in xylene and rehydrated in graded ethanol (5 min in 100%, 5 min in 95%, and 5 min in 75%) and then washed by PBS containing 0.3% Triton X-100 (Sigma-Aldrich) (PBST) for three times. Sections were pretreated with antigen retrieval with Tris/EDTA buffer pH 9.0, rinsed three times with PBST, incubated with 3% $H_2O_2$ in PBS at 37° C. for 10 min. After blocking with 5% goat serum (Cell Signaling Technology, 5425S) in PBST for 1 h, tissue slides were incubated at 4° C. overnight with primary antibodies as follows: Mettl3 (Abcam, ab195352), Mettl14 (Fisher Scientific, ABE1338MI), Stat1 (PROTEINTECH GROUP, 10144-2-AP), MSH2 (PROTEINTECH GROUP, 15520-1-AP), Ki-67 (Cell Signaling Technology, 12202T), and CD8 (Cell Signaling Technology, 98941T). Then, the sections were washed by PBST for five times, incubated with biotinylated goat anti-rabbit IgG (Vector laboratories, BA-1000) at 25° C. for 1 h and treated with AEC substrate kit (Vector laboratories, SK-4205) for 5 min and then counterstained with hematoxylin. Finally, all the mouse and human colon tissue slides were imaged. For the human colon cancer slides, images were obtained and semiquantitative evaluation of staining was scored as follows: score=percentage of malignant cells staining positive (0<10%; 1, 10-25%; 2, 25-50%; 3, >50%)×mean stain intensity (0-3) as previously defined (Lin et al, 2014).

| Genes Name | 5'-3' |
|---|---|
| Stat1 | CTATGAGCCCGACCCTATTA/GTCTCAGCTTGACAGTGAAC |
| Stat4 | ACCTAGAGACCAGCTCATT/CAAGTTCTGGGAGTCGTTAG |
| Irf1 | GATGGACTCAGCAGCTCTA/GCTGGAGTTATGTCCCTTTC |
| Irf4 | GCTGCATATCTGCCTGTATT/CTCAATGTTCTTCCTCTGTCC |
| Irf7 | AAGTGAGCCTCAGCAATG/GCAGAACCTGAAGCAAGA |
| Ccl3 | TCCTACAGCCGGAAGATT/GTTCCAGGTCAGTGATGTATT |
| Ccl4 | CCACTTCCTGCTGTTTCTCT/TTGGTCAGGAATACCACAGC |
| Ccl5 | CCCACGTCAAGGAGTATTTC/TCTTCTCTGGGTTGGCA |
| Ccl8 | GTCACCTGCTGCTTTCAT/GGGTCTACACAGAGAGACATA |
| Cxcl9 | TCGAGGAACCCTAGTGATAAG/TTGAGGTCTTTGAGGGATTTG |
| Cxcl10 | CATCCTGCTGGGTCTGAGTG/ATTCTCACTGGCCCGTCATC |
| Cxcl11 | GGCTGCGACAAAGTTGAAGT/CGAGCTTGCTTGGATCTGGG |
| Pdl1 | TGGTGGAGTATGGCAGCAAC/CCCAGTACACCACTAACGCA |
| Zbp1 | GCCTAGCCTTGATGAAAGAA/GAATACAGGAGTGGGTTCAC |
| Gapdh | GTCGGTGTGAACGGATTT/GGAGTCATACTGGAACATGTAG |
| Hprt1 | AACTTTGCTTTCCCTGGTTA/AACAAAGTCTGGCCTGTATC |
| Ctla4 | GAGTCTGTGTGGGTTCAAAC/AAAAGAAGAGTGAGCAGGGC |
| Stat1/m$^6$A | CACAAAATGGATTTTGTAAACAAAGAC/TACTAAAGTGACCGTTCTCCTC |
| Irf1m$^6$A | GGACATTGGGATAGGCATACAAC/GGCGGCAGCCTCACAGAG |

Statistical Analysis

Results were analyzed using Prism 5.0 software (GraphPad) and presented as mean f SEM (standard error) or mean f SD (standard deviation) as indicated. P values were calculated using Student's t-tests and considered to be statistically significance at $P<0.05$.

All primers used for qPCR and MeRIP-qPCR are listed.

Figure 103:
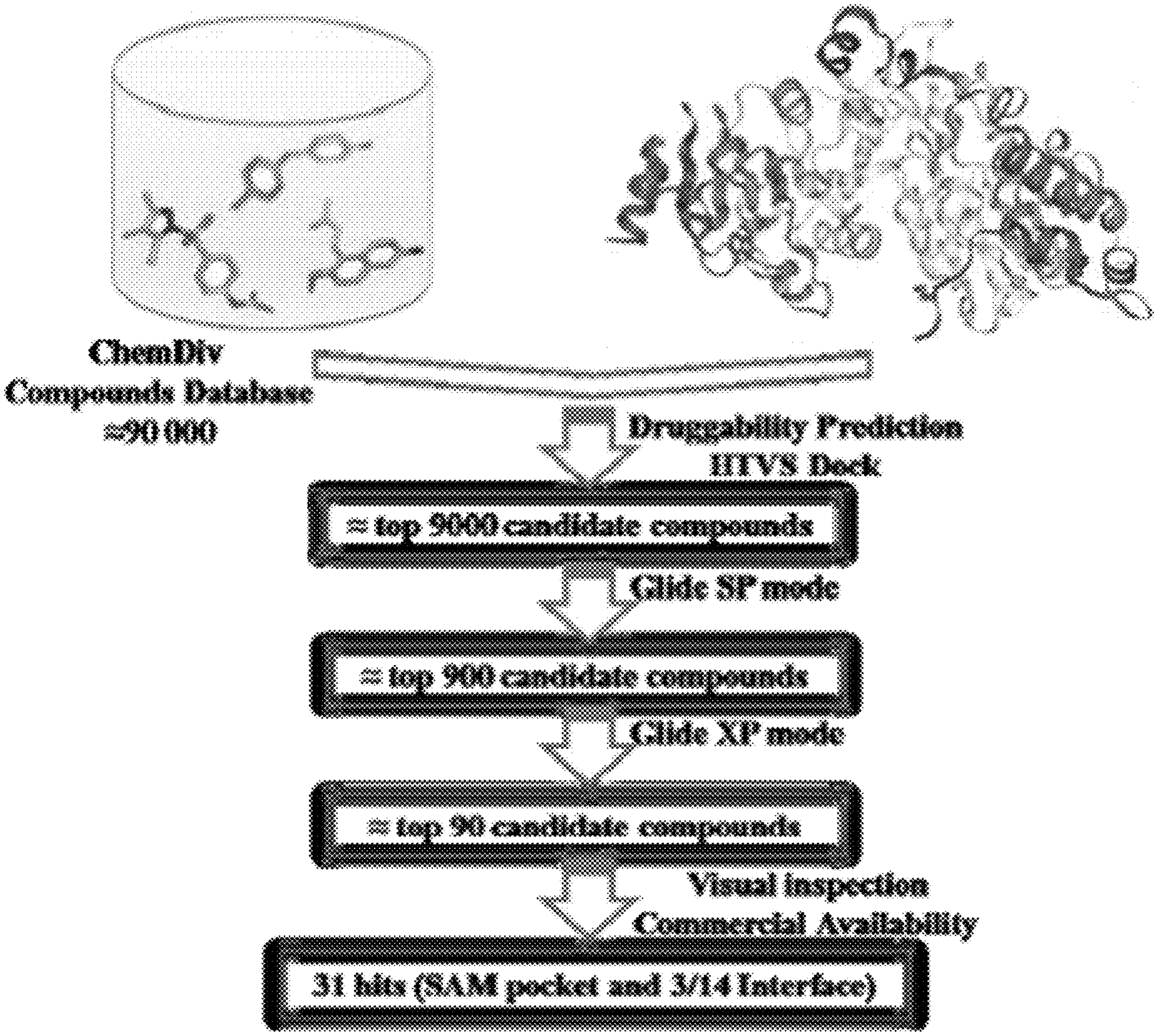
FIG. 103. In-silico virtual screening flow chart.

The first strategy used the structure-based in silico virtual screening, followed by medicinal chemistry optimization (FIG. 93 below). We utilized the Schrödinger Maestro to do the successive virtual screening to scale down the compound library volume from 90000 to 90 respectively by HTVS, Glide SP and Glide XP module. We selected the final 31 potential hit candidates for in vitro evaluation (FIG. 103).

REFERENCES

1. Alexandrov L B, Nik-Zainal S, Wedge D C, Aparicio S A, Behjati S, Biankin A V, Bignell G R, Bolli N, Borg A, Børresen-Dale A-L (2013) Signatures of mutational processes in human cancer. Nature 500: 415
2. Amsen D, de Visser K E, Town T (2009) Approaches to determine expression of inflammatory cytokines. In Inflammation and Cancer (Springer), pp. 107-142
3. Ayers M, Lunceford J, Nebozhyn M, Murphy E, Loboda A, Kaufman D R, Albright A, Cheng J D, Kang S P, Shankaran V et al (2017) IFN-gammarelated mRNA profile predicts clinical response to PD-1 blockade. J Clin Invest 127: 2930-2940
4. Barbieri I, Tzelepis K, Pandolfini L, Shi J, Millin-Zambrano G, Robson S C, Aspris D, Migliori V, Bannister A J, Han N (2017) Promoter-bound METTL3 maintains myeloid leukaemia by m6A-dependent translation control. Nature 552: 126
5. Castro F, Cardoso A P, Gongalves R M, Serre K, Oliveira M J (2018) Interferongamma at the crossroads of tumor immune surveillance or evasion. Front Immunol 9: 847
6. Chen M, Wei L, Law C T, Tsang F H C, Shen J, Cheng C L H, Tsang L H, Ho D W H, Chiu D K C, Lee J M F (2018) RNA N6-methyladenosine methyltransferase-like 3 promotes liver cancer progression through YTHDF2-dependent posttranscriptional silencing of SOCS2. Hepatology 67: 2254-2270
7. Cui Q, Shi H, Ye P, Li L, Qu Q, Sun G, Sun G, Lu Z, Huang Y, Yang C-G (2017) m6A RNA methylation regulates the self-renewal and tumorigenesis of glioblastoma stem cells. Cell Rep 18: 2622-2634
8. Deng X, Su R, Weng H, Huang H, Li Z, Chen J (2018) RNA N6-methyladenosine modification in cancers: current status and perspectives. Cell Res 28: 507-517
9. Deschoolmeester V, Baay M, Lardon F, Pauwels P, Peeters M (2011) Immune cells in colorectal cancer: prognostic relevance and role of MSI. Cancer Microenviron 4: 377-392
10. Dominissini D, Moshitch-Moshkovitz S, Schwartz S, Salmon-Divon M, Ungar L, Osenberg S, Cesarkas K, Jacob-Hirsch J, Amariglio N, Kupiec M et al (2012) Topology of the human and mouse m6A RNA methylomes revealed by m6A-seq. Nature 485: 201-206
11. Dunn G P, Bruce A T, Ikeda H, Old L J, Schreiber R D (2002) Cancer immunoediting: from immunosurveillance to tumor escape. Nat Immunol 3: 991
12. Ganesh K, Stadler Z K, Cercek A, Mendelsohn R B, Shia J, Segal N H, Diaz L A (2019) Immunotherapy in colorectal cancer: rationale, challenges and potential. Nat Rev Gastroenterol Hepatol 16: 361-375

13. Garcia-Diaz A, Shin D S, Moreno B H, Saco J, Escuin-Ordinas H, Rodriguez G A, Zaretsky J M, Sun L, Hugo W, Wang X (2017) Interferon receptor signaling pathways regulating PD-L1 and PD-L2 expression. Cell Rep 19: 1189-1201
14. Gorbachev A V, Kobayashi H, Kudo D, Tannenbaum C S, Finke J H, Shu S, Farber J M, Fairchild R L (2007) CXC chemokine ligand 9/monokine induced by IFNc production by tumor cells is critical for T cell-mediated suppression of cutaneous tumors. J Immunol 178: 2278-2286
15. Han D, Liu J, Chen C, Dong L, Liu Y, Chang R, Huang X, Liu Y, Wang J, Dougherty U (2019) Anti-tumour immunity controlled through mRNA m 6 A methylation and YTHDF1 in dendritic cells. Nature 566: 270
16. Honda K, Takaoka A, Taniguchi T (2006) Type I interferon gene induction by the interferon regulatory factor family of transcription factors. Immunity 25: 349-360
17. Hsu P J, Zhu Y, Ma H, Guo Y, Shi X, Liu Y, Qi M, Lu Z, Shi H, Wang J (2017) Ythdc2 is an N6-methyladenosine binding protein that regulates mammalian spermatogenesis. Cell Res 27: 1115
18. Jaffrey S R, Kharas M G (2017) Emerging links between m(6)A and misregulated mRNA methylation in cancer. Genome Med 9: 2
19. Jenkins R W, Barbie D A, Flaherty K T (2018) Mechanisms of resistance to immune checkpoint inhibitors. Br J Cancer 118: 9
20. Jia G, Fu Y, Zhao X, Dai Q, Zheng G, Yang Y, Yi C, Lindahl T, Pan T, Yang Y-G (2011) N6-methyladenosine in nuclear RNA is a major substrate of the obesity-associated FTO. Nat Chem Biol 7: 885
21. Khalil D N, Smith E L, Brentjens R J, Wolchok J D (2016) The future of cancer treatment: immunomodulation, CARs and combination immunotherapy. Nat Rev Clin Oncol 13: 273
22. Kim K, Skora A D, Li Z, Liu Q, Tam A J, Blosser R L, Diaz L A, Papadopoulos N, Kinzler K W, Vogelstein B (2014) Eradication of metastatic mouse cancers resistant to immune checkpoint blockade by suppression of myeloidderived cells. Proc Natl Acad Sci USA 111: 11774-11779
23. Koh C W Q, Goh Y T, Goh W S S (2019) Atlas of quantitative single-baseresolution N6-methyl-adenine methylomes. Nat Commun 10: 5636
24. Kowanetz M, Zou W, Gettinger S N, Koeppen H, Kockx M, Schmid P, Kadel E E III, Wistuba I, Chaft J, Rizvi N A et al (2018) Differential regulation of PD-L1 expression by immune and tumor cells in NSCLC and the response to treatment with atezolizumab (anti-PD-L1). Proc Natl Acad Sci USA 115: E10119-E10126
25. Le D T, Durham J N, Smith K N, Wang H, Bartlett B R, Aulakh L K, Lu S, Kemberling H, Wilt C, Luber B S et al (2017) Mismatch repair deficiency predicts response of solid tumors to PD-1 blockade. Science 357: 409-413
26. Li A, Chen Y—S, Ping X-L, Yang X, Xiao W, Yang Y, Sun H—Y, Zhu Q, Baidya P, Wang X (2017) Cytoplasmic m6A reader YTHDF3 promotes mRNA translation. Cell Res 27: 444
27. Li N, Kang Y, Wang L, Huff S, Tang R, Hui H, Agrawal K, Gonzalez G M, Wang Y, Patel S P et al (2020) ALKBH5 regulates anti-PD-1 therapy response by modulating lactate and suppressive immune cell accumulation in tumor microenvironment. Proc Natl Acad Sci USA 117: 20159-20170
28. Lichinchi G, Gao S, Saletore Y, Gonzalez G M, Bansal V, Wang Y, Mason C E, Rana T M (2016a) Dynamics of the human and viral m(6)A RNA methylomes during HIV-1 infection of T cells. Nat Microbiol 1: 16011
29. Lichinchi G, Zhao B S, Wu Y, Lu Z, Qin Y, He C, Rana T M (2016b) Dynamics of human and viral RNA methylation during zika virus infection. Cell Host Microbe 20: 666-673
30. Lichinchi G, Rana T M (2019) Profiling of N(6)-Methyladenosine in Zika Virus RNA and Host Cellular mRNA. Methods Mol Biol 1870: 209-218
31. Lichterfeld M, Xu G Y, Waring M T, Mui S K, Johnston M N, Cohen D, Addo M M, Zaunders J, Alter G, Pae E (2004) HIV-1-specific cytotoxicity is preferentially mediated by a subset of CD8+ T cells producing both interferon-c and tumor necrosis factor-a. Blood 104: 487-494
32. Lin Y, Zhang H, Liang J, Li K, Zhu W, Fu L, Wang F, Zheng X, Shi H, Wu S (2014) Identification and characterization of alphavirus M1 as a selective oncolytic virus targeting ZAP-defective human cancers. Proc Natl Acad Sci USA 111: E4504-E4512
33. Liu J, Yue Y, Han D, Wang X, Fu Y, Zhang L, Jia G, Yu M, Lu Z, Deng X (2014) A METTL3-METTL14 complex mediates mammalian nuclear RNA N 6-adenosine methylation. Nat Chem Biol 10: 93
34. Liu J, Harada B T, He C (2019) Regulation of gene expression by N(6)-methyladenosine in cancer. Trends Cell Biol 29: 487-499
35. Llosa N J, Cruise M, Tam A, Wicks E C, Hechenbleikner E M, Taube J M, Blosser R L, Fan H, Wang H, Luber B S (2015) The vigorous immune microenvironment of microsatellite instable colon cancer is balanced by multiple counter-inhibitory checkpoints. Cancer Discov 5:43-51
36. Ma J Z, Yang F, Zhou C C, Liu F, Yuan J H, Wang F, Wang T T, Xu Q G, Zhou W P, Sun S H (2017) METTL14 suppresses the metastatic potential of hepatocellular carcinoma by modulating N6methyladenosine-dependent primary MicroRNA processing. Hepatology 65: 529-543
37. Mandal R, Samstein R M, Lee K W, Havel J J, Wang H, Krishna C, Sabio E Y, Makarov V, Kuo F, Blecua P et al (2019) Genetic diversity of tumors with mismatch repair deficiency influences anti-PD-1 immunotherapy response. Science 364: 485-491
38. Manguso R T, Pope H W, Zimmer M D, Brown F D, Yates K B, Miller B C, Collins N B, Bi K, LaFleur M W, Juneja V (2017) In vivo CRISPR screening identifies Ptpn2 as a cancer immunotherapy target. Nature 547: 413
39. Meyer K D, Saletore Y, Zumbo P, Elemento O, Mason C E, Jaffrey S R (2012) Comprehensive analysis of mRNA methylation reveals enrichment in 30 UTRs and near stop codons. Cell 149: 1635-1646
40. Meyer K D, Jaffrey S R (2017) Rethinking m(6)A readers, writers, and erasers. Annu Rev Cell Dev Biol 33: 319-342
41. Mu Y, Yan X, Li D, Zhao D, Wang L, Wang X, Gao D, Yang J, Zhang H, Li Y (2018) NUPR1 maintains autolysosomal efflux by activating SNAP25 transcription in cancer cells. Autophagy 14: 654-670
42. Nachtergaele S, He C (2018) Chemical modifications in the life of an mRNA transcript. Annu Rev Genet 52: 349-372
43. Paliard X, de Waal Malefijt R, de Vries J E, Spits H (1988) Interleukin-4 mediates CDS induction on human CD4+ T-cell clones. Nature 335: 642
44. Pandiyan P, Hegel J K E, Krueger M, Quandt D, Brunner-Weinzierl M C (2007) High IFN-c production of individual CD8 T lymphocytes is controlled by CD152 (CTLA-4). J Immunol 178: 2132-2140
45. Panneerdoss S, Eedunuri V K, Yadav P, Timilsina S, Rajamanickam S, Viswanadhapalli S, Abdelfattah N, Onyeagucha B C, Cui X, Lai Z (2018) Cross-talk among writers, readers, and erasers of m6A regulates cancer growth and progression. Sci Adv 4: eaar8263
46. Pautz A, Art J, Hahn S, Nowag S, Voss C, Kleinert H (2010) Regulation of the expression of inducible nitric oxide synthase. Nitric Oxide 23: 75-93
47. Ping X-L, Sun B—F, Wang L, Xiao W, Yang X, Wang W-J, Adhikari S, Shi Y, Lv Y, Chen Y—S(2014) Mammalian WTAP is a regulatory subunit of the RNA N6-methyladenosine methyltransferase. Cell Res 24: 177
48. Ramana C V, Chatterjee-Kishore M, Nguyen H, Stark G R (2000) Complex roles of Stat1 in regulating gene expression. Oncogene 19: 2619
49. Ribas A, Wolchok J D (2018) Cancer immunotherapy using checkpoint blockade. Science 359: 1350-1355
50. Samstein R M, Lee C H, Shoushtari A N, Hellmann M D, Shen R, Janjigian Y Y, Barron D A, Zehir A, Jordan E J, Omuro A et al (2019) Tumor mutational load predicts survival after immunotherapy across multiple cancer types. Nat Genet 51: 202-206
51. Schreiber R D, Old L J, Smyth M J (2011) Cancer immunoediting: integrating immunity's roles in cancer suppression and promotion. Science 331: 1565-1570
52. Sharma P, Allison J P (2015) The future of immune checkpoint therapy. Science 348: 56-61
53. Sharma P, Hu-Lieskovan S, Wargo J A, Ribas A (2017) Primary, adaptive, and acquired resistance to cancer immunotherapy. Cell 168: 707-723
54. Sridharan V, Margalit D N, Lynch S A, Severgnini M, Zhou J, Chau N G, Rabinowits G, Lorch J H, Hammerman P S, Hodi F S (2016) Definitive chemoradiation alters the immunologic landscape and immune checkpoints in head and neck cancer. Br J Cancer 115: 252
55. Tokunaga R, Zhang W, Naseem M, Puccini A, Berger M D, Soni S, McSkane M, Baba H, Lenz H-J (2018) CXCL9, CXCL10, CXCL11/CXCR3 axis for immune activation—a target for novel cancer therapy. Cancer Treat Rev 63: 40-47
56. Townsend S E, Allison J P (1993) Tumor rejection after direct costimulation of CD8+ T cells by B7-transfected melanoma cells. Science 259: 368-370
57. Veinalde R, Grossardt C, Hartmann L, Bourgeois-Daigneault M-C, Bell J C, Jiger D, von Kalle C, Ungerechts G, Engeland C E (2017) Oncolytic measles virus encoding interleukin-12 mediates potent antitumor effects through T cell activation. Oncoimmunology 6: e1285992
58. Vu L P, Pickering B F, Cheng Y, Zaccara S, Nguyen D, Minuesa G, Chou T, Chow A, Saletore Y, MacKay M (2017) The N6-methyladenosine (m6A)-forming enzyme METTL3 controls myeloid differentiation of normal hematopoietic and leukemia cells. Nat Med 23: 1369
59. Wang X, Lu Z, Gomez A, Hon G C, Yue Y, Han D, Fu Y, Parisien M, Dai Q, Jia G (2014) N6-methyladenosine-dependent regulation of messenger RNA stability. Nature 505: 117
60. Wang X, Zhao B S, Roundtree I A, Lu Z, Han D, Ma H, Weng X, Chen K, Shi H, He C (2015) N6-methyladenosine modulates messenger RNA translation efficiency. Cell 161: 1388-1399
61. Wang H, Hu X, Huang M, Liu J, Gu Y, Ma L, Zhou Q, Cao X (2019) Mettl3-mediated mRNA m6A methylation promotes dendritic cell activation. Nat Commun 10: 1898
62. Wei L-H, Song P, Wang Y, Lu Z, Tang Q, Yu Q, Xiao Y, Zhang X, Duan H—C, Jia G (2018a) The m6A reader ECT2 controls trichome morphology by affecting mRNA stability in *Arabidopsis*. Plant Cell 30: 968-985
63. Wei S C, Duffy C R, Allison J P (2018b) Fundamental mechanisms of immune checkpoint blockade therapy. Cancer Discov 8: 1069-1086
64. Weng H, Huang H, Wu H, Qin X, Zhao B S, Dong L, Shi H, Skibbe J, Shen C, Hu C (2018) METTL14 inhibits hematopoietic stem/progenitor differentiation and promotes leukemogenesis via mRNA m6A modification. Cell Stem Cell 22: 191-205 e199
65. Wu F, Cheng W, Zhao F, Tang M, Diao Y, Xu R (2019) Association of N6-methyladenosine with viruses and related diseases. Virol J 16: 133
66. Xiao W, Adhikari S, Dahal U, Chen Y—S, Hao Y-J, Sun B—F, Sun H—Y, Li A, Ping X-L, Lai W-Y (2016) Nuclear m6A reader YTHDC1 regulates mRNA splicing. Mol Cell 61: 507-519
67. Yang S, Wei J, Cui Y—H, Park G, Shah P, Deng Y, Aplin A E, Lu Z, Hwang S, He C (2019) m6A mRNA demethylase FTO regulates melanoma tumorigenicity and response to anti-PD-1 blockade. Nat Commun 10: 2782
68. Yue Y, Liu J, He C (2015) RNA N6-methyladenosine methylation in posttranscriptional gene expression regulation. Genes Dev 29: 1343-1355
69. Zenke K, Muroi M, Tanamoto K I (2018) IRF1 supports DNA binding of STAT1 by promoting its phosphorylation. Immunol Cell Biol 96: 1095-1103
70. Zheng G, Dahl J A, Niu Y, Fedorcsak P, Huang C-M, Li C J, Vigbo C B, Shi Y, Wang W-L, Song S-H (2013) ALKBH5 is a mammalian RNA demethylase that impacts RNA metabolism and mouse fertility. Mol Cell 49: 18-29

Inhibition of Mettl3/14 activity assays were performed as described by Wang et al., 2016, Molecular Cell 63, 306-317).

Also See Example C12 for synthesis of non-limiting exemplary Mettl3/14 inhibitors described herein.

Example B7: PCIF1 Silencing/Editing Inhibits Cancers and Enhances Immunotherapy Abstract N6,2'-O-dimethyladenosine (m6Am) is an abundant RNA modification located adjacent to the 5'-end of mRNA 7-methylguanosine (m7G) cap structure. Phosphorylated CTD Interacting Factor 1 (PCIF1) is the methyl transferase that catalyzes m6A methylation on 2'-O-methylated A at the 5'-ends of mRNAs1-3. The role of m6Am RNA modification and the catalytic function of PCIF1 in regulating cancer is not known.

Here we show that PCIF1 silencing or CRSPR KO reduced tumor growth in melanoma and CRC as well as enhanced immunotherapy outcomes.

Introduction

RNA contains more than 100 chemical modifications and recent studies on their structure and function have led to a recent frontier in biology and medicine termed epitranscriptomics[1-3]. One of these modifications, N6-methyladenosine (m6A) is the most prevalent RNA modification in many species, including mammals and is found in 5'-UTR, 3'-UTRs, and stop codons[4-6]. The m6A modification is catalyzed by RNA methyltransferase complex containing METTL3 that catalyzes the addition of a methyl group at N6 position of adenosine which affects gene expression via regulation of RNA metabolism, function, and localization[7,8]. Another abundant RNA modification near the mRNA cap structure is a dimethylated adenosine, N6,2'-O-dimethyladenosine (m6Am)[9,10]. Since m6Am is found at the first transcribed nucleotide in ~30% of the cellular mRNAs, m6Am can have a major influence on gene expression of the transcriptome[10]. Recent studies have identified the Phosphorylated CTD Interacting Factor 1 (PCIF1) as the enzyme that catalyzes m6A methylation on 2'-O-methylated A at the 5'-ends of mRNAs[13].

REFERENCES

1. Akichika, S. et al. Cap-specific terminal N (6)-methylation of RNA by an RNA polymerase II-associated methyltransferase. *Science* 363, doi:10.1126/science.aav0080 (2019).
2. Boulias, K. et al. Identification of the m(6)Am Methyltransferase PCIF1 Reveals the Location and Functions of m(6)Am in the Transcriptome. *Mol Cell* 75, 631-643 e638, doi:10.1016/j.molcel.2019.06.006 (2019).
3. Sendinc, E. et al. PCIF1 Catalyzes m6Am mRNA Methylation to Regulate Gene Expression. *Mol Cell* 75, 620-630 e629, doi:10.1016/j.molcel.2019.05.030 (2019).
4. Meyer, K. D. et al. Comprehensive analysis of mRNA methylation reveals enrichment in 3' UTRs and near stop codons. *Cell* 149, 1635-1646, doi:10.1016/j.cell.2012.05.003 (2012).
5. Dominissini, D. et al. Topology of the human and mouse m6A RNA methylomes revealed by m6A-seq. *Nature* 485, 201-206, doi:10.1038/naturel 1112 (2012).
6. Schwartz, S. et al. Perturbation of m6A writers reveals two distinct classes of mRNA methylation at internal and 5' sites. *Cell Rep* 8, 284-296, doi:10.1016/j.celrep.2014.05.048 (2014).
7. Meyer, K. D. & Jaffrey, S. R. Rethinking m(6)A Readers, Writers, and Erasers. *Annu Rev Cell Dev Biol* 33, 319-342, doi:10.1146/annurev-cellbio-100616-060758 (2017).
8. Shi, H., Wei, J. & He, C. Where, When, and How: Context-Dependent Functions of RNA Methylation Writers, Readers, and Erasers. *Mol Cell* 74, 640-650, doi:10.1016/j.molcel.2019.04.025 (2019).
9. Keith, J. M., Ensinger, M. J. & Moss, B. HeLa cell RNA (2'-O-methyladenosine-N6-)-methyltransferase specific for the capped 5'-end of messenger RNA. *J Biol Chem* 253, 5033-5039 (1978).
10. Wei, C., Gershowitz, A. & Moss, B. N6, 02'-dimethyladenosine a novel methylated ribonucleoside next to the 5' terminal of animal cell and virus mRNAs. *Nature* 257, 251-253, doi:10.1038/257251a0 (1975).

Example B8: YHT Compounds in Colon Cancer

Figure 104:
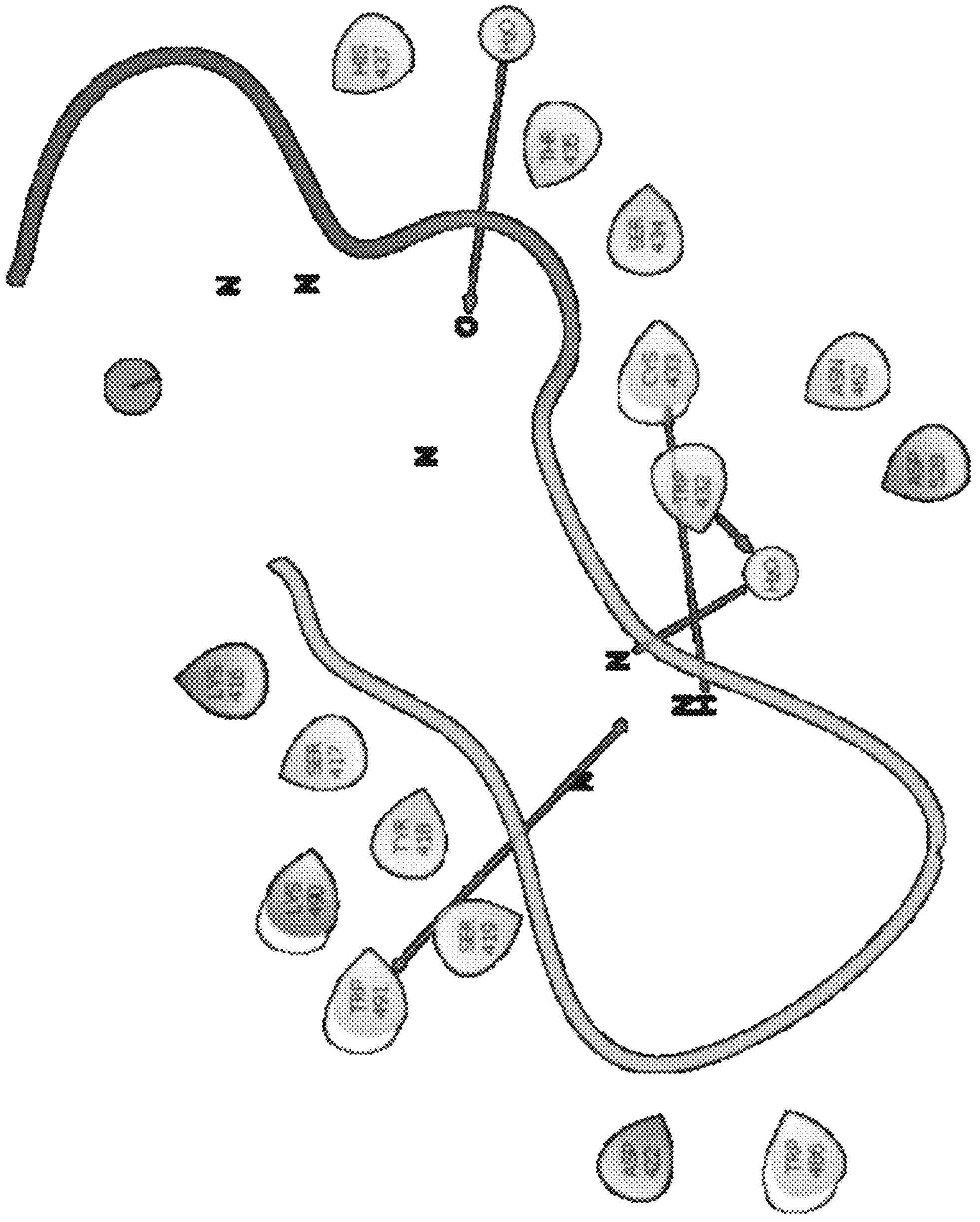
FIG. 104. Figure illustrating three potential libraries of compounds.
Figure 106:
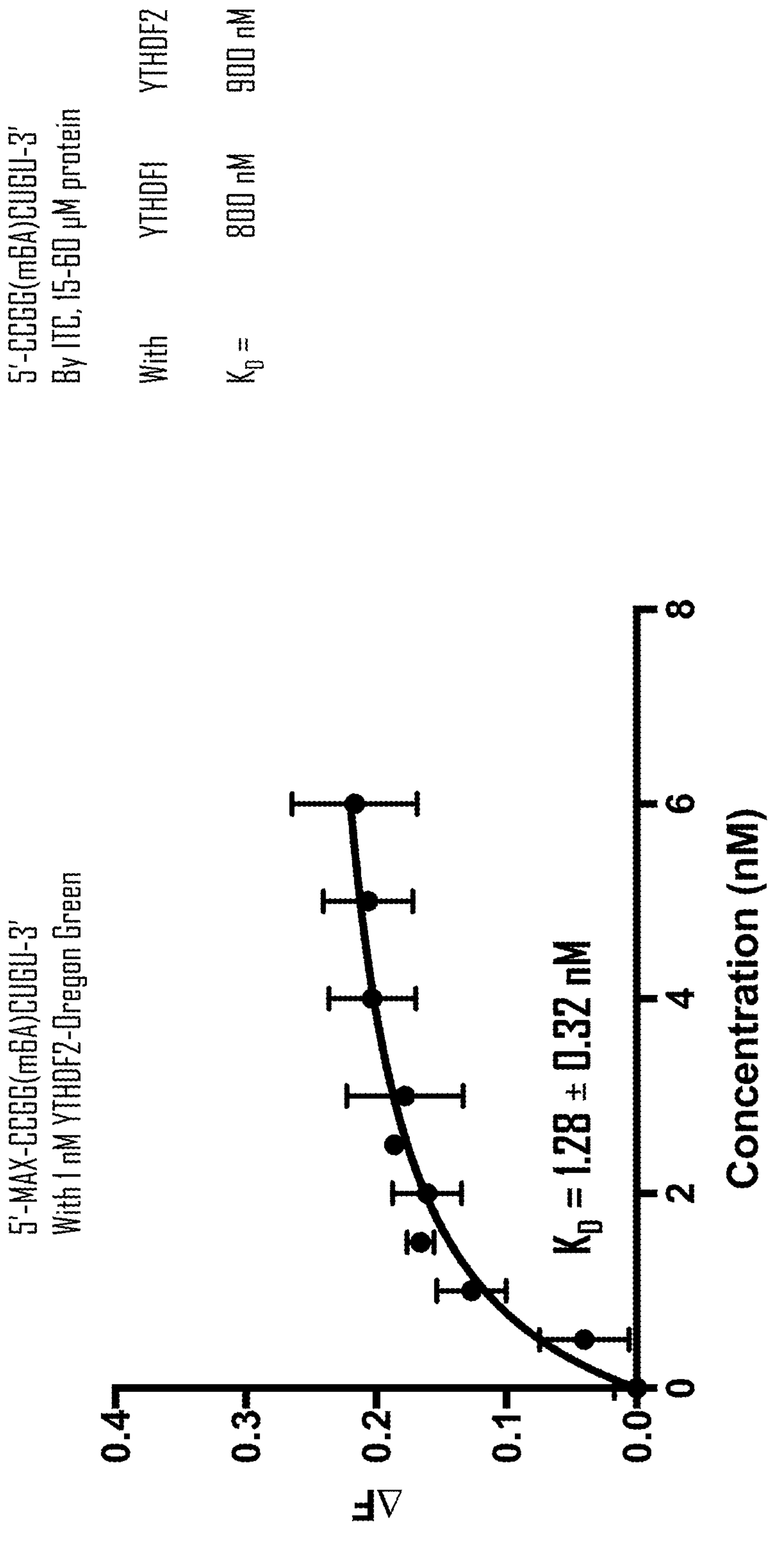
FIG. 106. Plot depicting assay validation statistics.
Figure 108:
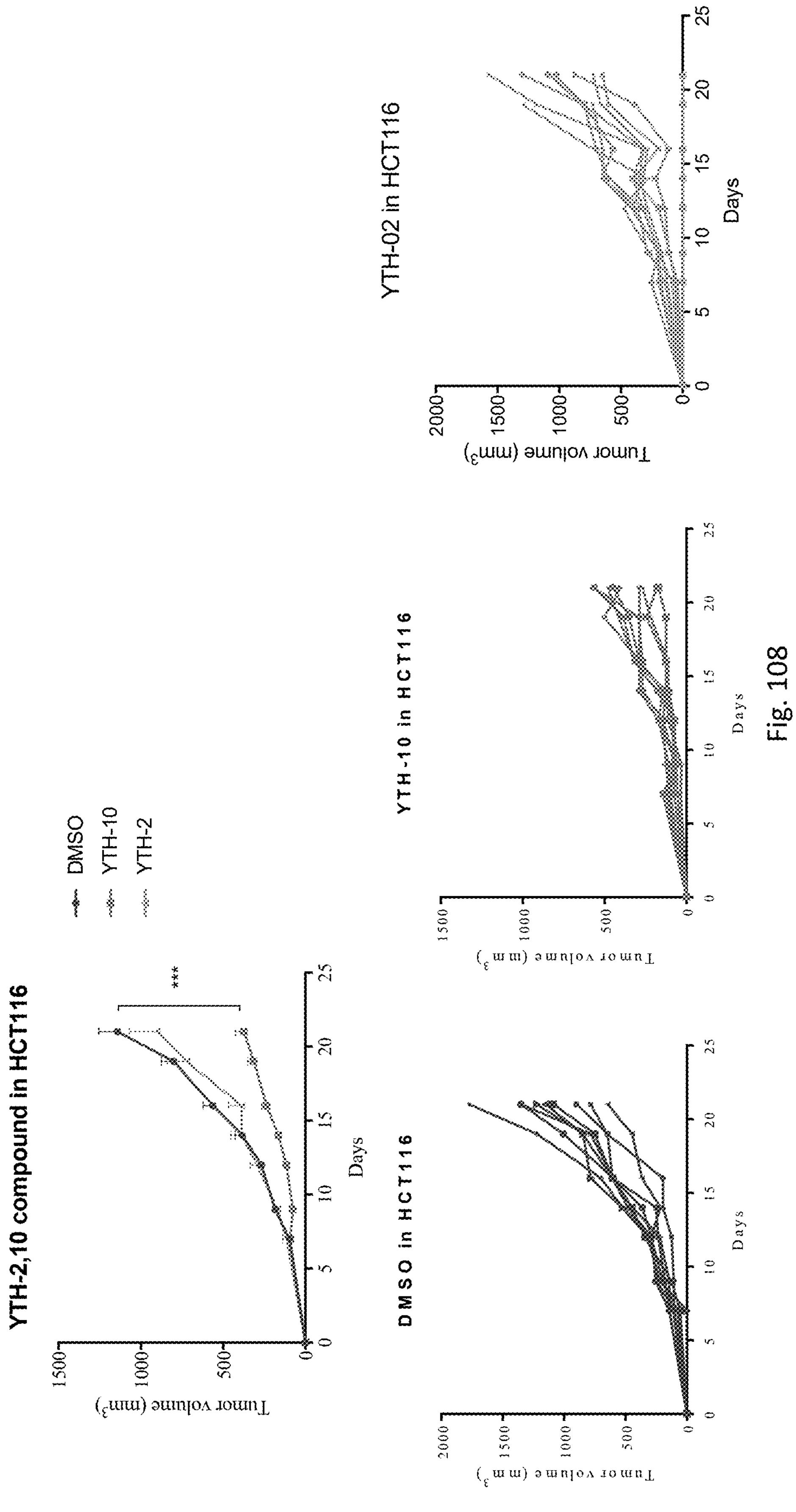
FIG. 108. Plots depicting impact of YHT compounds in mice.
Figure 109:
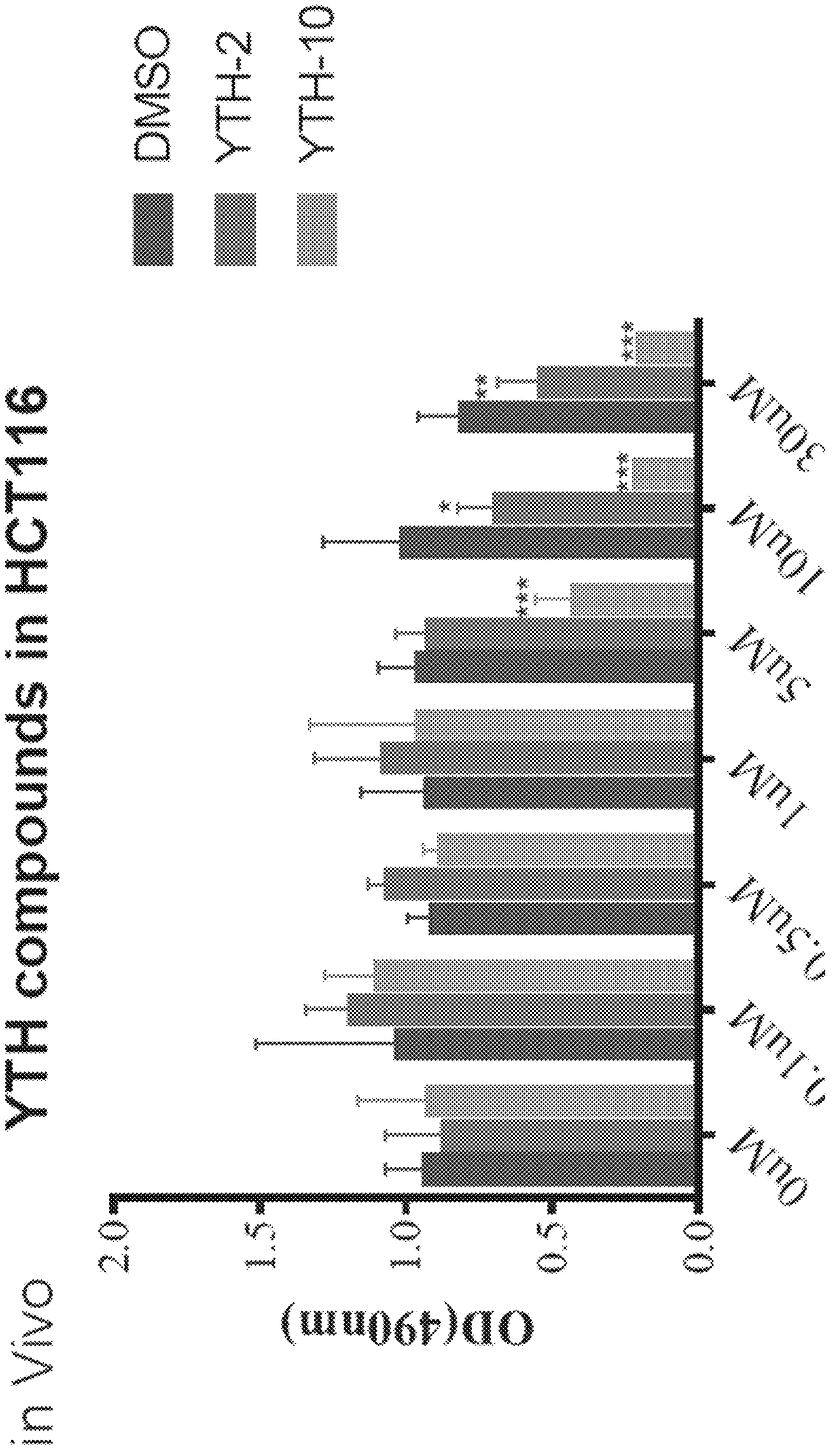
FIG. 109. Plots depicting impact of YHT compounds in mice.
Figure 109:
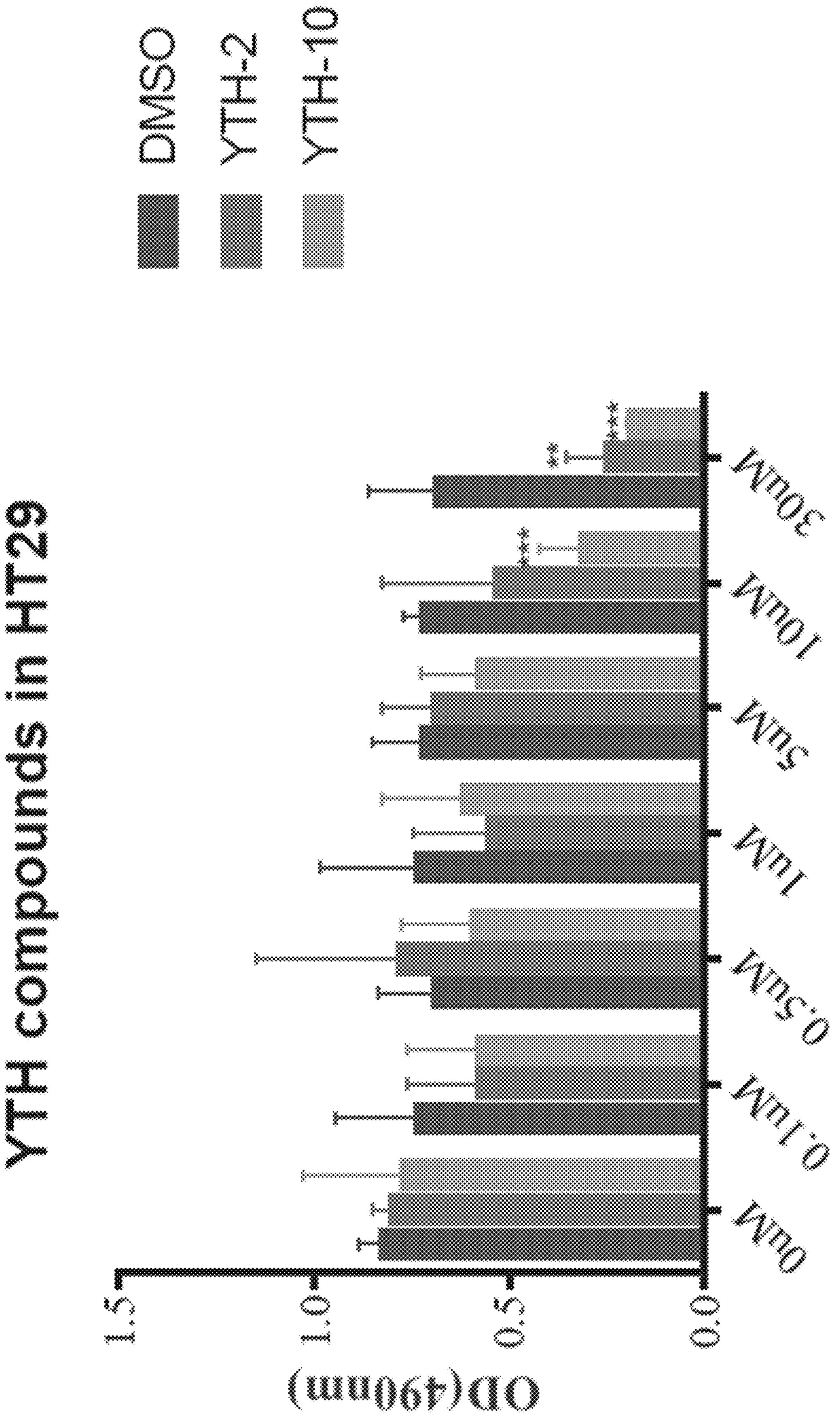
Figure 109:
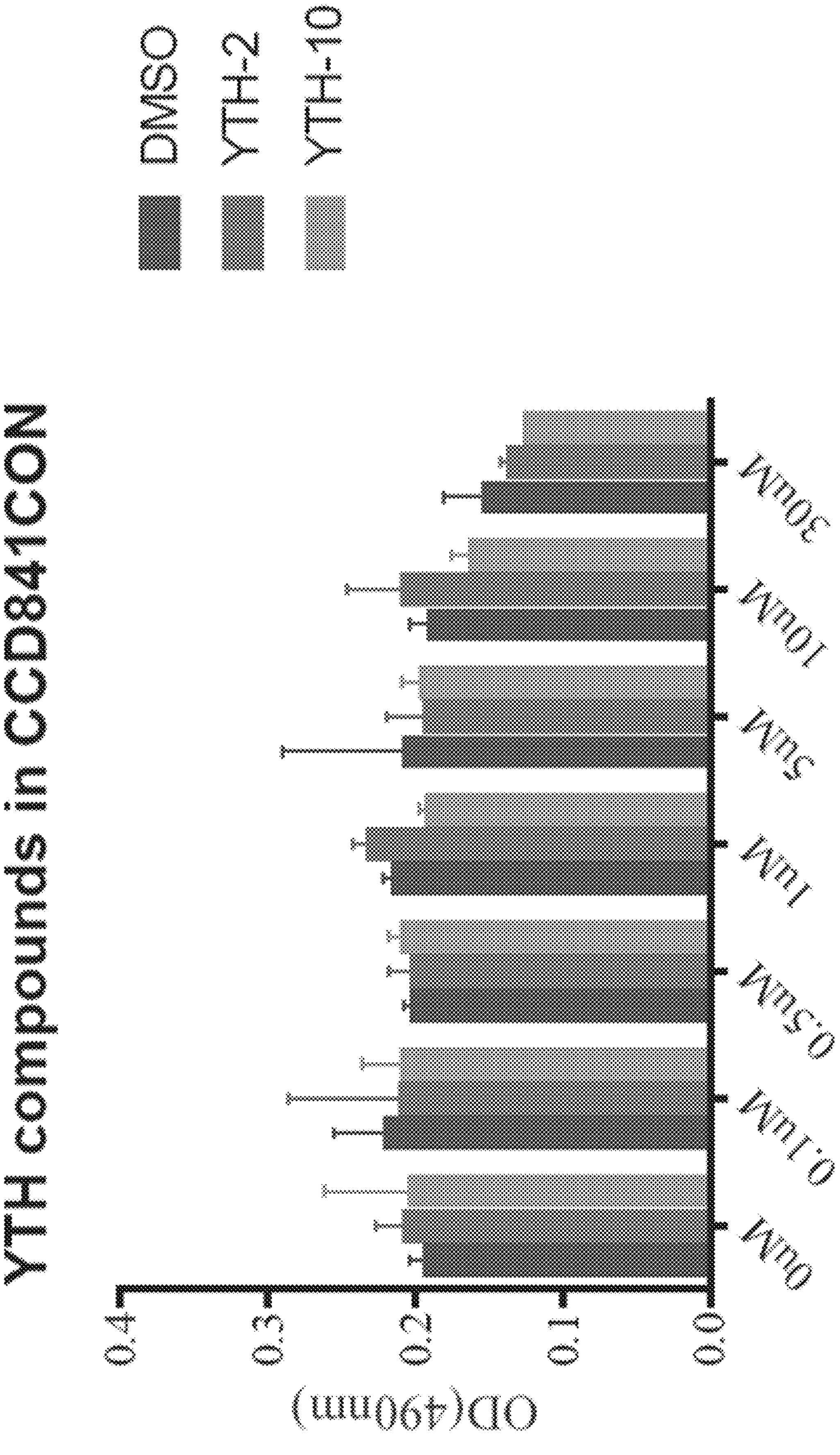
Figure 110:
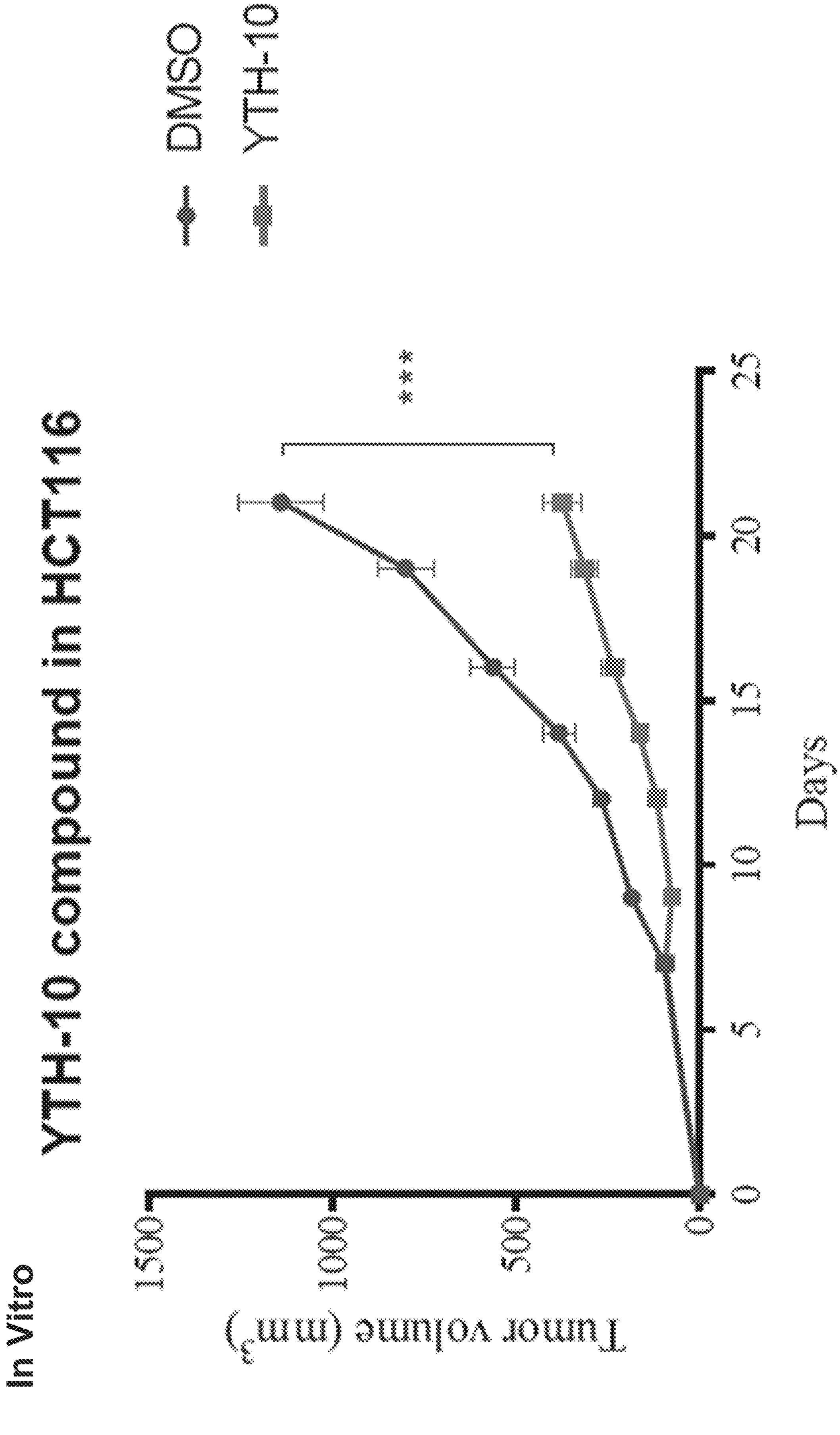
FIG. 110. Plots depicting impact of YHT compounds in mice.
Figure 110:
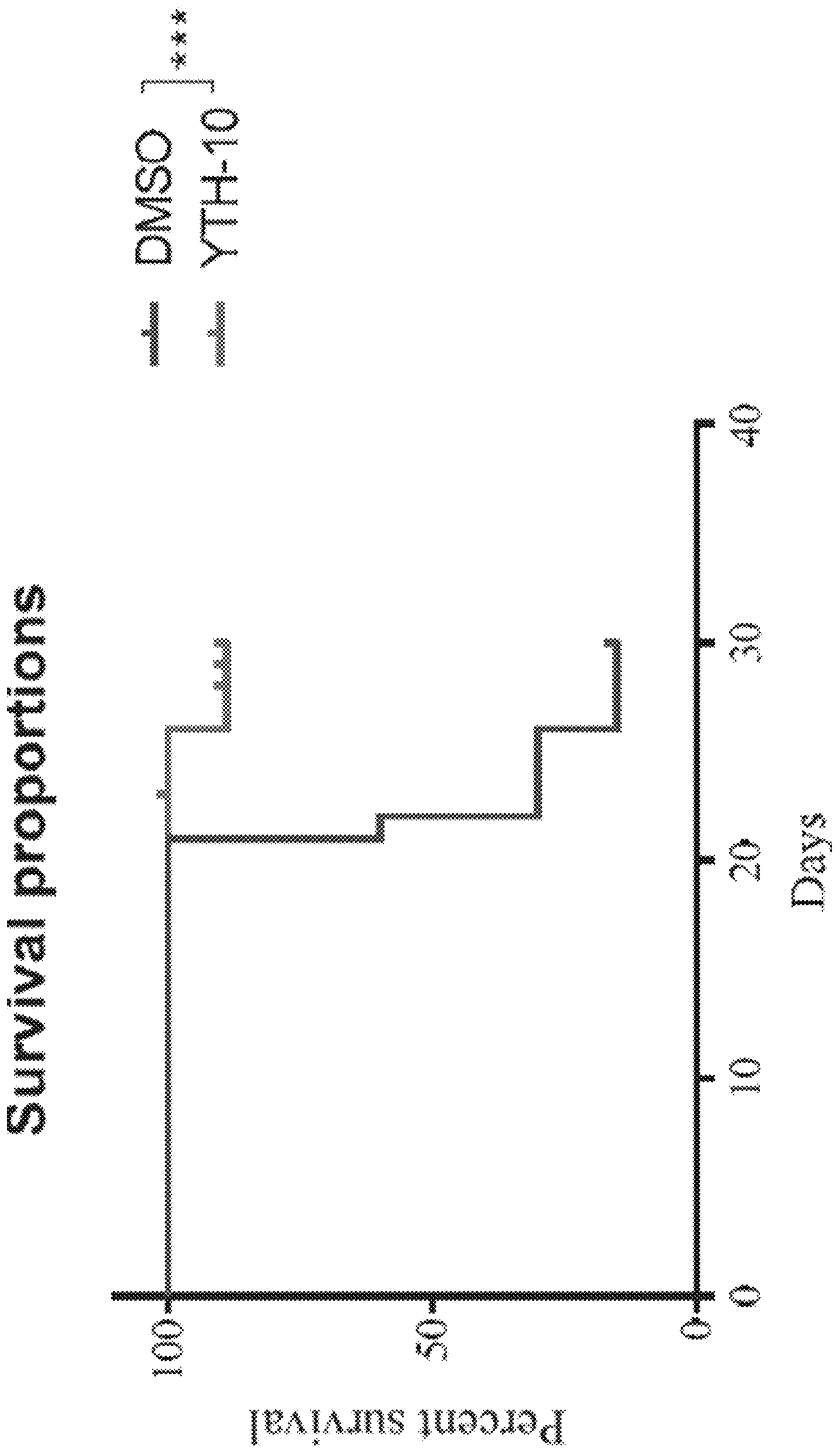
Figure 110:
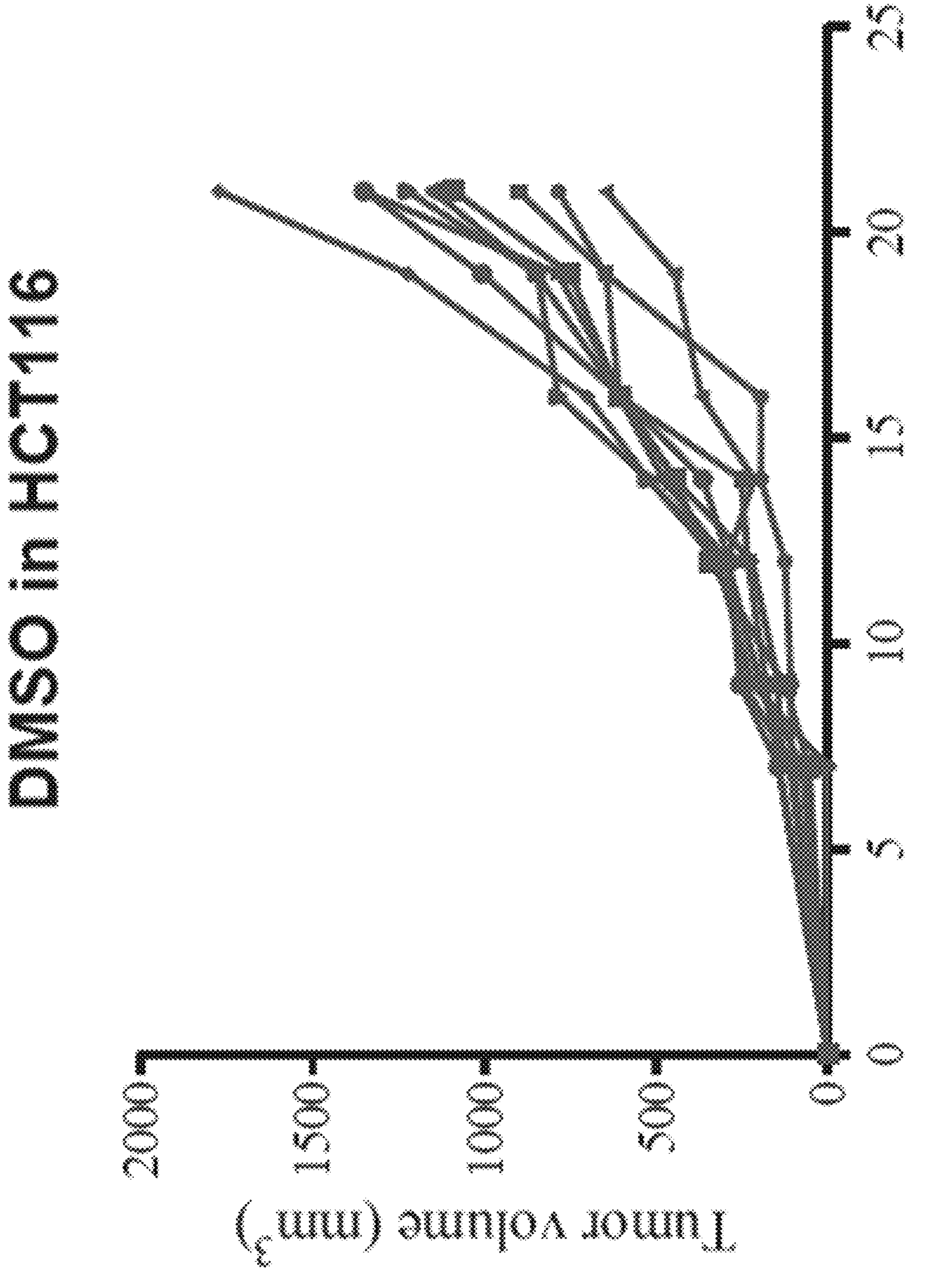
Figure 110:
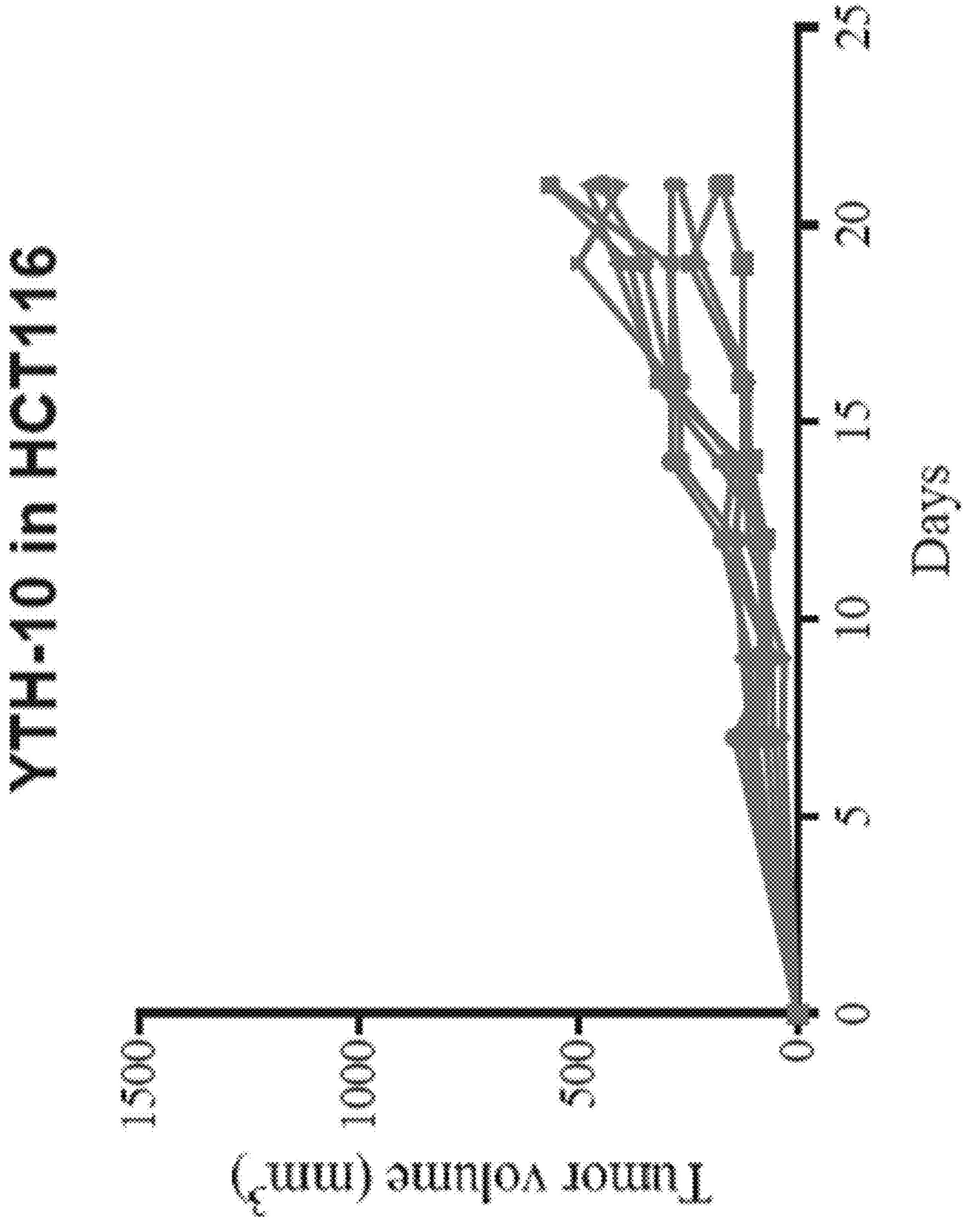
Figure 111:
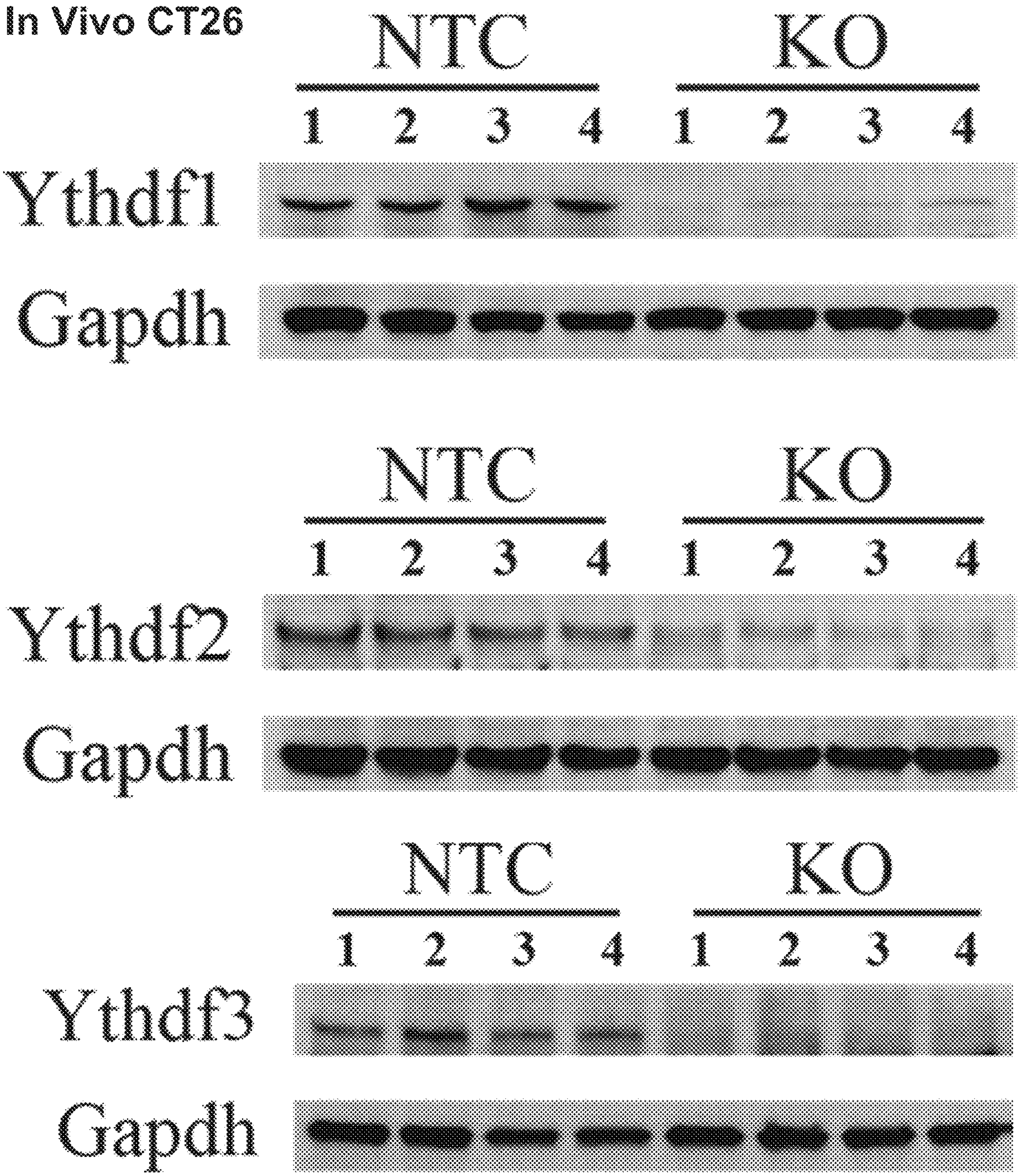
FIG. 111. Plots depicting impact of YHT compounds on tumors.
Figure 111:
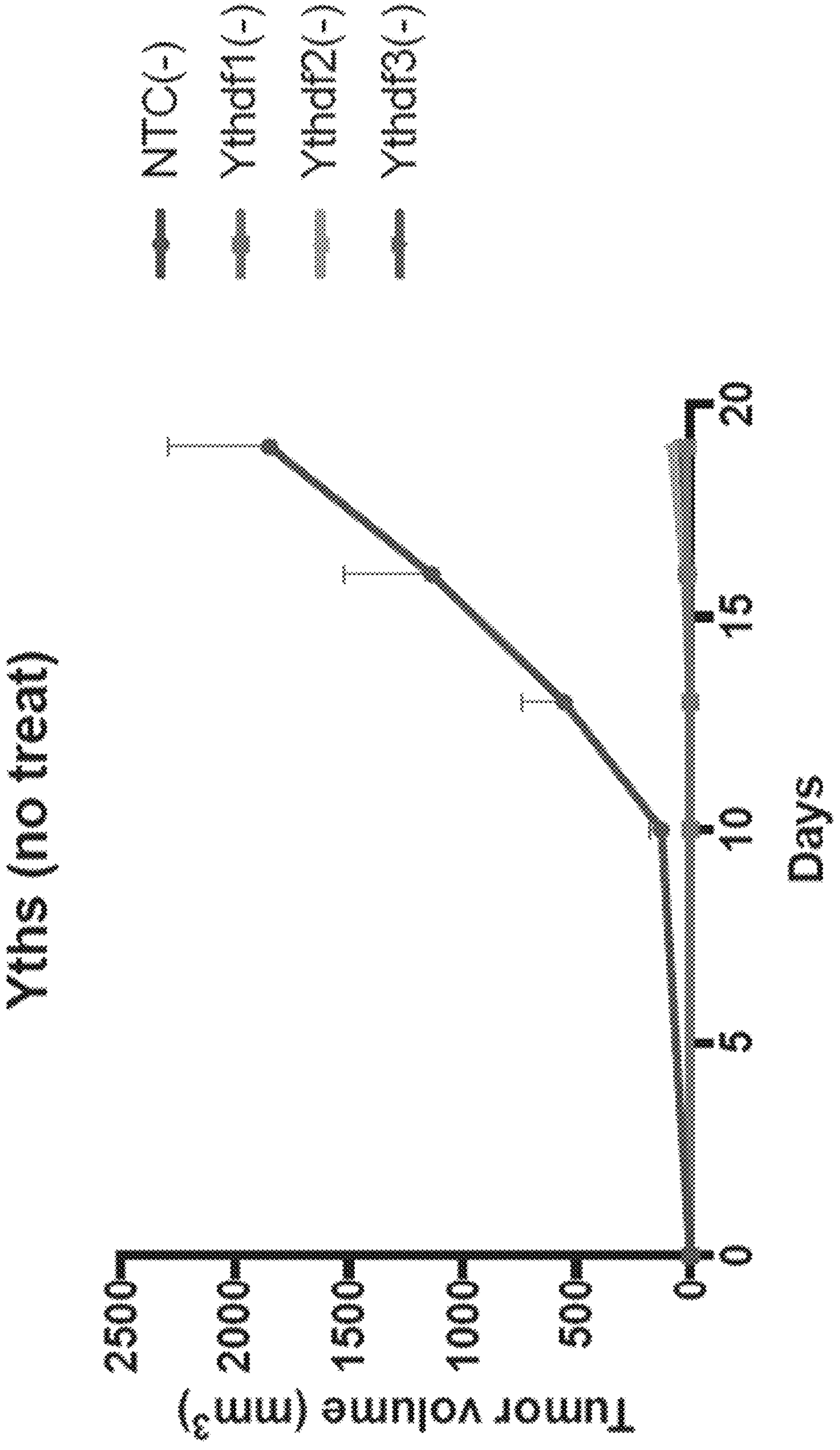

FIG. 104 shows three possible libraries that could be made. FIG. 105 depicts possible design and synthesis of compound libraries. In Vitro FRET assay development could yield a high throughput FRET assay to determine binding affinities for potential YHT inhibitors against YTHDF1, YTHDF2, YTHDF3, or other similar proteins. FIG. 106 shows YTH assay validation for MAX m6A RNA. FIG. 107 shows three YTH-like compounds or inhibitors and depicts the compound's KiF1, Kif2, and c log P. FIGS. 108 and 109 show impacts of YTH compounds and YTH-2,10 compound in HCT116 cells. FIG. 110 shows the impact of YTH on tumor compounds over time. Treatment start at Day 7 and treat mice every other day. FIG. 111 shows the impact of Ythdr (−) mice on tumor volume and in vivo mouse strain validation.

Example B9: PTPN2 Inhibitor and PD-1 Antibody Impact Melanoma Growth

Abstract

As immune checkpoint blockade treatments are only effective in a limited number of patients, additional strategies are needed to increase immunotherapy response. Protein tyrosine phosphatase receptor 2 PTPN2 deletion in B16 melanoma cells has been shown to sensitize tumors to immunotherapy treatment by enhancing interferon-γ IFNγ signaling, resulting in tumor growth suppression. Using in silico modeling and structure-based design, we synthesized ten small molecule inhibitors targeting PTPN2. We show that while these inhibitors are nontoxic as single agents, they induce growth suppression in B16 melanoma cells when combined with IFNγ treatment. Additionally, three inhibitors were shown to upregulate expression of T-cell chemokines CXCL11 and CCL5 when combined with IFNγ treatment and to induce expression of phosphorylated STAT1 consistent with PTPN2 deletion. These inhibitors present promising leads for future in vivo validation of PTPN2 inhibition as a mechanism to increase immunotherapy response.

Introduction

Tumors have adapted to avoid the immune system by expressing T-cell regulating receptors such as cytotoxic T-lymphocyte antigen 4 (CTLA-4) and programmed cell death protein 1 (PD-1).[1,2] When expressed on T cells and their ligands CD80/CD86, CTLA-4 and PD-1 effectively regulate T cell activation; however, when expressed on tumor cells these proteins inhibit T-cell signaling and promote tolerance and exhaustion of T cells, enabling immune evasion and tumor cell survival.[1,3] The development of antibodies and fusion proteins that target PD-1, PD-L1, and CTLA-4 has represented a breakthrough in cancer therapy by enabling T cell response to tumor antigens.[4,5] However, immune checkpoint blockade remains ineffective in most patients and those who do respond often develop resistance and experience relapse.[6] Strategies that sensitize resistant tumors to immune checkpoint blockade treatments are necessary to overcome the current limitations of this breakthrough therapy.

Immune checkpoint receptors such as PD-1 and CTLA-4 can suppress T-cell response (TCR) by recruiting phosphatases to counteract cell receptor-induced kinase signaling and co-stimulatory receptors such as CD28 on αβ T cells.[1,3] Protein tyrosine phosphatase N2 (PTPN2, also known as TCPTP) negatively regulates ap TCR signaling by dephosphorylating and inactivating the Src family kinase (SFK)[7,8]; PTPN2 also antagonizes cytokine signaling required for T-cell function, homeostasis, and differentiation by dephosphorylating and inactivating Janus-activated kinase (JAK)-1 and JAK-3, as well as their target substrates signal transducer and activator of transcription (STAT)-1, STAT-3, and STAT-5.[9-12] PTPN2-mediated dephosphorylation of STAT1 and JAK1 is also known to negatively regulate interferon-γ (IFNγ) signaling.[13-16] Manguso et. al demonstrated that loss of function of PTPN2 increased IFNγ signaling and antigen presentation to T cells while also inducing growth arrest in tumor cells in response to cytokines.[17] These results indicate that inhibition of PTPN2 could sensitize tumors to immunotherapy by invoking an IFNγ response.

To determine if PTPN2 inhibition could sensitize tumors to immunotherapy treatment, we sought to develop small molecule inhibitors of PTPN2 by in silico modeling and structure-based design. Ten inhibitors were synthesized in three steps and high yields. Stable PTPN2 knockout B16 melanoma cells were developed and treated with cytokines to replicate the phenotype reported in Manguso et. al. PTPN2 knockout B16 cells showed a marked increase in RNA expression of T cell chemokines CXCL11 and CCL5 and was observed to sensitize tumors to treatment with IFNγ, as reported.[17] Western blot analysis confirmed increased phosphorylation of STAT1, consistent with PTPN2 inhibition. Furthermore, wild type B16 melanoma cells treated with IFNγ and PTPN2 inhibitors PTP-5, 7, and 9 also showed upregulation of CXCL11 and CCL5 and increased phosphorylation of STAT1, as observed in the PTPN2-knockout B16 cells. While the inhibitors showed no cytotoxic effects as single agents, combined treatment with PTP-5, 7, or 9 and IFNγ significantly impaired tumor growth in a manner consistent with the IFNγ-treated PTPN2 knockout cells. This study identifies three PTPN2 inhibitors as potential leads for development as sensitizing agents to immunotherapy treatment.

Methods

Mice and Treatments

Seven- to nine-week-old wildtype female C57BL/6J mice were obtained from the Jackson laboratory. Mice were age-matched to be 7-12 weeks old at the time of tumor inoculation. $0.5\times10^6$ B16F10 melanoma cells were resuspended in phosphate-buffered saline (PBS, Gibco) and subcutaneously injected to the right flank of mice on day 0. On day 1 and 4, mice were vaccinated with irradiated (1 OOGy) GM-CSF-secreting B16 (GVAX) cells on the left flank to elicit an anti-tumor immune response. On day 6 and 9, all mice were intraperitoneally injected with PD-1 antibody. PTPN2 inhibitor (50 mg/kg diluted in DMSO, 1 OPI per mouse) or DMSO (1 OPI per mouse) was intratumorally injected to the two groups on day 10, 12 and 14. Tumors were measured every two days from day 7 until the time of death or day 18. When the tumor reached 2.0 cm in the longest dimension, the mouse was defined as death. Tumor volume (length×width2)/2. Mice were euthanized with $CO_2$ inhalation on the day of euthanasia.

Flowcytometry Analysis of Tumor-Infiltrating Lymphocytes

Tumors were dissected on the day when reached 2.0 cm length or day 18. The tumor tissues were weighed, mechanically diced, incubated with collagenase P (2 mg/ml, Sigma-Aldrich) and DNase I (50 pg/ml, Sigma-Aldrich) for 15 min and then pipetted into a single-cell suspension. Cells were filtered through a 70 pm filter (Corning). anti-mouse CD16/32 antibody (BioLegend) was used to block all samples. Dead cells were excluded by Zombie Aqua (BioLegend). All surface and intracellular markers were stained under per manufacturer's instruction. Single-color compensation controls and fluorescence-minus-one thresholds were used on RUO green to set gate margins. Group comparisons were performed using Student's t-test.

Results

In Silico Modeling and Structure-Based Design of PTPN2 Inhibitors

Figure 112:
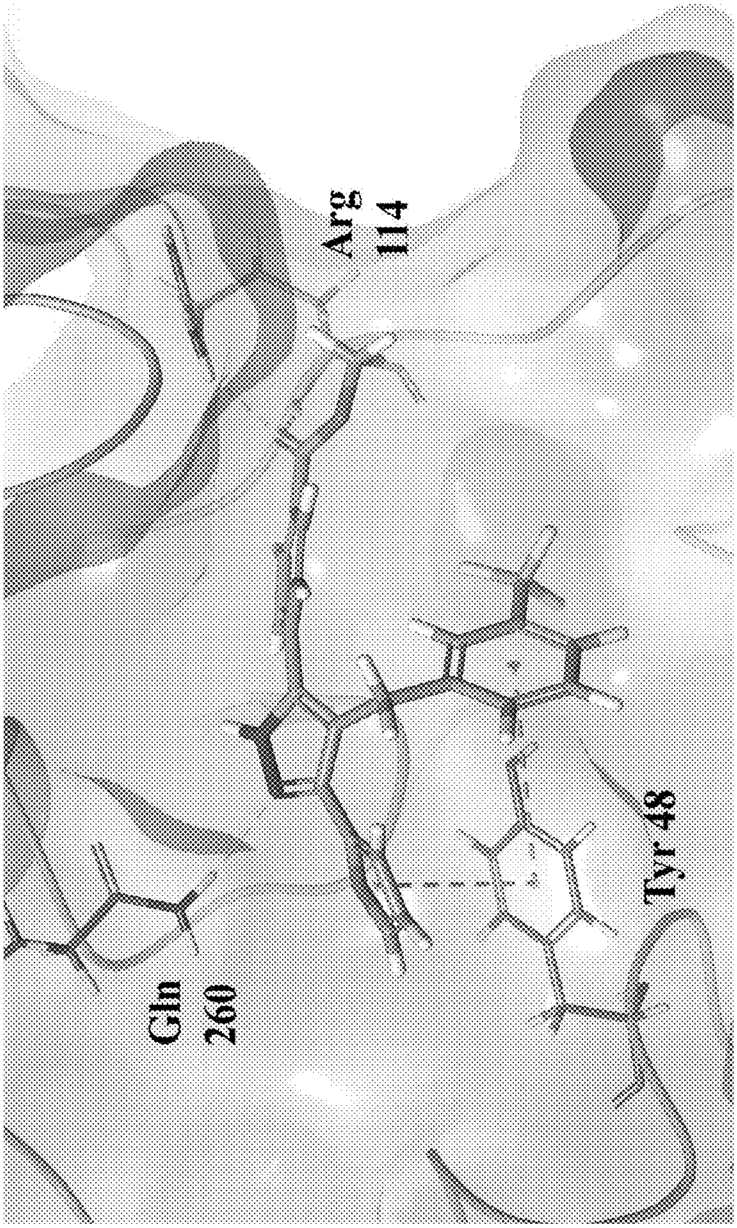
FIG. 112. Docking pose of PTPN2 inhibitor PTP-5 against the active site of PTPN2.
Figure 113A:
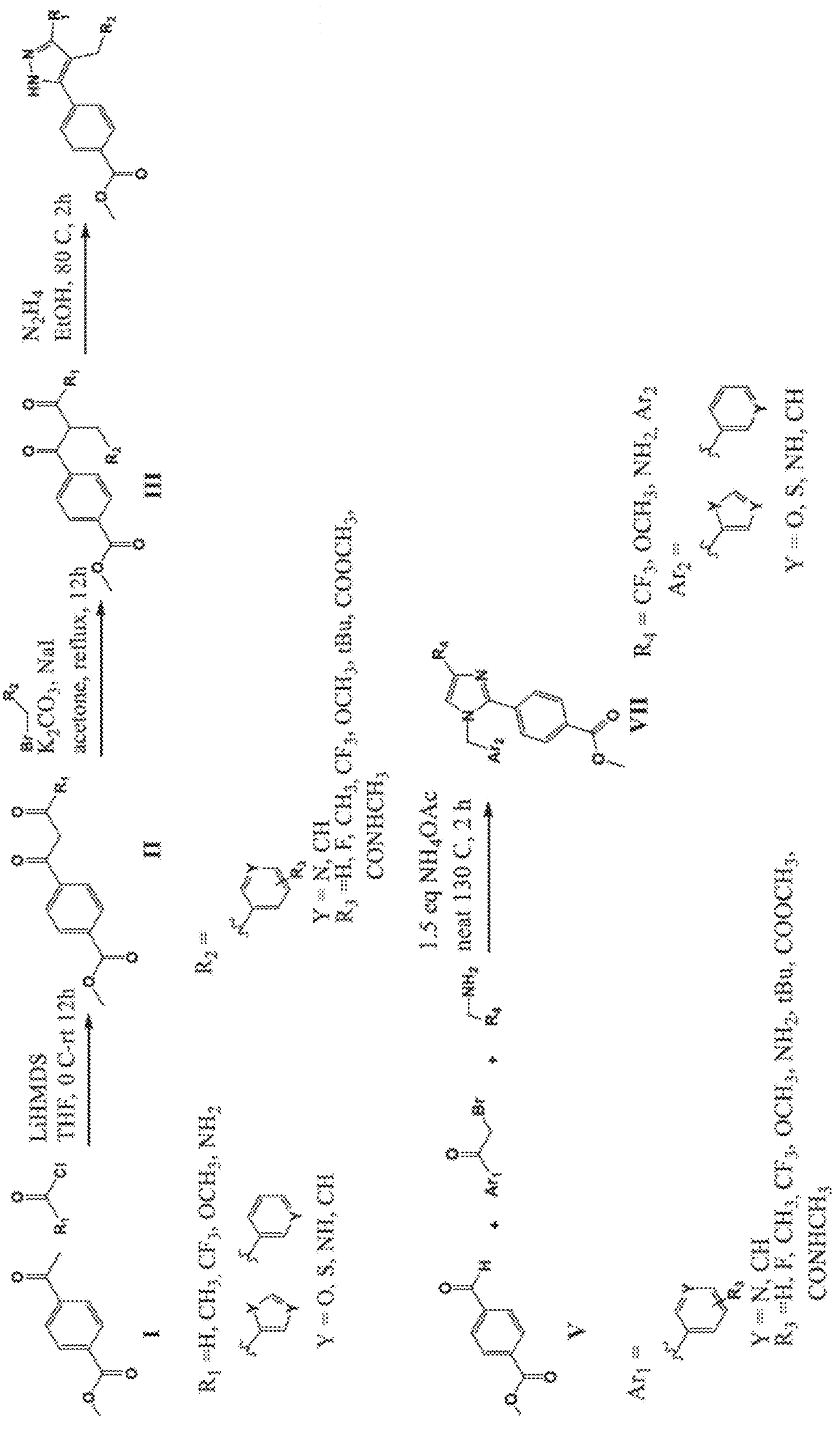
FIG. 113A-113B. Scheme of synthetic routes to PTPN2 inhibitors.
Figure 113B:
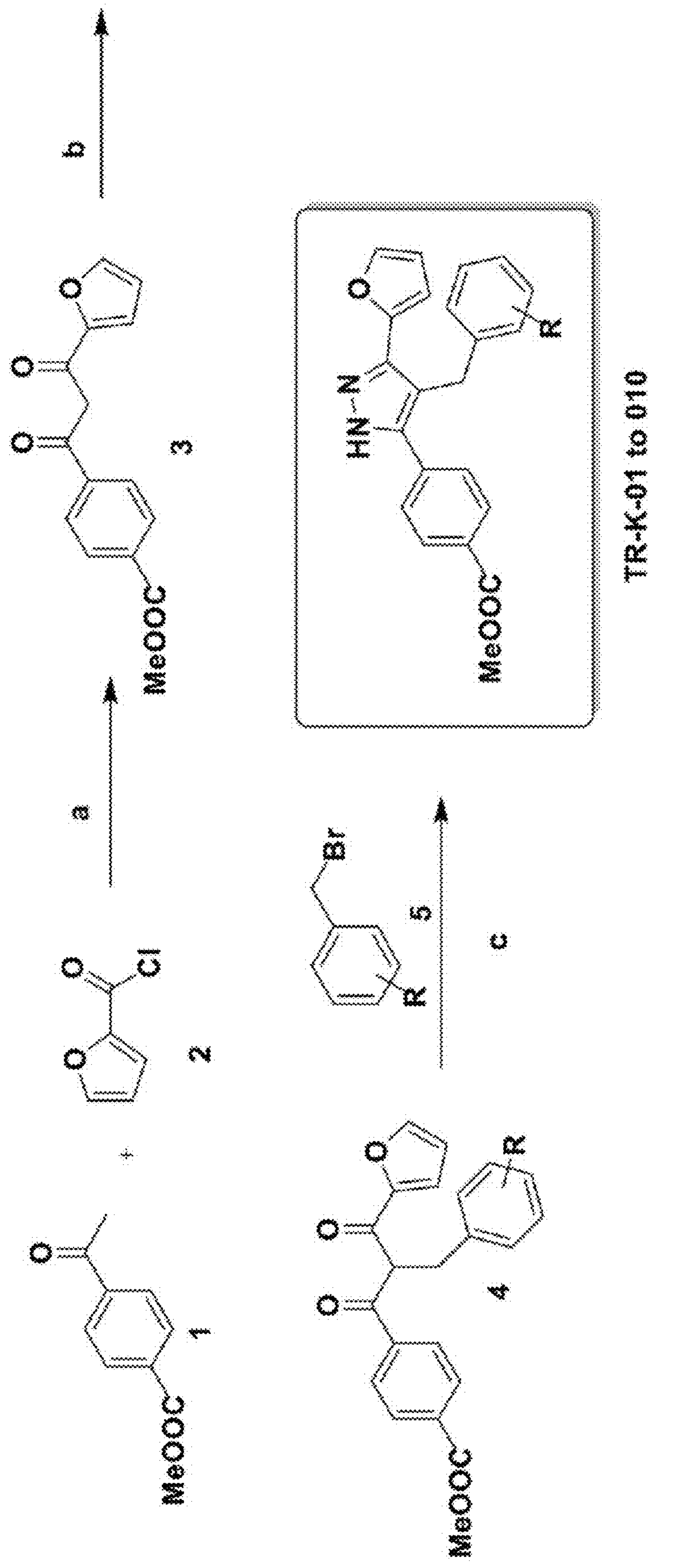
Figure 114A:
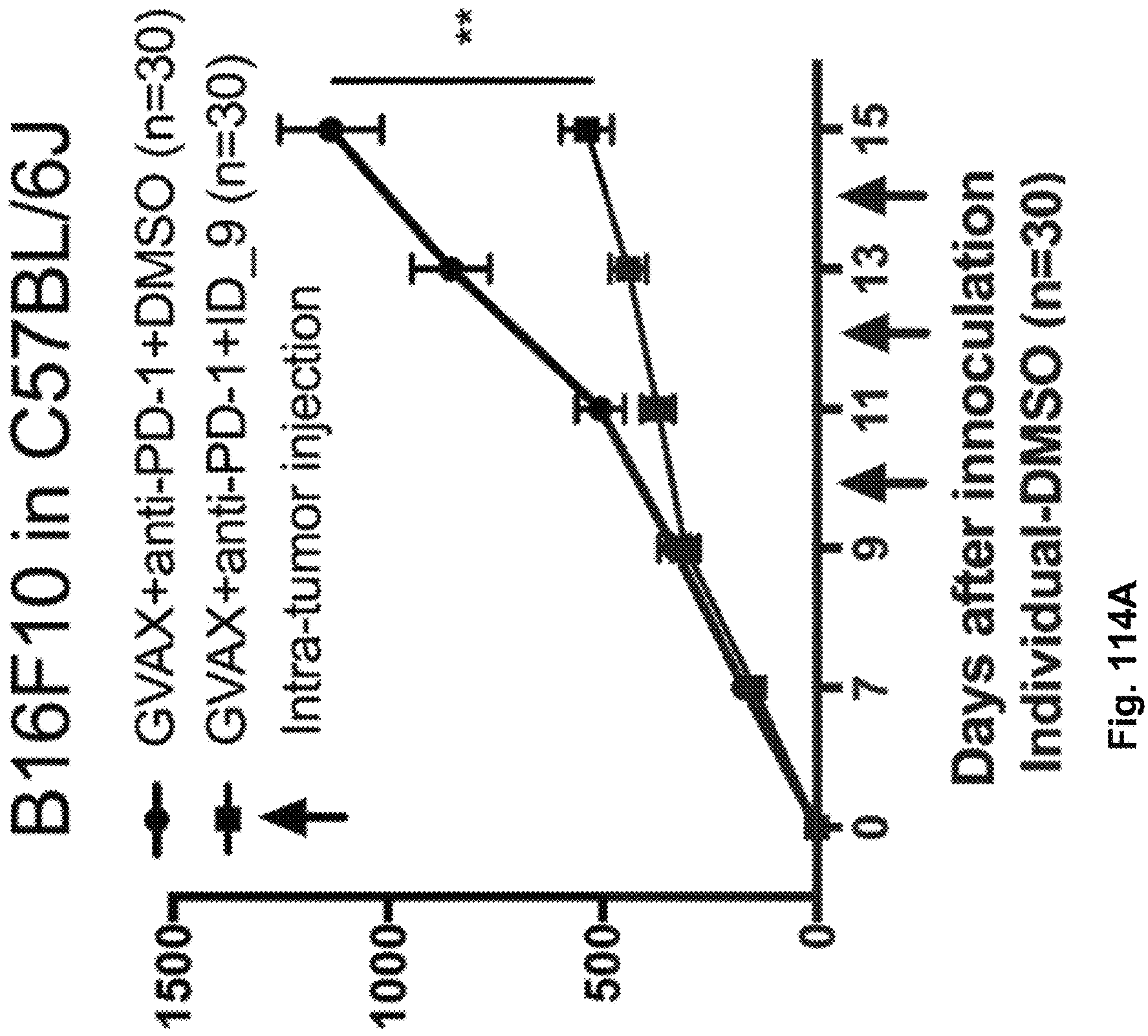
FIG. 114A-114D. Anti-PD-1 and PTPN2 inhibitor ID_9 synergistically reduce murine B16FI0 melanoma in vivo growth. (114A) C57BU6J mice bearing B16F10 derived melanoma were treated with GVAX (on day 1 and 4) plus anti-PD-1 (on day 6 and 9) combined with DMSO control or PTPN2 inhibitor ID_9 (on day 10, 12, and 14). ID_9 and anti-PD-1 combination drastically reduced average tumor volume upon three times ID_9 intratumor injection. (114B) Survival analysis of DMSO control group versus ID_9 group. ID_9 intratumor injection together with anti-PD-1 immunotherapy induced long-last protection to mice with B16F10 melanoma. (114C and 114D) Individual mouse tumor growth curve in DMSO control and ID_9 groups. Data are mean±SEM; n=30 mice per group. *P<0.05; P<0.01; *P<0.001; ****P<0.0001.
Figure 114B:
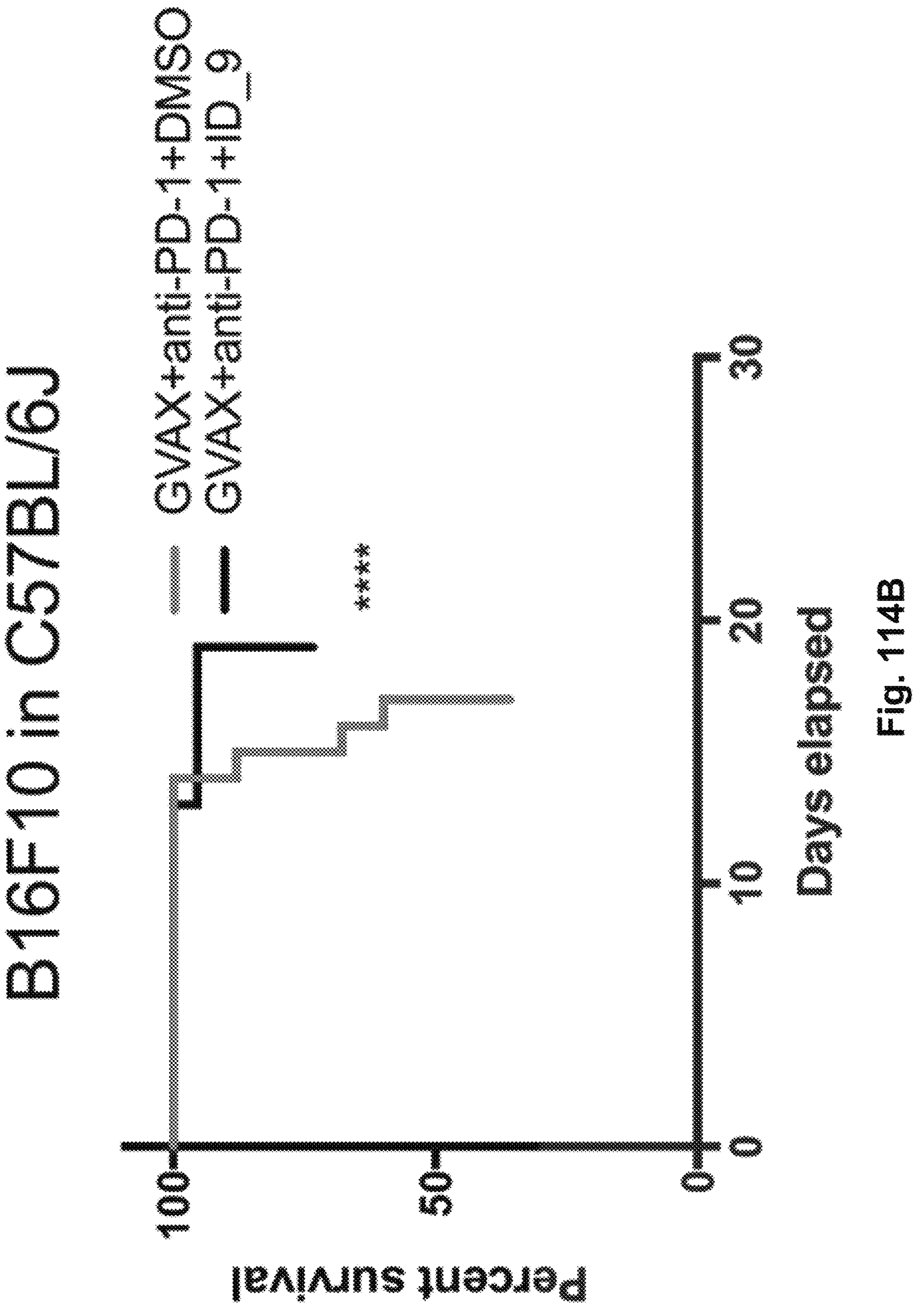
Figure 114C:
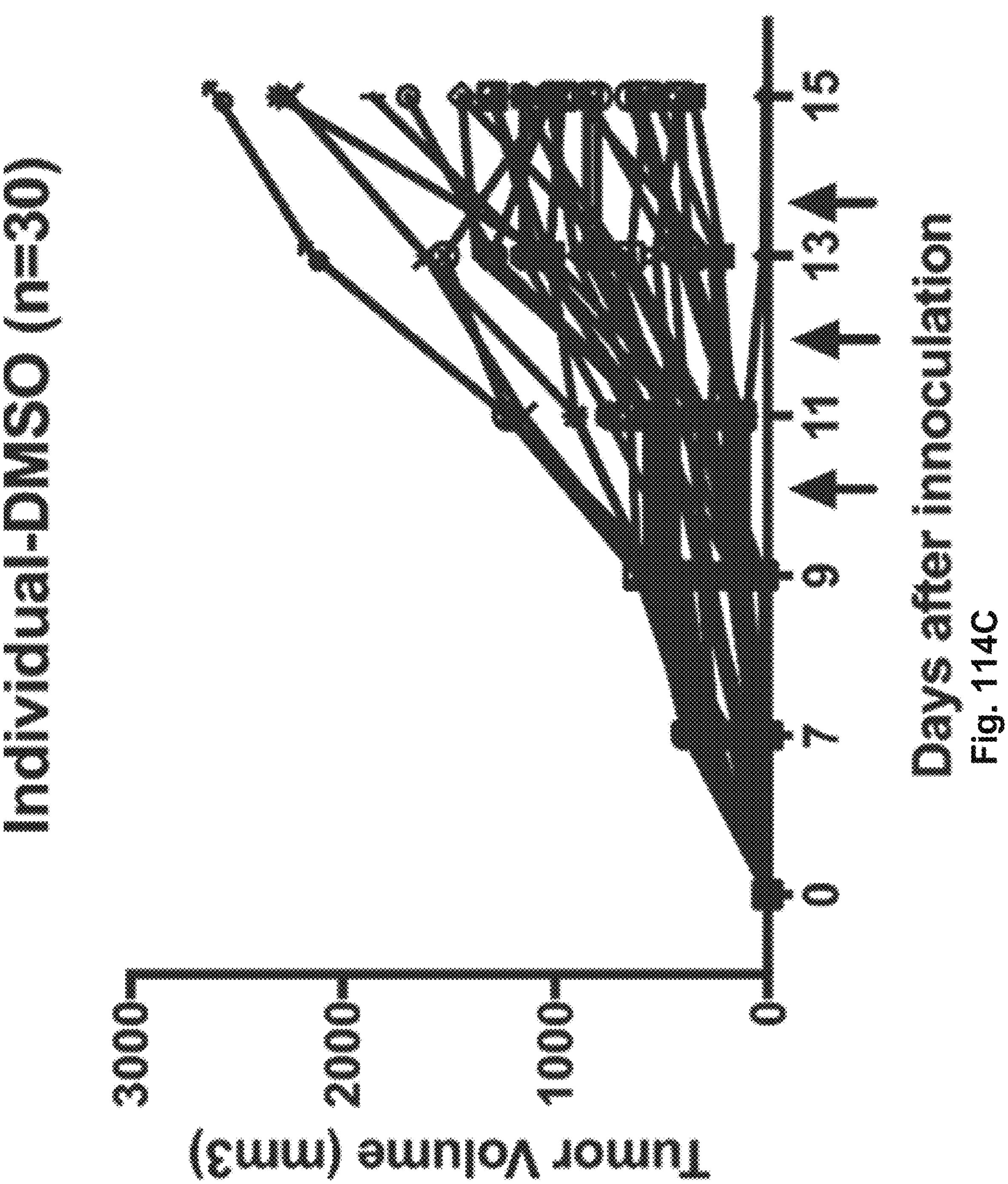
Figure 114D:
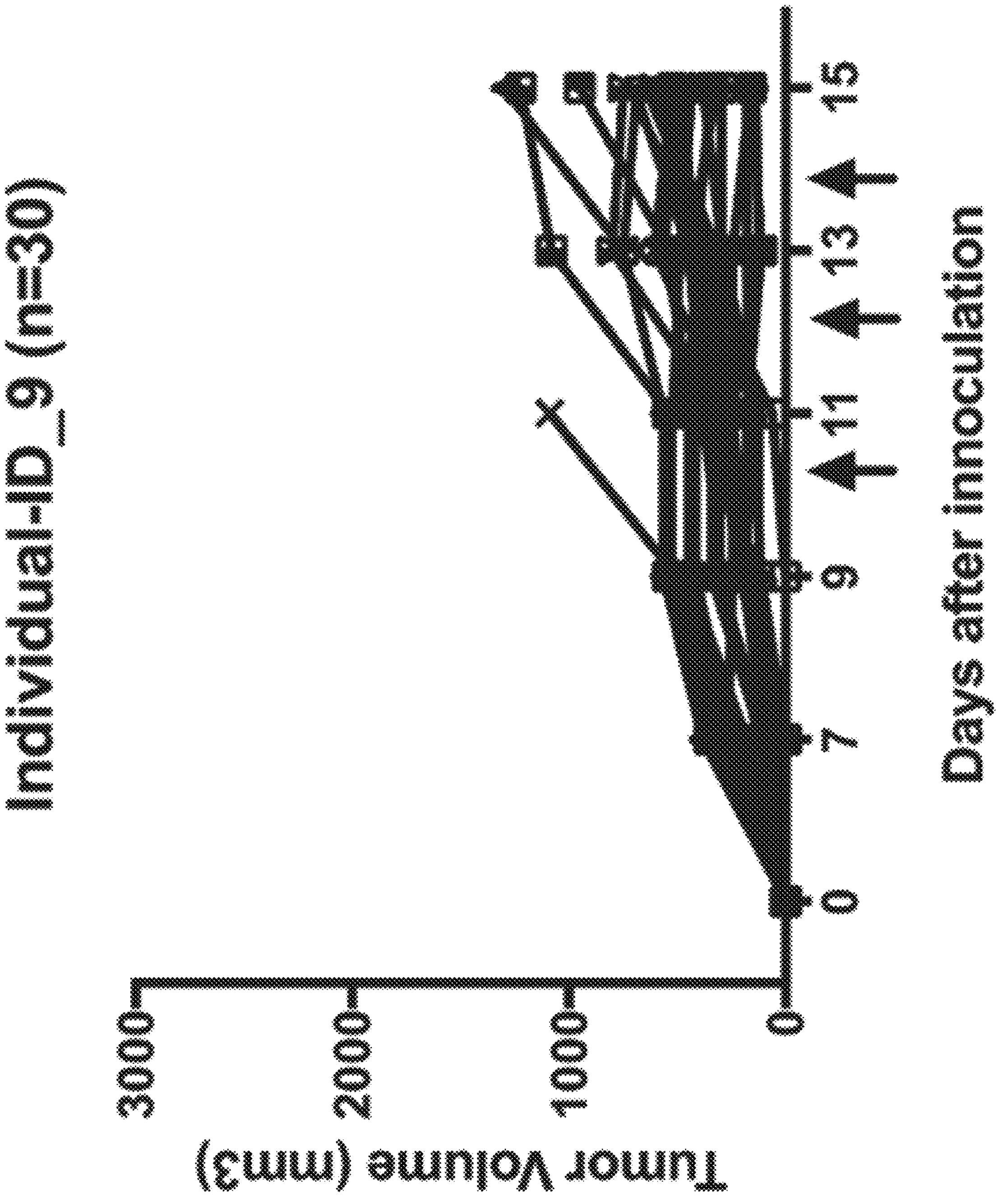

Previous reports have indicated that PTPN2 negatively regulates the IFNγ signaling pathway by inhibiting dephosphorylation of JAK1 and STAT1.[13-16] As such, we theorized that loss of function of PTPN2 would sensitize tumor cells to immunotherapy treatment by increasing IFNγ signaling, as reported previously in Manguso et al.[17] To determine if small molecule inhibitors were able to replicate the phenotype reported in Manguso et al., we first sought to identify PTPN2 inhibitors by in silico modeling and structure-based design. Despite the high sequence conservation across the PTP superfamily, selective small molecule inhibitors have been identified for homolog proteins PTP1B and SHP2 (also known as PTPN11) by exploiting small sequence variations in the periphery of the catalytic domain.[18-21] Using one such selective inhibitor of SHP2, PHPS1, we modeled potential inhibitors of PTPN2 in the Schrödinger software suite. Compounds were evaluated for their ability to interact with both the conserved HCX5R motif as well as residues at the periphery of the binding site, such as Tyr 48 or Gln 260 (FIG. 112). This strategy identified three PTPN2 inhibitors which were confirmed to sensitize B16 melanoma cells to IFNγ treatment without inducing cytotoxicity as single agents (FIG. 113). Our strategy in this proposal is to combine rational design with a variety of in vitro biochemical assays and cellular mechanism of action studies to optimize these preliminary leads and develop PTPN2 inhibitors as immunotherapy sensitizing agents.

PTPN2 Inhibitors Through Structure-Based Drug Design

The lead hits identified through the preliminary in silico modeling is optimized for potency and physicochemical properties using structure-based design prior to cell-based testing. Rational design of proposed inhibitors is incorporate a variety of medicinal chemistry techniques, including bioisosterism, scaffold hopping, and structure-activity relationship studies. Design will focus on increasing modeling interactions with key residues in both the HCX5R motif as well as residues at the periphery binding site. Synthesis will be performed as described in Scheme 1. This modular synthetic scheme will enable us to rapidly synthesize approximately 300 rationally designed compounds, all within 1-3 steps. Synthesis of compounds with the imidazole scaffold IV has already been completed in high yields (>75%).

Concomitantly, the log D value can be determined for inhibitors which are potent and selective. Meta-analyses of pharmaceutical drug development projects has identified the importance of log D in identifying compounds which are more likely to feature favorable clearance rates and membrane permeability; one such study found that compounds with a molecular weight of 350 g/mol and a log D of 1.5 had a 25% success rate of being advanced to clinical trials.

Combination of PTPN2 Inhibitor and PD-1 Antibody Impeded In Vivo Melanoma Growth To evaluate the in vivo effect of PTPN2 inhibitor ID 9 in combination with immune checkpoint blockades, we performed anti-PD-1 plus GVAX treatment to C57BL/6J mice with subcutaneously transplanted B16F10 melanoma (FIG. 114). After twice intraperitoneal PD-1 antibody challenge, the mice were injected with DMSO or PTPN2 inhibitor ID 9 intratumorally on day 10, 12 and 14. The tumor growth immediate y slowed down after the first ID 9 injection on day 10. The curves separated even more clearly after three times intratumoral treatment and finally resulted to significant difference in tumor volume on day 15 (FIG. 114A). ID 9 with PD-1 antibody synergistically prolonged overall survival time of mice compared to anti-PD-1 with DMSO control group (FIG. 114B). The individual mouse tumor growth curves are shown in FIGS. 112C and 112D. To conclude, PTPN2 inhibitor ID 9 synergistically with PD-1 antibody impeded melanoma in vivo growth in C57BL/6J mice.

Figure 115A:
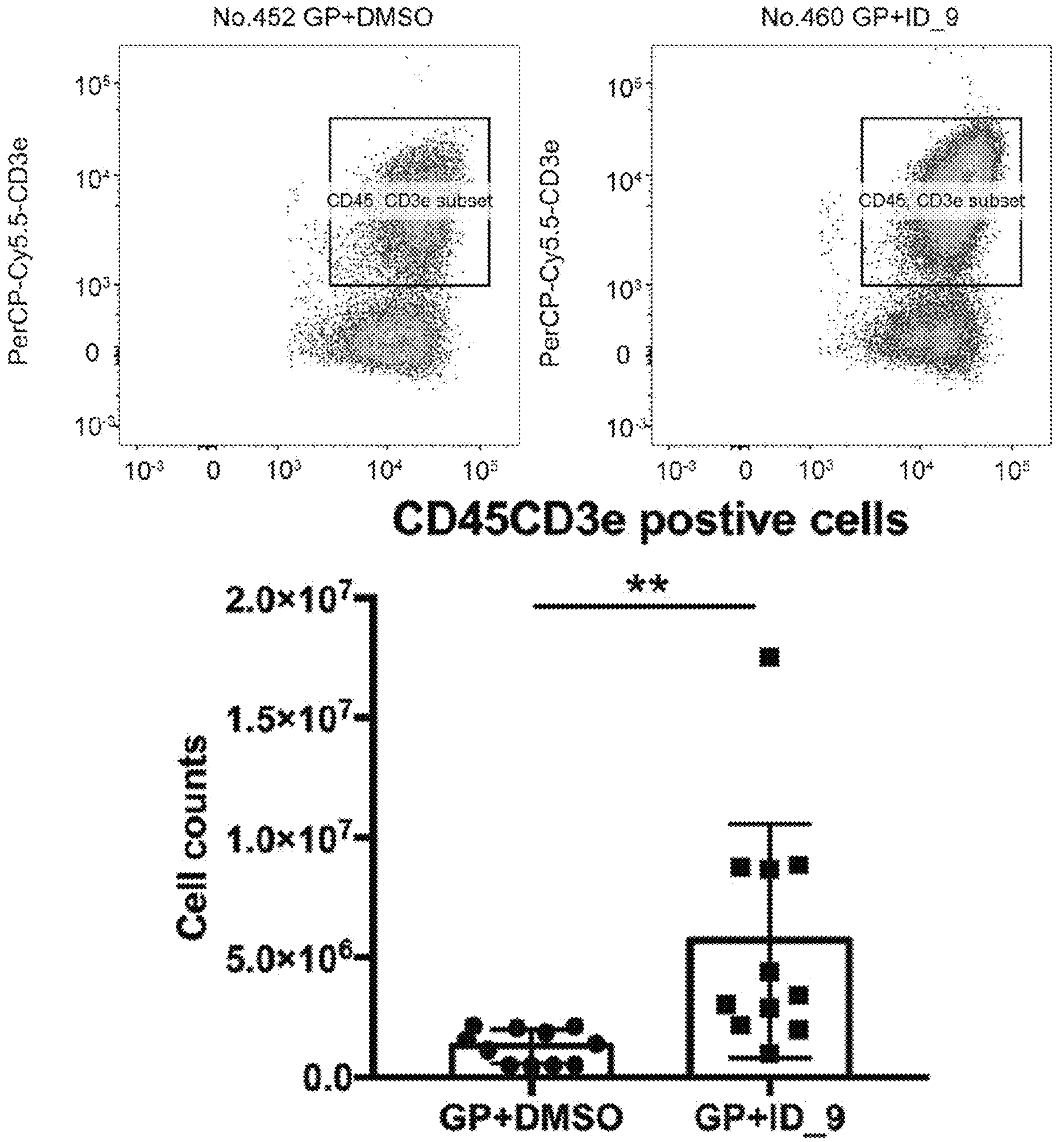
FIG. 115A-115C. anti-PD-1 and PTPN2 inhibitor ID_9 combination therapy increases intratumoral CD8 positive T cell infiltration. (115A) Representative FACS plots show ID_9 group tumor's total T cells (CD45 and CD3e positive) count increased after compound ID_9 intratumoral challenge. Summary FACS result indicates an average intratumoral T cells upregulation of ID_9 group compared to DMSO control. (115B) CD8 and CD4 positive T cells are shown in representative FACS plots. Intratumoral CD8+ T cells are especially enhanced in ID_9 group. (115C) Granzyme B positive ratio in CD8 T cells is upregulated upon ID_9 combination therapy. Data are mean±SD; Each dot in summary FACS represents one individual mouse; *P<0.05; P<0.01; P<0.001.
Figure 115B:
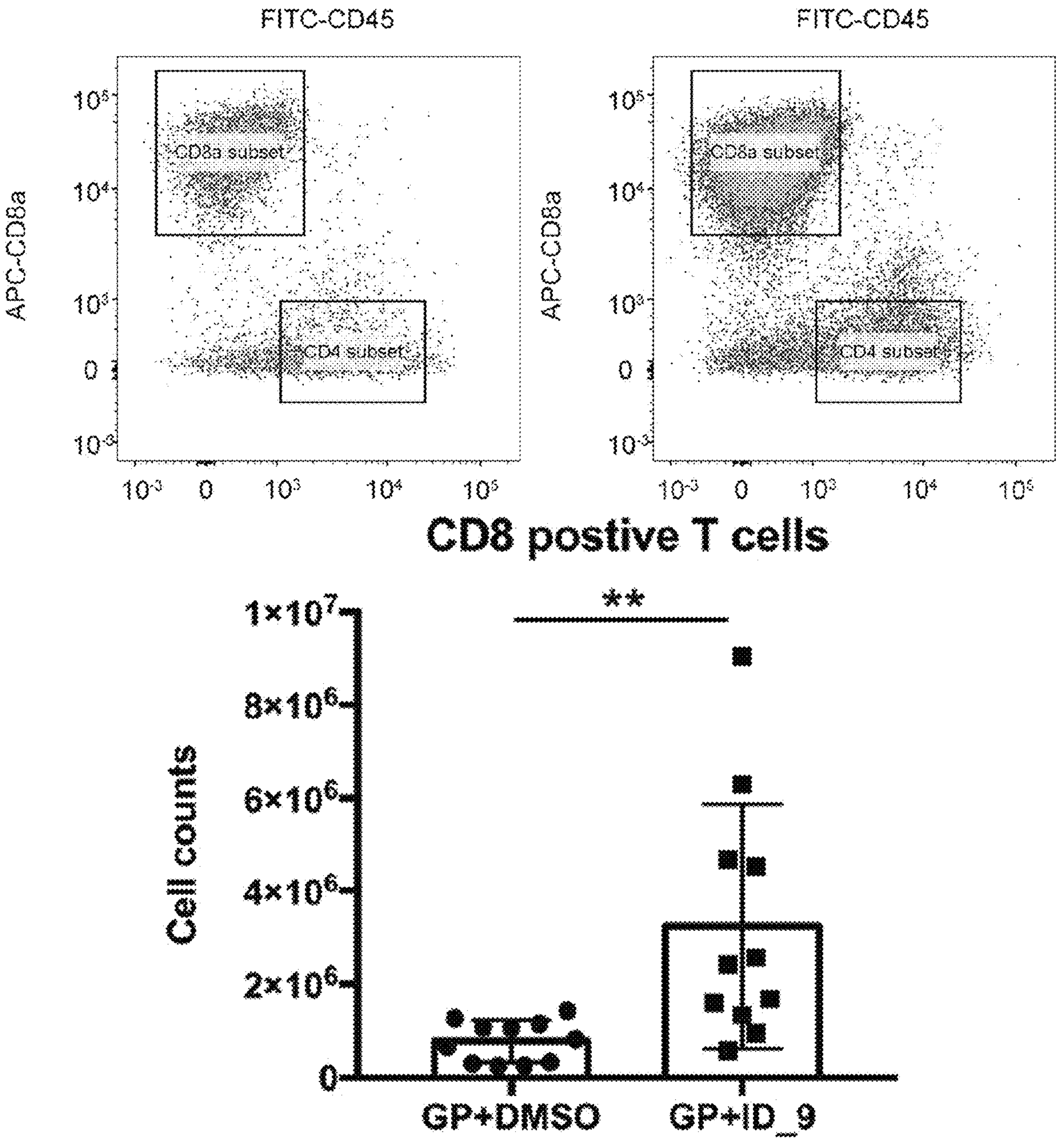
Figure 115C:
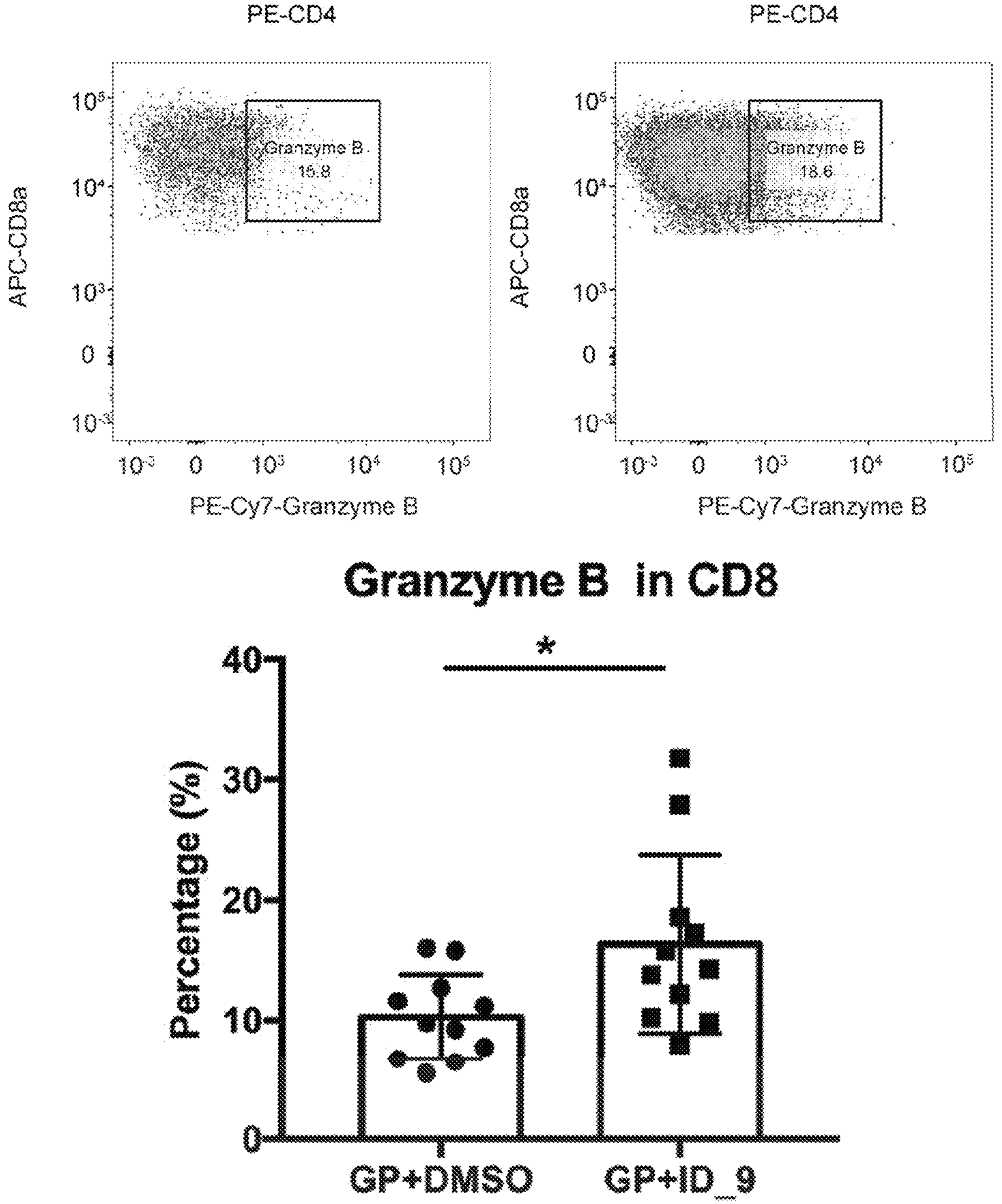
Figure 117:
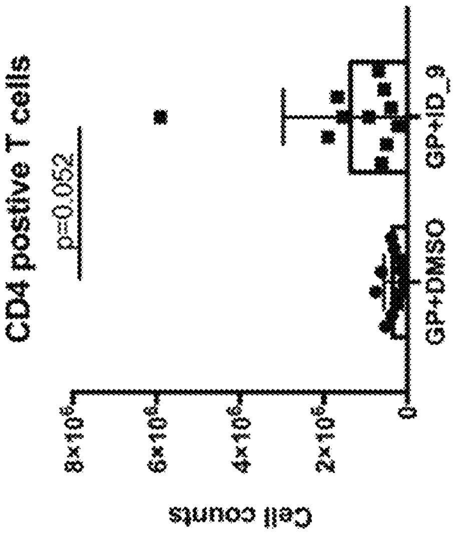
FIG. 117. CD4+ T cells didn't show significant change in most of the ID_9 treated group tumors.
Figure 121:
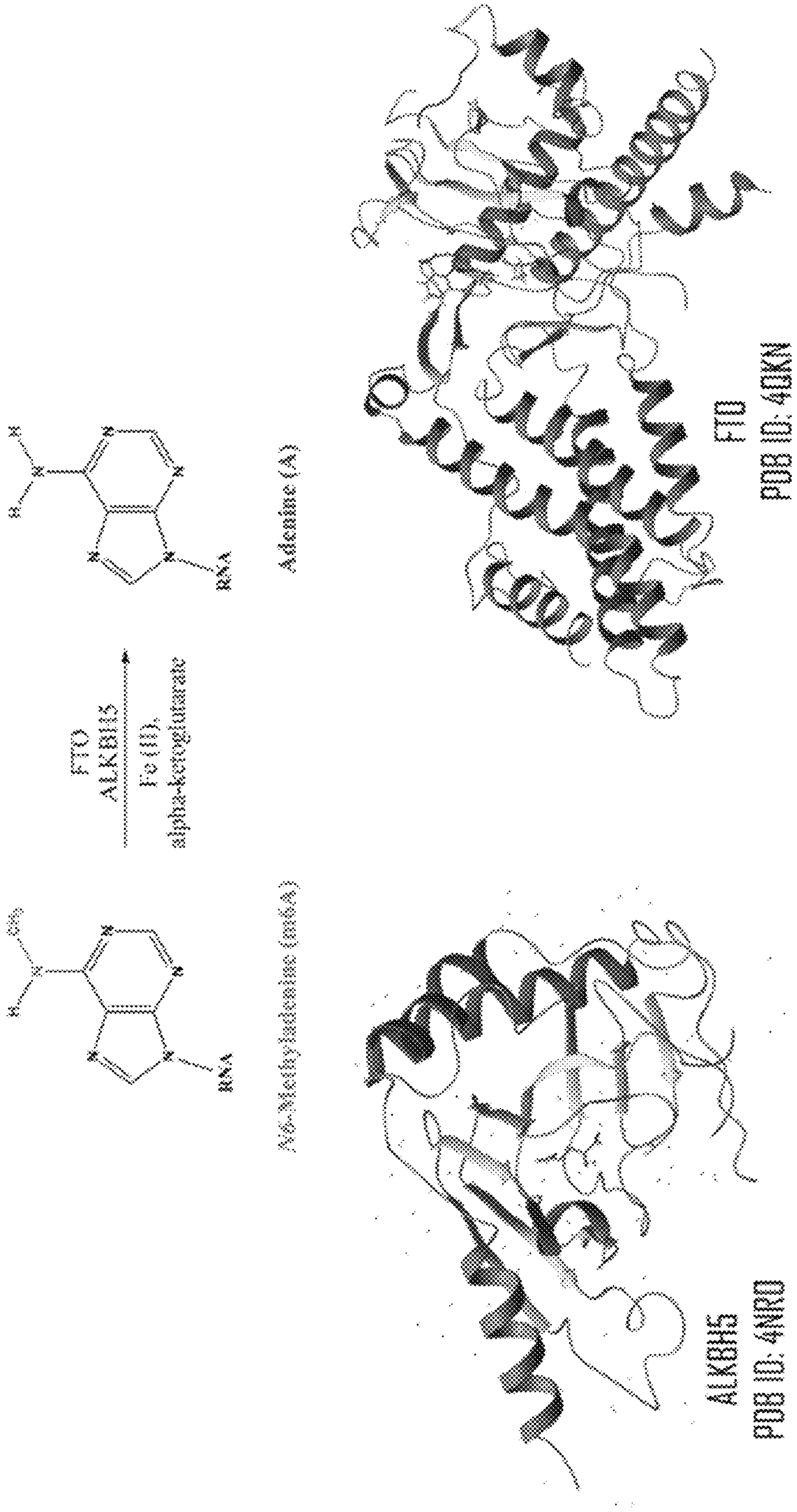
FIG. 121. Depiction of structure-based synthesis, and characterization of inhibitors of m6A RNA demethylases FTO and ALKBH5.
Figure 122:
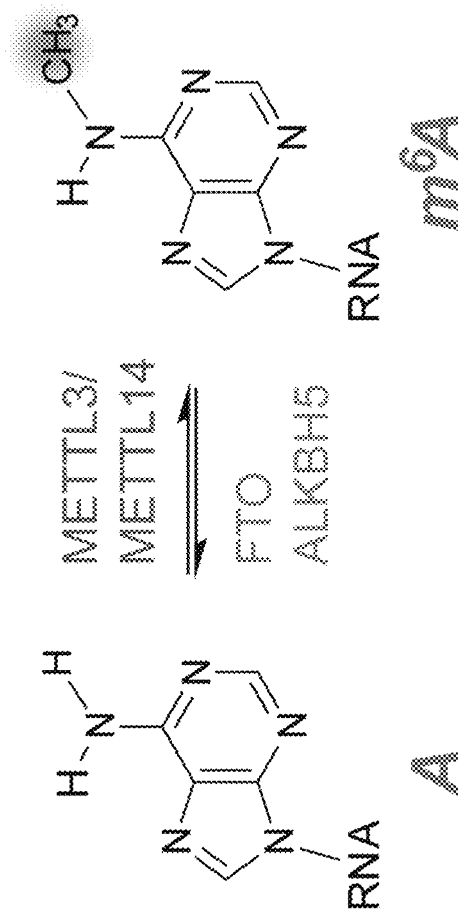
FIG. 122. Depiction of m6A modification. m6A RNA modification is a reversible process controlled by the methylation METTL3/METTL14 writer complex and the two Fe (II)-α-ketoglutarate dependent dioxygenases FTO and ALKBH5.
Figure 123A:
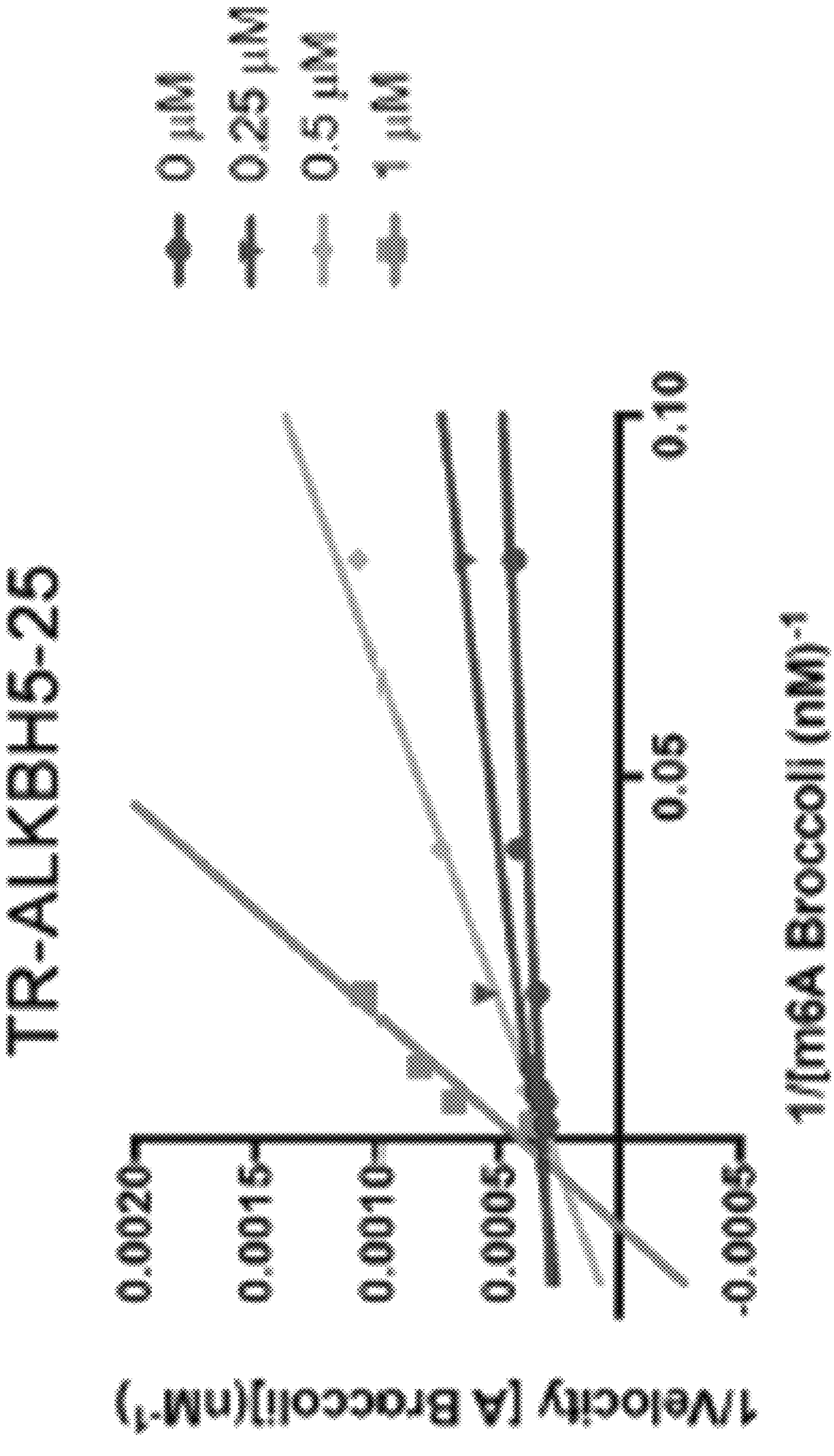
FIG. 123A-123E. Plots showing that sulfonamides inhibit ALKBH5 by multiple mechanisms.
Figure 123B:
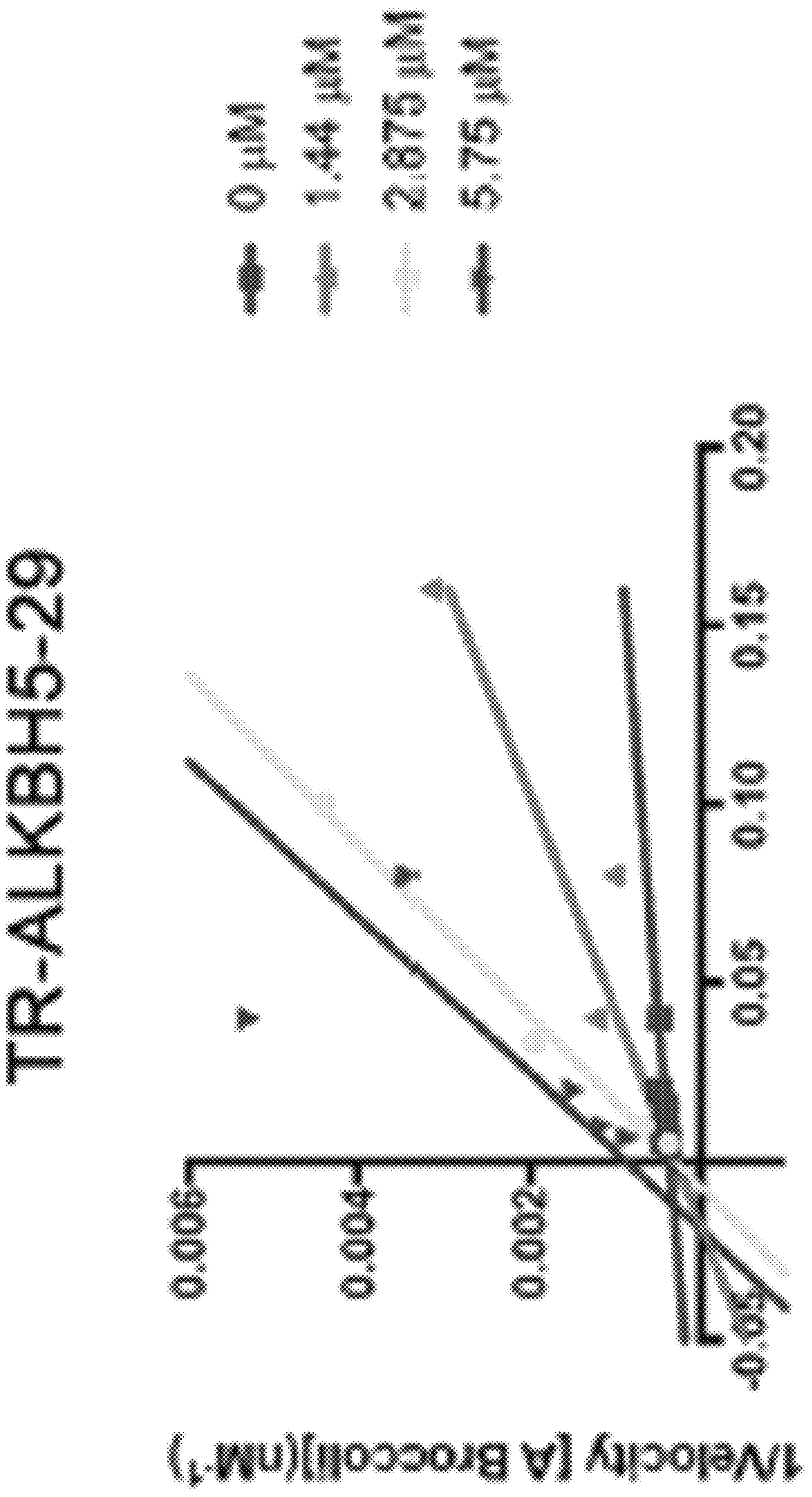
Figure 123C:
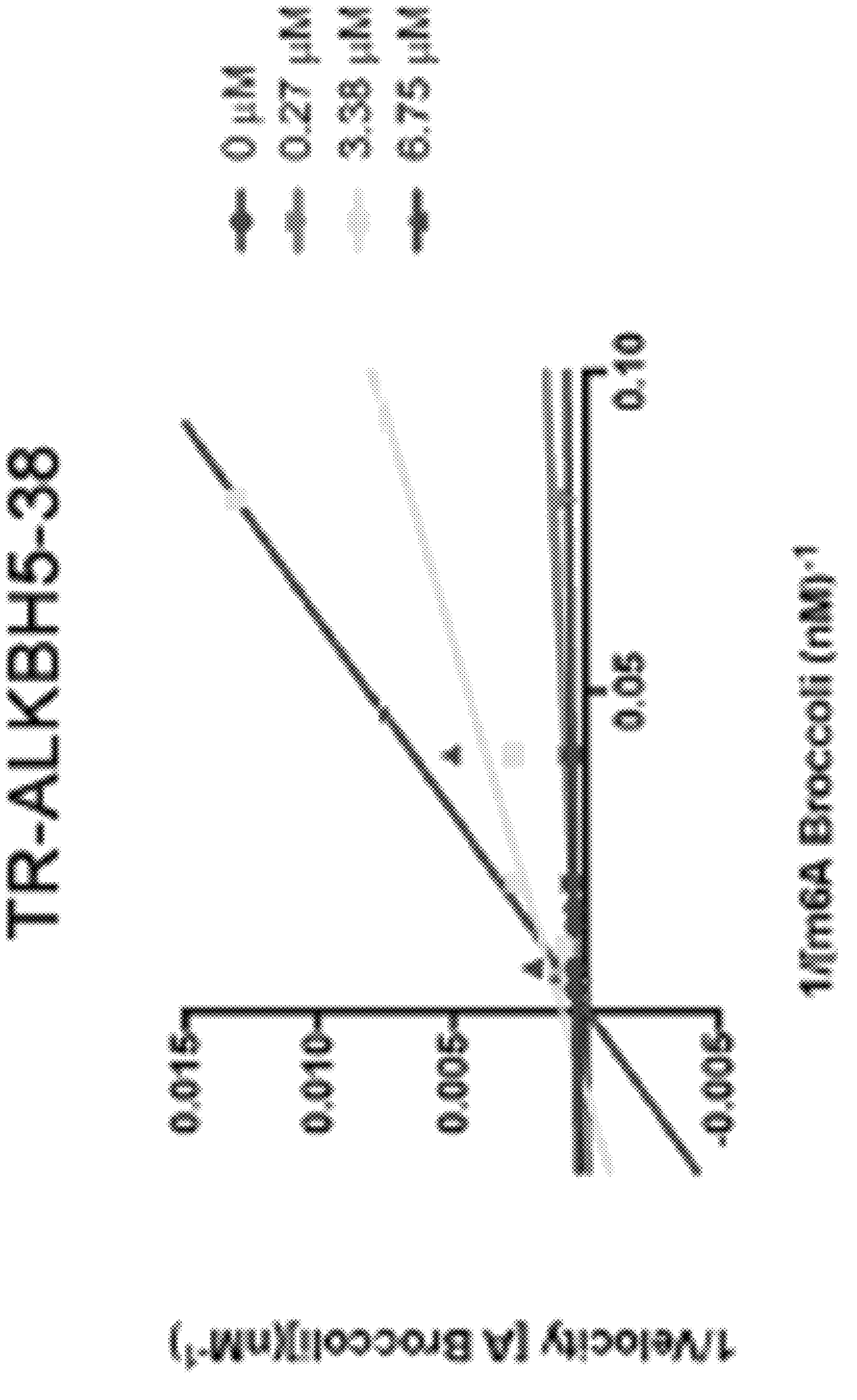
Figure 123D:
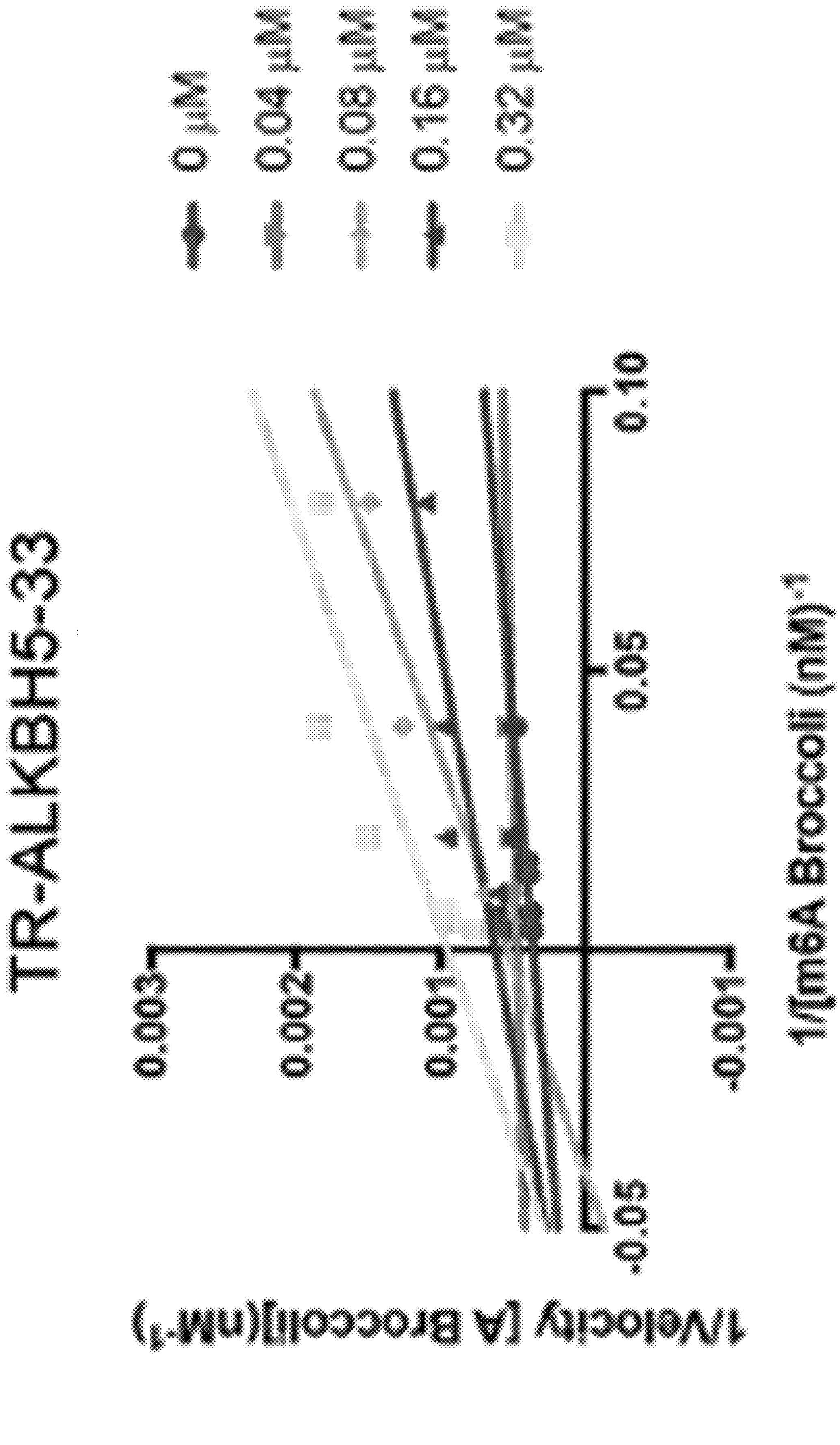
Figure 123E:
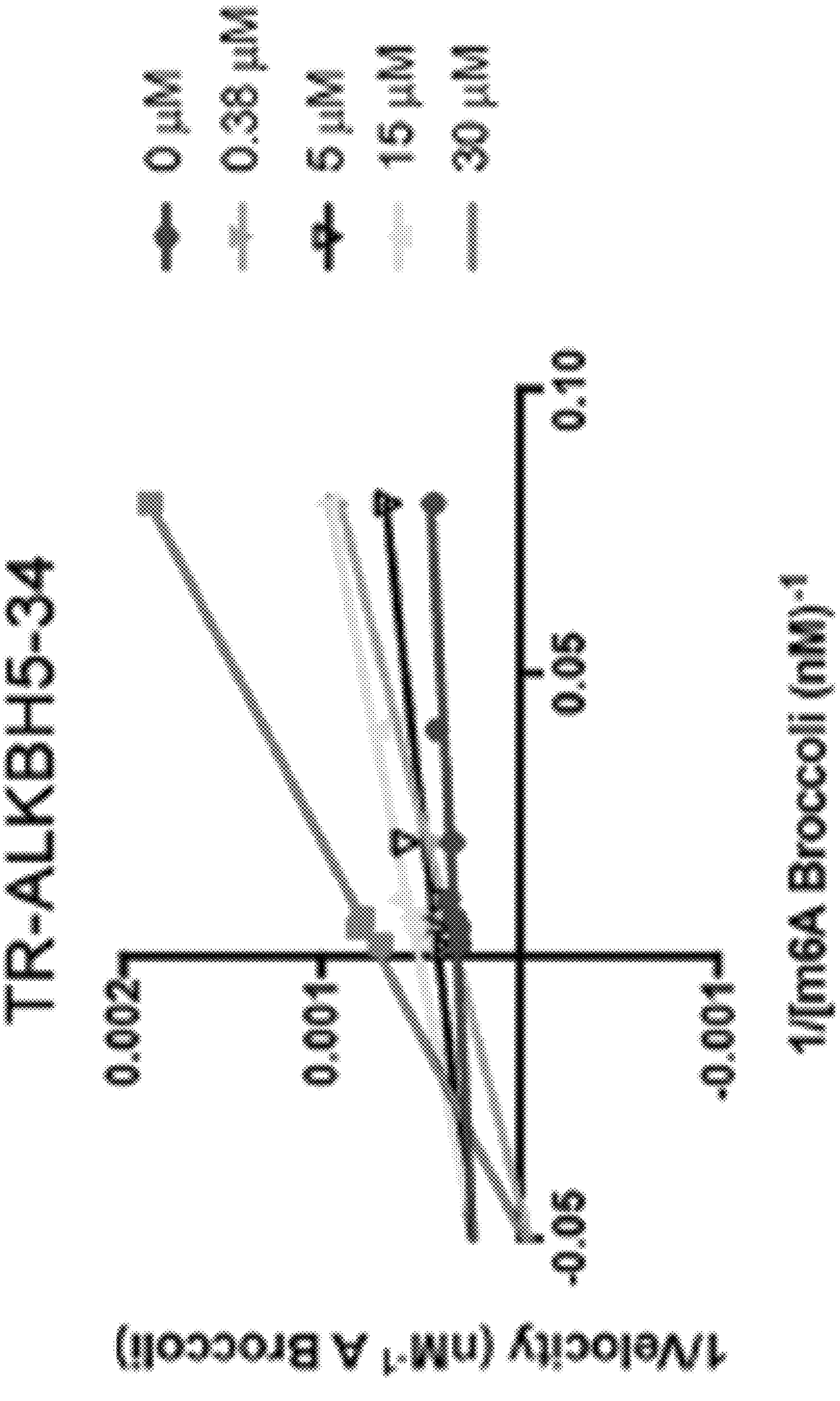

PTPN2 Inhibitor Synergistically Promoted Anti-PD-1 Immunotherapy's Efficacy by Recruiting CD8 Positive T Cells Tumors were finally dissected, stained and performed flowcytometry analysis. T lymphocytes were marked as CD45 and CD3e positive cells. More T cells were sorted in ID 9 compound treated group tumor tissues compared to DMSO group (FIG. 115A). Among the sorted T lymphocytes, CD8+ T cells exhibited drastic increase after ID 9 challenge. Most of the ID 9 group tumor tissues contained more than $2\times10^6$ CD8+ T cells while the DMSO control group tumor tissues had fewer than $2\times10^6$ (FIG. 115B). However, when counting CD4+ T cells, we didn't observe an analytically significant increase despite some upregulation in several samples (FIG. 117), which is consistent with the reported PTPN2 knockout model with cancer immunotherapy (1). The antitumor effect was also associated with an increase of Granzyme B expression in CD8+ T cell (FIG. 115C), indicating more activated CD8+ T cell in the tumor microenvironment (2).

PTPN2 Inhibitor Combined with Immunotherapy Prompted T Cell Chemokines

Figure 116A:
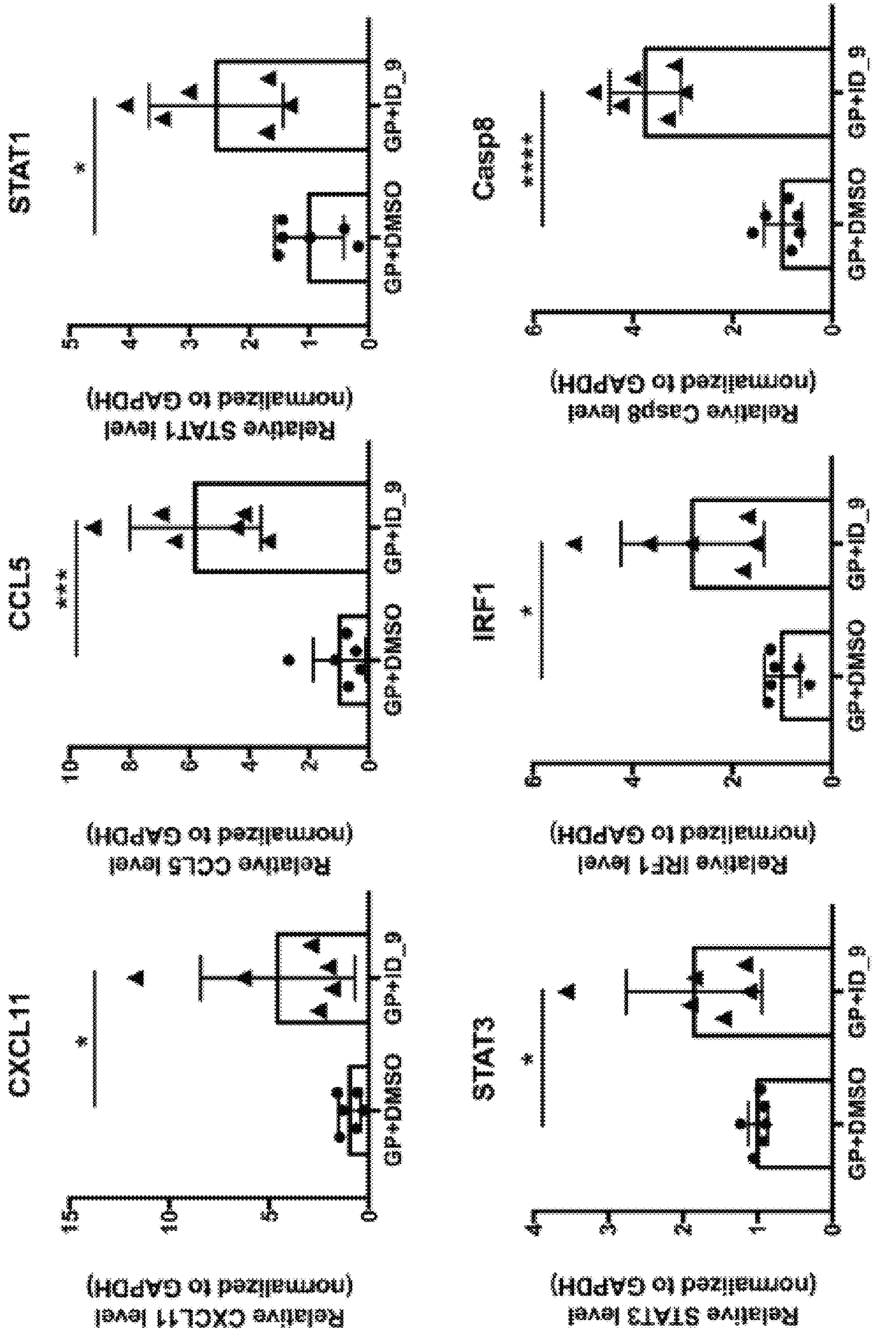
FIG. 116A-116B. anti-PD-1 and PTPN2 inhibitor ID_9 combination therapy enhances T cell chemokines and Stat1 phosphorylation. (116A) Quantitative PCR for mice tumor tissues indicates significant upregulation in CXCLII, CCL5, STATI, STAT3, IRFI and Caspase8 on RNA level after intratumoral injection of inhibitor ID 9. (116B) Both Stat1 and phosphorylated Stat1 increased on protein level upon ID_9 combination treatment. Data are mean±SD; Each dot in qPCR represents one individual mouse; *P<0.05; P<0.01; *P<0.001; ****P<0.0001.
Figure 116B:
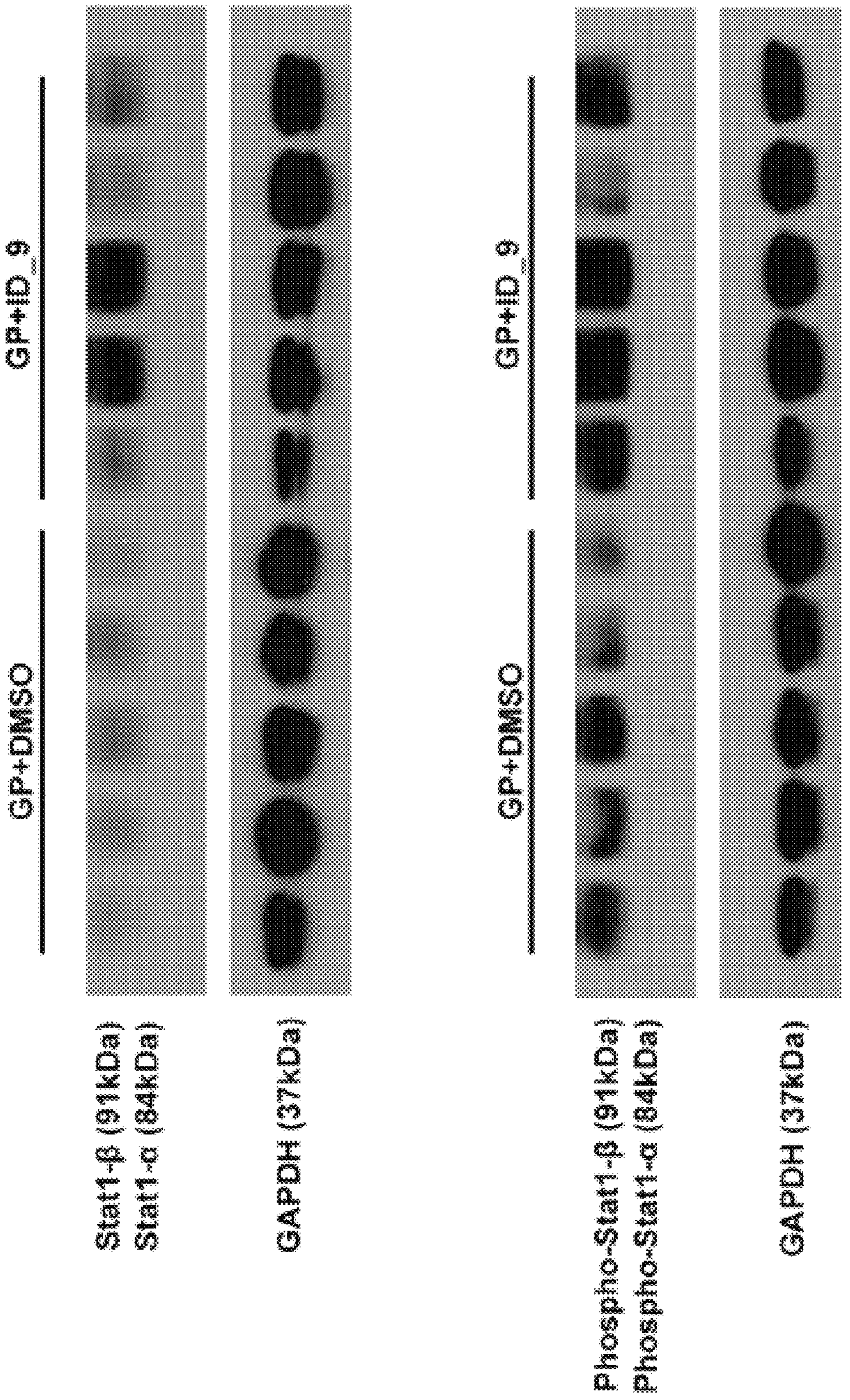

The transcriptional RNA levels in ID 9 treated tumors were analyzed in FIG. 116A. Consistent with the in vitro model, several T cell chemokines, for example, CXCLII and CCL5, are potentially involved in the in vivo T cell infiltration. Downstream pathway gene STATI STAT 3, IRFI and Caspase8 were also upregulated significantly. Similar to in vitro validation, DMSO control group combined with PD-1 antibody showed less Stat 1 than GP+ID 9 group tumors. ID 9 treated tumor also expressed higher phosphorylated-Stat1 than control (FIG. 116B), which re-confirmed the STAT1 upregulation in transcriptional mRNA level analyzed by quantitative RT-PCR in FIG. 116A. To conclude, the in vivo results exhibited the similar effect as confirmed in vitro. PTPN2 inhibitor ID 9 can potentially elicit a stronger antitumor response combined with anti-PD-1 immunotherapy in vivo.

FIG. 118 illustrates additional non-limiting exemplary PTPN2 inhibitors.

Also see: "Clinical and biological features of PTPN2-deleted adult and pediatric T-cell acute lymphoblastic leukemia" Blood Adv. 2019 Jul. 9; 3(13):1981-1988. doi: 10.1182/bloodadvances.2018028993; "PTPN2 induced by inflammatory response and oxidative stress contributed to glioma progression" J Cell Biochem. 2019 November; 120 (11):19044-19051. doi: 10.1002/jcb.29227; "PTPN2 as a promoter of colon carcinoma via reduction of inflammasome activation" Mol Cell Oncol. 2018 Jun. 6; 5(4):e1465013. doi: 10.1080/23723556.2018.1465013; "PTPN2 Regulates Inflammasome Activation and Controls Onset of Intestinal Inflammation and Colon Cancer" Cell Rep. 2018 Feb. 13; 22(7):1835-1848. doi: 10.1016/j.celrep.2018.01.052; and "Functional genomic landscape of cancer-intrinsic evasion of killing by T cells" Nature. 2020 October; 586(7827):120-126. doi: 10.1038/s41586-020-2746-2, each of which is incorporated herein by reference in its entirety.

REFERENCES

1. Manguso R T, Pope H W, Zimmer M D, Brown F D, Yates K B, Miller B C, et al. In vivo CRISPR screening identifies Ptpn2 as a cancer immunotherapy target. Nature. 3-8.
2. Nowacki™, Kuerten S, Zhang W, Shive C C, Kreher C R, Boehm 80, et al. 2. Granzyme B production distinguishes recently activated CD8(+) memory cells from resting memory cells. Cell Immunol. 2007; 247(1):36-48.
3. Pardoll, D. M. The blockade of immune checkpoints in cancer immunotherapy. Nat Rev Cancer 12, 252-264, doi:10.1038/nrc3239 (2012).
4. Ribas, A. & Wolchok, J. D. Cancer immunotherapy using checkpoint blockade. Science 359, 1350-1355, doi: 10.1126/science.aar4060 (2018).
5. Zappasodi, R., Merghoub, T. & Wolchok, J. D. Emerging Concepts for Immune Checkpoint Blockade-Based Combination Therapies. Cancer Cell 34, 690, doi:10.1016/j.ccell.2018.09.008 (2018).
6. Reck, M. et al. Pembrolizumab versus Chemotherapy for PD-L1-Positive Non-Small-Cell Lung Cancer. N Engl J Med 375, 1823-1833, doi:10.1056/NEJMoa1606774 (2016).
7. Wolchok, J. D. et al. Nivolumab plus ipilimumab in advanced melanoma. N Engl J Med 369, 122-133, doi: 10.1056/NEJMoa1302369 (2013).
8. Zaretsky, J. M. et al. Mutations Associated with Acquired Resistance to PD-1 Blockade in Melanoma. N Engl J Med 375, 819-829, doi:10.1056/NEJMoa1604958 (2016).
9. van Vliet, C. et al. Selective regulation of tumor necrosis factor-induced Erk signaling by Src family kinases and the T cell protein tyrosine phosphatase. Nat Immunol 6, 253-260, doi:10.1038/ni1169 (2005).
10. Wiede, F. et al. T cell protein tyrosine phosphatase attenuates T cell signaling to maintain tolerance in mice. J Clin Invest 121, 4758-4774, doi:10.1172/JCI59492 (2011).
11. ten Hoeve, J. et al. Identification of a nuclear Stat1 protein tyrosine phosphatase. Mol Cell Biol 22, 5662-5668, doi:10.1128/mcb.22.16.5662-5668.2002 (2002).
12. Simoncic, P. D., Lee-Loy, A., Barber, D. L., Tremblay, M. L. & McGlade, C. J. The T cell protein tyrosine phosphatase is a negative regulator of janus family kinases 1 and 3. Curr Biol 12, 446-453, doi:10.1016/s0960-9822(02)00697-8 (2002).
13. Kleppe, M. et al. PTPN2 negatively regulates oncogenic JAK1 in T-cell acute lymphoblastic leukemia. Blood 117, 7090-7098, doi:10.1182/blood-2010-10-314286 (2011).
14. Kleppe, M. et al. Mutation analysis of the tyrosine phosphatase PTPN2 in Hodgkin's lymphoma and T-cell non-Hodgkin's lymphoma. Haematologica 96, 1723-1727, doi:10.3324/haematol.2011.041921 (2011).
15. Wiede, F., La Gruta, N. L. & Tiganis, T. PTPN2 attenuates T-cell lymphopenia-induced proliferation. Nat Commun 5, 3073, doi:10.1038/ncomms4073 (2014).
16. Wiede, F., Ziegler, A., Zehn, D. & Tiganis, T. PTPN2 restrains CD8(+) T cell responses after antigen cross-presentation for the maintenance of peripheral tolerance in mice. J Autoimmun 53, 105-114, doi:10.1016/j.jaut.2014.05.008 (2014).
17. Wiede, F. et al. PTPN2 regulates T cell lineage commitment and alphabeta versus gammadelta specification. J Exp Med 214, 2733-2758, doi:10.1084/jem.20161903 (2017).
18. Wiede, F., Sacirbegovic, F., Leong, Y. A., Yu, D. & Tiganis, T. PTPN2-deficiency exacerbates T follicular helper cell and B cell responses and promotes the development of autoimmunity. J Autoimmun 76, 85-100, doi: 10.1016/j.jaut.2016.09.004 (2017).
19. Manguso, R. T. et al. In vivo CRISPR screening identifies Ptpn2 as a cancer immunotherapy target. Nature 547, 413-418, doi:10.1038/nature23270 (2017).
20. Tenev, T. et al. Both SH2 domains are involved in interaction of SHP-1 with the epidermal growth factor receptor but cannot confer receptor-directed activity to SHP-1/SHP-2 chimera. J Biol Chem 272, 5966-5973, doi:10.1074/jbc.272.9.5966 (1997).
21. O'Reilly, A. M. & Neel, B. G. Structural determinants of SHP-2 function and specificity in *Xenopus* mesoderm induction. Mol Cell Biol 18, 161-177, doi:10.1128/mcb.18.1.161 (1998).

22. Iversen, L. F. et al. Structure-based design of a low molecular weight, nonphosphorus, nonpeptide, and highly selective inhibitor of protein-tyrosine phosphatase 1B. J Biol Chem 275, 10300-10307, doi:10.1074/jbc.275.14.10300 (2000).

23. Asante-Appiah, E. et al. The YRD motif is a major determinant of substrate and inhibitor specificity in T-cell protein-tyrosine phosphatase. J Biol Chem 276, 26036-26043, doi:10.1074/jbc.M011697200 (2001).

Example B10: High Throughput Screen Test for Growth Inhibition

The High Throughput Screen method is described below. The endpoint readout of this assay is based upon quantitation of ATP as an indicator of viable cells.

Cell lines that have been preserved in liquid nitrogen are thawed and expanded in growth media (see Table 1-3). Once cells have reached expected doubling times, screening begins. Cells are seeded in growth media in black 384-well tissue culture treated plates at 500-1500 cells per well (as noted in Analyzer). Cells are equilibrated in assay plates via centrifugation and placed at 37° C. 5% $CO_2$ for twenty-four hours before treatment. At the time of treatment, a set of assay plates (which do not receive treatment) are collected and ATP levels are measured by adding CellTiter-Glo 2.0 (Promega) and luminescence read on Envision plate readers (Perkin Elmer). Assay plates are incubated with compound for 3 days and are then analysed using CellTiter-Glo 2.0. All data points are collected via automated processes and are subject to quality control and analysed using Horizon's software.

Growth Inhibition (GI) is utilized as a measure of cell growth. The GI percentages are calculated by applying the following test and equation:

If $T<V\_0$: $100*(1-(T-V\_0)/V\_0)$

If $T\geq V\_0$: $100*(1-(T-V\_0)/(V-V\_0))$ where T is the signal measure for a test article, V is the untreated/vehicle-treated control measure, and Vo is the untreated/vehicle control measure at time zero (also colloquially referred as T0 plates). This formula is derived from the Growth Inhibition calculation used in the National Cancer Institute's NCI-60 high throughput screen. For the purposes of this report, all data analysis was performed in Growth Inhibition (except where noted).

A GI reading of 0% represents no growth inhibition and would occur in instances where the T reading at 6 days is comparable to the V reading at the respective time period. A GI of 100% represents complete growth inhibition (cytostasis) and in this case cells treated with compound for 3 days would have the same endpoint reading as TO control cells. A GI of 200% represents complete death (cytotoxicity) of all cells in the culture well and in this case the T reading at 3 days will be lower than the TO control (values near or at zero).

Horizon also provides Inhibition as a measure of cell viability. Inhibition levels of 0% represent no inhibition of cell growth by treatment. Inhibition of 100% represents no doubling of cell numbers during the treatment window. Both cytostatic and cytotoxic treatments can yield an Inhibition percentage of 100%. Inhibition percentage is calculated as the following:

$I=1-T/U$ where T is the treated and U is the untreated/vehicle control.

| # | Cell Line | Tissue | Media |
|---|---|---|---|
| 1 | MCF7 | Breast | EMEM with 10% FBS and 0.01 mg/mL Human Insulin |
| 2 | SUM-159PT | Breast | Ham's F12 with 5% FBS, 10 mM HEPES, 5 μg/mL Insulin and 1 μg/mL Hydrocortisone |
| 3 | MDA-MB-231 | Breast | RPMI with 10% FBS |
| 4 | HCT-116 | Colorectal | McCoy's 5A with 10% FBS |
| 5 | SW480 | Colorectal | RPMI with 10% FBS |
| 6 | HEC-50B | Endometrium | EMEM with 15% FBS |
| 7 | Ishikawa | Endometrium | EMEM with 15% FBS and 1% NEAA |
| 8 | KYSE-70 | Esophagus | RPMI with 10% FBS |
| 9 | AGS | Gastric | Hams F12K with 10% FBS |
| 10 | SNU-16 | Gastric | RPMI with 10% FBS, 25 mM HEPES and 25 mM Sodium Bicarbonate |
| 11 | BICR 16 | Head and Neck | DMEM with 10% FBS and 0.4 μg/mL Hydrocortisone |
| 12 | PE-CA-PJ15 | Head and Neck | IMDM with 10% FBS |
| 13 | MOLT-4 | Leukemia | RPMI with 10% FBS |
| 14 | KASUMI-1 | Leukemia | RPMI with 10% FBS |
| 15 | MV-4-11 | Leukemia | IMDM with 10% FBS |
| 16 | A549 | Lung | Ham's F12K with 10% FBS |
| 17 | LUDLU-1 | Lung | RPMI with 10% FBS |
| 18 | NCI-H520 | Lung | RPMI with 10% FBS |
| 19 | A2780 | Ovary | RPMI with 10% FBS |
| 20 | SK-OV-3 | Ovary | McCoy's 5A with 10% FBS |
| 21 | Panc 04.03 | Pancreas | RPMI with 15% FBS and 10 units/mL Human Insulin |

Compound Panel.

| Chalice name | C-Number | MW | Top Assay Conc. (μM) | Dose points | Fold Dilution |
|---|---|---|---|---|---|
| TRANA1 | C-22122 | 218.32 | 50 | 9 | 3 |
| TRANA2 | C-22123 | 419.72 | 50 | 9 | 3 |
| TRANA3 | C-22124 | 367.72 | 50 | 9 | 3 |
| TRANA4 | C-22125 | 345.34 | 50 | 9 | 3 |
| TRANA5 | C-22126 | 328.47 | 50 | 9 | 3 |
| TRANA6 | C-22127 | 346.86 | 50 | 9 | 3 |
| TRANA7 | C-22128 | 364.85 | 50 | 9 | 3 |
| TRANA8 | C-22129 | 283.38 | 50 | 9 | 3 |
| TRANA9 | C-22130 | 254.34 | 50 | 9 | 3 |
| TRANA10 | C-22131 | 335.37 | 50 | 9 | 3 |

Reagents and Supplementation

| Item | Supplier |
|---|---|
| Bovine Insulin | Sigma |
| BSA | Sigma |
| CellTiter-Glo 2.0 | Promega |
| DMEM | ThermoFisher (Gibco) |
| DMSO | Sigma |
| F12 (Ham's F12) | ThermoFisher (Gibco) |
| F12K | ThermoFisher (Gibco) |
| FBS | ThermoFisher (Gibco) |
| HEPES | ThermoFisher (Gibco) |
| Human Insulin | Sigma |
| Hydrocortisone | Sigma |
| IMDM (Iscove's) | ThermoFisher (Gibco) |
| McCoy's 5A | ThermoFisher (Gibco) |
| MEM (EMEM) | ThermoFisher (Gibco) |
| NEAA | ThermoFisher (Gibco) |

-continued

| Item | Supplier |
|---|---|
| PBS | ThermoFisher (Gibco) |
| Penicillin-Streptomycin | ThermoFisher (Gibco) |
| RPMI | ThermoFisher (Gibco) |
| RPMI (ATCC Modified) | ThermoFisher (Gibco) |
| Sodium Bicarbonate | Sigma |
| Trypsin | ThermoFisher (Gibco) |

Growth Inhibition (GI) Values.

| Cell Line | Cancer Type | ALK-04 | TR-ALKBH5-25 | TR-ALKBH5-29 | TR-ALKBH5-34 | TR-FTO-38 N | TR-FTO-43 N | TR-FTO-49 N | TR-YTH-01 | TR-YTH-05 | TR-YTH-10 |
|---|---|---|---|---|---|---|---|---|---|---|---|
| MV4-11 | Leukemia | | 19.216 | 29.144 | 24.544 | | | | | | 23.158 |
| Kasumi-1 | Leukemia | | 22.121 | 25.241 | 42.616 | | 18.136 | | | | 10.784 |
| MOLT-4 | Leukemia | | 18.276 | 18.74 | 25.335 | 24.366 | 24.595 | 27.521 | | | 14.304 |
| A549 | LUSC | | 24.433 | 23.182 | | | | | | | 24.437 |
| NCI-H520 | LUSC | | 29.362 | 29.471 | 51.607 | | | | | | 24.266 |
| LUDLU-1 | LUSC | | 20.634 | 21.81 | 28.966 | 31.952 | 28.561 | | | | 20.311 |
| AGS | Gastric | | 23.222 | 14.577 | 53.95 | 23.3 | 21.005 | | | 6.35 | 21.842 |
| SNU-16 | Gastric | | 18.255 | 21.335 | 20.376 | 3.105 | 3.455 | 14.166 | 21.028 | | 2.703 |
| MDA-MB-231 | Breast (basal) | | 28.725 | 22.731 | | | | | | | |
| MC-F7 | Breast (luminal) | | 30.338 | 24.072 | 39.862 | | | | | | 24.642 |
| SUM159PT | Breast | | 9.996 | 12.44 | 23.148 | | | | | 8.629 | 56.597 |
| SKOV-3 | Ovarian | | 35.242 | | | | | | | | 25.341 |
| A2780 | Ovarian | | 17.889 | 19.059 | 25.014 | 29.918 | 21.94 | 24.707 | | 17.678 | 16.074 |
| HEC-50B | Endometrial (uterine) | | 35.525 | | | 14.018 | | | | | 37.217 |
| Ishikawa | Endometrial (uterine) | | 28.662 | | | | | | | | 22.531 |
| HCT-116 | Colon | | 20.676 | 23.338 | 24.491 | | 31.451 | | | | 21.453 |
| SW480 | Colon | | 22.301 | 24.107 | | | 28.499 | | | | 25.275 |
| KYSE70 | Esophagoel | | 19.384 | 22.725 | 21.228 | 23.468 | 20.992 | 26.991 | | 25.972 | 17.487 |
| BICR16 | Head and Neck | | 26.389 | 22.373 | 51.699 | 29.832 | 25.212 | | | | 12.966 |
| PECAPJ15 | Head and Neck | | 37.574 | 28.675 | | | | | | | 44.646 |
| Panc 04 03 | Pancreatic | | 20.087 | 22.544 | | | | | | | 28.024 |

| Cell Line | Cancer Type | ALK-04 | TR-ALKBH5-25 | TR-ALKBH5-29 | TR-ALKBH5-34 |
|---|---|---|---|---|---|
| MV4-11 | Leukemia | | 19.216 | 29.144 | 24.544 |
| Kasumi-1 | Leukemia | | 22.121 | 25.241 | 42.616 |
| MOLT-4 | Leukemia | | 18.276 | 18.74 | 25.335 |
| A549 | LUSC | | 24.433 | 23.182 | |
| NCI-H520 | LUSC | | 29.362 | 29.471 | 51.607 |
| LUDLU-1 | LUSC | | 20.634 | 21.81 | 28.966 |
| AGS | Gastric | | 23.222 | 14.577 | 53.95 |
| SNU-16 | Gastric | | 18.255 | 21.335 | 20.376 |
| MDA-MB-231 | Breast (basal) | | 28.725 | 22.731 | |
| MC-F7 | Breast (luminal) | | 30.338 | 24.072 | 39.862 |
| SUM159PT | Breast | | 9.996 | 12.44 | 23.148 |
| SKOV-3 | Ovarian | | 35.242 | | |
| A2780 | Ovarian | | 17.889 | 19.059 | 25.014 |
| HEC-50B | Endometrial (uterine) | | 35.525 | | |
| Ishikawa | Endometrial (uterine) | | 28.662 | | |
| HCT-116 | Colon | | 20.676 | 23.338 | 24.491 |
| SW480 | Colon | | 22.301 | 24.107 | |
| KYSE70 | Esophagoel | | 19.384 | 22.725 | 21.228 |
| BICR16 | Head and Neck | | 26.389 | 22.373 | 51.699 |
| PECAPJ15 | Head and Neck | | 37.574 | 28.675 | |
| Panc 04 03 | Pancreatic | | 20.087 | 22.544 | |

| Cell Line | Cancer Type | TR-FTO-38 N | TR-FTO-43 N | TR-FTO-49 N |
|---|---|---|---|---|
| MV4-11 | Leukemia | | | |
| Kasumi-1 | Leukemia | | 18.136 | |
| MOLT-4 | Leukemia | 24.366 | 24.595 | 27.521 |
| A549 | LUSC | | | |
| NCI-H520 | LUSC | | | |
| LUDLU-1 | LUSC | 31.952 | 28.561 | |
| AGS | Gastric | 23.3 | 21.005 | |
| SNU-16 | Gastric | 3.105 | 3.455 | 14.166 |
| MDA-MB-231 | Breast (basal) | | | |
| MC-F7 | Breast (luminal) | | | |
| SUM159PT | Breast | | | |
| SKOV-3 | Ovarian | | | |
| A2780 | Ovarian | 29.918 | 21.94 | 24.707 |
| HEC-50B | Endometrial (uterine) | 14.018 | | |
| Ishikawa | Endometrial (uterine) | | | |
| HCT-116 | Colon | | 31.451 | |
| SW480 | Colon | | 28.499 | |
| KYSE70 | Esophagoel | 23.468 | 20.992 | 26.991 |
| BICR16 | Head and Neck | 29.832 | 25.212 | |
| PECAPJ15 | Head and Neck | | | |
| Panc 04 03 | Pancreatic | | | |

| Cell Line | Cancer Type | TR-YTH-01 | TR-YTH-05 | TR-YTH-10 |
|---|---|---|---|---|
| MV4-11 | Leukemia | | | 23.158 |
| Kasumi-1 | Leukemia | | | 10.784 |
| MOLT-4 | Leukemia | | | 14.304 |
| A549 | LUSC | | | 24.437 |
| NCI-H520 | LUSC | | | 24.266 |
| LUDLU-1 | LUSC | | | 20.311 |
| AGS | Gastric | | 6.35 | 21.842 |
| SNU-16 | Gastric | 21.028 | | 2.703 |
| MDA-MB-231 | Breast (basal) | | | |
| MC-F7 | Breast (luminal) | | | 24.642 |
| SUM159PT | Breast | | 8.629 | 56.597 |
| SKOV-3 | Ovarian | | | 25.341 |
| A2780 | Ovarian | | 17.678 | 16.074 |
| HEC-50B | Endometrial (uterine) | | | 37.217 |
| Ishikawa | Endometrial (uterine) | | | 22.531 |
| HCT-116 | Colon | | | 21.453 |
| SW480 | Colon | | | 25.275 |
| KYSE70 | Esophagoel | | 25.972 | 17.487 |
| BICR16 | Head and Neck | | | 12.966 |
| PECAPJ15 | Head and Neck | | | 44.646 |
| Panc 04 03 | Pancreatic | | | 28.024 |

| Compound | LUDLU-1 | SUM159PT | A2780 | HCT-116 | KYSE-70 | Panc.04.03 | MOLT-4 | AGS |
|---|---|---|---|---|---|---|---|---|
| TRANA1 | ~100 | NDE | ~100 | >100 | ~100 | NDE | ~100 | NDE |
| TRANA2 | 20.72 | 17.42 | 22.48 | 22.64 | 20.52 | 19.79 | 19.25 | 22.53 |
| TRANA3 | 20.65 | 11.91 | 21.83 | 20.72 | 24.22 | 21.63 | 17.96 | 9.92 |
| TRANA4 | ~75 | 24.76 | 20.93 | ~75 | 21.65 | ~75 | 21.94 | ~75 |
| TRANA5 | ~75 | >100 | ~50 | ~75 | 25.93 | >100 | ~75 | ~30 |
| TRANA6 | 23.96 | >100 | 16.44 | ~75 | 23.97 | ~75 | 21.01 | 20.89 |
| TRANA7 | ~100 | >100 | 25 | ~75 | 25 | ~75 | ~75 | >100 |
| TRANA8 | >100 | NDE | >100 | NDE | >100 | NDE | >100 | >100 |
| TRANA9 | >100 | 15.82 | 22.46 | NDE | 28.55 | >100 | >100 | 3.9 |
| TRANA10 | 20.2 | ~75 | 13.64 | 20.75 | 18.86 | 27.64 | 20.5 | 23.93 |

| | LUSC<br>Any/All | Breast<br>ALKBH5 | Ovarian<br>ALKBH5 | Colon<br>ALKBH5/<br>YTH | Esophagoel<br>ALKBH5 | Pancreatic<br>? | Leukemia<br>FTO/YTH | Gastric<br>FTO/YTH |
|---|---|---|---|---|---|---|---|---|
| Chemo SOC | Cisplatin combos or Carboplatin + Paclitaxel | Nibs/ PARP inhibitors | Cisplatin | 5FU + oxalplatin, leucovorin other combos | Cisplatin + 5FU, carboplatin + paclitaxel | gemcitabine | Cytarabine | Paclitaxel combo, Cisplatin combo, 5-FU combo |
| EC50 | 5-8 uM | Olaparib 30 uM<br>cisplatin 5 uM<br>lapatinib 137 uM (cisplatin, oleparib approx 7 uM) | 2-40 uM | 5FU 2-10 uM<br>oxalplatin 2-20 uM | cisplatin 8 uM<br>oxalplatin 37 uM | gemcitabine <1 uM<br>cisplatin 20-26 uM<br>ocalplatin 3.5-10 uM | 0.25-3.5 uM | 5FU 28.8 uM<br>cisplatin 13.5-25 uM |

Compound Preparation and Evaluation

General Information: All reactions were performed in flame-dried round-bottomed or modified Schlenk flasks fitted with rubber septa under a positive pressure of argon, unless otherwise noted. Air- and moisture-sensitive liquids and solutions were transferred via syringe or stainless steel cannula. Solvents (methylene chloride, ether, tetrahydrofuran, benzene, and toluene) were purified using a Pure-Solv MD-5 Solvent Purification System (Innovative Technology). Where necessary, solvents were deoxygenated by sparging with nitrogen for at least 1 hour unless otherwise noted. All other reagents were used directly from the supplier without further purification unless otherwise noted. Organic solutions were concentrated by rotary evaporation at ~25 mbar in a water bath heated to 40° C. unless otherwise noted. Analytical thin-layer chromatography (TLC) was carried out using 0.2 mm commercial glass-coated silica gel plates (silica gel 60, F254, EMD chemical). Thin layer chromatography plates were visualized by exposure to ultraviolet light and/or exposure to iodine, or to an acidic solution of ceric ammonium molybdate, or a basic solution of potassium permanganate followed by heating on a hot plate. Gas chromatographs were measured using an Agilent 7820 GC. Mass spectra (MS) were obtained on a Karatos MS9, Autospec, or an Agilent 6150 and reported as m/z (relative intensity). Accurate masses are reported for the molecular ion [M+D]+ or [M+2D]2+.

Nuclear magnetic resonance spectra (1H-NMR and 13C-NMR) were recorded with a Varian Gemini (400 MHz, 1H at 400 MHz, 13C at 100 MHz, 500 MHz, 1H at 500 MHz, 13C at 125 MHz, or 600 MHz, 1H at 600 MHz, 13C at 150 MHz). For $CDCl_3$, and CD30D solutions, chemical shifts are reported as parts per million (ppm) referenced to residual protium or carbon of the solvent; CDCl3 δ 77.0 ppm, CD3OD δ 3.49 ppm, C6D6 δ 128.0 ppm, C5D4HN δ 7.19 ppm, C5D5N δ 135.9 ppm, and CD2HCN δ 1.93 ppm. Coupling constants are reported in Hertz (Hz). Data for 1H-NMR spectra are reported as follows: chemical shift (ppm, referenced to protium; (bs=broad singlet, s=singlet, br d=broad doublet, d=doublet, t=triplet, q=quartet, dd=doublet of doublets, td=triplet of doublets, ddd=doublet of doublet of doublets, m=multiplet, integration, and coupling constants (Hz)). HPLC purifications were performed on an Agilent 1200 series HPLC with a Supelco Analytical Discovery® C18 (25 cm×10 mm, 5 μm) RP-HPLC column unless otherwise noted.

Example C1

Procedures for the Preparation of Non-Limiting Exemplary FTO Inhibitors (e.g., Compounds of Formula (F1)):

General Procedure A for Suzuki-Miyaura Cross-Coupling Reactions

Scheme 1.

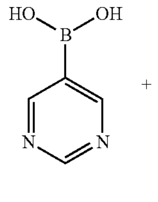

-continued

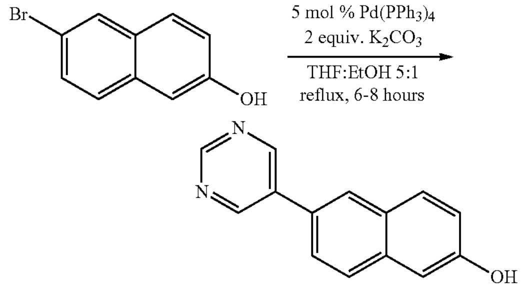

101 (FTO-1)

6-bromo-2-naphthol (0.900 g, 4.0 mmol), palladium tetrakisthriphenylphosphine (0.231 g, 0.02 mmol), and potassium carbonate (1.115 g, 8.0 mmol) were placed under nitrogen atmosphere, and dissolved in dry THF (20 mL) to obtain a dark red solution. A syringe was used to transfer pyrimidine-5-boronic acid (0.500 g, 4.0 mmol) in 5 mL dry THF to the stirring solution. The reaction was heated under reflux for 6 hours. The reaction mixture was filtered over Celite and the filter cake was washed with ethyl acetate. The filtrate was concentrated under reduced pressure to obtain the crude product as a yellow solid. The crude product was purified by silica gel column chromatography (Ethyl acetate: Hexanes 2:3, Rf=0.48). Following this procedure, twenty potential FTO inhibitors were obtained with an average yield of 54%.

Procedure B for Synthesis of tert-butyl (6-bromobenzo[d]thiazol-2-yl) carbamate 6-bromobenzo[d]thiazol-2-amine (0.458 g, 2 mmol) and $BOC_2O$ (1.2 eq, 2.4 mmol) were dissolved in THF (30 mL). 4-dimethylaminopyridine (DMAP, 0.1 equivalent) was added to the solution and the reaction was stirred for 3.5 hours at room temperature. The reaction mixture was diluted in ethyl acetate (100 mL) and washed with 0.25 M HCl (50 mL), 2 M $NaHCO_3$ (100 mL), and brine. The organic layers were dried by $Na_2SO_4$, filtered, then concentrated to obtain the crude product. The crude product was used for Suzuki coupling via general method A without further purification.

Procedure C for Boc Deprotection of tert-butyl (6-(2-methoxypyrimidin-5-yl)benzo[d]thiazol-2-yl) carbamate A solution of tert-butyl (6-(2-methoxypyrimidin-5-yl) benzo[d]thiazol-2-yl)carbamate (0.720 g, 2 mmol) in dioxane (40 mL) was treated with 4M HCl in dioxane and stirred at room temperature for 1 hour. The reaction mixture was concentrated, then dissolved in ethyl acetate (100 mL) and extracted with 10% $Na_2CO_3$ (50 mL) and brine (2×50 mL). The organic layers were dried with $Na_2SO_4$, filtered, and concentrated to obtain the crude product as a yellow solid. The crude product was purified by silica gel column chromatography (Ethyl acetate:Hexanes 2:3, Rf=0.48).

Compounds in Table 100 were synthesized following the methods above.

TABLE 100

| STRUCTURE | ENTRY NUMBER (NAME) | CHARACTERIZATION DATA |
|---|---|---|
| 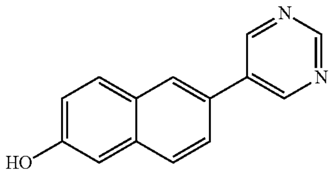 [SMILES: Oc1ccc2cc(-c3cncnc3)ccc2c1] | 101 (FTO-01) | 6-(pyrimidin-5-yl)naphthalen-2-ol. Prepared according to general procedure A. Yield 0.640 g, 2.88 mmol, 72%. Yellow solid, mp 230° C. $^{1}$H-NMR (600 MHz, d-DMSO): 9.93 (s, 1H), 9.25 (s, 2H), 9.17 (s, 1H), 8.03 (d, J = 2.0 Hz, 1H), 7.75 (d, J = 8.6 Hz, 1H), 7.65 (d, J = 8.6 Hz, 1H), 7.47 (dd, J = 8.8, 2.1 Hz, 1H), 7.45 (d, J = 8.8 Hz, 1H), 7.13 (d, J = 2.5 Hz, 1H). $^{13}$C-NMR (150 MHz, d-DMSO): 156.5, 155.3, 150.3, 150.3, 133.8, 132.8, 132.2, 130.0, 129.5, 129.4, 128.2, 125.2, 115.9, 109.5. HRMS (ESI, M+) m/z calculated for $C_{14}H_{10}N_2O$ 222.0793, found 222.0795. |
| 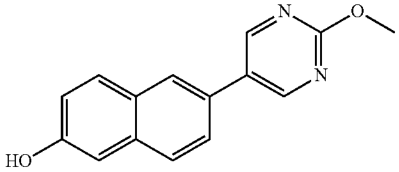 [SMILES: COc1ncc(-c2ccc3cc(O)ccc3c2)cn1] | 102 (FTO-02) | 6-(2-methoxypyrimidin-5-yl)naphthalen-2-ol. Prepared according to general procedure A. Yield 0.525 g, 2.8 mmol, 52%. Orange solid, mp 230° C. $^{1}$H-NMR (600 MHz, d-DMSO): 9.89 (s, 1H), 9.02 (s, 2H), 8.16 (d, J = 2.0 Hz, 1H), 7.82 (d, J = 8.7 Hz, 1H), 7.80 (d, J = 8.7 Hz, 1H), 7.76 (d, J = 2.5 Hz, 1H), 7.75 (d, J = 2.5 Hz, 1H), 7.15 (d, J = 2.6 Hz, 1H), 3.97 (s, 3H). $^{13}$C-NMR (150 MHz, d-DMSO): 157.8, 155.4, 155.4, 154.7, 133.9, 130.6, 129.3, 128.5, 128.2, 126.7, 125.5, 120.1, 115.9, 106.5, 56.0. HRMS (ESI, M+) m/z calculated for $C_{15}H_{12}N_2O_2$ 252.0899, found 252.0900. |
| 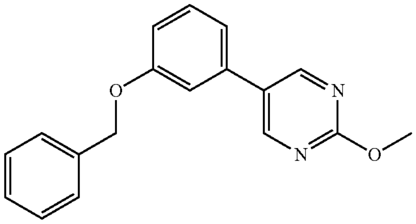 [SMILES: COc1ncc(-c2cccc(OCc3ccccc3)c2)cn1] | 103 (FTO-03) | 5-(3-(benzyloxy)phenyl)-2-methoxypyrimidine. Prepared according to general procedure A. Yield 0.588 g, 2.01 mmol, 51%. Yellow solid, mp 230° C. $^{1}$H-NMR (600 MHz, $CDCl_3$): 8.71 (s, 2H), 7.47 (d, J = 7.3 Hz, 2H), 7.42 (t, J = 7.4 Hz, 1 H), 7.41 (d, J = 6.1 Hz, 2H), 7.40 (d, J = 2.7 Hz, 1H), 7.36 (t, J = 7.3 Hz, 1H), 7.13 (d, J = 1.4 Hz, 2H), 7.04 (d, J = 1.6 Hz, 1 H), 5.14 (s, 2H), 4.07 (s, 3H). $^{13}$C-NMR (150 MHz, d-DMSO): 163.4, 159.7, 156.7, 156.7, 139.7, 136.6, 130.8, 130.8, 128.9, 128.9, 128.4, 127.8, 124.2, 118.4, 114.0, 113.2, 70.4, 55.0. HRMS (ESI, M+) m/z calculated for $C_{18}H_{16}N_2O_2$ 292.1212, found 292.1216 |
| 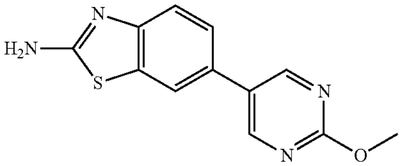 [SMILES: COc1ncc(-c2ccc3nc(N)sc3c2)cn1] | 104 (FTO-04) | 6-(2-methoxypyrimidin-5-yl)benzo[d]thiazol-2-amine. Prepared according to general procedure A from tert-butyl (6-bromobenzo[d]thiazol-2-yl)carbamate and (2-methoxypyrimidin-5-yl)boronic acid. FTO-04 was purified after Boc deprotection as described in procedure C. Yield 0.723 g, 2.80 mmol, 70%. Yellow solid, mp 230° C. $^{1}$H-NMR (600 MHz, d-DMSO): 8.82 (s, 2H), 7.71 (s, 2H), 7.60 (d, J = 8.3 Hz, 1H), 7.47 (d, J = 2.0 Hz, 1H), 7.14 (dd, J = 8.3, 2.0 Hz, 1H), 3.87 (s, 3H). $^{13}$C-NMR (150 MHz, d-DMSO): 168.7, 157.8, 155.2, 155.0, 155.0, 130.5, 123.8, 123.4, 120.6, 118.9, 55.1. HRMS (ESI, M+) m/z calculated for $C_{12}H_{10}N_4OS$ 258.0575, found 258.0580. |
| 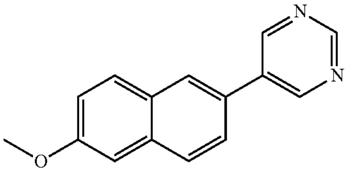 [SMILES: COc1ccc2cc(-c3cncnc3)ccc2c1] | 105 (FTO-05) | 5-(6-methoxynaphthalen-2-yl)pyrimidine. Prepared according ot general procedure A. Yield 0.595 g, 2.52 mmol, 63%. White solid, mp 230° C. $^{1}$H-NMR (600 MHz, d-DMSO): 9.26 (s, 2H), 9.19 (s, 1H), 8.35 (d, J = 1.1 Hz, 1H), 7.98 (d, J = 8.6 Hz, 1H), 7.92 (dd, J = 8.5, 2.1 Hz, 2H), 7.40 (d, J = 2.5 Hz, 1H), 7.24 (dd, J = 8.9, 2.6 Hz, 1H), 3.90 (s, 3H). $^{13}$C-NMR (150 MHz, d-DMSO): 157.7, 155.3, 150.3, 150.3, 135.0, 134.2, 133.9, 130.6, 129.3, 128.5, 126.7, 125.4, 120.1, 106.5, 56.0. HRMS (ESI, M+) m/z calculated for $C_{15}H_{12}N_2O$ 236.0950, found 236.0593. |
| 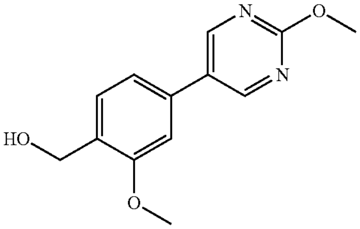 [SMILES: COc1ncc(-c2ccc(CO)c(OC)c2)cn1] | 106 (FTO-06) | (2-methoxy-4-(2-methoxypyrimidin-5-yl)phenyl)methanol. Prepared according to general procedure A. Yield 0.374 g, 1.52 mmol, 38%. White solid, mp 230° C. $^{1}$H-NMR (600 MHz, d-DMSO): 8.60 (s, 2H), 7.29 (d, J = 7.9 Hz, 1H), 7.13 (d, J = 1.6 Hz, 1H), 7.11 (t, J = 2.7 Hz, 1H), 5.10 (t, J = 5.6 Hz, 2H), 3.78 (s, 6H). $^{13}$C-NMR (150 MHz, d-DMSO): 163.4, 157.1, 148.9, 148.9, 136.2, 131.0, 129.1, 123.5, 113.9, 61.1, 5.8.1, 56.0. HRMS (ESI, M+) m/z calculated for $C_{13}H_{14}N_2O_3$ 246.1004, found 246.1009 |

TABLE 100-continued

| STRUCTURE | ENTRY NUMBER (NAME) | CHARACTERIZATION DATA |
| --- | --- | --- |
| 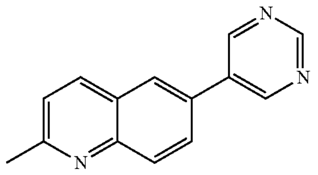 [SMILES: Cc1ccc2cc(-c3cncnc3)ccc2n1] | 107 (FTO-07) | 2-methyl-6-(pyrimidin-5-yl)quinolone. Prepared according to general procedure A. Yield 0.520 g, 2.35 mmol, 59%. White solid, mp 230° C. $^1$H-NMR (600 MHz, d-DMSO): 9.26 (s, 1H), 8.68 (s, 2H), 8.24 (d, J = 8.4 Hz, 1H), 8.23 (d, J = 2.2 Hz, 1H), 7.89 (d, J = 8.9 Hz, 1H), 7.83 (dd, J = 8.9, 2.2 Hz, 1H), 7.48 (d, J = 8.4 Hz, 1H), 2.73 (s, 3H). $^{13}$C-NMR (150 MHz, d-DMSO): 155.0, 154.8, 154.8, 150.5, 150.1, 141.9, 136.8, 130.7, 130.2, 128.7, 128.3, 125.9, 123.1, 24.0. HRMS (ESI, M+) m/z calculated for $C_{14}H_{11}N_3$ 221.0953, found 221.0958. |
| 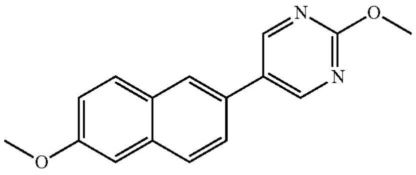 | 108 (FTO-08) | 2-methoxy-5-(6-methoxynaphthalen-2-yl)pyrimidine. Prepared according to general procedure A. Yield 0.266 g, 1.00 mmol, 25%. White solid, mp 230° C. $^1$H-NMR (600 MHz, d-DMSO): 9.05 (s, 2H), 8.23 (d, J = 1.1 Hz, 1H), 7.95 (d, J = 8.6 Hz, 1H), 7.93 (d, J = 2.1 Hz, 1H), 7.89 (d, J = 2.1 Hz, 1H), 7.37 (d, J = 2.5 Hz, 1H), 7.21 (dd, J = 8.9, 2.6 Hz, 1H), 3.97 (s, 3H), 3.89 (s, 3H). $^{13}$C-NMR (150 MHz, d-DMSO): 163.5, 157.5, 150.3, 150.3, 133.9, 130.8, 130.3, 129.5, 128.5, 128.3, 124.1, 120.4, 120.1, 106.7, 56.5, 56.0. HRMS (ESI, M+) m/z calculated for $C_{16}H_{14}N_2O_2$ 266.1055, found 266.1058. |
| 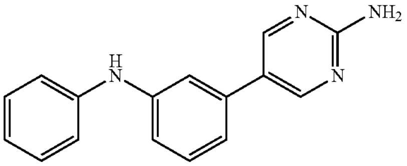 [SMILES: Nc1ncc(-c2cccc(Nc3ccccc3)c2)cn1] | 109 (FTO-09 | 5-(3-(phenylamino)phenyl)pyrimidin-2-amine. Prepared according to general procedure A. Yield 0.441 g, 1.68 mmol, 42%. Yellow solid, mp 230° C. $^1$H-NMR (600 MHz, d-DMSO): 8.37 (s, 2H), 7.27 (t, J = 7.9 Hz, 2H), 7.15 (t, J = 8.6 Hz, 2H), 7.08 (d, J = 7.6 Hz, 2H), 7.02 (dd, J = 8.2, 1.7 Hz, 1H), 6.92 (d, J = 8.9 Hz, 1H), 6.90 (t, J = 7.3 Hz, 1H). $^{13}$C-NMR (150 MHz, d-DMSO): 161.5, 150.2, 150.2, 140.1, 139.3, 137.2, 130.5, 129.9, 129.9, 121.4, 120.6, 120.6, 120.6, 120.4, 117.6, 117.6. HRMS (ESI, M+) m/z calculated for $C_{16}H_{14}N_4O$ 262.1218, found 262.1225. |
| 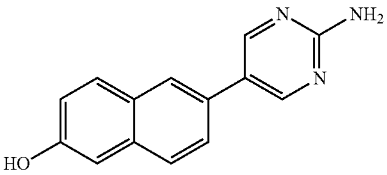 [SMILES: Nc1ncc(-c2ccc3cc(O)ccc3c2)cn1] | 110 (FTO-10) | 6-(2-aminopyrimidin-5-yl)naphthalen-2-ol. Prepared according to general procedure A. Yield 0.690 g, 2.91 mmol, 73%. Yellow solid, mp 230° C. $^1$H-NMR (600 MHz, d-DMSO): 8.66 (s, 2H), 8.20 (d, J = 6 Hz, 1H), 8.01 (s, 1H), 7.78 (d, J = 8.8 Hz, 1H), 7.73 (d, J = 8.6, 1H), 7.12 (d, J = 6 Hz, 1H), 7.09 (dd, J = 8.9, 2.4 Hz, 1H), 6.79 (s, 2H), 6.57 (s, 1H). $^{13}$C-NMR (150 MHz, d-DMSO): 158.8, 158.6, 156.5, 156.,5 134.1, 132.6, 130.1, 130.2, 127.6, 127.6, 124.7, 124.0, 122.1, 110.8. HRMS (ESI, M+) m/z calculated for $C_{14}H_{11}N_3O$ 237.0902, found 237.0900 |
| 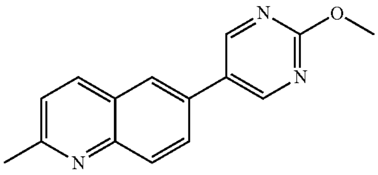 | 111 (FTO-11) | 6-(2-methoxypyrimidin-5-yl)-2-methylquinoline. Prepared according to general procedure A. Yield 0.302 g, 1.20 mmol, 30%. White solid, mp 230° C. $^1$H-NMR (600 MHz, d-DMSO): 8.53 (s, 2H), 7.96 (d, J = 8.4 Hz, 1H), 7.93 (d, J = 2.2 Hz, 1H), 7.89 (d, J = 8.9 Hz, 1H), 7.74 (dd, J = 8.9, 2.2 Hz, 1H), 7.31 (d, J = 8.4 Hz, 1H), 4.02 (s, 3H), 2.73 (s, 3H). $^{13}$C-NMR (150 MHz, d-DMSO): 163.4, 155.0, 154.8, 154.8, 150.5, 141.9, 136.8, 130.7, 128.7, 128.3, 125.9, 123.1, 118.4, 50.3, 21.0. HRMS (ESI, M+) m/z calculated for $C_{15}H_{13}N_3O$ 251.1059, found 251.1061. |
| 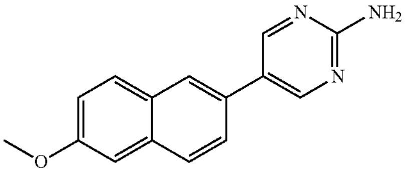 [SMILES: COc1ccc2cc(-c3cnc(N)nc3)ccc2c1] | 112 (FTO-12) | 5-(6-methoxynaphthalen-2-yl)pyrimidin-2-amine. Prepared according to general procedure A. Yield 0.543 g, 2.16 mmol, 54%. Yellow solid, mp 230° C. $^1$H-NMR (600 MHz, d-DMSO): 8.68 (s, 2H), 8.09 (d, J = 2.5 Hz, 1H), 7.87 (d, J = 8.8 Hz, 1H), 7.84 (d, J = 8.8 Hz, 1H), 7.75 (dd, J = 8.5, 1.9 Hz, 1H), 7.33 (d, J = 2.5 Hz, 1H), 7.18 (dd, J = 8.9, 2.5 Hz, 1H), 6.79 (s, 2H), 3.88 (s, 3H). $^{13}$C-NMR (150 MHz, d-DMSO): 163.4, 157.9, 156.6, 156.6, 133.9, 130.9, 130.4, 129.5, 128.5, 126.7, 123.8, 122.8, 106.5, 56.0, 25.8. HRMS (ESI, M+) m/z calculated for $C_{15}H_{13}N_3O$ 251.1059, found 251.1066. |

TABLE 100-continued

| STRUCTURE | ENTRY NUMBER (NAME) | CHARACTERIZATION DATA |
|---|---|---|
| 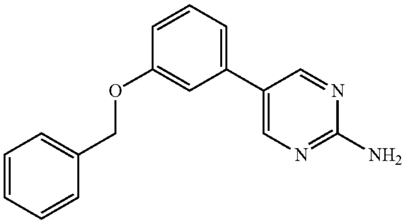 [SMILES: Nc1ncc(-c2cccc(OCc3ccccc3)c2)cn1] | 113 (FTO-13) | 5-(3-(benzyloxy)phenyl)pyrimidin-2-amine. Prepared according to general procedure A. Yield 0.566 g, 2.04 mmol, 51%. Yellow solid, mp_ 230° C. $^1$H-NMR (600 MHz, d-DMSO): 8.70 (s, 2H), 7.43 (d, J = 7.3 Hz, 2H), 7.42 (t, J = 7.4 Hz, 1 H), 7.40 (d, J = 6.1 Hz, 2H), 7.39 (d, J = 2.7 Hz, 1H), 7.36 (t, J = 7.3 Hz, 1H), 7.14 (d, J = 1.4 Hz, 2H), 7.04 (d, J = 1.6 Hz, 1 H), 6.79 (s, 2H), 5.05 (s, 2H). $^{13}$C-NMR (150 MHz, d-DMSO): 161.7, 159.7, 150.7, 150.7, 137.0, 136.6, 130.8, 128.9, 128.9, 128.4, 127.8, 127.8, 120.2, 118.4, 114.0, 113.2, 70.4. HRMS (ESI, M+) m/z calculated for $C_{17}H_{15}N_3O$ 277.1215, found 277.1223. |
| 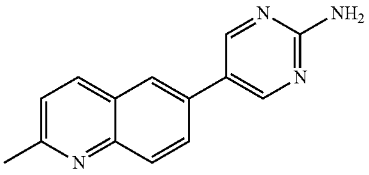 [SMILES: Cc1ccc2cc(-c3cnc(N)nc3)ccc2n1] | 114 (FTO-14) | 5-(2-methylquinolin-6-yl)pyrimidin-2-amine. Prepared according to general procedure A. Yield 0.784 g, 3.32 mmol, 83%. Yellow solid, mp 230° C. $^1$H-NMR (600 MHz, d-DMSO): 8.73 (s, 2H), 8.23 (d, J = 8.3 Hz, 1H), 8.18 (d, J = 8.8 Hz, 1H), 8.00 (d, J = 1.7 Hz, 1H),b7.94 (d, J = 8.7 Hz, 1H), 7.43 (d, J = 8.5 Hz, 1H), 6.87 (s, 2H), 2.65 (s, 3H). $^{13}$C-NMR (150 MHz, d-DMSO): 163.7, 157.9, 156.9, 156.9, 141.9, 138.6, 136.8, 130.7, 128.7, 128.3, 125.9, 123.1, 118.4, 25.5. HRMS (ESI, M+) m/z calculated for $C_{14}H_{12}N_4$ 236.1062, found 236.1070. |
| 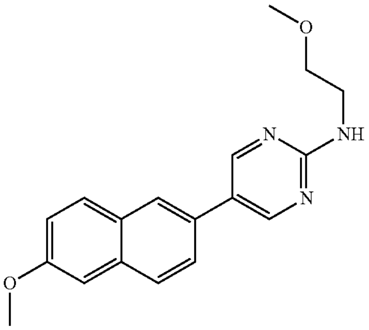 [SMILES: COCCNc1ncc(-c2ccc3cc(OC)ccc3c2)cn1] | 115 (FTO-15) | N-(2-methoxyethyl)-5-(6-methoxynaphthalen-2-yl)pyrimidin-2-amine. Prepared according to general procedure A. Yield 0.744 g, 2.52 mmol, 63%. Yellow solid, mp 230° C. $^1$H-NMR (600 MHz, d-DMSO): 8.41 (s, 2H), 8.00 (s, 1H), 7.83 (m, 2H), 7.80 (dd, J = 8.7, 2.5 Hz, 1H), 7.71 (dd, J = 8.5, 1.7 Hz, 1H), 7.30 (d, J = 2.3 Hz, 1H), 7.15 (dd, J = 8.9, 2.5 Hz, 1H), 6.73 (s, 1H), 3.87 (s, 3H), 3.48 (m, 2H), 3.27 (s, 3H). $^{13}$C-NMR (150 MHz, d-DMSO): 159.5, 156.7, 150.8, 150.8, 136.1, 134.1, 132.9, 129.7, 128.8, 127.9, 124.2, 120.3, 119.1, 109.7, 72.0, 58.7, 56.3, 43.5. HRMS (ESI, M+) m/z calculated for $C_{18}H_{19}N_3O_2$ 309.1477, found 309.14722 |
| 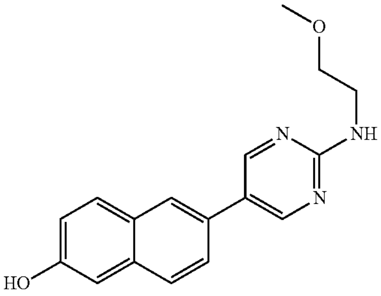 [SMILES: COCCNc1ncc(-c2ccc3cc(O)ccc3c2)cn1] | 116 (FTO-16) | 6-(2-((2-methoxyethyl)amino)pyrimidin-5-yl)naphthalen-2-ol. Prepared according to general procedure A. Yield 0.378 g, 1.28 mmol, 32%. Yellow solid, mp 230° C. $^1$H-NMR (600 MHz, d-DMSO): 8.29 (s, 2H), 7.93 (s, 1H), 7.68 (dd, J = 8.7, 2.5 Hz, 2H), 7.46 (d, J = 7.3 Hz, 1H), 7.39 (t, J = 7.7 Hz, 1H), 7.32 (t, J = 8.0, 1H), 6.90 (dd, J = 8.0, 2.0 Hz, 1H), 3.95 (s, 2H), 3.46 (s, 2H), 3.25 (s, 3H). $^{13}$C-NMR (150 MHz, d-DMSO): 159.9, 156.6, 150.3, 150.3, 134.1, 132.2, 130.3, 130.0, 129.0, 128.7, 125.7, 120.5, 116.4, 109.5, 71.8, 43.3, 56.9. HRMS (ESI, M+) m/z calculated for $C_{17}H_{17}N_3O_2$ 295.1321, found 295.1316 |
| 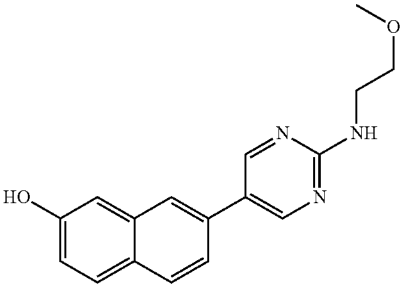 [SMILES: COCCNc1ncc(-c2ccc3ccc(O)cc3c2)cn1] | 117 (FTO-17) | 7-(2-((2-methoxyethyl)amino)pyrimidin-5-yl)naphthalen-2-ol. Prepared according to general procedure A. Yield 0.484 g, 1.68 mmol, 42%. Yellow solid, mp 230° C. $^1$H-NMR (600 MHz, d-DMSO): 8.41 (s, 2H), 7.90 (s, 1H), 7.84 (d, J = 8.4 Hz, 1H), 7.73 (d, J = 8.3 Hz, 1H), 7.64 (dd, J = 8.0, 2.0 Hz, 1H), 7.63 (d, J = 2.5 Hz, 1H), 7.39 (t, J = 7.7 Hz, 1H), 7.13 (d, J = 7.3 1H), 3.94 (s, 2H), 3.47 (s, 2H), 3.28 (s, 3H). $^{13}$C-NMR (150 MHz, d-DMSO): 160.2, 156.1, 150.1, 150.1, 135.7, 134.9, 130.0, 129.2, 127.5, 125.5, 124.1, 120.6, 118.8, 109.7, 71.6, 56.5, 43.1. HRMS (ESI, M+) m/z calculated for $C_{17}H_{17}N_3O_2$ 295.1321, found 295.1314. |

TABLE 100-continued

| STRUCTURE | ENTRY NUMBER (NAME) | CHARACTERIZATION DATA |
|---|---|---|
| 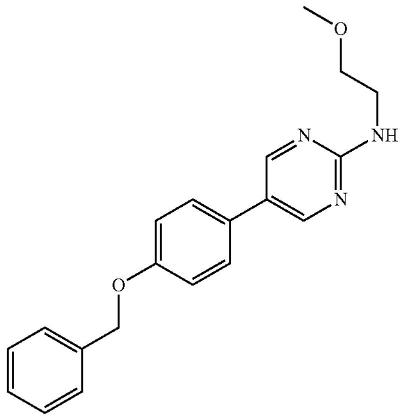 [SMILES: COCCNc1ncc(-c2ccc(OCc3ccccc3)cc2)cn1] | 118 (FTO-18) | 5-(4-(benzyloxy)phenyl)-N-(2-methoxyethyl)pyrimidin-2-amine. Prepared according to general procedure A. Yield 0.698 g, 2.08 mmol, 52%. Yellow solid, mp 230° C. $^{1}$H-NMR (600 MHz, d-DMSO): 8.29 (s, 2H), 7.93 (s, 1H), 7.68 (dd, J = 8.7, 2.5 Hz, 2 H), 7.46 (d, J = 7.3 Hz, 2H), 7.39 (t, J = 7.7 Hz, 2H), 7.32 (t, J = 8.0, 1H), 6.90 (dd, J = 8.0, 2.0 Hz, 2H), 5.16 (s, 2H), 3.95 (s, 2H), 3.46 (s, 2H), 3.25 (s, 3H). $^{13}$C-NMR (150 MHz, d-DMSO): 159.5, 158.8, 150.1, 150.1, 137.9, 136.6, 130.6, 128.9, 128.9, 128.4, 127.8, 127.8, 120.2, 118.4, 114.0, 113.2, 71.6, 70.7, 58.7, 43.1. HRMS (ESI, M+) m/z calculated for $C_{20}H_{21}N_3O_2$ 335.1634, found 334.1630. |
| 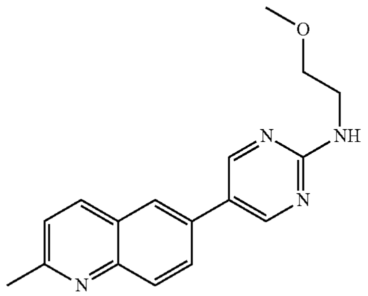 [SMILES: COCCNc1ncc(-c2ccc3nc(C)ccc3c2)cn1] | 119 (FTO-19) | N-(2-methoxyethyl)-5-(2-methylquinolin-6-yl)pyrimidin-2-amine. Prepared according to general procedure A. Yield 0.503 g, 1.71 mmol, 43%. Yellow solid, mp 230° C. $^{1}$H-NMR (600 MHz, d-DMSO): 8.70 (s, 2H), 8.24 (d, J = 8.3 Hz, 1H), 8.10 (d, J = 8.8 Hz, 1H), 8.01 (d, J = 1.7 Hz, 1H), 7.93 (s, 1H), 7.89 (d, J = 8.7 Hz, 1H), 7.44 (d, J = 8.5 Hz, 1H), 3.94 (s, 2H), 3.45 (s, 2H), 3.26 (s, 3H), 2.71 (s, 3H). $^{13}$C-NMR (150 MHz, d-DMSO): 159.8, 158.1, 151.2, 151.2, 150.1, 141.9, 135.6, 133.1, 128.7, 128.3, 125.9, 123.1, 120.2, 71.5, 58.7, 43.1, 25.5. HRMS (ESI, M+) m/z calculated for $C_{17}H_{18}N4_3O$ 294.1481, found 294.1485. |
| 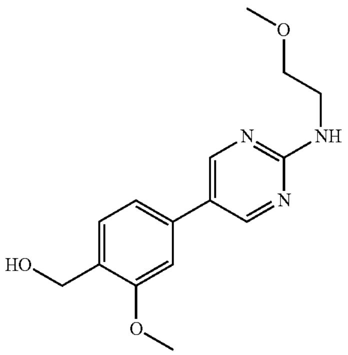 [SMILES: COCCNc1ncc(-c2ccc(CO)c(OC)c2)cn1] | 120 (FTO-20) | (2-methoxy-4-(2-((2-methoxyethyl)amino)pyrimidin-5-yl)phenyl)methanol. Prepared according to general procedure A. Yield 0.584 g, 2.02 mmol, 51%. Yellow solid, mp 230° C. $^{1}$H-NMR (600 MHz, d-DMSO): 8.68 (s, 2H), 7.93 (s, 1H), 7.30 (d, J = 7.9 Hz, 1H), 7.13 (d, J = 1.6 Hz, 1H), 7.11 (t, J = 2.7 Hz, 1H), 5.10 (t, J = 5.6 Hz, 2H), 3.94 (s, 2H), 3.77 (s, 3H), 3.45 (s, 2H), 3.26 (s, 3H). $^{13}$C-NMR (150 MHz, d-DMSO): 159.9, 157.1, 148.9, 148.9, 136.2, 131.0, 129.1, 123.5, 119.1, 113.9, 71.5, 61.1, 58.6, 58.1, 43.0. HRMS (ESI, M+) m/z calculated for $C_{15}H_{19}N_3O_3$ 289.1426, found 289.1430 |

Inhibition Data for Compounds of Table 100:

| Structure | Name | Enzymatic $IC_{50}$ FTO | Enzymatic $IC_{50}$ ALKBH5 |
|---|---|---|---|
| 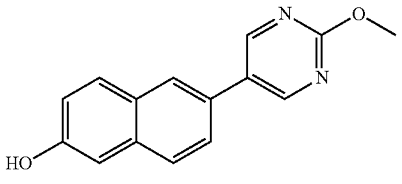 [SMILES: COc1ncc(-c2ccc3cc(O)ccc3c2)cn1] | FTO-2 | 2.18 ± 1.3 | 85.5 ± 5.7 |

-continued
| | | | |
|---|---|---|---|
| 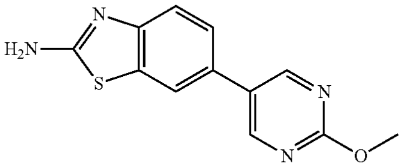 [SMILES: COc1ncc(-c2ccc3nc(N)sc3c2)cn1] | FTO-4 | 3.39 ± 2.5 | 39.4 ± 3.1 |
| 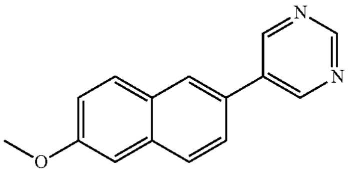 [SMILES: COc1ccc2cc(-c3cncnc3)ccc2c1] | FTO-5 | 13.38 ± 2.3 | >40 |
| 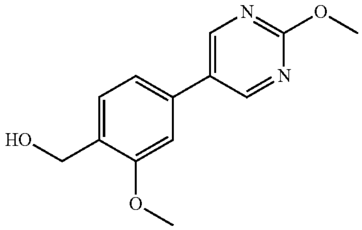 [SMILES: COc1ncc(-c2ccc(CO)c(OC)c2)cn1] | FTO-6 | 13.8 ± 2.4 | 64.4 ± 6.3 |
| 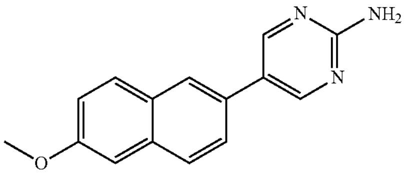 [SMILES: COc1ccc2cc(-c3cnc(N)nc3)ccc2c1] | FTO-12 | 18.3 ± 1.7 | >40 |
| 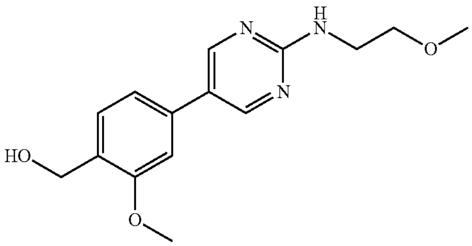 [SMILES: COCCNc1ncc(-c2ccc(CO)c(OC)c2)cn1] | FTO-20 | 17.2 ± 2.9 | 90.2 ± 7.8 |
| Structure | Name | Enzymatic $IC_{50}$ FTO |
|---|---|---|
| 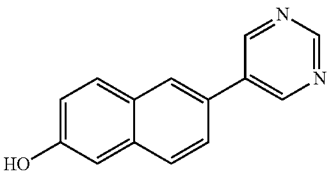 [SMILES: Oc1ccc2cc(-c3cncnc3)ccc2c1] | FTO-1 | 41.7 ± 12 |
| 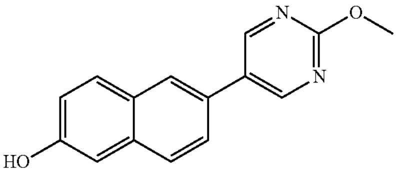 [SMILES: COc1ncc(-c2ccc3cc(O)ccc3c2)cn1] | FTO-2 | 2.18 ± 1.3 |

-continued
| | | |
|---|---|---|
| 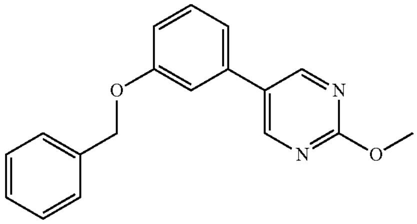 [SMILES: COc1ncc(-c2cccc(OCc3ccccc3)c2)cn1] | FTO-3 | — |
| 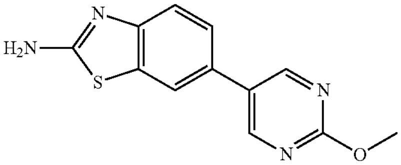 [SMILES: COc1ncc(-c2ccc3nc(N)sc3c2)cn1] | FTO-4 | 3.39 ± 2.5 |
| 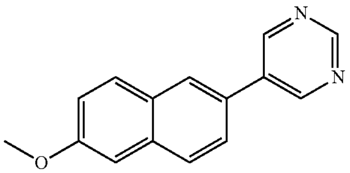 [SMILES: COc1ccc2cc(-c3cncnc3)ccc2c1] | FTO-5 | 13.38 ± 2.3 |
| 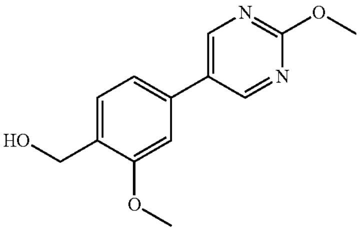 [SMILES: COc1ncc(-c2ccc(CO)c(OC)c2)cn1] | FTO-6 | 13.8 ± 2.4 |
| 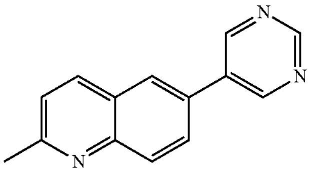 [SMILES: Cc1ccc2cc(-c3cncnc3)ccc2n1] | FTO-7 | 29.1 ± 2.4 |
| 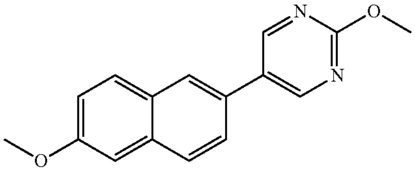 | FTO-8 | 16.0 ± 1.8 |
| 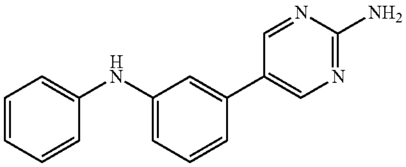 [SMILES: Nc1ncc(-c2cccc(Nc3ccccc3)c2)cn1] | FTO-9 | 43.8 ± 2.4 |
| 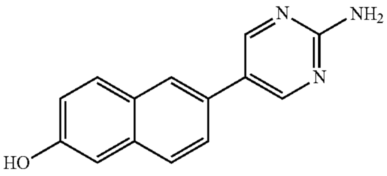 [SMILES: Nc1ncc(-c2ccc3cc(O)ccc3c2)cn1] | FTO-10 | 48.1 ± 3.5 |

-continued
| | | |
|---|---|---|
| 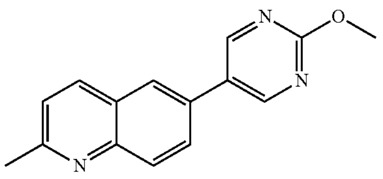 | FTO-11 | 11.3 ± 1.1 |
| 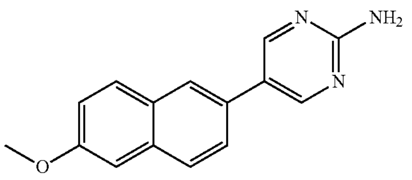 [SMILES: COc1ccc2cc(-c3cnc(N)nc3)ccc2c1] | FTO-12 | 18.3 ± 1.7 |
| 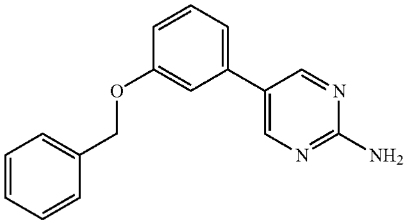 [SMILES: Nc1ncc(-c2cccc(OCc3ccccc3)c2)cn1] | FTO-13 | 36.7 ± 3.1 |
| 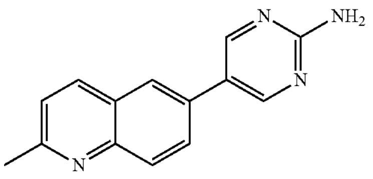 [SMILES: Cc1ccc2cc(-c3cnc(N)nc3)ccc2n1] | FTO-14 | 59.6 ± 4.8 |
| 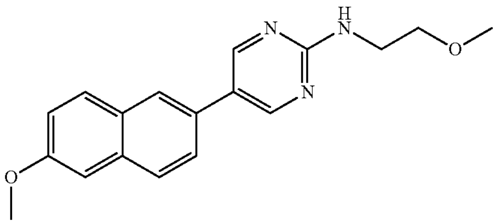 [SMILES: COCCNc1ncc(-c2ccc3cc(OC)ccc3c2)cn1] | FTO-15 | — |
| 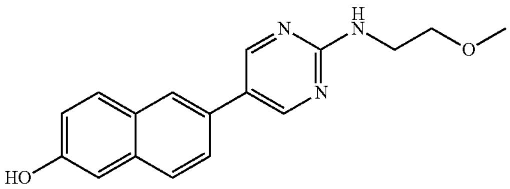 [SMILES: COCCNc1ncc(-c2ccc3cc(O)ccc3c2)cn1] | FTO-16 | 46.5 ± 3.1 |
| 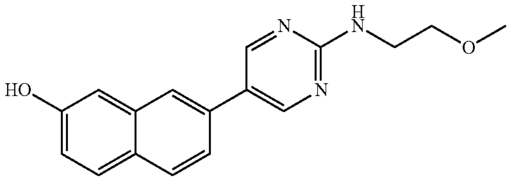 [SMILES: COCCNc1ncc(-c2ccc3ccc(O)cc3c2)cn1] | FTO-17 | 51.9 ± 4.7 |

-continued
| | | |
|---|---|---|
| 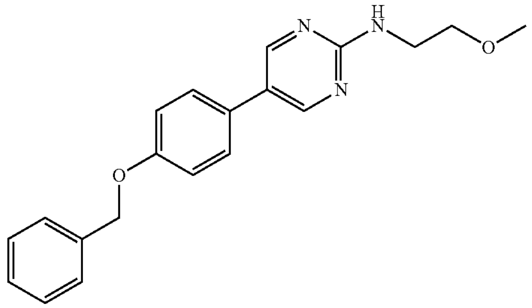 [SMILES: COCCNc1ncc(-c2ccc(OCc3ccccc3)cc2)cn1] | FTO-18 | 127.0 ± 5.9 |
| 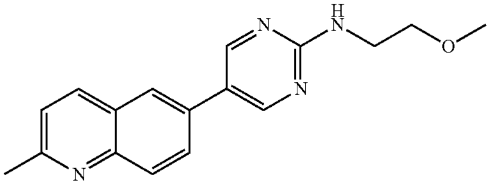 | FTO-19 | 25.2 ± 4.9 |
| 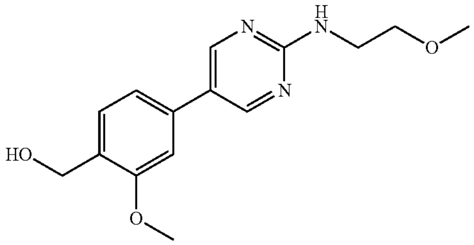 [SMILES: COCCNc1ncc(-c2ccc(CO)c(OC)c2)cn1] | FTO-20 | 17.2 ± 2.9 |
| Structure | Name | Enzymatic $IC_{50}$ ALKBH5 |
|---|---|---|
| 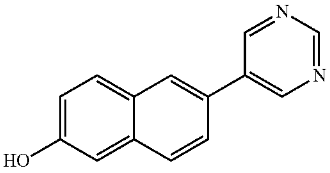 [SMILES: Oc1ccc2cc(-c3cncnc3)ccc2c1] | FTO-1 | >>40 |
| 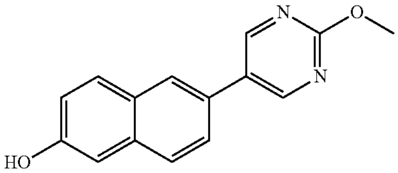 [SMILES: COc1ncc(-c2ccc3cc(O)ccc3c2)cn1] | FTO-2 | 85.5 ± 5.7 |
| 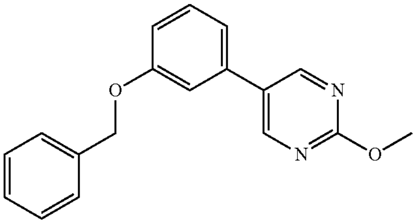 [SMILES: COc1ncc(-c2cccc(OCc3ccccc3)c2)cn1] | FTO-3 | — |

-continued
| | | |
|---|---|---|
| 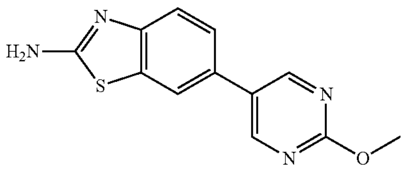 [SMILES: COc1ncc(-c2ccc3nc(N)sc3c2)cn1] | FTO-4 | 39.4 ± 3.1 |
| 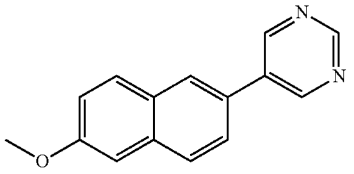 [SMILES: COc1ccc2cc(-c3cncnc3)ccc2c1] | FTO-5 | >>40 |
| 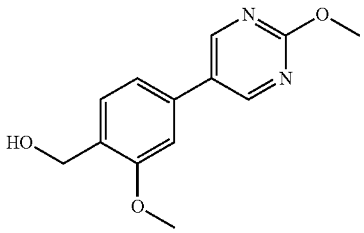 [SMILES: COc1ncc(-c2ccc(CO)c(OC)c2)cn1] | FTO-6 | 64.4 ± 6.3 |
| 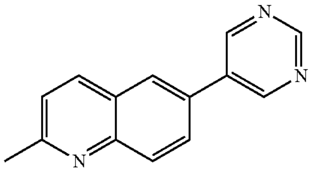 [SMILES: Cc1ccc2cc(-c3cncnc3)ccc2n1] | FTO-7 | >>>40 |
| 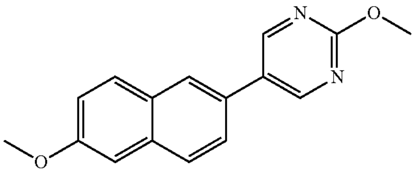 | FTO-8 | 16.4 ± 2.1 |
| 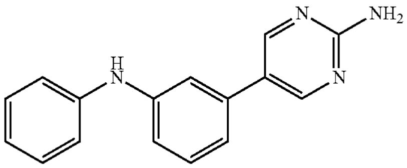 [SMILES: Nc1ncc(-c2cccc(Nc3ccccc3)c2)cn1] | FTO-9 | 5.2 ± 2.9 |
| 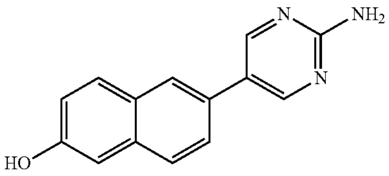 [SMILES: Nc1ncc(-c2ccc3cc(O)ccc3c2)cn1] | FTO-10 | 36.1 ± 3.1 |
| 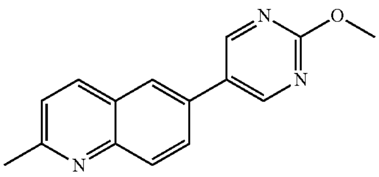 | FTO-11 | 19.5 ± 2.7 |

-continued
| | | |
|---|---|---|
| 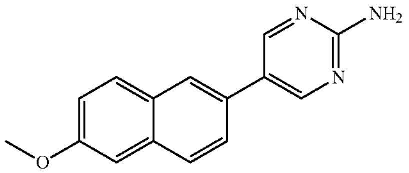 [SMILES: COc1ccc2cc(-c3cnc(N)nc3)ccc2c1] | FTO-12 | >>>40 |
| 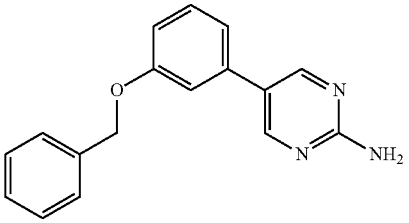 [SMILES: Nc1ncc(-c2cccc(OCc3ccccc3)c2)cn1] | FTO-13 | 14.9 ± 1.8 |
| 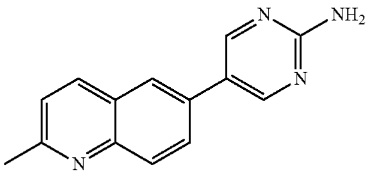 [SMILES: Cc1ccc2cc(-c3cnc(N)nc3)ccc2n1] | FTO-14 | 214.9 ± 9.6 |
| 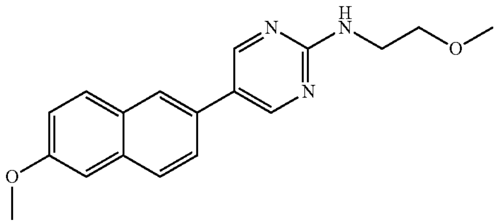 [SMILES: COCCNc1ncc(-c2ccc3cc(OC)ccc3c2)cn1] | FTO-15 | — |
| 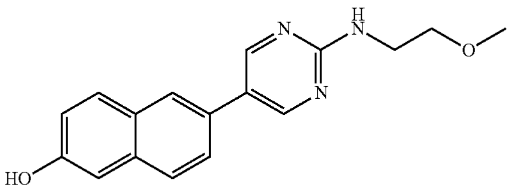 [SMILES: COCCNc1ncc(-c2ccc3cc(O)ccc3c2)cn1] | FTO-16 | 663.8 ± 31.4 |
| 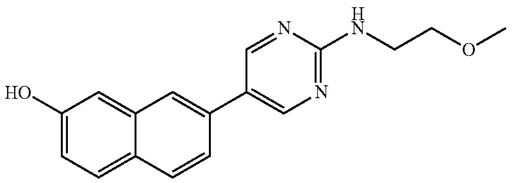 [SMILES: COCCNc1ncc(-c2ccc3ccc(O)cc3c2)cn1] | FTO-17 | 985.4 ± 29.8 |
| 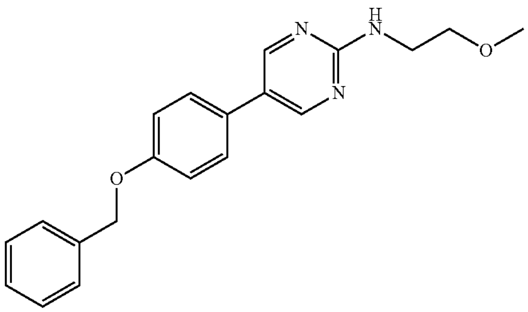 [SMILES: COCCNc1ncc(-c2ccc(OCc3ccccc3)cc2)cn1] | FTO-18 | >>>40 |

-continued
| | | |
|---|---|---|
| 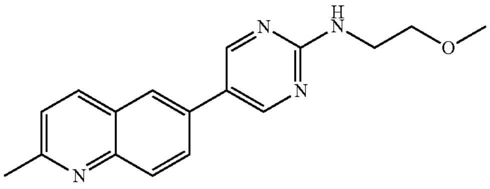 | FTO-19 | 53.5 ± 5.2 |
| 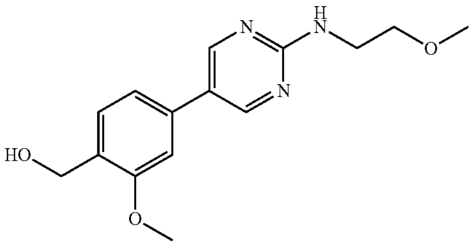 [SMILES: COCCNc1ncc(-c2ccc(CO)c(OC)c2)cn1] | FTO-20 | 90.2 ± 7.8 |
Inhibition Data for FTO Inhibitors of Table 100 against FTO and ALKBH5. C log P and permeability parameters calculated by QikProp.
| Structure | Entry Number (Name) | clogP (octanol/ water) | Permeability (nm/s) Caco-2 | Permeability (nm/s) MDCK | Enzymatic $IC_{50}$ FTO | Enzymatic $IC_{50}$ ALKBH5 |
|---|---|---|---|---|---|---|
| 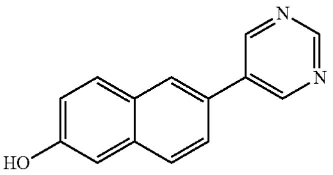 [SMILES: Oc1ccc2cc(-c3cncnc3)ccc2c1] | 101 (FTO-1) | 2.04 | 873 | 427 | 41.7 ± 1.2 | >40 |
| 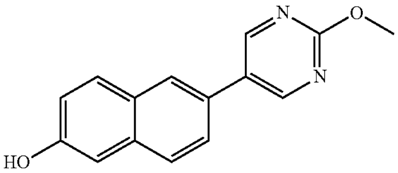 [SMILES: COc1ncc(-c2ccc3cc(O)ccc3c2)cn1] | 102 (FTO-2) | 3.00 | 1338 | 677 | 2.18 ± 1.3 | 85.5 ± 5.7 |
| 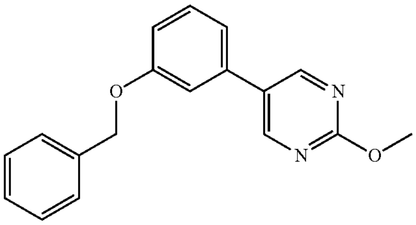 [SMILES: COc1ncc(-c2cccc(OCc3ccccc3)c2)cn1] | 103 (FTO-3) | 4.69 | 4410 | 2460 | ND | ND |
| 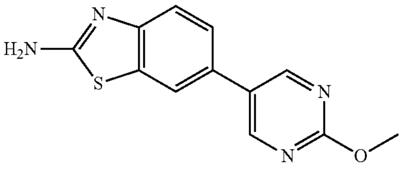 [SMILES: COc1ncc(-c2ccc3nc(N)sc3c2)cn1] | 104 (FTO-4) | 2.00 | 632 | 562 | 3.39 ± 2.5 | 39.4 ± 3.1 |

-continued
| Structure | Entry Number (Name) | clogP (octanol/ water) | Permeability (nm/s) Caco-2 | MDCK | Enzymatic $IC_{50}$ FTO | Enzymatic $IC_{50}$ ALKBH5 |
|---|---|---|---|---|---|---|
| 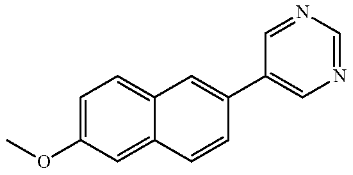 [SMILES: COc1ccc2cc(-c3cncnc3)ccc2c1] | 105 (FTO-5) | 2.67 | 2880 | 1552 | 13.38 ± 2.3 | >40 |
| 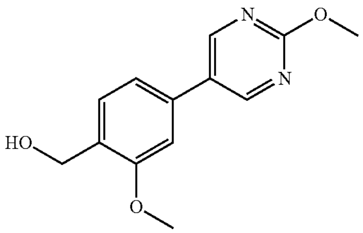 [SMILES: COc1ncc(-c2ccc(CO)c(OC)c2)cn1] | 106 (FTO-6) | 2.30 | 1335 | 665 | 13.8 ± 2.4 | 64.4 ± 6.3 |
| 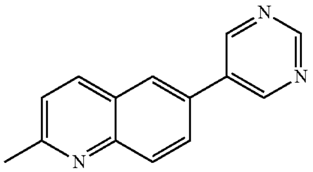 [SMILES: Cc1ccc2cc(-c3cncnc3)ccc2n1] | 107 (FTO-7) | 2.27 | 2101 | 1104 | 29.1 ± 2 .4 | >40 |
| 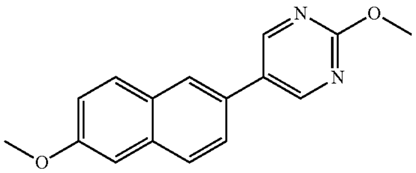 | 108 (FTO-8) | 3.75 | 4411 | 2460 | 10.0 ± 1.8 | 16.4 ± 2.1 |
| 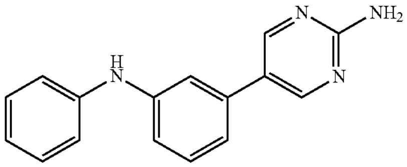 [SMILES: Nc1ncc(-c2cccc(Nc3ccccc3)c2)cn1] | 109 (FTO-9) | 2.79 | 624 | 297 | 43.8 ± 2.4 | 5.2 ± 2.9 |
| 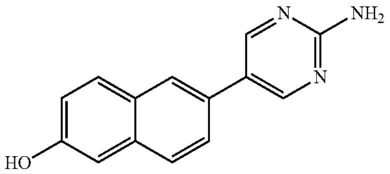 [SMILES: Nc1ncc(-c2ccc3cc(O)ccc3c2)cn1] | 110 (FTO-10) | 1.60 | 255 | 113 | 48.1 ± 3.5 | 36.1 ± 3.1 |
| 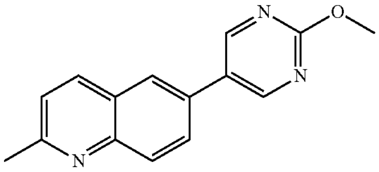 | 111 (FTO-11) | 3.35 | 321.8 | 1750 | 11.3 ± 1.1 | 19.5 ± 2.7 |

-continued
| Structure | Entry Number (Name) | clogP (octanol/ water) | Permeability (nm/s) Caco-2 | Permeability (nm/s) MDCK | Enzymatic $IC_{50}$ FTO | Enzymatic $IC_{50}$ ALKBH5 |
|---|---|---|---|---|---|---|
| 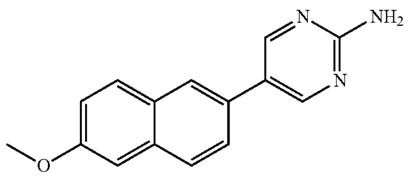 [SMILES: COc1ccc2cc(-c3cnc(N)nc3)ccc2c1] | 112 (FTO-12) | 2.48 | 842 | 411 | 18.3 ± 1.7 | >40 |
| 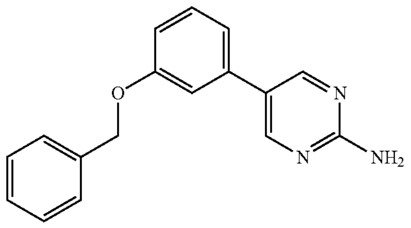 [SMILES: Nc1ncc(-c2cccc(OCc3ccccc3)c2)cn1] | 113 (FTO-13) | 3.37 | 842 | 411 | 36.7 ± 3.1 | 14.9 ± 1.8 |
| 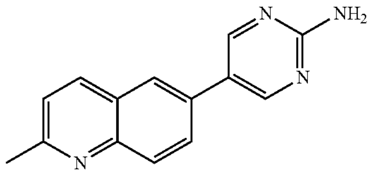 [SMILES: Cc1ccc2cc(-c3cnc(N)nc3)ccc2n1] | 114 (FTO-14) | 2.11 | 615 | 292 | 59.6 ± 4.8 | >40 |
| 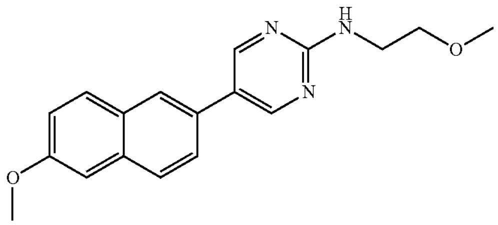 [SMILES: COCCNc1ncc(-c2ccc3cc(OC)ccc3c2)cn1] | 115 (FTO-15) | 3.45 | 963 | 475 | ND | ND |
| 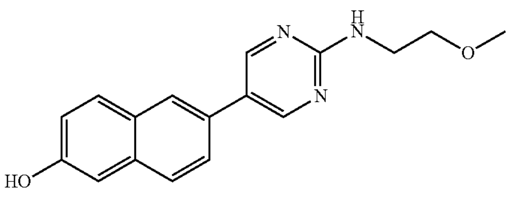 [SMILES: COCCNc1ncc(-c2ccc3cc(O)ccc3c2)cn1] | 116 (FTO-16) | 2.89 | 292 | 130 | 46.5 ± 3.1 | >40 |
| 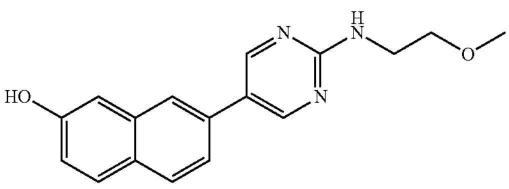 [SMILES: COCCNc1ncc(-c2ccc3ccc(O)cc3c2)cn1] | 117 (FTO-17) | 2.89 | 292 | 130 | 51.9 ± 4.7 | >40 |

-continued

| Structure | Entry Number (Name) | clogP (octanol/ water) | Permeability (nm/s) Caco-2 | MDCK | Enzymatic $IC_{50}$ FTO | Enzymatic $IC_{50}$ ALKBH5 |
|---|---|---|---|---|---|---|
| 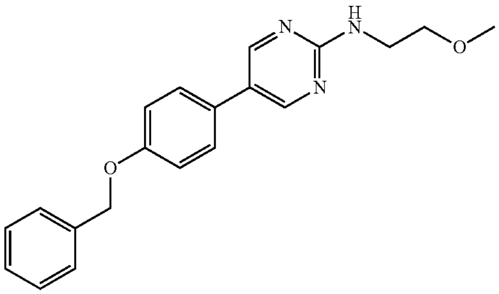 [SMILES: COCCNc1ncc(-c2ccc(OCc3ccccc3)cc2)cn1] | 118 (FTO-18) | 3.69 | 963 | 475 | >40 | >40 |
| 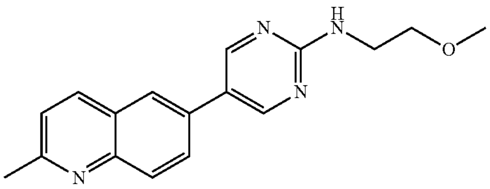 | 119 (FTO-19) | 2.44 | 702 | 337 | 25.2 ± 4.9 | 53.5 ± 5.2 |
| 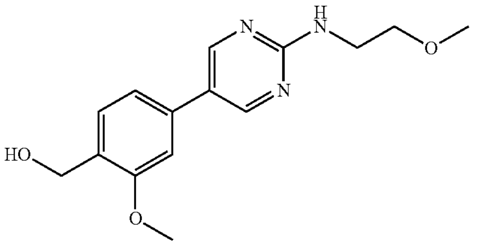 [SMILES: COCCNc1ncc(-c2ccc(CO)c(OC)c2)cn1] | 120 (FTO-20) | 1.21 | 287 | 128 | 17.2 ± 2.9 | 90.2 ± 7.8 |

ND = Not determined

Example C2

General Procedure for the Preparation of Non-Limiting Exemplary FTO Inhibitors (e.g., Compounds of Formula (F2)):

Scheme 2.

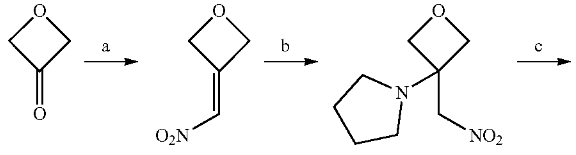

2 3

-continued

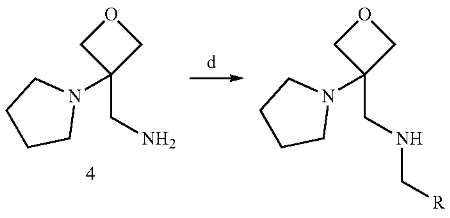

4 5

Reagents and conditions: a). oxetan-3-one; nitromethane, trimethylamine, methanesulfonyl chloride; 12 h., b). Pyrrolidine or 3-fluoropyrrolidine $NaHCO_3$, THF, 3 h., c). RaNi, THF, room temeperature, 3 h., d). Aldehyde, $NaBH_4$, 5 h.

Step a: 3-(nitromethylene)oxetane (2)

3-Oxetanone (130 μL, 2.03 mmol), nitromethane (154 μL, 2.85 mmol), and $NEt_3$ (57 μL, 0.41 mmol) were stirred at room temperature for 30 min then diluted with $CH_2Cl_2$ (10 mL) and cooled to −78° C. To this solution was added $NEt_3$ (565 μL, 4.05 mmol), followed by MsCl (157 μL, 2.03 mmol) dropwise over 10 min. The reaction mixture was stirred at −78° C. for 40 min. The reaction mixture was allowed to warm to room temperature and directly poured on a column. (15→25% EtOAc in hexane) provided compound (2) as a yellow oil.

Step b: 1-(3-(nitromethyl)oxetan-3-yl)pyrrolidine (3)

To a stirred solution of (2) (1 eq) in THF and followed by the addition of $NaHCO_3$ (1 eq.) and pyrrolidine (1 eq.). The reaction mixture was stirred for 1 h at room temperature. After completion of reaction the reaction mixture was filtered through celite bed. The solvent as evaporated under vacuum and the crude product was purified by column chromatography (EtOH:Hexane, 1:9→2:8) to give compound (3) as a liquid.

Step c: (3-(pyrrolidin-1-yl)oxetan-3-yl)methanamine (4)

To a stirred solution of (3) (1 eq.) in THF and followed by the addition of RaNi. The reaction mixture was stirred for 3 h under Hydrogen balloon. After completion of reaction, the reaction mixture was filtered through celite bed. The solvent was evaporated under vacuum and the crude product was purified by column chromatography (MeOH:DCM, 1:9→2:8) to give compound (4) as a liquid.

Step d: General Procedure for the Synthesis of Compounds. (5-58)

A two-necked round-bottomed flask was charged with compound (4) (1 eq.) in MeOH and followed by the addition of corresponding aldehyde (1 eq.). The reaction mixture was stirred at room temperature for 3 h and after completion of starting materials to the reaction mass add $NaBH_4$ (1.5 eq.) portion-wise. The reaction mass again stirred for 2 h at room temperature. After completion of reaction the excess of MeOH was removed and dissolve in water and extract with ethyl acetate. The organic layer was separate and $NaSO_4$ and filter and filtrate was concentrate under reduced pressure. The crude material was purified by flash column chromatography MeOH:DCM, 1:9→2:8) to give the final compound as a semi liquid.

Compounds in Table 200 were synthesized using the methods described above:

TABLE 200

| STRUCTURE | ENTRY NUMBER (NAME) | ANALYTICAL DATA |
|---|---|---|
| 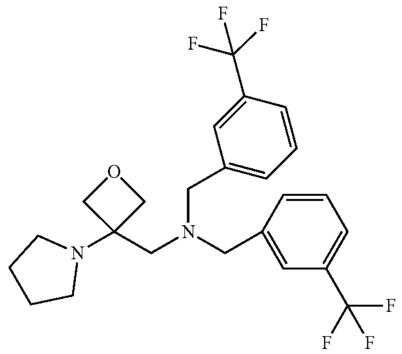 [SMILES: FC(F)(F)c1cccc(CN(Cc2cccc(C(F)(F)F)c2)CC2(N3CCCC3)COC2)c1] | 201 (TR-FTO-01-N) | $^1$H NMR (599 MHz, $CDCl_3$) δ 7.62 (s, 1H), 7.50 (d, J = 4.7 Hz, 2H), 7.43 (t, J = 7.6 Hz, 1H), 4.78 (d, J = 6.7 Hz, 1H), 4.39 (d, J = 6.5 Hz, 1H), 3.65 (s, 2H), 2.89 (s, 1H), 2.78 (s, 2H), 1.82 (s, 2H). $^{13}$C NMR (151 MHz, CDCl3) δ 140.69, 132.12, 130.71, 130.50, 128.67, 125.78, 125.76, 123.97, 123.95, 76.84, 63.16, 59.04, 58.52, 46.67, 23.86.; HRMS (ESI): m/z (%) = 473.2016 (M + $H^+$). Purity >98%. |
| 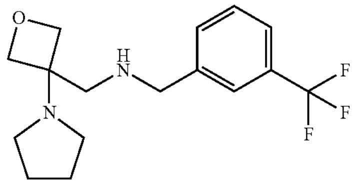 [SMILES: FC(F)(F)c1cccc(CNCC2(N3CCCC3)COC2)c1] | 202 (TR-FTO-02-N) | $^1$H NMR (600 MHz, CDCl3) δ 7.61 (d, J = 7.8 Hz, 1H), 7.53 (dd, J = 15.5, 7.7 Hz, 2H), 7.45 (dd, J = 14.1, 6.4 Hz, 1H), 4.80 (d, J = 6.6 Hz, 2H), 4.35 (d, J = 6.6 Hz, 2H), 3.90 (s, 2H), 2.95 (s, 2H), 2.71 (t, J = 6.4 Hz, 4H), 1.83-1.79 (m, 4H); $^{13}$C NMR (151 MHz, CDCl3) δ 141.58, 131.44, 128.80, 124.77, 124.75, 123.84, 123.81, 76.87, 62.56, 54.60, 53.45 46.80, 23.98; HRMS (ESI): m/z (%) = 315.1677 (M + $H^+$). Purity >96%. |
| 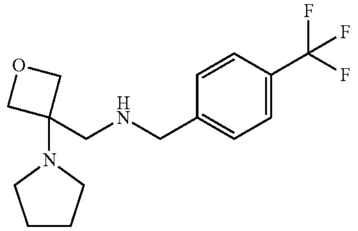 [SMILES: FC(F)(F)c1ccc(CNCC2(N3CCCC3)COC2)cc1] | 203 (TR-FTO-03-N) | $^1$H NMR (CD3OD): 1H NMR (600 MHz, CDCl3) δ 7.59 (d, J = 8.1 Hz, 1H), 7.46 (t, J = 8.7 Hz, 1H), 4.80 (d, J = 6.6 Hz, 1H), 4.35 (d, J = 6.6 Hz, 1H), 3.90 (s, 1H), 2.95 (s, 1H), 2.72 (t, J = 6.4 Hz, 2H), 1.83-1.79 (m, 2H); $^{13}$C NMR (151 MHz, CDCl3) δ 144.68, 129.32, 129.08, 128.28, 125.33, 125.30, 76.86, 62.55, 54.60, 53.48, 46.83, 24.00; HRMS (ESI): m/z (%) = 315.1679 (M + $H^+$). Purity >98%. |

TABLE 200-continued

| STRUCTURE | ENTRY NUMBER (NAME) | ANALYTICAL DATA |
|---|---|---|
| 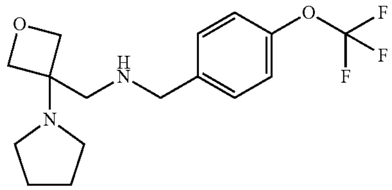 [SMILES: FC(F)(F)Oc1ccc(CNCC2(N3CCCC3)COC2)cc1] | 204 (TR-FTO-04-N) | $^1$H NMR (600 MHz, CDCl3) δ 7.37 (t, J = 7.6 Hz, 1H), 7.18 (d, J = 8.1 Hz, 1H), 4.80 (d, J = 6.6 Hz, 1H), 4.36 (d, J = 6.6 Hz, 1H), 3.84 (s, 1H), 2.96 (d, J = 5.8 Hz, 1H), 2.71 (t, J = 6.4 Hz, 2H), 1.82-1.79 (m, 2H); $^{13}$C NMR (151 MHz, CDCl3) δ 148.17, 139.30, 129.35, 120.95, 76.89, 62.53, 54.59, 53.20, 46.79, 23.99; HRMS (ESI): m/z (%) = 331.1627 (M + H$^+$). Purity >95%. |
| 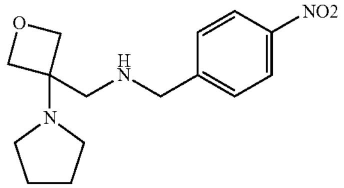 [SMILES: O=[N+]([O-])c1ccc(CNCC2(N3CCCC3)COC2)cc1] | 205 (TR-FTO-05-N) | $^1$H NMR (600 MHz, CDCl3) δ 8.22-8.18 (m, 1H), 7.54 (d, J = 8.6 Hz, 1H), 4.81 (d, J = 6.6 Hz, 1H), 4.35 (d, J = 6.6 Hz, 1H), 3.95 (s, 1H), 2.96 (s, 1H), 2.73 (t, J = 6.2 Hz, 2H), 1.84-1.80 (m, 2H); $^{13}$C NMR (151 MHz, CDCl3) δ 148.41, 147.06, 128.65, 123.63, 76.84, 62.59, 54.74, 53.27, 46.87, 24.02; HRMS (ESI): m/z (%) = 292.1656 (M + H$^+$). Purity >96%. |
| 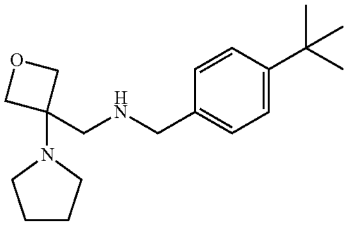 [SMILES: CC(C)(C)c1ccc(CNCC2(N3CCCC3)COC2)cc1] | 206 (TR-FTO-06-N) | $^1$H NMR (600 MHz, CDCl3) δ 7.37 (d, J = 8.3 Hz, 1H), 7.29-7.27 (m, 2H), 4.79 (d, J = 6.7 Hz, 2H), 4.38 (d, J = 6.6 Hz, 2H), 3.84 (s, 2H), 2.99 (d, J = 7.1 Hz, 2H), 2.69 (t, J = 6.4 Hz, 4H), 1.82-1.77 (m, 4H), 1.33 (s, 9H); $^{13}$C NMR (151 MHz, CDCl3) δ 149.95, 127.86, 125.34, 76.90, 62.54, 54.39, 53.53, 46.76, 34.53, 31.41, 23.99; HRMS (ESI): m/z (%) = 303.2428 (M + H$^+$). Purity >96%. |
| 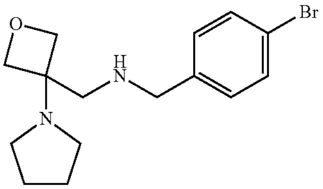 [SMILES: Brc1ccc(CNCC2(N3CCCC3)COC2)cc1] | 207 (TR-FTO-07-N) | $^1$H NMR (600 MHz, CDCl3) δ 7.47-7.43 (m, 1H), 7.22 (d, J = 8.3 Hz, 1H), 4.79 (d, J = 6.6 Hz, 1H), 4.34 (d, J = 6.6 Hz, 1H), 3.79 (s, 1H), 2.93 (s, 1H), 2.70 (t, J = 6.5 Hz, 2H), 1.82-1.79 (m, 2H); $^{13}$C NMR (151 MHz, CDCl3) δ 139.54, 131.44, 129.83, 120.67, 76.89, 62.54, 54.47, 53.28, 46.79, 24.00, HRMS (ESI): m/z (%) = 327.0888 (M + H$^+$). Purity >98%. |
| 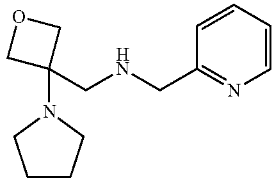 [SMILES: c1ccc(CNCC2(N3CCCC3)COC2)nc1] | 208 (TR-FTO-08-N) | $^1$H NMR (600 MHz, CDCl3) δ 8.55 (d, J = 4.6 Hz, 1H), 7.65 (td, J = 7.7, 1.7 Hz, 1H), 7.36 (d, J = 7.8 Hz 1H), 7.16 (dd, J = 7.1, 5.2 Hz, 1H), 4.80 (d, J = 6.6 Hz, 2H), 4.38 (d, J = 6.6 Hz, 2H), 3.97 (s, 2H), 3.01 (s, 2H), 2.73 (t, J = 6.2 Hz, 4H), 1.83-1.78 (m, 4H); $^{13}$C NMR (151 MHz, CDCl3) δ 159.97, 149.27, 136.51, 122.32, 122.01, 76.90, 62.59, 55.36, 54.84, 46.79, 24.00; HRMS (ESI): m/z (%) = 248.1759 (M + H$^+$). Purity >99%. |
| 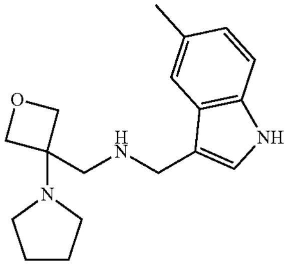 [SMILES: Cc1ccc2[nH]cc(CNCC3(N4CCCC4)COC3)c2c1] | 209 (TR-FTO-09-N) (TR-FTO-2) | $^1$H NMR (600 MHz, CDCl3) δ 8.30 (s, 1H), 7.44 (s, 1H), 7.28 (dd, J = 5.7, 2.5 Hz, 1H), 7.18 (d, J = 1.8 Hz, 1H), 7.04 (dd, J = 8.3, 1.0 Hz, 1H), 4.78 (d, J = 6.7 Hz, 2H), 4.40 (d, J = 6.7 Hz, 2H), 4.09 (s, 2H), 3.09 (s, 2H), 2.62 (t, J = 6.1 Hz, 4H), 2.47 (s, 3H), 1.75-1.70 (m, 4H); $^{13}$C NMR (151 MHz, CDCl3) δ 134.72, 128.98, 127.26, 123.91, 118.27, 110.98, 76.75, 62.21, 46.67, 44.60, 23.83, 21.52; HRMS (ESI): m/z (%) = 300.2070 (M + H$^+$). Purity >96%. |
| 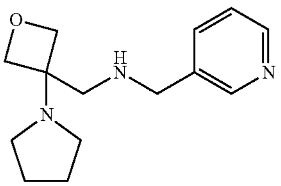 [SMILES: c1cncc(CNCC2(N3CCCC3)COC2)c1] | 210 (TR-FTO-010-N) | $^1$H NMR (600 MHz, CDCl3) δ 8.57 (t, J = 3.7 Hz, 2H), 8.52 (dd, J = 4.7, 1.3 Hz, 2H), 7.70 (d, J = 7.8 Hz, 2H), 7.28 (q, J = 4.7 Hz, 3H), 4.79 (d, J = 6.6 Hz, 4H), 4.35 (d, J = 6.6 Hz, 4H), 3.86 (s, 4H), 296 (s, 4H), 2.71 (t, J = 6.0 Hz, 8H), 1.82-1.79 (m, 8H); $^{13}$C 13C NMR (151 MHz, CDCl3) δ 149.76, 148.56, 135.81, 135.76, 123.45, 76.84, 62.56, 54.57, 51.32, 46.83, 24.00; HRMS (ESI): m/z (%) = 248.1759 (M + H$^+$). Purity >95%. |

TABLE 200-continued

| STRUCTURE | ENTRY NUMBER (NAME) | ANALYTICAL DATA |
|---|---|---|
| 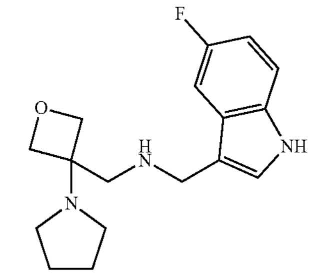 [SMILES: Fc1ccc2[nH]cc(CNCC3(N4CCCC4)COC3)c2c1] | 211 (TR-FTO-011-N) (TR-FTO-3) | $^1$H NMR (600 MHz, CDCl3) δ 8.41 (s, 1H), 7.33-7.28 (m, 2H), 7.27-7.25 (m, 1H), 6.95 (tt, J = 7.4, 3.7 Hz, 1H), 4.79 (d, J = 6.7 Hz, 2H), 4.39 (d, J = 6.7 Hz, 2H), 4.05 (s, 2H), 3.49 (s, 4H), 3.08 (s, 2H), 2.66 (t, J = 6.1 Hz, 4H), 1.78-1.74 (m, 4H); $^{13}$C NMR (151 MHz, CDCl3) δ 158.64, 157.08, 132.85, 127.52, 127.46, 112.02, 111.95, 110.72, 110.56, 103.82, 103.64, 76.75, 62.30, 53.99, 50.89, 46.77, 44.60, 23.87; HRMS (ESI): m/z (%) = 304.1819 (M + H$^+$). Purity >95%. |
| 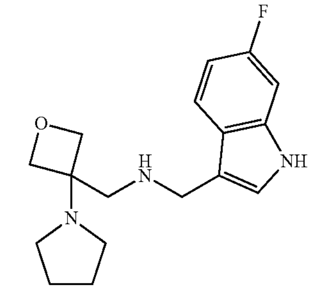 [SMILES: Fc1ccc2c(CNCC3(N4CCCC4)COC3)c[nH]c2c1] | 212 (TR-FTO-012-N) | $^1$H NMR (600 MHz, CDCl3) δ 8.45 (s, 1H), 7.59 (dd, J = 8.7, 5.3 Hz, 1H), 7.22 (s, 1H), 7.07 (dd, J = 9.6, 2.2 Hz, 1H), 6.91 (td, J = 9.3, 2.2 Hz, 1H), 4.78 (d, J = 6.7 Hz, 2H), 4.38 (d, J = 6.8 Hz, 2H), 4.10 (s, 2H), 3.09 (s, 2H), 2.64 (t, J = 6.0 Hz, 4H), 1.75-1.72 (m, 4H); $^{13}$C NMR (151 MHz, CDCl3) δ 160.85, 159.30, 136.38, 136.29, 123.64, 119.58, 119.51, 108.62, 108.46, 97.78, 97.52, 76.65, 62.24, 46.75, 44.45, 23.87; HRMS (ESI): m/z (%) = 304.1819 (M + H$^+$). Purity >94%. |
| 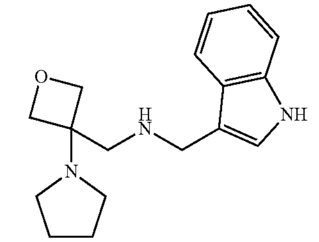 [SMILES: c1ccc2c(CNCC3(N4CCCC4)COC3)c[nH]c2c1] | 213 (TR-FTO-013-N) (TR-FTO-5) | $^1$H NMR (600 MHz, CDCl3) δ 8.36 (s, 1H), 7.67 (d, J = 7.9 Hz, 1H), 7.40 (d, J = 8.2 Hz, 1H), 7.28 (d, J = 4.5 Hz, 1H), 7.24-7.21 (m, 1H), 7.15 (dd, J = 11.1, 3.9 Hz, 1H), 4.77 (d, J = 6.8 Hz, 2H), 4.41-4.39 (m, 2H), 4.15 (s, 2H), 3.49 (d, J = 3.7 Hz, 2H), 3.12 (s, 2H), 2.61 (t, J = 5.9 Hz, 4H), 1.73-1.69 (m, 4H). $^{13}$C NMR (151 MHz, CDCl3) δ 136.36, 127.00, 122.39, 119.84, 118.57, 111.41, 62.14, 46.79, 46.72, 44.38, 23.83. HRMS (ESI): m/z (%) = 286.1916 (M + H$^+$). Purity >94%. |
| 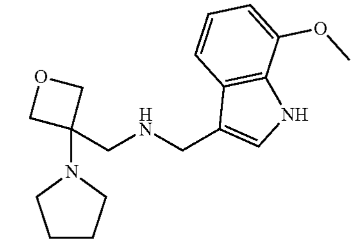 [SMILES: COc1cccc2c(CNCC3(N4CCCC4)COC3)c[nH]c12] | 214 (TR-FTO-014-N) | $^1$H NMR (600 MHz, CDCl3) δ 8.38 (s, 1H), 7.27-7.23 (m, 2H), 7.07 (t, J = 7.8 Hz, 1H), 6.67 (d, J = 7.7 Hz, 1H), 4.77 (d, J = 6.7 Hz, 2H), 4.40 (d, J = 6.7 Hz, 2H), 4.13 (s, 2H), 3.97 (s, 3H), 3.10 (s, 2H), 2.61 (t, J = 5.8 Hz, 4H), 1.73-1.70 (m, 4H); $^{13}$C NMR (151 MHz, CDCl3) δ 146.28, 128.42, 126.85, 120.34, 111.25, 102.10, 76.63, 62.11, 55.35, 46.69, 44.40, 23.82; HRMS (ESI): m/z (%) = 316.2018 (M + H$^+$). Purity >94% |
| 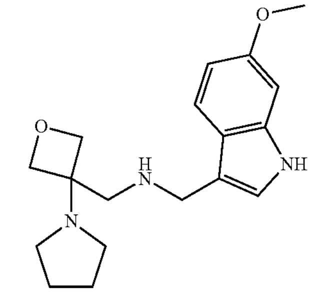 [SMILES: COc1ccc2c(CNCC3(N4CCCC4)COC3)c[nH]c2c1] | 215 (TR-FTO-015-N) | $^1$H NMR (600 MHz, CDCl3) δ 8.21 (s, 1H), 7.54 (d, J = 8.6 Hz, 1H), 7.16 (s, 1H), 6.90 (d, J = 2.1 Hz, 1H), 6.83 (dd, J = 8.6, 2.2 Hz, 1H), 4.78 (d, J = 6.8 Hz, 2H), 4.40 (d, J = 6.8 Hz, 2H), 4.11 (s, 2H), 3.87 (s, 3H), 3.11 (s, 2H), 2.62 (t, J = 5.7 Hz, 4H), 1.75-1.70 (m, 4H); $^{13}$C NMR (151 MHz, CDCl3) δ 156.68, 137.17, 121.36, 119.28, 109.83, 94.72, 76.62, 62.12, 55.70, 53.39, 50.91, 46.70, 44.44, 23.84; HRMS (ESI): m/z (%) = 316.2018 (M + H$^+$). Purity >94%. |

TABLE 200-continued

| STRUCTURE | ENTRY NUMBER (NAME) | ANALYTICAL DATA |
|---|---|---|
| 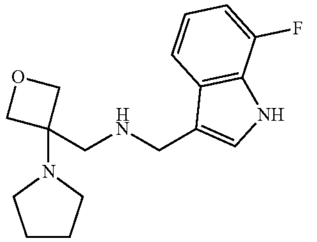 [SMILES: Fc1cccc2c(CNCC3(N4CCCC4)COC3)c[nH]c12] | 216 (TR-FTO-016-N) | $^{1}H$ NMR (600 MHz, CDCl3) δ 8.43 (s, 1H), 7.35 (d, J = 7.9 Hz, 1H), 7.17 (d, J = 2.0 Hz, 1H), 6.98-6.94 (m, 1H), 6.86-6.82 (m, 1H), 4.70 (d, J = 6.7 Hz, 2H), 4.31 (d, J = 6.7 Hz, 2H), 4.03 (s, 2H), 3.01 (s, 2H), 2.56 (t, J = 5.9 Hz, 4H), 1.67-1.64 (m, 4H); $^{13}C$ 13C NMR (151 MHz, CDCl3) δ 150.45, 148.85, 130.80, 124.78, 124.71, 120.04, 114.53, 107.17, 107.08, 76.69, 62.28, 46.75, 44.46, 23.86; HRMS (ESI): m/z (%) = 304.1820 (M + $H^+$). Purity >94%. |
| 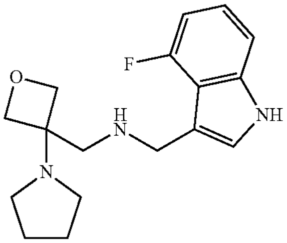 [SMILES: Fc1cccc2[nH]cc(CNCC3(N4CCCC4)COC3)c12] | 217 (TR-FTO-017-N) | $^{1}H$ NMR (600 MHz, CDCl3) δ 8.50 (s, 1H), 7.10-7.06 (m, 2H), 7.04-6.99 (m, 1H), 6.72-6.67 (m, 1H), 4.71 (d, J = 6.7 Hz, 2H), 4.33 (d, J = 6.7 Hz, 2H), 4.05 (s, 2H), 3.04 (s, 2H), 2.54 (t, J = 6.0 Hz, 4H), 1.68-1.64 (m, 4H); $^{13}C$ NMR (151 MHz, CDCl3) δ 157.78, 156.18, 139.27, 122.77, 115.64, 115.53, 107.64, 104.71, 104.62, 76.74, 62.15, 53.75, 46.65, 45.43, 23.82; HRMS (ESI): m/z (%) = 304.1820 (M + $H^+$). Purity >94%. |
| 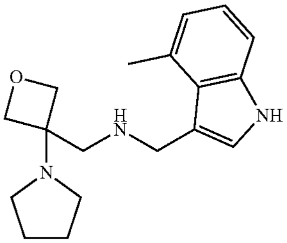 [SMILES: Cc1cccc2[nH]cc(CNCC3(N4CCCC4)COC3)c12] | 218 (TR-FTO-018-N) | $^{1}H$ NMR (600 MHz, CDCl3) δ 8.50 (s, 1H), 7.10-7.06 (m, 2H), 7.04-6.99 (m, 1H), 6.72-6.67 (m, 1H), 4.71 (d, J = 6.7 Hz, 2H), 4.33 (d, J = 6.7 Hz, 2H), 4.05 (s, 2H), 3.04 (s, 2H), 2.54 (t, J = 6.0 Hz, 4H), 1.68-1.64 (m, 4H); $^{13}C$ NMR (151 MHz, CDCl3) δ 137.04, 130.71, 125.68, 123.63, 122.16, 121.06, 109.17, 76.98, 62.58, 54.57, 46.77, 46.43, 23.93; HRMS (ESI): m/z (%) = 304.1820 (M + $H^+$). Purity >94%. |
| 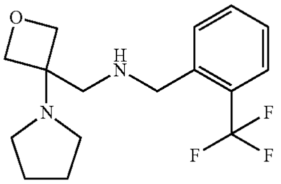 [SMILES: FC(F)(F)c1ccccc1CNCC1(N2CCCC2)COC1] | 219 (TR-FTO-019-N) | $^{1}H$ NMR (600 MHz, CDCl3) δ 7.70 (d, J = 7.7 Hz, 1H), 7.66 (d, J = 7.8 Hz, 1H), 7.55 (t, J = 7.6 Hz, 1H), 7.37 (t, J = 7.6 Hz, 1H), 4.82 (d, J = 6.6 Hz, 2H), 4.39 (d, J = 6.6 Hz, 2H), 4.02 (s, 2H), 3.02 (s, 2H), 2.72 (t, J = 6.3 Hz, 4H), 1.83-1.79 (m, 4H); $^{13}C$ NMR (151 MHz, CDCl3) δ 139.11, 131.91, 130.40, 128.44, 128.24, 126.91, 125.88, 125.84, 125.53, 123.71, 76.92, 62.52, 54.84, 49.94, 46.76, 23.98; HRMS (ESI): m/z (%) = 304.1820 (M + $H^+$). Purity >94%. |
| 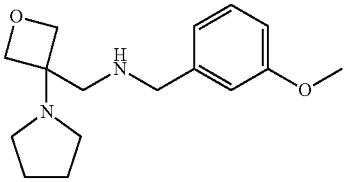 [SMILES: COc1cccc(CNCC2(N3CCCC3)COC2)c1] | 220 (TR-FTO-020-N) | $^{1}H$ NMR (600 MHz, CDCl3) δ 7.27 (dd, J = 10.9, 5.2 Hz, 1H), 6.93 (d, J = 7.2 Hz, 2H), 6.82 (dd, J = 7.5, 1.9 Hz, 1H), 4.80 (d, J = 6.6 Hz, 2H), 4.38 (d, J = 6.6 Hz, 2H), 3.84 (d, J = 2.8 Hz, 2H), 3.83 (s, 3H), 2.97 (s, 2H), 2.72 (t, J = 6.3 Hz, 4H), 1.83-1.79 (m, 4H); $^{13}C$ 13C NMR (151 MHz, CDCl3) δ 159.78, 141.84, 129.45, 120.50, 113.65, 112.47, 76.89, 62.56, 54.25, 53.80, 46.83, 24.01; HRMS (ESI): m/z (%) = 277.1911 (M + $H^+$). Purity >94%. |
| 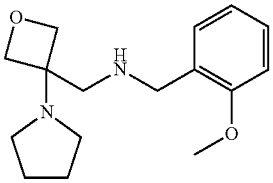 [SMILES: COc1ccccc1CNCC1(N2CCCC2)COC1] | 221 (TR-FTO-021-N) | $^{1}H$ NMR (600 MHz, CDCl3) δ 7.30-7.26 (m, 2H), 6.95 (t, J = 7.4 Hz, 1H), 6.89 (d, J = 8.1 Hz, 1H), 4.79 (d, J = 6.7 Hz, 2H), 4.42 (d, J = 6.7 Hz, 2H), 3.90 (d, J = 9.1 Hz, 2H), 3.85 (d, J = 6.7 Hz, 3H), 2.99 (s, 2H), 2.62 (t, J = 6.2 Hz, 4H), 1.80-1.76 (m, 4H); $^{13}C$ NMR (151 MHz, CDCl3) δ 157.73, 130.44, 128.83, 120.53, 110.20, 76.78, 62.21, 53.76, 49.42, 46.55, 23.93; HRMS (ESI): m/z (%) = 277.1911 (M + $H^+$). Purity >94%. |

TABLE 200-continued

| STRUCTURE | ENTRY NUMBER (NAME) | ANALYTICAL DATA |
|---|---|---|
| 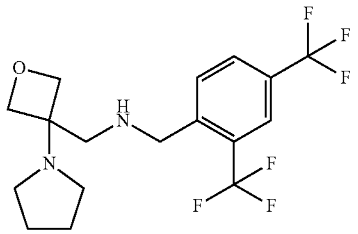 [SMILES: FC(F)(F)c1ccc(CNCC2(N3CCCC3)COC2)c(C(F)(F)F)c1] | 222 (TR-FTO-022-N) | $^1$H NMR (600 MHz, CDCl3) δ 7.85 (d, J = 8.1 Hz, 4H), 7.82 (s, 4H), 7.73 (d, J = 8.1 Hz, 4H), 4.74 (d, J = 6.6 Hz, 10H), 4.29 (d, J = 6.6 Hz, 9H), 3.98 (s, 9H), 2.93 (s, 9H), 2.66 (t, J = 5.8 Hz, 18H), 1.75-1.72 (m, 20H); $^{13}$C NMR (151 MHz, CDCl3) δ 143.73, 130.73, 129.57, 129.33, 128.74, 124.69, 122.90, 76.86, 62.56, 54.75, 49.11, 46.94, 23.86; HRMS (ESI): m/z (%) = 383.1554 (M + H+). Purity >94%. |
| 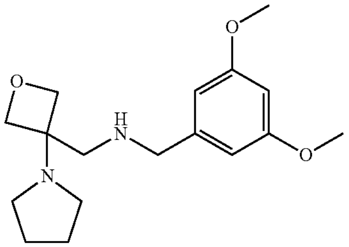 [SMILES: COc1cc(CNCC2(N3CCCC3)COC2)cc(OC)c1] | 223 (TR-FTO-023-N) aka (TR-FTO-028-N) | $^1$H NMR (600 MHz, CDCl3) δ 6.53 (d, J = 2.2 Hz, 2H), 6.38 (t, J = 2.2 Hz, 1H), 4.80 (d, J = 6.6 Hz, 2H), 4.38 (d, J = 6.6 Hz, 2H), 3.81 (s, 8H), 2.97 (s, 2H), 2.73 (t, J = 6.2 Hz, 4H), 1.83-1.80 (m, 4H); $^{13}$C NMR (151 MHz, CDCl3) δ 160.89, 142.73, 106.01, 98.99, 76.89, 62.60, 54.26, 53.95, 46.82, 24.01; HRMS (ESI): m/z (%) = 307.2016 (M + H$^+$). Purity >94%. |
| 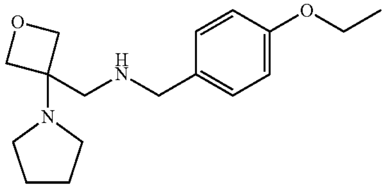 [SMILES: CCOc1ccc(CNCC2(N3CCCC3)COC2)cc1] | 224 (TR-FTO-024-N) | $^1$H NMR (600 MHz, CDCl3) δ 7.26 (d, J = 8.5 Hz, 2H), 6.88 (d, J = 8.5 Hz, 2H), 4.79 (d, J = 6.6 Hz, 2H), 4.38 (d, J = 6.6 Hz, 2H), 4.05 (q, J = 7.0 Hz, 2H), 3.81 (s, 2H), 2.97 (s, 2H), 2.70 (t, J = 6.1 Hz, 4H), 1.82-1.79 (m, 4H), 1.43 (t, J = 7.0 Hz, 3H); $^{13}$C NMR (151 MHz, CDCl3) δ 158.10, 129.41, 114.40, 76.90, 63.47, 62.55, 54.05, 53.20, 46.77, 24.03; HRMS (ESI): m/z (%) = 291.2068 (M + H$^+$). Purity >94%. |
| 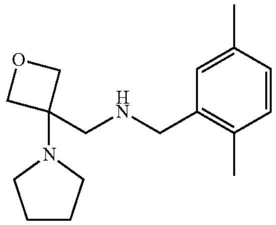 [SMILES: Cc1ccc(C)c(CNCC2(N3CCCC3)COC2)c1] | 225 (TR-FTO-025-N) | $^1$H NMR (600 MHz, CDCl3) δ 7.13 (s, 1H), 7.07 (d, J = 7.6 Hz, 1H), 7.00 (d, J = 7.5 Hz, 1H), 4.81 (d, J = 6.6 Hz, 2H), 4.41 (d, J = 6.6 Hz, 2H), 3.81 (s, 2H), 3.03 (s, 2H), 2.71 (t, J = 6.1 Hz, 4H), 2.33 (d, J = 5.0 Hz, 6H), 1.83-1.78 (m, 4H); $^{13}$C NMR (151 MHz, CDCl3) δ 137.93, 135.28, 133.24, 130.28, 129.56, 127.72, 76.91, 62.59, 54.79, 51.83, 46.76, 24.00; HRMS (ESI): m/z (%) = 275.2119 (M + H$^+$). Purity >94%. |
| 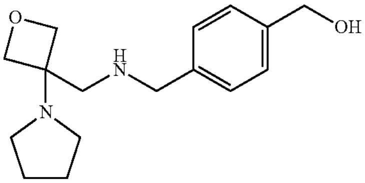 or Methyl ester | 226 (TR-FTO-026-N) | 1H NMR (600 MHz, CDCl3) δ 8.01 (t, J = 7.5 Hz, 1H), 7.43 (d, J = 8.1 Hz, 1H), 4.80 (d, J = 6.6 Hz, 1H), 4.36 (d, J = 6.6 Hz, 1H), 3.93 (s, 1H), 3.91 (s, 1H), 2.96 (s, 1H), 2.71 (t, J = 6.2 Hz, 2H), 1.83-1.79 (m, 2H); $^{13}$C NMR (151 MHz, CDCl3) δ 167.09, 145.94, 129.77, 128.86, 128.02, 76.90, 62.55, 54.54, 53.65, 46.83, 24.03; HRMS (ESI): m/z (%) = 277.1918 (M + H+). Purity >94%. |
| 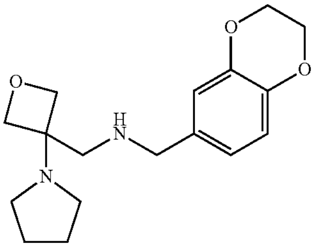 [SMILES: c1cc2c(cc1CNCC1(N3CCCC3)COC1)OCCO2] | 227 (TR-FTO-027-N) | $^1$H NMR (600 MHz, $CDCl_3$) δ 6.87 (d, J = 1.4 Hz, 1H), 6.83 (dt, J = 8.3, 4.9 Hz, 2H), 4.80 (d, J = 6.6 Hz, 2H), 4.83 (d, J = 6.6 Hz, 2H), 4.27 (s, 4H), 3.76 (s, 2H), 2.97 (s, 2H), 2.71 (t, J = 6.1 Hz, 4H), 1.84-1.80 (m, 4H); $^{13}$C NMR (151 MHz, CDCl3) δ 143.40, 142.52, 133.74, 121.13, 117.13, 116.98, 76.97, 64.43, 64.39, 62.56, 54.28, 53.32, 46.79, 24.02; HRMS (ESI): m/z (%) = 305.1859 (M + H$^+$). Purity >94%. |

TABLE 200-continued

| STRUCTURE | ENTRY NUMBER (NAME) | ANALYTICAL DATA |
|---|---|---|
| 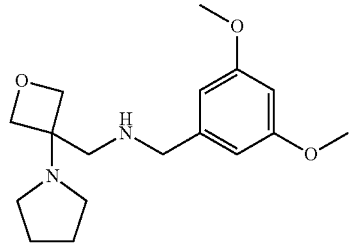 [SMILES: COc1cc(CNCC2(N3CCCC3)COC2)cc(OC)c1] | 228 (TR-FTO-028-N) aka (TR-FTO-023-N) | $^1$H NMR (600 MHz, CDCl3) δ 6.53 (d, J = 2.2 Hz, 2H), 6.38 (t, J = 2.2 Hz, 1H), 4.80 (d, J = 6.6 Hz, 2H), 4.38 (d, J = 6.6 Hz, 2H), 3.81 (s, 8H), 2.97 (s, 2H), 2.73 (t, J = 6.2 Hz, 4H), 1.84-1.79 (m, 4H); $^{13}$C NMR (151 MHz, CDCl3) δ 160.98, 142.57, 105.84, 99.06, 77.10, 62.57, 54.07, 53.94, 23.87; HRMS (ESI): m/z (%) = 307.2017 (M + H$^+$). Purity >94%. |
| 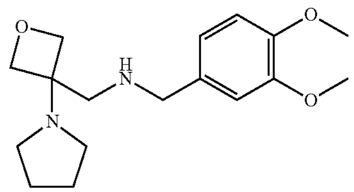 [SMILES: COc1ccc(CNCC2(N3CCCC3)COC2)cc1OC] | 229 (TR-FTO-029-N) | $^1$H NMR (600 MHz, CDCl3) δ 6.93 (d, J = 1.3 Hz, 1H), 6.86 (dt, J = 17.9, 4.8 Hz, 2H), 4.80 (d, J = 6.7 Hz, 2H), 4.37 (d, J = 6.6 Hz, 2H), 3.90 (d, J = 7.2 Hz, 6H), 3.81 (s, 2H), 2.96 (s, 2H), 2.71 (t, J = 6.1 Hz, 4H), 1.83-1.79 (m, 4H); $^{13}$C NMR (151 MHz, CDCl3) δ 148.97, 148.13, 132.40, 120.44, 111.26, 110.91, 76.86, 62.46, 53.97, 53.50, 46.80, 24.00; HRMS (ESI): m/z (%) = 307.2018 (M + H$^+$). Purity >94%. |
| 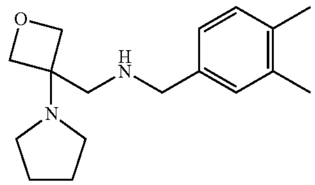 [SMILES: Cc1ccc(CNCC2(N3CCCC3)COC2)cc1C] | 230 (TR-FTO-030-N) | $^1$H NMR (600 MHz, CDCl3) δ 7.10 (dd, J = 21.2, 7.9 Hz, 3H), 4.80 (d, J = 6.6 Hz, 2H), 4.39 (d, J = 6.6 Hz, 2H), 3.82 (s, 2H), 2.98 (s, 2H), 2.70 (d, J = 5.7 Hz, 4H), 2.27 (d, J = 7.3 Hz, 6H), 1.81 (dd, J = 7.8, 4.7 Hz, 4H); $^{13}$C NMR (151 MHz, CDCl3) δ 136.66, 135.42, 129.72, 129.62, 125.68, 76.88, 62.49, 54.06, 53.48, 46.79, 24.01; HRMS (ESI): m/z (%) = 275.2121 (M + H$^+$). Purity >96%. |
| 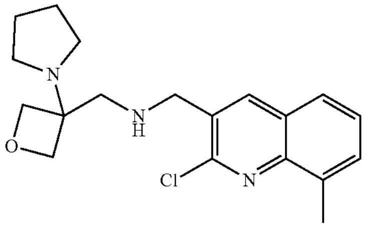 | 231 (TR-FTO-031-N) | $^1$H NMR (600 MHz, CDCl3) δ 8.95 (t, J = 5.3 Hz, 1H), 8.09 (d, J = 0.9 Hz, 1H), 7.68 (d, J = 8.1 Hz, 1H), 7.56 (d, J = 6.9 Hz, 1H), 7.48-7.40 (m, 1H), 4.81 (d, J = 6.6 Hz, 2H), 4.38 (d, J = 6.6 Hz, 2H), 4.07 (s, 2H), 3.03 (s, 2H), 2.84 (s, 3H), 2.74 (d, J = 5.7 Hz, 4H), 1.82 (dd, J = 7.6, 4.7 Hz, 4H); $^{13}$C NMR (151 MHz, CDCl3) δ 136.66, 135.42, 129.72, 129.62, 125.68, 76.88, 62.49, 54.06, 53.48, 46.79, 24.01; HRMS (ESI): m/z (%) = 312.2072 (M + H$^+$). Purity >94%. |
| 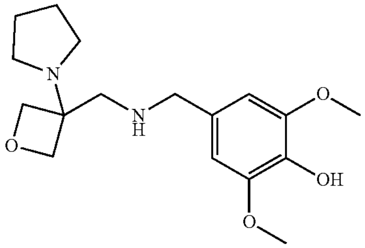 [SMILES: COc1cc(CNCC2(N3CCCC3)COC2)cc(OC)c1O] | 232 (TR-FTO-032-N) | $^1$H NMR (600 MHz, CDCl3) δ 6.64 (s, 1H), 4.81 (d, J = 6.7 Hz, 1H), 4.40 (d, J = 6.7 Hz, 1H), 3.91 (s, 3H), 3.84 (s, 1H), 3.00 (s, 1H), 2.73 (t, J = 6.0 Hz, 2H), 1.84-1.80 (m, 2H); $^{13}$C NMR (151 MHz, CDCl3) δ 147.14, 133.93, 104.98, 76.71, 62.42, 53.70, 46.85, 24.01; HRMS (ESI): m/z (%) = 323.1966 (M + H$^+$). Purity >97%. |
| 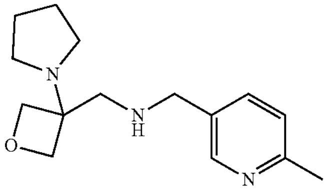 [SMILES: Cc1ccc(CNCC2(N3CCCC3)COC2)cn1] | 233 (TR-FTO-033-N) | $^1$H NMR (600 MHz, CDCl3) δ 8.43 (d, J = 1.6 Hz, 1H), 7.60 (dd, J = 7.9, 2.0 Hz, 1H), 7.15 (d, J = 7.9 Hz, 1H), 4.79 (d, J = 6.6 Hz, 2H), 4.35 (d, J = 6.6 Hz, 2H), 3.83 (s, 2H), 2.96 (s, 2H), 2.73 (t, J = 5.8 Hz, 4H), 2.56 (s, 3H), 1.83-1.80 (m, 4H); $^{13}$C NMR (151 MHz, CDCl3) δ 157.18, 148.97, 136.47, 132.51, 123.12, 76.84, 62.61, 54.36, 51.03, 46.88, 24.02; HRMS (ESI): m/z (%) = 262.1917 (M + H$^+$). Purity >95%. |

TABLE 200-continued

| STRUCTURE | ENTRY NUMBER (NAME) | ANALYTICAL DATA |
|---|---|---|
| 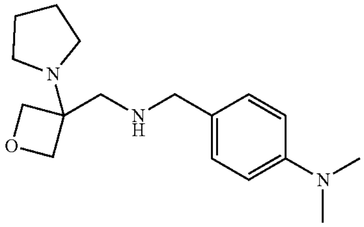 [SMILES: CN(C)c1ccc(CNCC2(N3CCCC3)COC2)cc1] | 234 (TR-FTO-034-N) | $^{1}$H NMR (600 MHz, CDCl3) δ 7.26 (d, J = 8.6 Hz, 1H), 6.74 (d, J = 8.6 Hz, 1H), 4.79 (d, J = 6.8 Hz, 1H), 4.41 (d, J = 6.8 Hz, 1H), 3.88 (s, 1H), 3.04 (s, 1H), 2.96 (s, 3H), 2.67 (t, J = 6.0 Hz, 2H), 1.81-1.78 (m, 2H); $^{13}$C NMR (151 MHz, CDCl3) δ 150.22, 129.65, 112.67, 76.64, 62.16, 52.66, 46.76, 40.71, 23.99; HRMS (ESI): m/z (%) = 290.2229 (M + H$^{+}$). Purity >98%. |
| 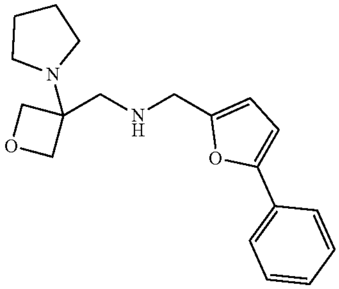 [SMILES: c1ccc(-c2ccc(CNCC3(N4CCCC4)COC3)o2)cc1] | 235 (TR-FTO-035-N) | $^{1}$H NMR (600 MHz, CDCl3) δ 7.66 (d, J = 7.6 Hz, 2H), 7.39 (t, J = 7.7 Hz, 2H), 7.26 (t, J = 7.4 Hz, 1H), 6.61 (d, J = 3.2 Hz, 1H), 6.30 (d, J = 3.2 Hz, 1H), 4.81 (d, J = 6.6 Hz, 2H), 4.39 (d, J = 6.6 Hz, 2H), 3.91 (s, 2H), 3.02 (d, J = 7.6 Hz, 2H), 2.70 (t, J = 5.9 Hz, 4H), 1.81-1.76 (m, 4H); $^{13}$C NMR (151 MHz, CDCl3) δ 153.63, 153.18, 130.90, 128.69, 127.20, 123.54, 76.90, 62.51, 54.00, 46.74, 46.21, 24.01; HRMS (ESI): m/z (%) = 313.1910 (M + H$^{+}$). Purity >97%. |
| 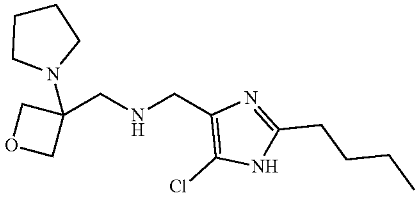 [SMILES: CCCCc1nc(CNCC2(N3CCCC3)COC2)c(Cl)[nH]1] | 236 (TR-FTO-036-N) | $^{1}$H NMR (600 MHz, CDCl3) δ 4.79 (t, J = 8.3 Hz, 2H), 4.38 (d, J = 6.8 Hz, 2H), 3.83 (s, 2H), 3.07 (s, 2H), 2.80 (s, 4H), 2.68-2.63 (m, 2H), 1.87 (t, J = 6.0 Hz, 4H), 1.68 (dt, J = 15.4, 7.7 Hz, 2H), 1.42-1.34 (m, 2H), 0.94 (t, J = 7.4 Hz, 3H); $^{13}$C NMR (151 MHz, CDCl3) δ 147.35, 76.60, 62.79, 54.24, 47.11, 42.81, 30.33, 28.59, 24.06, 22.36, 13.83; HRMS (ESI): m/z (%) = 327.1946 (M + H$^{+}$). Purity >95%. |
| 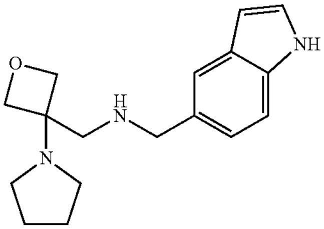 [SMILES: c1cc2cc(CNCC3(N4CCCC4)COC3)ccc2[nH]1] | 237 (TR-FTO-037-N) (TR-FTO-01) | $^{1}$H (600 MHz, CDCl3) δ 4.79 (t, J = 8.3 Hz, 2H), 4.38 (d, J = 6.8 Hz, 2H), 3.83 (s, 2H), 3.07 (s, 2H), 2.80 (s, 4H), 2.68-2.63 (m, 2H), 1.87 (t, J = 6.0 Hz, 4H), 1.68 (dt, J = 15.4, 7.7 Hz, 2H), 1.42-1.34 (m, 2H), 0.94 (t, J = 7.4 Hz, 3H); $^{13}$C NMR (151 MHz, CDCl3) δ 135.33, 127.98, 124.81, 122.72, 120.76, 111.33, 102.53, 76.72, 62.29, 53.90, 53.22, 46.77, 23.96; HRMS (ESI): m/z (%) = 286.1916 (M + H$^{+}$). Purity >98%. |
| 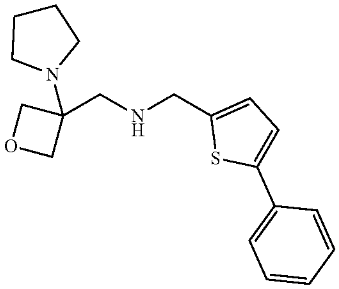 [SMILES: c1ccc(-c2ccc(CNCC3(N4CCCC4)COC3)s2)cc1] | 238 (TR-FTO-038-N) | $^{1}$H NMR (600 MHz, CDCl3) δ 7.60 (d, J = 7.4 Hz, 2H), 7.39 (t, J = 7.7 Hz, 2H), 7.30-7.26 (m, 2H), 7.18 (d, J = 3.6 Hz, 1H), 6.91 (d, J = 3.5 Hz, 1H), 4.82 (t, J = 6.2 Hz, 2H), 4.41 (d, J = 6.6 Hz, 2H), 4.06 (s, 2H), 3.05 (d, J = 11.3 Hz, 2H), 2.75 (t, J = 5.8 Hz, 4H), 1.84-1.80 (m, 4H); $^{13}$C NMR (151 MHz, CDCl3) δ 149.86, 143.61, 143.48, 134.54, 128.95, 128.84, 127.36, 126.25, 125.67, 122.67, 76.82, 76.48, 62.65, 53.85, 48.58, 46.90, 46.87, 24.03, 23.88; HRMS (ESI): m/z = 329.1683 (M + H$^{+}$). Purity >95%. |
| 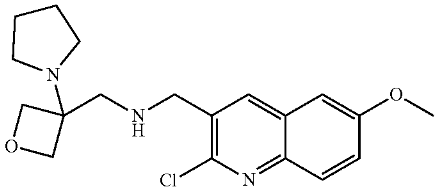 | 239 (TR-FTO-039-N) | $^{1}$H NMR (600 MHz, CDCl3) δ 8.67 (d, J = 1.9 Hz, 1H), 7.95-7.90 (m, 2H), 7.29-7.25 (m, 1H), 7.00 (t, J = 3.5 Hz, 1H), 4.73 (d, J = 6.6 Hz, 2H), 4.29 (d, J = 6.6 Hz, 2H), 3.95 (s, 2H), 3.87 (s, 3H), 2.94 (s, 2H), 2.65 (t, J = 5.8 Hz, 4H), 1.75-1.72 (m, 4H); $^{13}$C NMR (151 MHz, CDCl3) δ 157.93, 148.91, 143.62, 133.94, 133.39, 130.68, 129.04, 121.85, 105.03, 76.90, 55.60, 54.64, 51.62, 46.88, 24.05; HRMS (ESI): m/z (%) = 328.2020 (M + H$^{+}$). Purity >96%. |

TABLE 200-continued

| STRUCTURE | ENTRY NUMBER (NAME) | ANALYTICAL DATA |
| --- | --- | --- |
| 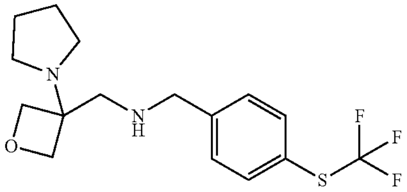 [SMILES: FC(F)(F)Sc1ccc(CNCC2(N3CCCC3)COC2)cc1] | 240 (TR-FTO-040-N) | $^1$H NMR (600 MHz, CDCl3) δ 7.64 (d, J = 8.0 Hz, 1H), 7.43 (d, J = 8.0 Hz, 1H), 4.81 (d, J = 6.6 Hz, 1H), 4.38 (d, J = 6.6 Hz, 1H), 3.89 (s, 1H), 2.98 (s, 1H), 2.73 (s, 2H), 1.84-1.80 (m, 3H); $^{13}$C NMR (151 MHz, CDCl3) δ 143.89, 136.48, 129.14, 76.86, 62.62, 54.65, 53.38, 46.86, 24.03; HRMS (ESI): m/z (%) = 347.1401 (M + H$^+$). Purity >97% |
| 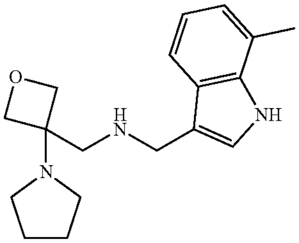 [SMILES: Cc1cccc2c(CNCC3(N4CCCC4)COC3)c[nH]c12] | 241 (TR-FTO-041-N) | $^1$H NMR (599 MHz, CDCl3) δ 8.13 (s, 1H), 7.54 (d, J = 7.8 Hz, 1H), 7.20 (d, J = 1.5 Hz, 1H), 7.07 (t, J = 7.5 Hz, 1H), 7.03 (d, J = 7.0 Hz, 1H), 4.79 (d, J = 6.6 Hz, 2H), 4.40 (d, J = 6.6 Hz, 2H), 4.08 (s, 2H), 3.08 (s, 2H), 2.67 (t, J = 5.9 Hz, 4H), 2.51 (s, 3H), 1.76 (d, J = 6.1 Hz, 4H); $^{13}$C NMR (151 MHz, CDCl3) δ 136.05, 126.67, 122.73, 122.69, 120.51, 119.82, 116.50, 76.93, 62.42, 54.34, 46.74, 44.87, 23.91, 16.72; HRMS (ESI): m/z (%) = 300.2072 (M + H$^+$). Purity >96%. |
| 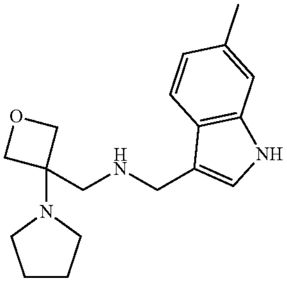 [SMILES: Cc1ccc2c(CNCC3(N4CCCC4)COC3)c[nH]c2c1] | 242 (TR-FTO-042-N) | $^1$H NMR (599 MHz, CDCl3) δ 8.26 (s, 1H), 7.56 (d, J = 8.1 Hz, 1H), 7.17 (s, 1H), 7.10 (s, 1H), 6.98 (d, J = 8.1 Hz, 1H), 4.79 (d, J = 6.6 Hz, 2H), 4.40 (d, J = 6.6 Hz, 2H), 4.07 (s, 2H), 3.09 (s, 2H), 2.66 (s, 4H), 2.48 (s, 3H), 1.75 (s, 4H); $^{13}$C NMR (151 MHz, CDCl3) δ 136.89, 131.97, 125.00, 122.44, 121.35, 118.40, 111.25, 76.91, 62.40, 54.32, 46.73, 44.74, 23.92, 21.78; HRMS (ESI): m/z (%) = 300.2072 (M + H$^+$). Purity >98%. |
| 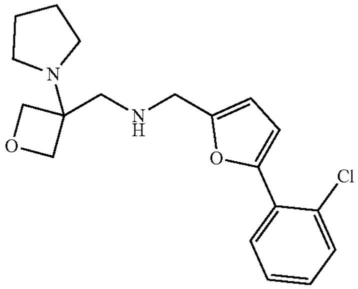 [SMILES: Clc1ccccc1-c1ccc(CNCC2(N3CCCC3)COC2)o1] | 243 (TR-FTO-043-N) | $^1$H NMR (599 MHz, CDCl3) δ 7.85 (d, J = 7.9 Hz, 1H), 7.44 (d, J = 8.0 Hz, 1H), 7.32 (t, J = 7.6 Hz, 1H), 7.20 (t, J = 7.7 Hz, 1H), 7.09 (d, J = 3.3 Hz, 1H), 6.36 (d, J = 3.2 Hz, 1H), 4.80 (d, J = 6.6 Hz, 2H), 4.40 (d, J = 6.6 Hz, 2H), 3.93 (s, 2H), 3.05 (s, 2H), 2.71 (s, 4H), 1.79 (d, J = 6.1 Hz, 4H); $^{13}$C NMR (151 MHz, CDCl3) δ 153.60, 149.48, 130.78, 129.85, 129.17, 127.89, 126.62, 126.85, 111.69, 109.59, 76.88, 62.59, 53.95, 46.80, 46.11, 24.00; HRMS (ESI): m/z (%) = 347.1520 (M + H$^+$). Purity >99%. |
| 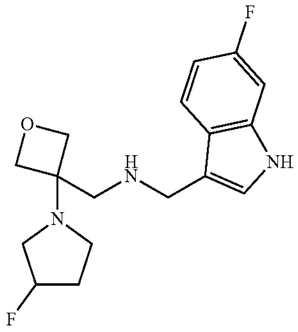 [SMILES: Fc1ccc2c(CNCC3(N4CCC(F)C4)COC3)c[nH]c2c1] | 244 (TR-FTO-044-N) | $^1$H NMR (599 MHz, CDCl3) δ 8.34 (s, 1H), 7.61 (dd, J = 8.6, 3.5 Hz, 1H), 7.20 (s, 1H), 7.07 (d, J = 9.6 Hz, 1H), 6.92 (t, J = 9.1 Hz, 1H), 5.14 (d, J = 55.7 Hz, 1H), 4.76 (dd, J = 18.9, 7.0 Hz, 2H), 4.42 (t, J = 7.7 Hz, 2H), 4.08 (s, 2H), 3.06 (d, J = 9.9 Hz, 2H), 3.00 (t, J = 5.6 Hz, 1H), 2.96 (s, 1H), 2.87 (t, J = 8.0 Hz, 1H), 2.71 (td, J = 8.1, 3.8 Hz, 1H), 2.13-1.91 (m, 2H); $^{13}$C NMR (151 MHz, CDCl3) δ 160.85, 159.23, 136.41, 123.68, 119.59, 119.51, 108.63, 108.38, 97.66, 97.44, 93.84, 92.62, 76.69, 62.13, 53.91, 53.80, 53.64, 45.12, 44.49, 32.68, 32.53, 29.76; HRMS (ESI): m/z (%) = 328.1728 (M + H$^+$). Purity >94%. |

TABLE 200-continued

| STRUCTURE | ENTRY NUMBER (NAME) | ANALYTICAL DATA |
|---|---|---|
| 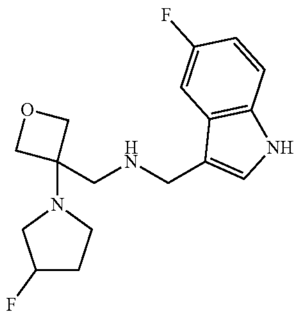 [SMILES: Fc1ccc2[nH]cc(CNCC3(N4CCC(F)C4)COC3)c2c1] | 245 (TR-FTO-045-N) | $^{1}$H NMR (599 MHz, CDCl3) δ 8.39 (s, 1H), 7.36-7.29 (m, 3H), 6.97 (t, J = 9.0 Hz, 1H), 5.15 (d, J = 54.8 Hz, 1H), 4.76 (dd, J = 19.4, 6.8 Hz, 2H), 4.42 (t, J = 7.1 Hz, 2H), 4.07 (s, 2H), 3.08 (s, 2H), 3.05-3.01 (m, 1H), 2.97 (d, J = 4.3 Hz, 1H), 2.89 (t, J = 6.9 Hz, 1H), 2.74 (td, J = 8.2, 3.7 Hz, 1H), 2.02 (ddd, J = 19.6, 14.1, 7.2 Hz, 2H); $^{13}$C NMR (151 MHz, CDCl3) δ 158.67, 157.11, 132.90, 127.55, 127.49, 125.20, 112.10, 112.03, 110.80, 110.63, 103.87, 103.71, 93.85, 92.69, 76.88, 76.70, 62.19, 53.97, 53.82, 53.59, 45.29, 45.16, 44.46, 32.69, 32.55, 29.76; HRMS (ESI): m/z (%) = 322.1730 (M + H$^{+}$). Purity >95%. |
| 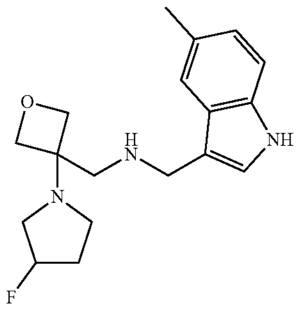 [SMILES: Cc1ccc2[nH]cc(CNCC3(N4CCC(F)C4)COC3)c2c1] | 246 (TR-FTO-046-N) | $^{1}$H NMR (599 MHz, CDCl3) δ 8.47 (s, 1H), 7.45 (s, 1H), 7.29 (d, J = 5.7 Hz, 1H), 7.24 (s, 1H), 7.05 (d, J = 8.3 Hz, 1H), 5.10 (d, J = 55.1 Hz, 1H), 4.75 (dd, J = 21.1, 6.9 Hz, 2H), 4.44 (t, J = 6.4 Hz, 2H), 4.13 (d, J = 2.9 Hz, 2H), 3.11 (d, J = 5.5 Hz, 2H), 2.98 (dd, J = 11.1, 6.8 Hz, 1H), 2.94-2.91 (m, 1H), 2.83 (dd, J = 15.8, 8.2 Hz, 1H), 2.69 (td, J = 8.2, 3.8 Hz, 1H), 2.48 (s, 3H), 2.05-1.93 (m, 2H); $^{13}$C NMR (151 MHz, CDCl3) δ 134.73, 129.12, 127.32, 124.07, 123.97, 118.16, 111.13, 93.80, 92.64, 76.69, 76.67, 62.01, 53.86, 53.75, 53.00, 45.04, 44.23, 32.64, 32.52, 21.58; HRMS (ESI): m/z (%) = 318.1978 (M + H$^{+}$). Purity >96%. |
| 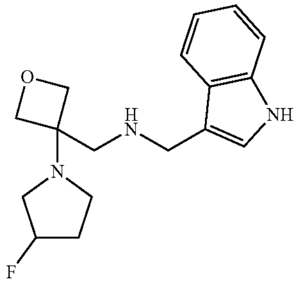 [SMILES: FC1CCN(C2(CNCc3c[nH]c4ccccc34)COC2)C1] | 247 (TR-FTO-047-N) | $^{1}$H NMR (599 MHz, CDCl3) δ 8.48 (s, 1H), 7.69 (d, J = 7.9 Hz, 1H), 7.40 (d, J = 8.2 Hz, 1H), 7.24 (dd, J = 17.0, 9.6 Hz, 2H), 7.16 (t, J = 7.5 Hz, 1H), 5.10 (d, J = 55.1 Hz, 1H), 4.75 (dd, J = 20.8, 6.9 Hz, 2H), 4.43 (d, J = 6.9 Hz, 2H), 4.14 (s, 2H), 3.10 (s, 2H), 2.98 (dd, J = 10.7, 6.8 Hz, 1H), 2.93 (t, J = 6.3 Hz, 1H), 2.84 (dd, J = 15.7, 8.4 Hz, 1H), 2.69 (td, J = 8.2, 3.6 Hz, 1H), 2.07-1.94 (m, 2H); $^{13}$C NMR (151 MHz, CDCl3) δ 136.41, 127.09, 123.70, 122.33, 119.80, 118.65, 111.49, 93.85, 92.69, 76.79, 76.71, 62.11, 53.92, 53.76, 53.31, 45.10, 44.33, 32.68, 32.54, 29.77; HRMS (ESI): m/z (%) = 304.1821 (M + H$^{+}$). Purity >94%. |
| 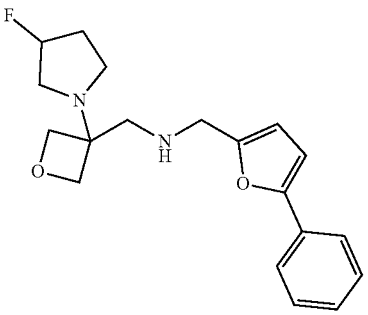 [SMILES: FC1CCN(C2(CNCc3ccc(-c4ccccc4)o3)COC2)C1] | 248 (TR-FTO-048-N) | $^{1}$H NMR (599 MHz, CDCl3) δ 7.66 (d, J = 8.1 Hz, 2H), 7.39 (t, J = 7.5 Hz, 2H), 7.27 (dd, J = 11.5, 4.1 Hz, 1H), 6.61 (d, J = 3.2 Hz, 1H), 6.30 (d, J = 3.1 Hz, 1H), 5.16 (d, J = 55.7 Hz, 1H), 4.77 (dd, J = 16.2, 6.8 Hz, 2H), 4.43 (dd, J = 14.4, 6.8 Hz, 2H), 3.91 (s, 2H), 3.07-2.99 (m, 4H), 2.91 (dd, J = 16.0, 8.1 Hz, 1H), 2.76 (td, J = 8.2, 3.9 Hz, 1H), 2.11-2.00 (m, 2H); $^{13}$C NMR (151 MHz, CDCl3) δ 153.55, 153.28, 130.81, 128.72, 127.26, 123.55, 109.53, 105.63, 93.90, 92.74, 76.89, 76.81, 62.39, 53.95, 53.79, 53.67, 46.10, 45.06, 32.75, 32.60; HRMS (ESI): m/z (%) = 331.1817 (M + H$^{+}$). Purity >98%. |

TABLE 200-continued

| STRUCTURE | ENTRY NUMBER (NAME) | ANALYTICAL DATA |
|---|---|---|
| 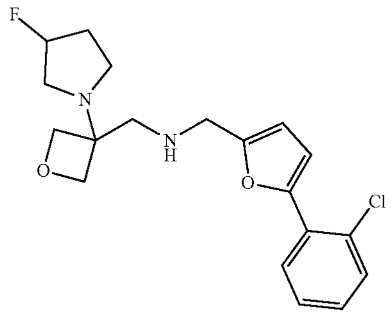 [SMILES: FC1CCN(C2(CNCc3ccc(-c4ccccc4Cl)o3)COC2)C1] | 249 (TR-FTO-049-N) | $^1$H NMR (599 MHz, CDCl3) δ 7.85 (d, J = 7.9 Hz, 1H), 7.45 (d, J = 8.0 Hz, 1H), 7.34-7.29 (m, 1H), 7.20 (t, J = 7.7 Hz, 1H), 7.09 (d, J = 3.2 Hz, 1H), 6.36 (d, J = 3.1 Hz, 1H), 5.16 (d, J = 55.0 Hz, 1H), 4.77 (dd, J = 15.9, 6.8 Hz, 2H), 4.43 (dd, J = 15.7, 6.8 Hz, 2H), 3.93 (s, 2H), 3.05 (d, J = 6.7 Hz, 3H), 3.00 (d, J = 6.4 Hz, 1H), 2.91 (dd, J = 16.1, 7.9 Hz, 1H), 2.75 (td, J = 8.3, 4.0 Hz, 1H), 2.12-1.98 (m, 2H); $^{13}$C NMR (151 MHz, CDCl3) δ 153.47, 149.55, 130.79, 129.92, 129.13, 127.95, 127.64, 126.89, 111.74, 109.67, 93.87, 92.70, 77.31, 77.10, 62.37, 53.96, 53.81, 53.68, 46.00, 45.08, 32.72, 32.57; HRMS (ESI): m/z (%) = 365.1427 (M + H$^+$). Purity >99%. |
| 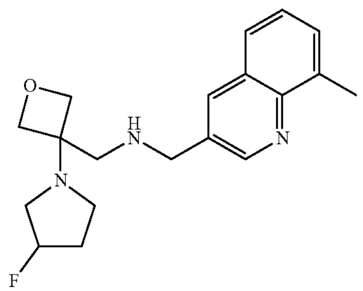 [SMILES: Cc1cccc2cc(CNCC3(N4CCC(F)C4)COC3)cnc12] | 250 (TR-FTO-050-N) | $^1$H NMR (599 MHz, CDCl3) δ 8.95 (d, J = 1.2 Hz, 2H), 8.08 (s, 2H), 7.67 (d, J = 8.1 Hz, 2H), 7.56 (d, J = 7.0 Hz, 2H), 7.45 (t, J = 7.6 Hz, 2H), 5.20 (d, J = 55.1 Hz, 2H), 4.77 (dd, J = 15.1, 6.8 Hz, 4H), 4.41 (dd, J = 18.4, 6.8 Hz, 4H), 4.06 (s, 4H), 3.07 (d, J = 3.2 Hz, 2H), 3.04-2.94 (m, 8H), 2.84 (s, 6H), 2.80 (td, J = 8.3, 3.9 Hz, 2H), 2.15-2.08 (m, 5H); $^{13}$C NMR (151 MHz, CDCl3) δ 150.31, 146.68, 136.97, 134.97, 132.55, 129.39, 127.98, 126.59, 125.75, 93.87, 92.71, 77.31, 77.10, 62.49, 54.23, 54.07, 53.92, 51.46, 45.27, 32.74, 32.59, 18.27; HRMS (ESI): m/z (%) = 330.1978 (M + H$^+$). Purity >98%. |
| 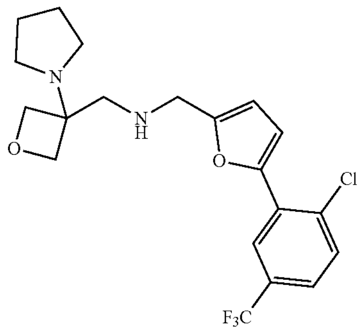 [SMILES: FC(F)(F)c1ccc(Cl)c(-c2ccc(CNCC3(N4CCCC4)COC3)o2)c1] | 251 (TR-FTO-051-N) | $^1$H NMR (599 MHz, CDCl3) δ 8.11 (s, 1H), 7.56 (d, J = 8.4 Hz, 1H), 7.42 (d, J = 8.3 Hz, 1H), 7.18 (dd, J = 10.1, 3.4 Hz, 1H), 6.39 (d, J = 3.3 Hz, 1H), 4.81 (d, J = 6.7 Hz, 2H), 4.40 (d, J = 6.7 Hz, 2H), 3.95 (s, 2H), 3.06 (s, 2H), 2.73 (s, 4H), 1.83-1.77 (m, 4H); $^{13}$C NMR (151 MHz, CDCl3) δ 154.69, 148.03, 131.41, 129.82, 124.27, 123.98, 113.11, 109.80, 76.82, 62.61, 54.12, 46.84, 46.15, 23.98; HRMS (ESI): m/z (%) = 415.1393 (M + H$^+$). Purity >98%. |
| 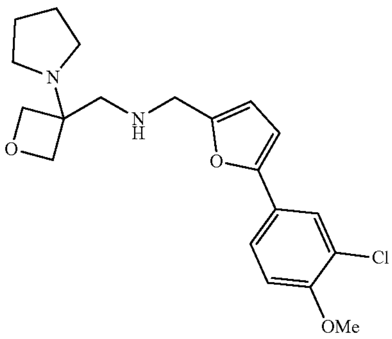 [SMILES: COc1ccc(-c2ccc(CNCC3(N4CCCC4)COC3)o2)cc1Cl] | 252 (TR-FTO-052-N) | $^1$H NMR (599 MHz, CDCl3) δ 7.67 (d, J = 2.0 Hz, 1H), 7.51 (d, J = 8.6 Hz, 1H), 6.94 (dt, J = 12.1, 6.0 Hz, 1H), 6.49 (d, J = 2.6 Hz, 1H), 6.28 (s, 1H), 4.80 (d, J = 6.5 Hz, 2H), 4.39 (dd, J = 6.6, 1.3 Hz, 2H), 3.94 (d, J = 1.9 Hz, 3H), 3.90 (s, 2H), 3.03 (s, 2H), 2.71 (s, 4H), 1.80 (s, 4H); $^{13}$C NMR (151 MHz, CDCl3) δ 154.15, 153.35, 151.90, 125.59, 124.83, 123.02, 122.80, 112.13, 109.58, 105.04, 76.86, 62.55, 56.28, 53.92, 46.77, 46.13, 24.02; HRMS (ESI): m/z (%) = 377.1626 (M + H$^+$). Purity >98%. |

TABLE 200-continued
| STRUCTURE | ENTRY NUMBER (NAME) | ANALYTICAL DATA |
|---|---|---|
| 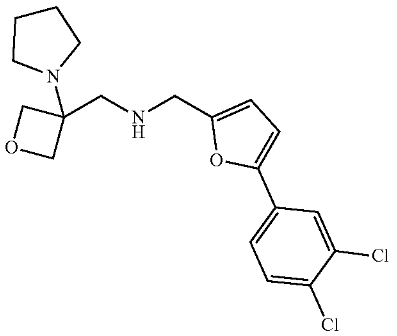 [SMILES: Clc1ccc(-c2ccc(CNCC3(N4CCCC4)COC3)o2)cc1Cl] | 253 (TR-FTO-053-N) | $^{1}H$ NMR (599 MHz, CDCl3) δ 7.73 (d, J = 1.7 Hz, 1H), 7.45 (dt, J = 14.4, 5.1 Hz, 2H), 6.62 (d, J = 3.3 Hz, 1H), 6.31 (d, J = 3.2 Hz, 1H), 4.80 (d, J = 6.7 Hz, 2H), 4.39 (d, J = 6.7 Hz, 2H), 3.90 (s, 2H), 3.03 (s, 2H), 2.73 (t, J = 5.9 Hz, 4H), 1.84-1.78 (m, 4H); $^{13}C$ NMR (151 MHz, CDCl3) δ 154.60, 150.87, 132.95, 130.74, 130.70, 125.19, 122.70, 109.75, 107.18, 76.83, 62.60, 54.04, 46.82, 46.19, 24.04; HRMS (ESI): m/z (%) = 381.1130 (M + $H^+$). Purity >99%. |
| 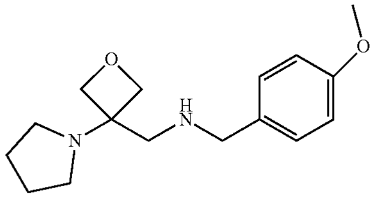 [SMILES: COc1ccc(CNCC2(N3CCCC3)COC2)cc1] | 254 (TR-FTO-04) | |
| 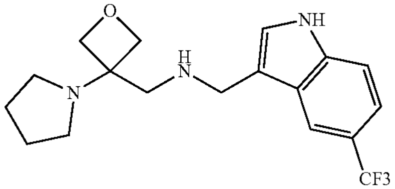 [SMILES: FC(F)(F)c1ccc2[nH]cc(CNCC3(N4CCCC4)COC3)c2c1] | 255 (TR-FTO-012) | |
| 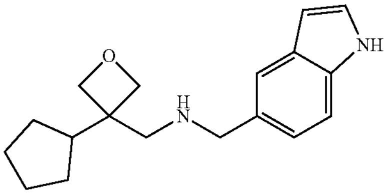 [SMILES: c1cc2cc(CNCC3(C4CCCC4)COC3)ccc2[nH]1] | 256 | |
| 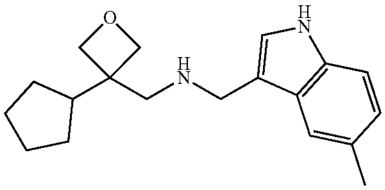 [SMILES: Cc1ccc2[nH]cc(CNCC3(C4CCCC4)COC3)c2c1] | 257 | |
| 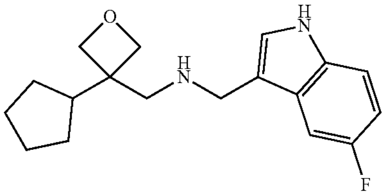 [SMILES: Fc1ccc2[nH]cc(CNCC3(C4CCCC4)COC3)c2c1] | 258 | |
| 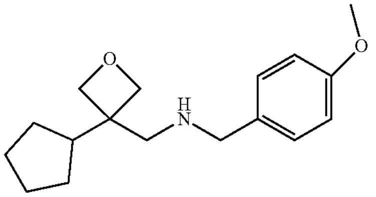 [SMILES: COc1ccc(CNCC2(C3CCCC3)COC2)cc1] | 259 | |

TABLE 200-continued
| STRUCTURE | ENTRY NUMBER (NAME) | ANALYTICAL DATA |
|---|---|---|
| 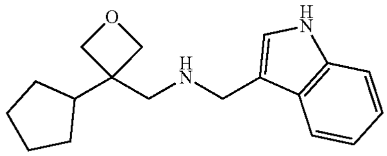 [SMILES: c1ccc2c(CNCC3(C4CCCC4)COC3)c[nH]c2c1] | 260 | |
| 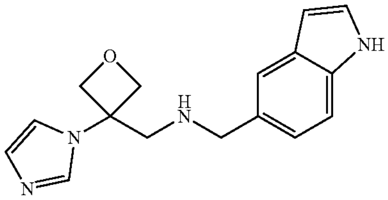 [SMILES: c1cn(C2(CNCc3ccc4[nH]ccc4c3)COC2)cn1] | 261 | |
| 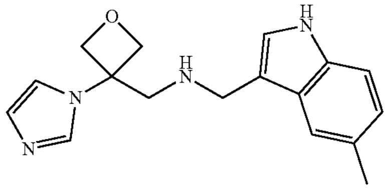 [SMILES: Cc1ccc2[nH]cc(CNCC3(n4ccnc4)COC3)c2c1] | 262 | |
| 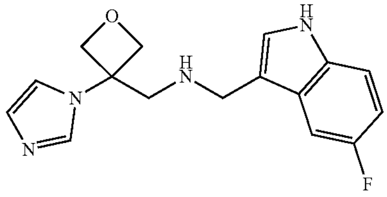 [SMILES: Fc1ccc2[nH]cc(CNCC3(n4ccnc4)COC3)c2c1] | 263 | |
| 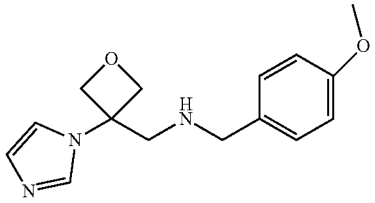 [SMILES: COc1ccc(CNCC2(n3ccnc3)COC2)cc1] | 264 | |
| 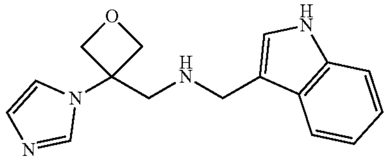 [SMILES: c1ccc2c(CNCC3(n4ccnc4)COC3)c[nH]c2c1] | 265 | |
| 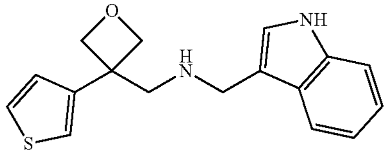 [SMILES: c1ccc2c(CNCC3(c4ccsc4)COC3)c[nH]c2c1] | 266 (1) | |
| 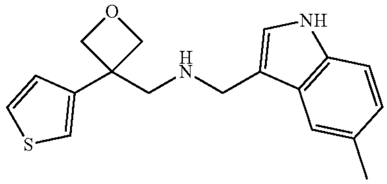 [SMILES: Cc1ccc2[nH]cc(CNCC3(c4ccsc4)COC3)c2c1] | 267 (2) | |

TABLE 200-continued
| STRUCTURE | ENTRY NUMBER (NAME) | ANALYTICAL DATA |
|---|---|---|
| 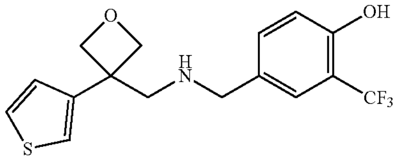 [SMILES: Oc1ccc(CNCC2(c3ccsc3)COC2)cc1C(F)(F)F] | 268 (3) | |
| 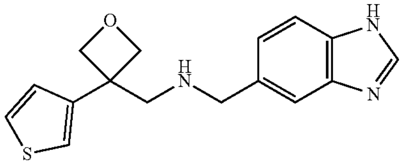 [SMILES: c1nc2cc(CNCC3(c4ccsc4)COC3)ccc2[nH]1] | 269 (4) | |
| 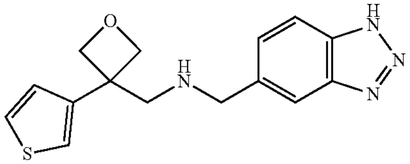 [SMILES: c1cc(C2(CNCc3ccc4[nH]nnc4c3)COC2)cs1] | 270 (5) | |
| 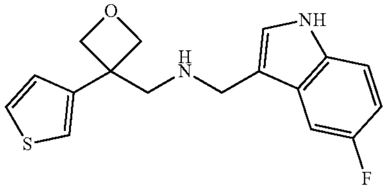 [SMILES: Fc1ccc2[nH]cc(CNCC3(c4ccsc4)COC3)c2c1] | 271 (6) | |
| 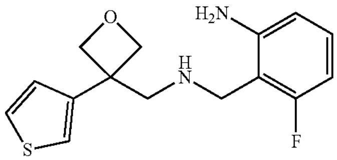 [SMILES: Nc1cccc(F)c1CNCC1(c2ccsc2)COC1] | 272 (7) | |
| 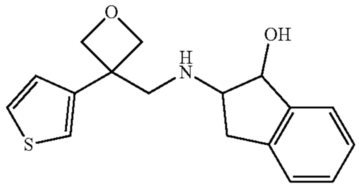 [SMILES: OC1c2ccccc2CC1NCC1(c2ccsc2)COC1] | 273 (8) | |
| 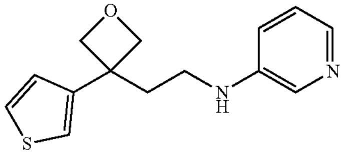 [SMILES: c1cncc(NCCC2(c3ccsc3)COC2)c1] | 274 (9) | |
| 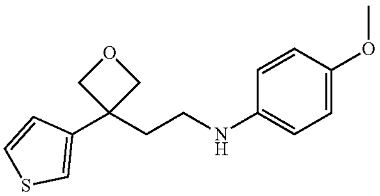 [SMILES: COc1ccc(NCCC2(c3ccsc3)COC2)cc1] | 275 (10) | |

TABLE 200-continued
| STRUCTURE | ENTRY NUMBER (NAME) | ANALYTICAL DATA |
|---|---|---|
| 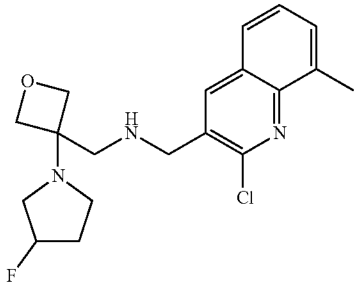 [SMILES: Cc1cccc2cc(CNCC3(N4CCC(F)C4)COC3)c(Cl)nc12] | 276 | |
Inhibition Data for Exemplary Compounds of Table 200
TABLE 200
COMPOUNDS INHIBITION DATA, contd.
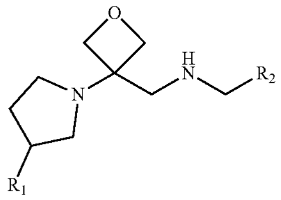
| Compound | $R_1$ | $R_2$ | FTO $IC_{50}$ (μM) | ALKBH5 $IC_{50}$ (μM) | elogD |
|---|---|---|---|---|---|
| TR-FTO-02 | H | 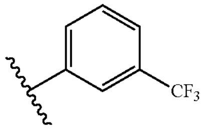 [SMILES: *c1cccc(C(F)(F)F)c1] | 4.3 | 19.5 | 1.02 |
| TR-FTO-09 | H | 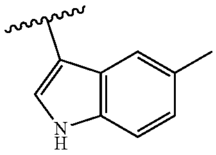 [SMILES: *c1c[nH]c2ccc(C)cc12] | 0.35 | >40 | 0.87 |
| TR-FTO-11 | H | 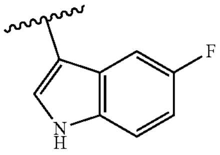 [SMILES: *c1c[nH]c2ccc(F)cc12] | 0.11 | 6.6 | 1.01 |
| TR-FTO-12 | H | 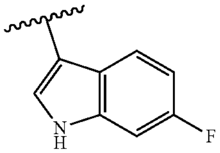 [SMILES: *c1c[nH]c2cc(F)ccc12] | 0.83 | 2.3 | 0.71 |
| TR-FTO-13 | H | 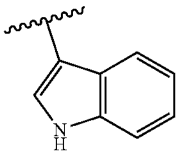 [SMILES: *c1c[nH]c2ccccc12] | 1.0 | >40 | 0.77 |

TABLE 200-continued
COMPOUNDS INHIBITION DATA, contd.
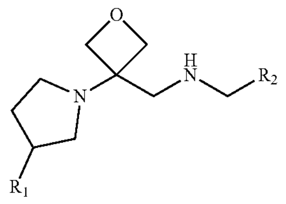
| Compound | $R_1$ | $R_2$ | FTO $IC_{50}$ (μM) | ALKBH5 $IC_{50}$ (μM) | elogD |
|---|---|---|---|---|---|
| TR-FTO-14 | H | 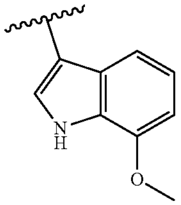 [SMILES: *c1c[nH]c2c(OC)cccc12] | 0.87 | >40 | 0.40 |
| TR-FTO-16 | H | 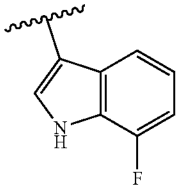 [SMILES: *c1c[nH]c2c(F)cccc12] | 2.2 | 0.87 | 0.70 |
| TR-FTO-17 | H | 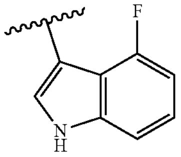 [SMILES: *c1c[nH]c2cccc(F)c12] | 1.3 | 2.5 | 0.64 |
| TR-FTO-18 | H | 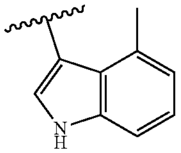 [SMILES: *c1c[nH]c2cccc(C)c12] | 1.1 | 41.3 | 0.71 |
| TR-FTO-27 | H | 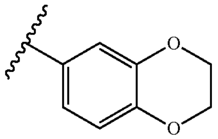 [SMILES: *c1ccc2c(c1)OCCO2] | 0.67 | 5.9 | 0.55 |
| TR-FTO-30 | H | 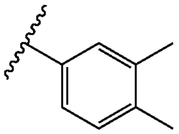 [SMILES: *c1ccc(C)c(C)c1] | 0.35 | 9.9 | 0.87 |
| TR-FTO-31 | H | 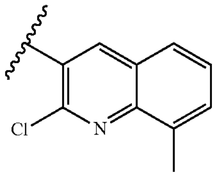 [SMILES: *c1cc2cccc(C)c2nc1Cl] | 0.95 | 51.2 | 1.56 |

TABLE 200-continued
COMPOUNDS INHIBITION DATA, contd.
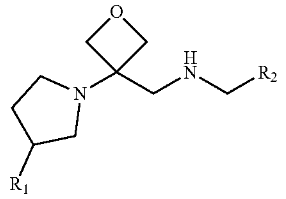
| Compound | $R_1$ | $R_2$ | FTO $IC_{50}$ (μM) | ALKBH5 $IC_{50}$ (μM) | elogD |
|---|---|---|---|---|---|
| TR-FTO-35 | H | 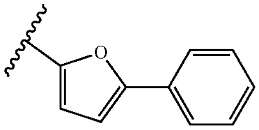 [SMILES: *c1ccc(-c2ccccc2)o1] | 0.07 | 55.0 | 1.14 |
| TR-FTO-37 | H | 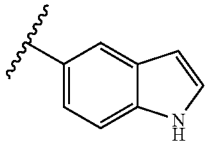 [SMILES: *c1ccc2[nH]ccc2c1] | 0.81 | 3.3 | 0.75 |
| TR-FTO-38 | H | 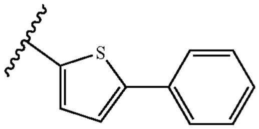 [SMILES: *c1ccc(-c2ccccc2)s1] | 0.27 | 3.4 | 1.57 |
| TR-FTO-39 | H | 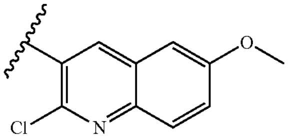 [SMILES: *c1cc2cc(OC)ccc2nc1Cl] | 1.7 | 0.92 | 1.12 |
| TR-FTO-40 | H | 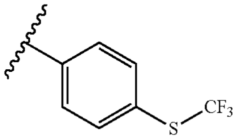 [SMILES: *c1ccc(SC(F)(F)F)cc1] | 0.16 | 3.0 | 1.29 |
| TR-FTO-42 | H | 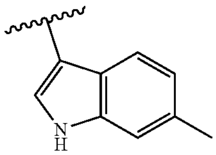 [SMILES: *c1c[nH]c2cc(C)ccc12] | 3.0 | 13.4 | 0.66 |
| TR-FTO-44 | F | 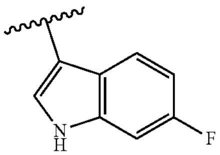 [SMILES: *c1c[nH]c2cc(F)ccc12] | 0.44 | 17.2 | 0.95 |
| TR-FTO-45 | F | 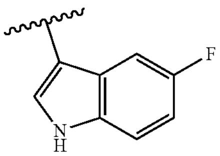 [SMILES: *c1c[nH]c2ccc(F)cc12] | 0.90 | 30.5 | 1.03 |

TABLE 200-continued
COMPOUNDS INHIBITION DATA, contd.
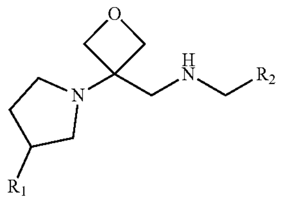
| Compound | $R_1$ | $R_2$ | FTO $IC_{50}$ (μM) | ALKBH5 $IC_{50}$ (μM) | elogD |
|---|---|---|---|---|---|
| TR-FTO-47 | F | 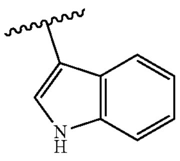 [SMILES: *c1c[nH]c2ccccc12] | 2.1 | >40 | 0.38 |
| TR-FTO-48 | F | 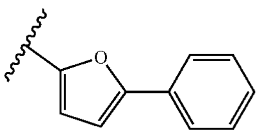 [SMILES: *c1ccc(-c2ccccc2)o1] | 2.0 | 2.6 | 1.34 |
TABLE 200 COMPOUNDS INHIBITION DATA, contd.
Example C3
General Procedure for the Preparation of Non-Limiting Exemplary FTO Inhibitors (e.g., Compounds of Formula (F3)):
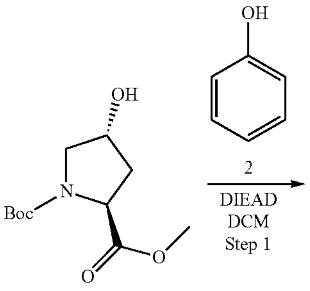
1
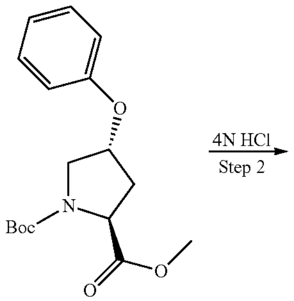
3
-continued
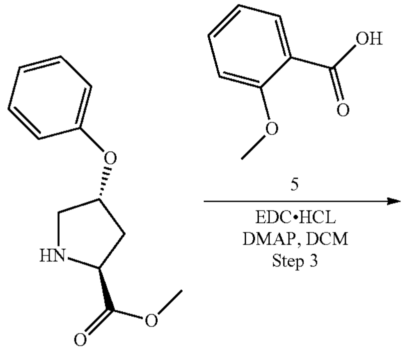
4
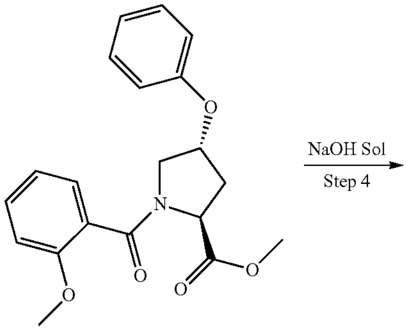
6

-continued
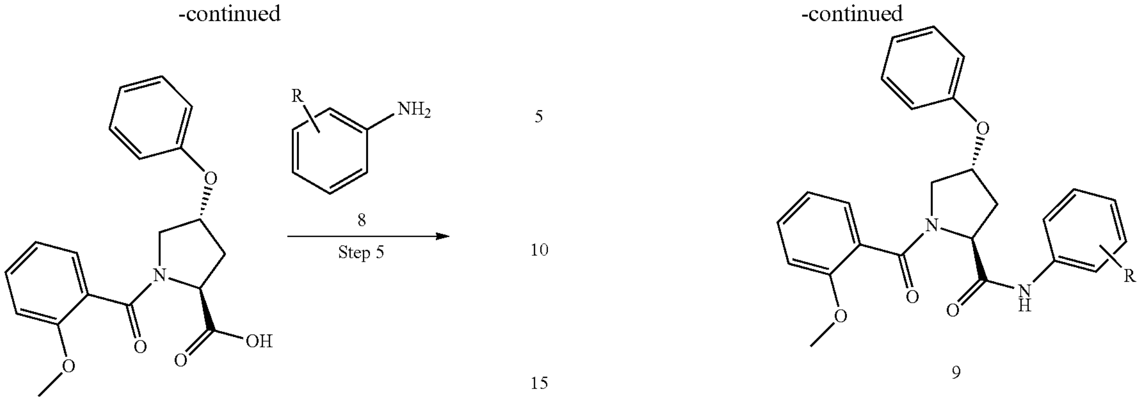
7
9
Non-Limiting Examples of FTO Inhibitors that can be Prepared Using the Methods Above:
TABLE 300
| STRUCTURE | ENTRY NUMBER (NAME) |
|---|---|
| 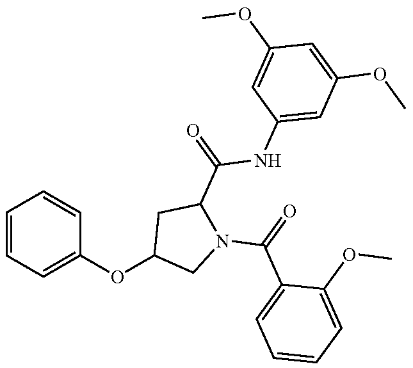 [SMILES: COc1cc(NC(=O)C2CC(Oc3ccccc3)CN2C(=O)c2ccccc2OC)cc(OC)c1] | 301 (TR-FTO-2-01) |
| 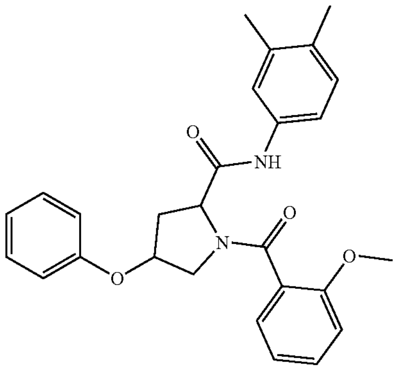 [SMILES: COc1ccccc1C(=O)N1CC(Oc2ccccc2)CC1C(=O)Nc1ccc(C)c(C)c1] | 302 (TR-FTO-2-02) |
| 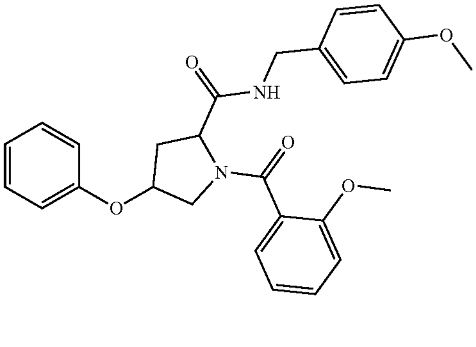 [SMILES: COc1ccc(CNC(=O)C2CC(Oc3ccccc3)CN2C(=O)c2ccccc2OC)cc1] | 303 (TR-FTO-2-03) |

TABLE 300-continued
| STRUCTURE | ENTRY NUMBER (NAME) |
| --- | --- |
| 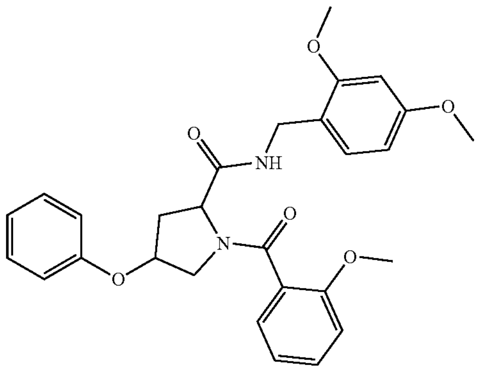 [SMILES: COc1ccc(CNC(=O)C2CC(Oc3ccccc3)CN2C(=O)c2ccccc2OC)c(OC)c1] | 304 (TR-FTO-2-04) |
| 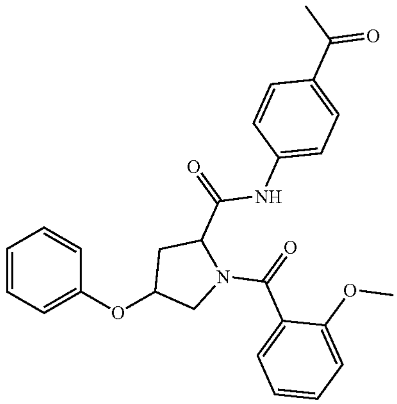 [SMILES: COc1ccccc1C(=O)N1CC(Oc2ccccc2)CC1C(=O)Nc1ccc(C(C)=O)cc1] | 305 (TR-FTO-2-05) |
| 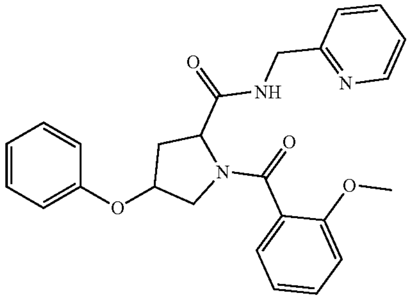 [SMILES: COc1ccccc1C(=O)N1CC(Oc2ccccc2)CC1C(=O)NCc1ccccn1] | 306 (TR-FTO-2-06) |
| 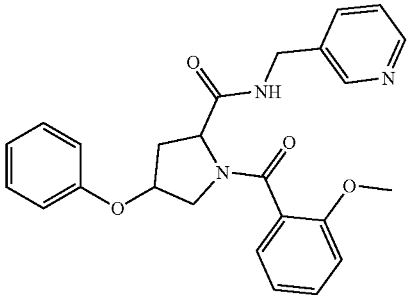 [SMILES: COc1ccccc1C(=O)N1CC(Oc2ccccc2)CC1C(=O)NCc1cccnc1] | 307 (TR-FTO-2-07) |

TABLE 300-continued
| STRUCTURE | ENTRY NUMBER (NAME) |
| --- | --- |
| 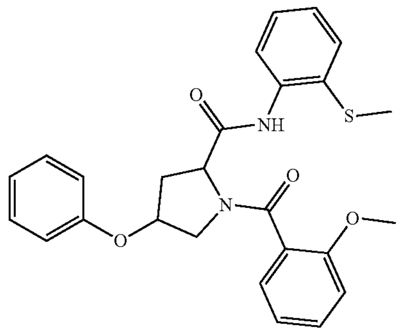 [SMILES: COc1ccccc1C(=O)N1CC(Oc2ccccc2)CC1C(=O)Nc1ccccc1SC] | 308 (TR-FTO-2-08) |
| 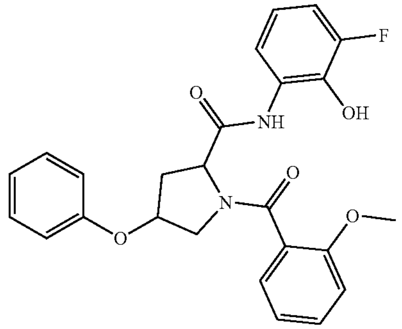 [SMILES: COc1ccccc1C(=O)N1CC(Oc2ccccc2)CC1C(=O)Nc1cccc(F)c1O] | 309 (TR-FTO-2-09) |
| 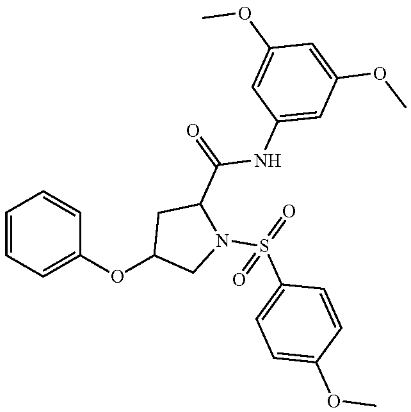 [SMILES: COc1ccc(S(=O)(=O)N2CC(Oc3ccccc3)CC2C(=O)Nc2cc(OC)cc(OC)c2)cc1] | 310 (TR-FTO-2-010) |
| 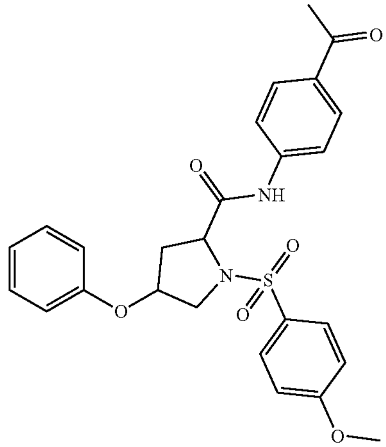 [SMILES: COc1ccc(S(=O)(=O)N2CC(Oc3ccccc3)CC2C(=O)Nc2ccc(C(C)=O)cc2)cc1] | 311 (TR-FTO-2-011) |

TABLE 300-continued
| STRUCTURE | ENTRY NUMBER (NAME) |
|---|---|
| 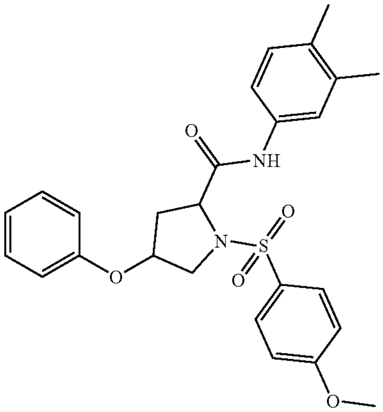 [SMILES: COc1ccc(S(=O)(=O)N2CC(Oc3ccccc3)CC2C(=O)Nc2ccc(C)c(C)c2)cc1] | 312 (TR-FTO-2-012) |
| 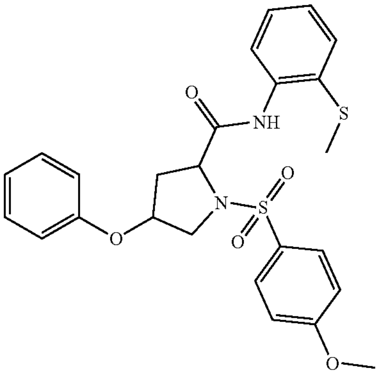 [SMILES: COc1ccc(S(=O)(=O)N2CC(Oc3ccccc3)CC2C(=O)Nc2ccccc2SC)cc1] | 313 (TR-FTO-2-013) |
| 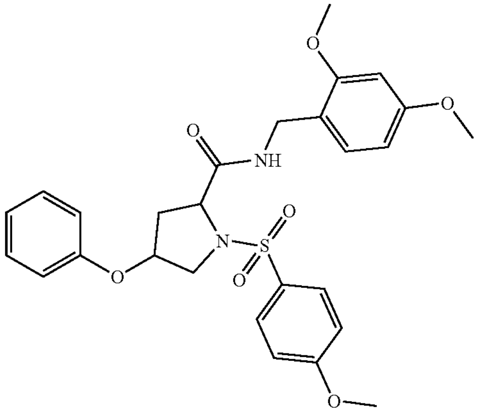 [SMILES: COc1ccc(S(=O)(=O)N2CC(Oc3ccccc3)CC2C(=O)NCc2ccc(OC)cc2OC)cc1] | 314 (TR-FTO-2-014) |
| 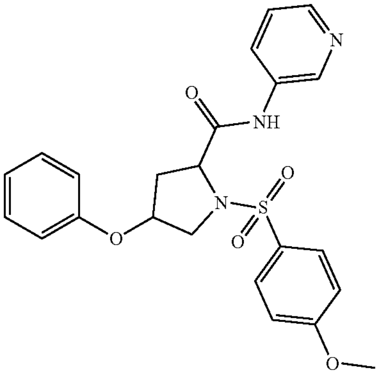 [SMILES: COc1ccc(S(=O)(=O)N2CC(Oc3ccccc3)CC2C(=O)Nc2cccnc2)cc1] | 315 (TR-FTO-2-015) |

TABLE 300-continued
| STRUCTURE | ENTRY NUMBER (NAME) |
|---|---|
| 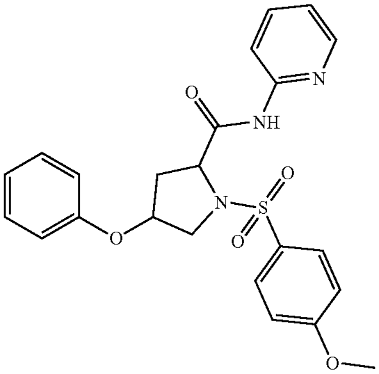 [SMILES: COc1ccc(S(=O)(=O)N2CC(Oc3ccccc3)CC2C(=O)Nc2ccccn2)cc1] | 316<br>(TR-FTO-2-016) |
| 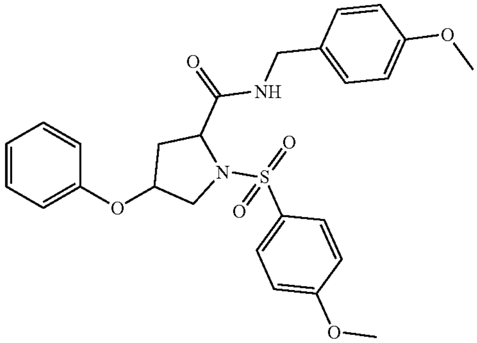 [SMILES: COc1ccc(CNC(=O)C2CC(Oc3ccccc3)CN2S(=O)(=O)c2ccc(OC)cc2)cc1] | 317<br>(TR-FTO-2-017) |
| 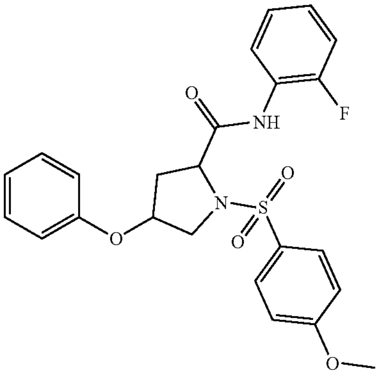 [SMILES: COc1ccc(S(=O)(=O)N2CC(Oc3ccccc3)CC2C(=O)Nc2ccccc2F)cc1] | 318<br>(TR-FTO-2-018) |
| 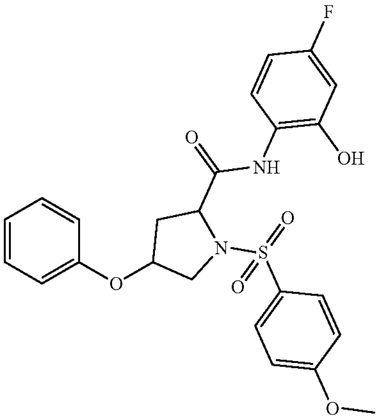 [SMILES: COc1ccc(S(=O)(=O)N2CC(Oc3ccccc3)CC2C(=O)Nc2ccc(F)cc2O)cc1] | 319<br>(TR-FTO-2-019) |

TABLE 300-continued
| STRUCTURE | ENTRY NUMBER (NAME) |
|---|---|
| 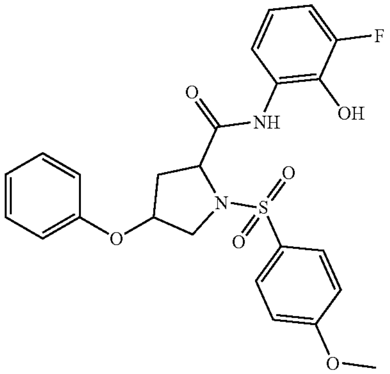 [SMILES: COc1ccc(S(=O)(=O)N2CC(Oc3ccccc3)CC2C(=O)Nc2cccc(F)c2O)cc1] | 320<br>(TR-FTO-2-020) |
| 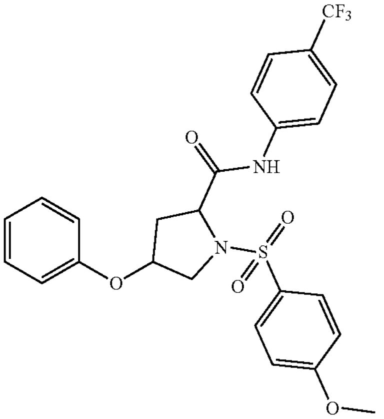 [SMILES: COc1ccc(S(=O)(=O)N2CC(Oc3ccccc3)CC2C(=O)Nc2ccc(C(F)(F)F)cc2)cc1] | 321<br>(TR-FTO-2-021) |
| 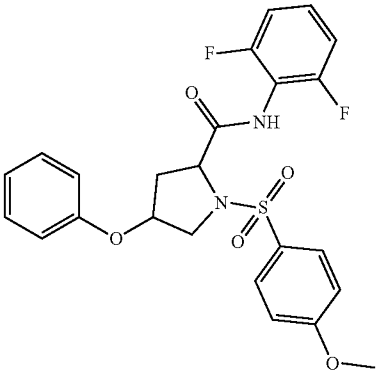 [SMILES: COc1ccc(S(=O)(=O)N2CC(Oc3ccccc3)CC2C(=O)Nc2c(F)cccc2F)cc1] | 322<br>(TR-FTO-2-022) |
| 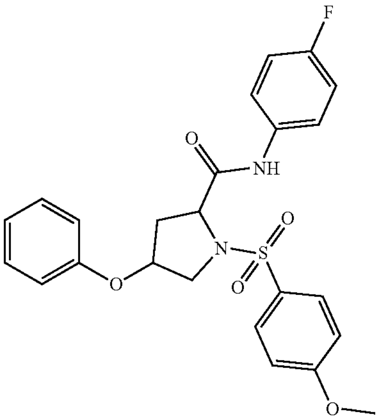 [SMILES: COc1ccc(S(=O)(=O)N2CC(Oc3ccccc3)CC2C(=O)Nc2ccc(F)cc2)cc1] | 323<br>(TR-FTO-2-023) |

TABLE 300-continued
| STRUCTURE | ENTRY NUMBER (NAME) |
|---|---|
| 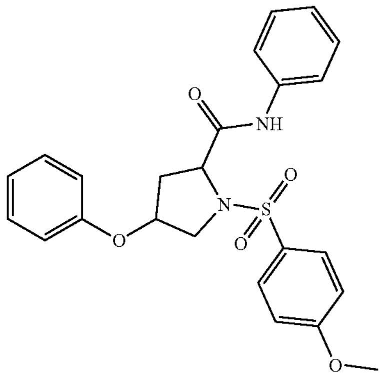 [SMILES: COc1ccc(S(=O)(=O)N2CC(Oc3ccccc3)CC2C(=O)Nc2ccccc2)cc1] | 324<br>(TR-FTO-2-024) |
Inhibition Data for Table 300 Compounds:
| | | | Permeability (nm/s) | | Enzymatic $IC_{50}$ |
|---|---|---|---|---|---|
| Structure | Name | clogP | Caco-2 | MDCK | FTO (μM) |
| 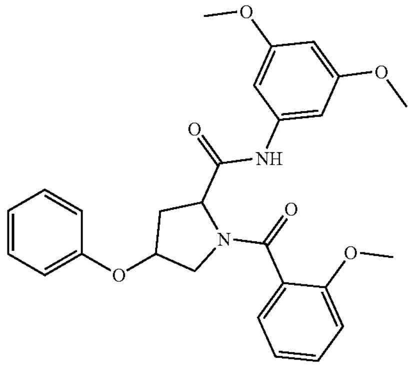 [SMILES: COc1cc(NC(=O)C2CC(Oc3ccccc3)CN2C(=O)c2ccccc2OC)cc(OC)c1] | TR-FTO 2-01 | 4.92 | 3581 | 1964 | 0.61 ± 0.17 |
| 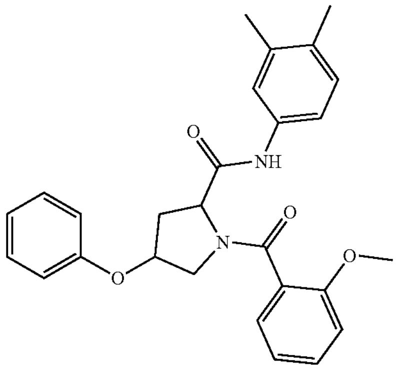 [SMILES: COc1ccccc1C(=O)N1CC(Oc2ccccc2)CC1C(=O)Nc1ccc(C)c(C)c1] | TR-FTO 2-02 | 5.27 | 2892 | 1559 | 0.19 ± 0.03 |

-continued
| Structure | Name | clogP | Permeability (nm/s) Caco-2 | MDCK | Enzymatic $IC_{50}$ FTO (μM) |
|---|---|---|---|---|---|
| 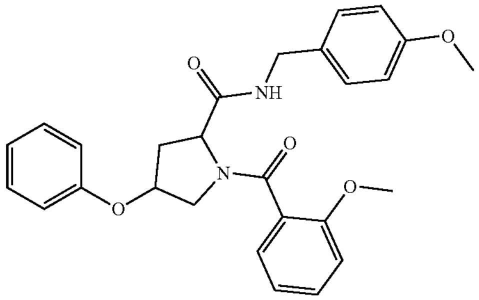 [SMILES: COc1ccc(CNC(=O)C2CC(Oc3ccccc3)CN2C(=O)c2ccccc2OC)cc1] | TR-FTO 2-03 | 4.56 | 2524 | 1733 | 1.24 ± 0.65 |
| 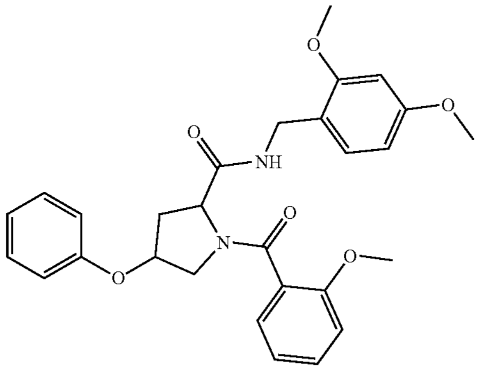 [SMILES: COc1ccc(CNC(=O)C2CC(Oc3ccccc3)CN2C(=O)c2ccccc2OC)c(OC)c1] | TR-FTO 2-04 | 4.30 | 1539 | 1355 | 6.67 ± 2.31 |
| 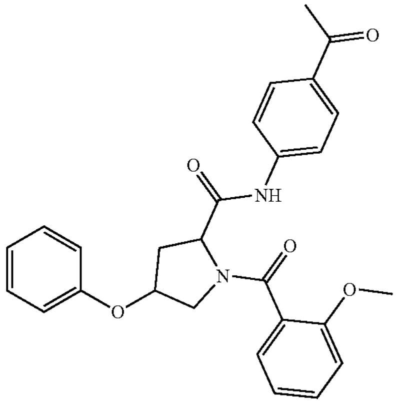 [SMILES: COc1ccccc1C(=O)N1CC(Oc2ccccc2)CC1C(=O)Nc1ccc(C(C)=O)cc1] | TR-FTO 2-05 | 4.19 | 1132 | 565 | 8.31 ± 2.07 |
| 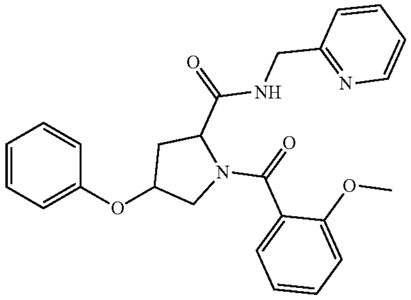 [SMILES: COc1ccccc1C(=O)N1CC(Oc2ccccc2)CC1C(=O)NCc1ccccn1] | TR-FTO 2-06 | 3.84 | 2391 | 1403 | 12.46 ± 2.70 |

-continued
| Structure | Name | clogP | Permeability (nm/s) Caco-2 | Permeability (nm/s) MDCK | Enzymatic IC$_{50}$ FTO (μM) |
|---|---|---|---|---|---|
| 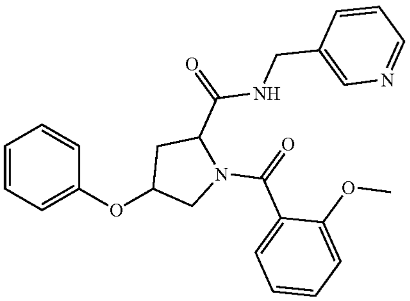 [SMILES: COc1ccccc1C(=O)N1CC(Oc2ccccc2)CC1C(=O)NCc1cccnc1] | TR-FTO 2-07 | 3.48 | 1835 | 1040 | 0.17 ± 0.03 |
| 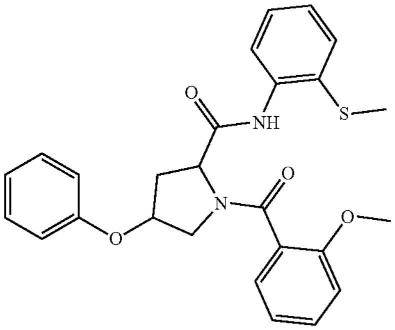 [SMILES: COc1ccccc1C(=O)N1CC(Oc2ccccc2)CC1C(=O)Nc1ccccc1SC] | TR-FTO 2-08 | 4.98 | 2524 | 2168 | 10.35 ± 2.29 |
| 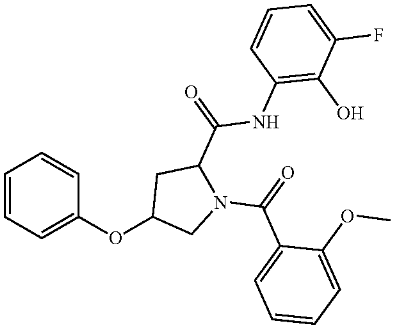 [SMILES: COc1ccccc1C(=O)N1CC(Oc2ccccc2)CC1C(=O)Nc1cccc(F)c1O] | TR-FTO 2-09 | 4.34 | 2541 | 2309 | >40 |
Example C4
General Procedure for the Preparation of YTH Inhibitors—Pyridyl Compounds.
Scheme 4.
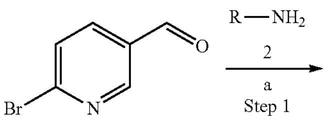
1
-continued
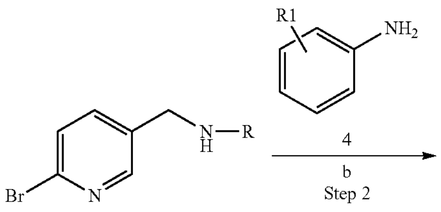
3

-continued

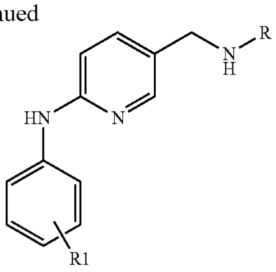

5

R = Cyclopropyl, Isopropyl

Reagents and conditions: a). $NaBH_4$, MeOH, 2 h., b) NaOtBu, $Pd(dba)_2$, Xanthophos, Toluene, 120° C.

Step 1: General Procedure for the Synthesis of Compounds. (5-58):

A two-necked round-bottomed flask was charged with 6-bromonicotinaldehyde (1) (1 eq.) and corresponding amine (2) (1 eq.) in methanol and stirred for 1 h at room temperature, followed by the addition of $NaBH_4$. The reaction mixture was stirred for 1 h at room temperature and after completion of starting materials, to the reaction mass add excess of water and ethyl acetate. The organic layer was separated and concentrated under reduced pressure. The crude material was purified by flash column chromatography ethyl acetate:hexane (50:50) to give the final compound (3).

Step 2: General Procedure for the Synthesis of Compounds. (TR-YTH-01-20):

A one-necked round-bottomed flask was fitted with a reflux condenser and with a magnetic stirrer. The flask was charged with corresponding (4) (1 mmol) and followed by the addition of $Pd(dba)_2$ catalyst (0.1 mmol), Xanthophos (0.01 mmol) and $^{t}$BuONa (2 mmol). The reaction mixture was left to stir at 120° C. for 12 h. After completion of reaction, to the reaction add excess of water and extract with ethyl acetate. The organic layer was separated and concentrated under reduced pressure. The crude material was purified by column chromatography (hexane:ethyl acetate 30:70) yielded compounds TR-YTH-01-20.

TABLE 400

| STRUCTURE | ENTRY NUMBER (NAME) | Analytical Data |
|---|---|---|
| 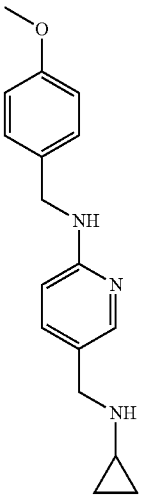 [SMILES: COc1ccc(CNc2ccc(CNC3CC3)cn2)cc1] | 401 (TR-YTH-01) | $^1$H NMR (599 MHz, CDCl3) δ 8.05 (d, J = 2.1 Hz, 1H), 7.41 (dd, J = 8.5, 2.3 Hz, 1H), 7.31-7.28 (m, 2H), 6.91-6.87 (m, 2H), 6.38 (d, J = 8.5 Hz, 1H), 4.44 (d, J = 5.7 Hz, 2H), 3.82 (s, 3H), 3.71 (s, 2H), 2.18-2.13 (m, 1H), 0.46 (td, J = 6.5, 4.4 Hz, 2H), 0.40-0.37 (m, 2H). $^{13}$C NMR (151 MHz, CDCl3) δ 158.74, 157.85, 131.11, 128.61, 124.69, 113.92, 55.91, 50.55, 45.85, 6.29. HRMS (ESI): m/z (%) = 284.1754 (M + $H^+$). Purity >98%. |
| 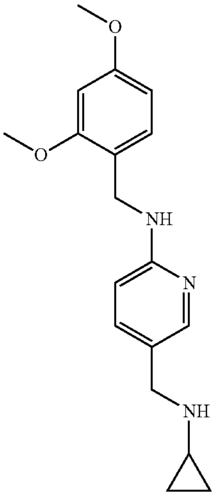 [SMILES: COc1ccc(CNc2ccc(CNC3CC3)cn2)c(OC)c1] | 402 (TR-YTH-02) | $^1$H NMR (600 MHz, CDCl3) δ 8.01 (s, 1H), 7.39 (dd, J = 8.3, 2.1 Hz, 1H), 7.22-7.18 (m, 1H), 6.47 (d, J = 2.2 Hz, 1H), 6.43-6.36 (m, 2H), 4.42-4.38 (m, 2H), 3.84 (d, J = 2.0 Hz, 3H), 3.80 (d, J = 2.0 Hz, 3H), 3.68 (d, J = 1.9 Hz, 2H), 2.14-2.08 (m, 1H), 0.44 (dd, J = 8.7, 4.6 Hz, 2H), 0.37 (s, 2H). $^{13}$C NMR (151 MHz, CDCl3) δ 158.39, 158.09, 124.19, 119.44, 55.30, 55.25, 50.55, 41.43, 6.25. HRMS (ESI): m/z (%) = 314.1861 (M + $H^+$). Purity >96%. |

TABLE 400-continued

| STRUCTURE | ENTRY NUMBER (NAME) | Analytical Data |
|---|---|---|
| 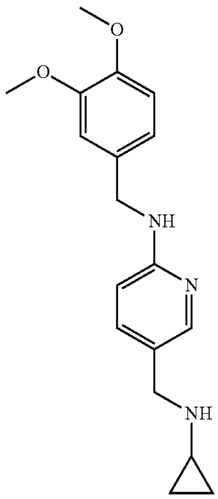 [SMILES: COc1ccc(CNc2ccc(CNC3CC3)cn2)cc1OC] | 403 (TR-YTH-03) | $^1$H NMR (600 MHz, CDCl3) δ 8.03 (d, J = 2.0 Hz, 1H), 7.40 (dd, J = 8.5, 2.3 Hz, 1H), 6.90 (dd, J = 4.0, 2.4 Hz, 2H), 6.84-6.81 (m, 1H), 6.37 (d, J = 8.5 Hz, 1H), 4.42 (d, J = 5.7 Hz, 2H), 3.87 (d, J = 7.5 Hz, 6H), 3.70 (s, 2H), 2.12 (dt, J = 10.2, 3.4 Hz, 1H), 0.44 (dt, J = 6.3, 2.9 Hz, 2H), 0.38-0.35 (m, 2H), 13C NMR (151 MHz, CDCl3) δ 157.97, 149.10, 148.18, 131.71, 124.62, 55.90, 55.81, 50.59, 46.28, 6.33, 6.33. HRMS (ESI): m/z (%) = 314.1861 (M + H+). Purity >98%. |
| 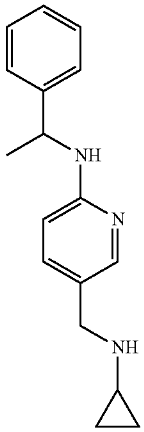 [SMILES: CC(Nc1ccc(CNC2CC2)cn1)c1ccccc1] | 404 (TR-YTH-04) | $^1$H NMR (600 MHz, CDCl3) δ 8.00 (s, 1H), 7.36 (d, J = 8.0 Hz, 2H), 7.34-7.29 (m, 3H), 7.26-7.22 (m, 1H), 6.17 (d, J = 8.5 Hz, 1H), 4.70 (p, J = 6.6 Hz, 1H), 3.65 (s, 2H), 2.12-2.07 (m, 1H), 1.55 (d, J = 6.7 Hz, 3H), 0.45-0.40 (m, 2H), 0.37-0.32 (m, 2H). $^{13}$C NMR (151 MHz, CDCl3) δ 157.35, 147.89, 144.77, 138.11, 128.65, 125.88, 124.69, 106.49, 50.64, 24.44, 6.41, 6.39. HRMS (ESI): m/z (%) = 268.1810 (M + H$^+$). Purity >98%. |
| 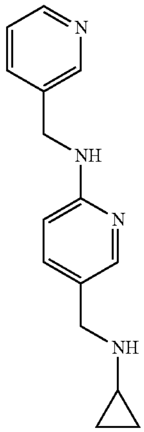 [SMILES: c1cncc(CNc2ccc(CNC3CC3)cn2)c1] | 405 (TR-YTH-05) | $^1$H NMR (600 MHz, CDCl3) δ 8.62 (s, 1H), 8.53-8.49 (m, 1H), 8.04 (s, 1H), 7.69 (dd, J = 7.8, 1.4 Hz, 1H), 7.43-7.40 (m, 1H), 7.27-7.23 (m, 1H), 6.38 (d, J = 8.4 Hz, 1H), 4.56 (d, J = 5.9 Hz, 2H), 3.70 (d, J = 1.8 Hz, 2H), 2.15-2.10 (m, 1H), 0.44 (tt, J = 6.2, 3.0 Hz, 2H), 0.39-0.34 (m, 2H). $^{13}$C NMR (151 MHz, CDCl3) δ 157.51, 155.89, 135.04, 129.16, 124.81, 50.53, 50.50, 48.87, 43.65, 6.43, 6.28. HRMS (ESI): m/z (%) = 255.1607 (M + H$^+$). Purity >97%. |

TABLE 400-continued

| STRUCTURE | ENTRY NUMBER (NAME) | Analytical Data |
|---|---|---|
| 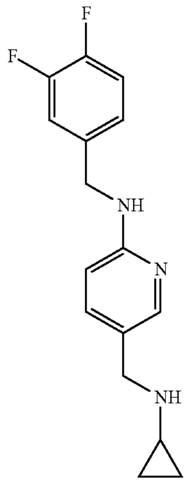 [SMILES: Fc1ccc(CNc2ccc(CNC3CC3)cn2)cc1F] | 406 (TR-YTH-06) | $^1$H NMR (600 MHz, CDCl3) δ 8.04 (d, J = 1.6 Hz, 1H), 7.41 (dd, J = 8.5, 2.2 Hz, 1H), 7.20-7.15 (m, 1H), 7.14-7.04 (m, 2H), 6.34 (d, J = 8.5 Hz, 1H), 4.49 (d, J = 6.0 Hz, 2H), 3.70 (s, 2H), 2.16-2.11 (m, 1H), 0.47-0.43 (m, 2H), 0.39-0.36 (m, 2H). $^{13}$C NMR (151 MHz, $CDCl_3$) δ 157.29, 148.55, 140.28, 130.48, 119.86, 50.43, 35.79, 6.99, 6.60. HRMS (ESI): m/z (%) = 290.1464 (M + $H^+$). Purity >99%. |
| 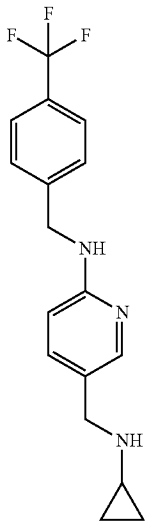 [SMILES: FC(F)(F)c1ccc(CNc2ccc(CNC3CC3)cn2)cc1] | 407 (TR-YTH-07) | $^1$H NMR (599 MHz, CDCl3) δ 8.06 (d, J = 2.1 Hz, 1H), 7.60 (d, J = 8.1 Hz, 2H), 7.49 (d, J = 8.0 Hz, 2H), 7.43 (dd, J = 8.5, 2.3 Hz, 1H), 6.37 (d, J = 8.5 Hz, 1H), 4.62 (d, J = 6.0 Hz, 2H), 3.72 (s, 2H), 2.17-2.13 (m, 1H), 0.46 (td, J = 6.5, 4.4 Hz, 2H), 0.40-0.36 (m, 2H). $^{13}$C NMR (151 MHz, CDCl3) 159.39, 148.09, 124.18, 117.44, 55.32, 55.25, 50.55, 41.43, 6.25. HRMS (ESI): m/z (%) = 322.1526 (M + $H^+$). Purity >99%. |
| 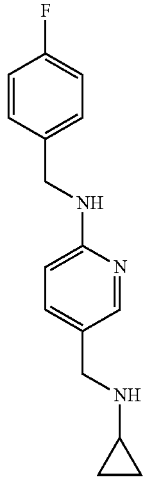 [SMILES: Fc1ccc(CNc2ccc(CNC3CC3)cn2)cc1] | 408 (TR-YTH-08) | $^1$H NMR (600 MHz, CDCl3) δ 8.04 (s, 1H), 7.40 (dd, J = 8.4, 1.8 Hz, 1H), 7.32 (dd, J = 7.9, 5.6 Hz, 2H), 7.02 (t, J = 8.6 Hz, 2H), 6.35 (d, J = 8.4 Hz, 1H), 4.48 (d, J = 5.8 Hz, 2H), 3.70 (s, 2H), 2.13 (ddd, J = 10.1, 6.9, 3.6 Hz, 1H), 0.47-0.43 (m, 2H), 0.38-0.55 (m, 2H). $^{13}$C NMR (151 MHz, CDCl3) δ 162.84, 160.90, 157.78, 147.57, 138.01, 135.00, 124.89, 50.62, 45.67, 6.38. HRMS (ESI): m/z (%) = 272.1560 (M + $H^+$). Purity >95% |

TABLE 400-continued

| STRUCTURE | ENTRY NUMBER (NAME) | Analytical Data |
|---|---|---|
| 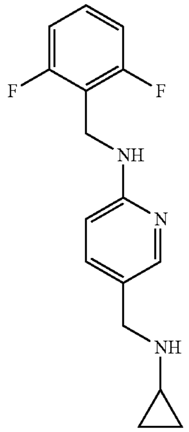 [SMILES: Fc1cccc(F)c1CNc1ccc(CNC2CC2)cn1] | 409 (TR-YTH-09) | $^{1}H$ NMR (599 MHz, CDCl3) δ 8.05 (s, 1H), 7.45 (d, J = 8.5 Hz, 1H), 7.23 (dt, J = 19.8, 6.5 Hz, 1H), 6.93-6.87 (m, 2H), 6.53 (d, J = 8.4 Hz, 1H), 4.60 (d, J = 5.8 Hz, 2H), 3.71 (s, 2H), 2.14 (td, J = 6.6, 3.5 Hz, 1H), 0.45 (dd, J = 6.2, 4.7 Hz, 2H), 0.41-0.38 (m, 2H). $^{13}C$ NMR (151 MHz, CDCl3) δ 149.55, 142.28, 130.48, 119.86, 55.60, 50.50, 45.43, 35.79, 6.39. HRMS (ESI): m/z (%) = 290.1464 (M + $H^+$). Purity >98%. |
| 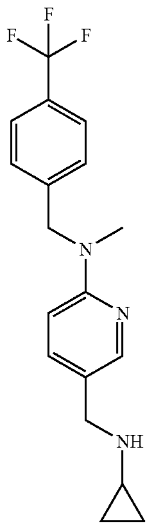 [SMILES: CN(Cc1ccc(C(F)(F)F)cc1)c1ccc(CNC2CC2)cn1] | 410 (TR-YTH-010) | $^{1}H$ NMR (599 MHz, CDCl3) δ 8.12 (d, J = 2.1 Hz, 1H), 7.57 (d, J = 8.1 Hz, 2H), 7.48 (dd, J = 8.6, 2.3 Hz, 1H), 7.35 (d, J = 8.0 Hz, 2H), 6.51 (d, J = 8.6 Hz, 1H), 4.89 (s, 2H), 3.74 (s, 2H), 3.07 (d, J = 2.2 Hz, 3H), 2.19-2.16 (m, 1H), 0.49-0.46 (m, 2H), 0.41 (d, J = 3.1 Hz, 2H). $^{13}C$ NMR (151 MHz, CDCl3) δ 157.98, 143.25, 123.88, 123.86, 52.96, 50.57, 36.39, 6.39. HRMS (ESI): m/z (%) = 336.1679 (M + $H^+$). Purity >95%. |
| 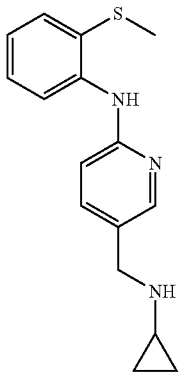 [SMILES: CSc1ccccc1Nc1ccc(CNC2CC2)cn1] | 411 (TR-YTH-011) | $^{1}H$ NMR (599 MHz, CDCl3) δ 8.20 (d, J = 1.9 Hz, 1H), 7.93 (d, J = 8.1 Hz, 1H), 7.53 (dd, J = 8.4, 2.1 Hz, 1H), 7.46 (t, J = 6.8 Hz, 1H), 7.26 (d, J = 7.6 Hz, 1H), 7.00 (t, J = 7.5 Hz, 1H), 6.85 (d, J = 8.4 Hz, 1H), 3.78 (s, 2H), 2.40 (s, 3H), 2.18 (dt, J = 9.8, 3.3 Hz, 1H), 0.50-0.45 (m, 2H), 0.41-0.38 (m, 2H). $^{13}C$ NMR (151 MHz, CDCl3) δ 154.72, 140.48, 131.86, 128.04, 127.41, 126.64, 122.54, 119.20, 109.45, 50.64, 29.99, 17.89, 6.49. HRMS (ESI): m/z (%) = 286.1374 (M + $H^+$). Purity 99%. |

TABLE 400-continued

| STRUCTURE | ENTRY NUMBER (NAME) | Analytical Data |
|---|---|---|
| 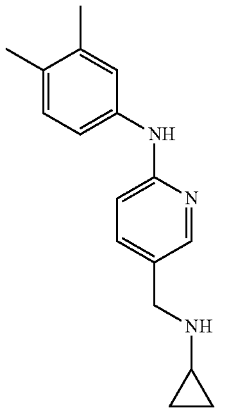 [SMILES: Cc1ccc(Nc2ccc(CNC3CC3)cn2)cc1C] | 412 (TR-YTH-012) | $^{1}H$ NMR (599 MHz, CDCl3) δ 8.12 (s, 1H), 7.47 (dd, J = 8.5, 2.2 Hz, 1H), 7.11 (d, J = 8.0 Hz, 1H), 7.09-7.04 (m, 2H), 6.84 (d, J = 8.5 Hz, 1H), 3.75 (s, 2H), 2.27 (d, J = 10.4 Hz, 6H), 2.17 (td, J = 6.6, 3.3 Hz, 1H), 0.49-0.45 (m, 2H), 0.41-0.38 (m, 2H). $^{13}C$ NMR (151 MHz, CDCl3) δ 155.90, 148.03, 138.31, 138.25, 137.54, 131.34, 130.32, 126.18, 122.47, 118.48, 107.61, 50.62, 19.97, 19.15, 6.43. HRMS (ESI): m/z (%) = 268.1809 (M + $H^+$). Purity >99%. |
| 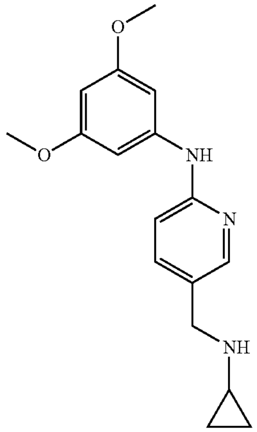 [SMILES: COc1cc(Nc2ccc(CNC3CC3)cn2)cc(OC)c1] | 413 (TR-YTH-013) | $^{1}H$ NMR (599 MHz, CDCl3) δ 8.17 (d, J = 2.2 Hz, 1H), 7.51 (dd, J = 8.5, 2.3 Hz, 1H), 6.94 (d, J = 8.5 Hz, 1H), 6.53 (d, J = 2.2 Hz, 2H), 6.19 (t, J = 2.1 Hz, 1H), 3.81 (s, 6H), 3.79-3.75 (m, 2H), 2.19-2.14 (m, 1H), 0.50-0.45 (m, 2H), 0.41-0.37 (m, 2H). $^{13}C$ NMR (151 MHz, CDCl3) δ 161.42, 154.92, 142.62, 138.28, 126.96, 98.16, 55.35, 50.58, 6.42, 6.40. HRMS (ESI): m/z (%) = 277.1261 (M + $H^+$). Purity >99%. |
| 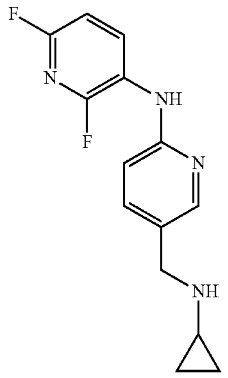 | 414 (TR-YTH-014) | $^{1}H$ NMR (599 MHz, CDCl3) δ 8.92 (ddd, J = 10.0, 8.5 7.2 Hz, 1H), 8.19 (d, J = 2.1 Hz, 1H), 7.58 (dd, J = 8.4, 2.3 Hz, 1H), 6.84 (dd, J = 8.6, 3.0 Hz, 1H), 6.72 (d, J = 8.4 Hz, 1H), 3.80 (s, 2H), 2.18-2.14 (m, 1H), 0.51-0.44 (m, 2H), 0.42-0.36 (m, 2H). $^{13}C$ NMR (151 MHz, CDCl3) δ 153.57, 138.45, 128.14, 50.52, 6.42. HRMS (ESI): m/z (%) = 300.1705 (M + $H^+$). Purity >99%. |

TABLE 400-continued

| STRUCTURE | ENTRY NUMBER (NAME) | Analytical Data |
|---|---|---|
| 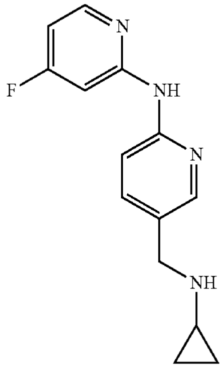 [SMILES: Fc1ccnc(Nc2ccc(CNC3CC3)cn2)c1] | 415 (TR-YTH-015) | $^1$H NMR (599 MHz, CDCl3) δ 8.24 (s, 1H), 8.21 (dd, J = 8.9, 5.7 Hz, 1H), 7.65 (dd, J = 11.7, 2.0 Hz, 1H), 7.61 (dd, J = 8.4, 2.0 Hz, 1H), 7.25 (d, J = 8.4 Hz, 1H), 6.62 (ddd, J = 7.7, 5.9, 2.0 Hz, 1H), 3.81 (s, 2H), 2.19-2.14 (m, 1H), 0.50-0.45 (m, 2H), 0.42-0.37 (m, 2H). $^{13}$C 13C NMR (151 MHz, CDCl3) δ 156.57, 156.49, 152.92, 147.32, 138.27, 50.58, 6.45. HRMS (ESI): m/z (%) = 259.1357 (M + H$^+$). Purity >99%. |
| 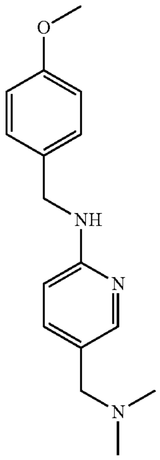 [SMILES: COc1ccc(CNc2ccc(CN(C)C)cn2)cc1] | 416 (TR-YTH-016) | $^1$H NMR (599 MHz, CDCl3) δ 8.00 (s, 1H), 7.54 (s, 1H), 7.30 (d, J = 8.6 Hz, 2H), 6.90 (d, J = 8.6 Hz, 2H), 6.42 (d, J = 8.6 Hz, 1H), 4.45 (d, J = 5.6 Hz, 2H), 3.82 (s, 3H), 3.46 (s, 2H), 2.35 (s, 6H). $^{13}$C NMR (151 MHz, CDCl3) δ 156.02, 148.75, 145.52, 137.23, 128.52, 126.20, 122.42, 106.42, 60.41, 55.03, 44.96, 24.44, 24.42. HRMS (ESI): m/z (%) = 272.1759 (M + H$^+$). Purity >95%. |
| 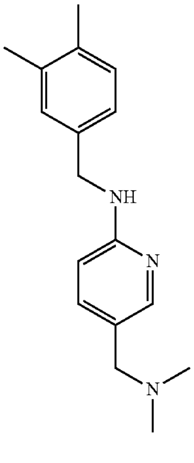 | 417 (TR-YTH-017) | $^1$H NMR (600 MHz, CDCl3) δ 8.05 (d, J = 2.1 Hz, 1H), 7.48 (dd, J = 8.5, 2.2 Hz, 1H), 7.11-7.03 (m, 3H), 6.85-6.81 (m, 1H), 6.49 (s, 1H), 3.35 (s, 2H), 2.25 (d, J = 10.7 Hz, 12H). $^{13}$C NMR (151 MHz, CDCl3) δ 159.53, 147.64, 136.52, 126.20, 106.56, 65.20, 55.55, 45.52, 24.54, 24.44. HRMS (ESI): m/z (%) = 256.1811 (M + H$^+$). Purity >99%. |

TABLE 400-continued

| STRUCTURE | ENTRY NUMBER (NAME) | Analytical Data |
| --- | --- | --- |
| 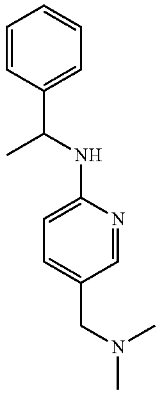 [SMILES: CC(Nc1ccc(CN(C)C)cn1)c1ccccc1] | 418 (TR-YTH-018) | $^1$H NMR (600 MHz, CDCl3) δ 7.95 (d, J = 2.1 Hz, 1H), 7.37 (d, J = 7.6 Hz, 2H), 7.34-7.30 (m, 3H), 7.24 (t, J = 7.2 Hz, 1H), 6.18 (d, J = 8.5 Hz, 1H), 4.95 (d, J = 5.9 Hz, 1H), 3.28-3.23 (m, 2H), 2.20 (s, 6H), 1.55 (d, J = 6.8 Hz, 3H). $^{13}$C NMR (151 MHz, CDCl3) δ 157.53, 148.64, 144.76, 138.84, 128.66, 127.01, 125.89, 122.74, 106.47, 61.02, 52.03, 44.96, 24.44, 24.42. HRMS (ESI): m/z (%) = 256.1811 (M + H$^+$). Purity >99%. |
| 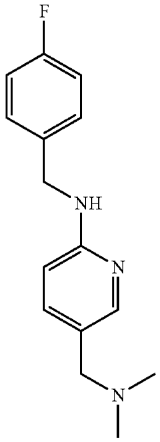 [SMILES: CN(C)Cc1ccc(NCc2ccc(F)cc2)nc1] | 419 (TR-YTH-019) | $^1$H NMR (600 MHz, CDCl3) δ 7.95 (d, J = 2.1 Hz, 1H), 7.37 (d, J = 7.6 Hz, 2H), 7.34-7.30 (m, 3H), 7.24 (t, J = 7.2 Hz, 1H), 6.18 (d, J = 8.5 Hz, 1H), 4.95 (d, J = 5.19 Hz, 1H), 3.28-3.23 (m, 2H), 2.20 (s, 6H). $^{13}$C NMR (151 MHz, CDCl3) δ 158.10, 147.24, 143.76, 136.52, 128.52, 127.20, 124.41, 122.74, 105.44, 60.02, 55.43, 44.10, 24.54, 24.44. HRMS (ESI): m/z (%) = 260.1599 (M + H$^+$). Purity >98%. |
| 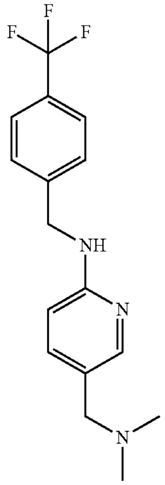 | 420 (TR-YTH-020) | $^1$H NMR (600 MHz, CDCl3) δ 7.99 (d, J = 2.0 Hz, 1H), 7.59 (d, J = 8.1 Hz, 2H), 7.48 (d, J = 8.0 Hz, 2H), 7.45 (d, J = 8.9 Hz, 1H), 6.37 (d, J = 8.5 Hz, 1H), 4.61 (d, J = 6.0 Hz, 2H), 3.33 (s, 2H), 2.25 (s, 6H). $^{13}$C NMR (151 MHz, CDCl3) δ 157.55, 149.64, 145.26, 138.56, 127.52, 126.23, 122.89, 106.86, 60.02, 52.23, 44.96, 24.40, 24.32. HRMS (ESI): m/z (%) = 310.1523 (M + H$^+$). Purity >98%. |

Inhibition Data for Compounds of Table 400 is Provided Below:
| Structure | | | | | Permeability (nm/s) | | $K_i$ (pM) | |
|---|---|---|---|---|---|---|---|---|
| $R_1$ | $R_2$ | $R_3$ | Name | clogP | Caco-2 | MDCK | YTHDF1 | YTHDF2 |
| 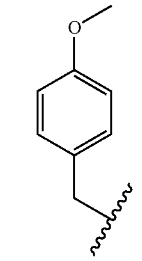 [SMILES: *Cc1ccc(OC)cc1] | H | 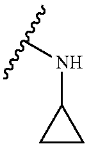 | TR-YTH-01 | 3.42 | 875 | 474 | 164 ± 21 | 102 ± 15 |
| 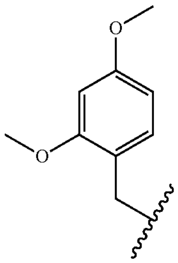 [SMILES: *Cc1ccc(OC)cc1OC] | H | 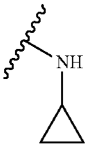 | TR-YTH-02 | 3.50 | 1051 | 577 | 229 ± 57 | 182 ± 69 |
| 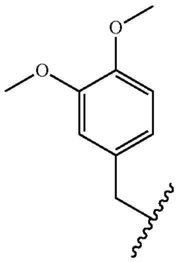 [SMILES: *Cc1ccc(OC)c(OC)c1] | H | 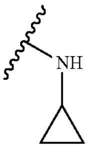 | TR-YTH-03 | 3.54 | 900 | 488 | 123 ± 6 | 85 ± 26 |
| 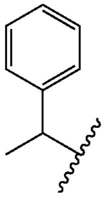 [SMILES: *C(C)c1ccccc1] | H | 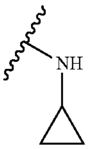 | TR-YTH-04 | 3.60 | 989 | 541 | 129 ± 6 | 100 ± 34 |
| 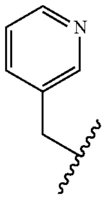 [SMILES: *Cc1cccnc1] | H | 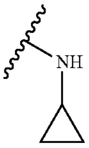 | TR-YTH-05 | 3.30 | 914 | 496 | 90 ± 10 | 70 ± 12 |
| 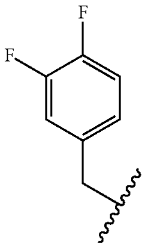 | H | 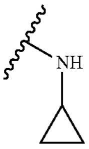 | TR-YTH-06 | 3.76 | 889 | 1477 | 285 ± 154 | 395 ± 51 |

-continued
| Structure | | | | | Permeability (nm/s) | | $K_i$ (pM) | |
|---|---|---|---|---|---|---|---|---|
| $R_1$ | $R_2$ | $R_3$ | Name | clogP | Caco-2 | MDCK | YTHDF1 | YTHDF2 |
| 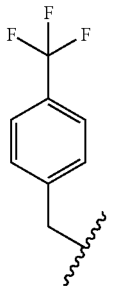 | H | 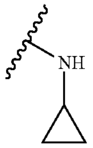 | TR-YTH-07 | 4.31 | 885 | 2116 | 162 ± 30 | 77 ± 18 |
| 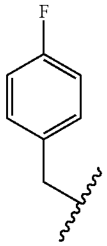 [SMILES: *Cc1ccc(F)cc1] | H | 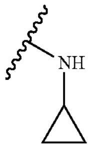 | TR-YTH-08 | 3.54 | 887 | 867 | 880 ± 194 | ND |
| 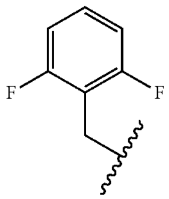 [SMILES: *Cc1c(F)cccc1F] | H | 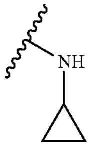 | TR-YTH-09 | 3.70 | 935 | 1282 | 281 ± 9 | 172 ± 49 |
| 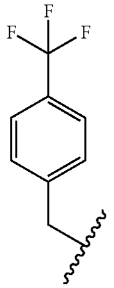 | $CH_3$ | 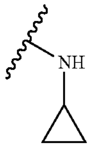 | TR-YTH-10 | 4.96 | 1490 | 3705 | 615 ± 107 | 106 ± 26 |
| 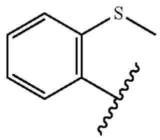 [SMILES: *c1ccccc1SC] | H | 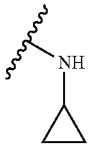 | TR-YTH-11 | 3.51 | 1058 | 861 | 13440 ± 4270 | 5590 ± 1400 |
| 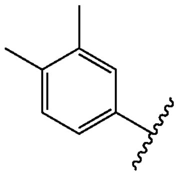 [SMILES: *c1ccc(C)c(C)c1] | H | 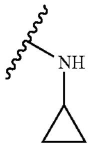 [SMILES: *NC1CC1] | TR-YTH-12 | 3.48 | 820 | 442 | 1421 ± 375 | 850 ± 115 |

-continued
| Structure | | | | | Permeability (nm/s) | | $K_i$ (pM) | |
|---|---|---|---|---|---|---|---|---|
| $R_1$ | $R_2$ | $R_3$ | Name | clogP | Caco-2 | MDCK | YTHDF1 | YTHDF2 |
| 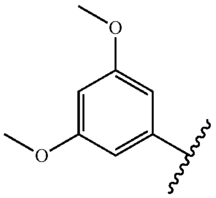 [SMILES: *c1cc(OC)cc(OC)c1] | H | 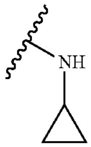 | TR-YTH-13 | 3.11 | 816 | 439 | 473 ± 95 | 150 ± 16 |
| 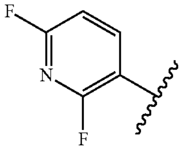 [SMILES: *c1ccc(F)nc1F] | H | 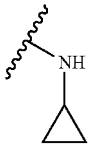 | TR-YTH-14 | 2.64 | 496 | 719 | 399 ± 40 | 128 ± 20 |
| 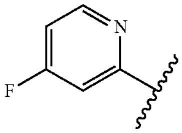 [SMILES: *c1cc(F)ccn1] | H | 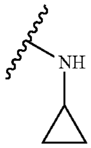 | TR-YTH-15 | 2.45 | 485 | 453 | 236 ± 51 | 145 ± 33 |
| 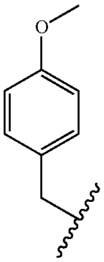 [SMILES: *Cc1ccc(OC)cc1] | H | 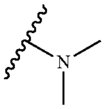 [SMILES: *N(C)C] | TR-YTH-16 | 3.31 | 1496 | 846 | 214 ± 50 | 179 ± 36 |
| 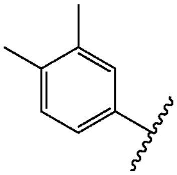 [SMILES: *c1ccc(C)c(C)c1] | H | 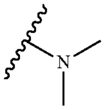 [SMILES: *N(C)C] | TR-YTH-17 | 3.42 | 1511 | 855 | 605 ± 104 | 333 ± 51 |
| 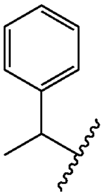 [SMILES: *C(C)c1ccccc1] | H | 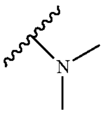 [SMILES: *N(C)C] | TR-YTH-18 | 3.43 | 1742 | 997 | 209 ± 27 | 95 ± 13 |
| 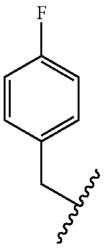 [SMILES: *Cc1ccc(F)cc1] | H | 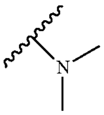 [SMILES: *N(C)C] | TR-YTH-19 | 3.44 | 1485 | 1512 | 391 ± 66 | 107 ± 19 |

-continued
| Structure | | | | | Permeability (nm/s) | | $K_i$ (pM) | |
|---|---|---|---|---|---|---|---|---|
| $R_1$ | $R_2$ | $R_3$ | Name | clogP | Caco-2 | MDCK | YTHDF1 | YTHDF2 |
| 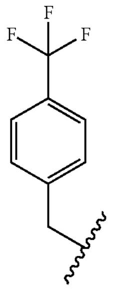 | H | 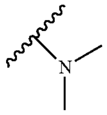 | TR-YTH-20 | 4.10 | 1499 | 3721 | ND | 266 ± 92 |
Ki Values for YTH Library Against YTHDF2
| Structure | Name | clogP | Caco-2 | MDCK | $K_i$ |
|---|---|---|---|---|---|
| 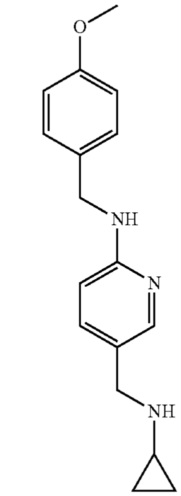 [SMILES: COc1ccc(CNc2ccc(CNC3CC3)cn2)cc1] | TR-YTH-01 | 3.42 | 875 | 474 | 102 ± 15 |
| 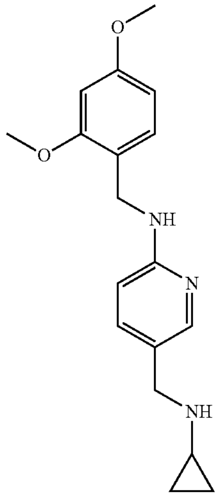 [SMILES: COc1ccc(CNc2ccc(CNC3CC3)cn2)c(OC)c1] | TR-YTH-02 | 3.50 | 1051 | 577 | 182 ± 69 |
-continued
| Structure | Name | clogP | Caco-2 | MDCK | $K_i$ |
|---|---|---|---|---|---|
| 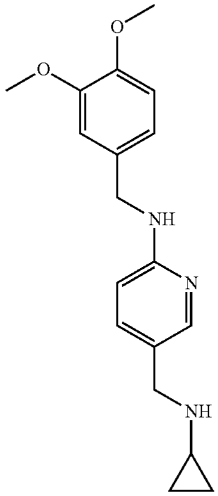 [SMILES: COc1ccc(CNc2ccc(CNC3CC3)cn2)cc1OC] | TR-YTH-03 | 3.54 | 900 | 488 | 85 ± 26 |
| 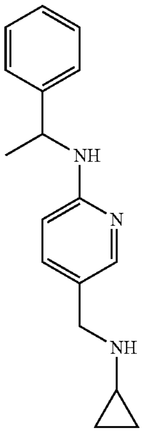 [SMILES: CC(Nc1ccc(CNC2CC2)cn1)c1ccccc1] | TR-YTH-04 | 3.60 | 989 | 541 | 100 ± 34 |

-continued
| Structure | Name | clogP | Caco-2 | MDCK | $K_i$ |
|---|---|---|---|---|---|
| 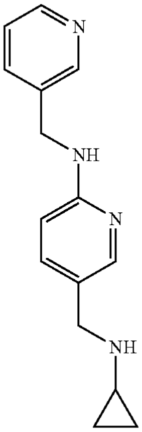 [SMILES: c1cncc(CNc2ccc(CNC3CC3)cn2)c1] | TR-YTH-05 | 3.30 | 914 | 496 | 70 ± 12 |
| 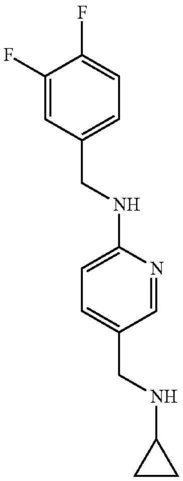 [SMILES: Fc1ccc(CNc2ccc(CNC3CC3)cn2)cc1F] | TR-YTH-06 | 3.76 | 889 | 1477 | 395 ± 51 |
| 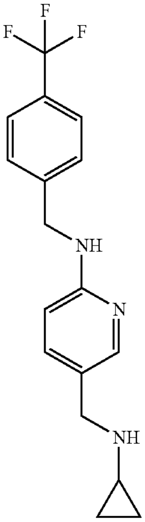 | TR-YTH-07 | 4.31 | 885 | 2116 | 77 ± 18 |
-continued
| Structure | Name | clogP | Caco-2 | MDCK | $K_i$ |
|---|---|---|---|---|---|
| 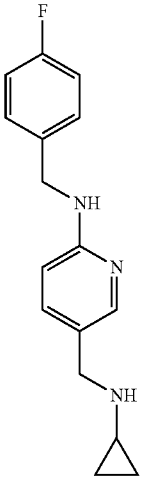 [SMILES: Fc1ccc(CNc2ccc(CNC3CC3)cn2)cc1] | TR-YTH-08 | 3.54 | 887 | 867 | ND |
| 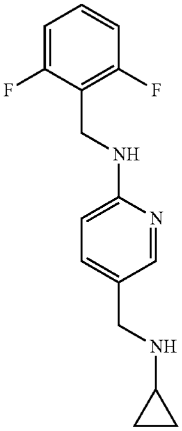 [SMILES: Fc1cccc(F)c1CNc1ccc(CNC2CC2)cn1] | TR-YTH-09 | 3.70 | 935 | 1282 | 172 ± 49 |
| 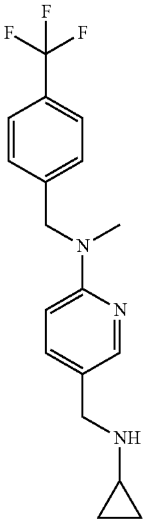 | TR-YTH-10 | 4.96 | 1490 | 3705 | 106 ± 26 |

Ki Values for YTH Library Against YTHDF2
| Structure | Name | clogP | Caco-2 | MDCK | $K_i$ |
|---|---|---|---|---|---|
| 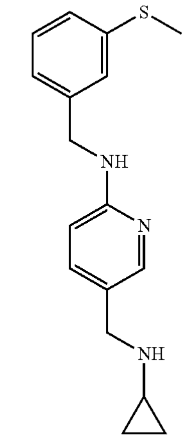 [SMILES: CSc1cccc(CNc2ccc(CNC3CC3)cn2)c1] | TR-YTH-11 | 3.51 | 1058 | 861 | 5590 ± 1400 |
| 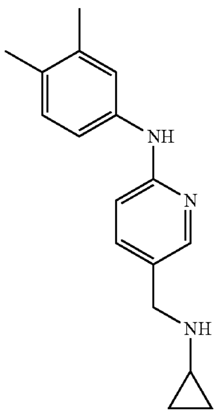 [SMILES: Cc1ccc(Nc2ccc(CNC3CC3)cn2)cc1C] | TR-YTH-12 | 3.48 | 820 | 442 | 850 ± 115 |
| 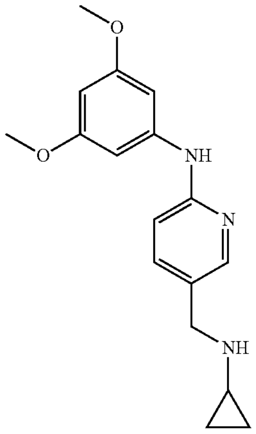 [SMILES: COc1cc(Nc2ccc(CNC3CC3)cn2)cc(OC)c1] | TR-YTH-13 | 3.11 | 816 | 439 | 150 ± 16 |
-continued
| Structure | Name | clogP | Caco-2 | MDCK | $K_i$ |
|---|---|---|---|---|---|
| 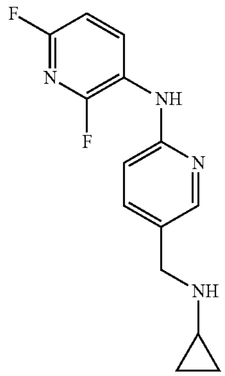 [SMILES: Fc1ccc(Nc2ccc(CNC3CC3)cn2)c(F)n1] | TR-YTH-14 | 2.64 | 496 | 719 | 128 ± 20 |
| 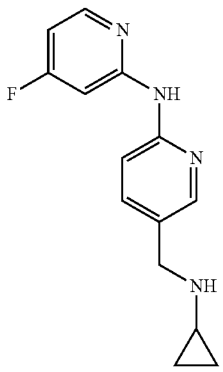 [SMILES: Fc1ccnc(Nc2ccc(CNC3CC3)cn2)c1] | TR-YTH-15 | 2.45 | 485 | 453 | 145 ± 33 |
| 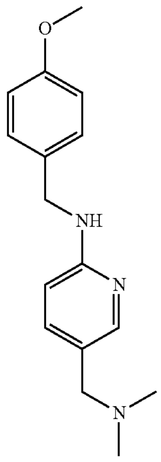 [SMILES: COc1ccc(CNc2ccc(CN(C)C)cn2)cc1] | TR-YTH-16 | 3.31 | 1496 | 846 | 179 ± 36 |
| 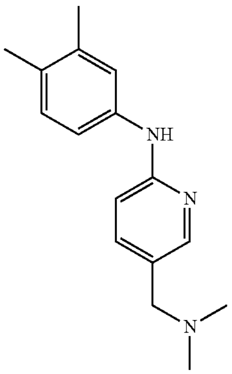 | TR-YTH-17 | 3.42 | 1511 | 855 | 333 ± 51 |

-continued
| Structure | Name | clogP | Caco-2 | MDCK | $K_i$ |
|---|---|---|---|---|---|
| 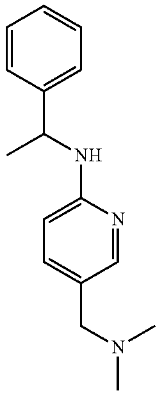 [SMILES: CC(Nc1ccc(CN(C)C)cn1)c1ccccc1] | TR-YTH-18 | 3.43 | 1742 | 997 | 95 ± 13 |
| 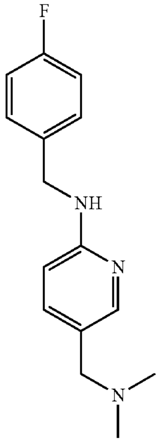 [SMILES: CN(C)Cc1ccc(NCc2ccc(F)cc2)nc1] | TR-YTH-19 | 3.44 | 1485 | 1512 | 107 ± 19 |
| 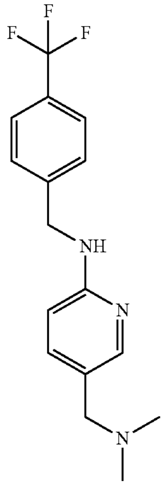 | TR-YTH-20 | 4.10 | 1499 | 3721 | 266 ± 92 |
Ki Values for YTH Library Against YTHDF2 and YTHDF1
| Structure | Name | $K_i$ YTHDF2 | $K_i$ YTHDF1 |
|---|---|---|---|
| 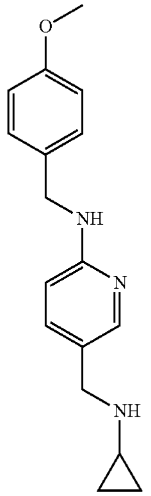 [SMILES: COc1ccc(CNc2ccc(CNC3CC3)cn2)cc1] | TR-YTH-01 | 102 ± 15 | 164 ± 21 |
| 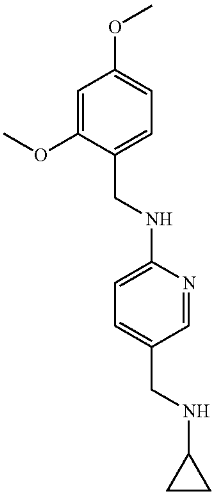 [SMILES: COc1ccc(CNc2ccc(CNC3CC3)cn2)c(OC)c1] | TR-YTH-02 | 182 ± 69 | 229 ± 57 |
| 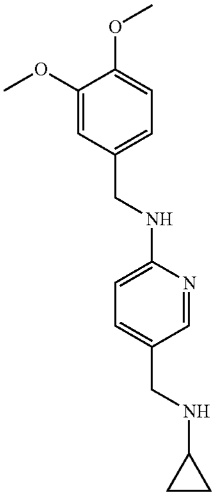 [SMILES: COc1ccc(CNc2ccc(CNC3CC3)cn2)cc1OC] | TR-YTH-03 | 85 ± 26 | 123 ± 6 |

-continued
| Structure | Name | $K_i$ YTHDF2 | $K_i$ YTHDF1 |
|---|---|---|---|
| 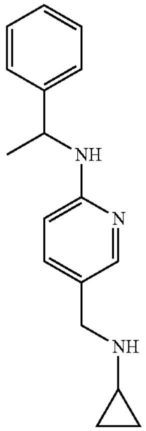 [SMILES: CC(Nc1ccc(CNC2CC2)cn1)c1ccccc1] | TR-YTH-04 | 100 ± 34 | 129 ± 6 |
| 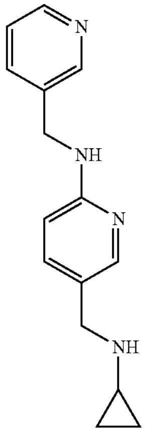 | TR-YTH-05 | 70 ± 12 | 90 ± 10 |
| 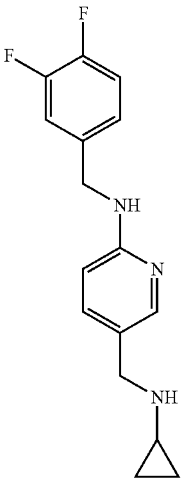 [SMILES: Fc1ccc(CNc2ccc(CNC3CC3)cn2)cc1F] | TR-YTH-06 | 395 ± 51 | 285 ± 154 |
-continued
| Structure | Name | $K_i$ YTHDF2 | $K_i$ YTHDF1 |
|---|---|---|---|
| 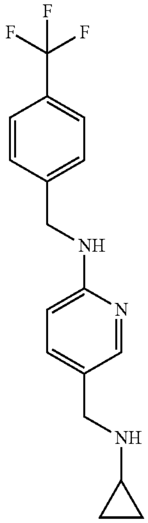 | TR-YTH-07 | 77 ± 18 | 162 ± 30 |
| 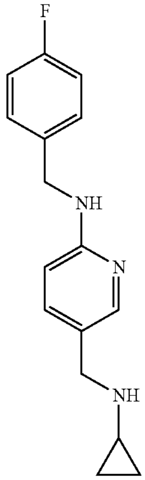 [SMILES: Fc1ccc(CNc2ccc(CNC3CC3)cn2)cc1] | TR-YTH-08 | ND | 880 ± 194 |
| 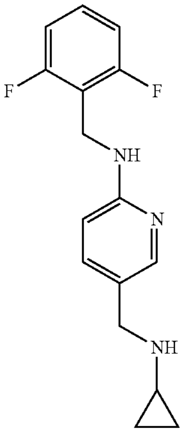 [SMILES: Fc1cccc(F)c1CNc1ccc(CNC2CC2)cn1] | TR-YTH-09 | 172 ± 49 | 281 ± 9 |

-continued
| Structure | Name | $K_i$ YTHDF2 | $K_i$ YTHDF1 |
|---|---|---|---|
| 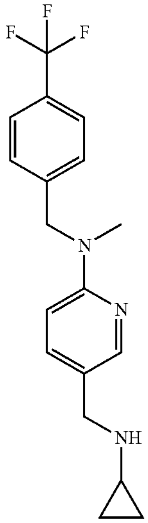 | TR-YTH-10 | 106 ± 26 | 615 ± 107 |
Ki Values for YTH Library Against YTHDF2 and YTHDF1
| Structure | Name | $K_i$ YTHDF2 | $K_i$ YTHDF1 |
|---|---|---|---|
| 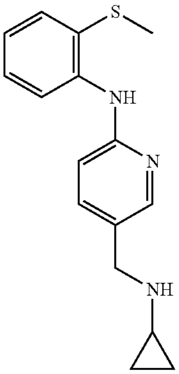 [SMILES: CSc1ccccc1Nc1ccc(CNC2CC2)cn1] | TR-YTH-11 | 5590 ± 1400 | 13440 ± 4270 |
| 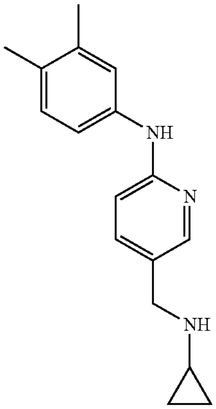 [SMILES: Cc1ccc(Nc2ccc(CNC3CC3)cn2)cc1C] | TR-YTH-12 | 850 ± 115 | 1421 ± 375 |
-continued
| Structure | Name | $K_i$ YTHDF2 | $K_i$ YTHDF1 |
|---|---|---|---|
| 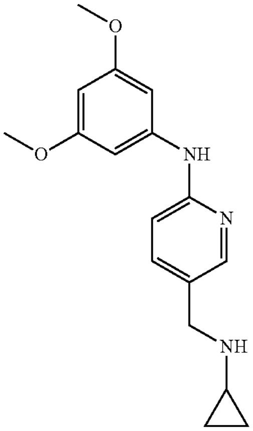 [SMILES: COc1cc(Nc2ccc(CNC3CC3)cn2)cc(OC)c1] | TR-YTH-13 | 150 ± 16 | 473 ± 95 |
| 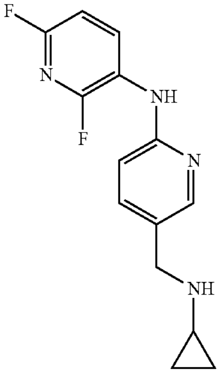 [SMILES: Fc1ccc(Nc2ccc(CNC3CC3)cn2)c(F)n1] | TR-YTH-14 | 128 ± 20 | 399 ± 40 |
| 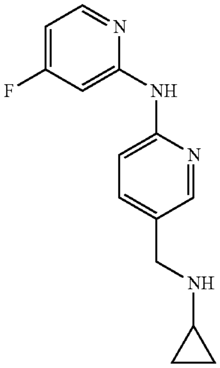 [SMILES: Fc1ccnc(Nc2ccc(CNC3CC3)cn2)c1] | TR-YTH-15 | 145 ± 33 | 236 ± 51 |

-continued
| Structure | Name | $K_i$ YTHDF2 | $K_i$ YTHDF1 |
|---|---|---|---|
| 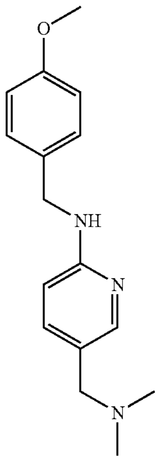 [SMILES: COc1ccc(CNc2ccc(CN(C)C)cn2)cc1] | TR-YTH-16 | 179 ± 36 | 214 ± 50 |
| 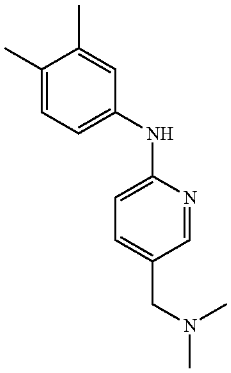 | TR-YTH-17 | 333 ± 51 | 605 ± 104 |
| 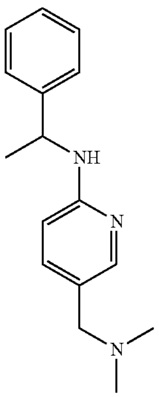 [SMILES: CC(Nc1ccc(CN(C)C)cn1)c1ccccc1] | TR-YTH-18 | 95 ± 13 | 209 ± 27 |
| 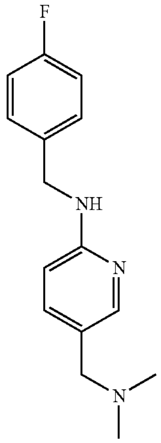 [SMILES: CN(C)Cc1ccc(NCc2ccc(F)cc2)nc1] | TR-YTH-19 | 107 ± 19 | 391 ± 66 |
| 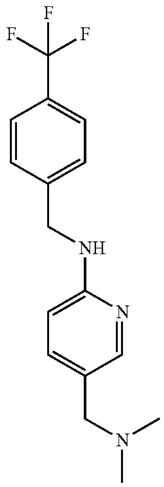 [SMILES: CN(C)Cc1ccc(NCc2ccc(C(F)(F)F)cc2)nc1] | TR-YTH-20 | 266 ± 92 | ND |
Example C5
Preparation of YTH Inhibitors (YTH "2" Inhibitors)
Scheme 5.
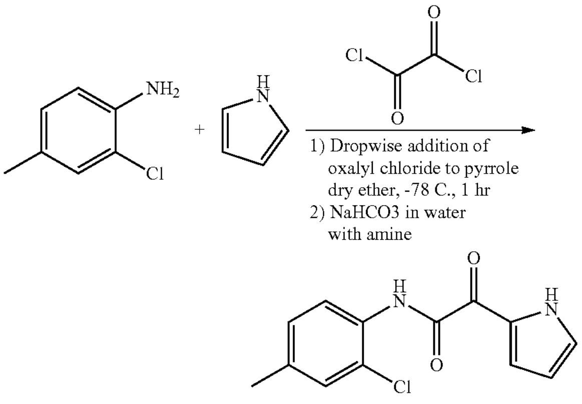
TR-YTH-03N TABLE 500
| STRUCTURE | ENTRY NUMBER (NAME) |
|---|---|
| 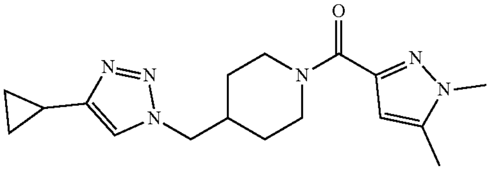 [SMILES: Cc1cc(C(=O)N2CCC(Cn3cc(C4CC4)nn3)CC2)nn1C] | 501 (TR-YTH2-01- aka (TR-YTH-06N) |
| 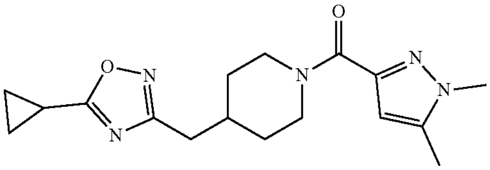 [SMILES: Cc1cc(C(=O)N2CCC(Cc3noc(C4CC4)n3)CC2)nn1C] | 502 (TR-YTH2-02- aka (TR-YTH-04N) |
| 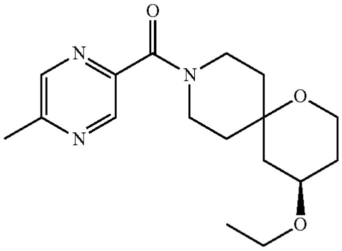 [SMILES: CCO[C@@H]1CCOC2(CCN(C(=O)c3cnc(C)cn3)CC2)C1] | 503 (TR-YTH2-03) |
| 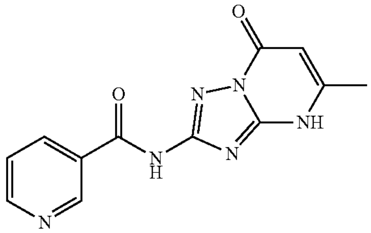 [SMILES: Cc1cc(=O)n2nc(NC(=O)c3cccnc3)nc2[nH]1] | 504 (TR-YTH2-04) |
| 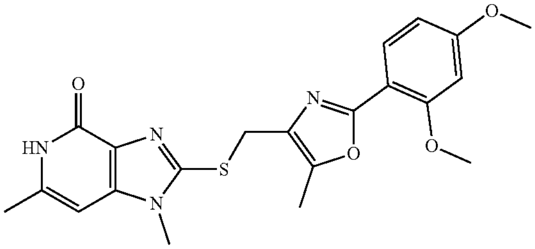 | 505 (TR-YTH2-05) |
| 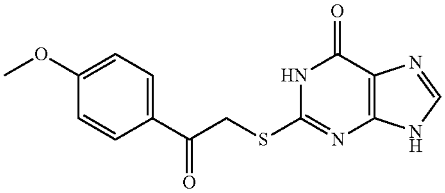 [SMILES: COc1ccc(C(=O)CSc2nc3[nH]cnc3c(=O)[nH]2)cc1] | 506 (TR-YTH2-06) |
| 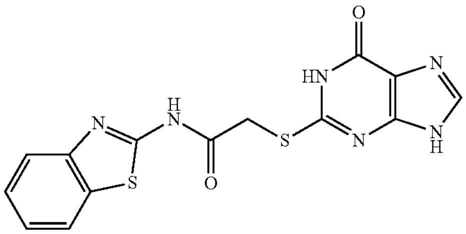 [SMILES: O=C(CSc1nc2[nH]cnc2c(=O)[nH]1)Nc1nc2ccccc2s1] | 507 (TR-YTH2-07) |

TABLE 500-continued
| STRUCTURE | ENTRY NUMBER (NAME) |
| --- | --- |
| 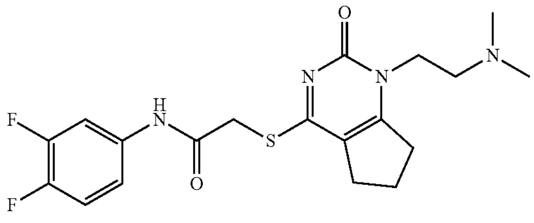 [SMILES: CN(C)CCn1c2c(c(SCC(=O)Nc3ccc(F)c(F)c3)nc1=O)CCC2] | 508 (TR-YTH2-08) |
| 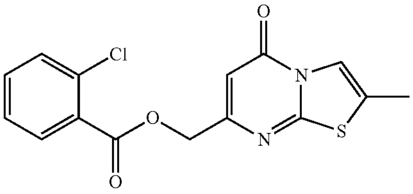 [SMILES: Cc1cn2c(=O)cc(COC(=O)c3ccccc3Cl)nc2s1] | 509 (TR-YTH2-09) |
| 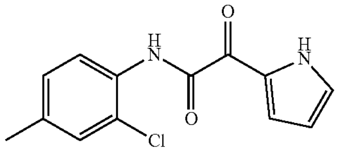 [SMILES: Cc1ccc(NC(=O)C(=O)c2ccc[nH]2)c(Cl)c1] | 510 (TR-YTH2-010-Ready) (TR-YTH-03N) |
| 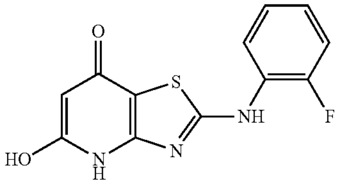 [SMILES: O=c1cc(O)[nH]c2nc(Nc3ccccc3F)sc12] | 511 (TR-YTH2-011) |
| 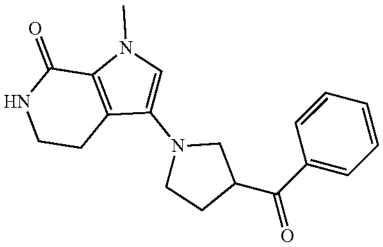 [SMILES: Cn1cc(N2CCC(C(=O)c3ccccc3)C2)c2c1C(=O)NCC2] | 512 (TR-YTH2-012) |

Inhibition Data for Compounds of Table 500: Enzymatic Ki Values—YTH Inhibitors
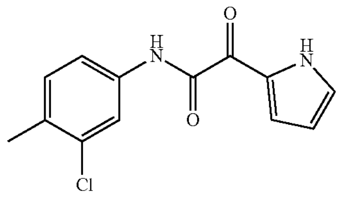
TR-YTH-03N
$K_iF1 = 0.94 \pm 0.62$ nM
$K_iF2 = 1.55 \pm 0.8$ nM
clogP = 3.12
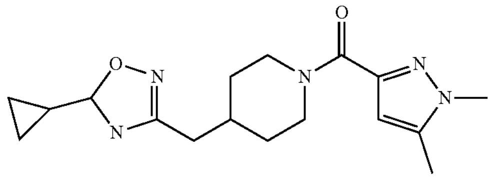
TR-YTH-04N
$K_iF1 = 497 \pm 44$ pM
$K_iF2 = 320 \pm 91$ pM
clogP = 2.58
-continued
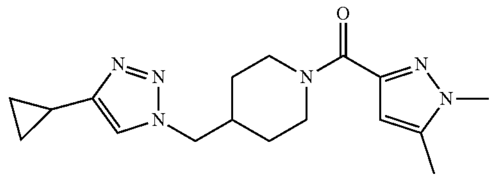
TR-YTH-05N
$K_iF1 = 333 \pm 48$ pM
$K_iF2 = 315 \pm 44$ pM
clogP = 3.08
Example C6
Preparation of TR-YTH-05N.
Scheme 6a.
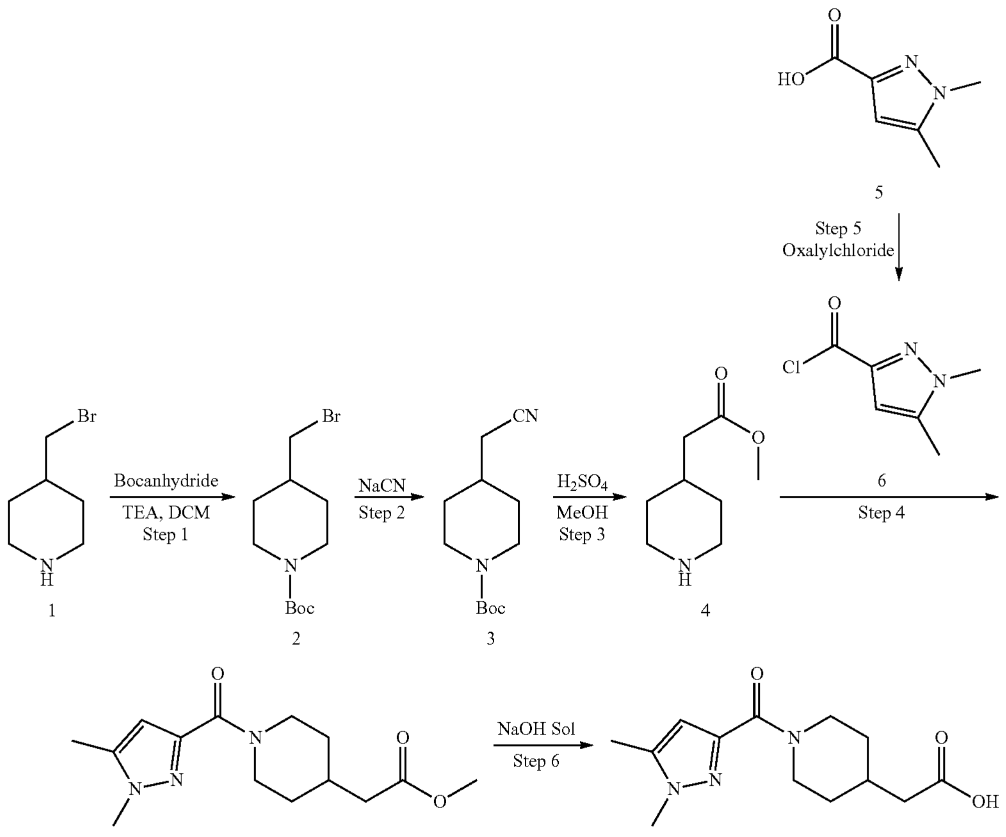

-continued
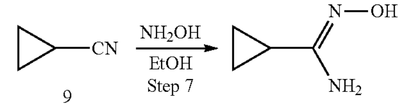
9
10
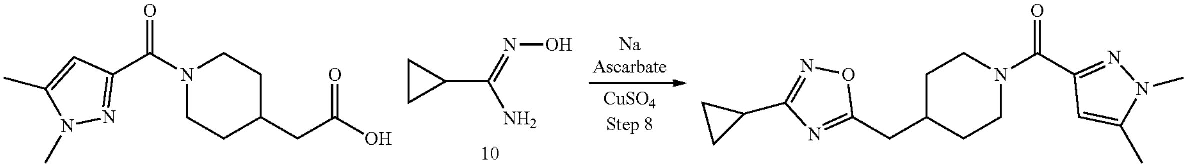
8
10
TR-YTH-05N
Preparation of TR-YTH-06N.
Scheme 6b.
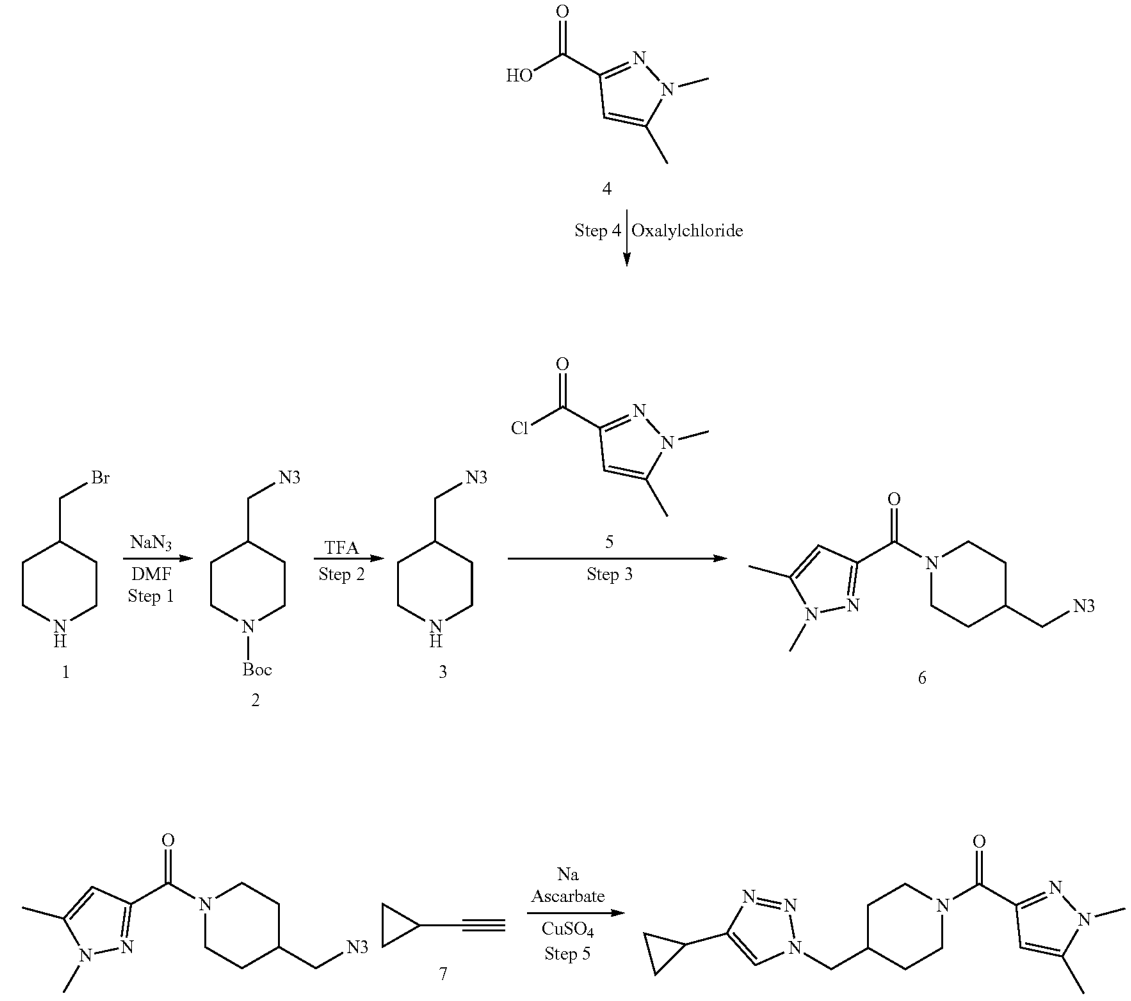
4
5
1
2
3
6
6
7
TR-YTH-06N The compounds in Table 600 are synthesized using similar methods as in Schemes 6a and 6b above.
TABLE 600
| STRUCTURE | ENTRY NUMBER (NAME) |
|---|---|
| 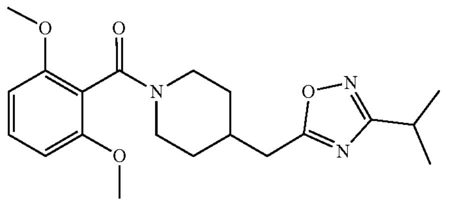 [SMILES: COc1cccc(OC)c1C(=O)N1CCC(Cc2nc(C(C)C)no2)CC1] | 601 (TR-YTH-2-01) |
| 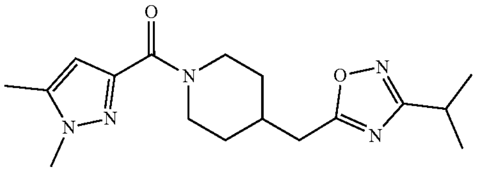 [SMILES: Cc1cc(C(=O)N2CCC(Cc3nc(C(C)C)no3)CC2)nn1C] | 602 (TR-YTH-2-02) |
| 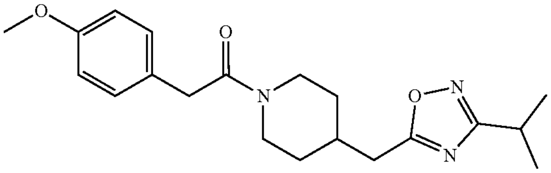 [SMILES: COc1ccc(CC(=O)N2CCC(Cc3nc(C(C)C)no3)CC2)cc1] | 603 (TR-YTH-2-03) |
| 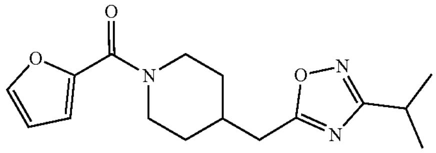 [SMILES: CC(C)c1noc(CC2CCN(C(=O)c3ccco3)CC2)n1] | 604 (TR-YTH-2-04) |
| 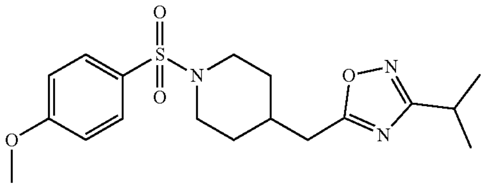 [SMILES: COc1ccc(S(=O)(=O)N2CCC(Cc3nc(C(C)C)no3)CC2)cc1] | 605 (TR-YTH-2-05) |
| 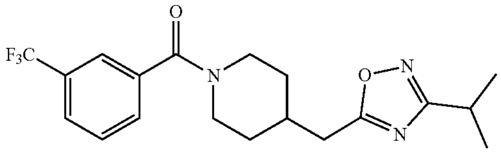 [SMILES: CC(C)c1noc(CC2CCN(C(=O)c3cccc(C(F)(F)F)c3)CC2)n1] | 606 (TR-YTH-2-06) |
| 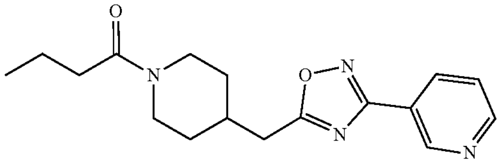 [SMILES: CCCC(=O)N1CCC(Cc2nc(-c3cccnc3)no2)CC1] | 607 (TR-YTH-2-07) |
| 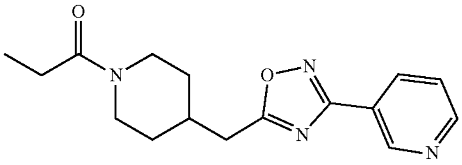 [SMILES: CCC(=O)N1CCC(Cc2nc(-c3cccnc3)no2)CC1] | 608 (TR-YTH-2-08) |

TABLE 600-continued
| STRUCTURE | ENTRY NUMBER (NAME) |
|---|---|
| 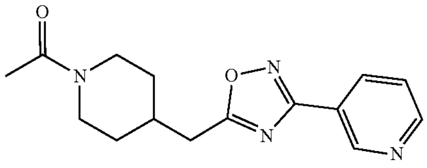 [SMILES: CC(=O)N1CCC(Cc2nc(-c3cccnc3)no2)CC1] | 609 (TR-YTH-2-09) |
| 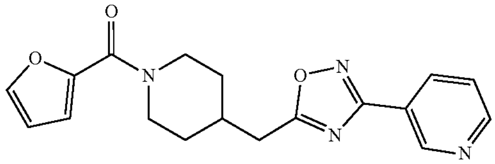 [SMILES: O=C(c1ccco1)N1CCC(Cc2nc(-c3cccnc3)no2)CC1] | 610 (TR-YTH-2-010) |
| 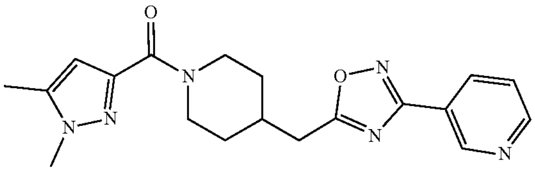 [SMILES: Cc1cc(C(=O)N2CCC(Cc3nc(-c4cccnc4)no3)CC2)nn1C] | 611 (TR-YTH-2-011) |
| 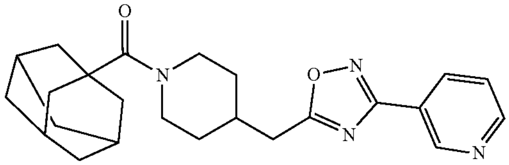 [SMILES: O=C(N1CCC(Cc2nc(-c3cccnc3)no2)CC1)C12CC3CC(CC(C3)C1)C2] | 612 (TR-YTH-2-012) |
| 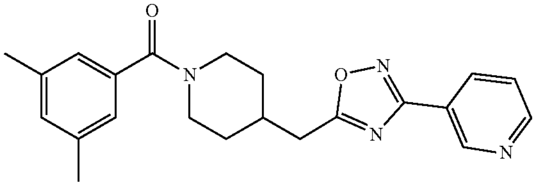 [SMILES: Cc1cc(C)cc(C(=O)N2CCC(Cc3nc(-c4cccnc4)no3)CC2)c1] | 613 (TR-YTH-2-013) |
| 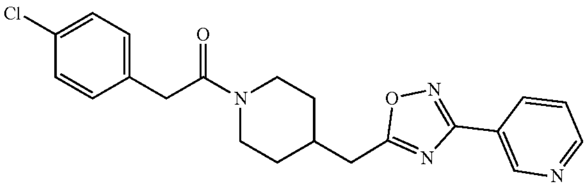 [SMILES: O=C(Cc1ccc(Cl)cc1)N1CCC(Cc2nc(-c3cccnc3)no2)CC1] | 614 (TR-YTH-2-014) |
| 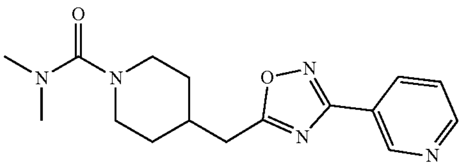 [SMILES: CN(C)C(=O)N1CCC(Cc2nc(-c3cccnc3)no2)CC1] | 615 (TR-YTH-2-015) |
| 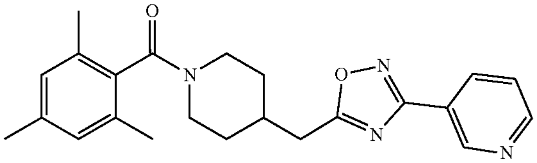 [SMILES: Cc1cc(C)c(C(=O)N2CCC(Cc3nc(-c4cccnc4)no3)CC2)c(C)c1] | 616 (TR-YTH-2-016) |

TABLE 600-continued
| STRUCTURE | ENTRY NUMBER (NAME) |
| --- | --- |
| 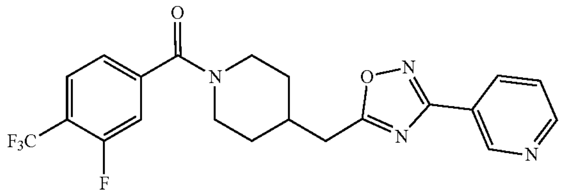 [SMILES: O=C(c1ccc(C(F)(F)F)c(F)c1)N1CCC(Cc2nc(-c3cccnc3)no2)CC1] | 617 (TR-YTH-2-017) |
| 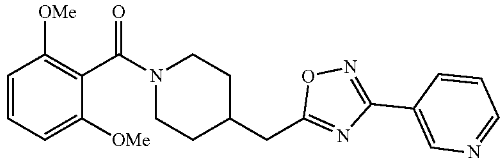 [SMILES: COc1cccc(OC)c1C(=O)N1CCC(Cc2nc(-c3cccnc3)no2)CC1] | 618 (TR-YTH-2-018) |
| 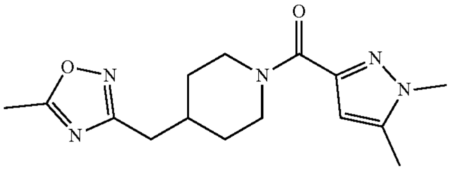 | 619 |
| 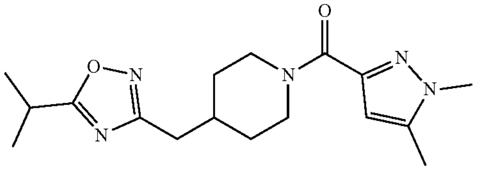 [SMILES: Cc1cc(C(=O)N2CCC(Cc3noc(C(C)C)n3)CC2)nn1C] | 620 |
| 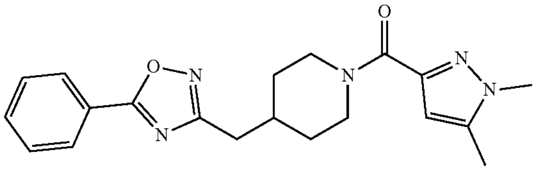 [SMILES: Cc1cc(C(=O)N2CCC(Cc3noc(-c4ccccc4)n3)CC2)nn1C] | 621 |
| 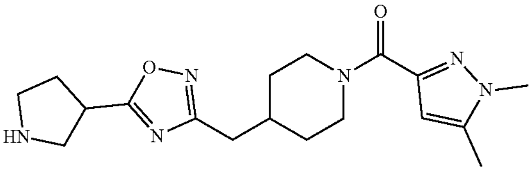 [SMILES: Cc1cc(C(=O)N2CCC(Cc3noc(C4CCNC4)n3)CC2)nn1C] | 622 |
| 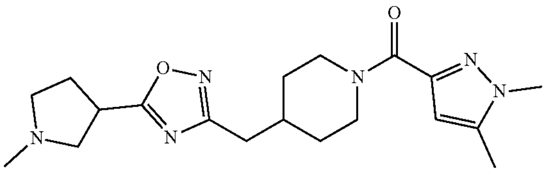 | 623 |
| 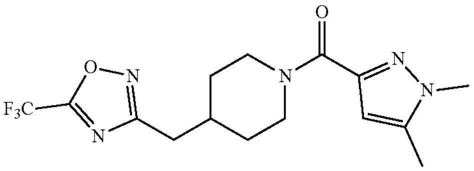 [SMILES: Cc1cc(C(=O)N2CCC(Cc3noc(C(F)(F)F)n3)CC2)nn1C] | 624 |

TABLE 600-continued
| STRUCTURE | ENTRY NUMBER (NAME) |
|---|---|
| 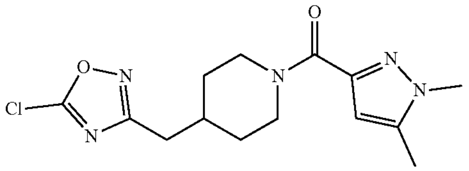 [SMILES: Cc1cc(C(=O)N2CCC(Cc3noc(Cl)n3)CC2)nn1C] | 625 |
| 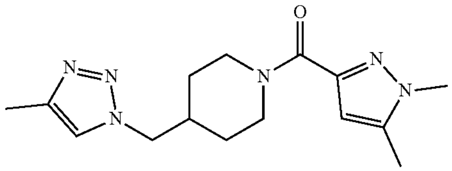 | 626 |
| 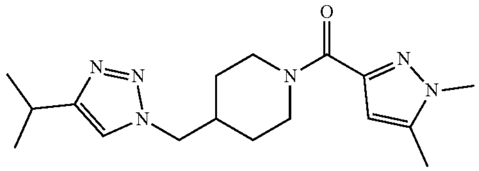 [SMILES: Cc1cc(C(=O)N2CCC(Cn3cc(C(C)C)nn3)CC2)nn1C] | 627 |
| 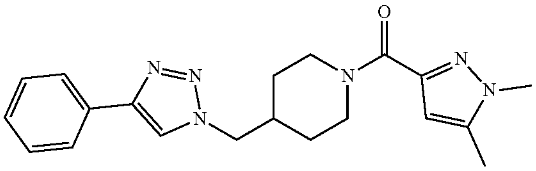 [SMILES: Cc1cc(C(=O)N2CCC(Cn3cc(-c4ccccc4)nn3)CC2)nn1C] | 628 |
| 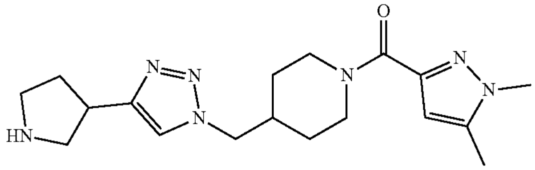 [SMILES: Cc1cc(C(=O)N2CCC(Cn3cc(C4CCNC4)nn3)CC2)nn1C] | 629 |
| 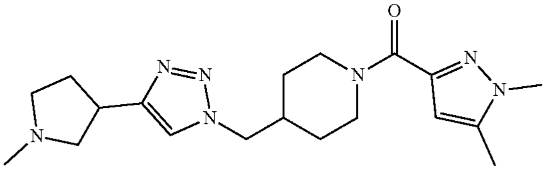 | 630 |
| 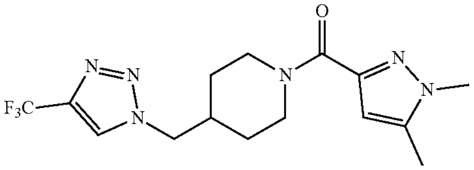 [SMILES: Cc1cc(C(=O)N2CCC(Cn3cc(C(F)(F)F)nn3)CC2)nn1C] | 631 |
| 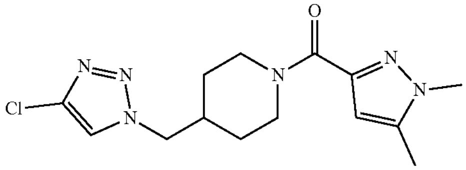 [SMILES: Cc1cc(C(=O)N2CCC(Cn3cc(Cl)nn3)CC2)nn1C] | 632 |

Example C7

General Procedure for the Preparation of Exemplary ALKBH5 Inhibitor (e.g., Compounds of Formula (A1) (e.g., Compounds of Table 700)):

Scheme 7.

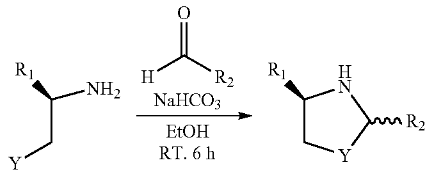

$R_1$ = H, COOH, $COOCH_3$
$R_2$ = Ar
Y = OH, SH

For example, the method of Scheme 7 can be used to synthesize:

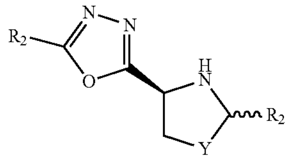

and/or the compounds in Table 700.

TABLE 700

| STRUCTURE | ENTRY NUMBER (NAME |
| --- | --- |
| 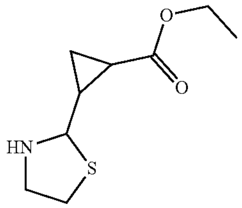 | 701 (ALK-01) |
| 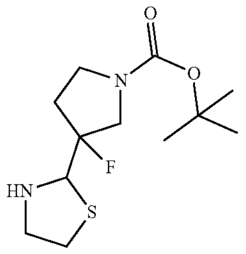 [SMILES: CC(C)(C)OC(=O)N1CCC(F)(C2NCCS2)C1] | 702 (ALK-02) |
| 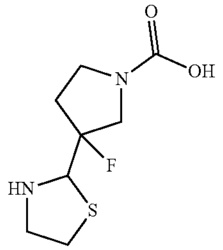 [SMILES: O=C(O)N1CCC(F)(C2NCCS2)C1] | 703 (ALK-03) |

TABLE 700-continued

| STRUCTURE | ENTRY NUMBER (NAME |
| --- | --- |
| 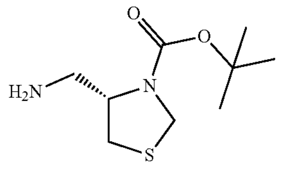 | 704 (ALK-04) |
| 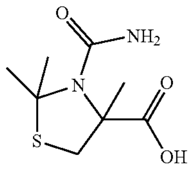 | 705 (ALK-05) |
| 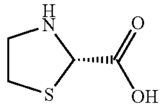 | 706 (ALK-06) |
| 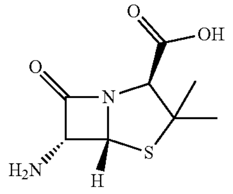 | 707 (ALK-07) |
| 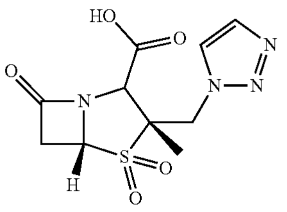 [SMILES: C[C@]1(Cn2ccnn2)C(C(=O)O)N2C(=O)C[C@H]2S1(=O)=O] | 708 (ALK-08) |
| 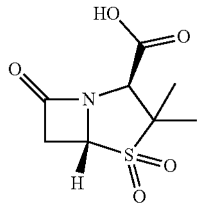 | 709 (ALK-09) |
| 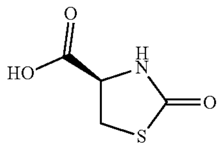 | 710 (ALK-10) |
| 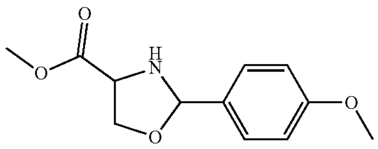 | 712 (ALK-12) |

TABLE 700-continued
| STRUCTURE | ENTRY NUMBER (NAME |
|---|---|
| 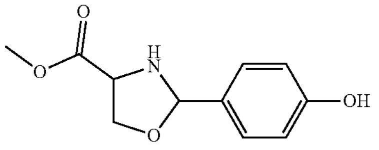 [SMILES: COC(=O)C1COC(c2ccc(O)cc2)N1] | 713 (ALK-13) |
| 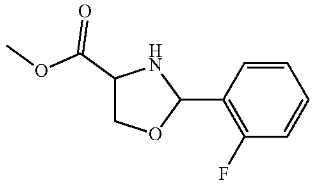 [SMILES: COC(=O)C1COC(c2ccccc2F)N1] | 714 (ALK-14) |
| 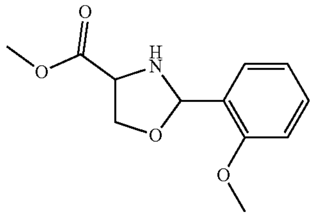 [SMILES: COC(=O)C1COC(c2ccccc2OC)N1] | 715 (ALK-15) |
| 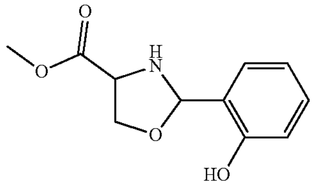 | 716 (ALK-16) |
| 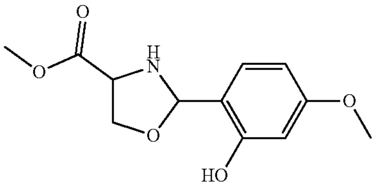 | 717 (ALK-17) |
| 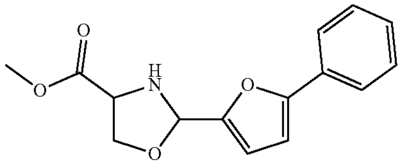 [SMILES: COC(=O)C1COC(c2ccc(-c3ccccc3)o2)N1] | 718 (ALK-18) |
| 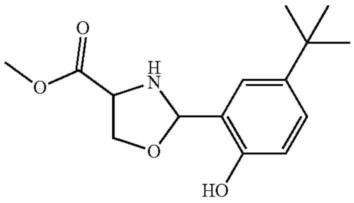 [SMILES: COC(=O)C1COC(c2cc(C(C)(C)C)ccc2O)N1] | 719 (ALK-19) |
| 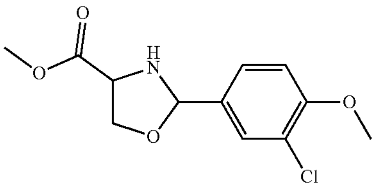 | 723 (ALK-23) |
TABLE 700-continued
| STRUCTURE | ENTRY NUMBER (NAME |
|---|---|
| 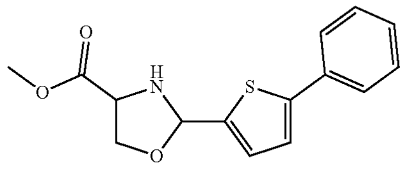 [SMILES: COC(=O)C1COC(c2ccc(-c3ccccc3)s2)N1] | 725 (ALK-25) |
| 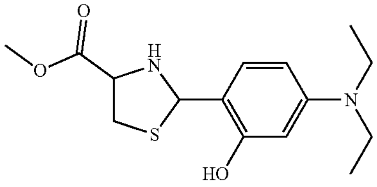 [SMILES: CCN(CC)c1ccc(C2NC(C(=O)OC)CS2)c(O)c1] | 730 (ALK-30) |
| 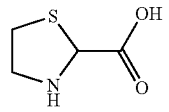 | |
| 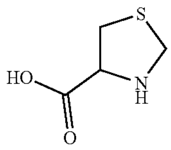 | |
| 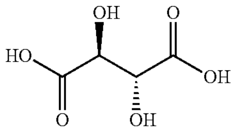 | |
| 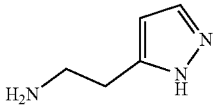 | |
| 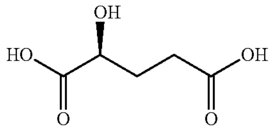 | |
| 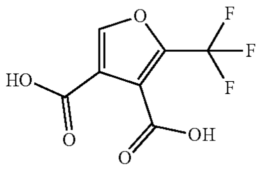 [SMILES: O=C(O)c1coc(C(F)(F)F)c1C(=O)O] | |

Inhibition Data for Compounds of Table 700:
TABLE 700
| COMPOUNDS INHIBITION DATA | | | | |
|---|---|---|---|---|
| Structure | Name | Enzymatic $IC_{50}$ ALKBH5 | Enzymatic $IC_{50}$ FTO | elogD |
| 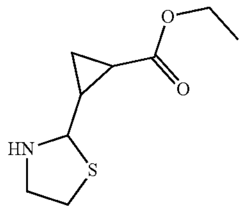 | ALK-01 | 17.5 ± 4.5 | >40 | 0.58 |
| 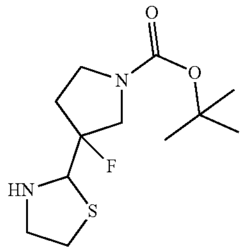 [SMILES: CC(C)(C)OC(=O)N1CCC(F)(C2NCCS2)C1] | ALK-02 | 16.6 ± 2.7 | >40 | 1.40 |
| 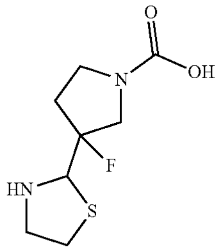 [SMILES: O=C(O)N1CCC(F)(C2NCCS2)C1] | ALK-03 | >40 | >40 | 0.62 |
| 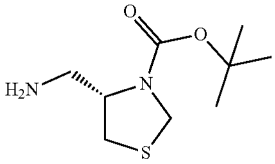 | ALK-04 | 0.9 ± 0.7 | >40 | 0.29 |
| 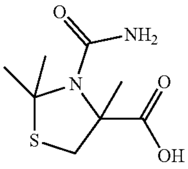 | ALK-05 | 19.8 ± 1.8 | >40 | 0.16 |
| 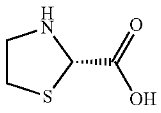 | ALK-06 | 8.8 ± 1.1 | >40 | 0.89 |
| 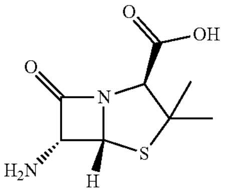 | ALK-07 | 10.0 ± 2.8 | >40 | 0.95 |

TABLE 700-continued
COMPOUNDS INHIBITION DATA
| Structure | Name | Enzymatic $IC_{50}$ ALKBH5 | Enzymatic $IC_{50}$ FTO | elogD |
|---|---|---|---|---|
| 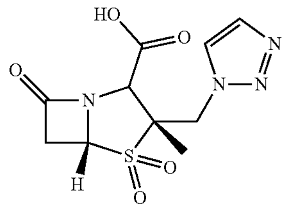 [SMILES: C[C@]1(Cn2ccnn2)C(C(=O)O)N2C(=O)C[C@H]2S1(=O)=O] | ALK-08 | 9.9 ± 1.3 | >40 | 0.36 |
| 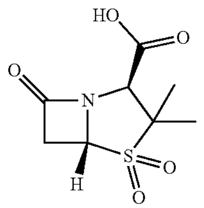 | ALK-09 | 3.8 ± 2.3 | >40 | 0.41 |
| 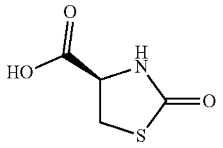 | ALK-10 | 1.7 ± 1.1 | >40 | 0.54 |
| 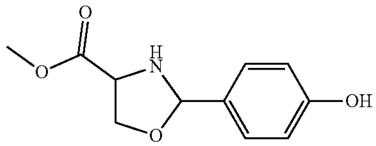 [SMILES: COC(=O)C1COC(c2ccc(O)cc2)N1] | ALK-13 | 6.7 ± 1.8 | >40 | 2.12 |
| 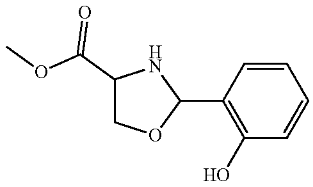 [SMILES: COC(=O)C1COC(c2ccccc2O)N1] | ALK-16 | 8.2 ± 2.3 | >40 | 1.44 |
| 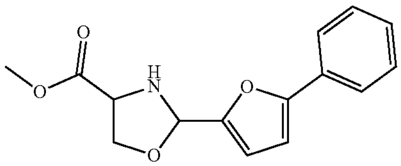 | ALK-18 | 5.4 ± 0.7 | 14.2 ± 3.1 | 0.73 |
| 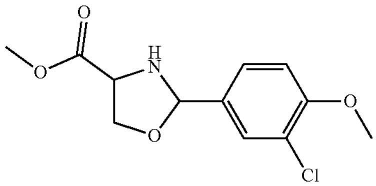 | ALK-23 | 2.8 ± 0.5 | >40 | 3.01 |
| 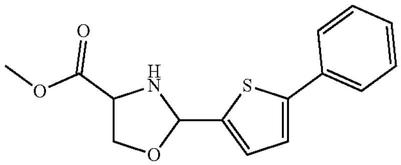 | ALK-25 | 0.9 ± 0.2 | >40 | 1.17 |

TABLE 700-continued
COMPOUNDS INHIBITION DATA
| Structure | Name | Enzymatic $IC_{50}$ ALKBH5 | Enzymatic $IC_{50}$ FTO | elogD |
|---|---|---|---|---|
| 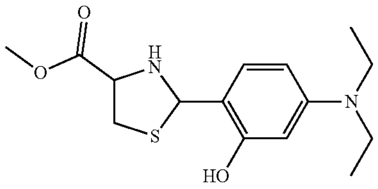 [SMILES: CCN(CC)c1ccc(C2NC(C(=O)OC)CS2)c(O)c1] | ALK-30 | 1.4 ± 0.4 | >40 | 0.67 |
| 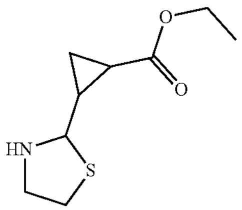 | ALK-01 | 17.5 | 103.3 | 0.58 |
| 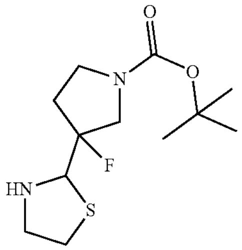 [SMILES: CC(C)(C)OC(=O)N1CCC(F)(C2NCCS2)C1] | ALK-02 | 16.6 | >40 | 1.40 |
| 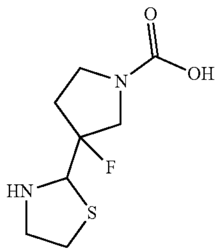 [SMILES: O=C(O)N1CCC(F)(C2NCCS2)C1] | ALK-03 | >40 | >40 | 0.62 |
| 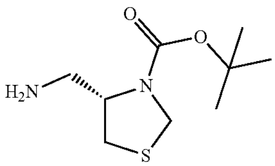 | ALK-04 | 0.9 | >40 | 0.29 |
| 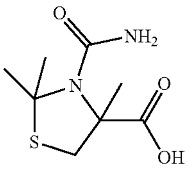 | ALK-05 | 19.8 | >40 | 0.16 |
| 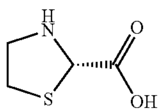 | ALK-06 | 7.95 | >40 | 0.89 |

TABLE 700-continued
| COMPOUNDS INHIBITION DATA | | | | |
|---|---|---|---|---|
| Structure | Name | Enzymatic $IC_{50}$ ALKBH5 | Enzymatic $IC_{50}$ FTO | elogD |
| 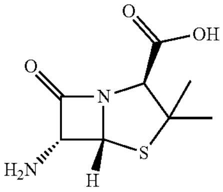 | ALK-07 | 10.0 | >40 | 0.95 |
| 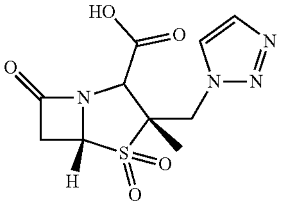 [SMILES: C[C@]1(Cn2ccnn2)C(C(=O)O)N2C(=O)C[C@H]2S1(=O)=O] | ALK-08 | 9.9 | >40 | 0.36 |
| 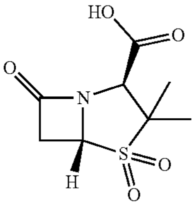 | ALK-09 | 5.7 | >40 | 0.41 |
| 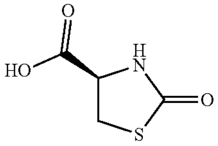 | ALK-10 | 1.7 | >40 | 0.54 |
Permeability Data and IC50
| Structure | Name | ClogP | Caco-2 | MDCK | logBB | Enzymatic $IC_{50}$ ALKBH5 |
|---|---|---|---|---|---|---|
| 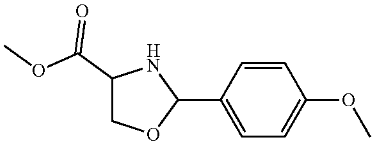 | ALK-12 | 1.05 | 523 | 271 | 0.20 | 16.7 ± 2.6 |
| 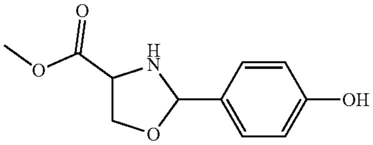 [SMILES: COC(=O)C1COC(c2ccc(O)cc2)N1] | ALK-13 | 0.25 | 161 | 76 | −0.24 | 6.7 ± 1.8 |
| 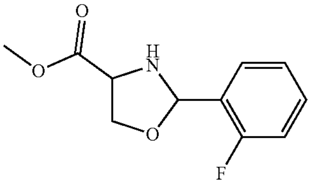 [SMILES: COC(=O)C1COC(c2ccccc2F)N1] | ALK-14 | 1.07 | 510 | 428 | 0.37 | 29.8 ± 2.9 |

-continued
| Structure | Name | ClogP | Caco-2 | MDCK | logBB | Enzymatic $IC_{50}$ ALKBH5 |
|---|---|---|---|---|---|---|
| 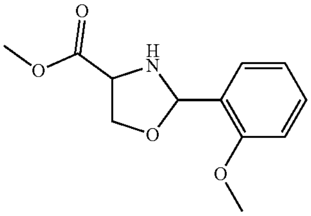 [SMILES: COC(=O)C1COC(c2ccccc2OC)N1] | ALK-15 | 0.96 | 491 | 258 | 0.20 | 18.2 ± 2.3 |
Permeability Data and IC50
| Structure | Name | ClogP | Caco-2 | MDCK | logBB | Enzymatic $IC_{50}$ ALKBH5 |
|---|---|---|---|---|---|---|
| 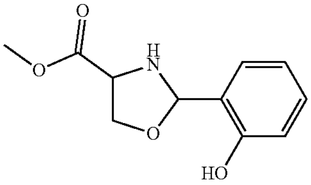 [SMILES: COC(=O)C1COC(c2ccccc2O)N1] | ALK-16 | 0.42 | 251 | 211 | −0.07 | 8.2 ± 2.3 |
| 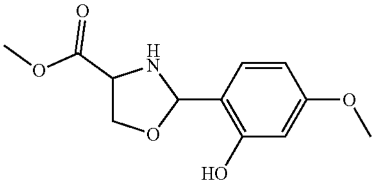 | ALK-17 | 0.44 | 218 | 105 | 0.20 | 18.2 ± 2.8 |
| 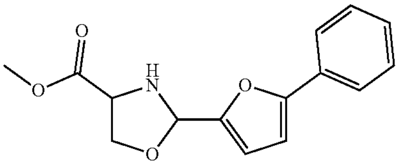 | ALK-18 | 1.88 | 518 | 105 | 0.24 | 5.4 ± 1.4 |
| 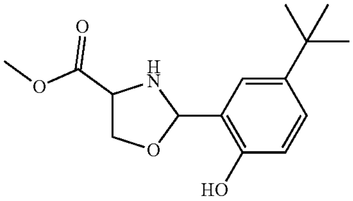 [SMILES: COC(=O)C1COC(c2cc(C(C)(C)C)ccc2O)N1] | ALK-19 | 1.49 | 218 | 105 | −0.23 | 24.0 ± 4.2 |

Example C8

General Procedure for the Preparation of ALKBH5 Inhibitors (e.g., Compounds of Formula (A2A), (A2B), and (A2C) (e.g., Compounds of Table 800)):

Scheme 8a.

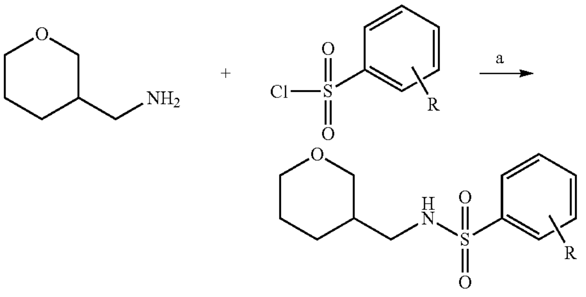

Scheme 8b.

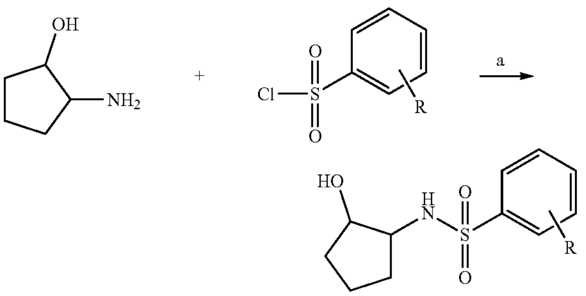

Schemes 8a, 8b, 8c.

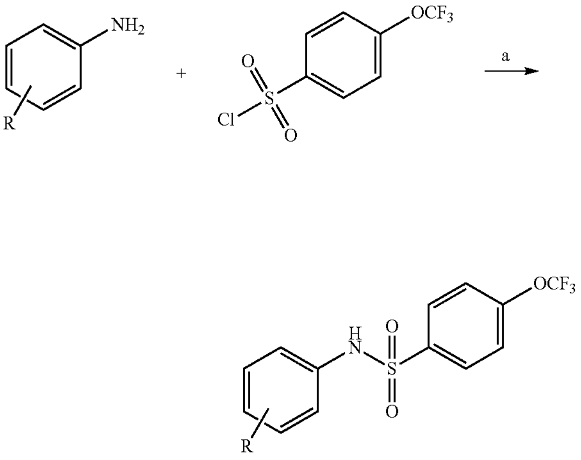

Reagents and conditions: a) Triethylamine, DCM, 1 h.

Step a. Synthesis of Compounds (5-58).

A two-necked round-bottomed flask was charged with corresponding sulfonylchloride (1 eq.) in DCM and followed by the addition of corresponding amine (1 eq.), and followed by the addition of TEA (1 eq.). The reaction mixture was stirred for 1 h at room temperature and after completion of starting materials to the reaction mass add excess of DCM and washed with brine and water. The organic layer was separate and concentrate under reduced pressure. The crude material was purified by flash column chromatography ethyl acetate:hexane (3:7) to give the final compound.

TABLE 800

| STRUCTURE | ENTRY NUMBER (NAME) | Analytical Data |
|---|---|---|
| 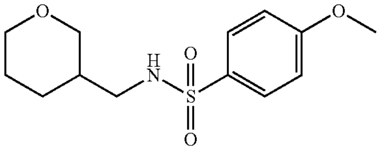 | 801 (TR-ALKBH5-01) | $^1$H NMR (600 MHz, CDCl3) δ 7.81-7.78 (m, 2H), 7.01-6.97 (m, 2H), 4.66 (t, J = 6.5 Hz, 1H), 3.89 (d, J = 3.7 Hz, 3H), 3.85-3.76 (m, 2H), 3.43-3.36 (m, 1H), 3.15 (dd, J = 11.3, 8.8 Hz, 1H), 2.84-2.80 (m, 2H), 1.82-1.72 (m, 2H), 1.62-1.52 (m, 2H), 1.26-1.22 (m, 1H). $^{13}$C NMR (151 MHz, CDCl3) δ 162.94, 131.25, 129.22, 114.36, 70.80, 68.45, 55.64, 45.20, 35.88, 27.02, 24.73. HRMS (ESI): m/z (%) = 339.9670 (M + H$^+$). Purity >98%. |
| 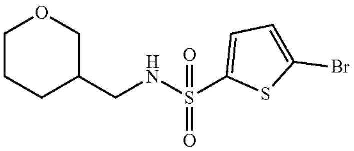 [SMILES: O=S(=O)(NCC1CCCOC1)c1ccc(Br)s1] | 802 (TR-ALKBH5-02) (TR-ALK-02) | $^1$H NMR (600 MHz, CDCl3) δ 7.37-7.35 (m, 1H), 7.09-7.07 (m, 1H), 4.78 (d, J = 4.6 Hz, 1H), 3.88-3.84 (m, 1H), 3.81 (dt, J = 11.2, 4.2 Hz, 1H), 3.48-3.42 (m, 1H), 3.22 (dd, J = 11.3, 8.4 Hz, 1H), 2.95 (td, J = 6.6, 4.3 Hz, 2H), 1.87-1.78 (m, 2H), 1.64 (t, J = 6.0 Hz, 1H), 1.60-1.55 (m, 1H), 1.34-1.28 (m, 1H). $^{13}$C NMR (151 MHz, CDCl3) δ 141.55, 132.28, 130.48, 119.86, 70.60, 68.50, 45.43, 35.79, 26.99, 24.60. HRMS (ESI): m/z (%) = 315.1677 (M + H$^+$). Purity >96%. |
| 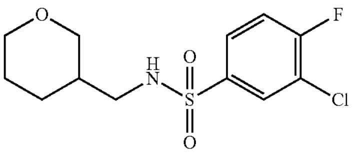 [SMILES: O=S(=O)(NCC1CCCOC1)c1ccc(F)c(Cl)c1] | 803 (TR-ALKBH5-03) | $^1$H NMR (600 MHz, CDCl3) δ 7.94 (dd, J = 6.6, 2.3 Hz, 1H), 7.77 (ddd, J = 8.6, 4.3, 2.3 Hz, 1H), 7.31-7.27 (m, 1H), 4.91 (t, J = 6.3 Hz, 1H), 3.86-3.77 (m, 2H), 3.47-3.41 (m, 1H), 3.20 (dd, J = 11.3, 8.4 Hz, 1H), 2.93-2.84 (m, 2H), 1.85-1.73 (m, 2H), 1.66-1.52 (m, 2H), 1.32-1.25 (m, 1H). $^{13}$C NMR (151 MHz, CDCl3) δ 161.45, 159.74, 136.98, 136.95, 130.01, 130.00, 127.53, 127.48, 122.58, 122.45, 117.62, 117.47, 70.57, 68.50, 45.23, 35.88, 26.91, 24.53. HRMS (ESI): m/z (%) = 308.0521 (M + H$^+$). Purity >98%. |

TABLE 800-continued

| STRUCTURE | ENTRY NUMBER (NAME) | Analytical Data |
| --- | --- | --- |
| 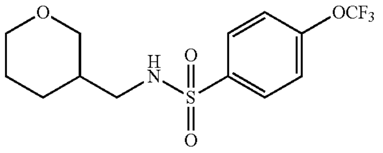 [SMILES: O=S(=O)(NCC1CCCOC1)c1ccc(OC(F)(F)F)cc1] | 804 (TR-ALKBH5-04) | $^1$H NMR (600 MHz, CDCl3) δ 7.94-7.90 (m, 2H), 7.36 (d, J = 8.6 Hz, 2H), 4.82 (t, J = 6.4 Hz, 1H), 3.86-3.75 (m, 2H), 3.46-3.39 (m, 1H), 3.19 (dd, J = 11.3, 8.4 Hz, 1H), 2.93-2.85 (m, 2H), 1.78 (dddd, J = 14.1, 12.0, 8.3, 4.0 Hz, 2H), 1.65-1.52 (m, 2H), 1.28 (ddd, J = 9.3, 8.3, 4.4 Hz, 1H). $^{13}$C NMR (151 MHz, CDCl3) δ 152.19, 152.18, 138.23, 129.21, 121.12, 121.11, 119.40, 70.61, 68.49, 68.48, 45.24, 35.90, 26.91, 24.54. HRMS (ESI): m/z (%) = 340.0825 (M + H$^+$). Purity >95%. |
| 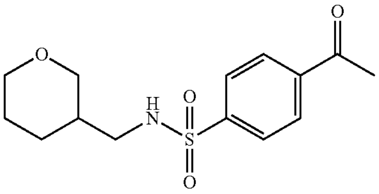 [SMILES: CC(=O)c1ccc(S(=O)(=O)NCC2CCCOC2)cc1] | 805 (TR-ALKBH5-05) | $^1$H NMR (600 MHz, CDCl3) δ 8.09 (d, J = 8.5 Hz, 2H), 7.96 (t, J = 6.1 Hz, 2H), 4.89 (t, J = 6.3 Hz, 1H), 3.85-3.76 (m, 2H), 3.45-3.39 (m, 1H), 3.18 (dd, J = 11.3, 8.5 Hz, 1H), 2.93-2.85 (m, 2H), 2.67 (s, 3H), 1.82-1.73 (m, 2H), 1.61 (ddd, J = 12.9, 8.9, 4.3 Hz, 1H), 1.57-1.49 (m, 1H), 1.30-1.25 (m, 1H). $^{13}$C NMR (151 MHz, CDCl3) δ 196.98, 196.98, 143.81, 140.03, 129.11, 129.10, 127.34, 70.60, 68.47, 45.26, 36.91, 26.99, 26.92, 24.56. HRMS (ESI): m/z (%) = 298.1110 (M + H$^+$). Purity >96%. |
| 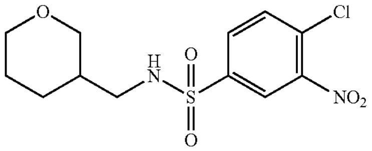 [SMILES: O=[N+]([O-])c1cc(S(=O)(=O)NCC2CCCOC2)ccc1Cl] | 806 (TR-ALKBH5-06) | $^1$H NMR (600 MHz, CDCl3) δ 8.35 (d, J = 2.1 Hz, 1H), 7.99 (dd, J = 8.4, 2.1 Hz, 1H), 7.75 (t, J = 6.4 Hz, 1H), 5.08 (t, J = 6.3 Hz, 1H), 3.86-3.76 (m, 2H), 3.50-3.43 (m, 1H), 3.23 (dd, J = 11.3, 8.2 Hz, 1H), 2.99-2.89 (m, 2H), 1.87-1.75 (m, 2H), 1.65 (ddt, J = 13.3, 8.7, 4.5 Hz, 1H), 1.60-1.53 (m, 1H), 1.35-1.28 (m, 1H). $^{13}$C NMR (151 MHz, CDCl3) δ 147.93, 140.30, 133.15, 131.71, 131.06, 124.40, 70.41, 68.53, 45.28, 35.88, 26.85, 24.41. HRMS (ESI): m/z (%) = 357.0284 (M + Na)$^+$. Purity >96%. |
| 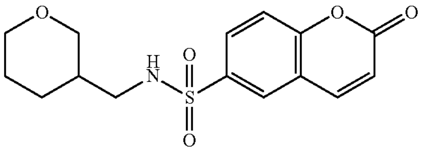 [SMILES: O=c1ccc2cc(S(=O)(=O)NCC3CCCOC3)ccc2o1] | 807 (TR-ALKBH5-07) | $^1$H NMR (600 MHz, CDCl3) δ 8.06 (d, J = 2.0 Hz, 1H), 7.99 (dd, J = 8.7, 2.1 Hz, 1H), 7.78 (d, J = 9.6 Hz, 1H), 7.47 (d, J = 8.7 Hz, 1H), 6.57 (d, J = 9.6 Hz, 1H), 4.94 (t, J = 6.3 Hz, 1H), 3.86-3.75 (m, 2H), 3.46-3.39 (m, 1H), 3.20 (dd, J = 11.3, 8.3 Hz, 1H), 2.93-2.86 (m, 2H), 1.83-1.74 (m, 2H), 1.62 (ddt, J = 13.0, 8.7, 4.4 Hz, 1H), 1.57-1.49 (m, 1H), 1.33-1.27 (m, 1H). $^{13}$C NMR (151 MHz, CDCl3) δ 159.63, 156.33, 142.77, 136.24, 130.02, 127.55, 119.00, 118.38, 118.12, 70.61, 68.47, 45.23, 35.91, 26.92, 24.55. HRMS (ESI): m/z (%) = 324.0902 (M + H$^+$). Purity >98%. |
| 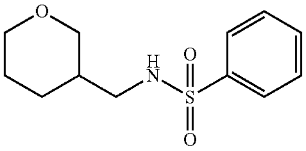 [SMILES: O=S(=O)(NCC1CCCOC1)c1ccccc1] | 808 (TR-ALKBH5-08) (TR-ALK-08) | $^1$H NMR (600 MHz, CDCl3) δ 7.87 (d, J = 7.5 Hz, 2H), 7.60 (t, J = 7.4 Hz 1H), 7.53 (t, J = 7.7 Hz, 2H), 4.89 (t, J = 6.3 Hz, 1H), 3.86-3.75 (m, 2H), 3.44-3.35 (m, 1H), 3.16 (dd, J = 11.2, 8.8 Hz, 1H), 2.89-2.82 (m, 2H), 1.83-1.73 (m, 2H), 1.63-1.50 (m, 2H), 1.30-1.25 (m, 1H). $^{13}$C NMR (151 MHz, CDCl3) δ 139.78, 132.76, 129.23, 127.02, 70.73, 68.45, 45.21, 35.95, 35.91, 26.96, 24.68. HRMS (ESI): m/z (%) = 256.1007 (M + H$^+$). Purity >99%. |
| 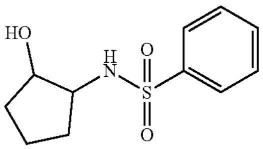 [SMILES: O=S(=O)(NC1CCCC1O)c1ccccc1] | 809 (TR-ALKBH5-09) | $^1$H NMR (600 MHz, CDCl3) δ 7.93-7.90 (m, 2H), 7.63-7.59 (m, 1H), 7.56-7.52 (m, 2H), 5.25-5.16 (m, 1H), 4.06 (dd, J = 13.5, 6.9 Hz, 1H), 3.31-3.22 (m, 1H), 2.03-1.96 (m, 1H), 1.89 (dtd, J = 13.1, 7.9, 5.1 Hz, 1H), 1.69-1.58 (m, 2H), 1.58-1.50 (m, 1H), 1.39-1.31 (m, 1H). $^{13}$C NMR (151 MHz, CDCl3) δ 139.90, 132.91, 129.27, 127.18, 78.13, 61.83, 31.24, 30.06, 19.86. HRMS (ESI): m/z (%) = 264.0670 (M + Na$^+$). Purity >96%. |
| 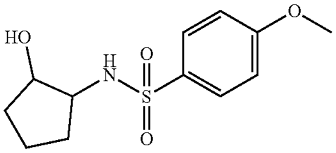 [SMILES: COc1ccc(S(=O)(=O)NC2CCCC2O)cc1] | 810 (TR-ALKBH5-010) | $^1$H NMR (600 MHz, CDCl3) δ 7.85-7.83 (m, 2H), 7.02-6.98 (m, 2H), 4.87 (d, J = 5.3 Hz, 1H), 4.06 (dd, J = 13.5, 6.9 Hz, 1H), 3.91-3.87 (m, 3H), 3.25-3.18 (m, 1H), 2.04-1.97 (m, 1H), 1.95-1.88 (m, 1H), 1.69-1.61 (m, 2H), 1.59-1.53 (m, 1H), 1.40-1.33 (m, 1H). $^{13}$C NMR (151 MHz, CDCl3) δ 163.07, 131.23, 129.43, 114.40, 78.29, 61.82, 31.37, 30.29, 19.92. HRMS (ESI): m/z (%) = 272.0955 (M + H$^+$). Purity >99%. |
| 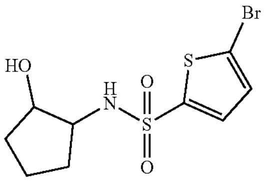 [SMILES: O=S(=O)(NC1CCCC1O)c1ccc(Br)s1] | 811 (TR-ALKBH5-011) | $^1$H NMR (600 MHz, CDCl3) δ 7.43-7.41 (m, 1H), 7.09 (d, J = 4.0 Hz, 1H), 5.17 (d, J = 4.5 Hz, 1H), 4.08 (dd, J = 13.3, 6.7 Hz, 1H), 3.41-3.32 (m, 1H), 2.06-2.00 (m, 2H), 1.76-1.65 (m, 2H), 1.59 (ddt, J = 13.3, 9.5, 6.6 Hz, 1H), 1.43 (dq, J = 12.7, 8.0 Hz, 1H). $^{13}$C 13C NMR (151 MHz, CDCl3) δ 141.47, 132.85, 130.60, 120.25, 78.13, 62.20, 31.44, 30.16, 20.01. HRMS (ESI): m/z (%) = 347.9336 (M + Na$^+$). Purity >98%. |

TABLE 800-continued

| STRUCTURE | ENTRY NUMBER (NAME) | Analytical Data |
|---|---|---|
| 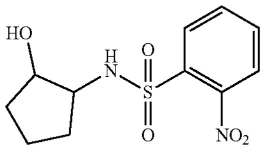 | 812 (TR-ALKBH5-012) | $^1$H NMR (600 MHz, CDCl3) δ 8.20-8.18 (m, 1H), 7.91-7.88 (m, 1H), 7.80-7.76 (m, 2H), 5.44 (d, J = 4.6 Hz, 1H), 3.48-3.40 (m, 1H), 2.04-1.95 (m, 2H), 1.74-1.67 (m, 2H), 1.58 (ddt, J = 13.3, 9.2, 6.5 Hz, 1H), 1.50-1.43 (m, 1H). $^{13}$C NMR (151 MHz, CDCl3) δ 148.00, 133.84, 133.65, 133.03, 131.42, 125.55, 78.27, 62.57, 60.52, 31.60, 30.40, 21.14, 20.15, 14.24. HRMS (ESI): m/z (%) = 309.0516 (M + Na$^+$). Purity >96%. |
| 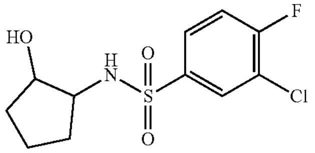 [SMILES: O=S(=O)(NC1CCCC1O)c1ccc(F)c(Cl)c1] | 813 (TR-ALKBH5-013) | $^1$H NMR (600 MHz, CDCl3) δ 7.99 (dd, J = 6.6, 2.3 Hz, 1H), 7.82 (ddd, J = 8.5, 4.3, 2.3 Hz, 1H), 7.31 (t, J = 8.5 Hz, 1H), 5.17 (d, J = 6.2 Hz, 1H), 4.06 (dd, J = 13.5, 6.9 Hz, 1H), 3.35-3.25 (m, 1H), 2.04-1.91 (m, 2H), 1.73-1.62 (m, 2H), 1.57 (ddt, J = 13.5, 9.5, 6.8 Hz, 1H), 1.37 (dq, J = 13.3, 8.5 Hz, 1H), $^{13}$C NMR (151 MHz, CDCl3) δ 141.47, 132.85, 130.60, 120.25, 78.13, 62.20, 31.44, 30.16, 20.01. HRMS (ESI): m/z (%) = 316.0185 (M + Na$^+$). Purity >97%. |
| 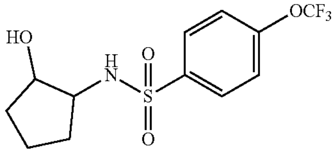 [SMILES: O=S(=O)(NC1CCCC1O)c1ccc(OC(F)(F)F)cc1] | 814 (TR-ALKBH5-014) | $^1$H NMR (600 MHz, CDCl3) δ 7.99-7.95 (m, 2H), 7.36 (d, J = 8.5 Hz, 2H), 5.16 (s, 1H), 4.07 (dd, J = 13.5, 6.9 Hz, 1H), 3.32-3.24 (m, 1H), 2.05-1.89 (m, 2H), 1.72-1.61 (m, 2H), 1.56 (ddt, J = 13.5, 9.5, 6.7 Hz, 1H), 1.37 (dq, J = 13.3, 8.5 Hz, 1H), $^{13}$C NMR (151 MHz, CDCl3) δ 152.28, 152.27, 138.30, 129.58, 129.39, 121.04, 78.11, 61.88, 31.29, 30.11, 19.81. HRMS (ESI): m/z (%) = 348.0489 (M + Na$^+$). Purity >96%. |
| 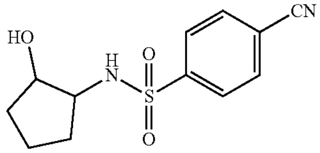 [SMILES: N#Cc1ccc(S(=O)(=O)NC2CCCC2O)cc1] | 815 (TR-ALKBH5-015) | $^1$H NMR (600 MHz, CDCl3) δ 8.19 (d, J = 7.9 Hz, 1H), 7.89 (d, J = 7.6 Hz, 1H), 7.81-7.77 (m, 1H), 7.72 (td, J = 7.5, 1.0 Hz, 1H), 5.46 (d, J = 7.6 Hz, 1H), 4.12-4.05 (m, 1H), 3.37-3.27 (m, 1H), 2.48 (d, J = 90.0 Hz, 1H), 2.00 (dt, J = 19.0, 6.2 Hz, 2H), 1.70-1.64 (m, 2H), 1.58-1.44 (m, 2H). $^{13}$C NMR (151 MHz, CDCl3) δ 143.11, 135.65, 135.13, 133.94, 133.50, 133.28, 132.73, 130.08, 122.59, 121.08, 116.36, 109.89, 77.94, 77.33, 77.19, 77.12, 76.91, 65.11, 62.02, 32.29, 31.36, 30.17, 27.26, 22.31, 19.94. HRMS (ESI): m/z (%) = 267.0803 (M + H$^+$). Purity >965%. |
| 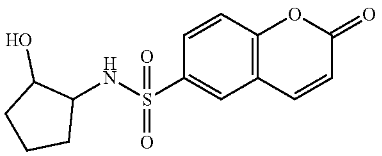 [SMILES: O=c1ccc2cc(S(=O)(=O)NC3CCCC3O)ccc2o1] | 816 (TR-ALKBH5-016) | $^1$H NMR (600 MHz, CDCl3) δ 8.06 (d, J = 2.1 Hz, 1H), 7.98 (dd, J = 8.7, 2.1 Hz, 1H), 7.79 (d, J = 9.6 Hz, 1H), 7.42 (d, J = 8.7 Hz, 1H), 6.51 (d, J = 9.6 Hz, 1H), 3.93 (dd, J = 13.2, 6.7 Hz, 1H), 3.21-3.15 (m, 1H), 1.95-1.79 (m, 2H), 1.63-1.55 (m, 2H), 1.47 (ddt, J = 11.1, 7.1, 5.5 Hz, 1H), 1.31 (dq, J = 13.4, 8.3 Hz, 1H). $^{13}$C NMR (151 MHz, DMSO) δ 159.79, 155.93, 144.25, 144.10, 138.12, 130.21, 130.09, 127.89, 127.74, 119.21, 76.50, 76.40, 40.41, 40.27, 40.13, 39.99, 39.86, 39.72, 39.58, 20.67. HRMS (ESI): m/z (%) = 332.0559 (M + Na$^+$). Purity >98%. |
| 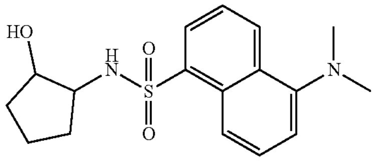 [SMILES: CN(C)c1cccc2c(S(=O)(=O)NC3CCCC3O)cccc12] | 817 (TR-ALKBH5-017) | $^1$H NMR (600 MHz, CDCl3) δ 8.57 (d, J = 8.5 Hz, 3H), 8.27 (dd, J = 11.5, 8.0 Hz, 6H), 7.60-7.52 (m, 6H), 7.20 (d, J = 7.5 Hz, 3H), 5.14 (dd, J = 24.3, 3.7 Hz, 3H), 4.05-3.98 (m, 3H), 3.24-3.13 (m, 2H), 2.90 (s, 20H), 2.79 (d, J = 2.1 Hz, 3H), 2.00-1.89 (m, 3H), 1.74 (dt, J = 13.4, 6.6 Hz, 4H), 1.56 (dd, J = 9.1, 5.0 Hz, 4H), 1.52-1.45 (m, 2H). $^{13}$C NMR (151 MHz, CDCl3) δ 171.35, 152.04, 134.50, 130.74, 129.95, 129.91, 129.58, 128.53, 123.31, 118.66, 115.29, 78.25, 62.07, 60.50, 45.47, 31.25, 30.18, 21.13, 19.87, 14.23. HRMS (ESI): m/z (%) = 335.1418 (M + H$^+$). Purity >96%. |
| 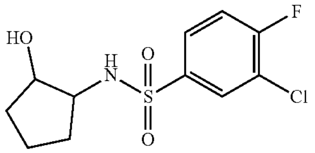 [SMILES: O=S(=O)(NC1CCCC1O)c1ccc(F)c(Cl)c1] | 818 (TR-ALKBH5-018) | $^1$H NMR (600 MHz, CDCl3) δ 7.99 (dd, J = 6.6, 2.2 Hz, 1H), 7.82 (ddd, J = 8.6, 4.2, 2.3 Hz, 1H), 7.30 (t, J = 8.5 Hz, 1H), 5.27 (d, J = 6.2 Hz, 1H), 4.06 (dd, J = 13.6, 6.9 Hz, 1H), 3.33-3.25 (m, 1H), 2.04-1.97 (m, 1H), 1.96-1.91 (m, 1H), 1.72-1.61 (m, 2H), 1.56 (ddt, J = 13.5, 9.5, 6.8 Hz, 1H), 1.37 (dq, J = 13.3, 8.5 Hz, 1H). $^{13}$C NMR (151 MHz, CDCl3) δ 161.55, 159.85, 137.08, 137.05, 130.16, 130.15, 127.78, 127.72, 122.58, 122.46, 117.64, 117.49, 78.16, 61.94, 31.39, 30.22, 19.86, 19.85. HRMS (ESI): m/z (%) = 316.0176 (M + Na$^+$). Purity >98%. |
| 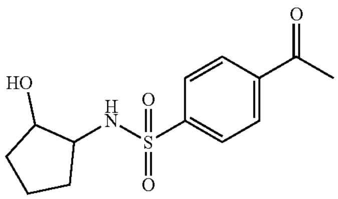 [SMILES: CC(=O)c1ccc(S(=O)(=O)NC2CCCC2O)cc1] | 819 (TR-ALKBH5-019) | $^1$H NMR (600 MHz, CDCl3) δ 8.10 (d, J = 8.2 Hz, 2H), 8.01 (d, J = 8.3 Hz, 2H), 5.03 (d, J = 5.9 Hz, 1H), 4.06 (q, J = 6.8 Hz, 1H), 3.33-3.24 (m, 1H), 2.67 (d, J = 5.9 Hz, 3H), 2.05-1.90 (m, 2H), 1.71-1.61 (m, 2H), 1.56 (ddt, J = 13.5, 9.5, 6.7 Hz, 1H), 1.37 (dq, J = 13.3, 8.5 Hz, 1H). $^{13}$C NMR (151 MHz, CDCl3) δ 197.05, 143.89, 140.14, 129.12, 127.54, 78.24, 62.00, 31.43, 30.31, 27.00, 19.90. HRMS (ESI): m/z (%) = 306.0768 (M + Na$^+$). Purity >95%. |

TABLE 800-continued

| STRUCTURE | ENTRY NUMBER (NAME) | Analytical Data |
|---|---|---|
| 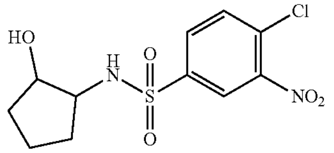 [SMILES: O=[N+]([O-])c1cc(S(=O)(=O)NC2CCCC2O)ccc1Cl] | 820 (TR-ALKBH5-020) | $^1$H NMR (600 MHz, CDCl3) δ 8.42 (d, J = 1.9 Hz, 1H), 8.04 (dd, J = 8.4, 2.0 Hz, 1H), 7.75 (d, J = 8.4 Hz, 1H), 5.04 (d, J = 6.3 Hz, 1H), 4.05 (q, J = 6.8 Hz, 1H), 3.40-3.33 (m, 1H), 2.03 (td, J = 13.5, 8.1, Hz, 2H), 1.75-1.67 (m, 2H), 1.61-1.55 (m, 1H), 1.41 (dq, J = 13.3, 8.6, Hz, 1H). $^{13}$C NMR (151 MHz, CDCl3) δ 147.86, 140.51, 133.10, 131.78, 131.32, 124.63, 78.01, 62.02, 31.39, 30.15, 19.75. HRMS (ESI): m/z (%) = 343.0122 (M + Na$^+$). Purity >96%. |
| 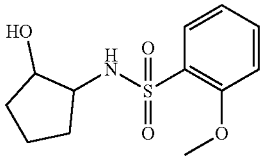 [SMILES: COc1ccccc1S(=O)(=O)NC1CCCC1O] | 821 (TR-ALKBH5-021) | $^1$H NMR (600 MHz, CDCl3) δ 7.93 (d, J = 7.7 Hz, 1H), 7.58 (t, J = 7.8 Hz, 1H), 7.11 (t, J = 7.5 Hz, 1H), 7.06 (d, J = 8.3 Hz, 1H), 5.16 (d, J = 4.2 Hz, 1H), 4.00 (s, 3H), 3.15-3.10 (m, 1H), 1.99 (dt, J = 14.1, 7.2 Hz, 1H), 1.85 (dt, J = 13.6, 6.7 Hz, 1H), 1.67-1.61 (m, 2H), 1.56-1.49 (m, 1H), 1.38 (dq, J = 13.2, 8.4 Hz, 1H). $^{13}$C NMR (151 MHz, CDCl3) δ 156.20, 134.88, 130.63, 126.95, 120.85, 112.21, 78.10, 62.03, 56.34, 31.24, 30.03, 19.97. HRMS (ESI): m/z (%) = 272.0952 (M + H$^+$). Purity >97%. |
| 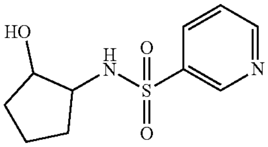 [SMILES: O=S(=O)(NC1CCCC1O)c1cccnc1] | 822 (TR-ALKBH5-022) | $^1$H NMR (599 MHz, CDCl3) δ 9.11 (s, 1H), 8.80 (d, J = 4.0 Hz, 1H), 8.26-8.21 (m, 1H), 7.51 (dd, J = 7.9, 4.9 Hz, 1H), 6.00 (s, 1H), 4.05 (q, J = 6.9 Hz, 1H), 3.40-3.32 (m, 1H), 2.02-1.91 (m, 2H), 1.72-1.60 (m, 2H), 1.55 (ddt, J = 13.5, 9.5, 6.8 Hz, 1H), 1.39 (ddd, J = 17.1, 13.3, 8.5 Hz, 1H). $^{13}$C NMR (151 MHz, CDCl3) δ 152.95, 147.87, 137.25, 135.26, 124.02, 77.82, 61.93, 31.32, 30.18, 19.78. HRMS (ESI): m/z (%) = 243.0801 (M + H$^+$). Purity >95% |
| 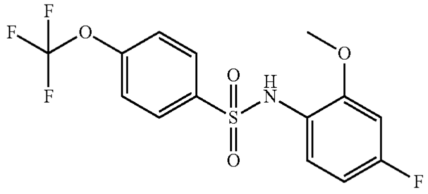 | 823 (TR-ALKBH5-023) | $^1$H NMR (599 MHz, CDCl3) δ 7.77-7.73 (m, 2H), 7.52 (dd, J = 8.8, 6.0 Hz, 1H), 7.25 (d, J = 8.6 Hz, 2H), 6.67 (td, J = 8.5, 2.6 Hz, 1H), 6.48 (dd, J = 9.9, 2.6 Hz, 1H), 3.54 (s, 3H). $^{13}$C NMR 13C (151 MHz, CDCl3) δ 162.11, 160.48, 152.28, 152.27, 151.94, 151.87, 137.28, 129.45, 125.14, 125.07, 121.06, 120.99, 120.97, 120.59, 119.35, 107.56, 107.41, 99.41, 99.23, 55.70. HRMS (ESI): m/z (%) = 288.0337 (M + Na$^+$). Purity >96%. |
| 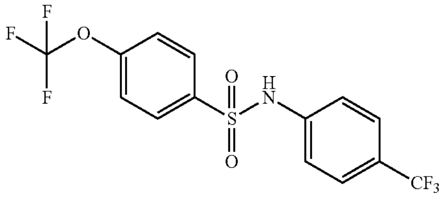 [SMILES: O=S(=O)(Nc1ccc(C(F)(F)F)cc1)c1ccc(OC(F)(F)F)cc1] | 824 (TR-ALKBH5-024) | $^1$H NMR (599 MHz, CDCl3) δ 7.95-7.91 (m, 2H), 7.71 (d, J = 8.3 Hz, 1H), 7.54 (d, J = 8.4 Hz, 2H), 7.32 (d, J = 8.4 Hz, 2H), 7.24 (d, J = 8.5 Hz, 2H). $^{13}$C NMR (151 MHz, CDCl3) δ 152.75, 139.43, 136.85, 129.42, 127.37, 127.15, 126.82, 126.80, 120.99, 120.04. HRMS (ESI): m/z (%) = 384.0134 (M − H$^-$). Purity >98%. |
| 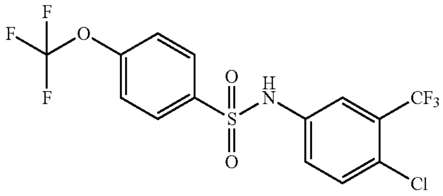 [SMILES: O=S(=O)(Nc1ccc(Cl)c(C(F)(F)F)c1)c1ccc(OC(F)(F)F)cc1] | 825 (TR-ALKBH5-025) | $^1$H NMR (599 MHz, CDCl3) δ 7.91-7.87 (m, 2H), 7.67 (s, 1H), 7.42 (d, J = 8.4 Hz, 2H), 7.33 (s, 1H), 7.31-7.27 (m, 1H). $^{13}$C NMR (151 MHz, CDCl3) δ 152.86, 136.51, 135.04, 132.64, 129.59, 129.44, 129.38, 129.05, 125.25, 123.04, 121.23, 121.07, 121.00, 120.37, 120.33, 119.28. HRMS (ESI): m/z (%) = 417.9744 (M − H$^-$). Purity >96%. |
| 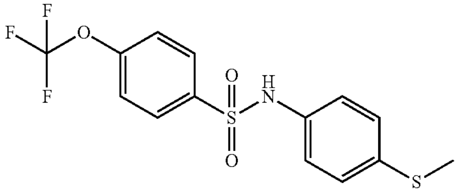 [SMILES: CSc1ccc(NS(=O)(=O)c2ccc(OC(F)(F)F)cc2)cc1] | 826 (TR-ALKBH5-026) | $^1$H NMR (599 MHz, CDCl3) δ 7.84-7.81 (m, 2H), 7.30-7.26 (m, 2H), 7.16 (d, J = 8.5 Hz, 2H), 7.03 (d, J = 8.6 Hz, 2H), 6.99 (s, 1H), 2.46 (s, 3H). $^{13}$C NMR (151 MHz, CDCl3) δ 152.42, 137.14, 136.48, 132.97, 129.44, 127.57, 123.18, 120.80, 15.97. HRMS (ESI): m/z (%) = 362.0138 (M − H$^-$). Purity >97%. |
| 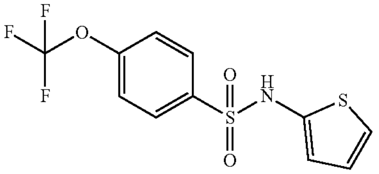 [SMILES: O=S(=O)(Nc1cccs1)c1ccc(OC(F)(F)F)cc1] | 827 (TR-ALKBH5-027) | $^1$H NMR (599 MHz, CDCl3) δ 8.10 (d, J = 8.9 Hz, 6H), 7.51 (d, J = 5.2 Hz, 3H), 7.32 (d, J = 8.4 Hz, 6H), 7.30-7.28 (m, 5H), 6.52 (d, J = 5.2 Hz, 3H). $^{13}$C NMR (151 MHz, CDCl3) δ 164.16, 154.29, 139.10, 132.69, 132.46, 128.65, 122.66, 120.64, 120.29, 106.71. HRMS (ESI): m/z (%) = 322.9780 (M − H$^-$). Purity >94%. |

TABLE 800-continued

| STRUCTURE | ENTRY NUMBER (NAME) | Analytical Data |
| --- | --- | --- |
| 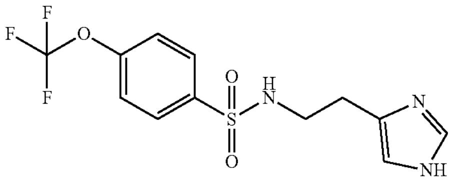 [SMILES: O=S(=O)(NCCc1c[nH]cn1)c1ccc(OC(F)(F)F)cc1] | 828 (TR-ALKBH5-028) | $^1$H NMR (599 MHz, CDCl3) δ 8.17-8.12 (m, 2H), 7.94 (d, J = 6.3 Hz, 1H), 7.90 (d, J = 8.8 Hz, 1H), 7.46 (d, J = 8.5 Hz, 2H), 7.41 (d, J = 8.5 Hz, 1H), 7.32 (d, J = 8.3 Hz, 1H), 3.37-3.13 (m, 2H), 2.72 (t, J = 6.1 Hz, 1H), 2.06 (s, 1H). $^{13}$C NMR (151 MHz, CDCl3) δ 153.92, 153.84, 152.08, 142.10, 142.03, 138.47, 135.62, 129.88, 129.54, 129.19, 128.01, 121.43, 121.18, 121.01, 120.71, 42.19, 27.48. HRMS (ESI): m/z (%) = 334.0482 (M − H$^-$). Purity >94%. |
| 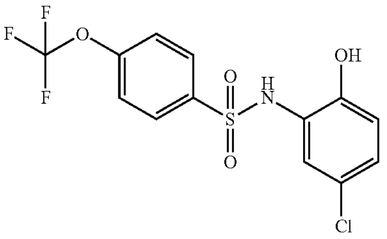 | 829 (TR-ALKBH5-029) | $^1$H NMR (599 MHz, CDCl3) δ 8.11 (d, J = 8.5 Hz, 2H), 7.54 (d, J = 8.3 Hz, 2H), 6.92 (d, J = 8.6 Hz, 1H), 6.87 (s, 1H), 6.75 (d, J = 8.5 Hz, 1H). $^{13}$C NMR (151 MHz, CDCl3) δ 133.36, 130.85, 123.82, 120.86, 118.20, 116.77. HRMS (ESI): m/z (%) = 367.9962 (M + H$^+$). Purity >95%. |
| 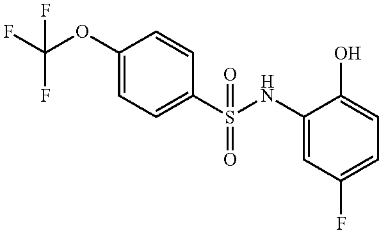 [SMILES: O=S(=O)(Nc1cc(F)ccc1O)c1ccc(OC(F)(F)F)cc1] | 830 (TR-ALKBH5-030) | $^1$H NMR (599 MHz, CDCl3) δ 7.98 (t, J = 8.3 Hz, 2H), 7.38 (t, J = 10.4 Hz, 2H), 6.80 (dt, J = 11.0, 5.5 Hz, 1H), 6.43 (dd, J = 9.8, 2.8 Hz, 1H), 6.33 (td, J = 8.9, 2.9 Hz, 1H). $^{13}$C NMR (151 MHz, CDCl3) δ 162.63, 161.00, 153.57, 141.21, 141.13, 133.37, 130.86, 124.02, 123.95, 120.83, 104.89, 104.73, 103.70, 103.53. HRMS (ESI): m/z (%) = 352.0255 (M + H$^+$). Purity >98%. |
| 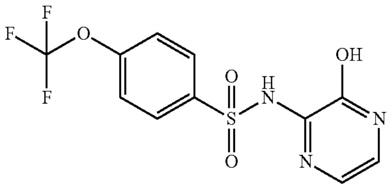 [SMILES: O=S(=O)(Nc1nccnc1O)c1ccc(OC(F)(F)F)cc1] | 831 (TR-ALKBH5-031) | $^1$H NMR (599 MHz, CDCl3) δ 7.99-7.95 (m, 3H), 7.41-7.37 (m, 2H), 7.26-7.22 (m, 1H), 6.65-6.60 (m, 1H). $^{13}$C NMR (151 MHz, CDCl3) δ 153.72, 152.09, 146.69, 133.27, 131.99, 130.77, 130.29, 121.00, 120.95, 113.98. HRMS (ESI): m/z (%) = 336.0339 (M + H$^+$). Purity >95%. |
| 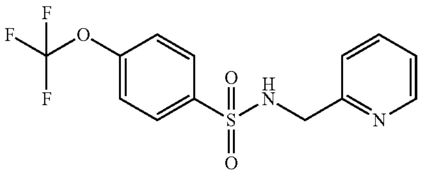 [SMILES: O=S(=O)(NCc1ccccn1)c1ccc(OC(F)(F)F)cc1] | 832 (TR-ALKBH5-032) | $^1$H NMR (599 MHz, CDCl3) δ 8.46-8.41 (m, 1H), 7.88 (d, J = 8.7 Hz, 2H), 7.60 (td, J = 7.7, 1.5 Hz, 1H), 7.24 (d, J = 8.6 Hz, 2H), 7.19-7.14 (m, 2H), 6.46 (s, 1H), 4.31 (d, J = 4.8 Hz, 2H). $^{13}$C NMR (151 MHz, CDCl3) δ 154.54, 151.91, 149.05, 138.39, 136.88, 129.28, 122.75, 122.09, 121.06, 120.88, 47.42. HRMS (ESI): m/z (%) = 333.0509 (M + H$^+$). Purity >97%. |
| 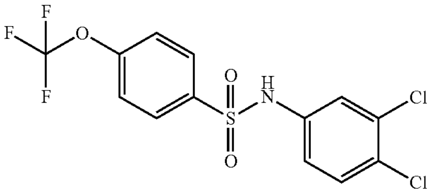 [SMILES: O=S(=O)(Nc1ccc(Cl)c(Cl)c1)c1ccc(OC(F)(F)F)cc1] | 833 (TR-ALKBH5-033) | $^1$H NMR (599 MHz, CDCl3) δ 7.89 (d, J = 8.8 Hz, 2H), 7.44 (d, J = 24.5 Hz, 1H), 7.33 (dd, J = 8.2, 6.5 Hz, 3H), 7.27-7.25 (m, 1H), 7.01-6.97 (m, 1H). $^{13}$C NMR (151 MHz, CDCl3) δ 152.76, 136.59, 135.51, 133.43, 131.12, 129.70, 129.43, 123.15, 121.01, 120.63. HRMS (ESI): m/z (%) = 383.9479 (M + H$^+$). Purity >96%. |
| 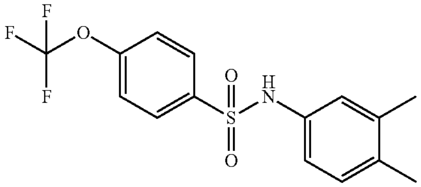 [SMILES: Cc1ccc(NS(=O)(=O)c2ccc(OC(F)(F)F)cc2)cc1C] | 834 (TR-ALKBH5-034) | $^1$H NMR (599 MHz, CDCl3) δ 7.83 (dd, J = 8.7, 1.2 Hz, 2H), 7.29-7.25 (m, 2H), 7.02 (d, J = 8.1 Hz, 1H), 6.87 (s, 1H), 6.82 (d, J = 7.9 Hz, 1H), 2.20 (d, J = 7.7 Hz, 6H). $^{13}$C NMR (151 MHz, CDCl3) δ 152.27, 137.94, 137.42, 134.65, 133.41, 130.42, 129.45, 123.86, 120.73, 119.86, 19.74, 19.17. HRMS (ESI): m/z (%) = 368.0541 (M + Na$^+$). Purity >95%. |

TABLE 800-continued

| STRUCTURE | ENTRY NUMBER (NAME) | Analytical Data |
|---|---|---|
| 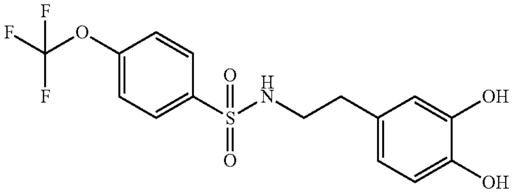 [SMILES: O=S(=O)(NCCc1ccc(O)c(O)c1)c1ccc(OC(F)(F)F)cc1] | 835 (TR-ALKBH5-035) | $^1$H NMR (599 MHz, CDCl3) δ 7.89 (t, J = 5.7 Hz, 2H), 7.87-7.81 (m, 4H), 7.35 (t, J = 7.9 Hz, 6H), 7.14 (d, J = 8.3 Hz, 1H), 7.12-7.07 (m, 2H), 5.00 (t, J = 6.3 Hz, 1H), 3.23 (q, J = 6.7 Hz, 2H), 2.82 (t, J = 6.8 Hz, 2H). $^{13}$C NMR (151 MHz, CDCl3) δ 153.65, 152.24, 140.92, 139.64, 139.00, 138.16, 133.25, 133.14, 130.81, 130.73, 129.17, 128.78, 124.88, 124.48, 121.10, 121.02, 120.87, 120.83, 119.36, 119.29, 43.76, 35.38. HRMS (ESI): m/z (%) = 843.0375 (M + $NH_4^+$). Purity >97%. |
| 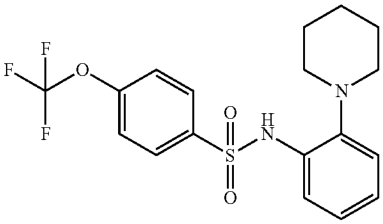 [SMILES: O=S(=O)(Nc1ccccc1N1CCCCC1)c1ccc(OC(F)(F)F)cc1] | 836 (TR-ALKBH5-036) | $^1$H NMR (599 MHz, CDCl3) δ 7.87 (d, J = 8.6 Hz, 2H), 7.62 (d, J = 8.0 Hz, 1H), 7.26 (d, J = 8.5 Hz, 2H), 7.11 (tt, J = 14.8, 7.4 Hz, 3H), 2.46 (s, 4H), 1.64 (s, 4H). $^{13}$C NMR (151 MHz, CDCl3) δ 152.26, 138.05, 132.62, 129.05, 122.00, 121.02, 120.84, 119.30, 54.17, 26.59. HRMS (ESI): m/z (%) = 401.1135 (M + $H^+$). Purity >96%. |
| 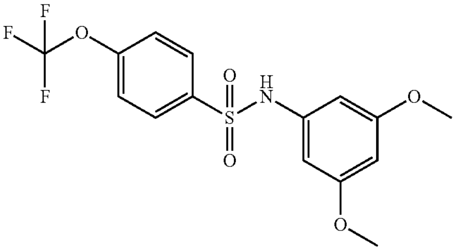 [SMILES: COc1cc(NS(=O)(=O)c2ccc(OC(F)(F)F)cc2)cc(OC)c1] | 837 (TR-ALKBH5-037) | $^1$H NMR (599 MHz, CDCl3) δ 7.92-7.88 (m, 2H), 7.31-7.27 (m, 2H), 6.92 (d, J = 2.1 Hz, 2H), 6.24 (t, J = 2.1 Hz, 1H), 3.73 (s, 6H). $^{13}$C NMR (151 MHz, CDCl3) δ 161.34, 152.43, 137.84, 137.17, 129.49, 121.04, 120.81, 119.31, 99.57, 97.53, 55.41. HRMS (ESI): m/z (%) = 378.0615 (M + $H^+$). Purity >98%. |
| 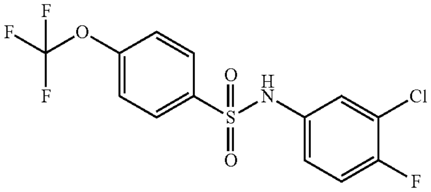 [SMILES: O=S(=O)(Nc1ccc(F)c(Cl)c1)c1ccc(OC(F)(F)F)cc1] | 838 (TR-ALKBH5-038) | $^1$H NMR (599 MHz, CDCl3) δ 7.86 (d, J = 8.8 Hz, 2H), 7.43 (s, 1H), 7.32 (d, J = 8.6 Hz, 2H), 7.22 (dd, J = 6.3, 2.5 Hz, 1H), 7.05 (t, J = 8.6 Hz, 1H), 7.02-6.98 (m, 1H). $^{13}$C NMR (151 MHz, CDCl3) δ 157.11, 155.46, 152.69, 136.58, 132.51, 132.49, 129.45, 124.74, 122.26, 122.21, 121.92, 121.79, 121.02, 120.96, 119.29, 117.32, 117.17. HRMS (ESI): m/z (%) = 367.9776 (M − $H^-$). Purity >97%. |
| 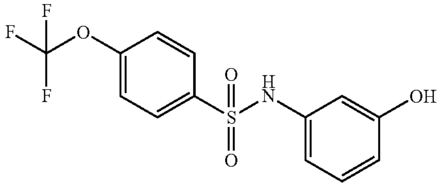 [SMILES: O=S(=O)(Nc1cccc(O)c1)c1ccc(OC(F)(F)F)cc1] | 839 (TR-ALKBH5-039) | $^1$H NMR (599 MHz, DMSO) δ 10.29 (s, 1H), 7.92-7.87 (m, 2H), 7.56 (d, J = 8.3 Hz, 2H), 7.01 (t, J = 8.1 Hz, 1H), 6.60 (t, J = 2.1 Hz, 1H), 6.54 (dd, J = 8.0, 1.3 Hz, 1H), 6.45 (dd, J = 8.0, 1.8 Hz, 1H). $^{13}$C NMR (151 MHz, CDCl3) δ 157.93, 148.91, 143.62, 133.49, 133.39, 130.68, 129.04, 121.85, 105.03, 76.90, 55.60, 54.64, 51.62, 46.88, 24.05. HRMS (ESI): m/z (%) = 332.0210 (M − $H^-$). Purity >98%. |
| 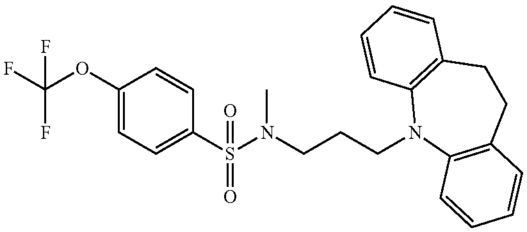 [SMILES: CN(CCCN1c2ccccc2CCc2ccccc21)S(=O)(=O)c1ccc(OC(F)(F)F)cc1] | 840 (TR-ALKBH5-040) | $^1$H NMR (599 MHz, CDCl3) δ 7.73 (d, J = 8.7 Hz, 2H), 7.29 (d, J = 1.9 Hz, 2H), 7.18-7.12 (m, 4H), 7.09 (d, J = 8.0 Hz, 2H), 6.97 (t, J = 7.3 Hz, 2H), 3.81 (t, J = 6.6 Hz, 2H), 3.18 (s, 4H), 3.14 (t, J = 7.2 Hz, 2H), 2.67 (s, 3H), 1.81 (p, J = 6.7 Hz, 2H). $^{13}$C NMR (151 MHz, CDCl3) δ 134.31, 129.99, 129.37, 126.52, 119.84, 48.25, 34.70, 32.10, 25.82. HRMS (ESI): m/z (%) = 491.1601 (M + $H^+$). Purity >97%. |
| 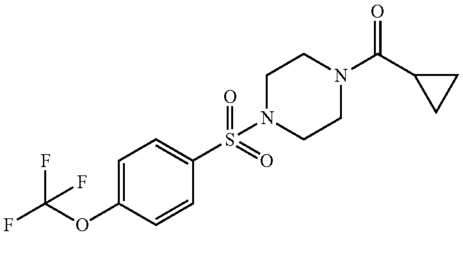 [SMILES: O=C(C1CC1)N1CCN(S(=O)(=O)c2ccc(OC(F)(F)F)cc2)CC1] | 841 (TR-ALKBH5-041) | $^1$H NMR (600 MHz, CDCl3) δ 7.83-7.79 (m, 1H), 7.39 (d, J = 8.4 Hz, 1H), 3.77 (d, J = 30.3 Hz, 2H), 3.06 (d, J = 33.4 Hz, 2H), 0.96-0.91 (m, 1H), 0.80-0.73 (m, 1H). $^{13}$C NMR (151 MHz, CDCl3) δ 172.09, 172.08, 152.54, 133.84, 129.87, 129.85, 121.07, 121.05, 10.89, 7.75. HRMS (ESI): m/z (%) = 379.932 (M + $H^+$). Purity >98%. |

TABLE 800-continued
| STRUCTURE | ENTRY NUMBER (NAME) | Analytical Data |
|---|---|---|
| 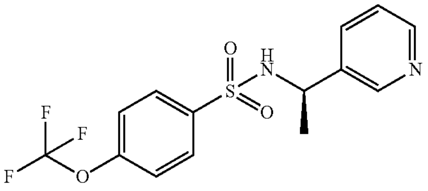 [SMILES: C[C@@H](NS(=O)(=O)c1ccc(OC(F)(F)F)cc1)c1cccnc1] | 842 (TR-ALKBH5-042) | $^{1}$H NMR (600 MHz, CDCl3) δ 8.41 (d, J = 12.6 Hz, 6H), 7.73-7.69 (m, 6H), 7.41 (d, J = 7.9 Hz, 3H), 7.19 (d, J = 8.3 Hz, 6H), 7.09 (dd, J = 7.7, 4.8 Hz, 3H), 4.61 (p, J = 6.8 Hz, 3H), 1.49 (d, J = 6.9 Hz, 10H). $^{13}$C NMR (151 MHz, CDCl3) δ 148.92, 147.96, 133.87, 129.18, 120.92, 51.67, 23.49. HRMS (ESI): m/z (%) = 347.0667 (M + H$^{+}$). Purity >98%. |
| 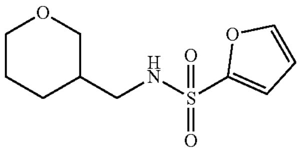 [SMILES: O=S(=O)(NCC1CCCOC1)c1ccco1] | 843 | |
| 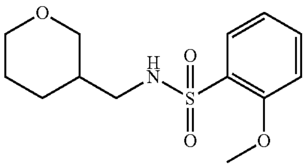 [SMILES: COc1ccccc1S(=O)(=O)NCC1CCCOC1] | 844 (TR-ALK-01) | |
| 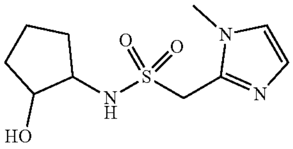 [SMILES: Cn1ccnc1CS(=O)(=O)NC1CCCC1O] | 845 | |
| 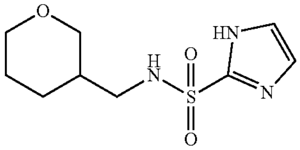 [SMILES: O=S(=O)(NCC1CCCOC1)c1ncc[nH]1] | 846 | |
| 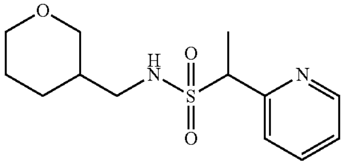 [SMILES: CC(c1ccccn1)S(=O)(=O)NCC1CCCOC1] | 847 | |
| 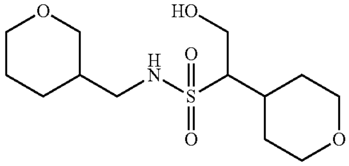 [SMILES: O=S(=O)(NCC1CCCOC1)C(CO)C1CCOCC1] | 848 | |
| 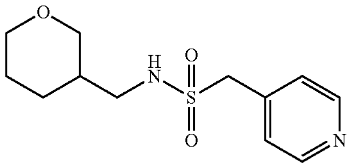 [SMILES: O=S(=O)(Cc1ccncc1)NCC1CCCOC1] | 849 | |

TABLE 800-continued
| STRUCTURE | ENTRY NUMBER (NAME) | Analytical Data |
| --- | --- | --- |
| 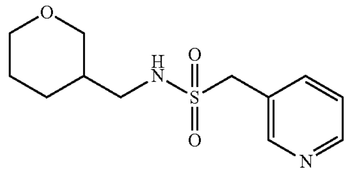 [SMILES: O=S(=O)(Cc1cccnc1)NCC1CCCOC1] | 850 | |
| 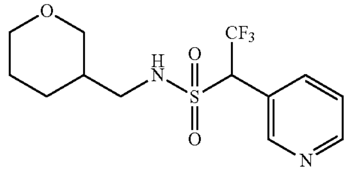 [SMILES: O=S(=O)(NCC1CCCOC1)C(c1cccnc1)C(F)(F)F] | 851 | |
| 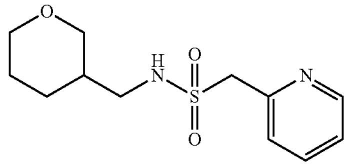 [SMILES: O=S(=O)(Cc1ccccn1)NCC1CCCOC1] | 852 | |
| 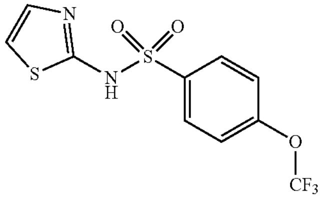 [SMILES: O=S(=O)(Nc1nccs1)c1ccc(OC(F)(F)F)cc1] | 853 | |
| 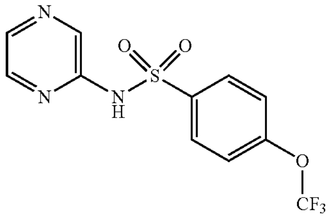 [SMILES: O=S(=O)(Nc1cnccn1)c1ccc(OC(F)(F)F)cc1] | 854 | |
| 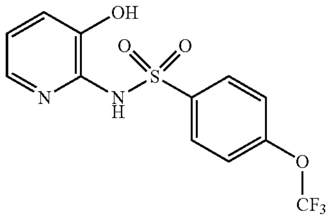 [SMILES: O=S(=O)(Nc1ncccc1O)c1ccc(OC(F)(F)F)cc1] | 855 | |
| 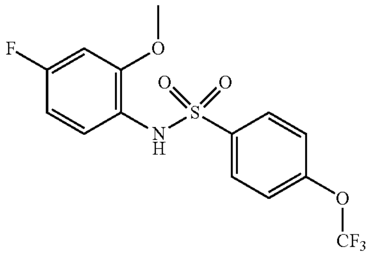 [SMILES: COc1cc(F)ccc1NS(=O)(=O)c1ccc(OC(F)(F)F)cc1] | 786 | |

TABLE 800-continued
| STRUCTURE | ENTRY NUMBER (NAME) | Analytical Data |
|---|---|---|
| 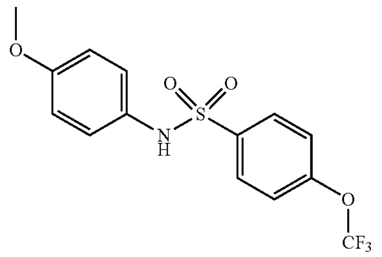 [SMILES: COc1ccc(NS(=O)(=O)c2ccc(OC(F)(F)F)cc2)cc1] | 857 | |
| 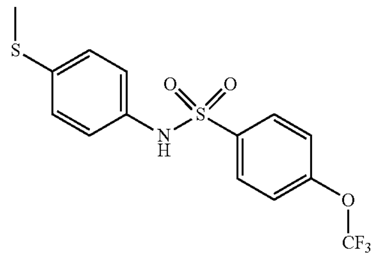 [SMILES: CSc1ccc(NS(=O)(=O)c2ccc(OC(F)(F)F)cc2)cc1] | 858 | |
| 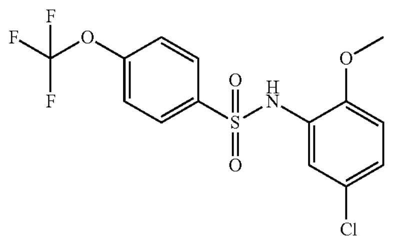 [SMILES: COc1ccc(Cl)cc1NS(=O)(=O)c1ccc(OC(F)(F)F)cc1] | 859 | |
| 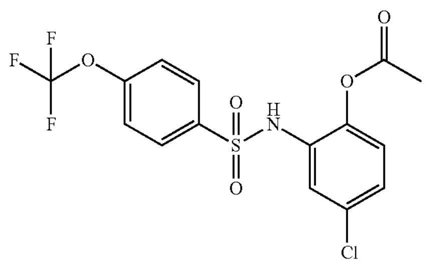 [SMILES: CC(=O)Oc1ccc(Cl)cc1NS(=O)(=O)c1ccc(OC(F)(F)F)cc1] | 860 | |
| 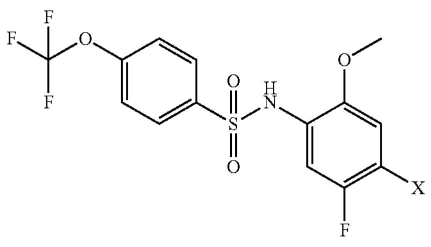 X = F | 861 | |

TABLE 800-continued
| STRUCTURE | ENTRY NUMBER (NAME) | Analytical Data |
|---|---|---|
| 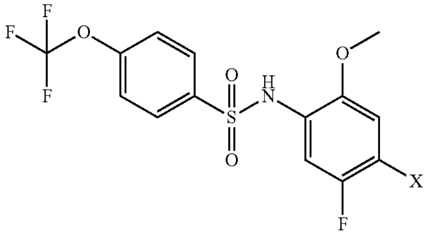 X = Cl | 862 | |
| 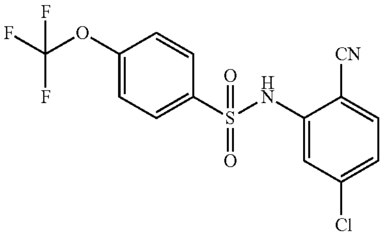 [SMILES: N#Cc1ccc(Cl)cc1NS(=O)(=O)c1ccc(OC(F)(F)F)cc1] | 863 | |
| 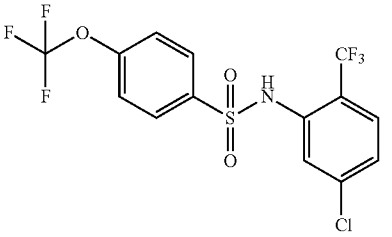 [SMILES: O=S(=O)(Nc1cc(Cl)ccc1C(F)(F)F)c1ccc(OC(F)(F)F)cc1] | 864 | |
| 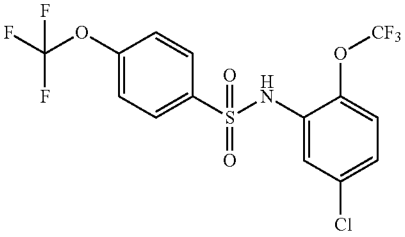 [SMILES: O=S(=O)(Nc1cc(Cl)ccc1OC(F)(F)F)c1ccc(OC(F)(F)F)cc1] | 865 | |
| 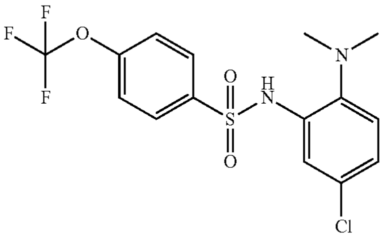 [SMILES: CN(C)c1ccc(Cl)cc1NS(=O)(=O)c1ccc(OC(F)(F)F)cc1] | 866 | |
| 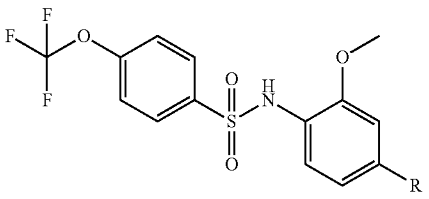 R = F | 867 | |

TABLE 800-continued
| STRUCTURE | ENTRY NUMBER (NAME) | Analytical Data |
|---|---|---|
| 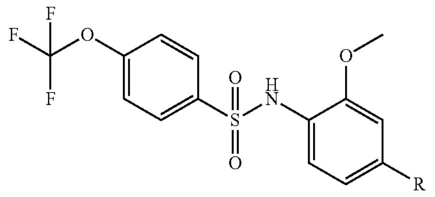 R = $CH_3$ | 868 | |
| 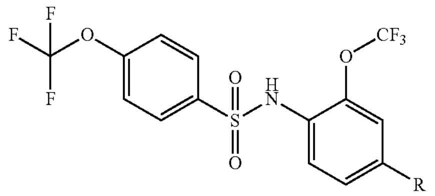 R = F | 869 | |
| 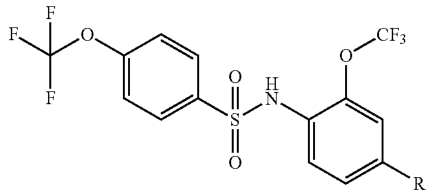 R = $CH_3$ | 870 | |
| 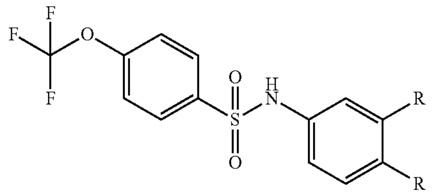 R = $CF_3$, $OCH_3$, $OCF_3$ | 871 | |
| 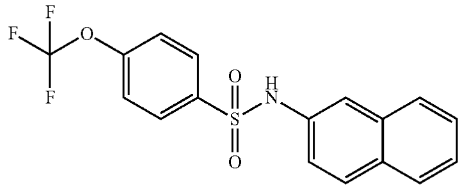 [SMILES: O=S(=O)(Nc1ccc2ccccc2c1)c1ccc(OC(F)(F)F)cc1] | 872 | |
| 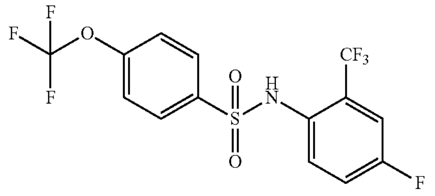 [SMILES: O=S(=O)(Nc1ccc(F)cc1C(F)(F)F)c1ccc(OC(F)(F)F)cc1] | 873 | |

TABLE 800-continued
| STRUCTURE | ENTRY NUMBER (NAME) | Analytical Data |
|---|---|---|
| 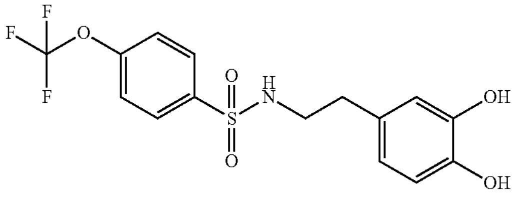 [SMILES: O=S(=O)(NCCc1ccc(O)c(O)c1)c1ccc(OC(F)(F)F)cc1] | | |
Inhibition Data for Compounds of Table 800
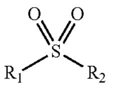
| Compound | $R_1$ | $R_2$ | ALKBH5 $IC_{50}$ (μM) | FTO $IC_{50}$ (μM) | elogD |
|---|---|---|---|---|---|
| TR-ALKBH5-04 | 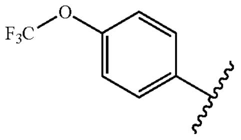 [SMILES: *c1ccc(OC(F)(F)F)cc1] | 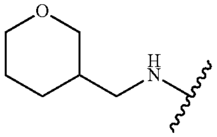 [SMILES: *NCC1CCCOC1] | 0.24 | 19.7 | 0.37 |
| TR-ALKBH5-05 | 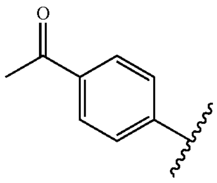 [SMILES: *c1ccc(C(C)=O)cc1] | 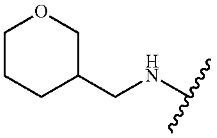 [SMILES: *NCC1CCCOC1] | 1.9 | >40 | 1.12 |
| TR-ALKBH5-08 | 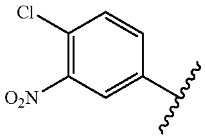 [SMILES: *c1ccc(Cl)c([N+](=O)[O-])c1] | 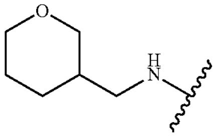 [SMILES: *NCC1CCCOC1] | 0.50 | 6.4 | 0.89 |
| TR-ALKBH5-25 | 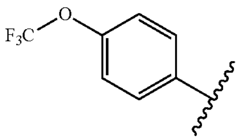 [SMILES: *c1ccc(OC(F)(F)F)cc1] | 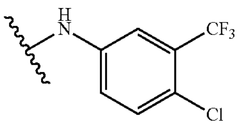 [SMILES: *Nc1ccc(Cl)c(C(F)(F)F)c1] | 1.6 | >40 | 1.50 |
| TR-ALKBH5-27 | 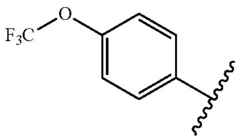 | 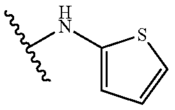 [SMILES: *Nc1cccs1] | 2.0 | >40 | 0.36 |
| TR-ALKBH5-29 | 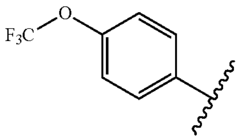 [SMILES: *c1ccc(OC(F)(F)F)cc1] | 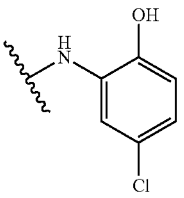 [SMILES: *Nc1cc(Cl)ccc1O] | 0.11 | >40 | 0.88 |

-continued
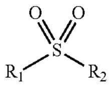
| Compound | $R_1$ | $R_2$ | ALKBH5 $IC_{50}$ (μM) | FTO $IC_{50}$ (μM) | elogD |
|---|---|---|---|---|---|
| TR-ALKBH5-30 | 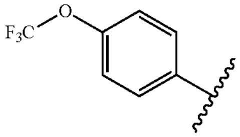 [SMILES: *c1ccc(OC(F)(F)F)cc1] | 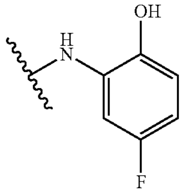 [SMILES: *Nc1cc(F)ccc1O] | 1.0 | >40 | 0.81 |
| TR-ALKBH5-31 | 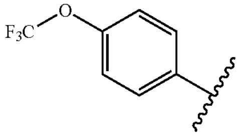 [SMILES: *c1ccc(OC(F)(F)F)cc1] | 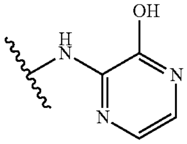 [SMILES: *Nc1nccnc1O] | 13.7 | >40 | 2.33 |
| TR-ALKBH5-32 | 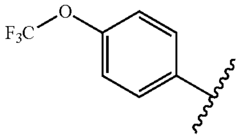 [SMILES: *c1ccc(OC(F)(F)F)cc1] | 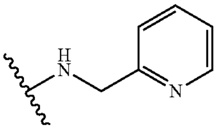 [SMILES: *NCc1ccccn1] | 2.2 | >40 | 2.25 |
| TR-ALKBH5-33 | 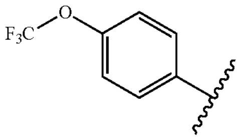 | 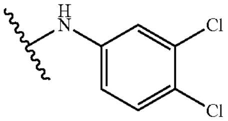 [SMILES: *Nc1ccc(Cl)c(Cl)c1] | 2.6 | >40 | 1.24 |
| TR-ALKBH5-34 | 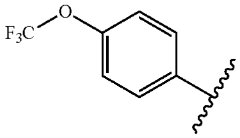 | 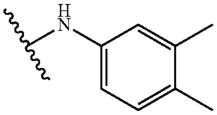 [SMILES: *Nc1ccc(C)c(C)c1] | 23.3 | >40 | 0.60 |
| TR-ALKBH5-36 | 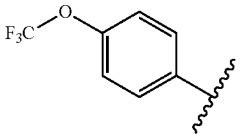 | 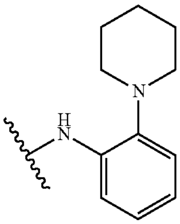 [SMILES: *Nc1ccccc1N1CCCCC1] | 0.40 | 23.2 | 1.13 |
| TR-ALKBH5-38 | 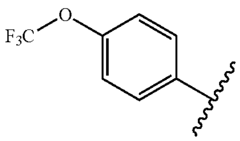 [SMILES: *c1ccc(OC(F)(F)F)cc1] | 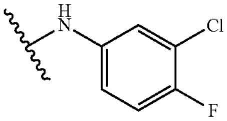 [SMILES: *Nc1ccc(F)c(Cl)c1] | 1.9 | 27.6 | 2.58 |
| TR-ALKBH5-39 | 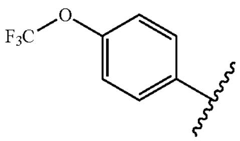 [SMILES: *c1ccc(OC(F)(F)F)cc1] | 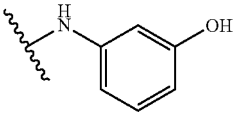 [SMILES: *Nc1cccc(O)c1] | 3.1 | >40 | 1.60 |

-continued
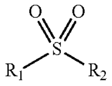
| Compound | $R_1$ | $R_2$ | ALKBH5 $IC_{50}$ (μM) | FTO $IC_{50}$ (μM) | elogD |
|---|---|---|---|---|---|
| TR-ALKBH5-40 | 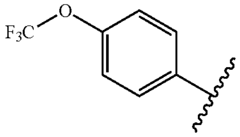 [SMILES: *c1ccc(OC(F)(F)F)cc1] | 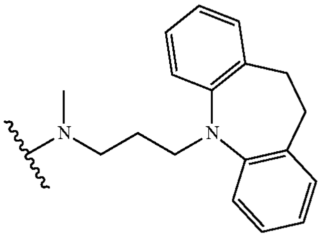 [SMILES: *N(C)CCCN1c2ccccc2CCc2ccccc21] | 2.3 | 59.4 | 2.05 |
| TR-ALKBH5-41 | 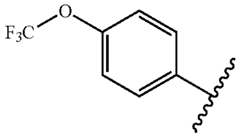 [SMILES: *c1ccc(OC(F)(F)F)cc1] | 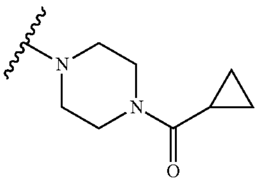 [SMILES: *N1CCN(C(=O)C2CC2)CC1] | 0.45 | >40 | 0.79 |
| TR-ALKBH5-42 | 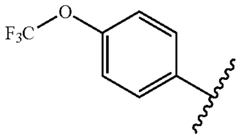 [SMILES: *c1ccc(OC(F)(F)F)cc1] | 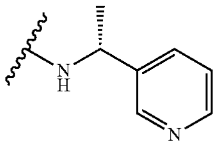 [SMILES: *N[C@H](C)c1cccnc1] | 0.25 | 285 | 0.83 |
Example C9
General Procedure for the Preparation of Non-Limiting ALKBH5 Inhibitors (e.g., Compounds of Formula (A3) (e.g., Compounds of Table 900)).
Scheme 9.
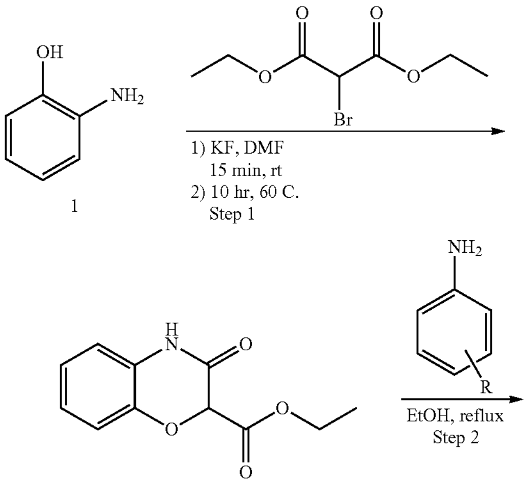
-continued
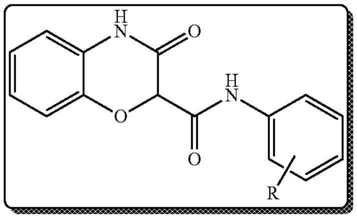
TABLE 900
| STRUCTURE | ENTRY NUMBER (NAME) |
|---|---|
| 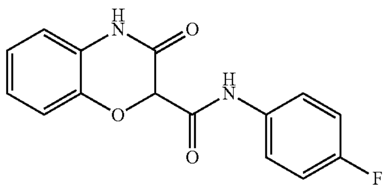 [SMILES: O=C(Nc1ccc(F)cc1)C1Oc2ccccc2NC1=O] | 901 (TR-ALK-2-01) |

TABLE 900-continued
| STRUCTURE | ENTRY NUMBER (NAME) |
|---|---|
| 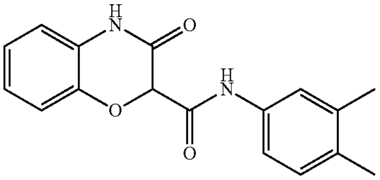 [SMILES: Cc1ccc(NC(=O)C2Oc3ccccc3NC2=O)cc1C] | 902 (TR-ALK-2-02) |
| 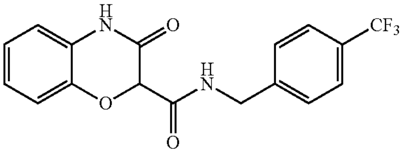 [SMILES: O=C(NCc1ccc(C(F)(F)F)cc1)C1Oc2ccccc2NC1=O] | 903 (TR-ALK-2-03) |
| 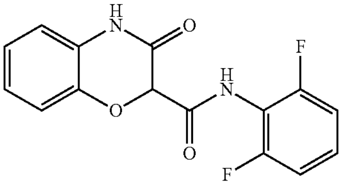 [SMILES: O=C1Nc2ccccc2OC1C(=O)Nc1c(F)cccc1F] | 904 (TR-ALK-2-04) |
| 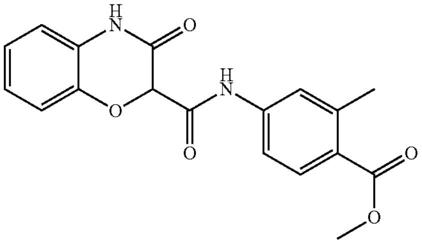 [SMILES: COC(=O)c1ccc(NC(=O)C2Oc3ccccc3NC2=O)cc1C] | 905 (TR-ALK-2-05) |
| 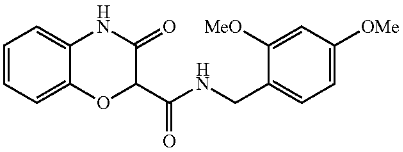 [SMILES: COc1ccc(CNC(=O)C2Oc3ccccc3NC2=O)c(OC)c1] | 906 (TR-ALK-2-06) |
| 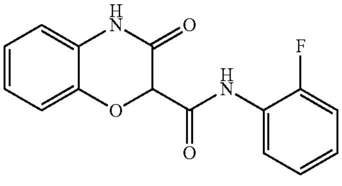 [SMILES: O=C(Nc1ccccc1F)C1Oc2ccccc2NC1=O] | 907 (TR-ALK-2-07) |
| 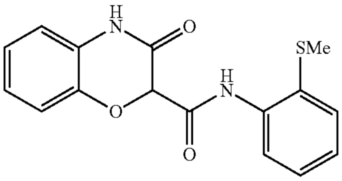 [SMILES: CSc1ccccc1NC(=O)C1Oc2ccccc2NC1=O] | 908 (TR-ALK-2-08) |
| 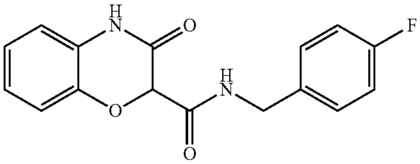 [SMILES: O=C(NCc1ccc(F)cc1)C1Oc2ccccc2NC1=O] | 909 (TR-ALK-2-09) |
| 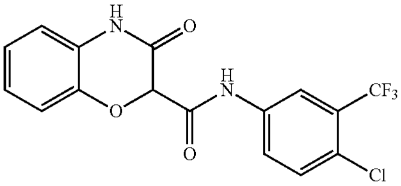 [SMILES: O=C(Nc1ccc(Cl)c(C(F)(F)F)c1)C1Oc2ccccc2NC1=O] | 910 (TR-ALK-2-010) |
| 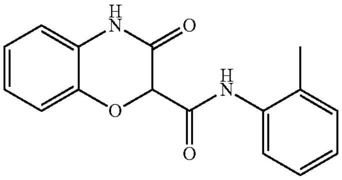 [SMILES: Cc1ccccc1NC(=O)C1Oc2ccccc2NC1=O] | 911 (TR-ALK-2-011) |
| 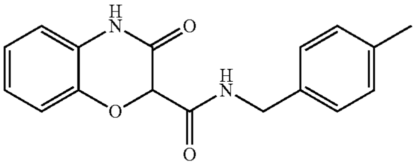 [SMILES: Cc1ccc(CNC(=O)C2Oc3ccccc3NC2=O)cc1] | 912 (TR-ALK-2-012) |
Example C10
General Procedure for the Preparation of Non-Limiting Exemplary PTPN2 Inhibitors (e.g., Compounds of Formula (PT1).
Scheme 10.
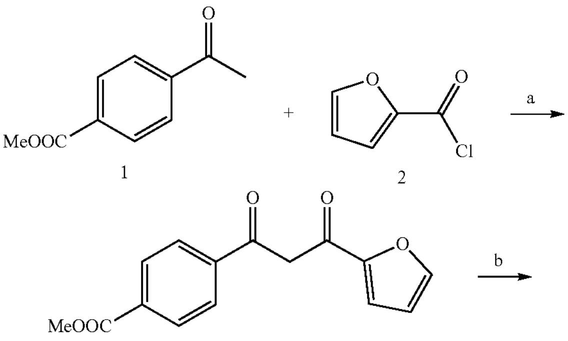
1 2 3

-continued

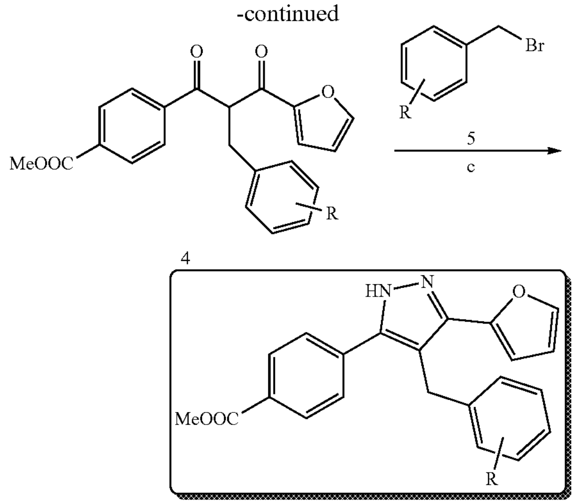

TR-K-01 to 010

Reagents and conditions: a). LiHMDS, THF, 0° C. to RT 12 h., c). $N_2H_4$, EtOH, 80° C., 2 h., b). $K_2CO_3$, NaI, acetone, reflux, 12 h.

Step a: methyl 4-(3-(furan-2-yl)-3-oxopropanoyl) benzoate (3)

A suspension of compound (1) (200 mg, 0.685 mmol) in dry THF (1.0 mL) was cooled at 0° C. under Argon atmosphere. After cooling, LiHMDS (0.685 mmol) was added dropwise to the reaction mass and stirred for 30 min at the same temperature. To this solution the furoylchloride (0.685 mmol) was dissolved in THF and added to the reaction mass and stirred for the 12 h at room temperature. Cold ethyl acetate (150 mL) and ice-water (50 mL) were added and the organic phase was separated. The aqueous phase was extracted with more ethyl acetate (100 mL) and the combined extracts were washed with water then brine, and dried over MgSO4. The solvents were evaporated and the residue was purified by column chromatography on silica gel (Ethyl acetate:Hexane, 1:9) yielded compound as a white solid. (85% yield).

Step b: General Procedure for the Synthesis of Compound (4)

To a stirred suspension of methyl 4-(3-(furan-2-yl)-3-oxopropanoyl) benzoate (1.0 g, 4.46 mmol), $K_2CO_3$ (0.67 g, 4.82 mmol) and NaI (0.73 g, 4.88 mmol) in dry acetone (15 ml) was added corresponding bromo compound (5) (5.2 mmol) dropwise, under nitrogen atmosphere. The mixture was stirred at reflux for 12 h. The reaction was monitored by TLC and after completion of the reaction it was cooled to room temperature and filtered through a celite pad. The filtrate was evaporated under vacuum and the residue was purified by silica gel column chromatography (95:5, hexane: ethyl acetate) to give the pure product (4) as a colourless solid in good yield.

Step c: General Procedure for the Synthesis of Compounds. (TR-K-01 to 010)

To a stirred solution of compound (4) (1 eq) in EtOH and followed by the addition of N2H4 (1 eq.). The reaction mixture was stirred for 2 h at 80° C. After completion of reaction the excess of EtOH was removed by rotovapour, and redissolved in water and extract with ethyl acetate and the organic layer was separate and concentrate under reduced pressure. The crude product was purified by column chromatography on silica gel (Ethyl acetate:Hexane, 1:1) yielded compound as a white solid. (65% yield).

TABLE 1000

| STRUCTURE | ENTRY NUMBER (NAME) | ANALYTICAL DATA |
|---|---|---|
| 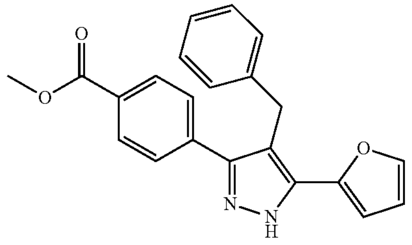 TR-K-01 | 1001 (TR-K-01) | 1H NMR (599 MHz, CDCl3) δ 8.01 (d, J = 8.1 Hz, 2H), 7.58 (d, J = 8.1 Hz, 2H), 7.44 (s, 1H), 7.32 (d, J = 7.4 Hz, 1H), 7.29 (d, J = 8.5 Hz, 1H), 7.23 (t, J = 7.3 Hz, 1H), 7.19 (d, J = 7.5 Hz, 2H), 6.43-6.36 (m, 2H), 4.18 (s, 2H), 3.93 (s, 3H). 13C NMR (151 MHz, CDCl3) δ 166.85, 142.26, 139.74, 130.00, 129.52, 128.85, 127.96, 127.49, 126.35, 112.82, 111.62, 107.67, 52.22, 29.62. HRMS (ESI): m/z (%) = 359.1388 (M + $H^+$). Purity >98%. |
| 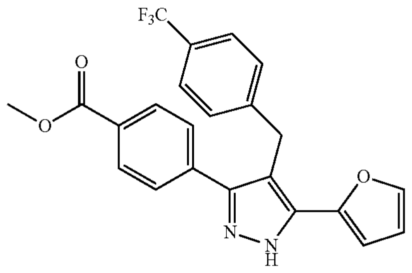 TR-K-02 | 1002 (TR-K-02) | 1H NMR (599 MHz, CDCl3) δ 8.04 (d, J = 8.3 Hz, 2H), 7.55 (dd, J = 11.5, 8.4 Hz, 4H), 7.47 (s, 1H), 7.29 (d, J = 8.5 Hz, 2H), 6.45 (dd, J = 3.3, 1.7 Hz, 1H), 6.38 (d, J = 3.3 Hz, 1H), 4.24 (s, 2H), 3.94 (s, 3H). 13C NMR (151 MHz, CDCl3) δ 166.74, 144.08, 130.17, 129.83, 128.25, 127.57, 125.71, 111.92, 107.56, 52.34, 29.35. HRMS (ESI): m/z (%) = 427.1263 (M + $H^+$). Purity >96%. |

TABLE 1000-continued

| STRUCTURE | ENTRY NUMBER (NAME) | ANALYTICAL DATA |
|---|---|---|
| 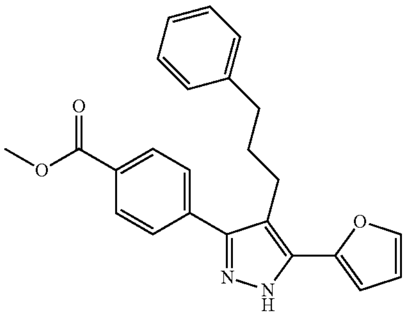 TR-K-03 | 1003 (TR-K-03) | 1H NMR (599 MHz, CDCl3) δ 8.08 (d, J = 8.1 Hz, 2H), 7.61 (d, J = 8.1 Hz, 2H), 7.48 (s, 1H), 7.30 (t, J = 5.5 Hz, 2H), 7.23 (d, J = 6.7 Hz, 1H), 7.15 (d, J = 7.3 Hz, 2H), 6.49 (s, 1H), 6.44 (s, 1H), 3.98 (s, 3H), 2.82-2.78 (m, 2H), 2.68 (t, J = 7.1 Hz, 2H), 1.94-1.89 (m, 2H). 13C NMR (151 MHz, MeOD) δ 157.38, 153.65, 149.87, 142.14, 124.89, 124.17, 120.21, 111.20, 91.70. HRMS (ESI): m/z (%) = 387.1701 (M + $H^+$). Purity >98%. |
| 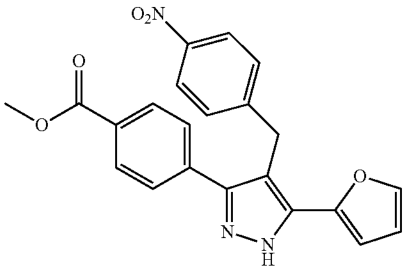 TR-K-04 | 1004 (TR-K-04) | 1H NMR (599 MHz, CDCl3) δ 8.15 (d, J = 8.4 Hz, 2H), 8.02 (d, J = 8.0 Hz, 2H), 7.50 (d, J = 7.9 Hz, 2H), 7.43 (s, 1H), 7.32 (d, J = 8.3 Hz, 2H), 6.42 (d, J = 21.0 Hz, 2H), 4.29 (s, 2H), 3.94 (s, 3H). 13C NMR (151 MHz, CDCl3) δ 166.62, 147.78, 146.68, 142.63, 130.20, 129.92, 128.69, 127.59, 124.02, 111.63, 111.42, 107.70, 52.57, 29.95. HRMS (ESI): m/z (%) = 404.1238 (M + $H^+$). Purity >95%. |
| 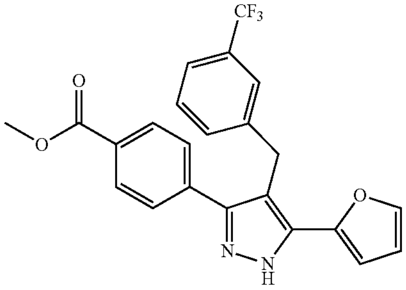 TR-K-05 | 1005 (TR-K-05) | 1H NMR (599 MHz, CDCl3) δ 8.04 (d, J = 8.2 Hz, 2H), 7.54 (d, J = 8.2 Hz, 2H), 7.49 (d, J = 7.7 Hz, 1H), 7.45 (d, J = 5.5 Hz, 2H), 7.40 (t, J = 7.7 Hz, 1H), 7.33 (d, J = 7.7 Hz, 1H), 6.45 (dd, J = 3.1, 1.7 Hz, 1H), 6.40 (d, J = 3.3 Hz, 1H), 4.24 (s, 2H), 3.94 (s, 3H). 13C NMR (151 MHz, CDCl3) δ 166.73, 140.83, 131.10, 130.85, 130.08, 129.83, 129.18, 127.62, 124.70, 123.31, 111.92, 111.69, 107.34, 52.34, 29.58. HRMS (ESI): m/z (%) = 427.1261 (M + $H^+$). Purity >96%. |
| 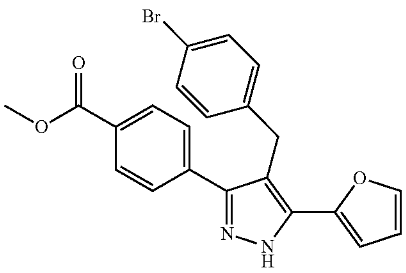 TR-K-06 | 1006 (TR-K-06) | 1H NMR (599 MHz, CDCl3) δ 8.04 (d, J = 8.3 Hz, 2H), 7.55 (d, J = 8.2 Hz, 2H), 7.46 (d, J = 1.1 Hz, 1H), 7.43 (d, J = 8.3 Hz, 2H), 7.06 (d, J = 8.3 Hz, 2H), 6.44 (dd, J = 3.2, 1.7 Hz, 1H), 6.38 (d, J = 3.3 Hz, 1H), 4.12 (s, 2H), 3.94 (s, 3H). 13C NMR (151 MHz, CDCl3) δ 166.73, 138.77, 131.79, 130.11, 129.71, 129.65, 127.57, 120.19, 112.22, 111.64, 107.77, 51.97, 29.13. HRMS (ESI): m/z (%) = 437.0491 (M + $H^+$). Purity >96%. |

TABLE 1000-continued

| STRUCTURE | ENTRY NUMBER (NAME) | ANALYTICAL DATA |
|---|---|---|
| 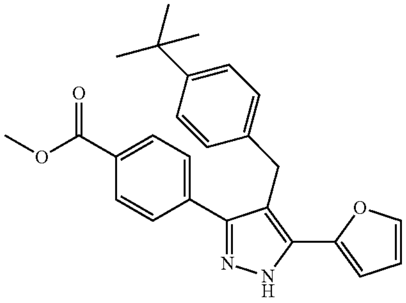 TR-K-07 | 1007 (TR-K-07) | 1H NMR (599 MHz, CDCl3) δ 8.04 (d, J = 8.2 Hz, 2H), 7.61 (d, J = 8.2 Hz, 2H), 7.47 (s, 1H), 7.32 (d, J = 8.2 Hz, 2H), 7.11 (d, J = 8.1 Hz, 2H), 6.46-6.40 (m, 2H), 4.14 (s, 2H), 3.94 (s, 3H), 1.32 (s, 10H). 13C NMR (151 MHz, CDCl3) δ 166.93, 149.03, 136.52, 130.11, 129.51, 127.62, 127.50, 125.63, 113.18, 111.70, 107.78, 52.12, 34.31, 31.31, 29.13. HRMS (ESI): m/z (%) = 415.2012 (M + H$^+$). Purity >98%. |
| 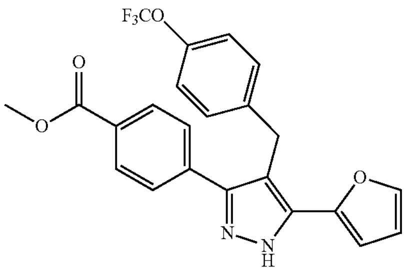 TR-K-08 | 1008 (TR-K-08) | 1H NMR (599 MHz, CDCl3) δ 8.04 (d, J = 8.1 Hz, 2H), 7.55 (d, J = 8.0 Hz, 2H), 7.46 (s, 1H), 7.19 (d, J = 8.4 Hz, 2H), 7.15 (d, J = 8.4 Hz, 2H), 6.47-6.38 (m, 2H), 4.18 (s, 2H), 3.94 (s, 3H). 13C NMR (151 MHz, CDCl3) δ 166.72, 138.49, 130.08, 129.77, 129.19, 127.64, 121.32, 111.71, 107.70, 52.34, 29.13. HRMS (ESI): m/z (%) = 443.1210 (M + H$^+$). Purity >99%. |
| 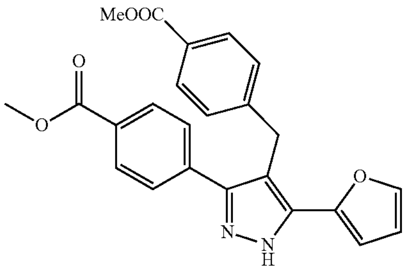 TR-K-09 | 1009 (TR-K-09) | 1H NMR (599 MHz, CDCl3) δ 7.97 (d, J = 8.1 Hz, 1H), 7.53 (d, J = 8.1 Hz, 1H), 7.47-7.42 (m, 1H), 7.27-7.23 (m, 1H), 6.43-6.35 (m, 1H), 4.23 (s, 1H), 3.92 (s, 1H), 3.89 (s, 1H). 13C NMR (151 MHz, MeOD) δ 155.97, 152.23, 125.25, 120.45, 116.82, 115.53, 108.29, 105.56, 90.19, 88.63, 83.89, 80.28, 73.55, 73.10, 71.87, 71.26, 45.77, 43.84, 30.94. HRMS (ESI): m/z (%) = 417.1445 (M + H$^+$). Purity >96%. |
| 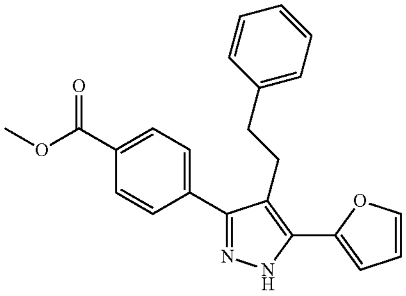 TR-K-010 | 1010 (TR-K-010) | 1H NMR (599 MHz, CDCl3) δ 8.12 (d, J = 8.4 Hz, 8H), 7.86 (d, J = 8.2 Hz, 8H), 7.55 (d, J = 7.4 Hz, 7H), 7.50 (s, 4H), 6.87 (s, 4H), 6.70 (dd, J = 9.4, 3.2 Hz, 6H), 6.55 (d, J = 20.7 Hz, 7H), 3.97 (s, 7H), 3.96 (s, 12H), 3.15-3.07 (m, 8H), 2.91-2.87 (m, 9H). 13C NMR (151 MHz, MeOD) δ 155.97, 152.23, 125.25, 120.45, 116.82, 115.53, 108.29, 105.56, 90.19, 88.63, 83.89, 80.28, 73.55, 73.10, 71.87, 71.26, 45.77, 43.84, 30.94. HRMS (ESI): m/z (%) = 373.1545 (M + H$^+$). Purity >96%. |

Example C11
Non-Limiting Examples of Mettl3 Inhibitors Include Compounds in Table 1100:
TABLE 1100
| STRUCTURE | ENTRY NUMBER (NAME) |
|---|---|
| 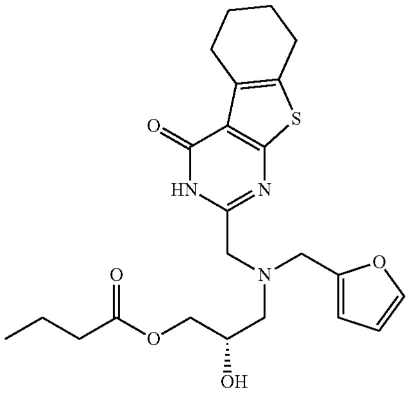 [SMILES: CCCC(=O)OC[C@@H](O)CN(Cc1nc2sc3c(c2c(=O)[nH]1)CCCC3)Cc1ccco1] | 1101 (Anticancer 2891) |
| 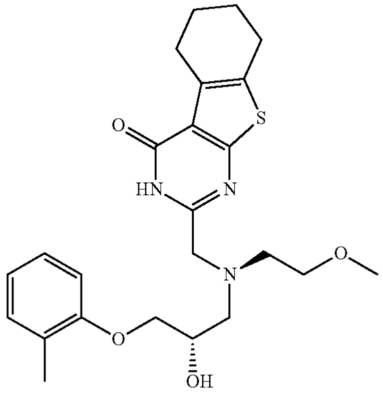 | 1102 (Anticancer 2888) |
| 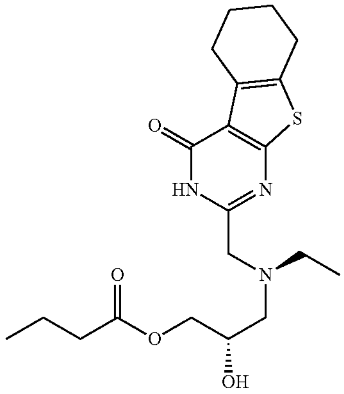 | 1103 (Anticancer 2858) |

TABLE 1100-continued
| STRUCTURE | ENTRY NUMBER (NAME) |
|---|---|
| 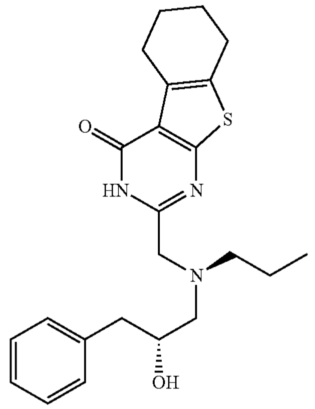 | 1104 (Anticancer 2862) |
| 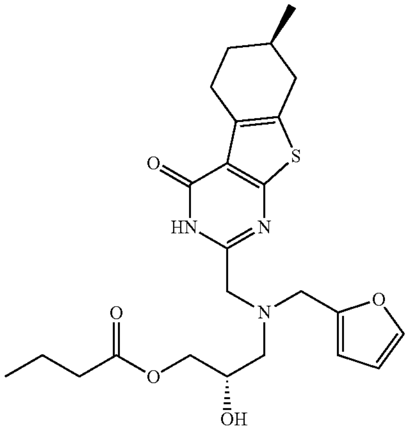 [SMILES: CCCC(=O)OC[C@@H](O)CN(Cc1nc2sc3c(c2c(=O)[nH]1)CC[C@@H](C)C3)Cc1ccco1] | 1105 (Anticancer 2913) |
| 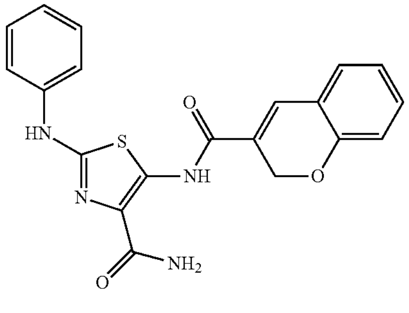 [SMILES: NC(=O)c1nc(Nc2ccccc2)sc1NC(=O)C1=Cc2ccccc2OC1] | 1106 (Anticancer 2010) |
| 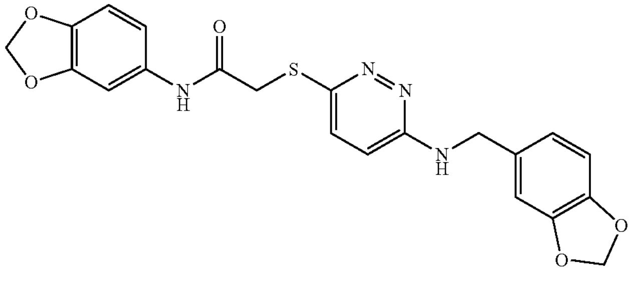 [SMILES: O=C(CSc1ccc(NCc2ccc3c(c2)OCO3)nn1)Nc1ccc2c(c1)OCO2] | 1107 (Anticancer 1497) |

TABLE 1100-continued
| STRUCTURE | ENTRY NUMBER (NAME) |
| --- | --- |
| 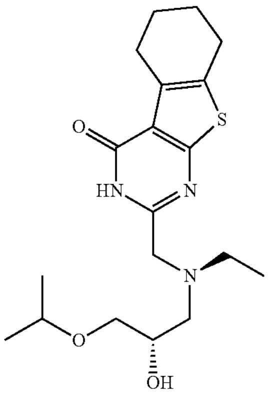 | 1108 (Anticancer 2914) |
| 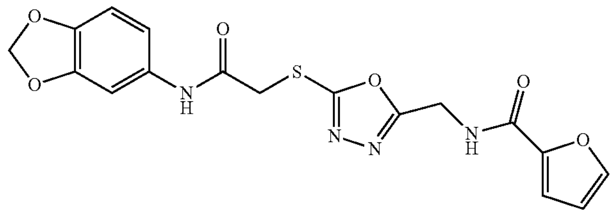 [SMILES: O=C(CSc1nnc(CNC(=O)c2ccco2)o1)Nc1ccc2c(c1)OCO2] | 1109 (Anticancer 334) |
| 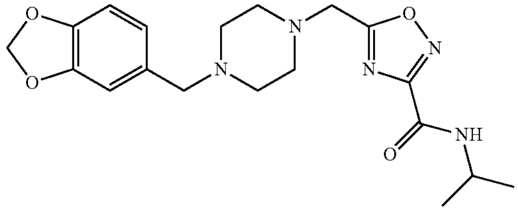 [SMILES: CC(C)NC(=O)c1noc(CN2CCN(Cc3ccc4c(c3)OCO4)CC2)n1] | 1110 (Anticancer 2919) |
| 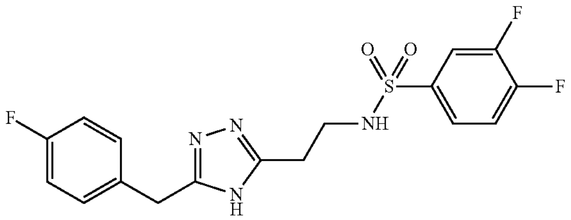 [SMILES: O=S(=O)(NCCc1nnc(Cc2ccc(F)cc2)[nH]1)c1ccc(F)c(F)c1] | 1111 (Anticancer 2000) |
| 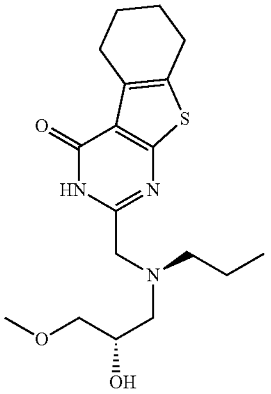 | 1112 (Anticancer 2879) |

TABLE 1100-continued
| STRUCTURE | ENTRY NUMBER (NAME) |
| --- | --- |
| 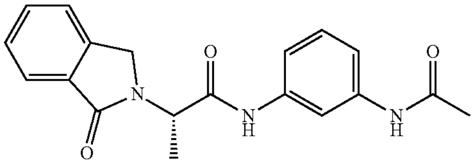 [SMILES: CC(=O)Nc1cccc(NC(=O)[C@H](C)N2Cc3ccccc3C2=O)c1] | 1113 (Anticancer 1151) |
| 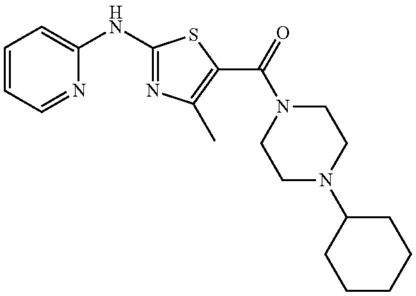 [SMILES: Cc1nc(Nc2ccccn2)sc1C(=O)N1CCN(C2CCCCC2)CC1] | 1114 (Anticancer 2640) |
| 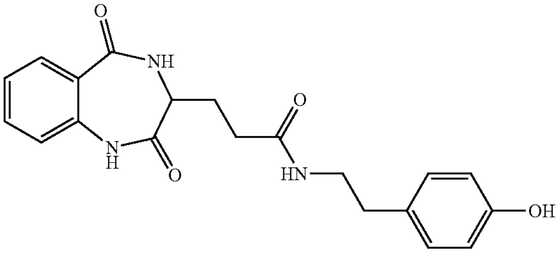 [SMILES: O=C(CCC1NC(=O)c2ccccc2NC1=O)NCCc1ccc(O)cc1] | 1115 (Anticancer 2221) |
| 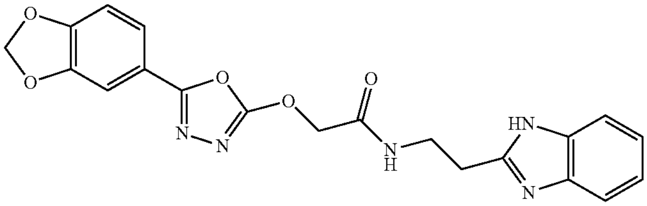 [SMILES: O=C(COc1nnc(-c2ccc3c(c2)OCO3)o1)NCCc1nc2ccccc2[nH]1] | 1116 (Anticancer 741) |
| 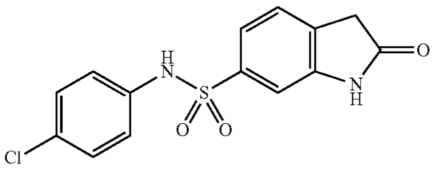 [SMILES: O=C1Cc2ccc(S(=O)(=O)Nc3ccc(Cl)cc3)cc2N1] | 1117 (Anticancer 390) |
| 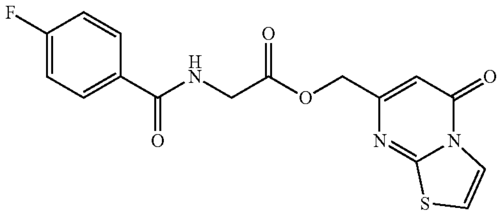 [SMILES: O=C(CNC(=O)c1ccc(F)cc1)OCc1cc(=O)n2ccsc2n1] | 1118 (Anticancer 1707) |

TABLE 1100-continued
| STRUCTURE | ENTRY NUMBER (NAME) |
|---|---|
| 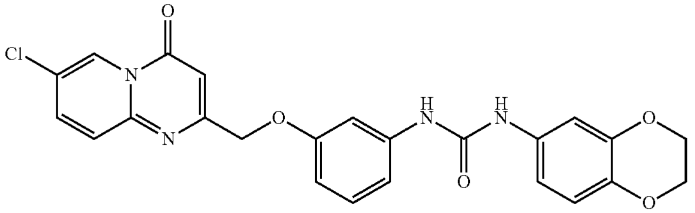 [SMILES: O=C(Nc1cccc(OCc2cc(=O)n3cc(Cl)ccc3n2)c1)Nc1ccc2c(c1)OCCO2] | 1119 (Anticancer 2022) |
| 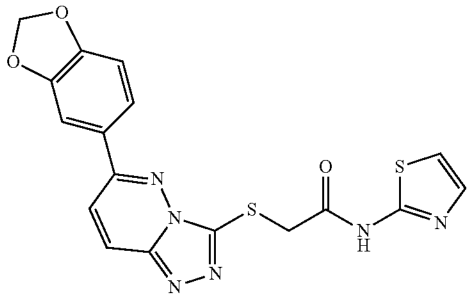 [SMILES: O=C(CSc1nnc2ccc(-c3ccc4c(c3)OCO4)nn12)Nc1nccs1] | 1120 (Anticancer 2106) |
| 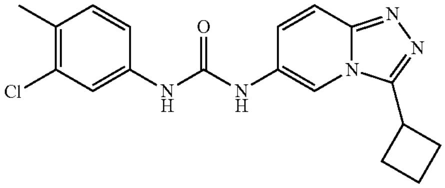 [SMILES: Cc1ccc(NC(=O)Nc2ccc3nnc(C4CCC4)n3c2)cc1Cl] | 1121 (Anticancer 2768) |
| 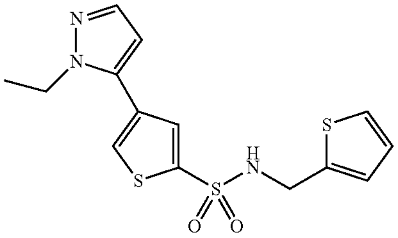 [SMILES: CCn1nccc1-c1csc(S(=O)(=O)NCc2cccs2)c1] | 1122 (Anticancer 2617) |
| 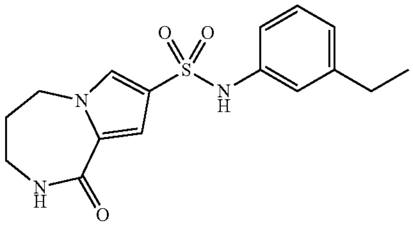 [SMILES: CCc1cccc(NS(=O)(=O)c2cc3n(c2)CCCNC3=O)c1] | 1123 (Anticancer 2788) |
| 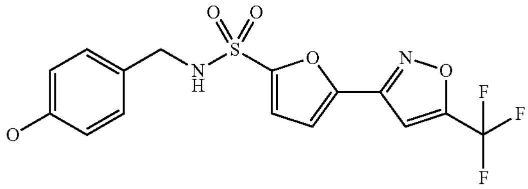 [SMILES: O=S(=O)(NCc1ccc(O)cc1)c1ccc(-c2cc(C(F)(F)F)on2)o1] | 1124 (Anticancer 1561) |

TABLE 1100-continued
| STRUCTURE | ENTRY NUMBER (NAME) |
|---|---|
| 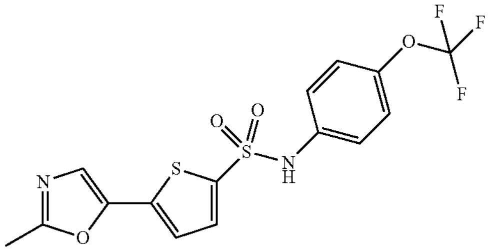 [SMILES: Cc1ncc(-c2ccc(S(=O)(=O)Nc3ccc(OC(F)(F)F)cc3)s2)o1] | 1125 (Anticancer 2380) |
| 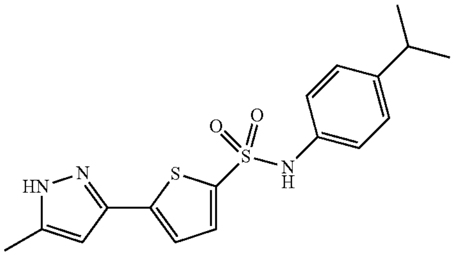 [SMILES: Cc1cc(-c2ccc(S(=O)(=O)Nc3ccc(C(C)C)cc3)s2)n[nH]1] | 1126 (Anticancer 2380) |
| 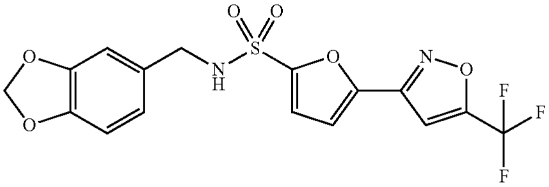 [SMILES: O=S(=O)(NCc1ccc2c(c1)OCO2)c1ccc(-c2cc(C(F)(F)F)on2)o1] | 1127 (Anticancer 1561) |
| 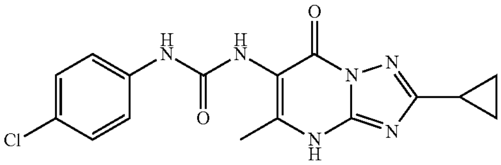 [SMILES: Cc1[nH]c2nc(C3CC3)nn2c(=O)c1NC(=O)Nc1ccc(Cl)cc1] | 1128 (Anticancer 2370) |
| 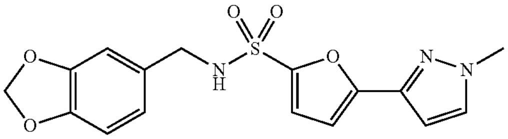 [SMILES: Cn1ccc(-c2ccc(S(=O)(=O)NCc3ccc4c(c3)OCO4)o2)n1] | 1129 (Anticancer 2613) |
| 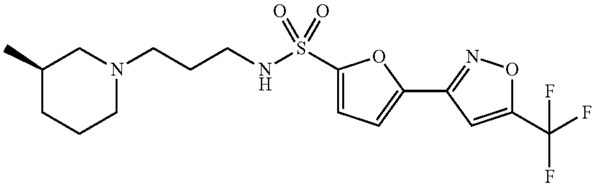 [SMILES: C[C@@H]1CCCN(CCCNS(=O)(=O)c2ccc(-c3cc(C(F)(F)F)on3)o2)C1] | 1130 (Anticancer 1633) |
| 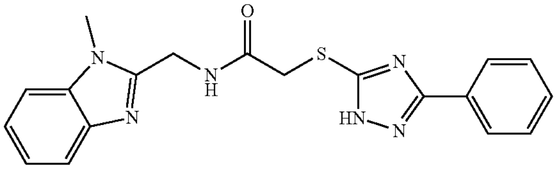 [SMILES: Cn1c(CNC(=O)CSc2nc(-c3ccccc3)n[nH]2)nc2ccccc21] | 1131 (Anticancer 2005) |

TABLE 1100-continued
| STRUCTURE | ENTRY NUMBER (NAME) |
|---|---|
| 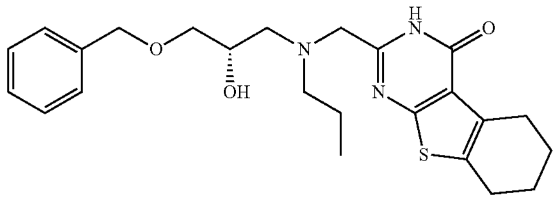 [SMILES: CCCN(Cc1nc2sc3c(c2c(=O)[nH]1)CCCC3)C[C@H](O)COCc1ccccc1] | 1132 (KDM 2861) |
| 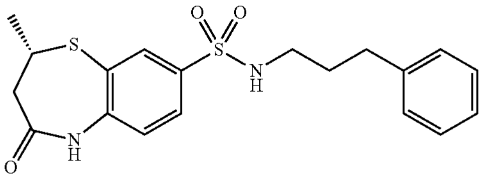 [SMILES: C[C@H]1CC(=O)Nc2ccc(S(=O)(=O)NCCCc3ccccc3)cc2S1] | 1133 (KDM 1802) |
| 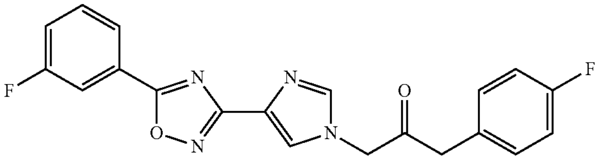 [SMILES: O=C(Cc1ccc(F)cc1)Cn1cnc(-c2noc(-c3cccc(F)c3)n2)c1] | 1134 (KDM 3415) |
| 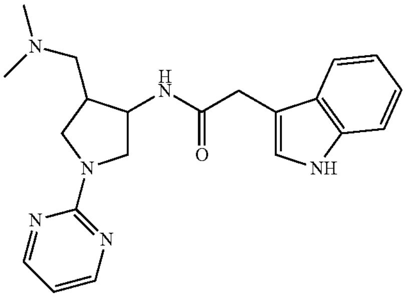 [SMILES: CN(C)CC1CN(c2ncccn2)CC1NC(=O)Cc1c[nH]c2ccccc12] | 1135 (Antiviral 4737) |
| 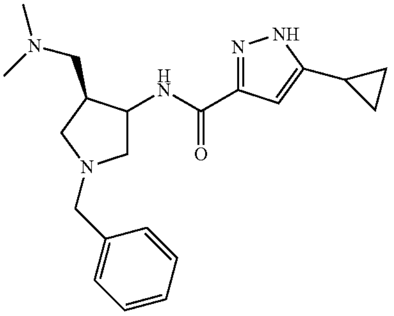 [SMILES: CN(C)C[C@@H]1CN(Cc2ccccc2)CC1NC(=O)c1cc(C2CC2)[nH]n1] | 1136 (Antiviral 4744) |
| 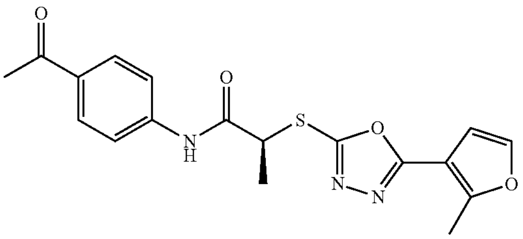 [SMILES: CC(=O)c1ccc(NC(=O)[C@H](C)Sc2nnc(-c3ccoc3C)o2)cc1] | 1137 (Anticancer 777) |

TABLE 1100-continued
| STRUCTURE | ENTRY NUMBER (NAME) |
|---|---|
| 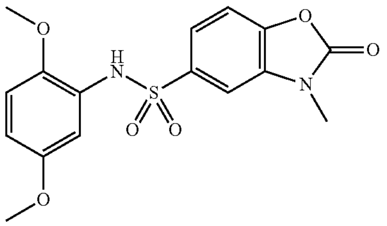 [SMILES: COc1ccc(OC)c(NS(=O)(=O)c2ccc3oc(=O)n(C)c3c2)c1] | 1138 (Anticancer 439) |
| 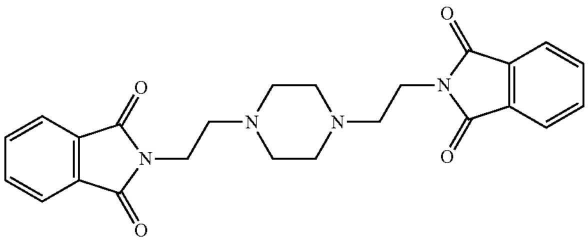 [SMILES: O=C1c2ccccc2C(=O)N1CCN1CCN(CCN2C(=O)c3ccccc3C2=O)CC1] | 1139 (Anticancer 1) |
| 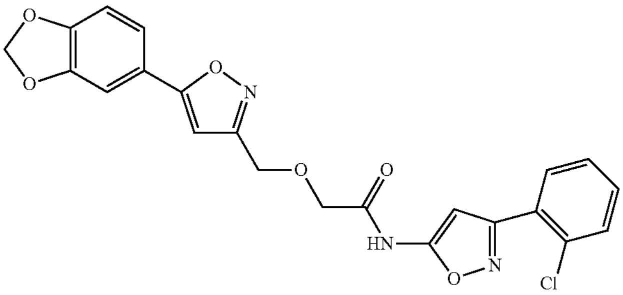 [SMILES: O=C(COCc1cc(-c2ccc3c(c2)OCO3)on1)Nc1cc(-c2ccccc2Cl)no1] | 1140 (Anticancer 1154) |
| 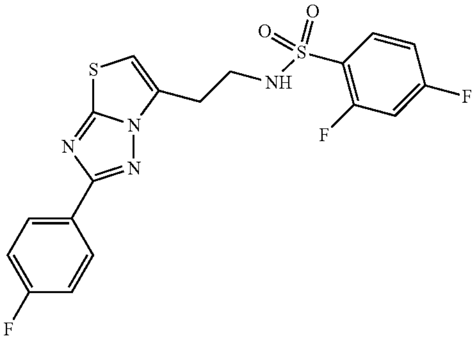 [SMILES: O=S(=O)(NCCc1csc2nc(-c3ccc(F)cc3)nn12)c1ccc(F)cc1F] | 1141 (Anticancer 2089) |
| 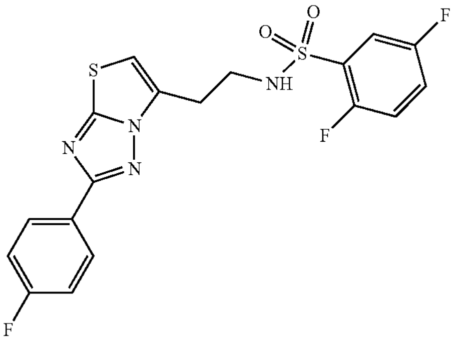 [SMILES: O=S(=O)(NCCc1csc2nc(-c3ccc(F)cc3)nn12)c1cc(F)ccc1F] | 1142 (Anticancer 2088) |

TABLE 1100-continued
| STRUCTURE | ENTRY NUMBER (NAME) |
| --- | --- |
| 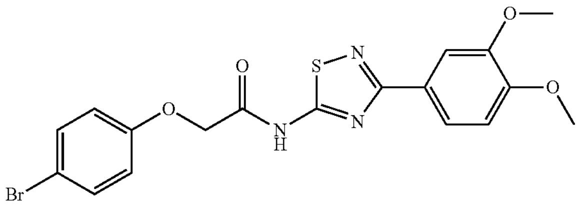 [SMILES: COc1ccc(-c2nsc(NC(=O)COc3ccc(Br)cc3)n2)cc1OC] | 1143 (Anticancer 772) |
| 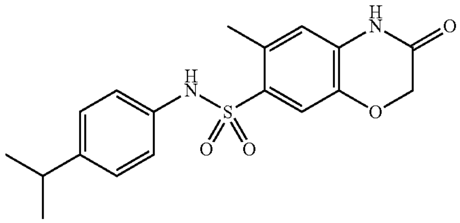 [SMILES: Cc1cc2c(cc1S(=O)(=O)Nc1ccc(C(C)C)cc1)OCC(=O)N2] | 1144 (Anticancer 1048) |
| 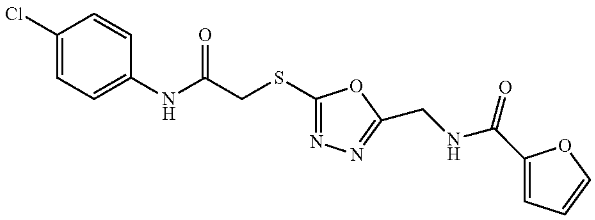 [SMILES: O=C(CSc1nnc(CNC(=O)c2ccco2)o1)Nc1ccc(Cl)cc1] | 1145 (Anticancer 335) |
| 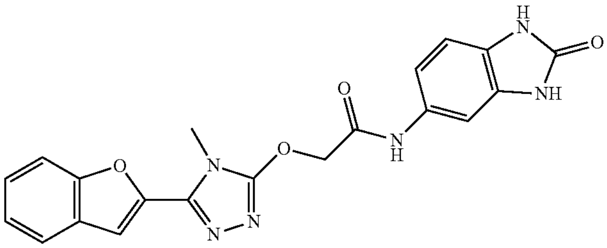 [SMILES: Cn1c(OCC(=O)Nc2ccc3[nH]c(=O)[nH]c3c2)nnc1-c1cc2ccccc2o1] | 1146 (Anticancer 2177) |
| 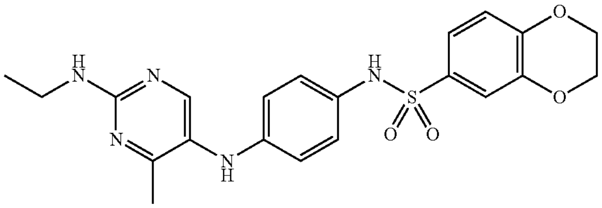 [SMILES: CCNc1ncc(Nc2ccc(NS(=O)(=O)c3ccc4c(c3)OCCO4)cc2)c(C)n1] | 1147 (Anticancer 903) |
| 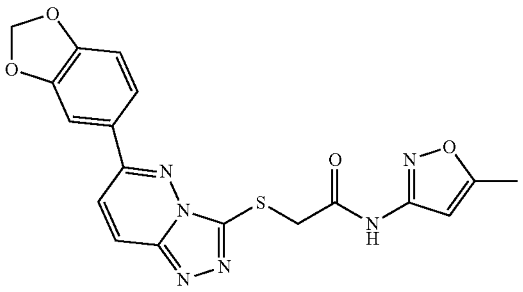 [SMILES: Cc1cc(NC(=O)CSc2nnc3ccc(-c4ccc5c(c4)OCO5)nn23)no1] | 1148 (Anticancer 2105) |

TABLE 1100-continued
| STRUCTURE | ENTRY NUMBER (NAME) |
|---|---|
| 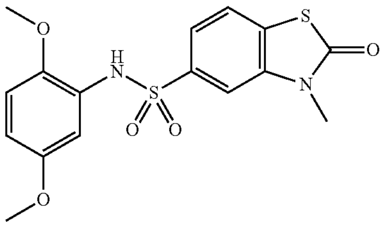 [SMILES: COc1ccc(OC)c(NS(=O)(=O)c2ccc3sc(=O)n(C)c3c2)c1] | 1149 (Anticancer 439) |
| 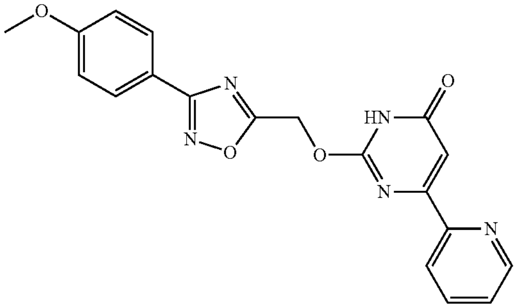 [SMILES: COc1ccc(-c2noc(COc3nc(-c4ccccn4)cc(=O)[nH]3)n2)cc1] | 1150 (Anticancer 2069) |
| 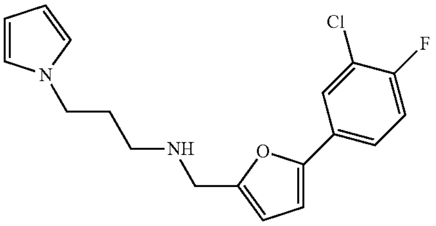 [SMILES: Fc1ccc(-c2ccc(CNCCCn3cccc3)o2)cc1Cl] | 1151 (Anticancer 921) |
| 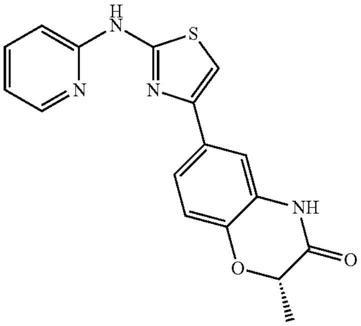 [SMILES: C[C@@H]1Oc2ccc(-c3csc(Nc4ccccn4)n3)cc2NC1=O] | 1152 (Anticancer 854) |
| 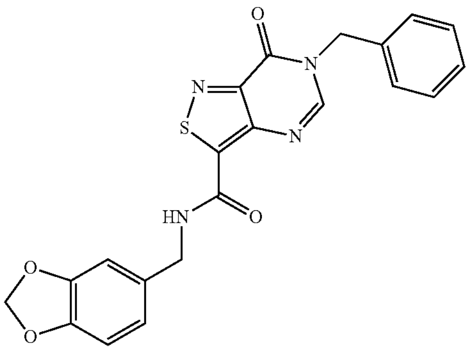 [SMILES: O=C(NCc1ccc2c(c1)OCO2)c1snc2c(=O)n(Cc3ccccc3)cnc12] | 1153 (Anticancer 2470) |

TABLE 1100-continued
| STRUCTURE | ENTRY NUMBER (NAME) |
|---|---|
| 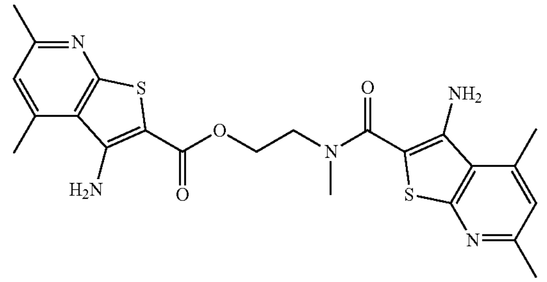 [SMILES: Cc1cc(C)c2c(N)c(C(=O)OCCN(C)C(=O)c3sc4nc(C)cc(C)c4c3N)sc2n1] | 1154 (Anticancer 159) |
| 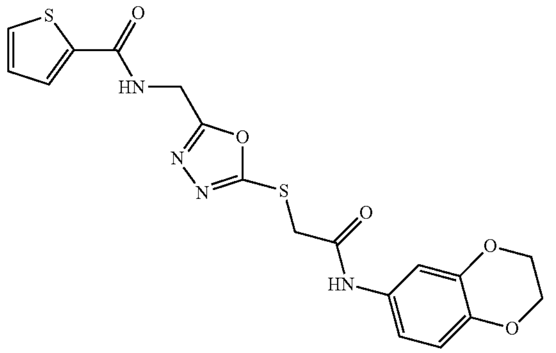 [SMILES: O=C(CSc1nnc(CNC(=O)c2cccs2)o1)Nc1ccc2c(c1)OCCO2] | 1155 (Anticancer 331) |
| 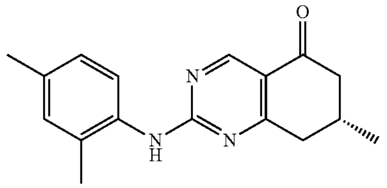 | 1156 (Anticancer 768) |
| 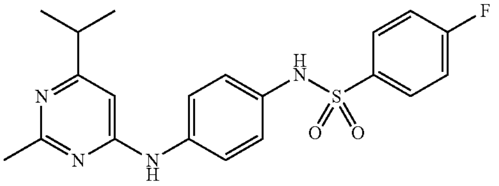 [SMILES: Cc1nc(Nc2ccc(NS(=O)(=O)c3ccc(F)cc3)cc2)cc(C(C)C)n1] | 1157 (Anticancer 847) |
| 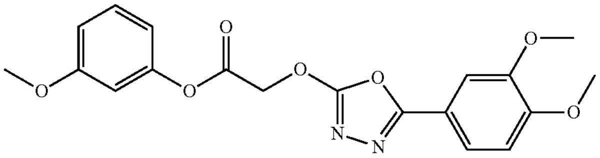 | 1158 (Anticancer 786) |
| 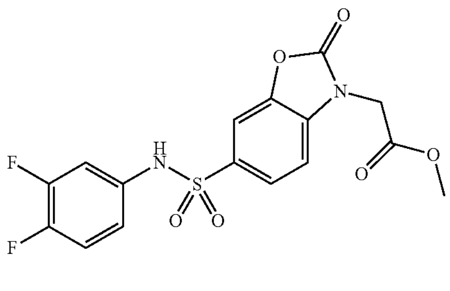 [SMILES: COC(=O)Cn1c(=O)oc2cc(S(=O)(=O)Nc3ccc(F)c(F)c3)ccc21] | 1159 (Anticancer 1290) |

TABLE 1100-continued
| STRUCTURE | ENTRY NUMBER (NAME) |
|---|---|
| 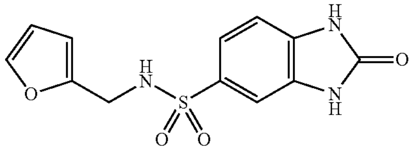 [SMILES: O=c1[nH]c2ccc(S(=O)(=O)NCc3ccco3)cc2[nH]1] | 1160 (Anticancer 2042) |
| 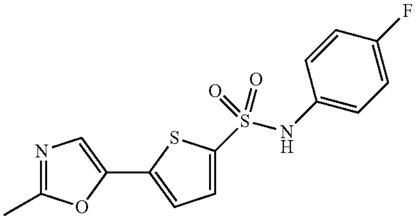 [SMILES: Cc1ncc(-c2ccc(S(=O)(=O)Nc3ccc(F)cc3)s2)o1] | 1161 (Anticancer 2376) |
| 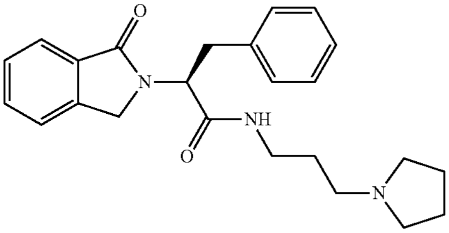 [SMILES: O=C(NCCCN1CCCC1)[C@H](Cc1ccccc1)N1Cc2ccccc2C1=O] | 1162 (Anticancer 1109) |
| 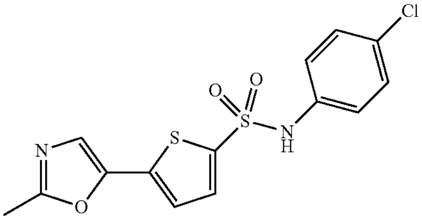 [SMILES: Cc1ncc(-c2ccc(S(=O)(=O)Nc3ccc(Cl)cc3)s2)o1] | 1163 (Anticancer 2373) |
| 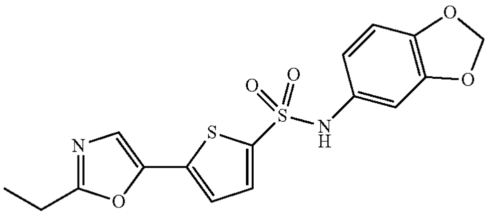 [SMILES: CCc1ncc(-c2ccc(S(=O)(=O)Nc3ccc4c(c3)OCO4)s2)o1] | 1164 (Anticancer 2376) |
| 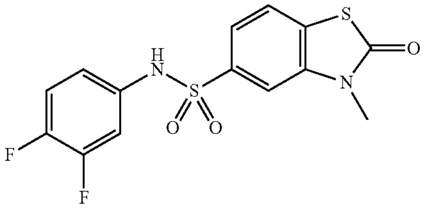 [SMILES: Cn1c(=O)sc2ccc(S(=O)(=O)Nc3ccc(F)c(F)c3)cc21] | 1165 (Anticancer 1499) |
| 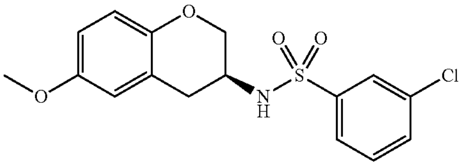 [SMILES: COc1ccc2c(c1)C[C@H](NS(=O)(=O)c1cccc(Cl)c1)CO2] | 1166 (Anticancer 1418) |

TABLE 1100-continued
| STRUCTURE | ENTRY NUMBER (NAME) |
|---|---|
| 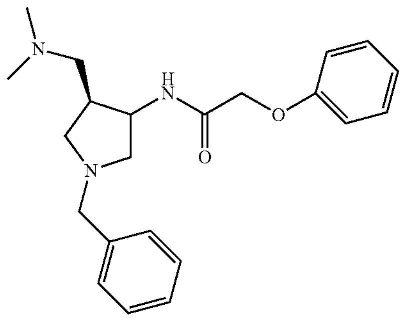 [SMILES: CN(C)C[C@@H]1CN(Cc2ccccc2)CC1NC(=O)COc1ccccc1] | 1167 (Antiviral 4370) |
| 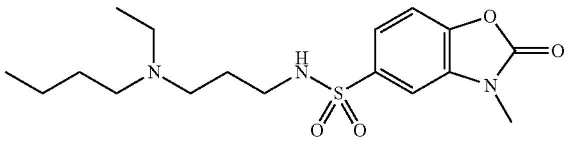 [SMILES: CCCCN(CC)CCCNS(=O)(=O)c1ccc2oc(=O)n(C)c2c1] | 1168 (Antiviral 699) |
| 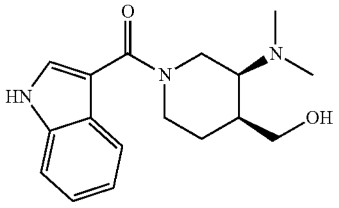 [SMILES: CN(C)[C@@H]1CN(C(=O)c2c[nH]c3ccccc23)CC[C@@H]1CO] | 1169 (PPI 1577) |
| 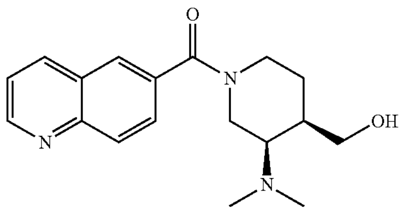 [SMILES: CN(C)[C@H]1CN(C(=O)c2ccc3ncccc3c2)CC[C@H]1CO] | 1170 (CNS 2713) |
| 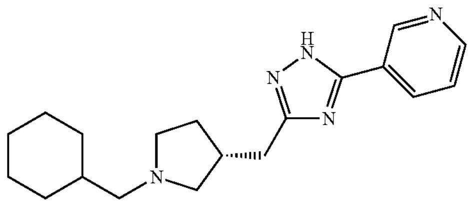 [SMILES: c1cncc(-c2nc(C[C@H]3CCN(CC4CCCCC4)C3)n[nH]2)c1] | 1171 (CNS 2626) |
| 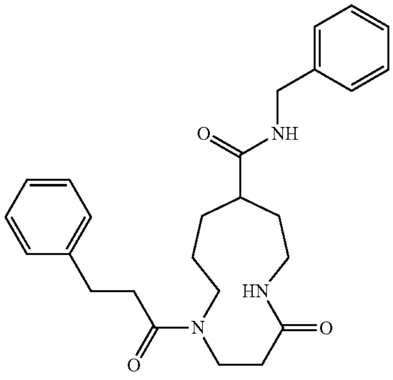 [SMILES: O=C1CCN(C(=O)CCc2ccccc2)CCCC(C(=O)NCc2ccccc2)CCN1] | 1172 (Macrocycle 121) |

TABLE 1100-continued
| STRUCTURE | ENTRY NUMBER (NAME) |
|---|---|
| 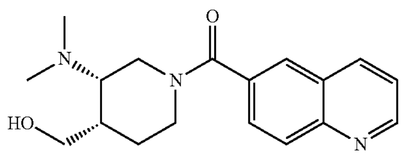 [SMILES: CN(C)[C@@H]1CN(C(=O)c2ccc3ncccc3c2)CC[C@@H]1CO] | 1173 (Beyone 4801) |
| 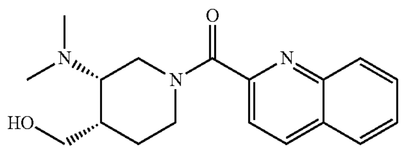 [SMILES: CN(C)[C@@H]1CN(C(=O)c2ccc3ccccc3n2)CC[C@@H]1CO] | 1174 (Beyond 4793) |
| 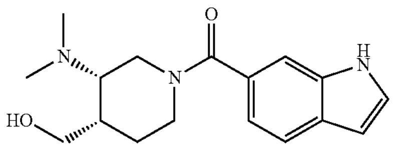 [SMILES: CN(C)[C@@H]1CN(C(=O)c2ccc3cc[nH]c3c2)CC[C@@H]1CO] | 1175 (Beyond 4797) |
| 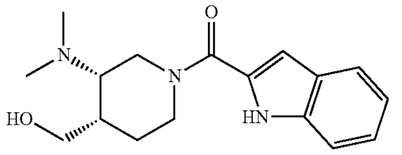 [SMILES: CN(C)[C@@H]1CN(C(=O)c2cc3ccccc3[nH]2)CC[C@@H]1CO] | 1176 (Beyond 4789) |
| 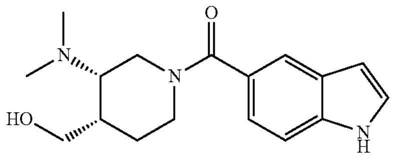 [SMILES: CN(C)[C@@H]1CN(C(=O)c2ccc3[nH]ccc3c2)CC[C@@H]1CO] | 1177 (Beyond 4798) |
| 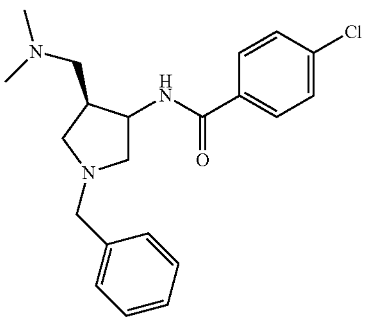 [SMILES: CN(C)C[C@@H]1CN(Cc2ccccc2)CC1NC(=O)c1ccc(Cl)cc1] | 1178 (Beyond 5078) |

Example C12
Procedure for the Preparation of Non-Limiting Exemplary Mettl3/14 Inhibitors (e.g., Compounds Having Formula (M1)).
Synthesis Route of Compound 1.
Scheme 12a.
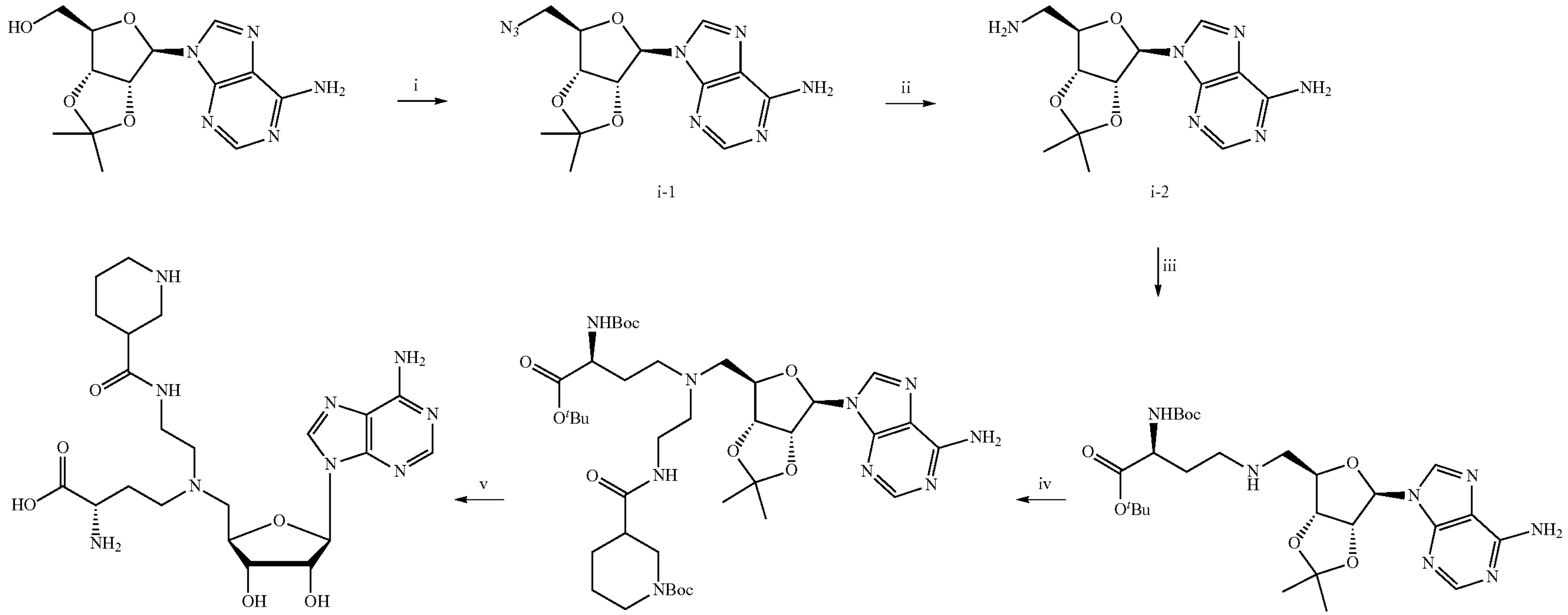
i-1
i-2
i-3
i-4
1
Reagents and conditions: i, a) Diphenylphosphoryl azide (DPPA), DBU, dioxane;
b) $NaN_3$, 15-crown-5; ii, $H_2$, Pd/C, MeOH; iii, BB-1, $NaBH(OAc)_3$, DCE; iv,
a) DIPEA, DMF, 50° C.; b) BB-2, $NaBH(OAc)_3$, AcOH; v, TFA:water:anisole (9:1:1).

Step i. Synthesis of Compound i1.

To a suspension of 2',3'-O-isopropylideneadenosine (2.0 g, 6.5 mmol, 1 eq.) in 1,4-dioxane (4 mL) was added DPPA (2.8 mL, 13 mmol, 2 eq.) and DBU (2.92 mL, 19.54 mmol, 3 eq.) at room temperature under $N_2$. The solution was stirred for 2 hours after which $NaN_3$ (2.12 g, 32.6 mmol, 5 eq.) and 15-crown-5 (128 μL, 0.65 mmol, 0.1 eq.) were added and the reaction mixture was heated to reflux. After 1.5 hours the solid was removed by filtration. The solvent was evaporated and the crude product was purified by column chromatography (Ethyl acetate/Hexanes=1:1, to dichloromethane:methanol=50:1, silica). After dried under vacuum, a light yellow solid (i1) was obtained.

$^1$H NMR (600 MHz, Chloroform-d) δ 8.35 (s, 1H), 7.92 (s, 1H), 6.11 (d, J=2.4 Hz, 1H), 5.85 (s, 2H), 5.46 (dd, J=6.3, 2.4 Hz, 1H), 5.06 (dd, J=6.4, 3.4 Hz, 1H), 4.38 (td, J=5.7, 3.3 Hz, 1H), 3.64-3.50 (m, 3H), 1.62 (s, 3H), 1.39 (s, 3H).

HRMS ($ESI^+$) calcd for $C_{13}H_{17}N_8O_3$ $[M+H]^+$ m/z 333.1418, found m/z 333.1419.

Step ii. Synthesis of Compound i2. To the adenosine azide derivative (i1) (500 mg, 1.6 mmol) in methanol (10 mL) was added Pd/C (100 mg). The reaction mixture was then placed under an atmosphere of H2 for 4 hours. After the completion of reduction reaction, the reaction mixture was filtered through a pad of celite to remove the Pd/C. Then the solvent was evaporated and the crude product (i2) was obtained and no further purification was performed to be used directly in the next step.

$^1$H NMR (600 MHz, Chloroform-d) δ 8.33 (s, 1H), 7.92 (s, 1H), 6.02 (d, J=3.0 Hz, 1H), 5.85 (s, 2H), 5.46 (dd, J=6.5, 3.0 Hz, 1H), 5.01 (dd, J=6.5, 3.5 Hz, 1H), 4.30-4.15 (m, 1H), 3.03 (dd, J=13.4, 4.5 Hz, 1H), 2.95 (dd, J=13.4, 6.0 Hz, 1H), 1.61 (s, 3H), 1.38 (s, 3H).

Step iii. Synthesis of Compound i3. Aldehyde BB-1 (273 mg, 1 mmol) and compound (i2) (306 mg, 1 mmol) were dissolved in DCE (10 mL). To this mixture was added $Na(OAc)_3BH$ (318 mg, 1.5 mmol) in small portions, with addition of further DCE to keep the suspension mobile. The mixture was stirred for 2 hours and the reaction monitored by TLC. Then the saturated $NaHCO_3$ solution (2 mL) was added and stirring continued for 30 minutes. The mixture was then poured into water and extract with DCM (3×20 mL). Then the combined organic extracts were dried over $MgSO_4$ and the solvent removed in vacuo. The product i3 was purified by column chromatography (MeOH/DCM=10:1 to 5:1) to give secondary amine as a white solid.

Step iv. Synthesis of Compound i4. Compound (i3) (56.4 mg, 0.1 mmol ) and aldehyde BB-2 (32.4 mg, 1.2 eq.) were dissolved in DMF (3 mL), then DIPEA (20 μL, 1.2 eq.) was added and the mixture was heated to 50° C. for 1 hour. After that the reaction was recovered to room temperature and NaBH(OAc)3 (53 mg, 2.5 eq.) was added into above in small amount of portions followed by the AcOH (8 μL) to adjust the pH to slight acid. Keep stirring until no reaction progression monitored by TLC. Saturated $NaHCO_3$ (5 mL) was added and then extracted by DCM (3×8 mL). Then the combined organic layers were washed by brine and subsequently subjected to the silica gel column chromatography (DCM/MeOH=20:1) purification to obtain the compound (i4).

Step v. Synthesis of Compound 1. The deprotection was taken up in a mixture solution (5 mL) consisted of TFA, water, anisole (ratio 9:1:1), the reaction was completed after 2 hours by the RP-HPLC monitoring. The solvent was mostly dried by N2 blowing left into a small portion and add $H_2O$ and MeCN to subsequently subject to the prep-RP-HPLC purification. Then the target peak collection was lyophilized by lyophilizer to give a fluffy white solid as the final compound (1).

Synthesis Route of Compound 2 and 3.

Scheme 12b.

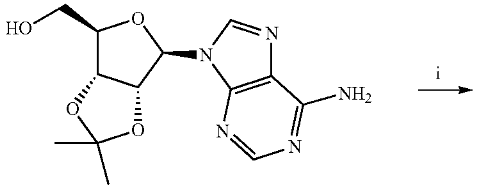

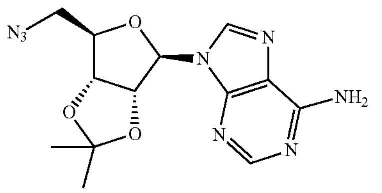

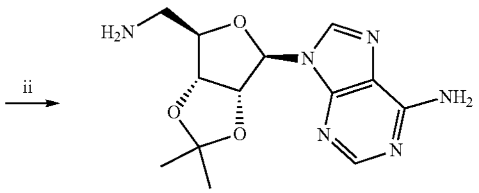

i-1 i-2

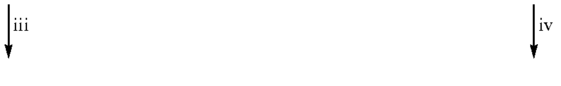

-continued

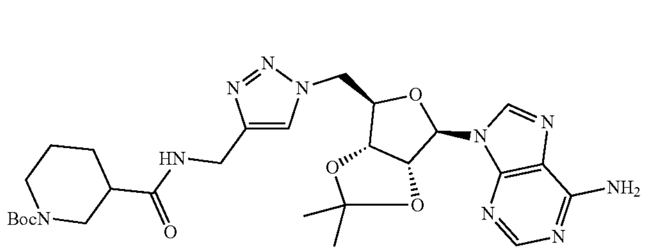

i-5 v

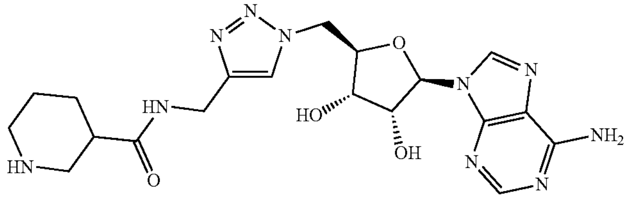

2

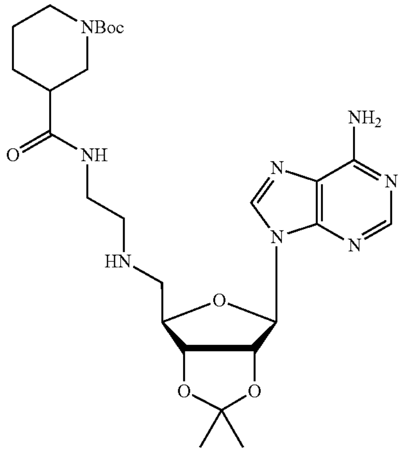

i-6 v

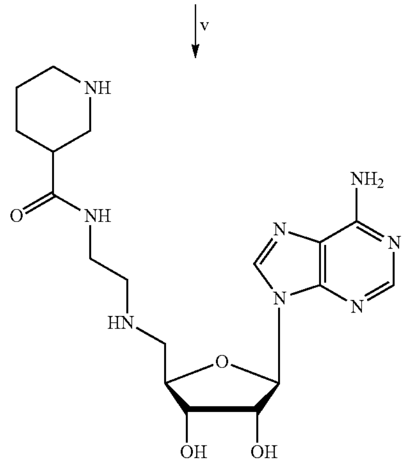

3

Reagents and conditions: i, a) Diphenylphosphoryl azide (DPPA), DBU, dioxane; b) $NaN_3$, 15-crown-5; ii, $H_2$, Pd/C, MeOH; iii, BB-3, $CuSO_4$•$5H_2O$, sodium ascorbate, $^t$BuOH:$H_2O$ = 2:1. iv, $NaBH(OAc)_3$, Triethylamine, DCM; v, TFA:water:anisole (90:5:5)

Step iii. Synthesis of Compound i-5.

Compound (i1) (70 mg, 0.21 mmol) and compound BB-3 (56 mg, 1 eq.) were dissolved in $^t$BuOH-$H_2O$ (3 mL/1.5 mL), then $CuSO_4$·$5H_2O$ (5.3 mg, 0.1 eq.) and sodium ascorbate were respectively added into the above mixture. The reaction was protected by N2 and stopped until the completion monitored by TLC. After 3 hours, ethyl acetate (8 mL) and water (6 mL) were added and after vigorously stirred for 5 minutes, all the mixture was transferred to the separating funnel, after vibrating and layering, the ethyl acetate layer was collected and concentrated which was subsequently subjected to the column chromatography purification (DCM/MeOH=20:1) to give white solid as the product (i5).

Synthesis of Compound (i6).

Step iv. A solution of compound (i2) (41 mg, 0.134 μmol) and compound BB-2 (40 mg, 1.1 eq.) in DCM (3 mL) at room temperature was stirred for 20 minutes. After the subsequent addition of Triethylamine (18 L, 1 eq.), NaBH (OAc)3 (57 mg, 2 eq.) was added in portions. Then the mixture was stirred for 3 hours. The saturated $Na_2CO_3$ was added to quench the reaction and keep continued stirring for 5 minutes. DCM was next used to extract (2×10 mL) and the collected combined organic solution was then concentrated, followed by the silica gel column chromatography by DCM/MeOH=20:1.

$^1$H NMR (600 MHz, Methanol-d4) δ 8.45 (s, 1H), 8.31-8.26 (m, 1H), 8.24 (s, 1H), 6.26 (d, J=2.5 Hz, 1H), 5.49-5.36 (m, 1H), 5.13 (dd, J=6.4, 3.4 Hz, 1H), 4.56-4.42 (m, 1H), 4.09-3.84 (m, 2H), 3.56-3.41 (m, 1H), 3.05-2.90 (m, 2H), 2.88-2.66 (m, 2H), 2.28-2.15 (m, 1H), 1.80 (dd, J=28.0, 12.7 Hz, 1H), 1.72-1.64 (m, 1H), 1.62 (s, 3H), 1.60-1.56 (m, 1H), 1.56-1.48 (m, 1H), 1.46-1.41 (m, 9H), 1.39 (s, 3H).

$^{13}$C NMR (151 MHz, Methanol-d4) δ 175.93, 175.79, 156.12, 152.69, 148.70, 140.85, 114.58, 90.80, 90.71, 83.87, 83.32, 82.30, 79.84, 49.40, 36.50, 27.26, 26.05, 24.10, 19.75.

Synthesis of Compound (2).

Step v. Compound (i5) was deprotected by the mixture solution TFA:H2O:Anisole (9:1:1) by vigorously stirring for 2 hours. RP-HPLC was used to monitor the completion of the deprotection then it was purified by prep-RP-HPLC. The collected component was lyophilized to give the white solid product compound (2).

Synthesis of Compound (3)

Step vi. Compound (i6) was deprotected by the mixture solution TFA:H2O:Anisole (9:1:1) by vigorously stirring for 2 hours. RP-HPLC was used to monitor the completion of the deprotection then it was purified by prep-RP-HPLC. The collected component was lyophilized to give the white solid product compound (3).

Synthesis Route of Compound (BB-1).

Scheme 12c.

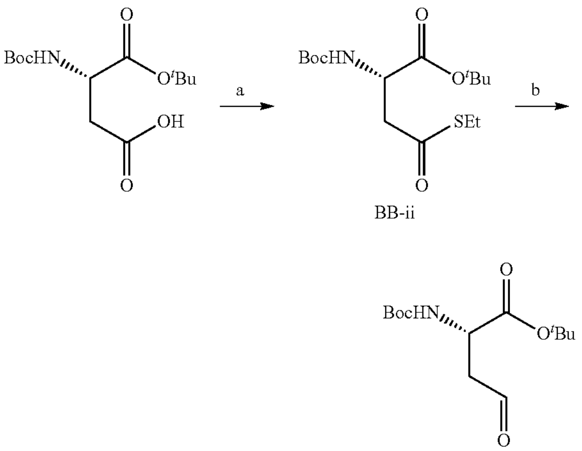

BB-ii

BB-1

Reagents and conditions: a) EtSH, DCC, DMAP, DCM, b) $Et_3SiH$, Pd/C, acetone.

Synthesis of Building Block (BB-1).

Step a. N-α-t-Boc-L-aspartic acid α-t-butylester (2.00 g, 6.92 mmol), DCC (1.71 g, 8.3 mmol), DMAP (84.0 mg, 690 μmol) and ethanethiol (562 μL, 472 mg, 7.61 mmol) were dissolved in DCM (70 mL) and stirred for 48 hours. The mixture was diluted with hexane (100 mL), filtered through a plug of celite and the solvent removed in vacuo. Purification was undertaken by column chromatography (10 to 20% ethyl acetate in hexanes) and removal of the solvent in vacuo afforded compound BB-i1.

$^1H$ NMR (599 MHz, Chloroform-d) δ 5.41 (d, J=8.4 Hz, 1H), 4.40 (d, J=8.9 Hz, 1H), 3.14 (dd, J=16.3, 4.9 Hz, 1H), 3.02 (dd, J=16.3, 4.8 Hz, 1H), 2.95-2.80 (m, 2H), 1.44 (s, 9H), 1.42 (s, 9H), 1.23 (t, J=7.4 Hz, 3H).

Step b. Compound BB-i1 (940 mg, 2.82 mmol) was dissolved in acetone (20 mL) at 0° C. To this was added 10% palladium on carbon (100 mg) and $Et_3SiH$ (2.25 mL, 1.64 g, 14.1 mmol). The reaction was maintained at between 10-20° C. and monitored by TLC (20% ethyl acetate in hexanes) which showed the starting material was consumed after 5 minutes. The mixture was filtered through celite and the solvents was removed in vacuo to yield the crude product. Purification by column chromatography (10 to 20% ethyl acetate in hexanes) and removal of the solvent in vacuo afforded compound (BB-1).

$^1H$ NMR (600 MHz, Chloroform-d) δ 9.72 (d, J=1.7 Hz, 1H), 5.35 (d, J=8.2 Hz, 1H), 4.50-4.34 (m, 1H), 3.00 (dd, J=18.0, 5.3 Hz, 1H), 2.93 (dd, J=17.9, 5.1 Hz, 1H), 1.44 (s, 9H), 1.43 (s, 9H).

$^{13}C$ NMR (151 MHz, Chloroform-d) δ 199.43, 169.96, 155.39, 82.72, 80.05, 49.35, 46.41, 29.72, 28.32.

HRMS ($ESI^+$) calcd for $C_{13}H_{23}NO_5$ $[M+Na]^+$ m/z 296.1468, found m/z 296.1467.

Synthetic Route of Compound BB2.

Scheme 12d.

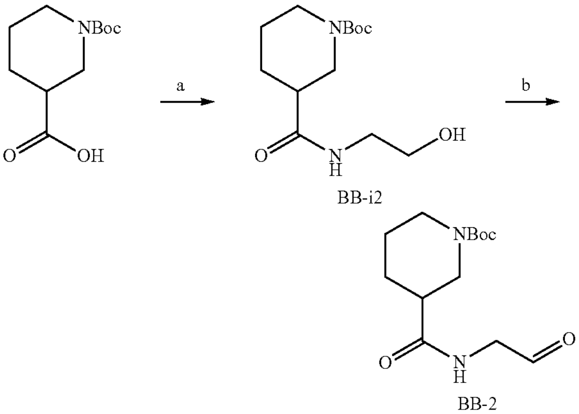

BB-i2

BB-2

Reagents and conditions: a), HATU, DIPEA, DCM; b) Dess-Martin periodinane, DCM

Synthesis of Building Block (BB-2).

Step a. Piperidine-1,3-dicarboxylic acid 1-tert-butyl ester (500 mg, 2.2 mmol), HATU (833 mg, 2.2 mmol) and Di-isopropylethylamine (761 μL, 4.4 mmol) were stirred in dry DCM (10 ml) in an ice bath for 5 min, then at room temperature for 5 min. Ethanolamine (198 μL, 3.28 mmol) was added and the reaction stirred at room temperature for 3 hours. The reaction was diluted with DCM (40 ml), washed with water (50 ml), the DCM layer separated and dried ($MgSO_4$) and concentrated. TLC visualized with $KMnO_4$. Compound BB-i2 was obtained by the silica gel column chromatography purification to give a clear oil.

$^1H$ NMR (600 MHz, Methanol-d4) δ 4.10-4.00 (m, 1H), 3.98 (d, J=13.4 Hz, 1H), 3.58 (t, J=5.8 Hz, 2H), 3.28 (t, J=5.9 Hz, 2H), 2.33 (tt, J=11.0, 3.9 Hz, 1H), 1.97-1.88 (m, 1H), 1.75-1.68 (m, 1H), 1.68-1.61 (m, 1H), 1.45 (s, 9H).

$^{13}C$ NMR (151 MHz, Methanol-d4) δ 174.98, 155.05, 79.82, 60.15, 53.40, 42.96, 41.44, 27.66, 27.25, 24.16.

HRMS ($ESI^+$) calcd for $C_{13}H_{24}N_2O_4$ $[M+Na]^+$ m/z 295.1628, found m/z 295.1630.

Step b. Then the next oxidation reaction was carried out. To a solution of compound BB-i2 (42 mg, 0.154 mmol) in dry DCM was added Dess-Martin reagent (370 mg, 5 eq.), stirring at room temperature for 1 hour and protected by N2. Then a saturated solution of $NaHCO_3$ was added to quench the reaction, the mixture was diluted with DCM subsequently. The organic phase was separated, dried and evaporated under vacuum to obtain the aldehyde BB-2, which would be used directly in the next step without further purification.

Synthetic Route of Compound BB-3.

Scheme 12e.

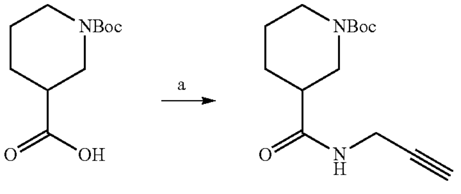

BB-3

Reagents and conditions: a), EDCl, HOBt, DCM

Synthesis of Building Block BB-3.

Step a. Piperidine-1,3-dicarboxylic acid 1-tert-butyl ester (500 mg, 2.2 mmol), EDCI (463 mg, 1.1 eq.), HOBt (323 mg, 1.1 eq.) were stirred in DCM (10 mL) at room temperature. After 5 minutes, propargylamine (155 μL, 1.1 eq.) was added dropwise into the above mixture. The solution was kept stirring until the complete consumption of starting material. After 2 hours, the reaction solution was washed successively by saturated $NaHCO_3$, brine. Then the organic solvent was concentrated and subsequently subjected to the column chromatography purification to obtain the BB-3.

$^1$H NMR (600 MHz, Methanol-d4) δ 4.07 (d, J=11.5 Hz, OH), 4.00 (dtd, J=13.3, 3.0, 1.5 Hz, 1H), 3.05-2.68 (m, 2H), 2.33 (tt, J=11.1, 3.9 Hz, 11H), 1.93 (dtd, J=11.5, 4.0, 2.0 Hz, 1H), 1.74 (d, J=13.4 Hz, 1H), 1.71-1.63 (m, 1H), 1.47 (s, 9H).

$^{13}$C NMR (151 MHz, Methanol-d4) δ 175.63, 156.43, 81.26, 80.57, 72.15, 44.12, 29.32, 28.90, 28.65, 25.85-25.19 (in).

HRMS (ESI$^+$) calcd for $C_{14}H_{22}N_2O_3$ $[M+Na]^+$ m/z 289.1523, found m/z 289.1525.

TABLE 1200

| STRUCTURE | ENTRY NUMBER (NAME) | ANALYTICAL DATA |
|---|---|---|
| 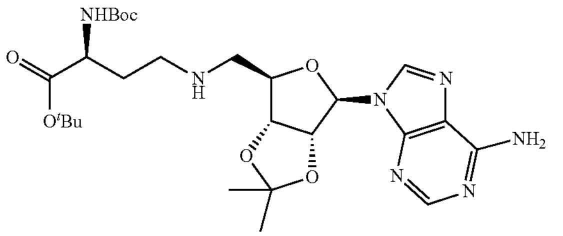 [SMILES: CC(C)(C)OC(=O)N[C@@H](CCNC[C@H]1O[C@@H](n2cnc3c(N)ncnc32)[C@@H]2OC(C)(C)O[C@@H]21)C(=O)OC(C)(C)C] | 1201 (2) | $^1$H NMR (600 MHz, Chloroform-d) δ 8.34 (s, 1H), 7.92 (s, 1H), 6.00-5.91 (m, 1H), 5.89 (s, 1H), 5.59 (s, 2H), 5.48 (s, 1H), 5.21-4.98 (m, 1H), 4.47-4.33 (m, 1H), 4.31-4.18 (m, 1H), 2.97 (s, 1H), 2.88-2.74 (m, 1H), 2.72-2.52 (m, 1H), 2.06-1.87 (m, 1H), 1.88-1.78 (m, 1H), 1.62-1.58 (m, 3H), 1.49-1.43 (m, 9H), 1.40 (s, 3H), 1.38 (s, 9H). HRMS (ESI$^+$) calcd for $C_{26}H_{42}N_7O_7$ $[M + H]^+$ m/z 564.3140, found m/z 564.3142. |
| 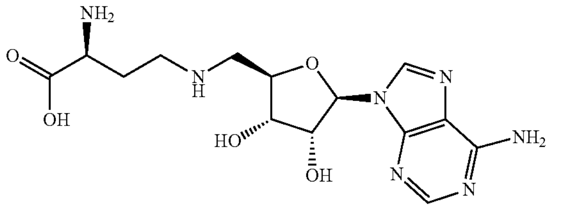 [SMILES: Nc1ncnc2c1ncn2[C@@H]1O[C@H](CNCC[C@H](N)C(=O)O)[C@@H](O)[C@H]1O] | 1202 (3) | |
| 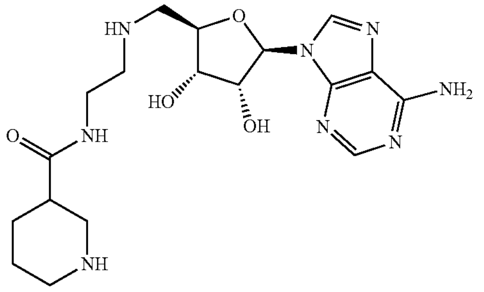 [SMILES: Nc1ncnc2c1ncn2[C@@H]1O[C@H](CNCCNC(=O)C2CCCNC2)[C@@H](O)[C@H]1O] | 1203 (4) | $^1$H NMR (600 MHz, Deuterium Oxide) δ 8.56-8.39 (m, 2H), 6.18 (d, J = 5.0 Hz, 1H), 4.93-4.87 (m, 1H), 4.55-4.42 (m, 2H), 3.66 (ddd, J = 13.2, 9.8, 3.4 Hz, 1H), 3.61-3.47 (m, 3H), 3.41-3.35 (m, 1H), 3.34-3.27 (m, 3H), 3.11-2.98 (m, 2H), 2.80-2.71 (m, 1H), 2.01-1.86 (m, 2H), 1.81-1.69 (m, 1H), 1.67-1.54 (m, 1H). $^{13}$C NMR (151 MHz, Deuterium Oxide) δ 175.54, 162.95, 150.77, 148.17, 145.62, 143.21, 119.39, 89.77, 79.44, 73.29, 71.43, 49.04, 47.29, 44.58, 43.83, 38.87, 35.76, 25.28, 20.58. HRMS (ESI$^+$) calcd for $C_{18}H_{28}N_8O_4$ $[M + H]^+$ m/z 421.2306, found m/z 421.2310. |
| 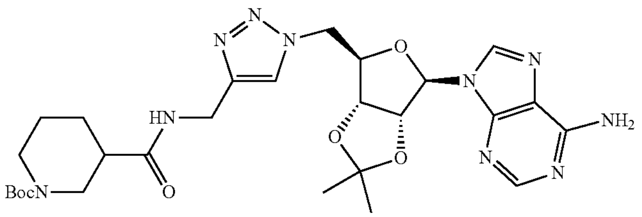 [SMILES: CC(C)(C)OC(=O)N1CCCC(C(=O)NCc2cn(C[C@H]3O[C@@H](n4cnc5c(N)ncnc54)[C@@H]4OC(C)(C)O[C@@H]43)nn2)C1] | 1204 (5) | $^1$H NMR (600 MHz, Methanol-d4) δ 8.25 (s, 1H), 8.19 (s, 1H), 7.60 (s, 1H), 6.22 (d, J = 1.6 Hz, 1H), 5.46 (dd, J = 5.9, 3.1 Hz, 1H), 5.20 (dd, J = 6.3, 3.6 Hz, 1H), 4.81-4.74 (m, 2H), 4.58 (ddd, J = 9.1, 7.1, 4.0 Hz, 1H), 4.39-4.27 (m, 2H), 4.01 (d, J = 12.1 Hz, 1H), 3.96 (d, J = 13.5 Hz, 1H), 2.28 (tt, J = 11.2, 3.9 Hz, 1H), 1.87-1.80 (m, 1H), 1.71-1.64 (m, 1H), 1.59 (s, 3H), 1.43 (s, 9H), 1.38 (s, 3H). $^{13}$C NMR (151 MHz, Methanol-d4) δ 174.52, 156.07, 154.99, 152.76, 140.74, 123.69, 114.52 (d, J = 1.7 Hz), 90.25, 90.21, 85.12, 83.85, 81.82, 81.79, 79.81, 53.40, 51.35, 42.72, 34.05, 27.25, 26.02, 24.12. HRMS (ESI$^+$) calcd for $C_{27}H_{38}N_{10}O_6$ $[M + H]^+$ m/z 599.3049, found m/z 599.3054 |

TABLE 1200-continued

| STRUCTURE | ENTRY NUMBER (NAME) | ANALYTICAL DATA |
|---|---|---|
| 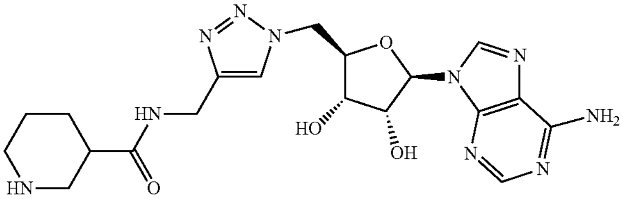 [SMILES: Nc1ncnc2c1ncn2[C@@H]1O[C@H](Cn2cc(CNC(=O)C3CCCNC3)nn2)[C@@H](O)[C@H]1O] | 1205 (6) | $^1$H NMR (600 MHz, Deuterium Oxide) δ 8.38 (s, 1H), 8.22 (s, 1H), 7.77 (d, J = 6.3 Hz, 1H), 6.09 (d, J = 3.4 Hz, 1H), 4.86-4.82 (m, 3H), 4.73-4.67 (m, 1H), 4.50 (s, 2H), 4.38-4.25 (m, 2H), 3.34 (ddd, J = 13.2, 9.8, 3.7 Hz, 1H), 3.30-3.22 (m, 1H), 3.13 (ddd, J = 12.6, 9.4, 2.8 Hz, 1H), 3.06-2.99 (m, 1H), 2.79-2.72 (m, 1H), 1.98-1.83 (m, 2H), 1.77-1.58 (m, 2H). $^{13}$C NMR (151 MHz, Deuterium Oxide) δ 174.34, 149.86, 147.99, 144.30, 144.26, 143.09, 143.06, 143.04, 143.00, 118.82, 89.14, 89.11, 81.69, 81.54, 73.11, 70.27, 50.66 (d, J = 4.9 Hz), 34.03, 25.41, 20.51. HRMS (ESI$^+$) calcd for $C_{19}H_{26}N_{10}O_4$ [M + H]$^+$ m/z 459.2211, found m/z 459.2218. |
| 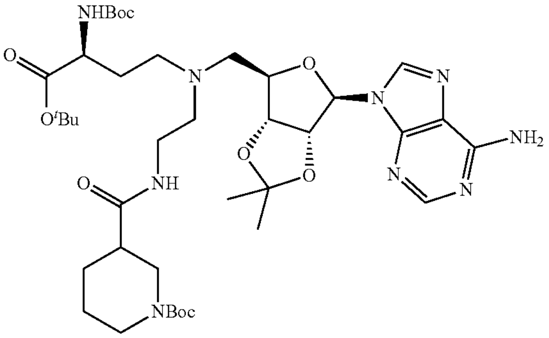 [SMILES: CC(C)(C)OC(=O)N[C@@H](CCN(CCNC(=O)C1CCCN(C(=O)OC(C)(C)C)C1)C[C@H]1O[C@@H](n2cnc3c(N)ncnc32)[C@@H]2OC(C)(C)O[C@@H]21)C(=O)OC(C)(C)C] | 1206 (7) | $^1$H NMR (600 MHz, Methanol-d4) δ 8.26 (d, J = 2.4 Hz, 1H), 8.23 (d, J = 2.1 Hz, 1H), 6.19 (s, 1H), 5.57-5.49 (m, 1H), 5.15-4.99 (m, 1H), 4.34-4.23 (m, 1H), 4.23-4.15 (m, 1H), 4.15-4.03 (m, 1H), 4.00 (d, J = 13.4 Hz, 1H), 3.28-3.16 (m, 1H), 3.13-3.03 (m, 1H), 2.94-2.79 (m, 2H), 2.78-2.67 (m, 1H), 2.68-2.54 (m, 3H), 2.49-2.39 (m, 2H), 2.37-2.25 (m, 1H), 2.07-1.82 (m, 2H), 1.74-1.54 (m, 7H), 1.49-1.43 (m, 27H), 1.40 (s, 3H). $^{13}$C NMR (151 MHz, Methanol-d4) δ 175.92, 174.05, 158.41, 158.34, 157.56, 156.52, 156.49, 150.31, 142.35, 120.87, 115.56, 92.05, 86.93, 86.81, 85.05, 82.72, 81.34, 81.27, 80.57, 53.77, 44.47, 38.51, 30.52, 29.04, 28.92, 28.81, 28.56, 28.44. HRMS (ESI$^+$) calcd for $C_{39}H_{63}N_9O_{10}$ [M + H]$^+$ m/z 818.4771, found m/z 818.4767 |
| 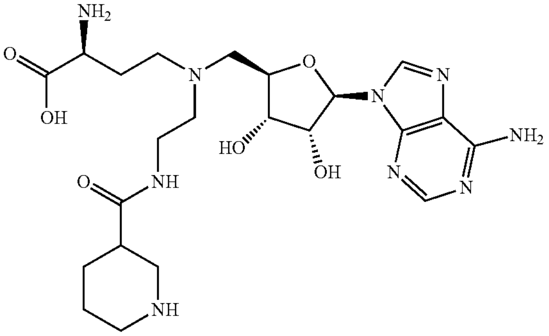 [SMILES: Nc1ncnc2c1ncn2[C@@H]1O[C@H](CN(CCNC(=O)C2CCCNC2)CC[C@H](N)C(=O)O)[C@@H](O)[C@H]1O] | 1206 (8) | $^1$H NMR (600 MHz, Deuterium Oxide) δ 8.45-8.27 (m, 2H), 6.10 (s, 1H), 4.85-4.76 (m, 1H), 4.51-4.38 (m, 2H), 3.79 (d, J = 9.6 Hz, 1H), 3.68 (s, 2H), 3.60-3.50 (m, 1H), 3.50-3.35 (m, 4H), 3.31 (d, J = 11.4 Hz, 2H), 3.25-3.16 (m, 1H), 3.03-2.87 (m, 2H), 2.68 (tt, J = 9.7, 5.0 Hz, 1H), 2.37-2.18 (m, 1H), 2.14-2.02 (m, 1H), 1.92-1.79 (m, 2H), 1.72-1.60 (m, 1H), 1.59-1.44 (m, 1H). $^{13}$C NMR (151 MHz, Deuterium Oxide) δ 175.28, 172.92, 151.10, 148.20, 146.09, 143.03, 119.29, 89.93, 87.20, 73.22, 72.72, 55.36, 52.93, 52.66, 38.90, 25.40, 24.59, 20.63. HRMS (ESI$^+$) calcd for $C_{22}H_{35}N_9O_6$ [M + H]$^+$ m/z 522.2783, found m/z 522.2784. |
| 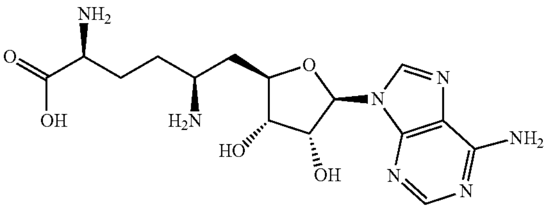 [SMILES: Nc1ncnc2c1ncn2[C@@H]1O[C@H](C[C@@H](N)CC[C@H](N)C(=O)O)[C@@H](O)[C@H]1O] | Senifungin | |

Example C13

General Synthetic Procedure for Non-Limiting Exemplary Mettl3/14 Inhibitors (e.g., Compounds of Formula (M2)): Synthetic Route of Quinazoline Derivatives.

Scheme 13a.

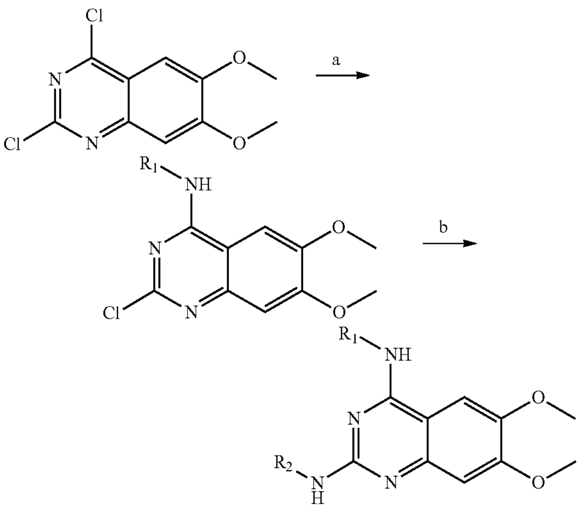

Reagents and conditions: a), $R_1$—$NH_2$, $K_2CO_3$, DMF, room temperature; b), $R_2$—$NH_2$, Sealed tube, 110° C., isoamyl alcohol.

Synthetic Procedure for Synthesis of JMC Compound.

To a solution of 2,4-dichloro-6,7-dimethoxyquinazoline (1 g, 3.8 mmol) in DMF (10 mL) were added $K_2CO_3$ (1.1 g, 8 mmol) and 4-methylpiperidin-1-amine (1 mL, 8 mmol). After being stirred for 2 h, the reaction was quenched with water and extracted with DCM (3×5 mL). The combined organic layers were dried over anhydrous $Na_2SO_4$, filtered, and concentrated under reduced pressure. Then the intermediate 6,7-dimethoxy-N-(1-methylpiperidin-4-yl)-2-chloroquinazolin-4-amine (JMC compound intermediate) was purified by silica gel column chromatography (MeOH/DCM=1:5).

$^1H$ NMR (600 MHz, Methanol-d4) δ 7.53 (s, 1H), 6.93 (s, 1H), 4.26 (tt, J=11.5, 4.2 Hz, 1H), 3.96 (s, 3H), 3.94 (s, 3H), 3.10 (dt, J=12.9, 3.3 Hz, 2H), 2.45 (s, 3H), 2.44-2.39 (m, 2H), 2.17-2.09 (m, 2H), 1.89-1.74 (m, 2H). $^{13}C$ NMR (151 MHz, Methanol-d4) δ 161.10, 156.89, 156.52, 150.57, 148.36, 108.25, 106.50, 102.89, 56.81, 56.52, 55.65, 45.75, 31.71. HRMS (ESI$^+$) calcd for $C_{16}H_{21}ClN_4O_2$ $[M+H]^+$ m/z 337.1426, found m/z 337.1428.

Next, the above intermediate (6,7-dimethoxy-N-(1-methylpiperidin-4-yl)-2-chloroquinazolin-4-amine (JMC compound intermediate)) (50 mg, 0.148 mmol) and hexamine hydrochloride (41 mg, 2 eq.) were dispersed in isoamyl alcohol (3 mL) in the sealed tube followed by the addition of DIPEA (78 μL, 3 eq.), heating the mixture to 110° C. and keeping stirring overnight. After being concentrated under reduced pressure to remove the solvents, the resulting residue was purified by prep-RP-HPLC (PRP-1 column) to yield the title compound. A linear gradient was used with 20% to 90% of MeCN (B) in $H_2O$ (with 0.1% TFA) (A).

Compound TR-Met3-13.

The title compound was prepared according to synthetic procedure for JMC compound. But the second step we used methyl piperidine-3-carboxylate and after the reaction we obtained the methyl ester-hydrolyzed TR-Met3-13.

Synthetic Route of TR-Met3-14.

Scheme 13b.

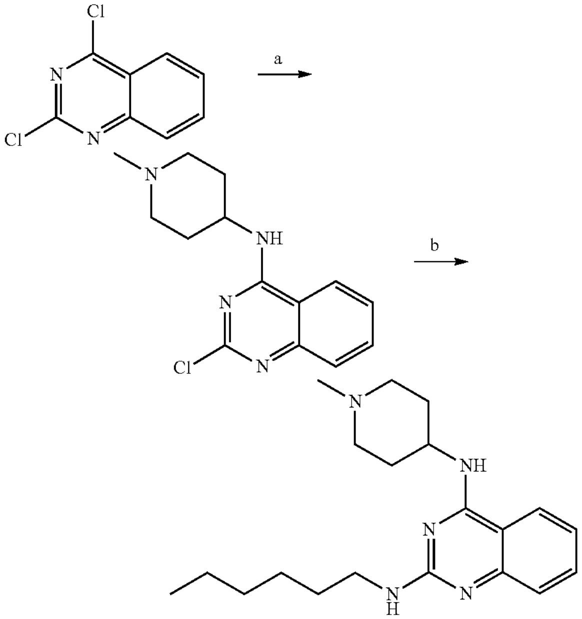

Reagents and conditions: a), $R_1$—$NH_2$, $K_2CO_3$, DMF, r.t.; b), $R_2$—$NH_2$, Sealed tube, 110° C., isoamyl alcohol.

Compound TR-Met3-14.

The title compound was prepared according to synthetic procedure for JMC compound but the starting material of quinazoline is 2,4-dichloro-quinazoline.

Compound TR-Met3-15

The title compound was prepared according to synthetic procedure for JMC compound.

Intermediate compound $^1H$ NMR (600 MHz, DMSO-d6) δ 7.29 (s, 1H), 7.17 (s, 1H), 4.08 (d, J=13.2 Hz, 1H), 3.91 (s, 3H), 3.90-3.89 (m, 4H), 2.77-2.72 (m, 1H), 1.99 (dt, J=10.2, 4.7 Hz, 1H), 1.86-1.73 (m, 2H), 1.72-1.60 (m, 1H).

Compound TR-Met3-16.

The title compound was prepared according to synthetic procedure for JMC compound.

Compound TR-Met3-17.

The title compound was prepared according to synthetic procedure for JMC compound.

Compound TR-Met3-18.

To a solution of 2,4-dichloro-6,7-dimethoxyquinazoline (100 mg, 0.38 mmol) in THF (4 mL) were added DIPEA (268 μL, 4 eq.) and hexamine hydrochloride (106 mg, 0.76 mmol). After being stirred for overnight, the reaction was concentrated under reduced pressure. Then the compound TR-Met3-17 was purified by silica gel column chromatography (Hexanes/ethyl acetate=2:1).

Synthetic Route of TR-Met3-19.

Scheme 13c.

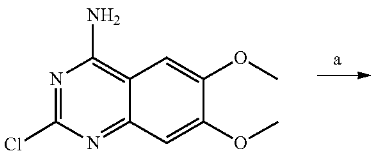

-continued

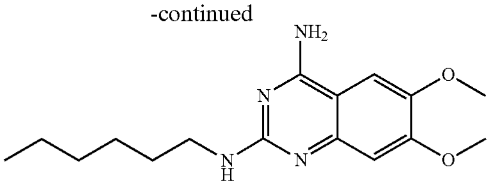

Reagents and conditions a), Hexamine hydrochloride, DIPEA, sealed tube, 110° C., isoamyl alcohol.

Compound TR-Met3-19.

2-Chloro-4-amino-6,7-dimethoxyquinazoline (50 mg, 0.208 mmol) and hexamine hydrochloride (57 mg, 2 eq.) were dispersed in isoamyl alcohol (3 mL) in the sealed tube followed by the addition of DIPEA (145 μL, 4 eq.), heating the mixture to 110° C. and keeping stirring overnight. Next the mixture was concentrated under reduced pressure and then add ethyl acetate, producing the precipitate and then it was filtered and washed 3 times by another portions of ethyl acetate, until the TLC showed the product point was pure. Compound TR-Met3-20.

TR-Met3-18 (60 mg, 0.185 mmol) and methyl piperidine-3-carboxylate (66.6 mg, 2 eq.) were mixed in 3 mL isoamyl alcohol in the sealed tube, keeping stirring under 110° C. oil bath atmosphere overnight. After being concentrated under reduced pressure to remove the solvents, the resulting residue was purified by prep-RP—HPLC (PRP-1 column) to yield the title compound. A linear gradient was used with 20% to 90% of MeCN (B) in $H_2O$ (with 0.1% TFA) (A) within 30 minutes.

Synthetic Route of TR-Met3-21.

Scheme 13d.

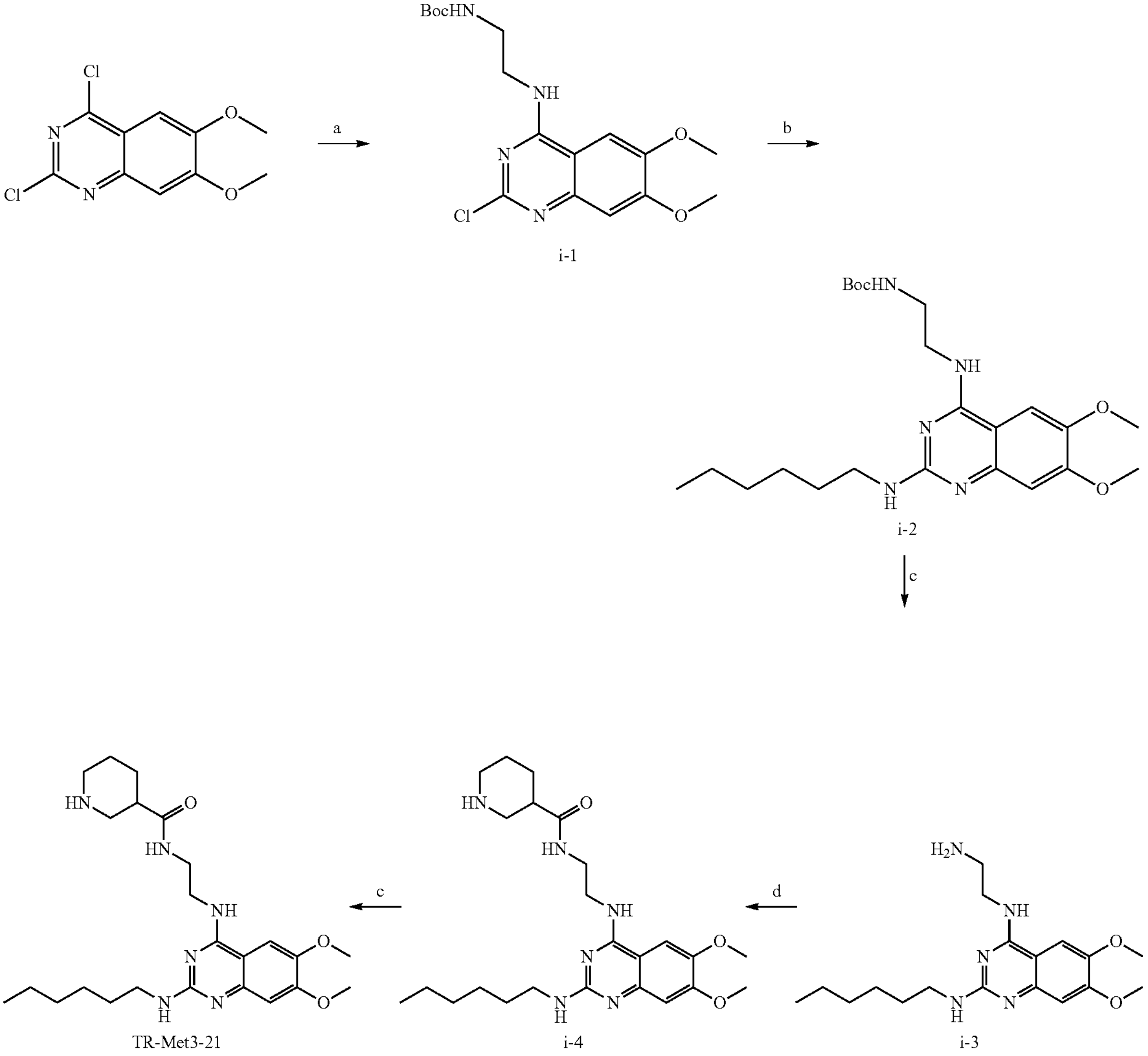

Reagents and conditions a), tert-butyl (2-aminoethyl)carbamate, $K_2CO_3$, DMF, r.t.; b), hexylamine, sealed tube, 110° C., isoamyl alcohol; c), 50% TFA in DCM; d), HATU, DIPEA, DMF.

Compound TR-Met3-21.

Step a: 2,4-Dichloro-6,7-dimethoxyquinazoline (500 mg, 1.93 mmol) and N-Boc-1,3-propanediamine (464 mg, 2.89 mmol, 1.5 eq.) were dissolved in DMF (8 mL), followed by the addition of $K_2CO_3$ (533 mg, 2 eq.). The mixture was stirred at room temperature for 2 hours until the reaction completion monitored by TLC. Then the mixture was diluted and blenched by 10 mL $H_2O$, subsequently DCM was used to wash and extract the target compound (3×15 mL), which was then concentrated under reduced pressure and subjected to the silica gel column chromatography purification to give the intermediate compound i-1 (ethyl acetate:Hexanes=1.5:1). $^1H$ NMR (600 MHz, Chloroform-d) δ 7.68 (s, 1H), 7.13 (s, 1H), 7.11 (s, 1H), 5.15 (s, 1H), 4.01 (s, 3H), 3.97 (s, 3H), 3.70 (q, J=4.5 Hz, 2H), 3.51 (q, J=5.9 Hz, 2H), 1.48-1.38 (m, 9H).

Step b: Next, compound i-1 (200 mg, 0.522 mmol) and hexylamine hydrochloride (108 mg, 0.784 mmol, 1.5 eq.) were mixed in isoamyl alcohol (2.5 mL) in sealed tube, DIPEA (318 μL) was subsequently added and the reaction was heated to 115° C., keeping stirring overnight. Cold ether (20 mL) was added to precipitate and after the centrifuge the below precipitated cake was purified by the silica gel column chromatography (ethyl acetate to DCM/MeOH=20:1 to 10:1) to give the intermediate compound i-2.

$^1H$ NMR (600 MHz, Chloroform-d) δ 8.82 (s, 1H), 7.84 (s, 1H), 7.39 (s, 1H), 6.82 (s, 1H), 5.54 (t, J=6.1 Hz, 1H), 3.99 (s, 3H), 3.93 (s, 3H), 3.76-3.66 (m, 2H), 3.59-3.50 (m, 2H), 3.48-3.37 (m, 2H), 1.61 (p, J=7.4 Hz, 2H), 1.42 (s, 9H), 1.36 (q, J=7.2 Hz, 2H), 1.32-1.20 (m, 4H), 0.86 (d, J=7.5 Hz, 3H).

Step c: Next the deprotection was taken up in 50% TFA in DCM for vigorously stirring 1 hour. Then the solvent was dried by the N2 blowing and subsequent in vacuo to obtain i-3 and it could be used in the next step directly without any further purification.

$^1H$ NMR (600 MHz, Methanol-d4) δ 7.50 (s, 1H), 6.97 (s, 1H), 3.96 (s, 3H), 3.94-3.87 (m, 5H), 3.49 (t, J=7.2 Hz, 2H), 3.30-3.26 (m, 2H), 1.68 (p, J=7.3 Hz, 2H), 1.48-1.41 (m, 2H), 1.40-1.33 (m, 4H), 0.96-0.89 (m, 3H).

Step d: Next, to a solution of 1-(tert-Butoxycarbonyl)-3-piperidinecarboxylic acid (37 mg, 0.16 mmol) in DMF (3 mL) was added successively HATU (61 mg, 1 eq.), DIPEA (56 μL, 2 eq.), keeping the mixture stirring at the ice-bath atmosphere for 5 minutes. Subsequently compound i-3 (55 mg, 0.16 mmol) dissolved in DMF (1 mL) was added into above mixture, then the reaction was recovered to room temperature to keep stirring. After 1 hour, the reaction was almost complete which was then bleached by $H_2O$ and DCM was used to extract the product 3 times. At last the combined organic layers were concentrated and subject to the silica gel column chromatography to obtain the compound i-4. Then the deprotection was performed in 50% TFA in DCM stirring for 1 hour. The crude residue was concentrated then subject to the Prep-RP-HPLC purification to give TR-Met3-21.

Synthesis Route of TR-Met3-22, TR-Met3-23.

Scheme 1e.

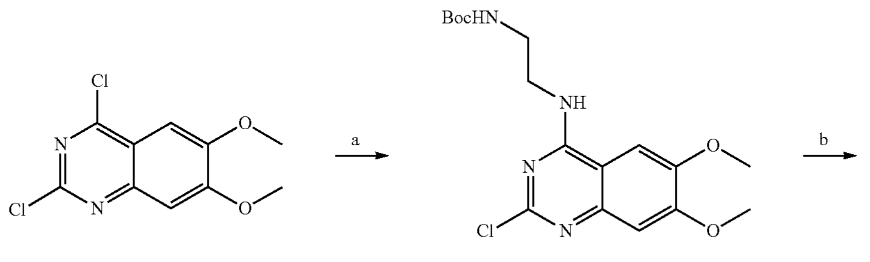

i-1

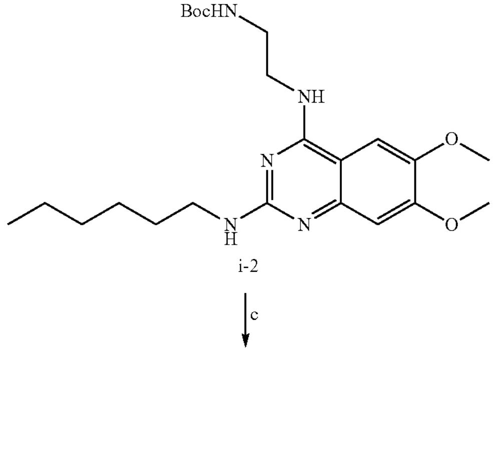

i-2

-continued

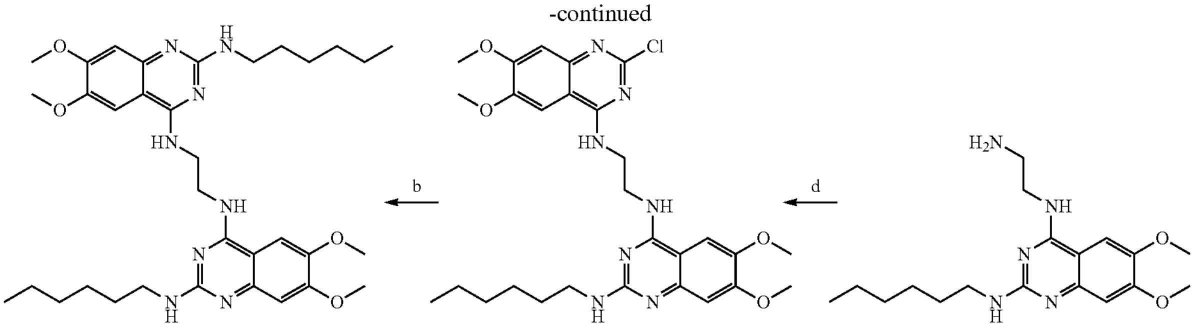

TR-Met-23 TR-Met-22 i-3

Reagents and conditions: a), tert-butyl (2-aminoethyl)carbamate, $K_2CO_3$, DMF, room temperature; b), hexylamine, sealed tube, 110° C., isoamyl alcohol; c), 50% TFA in DCM; d), 2,4-dichloro-6,7-dimethoxy-quinazoline, $K_2CO_3$, DMF, room temperature Compound TR-Met3-22.

Step d. Compound i-3 (72 mg, 1.0 eq.) and 2,4-Dichloro-6,7-dimethoxyquinazoline (54 mg, 0.207 mmol, 1 eq.) were dissolved in DMF (3 mL) which was followed by the addition of $K_2CO_3$ (114 mg, 4 eq.), the mixture was stirred at room temperature for 2 hours. Water and DCM was added above and the combined DCM (3×10 mL) layers were concentrated and purified thereafter by column chromatography (ethyl acetate to DCM:MeOH=20:1 to 10:1) to give the slight white solid TR-Met3-22.

Compound TR-Met3-23.

Step b. To a suspension of TR-Met3-22 (29 mg, 0.051 mmol) and hexylamine (8 p L, 1.2 eq.) in isoamyl alcohol (2.5 mL) in sealed tune was added DIPEA (22 p L, 2.5 eq.), keeping the mixture stirring under 120° C. for overnight. After being concentrated of the reactive solvents under reduced pressure, the resulting residue was purified by prep-RP—HPLC (PRP-1 column) to yield the title compound. A linear gradient was used with 20% to 90% of MeCN (B) in $H_2O$ (with 0.1% TFA) (A) within 20 minutes.

TABLE 1310

| STRUCTURE | ENTRY NUMBER (NAME) | ANALYTICAL DATA |
|---|---|---|
| 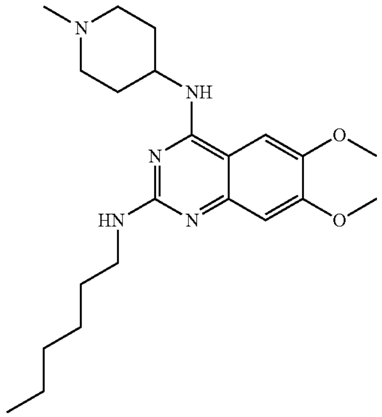 [SMILES: CCCCCCNc1nc(NC2CCN(C)CC2)c2cc(OC)c(OC)cc2n1] | JMC compound | |
| 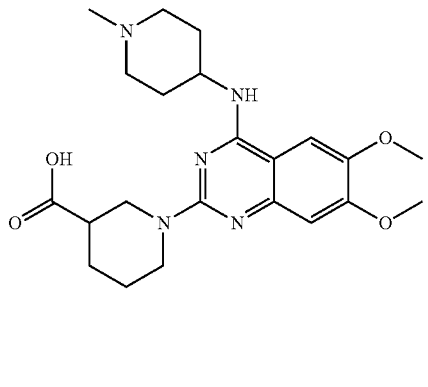 [SMILES: COc1cc2nc(N3CCCC(C(=O)O)C3)nc(NC3CCN(C)CC3)c2cc1OC] | 1313 (TR-Met3-13) | $^1H$ NMR (600 MHz, Deuterium Oxide) δ 7.13 (s, 1H), 6.62 (s, 1H), 4.38-4.14 (m, 1H), 4.01-3.86 (m, 1H), 3.60 (d, J = 12.6 Hz, 2H), 3.50-3.25 (m, 1H), 3.17 (t, J = 13.3 Hz, 2H), 2.87 (s, 3H), 2.47-2.39 (m, 1H), 2.31 (d, J = 16.0 Hz, 2H), 2.06-1.94 (m, 1H), 1.94-1.80 (m, 2H), 1.77 (s, 2H), 1.66-1.44 (m, 1H). $^{13}C$ NMR (151 MHz, Methanol-d4) δ 174.78, 158.92, 156.24, 151.17, 147.91, 135.97, 103.78, 102.19, 98.45, 55.84, 55.55, 53.45, 46.75, 46.70, 45.50, 42.50, 40.53, 28.40, 26.30, 23.53. HRMS ($ESI^+$) calcd for $C_{22}H_{31}N_5O_4$ $[M + H]^+$ m/z 430.2449, found m/z 430.2449. |

TABLE 1310-continued

| STRUCTURE | ENTRY NUMBER (NAME) | ANALYTICAL DATA |
|---|---|---|
| 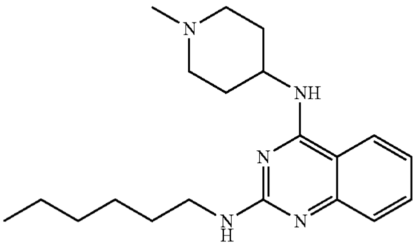 [SMILES: CCCCCCNc1nc(NC2CCN(C)CC2)c2ccccc2n1] | 1314 (TR-Met3-14) | $^1$H NMR (600 MHz, Chloroform-d) δ 8.00 (s, 1H), 7.95 (d, J = 8.2 Hz, 1H), 7.52 (dd, J = 8.4, 1.2 Hz, 1H), 7.44 (d, J = 8.4 Hz, 1H), 7.18-7.10 (m, 1H), 4.33 (dtt, J = 15.7, 11.0, 4.6 Hz, 1H), 3.45-3.34 (m, 2H), 3.25 (t, J = 10.2 Hz, 2H), 2.60-2.44 (m, 5H), 2.23-2.12 (m, 2H), 2.12-1.99 (m, 2H), 1.67-1.55 (m, 2H), 1.41-1.31 (m, 3H), 1.31-1.16 (m, 4H), 0.87 (d, J = 6.7 Hz, 3H). $^{13}$C NMR (151 MHz, Chloroform-d) δ 169.37, 160.01, 154.37, 140.96, 134.79, 123.09, 117.66, 109.27, 53.89, 47.65, 44.73, 41.40. HRMS (ESI$^+$) calcd for $C_{20}H_{31}N_5$ [M + H]$^+$ m/z 342.2652, found m/z 342.2650 |
| 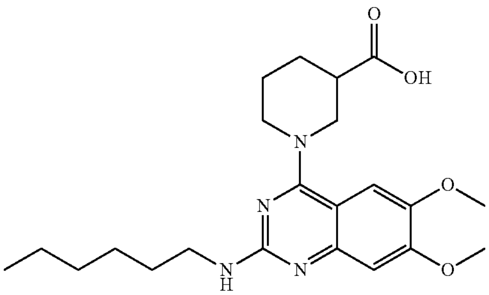 [SMILES: CCCCCCNc1nc(N2CCCC(C(=O)O)C2)c2cc(OC)c(OC)cc2n1] | 1315 (TR-Met3-15) | $^1$H NMR (600 MHz, Chloroform-d) δ 7.31 (s, 1H), 7.17 (s, 1H), 3.96 (s, 3H), 3.86 (s, 3H), 3.46 (dq, J = 13.3, 6.7 Hz, 1H), 3.39-3.22 (m, 1H), 2.81-2.63 (m, 1H), 2.38-2.12 (m, 1H), 2.11-1.85 (m, 1H), 1.77-1.69 (m, 1H), 1.64 (p, J = 7.4 Hz, 2H), 1.46-1.23 (m, 8H), 0.92 (t, J = 6.9 Hz, 3H). $^{13}$C NMR (151 MHz, Chloroform-d) δ 152.48, 106.29, 98.80, 56.23, 53.43, 49.45, 41.48, 31.59, 29.43, 26.75, 22.64, 14.08. HRM (ESI$^+$) calcd for $C_{22}H_{32}N_4O_4$ [M + H]$^+$ m/z 417.2496, found m/z 417.2497. |
| 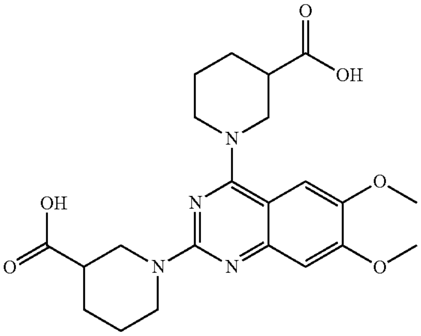 [SMILES: COc1cc2nc(N3CCCC(C(=O)O)C3)nc(N3CCCC(C(=O)O)C3)c2cc1OC] | 1316 (TR-Met3-16) | $^1$H NMR (599 MHz, Methanol-d4) δ 7.33 (d, J = 4.0 Hz, 1H), 7.16 (d, J = 1.6 Hz, 1H), 4.49-4.41 (m, 1H), 4.31-4.14 (m, 2H), 4.10-4.01 (m, 1H), 3.97 (s, 3H), 3.92 (s, 3H), 3.80 (tt, J = 14.7, 7.3 Hz, 2H), 3.68 (td, J = 13.9, 13.3, 7.3 Hz, 2H), 2.90-2.79 (m, 1H), 2.73-2.62 (m, 1H), 2.26-2.08 (m, 2H), 1.99-1.90 (m, 3H), 1.89-1.80 (m, 1H), 1.79-1.73 (m, 1H), 1.72-1.59 (m, 1H). $^{13}$C NMR (151 MHz, Methanol-d4) δ 175.01, 162.89, 156.14, 150.34, 146.71, 138.58, 106.65, 102.83, 98.66, 55.50, 51.12, 49.55, 46.60, 45.69-44.95 (m), 40.96, 40.57, 26.59, 24.06, 23.49. HRMS (ESI$^+$) calcd for $C_{22}H_{28}N_4O_6$ [M + H]$^+$ m/z 445.2082, found m/z 445.2080. |
| 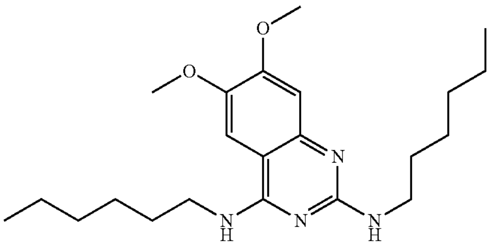 [SMILES: CCCCCCNc1nc(NCCCCCC)c2cc(OC)c(OC)cc2n1] | 1317 (TR-Met3-17) | $^1$H NMR (600 MHz, Chloroform-d) δ 8.45 (s, 1H), 7.66 (s, 1H), 7.56 (s, 1H), 6.65 (s, 1H), 4.03 (s, 3H), 3.89 (s, 3H), 3.71-3.50 (m, 2H), 3.47-3.18 (m, 2H), 1.73 (p, J = 7.6 Hz, 2H), 1.60 (p, J = 7.5 Hz, 2H), 1.34 (q, J = 7.1 Hz, 4H), 1.28-1.22 (m, 8H), 0.90-0.80 (m, 6H). $^{13}$C NMR (151 MHz, Chloroform-d) δ 159.39, 155.56, 153.07, 146.96, 134.99, 104.51, 102.21, 100.15, 57.18, 56.50, 41.98, 31.59, 31.53, 29.48, 29.04, 26.88, 26.65, 22.62, 22.58, 14.06, 14.01. HRMS (ESI$^+$) calcd for $C_{22}H_{36}N_4O_2$ [M + H]$^+$ m/z 389.2911, found m/z 389.2907. |
| 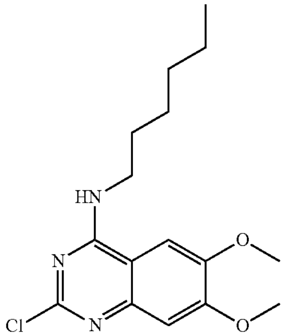 [SMILES: CCCCCCNc1nc(Cl)nc2cc(OC)c(OC)cc12] | 1318 (TR-Met3-18) | $^1$H NMR (599 MHz, Chloroform-d) δ 7.13 (s, 1H), 6.83 (s, 1H), 3.98 (s, 3H), 3.96 (s, 3H), 3.65 (td, J = 7.4, 5.5 Hz, 2H), 1.76-1.68 (m, 2H), 1.46-1.39 (m, 2H), 1.38-1.30 (m, 4H), 0.90 (d, J = 6.7 Hz, 3H). |

TABLE 1310-continued

| STRUCTURE | ENTRY NUMBER (NAME) | ANALYTICAL DATA |
|---|---|---|
| 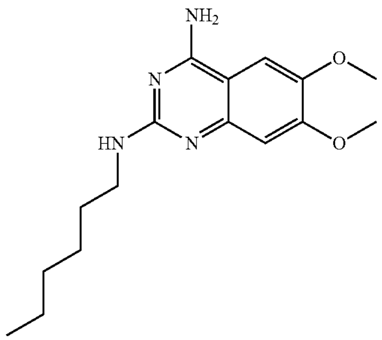 [SMILES: CCCCCCNc1nc(N)c2cc(OC)c(OC)cc2n1] | 1319 (TR-Met3-19) | $^1$H NMR (599 MHz, Methanol-d4) δ 7.52 (s, 1H), 6.94 (s, 1H), 3.96 (s, 3H), 3.91 (s, 3H), 3.55-3.40 (m, 2H), 1.66 (p, J = 7.6 Hz, 2H), 1.49-1.39 (m, 2H), 1.38-1.30 (m, 4H), 0.93 (p, J = 7.1, 4.6 Hz, 3H). $^{13}$C NMR (151 MHz, Methanol-d4) δ 135.93, 118.34, 111.09, 107.17, 104.24, 55.45, 41.63, 40.82, 3131, 26.21, 22.30, 12.95. HRMS (ESI$^+$) calcd for $C_{16}H_{24}N_4O_2$ $[M + H]^+$ m/z 305.1972, found m/z 305.1971 |
| 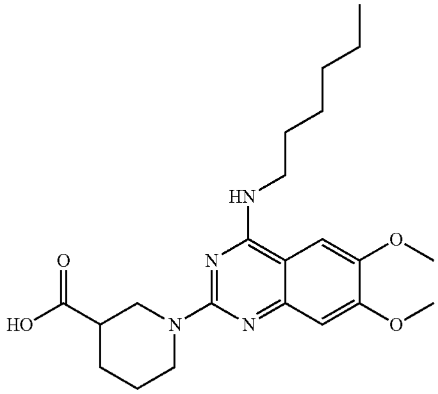 [SMILES: CCCCCCNc1nc(N2CCCC(C(=O)O)C2)nc2cc(OC)c(OC)cc12] | 1320 (TR-Met3-20) | $^1$H NMR (600 MHz, DMSO-d6) δ 7.69 (t, J = 5.6 Hz, 1H), 7.39 (s, 1H), 6.75 (s, 1H), 4.78 (dd, J = 12.9, 4.0 Hz, 1H), 4.60-4.51 (m, 1H), 3.82 (s, 3H), 3.80 (s, 3H), 3.45 (td, J = 7.3, 3.5 Hz, 2H), 2.96 (dd, J = 13.0, 10.5 Hz, 1H), 2.87 (td, J = 12.4, 2.9 Hz, 1H), 2.34 (tt, J = 10.8, 3.9 Hz, 1H), 1.99 (dt, J = 12.9, 4.3 Hz, 1H), 1.70-1.54 (m, 4H), 1.41 (dtd, J = 12.0, 8.3, 4.3 Hz, 1H), 1.36-1.24 (m, 6H), 0.86 (t, J = 6.7 Hz, 3H). HRMS (ESI$^+$) calcd for $C_{22}H_{32}N_4O_4$ $[M + H]^+$ m/z 417.2496, found m/z 417.2495. |
| 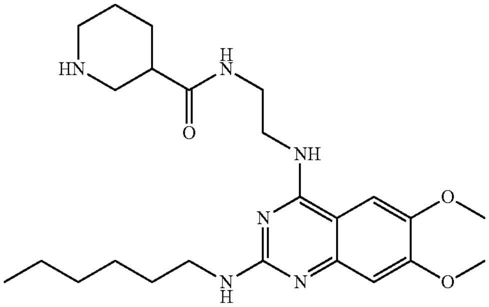 [SMILES: CCCCCCNc1nc(NCCNC(=O)C2CCCNC2)c2cc(OC)c(OC)cc2n1] | 1321 (TR-Met3-21) | $^1$H NMR (599 MHz, Methanol-d4) δ 7.50 (s, 1H), 6.92 (s, 1H), 3.96 (s, 3H), 3.92 (s, 3H), 3.78 (t, J = 6.2 Hz, 2H), 3.66-3.40 (m, 4H), 3.27 (dd, J = 12.9, 3.8 Hz, 1H), 3.22-3.19 (m, 1H), 3.16 (dd, J = 12.7, 8.7 Hz, 1H), 3.08-2.98 (m, 1H), 2.77-2.61 (m, 1H), 2.01-1.93 (m, 1H), 1.92-1.81 (m, 1H), 1.77-1.70 (m, 2H), 1.68 (q, J = 7.3 Hz, 2H), 1.47-1.41 (m, 2H), 1.39-1.28 (m, 4H), 0.92 (t, J = 4.3 Hz, 3H), HRMS (ESI$^+$) calcd for $C_{24}H_{38}N_6O_3$ $[M + H]^+$ m/z 459.3078, found m/z 459.3073. |
| 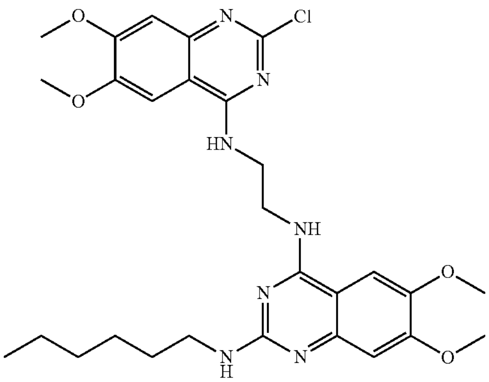 [SMILES: CCCCCCNc1nc(NCCNc2nc(Cl)nc3cc(OC)c(OC)cc23)c2cc(OC)c(OC)cc2n1] | 1322 TR-Met3-22 | 1H NMR (600 MHz, DMSO-d6) δ 8.51 (t, J = 5.6 Hz, 1H), 7.59 (s, 1H), 7.55 (s, 1H), 7.52 (s, 1H), 7.02 (s, 1H), 6.91 (s, 1H), 3.86 (s, 6H), 3.84-3.81 (m, 2H), 3.81 (s, 3H), 3.77 (s, 3H), 3.22 (q, J = 6.4 Hz, 2H), 1.48 (p, J = 7.5, 7.1 Hz, 2H), 1.31-1.08 (m, 6H), 0.89-0.71 (m, 3H). HRMS (ESI+) calcd for $C_{28}H_{36}ClN_7O_4$ [M + H]+ m/z 570.2590, found m/z 570.2581. |

TABLE 1310-continued

| STRUCTURE | ENTRY NUMBER (NAME) | ANALYTICAL DATA |
|---|---|---|
| 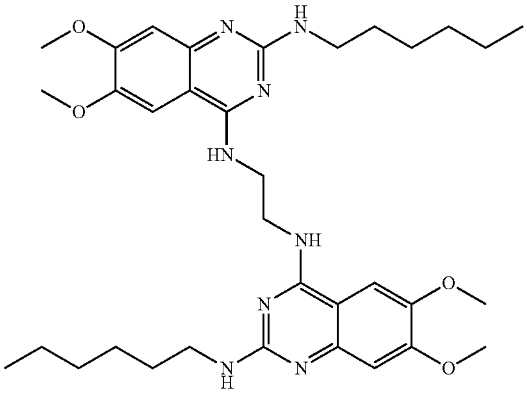 [SMILES: CCCCCCNc1nc(NCCNc2nc(NCCCCCC)nc3cc(OC)c(OC)cc23)c2cc(OC)c(OC)cc2n1] | 1323 (TR-Met3-23) | 1H NMR (600 MHz, Methanol-d4) δ 8.58 (s, 2H), 7.34 (s, 2H), 6.85 (s, 2H), 4.01 (s, 4H), 3.93 (s, 6H), 3.82 (s, 6H), 1.57 (p, J = 7.3 Hz, 4H), 1.43-1.19 (m, 12H), 0.96-0.78 (m, 6H). 13C NMR (151 MHz, Methanol-d4) δ 169.18, 160.29, 155.71, 146.76, 103.10, 102.63, 55.39, 55.30, 53.43, 40.88, 40.56, 31.40, 29.17, 26.40, 22.33, 13.06. HRMS (ESI+) calcd for $C_{34}H_{50}N_8O_4$ [M + H]+ m/z 635.4028, found m/z 635.4037. |

1. Zhang, G.; Richardson, S. L.; Mao, Y.; Huang, R. Design, synthesis, and kinetic analysis of potent protein N-terminal methyltransferase 1 inhibitors. *Org Biomol Chem* 2015, 13, 4149-54.
2. Hobley, G.; McKelvie, J. C.; Harmer, J. E.; Howe, J.; Oyston, P. C.; Roach, P. L. Development of rationally designed DNA N6 adenine methyltransferase inhibitors. *Bioorganic & Medicinal Chemistry Letters* 2012, 22, 3079-82.
3. Swarbrick, J. M.; Graeff, R.; Garnham, C.; Thomas, M. P.; Galione, A.; Potter, B. V. 'Click cyclic ADP-ribose': a neutral second messenger mimic. *Chem Commun* (*Camb*) 2014, 50, 2458-61.
4. Xiong, Y.; Li, F.; Babault, N.; Dong, A.; Zeng, H.; Wu, H.; Chen, X.; Arrowsmith, C. H.; Brown, P. J.; Liu, J.; Vedadi, M.; Jin, J. Discovery of Potent and Selective Inhibitors for G9a-Like Protein (GLP) Lysine Methyltransferase. *Journal Of Medicinal Chemistry* 2017, 60, 1876-1891.
5. Van Horn, K. S.; Burda, W. N.; Fleeman, R.; Shaw, L. N.; Manetsch, R. Antibacterial activity of a series of N2,N4-disubstituted quinazoline-2,4-diamines. *Journal Of Medicinal Chemistry* 2014, 57, 3075-93.
6. Ma, A.; Yu, W.; Li, F.; Bleich, R. M.; Herold, J. M.; Butler, K. V.; Norris, J. L.; Korboukh, V.; Tripathy, A.; Janzen, W. P.; Arrowsmith, C. H.; Frye, S. V.; Vedadi, M.; Brown, P. J.; Jin, J. Discovery of a selective, substrate-competitive inhibitor of the lysine methyltransferase SETD8. *Journal Of Medicinal Chemistry* 2014, 57, 6822-33.
7. Bouchut, A.; Rotili, D.; Pierrot, C.; Valente, S.; Lafitte, S.; Schultz, J.; Hoglund, U.; Mazzone, R.; Lucidi, A.; Fabrizi, G.; Pechalrieu, D.; Arimondo, P. B.; Skinner-Adams, T. S.; Chua, M. J.; Andrews, K. T.; Mai, A.; Khalife, J. Identification of novel quinazoline derivatives as potent antiplasmodial agents. *European Journal Of Medicinal Chemistry* 2019, 161, 277-291.

What is claimed is:
1. A compound selected from:
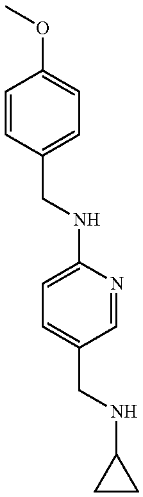,
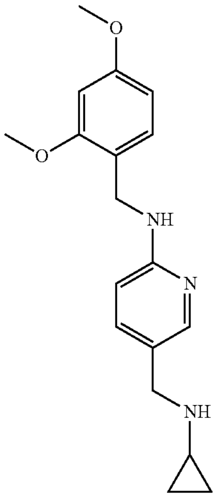,
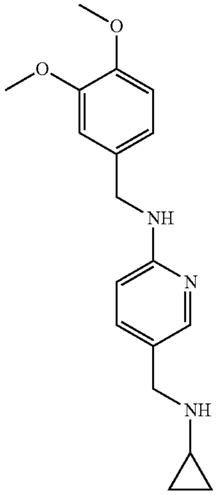,
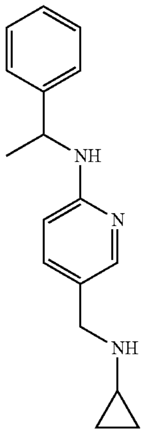,
-continued
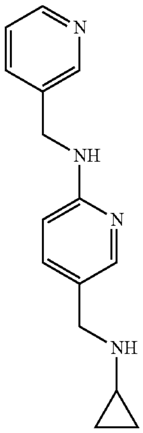,
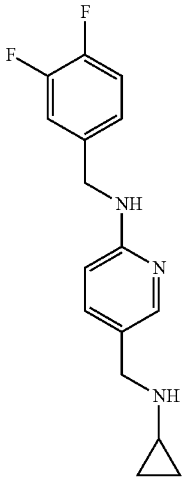,
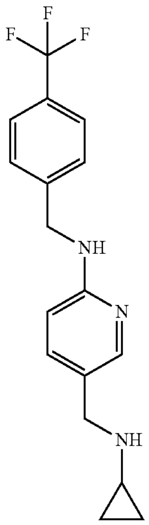,
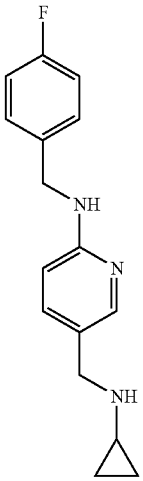,
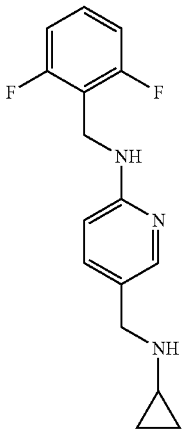,
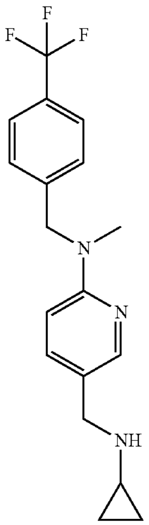, -continued
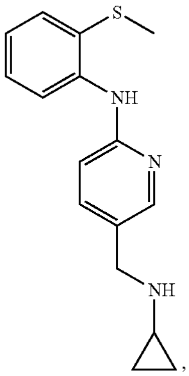,
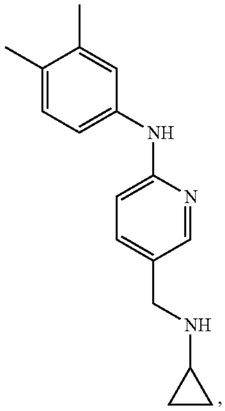,
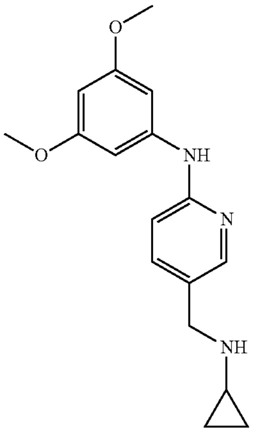,
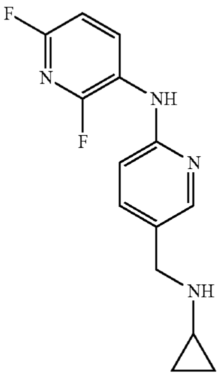,
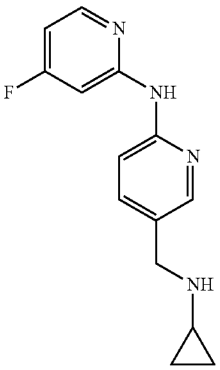,
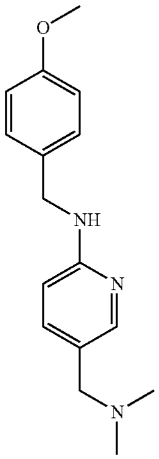,
-continued
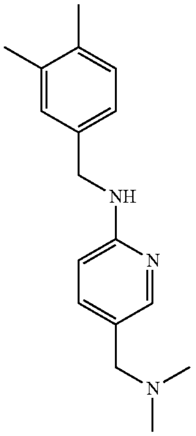,
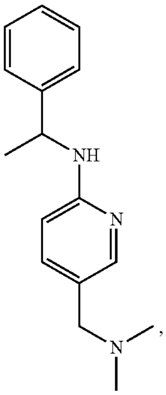,
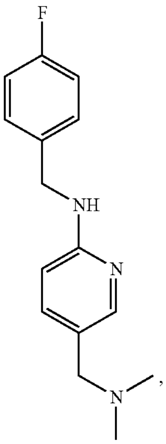, and
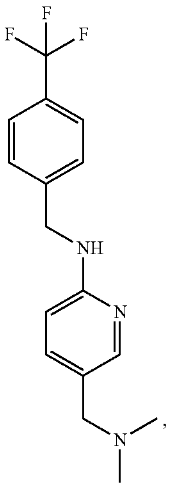,
or a pharmaceutically acceptable salt thereof.
2. The compound of claim 1, wherein the compound is selected from:
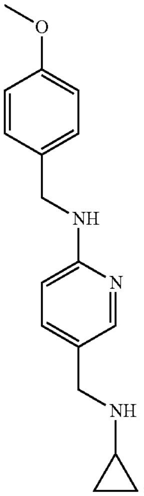,
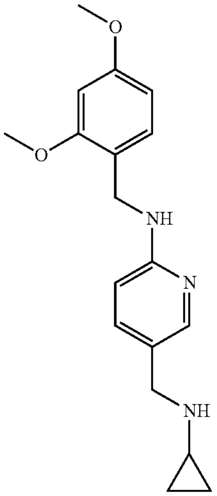, -continued
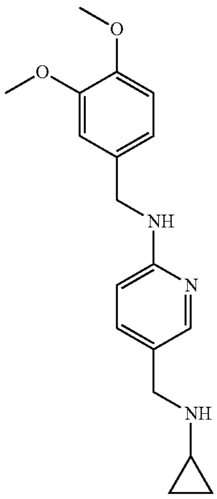,
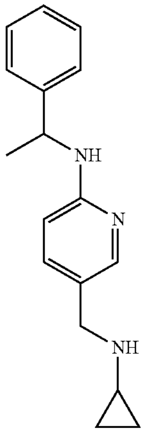,
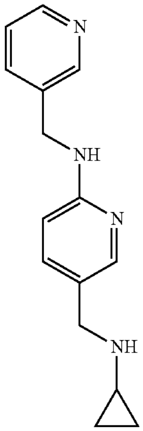,
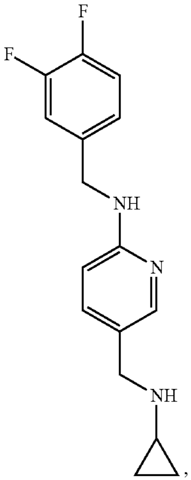,
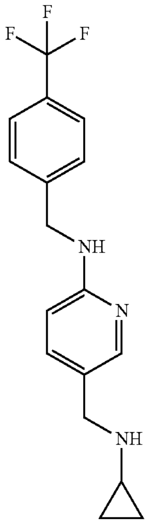,
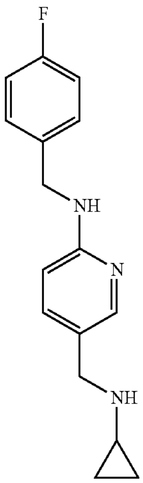,
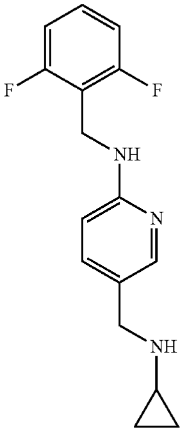,
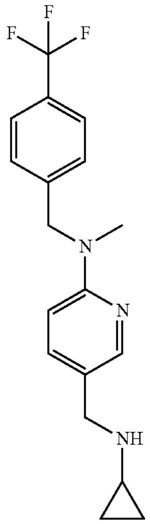,
-continued
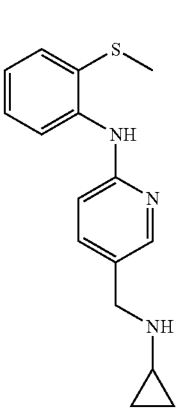,
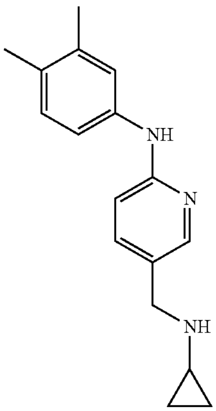,
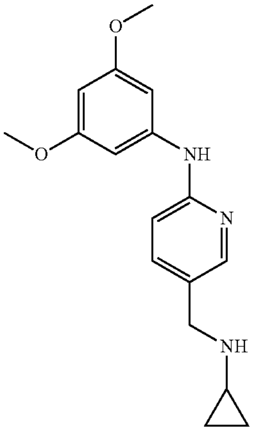,
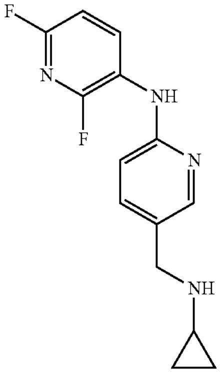,
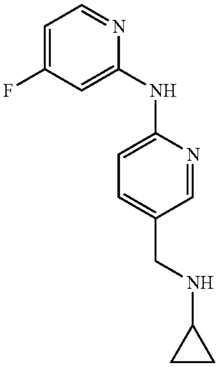,
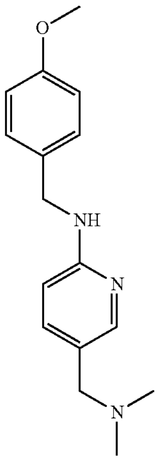, -continued
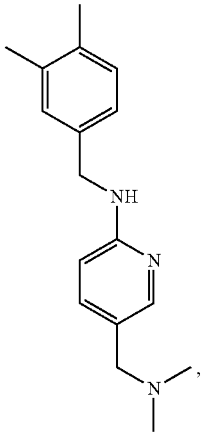
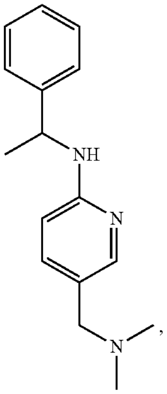
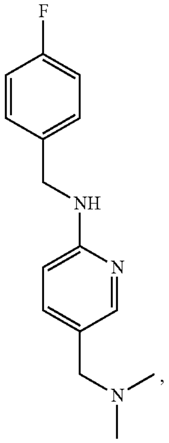
and
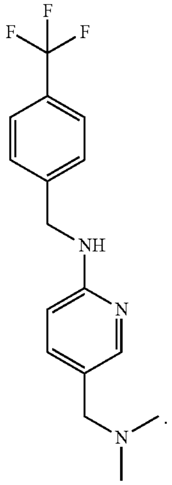
3. The compound of claim 1, wherein the compound is
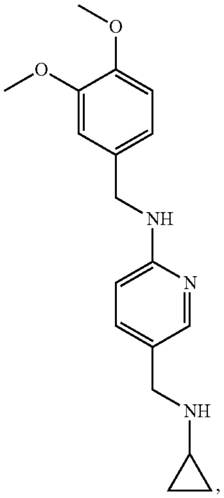 [SMILES: COc1ccc(CNc2ccc(CNC3CC3)cn2)cc1OC]
or a pharmaceutically acceptable salt thereof.
4. The compound of claim 1, wherein the compound is
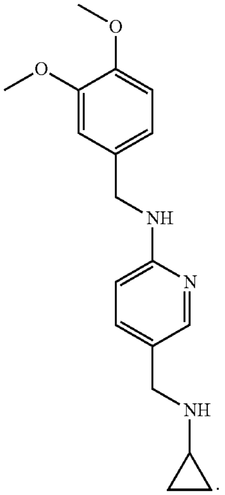 [SMILES: COc1ccc(CNc2ccc(CNC3CC3)cn2)cc1OC]
5. The compound of claim 1, wherein the compound is
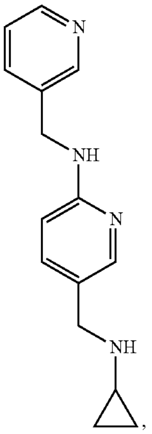 [SMILES: c1cncc(CNc2ccc(CNC3CC3)cn2)c1]
or a pharmaceutically acceptable salt thereof.
6. The compound of claim 1, wherein the compound is
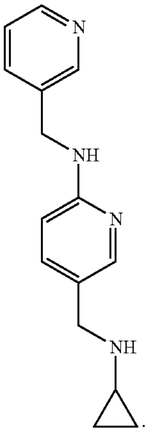 [SMILES: c1cncc(CNc2ccc(CNC3CC3)cn2)c1]

7. The compound of claim 1, wherein the compound is

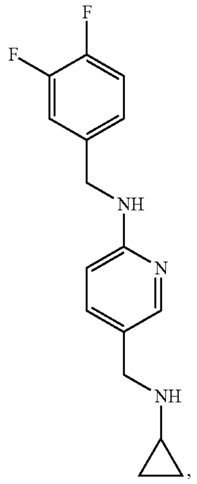 [SMILES: Fc1ccc(CNc2ccc(CNC3CC3)cn2)cc1F]

or a pharmaceutically acceptable salt thereof.

8. The compound of claim 1, wherein the compound is

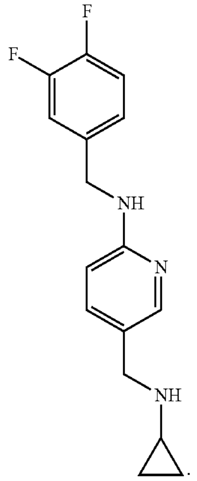 [SMILES: Fc1ccc(CNc2ccc(CNC3CC3)cn2)cc1F]

9. The compound of claim 1, wherein the compound is

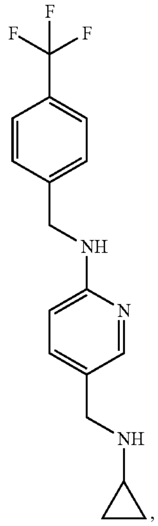

or a pharmaceutically acceptable salt thereof.

10. The compound of claim 1, wherein the compound is

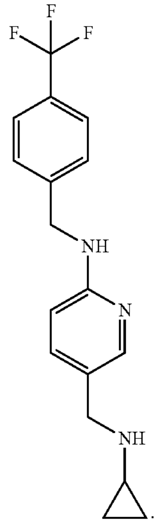 [SMILES: FC(F)(F)c1ccc(CNc2ccc(CNC3CC3)cn2)cc1]

11. The compound of claim 1, wherein the compound is

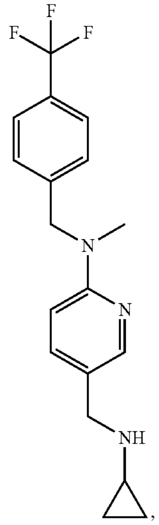 [SMILES: CN(Cc1ccc(C(F)(F)F)cc1)c1ccc(CNC2CC2)cn1]

or a pharmaceutically acceptable salt thereof.

12. The compound of claim 1, wherein the compound is
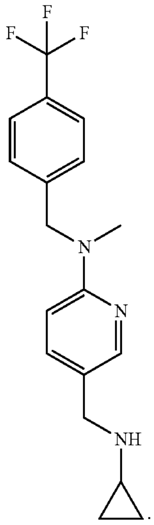
.
13. A compound selected from:
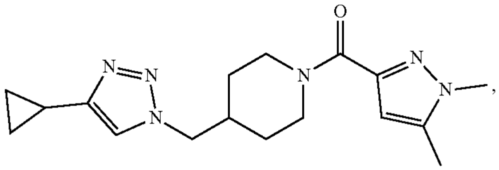
,
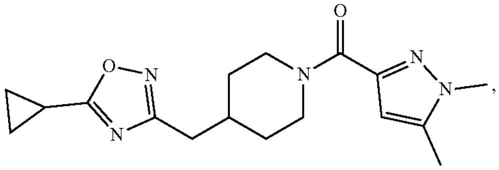
,
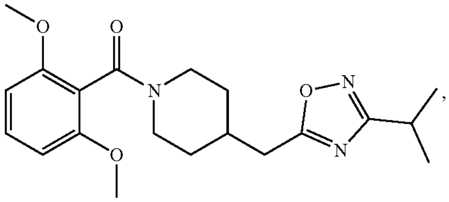
,
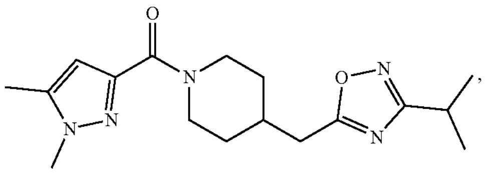
,
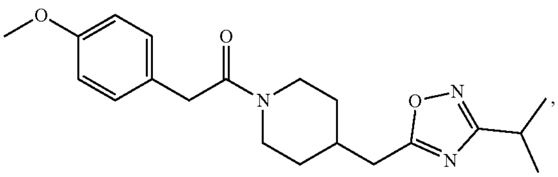
,
-continued
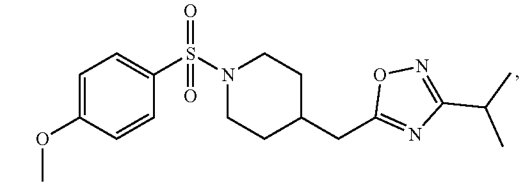
,
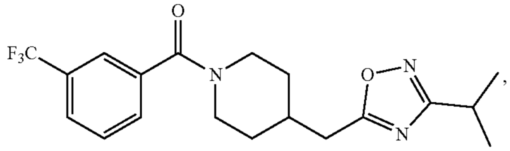
,
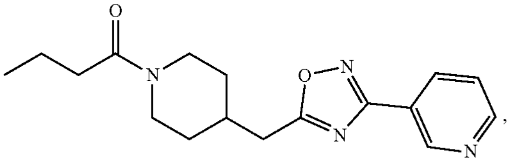
,
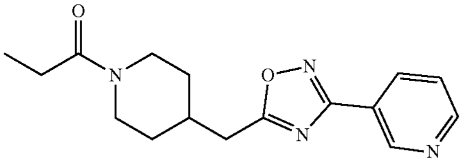
,
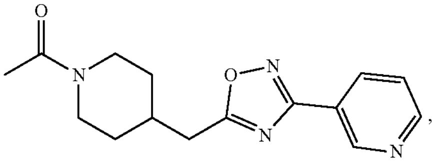
,
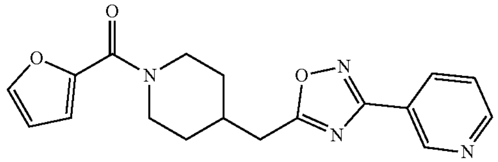
,
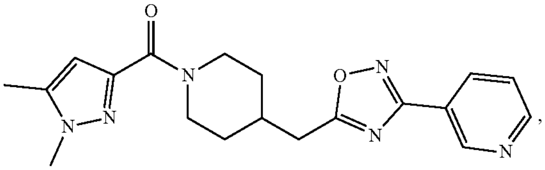
,
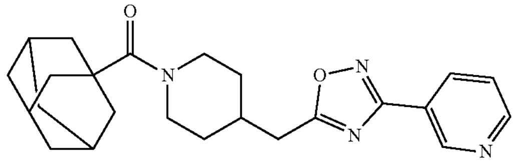
,
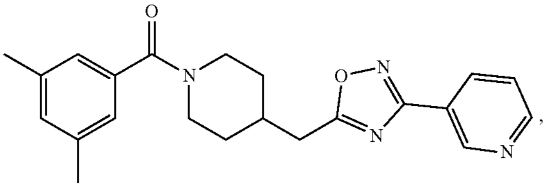
,
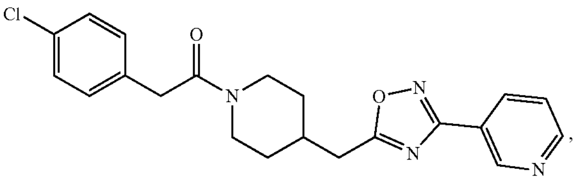
, -continued
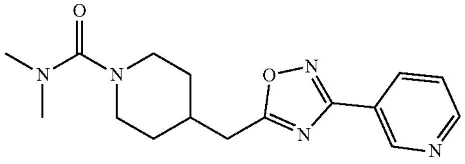,
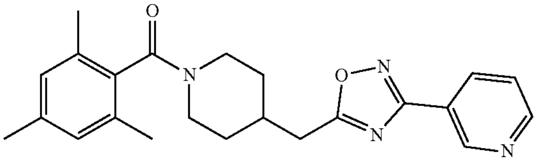,
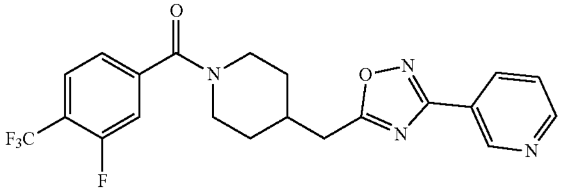,
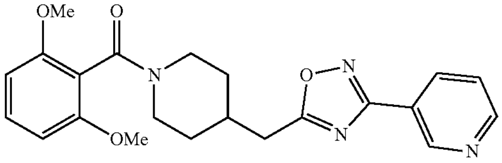,
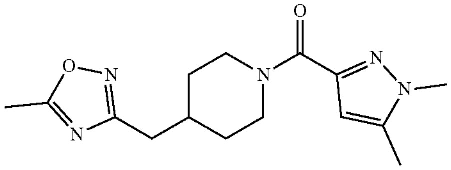,
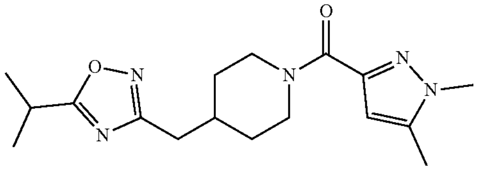,
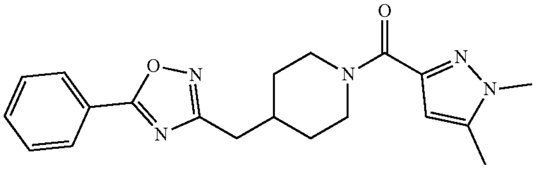,
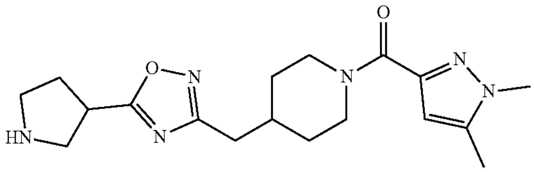,
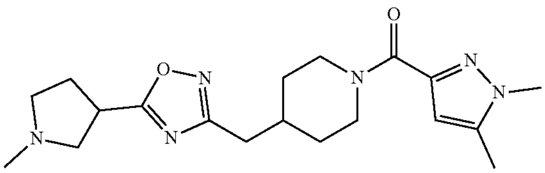,
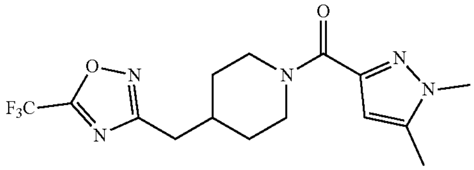,
-continued
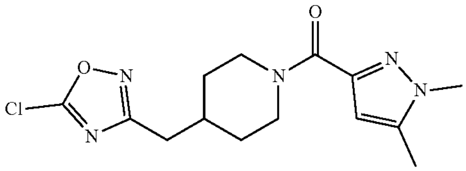,
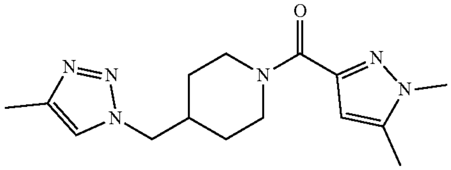,
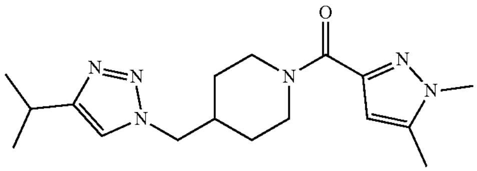,
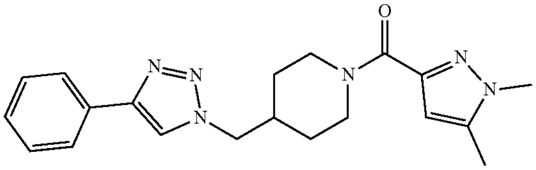,
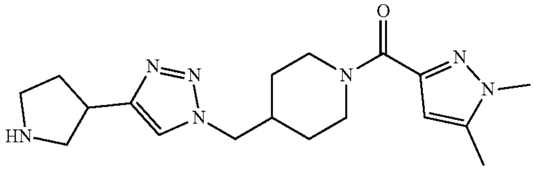,
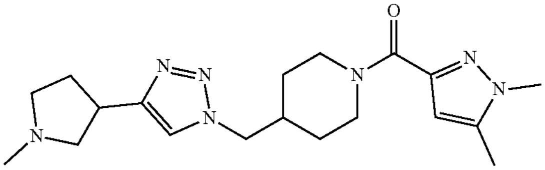,
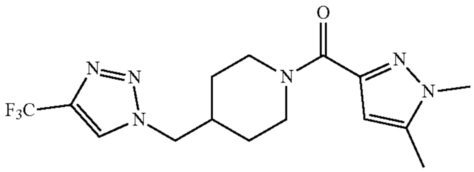, and
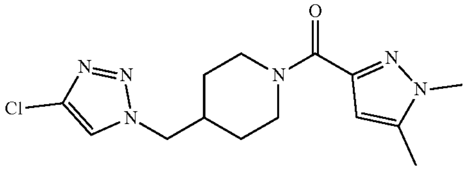,
or a pharmaceutically acceptable salt thereof.
14. The compound of claim 13, wherein the compound is selected from:
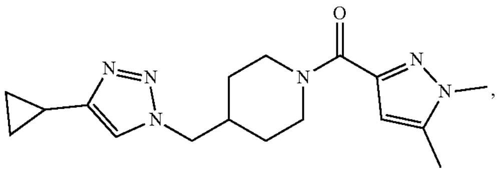, -continued
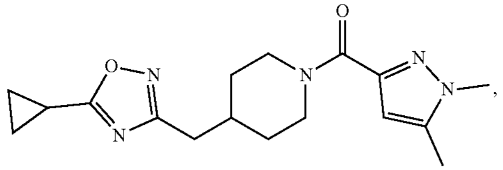
,
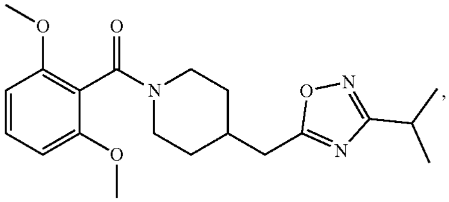
,
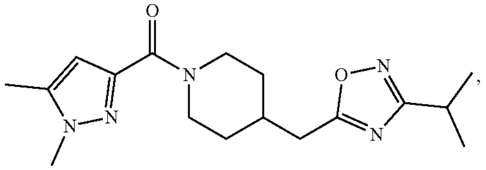
,
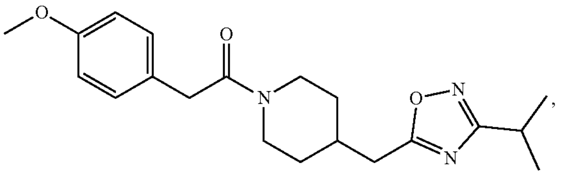
,
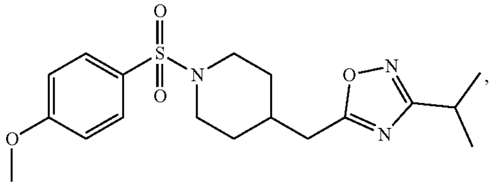
,
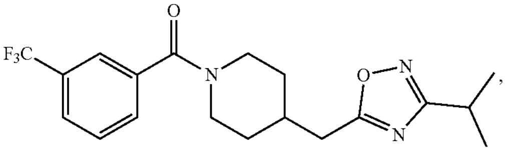
,
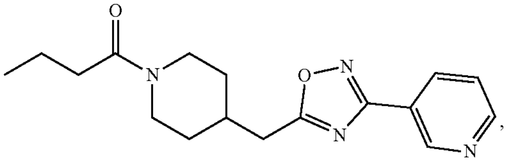
,
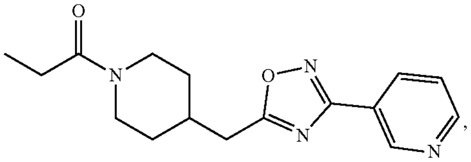
,
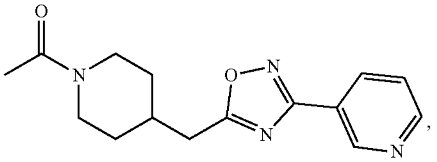
,
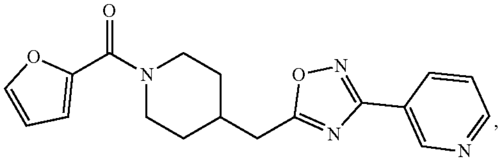
,
-continued
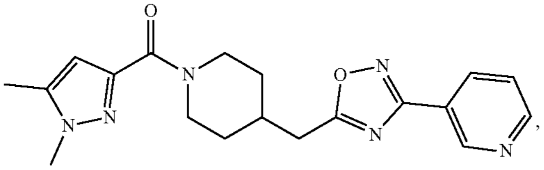
,
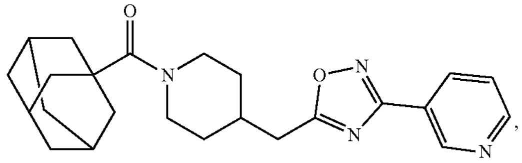
,
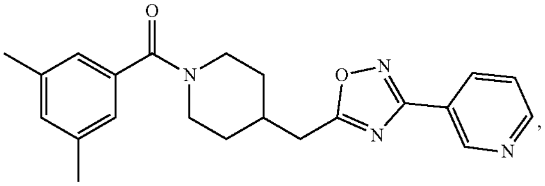
,
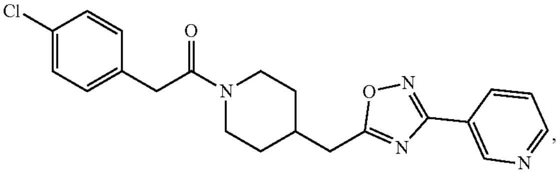
,
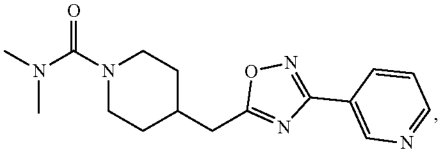
,
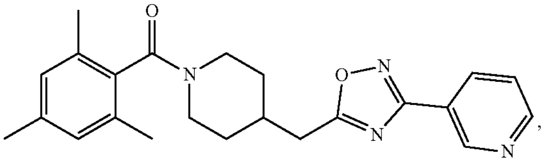
,
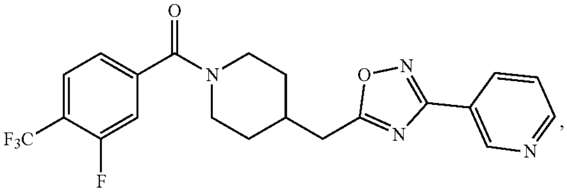
,
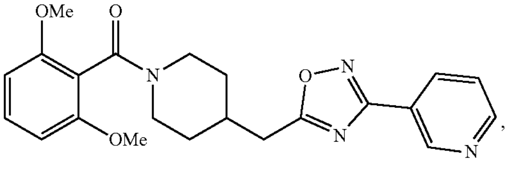
,
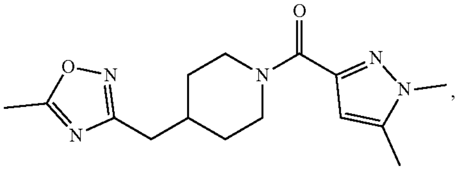
,
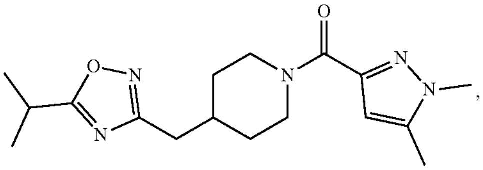
, -continued

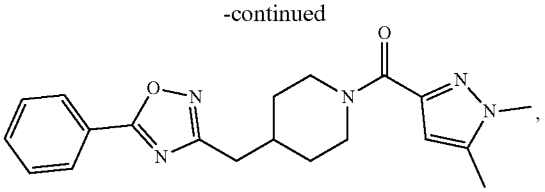

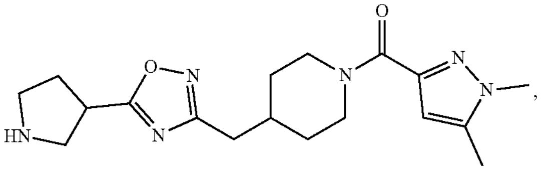

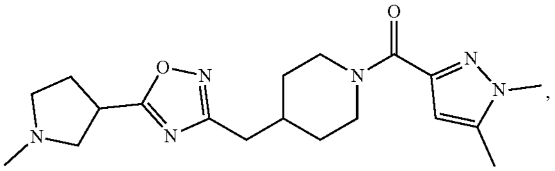

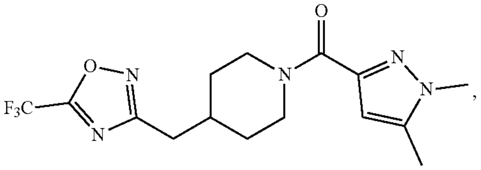

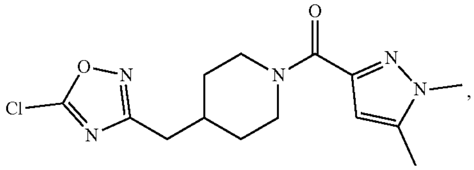

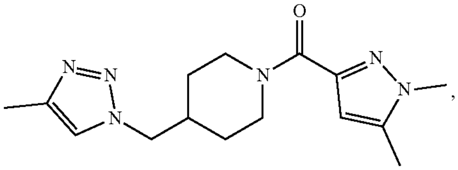

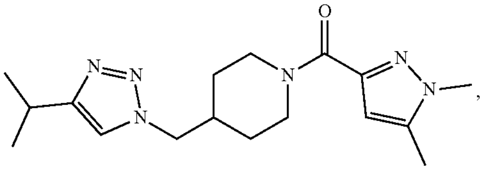

-continued

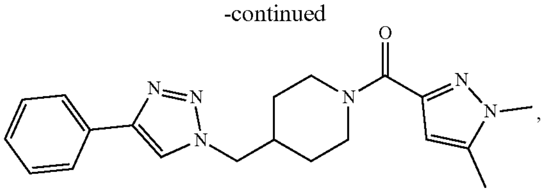

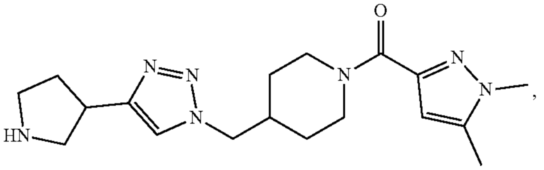

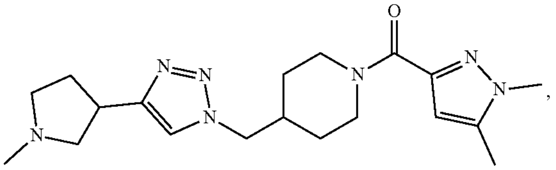

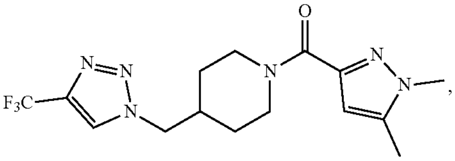

and

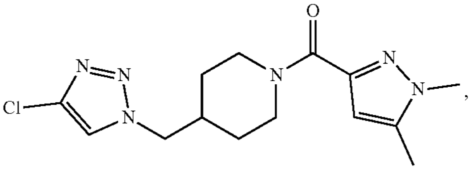

15. A method of treating a disease or disorder in a subject, wherein the disease or disorder is cancer, comprising administering to the subject a therapeutically effective amount of a compound of claim 1, or a pharmaceutically acceptable salt thereof.

16. A method of treating a disease or disorder in a subject, wherein the disease or disorder is cancer, comprising administering to the subject a therapeutically effective amount of a compound of claim 13, or a pharmaceutically acceptable salt thereof.

* * * * *